US009567581B2

(12) United States Patent
Lee et al.

(10) Patent No.: US 9,567,581 B2
(45) Date of Patent: Feb. 14, 2017

(54) SELECTIVE REACTIVATION OF GENES ON THE INACTIVE X CHROMOSOME

(71) Applicant: The General Hospital Corporation, Boston, MA (US)

(72) Inventors: Jeannie T. Lee, Boston, MA (US); Stefan Pinter, Cambridge, MA (US); Ruslan Sadreyev, Brookline, MA (US); Barry Kesner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/419,763

(22) PCT Filed: Aug. 7, 2013

(86) PCT No.: PCT/US2013/053948
§ 371 (c)(1),
(2) Date: Feb. 5, 2015

(87) PCT Pub. No.: WO2014/025887
PCT Pub. Date: Feb. 13, 2014

(65) Prior Publication Data
US 2015/0225717 A1 Aug. 13, 2015

Related U.S. Application Data

(60) Provisional application No. 61/680,616, filed on Aug. 7, 2012.

(51) Int. Cl.
A61K 48/00 (2006.01)
C12N 15/113 (2010.01)
C07H 21/00 (2006.01)
C07H 21/04 (2006.01)
C12N 15/11 (2006.01)

(52) U.S. Cl.
CPC ............. *C12N 15/113* (2013.01); *C07H 21/00* (2013.01); *C07H 21/04* (2013.01); *C12N 15/111* (2013.01); *C12N 2310/11* (2013.01); *C12N 2310/113* (2013.01); *C12N 2310/14* (2013.01); *C12N 2310/315* (2013.01); *C12N 2310/321* (2013.01); *C12N 2310/3231* (2013.01); *C12N 2310/341* (2013.01); *C12N 2310/3533* (2013.01); *C12N 2320/30* (2013.01)

(58) Field of Classification Search
CPC .................................................... A61K 48/00
See application file for complete search history.

(56) References Cited

FOREIGN PATENT DOCUMENTS

| WO | 2012/065143 | 5/2012 |
|---|---|---|
| WO | WO 2012/087983 | 6/2012 |
| WO | WO 2013/173608 | 11/2013 |

OTHER PUBLICATIONS

Zahnow et al. (Molecular Cell 39; Sep. 2010: 661-663).*
Grant et al., "Activation of the hprt gene on the inactive X chromosome in transformed diploid female Chinese hamster cells." Journal of Cell Science, 1989, 92, pp. 723-732.
International Search Report and Written Opinion dated Nov. 28, 2103 in international application No. PCT/US2013/053948, 6 pgs.
Bailey et al., "MEME: discovering and analyzing DNA and protein sequence motifs," Nucleic Acids Res. 2006, 34:W369-W373.
Bailey et al., "Molecular evidence for a relationship between LINE-1 elements and X chromosome inactivation: The Lyon repeat hypothesis," Proc Natl Acad Sci, Jun. 2000, 97: 6634-6639.
Barr and Moore, "Chromosomes, sex chromatin, and cancer," Proc. Can. Cancer Conf., 1957, 2:3-16.
Barski et al., "High-resolution profiling of histone methylations in the human genome," Cell, May 2007, 129:823-837.
Beletskii et al., "PNA interference mapping demonstrates functional domains in the noncoding RNA Xist," Proc. Natl. Acad. Sci., Jul. 2001, 98:9215-9220.
Berletch et al., "Escape from X inactivation in mice and humans," Genome Biol., 2010, 11:213.
Bernstein et al., "A bivalent chromatin structure marks key developmental genes in embryonic stem cells," Cell, Apr. 2006, 125:315-326.
Borah et al., "Further studies on the prognostic importance of Barr body frequency in human breast cancer: with discussion on its probable mechanism," J. Surg. Oncol., 1980, 13:1-7.
Boyer et al., "Polycomb complexes repress developmental regulators in murine embryonic stem cells," Nature, 2006, 441:349-353.
Brockdorff et al., "The product of the mouse Xist gene is a 15 kb inactive X-specific transcript containing no conserved ORF and located in the nucleus," Cell, Oct. 1992, 71:515-526.
Brown et al., "The human XIST gene: analysis of a 17 kb inactive X-specific RNA that contains conserved repeats and is highly localized within the nucleus," Cell, Oct. 1992, 71:527-542.
Camargo and Wang, "Cytogenetic evidence for the absence of an inactivated X chromosome in a human female (XX) breast carcinoma cell line," Hum. Genet., 1980, 55:81-5.
Cantrell et al., "X chromosome inactivation and Xist evolution in a rodent lacking LINE-1 activity," PLoS One, Jul. 2009, 4(7):e6252.
Carrel et al., "X-inactivation profile reveals extensive variability in X-linked gene expression in females," Nature, Mar. 2005, 434:400-404.
Chow et al., "LINE-1 activity in facultative heterochromatin formation during X chromosome inactivation," Cell, Jun. 2010, 141:956-969.
Chow et al., "Silencing of the mammalian X chromosome," Annual Review of Genomics and Human Genetics, Sep. 2005, 6:69-92.
Chureau et al., "Ftx is a non-coding RNA which affects Xist expression and chromatin structure within the X-inactivation center region," Hum Mol Genet, 2011, 20:705-718.
Clemson et al., "XIST RNA paints the inactive X chromosome at interphase: evidence for a novel RNA involved in nuclear/chromosome structure," J Cell Biol., Feb. 1996, 132:259-275.
Dinger et al., "NRED: a database of long noncoding RNA expression," Nucleic Acids Res., 2009, 37:D122-D126.
Dutrillaux et al., "Imbalance of sex chromosomes, with gain of early-replicating X, in human solid tumors," Int. J. Cancer, Oct. 1986, 38:475-9.
Engstrom et al., "Complex Loci in Human and Mouse Genomes," PLoS Genet., Apr. 2006, 2:e47.
(Continued)

*Primary Examiner* — Kimberly Chong
(74) *Attorney, Agent, or Firm* — Fish & Richardson P.C.

(57) ABSTRACT

Methods and compositions for selectively reactivating genes on the inactive X chromosome (Xi) in a locus-specific manner, e.g., genes associated with X-linked diseases, e.g., Rett Syndrome, Factor VIII or IX deficiency, Fragile X Syndrome, Duchenne muscular dystrophy, and PNH, in heterozygous females.

34 Claims, 24 Drawing Sheets

(56) References Cited

OTHER PUBLICATIONS

Falls et al., "Genomic Imprinting: Implications for Human Disease," Am. J. Pathol., Mar. 1999, 154:635-647.
Ganesan et al., "Abnormalities of the Inactive X Chromosome are a Common Feature of BRCA1 Mutant and Sporadic Basal-like Breast Cancer," Cold Spring Harb Symp Quant Biol., 2005, 70:93-7.
Gartler et al., "Mammalian X-chromosome inactivation," Annu Rev Genet, 1983, 17:155-190.
Germain, "Chapter 7: General aspects of X-linked diseases" in Fabry Disease: Perspectives from 5 Years of FOS. Mehta A, Beck M, Sunder-Plassmann G, editors. (Oxford: Oxford PharmaGenesis; 2006), 7 pages.
Ghosh and Shah, "Probable mechanism for the loss of Barr body in human female tumor with special reference to breast cancer," Med Hypotheses, Aug. 1981, 7:1099-104.
Ghosh and Shah, "Significance of the Barr body in human female tumors," Cancer Genet. Cytogenet., Nov. 1981, 4:269-74.
Ghosh et al., "Barr body frequency in esophageal cancer in Indian women," Acta. Cytol., 1983, 27:202-3.
Greenfield et al., "The UTX gene escapes X inactivation in mice and humans," Hum. Mol. Genet., 1998, 7:737-742.
Guttman et al., "Chromatin signature reveals over a thousand highly conserved large non-coding RNAs in mammals," Nature, Mar. 2009, 458(7235):223-7.
Guy et al., "Reversal of Neurological Defects in a Mouse Model of Rett Syndrome," Science, Feb. 2007, 315(5815):1143-7.
Hall, "Genomic imprinting: nature and clinical relevance," Annu. Rev. Med., 1997, 48:35-44.
Hasegawa et al., "The matrix protein hnRNP U is required for chromosomal localization of Xist RNA," Dev Cell, Sep. 2010, 19:469-476.
Helbig et al., "Scaffold attachment factor A (SAFA) is concentrated in inactive X chromosome territories through its RGG domain," Chromosoma, Dec. 2003, 112:173-182.
Huang et al., "Relationship of XIST Expression and Responses of Ovarian Cancer to Chemotherapy," Mol. Cancer Ther., Aug. 2002, 1:769-776.
International Preliminary Report on Patentability in International application No. PCT/US2013/053948, dated Feb. 10, 2015, 6 pages.
Jeon et al., "YY1 tethers Xist RNA to the inactive X nucleation center," Cell, Jul. 2011, 146:119-133.
Jia et al., "Genome-wide computational identification and manual annotation of human long noncoding RNA genes," RNA, 2010, 16(8):1478-1487.
Johnston et al., "Enox, a novel gene that maps 10 kb upstream of Xist and partially escapes X inactivation," Genomics, 2002, 80:236-244.
Kanhere et al., "Short RNAs are Transcribed from Repressed Polycomb Target Genes and Interact with Polycomb Repressive Complex-2," Molecular Cell, Jun. 2010, 38:675-688.
Kawakami et al., "Characterization of loss-of-inactive X in Klinefelter syndrome and female-derived cancer cells," Oncogene, 2004, 23:6163-6169.
Kawakami et al., "The roles of supernumerical X chromosomes and XIST expression in testicular germ cell tumors," J. Urol., Apr. 2003, 169:1546-52.
Kawakami et al., "XIST unmethylated DNA fragments in male-derived plasma as a tumour marker for testicular cancer," Lancet, Jan. 2004, 363:40-2.
Keane et al., "Mouse genomic variation and its effect on phenotypes and gene regulation," Nature, Sep. 2011, 477:289-294.
Khalil et al., "Many human large intergenic noncoding RNAs associate with chromatin-modifying complexes and affect gene expression," PNAS, Jul. 2009, 106(28):11675-11680.
Ku et al., "Genomewide analysis of PRC1 and PRC2 occupancy identifies two classes of bivalent domains," PLoS Genet., 2008, 4:e1000242.
Lalande, "Parental imprinting and human disease," Annu. Rev. Genet., 1996, 30:173-195.

Lee et al., "Chromatin immunoprecipitation and microarray-based analysis of protein location," Nat. Protoc., 2006, 1:729-748.
Lee et al., "Tsix, a gene antisense to Xist at the X-inactivation centre," Nat. Genet., Apr. 1999, 21:400-404.
Lee, "Gracefully ageing at 50, X-chromosome inactivation becomes a paradigm for RNA and chromatin control," Nat. Rev. Mol. Cell Biol., Dec. 2011, 12:815-826.
Liao et al., "Novel perspective: focusing on the X chromosome in reproductive cancers," Cancer Invest., 2003, 21:641-58.
Lipovich et al., "MacroRNA underdogs in a microRNA world: Evolutionary, regulatory, and biomedical significance of mammalian long non-protein-coding RNA," Biochim Biophys Acta., Sep. 2010, 1799(9):597-615.
Luo et al., "Transcriptomic and Genomic Analysis of Human Hepatocellular Carcinomas and Hepatoblastomas," Hepatology., Oct. 2006, 44(4):1012-24.
Lyon, "Imprinting and X-chromosome inactivation," Results Probl. Cell Differ., 1999, 25:73-90.
Lyon, "LINE-1 elements and X chromosome inactivation: a function for "junk" DNA?" Proc Natl Acad Sci., Jun. 2000, 97:6248-6249.
Lyon, "X-chromosome inactivation and human genetic disease," Acta. Paediatr. Suppl., 2002, 91(439):107-12.
Marks et al., "High-resolution analysis of epigenetic changes associated with X inactivation," Genome Res., 2009, 19:1361-1373.
Mikkelsen et al., "Genome-wide maps of chromatin state in pluripotent and lineage-committed cells," Nature, Aug. 2007, 448:553-560.
Moore and Barr, "The Sex Chromatin in Benign Tumours and Related Conditions in Man," Br. J. Cancer, Jun. 1955, 9:246-52.
Moore and Barr, "The sex chromatin in human malignant tissues," Br. J. Cancer, Sep. 1957, 11:384-90.
Moore et al., "The sex chromatin of the bovine freemartin," J Exp. Zool., Jun. 1957, 135:101-25.
Namekawa et al., "Two-step imprinted X inactivation: repeat versus genic silencing in the mouse," Mol. Cell Biol., Jul. 2010, 30:3187-3205.
Numata et al., "Comparative analysis of cis-encoded antisense RNAs in eukaryotes," Gene, May 2007, 392:134-141.
Numata et al., "Identification of novel endogenous antisense transcripts by DNA microarray analysis targeting complementary strand of annotated genes," BMC Genomics, Aug. 2009, 10:392.
Ogawa et al., "Intersection of the RNA interference and X-inactivation pathways," Science, Jun. 2008, 320:1336-1341.
Okada et al., "Comparative expression analysis uncovers novel features of endogenous antisense transcription," Hum. Mol. Genet., 2008, 17(11):1631-40.
Ørom et al., "Long Noncoding RNAs with Enhancer-like Function in Human Cells," Cell, Oct. 2010, 143(1):46-58.
Pandey et al., "Kcnq1ot1 antisense noncoding RNA mediates lineage-specific transcriptional silencing through chromatin-level regulation," Mol. Cell., Oct. 2008, 32(2):232-46.
Payer et al., "X chromosome dosage compensation: how mammals keep the balance," Annu. Rev. Genet., Sep. 2008, 42:733-772.
Pedersen et al., "Identification and Classification of Conserved RNA Secondary Structures in the Human Genome," PLoS Computat. Biol., Apr. 2006, 2(4):e33.
Plath et al., "Role of histone H3 lysine 27 methylation in X inactivation," Science, Apr. 2003, 300:131-135.
Plenge et al., "Skewed X-Chromosome Inactivation is a Common Feature of X-Linked Mental Retardation Disorders," Am. J. Hum. Genet., 2002, 71:168-173.
Ponting et al., "Evolution and Functions of Long Noncoding RNAs," Cell, Feb. 2009, 136(4):629-641.
Pullirsch et al., "The Trithorax group protein Ash2l and Saf-A are recruited to the inactive X chromosome at the onset of stable X inactivation," Development, Jan. 2010, 137:935-943.
Reinius et al., "Female-biased expression of long non-coding RNAs in domains that escape X-inactivation inactivation in mouse," BMC Genomics, 2010, 11:614.
Rosen et al., "Barr Body Distribution and Estrogen Receptor Protein in Mammary Carcinoma," Ann. Clin. Lab Sci., 1977, 7:491-9.

(56) References Cited

OTHER PUBLICATIONS

Rosok and Sioud, "Systematic identification of sense-antisense transcripts in mammalian cells," Nat Biotechnol. Jan. 2004, 22(1):104-8.
Seila et al., "Divergent Transcription from Active Promoters," Science, Dec. 2008, 322(5909):1849-51.
Silva et al., "Establishment of histone h3 methylation on the inactive X chromosome 5 requires transient recruitment of Eed-Enx1 polycomb group complexes," Dev. Cell, Apr. 2003, 4:481-495.
Simon and Kingston, "Mechanisms of polycomb gene silencing: knowns and unknowns," Nat. Rev. Mol. Cell Biol., Oct. 2009, 10:697-708.
Sirchia et al., "Loss of the Inactive X Chromosome and Replication of the Active X in BRCA1-Defective and Wild-type Breast Cancer Cells," Cancer Res., Mar. 2005, 65:2139-2146.
Spatz et al., "X-Chromosome Genetics and Human Cancer," Nat. Rev. Cancer, Aug. 2004, 4:617-29.
Splinter et al., "The inactive X chromosome adopts a unique three-dimensional conformation that is dependent on Xist RNA," Genes Dev., 2011, 25:1371-1383.
Tavares, "On the sex of cancer and teratomata cells," Lancet, May 1955, 268:948-9.
Tavares, "Sex chromatin in tumor cells," Acta Cytol., 1962, 6:90-4.
Tavares, "Sex chromatin in tumors," Medico (Porto), Jan. 1961, 12:97-100 (with English summary).
Tian et al., "The long noncoding RNA, Jpx, is a molecular switch for Xchromosome Inactivation," Cell, Oct. 2010, 143(3):390-403.
Torarinsson et al., "Thousands of corresponding human and mouse genomic regions unalignable in primary sequence contain common RNA structure," Genome Res., Jul. 2006, 16(7):885-889.
Tsai et al., "Long Noncoding RNA as Modular Scaffold of Histone Modification Complexes," Science, Aug. 2010, 329(5992):689-93.
Van den Veyver, "Skewed X Inactivation in X-Linked Disorders," Semin Reprod. Med., 2001, 19(2):183-91.
Wang et al., "Evidence of influence of genomic DNA sequence on human X chromosome inactivation," PLoS Comput. Biol., Sep. 2006, 2:e113.
Wang et al., "Two identical active X chromosomes in human mammary carcinoma cells," Cancer Genet. Cytogenet. Jun. 1990, 46:271-80.
Washietl et al., "Fast and reliable prediction of noncoding RNAs," Proc. Natl. Acad. Sci. USA, Feb. 2005, 102(7):2454-9.
Washietl et al., "Mapping of conserved RNA secondary structures predicts thousands of functional noncoding RNAs in the human genome," Nat. Biotechnol., Nov. 2005, 23(11):1383-90.
Wutz and Gribnau, "X inactivation Xplained," Curr. Opin. Genet. Dev., 2007. 17:387-393.
Yang et al., "Global survey of escape from X inactivation by RNA-sequencing in mouse," Genome Res., 2010, 20:614-622.
Yap et al., "Molecular Interplay of the Noncoding RNA ANRIL and Methylated Histone H3 Lysine 27 by Polycomb CBX7 in Transcriptional Silencing of INK4a," Mol. Cell, Jun. 2010, 38(5):662-74.
Yildirim et al., "Xist RNA is a Potent Suppressor of Hematologic Cancer in Mice," Cell, Feb. 2013, 152:727-742.
Zhang et al., "NATsDB: Natural Antisense Transcripts DataBase," Nucl. Acids Res., Nov. 2006, 35:D156-D161.
Zhao et al., "Genome-wide Identification of Polycomb-Associated RNAs by RIP-seq," Molecular Cell, Dec. 2010, 40:939-953.
Zhao et al., "Polycomb proteins targeted by a short repeat RNA to the mouse X chromosome," Science, Oct. 2008, 322:750-756.

\* cited by examiner

SELECTIVE REACTIVATION OF GENES ON THE INACTIVE X CHROMOSOME

CLAIM OF PRIORITY

This application is a U.S. National Phase Application under 35 U.S.C. §371 of International Patent Application No. PCT/US2013/053948, filed on Aug. 7, 2013, which claims the benefit of U.S. Patent Application Ser. No. 61/680,616, filed on Aug. 7, 2012, The entire contents of the foregoing are hereby incorporated by reference herein.

FEDERALLY SPONSORED RESEARCH OR DEVELOPMENT

This invention was made with Government support under Grant No. RO1-GM090278 awarded by the National Institutes of Health. The Government has certain rights in the invention.

TECHNICAL FIELD

This invention relates to methods and compositions for selectively reactivating genes on the inactive X chromosome (Xi), e.g., genes associated with X-linked diseases, e.g., Rett Syndrome, Factor VIII or IX deficiency, Fragile X Syndrome, Duchenne muscular dystrophy, and PNH, in heterozygous females carrying a mutated allele, in addition to a functional wildtype or hypomorphic allele.

BACKGROUND

X chromosome inactivation (XCI) achieves dosage balance in mammals by repressing one of two X chromosomes in females. X-linked diseases occur in females when a defective gene is present on the active X chromosome (Xa). In some cases, a normal, wild type copy of the gene is present on the inactive X chromosome (Xi), and the severity of the disease may depend on the prevalence (skewing) of inactivation of the X chromosome carrying the wild type gene. Reactivating the entire Xi is undesirable as cancers could arise as a result of X-chromosome gene overdosing (Yildirim et al., 2013, Cell 152: 727-742). Locus-specific reactivation of the non-disease silent allele on the Xi would be therapeutic in many cases of X-linked disease, such as Rett Syndrome.

SUMMARY

At least in part, the present invention is based on the discovery that, during XCI, the long noncoding Xist RNA and Polycomb proteins spread along the inactive X (Xi) to initiate chromosome-wide silencing. Although inactivation is known to commence at the X-inactivation center (Xic), how it propagates remains unknown. The present disclosure is based on an examination allele-specific binding of Polycomb repressive complex 2 (PRC2) and chromatin composition during XCI, which was used to generate a chromosome-wide profile of Xi and Xa (active X) at nucleosome-resolution. As described herein, initially, Polycomb proteins are localized to ~150 strong sites along the X and concentrated predominantly within bivalent domains coinciding with CpG islands ("canonical sites"). As XCI proceeds, ~4000 non-canonical sites are recruited, most of which are intergenic, non-bivalent, and lack CpG islands. Non-canonical sites cluster around the ~150 strong sites, and their H3K27me3 levels reflect a graded concentration originating from strong sites. This suggests that PRC2 and H3K27 methylation spread along a gradient unique to XCI. Thus, XCI is governed by a hierarchy of defined Polycomb stations that spread H3K27 methylation in cis.

A vast majority of the strong and moderate sites demonstrate transcription of at least one RNA, many of which are likely to be noncoding. Some overlap the previously described PRC2 transcriptome (Zhao et al., 2010, Molecular Cell; WO 2012/065143; and PCT/US2011/065939), but a large number does not.

Thus, in one aspect the invention provides methods for activating an inactive X-linked allele in a cell of a female heterozygous subject. The methods include administering to the cell an inhibitory oligonucleotide targeting one or more of a strong or moderate PRC2 or EZH2 or SUZ12 binding site as listed in Tables A, IVA-C or XIII-XV; and/or one or more of the transcripts associated with the PRC2 sites, as listed in Tables VI-IX, XVI-XVIII. In some embodiments, both an inhibitory oligonucleotide targeting a strong or moderate PRC2 or EZH2 or SUZ12 binding site, and an inhibitory oligonucleotide targeting a transcript associated with the same PRC2 site are administered.

In another aspect, the invention provides methods for activating an inactive X-linked allele in a cell, preferably a cell of a female heterozygous subject. The methods include administering to the cell one or more of:
(a) an inhibitory oligonucleotide targeting a strong or moderate PRC2 binding site (e.g., EZH2 or SUZ12 binding site, preferably a strong binding site) as listed in Tables A, IVA-C or XIII-XV, i.e., an oligo that is complementary or identical to a region within a strong or moderate PRC2 site, and/or
(b) an inhibitory oligonucleotide targeting (i.e., complementary to) a polycomb-associated RNA (pa-RNA) associated with the X-linked allele, e.g., a paRNA as set forth in Tables VI-IX or XVI-XVIII.

Although the end result is an activation or increase in gene expression, the oligonucleotides described herein are referred to as "inhibitory" because they inhibit the PRC2-mediated gene silencing, either by binding to either strand of the genomic DNA where the PRC2 complex binds (i.e., a strong or moderate site as described herein) and, without wishing to be bound by theory, inhibit binding of the PRC2 complex to that site, or because they bind to a paRNA as described herein and, without wishing to be bound by theory, inhibit the ability of the paRNA to silence the associated gene.

In some embodiments, the inactive X-linked allele is associated with an X-linked disorder, and the oligonucleotide is administered in a therapeutically effective amount.

In some embodiments, the cell is in a living subject.

In some embodiments, the inhibitory oligonucleotide is complementary or identical to at least 8 consecutive nucleotides of one or more of a strong or moderate PRC2 or EZH2 or SUZ12 binding site as listed in TABLES A, IV, XIII-XV; and/or one complementary to at least 8 consecutive nucleotides of one of the transcripts associated with the PRC2 sites, as listed in Tables VI-IX, XVI-XVIII.

In some embodiments, the oligonucleotide does not comprise three or more consecutive guanosine nucleotides. In some embodiments, the oligonucleotide does not comprise four or more consecutive guanosine nucleotides.

In some embodiments, the oligonucleotide is 8 to 30 nucleotides in length.

In some embodiments, at least one nucleotide of the oligonucleotide is a nucleotide analogue.

In some embodiments, at least one nucleotide of the oligonucleotide comprises a 2' O-methyl.

In some embodiments, each nucleotide of the oligonucleotide comprises a 2' O-methyl.

In some embodiments, the oligonucleotide comprises at least one ribonucleotide, at least one deoxyribonucleotide, or at least one bridged nucleotide. In some embodiments, the bridged nucleotide is a LNA nucleotide, a cEt nucleotide or a ENA modified nucleotide.

In some embodiments, each nucleotide of the oligonucleotide is a LNA nucleotide.

In some embodiments, the nucleotides of the oligonucleotide comprise 2'-fluoro-deoxyribonucleotides.

In some embodiments, the nucleotides of the oligonucleotide comprise 2'-O-methyl nucleotides.

In some embodiments, the nucleotides of the oligonucleotide comprise ENA nucleotide analogues.

In some embodiments, the nucleotides of the oligonucleotide comprise LNA nucleotides.

In some embodiments, the nucleotides of the oligonucleotide comprise comprising phosphorothioate internucleotide linkages between at least two nucleotides.

In some embodiments, the nucleotides of the oligonucleotide comprise phosphorothioate as internucleotide linkages between all nucleotides.

In some embodiments, the oligonucleotide is a gapmer or a mixmer.

In some embodiments, the oligonucleotide increases expression of mecp2.

In another aspect, the invention provides inhibitory oligonucleotides that are complementary to at least 8 consecutive nucleotides of one or more of a strong or moderate PRC2/EZH2 or SUZ12 binding site as listed in TABLES A, IV, XII-XV; and/or one or more of the transcripts associated with the PRC2 sites, as listed in Tables VI-IX, XVI-XVIII.

In some embodiments, the oligonucleotide does not comprise three or more consecutive guanosine nucleotides.

In some embodiments, the oligonucleotide does not comprise four or more consecutive guanosine nucleotides.

In some embodiments, the oligonucleotide is 8 to 30 nucleotides in length.

In some embodiments, at least one nucleotide of the oligonucleotide is a nucleotide analogue.

In some embodiments, at least one nucleotide of the oligonucleotide comprises a 2' O-methyl.

In some embodiments, each nucleotide of the oligonucleotide comprises a 2' O-methyl.

In some embodiments, the oligonucleotide comprises at least one ribonucleotide, at least one deoxyribonucleotide, or at least one bridged nucleotide.

In some embodiments, the bridged nucleotide is a LNA nucleotide, a cEt nucleotide or a ENA modified nucleotide.

In some embodiments, each nucleotide of the oligonucleotide is a LNA nucleotide.

In some embodiments, the nucleotides of the oligonucleotide comprise 2'-fluoro-deoxyribonucleotides.

In some embodiments, the nucleotides of the oligonucleotide comprise 2'-O-methyl nucleotides.

In some embodiments, the nucleotides of the oligonucleotide comprise ENA nucleotide analogues.

In some embodiments, the nucleotides of the oligonucleotide comprise LNA nucleotides.

In some embodiments, the nucleotides of the oligonucleotide comprise comprising phosphorothioate internucleotide linkages between at least two nucleotides.

In some embodiments, the nucleotides of the oligonucleotide comprise phosphorothioate internucleotide linkages between all nucleotides.

In some embodiments, the oligonucleotides are gapmers or mixmers.

In some embodiments, the oligonucleotide increases expression of mecp2.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

REFERENCE TO SEQUENCES SUBMITTED ON A COMPACT DISC

This application includes a compact disc containing a sequence listing. The sequence listing is identified on the compact disc as follows.

| Disc | File Name | Date of Creation | size (bytes) |
|---|---|---|---|
| 29539_0067WO1_1 | 29539_0067WO1_ST25.txt | Aug. 7, 2013 | 606,912 KB |

Figure 1A:
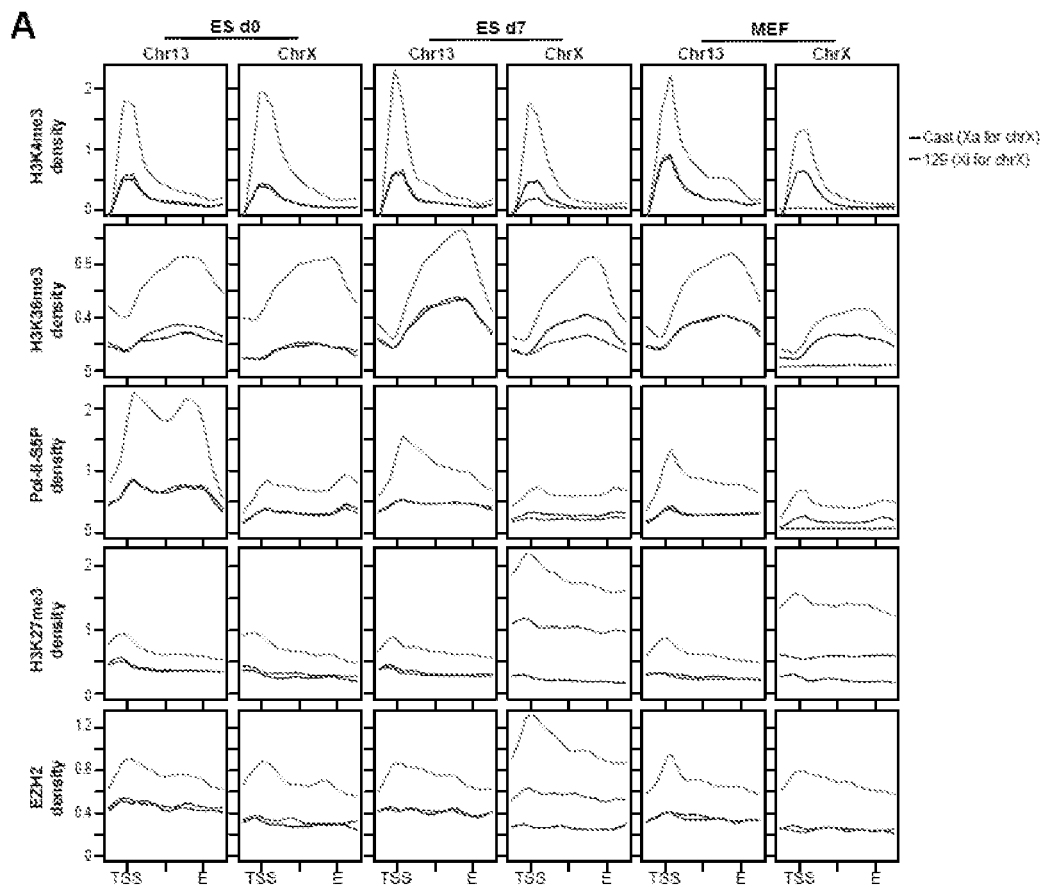
FIG. 1: Allelic Chromatin Profiles of Xa and Xi.

(A) Metagene analysis for chromatin epitopes on Chr13 and ChrX at indicated timepoints. Coverages were averaged over all genes (843 for Chr13, 1007 for ChrX) and scaled from TSS to 3' end, E. Profiles extend 3 kb upstream of TSS and 3 kb downstream of E. Densities were normalized to the average gene coverage over the chromosome.

(B,C) Pearson correlations for pairwise comparisons between epitopes were compared to a permutation-based random model and resulting Z-scores plotted in heatmaps. (B) plots MEF results. (C) plots ES d0 and d7 results. Numerical Z-scores are color-coded and scaled identically for all heatmaps. Yellow-red patches, significant positive correlation; blue patches, significant negative correlation. A white diagonal line separates Cast and 129 results.

FIG. 2: Many Strong EZH2 Sites are Defined Bivalent Domains.

(A) Characteristics of constant, acquired, and lost strong EZH2 sites on d0 and d7. The portion of sites lying within CpG islands is indicated by stripes.

(B) Changes in peak widths, densities (coverage per bp) for EZH2 and H3K27me3 between d0 and d7. Medians (turquoise, Chr13; orange, ChrX), 25-75 percentile (box) and 10-90 percentile (error bars) are shown.

(C) Allelic skewing of strong EZH2 sites. Numbers of sites skewing to Cast (blue) or 129 (red) are shown. Those with significant skewing (p<0.05, norm. approx. of binomial) are shown in darker blue and red. Grey bars, non-polymorphic sites (n/d, not determined).

(D) Summed coverage of EZH2 and H3K27me3 at strong and moderate sites as a percentage of total chromosomal coverage on d0 and d7 (left) and as absolute fold-increase (d7/d0, right).

FIG. 3: Moderate EZH2 Sites are Non-Canonical PRC2 Targets.

(A) Characteristics of moderate EZH2 sites on d0 and d7. The portion of sites overlapping CpG islands is indicated by stripes.

(B) Allelic skewing of moderate EZH2 sites. Numbers of sites skewing to Cast (blue) or 129 (red) are shown. Those with significant skewing (p<0.05, norm. approx. of binomial) are shown in darker blue and red. Grey bars, non-polymorphic sites (n/d, not determined).

(C) Changes in EZH2 and H3K27me3 densities between d0 and d7. Medians (turquoise, Chr13; orange, ChrX), 25-75 percentile (box) and 10-90 percentile (error bars) are shown.

(D) Metasite analysis for strong and moderate sites at indicated timepoints. Coverages were averaged over all strong (ChrX: 56, 147, 50 sites; Chr13: 79, 81, 83 sites for d0, d7 and MEFs) and moderate sites (ChrX: 1618, 4077, 1211 sites; chr13: 1241, 1041, 758 sites for d0, d7 and MEFs) and scaled from start to end. Profiles extend ±20 kb into flanks. Densities were normalized to the average site coverage over the chromosome.

FIG. 4: Relationship of Repetitive Elements to EZH2 Sites.

(A) Repeat classes enriched or depleted in strong sites, ±3 kb flanking strong sites and moderate sites are plotted by their level of enrichment (positive log 2 odds ratio) or depletion (negative). Different timepoints and chromosomes, as marked. Bubble sizes indicate the fraction of sites (Scale: 0.05, 0.2, 0.5, 1.0) containing a given repeat class (if enriched) or lacking it (if depleted). For example, LINE1 sequences are depleted across the board in most sites, hence their bubbles are large. Only statistically significant (Z>2.5) enrichment or depletion is shown (bubble sizes smaller than 0.05 indicate insignificance). The full data are listed in Table II for further reference.

(B-D) Log 2 odds ratios for significant (Z>2.5) enrichment and depletion of specific repeat types at (B) strong sites, (C) flanking (+/−3 kb) strong sites and (D) moderate sites. The full data are listed in Table III for further reference.

Figure 5A:
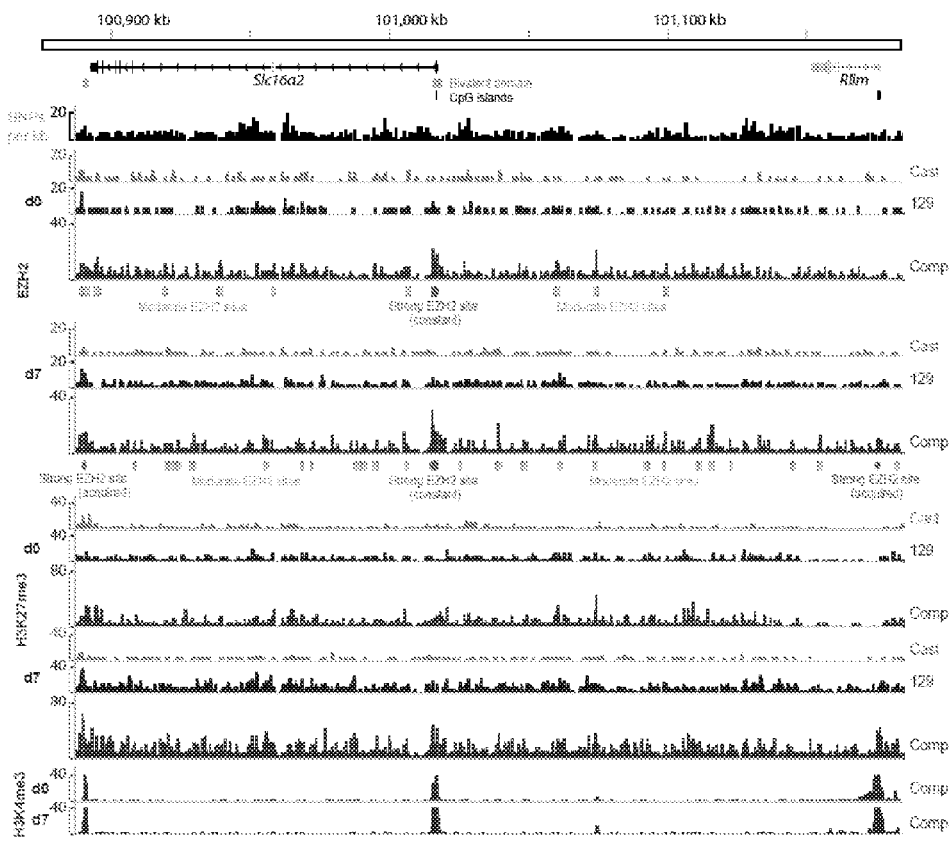

FIG. 5: Developmental Profile of the Slc16a2-Rnf12 Region.

(A) ES d0 and d7 profiles for Slc16a2-Rnf12 region.

(B) Three models for spreading of EZH2.

FIG. 6: Spread of H3K27me3 from EZH2 sites occurs in a distance-dependent manner.

(A) EZH2 and H3K27me3 densities from d0 and d7 were binned over Chr13 and ChrX positions to obtain correlation coefficients and Z scores from a permutation-based random model. Pearson R coefficients are indicated for the correlation of strong/moderate EZH2 sites (orange values) and H3K27me3/moderate EZH2 sites (black values). A purple triangle marks the location of the Xic.

(B,C) Smoothened trendlines of EZH2 (B) or H3K27me3 (C) densities at a given nucleosome-sized window of x-distance from the nearest strong site, on indicated days and chromosomes. Densities are plotted over a sliding 1 kb window with steps of 200 bp.

FIG. 7: A Hierarchy of EZH2 Sites, with Limited EZH2 Translocation and Long-Range H3K27Me3 Gradient.

(A) Smoothened trendlines of EZH2 densities at a moderate (mod) site at given distances (x-axis) from the nearest strong site, on indicated days and chromosomes.

(B) Smoothened trendlines of H3K27me3 densities at a moderate (mod) site at given distances (x-axis) from the nearest strong site, on indicated days and chromosomes. Color-coded triangles denote distance-at-half-maximum for each chromosomal timepoint.

(C) Depiction of the number of moderate (mod) sites at given distances from the nearest strong site on d0 and d7 for Chr13 and ChrX. Scale, bubble sizes represent fractions of 0.2, 0.05 and 0.02 of all mod sites. Each graphed bubble is summed over 40 kb bins. Pearson correlation coefficients (R) and Z scores (Fisher transformed) shown.

(D) Model and summary.

FIG. 8: X Chromosome State and Allelic Ratio in Differentiating ESCs and MEFs.

(A) Percentage of EZH2 and H3K27me3 immunofluorescence stained differentiating ES cells (d4, d7, d10 example images next to bar chart), Xist-RNA FISH and X chromosome paint in MEFs, demonstrating 1:1 state of Xi:Xa.

(B) Relative abundance of input DNA aligning to specific chromosomes normalized solely by chromosome length in d0, d7 and MEFs, demonstrating expected relative abundance near 1 for all samples (not accounting for mapability). Chromosomes 13 and X highlighted by MEF labels (0.98 and 0.84, respectively).

(C) Distribution of input coverage densities over 1 kb in d0, d7 and MEFs in composite (comp), cast and 129 tracks over chr13 (black) and chrX (red), demonstrating lack of right-ward shift expected in case of aneuploidy.

Figure 9:
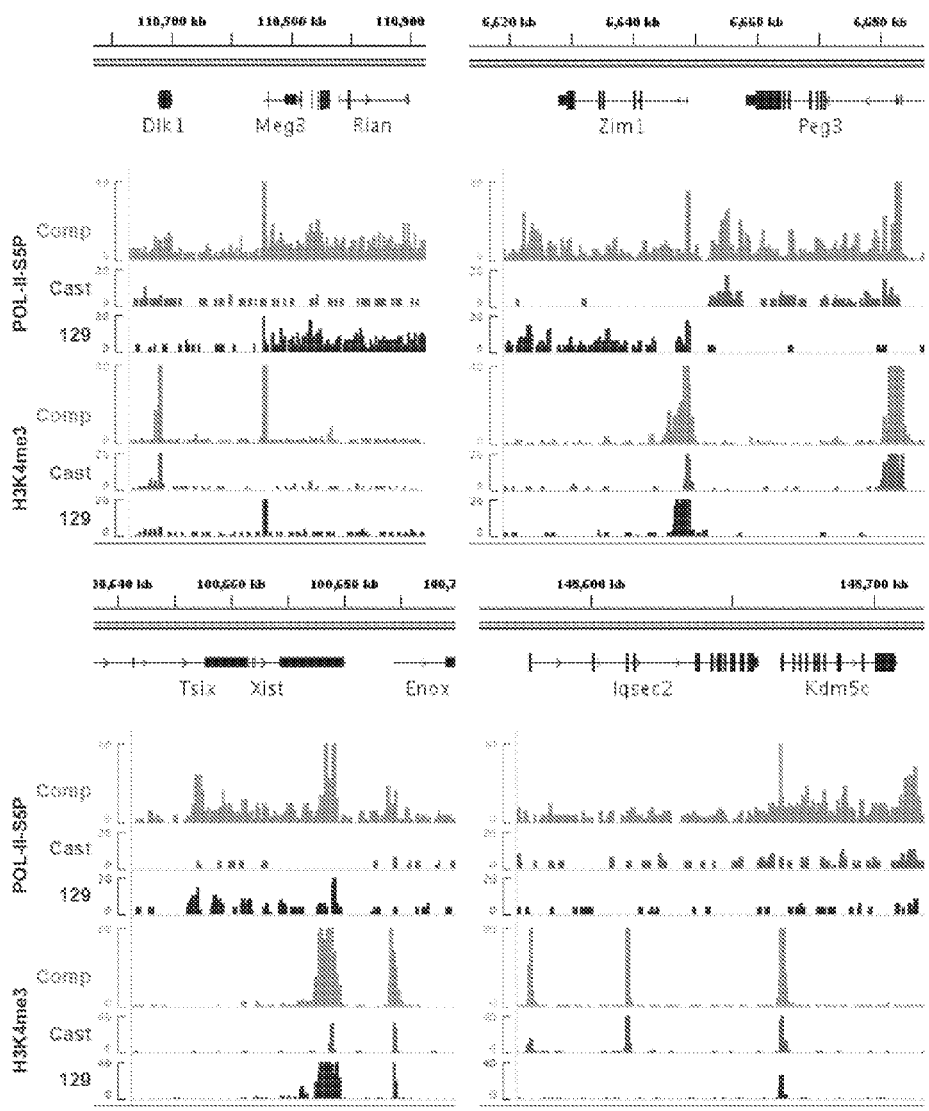

FIG. 9: Allele-Specific ChIP-Seq at Imprinted, Biallelic and X-Linked Loci.

Select ChIP-seq profiles for POL-II-S5P, H3K4me3, H3K27me3, and EZH2 epitopes in MEFs were mapped to Mus castaneus (Cast) or 129 alleles. Comp, composite track (Cast+129+neutral). While composite tracks indicate total epitope abundance, enrichment in the allele-specific tracks is a function of both epitope abundance and SNP density. Input-normalized coverage values are indicated on the y-axis and scaled identically between alleles.

Figures 10A, 10B:
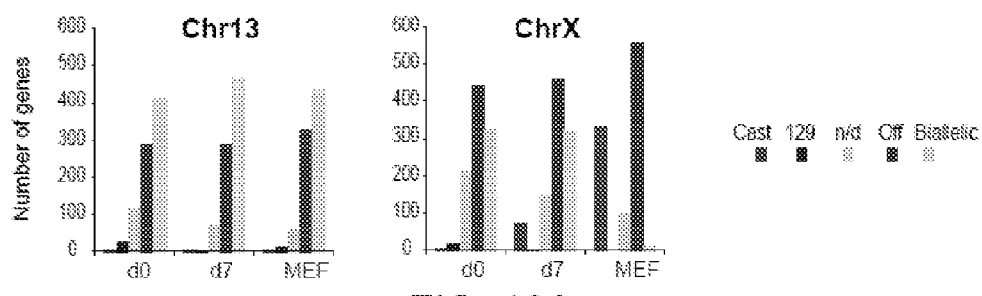
Figure 10C:
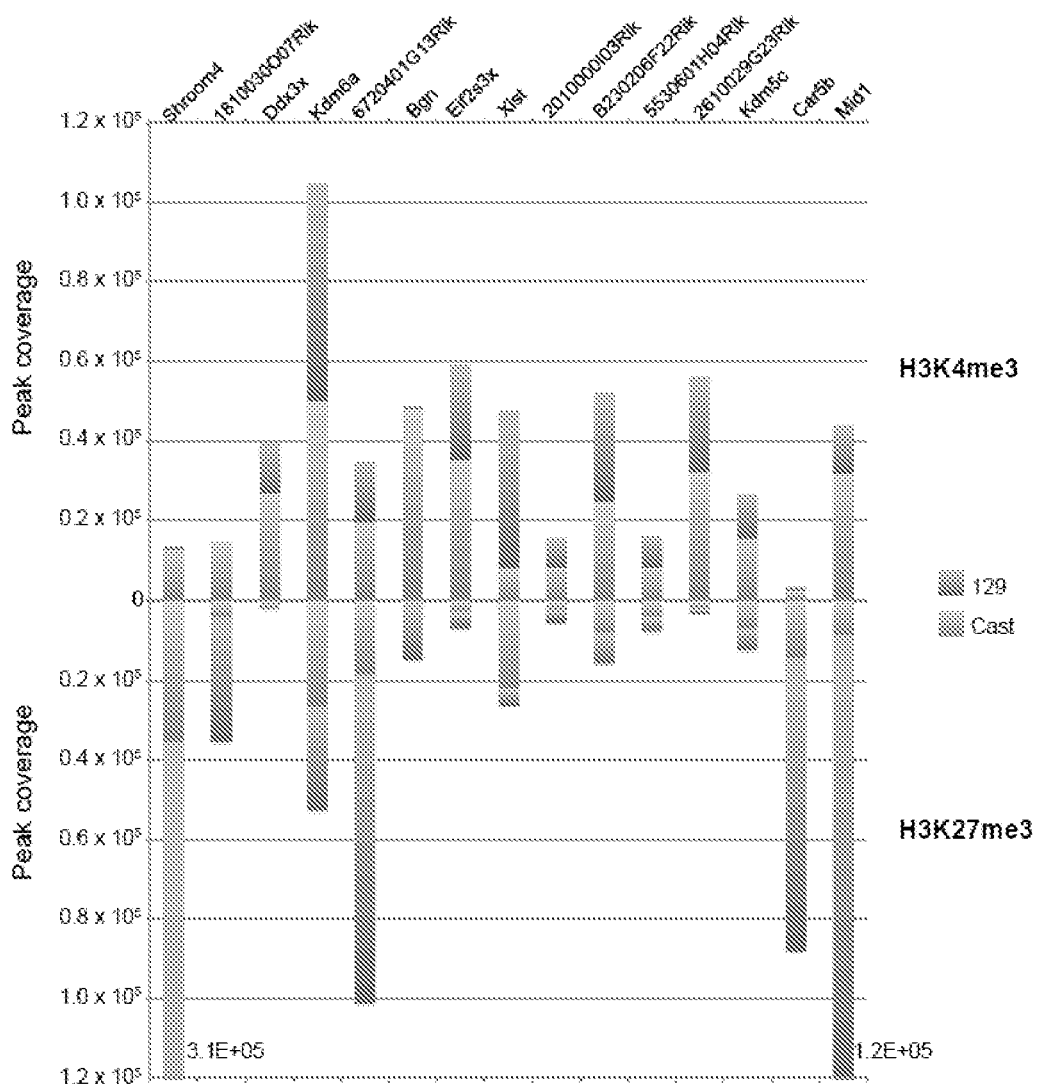

FIG. 10: Genes that Escape XCI.

(A) Classification of Chr13 and ChrX genes according to H3K4me3 status in d0, d7 and MEF, n/d, not determined due to lack of allele-specific polymorphisms. Peaks within 3 kb of an annotated TSS were scored for their allelic skew and significance (p<0.05, norm. approx. of binomial).

(B) Genes that escape XCI are shown with aliases, ChrX coordinates, and allelic skew values ranging 100% Cast to 100% 129 for H3K4me3 ChIP DNA. Composite values (comp) indicate total H3K4me3 coverage. X-linked genes marked with H3K4me3 in MEFs were classified as escapee candidates if allelic skew was not significant (p >0.05, binomial test) and/or had a maximal H3K4me3 coverage of >3000 over a given 1 kb window on the 129 allele. Escapee gene candidates predicted by RNA-seq (Yang et al., 2010) are also included in the table for comparison: 8 genes were identified in both studies (green), 4 specific to Yang et al. (2010)(yellow), and 3 specific to this study (blue).

(C) Allelic (Cast in blue, 129 in red) chromatin states of escapee gene candidates (in MEFs). Peak coverage of active mark H3K4me3 is shown on top, repressive mark H3K27me3 on the bottom (y-axis reversed to improve visualization).

Figure 11A:
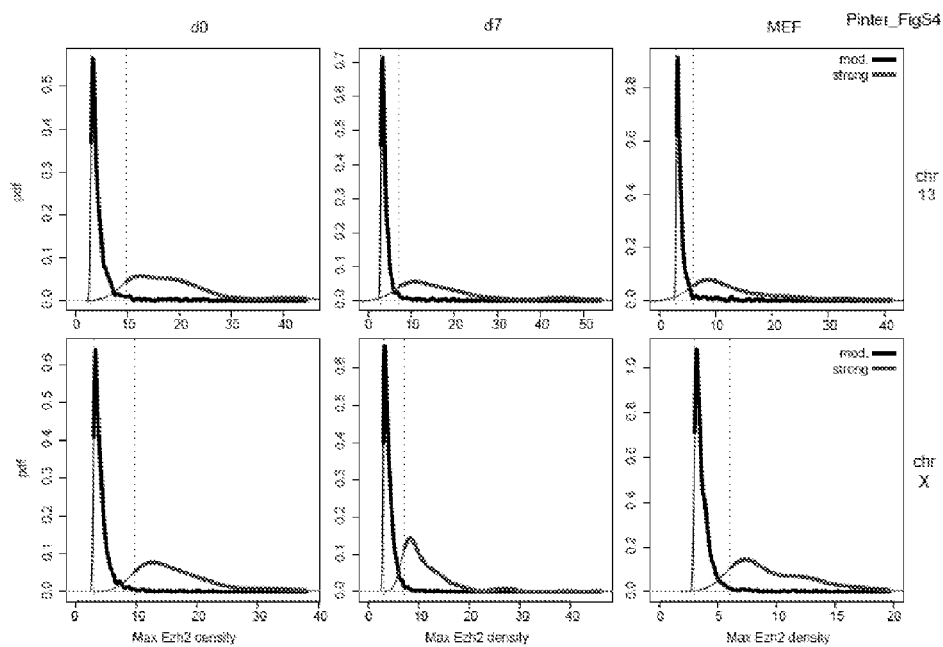
Figure 11B:
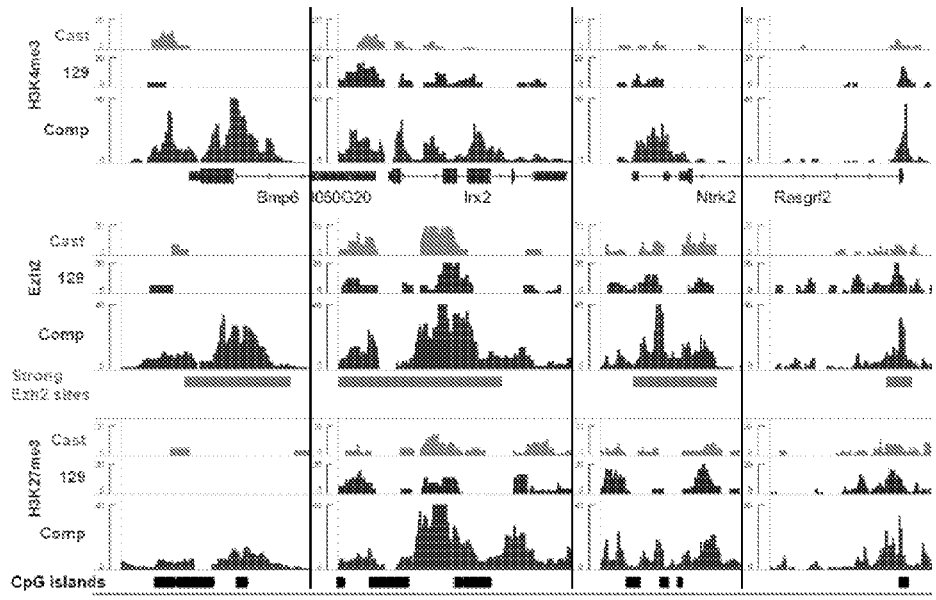

FIG. 11: Comparison of Strong EZH2 Sites.

(A) Distribution (as probability density function (pdf) on y-axis) of maximal EZH2 density (per 1 kb) on strong (red) and moderate (black) EZH2 sites on Chr13 and ChrX in d0, d7 and MEF cells. Two dotted threshold lines indicate the density cutoff for moderate (left) and strong EZH2 sites (right), thick lines indicate density of 1 kb windows that were above these cutoffs in moderate (black) and strong (red) EZH2 sites. Significance threshold ($p<10^{-5}$) for strong EZH2 sites was chosen such that the vast majority of moderate sites were excluded.

(B) Examples of previously identified (Ku, M et al. 2008) EZH2 targets in undifferentiated ES cells (d0) are called in our set of strong EZH2 sites (labeled in pink underneath composite EZH2 track in the middle): Bmp6, Irx2, Ntrk2 and Rasgrf2. All examples are bivalent (H3K4me3 tracks on top, H3K27me3 tracks on bottom) and contain CpG islands (labeled in black, last track).

Figure 12:
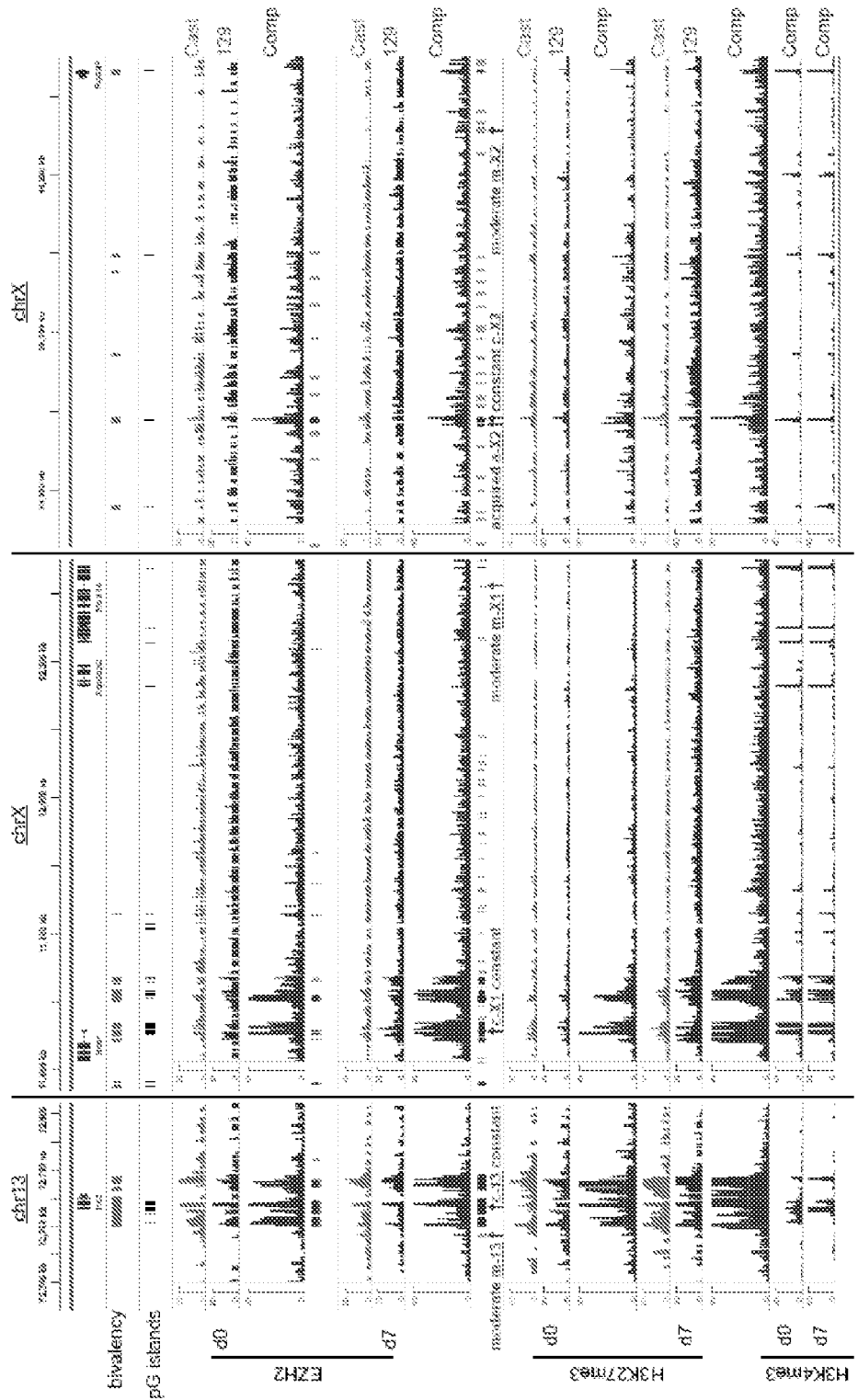

FIG. 12: Loci for Validation of Strong and Moderate EZH2 Sites.

Screenshots of EZH2 and H3K27me3 tracks from loci chosen for validation of strong and moderate EZH2 sites on Chr13 and ChrX. Purple arrows and labels identify sites assayed by allele-specific qPCR in FIG. 13 and include a strong (constant, c-13) and moderate site (m-13) on Chr13, three strong (acquired, a-X2 and constant, c-X1, c-X2) and two moderate sites (m-X1, m-X2) on ChrX.

Figure 13:
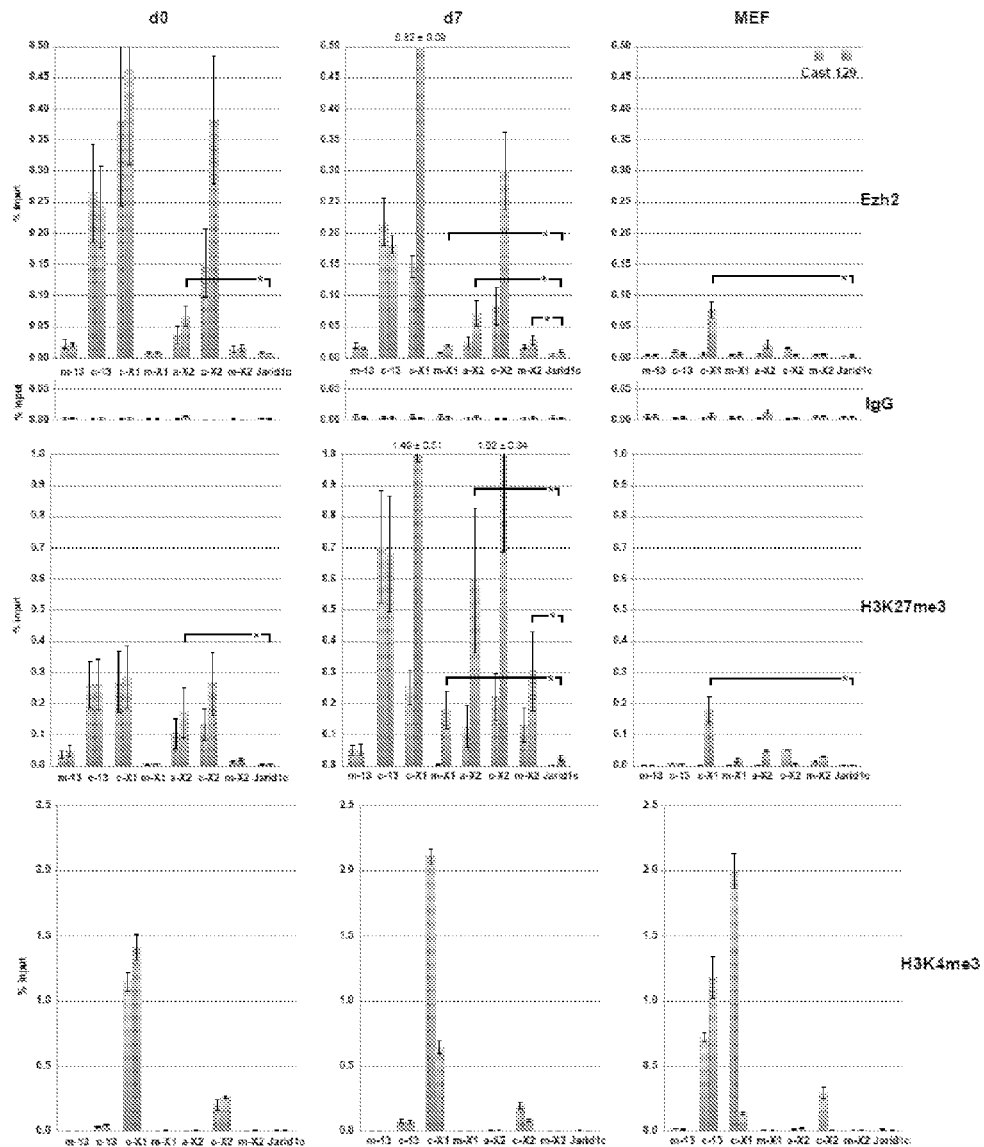

FIG. 13: Allele-Specific qPCR for Validation of Strong and Moderate EZH2 Sites.

Input and chromatin-immunoprecipitated (ChIP) DNA from EZH2, H3K27me3 and IgG ChIPs in d0, d7 and MEF cells (three biological replicates each) was amplified with primer sets (one universal, one allele-specific primer each) to the sites shown in FIG. 12. Error bars indicate standard error of Cast (blue) and 129 (red) means. A representative H3K4me3 ChIP sample was also included with error bars indicating standard error of three technical replicates. Asterisk indicates statistically significant difference ($p<0.05$, one-tailed Mann-Whitney U test) to the 129 signal at negative control locus in the gene body of escapee gene Jaridlc.

Figure 14:
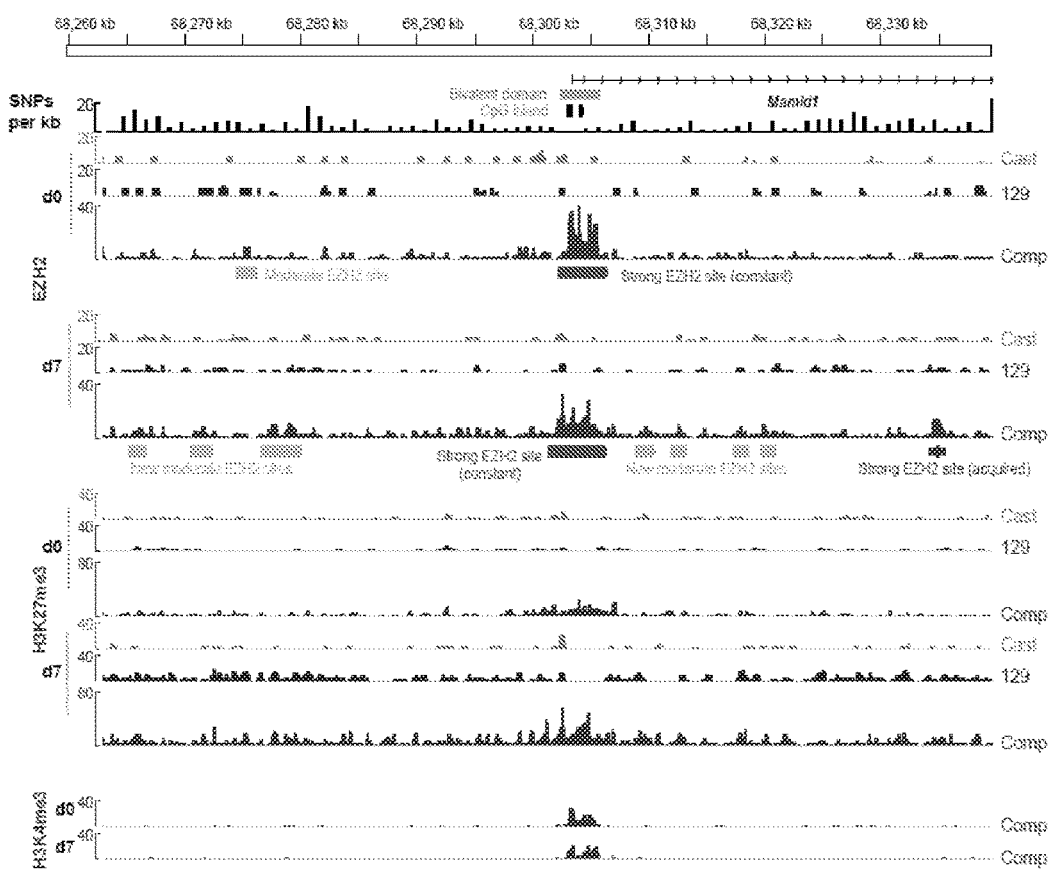

FIG. 14: Strong and Moderate EZH2 Site at the Xic-Distant Site, MamId1.

Screenshot of EZH2, H3K27me3, and H3K4me3 tracks in d0 and d7 cells at Mamid1, approximately 30 Mb from the Xic. As in FIG. 5, strong (constant and acquired) and moderate EZH2 sites are indicated underneath the composite (comp) EZH2 tracks, SNP (and Indel) density per 1 kb window above the epitope tracks.

Figure 15A:
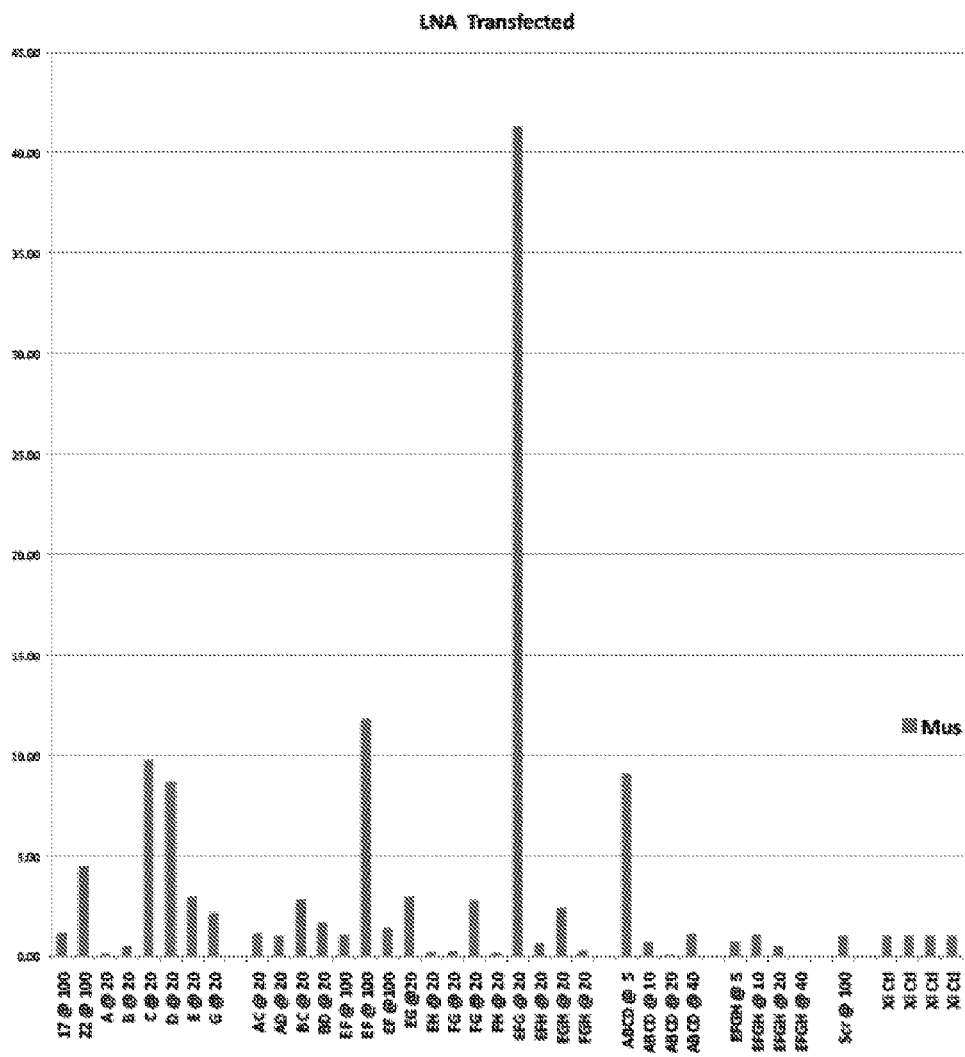
Figure 15B:
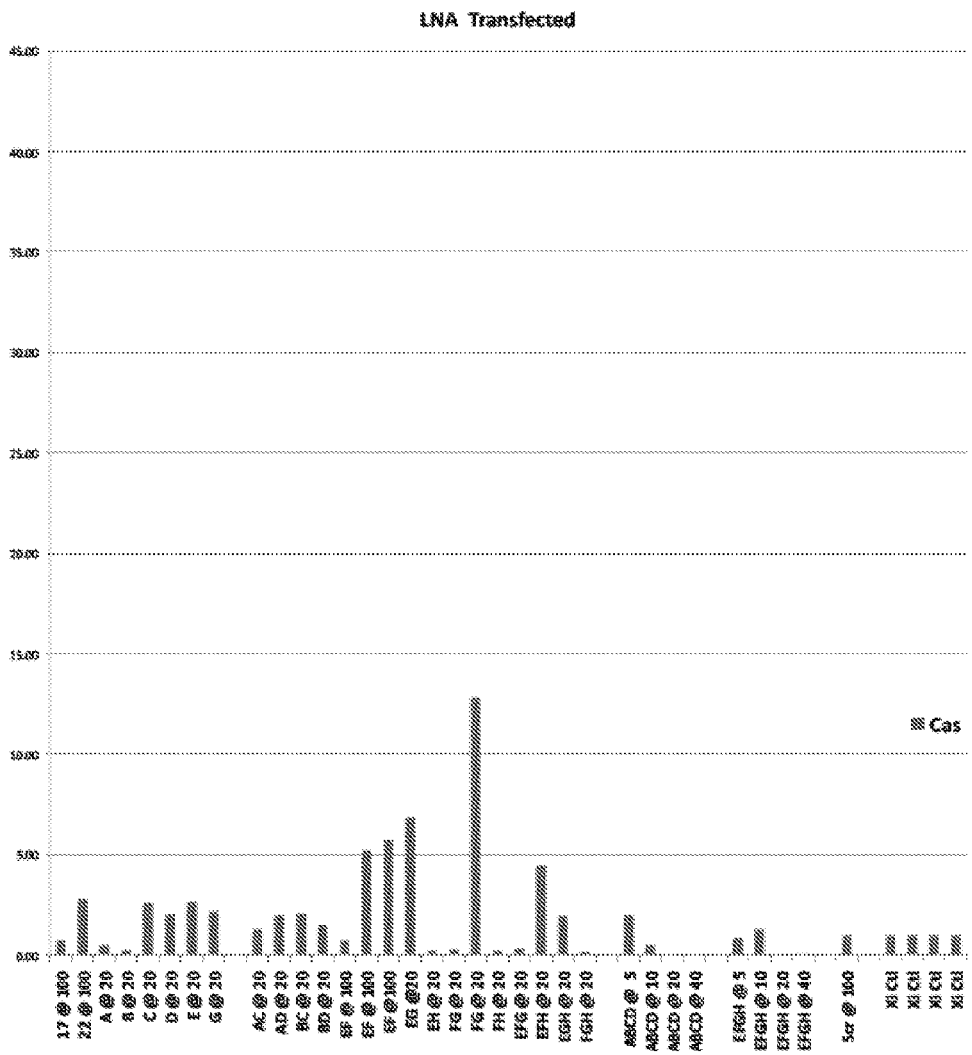

FIGS. 15A-B: Targeting Mecp2-AS or PRC2 Binding Sites Reactivates Expression

Bar graphs showing the results of with the untreated control set to a value of 1.0 and all others normalized to this value. LNA concentrations shown after each oligo in "nM". All values normalized to Gapdh control. Then the level of expression in untreated samples (Xi control, Xi ctrl) was set to a normalized value of 1.0. The results are shown at a single time point, 24 h post-LNA treatment. 15A, expression from the mus (Xi) chromosome; 15B, expression from the Castaneus X (active X), shown at the same scale as 15A.

DETAILED DESCRIPTION

XCI provides an excellent model by which to study Polycomb regulation and the role of long noncoding RNAs (lncRNA) in inducing facultative heterochromatin (Lyon, 1999; Wutz and Gribnau, 2007; Payer and Lee, 2008)(Lee, 2011). XCI is controlled by the X-inactivation center (Xic), an X-linked region that controls the counting of X chromosomes, the mutually exclusive choice of Xa and Xi, and the recruitment and propagation of silencing complexes. The 17-kb Xist RNA initiates the silencing step as it accumulates on the X (Brockdorff et al., 1992; Brown et al., 1992; Clemson et al., 1996). Although recent studies have shown that Xist RNA directly recruits Polycomb repressive complex 2 (PRC2) to the Xi (Zhao et al., 2008) and that loading of the Xist-PRC2 complex occurs first at a YY1-bound nucleation center located within the Xic (Jeon and Lee, 2011), how the silencing complexes spread throughout the X after this obligatory nucleation step remains a major unsolved problem. Because autosomes with ectopic Xic sequences are subject to long-range silencing (Wutz and Gribnau, 2007; Payer and Lee, 2008), it is thought that spreading elements cannot be unique to the X. One hypothesis suggests that repetitive elements of the LINE1 class facilitate spreading (Lyon, 2000). However, this hypothesis has been difficult to test, as linking repeats to locus-specific function has been complicated by their repetitive nature. Some studies have provided correlative evidence (Bailey et al., 2000; Wang et al., 2006; Chow et al., 2010), whereas others find that species lacking active LINE1s nonetheless possess XCI (Cantrell et al., 2009). Other classes of repeats may be more enriched on the X (Chow et al., 2005). Matrix-associated proteins, such as SAF-A/hnRNP-U, have also been proposed to facilitate spreading (Helbig and Fackelmayer, 2003; Hasegawa et al., 2010; Pullirsch et al., 2010), but a direct link has also not been demonstrated.

In general, the identification of spreading elements has been thwarted by the lack of high-throughput approaches that distinguish Xi and Xa at sufficient resolution. Epigenomic studies have primarily focused on male cells (Bernstein et al., 2006; Boyer et al., 2006; Barski et al., 2007; Mikkelsen et al., 2007; Ku et al., 2008), though one recent ChIP-seq analysis with partial allele-specific coverage used female mouse embryonic stem (ES) cells but without addressing PRC2 binding. The reported 1.2-fold enrichment of H3K27me3 on Xi (Marks et al., 2009) is unexpectedly low and at odds with intense cytological H3K27me3 immunostaining (Plath et al., 2003; Silva et al., 2003)—likely caused by low-density polymorphisms between Xi and Xa. As a result, the quest for an Xi chromatin state map and spreading elements has remained unrealized.

In principle, silencing complexes could initially load at the Xic and spread serially from nucleosome to nucleosome. Alternatively, they could spread outwardly via 'way stations' located at defined sites along the X that would anchor and relay silencing complexes (Gartler and Riggs, 1983). To test these models, an allele-specific ChIP-seq strategy was devised that enabled the generation of chromosome-wide developmental profiles at unprecedented allelic resolution. Reported herein is a high-density Xi chromatin state map and identification of discrete Polycomb stations.

A vast majority of the strong and moderate sites demonstrates transcription of at least one RNA, many of which are likely to be noncoding. The PRC2 site-associated RNAs can be noncoding (long noncoding RNA, lncRNA) or occasionally part of a coding mRNA; for simplicity, we will discuss them together as polycomb-associated RNA (paRNA) henceforth. Some overlap the previously described PRC2 transcriptome (Zhao et al., 2010, Molecular Cell; WO 2012/087983 and WO 2012/065143). In ES cells and MEFs, 20-25% of putative mouse paRNAs have not been previously described; and 43-45% those within mouse moderate sites are new.

Each strong site governs on average ~10 X-linked genes, and, without wishing to be bound by theory, it may be from these strong sites that local spreading of silencing occurs via moderate sites to encompass genes within the local domain. There is on average 20-30 moderate sites per strong site. PRC2 is first recruited to the strong sites. They are then passed on to moderate sites locally. Locally acting paRNAs within the moderate sites, in intergenic spaces, or within the genes themselves spread the repression to span the entire local gene cluster. Thus, paRNAs at strong and moderate sites are proposed to serve as cis-acting recruiting centers for PRC2. In some embodiments, the present methods include targeting paRNAs at strong and moderate sites to disrupt spreading or maintenance of inactivation at one or a few X-linked genes under the sphere of influence of the strong and moderate sites. In this manner, specific genes of interest on the inactive X could be reactivated to treat X-linked diseases, when the inactivated X chromosome bears a functional or hypomorphic copy of the gene.

paRNAs and paRNA Libraries

The present invention includes the individual paRNAs described herein, as well as libraries of paRNAs produced by methods described herein. In some embodiments, the paRNAs or libraries are in solution, or are lyophilized. In some embodiments, the libraries are bound to a substrate, e.g., wherein each member of the library is bound to an individually addressable member, e.g., an individual area on an array (e.g., a microarray), or a bead. The PRC2-interacting RNA transcript, although non-coding, may include a protein-coding sequence of bases if it is a distinct transcript that overlaps in position with a protein-coding reference gene (e.g. the gene whose expression is modulated in cis). In some embodiments, the paRNAs described herein differ from the endogenous molecule in one or more ways, e.g., they include more or fewer nucleotides, and/or include one or more of the modifications described herein for inhibitory nucleic acids, e.g., backbone or nucleoside modifications.

In one embodiment, a paRNA includes a nucleotide sequence that is at least about 85% or more homologous or identical to the entire length of a paRNA sequence shown herein, e.g., in any of Tables 1-4, or a fragment comprising at least 20 nt thereof (e.g., at least 25, 30, 35, 40, 50, 60, 70, 80, 90, or 100 nt thereof, e.g., at least 5%, 10%, 15%, 20%, 25%, 30%, 35%, 40%, 50% or more of the full length paRNA). In some embodiments, the nucleotide sequence is at least about 90%, 91%, 92%, 93%, 94%, 95%, 96%, 97%, 98%, 99% or 100% homologous or identical to a paRNA sequence shown herein. In some embodiments, the nucleotide sequence is at least about 85%, e.g., is at least about 90%, 91%, 92%, 93%, 94%, 95%, 96%, 97%, 98%, 99% or 100% homologous or identical to a paRNA sequence described herein, in a fragment thereof or a region that is much more conserved, such as Repeat A, but has lower sequence identity outside that region.

Mouse-to-human LiftOver analysis and analysis in the UCSC genome browser of syntenic positions indicate the existence of similar transcripts in the human genome. This process and LiftOver chains are generally described in Kent et al., *Proc. Nat'l Acad. Sci.*, 100(20) 11484-11489 (2003). Similar PRC2-interacting transcripts are believed to occur in the human system given the geographic and sequence similarities between the mouse and human transcripts. The data suggest that many if not all of the mouse PRC2-transcripts have direct counterparts in the human epigenome. Such direct counterparts in other species are termed "orthologous" herein. Empirically identified human paRNAs associated with the X chromosome, and strong and moderate binding sites in the X Chromosome, are described herein (see Example 10).

paRNAs may be functionally conserved without being highly conserved at the level of overall nucleotide identity. For example, mouse Xist shows only 76% overall nucleotide identity with human XIST using sliding 21-bp windows, or an overall sequence identity of only 60%. However, within specific functional domains, such as Repeat A, the degree of conservation can be >70% between different mammalian species. The crucial motif in Repeat A is the secondary structures formed by the repeat. A paRNA interacting with PRC2 may therefore be similarly low in overall conservation but still have conservation in secondary structure within specific domains of the RNA, and thereby demonstrate functional conservation with respect to recruitment of PRC2.

Calculations of homology or sequence identity between sequences (the terms are used interchangeably herein) are performed as follows.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 1000/%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5. There are several potential uses for the paRNAs described herein in the expanded PRC2 transcriptome: The RNAs themselves, or antagomirs and small molecules designed against them, can be utilized to modulate expression (either up or down) of Polycomb target genes. In addition, the paRNAs can be used to design and/or test inhibitory nucleic acids as described herein.

In various related aspects, including with respect to the targeting of paRNAs by LNA molecule, paRNAs can include endogenous cellular RNAs that are greater than 60 nt in length, e.g., greater than 100 nt, e.g., greater than 200 nt, have no positive-strand open reading frames greater than 100 amino acids in length, are identified as paRNAs by experimental evidence, and are distinct from known (smaller) functional-RNA classes (including but not limited to ribosomal, transfer, and small nuclear/nucleolar RNAs, siRNA, piRNA, and miRNA). See, e.g., Lipovich et al., "MacroRNA underdogs in a microRNA world: Evolutionary, regulatory, and biomedical significance of mammalian long non-protein-coding RNA" Biochimica et Biophysica Acta (2010) doi:10.1016/j.bbagrm.2010.10.001; Ponting et al., Cell 136(4):629-641 (2009), Jia et al., RNA 16 (8)

(2010) 1478-1487, Dinger et al., Nucleic Acids Res. 37 1685 (2009) D122-D126 (database issue); and references cited therein. paRNAs can include RNAs referred to as long RNA, large RNA, macro RNA, intergenic RNA, and Non-Coding Transcripts. The methods described herein can be used to target nuclear-localized paRNAs. Known classes of paRNAs include large intergenic non-coding RNAs (lincR-NAs, see, e.g., Guttman et al., Nature. 2009 Mar. 12; 458(7235):223-7. Epub 2009 Feb. 1, which describes over a thousand exemplary highly conserved large non-coding RNAs in mammals; and Khalil et al., PNAS 106(28)11675-11680 (2009)): promoter associated short RNAs (PASRs; see, e.g., Seila et al., Science. 2008 Dec. 19; 322(5909): 1849-51. Epub 2008 Dec. 4; Kanhere et al., Molecular Cell 38, 675-688, (2010)); endogenous antisense RNAs (see, e.g., Numata et al., BMC Genomics. 10:392 (2009); Okada et al., Hum Mol Genet. 17(11):1631-40 (2008); Numata et al., Gene 392(1-2):134-141 (2007); and Røsok and Sioud, Nat Biotechnol. 22(1): 104-8 (2004)); and RNAs that bind chromatin modifiers such as PRC2 and LSD1 (see, e.g., Tsai et al., Science. 2010 Aug. 6; 329(5992):689-93. Epub 2010 Jul. 8; and Zhao et al., Science. 2008 Oct. 31; 322(5902): 750-6).

Exemplary paRNAs include the lncRNAs XIST, TSIX, MALAT1, RNCR2, and HOTAIR. The sequences for more than 17,000 long human ncRNAs can be found in the NCode™ Long ncRNA Database on the Invitrogen website. Additional long ncRNAs can be identified using, e.g., manual published literature, Functional Annotation of Mouse (FANTOM3) project, Human Full-length cDNA Annotation Invitational (H-Invitational) project, antisense ncRNAs from cDNA and EST database for mouse and human using a computation pipeline (Zhang et al., Nucl. Acids Res. 35 (suppl 1): D156-D161 (2006); Engstrom et al., PLoS Genet. 2:e47 (2006)), human snoRNAs and scaR-NAs derived from snoRNA-LBME-db, RNAz (Washietl et al. 2005), Noncoding RNA Search (Torarinsson, et al. 2006), and EvoFold (Pedersen et al. 2006).

Disorders Associated with X-Inactivation

The present disclosure provides therapeutics for X-linked diseases formulated by designing inhibitory nucleic acids, e.g., oligonucleotides that bind to the strong or moderate PRC2 binding sites as described herein (on either strand), or oligonucleotides that are complementary to and thus bind to the transcripts that cross the PRC2 sites (paRNAs) described herein, to disrupt silencing of genes controlled by the PRC2 sites (e.g., all of the genes within a cluster), or to disrupt silencing of one specific gene. This methodology is useful in X-linked disorders, e.g., in heterozygous women who retain a wildtype copy of a gene on the Xi (See, e.g., Lyon, Acta Paediatr Suppl. 2002; 91(439):107-12; Carrell and Willard, Nature. 434(7031):400-4 (2005); den Veyver, Semin Reprod Med. 19(2):183-91 (2001)). Again, without wishing to be bound by theory, administration of an inhibitory nucleic acid (e.g., oligonucleotide) targeting a strong or moderate binding site is expected to prevent PRC2 recruitment to a specific X-linked gene cluster or to a specific gene on the inactive X, thereby reactivating the "good" or hypomorphic copy of the X-linked gene. As a result of X-inactivation, heterozygous females are mosaic for X-linked gene expression; some cells express genes from the maternal X and other cells express genes from the paternal X. The relative ratio of these two cell populations in a given female is frequently referred to as the "X-inactivation pattern." One cell population may be at a selective growth disadvantage, resulting in clonal outgrowth of cells with one or the other parental X chromosome active; this can cause significant deviation or skewing from an expected mean X-inactivation pattern (i.e., 50:50). See, e.g., Plenge et al., Am. J. Hum. Genet. 71:168-173 (2002) and references cited therein.

The present methods can be used to treat disorders associated with X-inactivation, which includes those listed in Table A.

TABLE A

| Disorder | OMIM # | Locus | Gene | K562 Suz12* | K562 Ezh2** | GM12878 Ezh2*** |
|---|---|---|---|---|---|---|
| Dent's disease 1 | 300009 | Xp11.22 | CLCN5 | seg_203 seg_204 seg_205 seg_206<br>seg_207 seg_208 seg_209 seg_210<br>seg_211 seg_212 seg_213 seg_214<br>seg_215 seg_216 seg_217 seg_218<br>seg_219 seg_220 seg_221 seg_222<br>seg_223 seg_224 seg_225 seg_226<br>seg_227 seg_228 seg_229 seg_230<br>seg_231 seg_232 seg_233 seg_234<br>seg_235 seg_236 seg_237 seg_238<br>seg_239 seg_240 seg_242 seg_243<br>seg_244 seg_245 seg_246 seg_247<br>seg_249 seg_250 seg_251 seg_252<br>seg_253 seg_254 seg_256 seg_257<br>seg_258 seg_259 seg_260 seg_261<br>seg_262 seg_263 seg_264 seg_265<br>seg_266 seg_267 seg_268 seg_269<br>seg_270 seg_271 seg_202 seg_241<br>seg_248 seg_255 | seg_224 seg_225 seg_226<br>seg_227 seg_228 seg_229<br>seg_230 seg_232 seg_234<br>seg_235 seg_236 seg_237<br>seg_238 seg_239 seg_240<br>seg_241 seg_242 seg_243<br>seg_245 seg_246 seg_247<br>seg_248 seg_249 seg_250<br>seg_251 seg_252 seg_253<br>seg_254 seg_255 seg_256<br>seg_257 seg_258 seg_259<br>seg_260 seg_262 seg_263<br>seg_265 seg_266 seg_267<br>seg_268 seg_269 seg_270<br>seg_271 seg_272 seg_273<br>seg_274 seg_275 seg_276<br>seg_277 seg_231<br>seg_233 seg_244 seg_261<br>seg_264 | seg_96 seg_97 seg_98<br>seg_99 seg_100<br>seg_101 seg_102<br>seg_103 seg_104<br>seg_105 seg_93<br>seg_95 |
| Testicular feminization syndrome | 300068 | Xq11-q12 | AR | seg_296 seg_297 seg_298 seg_300<br>seg_302 seg_305 seg_306 seg_307<br>seg_308 seg_309 seg_310 seg_311<br>seg_313 seg_314 seg_315 seg_316<br>seg_317 seg_318 seg_319 seg_320<br>seg_321 seg_322 seg_323 seg_324<br>seg_326 seg_328 seg_329 seg_330<br>seg_331 seg_332 seg_334 seg_335<br>seg_337 seg_338 seg_339 seg_340<br>seg_341 seg_342 seg_344 seg_345<br>seg_295 seg_299 seg_301 seg_303<br>seg_304 seg_312 seg_325 seg_327<br>seg_333 seg_336 seg_343 | seg_285 seg_286 seg_287<br>seg_290 seg_291 seg_292<br>seg_294 seg_295 seg_296<br>seg_297 seg_298 seg_299<br>seg_302 seg_303 seg_304<br>seg_305 seg_306 seg_307<br>seg_308 seg_309 seg_311<br>seg_312 seg_313 seg_288<br>seg_289 seg_293 seg_300<br>seg_301 seg_310 | seg_108 seg_109<br>seg_110 seg_111<br>seg_112 seg_113<br>seg_114 seg_115<br>seg_116 seg_117<br>seg_118 seg_119<br>seg_121 seg_122<br>seg_124 seg_125<br>seg_120 seg_123 |
| Addison's disease with cerebral sclerosis | 300100 | Xq28 | ABCD1 | seg_564 seg_566 seg_567 seg_568<br>seg_569 seg_571 seg_572 seg_574<br>seg_575 seg_576 seg_577 seg_578<br>seg_579 seg_580 seg_581 seg_582<br>seg_583 seg_584 seg_585 seg_586<br>seg_587 seg_588 seg_589 seg_590<br>seg_591 seg_592 seg_593 seg_594<br>seg_595 seg_596 seg_597 seg_599<br>seg_600 seg_601 seg_602 seg_603<br>seg_604 seg_605 seg_606 seg_607<br>seg_608 seg_609 seg_610 seg_611<br>seg_612 seg_613 seg_615 seg_616<br>seg_617 seg_618 seg_619 seg_620<br>seg_622 seg_623 seg_624 seg_625<br>seg_626 seg_627 seg_628 seg_629<br>seg_630 seg_631 seg_632 seg_633<br>seg_634 seg_635 seg_637 seg_638 | seg_504 seg_505 seg_506<br>seg_507 seg_508 seg_509<br>seg_510 seg_511 seg_512<br>seg_514 seg_515 seg_516<br>seg_517 seg_518 seg_520<br>seg_521 seg_522 seg_523<br>seg_524 seg_525 seg_526<br>seg_527 seg_528 seg_529<br>seg_530 seg_531 seg_532<br>seg_533 seg_534 seg_535<br>seg_536 seg_538 seg_539<br>seg_540 seg_542 seg_543<br>seg_544 seg_545 seg_546<br>seg_547 seg_548 seg_549<br>seg_550 seg_551 seg_552<br>seg_553 seg_554 seg_555<br>seg_556 seg_558 seg_559 | seg_209 seg_210<br>seg_211 seg_212<br>seg_213 seg_214<br>seg_215 |

TABLE A-continued

| Disorder | OMIM # | Locus | Gene | K562 Suz12* | K562 Ezh2** | GM12878 Ezh2*** |
|---|---|---|---|---|---|---|
| Adrenal hypoplasia | 300200 | XP21.3-p21.2 | DAX1 | seg_639 seg_641 seg_642 seg_644<br>seg_645 seg_646 seg_647 seg_648<br>seg_649 seg_650 seg_651 seg_652<br>seg_654 seg_655 seg_656 seg_657<br>seg_658 seg_659 seg_660 seg_661<br>seg_662 seg_663 seg_664 seg_665<br>seg_666 seg_565 seg_570 seg_573<br>seg_614 seg_621 seg_636 seg_640<br>seg_643 seg_598 seg_653 | seg_561 seg_562 seg_563<br>seg_564 seg_565 seg_566<br>seg_567 seg_568 seg_570<br>seg_572 seg_573 seg_574<br>seg_575 seg_576 seg_577<br>seg_578 seg_513 seg_519<br>seg_537 seg_541 seg_557<br>seg_569 seg_571 seg_560 | |
| siderius X-linked mental retardation syndrome | 300263 | Xp11.22 | PHF8 | seg_157 seg_159 seg_160 seg_161<br>seg_162 seg_163 seg_164 seg_158 | seg_198 seg_197 | seg_67 seg_69 seg_71<br>seg_72 seg_73 seg_74<br>seg_75 seg_76 seg_77<br>seg_78 seg_68 seg_70<br>seg_101 seg_102<br>seg_103 seg_104<br>seg_105 seg_106 |
| Agamma-globulinaemia, Bruton type | 300300 | Xq21.3-q22 | BTK | seg_222 seg_223 seg_224 seg_225<br>seg_226 seg_227 seg_228 seg_229<br>seg_230 seg_231 seg_232 seg_233<br>seg_234 seg_235 seg_236 seg_237<br>seg_238 seg_239 seg_240 seg_242<br>seg_243 seg_244 seg_245 seg_246<br>seg_247 seg_249 seg_250 seg_251<br>seg_252 seg_253 seg_254 seg_256<br>seg_257 seg_258 seg_259 seg_260<br>seg_261 seg_262 seg_263 seg_264<br>seg_265 seg_266 seg_267 seg_268<br>seg_269 seg_270 seg_271 seg_272<br>seg_273 seg_274 seg_275 seg_276<br>seg_277 seg_278 seg_279 seg_280<br>seg_281 seg_282 seg_284 seg_241<br>seg_248 seg_255 seg_283<br>seg_376 seg_377 seg_378 seg_379<br>seg_381 seg_382 seg_385 seg_386<br>seg_388 seg_389 seg_391 seg_392<br>seg_393 seg_394 seg_395 seg_396<br>seg_397 seg_398 seg_399 seg_400<br>seg_401 seg_402 seg_403 seg_404<br>seg_405 seg_380 seg_383 seg_387<br>seg_390 seg_384 | seg_247 seg_248 seg_249<br>seg_250 seg_251 seg_252<br>seg_253 seg_254 seg_255<br>seg_256 seg_257 seg_258<br>seg_259 seg_260 seg_262<br>seg_263 seg_265 seg_266<br>seg_267 seg_268 seg_269<br>seg_270 seg_271 seg_272<br>seg_275 seg_274 seg_275<br>seg_276 seg_277 seg_278<br>seg_279 seg_280 seg_281<br>seg_282 seg_283 seg_261<br>seg_264<br>seg_323 seg_324 seg_326<br>seg_327 seg_328 seg_329<br>seg_331 seg_332 seg_333<br>seg_334 seg_336 seg_337<br>seg_338 seg_339 seg_340<br>seg_341 seg_342 seg_343<br>seg_344 seg_345 seg_346<br>seg_347 seg_348 seg_321<br>seg_325 seg_330 seg_335 | seg_140 seg_141<br>seg_142 seg_143<br>seg_144 seg_145<br>seg_146 |
| Choroidoretinal degeneration | 300389 | Xp21.1 | RPGR | seg_165 seg_166 seg_167 seg_168<br>seg_169 seg_170 seg_171 seg_172<br>seg_173 seg_174 seg_175 seg_176<br>seg_177 seg_178 seg_179 seg_181<br>seg_182 seg_183 seg_184 seg_185<br>seg_186 seg_187 seg_188 seg_189<br>seg_191 seg_192 seg_193 seg_195<br>seg_196 seg_180 seg_190 seg_194 | seg_200 seg_201 seg_202<br>seg_203 seg_204 seg_205<br>seg_206 seg_207 seg_208<br>seg_210 seg_211 seg_212<br>seg_213 seg_214 seg_215<br>seg_216 seg_217 seg_218<br>seg_209 | seg_80 seg_81 seg_82<br>seg_83 seg_84 seg_85<br>seg_86 seg_87 seg_88<br>seg_89 seg_90 seg_91 |
| Choroidaemia | 300390 | Xq21.2 | CHM | seg_368 seg_369 seg_370 seg_371<br>seg_372 | | seg_136 seg_137 |
| Albinism, ocular | 300500 | Xp22.3 | OA1 | seg_50 seg_51 seg_52 seg_53 seg_54<br>seg_55 seg_56 seg_57 seg_58 seg_59<br>seg_60 seg_61 seg_63 seg_64 seg_65 | seg_56 seg_57 seg_58<br>seg_60 seg_61 seg_63<br>seg_64 seg_65 seg_66 | seg_9 seg_10 seg_11<br>seg_12 seg_13 seg_14<br>seg_16 seg_17 seg_18 |

TABLE A-continued

| Disorder | OMIM # | Locus | Gene | K562 Suz12* | K562 Ezh2** | GM12878 Ezh2*** |
|---|---|---|---|---|---|---|
| | | | | seg_66 seg_67 seg_68 seg_69 seg_70 | seg_67 seg_68 seg_69 | seg_19 seg_20 seg_21 |
| | | | | seg_71 seg_73 seg_74 seg_75 seg_76 | seg_70 seg_71 seg_72 | seg_22 seg_23 seg_24 |
| | | | | seg_77 seg_78 seg_79 seg_80 seg_81 | seg_73 seg_74 seg_75 | seg_25 seg_26 seg_27 |
| | | | | seg_82 seg_83 seg_84 seg_85 seg_86 | seg_76 seg_77 seg_78 | seg_28 seg_29 seg_30 |
| | | | | seg_87 seg_88 seg_89 seg_90 seg_91 | seg_79 seg_80 seg_81 | seg_31 seg_32 seg_33 |
| | | | | seg_62 seg_72 | seg_82 seg_83 seg_84 | seg_34 seg_15 |
| | | | | | seg_85 seg_36 seg_87 | |
| | | | | | seg_88 seg_89 seg_91 | |
| | | | | | seg_92 seg_93 seg_95 | |
| | | | | | seg_96 seg_97 seg_98 | |
| | | | | | seg_99 seg_100 seg_101 | |
| | | | | | seg_102 seg_103 seg_104 | |
| | | | | | seg_106 seg_107 seg_108 | |
| | | | | | seg_110 seg_59 seg_62 | |
| | | | | | seg_90 seg_94 seg_105 | |
| | | | | | seg_109 | |
| Dent's disease 2 | 300555 | Xq25-q26 | OCRL | seg_474 seg_475 seg_477 seg_478 | seg_420 seg_421 seg_422 | seg_185 seg_186 |
| | | | | seg_479 seg_480 seg_481 seg_482 | seg_423 seg_424 seg_425 | seg_187 seg_188 |
| | | | | seg_483 seg_484 seg_485 seg_486 | seg_426 seg_427 seg_428 | seg_189 seg_190 |
| | | | | seg_487 seg_488 seg_489 seg_490 | seg_429 seg_430 seg_431 | seg_191 seg_192 |
| | | | | seg_491 seg_492 seg_493 seg_494 | seg_432 seg_433 seg_434 | seg_183 |
| | | | | seg_495 seg_496 seg_497 seg_498 | seg_436 seg_438 seg_439 | |
| | | | | seg_499 seg_501 seg_502 seg_503 | seg_440 seg_441 seg_442 | |
| | | | | seg_476 seg_500 | seg_443 seg_435 seg_437 | |
| fragile X syndrome | 300624 | Xq27.3 | FMR1 | seg_561 seg_562 seg_563 seg_564 | seg_503 seg_504 seg_505 | seg_208 seg_209 |
| | | | | seg_566 seg_567 seg_568 seg_569 | seg_506 seg_507 seg_508 | seg_210 seg_211 |
| | | | | seg_571 seg_572 seg_574 seg_575 | seg_509 seg_510 seg_511 | seg_212 |
| | | | | seg_576 seg_577 seg_578 seg_579 | seg_512 seg_514 seg_515 | |
| | | | | seg_580 seg_581 seg_582 seg_583 | seg_516 seg_517 seg_518 | |
| | | | | seg_584 seg_585 seg_586 seg_587 | seg_520 seg_521 seg_522 | |
| | | | | seg_588 seg_589 seg_590 seg_591 | seg_523 seg_524 seg_525 | |
| | | | | seg_592 seg_593 seg_594 seg_595 | seg_526 seg_527 seg_528 | |
| | | | | seg_596 seg_597 seg_599 seg_560 | seg_529 seg_530 seg_531 | |
| | | | | seg_565 seg_570 seg_573 seg_598 | seg_532 seg_513 seg_519 | |
| Rett/Epileptic encephalopathy, early infantile, 2 | 300672 | Xp22.13 | CDKL5 | seg_83 seg_84 seg_85 seg_86 seg_87 | seg_96 seg_97 seg_98 | seg_31 seg_32 seg_33 |
| | | | | seg_88 seg_89 seg_90 seg_91 seg_92 | seg_99 seg_100 seg_101 | seg_34 seg_35 seg_36 |
| | | | | seg_93 seg_94 seg_95 seg_96 seg_97 | seg_102 seg_103 seg_104 | seg_37 seg_38 seg_39 |
| | | | | seg_98 seg_99 seg_100 seg_101 | seg_106 seg_107 seg_108 | seg_40 seg_41 seg_42 |
| | | | | seg_102 seg_103 seg_104 seg_105 | seg_110 seg_111 seg_112 | seg_43 seg_44 seg_45 |
| | | | | seg_106 seg_107 seg_108 seg_109 | seg_113 seg_114 seg_115 | seg_46 seg_47 seg_48 |
| | | | | seg_111 seg_112 seg_113 seg_114 | seg_117 seg_119 seg_120 | seg_49 seg_50 seg_51 |
| | | | | seg_115 seg_116 seg_117 seg_118 | seg_121 seg_122 seg_123 | seg_52 seg_53 seg_55 |
| | | | | seg_119 seg_121 seg_122 seg_124 | seg_124 seg_125 seg_126 | seg_56 seg_57 seg_58 |
| | | | | seg_125 seg_126 seg_127 seg_128 | seg_127 seg_128 seg_130 | seg_59 seg_61 seg_60 |
| | | | | seg_129 seg_131 seg_132 seg_133 | seg_131 seg_132 seg_133 | seg_54 |
| | | | | seg_134 seg_135 seg_136 seg_137 | seg_134 seg_135 seg_136 | |
| | | | | seg_138 seg_139 seg_110 seg_123 | seg_137 seg_138 seg_139 | |
| | | | | seg_130 seg_120 | seg_140 seg_141 seg_142 | |
| | | | | | seg_143 seg_144 seg_145 | |
| | | | | | seg_146 seg_147 seg_148 | |
| | | | | | seg_149 seg_150 seg_151 | |

TABLE A-continued

| Disorder | OMIM # | Locus | Gene | K562 Suz12* | K562 Ezh2** | GM12878 Ezh2*** |
|---|---|---|---|---|---|---|
| | | | | | seg_152 seg_153 seg_156 | |
| | | | | | seg_157 seg_158 seg_159 | |
| | | | | | seg_160 seg_161 seg_162 | |
| | | | | | seg_163 seg_164 seg_165 | |
| | | | | | seg_166 seg_167 seg_168 | |
| | | | | | seg_169 seg_171 seg_172 | |
| | | | | | seg_173 seg_174 seg_175 | |
| | | | | | seg_176 seg_177 seg_178 | |
| | | | | | seg_179 seg_180 seg_181 | |
| | | | | | seg_182 seg_183 seg_184 | |
| | | | | | seg_94 seg_105 seg_109 | |
| | | | | | seg_116 seg_118 seg_129 | |
| Albinism-deafness syndrome | 300700 | Xq26.3-q27.1 | ADFN | seg_434 seg_436 seg_437 seg_438 | seg_154 seg_155 seg_170 | seg_164 seg_165 |
| | | | | seg_440 seg_441 seg_442 seg_443 | seg_375 seg_376 seg_377 | seg_166 seg_167 |
| | | | | seg_444 seg_445 seg_446 seg_447 | seg_378 seg_379 seg_380 | seg_168 seg_169 |
| | | | | seg_448 seg_449 seg_450 seg_451 | seg_381 seg_382 seg_383 | seg_171 seg_172 |
| | | | | seg_452 seg_453 seg_454 seg_455 | seg_384 seg_385 seg_386 | seg_173 seg_174 |
| | | | | seg_456 seg_457 seg_458 seg_459 | seg_387 seg_388 seg_389 | seg_175 seg_176 |
| | | | | seg_460 seg_461 seg_462 seg_464 | seg_390 seg_391 seg_392 | seg_177 seg_178 |
| | | | | seg_465 seg_466 seg_435 seg_439 | seg_393 seg_394 seg_395 | seg_179 seg_180 |
| | | | | seg_463 seg_433 | seg_396 seg_397 seg_398 | seg_181 seg_170 |
| | | | | | seg_399 seg_400 seg_401 | |
| | | | | | seg_402 seg_403 seg_404 | |
| | | | | | seg_405 seg_406 seg_407 | |
| | | | | | seg_409 seg_410 seg_411 | |
| | | | | | seg_413 seg_414 seg_415 | |
| | | | | | seg_408 seg_412 | |
| paroxysmal nocturnal hemoglobinuria | 300818 | Xp22.2 | PIGA | seg_68 seg_89 seg_70 seg_71 seg_73 | seg_77 seg_78 seg_79 | seg_17 seg_18 seg_19 |
| | | | | seg_74 seg_75 seg_76 seg_77 seg_78 | seg_80 seg_81 seg_82 | seg_20 seg_21 seg_22 |
| | | | | seg_79 seg_80 seg_81 seg_82 seg_83 | seg_83 seg_84 seg_85 | seg_23 seg_24 seg_25 |
| | | | | seg_84 seg_85 seg_86 seg_87 seg_88 | seg_86 seg_87 seg_88 | seg_26 seg_27 seg_28 |
| | | | | seg_89 seg_90 seg_91 seg_92 seg_93 | seg_89 seg_91 seg_92 | seg_29 seg_30 seg_31 |
| | | | | seg_94 seg_95 seg_96 seg_97 seg_98 | seg_93 seg_95 seg_96 | seg_32 seg_33 seg_34 |
| | | | | seg_99 seg_100 seg_101 seg_102 | seg_97 seg_98 seg_99 | seg_35 seg_36 seg_37 |
| | | | | seg_103 seg_104 seg_105 seg_106 | seg_100 seg_101 seg_102 | seg_38 seg_39 seg_40 |
| | | | | seg_107 seg_108 seg_109 seg_111 | seg_103 seg_104 seg_106 | seg_41 seg_42 seg_43 |
| | | | | seg_112 seg_113 seg_114 seg_115 | seg_107 seg_108 seg_110 | seg_44 seg_45 seg_48 |
| | | | | seg_116 seg_117 seg_118 seg_119 | seg_111 seg_112 seg_113 | seg_47 seg_48 seg_49 |
| | | | | seg_121 seg_122 seg_124 seg_125 | seg_114 seg_115 seg_117 | seg_50 seg_51 seg_52 |
| | | | | seg_126 seg_127 seg_128 seg_129 | seg_119 seg_120 seg_121 | seg_53 seg_55 seg_56 |
| | | | | seg_72 seg_110 seg_123 seg_130 | seg_122 seg_123 seg_124 | seg_54 |
| | | | | seg_120 | seg_125 seg_126 seg_127 | |
| | | | | | seg_128 seg_130 seg_131 | |
| | | | | | seg_132 seg_133 seg_134 | |
| | | | | | seg_135 seg_136 seg_137 | |
| | | | | | seg_138 seg_139 seg_140 | |
| | | | | | seg_141 seg_142 seg_143 | |
| | | | | | seg_144 seg_145 seg_146 | |
| | | | | | seg_147 seg_148 seg_149 | |
| | | | | | seg_150 seg_151 seg_152 | |
| | | | | | seg_153 seg_156 seg_157 | |

TABLE A-continued

| Disorder | OMIM # | Locus | Gene | K562 Suz12* | K562 Ezh2** | GM12878 Ezh2*** |
|---|---|---|---|---|---|---|
| | | | | | seg_158 seg_159 seg_160 | |
| | | | | | seg_161 seg_162 seg_163 | |
| | | | | | seg_164 seg_165 seg_166 | |
| | | | | | seg_167 seg_168 seg_169 | |
| | | | | | seg_171 seg_172 seg_173 | |
| | | | | | seg_174 seg_175 seg_176 | |
| | | | | | seg_177 seg_178 seg_90 | |
| | | | | | seg_94 seg_105 seg_109 | |
| | | | | | seg_116 seg_118 seg_129 | |
| | | | | | seg_154 seg_155 seg_170 | |
| Aldrich syndrome | 301000 | Xp11.23-p11.22 | WAS | seg_199 seg_201 seg_203 seg_204 | seg_220 seg_221 seg_222 | seg_96 seg_97 seg_98 |
| | | | | seg_205 seg_206 seg_207 seg_208 | seg_223 seg_224 seg_225 | seg_99 seg_100 |
| | | | | seg_209 seg_210 seg_211 seg_212 | seg_226 seg_227 seg_228 | seg_101 seg_102 |
| | | | | seg_213 seg_214 seg_215 seg_216 | seg_229 seg_230 seg_232 | seg_103 seg_93 |
| | | | | seg_217 seg_218 seg_219 seg_220 | seg_234 seg_235 seg_236 | seg_95 |
| | | | | seg_221 seg_222 seg_223 seg_224 | seg_237 seg_238 seg_239 | |
| | | | | seg_225 seg_226 seg_227 seg_228 | seg_240 seg_241 seg_242 | |
| | | | | seg_229 seg_230 seg_231 seg_232 | seg_243 seg_245 seg_246 | |
| | | | | seg_233 seg_234 seg_235 seg_236 | seg_247 seg_248 seg_249 | |
| | | | | seg_237 seg_238 seg_239 seg_240 | seg_250 seg_251 seg_252 | |
| | | | | seg_242 seg_243 seg_244 seg_245 | seg_253 seg_254 seg_255 | |
| | | | | seg_246 seg_247 seg_249 seg_250 | seg_256 seg_257 seg_258 | |
| | | | | seg_251 seg_252 seg_253 seg_254 | seg_259 seg_260 seg_262 | |
| | | | | seg_256 seg_257 seg_258 seg_259 | seg_263 seg_265 seg_266 | |
| | | | | seg_260 seg_261 seg_262 seg_263 | seg_267 seg_268 seg_269 | |
| | | | | seg_264 seg_200 seg_202 seg_241 | seg_270 seg_271 seg_231 | |
| | | | | seg_248 seg_255 | seg_233 seg_244 seg_261 | |
| | | | | | seg_264 | |
| Alport syndrome | 301050 | Xq22.3 | COL4A5 | seg_394 seg_395 seg_396 seg_397 | seg_334 seg_336 seg_337 | seg_146 seg_148 |
| | | | | seg_398 seg_399 seg_400 seg_401 | seg_338 seg_339 seg_340 | seg_149 seg_150 |
| | | | | seg_402 seg_403 seg_404 seg_405 | seg_341 seg_342 seg_343 | seg_152 seg_156 |
| | | | | seg_406 seg_407 seg_408 seg_409 | seg_344 seg_345 seg_346 | seg_157 seg_158 |
| | | | | seg_410 seg_411 seg_412 seg_413 | seg_347 seg_348 seg_349 | seg_159 seg_160 |
| | | | | seg_414 seg_415 seg_417 seg_418 | seg_350 seg_351 seg_352 | seg_161 seg_162 |
| | | | | seg_419 seg_420 seg_421 seg_423 | seg_353 seg_355 seg_356 | seg_163 seg_164 |
| | | | | seg_425 seg_426 seg_427 seg_428 | seg_357 seg_358 seg_362 | seg_165 seg_166 |
| | | | | seg_431 seg_432 seg_434 seg_436 | seg_363 seg_364 seg_365 | seg_167 seg_168 |
| | | | | seg_437 seg_416 seg_422 seg_424 | seg_366 seg_367 seg_368 | seg_147 seg_153 |
| | | | | seg_429 seg_430 seg_435 seg_433 | seg_369 seg_370 seg_371 | seg_154 seg_155 |
| | | | | | seg_372 seg_373 seg_374 | seg_151 |
| | | | | | seg_375 seg_335 seg_354 | |
| Anaemia, hereditary hypochromic | 301300 | Xp11.21 | ALAS2 | seg_229 seg_230 seg_231 seg_232 | seg_359 seg_360 seg_361 | seg_101 seg_102 |
| | | | | seg_233 seg_234 seg_235 seg_236 | seg_252 seg_253 seg_254 | seg_103 seg_104 |
| | | | | seg_237 seg_238 seg_239 seg_240 | seg_255 seg_256 seg_257 | seg_105 seg_106 |
| | | | | seg_242 seg_243 seg_244 seg_245 | seg_258 seg_259 seg_260 | |
| | | | | seg_246 seg_247 seg_249 seg_250 | seg_262 seg_263 seg_265 | |
| | | | | seg_251 seg_252 seg_253 seg_254 | seg_266 seg_267 seg_268 | |
| | | | | seg_256 seg_257 seg_258 seg_259 | seg_269 seg_270 seg_271 | |
| | | | | seg_260 seg_261 seg_262 seg_263 | seg_272 seg_273 seg_274 | |
| | | | | seg_264 seg_265 seg_266 seg_267 | seg_275 seg_276 seg_277 | |
| | | | | | seg_278 seg_279 seg_280 | |

TABLE A-continued

| Disorder | OMIM # | Locus | Gene | K562 Suz12* | K562 Ezh2** | GM12878 Ezh2*** |
|---|---|---|---|---|---|---|
| Anemia, sideroblastic, with ataxia | 301310 | Xq13.3 | ABCB7 | seg_268 seg_269 seg_270 seg_271 seg_272 seg_273 seg_274 seg_275 seg_276 seg_277 seg_278 seg_279 seg_280 seg_281 seg_282 seg_284 seg_241 seg_248 seg_255 seg_283 seg_326 seg_328 seg_329 seg_330 seg_331 seg_332 seg_334 seg_335 seg_337 seg_338 seg_339 seg_340 seg_341 seg_342 seg_344 seg_345 seg_346 seg_347 seg_348 seg_349 seg_350 seg_351 seg_352 seg_353 seg_354 seg_356 seg_358 seg_359 seg_360 seg_361 seg_362 seg_363 seg_325 seg_327 seg_333 seg_336 | seg_281 seg_282 seg_283 seg_261 seg_264 seg_295 seg_296 seg_297 seg_298 seg_299 seg_302 seg_303 seg_304 seg_305 seg_306 seg_307 seg_308 seg_309 seg_311 seg_312 seg_313 seg_314 seg_315 seg_316 seg_317 seg_318 seg_319 seg_300 seg_301 seg_310 | seg_119 seg_121 seg_122 seg_124 seg_125 seg_126 seg_127 seg_123 seg_129 seg_130 seg_131 seg_133 seg_134 seg_120 seg_123 seg_132 |
| Fabry disease | 301500 | Xq22 | GLA | seg_343 seg_355 seg_357 seg_376 seg_377 seg_378 seg_379 seg_381 seg_382 seg_385 seg_386 seg_388 seg_389 seg_391 seg_392 seg_393 seg_394 seg_395 seg_396 seg_397 seg_398 seg_399 seg_400 seg_401 seg_402 seg_403 seg_404 seg_405 seg_380 seg_383 seg_387 seg_390 seg_384 | seg_323 seg_324 seg_326 seg_327 seg_328 seg_329 seg_331 seg_332 seg_333 seg_334 seg_336 seg_337 seg_338 seg_339 seg_340 seg_341 seg_342 seg_343 seg_344 seg_345 seg_346 seg_347 seg_348 seg_321 seg_325 seg_330 seg_335 | seg_140 seg_141 seg_142 seg_143 seg_144 seg_145 seg_146 |
| Spinal muscular atrophy 2 | 301830 | Xp11.23 | UBA1 | seg_197 seg_198 seg_199 seg_201 seg_203 seg_204 seg_205 seg_206 seg_207 seg_208 seg_209 seg_210 seg_211 seg_212 seg_213 seg_214 seg_215 seg_216 seg_217 seg_218 seg_219 seg_220 seg_221 seg_222 seg_223 seg_224 seg_225 seg_226 seg_227 seg_228 seg_229 seg_230 seg_231 seg_232 seg_233 seg_234 seg_235 seg_236 seg_237 seg_238 seg_239 seg_240 seg_242 seg_243 seg_244 seg_200 seg_202 seg_241 | seg_220 seg_221 seg_222 seg_223 seg_224 seg_225 seg_226 seg_227 seg_228 seg_229 seg_230 seg_232 seg_234 seg_235 seg_236 seg_237 seg_238 seg_239 seg_240 seg_241 seg_242 seg_243 seg_245 seg_246 seg_247 seg_248 seg_249 seg_250 seg_251 seg_252 seg_253 seg_254 seg_255 seg_256 seg_257 seg_231 seg_233 seg_244 | seg_94 seg_96 seg_97 seg_98 seg_99 seg_100 seg_93 seg_95 |
| Cataract, congenital | 302200 | Xp | CCT | seg_76 seg_77 seg_78 seg_79 seg_80 seg_81 seg_82 seg_83 seg_84 seg_85 seg_86 seg_87 seg_88 seg_89 seg_90 seg_91 seg_92 seg_93 seg_94 seg_95 seg_96 seg_97 seg_98 seg_99 seg_100 seg_101 seg_102 seg_103 seg_104 seg_105 seg_106 seg_107 seg_108 seg_109 seg_111 seg_112 seg_113 seg_114 seg_115 seg_116 seg_117 seg_118 seg_119 seg_121 seg_122 seg_124 seg_125 seg_126 seg_127 seg_128 seg_129 seg_131 seg_132 seg_133 seg_134 seg_110 seg_123 seg_130 seg_120 | seg_88 seg_89 seg_91 seg_92 seg_93 seg_95 seg_96 seg_97 seg_98 seg_99 seg_100 seg_101 seg_102 seg_103 seg_104 seg_106 seg_107 seg_108 seg_110 seg_111 seg_112 seg_113 seg_114 seg_115 seg_117 seg_120 seg_121 seg_122 seg_123 seg_124 seg_125 seg_126 seg_127 seg_128 seg_130 seg_131 seg_132 seg_133 seg_134 seg_135 seg_136 | seg_21 seg_22 seg_23 seg_24 seg_25 seg_26 seg_27 seg_28 seg_29 seg_30 seg_31 seg_32 seg_33 seg_34 seg_35 seg_36 seg_37 seg_38 seg_39 seg_40 seg_41 seg_42 seg_43 seg_44 seg_45 seg_46 seg_47 seg_48 seg_49 seg_50 seg_51 seg_52 seg_53 seg_55 seg_56 seg_57 seg_58 seg_59 seg_54 |

TABLE A-continued

| Disorder | OMIM # | Locus | Gene | K562 Suz12* | K562 Ezh2** | GM12878 Ezh2*** |
|---|---|---|---|---|---|---|
| | | | | | seg_137 seg_138 seg_139 | |
| | | | | | seg_140 seg_141 seg_142 | |
| | | | | | seg_143 seg_144 seg_145 | |
| | | | | | seg_146 seg_147 seg_148 | |
| | | | | | seg_149 seg_150 seg_151 | |
| | | | | | seg_152 seg_155 seg_156 | |
| | | | | | seg_157 seg_158 seg_159 | |
| | | | | | seg_160 seg_161 seg_162 | |
| | | | | | seg_163 seg_164 seg_165 | |
| | | | | | seg_166 seg_167 seg_168 | |
| | | | | | seg_169 seg_171 seg_172 | |
| | | | | | seg_173 seg_174 seg_175 | |
| | | | | | seg_176 seg_177 seg_178 | |
| | | | | | seg_179 seg_180 seg_181 | |
| | | | | | seg_182 seg_183 seg_184 | |
| | | | | | seg_90 seg_94 seg_105 | |
| | | | | | seg_109 seg_116 seg_118 | |
| | | | | | seg_129 seg_154 seg_155 | |
| | | | | | seg_170 | |
| Charcot-Marie-Tooth, peroneal | 302800 | Xq13.1 | GJB1 | seg_313 seg_314 seg_315 seg_316 | seg_287 seg_290 seg_291 | seg_114 seg_115 |
| | | | | seg_317 seg_318 seg_319 seg_320 | seg_292 seg_294 seg_295 | seg_116 seg_117 |
| | | | | seg_321 seg_322 seg_323 seg_324 | seg_296 seg_297 seg_298 | seg_118 seg_119 |
| | | | | seg_326 seg_328 seg_329 seg_330 | seg_299 seg_302 seg_303 | seg_121 seg_122 |
| | | | | seg_331 seg_332 seg_334 seg_335 | seg_304 seg_305 seg_306 | seg_124 seg_125 |
| | | | | seg_337 seg_338 seg_339 seg_340 | seg_307 seg_308 seg_309 | seg_126 seg_127 |
| | | | | seg_341 seg_342 seg_344 seg_345 | seg_311 seg_312 seg_313 | seg_120 seg_123 |
| | | | | seg_346 seg_347 seg_348 seg_349 | seg_314 seg_315 seg_316 | |
| | | | | seg_350 seg_351 seg_352 seg_353 | seg_317 seg_318 seg_319 | |
| | | | | seg_354 seg_356 seg_312 seg_325 | seg_288 seg_289 seg_293 | |
| | | | | seg_327 seg_333 seg_336 seg_343 | seg_300 seg_301 seg_310 | |
| | | | | seg_355 seg_357 | | |
| Spastic paraplegia | 303350 | Xq28 | L1CAM | seg_564 seg_566 seg_567 seg_568 | seg_504 seg_505 seg_506 | seg_209 seg_210 |
| | | | | seg_569 seg_571 seg_572 seg_574 | seg_507 seg_508 seg_509 | seg_211 seg_212 |
| | | | | seg_575 seg_576 seg_577 seg_578 | seg_510 seg_511 seg_512 | seg_213 seg_214 |
| | | | | seg_579 seg_580 seg_581 seg_582 | seg_514 seg_515 seg_516 | seg_215 |
| | | | | seg_583 seg_584 seg_585 seg_586 | seg_517 seg_518 seg_520 | |
| | | | | seg_587 seg_588 seg_589 seg_590 | seg_521 seg_522 seg_523 | |
| | | | | seg_591 seg_592 seg_593 seg_594 | seg_524 seg_525 seg_526 | |
| | | | | seg_595 seg_596 seg_597 seg_599 | seg_527 seg_528 seg_529 | |
| | | | | seg_600 seg_601 seg_602 seg_603 | seg_530 seg_531 seg_532 | |
| | | | | seg_604 seg_605 seg_606 seg_607 | seg_533 seg_534 seg_535 | |
| | | | | seg_608 seg_609 seg_610 seg_611 | seg_536 seg_538 seg_539 | |
| | | | | seg_612 seg_613 seg_615 seg_616 | seg_540 seg_542 seg_543 | |
| | | | | seg_617 seg_618 seg_619 seg_620 | seg_544 seg_545 seg_546 | |
| | | | | seg_622 seg_623 seg_624 seg_625 | seg_547 seg_548 seg_549 | |
| | | | | seg_626 seg_627 seg_628 seg_629 | seg_550 seg_551 seg_552 | |
| | | | | seg_630 seg_631 seg_632 seg_633 | seg_553 seg_554 seg_555 | |
| | | | | seg_634 seg_635 seg_637 seg_638 | seg_556 seg_558 seg_559 | |
| | | | | seg_639 seg_641 seg_642 seg_644 | seg_561 seg_562 seg_563 | |
| | | | | seg_645 seg_646 seg_647 seg_648 | seg_564 seg_565 seg_566 | |
| | | | | seg_649 seg_650 seg_651 seg_652 | seg_567 seg_568 seg_570 | |

TABLE A-continued

| Disorder | OMIM # | Locus | Gene | K562 Suz12* | K562 Ezh2** | GM12878 Ezh2*** |
|---|---|---|---|---|---|---|
| Colour blindness | 303800 | Xq28 | OPN1MW | seg_654 seg_655 seg_656 seg_657<br>seg_658 seg_659 seg_660 seg_661<br>seg_662 seg_663 seg_664 seg_665<br>seg_666 seg_565 seg_570 seg_573<br>seg_614 seg_621 seg_636 seg_640<br>seg_643 seg_598 seg_653<br>seg_567 seg_568 seg_569 seg_571<br>seg_572 seg_574 seg_575 seg_576<br>seg_577 seg_578 seg_579 seg_580<br>seg_581 seg_582 seg_583 seg_584<br>seg_585 seg_586 seg_587 seg_588<br>seg_589 seg_590 seg_591 seg_592<br>seg_593 seg_594 seg_595 seg_596<br>seg_597 seg_599 seg_600 seg_601<br>seg_602 seg_603 seg_604 seg_605<br>seg_606 seg_607 seg_608 seg_609<br>seg_610 seg_611 seg_612 seg_613<br>seg_615 seg_616 seg_617 seg_618<br>seg_619 seg_620 seg_622 seg_623<br>seg_624 seg_625 seg_626 seg_627<br>seg_628 seg_629 seg_630 seg_631<br>seg_632 seg_633 seg_634 seg_635<br>seg_637 seg_638 seg_639 seg_641<br>seg_642 seg_644 seg_645 seg_646<br>seg_647 seg_648 seg_649 seg_650<br>seg_651 seg_652 seg_654 seg_655<br>seg_656 seg_657 seg_658 seg_659<br>seg_660 seg_661 seg_662 seg_663<br>seg_664 seg_665 seg_666 seg_565<br>seg_570 seg_573 seg_614 seg_621<br>seg_636 seg_640 seg_643 seg_598<br>seg_653 | seg_572 seg_573 seg_574<br>seg_575 seg_576 seg_577<br>seg_578 seg_513 seg_519<br>seg_537 seg_541 seg_557<br>seg_563 seg_571 seg_560<br>seg_504 seg_505 seg_506<br>seg_507 seg_508 seg_509<br>seg_510 seg_511 seg_512<br>seg_514 seg_515 seg_516<br>seg_517 seg_518 seg_520<br>seg_521 seg_522 seg_523<br>seg_524 seg_525 seg_526<br>seg_527 seg_528 seg_529<br>seg_530 seg_531 seg_532<br>seg_533 seg_534 seg_535<br>seg_536 seg_538 seg_539<br>seg_540 seg_542 seg_543<br>seg_544 seg_545 seg_546<br>seg_547 seg_548 seg_549<br>seg_550 seg_551 seg_552<br>seg_553 seg_554 seg_555<br>seg_556 seg_558 seg_559<br>seg_561 seg_562 seg_563<br>seg_564 seg_565 seg_566<br>seg_567 seg_568 seg_570<br>seg_572 seg_573 seg_574<br>seg_575 seg_576 seg_577<br>seg_578 seg_513 seg_519<br>seg_537 seg_541 seg_557<br>seg_569 seg_571 seg_560 | seg_209 seg_210<br>seg_211 seg_212<br>seg_213 seg_214<br>seg_215 |
| Diabetes insipidus, nephrogenic | 304800 | Xq28 | AVPR2 | seg_564 seg_566 seg_567 seg_568<br>seg_569 seg_571 seg_572 seg_574<br>seg_575 seg_576 seg_577 seg_578<br>seg_579 seg_580 seg_581 seg_582<br>seg_583 seg_584 seg_585 seg_586<br>seg_587 seg_588 seg_589 seg_590<br>seg_591 seg_592 seg_593 seg_594<br>seg_595 seg_596 seg_597 seg_599<br>seg_600 seg_601 seg_602 seg_603<br>seg_604 seg_605 seg_606 seg_607<br>seg_608 seg_609 seg_610 seg_611<br>seg_612 seg_613 seg_615 seg_616<br>seg_617 seg_618 seg_619 seg_620<br>seg_622 seg_623 seg_624 seg_625<br>seg_626 seg_627 seg_628 seg_629<br>seg_630 seg_631 seg_632 seg_633<br>seg_634 seg_635 seg_637 seg_638<br>seg_639 seg_641 seg_642 seg_644<br>seg_645 seg_646 seg_647 seg_648 | seg_504 seg_505 seg_506<br>seg_507 seg_508 seg_509<br>seg_510 seg_511 seg_512<br>seg_514 seg_515 seg_516<br>seg_517 seg_518 seg_520<br>seg_521 seg_522 seg_523<br>seg_524 seg_525 seg_526<br>seg_527 seg_528 seg_529<br>seg_530 seg_531 seg_532<br>seg_533 seg_534 seg_535<br>seg_536 seg_538 seg_539<br>seg_540 seg_542 seg_543<br>seg_544 seg_545 seg_546<br>seg_547 seg_548 seg_549<br>seg_550 seg_551 seg_552<br>seg_553 seg_554 seg_555<br>seg_556 seg_558 seg_559<br>seg_561 seg_562 seg_563<br>seg_564 seg_565 seg_566 | seg_209 seg_210<br>seg_211 seg_212<br>seg_213 seg_214<br>seg_215 |

TABLE A-continued

| Disorder | OMIM # | Locus | Gene | K562 Suz12* | K562 Ezh2** | GM12878 Ezh2*** |
|---|---|---|---|---|---|---|
| | | | | seg_649 seg_650 seg_651 seg_652 | seg_567 seg_568 seg_569 seg_570 | |
| | | | | seg_654 seg_655 seg_656 seg_657 | seg_572 seg_573 seg_574 | |
| | | | | seg_658 seg_659 seg_660 seg_661 | seg_575 seg_576 seg_577 | |
| | | | | seg_662 seg_663 seg_664 seg_665 | seg_578 seg_513 seg_519 | |
| | | | | seg_666 seg_565 seg_570 seg_573 | seg_537 seg_541 seg_557 | |
| | | | | seg_614 seg_621 seg_636 seg_640 | seg_569 seg_571 seg_560 | |
| | | | | seg_643 seg_598 seg_653 | | |
| Dyskeratosis congenita | 305000 | Xq28 | DKC1 | seg_577 seg_578 seg_579 seg_580 | seg_511 seg_512 seg_514 | seg_210 seg_211 |
| | | | | seg_581 seg_582 seg_583 seg_584 | seg_515 seg_516 seg_517 | seg_212 seg_213 |
| | | | | seg_585 seg_586 seg_587 seg_588 | seg_518 seg_520 seg_521 | seg_214 seg_215 |
| | | | | seg_589 seg_590 seg_591 seg_592 | seg_522 seg_523 seg_524 | |
| | | | | seg_593 seg_594 seg_595 seg_596 | seg_525 seg_526 seg_527 | |
| | | | | seg_597 seg_599 seg_600 seg_601 | seg_528 seg_529 seg_530 | |
| | | | | seg_602 seg_603 seg_604 seg_605 | seg_531 seg_532 seg_533 | |
| | | | | seg_606 seg_607 seg_608 seg_609 | seg_534 seg_535 seg_536 | |
| | | | | seg_610 seg_611 seg_612 seg_613 | seg_538 seg_539 seg_540 | |
| | | | | seg_615 seg_616 seg_617 seg_618 | seg_542 seg_543 seg_544 | |
| | | | | seg_619 seg_620 seg_622 seg_623 | seg_545 seg_546 seg_547 | |
| | | | | seg_624 seg_625 seg_626 seg_627 | seg_548 seg_549 seg_550 | |
| | | | | seg_628 seg_629 seg_630 seg_631 | seg_551 seg_552 seg_553 | |
| | | | | seg_632 seg_633 seg_634 seg_635 | seg_554 seg_555 seg_556 | |
| | | | | seg_637 seg_638 seg_639 seg_641 | seg_558 seg_559 seg_561 | |
| | | | | seg_642 seg_644 seg_645 seg_646 | seg_562 seg_563 seg_564 | |
| | | | | seg_647 seg_648 seg_649 seg_650 | seg_565 seg_566 seg_567 | |
| | | | | seg_651 seg_652 seg_654 seg_655 | seg_568 seg_570 seg_572 | |
| | | | | seg_656 seg_657 seg_658 seg_659 | seg_573 seg_574 seg_575 | |
| | | | | seg_660 seg_661 seg_662 seg_663 | seg_576 seg_577 seg_578 | |
| | | | | seg_664 seg_665 seg_666 seg_614 | seg_513 seg_519 seg_537 | |
| | | | | seg_621 seg_636 seg_640 seg_643 | seg_541 seg_557 seg_569 | |
| | | | | seg_598 seg_653 | seg_571 seg_560 | |
| Ectodermal dysplasia, anhidrotic | 305100 | Xq12-q13.1 | ED1 | seg_310 seg_311 seg_313 seg_314 | seg_286 seg_287 seg_290 | seg_111 seg_112 |
| | | | | seg_315 seg_316 seg_317 seg_318 | seg_291 seg_292 seg_294 | seg_113 seg_114 |
| | | | | seg_319 seg_320 seg_321 seg_322 | seg_295 seg_296 seg_297 | seg_115 seg_116 |
| | | | | seg_323 seg_324 seg_326 seg_328 | seg_298 seg_299 seg_302 | seg_117 seg_118 |
| | | | | seg_329 seg_330 seg_331 seg_332 | seg_303 seg_304 seg_305 | seg_119 seg_121 |
| | | | | seg_334 seg_335 seg_337 seg_338 | seg_306 seg_307 seg_308 | seg_122 seg_124 |
| | | | | seg_339 seg_340 seg_341 seg_342 | seg_309 seg_311 seg_312 | seg_125 seg_126 |
| | | | | seg_344 seg_345 seg_346 seg_347 | seg_313 seg_314 seg_315 | seg_127 seg_120 |
| | | | | seg_348 seg_349 seg_350 seg_351 | seg_316 seg_317 seg_318 | seg_123 |
| | | | | seg_352 seg_353 seg_354 seg_356 | seg_319 seg_288 seg_289 | |
| | | | | seg_312 seg_325 seg_327 seg_333 | seg_293 seg_300 seg_301 | |
| | | | | seg_336 seg_343 seg_355 | seg_310 | |
| Faciogenital dysplasia (Aarskog syndrome) | 305400 | Xp11.21 | FGD1 | seg_226 seg_227 seg_228 seg_229 | seg_251 seg_252 seg_253 | seg_101 seg_102 |
| | | | | seg_230 seg_231 seg_232 seg_233 | seg_254 seg_255 seg_256 | seg_103 seg_104 |
| | | | | seg_234 seg_235 seg_236 seg_237 | seg_257 seg_258 seg_259 | seg_105 seg_106 |
| | | | | seg_238 seg_239 seg_240 seg_242 | seg_260 seg_262 seg_263 | |
| | | | | seg_243 seg_244 seg_245 seg_246 | seg_265 seg_266 seg_267 | |
| | | | | seg_247 seg_249 seg_250 seg_251 | seg_268 seg_269 seg_270 | |
| | | | | seg_252 seg_253 seg_254 seg_256 | seg_271 seg_272 seg_273 | |
| | | | | seg_257 seg_258 seg_259 seg_260 | seg_274 seg_275 seg_276 | |
| | | | | seg_261 seg_262 seg_263 seg_264 | seg_277 seg_278 seg_279 | |

TABLE A-continued

| Disorder | OMIM # | Locus | Gene | K562 Suz12* | K562 Ezh2** | GM12878 Ezh2*** |
|---|---|---|---|---|---|---|
| Glucose-6-phosphate dehydrogenase deficiency | 305900 | Xq28 | G6PD | seg_265 seg_266 seg_267 seg_268 seg_269 seg_270 seg_271 seg_272 seg_273 seg_274 seg_275 seg_276 seg_277 seg_278 seg_279 seg_280 seg_281 seg_282 seg_284 seg_241 seg_248 seg_255 seg_283 seg_574 seg_575 seg_576 seg_577 seg_578 seg_579 seg_580 seg_581 seg_582 seg_583 seg_584 seg_585 seg_586 seg_587 seg_588 seg_589 seg_590 seg_591 seg_592 seg_593 seg_594 seg_595 seg_596 seg_597 seg_599 seg_600 seg_601 seg_602 seg_603 seg_604 seg_605 seg_606 seg_607 seg_608 seg_609 seg_610 seg_611 seg_612 seg_613 seg_615 seg_616 seg_617 seg_618 seg_619 seg_620 seg_622 seg_623 seg_624 seg_625 seg_626 seg_627 seg_628 seg_629 seg_630 seg_631 seg_632 seg_633 seg_634 seg_635 seg_637 seg_638 seg_639 seg_641 seg_642 seg_644 seg_645 seg_646 seg_647 seg_648 seg_649 seg_650 seg_651 seg_652 seg_654 seg_655 seg_656 seg_657 seg_658 seg_659 seg_660 seg_661 seg_662 seg_663 seg_664 seg_665 seg_666 seg_573 seg_614 seg_621 seg_636 seg_640 seg_643 seg_598 seg_653 | seg_280 seg_281 seg_282 seg_283 seg_261 seg_264 seg_508 seg_509 seg_510 seg_511 seg_512 seg_514 seg_515 seg_516 seg_517 seg_518 seg_520 seg_521 seg_522 seg_523 seg_524 seg_525 seg_526 seg_527 seg_528 seg_529 seg_530 seg_531 seg_532 seg_533 seg_534 seg_535 seg_536 seg_538 seg_539 seg_540 seg_542 seg_543 seg_544 seg_545 seg_546 seg_547 seg_548 seg_549 seg_550 seg_551 seg_552 seg_553 seg_554 seg_555 seg_556 seg_558 seg_559 seg_561 seg_562 seg_563 seg_564 seg_565 seg_566 seg_567 seg_568 seg_570 seg_572 seg_573 seg_574 seg_575 seg_576 seg_577 seg_578 seg_513 seg_519 seg_537 seg_541 seg_557 seg_569 seg_571 seg_560 | seg_209 seg_210 seg_211 seg_212 seg_213 seg_214 seg_215 |
| Glycogen storage disease type VIII | 306000 | Xp22.2-p22.1 | PHKA2 | seg_91 seg_92 seg_93 seg_94 seg_95 seg_96 seg_97 seg_98 seg_99 seg_100 seg_101 seg_102 seg_103 seg_104 seg_105 seg_106 seg_107 seg_108 seg_109 seg_111 seg_112 seg_113 seg_114 seg_115 seg_116 seg_117 seg_118 seg_119 seg_121 seg_122 seg_124 seg_125 seg_126 seg_127 seg_128 seg_129 seg_131 seg_132 seg_133 seg_134 seg_135 seg_136 seg_137 seg_138 seg_139 seg_140 seg_141 seg_142 seg_110 seg_123 seg_130 seg_120 | seg_111 seg_112 seg_113 seg_114 seg_115 seg_117 seg_119 seg_120 seg_121 seg_122 seg_123 seg_124 seg_125 seg_126 seg_127 seg_128 seg_130 seg_131 seg_132 seg_133 seg_134 seg_135 seg_136 seg_137 seg_138 seg_139 seg_140 seg_141 seg_142 seg_143 seg_144 seg_145 seg_146 seg_147 seg_148 seg_149 seg_150 seg_151 seg_152 seg_153 seg_156 seg_157 seg_158 seg_159 seg_160 seg_161 seg_162 seg_163 seg_164 seg_165 seg_166 seg_167 seg_168 seg_169 seg_171 seg_172 seg_173 seg_174 seg_175 seg_176 seg_177 seg_178 seg_179 | seg_35 seg_36 seg_37 seg_38 seg_39 seg_40 seg_41 seg_42 seg_43 seg_44 seg_45 seg_46 seg_47 seg_48 seg_49 seg_50 seg_51 seg_52 seg_53 seg_55 seg_56 seg_57 seg_58 seg_59 seg_61 seg_60 seg_54 |

TABLE A-continued

| Disorder | OMIM # | Locus | Gene | K562 Suz12* | K562 Ezh2** | GM12878 Ezh2*** |
|---|---|---|---|---|---|---|
| Gonadal dysgenesis (XY female type) | 306100 | Xp22.11-p21.2 | GDXY | | seg_180 seg_181 seg_182<br>seg_183 seg_184 seg_185<br>seg_186 seg_109 seg_116<br>seg_118 seg_129 seg_154<br>seg_155 seg_170 | |
| Granulomatous disease (chronic) | 306400 | Xp21.1 | CYBB | seg_165 seg_166 seg_167 seg_168<br>seg_169 seg_170 seg_171 seg_172<br>seg_173 seg_174 seg_175 seg_176<br>seg_177 seg_178 seg_179 seg_181<br>seg_182 seg_183 seg_184 seg_185<br>seg_186 seg_187 seg_188 seg_189<br>seg_191 seg_192 seg_193 seg_195<br>seg_196 seg_180 seg_190 seg_194 | seg_200 seg_201 seg_202<br>seg_203 seg_204 seg_205<br>seg_206 seg_207 seg_208<br>seg_210 seg_211 seg_212<br>seg_213 seg_214 seg_215<br>seg_216 seg_217 seg_218<br>seg_209 | seg_79 seg_80 seg_81<br>seg_82 seg_83 seg_84<br>seg_85 seg_86 seg_87<br>seg_88 seg_89 seg_90<br>seg_91 |
| Haemophilia A | 306700 | Xq28 | F8 | seg_579 seg_580 seg_581 seg_582<br>seg_583 seg_584 seg_585 seg_586<br>seg_587 seg_588 seg_589 seg_590<br>seg_591 seg_592 seg_593 seg_594<br>seg_595 seg_596 seg_597 seg_599<br>seg_600 seg_601 seg_602 seg_603<br>seg_604 seg_605 seg_606 seg_607<br>seg_608 seg_609 seg_610 seg_611<br>seg_612 seg_613 seg_615 seg_616<br>seg_617 seg_618 seg_619 seg_620<br>seg_622 seg_623 seg_624 seg_625<br>seg_626 seg_627 seg_628 seg_629<br>seg_630 seg_631 seg_632 seg_633<br>seg_634 seg_635 seg_637 seg_638<br>seg_639 seg_641 seg_642 seg_644<br>seg_645 seg_646 seg_647 seg_648<br>seg_649 seg_650 seg_651 seg_652<br>seg_654 seg_655 seg_656 seg_657<br>seg_658 seg_659 seg_660 seg_661<br>seg_662 seg_663 seg_664 seg_665<br>seg_666 seg_614 seg_621 seg_636<br>seg_640 seg_643 seg_598 seg_653 | seg_512 seg_514 seg_515<br>seg_516 seg_517 seg_518<br>seg_520 seg_521 seg_522<br>seg_523 seg_524 seg_525<br>seg_526 seg_527 seg_528<br>seg_529 seg_530 seg_531<br>seg_532 seg_533 seg_534<br>seg_535 seg_536 seg_538<br>seg_539 seg_540 seg_542<br>seg_543 seg_544 seg_545<br>seg_546 seg_547 seg_548<br>seg_549 seg_550 seg_551<br>seg_552 seg_553 seg_554<br>seg_555 seg_556 seg_558<br>seg_553 seg_561 seg_562<br>seg_563 seg_564 seg_565<br>seg_566 seg_567 seg_568<br>seg_570 seg_572 seg_573<br>seg_574 seg_575 seg_576<br>seg_577 seg_578 seg_513<br>seg_519 seg_537 seg_541<br>seg_557 seg_569 seg_571<br>seg_560 | seg_210 seg_211<br>seg_212 seg_213<br>seg_214 seg_215 |
| Haemophilia B | 306900 | Xq27.1-q27.2 | F9 | seg_506 seg_507 seg_509 seg_510<br>seg_511 seg_512 seg_513 seg_514<br>seg_515 seg_516 seg_517 seg_518<br>seg_519 seg_520 seg_521 seg_522<br>seg_523 seg_524 seg_525 seg_526<br>seg_527 seg_528 seg_529 seg_530<br>seg_531 seg_532 seg_533 seg_534<br>seg_535 seg_536 seg_537 seg_538<br>seg_540 seg_541 seg_542 seg_543<br>seg_544 seg_545 seg_546 seg_547<br>seg_548 seg_549 seg_550 seg_551 | seg_445 seg_446 seg_447<br>seg_448 seg_449 seg_450<br>seg_451 seg_452 seg_453<br>seg_454 seg_456 seg_457<br>seg_459 seg_460 seg_462<br>seg_463 seg_464 seg_465<br>seg_466 seg_467 seg_469<br>seg_470 seg_471 seg_472<br>seg_473 seg_474 seg_475<br>seg_476 seg_478 seg_480<br>seg_481 seg_482 seg_484 | seg_194 seg_195<br>seg_196 seg_197<br>seg_198 seg_200<br>seg_201 seg_202<br>seg_203 seg_204<br>seg_205 seg_206<br>seg_199 |

TABLE A-continued

| Disorder | OMIM # | Locus | Gene | K562 Suz12* | K562 Ezh2** | GM12878 Ezh2*** |
|---|---|---|---|---|---|---|
| | | | | seg_552 seg_553 seg_554 seg_555 | seg_485 seg_486 seg_487 | |
| | | | | seg_557 seg_558 seg_559 seg_505 | seg_488 seg_489 seg_490 | |
| | | | | seg_508 seg_539 seg_556 | seg_491 seg_492 seg_493 | |
| | | | | | seg_496 seg_497 seg_498 | |
| | | | | | seg_499 seg_500 seg_501 | |
| | | | | | seg_502 seg_455 seg_458 | |
| | | | | | seg_468 seg_477 seg_479 | |
| | | | | | seg_483 seg_494 seg_495 | |
| Hydrocephalus (aqueduct stenosis) | 307000 | Xq28 | L1CAM | seg_564 seg_566 seg_567 seg_568 | seg_461 | |
| | | | | seg_569 seg_571 seg_572 seg_574 | seg_504 seg_505 seg_506 | seg_209 seg_210 |
| | | | | seg_575 seg_576 seg_577 seg_578 | seg_507 seg_508 seg_509 | seg_211 seg_212 |
| | | | | seg_579 seg_580 seg_581 seg_582 | seg_510 seg_511 seg_512 | seg_213 seg_214 |
| | | | | seg_583 seg_584 seg_585 seg_586 | seg_514 seg_515 seg_516 | seg_215 |
| | | | | seg_587 seg_588 seg_589 seg_590 | seg_517 seg_518 seg_520 | |
| | | | | seg_591 seg_592 seg_593 seg_594 | seg_521 seg_522 seg_523 | |
| | | | | seg_595 seg_596 seg_597 seg_599 | seg_524 seg_525 seg_526 | |
| | | | | seg_600 seg_601 seg_602 seg_603 | seg_527 seg_528 seg_529 | |
| | | | | seg_604 seg_605 seg_606 seg_607 | seg_530 seg_531 seg_532 | |
| | | | | seg_603 seg_609 seg_610 seg_611 | seg_533 seg_534 seg_535 | |
| | | | | seg_612 seg_613 seg_615 seg_616 | seg_536 seg_538 seg_539 | |
| | | | | seg_617 seg_618 seg_619 seg_620 | seg_540 seg_542 seg_543 | |
| | | | | seg_622 seg_623 seg_624 seg_625 | seg_544 seg_545 seg_546 | |
| | | | | seg_626 seg_627 seg_628 seg_629 | seg_547 seg_548 seg_549 | |
| | | | | seg_630 seg_631 seg_632 seg_633 | seg_550 seg_551 seg_552 | |
| | | | | seg_634 seg_635 seg_637 seg_638 | seg_553 seg_554 seg_555 | |
| | | | | seg_639 seg_641 seg_642 seg_644 | seg_556 seg_558 seg_555 | |
| | | | | seg_645 seg_646 seg_647 seg_648 | seg_561 seg_562 seg_563 | |
| | | | | seg_649 seg_650 seg_651 seg_652 | seg_564 seg_565 seg_566 | |
| | | | | seg_654 seg_655 seg_656 seg_657 | seg_567 seg_568 seg_570 | |
| | | | | seg_658 seg_659 seg_660 seg_661 | seg_572 seg_573 seg_574 | |
| | | | | seg_662 seg_663 seg_664 seg_665 | seg_575 seg_576 seg_577 | |
| | | | | seg_666 seg_565 seg_570 seg_573 | seg_578 seg_513 seg_519 | |
| | | | | seg_614 seg_621 seg_636 seg_640 | seg_537 seg_541 seg_557 | |
| | | | | seg_643 seg_598 seg_653 | seg_569 seg_571 seg_560 | |
| Hypophosphataemic rickets | 307800 | Xp22.2-p22.1 | PHEX | seg_100 seg_101 seg_102 seg_103 | seg_126 seg_127 seg_128 | seg_49 seg_50 seg_51 |
| | | | | seg_104 seg_105 seg_106 seg_107 | seg_130 seg_131 seg_132 | seg_52 seg_53 seg_55 |
| | | | | seg_108 seg_109 seg_111 seg_112 | seg_133 seg_134 seg_135 | seg_56 seg_57 seg_58 |
| | | | | seg_113 seg_114 seg_115 seg_116 | seg_136 seg_137 seg_138 | seg_59 seg_61 seg_62 |
| | | | | seg_117 seg_118 seg_119 seg_121 | seg_139 seg_140 seg_141 | seg_63 seg_64 seg_60 |
| | | | | seg_122 seg_124 seg_125 seg_126 | seg_142 seg_143 seg_144 | seg_65 seg_54 |
| | | | | seg_127 seg_128 seg_129 seg_131 | seg_145 seg_146 seg_147 | |
| | | | | seg_132 seg_133 seg_134 seg_135 | seg_148 seg_149 seg_150 | |
| | | | | seg_136 seg_137 seg_138 seg_139 | seg_151 seg_152 seg_153 | |
| | | | | seg_140 seg_141 seg_142 seg_143 | seg_156 seg_157 seg_158 | |
| | | | | seg_144 seg_145 seg_147 seg_148 | seg_159 seg_160 seg_161 | |
| | | | | seg_149 seg_150 seg_151 seg_153 | seg_162 seg_163 seg_164 | |
| | | | | seg_154 seg_155 seg_156 seg_110 | seg_165 seg_166 seg_167 | |
| | | | | seg_123 seg_130 seg_146 seg_120 | seg_168 seg_169 seg_171 | |
| | | | | seg_152 | seg_172 seg_173 seg_174 | |
| | | | | | seg_175 seg_176 seg_177 | |

TABLE A-continued

| Disorder | OMIM # | Locus | Gene | K562 Suz12* | K562 Ezh2** | GM12878 Ezh2*** |
|---|---|---|---|---|---|---|
| Lesch-Nyhan syndrome (hypoxanthine-guanine-phosphoribosyl transferase deficiency) | 308000 | Xq26-q27.2 | HPRT1 | seg_479 seg_480 seg_481 seg_482<br>seg_483 seg_484 seg_485 seg_486<br>seg_487 seg_488 seg_489 seg_490<br>seg_491 seg_492 seg_493 seg_494<br>seg_495 seg_496 seg_497 seg_498<br>seg_499 seg_501 seg_502 seg_503<br>seg_504 seg_506 seg_507 seg_509<br>seg_510 seg_511 seg_512 seg_513<br>seg_514 seg_515 seg_516 seg_517<br>seg_518 seg_519 seg_520 seg_521<br>seg_522 seg_523 seg_524 seg_525<br>seg_526 seg_527 seg_528 seg_529<br>seg_530 seg_531 seg_532 seg_533<br>seg_534 seg_535 seg_536 seg_537<br>seg_538 seg_540 seg_541 seg_542<br>seg_543 seg_544 seg_545 seg_546<br>seg_547 seg_548 seg_549 seg_500<br>seg_505 seg_508 seg_539 | seg_178 seg_179 seg_180<br>seg_181 seg_182 seg_183<br>seg_184 seg_185 seg_186<br>seg_187 seg_188 seg_189<br>seg_191 seg_192 seg_193<br>seg_195 seg_129 seg_154<br>seg_190 seg_155 seg_194<br>seg_170<br>seg_421 seg_422 seg_423<br>seg_424 seg_425 seg_426<br>seg_427 seg_428 seg_429<br>seg_430 seg_431 seg_432<br>seg_433 seg_434 seg_436<br>seg_438 seg_439 seg_440<br>seg_441 seg_442 seg_443<br>seg_444 seg_445 seg_446<br>seg_447 seg_448 seg_449<br>seg_450 seg_451 seg_452<br>seg_453 seg_454 seg_456<br>seg_457 seg_459 seg_460<br>seg_462 seg_463 seg_464<br>seg_465 seg_466 seg_467<br>seg_469 seg_470 seg_471<br>seg_472 seg_473 seg_474<br>seg_475 seg_476 seg_478<br>seg_480 seg_481 seg_482<br>seg_484 seg_485 seg_486<br>seg_487 seg_488 seg_489<br>seg_490 seg_491 seg_492<br>seg_493 seg_496 seg_497<br>seg_435 seg_437 seg_455<br>seg_458 seg_468 seg_477<br>seg_479 seg_483 seg_494<br>seg_495 seg_461 | seg_187 seg_188<br>seg_189 seg_190<br>seg_191 seg_192<br>seg_193 seg_194<br>seg_195 seg_196<br>seg_197 seg_198<br>seg_200 seg_201<br>seg_202 seg_203<br>seg_199 |
| Incontinentia pigmenti | 308300 | Xq28 | IKBKG | seg_574 seg_575 seg_576 seg_577<br>seg_578 seg_579 seg_580 seg_581<br>seg_582 seg_583 seg_584 seg_585<br>seg_586 seg_587 seg_588 seg_589<br>seg_590 seg_591 seg_592 seg_593<br>seg_594 seg_595 seg_596 seg_597<br>seg_599 seg_600 seg_601 seg_602<br>seg_603 seg_604 seg_605 seg_606<br>seg_607 seg_608 seg_609 seg_610<br>seg_611 seg_612 seg_613 seg_615<br>seg_616 seg_617 seg_618 seg_619<br>seg_620 seg_622 seg_623 seg_624<br>seg_625 seg_626 seg_627 seg_628<br>seg_629 seg_630 seg_631 seg_632<br>seg_633 seg_634 seg_635 seg_637<br>seg_638 seg_639 seg_641 seg_642<br>seg_644 seg_645 seg_646 seg_647 | seg_508 seg_509 seg_510<br>seg_511 seg_512 seg_514<br>seg_515 seg_516 seg_517<br>seg_518 seg_520 seg_521<br>seg_522 seg_523 seg_524<br>seg_525 seg_526 seg_527<br>seg_528 seg_529 seg_530<br>seg_531 seg_532 seg_533<br>seg_534 seg_535 seg_536<br>seg_538 seg_539 seg_540<br>seg_542 seg_543 seg_544<br>seg_545 seg_546 seg_547<br>seg_548 seg_549 seg_550<br>seg_551 seg_552 seg_553<br>seg_554 seg_555 seg_556<br>seg_558 seg_559 seg_561<br>seg_562 seg_563 seg_564 | seg_209 seg_210<br>seg_211 seg_212<br>seg_213 seg_214<br>seg_215 |

TABLE A-continued

| Disorder | OMIM # | Locus | Gene | K562 Suz12* | K562 Ezh2** | GM12878 Ezh2*** |
|---|---|---|---|---|---|---|
| | | | | seg_648 seg_649 seg_650 seg_651 | seg_565 seg_566 seg_567 | |
| | | | | seg_652 seg_654 seg_655 seg_656 | seg_568 seg_570 seg_572 | |
| | | | | seg_657 seg_658 seg_659 seg_660 | seg_573 seg_574 seg_575 | |
| | | | | seg_661 seg_662 seg_663 seg_664 | seg_576 seg_577 seg_578 | |
| | | | | seg_665 seg_666 seg_573 seg_614 | seg_513 seg_519 seg_537 | |
| | | | | seg_621 seg_636 seg_640 seg_643 | seg_541 seg_557 seg_569 | |
| | | | | seg_598 seg_653 | seg_571 seg_560 | |
| Kallmann syndrome | 308700 | Xp22.3 | KAL1 | seg_48 seg_49 seg_50 seg_51 seg_52 | seg_52 seg_53 seg_54 | seg_8 seg_9 seg_10 |
| | | | | seg_55 seg_54 seg_55 seg_56 seg_57 | seg_55 seg_56 seg_57 | seg_11 seg_12 seg_13 |
| | | | | seg_58 seg_59 seg_60 seg_61 seg_63 | seg_58 seg_60 seg_61 | seg_14 seg_16 seg_17 |
| | | | | seg_64 seg_65 seg_66 seg_67 seg_68 | seg_63 seg_64 seg_65 | seg_18 seg_19 seg_20 |
| | | | | seg_69 seg_70 seg_71 seg_73 seg_74 | seg_66 seg_67 seg_68 | seg_21 seg_22 seg_23 |
| | | | | seg_75 seg_76 seg_77 seg_78 seg_79 | seg_69 seg_70 seg_71 | seg_24 seg_25 seg_26 |
| | | | | seg_80 seg_81 seg_82 seg_83 seg_84 | seg_72 seg_73 seg_74 | seg_27 seg_28 seg_29 |
| | | | | seg_85 seg_47 seg_62 seg_72 | seg_75 seg_76 seg_77 | seg_15 |
| | | | | | seg_78 seg_79 seg_80 | |
| | | | | | seg_81 seg_82 seg_83 | |
| | | | | | seg_84 seg_85 seg_86 | |
| | | | | | seg_87 seg_88 seg_89 | |
| | | | | | seg_91 seg_92 seg_93 | |
| | | | | | seg_95 seg_96 seg_97 | |
| | | | | | seg_98 seg_59 seg_62 | |
| | | | | | seg_90 seg_94 | |
| Keratosis follicularis spinulosa | 308800 | Xp22.1 | SAT | seg_112 seg_113 seg_114 seg_115 | seg_145 seg_146 seg_147 | seg_56 seg_57 seg_58 |
| | | | | seg_116 seg_117 seg_118 seg_119 | seg_148 seg_149 seg_150 | seg_59 seg_61 seg_62 |
| | | | | seg_121 seg_122 seg_124 seg_125 | seg_151 seg_152 seg_153 | seg_63 seg_64 seg_60 |
| | | | | seg_126 seg_127 seg_128 seg_129 | seg_156 seg_157 seg_158 | seg_65 seg_54 |
| | | | | seg_131 seg_132 seg_133 seg_134 | seg_159 seg_160 seg_161 | |
| | | | | seg_135 seg_136 seg_137 seg_138 | seg_162 seg_163 seg_164 | |
| | | | | seg_139 seg_140 seg_141 seg_142 | seg_165 seg_166 seg_167 | |
| | | | | seg_143 seg_144 seg_145 seg_147 | seg_168 seg_169 seg_171 | |
| | | | | seg_148 seg_149 seg_150 seg_151 | seg_172 seg_173 seg_174 | |
| | | | | seg_153 seg_154 seg_155 seg_156 | seg_175 seg_176 seg_177 | |
| | | | | seg_157 seg_110 seg_123 seg_130 | seg_178 seg_179 seg_180 | |
| | | | | seg_146 seg_120 seg_152 | seg_181 seg_182 seg_183 | |
| | | | | | seg_184 seg_185 seg_186 | |
| | | | | | seg_187 seg_188 seg_189 | |
| | | | | | seg_191 seg_192 seg_193 | |
| | | | | | seg_195 seg_154 seg_170 | |
| Lowe (oculocerebrorenal) syndrome | 309000 | Xq26.1 | OCRL | seg_474 seg_475 seg_477 seg_478 | seg_420 seg_421 seg_422 | seg_185 seg_186 |
| | | | | seg_479 seg_480 seg_481 seg_482 | seg_423 seg_424 seg_425 | seg_187 seg_188 |
| | | | | seg_483 seg_484 seg_485 seg_486 | seg_426 seg_427 seg_428 | seg_189 seg_190 |
| | | | | seg_487 seg_488 seg_489 seg_490 | seg_429 seg_430 seg_431 | seg_191 seg_192 |
| | | | | seg_491 seg_492 seg_493 seg_494 | seg_432 seg_433 seg_434 | seg_183 |
| | | | | seg_495 seg_496 seg_497 seg_498 | seg_436 seg_438 seg_439 | |
| | | | | seg_499 seg_501 seg_502 seg_503 | seg_440 seg_441 seg_442 | |
| | | | | seg_476 seg_500 | seg_443 seg_435 seg_437 | |
| Menkes syndrome | 309400 | Xq12-q13 | ATP7A | seg_353 seg_354 seg_356 seg_358 | seg_317 seg_318 seg_319 | seg_128 seg_129 |
| | | | | seg_359 seg_360 seg_361 seg_362 | | seg_130 seg_131 |
| | | | | seg_363 seg_364 seg_365 seg_366 | | seg_133 seg_134 |

TABLE A-continued

| Disorder | OMIM # | Locus | Gene | K562 Suz12* | K562 Ezh2** | GM12878 Ezh2*** |
|---|---|---|---|---|---|---|
| Renpenning Syndrome | 309500 | Xp11.23 | PQBP1 | seg_355 seg_357<br>seg_199 seg_201 seg_203 seg_204<br>seg_205 seg_206 seg_207 seg_208<br>seg_209 seg_210 seg_211 seg_212<br>seg_213 seg_214 seg_215 seg_216<br>seg_217 seg_218 seg_219 seg_220<br>seg_221 seg_222 seg_223 seg_224<br>seg_225 seg_226 seg_227 seg_228<br>seg_229 seg_230 seg_231 seg_232<br>seg_233 seg_234 seg_235 seg_236<br>seg_237 seg_238 seg_239 seg_240<br>seg_242 seg_243 seg_244 seg_245<br>seg_246 seg_247 seg_249 seg_250<br>seg_251 seg_252 seg_253 seg_254<br>seg_256 seg_257 seg_258 seg_259<br>seg_260 seg_261 seg_262 seg_263<br>seg_264 seg_200 seg_202 seg_241<br>seg_248 seg_255 | seg_220 seg_221 seg_222<br>seg_223 seg_224 seg_225<br>seg_226 seg_227 seg_228<br>seg_229 seg_230 seg_232<br>seg_234 seg_235 seg_236<br>seg_237 seg_238 seg_239<br>seg_240 seg_241 seg_242<br>seg_243 seg_245 seg_246<br>seg_247 seg_248 seg_249<br>seg_250 seg_251 seg_252<br>seg_253 seg_254 seg_255<br>seg_256 seg_257 seg_258<br>seg_259 seg_260 seg_262<br>seg_263 seg_265 seg_266<br>seg_267 seg_268 seg_269<br>seg_270 seg_271 seg_231<br>seg_233 seg_244 seg_261<br>seg_264 | seg_135 seg_132<br>seg_96 seg_97 seg_98<br>seg_99 seg_100<br>seg_101 seg_102<br>seg_103 seg_104<br>seg_105 seg_93<br>seg_95 |
| Mental retardation, with or without fragile site (numerous specific types) | 309530 | Xp11.3-q21.1 | MRX1 | seg_218 seg_219 seg_220 seg_221<br>seg_222 seg_223 seg_224 seg_225<br>seg_226 seg_227 seg_228 seg_229<br>seg_230 seg_231 seg_232 seg_233<br>seg_234 seg_235 seg_236 seg_237<br>seg_238 seg_239 seg_240 seg_242<br>seg_243 seg_244 seg_245 seg_246<br>seg_247 seg_249 seg_250 seg_251<br>seg_252 seg_253 seg_254 seg_256<br>seg_257 seg_258 seg_259 seg_260<br>seg_261 seg_262 seg_263 seg_264<br>seg_265 seg_266 seg_267 seg_268<br>seg_269 seg_270 seg_271 seg_272<br>seg_273 seg_274 seg_275 seg_276<br>seg_277 seg_278 seg_279 seg_241<br>seg_248 seg_255 | seg_245 seg_246 seg_247<br>seg_248 seg_249 seg_250<br>seg_251 seg_252 seg_253<br>seg_254 seg_255 seg_256<br>seg_257 seg_258 seg_259<br>seg_260 seg_262 seg_263<br>seg_265 seg_266 seg_267<br>seg_268 seg_269 seg_270<br>seg_271 seg_272 seg_273<br>seg_274 seg_275 seg_276<br>seg_277 seg_278 seg_279<br>seg_280 seg_281 seg_282<br>seg_283 seg_244 seg_261<br>seg_264 | seg_101 seg_102<br>seg_103 seg_104<br>seg_105 seg_106 |
| Coffin-Lowry syndrome | 309580 | Xq13 | ATRX | seg_350 seg_351 seg_352 seg_353<br>seg_354 seg_356 seg_358 seg_359<br>seg_360 seg_361 seg_362 seg_363<br>seg_364 seg_365 seg_366 seg_355<br>seg_357 | seg_317 seg_318 seg_319 | |
| Microphthalmia with multiple anomalies (Lenz syndrome) | 309800 | Xq27-q28 | MAA | seg_561 seg_562 seg_563 seg_564<br>seg_566 seg_567 seg_568 seg_569<br>seg_571 seg_572 seg_574 seg_575<br>seg_576 seg_577 seg_578 seg_579<br>seg_580 seg_581 seg_582 seg_583<br>seg_584 seg_585 seg_586 seg_587<br>seg_588 seg_589 seg_590 seg_591<br>seg_592 seg_593 seg_594 seg_595<br>seg_596 seg_565 seg_560 seg_570<br>seg_573 | seg_503 seg_504 seg_505<br>seg_506 seg_507 seg_508<br>seg_509 seg_510 seg_511<br>seg_512 seg_514 seg_515<br>seg_516 seg_517 seg_518<br>seg_520 seg_521 seg_522<br>seg_523 seg_524 seg_525<br>seg_526 seg_527 seg_528<br>seg_529 seg_530 seg_531<br>seg_513 seg_519 | seg_208 seg_209<br>seg_210 seg_211<br>seg_212 |
| Muscular | 310300 | Xq28 | EMD | seg_567 seg_568 seg_569 seg_571 | seg_504 seg_505 seg_506 | seg_209 seg_210 |

TABLE A-continued

| Disorder | OMIM # | Locus | Gene | K562 Suz12* | K562 Ezh2** | GM12878 Ezh2*** |
|---|---|---|---|---|---|---|
| dystrophy (Becker, Duchenne and Emery-Dreifuss types) | | | | seg_572 seg_574 seg_575 seg_576<br>seg_577 seg_578 seg_579 seg_580<br>seg_581 seg_582 seg_583 seg_584<br>seg_585 seg_586 seg_587 seg_588<br>seg_589 seg_590 seg_591 seg_592<br>seg_593 seg_594 seg_595 seg_596<br>seg_597 seg_599 seg_600 seg_601<br>seg_602 seg_603 seg_604 seg_605<br>seg_606 seg_607 seg_608 seg_609<br>seg_610 seg_611 seg_612 seg_613<br>seg_615 seg_616 seg_617 seg_618<br>seg_619 seg_620 seg_622 seg_623<br>seg_624 seg_625 seg_626 seg_627<br>seg_628 seg_629 seg_630 seg_631<br>seg_632 seg_633 seg_634 seg_635<br>seg_637 seg_638 seg_639 seg_641<br>seg_642 seg_644 seg_645 seg_646<br>seg_647 seg_648 seg_649 seg_650<br>seg_651 seg_652 seg_654 seg_655<br>seg_656 seg_657 seg_658 seg_659<br>seg_660 seg_661 seg_662 seg_663<br>seg_664 seg_665 seg_666 seg_670<br>seg_573 seg_614 seg_621 seg_636<br>seg_640 seg_643 seg_598 seg_653 | seg_507 seg_508 seg_509<br>seg_510 seg_511 seg_512<br>seg_514 seg_515 seg_516<br>seg_517 seg_518 seg_520<br>seg_521 seg_522 seg_523<br>seg_524 seg_525 seg_526<br>seg_527 seg_528 seg_529<br>seg_530 seg_531 seg_532<br>seg_533 seg_534 seg_535<br>seg_536 seg_538 seg_539<br>seg_540 seg_542 seg_543<br>seg_544 seg_545 seg_546<br>seg_547 seg_548 seg_549<br>seg_550 seg_551 seg_552<br>seg_553 seg_554 seg_555<br>seg_556 seg_558 seg_559<br>seg_561 seg_562 seg_563<br>seg_564 seg_565 seg_566<br>seg_567 seg_568 seg_570<br>seg_572 seg_573 seg_574<br>seg_575 seg_576 seg_577<br>seg_578 seg_513 seg_519<br>seg_537 seg_541 seg_557<br>seg_569 seg_571 seg_560 | seg_211 seg_212<br>seg_213 seg_214<br>seg_215 |
| Myotubular myopathy | 310400 | Xq28 | MTM1 | seg_562 seg_563 seg_564 seg_566<br>seg_567 seg_568 seg_569 seg_571<br>seg_572 seg_574 seg_575 seg_576<br>seg_577 seg_578 seg_579 seg_580<br>seg_581 seg_582 seg_583 seg_584<br>seg_585 seg_586 seg_587 seg_588<br>seg_589 seg_590 seg_591 seg_592<br>seg_593 seg_594 seg_595 seg_596<br>seg_597 seg_599 seg_600 seg_601<br>seg_602 seg_603 seg_604 seg_605<br>seg_606 seg_607 seg_608 seg_609<br>seg_610 seg_611 seg_612 seg_613<br>seg_615 seg_616 seg_617 seg_618<br>seg_619 seg_620 seg_622 seg_623<br>seg_624 seg_625 seg_626 seg_627<br>seg_628 seg_629 seg_630 seg_631<br>seg_632 seg_633 seg_634 seg_635<br>seg_637 seg_638 seg_639 seg_641<br>seg_642 seg_644 seg_645 seg_646<br>seg_647 seg_648 seg_649 seg_650<br>seg_651 seg_652 seg_654 seg_655<br>seg_656 seg_657 seg_658 seg_659<br>seg_660 seg_661 seg_662 seg_560<br>seg_565 seg_570 seg_573 seg_614<br>seg_621 seg_636 seg_640 seg_643 | seg_504 seg_505 seg_506<br>seg_507 seg_508 seg_509<br>seg_510 seg_511 seg_512<br>seg_514 seg_515 seg_516<br>seg_517 seg_518 seg_520<br>seg_521 seg_522 seg_523<br>seg_524 seg_525 seg_526<br>seg_527 seg_528 seg_529<br>seg_530 seg_531 seg_532<br>seg_533 seg_534 seg_535<br>seg_536 seg_538 seg_539<br>seg_540 seg_542 seg_543<br>seg_544 seg_545 seg_546<br>seg_547 seg_548 seg_549<br>seg_550 seg_551 seg_552<br>seg_553 seg_554 seg_555<br>seg_556 seg_558 seg_559<br>seg_561 seg_562 seg_563<br>seg_564 seg_565 seg_566<br>seg_567 seg_568 seg_570<br>seg_572 seg_573 seg_574<br>seg_575 seg_576 seg_577<br>seg_513 seg_519 seg_537<br>seg_541 seg_557 seg_569 | seg_208 seg_209<br>seg_210 seg_211<br>seg_212 seg_213<br>seg_214 seg_215 |
| Night | 310500 | Xp11.4 | CSNB1 | seg_167 seg_168 seg_169 seg_170 | seg_200 seg_201 seg_202 | seg_80 seg_81 seg_82 |

TABLE A-continued

| Disorder | OMIM # | Locus | Gene | K562 Suz12* | K562 Ezh2** | GM12878 Ezh2*** |
|---|---|---|---|---|---|---|
| blindness, congenital stationary | | | | seg_171 seg_172 seg_173 seg_174 seg_175 seg_176 seg_177 seg_178 seg_179 seg_181 seg_182 seg_183 seg_184 seg_185 seg_186 seg_187 seg_188 seg_189 seg_191 seg_192 seg_193 seg_195 seg_196 seg_197 seg_198 seg_199 seg_201 seg_180 seg_190 seg_194 seg_200 | seg_203 seg_204 seg_205 seg_206 seg_207 seg_208 seg_210 seg_211 seg_212 seg_213 seg_214 seg_215 seg_216 seg_217 seg_218 seg_219 seg_220 seg_221 seg_222 seg_223 seg_224 seg_225 seg_209 | seg_83 seg_84 seg_85 seg_86 seg_87 seg_88 seg_89 seg_90 seg_91 seg_92 seg_94 seg_93 |
| Norrie's disease (pseudoglioma) | 310600 | Xp11.4 | NDP | seg_174 seg_175 seg_176 seg_177 seg_178 seg_179 seg_181 seg_182 seg_133 seg_184 seg_185 seg_186 seg_187 seg_188 seg_189 seg_191 seg_192 seg_193 seg_195 seg_196 seg_197 seg_198 seg_199 seg_201 seg_203 seg_204 seg_205 seg_206 seg_207 seg_208 seg_209 seg_210 seg_211 seg_212 seg_213 seg_214 seg_215 seg_216 seg_217 seg_180 seg_190 seg_194 seg_200 seg_202 | seg_208 seg_210 seg_211 seg_212 seg_213 seg_214 seg_215 seg_216 seg_217 seg_218 seg_219 seg_220 seg_221 seg_222 seg_223 seg_224 seg_225 seg_226 seg_227 seg_228 seg_229 seg_230 seg_232 seg_234 seg_235 seg_236 seg_237 seg_238 seg_239 seg_240 seg_241 seg_242 seg_243 seg_209 seg_231 seg_233 seg_244 | seg_85 seg_86 seg_87 seg_88 seg_89 seg_90 seg_91 seg_92 seg_94 seg_96 seg_97 seg_98 seg_99 seg_93 seg_95 |
| Nystagmus, oculomotor or 'jerky' | 310700 | Xq26-q27 | NYS1 | seg_475 seg_477 seg_478 seg_479 seg_480 seg_481 seg_482 seg_483 seg_484 seg_485 seg_486 seg_487 seg_488 seg_489 seg_490 seg_491 seg_492 seg_493 seg_494 seg_495 seg_496 seg_497 seg_498 seg_499 seg_501 seg_502 seg_503 seg_504 seg_506 seg_507 seg_509 seg_510 seg_511 seg_512 seg_513 seg_514 seg_515 seg_516 seg_517 seg_518 seg_519 seg_520 seg_521 seg_522 seg_523 seg_524 seg_525 seg_526 seg_527 seg_528 seg_529 seg_530 seg_531 seg_532 seg_533 seg_534 seg_535 seg_536 seg_537 seg_538 seg_540 seg_541 seg_542 seg_476 seg_500 seg_505 seg_508 seg_539 | seg_421 seg_422 seg_423 seg_424 seg_425 seg_426 seg_427 seg_428 seg_429 seg_430 seg_431 seg_432 seg_433 seg_434 seg_436 seg_438 seg_439 seg_440 seg_441 seg_442 seg_443 seg_444 seg_445 seg_446 seg_447 seg_448 seg_449 seg_450 seg_451 seg_452 seg_453 seg_454 seg_456 seg_457 seg_459 seg_460 seg_462 seg_463 seg_464 seg_465 seg_466 seg_467 seg_469 seg_470 seg_471 seg_472 seg_473 seg_474 seg_475 seg_476 seg_478 seg_480 seg_481 seg_482 seg_484 seg_485 seg_486 seg_487 seg_488 seg_489 seg_490 seg_491 seg_492 seg_493 seg_435 seg_437 seg_455 seg_458 seg_468 seg_477 seg_479 seg_483 seg_494 seg_461 | seg_186 seg_187 seg_188 seg_189 seg_190 seg_191 seg_192 seg_193 seg_194 seg_195 seg_196 seg_197 seg_198 seg_199 |
| Orofaciodigital syndrome (type I) | 311200 | Xp22.3-p22.2 | OFD1 | seg_52 seg_53 seg_54 seg_55 seg_56 seg_57 seg_58 seg_59 seg_60 seg_61 seg_63 seg_64 seg_65 seg_66 seg_67 seg_68 seg_69 seg_70 seg_71 seg_73 seg_74 seg_75 seg_76 seg_77 seg_78 | seg_56 seg_57 seg_58 seg_60 seg_61 seg_63 seg_64 seg_65 seg_66 seg_67 seg_68 seg_69 seg_70 seg_71 seg_72 | seg_14 seg_16 seg_17 seg_18 seg_19 seg_20 seg_21 seg_22 seg_23 seg_24 seg_25 seg_26 seg_27 seg_28 seg_29 |

TABLE A-continued

| Disorder | OMIM # | Locus | Gene | K562 Suz12* | K562 Ezh2** | GM12878 Ezh2*** |
|---|---|---|---|---|---|---|
| | | | | seg_79 seg_80 seg_81 seg_82 seg_83 | seg_73 seg_74 seg_75 | seg_30 seg_31 seg_32 |
| | | | | seg_84 seg_85 seg_86 seg_87 seg_88 | seg_76 seg_77 seg_78 | seg_33 seg_34 seg_35 |
| | | | | seg_89 seg_90 seg_91 seg_92 seg_93 | seg_79 seg_80 seg_81 | seg_36 seg_37 seg_38 |
| | | | | seg_94 seg_95 seg_96 seg_97 seg_98 | seg_82 seg_83 seg_84 | seg_39 seg_40 seg_41 |
| | | | | seg_99 seg_100 seg_101 seg_102 | seg_85 seg_86 seg_87 | seg_42 seg_43 seg_44 |
| | | | | seg_103 seg_104 seg_105 seg_106 | seg_88 seg_89 seg_91 | seg_45 seg_46 seg_47 |
| | | | | seg_107 seg_108 seg_109 seg_62 | seg_92 seg_93 seg_95 | seg_48 seg_49 seg_50 |
| | | | | seg_72 | seg_96 seg_97 seg_98 | seg_51 seg_52 seg_53 |
| | | | | | seg_99 seg_100 seg_101 | seg_15 |
| | | | | | seg_102 seg_103 seg_104 | |
| | | | | | seg_106 seg_107 seg_108 | |
| | | | | | seg_110 seg_111 seg_112 | |
| | | | | | seg_113 seg_114 seg_115 | |
| | | | | | seg_117 seg_119 seg_120 | |
| | | | | | seg_121 seg_122 seg_123 | |
| | | | | | seg_124 seg_125 seg_126 | |
| | | | | | seg_127 seg_128 seg_130 | |
| | | | | | seg_131 seg_132 seg_133 | |
| | | | | | seg_134 seg_135 seg_136 | |
| | | | | | seg_137 seg_138 seg_139 | |
| | | | | | seg_140 seg_141 seg_142 | |
| | | | | | seg_143 seg_59 seg_62 | |
| | | | | | seg_90 seg_94 seg_105 | |
| | | | | | seg_109 seg_116 seg_118 | |
| | | | | | seg_129 | |
| Ornithine transcarbamylase deficiency (type I hyperammonaemia) | 311250 | Xp21.1 | OTC | seg_165 seg_166 seg_167 seg_168 | seg_200 seg_201 seg_202 | seg_80 seg_81 seg_82 |
| | | | | seg_169 seg_170 seg_171 seg_172 | seg_203 seg_204 seg_205 | seg_83 seg_84 seg_85 |
| | | | | seg_173 seg_174 seg_175 seg_176 | seg_206 seg_207 seg_208 | seg_86 seg_87 seg_88 |
| | | | | seg_177 seg_178 seg_179 seg_181 | seg_210 seg_211 seg_212 | seg_89 seg_90 seg_91 |
| | | | | seg_182 seg_183 seg_184 seg_185 | seg_213 seg_214 seg_215 | seg_92 |
| | | | | seg_186 seg_187 seg_188 seg_189 | seg_216 seg_217 seg_218 | |
| | | | | seg_191 seg_192 seg_193 seg_195 | seg_209 | |
| | | | | seg_196 seg_180 seg_190 seg_194 | | |
| Phosphoglycerate kinase deficiency | 311800 | Xq13 | PGK1 | seg_353 seg_354 seg_356 seg_358 | seg_317 seg_318 seg_319 | seg_128 seg_129 |
| | | | | seg_359 seg_360 seg_361 seg_362 | | seg_130 seg_131 |
| | | | | seg_383 seg_364 seg_365 seg_366 | | seg_133 seg_134 |
| | | | | seg_355 seg_357 | | seg_135 seg_132 |
| Phosphoribosyl-pyrophosphate synthetase deficiency | 311850 | Xq22-q24 | PRPS1 | seg_392 seg_393 seg_394 seg_395 | seg_329 seg_331 seg_332 | seg_145 seg_146 |
| | | | | seg_396 seg_397 seg_398 seg_399 | seg_333 seg_334 seg_336 | seg_148 seg_149 |
| | | | | seg_400 seg_401 seg_402 seg_403 | seg_337 seg_338 seg_339 | seg_150 seg_152 |
| | | | | seg_404 seg_405 seg_406 seg_407 | seg_340 seg_341 seg_342 | seg_156 seg_157 |
| | | | | seg_408 seg_409 seg_410 seg_411 | seg_343 seg_344 seg_345 | seg_158 seg_159 |
| | | | | seg_412 seg_413 seg_414 seg_415 | seg_346 seg_347 seg_348 | seg_160 seg_161 |
| | | | | seg_417 seg_418 seg_419 seg_420 | seg_349 seg_350 seg_351 | seg_162 seg_163 |
| | | | | seg_421 seg_423 seg_425 seg_426 | seg_352 seg_353 seg_355 | seg_164 seg_165 |
| | | | | seg_427 seg_428 seg_431 seg_432 | seg_356 seg_357 seg_358 | seg_166 seg_147 |
| | | | | seg_434 seg_390 seg_416 seg_422 | seg_362 seg_363 seg_364 | seg_153 seg_154 |
| | | | | seg_424 seg_429 seg_430 seg_435 | seg_365 seg_366 seg_367 | seg_155 seg_151 |
| | | | | seg_433 | seg_368 seg_369 seg_370 | |
| | | | | | seg_371 seg_372 seg_373 | |
| | | | | | seg_374 seg_375 seg_330 | |

TABLE A-continued

| Disorder | OMIM # | Locus | Gene | K562 Suz12* | K562 Ezh2** | GM12878 Ezh2*** |
|---|---|---|---|---|---|---|
| Retinitis pigmentosa | 312610 | Xp21.1 | RPGR | seg_165 seg_166 seg_167 seg_168 seg_169 seg_170 seg_171 seg_172 seg_173 seg_174 seg_175 seg_176 seg_177 seg_178 seg_179 seg_181 seg_182 seg_183 seg_184 seg_185 seg_186 seg_187 seg_188 seg_189 seg_191 seg_192 seg_193 seg_195 seg_196 seg_180 seg_190 seg_194 | seg_335 seg_354 seg_359 seg_360 seg_361 seg_200 seg_201 seg_202 seg_203 seg_204 seg_205 seg_206 seg_207 seg_208 seg_210 seg_211 seg_212 seg_213 seg_214 seg_215 seg_216 seg_217 seg_218 seg_209 | seg_80 seg_81 seg_82 seg_83 seg_84 seg_85 seg_86 seg_87 seg_88 seg_89 seg_90 seg_91 |
| Retinoschisis | 312700 | Xp22.2-p22.1 | RS1 | seg_87 seg_88 seg_89 seg_90 seg_91 seg_92 seg_93 seg_94 seg_95 seg_96 seg_97 seg_98 seg_99 seg_100 seg_101 seg_102 seg_103 seg_104 seg_105 seg_106 seg_107 seg_108 seg_109 seg_111 seg_112 seg_113 seg_114 seg_115 seg_116 seg_117 seg_118 seg_119 seg_121 seg_122 seg_124 seg_125 seg_126 seg_127 seg_128 seg_129 seg_131 seg_132 seg_133 seg_134 seg_135 seg_136 seg_137 seg_138 seg_139 seg_140 seg_110 seg_123 seg_130 seg_120 | seg_101 seg_102 seg_103 seg_104 seg_106 seg_107 seg_108 seg_110 seg_111 seg_112 seg_113 seg_114 seg_115 seg_117 seg_119 seg_120 seg_121 seg_122 seg_123 seg_124 seg_125 seg_126 seg_127 seg_128 seg_130 seg_131 seg_132 seg_133 seg_134 seg_135 seg_136 seg_137 seg_138 seg_139 seg_140 seg_141 seg_142 seg_143 seg_144 seg_145 seg_146 seg_147 seg_148 seg_149 seg_150 seg_151 seg_152 seg_153 seg_156 seg_157 seg_158 seg_159 seg_160 seg_161 seg_162 seg_163 seg_164 seg_165 seg_166 seg_167 seg_168 seg_169 seg_171 seg_172 seg_173 seg_174 seg_175 seg_176 seg_177 seg_178 seg_179 seg_180 seg_181 seg_182 seg_183 seg_184 seg_185 seg_105 seg_109 seg_116 seg_118 seg_129 seg_154 seg_155 seg_170 | seg_31 seg_32 seg_33 seg_34 seg_35 seg_36 seg_37 seg_38 seg_39 seg_40 seg_41 seg_42 seg_43 seg_44 seg_45 seg_46 seg_47 seg_48 seg_49 seg_50 seg_51 seg_52 seg_53 seg_55 seg_56 seg_57 seg_58 seg_59 seg_61 seg_60 seg_54 |
| Rett syndrome | 312750 | Xq28, Xp22 | MECP2 | seg_564 seg_566 seg_567 seg_568 seg_569 seg_571 seg_572 seg_574 seg_575 seg_576 seg_577 seg_578 seg_579 seg_580 seg_581 seg_582 seg_583 seg_584 seg_585 seg_586 seg_587 seg_588 seg_589 seg_590 seg_591 seg_592 seg_593 seg_594 seg_595 seg_596 seg_597 seg_599 seg_600 seg_601 seg_602 seg_603 seg_604 seg_605 seg_606 seg_607 seg_608 seg_609 seg_610 seg_611 seg_612 seg_613 seg_615 seg_616 | seg_504 seg_505 seg_506 seg_507 seg_508 seg_509 seg_510 seg_511 seg_512 seg_514 seg_515 seg_516 seg_517 seg_518 seg_520 seg_521 seg_522 seg_523 seg_524 seg_525 seg_526 seg_527 seg_528 seg_529 seg_530 seg_531 seg_532 seg_533 seg_534 seg_535 seg_536 seg_538 seg_539 seg_540 seg_542 seg_543 | seg_209 seg_210 seg_211 seg_212 seg_213 seg_214 seg_215 |

TABLE A-continued

| Disorder | OMIM # | Locus | Gene | K562 Suz12* | K562 Ezh2** | GM12878 Ezh2*** |
|---|---|---|---|---|---|---|
| | | | | seg_617 seg_618 seg_619 seg_620 | seg_544 seg_545 seg_546 | |
| | | | | seg_622 seg_623 seg_624 seg_625 | seg_547 seg_548 seg_549 | |
| | | | | seg_626 seg_627 seg_628 seg_629 | seg_550 seg_551 seg_552 | |
| | | | | seg_630 seg_631 seg_632 seg_633 | seg_553 seg_554 seg_555 | |
| | | | | seg_634 seg_635 seg_637 seg_638 | seg_556 seg_558 seg_559 | |
| | | | | seg_639 seg_641 seg_642 seg_644 | seg_561 seg_562 seg_563 | |
| | | | | seg_645 seg_646 seg_647 seg_648 | seg_564 seg_565 seg_566 | |
| | | | | seg_649 seg_650 seg_651 seg_652 | seg_567 seg_568 seg_570 | |
| | | | | seg_654 seg_655 seg_656 seg_657 | seg_572 seg_573 seg_574 | |
| | | | | seg_658 seg_659 seg_660 seg_661 | seg_575 seg_576 seg_577 | |
| | | | | seg_662 seg_663 seg_664 seg_665 | seg_578 seg_513 seg_519 | |
| | | | | seg_666 seg_565 seg_570 seg_573 | seg_537 seg_541 seg_557 | |
| | | | | seg_614 seg_621 seg_636 seg_640 | seg_569 seg_571 seg_560 | |
| | | | | seg_643 seg_598 seg_653 | | |
| Muscular atrophy/ Dihydro-testosterone receptor deficiency | 313200 | Xq11-q12 | AR | seg_296 seg_297 seg_298 seg_300 | seg_285 seg_286 seg_287 | seg_108 seg_109 |
| | | | | seg_302 seg_305 seg_306 seg_307 | seg_290 seg_291 seg_292 | seg_110 seg_111 |
| | | | | seg_308 seg_309 seg_310 seg_311 | seg_294 seg_295 seg_296 | seg_112 seg_113 |
| | | | | seg_313 seg_314 seg_315 seg_316 | seg_297 seg_298 seg_299 | seg_114 seg_115 |
| | | | | seg_317 seg_318 seg_319 seg_320 | seg_302 seg_303 seg_304 | seg_116 seg_117 |
| | | | | seg_321 seg_322 seg_323 seg_324 | seg_305 seg_306 seg_307 | seg_118 seg_119 |
| | | | | seg_326 seg_328 seg_329 seg_330 | seg_308 seg_309 seg_311 | seg_121 seg_122 |
| | | | | seg_331 seg_332 seg_334 seg_335 | seg_312 seg_313 seg_288 | seg_124 seg_125 |
| | | | | seg_337 seg_338 seg_339 seg_340 | seg_289 seg_293 seg_300 | seg_120 seg_123 |
| | | | | seg_341 seg_342 seg_344 seg_345 | seg_301 seg_310 | |
| | | | | seg_295 seg_299 seg_301 seg_303 | | |
| | | | | seg_304 seg_312 seg_325 seg_327 | | |
| | | | | seg_333 seg_336 seg_343 | | |
| Spinal muscular atrophy | 313200 | Xq11-q12 | AR | seg_296 seg_297 seg_298 seg_300 | seg_285 seg_286 seg_287 | seg_108 seg_109 |
| | | | | seg_302 seg_305 seg_306 seg_307 | seg_290 seg_291 seg_292 | seg_110 seg_111 |
| | | | | seg_308 seg_309 seg_310 seg_311 | seg_294 seg_295 seg_296 | seg_112 seg_113 |
| | | | | seg_313 seg_314 seg_315 seg_316 | seg_297 seg_298 seg_299 | seg_114 seg_115 |
| | | | | seg_317 seg_318 seg_319 seg_320 | seg_302 seg_303 seg_304 | seg_116 seg_117 |
| | | | | seg_321 seg_322 seg_323 seg_324 | seg_305 seg_306 seg_307 | seg_118 seg_119 |
| | | | | seg_326 seg_328 seg_329 seg_330 | seg_308 seg_309 seg_311 | seg_121 seg_122 |
| | | | | seg_331 seg_332 seg_334 seg_335 | seg_312 seg_313 seg_288 | seg_124 seg_125 |
| | | | | seg_337 seg_338 seg_339 seg_340 | seg_289 seg_293 seg_300 | seg_120 seg_123 |
| | | | | seg_341 seg_342 seg_344 seg_345 | seg_301 seg_310 | |
| | | | | seg_295 seg_299 seg_301 seg_303 | | |
| | | | | seg_304 seg_312 seg_325 seg_327 | | |
| | | | | seg_333 seg_336 seg_343 | | |
| Spondyloepiphyseal dysplasia tarda | 313400 | Xp22.2-p22.1 | SEDL | seg_52 seg_53 seg_54 seg_55 seg_56 | seg_56 seg_57 seg_58 | seg_14 seg_16 seg_17 |
| | | | | seg_57 seg_58 seg_59 seg_60 seg_61 | seg_60 seg_61 seg_63 | seg_18 seg_19 seg_20 |
| | | | | seg_63 seg_64 seg_65 seg_66 seg_67 | seg_64 seg_65 seg_66 | seg_21 seg_22 seg_23 |
| | | | | seg_68 seg_69 seg_70 seg_71 seg_73 | seg_67 seg_68 seg_69 | seg_24 seg_25 seg_26 |
| | | | | seg_74 seg_75 seg_76 seg_77 seg_78 | seg_70 seg_71 seg_72 | seg_27 seg_28 seg_29 |
| | | | | seg_79 seg_80 seg_81 seg_82 seg_83 | seg_73 seg_74 seg_75 | seg_30 seg_31 seg_32 |
| | | | | seg_84 seg_85 seg_86 seg_87 seg_88 | seg_76 seg_77 seg_78 | seg_33 seg_34 seg_35 |
| | | | | seg_89 seg_90 seg_91 seg_92 seg_93 | seg_79 seg_80 seg_81 | seg_36 seg_37 seg_38 |
| | | | | seg_94 seg_95 seg_96 seg_97 seg_98 | seg_82 seg_83 seg_84 | seg_39 seg_40 seg_41 |
| | | | | seg_99 seg_100 seg_101 seg_102 | seg_85 seg_86 seg_87 | seg_42 seg_43 seg_44 |
| | | | | seg_103 seg_104 seg_105 seg_106 | seg_88 seg_89 seg_91 | seg_45 seg_46 seg_47 |

TABLE A-continued

| Disorder | OMIM # | Locus | Gene | K562 Suz12* | K562 Ezh2** | GM12878 Ezh2*** |
|---|---|---|---|---|---|---|
| | | | | seg_107 seg_108 seg_109 seg_62 seg_72 | seg_92 seg_93 seg_95 seg_96 seg_97 seg_98 seg_99 seg_100 seg_101 seg_102 seg_103 seg_104 seg_106 seg_107 seg_108 seg_110 seg_111 seg_112 seg_113 seg_114 seg_115 seg_117 seg_119 seg_120 seg_121 seg_122 seg_123 seg_124 seg_125 seg_126 seg_127 seg_128 seg_130 seg_131 seg_132 seg_133 seg_134 seg_135 seg_136 seg_137 seg_138 seg_139 seg_140 seg_141 seg_142 seg_143 seg_59 seg_62 seg_90 seg_94 seg_105 seg_109 seg_116 seg_118 seg_129 | seg_48 seg_49 seg_50 seg_51 seg_52 seg_53 seg_15 |
| Thrombocytopenia, hereditary | 313900 | Xp11.23-p11.22 | WAS | seg_199 seg_201 seg_203 seg_204 seg_205 seg_206 seg_207 seg_208 seg_209 seg_210 seg_211 seg_212 seg_213 seg_214 seg_215 seg_216 seg_217 seg_218 seg_219 seg_220 seg_221 seg_222 seg_223 seg_224 seg_225 seg_226 seg_227 seg_228 seg_229 seg_230 seg_231 seg_232 seg_233 seg_234 seg_235 seg_236 seg_237 seg_238 seg_239 seg_240 seg_242 seg_243 seg_244 seg_245 seg_246 seg_247 seg_249 seg_250 seg_251 seg_252 seg_253 seg_254 seg_256 seg_257 seg_258 seg_259 seg_260 seg_261 seg_262 seg_263 seg_264 seg_200 seg_202 seg_241 seg_248 seg_255 | seg_220 seg_221 seg_222 seg_223 seg_224 seg_225 seg_226 seg_227 seg_228 seg_225 seg_230 seg_232 seg_234 seg_235 seg_236 seg_237 seg_238 seg_239 seg_240 seg_241 seg_242 seg_243 seg_245 seg_246 seg_247 seg_248 seg_249 seg_250 seg_251 seg_252 seg_253 seg_254 seg_255 seg_256 seg_257 seg_258 seg_259 seg_260 seg_262 seg_263 seg_265 seg_266 seg_267 seg_268 seg_269 seg_270 seg_271 seg_231 seg_233 seg_244 seg_261 seg_264 | seg_96 seg_97 seg_98 seg_99 seg_100 seg_101 seg_102 seg_103 seg_93 seg_95 |
| Thyroxine-binding globulin, absence | 314200 | Xq22.2 | TBG | seg_382 seg_385 seg_386 seg_388 seg_389 seg_391 seg_392 seg_393 seg_394 seg_395 seg_396 seg_397 seg_398 seg_399 seg_400 seg_401 seg_402 seg_403 seg_404 seg_405 seg_406 seg_407 seg_408 seg_409 seg_410 seg_411 seg_412 seg_413 seg_414 seg_415 seg_417 seg_418 seg_419 seg_420 seg_421 seg_423 seg_425 seg_426 seg_427 seg_428 seg_431 seg_432 seg_380 seg_383 seg_387 seg_390 seg_416 seg_422 seg_424 seg_429 seg_430 seg_384 | seg_326 seg_327 seg_328 seg_329 seg_331 seg_332 seg_333 seg_334 seg_336 seg_337 seg_338 seg_339 seg_340 seg_341 seg_342 seg_343 seg_344 seg_345 seg_346 seg_347 seg_348 seg_349 seg_350 seg_351 seg_352 seg_353 seg_355 seg_356 seg_357 seg_358 seg_362 seg_363 seg_364 seg_365 seg_366 seg_367 seg_368 seg_369 seg_370 seg_371 seg_372 seg_373 | seg_145 seg_146 seg_148 seg_149 seg_150 seg_152 seg_156 seg_157 seg_158 seg_159 seg_160 seg_161 seg_162 seg_163 seg_147 seg_153 seg_154 seg_155 seg_151 |

TABLE A-continued

| Disorder | OMIM # | Locus | Gene | K562 Suz12* | K562 Ezh2** | GM12878 Ezh2*** |
|---|---|---|---|---|---|---|
| McLeod syndrome | 314850 | Xp21.1 | XK | seg_165 seg_166 seg_167 seg_168<br>seg_169 seg_170 seg_171 seg_172<br>seg_173 seg_174 seg_175 seg_176<br>seg_177 seg_178 seg_179 seg_181<br>seg_182 seg_183 seg_184 seg_185<br>seg_186 seg_187 seg_188 seg_189<br>seg_191 seg_192 seg_193 seg_195<br>seg_196 seg_180 seg_190 seg_194 | seg_325 seg_330 seg_335<br>seg_354 seg_359 seg_360<br>seg_361<br>seg_200 seg_201 seg_202<br>seg_203 seg_204 seg_205<br>seg_206 seg_207 seg_208<br>seg_210 seg_211 seg_212<br>seg_213 seg_214 seg_215<br>seg_216 seg_217 seg_218<br>seg_209 | seg_79 seg_80 seg_81<br>seg_82 seg_83 seg_84<br>seg_85 seg_86 seg_87<br>seg_88 seg_89 seg_90<br>seg_91 |

*Strong human Suz12/PRC2 binding sites identified in K562 cells, see table XIV.
**Strong human Ezh2/PRC2 binding sites identified in K562 cells, see table XIII.
***Strong human Ezh2/PRC2 binding sites identified in GM12878 cells, see table XV Table A was adapted in part from Germain, "Chapter 7: General aspects of X-linked diseases" in Fabry Disease: Perspectives from 5 Years of FOS. Mehta A, Beck M, Sunder-Plassmann G, editors. (Oxford: Oxford PharmaGenesis; 2006).

Methods of Targeting Genes on Xi

The methods described herein can be used to specifically re-activate one or more genes on Xi, by targeting paRNAs or genomic DNA at strong and/or moderate binding sites as described herein, to disrupt RNA-mediated silencing in cis on the inactive X-chromosome. The PRC2 site-associated RNAs can be noncoding (long noncoding RNA, lncRNA) or occasionally part of a coding mRNA; for simplicity, we will refer to them together as polycomb-associated RNAs (paRNAs) henceforth. The paRNAs described herein, including fragments thereof that are at least 20 nt in length, and inhibitory nucleic acids and small molecules targeting (e.g., complementary to) the paRNAs, or complementray or identical to a region within a strong or moderate binding site in the genome, can be used to modulate gene expression in a cell, e.g., a cancer cell, a stem cell, or other normal cell types for gene or epigenetic therapy. The nucleic acids used in the methods described herein are termed "inhibitory" because they inhibit the paRNA-mediated repression of a specified gene, either by binding to the paRNA itself (e.g., an antisense oligo that is complementary to the paRNA) or by binding to a strong or moderate PRC2 binding site as described herein (also termed an EZH2 or SUZ12 binding site herein) in the genome, and (without wishing to be bound by theory) preventing binding of the PRC2 complex and thus disrupting PRC2-mediated silencing in the region of the strong or moderate binding site. The inhibitory oligonucleotides that bind to a strong or moderate PRC2 binding site described herein can bind to either strand of the DNA, but preferably bind to the same strand to which the paRNA binds.

The cells can be in vitro, including ex vivo, or in vivo (e.g., in a subject who has cancer, e.g., a tumor). In some embodiments, the methods include introducing into the cell an inhibitory nucleic acid or a long non-coding RNA described herein that is modified in some way, e.g., an paRNA that differs from the endogenous paRNA by including one or more modifications to the backbone or bases as described herein for inhibitory nucleic acids. Such modified paRNAs are also within the scope of the present invention.

In some embodiments, the methods include introducing into the cell an inhibitory nucleic acid that specifically binds, or is complementary, to a strong or moderate binding site or a long non-coding RNA described herein. A nucleic acid that binds "specifically" binds primarily to the target, i.e., to the target DNA or paRNA or related paRNAs to inhibit regulatory function or binding of the paRNA but not of other non-target RNAs. The specificity of the nucleic acid interaction thus refers to its function (e.g., inhibiting the PRC2-associated repression of gene expression) rather than its hybridization capacity. Inhibitory nucleic acids may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. These methods can be used to treat an X-linked condition in a subject by administering to the subject a composition (e.g., as described herein) comprising an inhibitory nucleic acid that binds to a long non-coding RNA (e.g., an inhibitory nucleic acid that binds to a paRNA described herein) or to a strong or moderate PRC2 binding site that is associated with a disease gene. Examples of genes involved in X-linked diseases are shown in Table A.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a composition, e.g., a sterile composition, comprising an inhibitory nucleic acid that is complementary to an paRNA described herein. Inhibitory nucleic acids for use in practicing the methods described herein can be an antisense or small interfering RNA, including but not limited to an shRNA or siRNA. In some embodiments, the inhibitory nucleic acid is a modified nucleic acid polymer (e.g., a locked nucleic acid (LNA) molecule).

Inhibitory nucleic acids have been employed as therapeutic moieties in the treatment of disease states in animals, including humans. Inhibitory nucleic acids can be useful therapeutic modalities that can be configured to be useful in treatment regimes for the treatment of cells, tissues and animals, especially humans.

For therapeutics, an animal, preferably a human, suspected of having cancer is treated by administering an paRNA or inhibitory nucleic acid in accordance with this invention. For example, in one non-limiting embodiment, the methods comprise the step of administering to the animal in need of treatment, a therapeutically effective amount of an paRNA or inhibitory nucleic acid as described herein.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112. However, in some embodiments the inhibitory nucleic acid is not an miRNA, an stRNA, an shRNA, an siRNA, an RNAi, or a dsRNA.

In some embodiments, the inhibitory nucleic acids are 10 to 50, 13 to 50, or 13 to 30 nucleotides in length. One having ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such inhibitory nucleic acids; for example, an inhibitory nucleic acid 30 nucleotides in length may have a portion of 15 bases that is complementary to the targeted RNA. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense (complementary) portions of 12, 13, 14, 15, 16, 17, 18, 19, 20, 21, 22, 23, 24, 25, 26, 27, 28, 29 or 30 nucleotides in length, or any range therewithin.

Preferably the inhibitory nucleic acid comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the olyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties). Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues.

Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide. PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids. Examples of LNAs are described in WO 2008/043753 and WO2007031091 and include compounds of the following formula.

Scheme 1

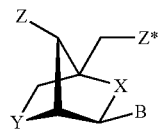

where X and Y are independently selected among the groups —O—, —S—, —N(H)—, N(R)—, —CH2- or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH═CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas Scheme 2

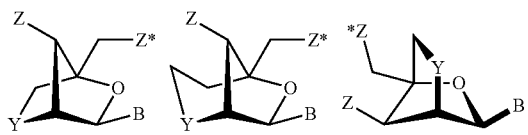

wherein Y is —O—, —S—, —NH—, or N(R$^H$); Z and Z* are independently selected among an internucleoside linkage, a terminal group or a protecting group: B constitutes a natural or non-natural nucleotide base moiety, and RH is selected from hydrogen and C$_{1-4}$-alkyl. Preferably, the Locked Nucleic Acid (LNA) used in an oligomeric compound, such as an antisense oligonucleotide, as described herein comprises at least one nucleotide comprises a Locked Nucleic Acid (LNA) unit according any of the formulas shown in Scheme 2 of PCT/DK2006/000512 (WO2007031091).

Preferably, the LNA used in the oligomer of the invention comprises internucleoside linkages selected from -0-P(O)$_2$—O—, —O—P(O,S)—O—, —O—P(S)$_2$—O—, —S—P(O)$_2$—O—, —S—P(O,S)—O—, —S—P(S)$_2$—O—, -0-P(O)$_2$—S—, —O—P(O,S)—S—, —S—P(O)$_2$—S—, —O—PO(R$^H$)—O—, —O—PO(OCH$_3$)—O—, —O—PO(NR$^H$)—O—, -0-PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown in scheme 3:

Scheme 3

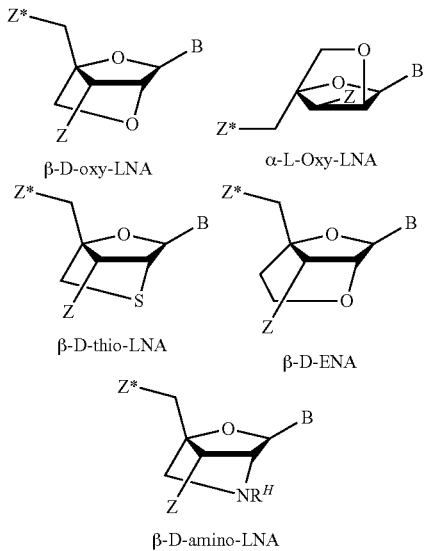

β-D-oxy-LNA    α-L-Oxy-LNA

β-D-thio-LNA    β-D-ENA

β-D-amino-LNA

The term "thio-LNA" comprises a locked nucleotide in which at least one of X or Y in the general formula above is selected from S or —CH2-S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH, —N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail below. One or more substituted sugar moieties can also be included, e.g., one of the following at the 2' position: OH, SH, SCH$_3$, F, OCN, OCH$_3$ OCH$_3$, OCH$_3$O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-CH$_2$CH$_2$OCH$_3$, also known as 2'-O-(2-methoxyethyl)](Martin et al, Helv. Chim. Acta, 1995, 78, 486). Other preferred modifications include 2'-methoxy (2'-O-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the as nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. For example, one or more inhibitory nucleic acids, of the same or different types, can be conjugated to each other; or inhibitory nucleic acids can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target paRNA, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an inhibitory nucleic acid is capable of hydrogen bonding with a base at the corresponding position of a paRNA, then the bases are considered to be complementary to each other at that position. 100% complementarity is not required. As noted above, inhibitory nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

In some embodiments, the location on a target paRNA to which an inhibitory nucleic acid hybridizes is a region to which a protein binding partner binds, as identified in Tables VI or VII. The identification of these strong or moderate binding sites, is described in Example 8 below. Routine methods can be used to design an inhibitory nucleic acid that binds to a selected strong or moderate binding site sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, methods of designing oligonucleotides similar to the inhibitory nucleic acids described herein, and various options for modified chemistries or formats, are exemplified in Lennox and Behlke, Gene Therapy (2011) 18: 1111-1120, which is incorporated herein by reference in its entirety, with the understanding that the inhibitory oligonucleotides of the present disclosure do not target miRNA 'seed regions'.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same paRNA beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target with complementary inhibitory nucleic acids.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an oligonucleotide is capable of hydrogen bonding with a nucleotide at the same position of a paRNA molecule, then the inhibitory nucleic acid and the paRNA are considered to be complementary to each other at that position. The inhibitory nucleic acids and the paRNA are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the inhibitory nucleic acid and the paRNA target. For example, if a base at one position of an inhibitory nucleic acid is capable of hydrogen bonding with a base at the corresponding position of a paRNA, then the bases are considered to be complementary to each other at that position. 100% complementarity is not required. It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target paRNA molecule interferes with the normal function of the target paRNA to cause a loss of activity (e.g., inhibiting PRC2-associated repression with consequent up-regulation of gene expression) and there is a sufficient degree of complementarity to avoid non-specific binding of the sequence to non-target paRNA sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an paRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to an paRNA are identified through routine experimentation. In general the inhibitory nucleic acids must retain specificity for their target, i.e., either do not directly bind to, or do not directly significantly affect expression levels of, transcripts other than the intended target.

Target-specific effects, with corresponding target-specific functional biological effects, are possible even when the inhibitory nucleic acid exhibits non-specific binding to a large number of non-target RNAs. For example, short 8 base long inhibitory nucleic acids that are fully complementary to a paRNA may have multiple 100% matches to hundreds of sequences in the genome, yet may produce target-specific effects, e.g. upregulation of a specific target gene through inhibition of PRC2 activity. 8-base inhibitory nucleic acids have been reported to prevent exon skipping with a high degree of specificity and reduced off-target effect. See Singh et al., RNA Biol., 2009; 6(3): 341-350. 8-base inhibitory nucleic acids have been reported to interfere with miRNA activity without significant off-target effects. See Obad et al., Nature Genetics, 2011; 43: 371-378.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNA molecules); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an paRNA in vitro, and are expected to inhibit the activity of PRC2 in vivo. Thus, oligonucleotides are chosen that are sufficiently complementary to the target, i.e., that hybridize sufficiently well and with sufficient biological functional specificity, to give the desired effect.

Modified Bases, Including Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acids (LNAs). Preferably, the modified nucleotides are part of locked nucleic acid molecules, including [alpha]-L-LNAs. LNAs include ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., paRNAs as described herein.

The modified base/LNA molecules can include molecules comprising, e.g., 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the paRNA. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of a modified base/LNA molecule; for example, a series of oligonucleotides of 10-30 nucleotides spanning the length of a target paRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the modified base/LNA molecules can be designed to target a specific region of the paRNA. For example, a specific functional region can be targeted, e.g., a region comprising a known RNA localization motif (i.e., a region complementary to the target nucleic acid on which the paRNA acts), or a region comprising a known protein binding region, e.g., a Polycomb (e.g., Polycomb Repressive Complex 2 (PRC2), comprised of H3K27 methylase EZH2, SUZ12, and EED)) or LSD1/CoREST/REST complex binding region (see, e.g., Tsai et al., Science. 2010 Aug. 6; 329(5992):689-93. Epub 2010 Jul. 8; and Zhao et al., Science. 2008 Oct. 31; 322(5902):750-6). Sarma et al., "Locked nucleic acids (LNAs) reveal sequence requirements and kinetics of Xist RNA localization to the X chromosome." PNAS published ahead of print Dec. 6, 2010, doi:10.1073/pnas.1009785107. Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

In a related aspect, the present disclosure demonstrates the ability of LNA molecules to displace a cis-acting nuclear long ncRNA with fast kinetics (e.g., RNA/PRC2 disassociation from the chromosome after 2, 5, 10 seconds up to 60 minutes as described herein)—a property that enables the modification and study of the function of long ncRNAs in ways not previously possible. Using 17 kb Xist RNA as a model, the present inventors showed that LNA molecules designed to specifically target the transcript leads to extremely rapid displacement of the RNA from the inactive X chromosome. Interestingly, while the RNA is displaced, transcript stability is not affected. Targeting different Xist regions has allowed the identification of a localization domain and show that Polycomb repressive complex 2 (PRC2) is displaced together with Xist. Thus, PRC2 depends on RNA for both initial targeting to and stable association with chromatin. Time-course analysis of RNA relocalization suggests that Xist and PRC2 spread along X at the same time but does not reach saturating levels for 24 hours, providing a window of opportunity to reprogram the chromatin, if necessary. It is remarkable that targeting a small region within a 17-kb RNA could produce such dramatic effects. The rapid effects suggest that the Xist RNA-protein complex may be anchored to the inactive X chromosome (Xi) chromatin via Repeat C. Alternatively, the LNA molecule's binding to Repeat C could change RNA conformation and interfere with a remote anchoring domain. While RNA displacement occurs with rapid kinetics, the recovery period is prolonged. Although full Xist clouds are restored within 8 hours, the full complement of PRC2 is not recovered for up to 24 hours. This implies that, during the spread of X chromosome inactivation (XCI), synthesis of the RNA is not the rate-limiting step; rather, it is the recruitment of associated silencing proteins such as PRC2. The rapid displacement of Xist and the slow kinetics of recovery provided a large window of opportunity to investigate Xist's spreading pattern relative to that of PRC2. Time-course analysis during the recovery phase indicates that Xist RNA binds most strongly near the Xist locus at first but spreads to the rest of Xi at the same time. Similarly, PRC2 is recruited synchronously throughout the X. Interestingly, neither Xist nor PRC2 levels reach saturation immediately, as the coating of Xist is not complete until t=8 hr and binding of PRC2 does not peak until t=24 hr. Combined, this analysis implies that establishment of chromosome-wide silencing may be relatively slow.

As demonstrated herein, LNA molecules can be used as a valuable tool to manipulate and aid analysis of long nuclear ncRNAs. Advantages offered by an LNA molecule-based system are the relatively low costs, easy delivery, and rapid action. While other inhibitory nucleic acids may exhibit effects after longer periods of time, LNA molecules exhibit effects that are more rapid, e.g., a comparatively early onset of activity, are fully reversible after a recovery period following the synthesis of new paRNA, and occur without causing substantial or substantially complete RNA cleavage or degradation. One or more of these design properties may be desired properties of the inhibitory nucleic acids of the invention. Additionally, LNA as molecules make possible the systematic targeting of domains within much longer nuclear transcripts. Although a PNA-based system has been described earlier, the effects on Xi were apparent only after 24 hours (Beletskii et al., Proc Natl Acad Sci USA 98:9215-9220 (2001)). The LNA technology enables high-throughput screens for functional analysis of long non-coding RNAs and also provides a novel tool to manipulate chromatin states in vivo for therapeutic applications.

In various related aspects, the methods described herein include using LNA molecules to target paRNAs for a number of uses, including as a research tool to probe the function of a specific paRNA, e.g., in vitro or in vivo. The methods include selecting one or more desired paRNAs, designing one or more LNA molecules that target the paRNA, providing the designed LNA molecule, and administering the LNA molecule to a cell or animal. The methods can optionally include selecting a region of the paRNA and designing one or more LNA molecules that target that region of the paRNA.

Aberrant imprinted gene expression is implicated in several diseases including Long QT syndrome, Beckwith-Wiedemann, Prader-Willi, and Angelman syndromes, as well as behavioral disorders and carcinogenesis (see, e.g., Falls et al., Am. J. Pathol. 154:635-647 (1999); Lalande, Annu Rev Genet 30:173-195 (1996); Hall Annu Rev Med. 48:35-44 (1997)). LNA molecules can be created to treat such imprinted diseases. As one example, the long QT Syndrome can be caused by a K+ gated Calcium-channel encoded by Kcnq1. This gene is regulated by its antisense counterpart, the long noncoding RNA, Kcnq1ot1 (Pandey et al., Mol Cell. 2008 Oct. 24; 32(2):232-46). Disease arises when Kcnq1ot1 is aberrantly expressed. LNA molecules can be created to downregulate Kcnq1ot1, thereby restoring expression of Kcnq1. As another example, LNA molecules could inhibit paRNA cofactors for polycomb complex chromatin modifiers to reverse the imprinted defect. From a commercial and clinical perspective, the timepoints between about 1 to 24 hours potentially define a window for epigenetic reprogramming. The advantage of the LNA system is that it works quickly, with a defined half-life, and is therefore reversible upon degradation of LNAs, at the same time that it provides a discrete timeframe during which epigenetic manipulations can be made. By targeting nuclear long ncRNAs, LNA molecules or similar polymers, e.g., xylo-LNAs, might be utilized to manipulate the chromatin state of cells in culture or in vivo, by transiently eliminating the regulatory RNA and associated proteins long enough to alter the underlying locus for therapeutic purposes. In particular, LNA molecules or similar polymers that specifically bind to, or are complementary to, PRC2-binding paRNA can prevent recruitment of PRC2 to a specific chromosomal locus, in a gene-specific fashion.

LNA molecules might also be administered in vivo to treat other human diseases, such as but not limited to cancer, neurological disorders, infections, inflammation, and myotonic dystrophy. For example, LNA molecules might be delivered to tumor cells to downregulate the biologic activity of a growth-promoting or oncogenic long nuclear ncRNA (e.g., Gtl2 or MALAT1 (Luo et al., Hepatology. 44(4):1012-24 (2006)), a paRNA associated with metastasis and is frequently upregulated in cancers). Repressive paRNAs downregulating tumor suppressors can also be targeted by LNA molecules to promote reexpression. For example, expression of the INK4b/ARF/INK4a tumor suppressor locus is controlled by Polycomb group proteins including PRC1 and PRC2 and repressed by the antisense noncoding RNA ANRIL (Yap et al., Mol Cell. 2010 Jun. 11; 38(5):662-74). ANRIL can be targeted by LNA molecules to promote reexpression of the INK4b/ARF/INK4a tumor suppressor. Some paRNA may be positive regulators of oncogenes. Such "activating paRNAs" have been described recently (e.g., Jpx (Tian et al., Cell. 143(3):390-403 (2010) and others (Ørom et al., Cell. 143(1):46-58 (2010)). Therefore, LNA molecules could be directed at these activating paRNAs to downregulate oncogenes. LNA molecules could also be delivered to inflammatory cells to downregulate regulatory paRNA that modulate the inflammatory or immune response. (e.g., LincRNA-Cox2, see Guttman et al., Nature. 458(7235):223-7. Epub 2009 Feb. 1 (2009)).

In still other related aspects, the LNA molecules targeting paRNAs described herein can be used to create animal or cell models of conditions associated with altered gene expression (e.g., as a result of altered epigenetics).

For example, it was first noticed about half a century ago that X chromosome changes are often seen in female reproductive cancers. Some 70% of breast carcinomas lack a 'Barr body', the cytologic hallmark of the inactive X chromosome (Xi), and instead harbor two or more active Xs (Xa). Additional X's are also a risk factor for men, as XXY men (Klinefelter Syndrome) have a 20- to 50-fold increased risk of breast cancer in a BRCA1 background. The X is also known to harbor a number of oncogenes. Supernumerary Xa's correlate with a poor prognosis and stand as one of the most common cytogenetic abnormalities not only in reproductive cancers but also in leukemias, lymphomas, and germ cell tumors of both sexes. See, e.g., Liao et al., Cancer Invest 21, 641-58 (2003); Spatz et al., Nat Rev Cancer 4, 617-29 (2004); Barr et al., Proc Can Cancer Conf 2, 3-16 (1957); Borah et al., J Surg Oncol 13, 1-7 (1980); Camargo and Wang, Hum Genet 55, 81-5 (1980); Dutrillaux et al., Int J Cancer 38, 475-9 (1986); Ghosh and Shah, Cancer Genet Cytogenet 4, 269-74 (1981); Ghosh and Shah, Med Hypotheses 7, 1099-104 (1981); Ghosh et al., Acta Cytol 27, 202-3 (1983); Huang et al., Mol Cancer Ther 1, 769-76 (2002); Kawakami et al., Lancet 363, 40-2 (2004); Kawakami et al., J Urol 169, 1546-52 (2003); Kawakami et al., Oncogene 23, 6163-9 (2004); Moore and Barr, Br J Cancer 9, 246-52 (1955); Moore and Barr, Br J Cancer 11, 384-90 (1957); Moore et al., J Exp Zool 135, 101-25 (1957); Rosen et al., Ann Clin Lab Sci 7, 491-9 (1977); Sirchia et al., Cancer Res 65, 2139-46 (2005); Tavares, Lancet 268, 948-9 (1955); Tavares, Medico (Porto) 12, 97-100 (1961); Tavares, Acta Cytol 6, 90-4 (1962); Wang et al., Cancer Genet Cytogenet 46, 271-80 (1990); and Ganesan et al., Cold Spring Harb Symp Quant Biol 70, 93-7 (2005).

See also PCT/US11/60493, which is incorporated by reference herein in its entirety.

Antagomirs

In some embodiments, the inhibitory nucleic acid is an antagomir. Antagomirs are chemically modified antisense oligonucleotides that can target an paRNA. For example, an antagomir for use in the methods described herein can include a nucleotide sequence sufficiently complementary to hybridize to an paRNA target sequence of about 12 to 25 nucleotides, preferably about 15 to 23 nucleotides.

In some embodiments, antagomirs include a cholesterol moiety, e.g., at the 3'-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2'-O-methylation of sugar and/or a phosphorothioate backbone. Phosphorothioate modifications provide protection against RNase or other nuclease activity and their lipophilicity contributes to enhanced tissue uptake. In some embodiments, the antagomir cam include six phosphorothioate backbone modifications; two phosphorothioates are located at the 5'-end and four at the 3'-end, but other patterns of phosphorothioate modification are also commonly employed and effective. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Krutzfeld et al. (2005) describe chemically engineered oligonucleotides, termed 'antagomirs', that are reported to be efficient and specific silencers of endogenous miRNAs in mice.

In general, the design of an antagomir avoids target RNA degradation due to the modified sugars present in the molecule. The presence of an unbroken string of unmodified sugars supports RNAseH recruitment and enzymatic activity. Thus, typically the design of an antagomir will include bases that contain modified sugar (e.g., LNA), at the ends or interspersed with natural ribose or deoxyribose nucleobases.

Antagomirs useful in the present methods can also be modified with respect to their length or otherwise the number of nucleotides making up the antagomir. In some embodiments, the antagomirs must retain specificity for their target, i.e., must not directly bind to, or directly significantly affect expression levels of, transcripts other than the intended target. In some embodiments, antagomirs may exhibit nonspecific binding that does not produce significant undesired biologic effect, e.g., the antagomirs do not affect expression levels of non-target transcripts or their association with regulatory proteins or regulatory RNAs.

Interfering RNA, Including siRNA/shRNA

In some embodiments, the inhibitory nucleic acid sequence that is complementary to an paRNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002): Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl.

Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly afftect expression levels of, transcripts other than the intended target.

Ribozymes

In some embodiments, the inhibitory nucleic acids are ribozymes. Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific paRNA targets within the background of cellular RNA. Such a cleavage event renders the paRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 MM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

Preferably, inhibitory nucleic acids of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444: Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the references cited therein.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

It is understood that any of the modified chemistries or formats of inhibitory nucleic acids described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning: A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part 1. Theory and Nucleic Acid Preparation, Tijssen, ed. Elsevier, N.Y. (1993).

Modification Patterns

In some embodiments, the inhibitory oligonucleotide comprises locked nucleic acids (LNA), ENA modified nucleotides, 2'-O-methyl nucleotides, or 2'-fluoro-deoxyribonucleotides. In some embodiments, the inhibitory oligonucleotide comprises alternating deoxyribonucleotides and 2'-fluoro-deoxyribonucleotides. In some embodiments, the inhibitory oligonucleotide comprises alternating deoxyribonucleotides and 2'-O-methyl nucleotides. In some embodiments, the inhibitory oligonucleotide comprises alternating deoxyribonucleotides and ENA modified nucleotides. In some embodiments, the inhibitory oligonucleotide comprises alternating deoxyribonucleotides and locked nucleic acid nucleotides. In some embodiments, the inhibitory oligonucleotide comprises alternating locked nucleic acid nucleotides and 2'-O-methyl nucleotides.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the inhibitory oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the oligonucleotide can have any combination of modifications as described herein.

As an example, the oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)xxXxXX, (X)xXxxXX, (X)xxXXxX, (X)xXxXXx, (X)xXxXxX, (X)xxXxXX, (X)xXxXxX and (X)XxXxXx, (d) (X)xxXXXX, (X)xXxXXX, (X)xXXxXX, (X)xXXXxX, (X)xXXXXx, (X)XxxXXX, (X)XxXxXX, (X)XxXXxX, (X)XxXXXx, (X)XxXXx, (X)XXxxXX, (X)XXxXxX, (X)XXxXXx, (X)XXXxxX, (X)XXXxXx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, the oligonucleotide is a gapmer (contain a central stretch (gap) of DNA monomers sufficiently long to induce RNase H cleavage, flanked by blocks of LNA modified nucleotides: see, e.g., Stanton et al., Nucleic Acid Ther. 2012. 22: 344-359; Nowotny et al., Cell, 121:1005-1016, 2005; Kurreck, European Journal of Biochemistry 270: 1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Orom et al., Gene. 2006 May 10; 3720:137-41).

Additional Sequence Structural Information

The inhibitory oligonucleotides described herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The inhibitory oligonucleotides have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than the gene of interest. The oligonucleotide is expected to have a reduced likelihood of having off-target effects. The threshold level of sequence identity may be 50%, 60%, 70%, 80%, 85%, 90%, 95%, 99% or 100% sequence identity.

The inhibitory oligonucleotides may have a sequence that is complementary to a region that encodes an RNA that forms a secondary structure comprising at least two single stranded loops. In some embodiments, oligonucleotides that are complementary to a region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the area of complementarity between the oligonucleotide and the nucleic acid region may be at a location of the PRC2 associated region that encodes at least a portion of at least one of the loops. In some embodiments, the predicted secondary structure RNA (e.g., paRNA) containing the nucleic acid region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The inhibitory oligonucleotide may have a sequence that is has greater than 30% G-C content, greater than 40% G-C content, greater than 50% G-C content, greater than 60% G-C content, greater than 70% G-C content, or greater than 80% G-C content. The inhibitory oligonucleotide may have a sequence that has up to 100% G-C content, up to 95% G-C content, up to 90% G-C content, or up to 80% G-C content.

The inhibitory oligonucleotide may be complementary to a chromosome of a different species (e.g., a mouse, rat, rabbit, goat, monkey, etc.) at a position that encompasses or that is in proximity to that species' homolog of the gene of interest. The inhibitory oligonucleotide may be complementary to a human genomic region encompassing or in proximity to the target gene and also be complementary to a mouse genomic region encompassing or in proximity to the mouse homolog of the target gene. Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease. In some embodiments, the region of complementarity of the inhibitory oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a paRNA disclosed in the tables provided herein. In some embodiments, the region of complementarity is complementary with at least 8 consecutive nucleotides of a paRNA disclosed in the tables provided herein.

Pharmaceutical Compositions

The methods described herein can include the administration of pharmaceutical compositions and formulations comprising inhibitory nucleic acid sequences designed to target an paRNA. In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum *acacia* and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

EXAMPLES

The invention is further described in the following examples, which do not limit the scope of the invention described in the claims.

Methods

The following methods were used in the Examples set forth below.

Cell Culture and ES Cell Differentiation

For MEFs, female F1(129S1×CAST/EiJ) embryos were harvested on E13.5 and fibroblasts were outgrown, immortalized with SV40 large T antigen, cloned, and those carrying an inactive $X^{129}$ were used. Female 16.7 ES cells (Lee et al., 1999) and $Tsix^{TST}/+$ (Ogawa et al., 2008) have been described. Differentiating ES cells were grown without LIF for 4 days, then plated for outgrowth until on d7.

ChIP-seq

ChIP samples were prepared and immunoprecipitated as described (Lee et al., 2006) using antibodies against H3K4me3 (Abcam, ab8580), H3K36me3 (Abcam, ab9050), H3K27me3 (Abcam, ab6002), EZH2 (Active Motif, 39639) and RNA polymerase II phosphorylated on Serine 5 of the C-terminal domain (Abeam, ab5131). ChIP DNA concentration was measured using the Quant-iT Picogreen dsDNA Assay kit (Invitrogen). DNA for Illumina sequencing was prepared according to Illumina instructions with minor modifications (ultrapure T4 DNA ligase (Enzymatics) for ligation, room-temperature purification of gel slices using QIAquick (Qiagen) spin columns and amplification using Phusion (NEB) GC buffer). Paired-end sequencing was carried out for 2× 36 cycles on a Genome Analyzer II (Illumina).

Allele-Specific Analysis

Mouse genome sequencing data (129S1/SvImJ and CAST/EiJ) from the Wellcome Trust Sanger Institute (sanger.ac.uk/resources/mouse/genomes/) aligned to the C57BL/6J reference genome (NCBI mm9) was screened for high quality single nucleotide polymorphisms (SNPs) and insertions/deletions indels. Variant genomes were constructed from mm9 using a total of 17,879,569 SNPs, 726,387 indels for CAST/EiJ, and 4,551,690 SNPs, 224,271 indels for 129S1/SvImJ. In total, the resulting CAST/EiJ and 129S1/SvImJ genomes differ in 22,095,665 SNPs and 948,567 indels. Read pairs were aligned to both genomes allowing for up to ~5 mismatches at high-quality bases or 2-4 small gaps using novoalign (Keightley et al., Genome Res. July 2009 19: 1195-1201). Each uniquely aligned pair to the CAST/EiJ genome was compared to the corresponding pair aligned to the 129S1/SvImJ genome. Pairs that differed significantly in alignment score due mismatches/gaps were classified as allele-specific and the better alignment retained. Pairs with identical alignment scores or scores that differed only slightly due to fragment length penalties were classified as neutral. Each experiment yields three tracks: Cast, 129, and composite (neutral, 129, Cast combined).

Generation of Coverage Maps and Enrichment Segments

Alignment coordinates were mapped to mm9 to permit comparisons to mm9 annotations. To calculate coverage, fragments defined by paired reads were included, discarding duplicate fragments. Coverage was normalized by input. Chromosomal segments that are likely to be enriched for a chromatin epitope were defined by analyzing significantly enriched overlapping 1 kb windows. The significance of the coverage enrichment in a window was determined based on the null model of paired-end fragments randomly shuffled across the chromosome.

To calculate coverage, fragments defined by paired reads were included, discarding duplicate fragments. The average fragment length was approximately 300-400 bp. The resulting positional coverage in each sample was normalized by the corresponding input coverage, with a pseudocount of 1: $n_{norm}=[(n+1)/(n_I+1)]*[N_I/N]$, where n, $n_I$, N, and $N_i$ are positional coverages in experiment and input, and total genome coverages in experiment and input, respectively.

To determine the likely regions of enrichment for chromatin modifications and EZH2, we used a window of 1 kb sliding over the chromosome length with the step of 50 bp. The significance of the window coverage at each position was assessed using the null model of randomly redistributed fragments. Specifically, each paired-end fragment at the given chromosome was assigned to a random location within this chromosome, followed by input normalization. The resulting normalized coverage of 1 Kb windows over all chromosomes was used to construct the random coverage distribution. Based on this distribution, P-value was assigned to the real window coverages. Windows with P-value below the significance cutoff were merged into segments, with up to 1 kb gap allowed between windows. The cutoff for calling significant window coverage was selected based on manual inspection of the segments produced at different cutoff values. The determined cutoffs showed high robustness between independent simulations.

Strongly covered segments for K4me3 and EZH2 were identified with the P-value cutoff of $10^{-5}$. Moderately covered segments for H3K27me3 and EZH2 were identified with absolute coverage cutoffs of 4.0 and 3.0 per position, respectively. Bivalent segments were identified in a similar fashion, with the requirement of a significant K4me3 coverage and a moderate K27me3 coverage within the same window.

Segments were classified as overlapping with K4me3 peaks, bivalent segments, and CpG islands if the corresponding feature occurred within 1 kb from the segment. CpG islands were defined by running EMBOSS 6.3.1 on unmasked genome with default parameters.

Chromosomal segments that are likely to be enriched for a chromatin modification or a DNA-binding protein were defined by merging adjacent significantly enriched 1 kb windows. The significance of the coverage enrichment in a window was determined based on the null model of originally aligned paired-end fragments being randomly shuffled across the chromosome.

Metagene and Metasite Profiles

The profiles of average coverage density over genes (metagene profiles) and over segments (metasite profiles) were constructed using normalization of profile densities so that the area under curve was proportional to the average gene/segment coverage at this chromosome. The profiles of average coverage density over genes (metagene profiles) and over sites were constructed as described before, with the exception for a different normalization that allows for the comparison of total gene/site coverage between alleles, chromosomes, and differentiation stages. Specifically, profile densities were normalized by the number of genes/sites at a given chromosome, so that the area under the curve is not equal to 1.0 but proportional to the average gene/site coverage at this chromosome.

Estimates of Density Map Correlations

Correlations between chromosomal density maps were calculated as Pearson correlation coefficients of coverages in non-overlapping windows, with estimates of statistical significance based on random permutation null model.

Correlations between chromosomal density maps were calculated based on the coverages of non-overlapping 1-5 kb windows over the entire chromosome. For the two compared marks, Pearson correlation coefficient was calculated on the sets of window coverages, and its statistical significance was estimated using random permutation null model. Specifically, $10^5$ simulations of random window shuffling were performed, resulting in the background distribution of Pearson correlation coefficients. This distribution was very well approximated by normal distribution (data not shown). The significance of the actual correlation of estimated as a Z-score based on the background distribution. We selected Z-score as a measure since many P-values for highly correlated marks were below computational precision and would appear as zero in the plots. Using Spearman rank correlation coefficients produced very similar results. Correlations between densities of different EZH2 and H3K27me3 sites were calculated in a similar fashion.

Estimates of Allelic Skew

Allelic skew of coverage at a given segment was analyzed by comparing allele-specific coverages at this segment. The significance of skew was estimated based on the normal distribution of effective numbers of allele-specific fragments.

Allelic skew of coverage at a given segment was analyzed by comparing allele-specific coverages at this segment. The significance of skew was estimated based on the normal distribution of effective numbers of allele-specific fragments. P-values were based on normal approximation of binomial distribution $N(np, np(1-p))$ where $p=0.5$ and n is the total effective number of fragments estimated from total coverage cov and average paired-end fragment length $<L>$: $n=cov/<L>$.

Repeat Enrichment Analysis

The significance of repeat enrichment or depletion was estimated against the distribution of RepeatMasker repeat numbers in the segments shuffled along the chromosome. Among the segments enriched for EZH2, we counted the number of segments overlapping different types of repeats defined by RepeatMasker in mm9 mouse genome. The significance of repeat enrichment or depletion was estimated against the distribution of repeat numbers in the segments shuffled along the chromosome (100 simulations).

Analysis of Coverage in Long-Range Vicinity of EZH2 Sites

The analysis of coverage trends in the megabase-scale vicinity of strong EZH2 sites was based on the coverage of 1 kb windows with 200 bp shift over the entire chromosome. For each window, the closest strong EZH2 segment was determined, and the window coverage was plotted against the distance to the closest segment. The trends of moderate site coverage around the strong sites were analyzed in a similar fashion.

Allele-Specific ChIP-qPCR

ChIPs were carried out as described above in biological triplicate for EZH2 and H3K27me3 from d0, d7 and MEF cells. Allele-specific primers were designed to discriminate at least 2 out the last 4 terminal (3') positions of the primer annealing site, and allele-specificity was confirmed using genomic DNA from pure Cast and 129 mice. Amplification was performed using 2× iQ Sybr green (Biorad) on a CFX96 instrument (Biorad) with the following protocol: 3 min at 95° C., then 45 cycles of 15 sec at 95° C., 15 sec at 58° C. and 30 sec at 72° C. Reactions using 129- and Cast-specific primers were set up in parallel from the same ChIP DNA dilution and contained one universal primer and one of two allele-specific primers (mus for 129, cas for Cast in primer name) at 250 nM:

| PRC2 site | Allele-specific primers | SEQUENCE | SEQ ID NO: |
|---|---|---|---|
| m-13: | p267-13m631musF: | GGC AGG GGT TAC TAC AGT AGA GTG | 3151 |
| | p268-13m631casF: | GGC AGG GGT TAC TAC AGT AGA GAA | 3152 |
| | p269-13m631R: | CAG CTC TGG GAA GGT TTT GTA TG | 3153 |
| c-13: | p270-13c47F | CCT GGT AGA GTC ACC TCC GGA CAG | 3154 |
| | p271-13c47musR | GAA CCT TTT CCC TCC AAG CCC AGA | 3155 |
| | p272-13c47casR | GAA CCT TTT CCC TCC AAG CCC CGC | 3156 |
| c-X1: | p276-Xc10F | CCT GCG ATC CGG CGC TTT G | 3157 |
| | p277-Xc10musR | CTC TCC CGA CCC CGC ACA CAT T | 3158 |
| | p278-Xc10casR | CTC TCC CGA CCC CGC ACA CGT C | 3159 |
| m-X1: | p283-Xm269musF | GGC TCA CAT TTG CAC TTT TTG CTA CG | 3160 |
| | p284-Xm269casF | GGC TCA CAT TTG CAC TTT TTG CTA AA | 3161 |
| | p285-Xm269R | GGG ATG AGG CGT CTG TGT TGG GTC | 3162 |
| a-X2: | p286-Xa76musF | CAC ATA AAA CAT CAA ACA GAA CAT GTG AGC | 3163 |
| | p287-Xa76casF | CAC ATA AAA CAT CAA ACA GAA CAT GTT AGA | 3164 |
| | p288-Xa76R | GGA CAC ACA AAT AGT GAC CTG GTG GC | 3165 |
| c-X2: | p289-Xc77musF | GCT TAG CGG ATT CCA TAC CCC AA | 3166 |
| | p290-Xc77casF | GCT TAG CGG ATT CCA TAC CCC CC | 3167 |
| | p291-Xc77R | GAG CAC ATT TTT AAG AAA ACC GAT GAC AG | 3168 |
| m-X2: | p295-Xm2240musF | GGA AGG GAA GTA ATT AAG CAA ACA CAA ACA | 3169 |
| | p296-Xm2240casF | GGA AGG GAA GTA ATT AAG CAA ACA CAT GG | 3170 |
| | p297-Xm2240R | CTC AAA GAA AAA AAA TAT CAT AAA AAC CAA ACT GTT TC | 3171 |
| Jarid1: | p298-intrJarid1cF | CAC TTC TTT TGT GCC TTA AGC ATT AGC | 3172 |
| | p299-intrJarid1cmusR | TCA CAC AGG TCA GAT ACA AAA AGT ATA GTT | 3173 |
| | p300-intrJarid1ccasR | TCA CAC AGG TCA GAT ACA AAA AGT ATA GCA | 3174 |

Example 1

Allele-Specific ChIP-seq

Figure 8A:
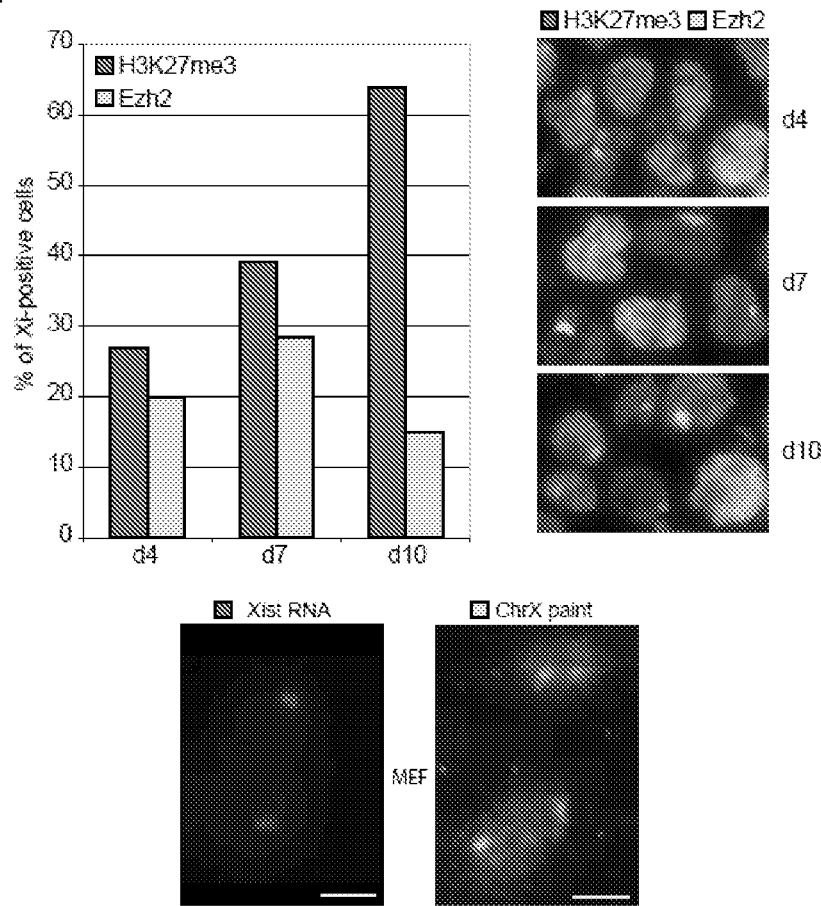
Figure 8B:
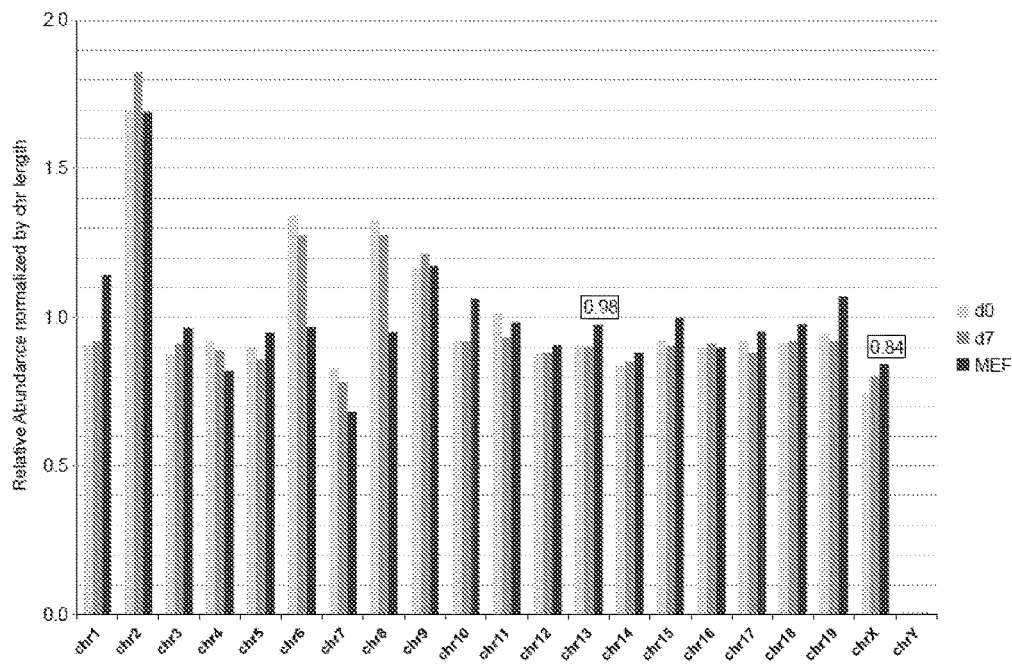
Figure 8C:
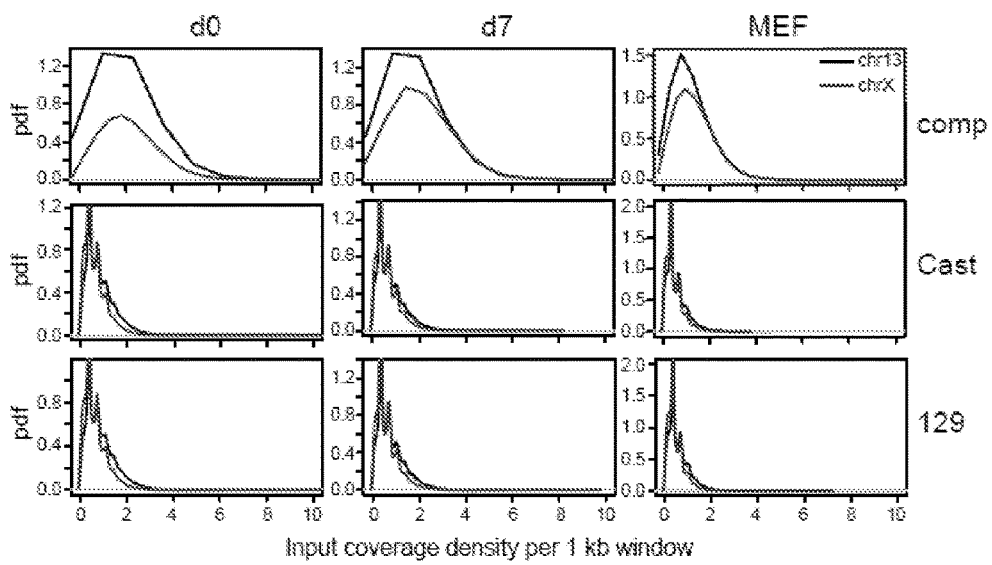

Mammalian PRC2 contains four core subunits, EED, SUZ12, RBAP48 (RBBP4 in mouse), and EZH2, the subunit responsible for trimethylating H3K27. Because Polycomb recruitment is a central feature of XCI (Plath et al., 2003; Silva et al., 2003; Zhao et al., 2008), we obtained allele-specific ChIP-seq profiles for EZH2 and H3K27me3 and compared them to those for activating marks, including holoenzyme POL-II-S5P (active POL-II), H3K4me3 (transcriptional initiation), and H3K36me3 (transcriptional elongation). To distinguish Xi from Xa, we used female cell lines carrying one X of Mus castaneus origin ($X^{Cast}$) and one of M. musculus 129 origin ($X^{129}$), and analyzed three developmental stages. First, we examined undifferentiated female ES cells (d0), which carry two Xa but recapitulate XCI during differentiation. Second, we examined differentiating ES cells on day 7 (d7), a timepoint corresponding to a mid-XCI state where ~40% of cells are establishing XCI (FIG. 8A). Disabling the Tsix allele on $X^{129}$ ($Tsix^{TST}$/+) (Ogawa et al., 2008) ensured inactivation of $X^{129}$ in the ES line. Third, we examined post-XCI, clonal hybrid female mouse embryonic fibroblasts (MEF; F1, ♂$X^{Cast}$×♀$X^{129}$) which have inactivated $X^{129}$. Approximately 0.6 million SNPs and insertions/deletions (indels) of ~23 million genomewide SNPs/indels between M. castaneus and M. musculus were used to distinguish $X^{Cast}$ and $X^{129}$ (Keane et al., 2011).

Using paired-end sequencing, 283% of all read pairs aligned uniquely and ~36% provided allele-specific information (Table I). All tracks (Cast, 129, Composite) were first normalized to their corresponding input controls to minimize potential artifacts stemming from differential chromosome compaction, crosslinking or sonication efficiencies, with ES and MEF input data mapping proportionally to chromosome length (FIG. 8B) and equally well to both homologs of ChrX and Chr13 (FIG. 8C); this showed that experimental bias between Xi and Xa was negligible. The composite track (comp) represents total epitope abundance, whereas Cast and 129 tracks reflect relative allelic abundance and local SNP densities (see Supplemental Methods). To validate our approach, we inspected loci with established mono- or bi-allelic expression (FIG. 9). At the imprinted Dlk1-Meg3 and Zim1-Peg3 loci, allele-specific H3K4me3 and POL-II-S5P profiles were consistent with known parent-of-origin effects. At the Xist promoter, H3K4me3 and POL-II-S5P were specifically enriched on $X^{129}$ (Xi). The opposite pattern was observed at Iqsec2, a gene subject to XCI. By contrast, biallelic H3K4me3 and POL-II-S5P enrichment was seen at the neighboring Jarid1c (Kdm5c), a gene known to escape XCI (Greenfield et al., 1998; Carrel and Willard, 2005). These results demonstrate the allele-specific nature of our ChIP-seq.

et al., 2010). Eight out of 11 genes appeared on both lists (e.g., Utx (Kdm6a), Jarid1c). Three noncoding genes, including Jpx (Enox), Ftx (B230206F22Rik) and 5530601H04Rik (FIG. 10B), appeared only in our study, though they had been shown by others to be biallelically expressed (Johnston et al., 2002; Reinius et al., 2010; Chureau et al., 2011). These results suggest that allele-specific ChIP-seq could be an effective method of identifying monoallelically expressed genes on a genome-wide scale.

Example 3

Allelic Profiles of Xa and Xi

We then performed metagene analysis to examine average epitope densities within genes on chromosomes X (ChrX) and 13 (Chr13). In 16.7 ES cells, Chr13 was the only autosome that is fully *M. castaneus* for one homologue and fully 129 for the other in $Tsix^{TST}/+$ ES cells (other autosomes have meiotically recombined in the F1 germline). For Chr13 genes, the marks of gene activation remained relatively constant and there was little allele-specific distinction before (d0 ES), during (d7 ES), and after (MEF) XCI. On both homologues, POL-II-S5P and H3K4me3 were enriched over promoters, and H3K36me3 occurred along the gene body, as expected.

By contrast, ChrX showed dynamic changes. While $X^{Cast}$ and $X^{129}$ profiles were similar on d0 (pre-XCI), they diverged significantly at d7 (mid-XCI) and remained distinct in MEFs (post-XCI)(FIG. 1A). Active marks (POL-11-S5P, H3K4me3, and H3K36me3) showed stereotypical enrichment on both homologues in the pre-XCI state (d0), but became substantially depleted on Xi ($X^{129}$) allele in d7 cells, dropping to about half of Xa ($X^{Cast}$) levels, as might be expected for a mid-XCI stage. In MEFs (post-XCI) the average composite values were reduced by ~50% and the Xi trace flatlined, consistent with complete loss of POL-II-S5P, H3K4me3, and H3K36me3 from Xi. Conversely, EZH2

TABLE I

Statistics for sequencing of input and indicated epitopes. ChIP-seq results for MEF, d0, and d7 ES cells showing all clusters and reads that are aligned, repetitive or unique, and allelic or neutral in millions and percent.

| celltype | epitope | clusters | aligned | | unique | | allelic | | neutral | |
|---|---|---|---|---|---|---|---|---|---|---|
| MEF | input 1 | 19.5 | 18.6 | 95% | 15.5 | 83% | 5.6 | 36% | 9.9 | 64% |
| MEF | input 2 | 28.7 | 27.5 | 96% | 23.1 | 84% | 8.5 | 37% | 14.6 | 63% |
| MEF | H3K27me3 | 17.9 | 17.0 | 95% | 15.2 | 89% | 5.5 | 36% | 9.7 | 64% |
| MEF | EZH2 | 21.9 | 19.8 | 90% | 16.8 | 85% | 6.1 | 36% | 10.7 | 64% |
| MEF | H3K4me3 | 20.4 | 19.4 | 95% | 17.9 | 93% | 5.5 | 31% | 12.5 | 69% |
| MEF | H3K36me3 | 17.2 | 16.5 | 96% | 14.4 | 87% | 5.1 | 36% | 9.2 | 64% |
| MEF | POL-II-S5 | 26.0 | 24.3 | 93% | 21.6 | 89% | 7.6 | 35% | 14.0 | 65% |
| ES d0 | input 1 | 32.5 | 31.3 | 96% | 26.0 | 83% | 9.5 | 36% | 16.5 | 64% |
| ES d0 | input 2 | 23.0 | 21.1 | 92% | 18.3 | 87% | 6.9 | 38% | 11.4 | 62% |
| ES d0 | H3K27me3 | 27.1 | 25.8 | 95% | 22.5 | 87% | 8.1 | 36% | 14.3 | 64% |
| ES d0 | EZH2 | 27.7 | 26.1 | 94% | 21.9 | 84% | 7.8 | 35% | 14.2 | 65% |
| ES d0 | H3K4me3 | 25.6 | 23.9 | 93% | 20.6 | 86% | 6.5 | 31% | 14.2 | 69% |
| ES d0 | H3K36me3 | 24.3 | 23.1 | 95% | 18.9 | 82% | 6.6 | 35% | 12.3 | 65% |
| ES d0 | POL-II-S5 | 29.3 | 27.9 | 95% | 24.4 | 88% | 8.5 | 35% | 16.0 | 65% |
| ES d7 | input | 29.7 | 28.6 | 96% | 23.7 | 83% | 8.4 | 35% | 15.3 | 65% |
| ES d7 | H3K27me3 | 30.6 | 28.8 | 94% | 25.3 | 88% | 8.6 | 34% | 16.7 | 66% |
| ES d7 | EZH2 | 29.1 | 27.5 | 94% | 23.0 | 84% | 8.2 | 36% | 14.8 | 64% |
| ES d7 | H3K4me3 | 26.2 | 24.8 | 95% | 22.7 | 92% | 7.1 | 31% | 15.6 | 69% |
| ES d7 | H3K36me3 | 29.5 | 28.2 | 96% | 21.6 | 77% | 6.8 | 32% | 14.8 | 68% |
| ES d7 | POL-II-S5 | 28.4 | 26.7 | 94% | 22.6 | 85% | 8.1 | 36% | 14.6 | 64% |
| | Average | 25.7 | 24.3 | 94.5% | 20.8 | 85.7% | 7.2 | 34.9% | 13.6 | 65.1% |
| | Stdev | 4.4 | 4.3 | 1.5% | 3.5 | 3.6% | 1.3 | 2.1% | 2.3 | 2.1% |

Example 2

Genes that Escape XCI

We used allele-specific profiles to identify genes that escape XCI by scoring H3K4me3 peaks within 3 kb of annotated transcriptional start sites (TSS) and noting allelic skews with statistical significance (p<0.05, normal approximation of binomial). Genes with significant $X^{Cast}$ (Xa) skewing were considered monoallelic. Genes with insignificant skewing or two-allele H3K4me3 enrichment were designated biallelic. Genes lacking H3K4me3 peaks within 3 kb of annotated promoters were considered repressed ("off"). Those lacking sufficient SNP density were excluded (not determined, "n/d"). On Chr13, ~400 out of 843 genes were biallelic, ~300 genes were off, ~100 were indeterminate (n/d), and few were monoallelic (FIG. 10A).

$X^{Cast}$ skewing was evident for almost all MEF genes (FIG. 10A), consistent with the genes being subject to XCI (Carrel and Willard, 2005; Berletch et al., 2010). Eleven genes showed biallelic H3K4me3 marks (FIG. 10B,C), in excellent agreement with recent expression analysis (Yang binding increased 2-fold on Xi between d0 and d7, and H3K27me3 levels increased 3-fold. On Xa ($X^{Cast}$), EZH2 and H3K27me3 levels stayed relatively constant. These results demonstrated de novo recruitment of EZH2 and H3K27 trimethylation en masse to X-genes during XCI. In post-XCI MEFs, however, allelic differences remained for H3K27me3 but EZH2 binding was not significantly enriched in genes on Xi over Xa. These results indicate that massive PRC2 recruitment occurs during the establishment phase of XCI, but maintenance does not require large amounts of genic PRC2, consistent with the already trimethylated state of H3K27 in post-XCI cells. It is possible that PRC2 on Xi is concentrated in nongenic regions.

Figure 1B:
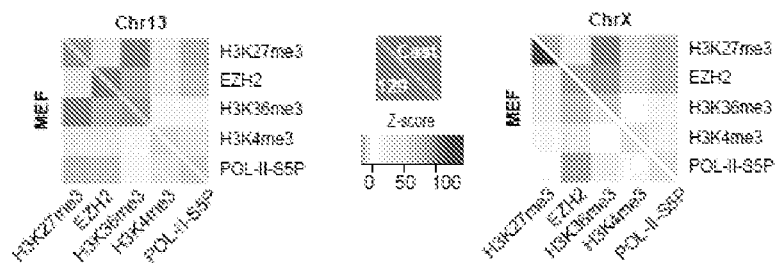
Figure 1C:
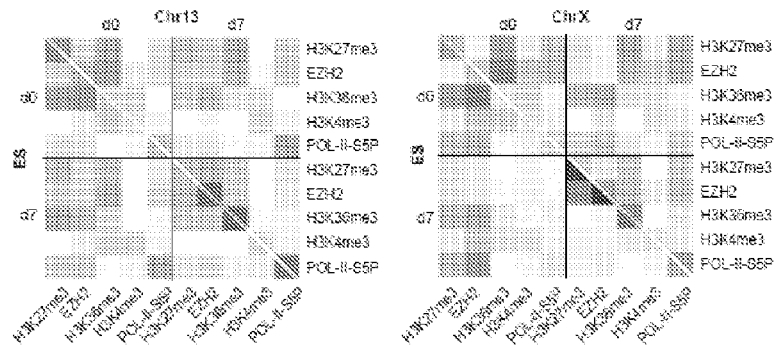

We then examined whole-chromosome coverages. Allelic heatmaps displayed positional correlations between different epitopes at different timepoints, with color-coded Z-scores representing the significance of the correlation estimated using a permutation-based random model (FIG. 1B,C). In MEF (FIG. 1B), allelic profiles for Chr13 were essentially identical (colors mirrored across the diagonal) with strong positive correlations of POL-II-S5P with H3K4me3 and H3K36me3, and good anti-correlations between POL-II-S5P/H3K36me3 and H3K27me3/EZH2. However, allelic profiles for ChrX were significantly different for a number of epitopes (discordant colors across the diagonal), consistent with XCI having occurred in MEFs. To ask what happens during XCI establishment, we examined d0 and d7 ES cells (FIG. 1C). Chr13 showed almost no allelic differences for any chromatin epitope, but significant allelic deviations were seen on ChrX. First, while the positive correlation between H3K27me3 and EZH2 on Xi was significant on d0 (Z-score=15), the correlation grew very strong on d7 (Z-score=96). Second, whereas H3K27me3/EZH2 were anti-correlated with active marks on d0, they became unexpectedly positively correlated on d7. Notably, the active marks showed high correlation between d0 and d7, suggesting that their density maps did not change dramatically. This dynamic of active versus repressive marks raised the intriguing possibility that, during XCI, EZH2 and H3K27me3 appear in domains marked by active POL-II and H3K4me3. This feature was Xi-specific, and absent on Xa and Chr13.

Example 4

Strong EZH2 Recruiting Sites on Xi are Bivalent Domains

Chromatin regions marked concurrently by H3K4me3 and H3K27me3 have been termed 'bivalent domains', typically associated with transcriptionally poised developmental genes in ES cells (Bernstein et al., 2006). In undifferentiated ES cells, CpG islands associated with bivalent domains account for most EZH2 sites (Ku et al., 2008), and H3K27me3 is rarely detected in the absence of H3K4me3 (Mikkelsen et al., 2007). We asked if EZH2 localization and H3K27me3 followed similar patterns on ChrX during XCI. On d0, most 'strong' EZH2 sites—defined as sites with significant EZH2 ChIP-seq coverage ($p<10^{-5}$ according to a permutation-based random model)—were often found within canonical bivalent domains (FIG. 2A), frequently coinciding with CpG islands (striped), as well as a few that were solely H3K27me3-marked. This was true for both ChrX and Chr13 and consistent with previous reports (Bernstein et al., 2006; Mikkelsen et al., 2007; Ku et al., 2008).

Figure 2A:
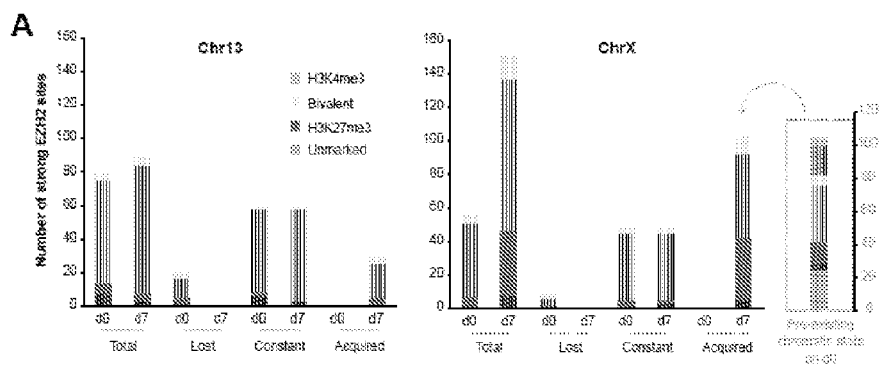
Figure 2B:
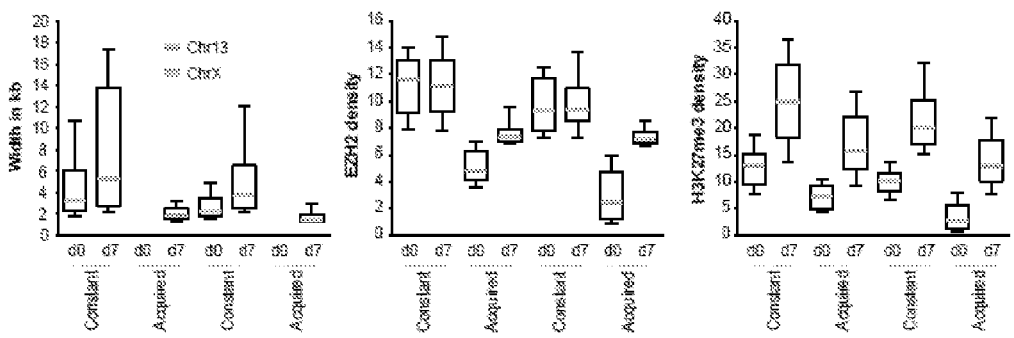
Figure 2C:
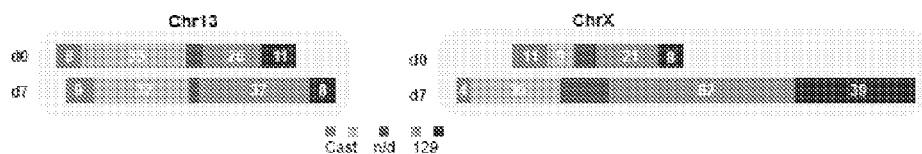

However, during cell differentiation and XCI, the chromatin composition and number of strong EZH2 sites diverged dramatically between ChrX and Chr13. On Chr13, 20 out of 79 of d0 EZH2 sites were lost and few new EZH2 sites were acquired (30). Almost all d7 sites were still bivalent domains associated with CpG islands (FIG. 2A). On the other hand, ChrX lost very few sites (8/48) and a large number (>100) of new EZH2 sites was acquired on d7. In contrast to constant sites, many acquired sites on ChrX were neither bivalent nor CpG islands. Among acquired sites, about half were already marked weakly by H3K27me3 on d0 but were below the significance cutoff for EZH2: the rest was previously marked solely by H3K4me3 or unmarked by either epitope (FIG. 2A, sidebar). Interestingly, strong EZH2 sites on both Chr13 and ChrX showed changes in widths of the sites, EZH2 densities, and H3K27me3 densities (FIG. 2B), which suggest a genome-wide increase in PRC2 activity from d0 and d7. Acquired sites on ChrX, however, may be key regulators of XCI, because they appear primarily on Xi during differentiation, as shown by allelic skewing of coverage (FIG. 2C).

Therefore, ChrX and Chr13 differed in several respects during XCI. First, ChrX gained a large number of EZH2 sites. Second, EZH2 binding on ChrX was allelically skewed (to future Xi). Third, whereas acquired and constant Chr13 sites were mostly bivalent, only about half of acquired X-linked sites were bivalent before XCI. Fourth, acquired sites on ChrX experienced larger increases in EZH2 and H3K27me3 densities than on Chr13. Given that many new EZH2 sites did not conform to the established paradigm of being bivalent, we suspected that non-canonical EZH2-binding sites may be central to the spread of XCI.

Example 5

Non-Canonical EZH2 Sites on Xi for Spreading

Figure 2D:
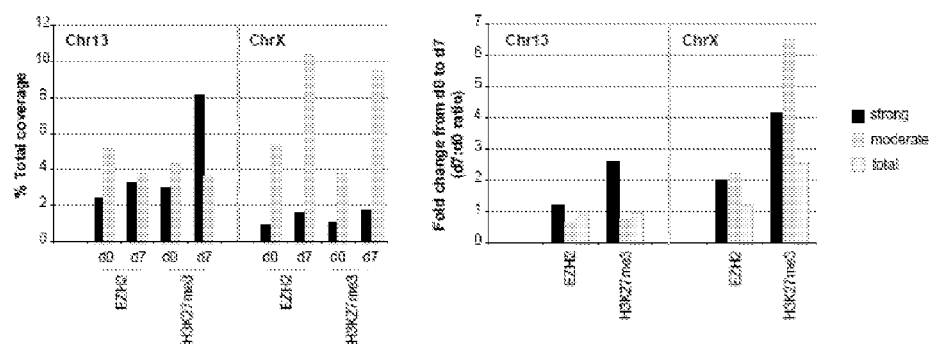
Figure 3A:
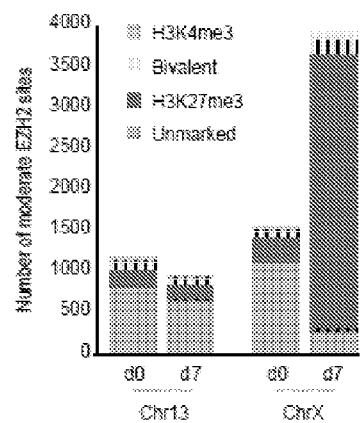
Figure 3B:
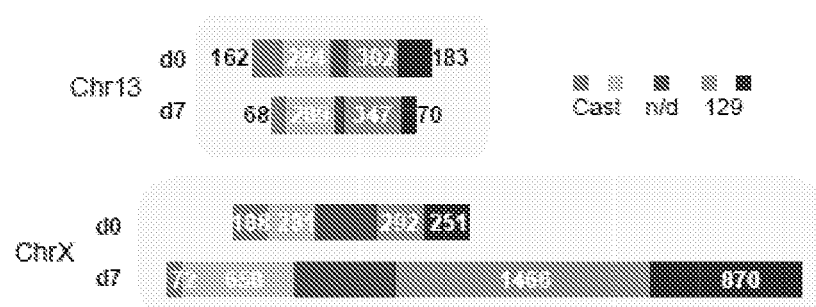
Figure 3C:
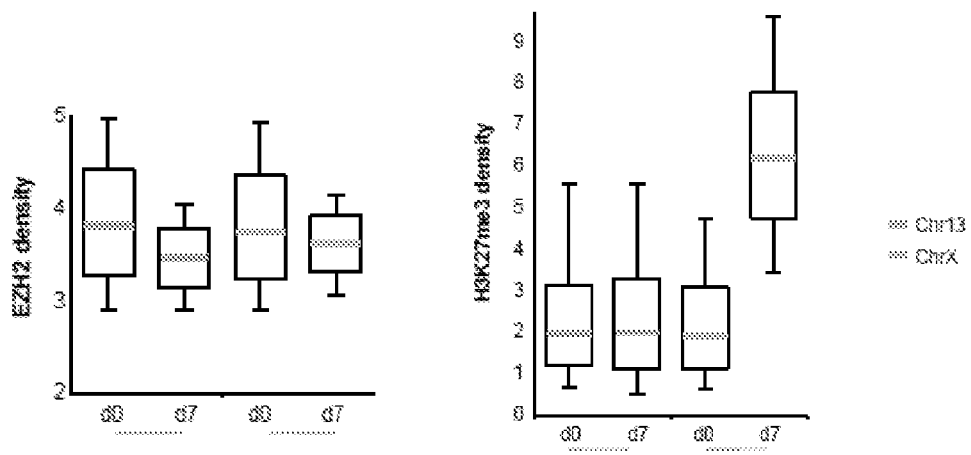
Figure 3D:
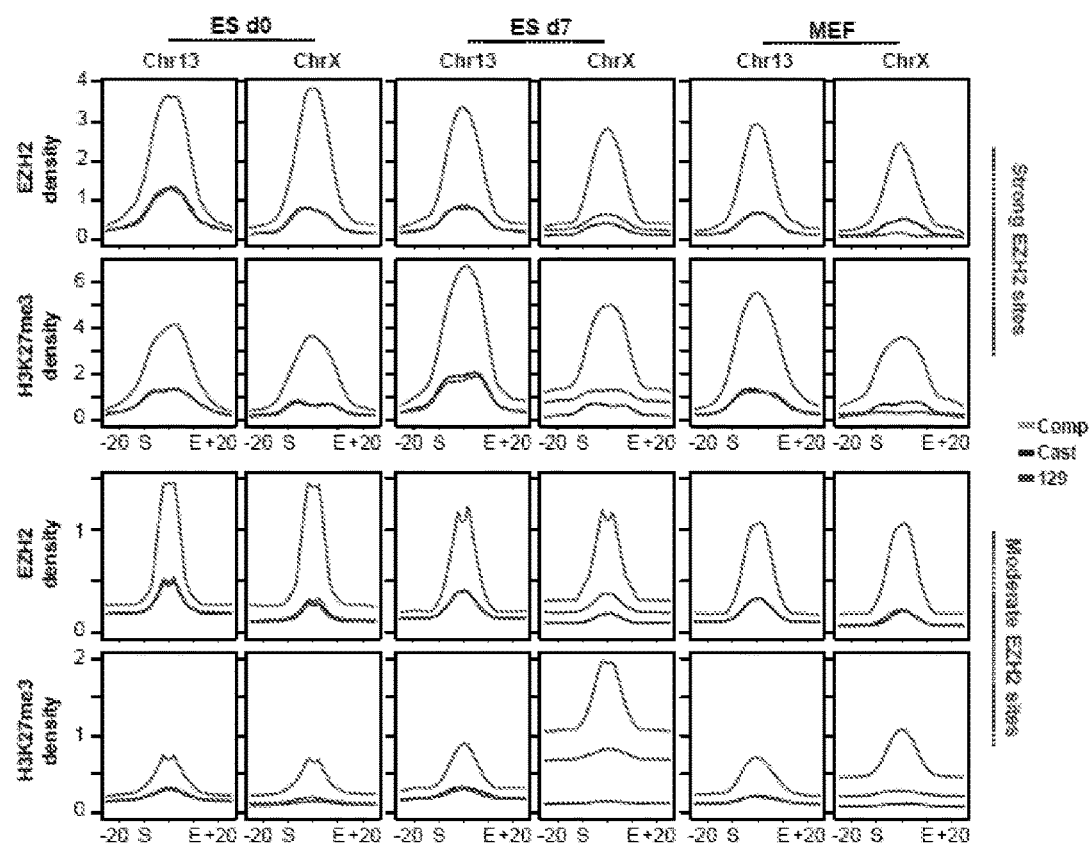
Figure 4A:
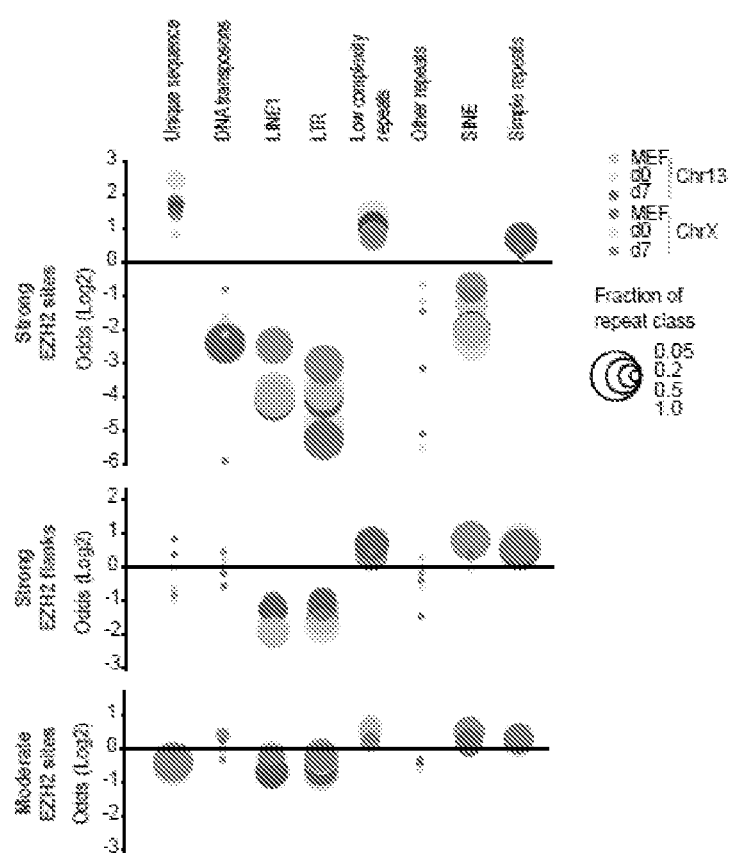
Figure 4B:
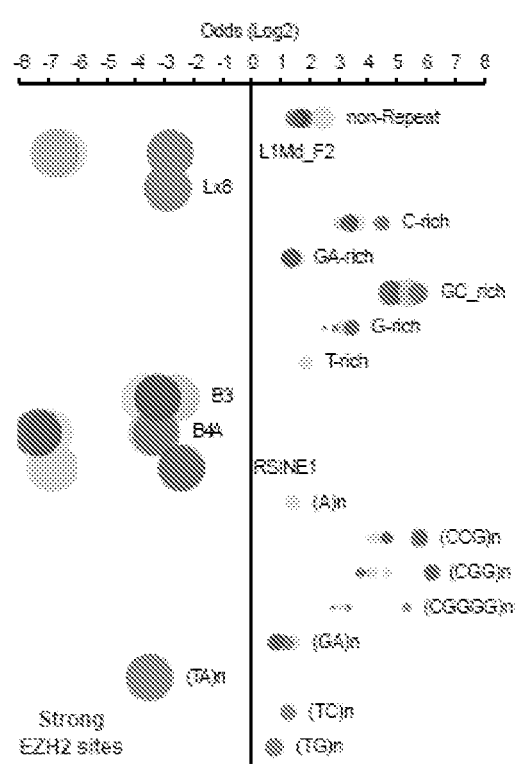
Figure 4C:
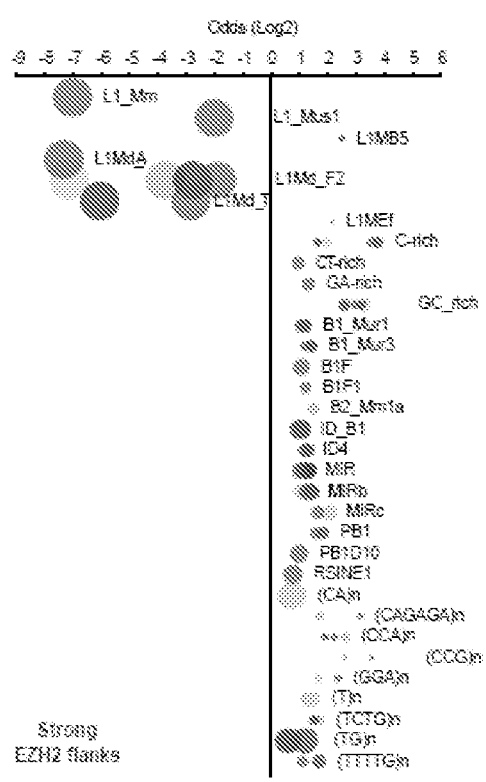
Figure 4D:
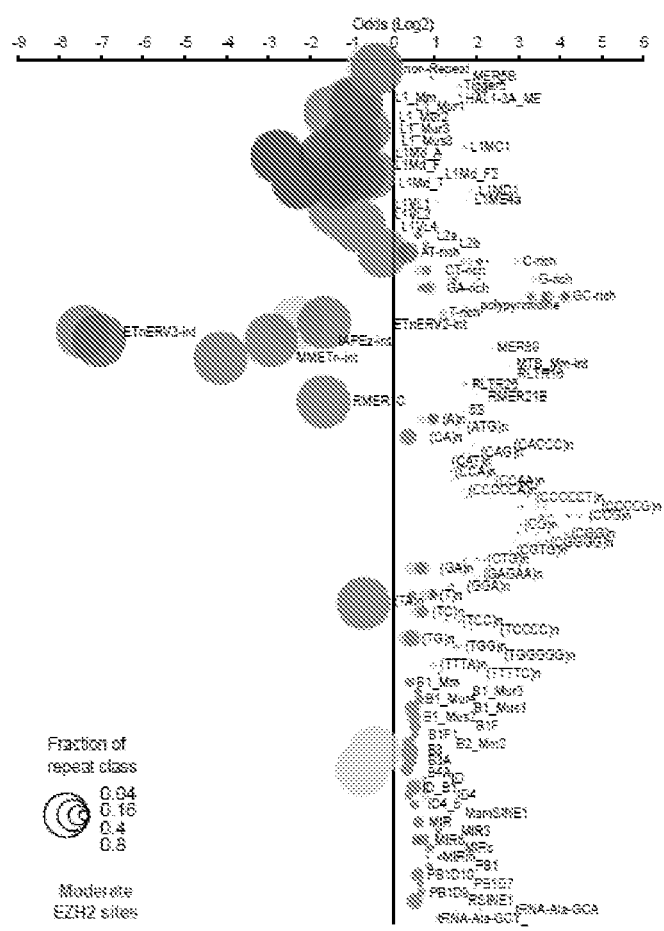

In light of de novo recruitment of non-canonical sites and the finding that many such sites were already weakly H3K27me3-positive (but below cutoff) on d0, we asked whether we might find additional functional EZH2 sites by relaxing the EZH2 enrichment threshold (FIG. 11A). We also noted that, although chromosome-wide coverages of EZH2 and H3K27me3 were greater for ChrX than Chr13 (d7), the cumulative coverages over strong sites accounted for a small fraction of total and were actually less for ChrX than Chr13 (FIG. 2D). By relaxing the cutoff to a density of >3/bp over a 1 kb window (equivalent top <0.03 according to random model) and excluding strong EZH2 sites ($p<10^{-5}$), we observed a large number of previously undetected sites, almost all of which were neither bivalent domains nor CpG islands (FIG. 3A). On ChrX, such 'moderate' or 'non-canonical' sites numbered at ~1500 on d0 and grew to ~4000 during XCI (d7). Moderate sites greatly exceeded strong sites in number and were mostly intergenic (~⅔, data not shown). Allelic profiles showed that the greatest gain occurred on $X^{129}$ (Xi) FIG. 3B). Although non-canonical sites also occurred on Chr13, their number was smaller and remained constant during cell differentiation. Furthermore, Chr13 sites showed little evidence of productive H3K27 trimethylation, whereas moderate ChrX sites were almost exclusively H3K27me3-marked (FIG. 3A,C). In fact, moderate sites on ChrX represented the lion's share of EZH2 activity during XCI. EZH2 and H3K27me3 levels summed over moderate sites far exceeded those over strong sites (FIG. 2D, left panel). The greatest change in H3K27me3 coverage between d0 and d7 was observed on these non-canonical sites (FIG. 2D, 3C, right panel). Taken together, these data indicate that massive acquisition of non-canonical EZH2 sites—both strong and moderate— defines XCI, and that non-canonical EZH2 sites (rather than bivalent sites) distinguish Xi from Xa and from autosomes. Though both bivalent and non-canonical sites are recruited during XCI, the latter best reflects the XCI-specific spread of PRC2 during cell differentiation.

Next, we experimentally validated the bioinformatically defined strong and moderate sites by performing allele-specific ChIP-qPCR on select loci from Chr13 and ChrX in d0/d7 ES cells and in MEF (FIG. 12, 13). Analysis of strong (constant and acquired) sites and moderate sites, revealed clear concordance between the ChIP-seq and ChIP-qPCR results for all tested epitopes, including EZH2, H3K27me3, and H3K4me3. First, strong sites (c-13, c-X1, c-X2) showed significantly greater enrichment by ChIP-qPCR than nearby moderate sites (m-13, m-X1, m-X2)(p<0.05, one-tailed Mann-Whitney U test). Second, allelic differences observed by ChIP-seq were reproduced by allelic-specific ChIP-qPCR. Finally, results from three biological replicates were consistent and showed significantly higher EZH2 and H3K27me3 binding at both strong and moderate sites than observed for an IgG pulldown control and the negative control escapee locus, Jaridlc (FIG. 13, * p<0.05, one-tailed Mann-Whitney U test). Thus, the ChIP-qPCR results validated our general approach to allele-specific ChIP-seq analysis.

To assess local spreading at strong and moderate sites, we plotted average EZH2 and H3K27me3 densities at binding sites ±20 kb of flanking sequence (FIG. 3D), with EZH2 sites being scaled from 0 to 1 between its start (S) and end (E) (metasite profile). On d0, no allelic differences were observed on ChrX and Chr13. On d7, strong allelic skew was observed on ChrX at both strong and moderate sites, and EZH2 and H3K27me3 densities were consistently greater on $X^{129}$ (Xi) than on $X^{Cast}$ (Xa), as expected. Interestingly, a flipped allelic skew was observed for strong sites in MEFs, occurring only in EZH2 levels and not in H3K27me3 levels. This is consistent with the notion that maintenance of H3K27me3 levels after the establishment of XCI requires only low levels of EZH2 at strong sites; on Xa, by contrast, higher levels of EZH2 may be continuously required for dynamic responses in X-linked gene expression. Most intriguingly, however, changes in EZH2 and H3K27me3 densities on d7 were greater at moderate than strong X-linked sites and occurred not only within the sites but also across >20 kb of flanking sequence bi-directionally (FIG. 3D), supporting the idea that non-canonical moderate sites are central to spreading of XCI.

Example 6

Relationship of EZH2 Sites to Repetitive Elements

We investigated whether the PRC2 sites share underlying sequence motifs. Given hypothesized roles for repetitive elements in spreading (Bailey et al., 2000; Lyon, 2000; Wang et al., 2006; Chow et al., 2010), we examined correlations with repeat classes (FIG. 4). Our paired-end sequencing approach enabled unique alignments of a large number of repeat-containing reads by virtue of being paired with a non-repetitive read. Strong sites were generally enriched in low-complexity repeats (d0, d7)(Z>2.5, permutation-based random model) and simple repeats (d7), but most simple repeats were GC-rich motifs typically found at CpG islands and bivalent domains (FIG. 4A,B; Tables II, III)(Ku et al., 2008). Short interspersed nuclear elements (SINE), long interspersed nuclear elements (LINE), and long-terminal repeats (LTR) were significantly under-represented. (TC)n and (TG)n repeats were over-represented specifically on ChrX, but <20% of strong EZH2 sites contained such repeats. Because flanking regions may play a role in spreading, we examined 3-kb flanks to either side of a strong site. Again, low-complexity and simple repeats were over-represented, and LINE1 and LTR were under-represented on both ChrX and Chr13 (FIG. 4A,C; Tables II, III). However, SINEs as a class were 1.7-fold enriched on ChrX in flanking regions, with enrichment occurring in >80% of flanking regions. This enrichment correlated with progression through XCI from d0 to d7. Moderate EZH2 sites similarly showed under-representation of LINE Is and LTRs, and modest over-representation of SINEs, low-complexity, and simple repeats (FIG. 4A,D; Tables II, III).

We performed similar analyses with known transcription factor consensus motifs. Several motifs were over-represented in EZH2 sites, but none were significantly enriched over a random model that took into account CpG content and proximity to gene promoters. De novo motif discovery using MEME (Bailey et al., 2006) retrieved only simple and low-complexity motifs, consistent with our repeat analysis. Taken together, while these data do not exclude a role for LINEs in other aspects of XCI (Chow et al., 2010; Namekawa et al., 2010), they do not support a direct role of LINEs in spreading EZH2. Positive association is instead seen for SINEs, low-complexity, and simple repeats.

TABLE II

Enriched and depleted repeat classes at EZH2 sites
Repeat classes significantly enriched or depleted at strong, strong-flanking (+/−3 kb) and moderate sites on d0, d7 and MEF are listed with odds ratios (inverted negative for depleted classes) and percentage of EZH2 sites containing (in case of enriched) or lacking (in case of depleted) a given repeat class. Only significantly enriched or depleted (Z ≥ 2.5) classes are listed with percentage, all others (Z < 2.5) are set to 0.0%.

|  | d0 odds ratio | % d0 sites | d7 odds ratio | % of d7 sites | MEF odds ratio | % of MEF sites |
|---|---|---|---|---|---|---|
| chr13-strong | | | | | | |
| Non-repeat | 1.8 | 0.0 | 3.4 | 17.3 | 1.8 | 0.0 |
| DNA transposon | −5.0 | 94.9 | −5.3 | 95.1 | −3.1 | 0.0 |
| LINE | −17.4 | 92.4 | −17.5 | 90.1 | −14.2 | 90.4 |
| LTR | −28.3 | 94.9 | −16.6 | 90.1 | −15.1 | 91.6 |
| Low_complexity | 2.6 | 60.8 | 2.1 | 51.9 | 2.1 | 56.6 |
| Others | −2.2 | 0.0 | −8.9 | 0.0 | −1.6 | 0.0 |
| SINE | −5.1 | 75.9 | −3.9 | 74.1 | −2.3 | 62.7 |
| Simple_repeat | 1.2 | 0.0 | 1.2 | 0.0 | 1.1 | 0.0 |
| chrX-strong | | | | | | |
| Non-repeat | 5.5 | 23.2 | 2.7 | 12.9 | 3.1 | 14.0 |
| DNA transposon | −4.4 | 0.0 | −1.8 | 3.0 | −68.6 | 0.0 |
| LINE | −15.9 | 92.9 | −5.5 | 78.9 | −16.4 | 90.0 |
| LTR | −13.8 | 94.6 | −8.2 | 91.2 | −38.3 | 98.0 |
| Low_complexity | 1.7 | 46.4 | 1.7 | 39.5 | 2.1 | 52.0 |
| Others | −45.4 | 0.0 | −2.8 | 3.0 | −34.6 | 0.0 |
| SINE | −4.1 | 78.6 | −1.7 | 58.5 | −4.0 | 82.0 |
| Simple_repeat | 1.4 | 0.0 | 1.6 | 64.6 | 1.6 | 58.0 |

|  | d0 odds ratio | d7 odds ratio | MEF odds ratio |
|---|---|---|---|
| chr13-flanking | | | |
| Non-repeat | −2.0 | 1.3 | −1.6 |
| DNA transposon | −1.5 | −1.5 | 1.1 |
| LINE | −3.5 | −2.4 | −2.4 |
| LTR | −3.4 | −2.0 | −2.2 |
| Low_complexity | 1.5 | 1.6 | 1.2 |

TABLE II-continued

Enriched and depleted repeat classes at EZH2 sites
Repeat classes significantly enriched or depleted at strong, strong-flanking (+/−3 kb) and moderate sites on d0, d7 and MEF are listed with odds ratios (inverted negative for depleted classes) and percentage of EZH2 sites containing (in case of enriched) or lacking (in case of depleted) a given repeat class. Only significantly enriched or depleted (Z ≥ 2.5) classes are listed with percentage, all others (Z < 2.5) are set to 0.0%.

| | | | |
|---|---|---|---|
| Others | −1.0 | −2.8 | 1.2 |
| SINE | −1.1 | 1.2 | 1.2 |
| Simple_repeat | 1.4 | 1.4 | 1.4 |
| chrX-flanking | | | |
| Non-repeat | −1.0 | −1.8 | 1.8 |
| DNA transposon | −1.0 | 1.4 | −1.2 |
| LINE | −3.9 | −2.1 | −3.9 |
| LTR | −3.4 | −2.2 | −2.9 |
| Low_complexity | 1.4 | 1.3 | 1.4 |
| Others | −1.5 | −1.1 | −1.4 |
| SINE | 1.2 | 1.7 | 1.3 |
| Simple_repeat | 1.6 | 1.5 | 1.5 |
| chr13-moderate | | | |
| Non-repeat | −1.2 | −1.1 | −1.1 |
| DNA transposon | −1.1 | −1.3 | 1.1 |
| LINE | −1.2 | −1.6 | −1.6 |
| LTR | −1.4 | −1.5 | −1.6 |
| Low_complexity | 1.4 | 1.4 | 1.6 |
| Others | −1.2 | −1.4 | −1.3 |
| SINE | −1.1 | −1.0 | −1.1 |
| Simple_repeat | 1.1 | 1.2 | 1.3 |
| chrX-moderate | | | |
| Non-repeat | −1.4 | −1.3 | −1.2 |
| DNA transposon | −1.1 | 1.3 | 1.2 |
| LINE | −1.1 | −1.2 | −1.1 |
| LTR | −1.2 | −1.2 | −1.3 |
| Low_complexity | 1.4 | 1.2 | 1.5 |
| Others | −1.5 | −1.3 | −1.3 |
| SINE | −1.0 | 1.4 | 1.1 |
| Simple_repeat | 1.2 | 1.3 | 1.2 |

TABLE III

Enriched and depleted repeat types at EZH2 sites
Repeat types significantly enriched or depleted at strong, strong-flanking (+/−3 kb) and moderate sites on d0, d7 and MEF are listed with odds ratios (inverted negative for depleted classes) and percentage of EZH2 sites containing (in case of enriched) or lacking (in case of depleted) a given repeat class. Only significantly enriched or depleted (Z ≥ 2.5) classes are listed with percentage, all others (Z < 2.5) are set to 0.0%.

| | Type | d0 odds ratio | % d0 sites | d7 odds ratio | % of d7 sites | MEF odds ratio | % of MEF sites |
|---|---|---|---|---|---|---|---|
| chr13-strong | | | | | | | |
| non-Repeat | . | 1.8 | 0.0 | 3.4 | 17.3 | 1.8 | 0.0 |
| L1Md_F2 | LINE | −90.1 | 100.0 | −109.7 | 100.0 | −82.2 | 0.0 |
| Lx8 | LINE | −83.2 | 0.0 | −10.3 | 0.0 | −6.6 | 0.0 |
| C-rich | Low_complexity | 12.3 | 12.7 | 10.4 | 13.6 | 8.2 | 6.0 |
| GA-rich | Low_complexity | 2.8 | 16.5 | 2.6 | 17.3 | 1.9 | 0.0 |
| GC-rich | Low_complexity | 36.3 | 29.1 | 27.9 | 28.4 | 42.8 | 33.7 |
| G-rich | Low_complexity | 8.9 | 8.9 | 10.9 | 11.1 | 3.1 | 0.0 |
| T-rich | Low_complexity | 3.7 | 7.6 | 2.5 | 0.0 | 1.1 | 0.0 |
| B3 | SINE | −12.8 | 98.7 | −9.5 | 97.5 | −6.0 | 97.6 |
| B4A | SINE | −126.1 | 100.0 | −165.0 | 100.0 | −10.9 | 98.8 |
| RSINE1 | SINE | −122.5 | 100.0 | −5.4 | 97.5 | −112.8 | 100.0 |
| (A)n | Simple_repeat | 2.7 | 10.1 | 1.8 | 0.0 | 2.2 | 0.0 |
| (CCG)n | Simple_repeat | 18.6 | 5.1 | 25.5 | 6.2 | 22.8 | 4.8 |
| (CGG)n | Simple_repeat | 18.2 | 3.8 | 13.5 | 3.7 | 16.2 | 2.4 |
| (CGGGG)n | Simple_repeat | 7.3 | 1.3 | 6.9 | 1.2 | 8.5 | 1.2 |
| (GA)n | Simple_repeat | 2.0 | 13.9 | 1.8 | 12.3 | 1.3 | 0.0 |
| (TA)n | Simple_repeat | −2.5 | 0.0 | −2.4 | 0.0 | −3.5 | 0.0 |
| (TC)n | Simple_repeat | 1.6 | 0.0 | 1.1 | 0.0 | −1.5 | 0.0 |
| (TG)n | Simple_repeat | −1.3 | 0.0 | −1.1 | 0.0 | 1.1 | 0.0 |
| chrX-strong | | | | | | | |
| non-Repeat | . | 5.5 | 23.2 | 2.7 | 12.9 | 3.1 | 14.0 |
| L1Md_F2 | LINE | −113.1 | 100.0 | −7.0 | 98.0 | −8.2 | 0.0 |
| Lx8 | LINE | −63.1 | 0.0 | −7.4 | 99.3 | −4.3 | 0.0 |
| C-rich | Low_complexity | 23.2 | 8.9 | 23.1 | 7.5 | 22.2 | 10.0 |
| GA-rich | Low_complexity | 2.7 | 0.0 | 2.3 | 5.4 | 2.8 | 0.0 |
| GC-rich | Low_complexity | 43.5 | 23.2 | 53.9 | 17.0 | 46.8 | 22.0 |
| G-rich | Low_complexity | 5.8 | 1.8 | 5.7 | 1.4 | 7.3 | 2.0 |
| T-rich | Low_complexity | −1.2 | 0.0 | −1.4 | 0.0 | 1.2 | 0.0 |
| B3 | SINE | −3.7 | 0.0 | −2.0 | 0.0 | −1.9 | 0.0 |
| B4A | SINE | −43.0 | 0.0 | −9.7 | 99.3 | −2.9 | 0.0 |
| RSINE1 | SINE | −5.2 | 0.0 | −2.8 | 0.0 | −3.8 | 0.0 |
| (A)n | Simple_repeat | 2.9 | 0.0 | 1.4 | 0.0 | 3.0 | 0.0 |
| (CCG)n | Simple_repeat | 17.5 | 3.6 | 57.6 | 6.8 | 54.6 | 14.0 |
| (CGG)n | Simple_repeat | 25.8 | 3.6 | 72.1 | 5.4 | 73.6 | 12.0 |
| (CGGGG)n | Simple_repeat | 9.2 | 1.8 | 40.7 | 3.4 | 10.0 | 2.0 |
| (GA)n | Simple_repeat | 2.6 | 10.7 | 2.3 | 8.8 | 1.5 | 0.0 |
| (TA)n | Simple_repeat | −4.6 | 0.0 | −11.4 | 99.3 | −36.1 | 0.0 |

TABLE III-continued

Enriched and depleted repeat types at EZH2 sites
Repeat types significantly enriched or depleted at strong, strong-flanking (+/−3 kb) and moderate sites on d0, d7 and MEF are listed with odds ratios (inverted negative for depleted classes) and percentage of EZH2 sites containing (in case of enriched) or lacking (in case of depleted) a given repeat class. Only significantly enriched or depleted (Z ≥ 2.5) classes are listed with percentage, all others (Z < 2.5) are set to 0.0%.

| | Type | d0 odds ratio | % d0 sites | d7 odds ratio | % of d7 sites | MEF odds ratio | % of MEF sites |
|---|---|---|---|---|---|---|---|
| (TC)n | Simple_repeat | 1.7 | 0.0 | 2.4 | 10.9 | −2.0 | 0.0 |
| (TG)n | Simple_repeat | 1.2 | 0.0 | 1.7 | 15.0 | 1.1 | 0.0 |
| chr13-flanking | | | | | | | |
| L1_Mm | LINE | −36.1 | 0.0 | −3.3 | 0.0 | −3.4 | 0.0 |
| L1_Mus1 | LINE | −2.8 | 0.0 | −1.5 | 0.0 | −5.6 | 0.0 |
| L1MB5 | LINE | 4.6 | 0.0 | 5.7 | 1.2 | 5.7 | 2.4 |
| L1Md_A | LINE | −1.9 | 0.0 | −40.4 | 0.0 | −3.7 | 0.0 |
| L1Md_F2 | LINE | −140.2 | 100.0 | −6.9 | 98.8 | −13.5 | 98.8 |
| L1Md_T | LINE | −5.9 | 0.0 | −66.7 | 100.0 | −3.3 | 0.0 |
| L1MEf | LINE | −9.5 | 0.0 | −9.8 | 0.0 | −9.9 | 0.0 |
| C-rich | Low_complexity | 4.0 | 6.3 | 3.1 | 4.9 | 1.5 | 0.0 |
| CT-rich | Low_complexity | 1.6 | 0.0 | 1.7 | 0.0 | 1.3 | 0.0 |
| GA-rich | Low_complexity | −1.1 | 0.0 | −1.0 | 0.0 | 1.1 | 0.0 |
| GC-rich | Low_complexity | 9.7 | 12.7 | 6.0 | 8.6 | −1.1 | 0.0 |
| B1_Mur1 | SINE | 1.5 | 0.0 | 2.3 | 12.3 | 1.0 | 0.0 |
| B1_Mur3 | SINE | 1.4 | 0.0 | 2.7 | 9.9 | 1.3 | 0.0 |
| B1F | SINE | −2.0 | 0.0 | −1.0 | 0.0 | 1.1 | 0.0 |
| B1F1 | SINE | −3.2 | 0.0 | −3.2 | 0.0 | 1.1 | 0.0 |
| B2_Mm1a | SINE | 1.1 | 0.0 | 1.4 | 0.0 | 2.8 | 8.4 |
| ID_B1 | SINE | 1.7 | 0.0 | 1.6 | 0.0 | 1.3 | 0.0 |
| ID4 | SINE | 1.8 | 0.0 | −1.1 | 0.0 | 1.7 | 0.0 |
| MIR | SINE | 1.7 | 0.0 | 2.5 | 16.0 | 2.5 | 14.5 |
| MIRb | SINE | 2.0 | 13.9 | 2.7 | 16.0 | 2.1 | 14.5 |
| MIRc | SINE | 4.0 | 12.7 | 1.8 | 0.0 | 4.2 | 14.5 |
| PB1 | SINE | 1.7 | 0.0 | 1.2 | 0.0 | −1.2 | 0.0 |
| PB1D10 | SINE | 1.2 | 0.0 | 1.6 | 0.0 | 1.1 | 0.0 |
| RSINE1 | SINE | −1.7 | 0.0 | −1.7 | 0.0 | 1.0 | 0.0 |
| (CA)n | Simple_repeat | 1.7 | 41.8 | 1.4 | 0.0 | 1.6 | 47.0 |
| (CAGAGA)n | Simple_repeat | 1.8 | 0.0 | 1.7 | 0.0 | 3.3 | 4.8 |
| (CCA)n | Simple_repeat | 2.5 | 0.0 | 3.7 | 3.7 | 6.1 | 6.0 |
| (CCG)n | Simple_repeat | 12.4 | 1.3 | 4.4 | 0.0 | −2.5 | 0.0 |
| (GGA)n | Simple_repeat | 3.2 | 5.1 | 1.6 | 0.0 | 2.3 | 0.0 |
| (T)n | Simple_repeat | 2.7 | 15.2 | 1.9 | 0.0 | 2.4 | 14.5 |
| (TCTG)n | Simple_repeat | 2.3 | 0.0 | 2.8 | 6.2 | 3.3 | 6.0 |
| (TG)n | Simple_repeat | 1.3 | 0.0 | 1.5 | 42.0 | 1.2 | 0.0 |
| (TTTTG)n | Simple_repeat | 1.6 | 0.0 | 2.2 | 0.0 | 1.6 | 0.0 |
| chrX-flanking | | | | | | | |
| L1_Mm | LINE | −48.1 | 0.0 | −129.4 | 100.0 | −41.9 | 0.0 |
| L1_Mus1 | LINE | −2.3 | 0.0 | −4.0 | 96.6 | −2.7 | 0.0 |
| L1MB5 | LINE | 1.5 | 0.0 | 5.7 | 2.7 | 1.6 | 0.0 |
| L1Md_A | LINE | −61.2 | 0.0 | −161.6 | 100.0 | −54.5 | 0.0 |
| L1Md_F2 | LINE | −3.8 | 92.9 | −3.7 | 91.2 | −2.3 | 0.0 |
| L1Md_T | LINE | −7.8 | 0.0 | −7.1 | 98.0 | −3.7 | 0.0 |
| L1MEf | LINE | 3.6 | 0.0 | 4.5 | 1.4 | −4.9 | 0.0 |
| C-rich | Low_complexity | 5.1 | 3.6 | 11.8 | 6.1 | 13.8 | 8.0 |
| CT-rich | Low_complexity | 2.0 | 0.0 | 1.9 | 10.9 | 2.3 | 0.0 |
| GA-rich | Low_complexity | 1.3 | 0.0 | 2.5 | 10.9 | 2.2 | 0.0 |
| GC-rich | Low_complexity | 23.5 | 12.5 | 7.7 | 5.4 | 9.1 | 6.0 |
| B1_Mur1 | SINE | 1.3 | 0.0 | 2.1 | 11.6 | 1.7 | 0.0 |
| B1_Mur3 | SINE | −23.7 | 0.0 | 2.3 | 7.5 | 1.5 | 0.0 |
| B1F | SINE | −1.1 | 0.0 | 2.1 | 18.4 | 2.0 | 0.0 |
| B1F1 | SINE | 1.5 | 0.0 | 2.3 | 8.8 | 1.3 | 0.0 |
| B2_Mm1a | SINE | −1.2 | 0.0 | 1.8 | 0.0 | 2.7 | 0.0 |
| ID_B1 | SINE | −1.0 | 0.0 | 2.0 | 25.9 | 2.1 | 24.0 |
| ID4 | SINE | −1.5 | 0.0 | 2.3 | 12.2 | 2.5 | 12.0 |
| MIR | SINE | 1.8 | 0.0 | 2.0 | 16.3 | 2.3 | 20.0 |
| MIRb | SINE | 2.2 | 17.9 | 2.5 | 21.1 | 1.7 | 0.0 |
| MIRc | SINE | 3.1 | 10.7 | 3.1 | 10.9 | 2.1 | 0.0 |
| PB1 | SINE | 2.7 | 0.0 | 3.0 | 8.8 | 3.5 | 10.0 |
| PB1D10 | SINE | 2.1 | 19.6 | 2.0 | 21.1 | 1.2 | 0.0 |
| RSINE1 | SINE | 1.7 | 0.0 | 1.7 | 24.5 | 1.1 | 0.0 |
| (CA)n | Simple_repeat | 1.3 | 0.0 | 1.1 | 0.0 | 1.0 | 0.0 |
| (CAGAGA)n | Simple_repeat | −10.4 | 0.0 | 8.9 | 2.7 | −9.6 | 0.0 |
| (CCA)n | Simple_repeat | 3.6 | 0.0 | 4.7 | 4.1 | −5.5 | 0.0 |
| (CCG)n | Simple_repeat | 29.0 | 8.9 | 6.0 | 1.4 | 11.7 | 2.0 |
| (GGA)n | Simple_repeat | 3.4 | 0.0 | 5.1 | 4.1 | 2.0 | 0.0 |
| (T)n | Simple_repeat | 2.1 | 0.0 | 1.2 | 0.0 | 2.4 | 0.0 |
| (TCTG)n | Simple_repeat | −6.1 | 0.0 | 2.4 | 0.0 | 1.9 | 0.0 |
| (TG)n | Simple_repeat | 2.5 | 51.8 | 1.6 | 34.0 | 2.3 | 44.0 |
| (TTTTG)n | Simple_repeat | −2.2 | 0.0 | 2.2 | 8.2 | 3.2 | 12.0 |

TABLE III-continued

Enriched and depleted repeat types at EZH2 sites
Repeat types significantly enriched or depleted at strong, strong-flanking (+/−3 kb) and moderate sites
on d0, d7 and MEF are listed with odds ratios (inverted negative for depleted classes) and percentage of EZH2
sites containing (in case of enriched) or lacking (in case of depleted) a given repeat class. Only significantly
enriched or depleted (Z ≥ 2.5) classes are listed with percentage, all others (Z < 2.5) are set to 0.0%.

| | Type | d0 odds ratio | % d0 sites | d7 odds ratio | % of d7 sites | MEF odds ratio | % of MEF sites |
|---|---|---|---|---|---|---|---|
| chr13-moderate | | | | | | | |
| non-Repeat | . | −1.2 | 0.0 | −1.1 | 0.0 | −1.1 | 0.0 |
| MER5B | DNA | 1.5 | 0.0 | 1.1 | 0.0 | 1.0 | 0.0 |
| Tigger5 | DNA | 1.1 | 0.0 | 1.5 | 0.0 | −36.4 | 0.0 |
| HAL1-3A_ME | LINE | −2.4 | 0.0 | −1.2 | 0.0 | −1.3 | 0.0 |
| L1_Mm | LINE | 1.1 | 0.0 | −2.2 | 0.0 | −3.6 | 0.0 |
| L1_Mur1 | LINE | −1.6 | 0.0 | −2.4 | 0.0 | −3.3 | 0.0 |
| L1_Mur2 | LINE | −2.3 | 0.0 | −1.7 | 0.0 | −1.3 | 0.0 |
| L1_Mur3 | LINE | −1.0 | 0.0 | −1.6 | 0.0 | −1.9 | 0.0 |
| L1_Mus3 | LINE | −1.8 | 0.0 | −2.1 | 98.9 | −1.1 | 0.0 |
| L1MC1 | LINE | 1.1 | 0.0 | −1.4 | 0.0 | 1.5 | 0.0 |
| L1Md_A | LINE | −1.8 | 0.0 | −6.9 | 99.7 | −6.8 | 99.7 |
| L1Md_F | LINE | −1.3 | 0.0 | −1.6 | 0.0 | −45.5 | 0.0 |
| L1Md_F2 | LINE | 1.1 | 0.0 | −2.1 | 97.0 | −2.6 | 97.8 |
| L1Md_T | LINE | −1.4 | 0.0 | −4.8 | 99.3 | −4.6 | 99.3 |
| L1MD1 | LINE | −2.6 | 0.0 | 1.2 | 0.0 | −17.0 | 0.0 |
| L1ME4a | LINE | 3.5 | 0.3 | 2.3 | 0.0 | 1.1 | 0.0 |
| L1VL1 | LINE | 1.1 | 0.0 | −28.2 | 0.0 | 1.1 | 0.0 |
| L1VL2 | LINE | 1.4 | 0.0 | −1.2 | 0.0 | −2.9 | 0.0 |
| L1VL4 | LINE | −2.5 | 0.0 | −1.7 | 0.0 | −2.3 | 0.0 |
| L2a | LINE | 1.1 | 0.0 | −1.2 | 0.0 | −1.8 | 0.0 |
| L2b | LINE | 1.3 | 0.0 | 1.4 | 0.0 | 1.1 | 0.0 |
| AT_rich | Low_complexity | 1.0 | 0.0 | 1.0 | 0.0 | 1.1 | 0.0 |
| C-rich | Low_complexity | 3.6 | 1.6 | 4.2 | 1.8 | 3.2 | 1.3 |
| CT-rich | Low_complexity | 1.2 | 0.0 | 1.4 | 0.0 | 1.2 | 0.0 |
| G-rich | Low_complexity | 2.6 | 1.1 | 2.8 | 1.2 | 2.1 | 0.0 |
| GA-rich | Low_complexity | 1.3 | 0.0 | 1.1 | 0.0 | 1.9 | 5.7 |
| GC-rich | Low_complexity | 9.9 | 3.9 | 12.9 | 4.6 | 17.4 | 5.9 |
| polypyrimidine | Low_complexity | 1.6 | 0.0 | 1.4 | 0.0 | 1.7 | 0.0 |
| T-rich | Low_complexity | 1.5 | 0.0 | 1.4 | 0.0 | 2.3 | 2.2 |
| ETnERV2-int | LTR | −7.1 | 0.0 | −1.6 | 0.0 | −42.3 | 0.0 |
| ETnERV3-int | LTR | −16.5 | 0.0 | −14.4 | 0.0 | −9.2 | 0.0 |
| IAPEz-int | LTR | −1.7 | 0.0 | −6.1 | 0.0 | −8.0 | 0.0 |
| MER89 | LTR | 1.6 | 0.0 | −12.2 | 0.0 | −8.4 | 0.0 |
| MMETn-int | LTR | −41.0 | 0.0 | −3.6 | 0.0 | −24.9 | 0.0 |
| MTB_Mm-int | LTR | −1.0 | 0.0 | −9.3 | 0.0 | −6.4 | 0.0 |
| RLTR16 | LTR | 1.2 | 0.0 | −31.1 | 0.0 | 1.7 | 0.0 |
| RLTR26 | LTR | −1.0 | 0.0 | 1.9 | 0.0 | −1.0 | 0.0 |
| RMER21B | LTR | 1.3 | 0.0 | −1.2 | 0.0 | 1.5 | 0.0 |
| RMER1C | Other | −1.1 | 0.0 | −1.8 | 0.0 | −2.2 | 0.0 |
| 5S | rRNA | 2.1 | 0.0 | −9.1 | 0.0 | −5.8 | 0.0 |
| (A)n | Simple_repeat | 1.5 | 0.0 | 1.9 | 4.1 | 1.6 | 0.0 |
| (ATG)n | Simple_repeat | −2.1 | 0.0 | 1.6 | 0.0 | −13.6 | 0.0 |
| (CA)n | Simple_repeat | 1.1 | 0.0 | 1.2 | 0.0 | 1.2 | 0.0 |
| (CACCC)n | Simple_repeat | 1.8 | 0.0 | 1.1 | 0.0 | 1.4 | 0.0 |
| (CAG)n | Simple_repeat | 1.6 | 0.0 | 2.2 | 0.0 | −1.1 | 0.0 |
| (CAT)n | Simple_repeat | −1.5 | 0.0 | 1.2 | 0.0 | −1.6 | 0.0 |
| (CCA)n | Simple_repeat | 1.3 | 0.0 | 2.0 | 0.0 | 2.5 | 0.0 |
| (CCAA)n | Simple_repeat | −1.3 | 0.0 | 1.0 | 0.0 | 1.4 | 0.0 |
| (CCCCCA)n | Simple_repeat | 3.1 | 0.6 | 1.6 | 0.0 | 3.3 | 0.0 |
| (CCCCCT)n | Simple_repeat | 2.8 | 0.0 | 3.4 | 0.3 | 3.6 | 0.0 |
| (CCCCG)n | Simple_repeat | 11.0 | 0.7 | 8.5 | 0.6 | 12.4 | 0.8 |
| (CCG)n | Simple_repeat | 12.1 | 0.9 | 13.7 | 1.0 | 22.4 | 1.2 |
| (CG)n | Simple_repeat | 5.9 | 0.3 | 6.0 | 0.4 | 5.4 | 0.3 |
| (CGG)n | Simple_repeat | 5.1 | 0.3 | 8.0 | 0.5 | 10.8 | 0.5 |
| (CGGGG)n | Simple_repeat | 9.5 | 0.3 | 11.4 | 0.4 | 7.5 | 0.3 |
| (CGTG)n | Simple_repeat | −1.0 | 0.0 | 2.3 | 0.0 | 1.6 | 0.0 |
| (CTG)n | Simple_repeat | 1.7 | 0.0 | 3.3 | 0.5 | 4.1 | 0.5 |
| (GA)n | Simple_repeat | 1.4 | 5.2 | 1.3 | 0.0 | 1.6 | 5.9 |
| (GAGAA)n | Simple_repeat | 4.0 | 0.6 | 2.2 | 0.0 | 2.1 | 0.0 |
| (GGA)n | Simple_repeat | 1.8 | 0.0 | 1.4 | 0.0 | −1.2 | 0.0 |
| (T)n | Simple_repeat | 1.8 | 3.6 | 1.9 | 3.7 | 1.7 | 3.2 |
| (TA)n | Simple_repeat | −1.3 | 0.0 | −1.4 | 0.0 | 1.0 | 0.0 |
| (TC)n | Simple_repeat | 1.2 | 0.0 | 1.1 | 0.0 | 1.3 | 0.0 |
| (TCC)n | Simple_repeat | 1.2 | 0.0 | 1.2 | 0.0 | −1.2 | 0.0 |
| (TCCCC)n | Simple_repeat | 1.3 | 0.0 | 2.3 | 0.0 | 2.3 | 0.0 |
| (TG)n | Simple_repeat | 1.0 | 0.0 | 1.1 | 0.0 | 1.2 | 0.0 |
| (TGG)n | Simple_repeat | 3.0 | 1.0 | 2.8 | 1.0 | 1.8 | 0.0 |
| (TGGGGG)n | Simple_repeat | 2.4 | 0.0 | 2.1 | 0.0 | 1.6 | 0.0 |
| (TTTA)n | Simple_repeat | 1.4 | 0.0 | 1.4 | 0.0 | −1.1 | 0.0 |
| (TTTTC)n | Simple_repeat | 1.1 | 0.0 | 1.2 | 0.0 | −1.8 | 0.0 |

TABLE III-continued

Enriched and depleted repeat types at EZH2 sites
Repeat types significantly enriched or depleted at strong, strong-flanking (+/−3 kb) and moderate sites
on d0, d7 and MEF are listed with odds ratios (inverted negative for depleted classes) and percentage of EZH2
sites containing (in case of enriched) or lacking (in case of depleted) a given repeat class. Only significantly
enriched or depleted (Z ≥ 2.5) classes are listed with percentage, all others (Z < 2.5) are set to 0.0%.

| | Type | d0 odds ratio | % d0 sites | d7 odds ratio | % of d7 sites | MEF odds ratio | % of MEF sites |
|---|---|---|---|---|---|---|---|
| B1_Mm | SINE | −1.2 | 0.0 | 1.3 | 0.0 | −1.2 | 0.0 |
| B1_Mur3 | SINE | 1.1 | 0.0 | 1.1 | 0.0 | −1.3 | 0.0 |
| B1_Mur4 | SINE | −1.1 | 0.0 | 1.1 | 0.0 | −1.0 | 0.0 |
| B1_Mus1 | SINE | 1.1 | 0.0 | −1.1 | 0.0 | −1.4 | 0.0 |
| B1_Mus2 | SINE | 1.1 | 0.0 | −1.1 | 0.0 | −1.2 | 0.0 |
| B1F | SINE | −1.2 | 0.0 | 1.1 | 0.0 | 1.0 | 0.0 |
| B1F1 | SINE | −1.7 | 0.0 | −1.1 | 0.0 | −1.7 | 0.0 |
| B2_Mm2 | SINE | −1.1 | 0.0 | −1.3 | 0.0 | −1.1 | 0.0 |
| B3 | SINE | −1.4 | 93.2 | −1.0 | 0.0 | −1.1 | 0.0 |
| B3A | SINE | −1.1 | 0.0 | −1.0 | 0.0 | −1.2 | 0.0 |
| B4A | SINE | −1.2 | 0.0 | −1.3 | 0.0 | −1.0 | 0.0 |
| ID | SINE | −1.3 | 0.0 | −1.1 | 0.0 | −1.2 | 0.0 |
| ID_B1 | SINE | −1.1 | 0.0 | 1.3 | 0.0 | 1.0 | 0.0 |
| ID4 | SINE | 1.7 | 2.8 | 1.0 | 0.0 | −1.1 | 0.0 |
| ID4_b | SINE | −1.3 | 0.0 | −1.2 | 0.0 | −1.6 | 0.0 |
| MamSINE1 | SINE | −3.9 | 0.0 | −4.0 | 0.0 | 3.8 | 0.0 |
| MIR | SINE | 1.3 | 0.0 | −1.1 | 0.0 | 1.2 | 0.0 |
| MIR3 | SINE | −1.1 | 0.0 | 1.5 | 0.0 | −1.7 | 0.0 |
| MIRb | SINE | 1.0 | 0.0 | −1.2 | 0.0 | −1.4 | 0.0 |
| MIRc | SINE | 1.1 | 0.0 | 1.2 | 0.0 | 1.4 | 0.0 |
| MIRm | SINE | 1.3 | 0.0 | 2.2 | 1.1 | 2.5 | 0.0 |
| PB1 | SINE | 1.0 | 0.0 | 1.3 | 0.0 | −1.8 | 0.0 |
| PB1D10 | SINE | −1.2 | 0.0 | −1.0 | 0.0 | −1.1 | 0.0 |
| PB1D7 | SINE | −1.2 | 0.0 | 1.2 | 0.0 | 1.2 | 0.0 |
| PB1D9 | SINE | −1.1 | 0.0 | −1.3 | 0.0 | −1.4 | 0.0 |
| RSINE1 | SINE | −1.2 | 0.0 | −1.2 | 0.0 | −1.4 | 0.0 |
| tRNA-Ala-GCA | tRNA | 1.2 | 0.0 | −7.6 | 0.0 | −5.8 | 0.0 |
| tRNA-Ala-GCY | tRNA | −2.1 | 0.0 | 2.0 | 0.0 | −1.2 | 0.0 |
| chrX-moderate | | | | | | | |
| non-Repeat | . | −1.4 | 96.4 | −1.3 | 95.8 | −1.2 | 0.0 |
| MER5B | DNA | −1.1 | 0.0 | 1.9 | 0.9 | 1.3 | 0.0 |
| Tigger5 | DNA | −1.3 | 0.0 | −1.1 | 0.0 | 3.0 | 0.4 |
| HAL1-3A_ME | LINE | 1.5 | 0.0 | 1.2 | 0.0 | 3.1 | 0.7 |
| L1_Mm | LINE | −1.4 | 0.0 | −2.0 | 98.7 | −1.9 | 98.7 |
| L1_Mur1 | LINE | −1.1 | 0.0 | −2.8 | 99.6 | −1.4 | 0.0 |
| L1_Mur2 | LINE | −1.1 | 0.0 | −2.0 | 98.8 | −1.3 | 0.0 |
| L1_Mur3 | LINE | −1.1 | 0.0 | −1.6 | 98.1 | 1.1 | 0.0 |
| L1_Mus3 | LINE | −1.4 | 0.0 | −1.9 | 97.8 | −1.9 | 97.9 |
| L1MC1 | LINE | −1.5 | 0.0 | 1.1 | 0.0 | 3.3 | 0.6 |
| L1Md_A | LINE | −1.5 | 0.0 | −2.8 | 98.6 | −3.1 | 99.0 |
| L1Md_F | LINE | −1.4 | 0.0 | −2.0 | 99.2 | −1.1 | 0.0 |
| L1Md_F2 | LINE | 1.1 | 0.0 | −1.5 | 91.7 | −1.7 | 93.1 |
| L1Md_T | LINE | −1.1 | 0.0 | −3.4 | 98.5 | −2.6 | 98.2 |
| L1MD1 | LINE | 3.6 | 0.3 | −1.5 | 0.0 | 1.5 | 0.0 |
| L1ME4a | LINE | 1.0 | 0.0 | 2.1 | 0.3 | −1.8 | 0.0 |
| L1VL1 | LINE | −3.6 | 0.0 | −2.6 | 99.8 | −1.0 | 0.0 |
| L1VL2 | LINE | −1.9 | 0.0 | −2.1 | 99.6 | −2.3 | 0.0 |
| L1VL4 | LINE | −1.1 | 0.0 | −1.8 | 99.3 | −1.9 | 0.0 |
| L2a | LINE | −1.4 | 0.0 | 1.5 | 2.8 | 1.4 | 0.0 |
| L2b | LINE | −1.4 | 0.0 | 1.7 | 1.2 | 1.3 | 0.0 |
| AT-rich | Low_complexity | 1.1 | 0.0 | −1.2 | 87.0 | 1.3 | 15.3 |
| C-rich | Low_complexity | 7.8 | 1.4 | 4.0 | 0.7 | 4.8 | 0.8 |
| CT-rich | Low_complexity | 1.5 | 3.2 | 1.7 | 3.3 | 1.1 | 0.0 |
| G-rich | Low_complexity | 10.4 | 1.2 | 4.2 | 0.6 | 4.0 | 0.4 |
| GA-rich | Low_complexity | 1.8 | 3.5 | 1.8 | 3.5 | 1.6 | 1.8 |
| GC-rich | Low_complexity | 13.9 | 2.1 | 9.9 | 1.7 | 17.5 | 2.1 |
| polypyrimidine | Low_complexity | 3.3 | 0.3 | 1.3 | 0.0 | 2.9 | 0.0 |
| T-rich | Low_complexity | 1.4 | 0.0 | 1.1 | 0.0 | 1.6 | 0.0 |
| ETnERV2-int | LTR | −5.0 | 99.8 | −3.1 | 99.7 | −4.2 | 0.0 |
| ETnERV3-int | LTR | −2.3 | 0.0 | −174.2 | 100.0 | −46.8 | 0.0 |
| IAPEz-int | LTR | −3.1 | 0.0 | −7.6 | 99.9 | −132.8 | 100.0 |
| MER89 | LTR | 1.9 | 0.0 | 5.1 | 0.1 | −4.3 | 0.0 |
| MMETn-int | LTR | −2.4 | 0.0 | −17.6 | 100.0 | −1.7 | 0.0 |
| MTB_Mm-int | LTR | −4.4 | 0.0 | 6.9 | 0.1 | −3.4 | 0.0 |
| RLTR16 | LTR | 4.5 | 0.2 | 1.3 | 0.0 | 1.1 | 0.0 |
| RLTR26 | LTR | −1.7 | 0.0 | 1.1 | 0.0 | 3.3 | 0.7 |
| RMER21B | LTR | 4.1 | 0.2 | 1.9 | 0.0 | 1.3 | 0.0 |
| RMER1C | Other | −1.6 | 0.0 | −3.2 | 99.7 | −2.0 | 0.0 |
| 5S | rRNA | −13.2 | 0.0 | 3.3 | 0.2 | −9.3 | 0.0 |
| (A)n | Simple_repeat | 1.6 | 2.4 | 1.3 | 0.0 | 1.6 | 0.0 |
| (ATG)n | Simple_repeat | 3.0 | 0.4 | −1.1 | 0.0 | −1.5 | 0.0 |

TABLE III-continued

Enriched and depleted repeat types at EZH2 sites
Repeat types significantly enriched or depleted at strong, strong-flanking (+/−3 kb) and moderate sites on d0, d7 and MEF are listed with odds ratios (inverted negative for depleted classes) and percentage of EZH2 sites containing (in case of enriched) or lacking (in case of depleted) a given repeat class. Only significantly enriched or depleted (Z ≥ 2.5) classes are listed with percentage, all others (Z < 2.5) are set to 0.0%.

|  | Type | d0 odds ratio | % d0 sites | d7 odds ratio | % of d7 sites | MEF odds ratio | % of MEF sites |
|---|---|---|---|---|---|---|---|
| (CA)n | Simple_repeat | 1.2 | 0.0 | 1.3 | 9.2 | 1.3 | 0.0 |
| (CACCC)n | Simple_repeat | 3.5 | 0.0 | 3.8 | 0.2 | 4.0 | 0.0 |
| (CAG)n | Simple_repeat | 3.6 | 0.4 | 3.2 | 0.4 | −1.2 | 0.0 |
| (CAT)n | Simple_repeat | 1.4 | 0.0 | 2.4 | 0.3 | −1.2 | 0.0 |
| (CCA)n | Simple_repeat | 1.2 | 0.0 | 1.6 | 0.0 | 2.6 | 0.6 |
| (CCAA)n | Simple_repeat | 1.9 | 0.0 | 2.7 | 0.3 | 1.8 | 0.0 |
| (CCCCCA)n | Simple_repeat | 1.2 | 0.0 | −1.0 | 0.0 | −6.2 | 0.0 |
| (CCCCCT)n | Simple_repeat | 1.8 | 0.0 | 5.1 | 0.2 | 2.7 | 0.0 |
| (CCCCG)n | Simple_repeat | 10.7 | 0.2 | 8.1 | 0.1 | 8.4 | 0.2 |
| (CCG)n | Simple_repeat | 11.4 | 0.6 | 12.0 | 0.6 | 18.5 | 0.8 |
| (CG)n | Simple_repeat | 6.5 | 0.3 | 4.5 | 0.2 | 8.4 | 0.3 |
| (CGG)n | Simple_repeat | 13.3 | 0.5 | 13.3 | 0.5 | 17.8 | 0.6 |
| (CGGGG)n | Simple_repeat | 12.4 | 0.3 | 10.7 | 0.2 | 12.8 | 0.3 |
| (CGTG)n | Simple_repeat | −5.1 | 0.0 | 7.1 | 0.2 | 2.6 | 0.0 |
| (CTG)n | Simple_repeat | 2.2 | 0.0 | 4.6 | 0.4 | 4.0 | 0.4 |
| (GA)n | Simple_repeat | 1.4 | 4.1 | 1.6 | 4.7 | 1.5 | 0.0 |
| (GAGAA)n | Simple_repeat | −1.7 | 0.0 | −1.3 | 0.0 | 2.6 | 0.0 |
| (GGA)n | Simple_repeat | 1.7 | 0.0 | 2.6 | 0.7 | 2.7 | 0.7 |
| (T)n | Simple_repeat | 1.7 | 2.7 | 1.4 | 2.2 | 1.3 | 0.0 |
| (TA)n | Simple_repeat | −1.0 | 0.0 | −1.6 | 96.9 | −1.2 | 0.0 |
| (TC)n | Simple_repeat | 1.5 | 4.5 | 1.6 | 5.1 | 1.3 | 0.0 |
| (TCC)n | Simple_repeat | 1.6 | 0.0 | 2.4 | 0.7 | 3.0 | 0.7 |
| (TCCCC)n | Simple_repeat | 1.4 | 0.0 | 3.7 | 0.1 | 2.2 | 0.0 |
| (TG)n | Simple_repeat | 1.2 | 8.7 | 1.4 | 9.8 | 1.1 | 0.0 |
| (TGG)n | Simple_repeat | 1.7 | 0.0 | 1.6 | 0.0 | −1.2 | 0.0 |
| (TGGGGG)n | Simple_repeat | 2.4 | 0.0 | 3.5 | 0.1 | 1.9 | 0.0 |
| (TTTA)n | Simple_repeat | 2.0 | 1.8 | −1.1 | 0.0 | 1.5 | 0.0 |
| (TTTTC)n | Simple_repeat | −2.2 | 0.0 | 2.2 | 0.6 | 1.3 | 0.0 |
| B1_Mm | SINE | −1.1 | 0.0 | 1.3 | 3.4 | 1.1 | 0.0 |
| B1_Mur3 | SINE | −1.1 | 0.0 | 1.5 | 2.0 | 1.2 | 0.0 |
| B1_Mur4 | SINE | −1.1 | 0.0 | 1.6 | 3.3 | −1.2 | 0.0 |
| B1_Mus1 | SINE | −1.0 | 0.0 | 1.4 | 7.6 | 1.2 | 0.0 |
| B1_Mus2 | SINE | 1.0 | 0.0 | 1.4 | 5.4 | −1.0 | 0.0 |
| B1F | SINE | 1.1 | 0.0 | 1.4 | 4.6 | −1.1 | 0.0 |
| B1F1 | SINE | −1.6 | 0.0 | 1.4 | 2.0 | 1.0 | 0.0 |
| B2_Mm2 | SINE | 1.2 | 0.0 | 1.3 | 5.3 | 1.2 | 0.0 |
| B3 | SINE | −1.0 | 0.0 | 1.3 | 10.1 | 1.2 | 0.0 |
| B3A | SINE | −1.0 | 0.0 | 1.3 | 5.7 | 1.1 | 0.0 |
| B4A | SINE | −1.7 | 97.3 | 1.3 | 5.4 | −1.0 | 0.0 |
| ID | SINE | −1.5 | 0.0 | 1.7 | 0.9 | −1.9 | 0.0 |
| ID_B1 | SINE | −1.0 | 0.0 | 1.4 | 8.1 | −1.1 | 0.0 |
| ID4 | SINE | −1.4 | 0.0 | 1.3 | 2.2 | 1.4 | 0.0 |
| ID4_b | SINE | 1.0 | 0.0 | 1.4 | 2.8 | 1.1 | 0.0 |
| MamSINE1 | SINE | −11.8 | 0.0 | 2.6 | 0.2 | −8.9 | 0.0 |
| MIR | SINE | 1.3 | 0.0 | 1.5 | 4.4 | 1.2 | 0.0 |
| MIR3 | SINE | 1.4 | 0.0 | 2.1 | 1.7 | 1.3 | 0.0 |
| MIRb | SINE | 1.1 | 0.0 | 1.7 | 4.4 | 1.5 | 3.3 |
| MIRc | SINE | 1.4 | 0.0 | 1.8 | 2.5 | 1.3 | 0.0 |
| MIRm | SINE | 1.5 | 0.0 | 1.8 | 0.8 | 1.2 | 0.0 |
| PB1 | SINE | −1.1 | 0.0 | 1.8 | 1.7 | −1.4 | 0.0 |
| PB1D10 | SINE | −1.1 | 0.0 | 1.5 | 5.8 | 1.3 | 0.0 |
| PB1D7 | SINE | 1.1 | 0.0 | 1.6 | 2.1 | 1.3 | 0.0 |
| PB1D9 | SINE | 1.2 | 0.0 | 1.6 | 2.4 | 1.1 | 0.0 |
| RSINE1 | SINE | −1.1 | 0.0 | 1.4 | 8.0 | 1.1 | 0.0 |
| tRNA-Ala-GCA | tRNA | −1.0 | 0.0 | 2.9 | 0.1 | 4.3 | 0.2 |
| tRNA-Ala-GCY | tRNA | −1.5 | 0.0 | 2.1 | 0.4 | 1.6 | 0.0 |

Example 7

A Hierarchy of EZH2 Sites

Figure 5B:
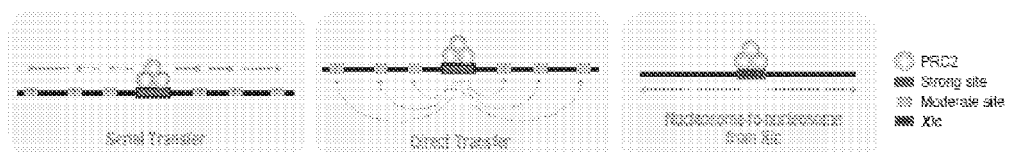

What is the relationship between strong and moderate sites and how does spreading occur between them? Exemplified by the Slc16a2-Rnf12 (Rlim) region (FIG. 5A) and the MamId1 locus (FIG. 14), bivalent domains show high EZH2 coverage on d0. During XCI, new strong sites were acquired (non-bivalent for MamId1 in FIG. 14, two bivalent ones in FIG. 5) and multiple closely-spaced moderate sites appeared near pre-existing strong sites, concurrently with increased density of H3K27me3. With one strong site for every 20-40 moderate sites, we hypothesize that strong sites might serve as recruiting 'hubs' from which EZH2 is passed onto adjacent moderate sites. Three models of spreading are possible (FIG. 5B). EZH2 may be relayed from a strong site to multiple adjacent moderate sites through 'serial transfer'. Alternatively, a strong site could relay EZH2 to moderate sites via 'direct transfer' through long-range 3D interactions. Finally, moderate and strong sites may not be functionally linked and spreading could instead occur nucleosome-by-nucleosome from the Xic.

To gain insight, densities of strong and moderate EZH2 sites and H3K27me3 were calculated over the lengths of Chr13 and ChrX (FIG. 6A) and analyzed positional correlations and significance (Pearson R and Z) between moderate EZH2 sites and strong sites, as well as moderate sites and H3K27me3. On d0, these correlations had only borderline significance on both Chr13 and ChrX. On d7, correlations were unchanged for Chr13 but increased greatly on ChrX (Note overlapping red, orange, and black lines from d0 to d7). The correlation of H3K27me3 with moderate sites was especially strong (black R=0.76, Z=13.2) and was highly significant even at small bin sizes (0.5 Mb). These data contain two separable observations regarding possible modes of XCI spreading: First, the presence of distinct peaks lacking height order (i.e. largest to smallest from Xic to telomere) in EZH2 and H3K27me3 densities over ChrX on d7 argues against nucleosome-by-nucleosome spreading of XCI, which might be expected to manifest as a continuous chromosomal gradient descending from the Xic. Second, the XCI-specific increase in positional correlation illustrates that moderate sites cluster near strong sites on ChrX on d7, an event highly unlikely to be due to chance (Z=8.2). Thus, we suggest a functional link between strong and moderate EZH2 sites, perhaps with strong sites seeding moderate sites in their vicinity to spread H3K27me3.

Figure 6B:
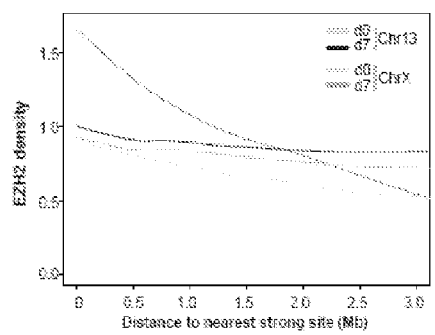
Figure 6C:
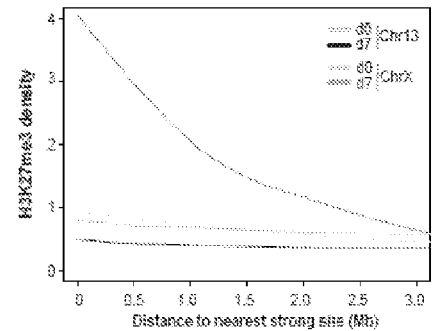
Figure 7A:
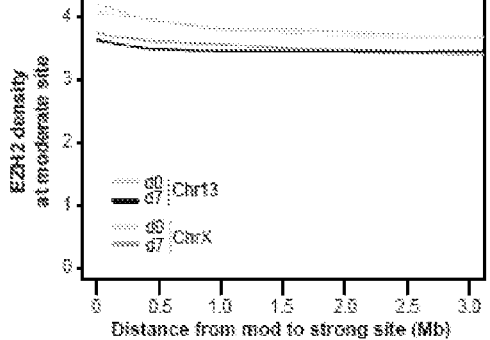

Both serial and direct transfer models (FIG. 5B) might predict a sensitivity of spreading to physical distance. To ask how EZH2 and H3K27me3 densities of a sliding window change as a function of distance from the nearest strong EZH2 site, we plotted trendlines of EZH2 and H3K27me3 densities over megabase-scale distances (FIGS. 6B,C). On Chr13, EZH2 and H3K27me3 densities did not correlate with distance from the nearest strong site on either d0 or d7. The d0 ChrX profile looked nearly identical to those of Chr13. On d7 however, EZH2 and H3K27me3 densities increased dramatically around strong sites (near 0, FIG. 6B,C), consistent with metagene and metasite profiles (FIG. 1,3). Intriguingly, these densities decayed with distance from the nearest strong site. EZH2 densities dropped 3-fold down to baseline by 3 Mb, and H3K27me3 densities dropped 4-fold over the same distance. These observations revealed a gradient of EZH2 binding and catalytic activity around strong sites, arguing for distance-dependent effects at the megabase-scale specific to ChrX during XCI. Are EZH2 and H3K27me3 densities of a given moderate site also sensitive to physical distance between strong and moderate sites? On Chr13, similar to trendlines for overall coverage densities (FIGS. 6B,C), EZH2 and H3K27me3 densities at moderate sites did not correlate with distance to the nearest strong site on either d0 or d7 (FIG. 7A,B). This was also the case for ChrX on d0. Analysis of ChrX on d7 revealed that the H3K27me3 trendline for moderate sites (FIG. 7B) displayed a similar decay (FIG. 6C) in H3K27me3 density with increasing distance to the nearest strong site. Importantly, the EZH2 trendline showed no significant distance-dependent effect at all over 0-3 Mb (FIG. 7A,B).

Figure 6A:
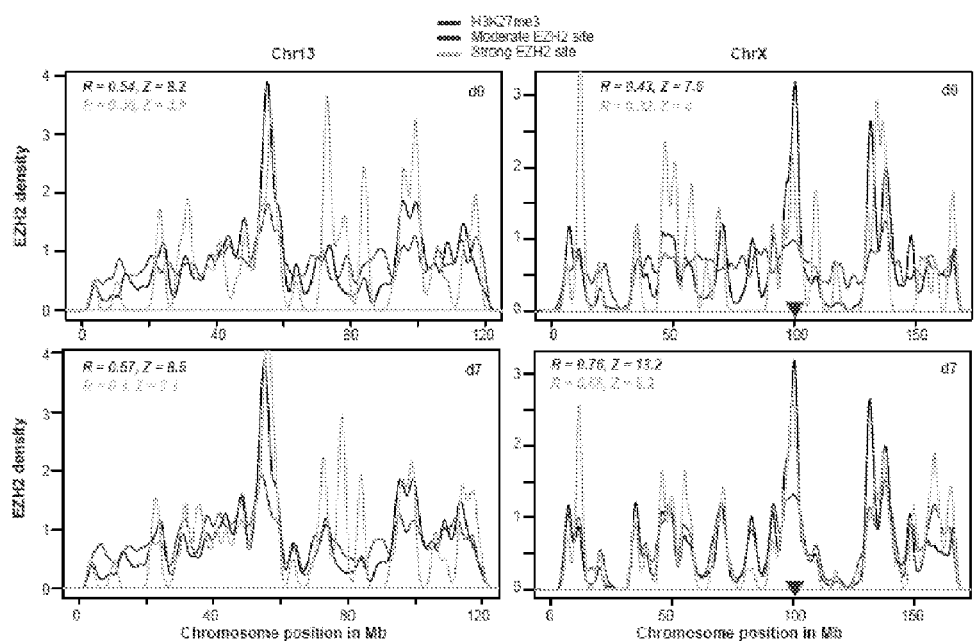
Figure 7B:
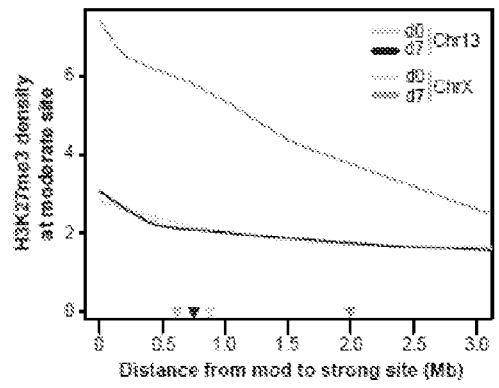
Figure 7C:
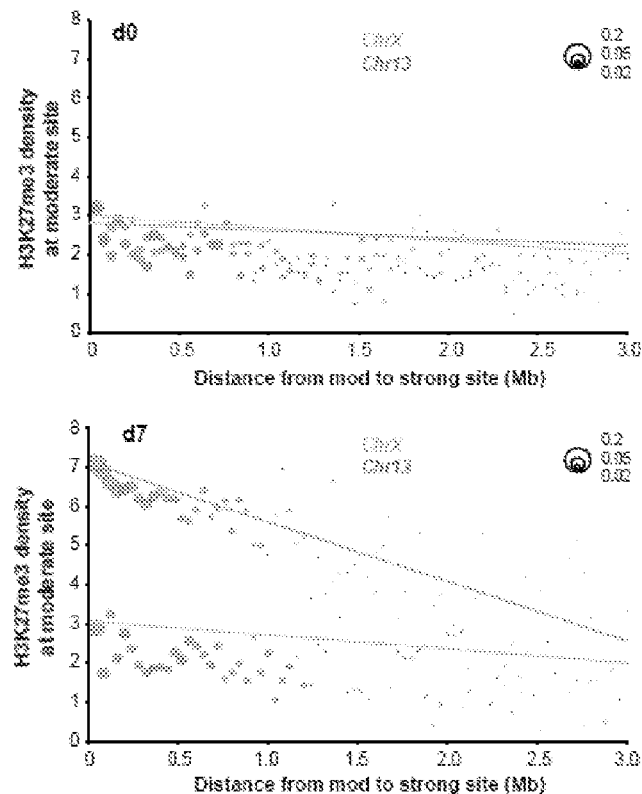
Figure 7D:
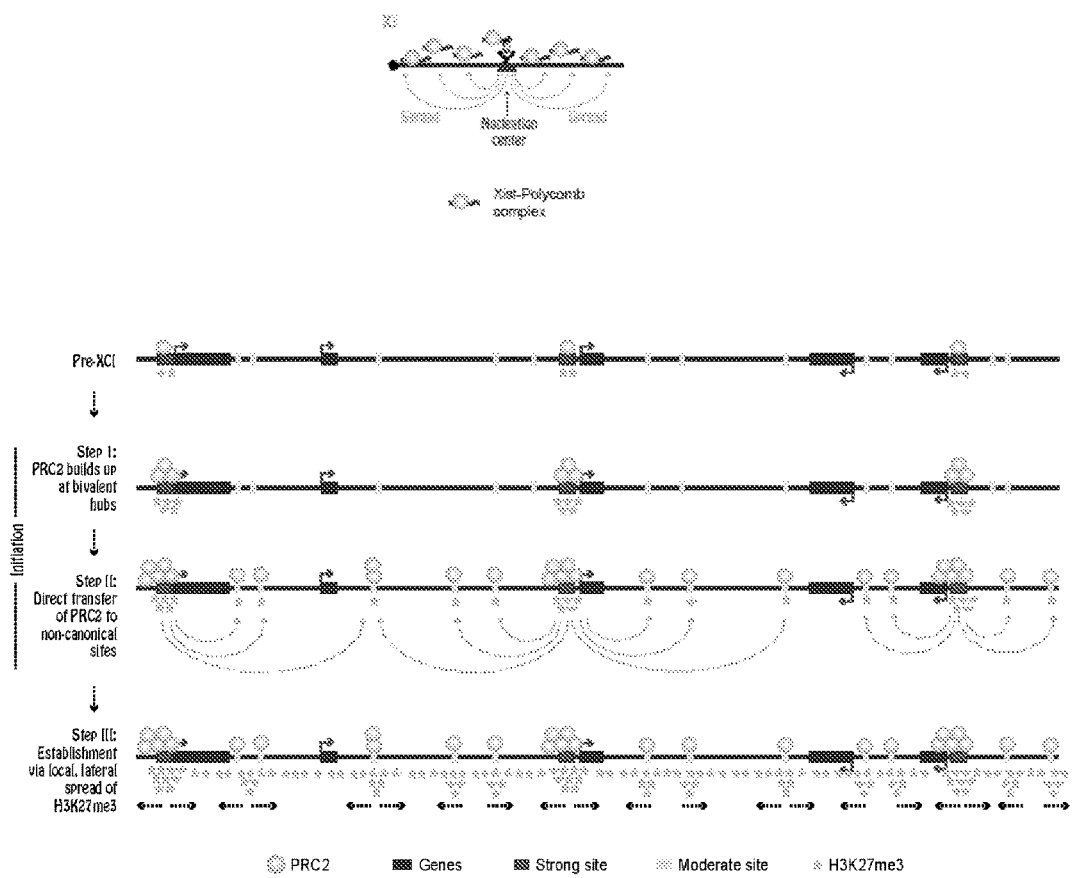

Moderate sites tend to be located close (<1 Mb) to strong sites (FIG. 6A, 7C). This trend was especially pronounced on ChrX on d7 (FIG. 7C, with the largest fraction of all sites clustered within a distance of 0.5 Mb from closest strong site), suggesting acquisition of moderate sites during XCI in the vicinity of strong sites. Importantly, H3K27me3 densities of moderate sites decay with increasing distance to the closest strong site only on ChrX on d7, as seen for both trendlines fitted to raw data (FIG. 7A,B) as well as medians of densities binned over a set distances (FIG. 7C, 40-kb bins). For a numerical characteristic of this long-range effect, we conservatively estimated the radius of the "sphere of influence" of strong EZH2 sites on neighboring moderate sites by calculating the distance-at-half-maximum for the density trendlines. For Chr13 on both days and ChrX on d0, the range was small (0.6-0.8 Mb; FIG. 7B triangles). In contrast, the range for ChrX on d7 was 3-fold greater (2.0 Mb). These data show that, during XCI, there is significant growth of moderate sites around strong sites and that, furthermore, there is substantial increase in the sphere of influence of a given strong site. The general EZH2 and H3K27me3 gradient (FIG. 6B,C) likely resulted from clustering of as moderate sites around strong sites (FIG. 7C). Importantly, the H3K27me3 density of each moderate site decreased with increasing distance from the closest strong site, specifically on ChrX on d7 (FIG. 7B,C). The lack of a similar gradient for EZH2 (FIG. 7A) suggests that EZH2 is not relayed in serial fashion from strong site to proximal moderate site and on to distal moderate site, because EZH2 densities of moderate sites would decay with increasing distance. Instead, the data are most consistent with the notion that strong sites are directly seeding moderate sites nearby, transferring discrete quantities of EZH2 directly from strong to moderate site, rather than spreading EZH2 linearly in a nucleosome-to-nucleosome fashion. Therefore, of the three potential models in FIG. 5B, we favor a direct transfer model in which XCI spreading occurs in a three-step process (FIG. 7D).

Tables IVA-C present the full list of strong (TVA) and moderate (IVB and IVC) EZH2 sites on mouse ChrX. Table IVB presents those mouse moderate binding sites with human liftover sites, and the SEQ ID NOs. corresponding to those human liftover sites. Table IVC presents mouse moderate binding sites without human liftover sites.

For Table IVA: 0, day 0 ES cells: 7, day 7 ES cells; M, MEF cells.

TABLE IVA

| | mouse | | human | | | HUMAN |
|---|---|---|---|---|---|---|
| Day/cell | start | stop | start | stop | name | SEQ ID NO: |
| 0 | 6355750 | 6357250 | 50212545 | 50213682 | X__d0seg__1 | 5933 |
| 0 | 11581050 | 11582400 | 39870650 | 39872160 | X__d0seg__2 | 5934 |
| 0 | 11654250 | 11656500 | 39953733 | 39956003 | X__d0seg__3 | 5935 |
| 0 | 11658000 | 11659650 | 39957538 | 39959198 | X__d0seg__4 | 5936 |
| 0 | 11661300 | 11669900 | 39960989 | 39970382 | X__d0seg__5 | 5937 |
| 0 | 11702200 | 11711600 | 40002293 | 40012108 | X__d0seg__6 | 5938 |
| 0 | 13063000 | 13064350 | 41332668 | 41334037 | X__d0seg__7 | 5939 |
| 0 | 19636150 | 19637850 | 46432902 | 46434381 | X__d0seg__8 | 5940 |
| 0 | 34588150 | 34590950 | 118891849 | 118895631 | X__d0seg__9 | 5941 |
| 0 | 35603800 | 35605650 | 119443498 | 119445332 | X__d0seg__10 | 5942 |
| 0 | 45387450 | 45388650 | 128788385 | 128789539 | X__d0seg__11 | 5943 |

TABLE IVA-continued

| | mouse | | human | | | HUMAN |
|---|---|---|---|---|---|---|
| Day/cell | start | stop | start | stop | name | SEQ ID NO: |
| 0 | 46837700 | 46839500 | 130206324 | 130208164 | X__d0seg__12 | 5944 |
| 0 | 46845400 | 46846850 | 130214751 | 130216122 | X__d0seg__13 | 5945 |
| 0 | 47252550 | 47253750 | none | none | X__d0seg__14 | |
| 0 | 49032200 | 49035300 | 132089948 | 132093140 | X__d0seg__15 | 5946 |
| 0 | 50411050 | 50413200 | 133684370 | 133686238 | X__d0seg__16 | 5947 |
| 0 | 51077050 | 51079600 | none | none | X__d0seg__17 | |
| 0 | 51278000 | 51279750 | none | none | X__d0seg__18 | |
| 0 | 55170850 | 55174500 | 136507747 | 136511479 | X__d0seg__19 | 5948 |
| 0 | 56819550 | 56821700 | 138285559 | 138287629 | X__d0seg__20 | 5949 |
| 0 | 58143800 | 58145750 | 139584389 | 139586382 | X__d0seg__21 | 5950 |
| 0 | 58147400 | 58150150 | 139588021 | 139591349 | X__d0seg__22 | 5951 |
| 0 | 63905800 | 63907600 | 144902694 | 144904464 | X__d0seg__23 | 5952 |
| 0 | 68302550 | 68306150 | 149530837 | 149534342 | X__d0seg__24 | 5953 |
| 0 | 68914200 | 68919300 | 150342031 | 150347910 | X__d0seg__25 | 5954 |
| 0 | 70666600 | 70668850 | 152685724 | 152687813 | X__d0seg__26 | 5955 |
| 0 | 90526850 | 90544850 | 25020529 | 25039134 | X__d0seg__27 | 5956 |
| 0 | 91610450 | 91612400 | 23925910 | 23927984 | X__d0seg__28 | 5957 |
| 0 | 95343200 | 95348050 | 66762975 | 66767942 | X__d0seg__29 | 5958 |
| 0 | 96331100 | 96333000 | 68048502 | 68050400 | X__d0seg__30 | 5959 |
| 0 | 98890350 | 98893700 | 70798488 | 70799686 | X__d0seg__31 | 5960 |
| 0 | 99043550 | 99046750 | 71129147 | 71132812 | X__d0seg__32 | 5961 |
| 0 | 99445650 | 99449150 | 71524940 | 71528621 | X__d0seg__33 | 5962 |
| 0 | 101015800 | 101017750 | 73640853 | 73642890 | X__d0seg__34 | 5963 |
| 0 | 102957600 | 102962150 | 76703692 | 76705284 | X__d0seg__35 | 5964 |
| 0 | 108010200 | 108013400 | 82763729 | 82767068 | X__d0seg__36 | 5965 |
| 0 | 109009250 | 109010600 | none | none | X__d0seg__37 | |
| 0 | 109715300 | 109716400 | 84499950 | 84501037 | X__d0seg__38 | 5966 |
| 0 | 117403550 | 117406500 | 91033972 | 91036917 | X__d0seg__39 | 5967 |
| 0 | 130219100 | 130222100 | 99660982 | 99663892 | X__d0seg__40 | 5968 |
| 0 | 130223500 | 130226150 | 99665247 | 99667700 | X__d0seg__41 | 5969 |
| 0 | 133633250 | 133635300 | none | none | X__d0seg__42 | |
| 0 | 133638650 | 133640400 | none | none | X__d0seg__43 | |
| 0 | 133652750 | 133658500 | 103498701 | 103501568 | X__d0seg__44 | 5970 |
| 0 | 134102600 | 134106900 | 103808481 | 103812486 | X__d0seg__45 | 5971 |
| 0 | 135446700 | 135448600 | 105064204 | 105066146 | X__d0seg__46 | 5972 |
| 0 | 136595250 | 136597000 | none | none | X__d0seg__47 | |
| 0 | 136811000 | 136814500 | 106691670 | 106694899 | X__d0seg__48 | 5973 |
| 0 | 137131700 | 137133550 | 107017375 | 107019086 | X__d0seg__49 | 5974 |
| 0 | 138155450 | 138160200 | 107975156 | 107980031 | X__d0seg__50 | 5975 |
| 0 | 152058400 | 152060300 | 23350696 | 23352468 | X__d0seg__51 | 5976 |
| 0 | 154479100 | 154481450 | 21392303 | 21394736 | X__d0seg__52 | 5977 |
| 0 | 158345400 | 158346750 | 17673909 | 17675213 | X__d0seg__53 | 5978 |
| 0 | 164560750 | 164562150 | 12155682 | 12157098 | X__d0seg__54 | 5979 |
| 0 | 165232450 | 165234650 | 11682453 | 11684741 | X__d0seg__55 | 5980 |
| 0 | 166317850 | 166318900 | 10587335 | 10588320 | X__d0seg__56 | 5981 |
| 7 | 6355950 | 6357900 | 50211824 | 50213570 | X__d7seg__1 | 5982 |
| 7 | 7121100 | 7122700 | none | none | X__d7seg__2 | |
| 7 | 7498450 | 7502200 | 48687634 | 48692237 | X__d7seg__3 | 5983 |
| 7 | 10294900 | 10296300 | 38663737 | 38665158 | X__d7seg__4 | 5984 |
| 7 | 11241850 | 11243350 | 39548159 | 39549617 | X__d7seg__5 | 5985 |
| 7 | 11382900 | 11384550 | 39678763 | 39680514 | X__d7seg__6 | 5986 |
| 7 | 11576800 | 11584500 | 39866133 | 39874292 | X__d7seg__7 | 5987 |
| 7 | 11618350 | 11619550 | 39916154 | 39916960 | X__d7seg__8 | 5988 |
| 7 | 11642600 | 11648900 | 39941590 | 39948337 | X__d7seg__9 | 5989 |
| 7 | 11650000 | 11672900 | 39949546 | 39972450 | X__d7seg__10 | 5990 |
| 7 | 11699450 | 11718900 | 39999868 | 40018589 | X__d7seg__11 | 5991 |
| 7 | 11727350 | 11738450 | 40025540 | 40037252 | X__d7seg__12 | 5992 |
| 7 | 12338750 | 12340000 | 40594595 | 40595937 | X__d7seg__13 | 5993 |
| 7 | 13062600 | 13063900 | 41332467 | 41333587 | X__d7seg__14 | 5994 |
| 7 | 13423950 | 13425200 | 41782998 | 41784181 | X__d7seg__15 | 5995 |
| 7 | 19636100 | 19638650 | 46432902 | 46435184 | X__d7seg__16 | 5996 |
| 7 | 20194000 | 20195500 | 47003630 | 47005197 | X__d7seg__17 | 5997 |
| 7 | 33430850 | 33432050 | 117631803 | 117632878 | X__d7seg__18 | 5998 |
| 7 | 33867300 | 33870050 | 118107473 | 118110151 | X__d7seg__19 | 5999 |
| 7 | 34587350 | 34590550 | 118891276 | 118894307 | X__d7seg__20 | 6000 |
| 7 | 35533400 | 35534750 | none | none | X__d7seg__21 | |
| 7 | 35603700 | 35606500 | 119443375 | 119446145 | X__d7seg__22 | 6001 |
| 7 | 38753650 | 38755500 | 122317397 | 122319184 | X__d7seg__23 | 6002 |
| 7 | 39878950 | 39880250 | none | none | X__d7seg__24 | |
| 7 | 40779750 | 40784250 | 124335918 | 124340213 | X__d7seg__25 | 6003 |
| 7 | 45385700 | 45389400 | 128786671 | 128790322 | X__d7seg__26 | 6004 |
| 7 | 45638750 | 45640750 | 129066389 | 129068773 | X__d7seg__27 | 6005 |
| 7 | 45693200 | 45698600 | 129112930 | 129118262 | X__d7seg__28 | 6006 |
| 7 | 45805150 | 45807500 | 129242747 | 129244939 | X__d7seg__29 | 6007 |
| 7 | 46079400 | 46080700 | none | none | X__d7seg__30 | |
| 7 | 46829050 | 46830450 | 130197943 | 130199420 | X__d7seg__31 | 6008 |

TABLE IVA-continued

| Day/cell | mouse start | mouse stop | human start | human stop | name | HUMAN SEQ ID NO: |
|---|---|---|---|---|---|---|
| 7 | 46845400 | 46848150 | 130214751 | 130217434 | X__d7seg__32 | 6009 |
| 7 | 48647950 | 48648950 | none | none | X__d7seg__33 | |
| 7 | 49033400 | 49035850 | 132091169 | 132093740 | X__d7seg__34 | 6010 |
| 7 | 49515800 | 49517700 | 132546731 | 132548722 | X__d7seg__35 | 6011 |
| 7 | 49966800 | 49968050 | 133119292 | 133120452 | X__d7seg__36 | 6012 |
| 7 | 50410150 | 50413500 | 133683549 | 133686542 | X__d7seg__37 | 6013 |
| 7 | 51077150 | 51079700 | none | none | X__d7seg__38 | |
| 7 | 51277000 | 51280800 | none | none | X__d7seg__39 | |
| 7 | 54755800 | 54757950 | 136114934 | 136117115 | X__d7seg__40 | 6014 |
| 7 | 54924750 | 54926300 | none | none | X__d7seg__41 | |
| 7 | 55031150 | 55032750 | 136362871 | 136364401 | X__d7seg__42 | 6015 |
| 7 | 55169850 | 55176350 | 136506771 | 136513469 | X__d7seg__43 | 6016 |
| 7 | 55279850 | 55281950 | 136644296 | 136646423 | X__d7seg__44 | 6017 |
| 7 | 55283050 | 55287350 | 136647551 | 136651893 | X__d7seg__45 | 6018 |
| 7 | 56818750 | 56823950 | 138284776 | 138290162 | X__d7seg__46 | 6019 |
| 7 | 57428850 | 57430650 | 138771932 | 138772950 | X__d7seg__47 | 6020 |
| 7 | 58052150 | 58053850 | 139471899 | 139473730 | X__d7seg__48 | 6021 |
| 7 | 58143750 | 58152800 | 139584340 | 139594145 | X__d7seg__49 | 6022 |
| 7 | 66613300 | 66615500 | 147581916 | 147584207 | X__d7seg__50 | 6023 |
| 7 | 68301750 | 68305800 | 149530084 | 149534002 | X__d7seg__51 | 6024 |
| 7 | 68334300 | 68335700 | 149578687 | 149580006 | X__d7seg__52 | 6025 |
| 7 | 68914500 | 68919750 | 150342370 | 150348293 | X__d7seg__53 | 6026 |
| 7 | 70666200 | 70668550 | 152685054 | 152687512 | X__d7seg__54 | 6027 |
| 7 | 70880850 | 70883000 | 152907833 | 152909967 | X__d7seg__55 | 6028 |
| 7 | 70884700 | 70886100 | 152912593 | 152913737 | X__d7seg__56 | 6029 |
| 7 | 71124850 | 71126000 | 153150311 | 153151480 | X__d7seg__57 | 6030 |
| 7 | 71597850 | 71598950 | 153706412 | 153707323 | X__d7seg__58 | 6031 |
| 7 | 72387600 | 72388700 | none | none | X__d7seg__59 | |
| 7 | 74677100 | 74678400 | 9309273 | 9310019 | X__d7seg__60 | 6032 |
| 7 | 80732150 | 80733300 | none | none | X__d7seg__61 | |
| 7 | 83217150 | 83218700 | 30494898 | 30495893 | X__d7seg__62 | 6033 |
| 7 | 90526600 | 90546650 | 25018602 | 25039378 | X__d7seg__63 | 6034 |
| 7 | 91610200 | 91612500 | 23925811 | 23928130 | X__d7seg__64 | 6035 |
| 7 | 91881050 | 91882300 | 51486154 | 51487415 | X__d7seg__65 | 6036 |
| 7 | 94121300 | 94122300 | none | none | X__d7seg__66 | |
| 7 | 95343750 | 95348350 | 66763547 | 66768258 | X__d7seg__67 | 6037 |
| 7 | 95361600 | 95362800 | 66783391 | 66784225 | X__d7seg__68 | 6038 |
| 7 | 96638500 | 96639900 | 68356970 | 68358498 | X__d7seg__69 | 6039 |
| 7 | 96662350 | 96663600 | 68381596 | 68382930 | X__d7seg__70 | 6040 |
| 7 | 97170850 | 97172350 | 68835881 | 68837401 | X__d7seg__71 | 6041 |
| 7 | 97280900 | 97282650 | 68948351 | 68949247 | X__d7seg__72 | 6042 |
| 7 | 98577750 | 98581100 | 70441491 | 70445186 | X__d7seg__73 | 6043 |
| 7 | 98834700 | 98835950 | 70752200 | 70753489 | X__d7seg__74 | 6044 |
| 7 | 98890600 | 98894100 | 70798488 | 70799686 | X__d7seg__75 | 6045 |
| 7 | 99041000 | 99042800 | 71126674 | 71128573 | X__d7seg__76 | 6046 |
| 7 | 99044000 | 99047000 | 71129999 | 71133070 | X__d7seg__77 | 6047 |
| 7 | 99264900 | 99267200 | 71350158 | 71352516 | X__d7seg__78 | 6048 |
| 7 | 99440900 | 99449050 | 71520048 | 71528514 | X__d7seg__79 | 6049 |
| 7 | 99640600 | 99641850 | 71731757 | 71733094 | X__d7seg__80 | 6050 |
| 7 | 100516300 | 100519250 | 72666458 | 72669490 | X__d7seg__81 | 6051 |
| 7 | 100549750 | 100551250 | 72780982 | 72782399 | X__d7seg__82 | 6052 |
| 7 | 100643850 | 100646150 | 73014340 | 73015090 | X__d7seg__83 | 6053 |
| 7 | 100889450 | 100891200 | 73755360 | 73757355 | X__d7seg__84 | 6054 |
| 7 | 101014850 | 101017550 | 73641056 | 73643867 | X__d7seg__85 | 6055 |
| 7 | 101175150 | 101176800 | 73832957 | 73834636 | X__d7seg__86 | 6056 |
| 7 | 102315250 | 102317050 | 75647562 | 75649460 | X__d7seg__87 | 6057 |
| 7 | 102957400 | 102962250 | 76703692 | 76705391 | X__d7seg__88 | 6058 |
| 7 | 103414650 | 103415900 | 77394772 | 77395913 | X__d7seg__89 | 6059 |
| 7 | 104871650 | 104873100 | 79277162 | 79278723 | X__d7seg__90 | 6060 |
| 7 | 106380700 | 106381950 | 80604122 | 80604916 | X__d7seg__91 | 6061 |
| 7 | 108009100 | 108013200 | 82762609 | 82766870 | X__d7seg__92 | 6062 |
| 7 | 109714550 | 109716500 | 84499233 | 84501149 | X__d7seg__93 | 6063 |
| 7 | 117403500 | 117405800 | 91033931 | 91036207 | X__d7seg__94 | 6064 |
| 7 | 126283950 | 126284950 | 95939522 | 95940514 | X__d7seg__95 | 6065 |
| 7 | 130218250 | 130227050 | 99660156 | 99668596 | X__d7seg__96 | 6066 |
| 7 | 130515100 | 130516400 | 99985953 | 99987187 | X__d7seg__97 | 6067 |
| 7 | 131291750 | 131293650 | 100878751 | 100880488 | X__d7seg__98 | 6068 |
| 7 | 131498150 | 131499850 | none | none | X__d7seg__99 | |
| 7 | 133201000 | 133202800 | 102862894 | 102864714 | X__d7seg__100 | 6069 |
| 7 | 133633550 | 133635650 | none | none | X__d7seg__101 | |
| 7 | 133638950 | 133640150 | none | none | X__d7seg__102 | |
| 7 | 133652000 | 133656050 | 103497966 | 103500889 | X__d7seg__103 | 6070 |
| 7 | 134103900 | 134107150 | 103809534 | 103812755 | X__d7seg__104 | 6071 |
| 7 | 135269700 | 135271350 | 104892432 | 104893265 | X__d7seg__105 | 6072 |
| 7 | 135642200 | 135643400 | 105302644 | 105303360 | X__d7seg__106 | 6073 |
| 7 | 136594950 | 136598150 | none | none | X__d7seg__107 | |

TABLE IVA-continued

| Day/cell | mouse start | mouse stop | human start | human stop | name | HUMAN SEQ ID NO: |
|---|---|---|---|---|---|---|
| 7 | 136810300 | 136814100 | 106690970 | 106694548 | X__d7seg__108 | 6074 |
| 7 | 137131450 | 137137100 | 107017134 | 107022121 | X__d7seg__109 | 6075 |
| 7 | 137199700 | 137201550 | 107069547 | 107072468 | X__d7seg__110 | 6076 |
| 7 | 137586800 | 137587850 | none | none | X__d7seg__111 | |
| 7 | 137950500 | 137951900 | none | none | X__d7seg__112 | |
| 7 | 138155350 | 138161850 | 107975050 | 107981731 | X__d7seg__113 | 6077 |
| 7 | 138739450 | 138740600 | 108867092 | 108868281 | X__d7seg__114 | 6078 |
| 7 | 139827900 | 139829450 | 110038531 | 110040094 | X__d7seg__115 | 6079 |
| 7 | 140152250 | 140153450 | none | none | X__d7seg__116 | |
| 7 | 141121300 | 141125200 | 111324058 | 111328035 | X__d7seg__117 | 6080 |
| 7 | 143394550 | 143398700 | 113816106 | 113820202 | X__d7seg__118 | 6081 |
| 7 | 148578700 | 148580800 | 53348416 | 53350615 | X__d7seg__119 | 6082 |
| 7 | 149406500 | 149407950 | none | none | X__d7seg__120 | |
| 7 | 149412300 | 149413650 | none | none | X__d7seg__121 | |
| 7 | 150022350 | 150023850 | none | none | X__d7seg__122 | |
| 7 | 150194300 | 150195450 | none | none | X__d7seg__123 | |
| 7 | 152056300 | 152061350 | 23349575 | 23354523 | X__d7seg__124 | 6083 |
| 7 | 154381450 | 154382500 | none | none | X__d7seg__125 | |
| 7 | 154478950 | 154481700 | 21392077 | 21394905 | X__d7seg__126 | 6084 |
| 7 | 155693950 | 155696050 | 20282889 | 20284842 | X__d7seg__127 | 6085 |
| 7 | 155852450 | 155854200 | 20133605 | 20135150 | X__d7seg__128 | 6086 |
| 7 | 156828250 | 156830300 | 19138526 | 19141115 | X__d7seg__129 | 6087 |
| 7 | 157347550 | 157349050 | 18539561 | 18540409 | X__d7seg__130 | 6088 |
| 7 | 157378650 | 157380150 | 18508174 | 18509130 | X__d7seg__131 | 6089 |
| 7 | 158154950 | 158158400 | 17875998 | 17879464 | X__d7seg__132 | 6090 |
| 7 | 158163800 | 158164950 | 17869593 | 17870743 | X__d7seg__133 | 6091 |
| 7 | 158346050 | 158347950 | 17672666 | 17674598 | X__d7seg__134 | 6092 |
| 7 | 158478550 | 158479650 | 17524940 | 17526056 | X__d7seg__135 | 6093 |
| 7 | 158596100 | 158598350 | 17392900 | 17395147 | X__d7seg__136 | 6094 |
| 7 | 160197550 | 160199400 | none | none | X__d7seg__137 | |
| 7 | 160345550 | 160347000 | 15873003 | 15874465 | X__d7seg__138 | 6095 |
| 7 | 160682000 | 160683400 | 15530416 | 15532882 | X__d7seg__139 | 6096 |
| 7 | 162675550 | 162678650 | 13955103 | 13958196 | X__d7seg__140 | 6097 |
| 7 | 163645450 | 163647650 | 12992638 | 12994912 | X__d7seg__141 | 6098 |
| 7 | 164318000 | 164319200 | 12379109 | 12380073 | X__d7seg__142 | 6099 |
| 7 | 164513650 | 164514900 | 12203435 | 12204396 | X__d7seg__143 | 6100 |
| 7 | 165222300 | 165223600 | 11689875 | 11691335 | X__d7seg__144 | 6101 |
| 7 | 165232500 | 165235950 | 11680989 | 11684700 | X__d7seg__145 | 6102 |
| 7 | 165474950 | 165476250 | 11444197 | 11445529 | X__d7seg__146 | 6103 |
| 7 | 166425950 | 166427250 | 10417297 | 10418060 | X__d7seg__147 | 6104 |
| M | 6354500 | 6357650 | 50212150 | 50214751 | Mseg__1 | 6105 |
| M | 11383500 | 11385150 | 39679408 | 39681127 | Mseg__2 | 6106 |
| M | 11663400 | 11667900 | 39963187 | 39967867 | Mseg__3 | 6107 |
| M | 11716850 | 11718450 | 40017048 | 40018389 | Mseg__4 | 6108 |
| M | 33867050 | 33870000 | 118107246 | 118110101 | Mseg__5 | 6109 |
| M | 34588050 | 34590250 | 118891747 | 118894003 | Mseg__6 | 6110 |
| M | 36147950 | 36149450 | 119915712 | 119916185 | Mseg__7 | 6111 |
| M | 48194000 | 48195550 | 131156656 | 131158215 | Mseg__8 | 6112 |
| M | 49965700 | 49968450 | 133118192 | 133121172 | Mseg__9 | 6113 |
| M | 51278600 | 51280350 | none | none | Mseg__10 | |
| M | 55170200 | 55172300 | 136507079 | 136509288 | Mseg__11 | 6114 |
| M | 55173350 | 55174750 | 136510352 | 136511728 | Mseg__12 | 6115 |
| M | 55271400 | 55273350 | 136631672 | 136633482 | Mseg__13 | 6116 |
| M | 55280300 | 55287050 | 136644722 | 136651581 | Mseg__14 | 6117 |
| M | 55290550 | 55292350 | 136655150 | 136657164 | Mseg__15 | 6118 |
| M | 57431400 | 57432800 | 138773758 | 138774995 | Mseg__16 | 6119 |
| M | 58144150 | 58149000 | 139584764 | 139589645 | Mseg__17 | 6120 |
| M | 68914150 | 68919150 | 150341980 | 150347692 | Mseg__18 | 6121 |
| M | 70747800 | 70749800 | 152782594 | 152784456 | Mseg__19 | 6122 |
| M | 85396250 | 85397400 | none | none | Mseg__20 | |
| M | 90492700 | 90494500 | 25071294 | 25072254 | Mseg__21 | 6123 |
| M | 90526400 | 90527900 | 25038048 | 25039598 | Mseg__22 | 6124 |
| M | 90529250 | 90530700 | 25035237 | 25036755 | Mseg__23 | 6125 |
| M | 90532900 | 90536800 | 25028850 | 25032991 | Mseg__24 | 6126 |
| M | 90539250 | 90544950 | 25020386 | 25026336 | Mseg__25 | 6127 |
| M | 98579350 | 98580950 | 70443345 | 70445034 | Mseg__26 | 6128 |
| M | 99044100 | 99046300 | 71130118 | 71132470 | Mseg__27 | 6129 |
| M | 99445250 | 99447450 | 71524416 | 71526952 | Mseg__28 | 6130 |
| M | 100380800 | 100382350 | 72433479 | 72435048 | Mseg__29 | 6131 |
| M | 100517100 | 100518450 | 72667291 | 72668591 | Mseg__30 | 6132 |
| M | 100642000 | 100644900 | none | none | Mseg__31 | |
| M | 101394600 | 101397000 | 74143561 | 74145754 | Mseg__32 | 6133 |
| M | 117405950 | 117407000 | 91036360 | 91037375 | Mseg__33 | 6134 |
| M | 119510000 | 119511250 | 92927719 | 92928844 | Mseg__34 | 6135 |
| M | 127858650 | 127859800 | 97533217 | 97534152 | Mseg__35 | 6136 |
| M | 133651850 | 133655750 | 103497517 | 103500629 | Mseg__36 | 6137 |

TABLE IVA-continued

| Day/cell | mouse start | mouse stop | human start | human stop | name | HUMAN SEQ ID NO: |
|---|---|---|---|---|---|---|
| M | 136595100 | 136597800 | none | none | Mseg_37 | |
| M | 136811700 | 136813750 | 106692325 | 106694186 | Mseg_38 | 6138 |
| M | 137134350 | 137135400 | 107019665 | 107020545 | Mseg_39 | 6139 |
| M | 138155700 | 138161850 | 107975434 | 107981731 | Mseg_40 | 6140 |
| M | 141123000 | 141124650 | 111325775 | 111327435 | Mseg_41 | 6141 |
| M | 143397150 | 143398250 | 113818658 | 113819740 | Mseg_42 | 6142 |
| M | 152056200 | 152059650 | 23351204 | 23354627 | Mseg_43 | 6143 |
| M | 154479800 | 154481850 | 21391910 | 21394015 | Mseg_44 | 6144 |
| M | 155851900 | 155854000 | 20133820 | 20135681 | Mseg_45 | 6145 |
| M | 158154850 | 158156600 | 17877847 | 17879563 | Mseg_46 | 6146 |
| M | 158345700 | 158347450 | 17673177 | 17674917 | Mseg_47 | 6147 |
| M | 159080700 | 159082100 | 16964311 | 16965735 | Mseg_48 | 6148 |
| M | 160197950 | 160200150 | none | none | Mseg_49 | |
| M | 165232950 | 165234750 | 11682353 | 11684132 | Mseg_50 | 6149 |

For Table IIVB: 0, day 0 ES cells; 7, day 7 ES cells; M, MEF cells. The SEQ NOs. are for the human liftover sequences corresponding to the empirically identified mouse binding sites.

TABLE IVB

Mouse Binding Sites with Human Liftovers

| Cell/Day | Mouse Start | Mouse end | Human start | Human end | Segment name | SEQ ID NO: |
|---|---|---|---|---|---|---|
| 0 | 5498050 | 5499850 | 51384621 | 51385743 | d0Mseg12 | 6150 |
| 0 | 5626750 | 5628600 | 51237102 | 51237727 | d0Mseg15 | 6151 |
| 0 | 5658250 | 5660100 | 51150260 | 51151798 | d0Mseg16 | 6152 |
| 0 | 5668400 | 5670100 | 51138480 | 51140100 | d0Mseg17 | 6153 |
| 0 | 5748000 | 5749900 | 51075870 | 51076838 | d0Mseg18 | 6154 |
| 0 | 6269800 | 6271650 | 50271710 | 50272155 | d0Mseg21 | 6155 |
| 0 | 6311700 | 6313400 | 50259828 | 50260498 | d0Mseg22 | 6156 |
| 0 | 6355350 | 6359100 | 50210609 | 50214087 | d0Mseg23 | 6157 |
| 0 | 6439500 | 6441200 | 50178893 | 50180814 | d0Mseg24 | 6158 |
| 0 | 6621650 | 6623350 | 49967916 | 49968685 | d0Mseg25 | 6159 |
| 0 | 6894000 | 6895750 | 49687889 | 49689724 | d0Mseg26 | 6160 |
| 0 | 6926950 | 6928600 | 49664202 | 49664943 | d0Mseg27 | 6161 |
| 0 | 6943500 | 6945150 | 49652496 | 49653779 | d0Mseg28 | 6162 |
| 0 | 6951300 | 6952700 | 49644353 | 49645597 | d0Mseg29 | 6163 |
| 0 | 6954450 | 6956600 | 49640185 | 49642591 | d0Mseg30 | 6164 |
| 0 | 7192150 | 7194200 | 49079555 | 49082334 | d0Mseg31 | 6165 |
| 0 | 7216650 | 7218550 | 49053974 | 49055791 | d0Mseg32 | 6166 |
| 0 | 7248700 | 7250350 | 49025447 | 49028034 | d0Mseg33 | 6167 |
| 0 | 7542700 | 7544550 | 48645436 | 48646897 | d0Mseg34 | 6168 |
| 0 | 8713600 | 8714850 | 37377045 | 37377723 | d0Mseg44 | 6169 |
| 0 | 8819600 | 8821400 | 37507349 | 37511839 | d0Mseg45 | 6170 |
| 0 | 9113750 | 9115350 | 37576100 | 37576664 | d0Mseg46 | 6171 |
| 0 | 9645550 | 9647250 | 38032241 | 38034190 | d0Mseg50 | 6172 |
| 0 | 9651300 | 9653000 | 38037944 | 38039779 | d0Mseg51 | 6173 |
| 0 | 9692900 | 9694950 | 38078201 | 38080297 | d0Mseg53 | 6174 |
| 0 | 9755150 | 9756900 | 38149973 | 38150474 | d0Mseg54 | 6175 |
| 0 | 9867700 | 9869400 | 38249973 | 38251585 | d0Mseg55 | 6176 |
| 0 | 10020200 | 10022150 | 38364806 | 38366637 | d0Mseg56 | 6177 |
| 0 | 10061900 | 10063850 | 38420306 | 38422352 | d0Mseg57 | 6178 |
| 0 | 10076700 | 10077700 | 38438460 | 38439366 | d0Mseg58 | 6179 |
| 0 | 10078900 | 10080600 | 38439858 | 38441923 | d0Mseg59 | 6180 |
| 0 | 10121350 | 10122750 | 38480547 | 38482022 | d0Mseg60 | 6181 |
| 0 | 10279550 | 10281150 | 38649265 | 38650920 | d0Mseg62 | 6182 |
| 0 | 10386900 | 10388750 | 38765167 | 38766457 | d0Mseg63 | 6183 |
| 0 | 10538600 | 10540100 | 38899029 | 38900549 | d0Mseg64 | 6184 |
| 0 | 10561550 | 10563100 | 38912277 | 38913350 | d0Mseg65 | 6185 |
| 0 | 10626900 | 10628650 | 38981715 | 38982441 | d0Mseg66 | 6186 |
| 0 | 10874500 | 10876100 | 39220834 | 39221777 | d0Mseg67 | 6187 |
| 0 | 10981850 | 10983550 | 39298806 | 39300497 | d0Mseg68 | 6188 |
| 0 | 11068300 | 11070450 | 39375066 | 39377627 | d0Mseg69 | 6189 |
| 0 | 11240150 | 11243650 | 39546298 | 39549617 | d0Mseg70 | 6190 |
| 0 | 11283650 | 11285000 | 39588385 | 39589768 | d0Mseg71 | 6191 |
| 0 | 11354250 | 11356100 | 39645601 | 39653225 | d0Mseg73 | 6192 |
| 0 | 11375100 | 11376200 | 39670709 | 39671699 | d0Mseg74 | 6193 |
| 0 | 11383350 | 11385400 | 39679261 | 39681394 | d0Mseg75 | 6194 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 11387500 | 11390550 | 39687004 | 39690176 | d0Mseg76 | 6195 |
| 0 | 11413850 | 11415500 | 39711808 | 39713462 | d0Mseg77 | 6196 |
| 0 | 11506750 | 11508550 | 39800944 | 39802652 | d0Mseg78 | 6197 |
| 0 | 11510300 | 11511900 | 39804787 | 39806020 | d0Mseg79 | 6198 |
| 0 | 11516600 | 11518550 | 39808913 | 39810205 | d0Mseg80 | 6199 |
| 0 | 11573900 | 11584350 | 39862889 | 39874130 | d0Mseg81 | 6200 |
| 0 | 11645350 | 11646550 | 39944588 | 39945914 | d0Mseg82 | 6201 |
| 0 | 11652900 | 11671400 | 39952327 | 39971371 | d0Mseg83 | 6202 |
| 0 | 11701800 | 11718950 | 40001909 | 40018589 | d0Mseg84 | 6203 |
| 0 | 11731500 | 11733350 | 40030026 | 40032134 | d0Mseg85 | 6204 |
| 0 | 11735400 | 11737750 | 40034243 | 40036599 | d0Mseg86 | 6205 |
| 0 | 11828200 | 11830050 | 40124432 | 40126931 | d0Mseg87 | 6206 |
| 0 | 11874350 | 11876050 | 40171654 | 40173026 | d0Mseg88 | 6207 |
| 0 | 11919050 | 11920800 | 40222540 | 40225263 | d0Mseg89 | 6208 |
| 0 | 13062550 | 13064850 | 41332467 | 41334385 | d0Mseg93 | 6209 |
| 0 | 13127000 | 13128000 | 41413718 | 41414777 | d0Mseg94 | 6210 |
| 0 | 13169700 | 13171350 | 41478429 | 41480000 | d0Mseg95 | 6211 |
| 0 | 13228200 | 13230000 | 41561029 | 41563513 | d0Mseg96 | 6212 |
| 0 | 13260850 | 13262550 | 41605553 | 41608150 | d0Mseg97 | 6213 |
| 0 | 13423650 | 13425450 | 41782693 | 41784443 | d0Mseg98 | 6214 |
| 0 | 13498950 | 13500800 | 41843824 | 41845252 | d0Mseg99 | 6215 |
| 0 | 13702300 | 13704050 | 41957723 | 41959332 | d0Mseg100 | 6216 |
| 0 | 13847550 | 13849400 | 42072561 | 42073365 | d0Mseg101 | 6217 |
| 0 | 14115400 | 14117050 | 42256207 | 42258188 | d0Mseg104 | 6218 |
| 0 | 14250650 | 14252100 | 42385818 | 42386012 | d0Mseg105 | 6219 |
| 0 | 14686750 | 14688450 | 42634126 | 42637274 | d0Mseg107 | 6220 |
| 0 | 14828200 | 14829850 | 42697133 | 42697663 | d0Mseg109 | 6221 |
| 0 | 14830900 | 14832600 | 42692356 | 42692645 | d0Mseg110 | 6222 |
| 0 | 14924600 | 14926300 | 42763595 | 42771532 | d0Mseg111 | 6223 |
| 0 | 15457800 | 15459500 | 43085068 | 43086778 | d0Mseg115 | 6224 |
| 0 | 15488400 | 15490100 | 43093809 | 43094667 | d0Mseg116 | 6225 |
| 0 | 16064950 | 16066500 | 43437190 | 43438047 | d0Mseg118 | 6226 |
| 0 | 16098550 | 16100350 | 145890788 | 145891496 | d0Mseg119 | 6227 |
| 0 | 16291950 | 16293550 | 43630279 | 43634460 | d0Mseg120 | 6228 |
| 0 | 16467700 | 16469700 | 43814337 | 43816308 | d0Mseg121 | 6229 |
| 0 | 16512450 | 16514150 | 43855852 | 43856472 | d0Mseg122 | 6230 |
| 0 | 17462100 | 17463800 | 102931764 | 102931959 | d0Mseg125 | 6231 |
| 0 | 17565900 | 17566950 | 44622555 | 44623924 | d0Mseg126 | 6232 |
| 0 | 17733350 | 17734550 | 44724938 | 44726299 | d0Mseg127 | 6233 |
| 0 | 18828500 | 18830200 | 45722726 | 45724726 | d0Mseg138 | 6234 |
| 0 | 18957250 | 18958850 | 45817006 | 45832328 | d0Mseg140 | 6235 |
| 0 | 19558200 | 19559450 | 46284530 | 46285072 | d0Mseg144 | 6236 |
| 0 | 19633850 | 19638150 | 46432902 | 46434681 | d0Mseg147 | 6237 |
| 0 | 19779950 | 19781600 | 46539229 | 46541241 | d0Mseg149 | 6238 |
| 0 | 20088800 | 20090600 | 46914256 | 46916022 | d0Mseg151 | 6239 |
| 0 | 20124450 | 20127600 | 46937281 | 46940639 | d0Mseg152 | 6240 |
| 0 | 21131900 | 21133650 | 115398655 | 115400110 | d0Mseg156 | 6241 |
| 0 | 21172800 | 21174400 | 115457948 | 115472259 | d0Mseg157 | 6242 |
| 0 | 21293650 | 21295250 | 115569207 | 115571604 | d0Mseg158 | 6243 |
| 0 | 21859100 | 21861000 | 116088373 | 116089315 | d0Mseg163 | 6244 |
| 0 | 22127700 | 22129500 | 116379235 | 116380628 | d0Mseg168 | 6245 |
| 0 | 22140050 | 22141700 | 116393220 | 116393816 | d0Mseg169 | 6246 |
| 0 | 22176700 | 22178250 | 116444897 | 116445300 | d0Mseg170 | 6247 |
| 0 | 22214750 | 22216350 | 116504858 | 116506369 | d0Mseg171 | 6248 |
| 0 | 22439500 | 22440700 | 116681128 | 116681830 | d0Mseg173 | 6249 |
| 0 | 22653150 | 22654700 | 116890499 | 116897650 | d0Mseg174 | 6250 |
| 0 | 22669150 | 22670750 | 116904891 | 116906150 | d0Mseg175 | 6251 |
| 0 | 22673300 | 22675100 | 116909986 | 116911046 | d0Mseg176 | 6252 |
| 0 | 22821650 | 22822700 | 117051368 | 117051896 | d0Mseg177 | 6253 |
| 0 | 22935400 | 22936800 | 117244223 | 117246416 | d0Mseg178 | 6254 |
| 0 | 22938700 | 22940600 | 117247748 | 117249078 | d0Mseg179 | 6255 |
| 0 | 23051650 | 23053550 | 117330906 | 117331130 | d0Mseg180 | 6256 |
| 0 | 23264800 | 23266550 | 117474321 | 117475532 | d0Mseg182 | 6257 |
| 0 | 23519450 | 23521100 | 127076727 | 127077736 | d0Mseg183 | 6258 |
| 0 | 33649800 | 33653650 | 117860276 | 117862945 | d0Mseg200 | 6259 |
| 0 | 33864350 | 33870000 | 118103194 | 118110101 | d0Mseg201 | 6260 |
| 0 | 34284900 | 34286250 | 118534368 | 118535141 | d0Mseg204 | 6261 |
| 0 | 34476050 | 34477400 | 118777825 | 118778830 | d0Mseg206 | 6262 |
| 0 | 34587050 | 34591300 | 118890977 | 118896264 | d0Mseg208 | 6263 |
| 0 | 34670100 | 34671800 | 119072042 | 119073223 | d0Mseg209 | 6264 |
| 0 | 35564300 | 35565300 | 119403850 | 119405074 | d0Mseg221 | 6265 |
| 0 | 35598700 | 35600500 | 119438010 | 119439841 | d0Mseg222 | 6266 |
| 0 | 35603150 | 35606150 | 119442759 | 119445796 | d0Mseg223 | 6267 |
| 0 | 35611300 | 35613100 | 119451846 | 119453474 | d0Mseg224 | 6268 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 35690850 | 35691850 | 119517726 | 119518291 | d0Mseg225 | 6269 |
| 0 | 35754350 | 35756050 | 119561427 | 119562856 | d0Mseg226 | 6270 |
| 0 | 35819150 | 35820850 | 119614477 | 119615648 | d0Mseg227 | 6271 |
| 0 | 36039400 | 36041250 | 119842373 | 119842929 | d0Mseg228 | 6272 |
| 0 | 36173350 | 36174900 | 119932892 | 119933252 | d0Mseg230 | 6273 |
| 0 | 36654450 | 36656100 | 120330537 | 120332343 | d0Mseg236 | 6274 |
| 0 | 36876550 | 36878100 | 120528235 | 120530237 | d0Mseg238 | 6275 |
| 0 | 37793150 | 37794800 | 121250458 | 121253285 | d0Mseg242 | 6276 |
| 0 | 37844400 | 37846150 | 121330934 | 121337734 | d0Mseg244 | 6277 |
| 0 | 38469450 | 38470650 | 122066574 | 122067437 | d0Mseg251 | 6278 |
| 0 | 38594850 | 38596500 | 122206545 | 122207118 | d0Mseg253 | 6279 |
| 0 | 38753000 | 38757450 | 122316744 | 122321135 | d0Mseg254 | 6280 |
| 0 | 38815700 | 38817400 | 122375517 | 122378159 | d0Mseg255 | 6281 |
| 0 | 38868850 | 38870550 | 122423590 | 122427671 | d0Mseg256 | 6282 |
| 0 | 39067900 | 39069500 | 122660711 | 122661389 | d0Mseg257 | 6283 |
| 0 | 39302700 | 39304500 | 122883575 | 122883897 | d0Mseg259 | 6284 |
| 0 | 39616700 | 39618350 | 123221188 | 123223377 | d0Mseg262 | 6285 |
| 0 | 39625200 | 39626900 | 123230623 | 123233048 | d0Mseg263 | 6286 |
| 0 | 39686050 | 39687600 | 123343412 | 123345001 | d0Mseg265 | 6287 |
| 0 | 39714050 | 39715750 | 123364511 | 123365673 | d0Mseg266 | 6288 |
| 0 | 40013950 | 40015100 | 123633862 | 123635113 | d0Mseg267 | 6289 |
| 0 | 40098550 | 40100400 | 123708500 | 123709575 | d0Mseg268 | 6290 |
| 0 | 40143600 | 40145300 | 123750446 | 123751745 | d0Mseg269 | 6291 |
| 0 | 40151400 | 40153000 | 123759059 | 123762887 | d0Mseg270 | 6292 |
| 0 | 40186550 | 40188250 | 123794765 | 123795552 | d0Mseg271 | 6293 |
| 0 | 40210550 | 40211550 | 123809222 | 123809677 | d0Mseg272 | 6294 |
| 0 | 40407600 | 40409250 | 124006420 | 124007290 | d0Mseg274 | 6295 |
| 0 | 40472500 | 40474400 | 124062911 | 124063665 | d0Mseg275 | 6296 |
| 0 | 40558600 | 40560400 | 124137181 | 124146965 | d0Mseg276 | 6297 |
| 0 | 40779800 | 40783250 | 124335968 | 124339222 | d0Mseg279 | 6298 |
| 0 | 40786750 | 40788350 | 124341501 | 124341841 | d0Mseg280 | 6299 |
| 0 | 40806250 | 40807950 | 124361834 | 124362744 | d0Mseg281 | 6300 |
| 0 | 40866400 | 40868350 | 124375759 | 124376574 | d0Mseg282 | 6301 |
| 0 | 40961850 | 40963850 | 124470423 | 124472361 | d0Mseg283 | 6302 |
| 0 | 41039500 | 41041250 | 124511669 | 124513421 | d0Mseg284 | 6303 |
| 0 | 41323900 | 41325550 | 124805056 | 124805341 | d0Mseg285 | 6304 |
| 0 | 41497750 | 41499050 | 124951426 | 124951961 | d0Mseg287 | 6305 |
| 0 | 41720000 | 41721850 | 125298738 | 125300600 | d0Mseg289 | 6306 |
| 0 | 43931600 | 43933350 | 127539134 | 127539717 | d0Mseg306 | 6307 |
| 0 | 44562750 | 44564400 | 128049207 | 128050510 | d0Mseg311 | 6308 |
| 0 | 44584200 | 44585750 | 128061267 | 128061602 | d0Mseg312 | 6309 |
| 0 | 44813650 | 44815200 | 128244188 | 128245366 | d0Mseg313 | 6310 |
| 0 | 44831400 | 44835800 | 128258218 | 128261991 | d0Mseg314 | 6311 |
| 0 | 44885300 | 44887200 | 128287706 | 128288820 | d0Mseg315 | 6312 |
| 0 | 44953550 | 44955250 | 128357475 | 128359345 | d0Mseg316 | 6313 |
| 0 | 45226500 | 45228200 | 128638231 | 128640008 | d0Mseg318 | 6314 |
| 0 | 45297750 | 45299550 | 128704573 | 128708498 | d0Mseg319 | 6315 |
| 0 | 45385750 | 45389250 | 128786719 | 128790159 | d0Mseg320 | 6316 |
| 0 | 45488450 | 45490400 | 128901741 | 128903749 | d0Mseg321 | 6317 |
| 0 | 45505050 | 45506850 | 128918350 | 128920545 | d0Mseg322 | 6318 |
| 0 | 45664900 | 45666900 | 129087730 | 129090199 | d0Mseg323 | 6319 |
| 0 | 45696250 | 45699200 | 129115939 | 129118858 | d0Mseg324 | 6320 |
| 0 | 45807950 | 45809750 | 129245394 | 129247932 | d0Mseg325 | 6321 |
| 0 | 46132200 | 46133450 | 129558859 | 129559167 | d0Mseg328 | 6322 |
| 0 | 46178900 | 46180600 | 129609706 | 129609943 | d0Mseg330 | 6323 |
| 0 | 46223250 | 46224300 | 129641548 | 129642386 | d0Mseg331 | 6324 |
| 0 | 46424000 | 46425650 | 129824019 | 129825338 | d0Mseg332 | 6325 |
| 0 | 46788250 | 46790300 | 130160250 | 130160610 | d0Mseg338 | 6326 |
| 0 | 46792650 | 46794150 | 130162565 | 130164136 | d0Mseg339 | 6327 |
| 0 | 46830500 | 46832150 | 130199469 | 130201066 | d0Mseg340 | 6328 |
| 0 | 46833300 | 46835250 | 130202016 | 130204177 | d0Mseg341 | 6329 |
| 0 | 46837150 | 46840150 | 130205732 | 130208956 | d0Mseg342 | 6330 |
| 0 | 46844900 | 46849150 | 130214214 | 130218472 | d0Mseg343 | 6331 |
| 0 | 47117100 | 47118950 | 130390764 | 130392077 | d0Mseg345 | 6332 |
| 0 | 47163200 | 47165050 | 130431899 | 130432414 | d0Mseg346 | 6333 |
| 0 | 47250800 | 47254300 | 130471174 | 130471612 | d0Mseg347 | 6334 |
| 0 | 47292300 | 47294250 | 130491898 | 130492160 | d0Mseg348 | 6335 |
| 0 | 47296350 | 47297700 | 130493341 | 130494538 | d0Mseg349 | 6336 |
| 0 | 47311250 | 47313150 | 130497500 | 130498116 | d0Mseg350 | 6337 |
| 0 | 47517150 | 47518900 | 130678615 | 130678963 | d0Mseg353 | 6338 |
| 0 | 48215300 | 48217100 | 131179423 | 131181280 | d0Mseg357 | 6339 |
| 0 | 48256150 | 48260450 | 131220943 | 131225525 | d0Mseg358 | 6340 |
| 0 | 48301750 | 48302950 | 131278014 | 131278763 | d0Mseg359 | 6341 |
| 0 | 48418100 | 48419850 | 131426674 | 131427999 | d0Mseg361 | 6342 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 48488050 | 48489200 | 131531145 | 131531727 | d0Mseg362 | 6343 |
| 0 | 48560650 | 48561800 | 131625511 | 131627275 | d0Mseg363 | 6344 |
| 0 | 48579050 | 48580700 | 131643579 | 131643804 | d0Mseg364 | 6345 |
| 0 | 48711450 | 48713150 | 131731336 | 131733099 | d0Mseg365 | 6346 |
| 0 | 49019800 | 49021500 | 132076121 | 132077158 | d0Mseg366 | 6347 |
| 0 | 49030900 | 49035950 | 132088516 | 132093838 | d0Mseg367 | 6348 |
| 0 | 49041550 | 49043400 | 132099266 | 132100904 | d0Mseg368 | 6349 |
| 0 | 49054850 | 49056700 | 132111953 | 132114009 | d0Mseg369 | 6350 |
| 0 | 49115350 | 49116900 | 132166372 | 132167098 | d0Mseg370 | 6351 |
| 0 | 49449550 | 49451250 | 132477256 | 132479068 | d0Mseg373 | 6352 |
| 0 | 49470850 | 49472300 | 132501369 | 132502597 | d0Mseg374 | 6353 |
| 0 | 49516400 | 49519950 | 132547340 | 132550971 | d0Mseg375 | 6354 |
| 0 | 49568750 | 49570250 | 132612063 | 132615648 | d0Mseg376 | 6355 |
| 0 | 49947550 | 49949450 | 133098516 | 133100926 | d0Mseg377 | 6356 |
| 0 | 49965700 | 49967650 | 133118192 | 133120136 | d0Mseg378 | 6357 |
| 0 | 50117350 | 50118350 | 133324614 | 133325151 | d0Mseg380 | 6358 |
| 0 | 50151750 | 50153450 | 133379324 | 133380833 | d0Mseg381 | 6359 |
| 0 | 50389850 | 50391600 | 133646432 | 133647389 | d0Mseg384 | 6360 |
| 0 | 50402300 | 50404150 | 133675065 | 133677098 | d0Mseg385 | 6361 |
| 0 | 50410900 | 50414450 | 133684229 | 133687679 | d0Mseg386 | 6362 |
| 0 | 50426350 | 50427400 | 133702755 | 133703787 | d0Mseg387 | 6363 |
| 0 | 50680600 | 50682400 | 134010628 | 134011331 | d0Mseg389 | 6364 |
| 0 | 51041250 | 51042750 | 134579038 | 134579956 | d0Mseg396 | 6365 |
| 0 | 53613650 | 53615500 | 134492594 | 134493655 | d0Mseg415 | 6366 |
| 0 | 53938600 | 53940400 | 135159035 | 135159827 | d0Mseg417 | 6367 |
| 0 | 53985300 | 53986300 | 135229962 | 135231013 | d0Mseg418 | 6368 |
| 0 | 54085350 | 54088900 | 135343978 | 135347694 | d0Mseg419 | 6369 |
| 0 | 54090400 | 54091450 | 135349194 | 135349917 | d0Mseg420 | 6370 |
| 0 | 54577950 | 54580050 | 135848013 | 135850107 | d0Mseg421 | 6371 |
| 0 | 54755300 | 54757550 | 136114195 | 136116742 | d0Mseg422 | 6372 |
| 0 | 54759150 | 54760800 | 136118238 | 136119738 | d0Mseg423 | 6373 |
| 0 | 54833200 | 54834950 | 136181494 | 136182057 | d0Mseg424 | 6374 |
| 0 | 54857650 | 54859300 | 136196146 | 136196356 | d0Mseg425 | 6375 |
| 0 | 55043850 | 55045500 | 136378478 | 136379954 | d0Mseg426 | 6376 |
| 0 | 55170200 | 55176300 | 136507079 | 136513398 | d0Mseg428 | 6377 |
| 0 | 55269650 | 55271500 | 136629395 | 136631796 | d0Mseg430 | 6378 |
| 0 | 55515950 | 55517600 | 136932196 | 136932407 | d0Mseg433 | 6379 |
| 0 | 55627450 | 55629150 | 137004678 | 137005621 | d0Mseg434 | 6380 |
| 0 | 55825650 | 55827350 | 137217567 | 137219377 | d0Mseg435 | 6381 |
| 0 | 55863150 | 55864900 | 137263518 | 137264410 | d0Mseg436 | 6382 |
| 0 | 55903200 | 55904850 | 137287637 | 137288858 | d0Mseg437 | 6383 |
| 0 | 55972200 | 55974150 | 137369544 | 137371625 | d0Mseg438 | 6384 |
| 0 | 56086950 | 56088600 | 137481110 | 137482124 | d0Mseg439 | 6385 |
| 0 | 56309350 | 56311000 | 137708870 | 137709448 | d0Mseg440 | 6386 |
| 0 | 56371000 | 56372750 | 137779385 | 137780630 | d0Mseg441 | 6387 |
| 0 | 56386200 | 56388200 | 137792166 | 137794140 | d0Mseg442 | 6388 |
| 0 | 56489150 | 56490650 | 137924802 | 137926367 | d0Mseg443 | 6389 |
| 0 | 56693500 | 56695500 | 138159571 | 138161025 | d0Mseg445 | 6390 |
| 0 | 56819200 | 56822050 | 138285209 | 138288246 | d0Mseg446 | 6391 |
| 0 | 56873550 | 56874550 | 138351055 | 138352012 | d0Mseg447 | 6392 |
| 0 | 57038750 | 57040500 | 138470872 | 138471659 | d0Mseg448 | 6393 |
| 0 | 57087450 | 57088900 | 138506335 | 138507792 | d0Mseg449 | 6394 |
| 0 | 57301100 | 57302800 | 138660159 | 138660376 | d0Mseg451 | 6395 |
| 0 | 57393900 | 57397600 | 138716399 | 138721615 | d0Mseg452 | 6396 |
| 0 | 57430250 | 57431950 | 138772601 | 138774240 | d0Mseg453 | 6397 |
| 0 | 57647950 | 57649500 | 139006792 | 139007745 | d0Mseg454 | 6398 |
| 0 | 57659050 | 57661050 | 139016306 | 139018771 | d0Mseg455 | 6399 |
| 0 | 57801250 | 57803450 | 139173958 | 139176577 | d0Mseg457 | 6400 |
| 0 | 57865700 | 57867350 | 139225313 | 139226165 | d0Mseg458 | 6401 |
| 0 | 58013450 | 58015150 | 139427332 | 139427725 | d0Mseg459 | 6402 |
| 0 | 58042800 | 58044650 | 139453825 | 139457542 | d0Mseg460 | 6403 |
| 0 | 58081850 | 58083550 | 139517527 | 139520017 | d0Mseg461 | 6404 |
| 0 | 58127500 | 58129500 | 139570393 | 139571700 | d0Mseg463 | 6405 |
| 0 | 58132850 | 58134850 | 139573188 | 139574373 | d0Mseg464 | 6406 |
| 0 | 58142300 | 58152450 | 139582747 | 139593795 | d0Mseg465 | 6407 |
| 0 | 58737250 | 58739000 | 140549902 | 140551253 | d0Mseg468 | 6408 |
| 0 | 58771150 | 58772950 | 140502362 | 140503638 | d0Mseg469 | 6409 |
| 0 | 59181150 | 59182400 | 140648434 | 140650828 | d0Mseg471 | 6410 |
| 0 | 59283000 | 59284650 | 140729589 | 140730359 | d0Mseg473 | 6411 |
| 0 | 59311400 | 59313150 | 140752455 | 140755267 | d0Mseg474 | 6412 |
| 0 | 59348750 | 59350450 | 140801407 | 140802195 | d0Mseg475 | 6413 |
| 0 | 60103250 | 60105100 | 141547249 | 141548140 | d0Mseg485 | 6414 |
| 0 | 60730100 | 60731850 | 142072550 | 142073142 | d0Mseg492 | 6415 |
| 0 | 61008200 | 61010050 | 142312563 | 142312854 | d0Mseg498 | 6416 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 61151200 | 61152950 | 142400730 | 142401528 | d0Mseg501 | 6417 |
| 0 | 61527650 | 61531700 | 142720286 | 142724493 | d0Mseg503 | 6418 |
| 0 | 61825450 | 61827050 | 143032965 | 143033272 | d0Mseg505 | 6419 |
| 0 | 62320050 | 62321700 | 143568554 | 143570206 | d0Mseg511 | 6420 |
| 0 | 62856500 | 62858100 | 144163597 | 144164556 | d0Mseg515 | 6421 |
| 0 | 62949100 | 62950700 | 144253347 | 144255281 | d0Mseg516 | 6422 |
| 0 | 62996700 | 62998050 | 144301426 | 144302229 | d0Mseg517 | 6423 |
| 0 | 63407100 | 63408750 | 144516735 | 144517061 | d0Mseg523 | 6424 |
| 0 | 63567050 | 63568950 | 144629942 | 144630384 | d0Mseg527 | 6425 |
| 0 | 63778100 | 63779750 | 144808645 | 144810883 | d0Mseg528 | 6426 |
| 0 | 63901200 | 63903850 | 144898111 | 144900677 | d0Mseg530 | 6427 |
| 0 | 63905500 | 63907900 | 144902364 | 144904761 | d0Mseg531 | 6428 |
| 0 | 64136900 | 64138700 | 145221785 | 145223055 | d0Mseg533 | 6429 |
| 0 | 64179400 | 64181150 | 145252196 | 145253968 | d0Mseg534 | 6430 |
| 0 | 64825300 | 64827050 | 145821989 | 145823194 | d0Mseg539 | 6431 |
| 0 | 65072450 | 65074100 | 146034483 | 146035113 | d0Mseg541 | 6432 |
| 0 | 65174700 | 65176100 | 146185425 | 146186095 | d0Mseg543 | 6433 |
| 0 | 65407200 | 65408950 | 146545245 | 146545932 | d0Mseg546 | 6434 |
| 0 | 65503700 | 65505350 | 146614980 | 146616114 | d0Mseg549 | 6435 |
| 0 | 65954350 | 65956200 | 147015185 | 147017317 | d0Mseg551 | 6436 |
| 0 | 66120050 | 66121650 | 147154382 | 147155922 | d0Mseg553 | 6437 |
| 0 | 66203350 | 66205150 | 147214580 | 147215862 | d0Mseg554 | 6438 |
| 0 | 66261200 | 66262650 | 147243281 | 147244824 | d0Mseg555 | 6439 |
| 0 | 66559800 | 66561650 | 147527136 | 147529353 | d0Mseg558 | 6440 |
| 0 | 66575100 | 66576800 | 147544151 | 147544709 | d0Mseg559 | 6441 |
| 0 | 66584550 | 66586300 | 147552460 | 147553518 | d0Mseg560 | 6442 |
| 0 | 66591350 | 66593000 | 147554689 | 147558186 | d0Mseg561 | 6443 |
| 0 | 66612250 | 66615350 | 147580806 | 147584059 | d0Mseg562 | 6444 |
| 0 | 66686400 | 66688000 | 147653591 | 147654308 | d0Mseg563 | 6445 |
| 0 | 66796250 | 66798350 | 147743228 | 147744195 | d0Mseg564 | 6446 |
| 0 | 66864650 | 66866250 | 147809791 | 147811048 | d0Mseg565 | 6447 |
| 0 | 67074300 | 67076100 | 148021921 | 148024772 | d0Mseg566 | 6448 |
| 0 | 67243850 | 67245850 | 148198540 | 148200273 | d0Mseg568 | 6449 |
| 0 | 67449250 | 67450400 | 148406820 | 148406976 | d0Mseg570 | 6450 |
| 0 | 67953150 | 67954850 | 149215097 | 149215558 | d0Mseg572 | 6451 |
| 0 | 68177400 | 68179150 | 149423320 | 149425118 | d0Mseg573 | 6452 |
| 0 | 68241150 | 68242650 | 149468454 | 149469389 | d0Mseg575 | 6453 |
| 0 | 68274550 | 68276250 | 149502014 | 149502544 | d0Mseg576 | 6454 |
| 0 | 68302300 | 68306450 | 149530447 | 149534656 | d0Mseg577 | 6455 |
| 0 | 68912550 | 68919950 | 150340243 | 150348493 | d0Mseg582 | 6456 |
| 0 | 69008800 | 69010950 | 150476931 | 150479631 | d0Mseg585 | 6457 |
| 0 | 69019700 | 69021550 | 150506080 | 150506410 | d0Mseg586 | 6458 |
| 0 | 69036350 | 69037700 | 150528414 | 150529663 | d0Mseg587 | 6459 |
| 0 | 69518500 | 69520300 | 151141496 | 151143350 | d0Mseg588 | 6460 |
| 0 | 69593150 | 69594850 | 151253649 | 151254915 | d0Mseg589 | 6461 |
| 0 | 70170200 | 70171300 | 152013627 | 152014200 | d0Mseg592 | 6462 |
| 0 | 70655800 | 70657950 | 152676293 | 152678338 | d0Mseg598 | 6463 |
| 0 | 70664550 | 70669500 | 152684240 | 152688407 | d0Mseg599 | 6464 |
| 0 | 70692950 | 70694650 | 152721396 | 152723065 | d0Mseg600 | 6465 |
| 0 | 70711750 | 70713450 | 152741138 | 152742758 | d0Mseg601 | 6466 |
| 0 | 70749800 | 70751750 | 152784456 | 152786356 | d0Mseg602 | 6467 |
| 0 | 70762700 | 70764300 | 152796863 | 152798278 | d0Mseg603 | 6468 |
| 0 | 70855400 | 70859850 | 152887498 | 152889256 | d0Mseg604 | 6469 |
| 0 | 70880300 | 70883850 | 152907310 | 152911630 | d0Mseg605 | 6470 |
| 0 | 71522150 | 71523800 | 153633517 | 153633972 | d0Mseg608 | 6471 |
| 0 | 71559800 | 71561550 | 153673805 | 153675928 | d0Mseg609 | 6472 |
| 0 | 72683300 | 72684900 | 154319084 | 154320539 | d0Mseg616 | 6473 |
| 0 | 73271250 | 73273150 | 114681544 | 114682421 | d0Mseg625 | 6474 |
| 0 | 73403300 | 73405000 | 114539896 | 114541084 | d0Mseg627 | 6475 |
| 0 | 73945100 | 73946750 | 8809113 | 8810780 | d0Mseg629 | 6476 |
| 0 | 74204800 | 74205950 | 8918925 | 8919933 | d0Mseg633 | 6477 |
| 0 | 74354100 | 74355950 | 9097939 | 9098658 | d0Mseg635 | 6478 |
| 0 | 74479650 | 74481500 | 9165561 | 9166569 | d0Mseg639 | 6479 |
| 0 | 74835300 | 74837050 | 9541007 | 9542010 | d0Mseg640 | 6480 |
| 0 | 74887150 | 74888850 | 9622451 | 9652183 | d0Mseg641 | 6481 |
| 0 | 75814350 | 75816000 | 37220133 | 37221031 | d0Mseg648 | 6482 |
| 0 | 76153600 | 76155300 | 36879028 | 36880035 | d0Mseg652 | 6483 |
| 0 | 76204350 | 76205550 | 36846998 | 36847199 | d0Mseg653 | 6484 |
| 0 | 76509050 | 76510700 | 36404171 | 36404660 | d0Mseg654 | 6485 |
| 0 | 76733150 | 76734800 | 35993028 | 35994758 | d0Mseg655 | 6486 |
| 0 | 76753500 | 76755200 | 35970094 | 35971592 | d0Mseg656 | 6487 |
| 0 | 76810650 | 76812150 | 35905727 | 35906658 | d0Mseg658 | 6488 |
| 0 | 77574200 | 77576000 | 35150260 | 35160500 | d0Mseg665 | 6489 |
| 0 | 77684450 | 77686200 | 36740892 | 36744682 | d0Mseg668 | 6490 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 78741350 | 78745900 | 34356727 | 34359854 | d0Mseg678 | 6491 |
| 0 | 78872550 | 78873800 | 34285580 | 34286028 | d0Mseg682 | 6492 |
| 0 | 79215650 | 79217350 | 33997931 | 33998333 | d0Mseg684 | 6493 |
| 0 | 79557900 | 79559550 | 33741409 | 33743186 | d0Mseg693 | 6494 |
| 0 | 79857600 | 79859300 | 33452012 | 33453109 | d0Mseg696 | 6495 |
| 0 | 80254150 | 80255950 | 33185083 | 33186115 | d0Mseg698 | 6496 |
| 0 | 80318500 | 80320200 | 33105869 | 33108524 | d0Mseg699 | 6497 |
| 0 | 81251850 | 81253650 | 32239306 | 32242454 | d0Mseg704 | 6498 |
| 0 | 81255150 | 81257300 | 32237572 | 32237818 | d0Mseg705 | 6499 |
| 0 | 81479450 | 81480900 | 32015529 | 32016547 | d0Mseg706 | 6500 |
| 0 | 81487750 | 81489450 | 32009808 | 32010769 | d0Mseg707 | 6501 |
| 0 | 81590050 | 81591800 | 31917168 | 31919036 | d0Mseg708 | 6502 |
| 0 | 81990300 | 81992050 | 31553874 | 31554846 | d0Mseg709 | 6503 |
| 0 | 82018750 | 82020400 | 31524098 | 31525749 | d0Mseg710 | 6504 |
| 0 | 82195400 | 82196700 | 31357619 | 31359042 | d0Mseg711 | 6505 |
| 0 | 82403700 | 82405400 | 31181011 | 31182728 | d0Mseg712 | 6506 |
| 0 | 82654100 | 82658600 | 31006282 | 31009137 | d0Mseg713 | 6507 |
| 0 | 82689550 | 82691450 | 30979166 | 30980310 | d0Mseg714 | 6508 |
| 0 | 82720400 | 82722100 | 30966768 | 30968131 | d0Mseg715 | 6509 |
| 0 | 82879550 | 82881300 | 30845268 | 30845816 | d0Mseg717 | 6510 |
| 0 | 82953250 | 82954900 | 30743635 | 30745063 | d0Mseg718 | 6511 |
| 0 | 83389350 | 83391000 | 30391141 | 30393316 | d0Mseg720 | 6512 |
| 0 | 83459650 | 83462050 | 30305447 | 30310141 | d0Mseg721 | 6513 |
| 0 | 83498100 | 83499800 | 30266572 | 30268308 | d0Mseg722 | 6514 |
| 0 | 83676450 | 83678100 | 30216814 | 30217402 | d0Mseg726 | 6515 |
| 0 | 83996250 | 83998050 | 29966349 | 29967290 | d0Mseg731 | 6516 |
| 0 | 84145500 | 84147050 | 29818530 | 29819770 | d0Mseg732 | 6517 |
| 0 | 84170700 | 84172800 | 29799731 | 29801818 | d0Mseg733 | 6518 |
| 0 | 84247650 | 84249250 | 29742448 | 29743818 | d0Mseg734 | 6519 |
| 0 | 84276950 | 84278650 | 29701349 | 29703758 | d0Mseg735 | 6520 |
| 0 | 84351200 | 84352850 | 29632179 | 29632621 | d0Mseg736 | 6521 |
| 0 | 84517450 | 84519150 | 29452057 | 29453170 | d0Mseg738 | 6522 |
| 0 | 84557200 | 84558650 | 29408052 | 29409423 | d0Mseg739 | 6523 |
| 0 | 84653350 | 84655100 | 29305622 | 29306211 | d0Mseg740 | 6524 |
| 0 | 84720450 | 84722200 | 29247582 | 29248603 | d0Mseg741 | 6525 |
| 0 | 84815150 | 84816800 | 29145261 | 29147611 | d0Mseg742 | 6526 |
| 0 | 84860400 | 84862250 | 29093880 | 29095196 | d0Mseg743 | 6527 |
| 0 | 85012200 | 85013650 | 28928792 | 28931035 | d0Mseg744 | 6528 |
| 0 | 85032750 | 85034050 | 28908715 | 28909224 | d0Mseg745 | 6529 |
| 0 | 85124800 | 85126400 | 28820332 | 28821634 | d0Mseg747 | 6530 |
| 0 | 85176650 | 85178350 | 28786018 | 28786623 | d0Mseg748 | 6531 |
| 0 | 85206500 | 85207750 | 28754563 | 28756386 | d0Mseg749 | 6532 |
| 0 | 85288700 | 85290550 | 28675711 | 28679552 | d0Mseg750 | 6533 |
| 0 | 85314350 | 85316000 | 28646138 | 28647295 | d0Mseg751 | 6534 |
| 0 | 85358400 | 85361750 | 28604766 | 28608155 | d0Mseg752 | 6535 |
| 0 | 85364600 | 85366300 | 28600255 | 28601965 | d0Mseg753 | 6536 |
| 0 | 85792550 | 85794200 | 28299807 | 28300150 | d0Mseg757 | 6537 |
| 0 | 86389550 | 86391150 | 27957716 | 27958166 | d0Mseg762 | 6538 |
| 0 | 86412650 | 86414350 | 27939569 | 27940357 | d0Mseg763 | 6539 |
| 0 | 86989450 | 86991200 | 27489658 | 27490404 | d0Mseg766 | 6540 |
| 0 | 86999250 | 87000950 | 27478311 | 27480059 | d0Mseg767 | 6541 |
| 0 | 87263750 | 87265550 | 27234699 | 27235412 | d0Mseg771 | 6542 |
| 0 | 87459700 | 87461400 | 27105417 | 27107248 | d0Mseg774 | 6543 |
| 0 | 87753950 | 87756000 | 26869569 | 26869857 | d0Mseg778 | 6544 |
| 0 | 87925000 | 87926600 | 26652168 | 26652786 | d0Mseg782 | 6545 |
| 0 | 88192750 | 88194400 | 26465880 | 26466400 | d0Mseg786 | 6546 |
| 0 | 89312450 | 89314100 | 26180439 | 26180674 | d0Mseg800 | 6547 |
| 0 | 89465500 | 89467150 | 26031327 | 26031720 | d0Mseg802 | 6548 |
| 0 | 89650200 | 89652200 | 25802345 | 25805653 | d0Mseg805 | 6549 |
| 0 | 89717750 | 89718750 | 25731163 | 25732194 | d0Mseg806 | 6550 |
| 0 | 89738800 | 89740450 | 25695054 | 25699634 | d0Mseg807 | 6551 |
| 0 | 89880500 | 89882250 | 25523309 | 25523987 | d0Mseg809 | 6552 |
| 0 | 90278350 | 90280050 | 25197574 | 25199546 | d0Mseg811 | 6553 |
| 0 | 90294900 | 90296650 | 25182507 | 25184534 | d0Mseg812 | 6554 |
| 0 | 90519400 | 90521250 | 25044877 | 25046103 | d0Mseg814 | 6555 |
| 0 | 90525450 | 90546350 | 25018910 | 25040467 | d0Mseg815 | 6556 |
| 0 | 90930950 | 90932600 | 24656096 | 24657532 | d0Mseg816 | 6557 |
| 0 | 91413950 | 91415650 | 24100595 | 24101004 | d0Mseg818 | 6558 |
| 0 | 91477600 | 91479550 | 24044199 | 24045531 | d0Mseg819 | 6559 |
| 0 | 91484400 | 91488600 | 24033530 | 24039170 | d0Mseg820 | 6560 |
| 0 | 91608900 | 91612700 | 23925605 | 23928770 | d0Mseg821 | 6561 |
| 0 | 91799000 | 91800800 | 51601228 | 51601466 | d0Mseg824 | 6562 |
| 0 | 92639800 | 92641550 | 63425250 | 63426814 | d0Mseg830 | 6563 |
| 0 | 92723300 | 92725200 | 63564001 | 63566849 | d0Mseg832 | 6564 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 92839200 | 92841000 | 64140517 | 64141987 | d0Mseg834 | 6565 |
| 0 | 93136000 | 93137650 | 64738085 | 64739731 | d0Mseg836 | 6566 |
| 0 | 93660200 | 93662150 | 65391584 | 65392550 | d0Mseg841 | 6567 |
| 0 | 93906200 | 93908200 | 65654925 | 65656563 | d0Mseg845 | 6568 |
| 0 | 94538700 | 94540250 | 65824332 | 65825740 | d0Mseg853 | 6569 |
| 0 | 94580000 | 94582300 | 65870522 | 65870853 | d0Mseg854 | 6570 |
| 0 | 94817600 | 94819350 | 66116387 | 66116875 | d0Mseg856 | 6571 |
| 0 | 94846650 | 94848350 | 66133132 | 66134850 | d0Mseg857 | 6572 |
| 0 | 95342400 | 95349050 | 66762307 | 66769132 | d0Mseg865 | 6573 |
| 0 | 95823750 | 95825500 | 67318031 | 67319044 | d0Mseg869 | 6574 |
| 0 | 96084100 | 96086200 | 67651012 | 67653565 | d0Mseg870 | 6575 |
| 0 | 96211300 | 96213200 | 67884482 | 67886322 | d0Mseg872 | 6576 |
| 0 | 96237950 | 96240650 | 67913458 | 67916124 | d0Mseg873 | 6577 |
| 0 | 96329750 | 96333550 | 68047196 | 68050996 | d0Mseg875 | 6578 |
| 0 | 96342550 | 96343850 | 68060181 | 68061523 | d0Mseg876 | 6579 |
| 0 | 96393800 | 96395100 | 68113958 | 68115329 | d0Mseg877 | 6580 |
| 0 | 96411000 | 96412800 | 68130958 | 68133362 | d0Mseg878 | 6581 |
| 0 | 96421600 | 96423300 | 68143108 | 68146669 | d0Mseg879 | 6582 |
| 0 | 96428000 | 96429850 | 68150769 | 68152786 | d0Mseg880 | 6583 |
| 0 | 96512700 | 96514600 | 68235986 | 68238549 | d0Mseg881 | 6584 |
| 0 | 96579250 | 96581150 | 68298297 | 68298617 | d0Mseg883 | 6585 |
| 0 | 96593500 | 96595100 | 68310297 | 68311868 | d0Mseg884 | 6586 |
| 0 | 96599750 | 96601450 | 68315355 | 68317029 | d0Mseg885 | 6587 |
| 0 | 96608150 | 96609450 | 68324375 | 68325513 | d0Mseg886 | 6588 |
| 0 | 96625050 | 96626650 | 68342396 | 68344299 | d0Mseg887 | 6589 |
| 0 | 96627800 | 96630250 | 68346564 | 68349617 | d0Mseg888 | 6590 |
| 0 | 96725450 | 96727150 | 68448086 | 68449933 | d0Mseg889 | 6591 |
| 0 | 96763250 | 96765100 | 68497972 | 68500183 | d0Mseg890 | 6592 |
| 0 | 96848650 | 96850350 | 68602279 | 68603945 | d0Mseg891 | 6593 |
| 0 | 97159500 | 97161350 | 68826620 | 68826999 | d0Mseg893 | 6594 |
| 0 | 97379000 | 97380100 | 69020662 | 69022721 | d0Mseg894 | 6595 |
| 0 | 97503950 | 97505850 | 69175650 | 69177751 | d0Mseg895 | 6596 |
| 0 | 97676850 | 97678550 | 69318580 | 69319059 | d0Mseg896 | 6597 |
| 0 | 97803250 | 97804250 | 69490538 | 69491298 | d0Mseg897 | 6598 |
| 0 | 97932300 | 97934150 | 69650015 | 69653471 | d0Mseg898 | 6599 |
| 0 | 97963050 | 97964500 | 69664670 | 69666136 | d0Mseg900 | 6600 |
| 0 | 97965650 | 97967350 | 69667355 | 69669161 | d0Mseg901 | 6601 |
| 0 | 98046500 | 98048050 | 69774027 | 69775248 | d0Mseg902 | 6602 |
| 0 | 98415650 | 98417450 | 70285879 | 70287822 | d0Mseg907 | 6603 |
| 0 | 98450050 | 98452150 | 70316252 | 70318356 | d0Mseg908 | 6604 |
| 0 | 98514100 | 98516200 | 70387695 | 70390584 | d0Mseg909 | 6605 |
| 0 | 98570350 | 98571800 | 70432843 | 70434018 | d0Mseg910 | 6606 |
| 0 | 98581000 | 98583000 | 70445087 | 70447666 | d0Mseg911 | 6607 |
| 0 | 98610750 | 98612550 | 70469534 | 70471333 | d0Mseg912 | 6608 |
| 0 | 98753750 | 98755400 | 70613505 | 70614236 | d0Mseg913 | 6609 |
| 0 | 98886600 | 98887850 | 150565726 | 150573806 | d0Mseg914 | 6610 |
| 0 | 98889950 | 98894050 | 70798488 | 70799686 | d0Mseg915 | 6611 |
| 0 | 98964500 | 98966350 | 70869746 | 70871110 | d0Mseg916 | 6612 |
| 0 | 99034950 | 99038350 | 71115819 | 71116564 | d0Mseg918 | 6613 |
| 0 | 99041700 | 99049300 | 71127413 | 71135129 | d0Mseg919 | 6614 |
| 0 | 99060700 | 99062300 | 71145126 | 71146461 | d0Mseg920 | 6615 |
| 0 | 99071200 | 99073100 | 71155218 | 71156780 | d0Mseg921 | 6616 |
| 0 | 99095300 | 99096550 | 71175644 | 71176356 | d0Mseg922 | 6617 |
| 0 | 99134200 | 99136050 | 71221238 | 71222506 | d0Mseg924 | 6618 |
| 0 | 99149850 | 99151550 | 71238722 | 71240542 | d0Mseg925 | 6619 |
| 0 | 99285100 | 99286750 | 71370737 | 71372518 | d0Mseg926 | 6620 |
| 0 | 99383000 | 99384700 | 71495186 | 71497106 | d0Mseg929 | 6621 |
| 0 | 99444050 | 99451350 | 71522808 | 71530160 | d0Mseg930 | 6622 |
| 0 | 99486400 | 99488250 | 71558772 | 71560626 | d0Mseg931 | 6623 |
| 0 | 99566000 | 99567800 | 71633358 | 71635362 | d0Mseg932 | 6624 |
| 0 | 99603150 | 99604800 | 71686760 | 71688246 | d0Mseg933 | 6625 |
| 0 | 99640350 | 99642100 | 71731741 | 71733679 | d0Mseg934 | 6626 |
| 0 | 99812450 | 99814300 | 71887027 | 71887547 | d0Mseg935 | 6627 |
| 0 | 100125900 | 100127750 | 72159986 | 72161955 | d0Mseg936 | 6628 |
| 0 | 100381100 | 100382950 | 72433780 | 72435567 | d0Mseg939 | 6629 |
| 0 | 100516550 | 100518450 | 72666744 | 72668591 | d0Mseg941 | 6630 |
| 0 | 100818300 | 100820300 | 73512719 | 73513769 | d0Mseg946 | 6631 |
| 0 | 100884300 | 100885450 | 73592095 | 73593215 | d0Mseg947 | 6632 |
| 0 | 100888500 | 100892400 | 73754118 | 73757872 | d0Mseg948 | 6633 |
| 0 | 100894150 | 100896200 | 73749869 | 73752364 | d0Mseg949 | 6634 |
| 0 | 100918650 | 100920300 | 73733005 | 73733622 | d0Mseg950 | 6635 |
| 0 | 100938350 | 100940150 | 73712704 | 73714413 | d0Mseg951 | 6636 |
| 0 | 101006150 | 101007750 | 73652321 | 73654311 | d0Mseg953 | 6637 |
| 0 | 101015150 | 101018500 | 73640388 | 73643571 | d0Mseg954 | 6638 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 0 | 101073800 | 101075500 | 73755542 | 73759009 | d0Mseg956 | 6639 |
| 0 | 101287250 | 101288950 | 73972760 | 73973792 | d0Mseg961 | 6640 |
| 0 | 101443250 | 101445100 | 74189480 | 74222078 | d0Mseg962 | 6641 |
| 0 | 101673000 | 101674850 | 74448601 | 74462106 | d0Mseg964 | 6642 |
| 0 | 102008000 | 102009850 | 74956843 | 74957815 | d0Mseg967 | 6643 |
| 0 | 102012300 | 102013950 | 74968256 | 74969482 | d0Mseg968 | 6644 |
| 0 | 102049500 | 102051050 | 75002015 | 75003554 | d0Mseg969 | 6645 |
| 0 | 102280200 | 102281900 | 75404165 | 75404915 | d0Mseg972 | 6646 |
| 0 | 102315950 | 102317000 | 75648324 | 75649410 | d0Mseg973 | 6647 |
| 0 | 102608250 | 102610100 | 76280646 | 76282009 | d0Mseg976 | 6648 |
| 0 | 102956950 | 102963400 | 76703692 | 76706545 | d0Mseg979 | 6649 |
| 0 | 103303400 | 103305100 | 77287226 | 77289103 | d0Mseg980 | 6650 |
| 0 | 103413750 | 103416550 | 77393560 | 77396497 | d0Mseg983 | 6651 |
| 0 | 103799950 | 103801400 | 77585135 | 77585894 | d0Mseg991 | 6652 |
| 0 | 103896700 | 103898600 | 77770237 | 77771313 | d0Mseg993 | 6653 |
| 0 | 104115650 | 104117700 | 78002891 | 78004882 | d0Mseg995 | 6654 |
| 0 | 104597350 | 104598850 | 78621398 | 78623011 | d0Mseg1000 | 6655 |
| 0 | 104703700 | 104705400 | 78813367 | 78814999 | d0Mseg1001 | 6656 |
| 0 | 104872050 | 104873900 | 79277582 | 79279571 | d0Mseg1003 | 6657 |
| 0 | 105014200 | 105015850 | 79595049 | 79596388 | d0Mseg1004 | 6658 |
| 0 | 105933200 | 105935100 | 79926813 | 79928864 | d0Mseg1013 | 6659 |
| 0 | 105952000 | 105953600 | 79943931 | 79945929 | d0Mseg1014 | 6660 |
| 0 | 106178250 | 106179900 | 80316735 | 80317343 | d0Mseg1015 | 6661 |
| 0 | 106206050 | 106207850 | 80374090 | 80376305 | d0Mseg1016 | 6662 |
| 0 | 106227350 | 106229250 | 80389747 | 80415164 | d0Mseg1017 | 6663 |
| 0 | 106655900 | 106657650 | 80850892 | 80851694 | d0Mseg1022 | 6664 |
| 0 | 106998250 | 107000200 | 81377385 | 81379460 | d0Mseg1026 | 6665 |
| 0 | 107491600 | 107492950 | 81956311 | 81957710 | d0Mseg1028 | 6666 |
| 0 | 107515000 | 107516800 | 81980538 | 81982179 | d0Mseg1029 | 6667 |
| 0 | 107890800 | 107892700 | 82586210 | 82588204 | d0Mseg1032 | 6668 |
| 0 | 107917250 | 107918900 | 82606575 | 82608531 | d0Mseg1033 | 6669 |
| 0 | 108008800 | 108013900 | 82762302 | 82767614 | d0Mseg1035 | 6670 |
| 0 | 108623600 | 108625500 | 83484874 | 83487065 | d0Mseg1038 | 6671 |
| 0 | 108633600 | 108635250 | 83494837 | 83496129 | d0Mseg1039 | 6672 |
| 0 | 108648550 | 108650250 | 83505320 | 83508862 | d0Mseg1041 | 6673 |
| 0 | 108699950 | 108701200 | 83585647 | 83587388 | d0Mseg1042 | 6674 |
| 0 | 108782850 | 108784250 | 83727825 | 83729519 | d0Mseg1044 | 6675 |
| 0 | 109353850 | 109355800 | 84227965 | 84231580 | d0Mseg1050 | 6676 |
| 0 | 109423150 | 109424950 | 84256948 | 84258838 | d0Mseg1052 | 6677 |
| 0 | 109713750 | 109717050 | 84498457 | 84501673 | d0Mseg1054 | 6678 |
| 0 | 109871500 | 109872550 | 84689438 | 84690082 | d0Mseg1055 | 6679 |
| 0 | 110118950 | 110120750 | 85033538 | 85033826 | d0Mseg1056 | 6680 |
| 0 | 110140750 | 110142450 | 85084462 | 85086230 | d0Mseg1057 | 6681 |
| 0 | 110421100 | 110422800 | 85412681 | 85416710 | d0Mseg1059 | 6682 |
| 0 | 110801700 | 110803500 | 85933710 | 85934289 | d0Mseg1061 | 6683 |
| 0 | 110851000 | 110852750 | 85990473 | 85990766 | d0Mseg1062 | 6684 |
| 0 | 111700150 | 111701800 | 86956298 | 86959701 | d0Mseg1066 | 6685 |
| 0 | 112401200 | 112403200 | 87315126 | 87315926 | d0Mseg1071 | 6686 |
| 0 | 113059400 | 113060700 | 87695980 | 87696230 | d0Mseg1076 | 6687 |
| 0 | 113845100 | 113846850 | 88310419 | 88310868 | d0Mseg1080 | 6688 |
| 0 | 113917550 | 113919350 | 88263023 | 88263833 | d0Mseg1081 | 6689 |
| 0 | 114314750 | 114316350 | 88442229 | 88443387 | d0Mseg1083 | 6690 |
| 0 | 115703400 | 115705000 | 89319230 | 89320498 | d0Mseg1089 | 6691 |
| 0 | 115959150 | 115960350 | 89590007 | 89590892 | d0Mseg1091 | 6692 |
| 0 | 116295150 | 116296800 | 89865088 | 89865907 | d0Mseg1096 | 6693 |
| 0 | 116315700 | 116317450 | 89900830 | 89911110 | d0Mseg1097 | 6694 |
| 0 | 116511800 | 116513400 | 90067520 | 90067991 | d0Mseg1100 | 6695 |
| 0 | 117048900 | 117050550 | 90697489 | 90698453 | d0Mseg1107 | 6696 |
| 0 | 117089400 | 117091200 | 90730944 | 90736294 | d0Mseg1108 | 6697 |
| 0 | 117278850 | 117280300 | 90916891 | 90919777 | d0Mseg1111 | 6698 |
| 0 | 117377550 | 117379450 | 91016340 | 91017764 | d0Mseg1112 | 6699 |
| 0 | 117401400 | 117407150 | 91031842 | 91037540 | d0Mseg1113 | 6700 |
| 0 | 117644600 | 117647700 | 91346072 | 91354230 | d0Mseg1115 | 6701 |
| 0 | 117768800 | 117770600 | 91547393 | 91548215 | d0Mseg1116 | 6702 |
| 0 | 119120350 | 119122050 | 92660966 | 92661229 | d0Mseg1125 | 6703 |
| 0 | 119151350 | 119153150 | 92701270 | 92702362 | d0Mseg1126 | 6704 |
| 0 | 119252400 | 119253650 | 92772141 | 92772699 | d0Mseg1129 | 6705 |
| 0 | 119277800 | 119279600 | 92792140 | 92793911 | d0Mseg1130 | 6706 |
| 0 | 119499300 | 119501050 | 92909526 | 92910271 | d0Mseg1132 | 6707 |
| 0 | 119623200 | 119624900 | 93021134 | 93022275 | d0Mseg1134 | 6708 |
| 0 | 119774200 | 119775900 | 93085263 | 93086408 | d0Mseg1136 | 6709 |
| 0 | 119924950 | 119926650 | 93288572 | 93290474 | d0Mseg1137 | 6710 |
| 0 | 123235550 | 123237150 | 93668059 | 93668633 | d0Mseg1156 | 6711 |
| 0 | 124986350 | 124990400 | 94938081 | 94942255 | d0Mseg1170 | 6712 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 125348250 | 125349850 | 95209971 | 95210989 | d0Mseg1173 | 6713 |
| 0 | 126591250 | 126592900 | 96338747 | 96342353 | d0Mseg1181 | 6714 |
| 0 | 126738250 | 126739450 | 96515899 | 96521050 | d0Mseg1182 | 6715 |
| 0 | 127136000 | 127137750 | 96958145 | 96959898 | d0Mseg1183 | 6716 |
| 0 | 127309150 | 127311100 | 97067208 | 97067837 | d0Mseg1184 | 6717 |
| 0 | 127573000 | 127574700 | 97252973 | 97256101 | d0Mseg1185 | 6718 |
| 0 | 127650050 | 127651700 | 97335209 | 97336831 | d0Mseg1186 | 6719 |
| 0 | 127728000 | 127729800 | 97416576 | 97417848 | d0Mseg1187 | 6720 |
| 0 | 128054100 | 128055850 | 97702907 | 97704933 | d0Mseg1189 | 6721 |
| 0 | 128386750 | 128388450 | 98011360 | 98012327 | d0Mseg1191 | 6722 |
| 0 | 128421550 | 128423350 | 98026625 | 98027329 | d0Mseg1192 | 6723 |
| 0 | 128541000 | 128543000 | 98153780 | 98154681 | d0Mseg1193 | 6724 |
| 0 | 128554500 | 128556200 | 98176607 | 98177200 | d0Mseg1194 | 6725 |
| 0 | 128895350 | 128897000 | 98420777 | 98425614 | d0Mseg1197 | 6726 |
| 0 | 129333950 | 129336300 | 98868946 | 98869357 | d0Mseg1198 | 6727 |
| 0 | 129419100 | 129420750 | 98939503 | 98939769 | d0Mseg1199 | 6728 |
| 0 | 129959400 | 129960500 | 99375776 | 99376091 | d0Mseg1203 | 6729 |
| 0 | 130195200 | 130196750 | 99637105 | 99638248 | d0Mseg1204 | 6730 |
| 0 | 130204800 | 130206600 | 99646054 | 99647626 | d0Mseg1205 | 6731 |
| 0 | 130218450 | 130226750 | 99660339 | 99668308 | d0Mseg1206 | 6732 |
| 0 | 130289950 | 130291600 | 99734427 | 99736686 | d0Mseg1207 | 6733 |
| 0 | 130430550 | 130432400 | 99889879 | 99891230 | d0Mseg1210 | 6734 |
| 0 | 130447400 | 130449200 | 99903304 | 99905140 | d0Mseg1211 | 6735 |
| 0 | 130462700 | 130464300 | 99921423 | 99923033 | d0Mseg1212 | 6736 |
| 0 | 130696700 | 130698350 | 100183556 | 100185633 | d0Mseg1213 | 6737 |
| 0 | 130938150 | 130940950 | 100473406 | 100476707 | d0Mseg1214 | 6738 |
| 0 | 131008150 | 131010000 | 100545375 | 100546418 | d0Mseg1215 | 6739 |
| 0 | 131290750 | 131291800 | 100877742 | 100878801 | d0Mseg1218 | 6740 |
| 0 | 131426400 | 131427850 | 101005754 | 101006338 | d0Mseg1221 | 6741 |
| 0 | 131468850 | 131470800 | 101060331 | 101079314 | d0Mseg1222 | 6742 |
| 0 | 131486050 | 131490050 | 101092954 | 101095762 | d0Mseg1223 | 6743 |
| 0 | 131558550 | 131560250 | 101215897 | 101216526 | d0Mseg1226 | 6744 |
| 0 | 131744200 | 131746500 | 101396423 | 101398365 | d0Mseg1228 | 6745 |
| 0 | 132128400 | 132130250 | 101634963 | 101635181 | d0Mseg1234 | 6746 |
| 0 | 132443300 | 132444950 | 102026471 | 102026806 | d0Mseg1237 | 6747 |
| 0 | 132699650 | 132700900 | 102504962 | 102505385 | d0Mseg1240 | 6748 |
| 0 | 132702150 | 132706250 | 102506557 | 102509611 | d0Mseg1241 | 6749 |
| 0 | 133173150 | 133174550 | 102809378 | 102809962 | d0Mseg1244 | 6750 |
| 0 | 133201850 | 133203600 | 102863759 | 102865597 | d0Mseg1246 | 6751 |
| 0 | 133225300 | 133227050 | 102893114 | 102894204 | d0Mseg1247 | 6752 |
| 0 | 133259450 | 133261350 | 102923252 | 102926503 | d0Mseg1248 | 6753 |
| 0 | 133320000 | 133321650 | 102989190 | 102991061 | d0Mseg1249 | 6754 |
| 0 | 133461350 | 133464150 | 103159141 | 103159839 | d0Mseg1250 | 6755 |
| 0 | 133527350 | 133528800 | 103356849 | 103358437 | d0Mseg1251 | 6756 |
| 0 | 133651350 | 133659100 | 103497403 | 103501568 | d0Mseg1254 | 6757 |
| 0 | 133867150 | 133868900 | 103672189 | 103672769 | d0Mseg1259 | 6758 |
| 0 | 134099100 | 134107350 | 103799771 | 103812994 | d0Mseg1262 | 6759 |
| 0 | 134277700 | 134279100 | 103983757 | 103984495 | d0Mseg1264 | 6760 |
| 0 | 134704850 | 134706650 | 104435078 | 104437310 | d0Mseg1267 | 6761 |
| 0 | 134947050 | 134948700 | 104646829 | 104647833 | d0Mseg1269 | 6762 |
| 0 | 134964050 | 134965750 | 104660717 | 104661858 | d0Mseg1271 | 6763 |
| 0 | 134975950 | 134977150 | 104671819 | 104672746 | d0Mseg1272 | 6764 |
| 0 | 134988850 | 134990650 | 104683910 | 104686108 | d0Mseg1273 | 6765 |
| 0 | 135301150 | 135302700 | 104941956 | 104943185 | d0Mseg1277 | 6766 |
| 0 | 135327950 | 135329550 | 104963624 | 104964823 | d0Mseg1278 | 6767 |
| 0 | 135445450 | 135450300 | 105063274 | 105067884 | d0Mseg1279 | 6768 |
| 0 | 135464700 | 135466450 | 105086269 | 105087503 | d0Mseg1280 | 6769 |
| 0 | 135504950 | 135506500 | 105144680 | 105149446 | d0Mseg1281 | 6770 |
| 0 | 135613150 | 135615050 | 105276126 | 105277717 | d0Mseg1284 | 6771 |
| 0 | 135751150 | 135752450 | 105420847 | 105422046 | d0Mseg1288 | 6772 |
| 0 | 136014900 | 136015950 | 105855188 | 105856078 | d0Mseg1291 | 6773 |
| 0 | 136108300 | 136109900 | 105945940 | 105946917 | d0Mseg1293 | 6774 |
| 0 | 136144900 | 136146850 | 105969711 | 105971612 | d0Mseg1294 | 6775 |
| 0 | 136219200 | 136221300 | 106045583 | 106047409 | d0Mseg1295 | 6776 |
| 0 | 136404100 | 136407250 | 106241425 | 106243936 | d0Mseg1296 | 6777 |
| 0 | 136681900 | 136683600 | 106545632 | 106546670 | d0Mseg1298 | 6778 |
| 0 | 136711950 | 136713450 | 106581560 | 106582257 | d0Mseg1299 | 6779 |
| 0 | 136798700 | 136800050 | 106681941 | 106682647 | d0Mseg1300 | 6780 |
| 0 | 136809900 | 136814900 | 106690547 | 106695325 | d0Mseg1301 | 6781 |
| 0 | 136825150 | 136826950 | 106705878 | 106707101 | d0Mseg1302 | 6782 |
| 0 | 136846800 | 136848700 | 106728011 | 106728776 | d0Mseg1303 | 6783 |
| 0 | 136873950 | 136877750 | 106747501 | 106750911 | d0Mseg1304 | 6784 |
| 0 | 136950200 | 136953900 | 106817595 | 106819913 | d0Mseg1305 | 6785 |
| 0 | 136960100 | 136961800 | 106839200 | 106840176 | d0Mseg1306 | 6786 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 0 | 136965450 | 136971200 | 106843893 | 106850147 | d0Mseg1307 | 6787 |
| 0 | 136987850 | 136989650 | 106861515 | 106861895 | d0Mseg1308 | 6788 |
| 0 | 137044750 | 137046600 | 106919655 | 106921361 | d0Mseg1309 | 6789 |
| 0 | 137109800 | 137111500 | 106993783 | 106995539 | d0Mseg1310 | 6790 |
| 0 | 137131250 | 137136400 | 107016901 | 107021572 | d0Mseg1311 | 6791 |
| 0 | 137198250 | 137201550 | 107068108 | 107072468 | d0Mseg1314 | 6792 |
| 0 | 137234450 | 137236450 | 107103259 | 107106148 | d0Mseg1315 | 6793 |
| 0 | 137269050 | 137270800 | 107145234 | 107147012 | d0Mseg1316 | 6794 |
| 0 | 137272400 | 137274200 | 107148183 | 107150272 | d0Mseg1317 | 6795 |
| 0 | 137344250 | 137345450 | 107222583 | 107223451 | d0Mseg1318 | 6796 |
| 0 | 137418950 | 137420250 | 107272383 | 107273135 | d0Mseg1320 | 6797 |
| 0 | 137475450 | 137477100 | 107324457 | 107324673 | d0Mseg1321 | 6798 |
| 0 | 137509750 | 137511450 | 107360053 | 107361701 | d0Mseg1322 | 6799 |
| 0 | 137674500 | 137676400 | 107472475 | 107473950 | d0Mseg1323 | 6800 |
| 0 | 137699150 | 137700900 | 107491922 | 107494242 | d0Mseg1325 | 6801 |
| 0 | 137765550 | 137767100 | 107555769 | 107556399 | d0Mseg1327 | 6802 |
| 0 | 137884100 | 137885750 | 107652591 | 107654374 | d0Mseg1329 | 6803 |
| 0 | 137901400 | 137903050 | 107670265 | 107672930 | d0Mseg1330 | 6804 |
| 0 | 137907400 | 137909100 | 107680345 | 107682178 | d0Mseg1331 | 6805 |
| 0 | 137913050 | 137914700 | 107686110 | 107687970 | d0Mseg1332 | 6806 |
| 0 | 138094300 | 138098200 | 107914252 | 107916568 | d0Mseg1333 | 6807 |
| 0 | 138128300 | 138129950 | 107943938 | 107945667 | d0Mseg1334 | 6808 |
| 0 | 138148950 | 138150550 | 107967515 | 107970175 | d0Mseg1335 | 6809 |
| 0 | 138155150 | 138162600 | 107974881 | 107982840 | d0Mseg1336 | 6810 |
| 0 | 138186550 | 138188350 | 108049972 | 108050213 | d0Mseg1338 | 6811 |
| 0 | 138365600 | 138367300 | 108432612 | 108434501 | d0Mseg1342 | 6812 |
| 0 | 138523550 | 138525200 | 108619278 | 108621100 | d0Mseg1343 | 6813 |
| 0 | 138545600 | 138547700 | 108641869 | 108643544 | d0Mseg1344 | 6814 |
| 0 | 138662450 | 138664250 | 108779852 | 108781402 | d0Mseg1345 | 6815 |
| 0 | 138738550 | 138740750 | 108866096 | 108868429 | d0Mseg1347 | 6816 |
| 0 | 138882800 | 138884650 | 109036295 | 109036891 | d0Mseg1348 | 6817 |
| 0 | 138972450 | 138974350 | 109132872 | 109133904 | d0Mseg1349 | 6818 |
| 0 | 139112450 | 139116200 | 109240267 | 109246096 | d0Mseg1354 | 6819 |
| 0 | 139247600 | 139249350 | 109393888 | 109394126 | d0Mseg1355 | 6820 |
| 0 | 139305450 | 139307200 | 109451407 | 109453314 | d0Mseg1356 | 6821 |
| 0 | 139340500 | 139341700 | 109499852 | 109502000 | d0Mseg1357 | 6822 |
| 0 | 139392650 | 139393800 | 109552718 | 109553654 | d0Mseg1358 | 6823 |
| 0 | 139401350 | 139403400 | 109561393 | 109563282 | d0Mseg1359 | 6824 |
| 0 | 139494050 | 139496650 | 109657053 | 109659686 | d0Mseg1360 | 6825 |
| 0 | 139514050 | 139515750 | 109674380 | 109676104 | d0Mseg1361 | 6826 |
| 0 | 139555750 | 139557700 | 109714935 | 109716033 | d0Mseg1362 | 6827 |
| 0 | 139720350 | 139721850 | 109917218 | 109918796 | d0Mseg1363 | 6828 |
| 0 | 139827450 | 139829450 | 110038100 | 110040094 | d0Mseg1365 | 6829 |
| 0 | 139962000 | 139964450 | 110195335 | 110197319 | d0Mseg1366 | 6830 |
| 0 | 140171650 | 140173500 | 110409080 | 110411343 | d0Mseg1367 | 6831 |
| 0 | 140236000 | 140237700 | 110487602 | 110489252 | d0Mseg1368 | 6832 |
| 0 | 140323050 | 140324700 | 110597361 | 110599205 | d0Mseg1369 | 6833 |
| 0 | 140336000 | 140337650 | 110614330 | 110616194 | d0Mseg1370 | 6834 |
| 0 | 140956750 | 140958450 | 111191291 | 111195694 | d0Mseg1374 | 6835 |
| 0 | 141121700 | 141124950 | 111324455 | 111327763 | d0Mseg1375 | 6836 |
| 0 | 141143000 | 141144700 | 111339366 | 111340349 | d0Mseg1376 | 6837 |
| 0 | 141781200 | 141783100 | 111921282 | 111922819 | d0Mseg1382 | 6838 |
| 0 | 141847200 | 141848450 | 111986158 | 111987296 | d0Mseg1383 | 6839 |
| 0 | 142126650 | 142128400 | 112290439 | 112291383 | d0Mseg1384 | 6840 |
| 0 | 142137000 | 142138800 | 112318621 | 112319362 | d0Mseg1385 | 6841 |
| 0 | 142421600 | 142423450 | 112599067 | 112600494 | d0Mseg1387 | 6842 |
| 0 | 142755450 | 142757200 | 113011194 | 113012415 | d0Mseg1390 | 6843 |
| 0 | 142997200 | 142998850 | 113319750 | 113320204 | d0Mseg1393 | 6844 |
| 0 | 143059550 | 143061300 | 113385304 | 113387105 | d0Mseg1395 | 6845 |
| 0 | 143231600 | 143233300 | 113661602 | 113662646 | d0Mseg1398 | 6846 |
| 0 | 143393450 | 143395700 | 113815080 | 113817326 | d0Mseg1399 | 6847 |
| 0 | 143396950 | 143401150 | 113818463 | 113821894 | d0Mseg1400 | 6848 |
| 0 | 143449950 | 143451400 | 113901516 | 113902923 | d0Mseg1401 | 6849 |
| 0 | 143577250 | 143578400 | 114039214 | 114045591 | d0Mseg1402 | 6850 |
| 0 | 143931450 | 143933250 | 114391306 | 114393176 | d0Mseg1408 | 6851 |
| 0 | 143977650 | 143979250 | 114461446 | 114462674 | d0Mseg1409 | 6852 |
| 0 | 146168000 | 146169550 | 114737725 | 114738742 | d0Mseg1417 | 6853 |
| 0 | 146280800 | 146282350 | 114538969 | 114540129 | d0Mseg1419 | 6854 |
| 0 | 147116650 | 147118250 | 54929258 | 54933331 | d0Mseg1429 | 6855 |
| 0 | 147797700 | 147798950 | 54195261 | 54195972 | d0Mseg1433 | 6856 |
| 0 | 148422700 | 148424000 | 53467423 | 53467726 | d0Mseg1435 | 6857 |
| 0 | 148428050 | 148429750 | 53462780 | 53464180 | d0Mseg1436 | 6858 |
| 0 | 148577250 | 148580800 | 53348416 | 53352759 | d0Mseg1438 | 6859 |
| 0 | 148788900 | 148790500 | 53097066 | 53098921 | d0Mseg1439 | 6860 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 0 | 149042400 | 149046100 | 9916073 | 9917528 | d0Mseg1440 | 6861 |
| 0 | 149137450 | 149139100 | 9834324 | 9835006 | d0Mseg1441 | 6862 |
| 0 | 149797550 | 149799350 | 56261656 | 56262877 | d0Mseg1446 | 6863 |
| 0 | 149828100 | 149830000 | 56311581 | 56313823 | d0Mseg1447 | 6864 |
| 0 | 149925500 | 149926950 | 56582908 | 56584454 | d0Mseg1449 | 6865 |
| 0 | 150160400 | 150162250 | 56758648 | 56759758 | d0Mseg1451 | 6866 |
| 0 | 150329350 | 150331100 | 57002874 | 57005781 | d0Mseg1453 | 6867 |
| 0 | 151558100 | 151560950 | 9935198 | 9936384 | d0Mseg1464 | 6868 |
| 0 | 151699000 | 151700650 | 23759018 | 23759699 | d0Mseg1465 | 6869 |
| 0 | 151994050 | 151995850 | 23421953 | 23422453 | d0Mseg1467 | 6870 |
| 0 | 152056150 | 152064650 | 23347044 | 23354675 | d0Mseg1468 | 6871 |
| 0 | 152676600 | 152677700 | 22949204 | 22949507 | d0Mseg1473 | 6872 |
| 0 | 152771850 | 152773500 | 22877650 | 22879623 | d0Mseg1474 | 6873 |
| 0 | 152909100 | 152910850 | 22754525 | 22755136 | d0Mseg1475 | 6874 |
| 0 | 153350750 | 153352600 | 22423386 | 22424736 | d0Mseg1477 | 6875 |
| 0 | 154348700 | 154350350 | 21542638 | 21544400 | d0Mseg1482 | 6876 |
| 0 | 154357100 | 154358800 | 21533589 | 21535664 | d0Mseg1483 | 6877 |
| 0 | 154478700 | 154481800 | 21391966 | 21395196 | d0Mseg1484 | 6878 |
| 0 | 154562500 | 154564150 | 21311881 | 21312415 | d0Mseg1487 | 6879 |
| 0 | 155066450 | 155067650 | 20806235 | 20808355 | d0Mseg1491 | 6880 |
| 0 | 155296500 | 155298300 | 20582759 | 20584743 | d0Mseg1494 | 6881 |
| 0 | 155359050 | 155360800 | 20548201 | 20549780 | d0Mseg1496 | 6882 |
| 0 | 155604950 | 155606650 | 20368678 | 20370276 | d0Mseg1498 | 6883 |
| 0 | 155683800 | 155685400 | 20298827 | 20300257 | d0Mseg1499 | 6884 |
| 0 | 155748150 | 155750000 | 20227385 | 20228616 | d0Mseg1500 | 6885 |
| 0 | 155814300 | 155816300 | 20153593 | 20156750 | d0Mseg1501 | 6886 |
| 0 | 155947100 | 155948550 | 20014121 | 20014507 | d0Mseg1503 | 6887 |
| 0 | 156064800 | 156066350 | 19904673 | 19906249 | d0Mseg1505 | 6888 |
| 0 | 156071600 | 156073250 | 19895889 | 19898567 | d0Mseg1506 | 6889 |
| 0 | 156115150 | 156117050 | 19857775 | 19858433 | d0Mseg1507 | 6890 |
| 0 | 156151400 | 156153250 | 19810140 | 19812996 | d0Mseg1508 | 6891 |
| 0 | 156156250 | 156158000 | 19805306 | 19807598 | d0Mseg1509 | 6892 |
| 0 | 156258050 | 156259200 | 19708990 | 19710443 | d0Mseg1510 | 6893 |
| 0 | 156276550 | 156280250 | 19687382 | 19690843 | d0Mseg1511 | 6894 |
| 0 | 156408900 | 156410700 | 19554897 | 19556072 | d0Mseg1512 | 6895 |
| 0 | 156637800 | 156639450 | 19318361 | 19318925 | d0Mseg1513 | 6896 |
| 0 | 156827750 | 156829650 | 19139573 | 19141668 | d0Mseg1514 | 6897 |
| 0 | 156944150 | 156945850 | 18983886 | 18996976 | d0Mseg1515 | 6898 |
| 0 | 156955350 | 156957000 | 18978106 | 18979198 | d0Mseg1516 | 6899 |
| 0 | 156960750 | 156962400 | 18971441 | 18973047 | d0Mseg1517 | 6900 |
| 0 | 157126700 | 157128150 | 18764319 | 18764930 | d0Mseg1518 | 6901 |
| 0 | 157172500 | 157174300 | 18717813 | 18719134 | d0Mseg1519 | 6902 |
| 0 | 157602750 | 157604400 | 18368053 | 18370767 | d0Mseg1523 | 6903 |
| 0 | 157935200 | 157936850 | 18061056 | 18064895 | d0Mseg1526 | 6904 |
| 0 | 157975300 | 157976950 | 18021341 | 18022610 | d0Mseg1527 | 6905 |
| 0 | 157990200 | 157991450 | 18018059 | 18018555 | d0Mseg1528 | 6906 |
| 0 | 158047700 | 158049250 | 17965345 | 17966494 | d0Mseg1529 | 6907 |
| 0 | 158154500 | 158157650 | 17876885 | 17879805 | d0Mseg1530 | 6908 |
| 0 | 158164200 | 158165200 | 17869342 | 17870336 | d0Mseg1531 | 6909 |
| 0 | 158226150 | 158227850 | 17807246 | 17808941 | d0Mseg1532 | 6910 |
| 0 | 158344800 | 158348150 | 17672476 | 17675850 | d0Mseg1533 | 6911 |
| 0 | 158357400 | 158359050 | 17659247 | 17661046 | d0Mseg1534 | 6912 |
| 0 | 158493300 | 158494950 | 17503094 | 17504675 | d0Mseg1535 | 6913 |
| 0 | 158513400 | 158514600 | 17486213 | 17487444 | d0Mseg1536 | 6914 |
| 0 | 158595800 | 158598300 | 17392951 | 17395448 | d0Mseg1537 | 6915 |
| 0 | 158643700 | 158645550 | 17357905 | 17359795 | d0Mseg1538 | 6916 |
| 0 | 159025000 | 159026750 | 17005964 | 17008778 | d0Mseg1540 | 6917 |
| 0 | 159080450 | 159082100 | 16964311 | 16965994 | d0Mseg1542 | 6918 |
| 0 | 159444450 | 159446550 | 16629904 | 16630822 | d0Mseg1543 | 6919 |
| 0 | 159604800 | 159606500 | 16472299 | 16473220 | d0Mseg1544 | 6920 |
| 0 | 159877900 | 159879650 | 16214151 | 16215502 | d0Mseg1545 | 6921 |
| 0 | 160072000 | 160073850 | 16082385 | 16083637 | d0Mseg1546 | 6922 |
| 0 | 160416050 | 160417900 | 15800274 | 15800905 | d0Mseg1549 | 6923 |
| 0 | 160428250 | 160430050 | 15790292 | 15792526 | d0Mseg1550 | 6924 |
| 0 | 160787650 | 160789400 | 15415928 | 15417243 | d0Mseg1552 | 6925 |
| 0 | 160938850 | 160940250 | 15292565 | 15293587 | d0Mseg1553 | 6926 |
| 0 | 160957300 | 160959250 | 15276411 | 15276976 | d0Mseg1554 | 6927 |
| 0 | 161023850 | 161025300 | 15221827 | 15222933 | d0Mseg1555 | 6928 |
| 0 | 161239100 | 161240850 | 15083146 | 15084874 | d0Mseg1556 | 6929 |
| 0 | 161607600 | 161609800 | 14712401 | 14715636 | d0Mseg1558 | 6930 |
| 0 | 161656300 | 161658050 | 14667879 | 14669135 | d0Mseg1559 | 6931 |
| 0 | 161781000 | 161782750 | 14526619 | 14533219 | d0Mseg1560 | 6932 |
| 0 | 161999650 | 162000750 | 14397763 | 14399069 | d0Mseg1563 | 6933 |
| 0 | 162065050 | 162067000 | 14372294 | 14373947 | d0Mseg1564 | 6934 |

TABLE IVB-continued

Mouse Binding Sites with Human Liftovers

| Cell/ Day | Mouse Start | Mouse end | Human start | Human end | Segment name | SEQ ID NO: |
|---|---|---|---|---|---|---|
| 0 | 162119800 | 162120900 | 14339340 | 14340408 | d0Mseg1565 | 6935 |
| 0 | 162591150 | 162592800 | 14059808 | 14063365 | d0Mseg1566 | 6936 |
| 0 | 162675900 | 162679050 | 13954693 | 13957841 | d0Mseg1568 | 6937 |
| 0 | 162784900 | 162786600 | 13831452 | 13833007 | d0Mseg1569 | 6938 |
| 0 | 162806950 | 162808800 | 13805983 | 13807381 | d0Mseg1570 | 6939 |
| 0 | 162861400 | 162863100 | 13767456 | 13768255 | d0Mseg1571 | 6940 |
| 0 | 162958300 | 162959950 | 13662381 | 13664259 | d0Mseg1572 | 6941 |
| 0 | 163218700 | 163220500 | 13393389 | 13394599 | d0Mseg1575 | 6942 |
| 0 | 163289200 | 163290800 | 13351902 | 13352895 | d0Mseg1576 | 6943 |
| 0 | 163769750 | 163770850 | 12883751 | 12884144 | d0Mseg1578 | 6944 |
| 0 | 163963000 | 163964650 | 12690276 | 12691336 | d0Mseg1580 | 6945 |
| 0 | 164002400 | 164006150 | 12655929 | 12658937 | d0Mseg1581 | 6946 |
| 0 | 164355400 | 164357300 | 12338108 | 12340755 | d0Mseg1582 | 6947 |
| 0 | 164554800 | 164556500 | 12161288 | 12161947 | d0Mseg1584 | 6948 |
| 0 | 164560050 | 164562900 | 12154917 | 12157768 | d0Mseg1585 | 6949 |
| 0 | 164576350 | 164578150 | 12148441 | 12149581 | d0Mseg1586 | 6950 |
| 0 | 164858150 | 164859750 | 11917226 | 11921091 | d0Mseg1589 | 6951 |
| 0 | 164865650 | 164866850 | 11910227 | 11910735 | d0Mseg1590 | 6952 |
| 0 | 164917300 | 164919050 | 11886934 | 11887134 | d0Mseg1591 | 6953 |
| 0 | 165193100 | 165194650 | 11713997 | 11715593 | d0Mseg1593 | 6954 |
| 0 | 165230800 | 165236400 | 11680395 | 11685724 | d0Mseg1594 | 6955 |
| 0 | 165241550 | 165243500 | 11672938 | 11674373 | d0Mseg1595 | 6956 |
| 0 | 165263750 | 165265800 | 11652442 | 11652722 | d0Mseg1596 | 6957 |
| 0 | 165328850 | 165330550 | 11588243 | 11590167 | d0Mseg1598 | 6958 |
| 0 | 165333350 | 165335100 | 11583458 | 11584689 | d0Mseg1599 | 6959 |
| 0 | 165379500 | 165381300 | 11535393 | 11544684 | d0Mseg1601 | 6960 |
| 0 | 165499850 | 165501750 | 11421936 | 11423685 | d0Mseg1602 | 6961 |
| 0 | 165557250 | 165559100 | 11361230 | 11363506 | d0Mseg1604 | 6962 |
| 0 | 165655850 | 165658650 | 11272295 | 11276341 | d0Mseg1605 | 6963 |
| 0 | 165659950 | 165661900 | 11269025 | 11271106 | d0Mseg1606 | 6964 |
| 0 | 165713750 | 165715650 | 11176443 | 11178107 | d0Mseg1607 | 6965 |
| 0 | 165722250 | 165724100 | 11170391 | 11171289 | d0Mseg1608 | 6966 |
| 0 | 166188300 | 166189850 | 10728146 | 10729457 | d0Mseg1612 | 6967 |
| 0 | 166195050 | 166196800 | 10724058 | 10724983 | d0Mseg1613 | 6968 |
| 0 | 166317100 | 166319550 | 10586688 | 10589069 | d0Mseg1615 | 6969 |
| 0 | 166384600 | 166386250 | 10509459 | 10511131 | d0Mseg1616 | 6970 |
| 0 | 166416250 | 166418300 | 10452095 | 10461012 | d0Mseg1617 | 6971 |
| 7 | 4919200 | 4920300 | 57160216 | 57160722 | d7Mseg4 | 6972 |
| 7 | 5626950 | 5628900 | 51236461 | 51237600 | d7Mseg11 | 6973 |
| 7 | 5657900 | 5660200 | 51150174 | 51152241 | d7Mseg12 | 6974 |
| 7 | 5748450 | 5749700 | 51076070 | 51076838 | d7Mseg17 | 6975 |
| 7 | 5826100 | 5827650 | 50744939 | 50745432 | d7Mseg19 | 6976 |
| 7 | 5919250 | 5921000 | 50617610 | 50618797 | d7Mseg23 | 6977 |
| 7 | 5968250 | 5969600 | 50569762 | 50571083 | d7Mseg24 | 6978 |
| 7 | 5976300 | 5978850 | 50555318 | 50558012 | d7Mseg25 | 6979 |
| 7 | 6098950 | 6100700 | 50434563 | 50436098 | d7Mseg27 | 6980 |
| 7 | 6308000 | 6309750 | 50262948 | 50264696 | d7Mseg30 | 6981 |
| 7 | 6345300 | 6347250 | 50219848 | 50221873 | d7Mseg31 | 6982 |
| 7 | 6350900 | 6352100 | 50217495 | 50218757 | d7Mseg32 | 6983 |
| 7 | 6353350 | 6359000 | 50210631 | 50215940 | d7Mseg33 | 6984 |
| 7 | 6446650 | 6448650 | 50171668 | 50173248 | d7Mseg34 | 6985 |
| 7 | 6471200 | 6472550 | 50146277 | 50147919 | d7Mseg35 | 6986 |
| 7 | 6486000 | 6487450 | 50131182 | 50131462 | d7Mseg36 | 6987 |
| 7 | 6525650 | 6526650 | 50107802 | 50108249 | d7Mseg39 | 6988 |
| 7 | 6536400 | 6538150 | 50096153 | 50096484 | d7Mseg40 | 6989 |
| 7 | 6585600 | 6586850 | 50051876 | 50052868 | d7Mseg42 | 6990 |
| 7 | 6660300 | 6662050 | 49948999 | 49951180 | d7Mseg44 | 6991 |
| 7 | 6670300 | 6672050 | 49929734 | 49930439 | d7Mseg45 | 6992 |
| 7 | 6680150 | 6681850 | 49923698 | 49924970 | d7Mseg46 | 6993 |
| 7 | 6683750 | 6685450 | 49921526 | 49923467 | d7Mseg47 | 6994 |
| 7 | 6728500 | 6730300 | 49864177 | 49864647 | d7Mseg52 | 6995 |
| 7 | 6747350 | 6748450 | 49845184 | 49846559 | d7Mseg53 | 6996 |
| 7 | 6810850 | 6812050 | 49780895 | 49781541 | d7Mseg56 | 6997 |
| 7 | 6816950 | 6818100 | 49774742 | 49776244 | d7Mseg57 | 6998 |
| 7 | 6828500 | 6830200 | 49763406 | 49764017 | d7Mseg58 | 6999 |
| 7 | 6875550 | 6876800 | 49715264 | 49716838 | d7Mseg59 | 7000 |
| 7 | 6891050 | 6892950 | 49690808 | 49693591 | d7Mseg61 | 7001 |
| 7 | 6895500 | 6897000 | 49686587 | 49688141 | d7Mseg62 | 7002 |
| 7 | 6928500 | 6932850 | 49658144 | 49664262 | d7Mseg65 | 7003 |
| 7 | 6937850 | 6939600 | 49657320 | 49657656 | d7Mseg66 | 7004 |
| 7 | 6952250 | 6954400 | 49642648 | 49644647 | d7Mseg67 | 7005 |
| 7 | 6955550 | 6957350 | 49638826 | 49641464 | d7Mseg68 | 7006 |
| 7 | 6963750 | 6965650 | 49628587 | 49629146 | d7Mseg69 | 7007 |
| 7 | 6991300 | 6995150 | 49608034 | 49612678 | d7Mseg71 | 7008 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 7046200 | 7047250 | 49525191 | 49525883 | d7Mseg73 | 7009 |
| 7 | 7048850 | 7050400 | 49519739 | 49522241 | d7Mseg74 | 7010 |
| 7 | 7066600 | 7068400 | 49489990 | 49490861 | d7Mseg75 | 7011 |
| 7 | 7132850 | 7137250 | 49143045 | 49147196 | d7Mseg82 | 7012 |
| 7 | 7184950 | 7189050 | 49084517 | 49089284 | d7Mseg83 | 7013 |
| 7 | 7191200 | 7192550 | 49081908 | 49083307 | d7Mseg84 | 7014 |
| 7 | 7202000 | 7203350 | 49071000 | 49072200 | d7Mseg85 | 7015 |
| 7 | 7224100 | 7226000 | 49047902 | 49048316 | d7Mseg86 | 7016 |
| 7 | 7235300 | 7236750 | 49040281 | 49041666 | d7Mseg87 | 7017 |
| 7 | 7243800 | 7245550 | 49031105 | 49033077 | d7Mseg88 | 7018 |
| 7 | 7247400 | 7252650 | 49022108 | 49029321 | d7Mseg89 | 7019 |
| 7 | 7312600 | 7314300 | 48921702 | 48922985 | d7Mseg91 | 7020 |
| 7 | 7339050 | 7341000 | 48899815 | 48901760 | d7Mseg93 | 7021 |
| 7 | 7365650 | 7367450 | 48858339 | 48860456 | d7Mseg95 | 7022 |
| 7 | 7387900 | 7390200 | 48837395 | 48839300 | d7Mseg96 | 7023 |
| 7 | 7391350 | 7392600 | 48834448 | 48835534 | d7Mseg97 | 7024 |
| 7 | 7400300 | 7401900 | 48825746 | 48827390 | d7Mseg98 | 7025 |
| 7 | 7412700 | 7414150 | 48819326 | 48821035 | d7Mseg99 | 7026 |
| 7 | 7418000 | 7419950 | 48814126 | 48816442 | d7Mseg100 | 7027 |
| 7 | 7440000 | 7441800 | 48795210 | 48796608 | d7Mseg101 | 7028 |
| 7 | 7451100 | 7452750 | 48779299 | 48780881 | d7Mseg102 | 7029 |
| 7 | 7454750 | 7456800 | 48775061 | 48776976 | d7Mseg103 | 7030 |
| 7 | 7463050 | 7464950 | 48766679 | 48767097 | d7Mseg104 | 7031 |
| 7 | 7475700 | 7477250 | 48754429 | 48755835 | d7Mseg105 | 7032 |
| 7 | 7497150 | 7506950 | 48683656 | 48693840 | d7Mseg106 | 7033 |
| 7 | 7522550 | 7524350 | 48661089 | 48663231 | d7Mseg107 | 7034 |
| 7 | 7585350 | 7587000 | 48627487 | 48629164 | d7Mseg110 | 7035 |
| 7 | 7593400 | 7596300 | 48620066 | 48623525 | d7Mseg111 | 7036 |
| 7 | 7708050 | 7709850 | 48455983 | 48457509 | d7Mseg120 | 7037 |
| 7 | 7734300 | 7736350 | 48415234 | 48416872 | d7Mseg122 | 7038 |
| 7 | 7752200 | 7753550 | 48397691 | 48398967 | d7Mseg123 | 7039 |
| 7 | 7769500 | 7771450 | 48378718 | 48380778 | d7Mseg124 | 7040 |
| 7 | 7782550 | 7784550 | 48365855 | 48368480 | d7Mseg125 | 7041 |
| 7 | 7786050 | 7787900 | 48363329 | 48364503 | d7Mseg126 | 7042 |
| 7 | 7848100 | 7849900 | 48325341 | 48327201 | d7Mseg128 | 7043 |
| 7 | 8157250 | 8158850 | 47935546 | 47936172 | d7Mseg135 | 7044 |
| 7 | 8380200 | 8381750 | 48213767 | 48214988 | d7Mseg137 | 7045 |
| 7 | 8775150 | 8778300 | 37429655 | 37431928 | d7Mseg139 | 7046 |
| 7 | 8849400 | 8851350 | 37544530 | 37546944 | d7Mseg140 | 7047 |
| 7 | 8856650 | 8858250 | 37551344 | 37552816 | d7Mseg141 | 7048 |
| 7 | 9109150 | 9110850 | 37594744 | 37596273 | d7Mseg143 | 7049 |
| 7 | 9239450 | 9240700 | 37706179 | 37707339 | d7Mseg145 | 7050 |
| 7 | 9324450 | 9326300 | 37764706 | 37766660 | d7Mseg147 | 7051 |
| 7 | 9353300 | 9354950 | 37791612 | 37791830 | d7Mseg148 | 7052 |
| 7 | 9447500 | 9449300 | 37875007 | 37875775 | d7Mseg151 | 7053 |
| 7 | 9459500 | 9461200 | 37885299 | 37890916 | d7Mseg152 | 7054 |
| 7 | 9491700 | 9493550 | 37931961 | 37933104 | d7Mseg153 | 7055 |
| 7 | 9644450 | 9645850 | 38031037 | 38032469 | d7Mseg154 | 7056 |
| 7 | 9657250 | 9659000 | 38042981 | 38044301 | d7Mseg155 | 7057 |
| 7 | 9670650 | 9672300 | 38055423 | 38056959 | d7Mseg156 | 7058 |
| 7 | 9720800 | 9722100 | 38099711 | 38100267 | d7Mseg158 | 7059 |
| 7 | 9730750 | 9732050 | 38116930 | 38117426 | d7Mseg159 | 7060 |
| 7 | 9777950 | 9779250 | 38163267 | 38164002 | d7Mseg160 | 7061 |
| 7 | 9824350 | 9827850 | 38207031 | 38209915 | d7Mseg161 | 7062 |
| 7 | 9890700 | 9892450 | 38271696 | 38274039 | d7Mseg162 | 7063 |
| 7 | 9912400 | 9914300 | 38285245 | 38288555 | d7Mseg164 | 7064 |
| 7 | 9944800 | 9946350 | 38315820 | 38316547 | d7Mseg165 | 7065 |
| 7 | 9997500 | 9998500 | 38352389 | 38352638 | d7Mseg168 | 7066 |
| 7 | 10002350 | 10004250 | 38355720 | 38358180 | d7Mseg169 | 7067 |
| 7 | 10060250 | 10063600 | 38418377 | 38422130 | d7Mseg170 | 7068 |
| 7 | 10084950 | 10086050 | 38446820 | 38447963 | d7Mseg171 | 7069 |
| 7 | 10168100 | 10170150 | 38541308 | 38544218 | d7Mseg172 | 7070 |
| 7 | 10203850 | 10205850 | 38591107 | 38591584 | d7Mseg173 | 7071 |
| 7 | 10226400 | 10227450 | 38611454 | 38613048 | d7Mseg174 | 7072 |
| 7 | 10281150 | 10284050 | 38650920 | 38652786 | d7Mseg175 | 7073 |
| 7 | 10294100 | 10296950 | 38662899 | 38665833 | d7Mseg176 | 7074 |
| 7 | 10389250 | 10390700 | 38768023 | 38771332 | d7Mseg177 | 7075 |
| 7 | 10397150 | 10399350 | 38775666 | 38778304 | d7Mseg178 | 7076 |
| 7 | 10418750 | 10419900 | 38799248 | 38800576 | d7Mseg179 | 7077 |
| 7 | 10430700 | 10432300 | 38818074 | 38820660 | d7Mseg180 | 7078 |
| 7 | 10435150 | 10437000 | 38825619 | 38826855 | d7Mseg181 | 7079 |
| 7 | 10479200 | 10480700 | 38868554 | 38870645 | d7Mseg182 | 7080 |
| 7 | 10519400 | 10521250 | 38893561 | 38895789 | d7Mseg183 | 7081 |
| 7 | 10539100 | 10540750 | 38899527 | 38901207 | d7Mseg184 | 7082 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 10569100 | 10571100 | 38923681 | 38925811 | d7Mseg185 | 7083 |
| 7 | 10572450 | 10573450 | 38926904 | 38927597 | d7Mseg186 | 7084 |
| 7 | 10625250 | 10626450 | 38979108 | 38981312 | d7Mseg188 | 7085 |
| 7 | 10637200 | 10639050 | 38983928 | 38985478 | d7Mseg189 | 7086 |
| 7 | 10652650 | 10654550 | 38994641 | 38996417 | d7Mseg190 | 7087 |
| 7 | 10664350 | 10666100 | 39008576 | 39010042 | d7Mseg191 | 7088 |
| 7 | 10676000 | 10677500 | 39019149 | 39020705 | d7Mseg192 | 7089 |
| 7 | 10679900 | 10684450 | 39023735 | 39028517 | d7Mseg193 | 7090 |
| 7 | 10710850 | 10713950 | 39058972 | 39061038 | d7Mseg194 | 7091 |
| 7 | 10773550 | 10775350 | 39102800 | 39104320 | d7Mseg196 | 7092 |
| 7 | 10786800 | 10788450 | 39117537 | 39118597 | d7Mseg197 | 7093 |
| 7 | 10832450 | 10837400 | 39169692 | 39173123 | d7Mseg199 | 7094 |
| 7 | 10838450 | 10839750 | 39173732 | 39174552 | d7Mseg200 | 7095 |
| 7 | 10929250 | 10931150 | 39245592 | 39246809 | d7Mseg201 | 7096 |
| 7 | 10938550 | 10941850 | 39253468 | 39256612 | d7Mseg202 | 7097 |
| 7 | 10960350 | 10961750 | 39275115 | 39275792 | d7Mseg203 | 7098 |
| 7 | 10988400 | 10989700 | 39306374 | 39307684 | d7Mseg204 | 7099 |
| 7 | 11021950 | 11023600 | 39337369 | 39338594 | d7Mseg206 | 7100 |
| 7 | 11028900 | 11030600 | 39342102 | 39342959 | d7Mseg207 | 7101 |
| 7 | 11051300 | 11052550 | 39361046 | 39362068 | d7Mseg208 | 7102 |
| 7 | 11058200 | 11059250 | 39366332 | 39367121 | d7Mseg209 | 7103 |
| 7 | 11064800 | 11066500 | 39372179 | 39373276 | d7Mseg210 | 7104 |
| 7 | 11068300 | 11072800 | 39375066 | 39379407 | d7Mseg211 | 7105 |
| 7 | 11090550 | 11091550 | 39396438 | 39397330 | d7Mseg212 | 7106 |
| 7 | 11115550 | 11116750 | 39424110 | 39425012 | d7Mseg213 | 7107 |
| 7 | 11162050 | 11163850 | 39467640 | 39469169 | d7Mseg214 | 7108 |
| 7 | 11176250 | 11177400 | 39490538 | 39491203 | d7Mseg215 | 7109 |
| 7 | 11187100 | 11188550 | 39499396 | 39499576 | d7Mseg216 | 7110 |
| 7 | 11191950 | 11193200 | 39501963 | 39502500 | d7Mseg217 | 7111 |
| 7 | 11197900 | 11199750 | 39504268 | 39505878 | d7Mseg218 | 7112 |
| 7 | 11208250 | 11210100 | 39512928 | 39514596 | d7Mseg219 | 7113 |
| 7 | 11212150 | 11213550 | 39516204 | 39517585 | d7Mseg220 | 7114 |
| 7 | 11232050 | 11233750 | 39537141 | 39538884 | d7Mseg221 | 7115 |
| 7 | 11237650 | 11247250 | 39544480 | 39551310 | d7Mseg222 | 7116 |
| 7 | 11252400 | 11253650 | 39560450 | 39561655 | d7Mseg223 | 7117 |
| 7 | 11358400 | 11359950 | 39654968 | 39656319 | d7Mseg225 | 7118 |
| 7 | 11371200 | 11373400 | 39667213 | 39668810 | d7Mseg226 | 7119 |
| 7 | 11374650 | 11376900 | 39670260 | 39672213 | d7Mseg227 | 7120 |
| 7 | 11378700 | 11386050 | 39674037 | 39682459 | d7Mseg228 | 7121 |
| 7 | 11416400 | 11417400 | 39714651 | 39715661 | d7Mseg229 | 7122 |
| 7 | 11421800 | 11423650 | 39719104 | 39720500 | d7Mseg230 | 7123 |
| 7 | 11446100 | 11450800 | 39742764 | 39746068 | d7Mseg231 | 7124 |
| 7 | 11459800 | 11461250 | 39754970 | 39756487 | d7Mseg232 | 7125 |
| 7 | 11490400 | 11492200 | 39784048 | 39785370 | d7Mseg233 | 7126 |
| 7 | 11495000 | 11496600 | 39788283 | 39789511 | d7Mseg234 | 7127 |
| 7 | 11567500 | 11571150 | 39854650 | 39859973 | d7Mseg235 | 7128 |
| 7 | 11574050 | 11589650 | 39863015 | 39879253 | d7Mseg236 | 7129 |
| 7 | 11617850 | 11620050 | 39915391 | 39917570 | d7Mseg238 | 7130 |
| 7 | 11642000 | 11673350 | 39941129 | 39972450 | d7Mseg239 | 7131 |
| 7 | 11675550 | 11677300 | 39976333 | 39977956 | d7Mseg240 | 7132 |
| 7 | 11695450 | 11696850 | 39995907 | 39997208 | d7Mseg242 | 7133 |
| 7 | 11698650 | 11720400 | 39999141 | 40019359 | d7Mseg243 | 7134 |
| 7 | 11721450 | 11722850 | 40021692 | 40022803 | d7Mseg244 | 7135 |
| 7 | 11726100 | 11739000 | 40024406 | 40037420 | d7Mseg245 | 7136 |
| 7 | 11760250 | 11761950 | 40054618 | 40055714 | d7Mseg247 | 7137 |
| 7 | 11801050 | 11802800 | 40107276 | 40107980 | d7Mseg248 | 7138 |
| 7 | 11833300 | 11834300 | 40128653 | 40128938 | d7Mseg249 | 7139 |
| 7 | 11838450 | 11839900 | 40135692 | 40136444 | d7Mseg250 | 7140 |
| 7 | 11843050 | 11844200 | 40138318 | 40138753 | d7Mseg251 | 7141 |
| 7 | 11863000 | 11868200 | 40157276 | 40160609 | d7Mseg252 | 7142 |
| 7 | 11883950 | 11885700 | 40181571 | 40182123 | d7Mseg253 | 7143 |
| 7 | 11932600 | 11934150 | 40239920 | 40240785 | d7Mseg255 | 7144 |
| 7 | 11946300 | 11950100 | 40248967 | 40253015 | d7Mseg256 | 7145 |
| 7 | 11977700 | 11980200 | 40280783 | 40281602 | d7Mseg258 | 7146 |
| 7 | 12002700 | 12004650 | 40303252 | 40305380 | d7Mseg259 | 7147 |
| 7 | 12019850 | 12022050 | 40319011 | 40319811 | d7Mseg260 | 7148 |
| 7 | 12041400 | 12043050 | 40331180 | 40332263 | d7Mseg262 | 7149 |
| 7 | 12049600 | 12051000 | 40339085 | 40341064 | d7Mseg263 | 7150 |
| 7 | 12052750 | 12054400 | 40343345 | 40344750 | d7Mseg264 | 7151 |
| 7 | 12061950 | 12063350 | 40349057 | 40350009 | d7Mseg265 | 7152 |
| 7 | 12090500 | 12092350 | 40377973 | 40380095 | d7Mseg266 | 7153 |
| 7 | 12232600 | 12234150 | 40486843 | 40487915 | d7Mseg267 | 7154 |
| 7 | 12310600 | 12312200 | 40566770 | 40567505 | d7Mseg269 | 7155 |
| 7 | 12338300 | 12340450 | 40594156 | 40596414 | d7Mseg270 | 7156 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 12347950 | 12349600 | 40604159 | 40604615 | d7Mseg271 | 7157 |
| 7 | 12369900 | 12371500 | 40606233 | 40606815 | d7Mseg272 | 7158 |
| 7 | 12423300 | 12425350 | 40712570 | 40713485 | d7Mseg273 | 7159 |
| 7 | 12435350 | 12437200 | 40731055 | 40732055 | d7Mseg274 | 7160 |
| 7 | 12522600 | 12524250 | 40789135 | 40791339 | d7Mseg280 | 7161 |
| 7 | 12569750 | 12571500 | 40859418 | 40861263 | d7Mseg281 | 7162 |
| 7 | 12581500 | 12584750 | 40873621 | 40874134 | d7Mseg282 | 7163 |
| 7 | 12603250 | 12604900 | 40888184 | 40889457 | d7Mseg284 | 7164 |
| 7 | 12648150 | 12650200 | 40944126 | 40946037 | d7Mseg286 | 7165 |
| 7 | 12656000 | 12657100 | 40950910 | 40951267 | d7Mseg287 | 7166 |
| 7 | 12811500 | 12815100 | 41147804 | 41148733 | d7Mseg290 | 7167 |
| 7 | 12948050 | 12949450 | 41260825 | 41264696 | d7Mseg295 | 7168 |
| 7 | 13055650 | 13056800 | 41316705 | 41318489 | d7Mseg298 | 7169 |
| 7 | 13062200 | 13066850 | 41329525 | 41335673 | d7Mseg299 | 7170 |
| 7 | 13069500 | 13071400 | 41338104 | 41340490 | d7Mseg300 | 7171 |
| 7 | 13073650 | 13074650 | 41342772 | 41343281 | d7Mseg301 | 7172 |
| 7 | 13182350 | 13184100 | 41493335 | 41493765 | d7Mseg302 | 7173 |
| 7 | 13193700 | 13194750 | 41520244 | 41521169 | d7Mseg303 | 7174 |
| 7 | 13212100 | 13215400 | 41550721 | 41553690 | d7Mseg304 | 7175 |
| 7 | 13235900 | 13237400 | 41579472 | 41580366 | d7Mseg305 | 7176 |
| 7 | 13239550 | 13241650 | 41583548 | 41585092 | d7Mseg306 | 7177 |
| 7 | 13289250 | 13291300 | 41643312 | 41645899 | d7Mseg307 | 7178 |
| 7 | 13294150 | 13295850 | 41648292 | 41651109 | d7Mseg308 | 7179 |
| 7 | 13317450 | 13319100 | 41666420 | 41674580 | d7Mseg309 | 7180 |
| 7 | 13414900 | 13415950 | 41770688 | 41772438 | d7Mseg310 | 7181 |
| 7 | 13417000 | 13418800 | 41773924 | 41778067 | d7Mseg311 | 7182 |
| 7 | 13422100 | 13425750 | 41781169 | 41784742 | d7Mseg312 | 7183 |
| 7 | 13433750 | 13435550 | 41901773 | 41902195 | d7Mseg313 | 7184 |
| 7 | 13466700 | 13468450 | 41811104 | 41813067 | d7Mseg315 | 7185 |
| 7 | 13501800 | 13503300 | 41856146 | 41856869 | d7Mseg316 | 7186 |
| 7 | 13642200 | 13644000 | 41930439 | 41931106 | d7Mseg317 | 7187 |
| 7 | 13715550 | 13716700 | 41969408 | 41970649 | d7Mseg318 | 7188 |
| 7 | 13844250 | 13846050 | 42068049 | 42069560 | d7Mseg320 | 7189 |
| 7 | 13853450 | 13854850 | 42076961 | 42077776 | d7Mseg321 | 7190 |
| 7 | 13926150 | 13927150 | 42131618 | 42132033 | d7Mseg322 | 7191 |
| 7 | 13945150 | 13946700 | 42148562 | 42149286 | d7Mseg323 | 7192 |
| 7 | 14852250 | 14853750 | 42730771 | 42734853 | d7Mseg327 | 7193 |
| 7 | 15822650 | 15824200 | 43325725 | 43326563 | d7Mseg332 | 7194 |
| 7 | 16161900 | 16163300 | 43488079 | 43488763 | d7Mseg336 | 7195 |
| 7 | 16195350 | 16197100 | 43513805 | 43515723 | d7Mseg337 | 7196 |
| 7 | 16381150 | 16382150 | 43731901 | 43732198 | d7Mseg338 | 7197 |
| 7 | 16462950 | 16464350 | 43808335 | 43809503 | d7Mseg339 | 7198 |
| 7 | 16482850 | 16484150 | 43826920 | 43828218 | d7Mseg340 | 7199 |
| 7 | 16527800 | 16529350 | 43864258 | 43865486 | d7Mseg341 | 7200 |
| 7 | 16552300 | 16553450 | 43881947 | 43882897 | d7Mseg342 | 7201 |
| 7 | 16575400 | 16577150 | 43901708 | 43903520 | d7Mseg344 | 7202 |
| 7 | 16582150 | 16583800 | 43906988 | 43908657 | d7Mseg345 | 7203 |
| 7 | 16681850 | 16683350 | 43977637 | 43978568 | d7Mseg346 | 7204 |
| 7 | 16746500 | 16748600 | 44046438 | 44048611 | d7Mseg347 | 7205 |
| 7 | 16819050 | 16820700 | 44131566 | 44132079 | d7Mseg348 | 7206 |
| 7 | 16988650 | 16989750 | 44253170 | 44253353 | d7Mseg351 | 7207 |
| 7 | 17064900 | 17066300 | 44338445 | 44338815 | d7Mseg352 | 7208 |
| 7 | 17142450 | 17143700 | 44394022 | 44396420 | d7Mseg354 | 7209 |
| 7 | 17147650 | 17149850 | 44400354 | 44402597 | d7Mseg355 | 7210 |
| 7 | 17261500 | 17263250 | 44481793 | 44482972 | d7Mseg357 | 7211 |
| 7 | 17278350 | 17279950 | 44503095 | 44503525 | d7Mseg358 | 7212 |
| 7 | 17283050 | 17284700 | 44507655 | 44508039 | d7Mseg359 | 7213 |
| 7 | 18036550 | 18038200 | 45058417 | 45059889 | d7Mseg362 | 7214 |
| 7 | 18452800 | 18454350 | 45368150 | 45369336 | d7Mseg365 | 7215 |
| 7 | 18731250 | 18732950 | 45613816 | 45615723 | d7Mseg366 | 7216 |
| 7 | 18849650 | 18851250 | 45738248 | 45744907 | d7Mseg367 | 7217 |
| 7 | 18891650 | 18893150 | 45767561 | 45769610 | d7Mseg368 | 7218 |
| 7 | 19598100 | 19599850 | 46414440 | 46415684 | d7Mseg371 | 7219 |
| 7 | 19635850 | 19639100 | 46432902 | 46435740 | d7Mseg374 | 7220 |
| 7 | 19693100 | 19694200 | 46476607 | 46477107 | d7Mseg377 | 7221 |
| 7 | 19867400 | 19869550 | 46617058 | 46619162 | d7Mseg379 | 7222 |
| 7 | 19987450 | 19988450 | 46759672 | 46760964 | d7Mseg381 | 7223 |
| 7 | 20001050 | 20006900 | 46770003 | 46775398 | d7Mseg382 | 7224 |
| 7 | 20133150 | 20134700 | 46949051 | 46949237 | d7Mseg387 | 7225 |
| 7 | 20138900 | 20140300 | 46952547 | 46958116 | d7Mseg388 | 7226 |
| 7 | 20193650 | 20196400 | 47003141 | 47006163 | d7Mseg391 | 7227 |
| 7 | 20233200 | 20236300 | 47049742 | 47051013 | d7Mseg392 | 7228 |
| 7 | 20245850 | 20247250 | 47058479 | 47060229 | d7Mseg393 | 7229 |
| 7 | 20294250 | 20296200 | 47103171 | 47106480 | d7Mseg394 | 7230 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 20354150 | 20355950 | 47229058 | 47230076 | d7Mseg397 | 7231 |
| 7 | 20445800 | 20447000 | 47439532 | 47441360 | d7Mseg398 | 7232 |
| 7 | 20450950 | 20454550 | 47445473 | 47447504 | d7Mseg399 | 7233 |
| 7 | 20517100 | 20518950 | 47499377 | 47500949 | d7Mseg400 | 7234 |
| 7 | 20538000 | 20539700 | 47517836 | 47518881 | d7Mseg401 | 7235 |
| 7 | 20691650 | 20693300 | 47966246 | 47967479 | d7Mseg405 | 7236 |
| 7 | 20696050 | 20697700 | 47969860 | 47972005 | d7Mseg406 | 7237 |
| 7 | 20891950 | 20893000 | 115009363 | 115009510 | d7Mseg412 | 7238 |
| 7 | 21127250 | 21128250 | 115396570 | 115397412 | d7Mseg417 | 7239 |
| 7 | 21131650 | 21133000 | 115398546 | 115399304 | d7Mseg418 | 7240 |
| 7 | 21202600 | 21204400 | 115494915 | 115495182 | d7Mseg420 | 7241 |
| 7 | 21233100 | 21234900 | 115516513 | 115516900 | d7Mseg421 | 7242 |
| 7 | 21292700 | 21294650 | 115568307 | 115570380 | d7Mseg425 | 7243 |
| 7 | 21436250 | 21437800 | 115681925 | 115682289 | d7Mseg428 | 7244 |
| 7 | 22387850 | 22388950 | 116649096 | 116649382 | d7Mseg437 | 7245 |
| 7 | 22571250 | 22572850 | 116821470 | 116822793 | d7Mseg439 | 7246 |
| 7 | 22837700 | 22839200 | 117078647 | 117079978 | d7Mseg440 | 7247 |
| 7 | 22935000 | 22937600 | 117244072 | 117246963 | d7Mseg441 | 7248 |
| 7 | 22941050 | 22942750 | 117249549 | 117251350 | d7Mseg442 | 7249 |
| 7 | 23381300 | 23382650 | 117582148 | 117583490 | d7Mseg446 | 7250 |
| 7 | 23395650 | 23396900 | 117630091 | 117630424 | d7Mseg447 | 7251 |
| 7 | 33386350 | 33387650 | 117593398 | 117593729 | d7Mseg459 | 7252 |
| 7 | 33428350 | 33432700 | 117629279 | 117633627 | d7Mseg461 | 7253 |
| 7 | 33484000 | 33485450 | 117676445 | 117677328 | d7Mseg462 | 7254 |
| 7 | 33575050 | 33576650 | 117775756 | 117776815 | d7Mseg463 | 7255 |
| 7 | 33647150 | 33648600 | 117857986 | 117859061 | d7Mseg464 | 7256 |
| 7 | 33668750 | 33669800 | 117878823 | 117879810 | d7Mseg465 | 7257 |
| 7 | 33672750 | 33673950 | 117883334 | 117883830 | d7Mseg466 | 7258 |
| 7 | 33704450 | 33705450 | 117919442 | 117920997 | d7Mseg468 | 7259 |
| 7 | 33730600 | 33732100 | 117954118 | 117954666 | d7Mseg469 | 7260 |
| 7 | 33737800 | 33739550 | 117959581 | 117961051 | d7Mseg470 | 7261 |
| 7 | 33773400 | 33774550 | 117995961 | 117997013 | d7Mseg472 | 7262 |
| 7 | 33780800 | 33782750 | 118004575 | 118006522 | d7Mseg473 | 7263 |
| 7 | 33827600 | 33829800 | 118080596 | 118084083 | d7Mseg474 | 7264 |
| 7 | 33855600 | 33857800 | 118095782 | 118096900 | d7Mseg477 | 7265 |
| 7 | 33862700 | 33871850 | 118101866 | 118111814 | d7Mseg478 | 7266 |
| 7 | 33873450 | 33875200 | 118113897 | 118116777 | d7Mseg479 | 7267 |
| 7 | 33898700 | 33900300 | 118148269 | 118150073 | d7Mseg480 | 7268 |
| 7 | 33920300 | 33921600 | 118172291 | 118172812 | d7Mseg482 | 7269 |
| 7 | 33975600 | 33977150 | 118227046 | 118229060 | d7Mseg484 | 7270 |
| 7 | 34031750 | 34033500 | 118257496 | 118264547 | d7Mseg485 | 7271 |
| 7 | 34052700 | 34054400 | 118283650 | 118286784 | d7Mseg486 | 7272 |
| 7 | 34067300 | 34068850 | 118305035 | 118305865 | d7Mseg487 | 7273 |
| 7 | 34090800 | 34093000 | 118323795 | 118325483 | d7Mseg488 | 7274 |
| 7 | 34108000 | 34109600 | 118338209 | 118340743 | d7Mseg489 | 7275 |
| 7 | 34136250 | 34139900 | 118368672 | 118372101 | d7Mseg490 | 7276 |
| 7 | 34158350 | 34160000 | 118388420 | 118390110 | d7Mseg491 | 7277 |
| 7 | 34184100 | 34185750 | 118406356 | 118407906 | d7Mseg492 | 7278 |
| 7 | 34228000 | 34229600 | 118458424 | 118458708 | d7Mseg494 | 7279 |
| 7 | 34353300 | 34354950 | 118625326 | 118626697 | d7Mseg495 | 7280 |
| 7 | 34403300 | 34405050 | 118693657 | 118699484 | d7Mseg496 | 7281 |
| 7 | 34414150 | 34417000 | 118708339 | 118710452 | d7Mseg497 | 7282 |
| 7 | 34419600 | 34421400 | 118713662 | 118715210 | d7Mseg498 | 7283 |
| 7 | 34433800 | 34435500 | 118728431 | 118731317 | d7Mseg499 | 7284 |
| 7 | 34441550 | 34443350 | 118738473 | 118740315 | d7Mseg500 | 7285 |
| 7 | 34501550 | 34504600 | 118795625 | 118796773 | d7Mseg502 | 7286 |
| 7 | 34522900 | 34524600 | 118819332 | 118821047 | d7Mseg503 | 7287 |
| 7 | 34527100 | 34529100 | 118824399 | 118826793 | d7Mseg504 | 7288 |
| 7 | 34531600 | 34533800 | 118829603 | 118834092 | d7Mseg505 | 7289 |
| 7 | 34550400 | 34551750 | 118859419 | 118861475 | d7Mseg507 | 7290 |
| 7 | 34564100 | 34566100 | 118869106 | 118869399 | d7Mseg508 | 7291 |
| 7 | 34587000 | 34591300 | 118890936 | 118896264 | d7Mseg511 | 7292 |
| 7 | 34624750 | 34626550 | 118925117 | 118925935 | d7Mseg514 | 7293 |
| 7 | 34648750 | 34650650 | 118985452 | 118987309 | d7Mseg515 | 7294 |
| 7 | 34673650 | 34675350 | 119071240 | 119071966 | d7Mseg517 | 7295 |
| 7 | 34702450 | 34704050 | 119037211 | 119037689 | d7Mseg518 | 7296 |
| 7 | 34731800 | 34733550 | 119003071 | 119005156 | d7Mseg519 | 7297 |
| 7 | 34827500 | 34829300 | 119126327 | 119126654 | d7Mseg520 | 7298 |
| 7 | 35209150 | 35212350 | 119255084 | 119257269 | d7Mseg534 | 7299 |
| 7 | 35228400 | 35230250 | 103497232 | 103497572 | d7Mseg536 | 7300 |
| 7 | 35455350 | 35457350 | 119370616 | 119371100 | d7Mseg546 | 7301 |
| 7 | 35463200 | 35464950 | 119252585 | 119254350 | d7Mseg547 | 7302 |
| 7 | 35511900 | 35513750 | 119071822 | 119072627 | d7Mseg549 | 7303 |
| 7 | 35542250 | 35544050 | 119383881 | 119385797 | d7Mseg552 | 7304 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 35564450 | 35566250 | 119404045 | 119405506 | d7Mseg553 | 7305 |
| 7 | 35584500 | 35586200 | 119424706 | 119425002 | d7Mseg554 | 7306 |
| 7 | 35591750 | 35593000 | 119430294 | 119431616 | d7Mseg555 | 7307 |
| 7 | 35602250 | 35609250 | 119441828 | 119448975 | d7Mseg556 | 7308 |
| 7 | 35735200 | 35737100 | 119553661 | 119554103 | d7Mseg560 | 7309 |
| 7 | 35825700 | 35827700 | 119619292 | 119620676 | d7Mseg562 | 7310 |
| 7 | 35869400 | 35871050 | 119641379 | 119642065 | d7Mseg565 | 7311 |
| 7 | 35896800 | 35898250 | 119672193 | 119672859 | d7Mseg566 | 7312 |
| 7 | 35945450 | 35947350 | 119725232 | 119726155 | d7Mseg568 | 7313 |
| 7 | 35960900 | 35962650 | 119742375 | 119742750 | d7Mseg569 | 7314 |
| 7 | 35973250 | 35974650 | 119751898 | 119752609 | d7Mseg570 | 7315 |
| 7 | 35982450 | 35984200 | 119758334 | 119759895 | d7Mseg571 | 7316 |
| 7 | 36039550 | 36042550 | 119842373 | 119842993 | d7Mseg573 | 7317 |
| 7 | 36084100 | 36085850 | 119877050 | 119880086 | d7Mseg574 | 7318 |
| 7 | 36658950 | 36660600 | 120349685 | 120349979 | d7Mseg580 | 7319 |
| 7 | 36821100 | 36822400 | 120466341 | 120467733 | d7Mseg583 | 7320 |
| 7 | 36835550 | 36837350 | 120473721 | 120474695 | d7Mseg584 | 7321 |
| 7 | 36993850 | 36995400 | 120609826 | 120610565 | d7Mseg586 | 7322 |
| 7 | 37274050 | 37275600 | 120711913 | 120713294 | d7Mseg590 | 7323 |
| 7 | 37277550 | 37279100 | 120714476 | 120714928 | d7Mseg591 | 7324 |
| 7 | 37307350 | 37308800 | 120742981 | 120743299 | d7Mseg592 | 7325 |
| 7 | 37373650 | 37375200 | 120795834 | 120796051 | d7Mseg594 | 7326 |
| 7 | 37843950 | 37845700 | 121330777 | 121331054 | d7Mseg602 | 7327 |
| 7 | 37874600 | 37875950 | 121383448 | 121383639 | d7Mseg603 | 7328 |
| 7 | 37942000 | 37943700 | 121449882 | 121450471 | d7Mseg605 | 7329 |
| 7 | 38168150 | 38169300 | 121757691 | 121758017 | d7Mseg609 | 7330 |
| 7 | 38352450 | 38354000 | 121964465 | 121964998 | d7Mseg611 | 7331 |
| 7 | 38571600 | 38573450 | 122131571 | 122132305 | d7Mseg616 | 7332 |
| 7 | 38712650 | 38714550 | 122273746 | 122275607 | d7Mseg617 | 7333 |
| 7 | 38753250 | 38755800 | 122316995 | 122319507 | d7Mseg619 | 7334 |
| 7 | 38761350 | 38763200 | 122325082 | 122327163 | d7Mseg620 | 7335 |
| 7 | 38775950 | 38777250 | 122337917 | 122338900 | d7Mseg621 | 7336 |
| 7 | 38785900 | 38787550 | 122347462 | 122349577 | d7Mseg622 | 7337 |
| 7 | 38788900 | 38790750 | 122350981 | 122352780 | d7Mseg623 | 7338 |
| 7 | 38808100 | 38809850 | 122368598 | 122370508 | d7Mseg624 | 7339 |
| 7 | 38817000 | 38818050 | 122377739 | 122378848 | d7Mseg625 | 7340 |
| 7 | 38868750 | 38870050 | 122423489 | 122424235 | d7Mseg626 | 7341 |
| 7 | 38901000 | 38902250 | 122465474 | 122466479 | d7Mseg627 | 7342 |
| 7 | 38940400 | 38942100 | 122527672 | 122529277 | d7Mseg628 | 7343 |
| 7 | 38953700 | 38955450 | 122541332 | 122543459 | d7Mseg629 | 7344 |
| 7 | 38957650 | 38958750 | 122545664 | 122546196 | d7Mseg630 | 7345 |
| 7 | 39069250 | 39070850 | 122661389 | 122661962 | d7Mseg631 | 7346 |
| 7 | 39095350 | 39096500 | 46299690 | 46300174 | d7Mseg632 | 7347 |
| 7 | 39147150 | 39148600 | 122733877 | 122734840 | d7Mseg634 | 7348 |
| 7 | 39191000 | 39192100 | 122771658 | 122773001 | d7Mseg635 | 7349 |
| 7 | 39224500 | 39226200 | 122828869 | 122830963 | d7Mseg637 | 7350 |
| 7 | 39262300 | 39268050 | 122863887 | 122867232 | d7Mseg638 | 7351 |
| 7 | 39306500 | 39310050 | 122886899 | 122889059 | d7Mseg640 | 7352 |
| 7 | 39458200 | 39459550 | 123041080 | 123042455 | d7Mseg645 | 7353 |
| 7 | 39473150 | 39474350 | 123057506 | 123058040 | d7Mseg646 | 7354 |
| 7 | 39561750 | 39562950 | 123163515 | 123163722 | d7Mseg647 | 7355 |
| 7 | 39603900 | 39605650 | 123200413 | 123200673 | d7Mseg648 | 7356 |
| 7 | 39645100 | 39646850 | 123264005 | 123265635 | d7Mseg649 | 7357 |
| 7 | 39703750 | 39705500 | 123356474 | 123357325 | d7Mseg652 | 7358 |
| 7 | 39748100 | 39750750 | 123386144 | 123389400 | d7Mseg654 | 7359 |
| 7 | 39795050 | 39796800 | 123420095 | 123420917 | d7Mseg655 | 7360 |
| 7 | 39822450 | 39824800 | 123439590 | 123441675 | d7Mseg657 | 7361 |
| 7 | 39827750 | 39829750 | 123443185 | 123445037 | d7Mseg658 | 7362 |
| 7 | 39854100 | 39855100 | 123478354 | 123479725 | d7Mseg659 | 7363 |
| 7 | 39861700 | 39863550 | 123488709 | 123491917 | d7Mseg660 | 7364 |
| 7 | 39878250 | 39880750 | 123507531 | 123509464 | d7Mseg661 | 7365 |
| 7 | 39910500 | 39911500 | 123540576 | 123541595 | d7Mseg662 | 7366 |
| 7 | 39961400 | 39962950 | 123587036 | 123588661 | d7Mseg663 | 7367 |
| 7 | 39999550 | 40000600 | 123619042 | 123620125 | d7Mseg664 | 7368 |
| 7 | 40021500 | 40023500 | 123640842 | 123642232 | d7Mseg665 | 7369 |
| 7 | 40138700 | 40140100 | 123745775 | 123748264 | d7Mseg667 | 7370 |
| 7 | 40194800 | 40196600 | 123800549 | 123801153 | d7Mseg668 | 7371 |
| 7 | 40251250 | 40252250 | 123837406 | 123838243 | d7Mseg669 | 7372 |
| 7 | 40270800 | 40271800 | 123855470 | 123856915 | d7Mseg670 | 7373 |
| 7 | 40339850 | 40341450 | 123924457 | 123926086 | d7Mseg671 | 7374 |
| 7 | 40391050 | 40392400 | 123980204 | 123981603 | d7Mseg674 | 7375 |
| 7 | 40491100 | 40492900 | 124076824 | 124078653 | d7Mseg675 | 7376 |
| 7 | 40512300 | 40515500 | 124093055 | 124093930 | d7Mseg676 | 7377 |
| 7 | 40643550 | 40644950 | 124218781 | 124220388 | d7Mseg677 | 7378 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 40779300 | 40784650 | 124335476 | 124340593 | d7Mseg678 | 7379 |
| 7 | 40786450 | 40789800 | 124341501 | 124343669 | d7Mseg679 | 7380 |
| 7 | 40895000 | 40897000 | 124392274 | 124393404 | d7Mseg680 | 7381 |
| 7 | 41626100 | 41627650 | 125183879 | 125184824 | d7Mseg686 | 7382 |
| 7 | 41720000 | 41722700 | 125298738 | 125301534 | d7Mseg688 | 7383 |
| 7 | 41725600 | 41727250 | 125305425 | 125306666 | d7Mseg689 | 7384 |
| 7 | 41739700 | 41741100 | 125315494 | 125316590 | d7Mseg691 | 7385 |
| 7 | 41778450 | 41780000 | 125345143 | 125345434 | d7Mseg692 | 7386 |
| 7 | 41975350 | 41976400 | 125536880 | 125537343 | d7Mseg695 | 7387 |
| 7 | 42141450 | 42143550 | 125685070 | 125686968 | d7Mseg698 | 7388 |
| 7 | 42551450 | 42552950 | 126072188 | 126072400 | d7Mseg702 | 7389 |
| 7 | 42742700 | 42744450 | 126256720 | 126259105 | d7Mseg704 | 7390 |
| 7 | 43681750 | 43682900 | 127185574 | 127186509 | d7Mseg719 | 7391 |
| 7 | 43718650 | 43720150 | 127369845 | 127370845 | d7Mseg720 | 7392 |
| 7 | 43826700 | 43827950 | 127457557 | 127458870 | d7Mseg722 | 7393 |
| 7 | 43924000 | 43925700 | 127537074 | 127538042 | d7Mseg726 | 7394 |
| 7 | 43944700 | 43946500 | 127558022 | 127562464 | d7Mseg727 | 7395 |
| 7 | 43969150 | 43975550 | 127574007 | 127574767 | d7Mseg728 | 7396 |
| 7 | 44013750 | 44014950 | 127615704 | 127616060 | d7Mseg730 | 7397 |
| 7 | 44162300 | 44163900 | 127751803 | 127753111 | d7Mseg731 | 7398 |
| 7 | 44168000 | 44169200 | 127760101 | 127761053 | d7Mseg732 | 7399 |
| 7 | 44179150 | 44180900 | 127762335 | 127764008 | d7Mseg733 | 7400 |
| 7 | 44236850 | 44238650 | 127816537 | 127818349 | d7Mseg735 | 7401 |
| 7 | 44244700 | 44245700 | 127826431 | 127827406 | d7Mseg736 | 7402 |
| 7 | 44266850 | 44267850 | 127843131 | 127844280 | d7Mseg737 | 7403 |
| 7 | 44315300 | 44316300 | 127881040 | 127882035 | d7Mseg738 | 7404 |
| 7 | 44356550 | 44358500 | 127933880 | 127934275 | d7Mseg740 | 7405 |
| 7 | 44365000 | 44366600 | 127937955 | 127940329 | d7Mseg741 | 7406 |
| 7 | 44443800 | 44445600 | 127991458 | 127992746 | d7Mseg743 | 7407 |
| 7 | 44451750 | 44453500 | 127997200 | 127997763 | d7Mseg744 | 7408 |
| 7 | 44527000 | 44528850 | 128029686 | 128030431 | d7Mseg745 | 7409 |
| 7 | 44611100 | 44613100 | 128080017 | 128082507 | d7Mseg746 | 7410 |
| 7 | 44614550 | 44615900 | 128083922 | 128085314 | d7Mseg747 | 7411 |
| 7 | 44636950 | 44638700 | 128102810 | 128104628 | d7Mseg749 | 7412 |
| 7 | 44645400 | 44646550 | 128109278 | 128110437 | d7Mseg750 | 7413 |
| 7 | 44675000 | 44676400 | 128158625 | 128159046 | d7Mseg751 | 7414 |
| 7 | 44742200 | 44743750 | 128210114 | 128211421 | d7Mseg752 | 7415 |
| 7 | 44752900 | 44754950 | 128225301 | 128225941 | d7Mseg753 | 7416 |
| 7 | 44762600 | 44763650 | 128228412 | 128229418 | d7Mseg754 | 7417 |
| 7 | 44818750 | 44819750 | 128249704 | 128250478 | d7Mseg757 | 7418 |
| 7 | 44885000 | 44886400 | 128287402 | 128288714 | d7Mseg759 | 7419 |
| 7 | 44918400 | 44919450 | 128327828 | 128328289 | d7Mseg760 | 7420 |
| 7 | 45115150 | 45116750 | 128527794 | 128534377 | d7Mseg763 | 7421 |
| 7 | 45139750 | 45140850 | 128562667 | 128563010 | d7Mseg764 | 7422 |
| 7 | 45149600 | 45151450 | 128564761 | 128566767 | d7Mseg765 | 7423 |
| 7 | 45206100 | 45207900 | 128624361 | 128626077 | d7Mseg766 | 7424 |
| 7 | 45238850 | 45239850 | 128651514 | 128652188 | d7Mseg767 | 7425 |
| 7 | 45243800 | 45248200 | 128655532 | 128659505 | d7Mseg768 | 7426 |
| 7 | 45343350 | 45345400 | 128740271 | 128740722 | d7Mseg772 | 7427 |
| 7 | 45347700 | 45349600 | 128743374 | 128745042 | d7Mseg773 | 7428 |
| 7 | 45370000 | 45373100 | 128768526 | 128771016 | d7Mseg775 | 7429 |
| 7 | 45378400 | 45380150 | 128779312 | 128781102 | d7Mseg776 | 7430 |
| 7 | 45382100 | 45392250 | 128783256 | 128794419 | d7Mseg777 | 7431 |
| 7 | 45421950 | 45423050 | 128826449 | 128828388 | d7Mseg779 | 7432 |
| 7 | 45470150 | 45471350 | 128880233 | 128881408 | d7Mseg780 | 7433 |
| 7 | 45486550 | 45488200 | 128898092 | 128901517 | d7Mseg781 | 7434 |
| 7 | 45505450 | 45507250 | 128919171 | 128921423 | d7Mseg782 | 7435 |
| 7 | 45523500 | 45524800 | 128937383 | 128938592 | d7Mseg783 | 7436 |
| 7 | 45549600 | 45550900 | 128964584 | 128965390 | d7Mseg784 | 7437 |
| 7 | 45553900 | 45555650 | 128968663 | 128970954 | d7Mseg785 | 7438 |
| 7 | 45638100 | 45641300 | 129065731 | 129069327 | d7Mseg788 | 7439 |
| 7 | 45663150 | 45665200 | 129086083 | 129088051 | d7Mseg790 | 7440 |
| 7 | 45667150 | 45672900 | 129090445 | 129096500 | d7Mseg791 | 7441 |
| 7 | 45686100 | 45687700 | 129107765 | 129108269 | d7Mseg792 | 7442 |
| 7 | 45690600 | 45700600 | 129110140 | 129120295 | d7Mseg793 | 7443 |
| 7 | 45702350 | 45703850 | 129122297 | 129124820 | d7Mseg794 | 7444 |
| 7 | 45718350 | 45720100 | 129144003 | 129146043 | d7Mseg795 | 7445 |
| 7 | 45765800 | 45767350 | 129198856 | 129200204 | d7Mseg796 | 7446 |
| 7 | 45799100 | 45810800 | 129237506 | 129249292 | d7Mseg797 | 7447 |
| 7 | 45812150 | 45814800 | 129251212 | 129253769 | d7Mseg798 | 7448 |
| 7 | 45816000 | 45817700 | 129254822 | 129256413 | d7Mseg799 | 7449 |
| 7 | 45866650 | 45868500 | 129299763 | 129301830 | d7Mseg800 | 7450 |
| 7 | 45871600 | 45873900 | 129304821 | 129307190 | d7Mseg801 | 7451 |
| 7 | 45882850 | 45884650 | 129318283 | 129319851 | d7Mseg802 | 7452 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 45886350 | 45888400 | 129328069 | 129329868 | d7Mseg803 | 7453 |
| 7 | 45948000 | 45953650 | 129403820 | 129431849 | d7Mseg805 | 7454 |
| 7 | 45973350 | 45975050 | 129468409 | 129469605 | d7Mseg806 | 7455 |
| 7 | 45976250 | 45977750 | 129473417 | 129474708 | d7Mseg807 | 7456 |
| 7 | 46023700 | 46025550 | 129515667 | 129517638 | d7Mseg808 | 7457 |
| 7 | 46034900 | 46036450 | 129526974 | 129527389 | d7Mseg809 | 7458 |
| 7 | 46132550 | 46133550 | 129558859 | 129559167 | d7Mseg812 | 7459 |
| 7 | 46223150 | 46225050 | 129641466 | 129643348 | d7Mseg817 | 7460 |
| 7 | 46262450 | 46265700 | 129685489 | 129688485 | d7Mseg818 | 7461 |
| 7 | 46270350 | 46272450 | 129689470 | 129690075 | d7Mseg819 | 7462 |
| 7 | 46349200 | 46350350 | 129740640 | 129741686 | d7Mseg820 | 7463 |
| 7 | 46382450 | 46384200 | 129775346 | 129778554 | d7Mseg821 | 7464 |
| 7 | 46532500 | 46534100 | 129926807 | 129927787 | d7Mseg822 | 7465 |
| 7 | 46567450 | 46571000 | 129963488 | 129966125 | d7Mseg823 | 7466 |
| 7 | 46572050 | 46573150 | 129966813 | 129967901 | d7Mseg824 | 7467 |
| 7 | 46582650 | 46583850 | 129980034 | 129984481 | d7Mseg825 | 7468 |
| 7 | 46594300 | 46595950 | 129998253 | 129999658 | d7Mseg826 | 7469 |
| 7 | 46626700 | 46628000 | 130021285 | 130022621 | d7Mseg827 | 7470 |
| 7 | 46634500 | 46636050 | 130029235 | 130030553 | d7Mseg828 | 7471 |
| 7 | 46671500 | 46673050 | 130073295 | 130073496 | d7Mseg829 | 7472 |
| 7 | 46674600 | 46676050 | 130078270 | 130079177 | d7Mseg830 | 7473 |
| 7 | 46726050 | 46727550 | 130125961 | 130126274 | d7Mseg831 | 7474 |
| 7 | 46737200 | 46739400 | 130135006 | 130140805 | d7Mseg832 | 7475 |
| 7 | 46816350 | 46817750 | 130184629 | 130186078 | d7Mseg833 | 7476 |
| 7 | 46823100 | 46825000 | 130191661 | 130193575 | d7Mseg834 | 7477 |
| 7 | 46826600 | 46830900 | 130195347 | 130199871 | d7Mseg835 | 7478 |
| 7 | 46835350 | 46841700 | 130204271 | 130210819 | d7Mseg836 | 7479 |
| 7 | 46844950 | 46849750 | 130214253 | 130219020 | d7Mseg837 | 7480 |
| 7 | 47150550 | 47152600 | 130422906 | 130424949 | d7Mseg844 | 7481 |
| 7 | 47186750 | 47187950 | 130439140 | 130439609 | d7Mseg845 | 7482 |
| 7 | 47278100 | 47279800 | 130480780 | 130481986 | d7Mseg851 | 7483 |
| 7 | 47292850 | 47294550 | 130491902 | 130492452 | d7Mseg853 | 7484 |
| 7 | 47364850 | 47366600 | 130534553 | 130536454 | d7Mseg855 | 7485 |
| 7 | 47424250 | 47428350 | 130726734 | 130729236 | d7Mseg857 | 7486 |
| 7 | 47430650 | 47432200 | 130723771 | 130724975 | d7Mseg858 | 7487 |
| 7 | 47472750 | 47474200 | 130698377 | 130698983 | d7Mseg859 | 7488 |
| 7 | 47560000 | 47561650 | 130653757 | 130658153 | d7Mseg862 | 7489 |
| 7 | 47782200 | 47783800 | 130554282 | 130555150 | d7Mseg872 | 7490 |
| 7 | 47858850 | 47860050 | 130773271 | 130774095 | d7Mseg874 | 7491 |
| 7 | 47929100 | 47930850 | 130875045 | 130875479 | d7Mseg875 | 7492 |
| 7 | 48040400 | 48041550 | 130994804 | 130995795 | d7Mseg883 | 7493 |
| 7 | 48109200 | 48110900 | 131069398 | 131069895 | d7Mseg885 | 7494 |
| 7 | 48119250 | 48121250 | 131078768 | 131079448 | d7Mseg886 | 7495 |
| 7 | 48144000 | 48145800 | 131109912 | 131112139 | d7Mseg887 | 7496 |
| 7 | 48179700 | 48180700 | 131140703 | 131142091 | d7Mseg888 | 7497 |
| 7 | 48185150 | 48186950 | 131147312 | 131149548 | d7Mseg889 | 7498 |
| 7 | 48189850 | 48198300 | 131152397 | 131161050 | d7Mseg890 | 7499 |
| 7 | 48203050 | 48204800 | 131166679 | 131167984 | d7Mseg891 | 7500 |
| 7 | 48226550 | 48227700 | 131192271 | 131193226 | d7Mseg892 | 7501 |
| 7 | 48234100 | 48236000 | 131198499 | 131199901 | d7Mseg893 | 7502 |
| 7 | 48277100 | 48278750 | 131243804 | 131245698 | d7Mseg894 | 7503 |
| 7 | 48320550 | 48321850 | 131305442 | 131306511 | d7Mseg896 | 7504 |
| 7 | 48334450 | 48335700 | 131315268 | 131316204 | d7Mseg897 | 7505 |
| 7 | 48344800 | 48346450 | 131322527 | 131324095 | d7Mseg898 | 7506 |
| 7 | 48367900 | 48369550 | 131347929 | 131349656 | d7Mseg899 | 7507 |
| 7 | 48371400 | 48373300 | 131351609 | 131353535 | d7Mseg900 | 7508 |
| 7 | 48378450 | 48380300 | 131359006 | 131360241 | d7Mseg901 | 7509 |
| 7 | 48392950 | 48394800 | 131376959 | 131377597 | d7Mseg903 | 7510 |
| 7 | 48427250 | 48428700 | 131448759 | 131449344 | d7Mseg904 | 7511 |
| 7 | 48519050 | 48520750 | 131574679 | 131576849 | d7Mseg905 | 7512 |
| 7 | 48526400 | 48527750 | 131590554 | 131591574 | d7Mseg906 | 7513 |
| 7 | 48556700 | 48560700 | 131621640 | 131625568 | d7Mseg907 | 7514 |
| 7 | 48567300 | 48569250 | 131633733 | 131636080 | d7Mseg908 | 7515 |
| 7 | 48601650 | 48603300 | 131672522 | 131673737 | d7Mseg910 | 7516 |
| 7 | 48714350 | 48716050 | 131736184 | 131738217 | d7Mseg915 | 7517 |
| 7 | 48720150 | 48721750 | 131742492 | 131744045 | d7Mseg916 | 7518 |
| 7 | 48723650 | 48725300 | 131745751 | 131746705 | d7Mseg917 | 7519 |
| 7 | 48730150 | 48731200 | 131751997 | 131752578 | d7Mseg918 | 7520 |
| 7 | 48751350 | 48753150 | 131771008 | 131772879 | d7Mseg919 | 7521 |
| 7 | 48767250 | 48769150 | 131791107 | 131792497 | d7Mseg921 | 7522 |
| 7 | 48775650 | 48777650 | 131797691 | 131799242 | d7Mseg922 | 7523 |
| 7 | 48822850 | 48824550 | 131840659 | 131842489 | d7Mseg923 | 7524 |
| 7 | 48826100 | 48827150 | 131843770 | 131844771 | d7Mseg924 | 7525 |
| 7 | 48842250 | 48844350 | 131865225 | 131867486 | d7Mseg925 | 7526 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 48856950 | 48858850 | 131881678 | 131883985 | d7Mseg926 | 7527 |
| 7 | 48864750 | 48866400 | 131890217 | 131891614 | d7Mseg927 | 7528 |
| 7 | 48897650 | 48899400 | 131935120 | 131936820 | d7Mseg928 | 7529 |
| 7 | 48909100 | 48910850 | 131950298 | 131951553 | d7Mseg929 | 7530 |
| 7 | 48931250 | 48933000 | 131967192 | 131968841 | d7Mseg930 | 7531 |
| 7 | 48964850 | 48966550 | 132010214 | 132011982 | d7Mseg931 | 7532 |
| 7 | 48968750 | 48970550 | 132014619 | 132018738 | d7Mseg932 | 7533 |
| 7 | 49021000 | 49022250 | 132077029 | 132080830 | d7Mseg934 | 7534 |
| 7 | 49029050 | 49041550 | 132086353 | 132099266 | d7Mseg935 | 7535 |
| 7 | 49059000 | 49060800 | 132116444 | 132117784 | d7Mseg937 | 7536 |
| 7 | 49074200 | 49078150 | 132132815 | 132135689 | d7Mseg938 | 7537 |
| 7 | 49112650 | 49115450 | 132164748 | 132165878 | d7Mseg939 | 7538 |
| 7 | 49129950 | 49131100 | 132202644 | 132203348 | d7Mseg940 | 7539 |
| 7 | 49132950 | 49134700 | 132205610 | 132206138 | d7Mseg941 | 7540 |
| 7 | 49147550 | 49149200 | 132221481 | 132222936 | d7Mseg942 | 7541 |
| 7 | 49154200 | 49156050 | 132231108 | 132231426 | d7Mseg943 | 7542 |
| 7 | 49225950 | 49227800 | 132308890 | 132310144 | d7Mseg947 | 7543 |
| 7 | 49245000 | 49248550 | 132328592 | 132331618 | d7Mseg948 | 7544 |
| 7 | 49266800 | 49268400 | 132350187 | 132353685 | d7Mseg949 | 7545 |
| 7 | 49309800 | 49311100 | 148628962 | 148631469 | d7Mseg951 | 7546 |
| 7 | 49332650 | 49334500 | 132371196 | 132373666 | d7Mseg954 | 7547 |
| 7 | 49368650 | 49370350 | 132395499 | 132398844 | d7Mseg955 | 7548 |
| 7 | 49404000 | 49405600 | 132434517 | 132436079 | d7Mseg956 | 7549 |
| 7 | 49450750 | 49452200 | 132478916 | 132480717 | d7Mseg957 | 7550 |
| 7 | 49459650 | 49461300 | 132491788 | 132492348 | d7Mseg958 | 7551 |
| 7 | 49463800 | 49465500 | 132494617 | 132495838 | d7Mseg959 | 7552 |
| 7 | 49476500 | 49478250 | 132506352 | 132507136 | d7Mseg960 | 7553 |
| 7 | 49498900 | 49500600 | 132528398 | 132529030 | d7Mseg961 | 7554 |
| 7 | 49510100 | 49511850 | 132540421 | 132542440 | d7Mseg962 | 7555 |
| 7 | 49515500 | 49518450 | 132546425 | 132549459 | d7Mseg963 | 7556 |
| 7 | 49576600 | 49578100 | 132627205 | 132628175 | d7Mseg964 | 7557 |
| 7 | 49590900 | 49592850 | 132637092 | 132637290 | d7Mseg965 | 7558 |
| 7 | 49617900 | 49619800 | 132660401 | 132662237 | d7Mseg966 | 7559 |
| 7 | 49632850 | 49634350 | 132677567 | 132681410 | d7Mseg967 | 7560 |
| 7 | 49699050 | 49700750 | 132781018 | 132782176 | d7Mseg969 | 7561 |
| 7 | 49702600 | 49703900 | 132784341 | 132785336 | d7Mseg970 | 7562 |
| 7 | 49717400 | 49719150 | 132793527 | 132796169 | d7Mseg971 | 7563 |
| 7 | 49727200 | 49729600 | 132810230 | 132812693 | d7Mseg972 | 7564 |
| 7 | 49748000 | 49749700 | 132831845 | 132833357 | d7Mseg973 | 7565 |
| 7 | 49753650 | 49755450 | 132839915 | 132843768 | d7Mseg974 | 7566 |
| 7 | 49760650 | 49762350 | 132858473 | 132860076 | d7Mseg975 | 7567 |
| 7 | 49775500 | 49776800 | 132880685 | 132881912 | d7Mseg976 | 7568 |
| 7 | 49791000 | 49792600 | 132903731 | 132905101 | d7Mseg977 | 7569 |
| 7 | 49810050 | 49811400 | 132930423 | 132931256 | d7Mseg978 | 7570 |
| 7 | 49839400 | 49841300 | 132968858 | 132970519 | d7Mseg980 | 7571 |
| 7 | 49849000 | 49850650 | 132979775 | 132981699 | d7Mseg981 | 7572 |
| 7 | 49886850 | 49888500 | 133026214 | 133027755 | d7Mseg982 | 7573 |
| 7 | 49915100 | 49916650 | 133063791 | 133066065 | d7Mseg983 | 7574 |
| 7 | 49964750 | 49970250 | 133117306 | 133123010 | d7Mseg984 | 7575 |
| 7 | 49984450 | 49986150 | 133138165 | 133139953 | d7Mseg985 | 7576 |
| 7 | 49988900 | 49990250 | 133142277 | 133143895 | d7Mseg986 | 7577 |
| 7 | 50001500 | 50003050 | 133157026 | 133158739 | d7Mseg987 | 7578 |
| 7 | 50013800 | 50014850 | 133172408 | 133172881 | d7Mseg988 | 7579 |
| 7 | 50096650 | 50098550 | 133305238 | 133307374 | d7Mseg990 | 7580 |
| 7 | 50141400 | 50143600 | 133367377 | 133370553 | d7Mseg991 | 7581 |
| 7 | 50146600 | 50148250 | 133374229 | 133375409 | d7Mseg992 | 7582 |
| 7 | 50153450 | 50155050 | 133380833 | 133381987 | d7Mseg993 | 7583 |
| 7 | 50157250 | 50159100 | 133383651 | 133385748 | d7Mseg994 | 7584 |
| 7 | 50165250 | 50170650 | 133396268 | 133398976 | d7Mseg995 | 7585 |
| 7 | 50226750 | 50228450 | 133476263 | 133476568 | d7Mseg997 | 7586 |
| 7 | 50238900 | 50240650 | 85340660 | 85340880 | d7Mseg999 | 7587 |
| 7 | 50264950 | 50267500 | 133506826 | 133509357 | d7Mseg1001 | 7588 |
| 7 | 50340900 | 50342400 | 133593795 | 133595251 | d7Mseg1003 | 7589 |
| 7 | 50407500 | 50413850 | 133680727 | 133686885 | d7Mseg1004 | 7590 |
| 7 | 50426500 | 50427800 | 133702985 | 133704563 | d7Mseg1005 | 7591 |
| 7 | 50464700 | 50467750 | 133751955 | 133755782 | d7Mseg1006 | 7592 |
| 7 | 50469100 | 50470800 | 133757148 | 133758461 | d7Mseg1007 | 7593 |
| 7 | 50479950 | 50482900 | 133766270 | 133771004 | d7Mseg1008 | 7594 |
| 7 | 50489150 | 50493350 | 133779974 | 133784547 | d7Mseg1009 | 7595 |
| 7 | 50495400 | 50497150 | 133786974 | 133788968 | d7Mseg1010 | 7596 |
| 7 | 50504750 | 50506250 | 133796368 | 133797936 | d7Mseg1011 | 7597 |
| 7 | 50516350 | 50517550 | 133806333 | 133807526 | d7Mseg1012 | 7598 |
| 7 | 50519200 | 50521300 | 133808900 | 133811153 | d7Mseg1013 | 7599 |
| 7 | 50545650 | 50547350 | 133846911 | 133848813 | d7Mseg1014 | 7600 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 50561150 | 50562700 | 133863567 | 133865861 | d7Mseg1015 | 7601 |
| 7 | 50603850 | 50605350 | 133911878 | 133913761 | d7Mseg1016 | 7602 |
| 7 | 50639650 | 50641450 | 133953300 | 133956274 | d7Mseg1017 | 7603 |
| 7 | 50643600 | 50645150 | 133960537 | 133962077 | d7Mseg1018 | 7604 |
| 7 | 50673600 | 50675450 | 134003552 | 134005656 | d7Mseg1019 | 7605 |
| 7 | 50712000 | 50713100 | 134034393 | 134035131 | d7Mseg1020 | 7606 |
| 7 | 50954900 | 50956200 | 134173012 | 134173437 | d7Mseg1029 | 7607 |
| 7 | 51038850 | 51040850 | 134580347 | 134581420 | d7Mseg1032 | 7608 |
| 7 | 53477850 | 53479750 | 134314823 | 134317752 | d7Mseg1046 | 7609 |
| 7 | 53535550 | 53536750 | 134480236 | 134481187 | d7Mseg1048 | 7610 |
| 7 | 53618100 | 53619850 | 134496269 | 134497771 | d7Mseg1050 | 7611 |
| 7 | 53715350 | 53716700 | 134661219 | 134662437 | d7Mseg1056 | 7612 |
| 7 | 53719800 | 53720900 | 134665148 | 134665788 | d7Mseg1057 | 7613 |
| 7 | 53850250 | 53852000 | 135055068 | 135057268 | d7Mseg1060 | 7614 |
| 7 | 53862950 | 53864950 | 135067584 | 135069491 | d7Mseg1062 | 7615 |
| 7 | 53867000 | 53868100 | 135071580 | 135071738 | d7Mseg1063 | 7616 |
| 7 | 53872150 | 53873200 | 135075480 | 135076643 | d7Mseg1064 | 7617 |
| 7 | 53903650 | 53905750 | 135111009 | 135113266 | d7Mseg1065 | 7618 |
| 7 | 53916600 | 53919150 | 135128877 | 135130681 | d7Mseg1066 | 7619 |
| 7 | 53924250 | 53925900 | 135138366 | 135141056 | d7Mseg1067 | 7620 |
| 7 | 53927400 | 53929150 | 135142875 | 135143824 | d7Mseg1068 | 7621 |
| 7 | 53934300 | 53935300 | 135149326 | 135150157 | d7Mseg1069 | 7622 |
| 7 | 53937550 | 53939550 | 135158855 | 135159827 | d7Mseg1070 | 7623 |
| 7 | 53960850 | 53962400 | 135194420 | 135195116 | d7Mseg1071 | 7624 |
| 7 | 53964550 | 53966300 | 135197019 | 135199821 | d7Mseg1072 | 7625 |
| 7 | 53983050 | 53986450 | 135226914 | 135231187 | d7Mseg1073 | 7626 |
| 7 | 53994800 | 53996200 | 135237335 | 135239141 | d7Mseg1074 | 7627 |
| 7 | 53999200 | 54001250 | 135243641 | 135245538 | d7Mseg1075 | 7628 |
| 7 | 54025000 | 54026150 | 135273261 | 135274425 | d7Mseg1076 | 7629 |
| 7 | 54064600 | 54066250 | 135314577 | 135318282 | d7Mseg1077 | 7630 |
| 7 | 54076350 | 54077600 | 135335304 | 135335746 | d7Mseg1078 | 7631 |
| 7 | 54097050 | 54098900 | 135356262 | 135358301 | d7Mseg1079 | 7632 |
| 7 | 54158750 | 54160600 | 135421910 | 135422840 | d7Mseg1081 | 7633 |
| 7 | 54166700 | 54168050 | 135426964 | 135428335 | d7Mseg1082 | 7634 |
| 7 | 54183300 | 54184850 | 135443734 | 135445050 | d7Mseg1083 | 7635 |
| 7 | 54200850 | 54202450 | 135467765 | 135469685 | d7Mseg1084 | 7636 |
| 7 | 54280650 | 54281650 | 135547604 | 135548845 | d7Mseg1085 | 7637 |
| 7 | 54289050 | 54290150 | 135557237 | 135558334 | d7Mseg1086 | 7638 |
| 7 | 54296300 | 54297750 | 135570154 | 135571569 | d7Mseg1087 | 7639 |
| 7 | 54301850 | 54303250 | 135575859 | 135576441 | d7Mseg1088 | 7640 |
| 7 | 54393400 | 54395000 | 135669405 | 135670466 | d7Mseg1089 | 7641 |
| 7 | 54397950 | 54399000 | 135674353 | 135675699 | d7Mseg1090 | 7642 |
| 7 | 54459050 | 54462150 | 135725439 | 135727688 | d7Mseg1091 | 7643 |
| 7 | 54492950 | 54494750 | 135758145 | 135759853 | d7Mseg1092 | 7644 |
| 7 | 54589300 | 54590950 | 135861227 | 135862302 | d7Mseg1094 | 7645 |
| 7 | 54644100 | 54645900 | 135961061 | 135962620 | d7Mseg1095 | 7646 |
| 7 | 54662150 | 54663950 | 135991728 | 135992427 | d7Mseg1096 | 7647 |
| 7 | 54691650 | 54692750 | 136044641 | 136045232 | d7Mseg1097 | 7648 |
| 7 | 54715200 | 54716550 | 136073919 | 136075950 | d7Mseg1098 | 7649 |
| 7 | 54726000 | 54727900 | 136084944 | 136085335 | d7Mseg1099 | 7650 |
| 7 | 54754050 | 54761400 | 136112939 | 136120284 | d7Mseg1101 | 7651 |
| 7 | 54791700 | 54793500 | 136152572 | 136153345 | d7Mseg1102 | 7652 |
| 7 | 54796000 | 54797400 | 136156162 | 136156860 | d7Mseg1103 | 7653 |
| 7 | 54804350 | 54805950 | 136163511 | 136164395 | d7Mseg1104 | 7654 |
| 7 | 54834600 | 54835700 | 136181856 | 136182411 | d7Mseg1105 | 7655 |
| 7 | 54906100 | 54907850 | 136259090 | 136260020 | d7Mseg1107 | 7656 |
| 7 | 54924500 | 54928600 | 136275697 | 136276727 | d7Mseg1108 | 7657 |
| 7 | 54942450 | 54944400 | 136291604 | 136292916 | d7Mseg1110 | 7658 |
| 7 | 54960150 | 54961950 | 136314648 | 136316454 | d7Mseg1111 | 7659 |
| 7 | 54964100 | 54965200 | 136318623 | 136319826 | d7Mseg1112 | 7660 |
| 7 | 55015750 | 55017950 | 136351182 | 136351991 | d7Mseg1114 | 7661 |
| 7 | 55019600 | 55021450 | 136353477 | 136355332 | d7Mseg1115 | 7662 |
| 7 | 55022500 | 55024050 | 136356403 | 136358052 | d7Mseg1116 | 7663 |
| 7 | 55025350 | 55027300 | 136359061 | 136359620 | d7Mseg1117 | 7664 |
| 7 | 55030850 | 55033150 | 136362617 | 136364448 | d7Mseg1118 | 7665 |
| 7 | 55089150 | 55090950 | 136417645 | 136419891 | d7Mseg1119 | 7666 |
| 7 | 55120600 | 55121950 | 136445911 | 136447290 | d7Mseg1120 | 7667 |
| 7 | 55128200 | 55129450 | 136455576 | 136456734 | d7Mseg1121 | 7668 |
| 7 | 55144900 | 55147800 | 136468567 | 136474795 | d7Mseg1122 | 7669 |
| 7 | 55165850 | 55167000 | 136502892 | 136504178 | d7Mseg1123 | 7670 |
| 7 | 55168950 | 55177100 | 136505919 | 136514806 | d7Mseg1124 | 7671 |
| 7 | 55207400 | 55209450 | 136563921 | 136565929 | d7Mseg1125 | 7672 |
| 7 | 55253850 | 55255450 | 136618653 | 136619145 | d7Mseg1127 | 7673 |
| 7 | 55266700 | 55274450 | 136627220 | 136635572 | d7Mseg1128 | 7674 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 55279400 | 55288000 | 136643868 | 136652525 | d7Mseg1129 | 7675 |
| 7 | 55290400 | 55296750 | 136654976 | 136660703 | d7Mseg1130 | 7676 |
| 7 | 55333950 | 55334950 | 136715789 | 136715952 | d7Mseg1131 | 7677 |
| 7 | 55339150 | 55340950 | 136719131 | 136720945 | d7Mseg1132 | 7678 |
| 7 | 55363350 | 55364400 | 136751326 | 136751520 | d7Mseg1133 | 7679 |
| 7 | 55405850 | 55408900 | 136826935 | 136829749 | d7Mseg1134 | 7680 |
| 7 | 55429950 | 55431350 | 136862340 | 136862778 | d7Mseg1135 | 7681 |
| 7 | 55549800 | 55551400 | 136955123 | 136955885 | d7Mseg1136 | 7682 |
| 7 | 55566800 | 55568000 | 136968911 | 136969767 | d7Mseg1137 | 7683 |
| 7 | 55570750 | 55572600 | 136970720 | 136972460 | d7Mseg1138 | 7684 |
| 7 | 55575400 | 55576800 | 136976994 | 136978460 | d7Mseg1139 | 7685 |
| 7 | 55678100 | 55680050 | 137028011 | 137029479 | d7Mseg1143 | 7686 |
| 7 | 55815000 | 55816600 | 137199358 | 137199980 | d7Mseg1145 | 7687 |
| 7 | 55820100 | 55824600 | 137214226 | 137215956 | d7Mseg1146 | 7688 |
| 7 | 55829300 | 55831000 | 137222067 | 137225943 | d7Mseg1147 | 7689 |
| 7 | 55922900 | 55924550 | 137302554 | 137302869 | d7Mseg1149 | 7690 |
| 7 | 56087450 | 56089600 | 137481607 | 137482124 | d7Mseg1155 | 7691 |
| 7 | 56197550 | 56199050 | 141236541 | 141237108 | d7Mseg1157 | 7692 |
| 7 | 56303600 | 56305250 | 137684872 | 137685102 | d7Mseg1160 | 7693 |
| 7 | 56386000 | 56388000 | 137791961 | 137793923 | d7Mseg1161 | 7694 |
| 7 | 56396550 | 56398250 | 137803543 | 137804171 | d7Mseg1162 | 7695 |
| 7 | 56418350 | 56421350 | 137820604 | 137823585 | d7Mseg1163 | 7696 |
| 7 | 56433550 | 56435150 | 137839612 | 137840973 | d7Mseg1164 | 7697 |
| 7 | 56436750 | 56438550 | 137843249 | 137844889 | d7Mseg1165 | 7698 |
| 7 | 56443200 | 56445900 | 137853682 | 137855941 | d7Mseg1166 | 7699 |
| 7 | 56459200 | 56460950 | 137869395 | 137869679 | d7Mseg1167 | 7700 |
| 7 | 56468400 | 56471100 | 137885931 | 137887422 | d7Mseg1168 | 7701 |
| 7 | 56519000 | 56520150 | 137950130 | 137950678 | d7Mseg1169 | 7702 |
| 7 | 56534600 | 56536550 | 137966945 | 137968677 | d7Mseg1170 | 7703 |
| 7 | 56563100 | 56564950 | 137980791 | 137982487 | d7Mseg1171 | 7704 |
| 7 | 56613300 | 56615000 | 138027080 | 138028952 | d7Mseg1172 | 7705 |
| 7 | 56689000 | 56691500 | 138155772 | 138157271 | d7Mseg1174 | 7706 |
| 7 | 56725550 | 56726900 | 138179819 | 138181542 | d7Mseg1175 | 7707 |
| 7 | 56727950 | 56729100 | 138181772 | 138182052 | d7Mseg1176 | 7708 |
| 7 | 56734200 | 56735350 | 138190457 | 138190837 | d7Mseg1177 | 7709 |
| 7 | 56759550 | 56760950 | 138213396 | 138214940 | d7Mseg1178 | 7710 |
| 7 | 56817950 | 56824200 | 138284113 | 138290320 | d7Mseg1179 | 7711 |
| 7 | 56835900 | 56837950 | 138302267 | 138304129 | d7Mseg1180 | 7712 |
| 7 | 56841550 | 56842900 | 138306749 | 138308006 | d7Mseg1181 | 7713 |
| 7 | 56939950 | 56941400 | 138368358 | 138368667 | d7Mseg1183 | 7714 |
| 7 | 56958200 | 56959950 | 138378925 | 138380442 | d7Mseg1184 | 7715 |
| 7 | 57026800 | 57027950 | 138452521 | 138452728 | d7Mseg1186 | 7716 |
| 7 | 57051400 | 57053650 | 138473286 | 138473849 | d7Mseg1187 | 7717 |
| 7 | 57155850 | 57158250 | 138531976 | 138532890 | d7Mseg1193 | 7718 |
| 7 | 57259500 | 57261250 | 138620974 | 138621523 | d7Mseg1194 | 7719 |
| 7 | 57268650 | 57270650 | 138629849 | 138631276 | d7Mseg1195 | 7720 |
| 7 | 57342400 | 57344350 | 138681973 | 138682655 | d7Mseg1196 | 7721 |
| 7 | 57391850 | 57393700 | 138714941 | 138716185 | d7Mseg1197 | 7722 |
| 7 | 57428450 | 57434700 | 138771735 | 138780855 | d7Mseg1198 | 7723 |
| 7 | 57438600 | 57440300 | 138784285 | 138784635 | d7Mseg1199 | 7724 |
| 7 | 57545250 | 57547100 | 138880576 | 138882549 | d7Mseg1200 | 7725 |
| 7 | 57548650 | 57550300 | 138884694 | 138886798 | d7Mseg1201 | 7726 |
| 7 | 57574850 | 57576750 | 138909129 | 138909629 | d7Mseg1202 | 7727 |
| 7 | 57610200 | 57612800 | 138954829 | 138955383 | d7Mseg1203 | 7728 |
| 7 | 57632800 | 57634100 | 138988196 | 138990271 | d7Mseg1204 | 7729 |
| 7 | 57655000 | 57659550 | 139012164 | 139017130 | d7Mseg1205 | 7730 |
| 7 | 57667000 | 57668600 | 139026626 | 139027927 | d7Mseg1206 | 7731 |
| 7 | 57723000 | 57724000 | 139055531 | 139055991 | d7Mseg1208 | 7732 |
| 7 | 57799400 | 57803350 | 139172227 | 139176447 | d7Mseg1212 | 7733 |
| 7 | 57816150 | 57817150 | 139186360 | 139187124 | d7Mseg1213 | 7734 |
| 7 | 57820600 | 57822300 | 139190009 | 139192320 | d7Mseg1214 | 7735 |
| 7 | 57897000 | 57898600 | 139246106 | 139247243 | d7Mseg1215 | 7736 |
| 7 | 57924600 | 57926050 | 139265900 | 139266606 | d7Mseg1216 | 7737 |
| 7 | 57941900 | 57943700 | 139279344 | 139280405 | d7Mseg1217 | 7738 |
| 7 | 57970300 | 57971950 | 139329689 | 139331596 | d7Mseg1219 | 7739 |
| 7 | 58016500 | 58017800 | 139428337 | 139428642 | d7Mseg1220 | 7740 |
| 7 | 58023150 | 58027350 | 139435386 | 139438602 | d7Mseg1221 | 7741 |
| 7 | 58029900 | 58031700 | 139440158 | 139441944 | d7Mseg1222 | 7742 |
| 7 | 58051850 | 58054150 | 139471603 | 139473881 | d7Mseg1223 | 7743 |
| 7 | 58055850 | 58057250 | 139474933 | 139485755 | d7Mseg1224 | 7744 |
| 7 | 58090000 | 58091400 | 139527124 | 139528588 | d7Mseg1225 | 7745 |
| 7 | 58093400 | 58095200 | 139530686 | 139532366 | d7Mseg1226 | 7746 |
| 7 | 58140550 | 58155350 | 139580490 | 139597036 | d7Mseg1227 | 7747 |
| 7 | 58165000 | 58167100 | 139606013 | 139608635 | d7Mseg1228 | 7748 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 58384850 | 58386550 | 139813773 | 139815971 | d7Mseg1231 | 7749 |
| 7 | 58465000 | 58466750 | 139909059 | 139910219 | d7Mseg1233 | 7750 |
| 7 | 58525200 | 58526900 | 139944578 | 139945782 | d7Mseg1234 | 7751 |
| 7 | 58663700 | 58665150 | 140028027 | 140028808 | d7Mseg1237 | 7752 |
| 7 | 58669750 | 58671600 | 140034198 | 140035090 | d7Mseg1238 | 7753 |
| 7 | 58675550 | 58677350 | 140040110 | 140041802 | d7Mseg1239 | 7754 |
| 7 | 58902100 | 58904000 | 140377605 | 140378501 | d7Mseg1243 | 7755 |
| 7 | 58934950 | 58936400 | 140317220 | 140317391 | d7Mseg1246 | 7756 |
| 7 | 58952850 | 58954350 | 140290024 | 140293902 | d7Mseg1248 | 7757 |
| 7 | 58957950 | 58959600 | 140274917 | 140275522 | d7Mseg1249 | 7758 |
| 7 | 58964100 | 58965700 | 140268009 | 140269956 | d7Mseg1250 | 7759 |
| 7 | 59377900 | 59379350 | 140817693 | 140818068 | d7Mseg1252 | 7760 |
| 7 | 59654450 | 59656000 | 141152255 | 141152448 | d7Mseg1254 | 7761 |
| 7 | 59732000 | 59733550 | 141043698 | 141044410 | d7Mseg1255 | 7762 |
| 7 | 60257750 | 60259350 | 141645503 | 141645843 | d7Mseg1260 | 7763 |
| 7 | 60328950 | 60330400 | 141697400 | 141697914 | d7Mseg1261 | 7764 |
| 7 | 60333600 | 60334700 | 141701687 | 141702583 | d7Mseg1262 | 7765 |
| 7 | 60358800 | 60360600 | 141734606 | 141734949 | d7Mseg1263 | 7766 |
| 7 | 60551350 | 60553250 | 141918750 | 141919340 | d7Mseg1264 | 7767 |
| 7 | 60615600 | 60617300 | 141983211 | 141983387 | d7Mseg1265 | 7768 |
| 7 | 60907800 | 60909550 | 142176537 | 142176875 | d7Mseg1266 | 7769 |
| 7 | 61149350 | 61150750 | 142399415 | 142400245 | d7Mseg1269 | 7770 |
| 7 | 61524000 | 61530100 | 142716690 | 142722819 | d7Mseg1271 | 7771 |
| 7 | 63358150 | 63359900 | 144466717 | 144467918 | d7Mseg1279 | 7772 |
| 7 | 63846600 | 63848250 | 144844453 | 144847661 | d7Mseg1282 | 7773 |
| 7 | 63854000 | 63856750 | 144856740 | 144857718 | d7Mseg1283 | 7774 |
| 7 | 63900800 | 63905250 | 144897705 | 144902105 | d7Mseg1284 | 7775 |
| 7 | 63906250 | 63908900 | 144903114 | 144905761 | d7Mseg1285 | 7776 |
| 7 | 63928000 | 63929650 | 144926400 | 144926929 | d7Mseg1286 | 7777 |
| 7 | 64138700 | 64140250 | 145223055 | 145224629 | d7Mseg1289 | 7778 |
| 7 | 64451200 | 64453150 | 145458604 | 145459922 | d7Mseg1291 | 7779 |
| 7 | 64472650 | 64473800 | 145487301 | 145488595 | d7Mseg1292 | 7780 |
| 7 | 65497350 | 65499300 | 146607457 | 146608792 | d7Mseg1298 | 7781 |
| 7 | 65896600 | 65898050 | 146924168 | 146928985 | d7Mseg1306 | 7782 |
| 7 | 65902700 | 65905800 | 146933222 | 146940547 | d7Mseg1307 | 7783 |
| 7 | 65915350 | 65916650 | 146947717 | 146956114 | d7Mseg1308 | 7784 |
| 7 | 65930300 | 65933100 | 146992254 | 146994838 | d7Mseg1309 | 7785 |
| 7 | 66305550 | 66307300 | 147288427 | 147289227 | d7Mseg1320 | 7786 |
| 7 | 66361850 | 66362900 | 147330986 | 147331400 | d7Mseg1321 | 7787 |
| 7 | 66364600 | 66365700 | 147332932 | 147333643 | d7Mseg1322 | 7788 |
| 7 | 66390250 | 66391650 | 147351653 | 147353040 | d7Mseg1323 | 7789 |
| 7 | 66406550 | 66408250 | 147372678 | 147372973 | d7Mseg1324 | 7790 |
| 7 | 66611300 | 66617600 | 147579836 | 147586312 | d7Mseg1329 | 7791 |
| 7 | 66622250 | 66624200 | 147590811 | 147592758 | d7Mseg1330 | 7792 |
| 7 | 66646150 | 66647800 | 147615213 | 147616214 | d7Mseg1331 | 7793 |
| 7 | 66759400 | 66761050 | 147719435 | 147721104 | d7Mseg1332 | 7794 |
| 7 | 66880800 | 66882300 | 147833273 | 147834183 | d7Mseg1335 | 7795 |
| 7 | 66908150 | 66909650 | 147851588 | 147853287 | d7Mseg1336 | 7796 |
| 7 | 66913250 | 66914700 | 147856589 | 147864319 | d7Mseg1337 | 7797 |
| 7 | 66978700 | 66980300 | 147925058 | 147926809 | d7Mseg1340 | 7798 |
| 7 | 66997750 | 66999000 | 147946438 | 147947572 | d7Mseg1341 | 7799 |
| 7 | 67067550 | 67069150 | 148015670 | 148017370 | d7Mseg1342 | 7800 |
| 7 | 67113250 | 67114850 | 148062880 | 148063791 | d7Mseg1343 | 7801 |
| 7 | 67132650 | 67134100 | 148083832 | 148085381 | d7Mseg1344 | 7802 |
| 7 | 67204900 | 67206350 | 148141610 | 148142956 | d7Mseg1347 | 7803 |
| 7 | 67211750 | 67213450 | 148148674 | 148150153 | d7Mseg1348 | 7804 |
| 7 | 67216400 | 67217650 | 148151702 | 148152010 | d7Mseg1349 | 7805 |
| 7 | 67231000 | 67232850 | 148184311 | 148185873 | d7Mseg1351 | 7806 |
| 7 | 67398850 | 67400400 | 148355268 | 148356853 | d7Mseg1354 | 7807 |
| 7 | 67539950 | 67541950 | 148479700 | 148480642 | d7Mseg1356 | 7808 |
| 7 | 67582850 | 67584700 | 148551742 | 148553461 | d7Mseg1357 | 7809 |
| 7 | 67608200 | 67609500 | 148574205 | 148575872 | d7Mseg1358 | 7810 |
| 7 | 67615850 | 67617800 | 148584521 | 148586400 | d7Mseg1359 | 7811 |
| 7 | 67623250 | 67624750 | 148592205 | 148607263 | d7Mseg1360 | 7812 |
| 7 | 67729150 | 67730900 | 148712174 | 148714034 | d7Mseg1361 | 7813 |
| 7 | 67795200 | 67796600 | 148662163 | 148662484 | d7Mseg1362 | 7814 |
| 7 | 67858400 | 67860050 | 149143513 | 149144925 | d7Mseg1363 | 7815 |
| 7 | 67861650 | 67863400 | 149146670 | 149148115 | d7Mseg1364 | 7816 |
| 7 | 67922900 | 67924650 | 149187024 | 149187514 | d7Mseg1365 | 7817 |
| 7 | 68072950 | 68074700 | 149313658 | 149315427 | d7Mseg1368 | 7818 |
| 7 | 68099650 | 68100700 | 149350667 | 149351773 | d7Mseg1369 | 7819 |
| 7 | 68144700 | 68146150 | 149374855 | 149375923 | d7Mseg1370 | 7820 |
| 7 | 68170850 | 68172300 | 149413480 | 149414297 | d7Mseg1371 | 7821 |
| 7 | 68176350 | 68177600 | 149421989 | 149423304 | d7Mseg1372 | 7822 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 68189050 | 68190950 | 149431047 | 149431717 | d7Mseg1373 | 7823 |
| 7 | 68195750 | 68197250 | 149435111 | 149436178 | d7Mseg1374 | 7824 |
| 7 | 68198500 | 68200200 | 149437096 | 149438842 | d7Mseg1375 | 7825 |
| 7 | 68208500 | 68210500 | 149449297 | 149449967 | d7Mseg1376 | 7826 |
| 7 | 68265250 | 68266700 | 149493557 | 149494011 | d7Mseg1378 | 7827 |
| 7 | 68270550 | 68272400 | 149496841 | 149498434 | d7Mseg1379 | 7828 |
| 7 | 68276750 | 68280150 | 149503063 | 149506784 | d7Mseg1380 | 7829 |
| 7 | 68301500 | 68306350 | 149529896 | 149534532 | d7Mseg1381 | 7830 |
| 7 | 68308900 | 68310600 | 149538744 | 149540733 | d7Mseg1382 | 7831 |
| 7 | 68311900 | 68313400 | 149544584 | 149545741 | d7Mseg1383 | 7832 |
| 7 | 68333900 | 68336250 | 149578145 | 149580412 | d7Mseg1386 | 7833 |
| 7 | 68421150 | 68422750 | 149693513 | 149694494 | d7Mseg1387 | 7834 |
| 7 | 68439400 | 68440850 | 149711461 | 149712599 | d7Mseg1388 | 7835 |
| 7 | 68454750 | 68456200 | 149720466 | 149721028 | d7Mseg1390 | 7836 |
| 7 | 68471600 | 68473100 | 149741492 | 149743052 | d7Mseg1391 | 7837 |
| 7 | 68633300 | 68635200 | 149883887 | 149886078 | d7Mseg1395 | 7838 |
| 7 | 68665450 | 68670600 | 149924231 | 149931862 | d7Mseg1396 | 7839 |
| 7 | 68678000 | 68679400 | 149939545 | 149941100 | d7Mseg1397 | 7840 |
| 7 | 68684750 | 68691750 | 149947424 | 149962499 | d7Mseg1398 | 7841 |
| 7 | 68734600 | 68736000 | 150046939 | 150047592 | d7Mseg1400 | 7842 |
| 7 | 68783600 | 68787550 | 150109177 | 150110952 | d7Mseg1402 | 7843 |
| 7 | 68792300 | 68794350 | 150119455 | 150121165 | d7Mseg1403 | 7844 |
| 7 | 68805250 | 68809850 | 150146454 | 150152649 | d7Mseg1404 | 7845 |
| 7 | 68840200 | 68841600 | 150238332 | 150238685 | d7Mseg1405 | 7846 |
| 7 | 68865650 | 68867400 | 150256220 | 150257046 | d7Mseg1407 | 7847 |
| 7 | 68902450 | 68903750 | 150322055 | 150323006 | d7Mseg1410 | 7848 |
| 7 | 68914050 | 68921750 | 150341933 | 150350499 | d7Mseg1411 | 7849 |
| 7 | 68954400 | 68956100 | 150408671 | 150410009 | d7Mseg1413 | 7850 |
| 7 | 69022500 | 69023900 | 150506946 | 150508443 | d7Mseg1415 | 7851 |
| 7 | 69061200 | 69063200 | 150564437 | 150567623 | d7Mseg1416 | 7852 |
| 7 | 69084450 | 69085600 | 150588488 | 150589043 | d7Mseg1417 | 7853 |
| 7 | 69151500 | 69152900 | 150750968 | 150751575 | d7Mseg1420 | 7854 |
| 7 | 69184700 | 69186150 | 150842348 | 150845127 | d7Mseg1421 | 7855 |
| 7 | 69209400 | 69210650 | 150865018 | 150866747 | d7Mseg1424 | 7856 |
| 7 | 69227100 | 69228350 | 150880672 | 150881495 | d7Mseg1425 | 7857 |
| 7 | 69236750 | 69237750 | 150894771 | 150895880 | d7Mseg1426 | 7858 |
| 7 | 69290650 | 69292550 | 150935839 | 150936869 | d7Mseg1428 | 7859 |
| 7 | 69331700 | 69333400 | 150956748 | 150957438 | d7Mseg1431 | 7860 |
| 7 | 69385050 | 69386650 | 150986516 | 150988072 | d7Mseg1433 | 7861 |
| 7 | 69496400 | 69500700 | 151120596 | 151121345 | d7Mseg1435 | 7862 |
| 7 | 69517250 | 69520800 | 151139787 | 151143870 | d7Mseg1436 | 7863 |
| 7 | 69671600 | 69673050 | 151329766 | 151331282 | d7Mseg1443 | 7864 |
| 7 | 69679100 | 69680750 | 151335852 | 151337243 | d7Mseg1445 | 7865 |
| 7 | 69686250 | 69688050 | 151355395 | 151356349 | d7Mseg1446 | 7866 |
| 7 | 69732550 | 69733600 | 151411738 | 151412413 | d7Mseg1448 | 7867 |
| 7 | 69747800 | 69749500 | 151434940 | 151435571 | d7Mseg1449 | 7868 |
| 7 | 69811900 | 69813100 | 151538287 | 151538923 | d7Mseg1451 | 7869 |
| 7 | 69900350 | 69901900 | 151618590 | 151620055 | d7Mseg1453 | 7870 |
| 7 | 70046950 | 70050650 | 151785671 | 151787478 | d7Mseg1457 | 7871 |
| 7 | 70069750 | 70071700 | 151805524 | 151807629 | d7Mseg1458 | 7872 |
| 7 | 70142150 | 70144350 | 151979703 | 151983157 | d7Mseg1461 | 7873 |
| 7 | 70153300 | 70154550 | 151989218 | 151990282 | d7Mseg1462 | 7874 |
| 7 | 70193800 | 70195550 | 152027256 | 152028431 | d7Mseg1463 | 7875 |
| 7 | 70220350 | 70221800 | 152056041 | 152056981 | d7Mseg1464 | 7876 |
| 7 | 70232550 | 70233700 | 152066464 | 152067633 | d7Mseg1465 | 7877 |
| 7 | 70257400 | 70259250 | 152113641 | 152129138 | d7Mseg1466 | 7878 |
| 7 | 70276250 | 70277250 | 152141408 | 152142118 | d7Mseg1469 | 7879 |
| 7 | 70307450 | 70311500 | 152223647 | 152226743 | d7Mseg1471 | 7880 |
| 7 | 70472950 | 70474700 | 154611555 | 154612779 | d7Mseg1475 | 7881 |
| 7 | 70487400 | 70488950 | 152517384 | 152517665 | d7Mseg1476 | 7882 |
| 7 | 70576900 | 70578150 | 152574778 | 152575327 | d7Mseg1478 | 7883 |
| 7 | 70580600 | 70583700 | 152585591 | 152587627 | d7Mseg1479 | 7884 |
| 7 | 70601650 | 70603300 | 152615594 | 152617358 | d7Mseg1481 | 7885 |
| 7 | 70640300 | 70642000 | 152661058 | 152662637 | d7Mseg1485 | 7886 |
| 7 | 70655550 | 70660200 | 152676030 | 152680458 | d7Mseg1486 | 7887 |
| 7 | 70664850 | 70671150 | 152684240 | 152690372 | d7Mseg1487 | 7888 |
| 7 | 70679100 | 70681100 | 152709968 | 152711880 | d7Mseg1488 | 7889 |
| 7 | 70702900 | 70704800 | 152731556 | 152736608 | d7Mseg1489 | 7890 |
| 7 | 70723900 | 70725000 | 152755709 | 152756746 | d7Mseg1490 | 7891 |
| 7 | 70726950 | 70728100 | 152758939 | 152759515 | d7Mseg1491 | 7892 |
| 7 | 70743300 | 70746000 | 152776894 | 152780147 | d7Mseg1492 | 7893 |
| 7 | 70748300 | 70751550 | 152783051 | 152786127 | d7Mseg1493 | 7894 |
| 7 | 70757200 | 70759150 | 152791666 | 152793578 | d7Mseg1494 | 7895 |
| 7 | 70767850 | 70769300 | 152801185 | 152802481 | d7Mseg1495 | 7896 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 70781750 | 70783700 | 152814373 | 152815781 | d7Mseg1496 | 7897 |
| 7 | 70794950 | 70796450 | 152824516 | 152825346 | d7Mseg1497 | 7898 |
| 7 | 70812950 | 70814750 | 152842547 | 152844430 | d7Mseg1498 | 7899 |
| 7 | 70860100 | 70861950 | 152889319 | 152890840 | d7Mseg1502 | 7900 |
| 7 | 70875500 | 70877250 | 152902517 | 152904457 | d7Mseg1503 | 7901 |
| 7 | 70880250 | 70886600 | 152907256 | 152914605 | d7Mseg1504 | 7902 |
| 7 | 70905400 | 70911700 | 152939259 | 152940828 | d7Mseg1506 | 7903 |
| 7 | 70919050 | 70921750 | 152953952 | 152956569 | d7Mseg1507 | 7904 |
| 7 | 70933800 | 70935300 | 152968165 | 152969856 | d7Mseg1508 | 7905 |
| 7 | 70948600 | 70949900 | 152978675 | 152979290 | d7Mseg1509 | 7906 |
| 7 | 70980950 | 70982700 | 153007419 | 153008992 | d7Mseg1510 | 7907 |
| 7 | 71012250 | 71013900 | 153039280 | 153040901 | d7Mseg1513 | 7908 |
| 7 | 71069800 | 71072250 | 153095872 | 153098097 | d7Mseg1515 | 7909 |
| 7 | 71109050 | 71113450 | 153136083 | 153139765 | d7Mseg1516 | 7910 |
| 7 | 71120500 | 71121700 | 153146752 | 153147992 | d7Mseg1517 | 7911 |
| 7 | 71124250 | 71126750 | 153149710 | 153152251 | d7Mseg1518 | 7912 |
| 7 | 71149300 | 71150850 | 153184225 | 153185985 | d7Mseg1520 | 7913 |
| 7 | 71154300 | 71156050 | 153189067 | 153191013 | d7Mseg1521 | 7914 |
| 7 | 71159150 | 71160750 | 153193580 | 153193885 | d7Mseg1522 | 7915 |
| 7 | 71161900 | 71162900 | 153195212 | 153196011 | d7Mseg1523 | 7916 |
| 7 | 71165700 | 71168200 | 153198707 | 153201262 | d7Mseg1524 | 7917 |
| 7 | 71194550 | 71196000 | 153219530 | 153220953 | d7Mseg1525 | 7918 |
| 7 | 71210350 | 71212250 | 153235226 | 153237200 | d7Mseg1526 | 7919 |
| 7 | 71223000 | 71225100 | 153250317 | 153251338 | d7Mseg1527 | 7920 |
| 7 | 71283100 | 71284300 | 153298540 | 153300521 | d7Mseg1529 | 7921 |
| 7 | 71292500 | 71294500 | 153316742 | 153324650 | d7Mseg1530 | 7922 |
| 7 | 71335250 | 71336950 | 153370538 | 153371498 | d7Mseg1532 | 7923 |
| 7 | 71382350 | 71384100 | 153418367 | 153418693 | d7Mseg1533 | 7924 |
| 7 | 71386600 | 71389900 | 153420655 | 153422775 | d7Mseg1534 | 7925 |
| 7 | 71459950 | 71461300 | 153562710 | 153563290 | d7Mseg1535 | 7926 |
| 7 | 71489000 | 71492050 | 153596991 | 153599880 | d7Mseg1536 | 7927 |
| 7 | 71499550 | 71501250 | 153606662 | 153608766 | d7Mseg1537 | 7928 |
| 7 | 71525800 | 71528950 | 153636851 | 153640773 | d7Mseg1538 | 7929 |
| 7 | 71544200 | 71546300 | 153658402 | 153660981 | d7Mseg1539 | 7930 |
| 7 | 71549400 | 71551350 | 153664294 | 153666201 | d7Mseg1540 | 7931 |
| 7 | 71566400 | 71568000 | 153679299 | 153679715 | d7Mseg1541 | 7932 |
| 7 | 71572900 | 71574500 | 153686143 | 153686719 | d7Mseg1542 | 7933 |
| 7 | 71597350 | 71599550 | 153706025 | 153707374 | d7Mseg1543 | 7934 |
| 7 | 71673000 | 71675050 | 153773591 | 153775852 | d7Mseg1547 | 7935 |
| 7 | 71693150 | 71694750 | 153792146 | 153794634 | d7Mseg1548 | 7936 |
| 7 | 71991550 | 71992850 | 153706095 | 153706314 | d7Mseg1554 | 7937 |
| 7 | 72211950 | 72213350 | 153705935 | 153706160 | d7Mseg1558 | 7938 |
| 7 | 72290150 | 72291950 | 153956437 | 153958245 | d7Mseg1561 | 7939 |
| 7 | 72333300 | 72334800 | 153982106 | 153982301 | d7Mseg1562 | 7940 |
| 7 | 72369350 | 72371100 | 154019364 | 154020441 | d7Mseg1563 | 7941 |
| 7 | 72409000 | 72410950 | 154060856 | 154061237 | d7Mseg1565 | 7942 |
| 7 | 72456150 | 72457900 | 154089731 | 154092130 | d7Mseg1566 | 7943 |
| 7 | 72557650 | 72561700 | 154180211 | 154181981 | d7Mseg1568 | 7944 |
| 7 | 72639750 | 72640950 | 154282973 | 154284279 | d7Mseg1570 | 7945 |
| 7 | 72732250 | 72734250 | 154372800 | 154373844 | d7Mseg1573 | 7946 |
| 7 | 72758200 | 72760250 | 154444032 | 154445346 | d7Mseg1574 | 7947 |
| 7 | 72786450 | 72787600 | 154471601 | 154471774 | d7Mseg1576 | 7948 |
| 7 | 72821850 | 72824150 | 154492014 | 154494231 | d7Mseg1577 | 7949 |
| 7 | 73053450 | 73054650 | 114861747 | 114862637 | d7Mseg1579 | 7950 |
| 7 | 73110250 | 73112150 | 114806989 | 114808563 | d7Mseg1580 | 7951 |
| 7 | 73115600 | 73117100 | 114798581 | 114799081 | d7Mseg1581 | 7952 |
| 7 | 73118600 | 73123600 | 114793735 | 114797278 | d7Mseg1582 | 7953 |
| 7 | 73147200 | 73148700 | 114768567 | 114769647 | d7Mseg1583 | 7954 |
| 7 | 73314150 | 73315500 | 114656166 | 114657201 | d7Mseg1585 | 7955 |
| 7 | 73332800 | 73334600 | 114641567 | 114641991 | d7Mseg1586 | 7956 |
| 7 | 73954550 | 73956650 | 8811634 | 8812303 | d7Mseg1592 | 7957 |
| 7 | 74652300 | 74654250 | 9269573 | 9270527 | d7Mseg1599 | 7958 |
| 7 | 74664750 | 74666050 | 9297790 | 9299098 | d7Mseg1600 | 7959 |
| 7 | 74676700 | 74678750 | 9309273 | 9310398 | d7Mseg1601 | 7960 |
| 7 | 74691600 | 74693200 | 9320690 | 9322503 | d7Mseg1602 | 7961 |
| 7 | 74920750 | 74922600 | 9933562 | 9935438 | d7Mseg1605 | 7962 |
| 7 | 75725050 | 75728900 | 37285441 | 37294049 | d7Mseg1612 | 7963 |
| 7 | 75828600 | 75830000 | 37207650 | 37209172 | d7Mseg1613 | 7964 |
| 7 | 76511500 | 76513000 | 36401010 | 36403291 | d7Mseg1616 | 7965 |
| 7 | 77182850 | 77184600 | 35485673 | 35486457 | d7Mseg1619 | 7966 |
| 7 | 78310450 | 78311900 | 34680178 | 34682234 | d7Mseg1626 | 7967 |
| 7 | 78315700 | 78317600 | 34673891 | 34675816 | d7Mseg1627 | 7968 |
| 7 | 78342250 | 78344000 | 34644750 | 34646160 | d7Mseg1628 | 7969 |
| 7 | 78362300 | 78364000 | 34627960 | 34628369 | d7Mseg1629 | 7970 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 79623400 | 79624600 | 33687656 | 33687877 | d7Mseg1634 | 7971 |
| 7 | 80205750 | 80207700 | 33216156 | 33217581 | d7Mseg1639 | 7972 |
| 7 | 80405800 | 80407550 | 33013820 | 33016706 | d7Mseg1641 | 7973 |
| 7 | 80469300 | 80471000 | 32948473 | 32949339 | d7Mseg1642 | 7974 |
| 7 | 80502150 | 80503600 | 32924975 | 32926317 | d7Mseg1643 | 7975 |
| 7 | 80510700 | 80511800 | 32914363 | 32915119 | d7Mseg1644 | 7976 |
| 7 | 80600000 | 80602050 | 32853369 | 32853783 | d7Mseg1647 | 7977 |
| 7 | 80779100 | 80780800 | 32792070 | 32795908 | d7Mseg1655 | 7978 |
| 7 | 80803250 | 80804700 | 32784908 | 32785324 | d7Mseg1656 | 7979 |
| 7 | 80975500 | 80977300 | 32561342 | 32562574 | d7Mseg1657 | 7980 |
| 7 | 81017800 | 81018850 | 32518838 | 32520032 | d7Mseg1660 | 7981 |
| 7 | 81145450 | 81146700 | 32388926 | 32389220 | d7Mseg1663 | 7982 |
| 7 | 81204800 | 81206050 | 32314046 | 32315086 | d7Mseg1664 | 7983 |
| 7 | 81322550 | 81323600 | 32171957 | 32173025 | d7Mseg1666 | 7984 |
| 7 | 81439050 | 81440650 | 32052274 | 32052799 | d7Mseg1668 | 7985 |
| 7 | 81500700 | 81501800 | 31995704 | 31996870 | d7Mseg1669 | 7986 |
| 7 | 81524300 | 81525350 | 31980546 | 31981019 | d7Mseg1670 | 7987 |
| 7 | 81574650 | 81575850 | 31931494 | 31931718 | d7Mseg1671 | 7988 |
| 7 | 81640900 | 81642200 | 31874352 | 31875671 | d7Mseg1672 | 7989 |
| 7 | 81706400 | 81708100 | 31798558 | 31801977 | d7Mseg1674 | 7990 |
| 7 | 81801850 | 81803450 | 31723606 | 31725336 | d7Mseg1676 | 7991 |
| 7 | 81845550 | 81847150 | 31674006 | 31675164 | d7Mseg1677 | 7992 |
| 7 | 81904250 | 81905500 | 31632349 | 31633483 | d7Mseg1678 | 7993 |
| 7 | 81913850 | 81915450 | 31623538 | 31625254 | d7Mseg1679 | 7994 |
| 7 | 81945100 | 81946900 | 31589196 | 31590001 | d7Mseg1680 | 7995 |
| 7 | 81951100 | 81952750 | 31581527 | 31583745 | d7Mseg1681 | 7996 |
| 7 | 81966100 | 81970350 | 31567380 | 31572011 | d7Mseg1682 | 7997 |
| 7 | 82019050 | 82020750 | 31523363 | 31525440 | d7Mseg1683 | 7998 |
| 7 | 82023200 | 82024850 | 31518190 | 31520702 | d7Mseg1684 | 7999 |
| 7 | 82033700 | 82034700 | 31508175 | 31509497 | d7Mseg1685 | 8000 |
| 7 | 82101200 | 82104600 | 31455040 | 31457069 | d7Mseg1686 | 8001 |
| 7 | 82113500 | 82116250 | 31446166 | 31447521 | d7Mseg1688 | 8002 |
| 7 | 82120150 | 82121800 | 31443541 | 31444319 | d7Mseg1689 | 8003 |
| 7 | 82137150 | 82138800 | 31426405 | 31428639 | d7Mseg1690 | 8004 |
| 7 | 82153650 | 82155400 | 31407167 | 31407699 | d7Mseg1692 | 8005 |
| 7 | 82156750 | 82158350 | 31403055 | 31405363 | d7Mseg1693 | 8006 |
| 7 | 82160400 | 82161450 | 31394111 | 31395069 | d7Mseg1694 | 8007 |
| 7 | 82187000 | 82189200 | 31367039 | 31368918 | d7Mseg1695 | 8008 |
| 7 | 82193550 | 82195250 | 31359217 | 31360463 | d7Mseg1696 | 8009 |
| 7 | 82208450 | 82209950 | 31346666 | 31347488 | d7Mseg1697 | 8010 |
| 7 | 82266550 | 82267550 | 31299175 | 31299619 | d7Mseg1698 | 8011 |
| 7 | 82288700 | 82290450 | 31288167 | 31289445 | d7Mseg1700 | 8012 |
| 7 | 82293700 | 82295000 | 31283765 | 31285017 | d7Mseg1701 | 8013 |
| 7 | 82311400 | 82313150 | 31262056 | 31262987 | d7Mseg1702 | 8014 |
| 7 | 82347800 | 82349650 | 31228686 | 31230254 | d7Mseg1703 | 8015 |
| 7 | 82367700 | 82368950 | 31208078 | 31210281 | d7Mseg1704 | 8016 |
| 7 | 82381500 | 82382800 | 31203831 | 31204993 | d7Mseg1706 | 8017 |
| 7 | 82458050 | 82459200 | 31129523 | 31130334 | d7Mseg1707 | 8018 |
| 7 | 82499650 | 82501400 | 31103829 | 31105595 | d7Mseg1709 | 8019 |
| 7 | 82514350 | 82516200 | 31089080 | 31090136 | d7Mseg1710 | 8020 |
| 7 | 82611550 | 82613500 | 31028230 | 31028614 | d7Mseg1713 | 8021 |
| 7 | 82670750 | 82672600 | 30994106 | 30994438 | d7Mseg1714 | 8022 |
| 7 | 82722950 | 82724800 | 30964512 | 30966028 | d7Mseg1715 | 8023 |
| 7 | 82777700 | 82779100 | 30934995 | 30935435 | d7Mseg1717 | 8024 |
| 7 | 82814050 | 82815900 | 30909800 | 30911227 | d7Mseg1718 | 8025 |
| 7 | 82818550 | 82821050 | 30905717 | 30908241 | d7Mseg1719 | 8026 |
| 7 | 82822500 | 82823700 | 30903337 | 30904238 | d7Mseg1720 | 8027 |
| 7 | 82840650 | 82842250 | 30887863 | 30889071 | d7Mseg1721 | 8028 |
| 7 | 83000700 | 83002300 | 30691250 | 30692397 | d7Mseg1725 | 8029 |
| 7 | 83124500 | 83126300 | 30587135 | 30588936 | d7Mseg1728 | 8030 |
| 7 | 83154000 | 83155400 | 30545924 | 30546443 | d7Mseg1729 | 8031 |
| 7 | 83175650 | 83177900 | 30523272 | 30524982 | d7Mseg1730 | 8032 |
| 7 | 83216350 | 83219100 | 30494499 | 30495893 | d7Mseg1731 | 8033 |
| 7 | 83223300 | 83224950 | 30490834 | 30491249 | d7Mseg1732 | 8034 |
| 7 | 83322100 | 83323300 | 30431946 | 30432759 | d7Mseg1736 | 8035 |
| 7 | 83418600 | 83420450 | 30346214 | 30349503 | d7Mseg1738 | 8036 |
| 7 | 83435400 | 83438050 | 30326575 | 30329333 | d7Mseg1739 | 8037 |
| 7 | 83455400 | 83457350 | 30310417 | 30311435 | d7Mseg1741 | 8038 |
| 7 | 83538650 | 83540550 | 30271481 | 30272220 | d7Mseg1742 | 8039 |
| 7 | 83591000 | 83592600 | 30260066 | 30260444 | d7Mseg1745 | 8040 |
| 7 | 83657050 | 83660550 | 30223406 | 30223935 | d7Mseg1747 | 8041 |
| 7 | 83662450 | 83663850 | 30221416 | 30221910 | d7Mseg1748 | 8042 |
| 7 | 83705650 | 83706850 | 30191069 | 30192090 | d7Mseg1750 | 8043 |
| 7 | 83722800 | 83724100 | 30182052 | 30182634 | d7Mseg1752 | 8044 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 83933100 | 83934650 | 30046019 | 30048010 | d7Mseg1755 | 8045 |
| 7 | 83964950 | 83966050 | 30020273 | 30021117 | d7Mseg1756 | 8046 |
| 7 | 83993000 | 83994650 | 29972392 | 29973517 | d7Mseg1757 | 8047 |
| 7 | 84016650 | 84018200 | 29947032 | 29949358 | d7Mseg1758 | 8048 |
| 7 | 84030400 | 84032150 | 29936884 | 29938351 | d7Mseg1759 | 8049 |
| 7 | 84063450 | 84064700 | 29905105 | 29907099 | d7Mseg1760 | 8050 |
| 7 | 84110900 | 84112050 | 29859501 | 29869736 | d7Mseg1762 | 8051 |
| 7 | 84144500 | 84146000 | 29819270 | 29820348 | d7Mseg1763 | 8052 |
| 7 | 84203350 | 84207100 | 29777427 | 29780471 | d7Mseg1764 | 8053 |
| 7 | 84270150 | 84271300 | 29712683 | 29714088 | d7Mseg1765 | 8054 |
| 7 | 84314300 | 84316150 | 29657466 | 29658758 | d7Mseg1766 | 8055 |
| 7 | 84354400 | 84357800 | 29627662 | 29628295 | d7Mseg1767 | 8056 |
| 7 | 84469100 | 84470600 | 29479128 | 29480484 | d7Mseg1769 | 8057 |
| 7 | 84574750 | 84576600 | 29378523 | 29379850 | d7Mseg1770 | 8058 |
| 7 | 84591350 | 84592850 | 29370767 | 29371119 | d7Mseg1771 | 8059 |
| 7 | 84634800 | 84637850 | 29329300 | 29332544 | d7Mseg1774 | 8060 |
| 7 | 84684050 | 84685750 | 29280872 | 29285585 | d7Mseg1775 | 8061 |
| 7 | 84713100 | 84714600 | 29252778 | 29253973 | d7Mseg1776 | 8062 |
| 7 | 84898700 | 84900250 | 29064653 | 29066395 | d7Mseg1779 | 8063 |
| 7 | 84908500 | 84910350 | 29052618 | 29054994 | d7Mseg1780 | 8064 |
| 7 | 84947200 | 84948550 | 29016552 | 29017744 | d7Mseg1781 | 8065 |
| 7 | 84977000 | 84978550 | 28982631 | 28983787 | d7Mseg1782 | 8066 |
| 7 | 85066100 | 85067800 | 89176629 | 89177426 | d7Mseg1785 | 8067 |
| 7 | 85132350 | 85134100 | 28809368 | 28811536 | d7Mseg1786 | 8068 |
| 7 | 85148700 | 85150250 | 28797367 | 28798373 | d7Mseg1787 | 8069 |
| 7 | 85160000 | 85161250 | 28793576 | 28793827 | d7Mseg1788 | 8070 |
| 7 | 85253750 | 85255600 | 28712224 | 28713482 | d7Mseg1789 | 8071 |
| 7 | 85352350 | 85353850 | 28612592 | 28613823 | d7Mseg1790 | 8072 |
| 7 | 85366200 | 85367850 | 28598697 | 28600326 | d7Mseg1791 | 8073 |
| 7 | 85386150 | 85387750 | 28582850 | 28583331 | d7Mseg1792 | 8074 |
| 7 | 85412500 | 85413750 | 28564875 | 28566470 | d7Mseg1793 | 8075 |
| 7 | 85697550 | 85699300 | 28374271 | 28374639 | d7Mseg1796 | 8076 |
| 7 | 85854400 | 85855850 | 28277627 | 28278498 | d7Mseg1797 | 8077 |
| 7 | 85997650 | 85999700 | 28218619 | 28220150 | d7Mseg1798 | 8078 |
| 7 | 87456250 | 87457700 | 27109563 | 27109810 | d7Mseg1808 | 8079 |
| 7 | 88214600 | 88216350 | 26462918 | 26463788 | d7Mseg1811 | 8080 |
| 7 | 88611450 | 88613000 | 26190646 | 26191846 | d7Mseg1813 | 8081 |
| 7 | 89357750 | 89359700 | 26167590 | 26168733 | d7Mseg1817 | 8082 |
| 7 | 89617250 | 89619050 | 25843233 | 25844918 | d7Mseg1818 | 8083 |
| 7 | 89661350 | 89662950 | 25784713 | 25785054 | d7Mseg1819 | 8084 |
| 7 | 89677300 | 89679000 | 25765103 | 25765582 | d7Mseg1820 | 8085 |
| 7 | 89711900 | 89713300 | 25733771 | 25734747 | d7Mseg1821 | 8086 |
| 7 | 89725400 | 89726850 | 25721339 | 25721715 | d7Mseg1822 | 8087 |
| 7 | 89753550 | 89754600 | 25673264 | 25680466 | d7Mseg1823 | 8088 |
| 7 | 89777800 | 89778950 | 25634289 | 25635158 | d7Mseg1824 | 8089 |
| 7 | 89827250 | 89828800 | 25564129 | 25565592 | d7Mseg1825 | 8090 |
| 7 | 89939950 | 89941550 | 25471542 | 25471872 | d7Mseg1827 | 8091 |
| 7 | 89954050 | 89955800 | 25463144 | 25463717 | d7Mseg1828 | 8092 |
| 7 | 89966400 | 89967950 | 25460338 | 25461852 | d7Mseg1829 | 8093 |
| 7 | 89983750 | 89985350 | 25450883 | 25451348 | d7Mseg1831 | 8094 |
| 7 | 90037450 | 90039000 | 25399192 | 25400180 | d7Mseg1832 | 8095 |
| 7 | 90054850 | 90056400 | 25373509 | 25374393 | d7Mseg1833 | 8096 |
| 7 | 90198450 | 90199800 | 25257535 | 25259103 | d7Mseg1836 | 8097 |
| 7 | 90266200 | 90268050 | 25206553 | 25206758 | d7Mseg1840 | 8098 |
| 7 | 90305150 | 90306900 | 25172141 | 25172448 | d7Mseg1841 | 8099 |
| 7 | 90353100 | 90354600 | 25122790 | 25123945 | d7Mseg1842 | 8100 |
| 7 | 90402900 | 90404000 | 145892354 | 145892535 | d7Mseg1844 | 8101 |
| 7 | 90506300 | 90507600 | 25062850 | 25063217 | d7Mseg1847 | 8102 |
| 7 | 90518950 | 90520700 | 25045379 | 25046103 | d7Mseg1848 | 8103 |
| 7 | 90523800 | 90549300 | 25016147 | 25042007 | d7Mseg1849 | 8104 |
| 7 | 90562400 | 90563700 | 24999621 | 25000903 | d7Mseg1850 | 8105 |
| 7 | 90663350 | 90664650 | 24908612 | 24909571 | d7Mseg1853 | 8106 |
| 7 | 90668650 | 90670400 | 24899649 | 24902937 | d7Mseg1854 | 8107 |
| 7 | 90705050 | 90706900 | 24861601 | 24863356 | d7Mseg1855 | 8108 |
| 7 | 90791750 | 90793450 | 24780008 | 24781739 | d7Mseg1856 | 8109 |
| 7 | 90836900 | 90838650 | 24745220 | 24745897 | d7Mseg1857 | 8110 |
| 7 | 90921800 | 90923650 | 24661635 | 24664088 | d7Mseg1860 | 8111 |
| 7 | 90930800 | 90932450 | 24656243 | 24657532 | d7Mseg1861 | 8112 |
| 7 | 90934450 | 90935450 | 24652415 | 24653275 | d7Mseg1862 | 8113 |
| 7 | 90947350 | 90949000 | 24635076 | 24637271 | d7Mseg1863 | 8114 |
| 7 | 90976400 | 90978000 | 24595934 | 24598475 | d7Mseg1864 | 8115 |
| 7 | 90994400 | 90995900 | 24575595 | 24577634 | d7Mseg1865 | 8116 |
| 7 | 91038400 | 91039950 | 24530959 | 24531974 | d7Mseg1866 | 8117 |
| 7 | 91076600 | 91079100 | 24481557 | 24484295 | d7Mseg1867 | 8118 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 91089650 | 91090900 | 24466578 | 24468076 | d7Mseg1868 | 8119 |
| 7 | 91098500 | 91102550 | 24457070 | 24462021 | d7Mseg1869 | 8120 |
| 7 | 91105400 | 91107050 | 24445396 | 24446221 | d7Mseg1870 | 8121 |
| 7 | 91120450 | 91122200 | 24423079 | 24424730 | d7Mseg1871 | 8122 |
| 7 | 91135950 | 91137400 | 24411015 | 24412569 | d7Mseg1873 | 8123 |
| 7 | 91145200 | 91146800 | 24399106 | 24405445 | d7Mseg1874 | 8124 |
| 7 | 91155700 | 91157600 | 24388624 | 24390656 | d7Mseg1875 | 8125 |
| 7 | 91200650 | 91202450 | 24350993 | 24351520 | d7Mseg1878 | 8126 |
| 7 | 91224850 | 91226700 | 24331136 | 24331586 | d7Mseg1879 | 8127 |
| 7 | 91243700 | 91245300 | 24310317 | 24312581 | d7Mseg1881 | 8128 |
| 7 | 91247550 | 91250050 | 24306545 | 24309572 | d7Mseg1882 | 8129 |
| 7 | 91324250 | 91326300 | 24226912 | 24229377 | d7Mseg1885 | 8130 |
| 7 | 91371750 | 91372750 | 24164211 | 24164875 | d7Mseg1886 | 8131 |
| 7 | 91384050 | 91385400 | 24153179 | 24154308 | d7Mseg1887 | 8132 |
| 7 | 91387900 | 91389650 | 24144138 | 24146698 | d7Mseg1888 | 8133 |
| 7 | 91458400 | 91459850 | 24069834 | 24072674 | d7Mseg1890 | 8134 |
| 7 | 91480150 | 91482300 | 24041384 | 24043582 | d7Mseg1891 | 8135 |
| 7 | 91493550 | 91494850 | 24028645 | 24029306 | d7Mseg1892 | 8136 |
| 7 | 91504350 | 91506250 | 24019124 | 24020452 | d7Mseg1893 | 8137 |
| 7 | 91507950 | 91509400 | 24016865 | 24018314 | d7Mseg1894 | 8138 |
| 7 | 91519100 | 91520800 | 24004075 | 24005729 | d7Mseg1895 | 8139 |
| 7 | 91570500 | 91572250 | 23970986 | 23972049 | d7Mseg1898 | 8140 |
| 7 | 91573500 | 91575050 | 23968425 | 23969197 | d7Mseg1899 | 8141 |
| 7 | 91587900 | 91591400 | 23950576 | 23955983 | d7Mseg1900 | 8142 |
| 7 | 91594150 | 91595200 | 23943839 | 23944757 | d7Mseg1901 | 8143 |
| 7 | 91609400 | 91614150 | 23922176 | 23928640 | d7Mseg1904 | 8144 |
| 7 | 91627200 | 91628500 | 23896303 | 23897718 | d7Mseg1905 | 8145 |
| 7 | 91631600 | 91633200 | 23892373 | 23892878 | d7Mseg1906 | 8146 |
| 7 | 91704850 | 91706550 | 51810636 | 51813361 | d7Mseg1909 | 8147 |
| 7 | 91782700 | 91784350 | 51639768 | 51641671 | d7Mseg1915 | 8148 |
| 7 | 91786200 | 91788100 | 51635990 | 51637836 | d7Mseg1916 | 8149 |
| 7 | 91797150 | 91798200 | 51599825 | 51600417 | d7Mseg1918 | 8150 |
| 7 | 91880500 | 91882850 | 51485471 | 51487965 | d7Mseg1921 | 8151 |
| 7 | 91890300 | 91892050 | 51491994 | 51492629 | d7Mseg1923 | 8152 |
| 7 | 91973300 | 91975100 | 57621606 | 57623474 | d7Mseg1928 | 8153 |
| 7 | 92219900 | 92223600 | 62568906 | 62571967 | d7Mseg1940 | 8154 |
| 7 | 92248350 | 92249450 | 62858799 | 62862742 | d7Mseg1941 | 8155 |
| 7 | 92264050 | 92265750 | 62883670 | 62884994 | d7Mseg1942 | 8156 |
| 7 | 92268250 | 92269900 | 62887454 | 62888850 | d7Mseg1943 | 8157 |
| 7 | 92276150 | 92277550 | 62898076 | 62898866 | d7Mseg1944 | 8158 |
| 7 | 92302350 | 92304150 | 62921716 | 62922221 | d7Mseg1945 | 8159 |
| 7 | 92327050 | 92330100 | 62945390 | 62949127 | d7Mseg1947 | 8160 |
| 7 | 92335250 | 92337200 | 62956371 | 62956737 | d7Mseg1948 | 8161 |
| 7 | 92350650 | 92352250 | 62963439 | 62964846 | d7Mseg1949 | 8162 |
| 7 | 92365400 | 92367650 | 62976676 | 62978772 | d7Mseg1950 | 8163 |
| 7 | 92501150 | 92502200 | 63072637 | 63073497 | d7Mseg1953 | 8164 |
| 7 | 92535850 | 92538050 | 63138696 | 63138975 | d7Mseg1954 | 8165 |
| 7 | 92620600 | 92623150 | 63409908 | 63412464 | d7Mseg1955 | 8166 |
| 7 | 92638300 | 92640200 | 63423584 | 63425660 | d7Mseg1956 | 8167 |
| 7 | 92653450 | 92654950 | 63430922 | 63431904 | d7Mseg1958 | 8168 |
| 7 | 92672200 | 92673400 | 63449218 | 63450416 | d7Mseg1959 | 8169 |
| 7 | 92718000 | 92719900 | 63492505 | 63556332 | d7Mseg1964 | 8170 |
| 7 | 92880300 | 92881900 | 64233968 | 64235103 | d7Mseg1969 | 8171 |
| 7 | 92906500 | 92907900 | 64253522 | 64255559 | d7Mseg1970 | 8172 |
| 7 | 93131150 | 93133000 | 64732941 | 64734885 | d7Mseg1976 | 8173 |
| 7 | 93203200 | 93204750 | 64802920 | 64803138 | d7Mseg1978 | 8174 |
| 7 | 93207000 | 93208750 | 64807716 | 64808948 | d7Mseg1979 | 8175 |
| 7 | 93215900 | 93217900 | 64816291 | 64818878 | d7Mseg1980 | 8176 |
| 7 | 93246950 | 93248000 | 64855009 | 64855155 | d7Mseg1981 | 8177 |
| 7 | 93281700 | 93283200 | 64872074 | 64873274 | d7Mseg1983 | 8178 |
| 7 | 93285700 | 93287100 | 64875932 | 64876929 | d7Mseg1984 | 8179 |
| 7 | 93291150 | 93293200 | 64887278 | 64888973 | d7Mseg1985 | 8180 |
| 7 | 93315000 | 93316100 | 64907980 | 64908886 | d7Mseg1986 | 8181 |
| 7 | 93346550 | 93347800 | 64948633 | 64949241 | d7Mseg1988 | 8182 |
| 7 | 93440500 | 93442200 | 65241111 | 65241477 | d7Mseg1989 | 8183 |
| 7 | 93508350 | 93510150 | 65291129 | 65297937 | d7Mseg1992 | 8184 |
| 7 | 93512100 | 93513500 | 65301609 | 65302187 | d7Mseg1993 | 8185 |
| 7 | 93690650 | 93693400 | 65416207 | 65417741 | d7Mseg2000 | 8186 |
| 7 | 93720300 | 93721400 | 65421692 | 65422052 | d7Mseg2002 | 8187 |
| 7 | 94144800 | 94146200 | 25077998 | 25078404 | d7Mseg2012 | 8188 |
| 7 | 94539900 | 94541650 | 65825376 | 65830256 | d7Mseg2020 | 8189 |
| 7 | 94543350 | 94545000 | 65831462 | 65832032 | d7Mseg2021 | 8190 |
| 7 | 94569650 | 94571350 | 65856296 | 65857881 | d7Mseg2022 | 8191 |
| 7 | 94595000 | 94596450 | 65896420 | 65897702 | d7Mseg2023 | 8192 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 94898350 | 94899700 | 66268475 | 66269224 | d7Mseg2031 | 8193 |
| 7 | 95048400 | 95049750 | 66429855 | 66431225 | d7Mseg2035 | 8194 |
| 7 | 95343100 | 95348700 | 66762816 | 66768622 | d7Mseg2041 | 8195 |
| 7 | 95356200 | 95357350 | 66777176 | 66778471 | d7Mseg2042 | 8196 |
| 7 | 95359200 | 95363200 | 66780392 | 66784533 | d7Mseg2043 | 8197 |
| 7 | 95365300 | 95366500 | 66786951 | 66788335 | d7Mseg2044 | 8198 |
| 7 | 95392450 | 95394200 | 66801391 | 66801846 | d7Mseg2045 | 8199 |
| 7 | 95410200 | 95412650 | 66815685 | 66818002 | d7Mseg2046 | 8200 |
| 7 | 95444050 | 95445800 | 66856637 | 66862349 | d7Mseg2047 | 8201 |
| 7 | 95462400 | 95464100 | 66878061 | 66885225 | d7Mseg2048 | 8202 |
| 7 | 95727100 | 95728350 | 67222834 | 67226420 | d7Mseg2052 | 8203 |
| 7 | 95823500 | 95825200 | 67317924 | 67319044 | d7Mseg2053 | 8204 |
| 7 | 95830100 | 95831850 | 67321049 | 67326678 | d7Mseg2054 | 8205 |
| 7 | 95835750 | 95837700 | 67331257 | 67333459 | d7Mseg2055 | 8206 |
| 7 | 95891350 | 95892850 | 67412773 | 67413621 | d7Mseg2056 | 8207 |
| 7 | 95895800 | 95897400 | 67415737 | 67417169 | d7Mseg2057 | 8208 |
| 7 | 95952500 | 95953900 | 67490880 | 67491934 | d7Mseg2058 | 8209 |
| 7 | 95970150 | 95972050 | 67499282 | 67500170 | d7Mseg2059 | 8210 |
| 7 | 96025050 | 96028150 | 67573493 | 67575208 | d7Mseg2062 | 8211 |
| 7 | 96064150 | 96065850 | 67634164 | 67635569 | d7Mseg2063 | 8212 |
| 7 | 96075650 | 96077150 | 67644046 | 67644579 | d7Mseg2064 | 8213 |
| 7 | 96085450 | 96087300 | 67652738 | 67654501 | d7Mseg2065 | 8214 |
| 7 | 96130800 | 96134100 | 67717473 | 67719790 | d7Mseg2066 | 8215 |
| 7 | 96194900 | 96196650 | 67861015 | 67865555 | d7Mseg2067 | 8216 |
| 7 | 96219650 | 96221300 | 67893442 | 67896086 | d7Mseg2068 | 8217 |
| 7 | 96236650 | 96240350 | 67911949 | 67915944 | d7Mseg2070 | 8218 |
| 7 | 96253900 | 96255650 | 67929335 | 67932242 | d7Mseg2071 | 8219 |
| 7 | 96262550 | 96264000 | 67938712 | 67940193 | d7Mseg2072 | 8220 |
| 7 | 96280250 | 96281850 | 67987006 | 67988140 | d7Mseg2073 | 8221 |
| 7 | 96283150 | 96284250 | 67979456 | 67979961 | d7Mseg2074 | 8222 |
| 7 | 96311150 | 96312200 | 68007550 | 68008359 | d7Mseg2075 | 8223 |
| 7 | 96329150 | 96335250 | 68046540 | 68052833 | d7Mseg2076 | 8224 |
| 7 | 96339300 | 96340850 | 68056981 | 68058679 | d7Mseg2077 | 8225 |
| 7 | 96354750 | 96356500 | 68073715 | 68075288 | d7Mseg2078 | 8226 |
| 7 | 96359900 | 96362900 | 68080278 | 68081906 | d7Mseg2079 | 8227 |
| 7 | 96372950 | 96376750 | 68091432 | 68094968 | d7Mseg2080 | 8228 |
| 7 | 96385500 | 96387750 | 68104397 | 68108103 | d7Mseg2081 | 8229 |
| 7 | 96401400 | 96406950 | 68123984 | 68126672 | d7Mseg2082 | 8230 |
| 7 | 96410200 | 96414200 | 68130121 | 68135290 | d7Mseg2083 | 8231 |
| 7 | 96419350 | 96421350 | 68140710 | 68142796 | d7Mseg2084 | 8232 |
| 7 | 96433000 | 96434500 | 68156949 | 68157926 | d7Mseg2085 | 8233 |
| 7 | 96466500 | 96468350 | 68197227 | 68199285 | d7Mseg2086 | 8234 |
| 7 | 96471250 | 96473500 | 68202131 | 68203415 | d7Mseg2087 | 8235 |
| 7 | 96474600 | 96475900 | 68203673 | 68204996 | d7Mseg2088 | 8236 |
| 7 | 96482000 | 96484550 | 68211052 | 68213625 | d7Mseg2089 | 8237 |
| 7 | 96488250 | 96490100 | 68217396 | 68219169 | d7Mseg2090 | 8238 |
| 7 | 96501050 | 96504450 | 68229421 | 68230638 | d7Mseg2091 | 8239 |
| 7 | 96508650 | 96510100 | 68232377 | 68234110 | d7Mseg2092 | 8240 |
| 7 | 96514400 | 96519550 | 68238280 | 68242769 | d7Mseg2093 | 8241 |
| 7 | 96528850 | 96530700 | 68250786 | 68252528 | d7Mseg2094 | 8242 |
| 7 | 96532750 | 96534600 | 68254548 | 68256558 | d7Mseg2095 | 8243 |
| 7 | 96536200 | 96537300 | 68258172 | 68258517 | d7Mseg2096 | 8244 |
| 7 | 96556600 | 96559700 | 68284195 | 68287196 | d7Mseg2097 | 8245 |
| 7 | 96563150 | 96564450 | 68289811 | 68290622 | d7Mseg2098 | 8246 |
| 7 | 96583200 | 96585150 | 68300263 | 68301956 | d7Mseg2100 | 8247 |
| 7 | 96605800 | 96607350 | 68322130 | 68323513 | d7Mseg2101 | 8248 |
| 7 | 96617350 | 96618650 | 68334725 | 68336057 | d7Mseg2102 | 8249 |
| 7 | 96624550 | 96625750 | 68341868 | 68343177 | d7Mseg2103 | 8250 |
| 7 | 96627450 | 96630050 | 68345579 | 68349402 | d7Mseg2104 | 8251 |
| 7 | 96638050 | 96640450 | 68356517 | 68359344 | d7Mseg2105 | 8252 |
| 7 | 96653450 | 96657150 | 68372372 | 68375711 | d7Mseg2106 | 8253 |
| 7 | 96661850 | 96664000 | 68381099 | 68383370 | d7Mseg2107 | 8254 |
| 7 | 96671250 | 96674900 | 68391241 | 68397518 | d7Mseg2108 | 8255 |
| 7 | 96712800 | 96715550 | 68435790 | 68438454 | d7Mseg2109 | 8256 |
| 7 | 96718950 | 96720500 | 68442668 | 68444375 | d7Mseg2110 | 8257 |
| 7 | 96721550 | 96723400 | 68445249 | 68445994 | d7Mseg2111 | 8258 |
| 7 | 96725100 | 96726500 | 68447770 | 68449225 | d7Mseg2112 | 8259 |
| 7 | 96727800 | 96729800 | 68450428 | 68452638 | d7Mseg2113 | 8260 |
| 7 | 96759100 | 96765450 | 68494416 | 68500658 | d7Mseg2114 | 8261 |
| 7 | 96768800 | 96769900 | 68504488 | 68505594 | d7Mseg2115 | 8262 |
| 7 | 96802500 | 96806500 | 68537903 | 68541912 | d7Mseg2116 | 8263 |
| 7 | 96807800 | 96810150 | 68543931 | 68546254 | d7Mseg2117 | 8264 |
| 7 | 96819550 | 96820800 | 68576838 | 68578203 | d7Mseg2118 | 8265 |
| 7 | 96852700 | 96854500 | 68606495 | 68608563 | d7Mseg2120 | 8266 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 96863100 | 96864900 | 68615809 | 68616322 | d7Mseg2121 | 8267 |
| 7 | 96879900 | 96881300 | 68620567 | 68621673 | d7Mseg2123 | 8268 |
| 7 | 96885400 | 96887250 | 68624565 | 68624977 | d7Mseg2124 | 8269 |
| 7 | 97005750 | 97007150 | 68715073 | 68716790 | d7Mseg2129 | 8270 |
| 7 | 97013850 | 97018550 | 68722532 | 68727304 | d7Mseg2130 | 8271 |
| 7 | 97041350 | 97042850 | 68749465 | 68751017 | d7Mseg2131 | 8272 |
| 7 | 97069150 | 97070600 | 68775724 | 68776933 | d7Mseg2132 | 8273 |
| 7 | 97125900 | 97127050 | 68808398 | 68808527 | d7Mseg2134 | 8274 |
| 7 | 97159850 | 97161350 | 68826620 | 68826999 | d7Mseg2135 | 8275 |
| 7 | 97168850 | 97172800 | 68833901 | 68837825 | d7Mseg2136 | 8276 |
| 7 | 97177000 | 97179000 | 68842254 | 68842905 | d7Mseg2137 | 8277 |
| 7 | 97202850 | 97204950 | 68853848 | 68855353 | d7Mseg2138 | 8278 |
| 7 | 97208150 | 97209700 | 68859907 | 68861111 | d7Mseg2139 | 8279 |
| 7 | 97276550 | 97278050 | 68948234 | 68948610 | d7Mseg2143 | 8280 |
| 7 | 97280450 | 97283100 | 68948351 | 68949764 | d7Mseg2144 | 8281 |
| 7 | 97353500 | 97355250 | 69001106 | 69002584 | d7Mseg2147 | 8282 |
| 7 | 97362850 | 97364600 | 69011200 | 69013384 | d7Mseg2148 | 8283 |
| 7 | 97373250 | 97374350 | 69015266 | 69015394 | d7Mseg2149 | 8284 |
| 7 | 97394350 | 97396150 | 69049359 | 69050825 | d7Mseg2150 | 8285 |
| 7 | 97419350 | 97421050 | 69096631 | 69097564 | d7Mseg2152 | 8286 |
| 7 | 97497450 | 97499150 | 69168894 | 69171682 | d7Mseg2153 | 8287 |
| 7 | 97631750 | 97633600 | 69288461 | 69290629 | d7Mseg2155 | 8288 |
| 7 | 97667400 | 97669350 | 69308113 | 69310041 | d7Mseg2158 | 8289 |
| 7 | 97696900 | 97698350 | 69364403 | 69366499 | d7Mseg2159 | 8290 |
| 7 | 97714300 | 97715900 | 69389319 | 69391386 | d7Mseg2160 | 8291 |
| 7 | 97754950 | 97756900 | 69443401 | 69443775 | d7Mseg2162 | 8292 |
| 7 | 97764150 | 97765750 | 69451053 | 69452103 | d7Mseg2163 | 8293 |
| 7 | 97800350 | 97801900 | 69487943 | 69489149 | d7Mseg2164 | 8294 |
| 7 | 97825850 | 97827400 | 69513101 | 69516256 | d7Mseg2165 | 8295 |
| 7 | 97861050 | 97862200 | 69550045 | 69550609 | d7Mseg2167 | 8296 |
| 7 | 97917850 | 97919000 | 69633087 | 69634269 | d7Mseg2168 | 8297 |
| 7 | 97927300 | 97928500 | 69644718 | 69645993 | d7Mseg2169 | 8298 |
| 7 | 97936300 | 97938350 | 69655173 | 69656658 | d7Mseg2170 | 8299 |
| 7 | 97962150 | 97963800 | 69663823 | 69665432 | d7Mseg2171 | 8300 |
| 7 | 97966450 | 97968300 | 69668211 | 69670157 | d7Mseg2172 | 8301 |
| 7 | 97970300 | 97972150 | 69672663 | 69674498 | d7Mseg2173 | 8302 |
| 7 | 97997000 | 98000650 | 69703880 | 69710197 | d7Mseg2174 | 8303 |
| 7 | 98082000 | 98083800 | 69830718 | 69831067 | d7Mseg2177 | 8304 |
| 7 | 98152700 | 98154150 | 69904476 | 69905520 | d7Mseg2180 | 8305 |
| 7 | 98228300 | 98230100 | 70073369 | 70073685 | d7Mseg2183 | 8306 |
| 7 | 98271000 | 98272400 | 70141064 | 70141627 | d7Mseg2187 | 8307 |
| 7 | 98404900 | 98406900 | 70276693 | 70278683 | d7Mseg2192 | 8308 |
| 7 | 98417000 | 98418400 | 70287366 | 70288797 | d7Mseg2193 | 8309 |
| 7 | 98449350 | 98457550 | 70315553 | 70324518 | d7Mseg2194 | 8310 |
| 7 | 98479950 | 98481450 | 70348213 | 70349616 | d7Mseg2195 | 8311 |
| 7 | 98495800 | 98497550 | 70365970 | 70367836 | d7Mseg2196 | 8312 |
| 7 | 98500850 | 98504650 | 70371755 | 70375526 | d7Mseg2197 | 8313 |
| 7 | 98515000 | 98516000 | 70389346 | 70390386 | d7Mseg2198 | 8314 |
| 7 | 98542750 | 98544500 | 70418460 | 70419705 | d7Mseg2199 | 8315 |
| 7 | 98577550 | 98581400 | 70441291 | 70445407 | d7Mseg2201 | 8316 |
| 7 | 98597100 | 98598750 | 70457979 | 70458617 | d7Mseg2202 | 8317 |
| 7 | 98601950 | 98603150 | 70461671 | 70462613 | d7Mseg2203 | 8318 |
| 7 | 98606800 | 98608250 | 70465443 | 70466971 | d7Mseg2204 | 8319 |
| 7 | 98610700 | 98612200 | 70469484 | 70470980 | d7Mseg2205 | 8320 |
| 7 | 98614550 | 98616450 | 70473386 | 70475393 | d7Mseg2206 | 8321 |
| 7 | 98632000 | 98633450 | 70510317 | 70510760 | d7Mseg2207 | 8322 |
| 7 | 98664300 | 98665850 | 70546542 | 70547433 | d7Mseg2208 | 8323 |
| 7 | 98834250 | 98836650 | 70751717 | 70754177 | d7Mseg2212 | 8324 |
| 7 | 98885050 | 98886650 | 150573759 | 150575541 | d7Mseg2213 | 8325 |
| 7 | 98890100 | 98894700 | 70798488 | 70799686 | d7Mseg2214 | 8326 |
| 7 | 98896200 | 98897900 | 70812316 | 70817013 | d7Mseg2215 | 8327 |
| 7 | 98921200 | 98922900 | 70832267 | 70833024 | d7Mseg2216 | 8328 |
| 7 | 98930900 | 98931950 | 70839985 | 70841756 | d7Mseg2217 | 8329 |
| 7 | 98965550 | 98967650 | 70870234 | 70872536 | d7Mseg2220 | 8330 |
| 7 | 98985950 | 98987350 | 70883129 | 70884479 | d7Mseg2222 | 8331 |
| 7 | 99040300 | 99051650 | 71125932 | 71136845 | d7Mseg2226 | 8332 |
| 7 | 99052850 | 99055500 | 71136951 | 71140016 | d7Mseg2227 | 8333 |
| 7 | 99057850 | 99061200 | 71143219 | 71145254 | d7Mseg2228 | 8334 |
| 7 | 99068150 | 99069450 | 71151999 | 71153362 | d7Mseg2229 | 8335 |
| 7 | 99074300 | 99075900 | 71159454 | 71160561 | d7Mseg2230 | 8336 |
| 7 | 99082500 | 99085400 | 71168029 | 71170297 | d7Mseg2231 | 8337 |
| 7 | 99095050 | 99096550 | 71175419 | 71176356 | d7Mseg2232 | 8338 |
| 7 | 99115600 | 99117300 | 71195136 | 71195784 | d7Mseg2234 | 8339 |
| 7 | 99124050 | 99125700 | 71210993 | 71212777 | d7Mseg2235 | 8340 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 99131150 | 99132900 | 71217094 | 71219660 | d7Mseg2236 | 8341 |
| 7 | 99138750 | 99140400 | 71225252 | 71225858 | d7Mseg2237 | 8342 |
| 7 | 99147350 | 99148700 | 71236183 | 71237644 | d7Mseg2238 | 8343 |
| 7 | 99213350 | 99215050 | 71300266 | 71302062 | d7Mseg2239 | 8344 |
| 7 | 99227050 | 99230800 | 71314616 | 71318626 | d7Mseg2240 | 8345 |
| 7 | 99233150 | 99234700 | 71321561 | 71323027 | d7Mseg2241 | 8346 |
| 7 | 99239300 | 99241650 | 71328369 | 71331157 | d7Mseg2242 | 8347 |
| 7 | 99264250 | 99267600 | 71349533 | 71352894 | d7Mseg2243 | 8348 |
| 7 | 99270150 | 99274150 | 71355176 | 71359620 | d7Mseg2244 | 8349 |
| 7 | 99286300 | 99288050 | 71372238 | 71373440 | d7Mseg2245 | 8350 |
| 7 | 99308450 | 99310450 | 71393655 | 71394970 | d7Mseg2247 | 8351 |
| 7 | 99352000 | 99354000 | 71458371 | 71460230 | d7Mseg2248 | 8352 |
| 7 | 99379100 | 99380400 | 71492402 | 71492552 | d7Mseg2249 | 8353 |
| 7 | 99383950 | 99385400 | 71496383 | 71498018 | d7Mseg2250 | 8354 |
| 7 | 99388600 | 99390750 | 71498578 | 71499771 | d7Mseg2251 | 8355 |
| 7 | 99435300 | 99437150 | 71515409 | 71516273 | d7Mseg2254 | 8356 |
| 7 | 99440450 | 99455050 | 71519113 | 71533421 | d7Mseg2255 | 8357 |
| 7 | 99475150 | 99476800 | 71546880 | 71547704 | d7Mseg2258 | 8358 |
| 7 | 99481200 | 99483150 | 71550607 | 71553137 | d7Mseg2259 | 8359 |
| 7 | 99501850 | 99503100 | 71570161 | 71571705 | d7Mseg2260 | 8360 |
| 7 | 99541150 | 99543000 | 71609615 | 71612031 | d7Mseg2261 | 8361 |
| 7 | 99596300 | 99598150 | 71679896 | 71682070 | d7Mseg2262 | 8362 |
| 7 | 99613250 | 99615000 | 71696761 | 71698836 | d7Mseg2263 | 8363 |
| 7 | 99622100 | 99623700 | 71707652 | 71708980 | d7Mseg2264 | 8364 |
| 7 | 99639950 | 99642550 | 71731355 | 71734116 | d7Mseg2265 | 8365 |
| 7 | 99698550 | 99700350 | 71790140 | 71792558 | d7Mseg2267 | 8366 |
| 7 | 99701750 | 99703400 | 71794120 | 71795437 | d7Mseg2268 | 8367 |
| 7 | 99727800 | 99729300 | 71822066 | 71822395 | d7Mseg2269 | 8368 |
| 7 | 99782050 | 99783150 | 71864638 | 71865814 | d7Mseg2270 | 8369 |
| 7 | 99838800 | 99841900 | 71933637 | 71937216 | d7Mseg2272 | 8370 |
| 7 | 99875550 | 99877400 | 71989055 | 71989710 | d7Mseg2275 | 8371 |
| 7 | 99879050 | 99881450 | 71999810 | 72001519 | d7Mseg2276 | 8372 |
| 7 | 99886500 | 99888050 | 72005806 | 72007577 | d7Mseg2277 | 8373 |
| 7 | 99974150 | 99977700 | 72089339 | 72094040 | d7Mseg2281 | 8374 |
| 7 | 100022700 | 100026500 | 72062507 | 72065178 | d7Mseg2285 | 8375 |
| 7 | 100075400 | 100076900 | 72092925 | 72094412 | d7Mseg2290 | 8376 |
| 7 | 100124700 | 100126550 | 72159049 | 72160676 | d7Mseg2291 | 8377 |
| 7 | 100213550 | 100217000 | 72293831 | 72295143 | d7Mseg2297 | 8378 |
| 7 | 100504850 | 100506850 | 72661883 | 72662491 | d7Mseg2309 | 8379 |
| 7 | 100515700 | 100520900 | 72666040 | 72670879 | d7Mseg2310 | 8380 |
| 7 | 100525950 | 100527850 | 72675705 | 72677950 | d7Mseg2311 | 8381 |
| 7 | 100549400 | 100551600 | 72780739 | 72782789 | d7Mseg2313 | 8382 |
| 7 | 100583300 | 100585600 | 72899465 | 72901608 | d7Mseg2314 | 8383 |
| 7 | 100611750 | 100613350 | 72957893 | 72958979 | d7Mseg2316 | 8384 |
| 7 | 100640950 | 100647050 | 73014340 | 73031761 | d7Mseg2320 | 8385 |
| 7 | 100816450 | 100818000 | 73510591 | 73512552 | d7Mseg2325 | 8386 |
| 7 | 100885800 | 100893650 | 73752843 | 73758155 | d7Mseg2326 | 8387 |
| 7 | 100907700 | 100909200 | 73738762 | 73740766 | d7Mseg2327 | 8388 |
| 7 | 100919650 | 100925050 | 73728433 | 73733622 | d7Mseg2328 | 8389 |
| 7 | 100928450 | 100930450 | 73723754 | 73725689 | d7Mseg2329 | 8390 |
| 7 | 100968200 | 100969200 | 73686886 | 73687446 | d7Mseg2331 | 8391 |
| 7 | 100971950 | 100972950 | 73685082 | 73685751 | d7Mseg2332 | 8392 |
| 7 | 100987700 | 100992000 | 73670146 | 73675778 | d7Mseg2333 | 8393 |
| 7 | 100994700 | 100996250 | 73665735 | 73667219 | d7Mseg2334 | 8394 |
| 7 | 101005850 | 101007250 | 73653443 | 73654615 | d7Mseg2335 | 8395 |
| 7 | 101014400 | 101019350 | 73639879 | 73644269 | d7Mseg2336 | 8396 |
| 7 | 101073300 | 101075150 | 73755977 | 73759178 | d7Mseg2341 | 8397 |
| 7 | 101154450 | 101156000 | 73807484 | 73809475 | d7Mseg2348 | 8398 |
| 7 | 101174700 | 101177750 | 73832504 | 73835755 | d7Mseg2349 | 8399 |
| 7 | 101182400 | 101184050 | 73842700 | 73843533 | d7Mseg2350 | 8400 |
| 7 | 101194400 | 101195550 | 73852053 | 73852303 | d7Mseg2351 | 8401 |
| 7 | 101205000 | 101206450 | 73885143 | 73885336 | d7Mseg2353 | 8402 |
| 7 | 101248550 | 101249900 | 73930218 | 73930486 | d7Mseg2358 | 8403 |
| 7 | 101276100 | 101277650 | 73956732 | 73958294 | d7Mseg2359 | 8404 |
| 7 | 101337850 | 101339050 | 74030026 | 74030809 | d7Mseg2361 | 8405 |
| 7 | 101392900 | 101398450 | 74141967 | 74147202 | d7Mseg2362 | 8406 |
| 7 | 101431300 | 101432800 | 74171676 | 74178727 | d7Mseg2363 | 8407 |
| 7 | 101483900 | 101485600 | 74277919 | 74279589 | d7Mseg2366 | 8408 |
| 7 | 101554450 | 101558800 | 74342555 | 74343332 | d7Mseg2369 | 8409 |
| 7 | 101593950 | 101595750 | 74371003 | 74371237 | d7Mseg2371 | 8410 |
| 7 | 101607300 | 101608650 | 74374996 | 74375546 | d7Mseg2372 | 8411 |
| 7 | 101612450 | 101614850 | 74378128 | 74378754 | d7Mseg2373 | 8412 |
| 7 | 101619150 | 101621000 | 74381236 | 74381481 | d7Mseg2374 | 8413 |
| 7 | 101672450 | 101674900 | 74448094 | 74462186 | d7Mseg2376 | 8414 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 101678000 | 101679800 | 74493782 | 74495431 | d7Mseg2377 | 8415 |
| 7 | 101682450 | 101685050 | 74497607 | 74506385 | d7Mseg2378 | 8416 |
| 7 | 101728100 | 101729700 | 74579675 | 74580110 | d7Mseg2380 | 8417 |
| 7 | 101758400 | 101759850 | 74641629 | 74642387 | d7Mseg2381 | 8418 |
| 7 | 101770400 | 101772100 | 74652160 | 74665048 | d7Mseg2382 | 8419 |
| 7 | 101805700 | 101809800 | 74701687 | 74702847 | d7Mseg2384 | 8420 |
| 7 | 101828350 | 101830050 | 74726161 | 74726408 | d7Mseg2385 | 8421 |
| 7 | 101858200 | 101859850 | 74738139 | 74738745 | d7Mseg2387 | 8422 |
| 7 | 101880900 | 101882600 | 74789202 | 74790481 | d7Mseg2388 | 8423 |
| 7 | 101887550 | 101889350 | 74816195 | 74825768 | d7Mseg2389 | 8424 |
| 7 | 101963650 | 101964850 | 74875823 | 74875982 | d7Mseg2395 | 8425 |
| 7 | 102007850 | 102009400 | 74956843 | 74957267 | d7Mseg2397 | 8426 |
| 7 | 102047050 | 102052750 | 74999999 | 75005276 | d7Mseg2398 | 8427 |
| 7 | 102148350 | 102149850 | 75204566 | 75206237 | d7Mseg2403 | 8428 |
| 7 | 102378650 | 102382900 | 75912882 | 75929363 | d7Mseg2415 | 8429 |
| 7 | 102402700 | 102403750 | 75938956 | 75954332 | d7Mseg2416 | 8430 |
| 7 | 102535150 | 102537200 | 76083865 | 76085210 | d7Mseg2418 | 8431 |
| 7 | 102565500 | 102566550 | 76197089 | 76198122 | d7Mseg2419 | 8432 |
| 7 | 102569400 | 102572600 | 76207160 | 76223209 | d7Mseg2420 | 8433 |
| 7 | 102586150 | 102587200 | 76233910 | 76235036 | d7Mseg2421 | 8434 |
| 7 | 102590900 | 102592150 | 76239172 | 76239969 | d7Mseg2422 | 8435 |
| 7 | 102623800 | 102625000 | 76320166 | 76320459 | d7Mseg2423 | 8436 |
| 7 | 102650750 | 102652450 | 76340173 | 76340697 | d7Mseg2424 | 8437 |
| 7 | 102740800 | 102742100 | 76395020 | 76395967 | d7Mseg2427 | 8438 |
| 7 | 102760000 | 102761900 | 76437917 | 76439779 | d7Mseg2429 | 8439 |
| 7 | 102869600 | 102871550 | 76618006 | 76619942 | d7Mseg2431 | 8440 |
| 7 | 102873250 | 102874850 | 76620537 | 76621892 | d7Mseg2432 | 8441 |
| 7 | 102956950 | 102964600 | 76703692 | 76707202 | d7Mseg2437 | 8442 |
| 7 | 102968450 | 102970900 | 76710891 | 76713740 | d7Mseg2438 | 8443 |
| 7 | 102987500 | 102989000 | 76748802 | 76757219 | d7Mseg2440 | 8444 |
| 7 | 102995600 | 102997350 | 76763912 | 76776911 | d7Mseg2441 | 8445 |
| 7 | 103002000 | 103003600 | 76782112 | 76789587 | d7Mseg2442 | 8446 |
| 7 | 103106750 | 103108550 | 76995713 | 77031704 | d7Mseg2443 | 8447 |
| 7 | 103164400 | 103166100 | 77082606 | 77083367 | d7Mseg2445 | 8448 |
| 7 | 103217400 | 103219450 | 77161601 | 77163026 | d7Mseg2446 | 8449 |
| 7 | 103277800 | 103279600 | 77242372 | 77243656 | d7Mseg2448 | 8450 |
| 7 | 103282650 | 103283900 | 77253611 | 77254234 | d7Mseg2449 | 8451 |
| 7 | 103403950 | 103405250 | 77387224 | 77389035 | d7Mseg2452 | 8452 |
| 7 | 103413900 | 103416300 | 77393634 | 77396311 | d7Mseg2453 | 8453 |
| 7 | 103540550 | 103542000 | 77452315 | 77452656 | d7Mseg2455 | 8454 |
| 7 | 103632900 | 103634000 | 77426690 | 77427277 | d7Mseg2461 | 8455 |
| 7 | 103644300 | 103645400 | 77456105 | 77456862 | d7Mseg2462 | 8456 |
| 7 | 103830700 | 103832900 | 77687818 | 77688543 | d7Mseg2470 | 8457 |
| 7 | 103992000 | 103993800 | 77811799 | 77829155 | d7Mseg2477 | 8458 |
| 7 | 103996250 | 103997400 | 77831167 | 77832199 | d7Mseg2478 | 8459 |
| 7 | 104004550 | 104006250 | 77854767 | 77860727 | d7Mseg2479 | 8460 |
| 7 | 104032750 | 104034450 | 77911905 | 77913589 | d7Mseg2481 | 8461 |
| 7 | 104035900 | 104037300 | 77914841 | 77916404 | d7Mseg2482 | 8462 |
| 7 | 104063850 | 104065350 | 77943574 | 77944393 | d7Mseg2484 | 8463 |
| 7 | 104092400 | 104093650 | 77963021 | 77964221 | d7Mseg2485 | 8464 |
| 7 | 104133900 | 104135500 | 78024094 | 78025716 | d7Mseg2486 | 8465 |
| 7 | 104151500 | 104153250 | 78063296 | 78064371 | d7Mseg2487 | 8466 |
| 7 | 104173900 | 104175100 | 78082496 | 78082929 | d7Mseg2488 | 8467 |
| 7 | 104286000 | 104287750 | 78202292 | 78206529 | d7Mseg2491 | 8468 |
| 7 | 104359700 | 104361000 | 78334790 | 78335538 | d7Mseg2495 | 8469 |
| 7 | 104416450 | 104418150 | 78366326 | 78368112 | d7Mseg2496 | 8470 |
| 7 | 104451600 | 104453900 | 78400489 | 78402691 | d7Mseg2498 | 8471 |
| 7 | 104492150 | 104493450 | 78430844 | 78431978 | d7Mseg2499 | 8472 |
| 7 | 104589800 | 104591100 | 78614809 | 78615152 | d7Mseg2501 | 8473 |
| 7 | 104605300 | 104607100 | 78628893 | 78631926 | d7Mseg2502 | 8474 |
| 7 | 104871000 | 104873650 | 79276534 | 79279315 | d7Mseg2507 | 8475 |
| 7 | 105005250 | 105006800 | 79586593 | 79587093 | d7Mseg2509 | 8476 |
| 7 | 105050800 | 105052150 | 79674840 | 79675962 | d7Mseg2510 | 8477 |
| 7 | 105075950 | 105077000 | 79709790 | 79710462 | d7Mseg2511 | 8478 |
| 7 | 106019450 | 106021400 | 80047116 | 80050237 | d7Mseg2522 | 8479 |
| 7 | 106089900 | 106091600 | 80208570 | 80209393 | d7Mseg2524 | 8480 |
| 7 | 106200850 | 106202150 | 80370403 | 80371112 | d7Mseg2528 | 8481 |
| 7 | 106208200 | 106209950 | 80376643 | 80378532 | d7Mseg2529 | 8482 |
| 7 | 106224900 | 106226300 | 80385189 | 80386503 | d7Mseg2531 | 8483 |
| 7 | 106232200 | 106233450 | 80419031 | 80419449 | d7Mseg2532 | 8484 |
| 7 | 106292100 | 106293250 | 80458875 | 80460054 | d7Mseg2533 | 8485 |
| 7 | 106299600 | 106301100 | 80468793 | 80469865 | d7Mseg2534 | 8486 |
| 7 | 106328050 | 106329950 | 80506047 | 80506741 | d7Mseg2535 | 8487 |
| 7 | 106380250 | 106382450 | 80603611 | 80605371 | d7Mseg2538 | 8488 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 106749050 | 106750450 | 80914954 | 80915477 | d7Mseg2543 | 8489 |
| 7 | 106823400 | 106825250 | 81022391 | 81022706 | d7Mseg2544 | 8490 |
| 7 | 106910800 | 106912600 | 81167029 | 81168155 | d7Mseg2545 | 8491 |
| 7 | 107161400 | 107163050 | 81685036 | 81685431 | d7Mseg2548 | 8492 |
| 7 | 107168000 | 107169000 | 81699524 | 81699963 | d7Mseg2549 | 8493 |
| 7 | 107549250 | 107550300 | 82021434 | 82024108 | d7Mseg2552 | 8494 |
| 7 | 107848000 | 107849900 | 82529123 | 82530770 | d7Mseg2555 | 8495 |
| 7 | 107858700 | 107861400 | 82558395 | 82559319 | d7Mseg2556 | 8496 |
| 7 | 107914500 | 107915550 | 82605146 | 82605290 | d7Mseg2557 | 8497 |
| 7 | 107962200 | 107963600 | 82699693 | 82700272 | d7Mseg2559 | 8498 |
| 7 | 108008300 | 108014500 | 82761881 | 82768249 | d7Mseg2563 | 8499 |
| 7 | 108018250 | 108019500 | 82771728 | 82772652 | d7Mseg2564 | 8500 |
| 7 | 108504700 | 108505750 | 83319992 | 83320825 | d7Mseg2569 | 8501 |
| 7 | 108605150 | 108606950 | 83472107 | 83473784 | d7Mseg2570 | 8502 |
| 7 | 108623050 | 108624950 | 83484874 | 83486458 | d7Mseg2571 | 8503 |
| 7 | 108627050 | 108628250 | 83488665 | 83489636 | d7Mseg2572 | 8504 |
| 7 | 108648150 | 108649850 | 83505320 | 83508447 | d7Mseg2573 | 8505 |
| 7 | 108653050 | 108654400 | 83511697 | 83512866 | d7Mseg2574 | 8506 |
| 7 | 108655700 | 108656900 | 83514401 | 83515341 | d7Mseg2575 | 8507 |
| 7 | 108723450 | 108724650 | 83611024 | 83612099 | d7Mseg2576 | 8508 |
| 7 | 108738050 | 108739900 | 83617262 | 83618183 | d7Mseg2577 | 8509 |
| 7 | 108766950 | 108768750 | 83699598 | 83700113 | d7Mseg2579 | 8510 |
| 7 | 108812150 | 108813450 | 83764530 | 83765579 | d7Mseg2580 | 8511 |
| 7 | 108815200 | 108817000 | 83765964 | 83768458 | d7Mseg2581 | 8512 |
| 7 | 109207250 | 109208650 | 83972876 | 83974143 | d7Mseg2590 | 8513 |
| 7 | 109359450 | 109361000 | 84235670 | 84238403 | d7Mseg2593 | 8514 |
| 7 | 109432450 | 109434250 | 84287702 | 84288484 | d7Mseg2598 | 8515 |
| 7 | 109459500 | 109461000 | 84306165 | 84307508 | d7Mseg2600 | 8516 |
| 7 | 109467550 | 109469200 | 84321914 | 84322609 | d7Mseg2601 | 8517 |
| 7 | 109470750 | 109472300 | 84324158 | 84325079 | d7Mseg2602 | 8518 |
| 7 | 109609700 | 109611500 | 84399238 | 84400141 | d7Mseg2603 | 8519 |
| 7 | 109622850 | 109624750 | 84400283 | 84400578 | d7Mseg2604 | 8520 |
| 7 | 109707900 | 109717600 | 84495477 | 84502272 | d7Mseg2608 | 8521 |
| 7 | 109723050 | 109725450 | 84507381 | 84508339 | d7Mseg2609 | 8522 |
| 7 | 109751800 | 109753050 | 84531624 | 84533356 | d7Mseg2610 | 8523 |
| 7 | 109808700 | 109810300 | 84631152 | 84632882 | d7Mseg2612 | 8524 |
| 7 | 109868000 | 109869800 | 84686651 | 84687968 | d7Mseg2614 | 8525 |
| 7 | 110039800 | 110040950 | 84825450 | 84826699 | d7Mseg2616 | 8526 |
| 7 | 110063550 | 110065600 | 84867079 | 84885987 | d7Mseg2618 | 8527 |
| 7 | 110097450 | 110098850 | 84959582 | 84960682 | d7Mseg2619 | 8528 |
| 7 | 110206600 | 110208550 | 85181784 | 85182679 | d7Mseg2620 | 8529 |
| 7 | 110410900 | 110414150 | 85402510 | 85405628 | d7Mseg2622 | 8530 |
| 7 | 110421350 | 110423100 | 85412968 | 85417097 | d7Mseg2623 | 8531 |
| 7 | 110434200 | 110438350 | 85441340 | 85448782 | d7Mseg2624 | 8532 |
| 7 | 110450000 | 110451600 | 85464759 | 85465555 | d7Mseg2625 | 8533 |
| 7 | 110538150 | 110539200 | 85586561 | 85587237 | d7Mseg2626 | 8534 |
| 7 | 110553950 | 110555000 | 85616690 | 85618075 | d7Mseg2627 | 8535 |
| 7 | 110575100 | 110576850 | 85642414 | 85642689 | d7Mseg2628 | 8536 |
| 7 | 110616900 | 110618350 | 85716922 | 85718257 | d7Mseg2630 | 8537 |
| 7 | 110753150 | 110754500 | 85905658 | 85909321 | d7Mseg2633 | 8538 |
| 7 | 110905600 | 110907200 | 86030155 | 86033030 | d7Mseg2634 | 8539 |
| 7 | 110923450 | 110925100 | 86062880 | 86064510 | d7Mseg2635 | 8540 |
| 7 | 110992500 | 110994200 | 86141119 | 86141430 | d7Mseg2637 | 8541 |
| 7 | 111432050 | 111433500 | 86575877 | 86576380 | d7Mseg2641 | 8542 |
| 7 | 111670700 | 111672500 | 86918130 | 86920065 | d7Mseg2642 | 8543 |
| 7 | 111761550 | 111763500 | 86990867 | 86991666 | d7Mseg2645 | 8544 |
| 7 | 112320000 | 112321600 | 87224641 | 87225114 | d7Mseg2650 | 8545 |
| 7 | 114815700 | 114817050 | 88879007 | 88880234 | d7Mseg2662 | 8546 |
| 7 | 117047500 | 117048950 | 90696104 | 90697538 | d7Mseg2673 | 8547 |
| 7 | 117401350 | 117410000 | 91031793 | 91040211 | d7Mseg2675 | 8548 |
| 7 | 117418450 | 117419650 | 91051219 | 91052327 | d7Mseg2676 | 8549 |
| 7 | 117485300 | 117486350 | 91097262 | 91097369 | d7Mseg2677 | 8550 |
| 7 | 117621350 | 117622500 | 91332196 | 91332690 | d7Mseg2678 | 8551 |
| 7 | 117727850 | 117729300 | 91480685 | 91484712 | d7Mseg2679 | 8552 |
| 7 | 117774500 | 117775650 | 91568504 | 91571115 | d7Mseg2680 | 8553 |
| 7 | 117860550 | 117862050 | 91658180 | 91659113 | d7Mseg2681 | 8554 |
| 7 | 117913350 | 117915150 | 91711855 | 91712846 | d7Mseg2682 | 8555 |
| 7 | 118586200 | 118587600 | 92212152 | 92213302 | d7Mseg2686 | 8556 |
| 7 | 119162950 | 119164650 | 92717855 | 92718276 | d7Mseg2690 | 8557 |
| 7 | 119266400 | 119267850 | 92782682 | 92784115 | d7Mseg2691 | 8558 |
| 7 | 119736800 | 119738500 | 93068622 | 93069012 | d7Mseg2693 | 8559 |
| 7 | 119907250 | 119909200 | 93247833 | 93248134 | d7Mseg2694 | 8560 |
| 7 | 120006850 | 120008600 | 93345203 | 93345625 | d7Mseg2695 | 8561 |
| 7 | 125055400 | 125056400 | 94987525 | 94988280 | d7Mseg2704 | 8562 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 125103800 | 125105100 | 95012096 | 95015191 | d7Mseg2705 | 8563 |
| 7 | 125289650 | 125290750 | 95164485 | 95165039 | d7Mseg2708 | 8564 |
| 7 | 125700950 | 125702650 | 95507790 | 95518748 | d7Mseg2711 | 8565 |
| 7 | 126029800 | 126031850 | 95730504 | 95732656 | d7Mseg2713 | 8566 |
| 7 | 126283350 | 126285600 | 95938881 | 95941157 | d7Mseg2714 | 8567 |
| 7 | 126415300 | 126416500 | 96099251 | 96100453 | d7Mseg2715 | 8568 |
| 7 | 126472700 | 126474250 | 96166158 | 96167631 | d7Mseg2716 | 8569 |
| 7 | 126480700 | 126482400 | 96176517 | 96177168 | d7Mseg2717 | 8570 |
| 7 | 126642750 | 126645500 | 96395621 | 96400962 | d7Mseg2718 | 8571 |
| 7 | 126739100 | 126740850 | 96520889 | 96522300 | d7Mseg2719 | 8572 |
| 7 | 126763100 | 126765000 | 96559133 | 96562065 | d7Mseg2720 | 8573 |
| 7 | 126822150 | 126823800 | 96637215 | 96638184 | d7Mseg2721 | 8574 |
| 7 | 126836250 | 126837850 | 96653618 | 96654964 | d7Mseg2722 | 8575 |
| 7 | 126858800 | 126860200 | 96679453 | 96680245 | d7Mseg2723 | 8576 |
| 7 | 126891500 | 126895700 | 96723510 | 96726970 | d7Mseg2724 | 8577 |
| 7 | 126948400 | 126950150 | 96802366 | 96803109 | d7Mseg2725 | 8578 |
| 7 | 126989050 | 126990400 | 96848062 | 96848525 | d7Mseg2726 | 8579 |
| 7 | 127040350 | 127041450 | 96894689 | 96895992 | d7Mseg2727 | 8580 |
| 7 | 127064700 | 127065800 | 96913549 | 96914466 | d7Mseg2729 | 8581 |
| 7 | 127100200 | 127102250 | 96933172 | 96934365 | d7Mseg2730 | 8582 |
| 7 | 127140700 | 127141900 | 96962872 | 96968041 | d7Mseg2731 | 8583 |
| 7 | 127204150 | 127206000 | 97011925 | 97012530 | d7Mseg2732 | 8584 |
| 7 | 127220400 | 127221450 | 97028126 | 97028265 | d7Mseg2733 | 8585 |
| 7 | 127296550 | 127298350 | 97061168 | 97062423 | d7Mseg2734 | 8586 |
| 7 | 127430050 | 127431800 | 97139667 | 97139969 | d7Mseg2735 | 8587 |
| 7 | 127614750 | 127616250 | 97291427 | 97292979 | d7Mseg2739 | 8588 |
| 7 | 127621850 | 127623800 | 97297043 | 97316629 | d7Mseg2740 | 8589 |
| 7 | 127643050 | 127645050 | 97329130 | 97331128 | d7Mseg2741 | 8590 |
| 7 | 127968550 | 127970100 | 97612010 | 97613239 | d7Mseg2745 | 8591 |
| 7 | 128168300 | 128169750 | 97770470 | 97770746 | d7Mseg2747 | 8592 |
| 7 | 128180100 | 128181600 | 97776995 | 97785666 | d7Mseg2748 | 8593 |
| 7 | 128281100 | 128282150 | 97892974 | 97894015 | d7Mseg2749 | 8594 |
| 7 | 128329300 | 128330850 | 97937798 | 97938085 | d7Mseg2750 | 8595 |
| 7 | 128455300 | 128458800 | 98053260 | 98056499 | d7Mseg2752 | 8596 |
| 7 | 128508750 | 128510050 | 98133946 | 98135139 | d7Mseg2753 | 8597 |
| 7 | 128701050 | 128703300 | 98262223 | 98264357 | d7Mseg2755 | 8598 |
| 7 | 128981250 | 128982900 | 98550719 | 98552396 | d7Mseg2758 | 8599 |
| 7 | 128989150 | 128990850 | 98558699 | 98560432 | d7Mseg2759 | 8600 |
| 7 | 129008350 | 129009500 | 98585324 | 98587034 | d7Mseg2760 | 8601 |
| 7 | 129277750 | 129278800 | 98853809 | 98854176 | d7Mseg2766 | 8602 |
| 7 | 129316000 | 129317400 | 98860259 | 98861376 | d7Mseg2768 | 8603 |
| 7 | 129397800 | 129399700 | 98918161 | 98919241 | d7Mseg2771 | 8604 |
| 7 | 129452100 | 129455450 | 98955784 | 98956458 | d7Mseg2772 | 8605 |
| 7 | 129497450 | 129498500 | 98989295 | 98990065 | d7Mseg2773 | 8606 |
| 7 | 129520900 | 129522850 | 99007744 | 99008695 | d7Mseg2774 | 8607 |
| 7 | 129720350 | 129721950 | 99211855 | 99212475 | d7Mseg2779 | 8608 |
| 7 | 129826550 | 129828250 | 99284420 | 99285145 | d7Mseg2782 | 8609 |
| 7 | 130000950 | 130002950 | 99432713 | 99438445 | d7Mseg2784 | 8610 |
| 7 | 130062950 | 130064800 | 99480168 | 99481316 | d7Mseg2785 | 8611 |
| 7 | 130157800 | 130159000 | 99594826 | 99596018 | d7Mseg2789 | 8612 |
| 7 | 130168100 | 130171500 | 99606301 | 99609897 | d7Mseg2790 | 8613 |
| 7 | 130189450 | 130191150 | 99631450 | 99633088 | d7Mseg2791 | 8614 |
| 7 | 130209200 | 130211750 | 99650863 | 99653061 | d7Mseg2792 | 8615 |
| 7 | 130215450 | 130229700 | 99657327 | 99671435 | d7Mseg2793 | 8616 |
| 7 | 130307600 | 130308750 | 99749651 | 99750622 | d7Mseg2795 | 8617 |
| 7 | 130359600 | 130361100 | 99779295 | 99780077 | d7Mseg2798 | 8618 |
| 7 | 130396500 | 130400750 | 99851667 | 99855846 | d7Mseg2799 | 8619 |
| 7 | 130402050 | 130403300 | 99859117 | 99860668 | d7Mseg2800 | 8620 |
| 7 | 130404500 | 130406400 | 99861906 | 99863702 | d7Mseg2801 | 8621 |
| 7 | 130419250 | 130423150 | 99877591 | 99882417 | d7Mseg2802 | 8622 |
| 7 | 130453500 | 130454700 | 99909306 | 99910520 | d7Mseg2803 | 8623 |
| 7 | 130496700 | 130498350 | 99956960 | 99962291 | d7Mseg2804 | 8624 |
| 7 | 130509250 | 130511200 | 99980485 | 99981774 | d7Mseg2805 | 8625 |
| 7 | 130514450 | 130517050 | 99985303 | 99987553 | d7Mseg2806 | 8626 |
| 7 | 130553650 | 130555500 | 100023838 | 100024048 | d7Mseg2808 | 8627 |
| 7 | 130628400 | 130630050 | 100104722 | 100105611 | d7Mseg2810 | 8628 |
| 7 | 130650450 | 130652250 | 100132725 | 100135550 | d7Mseg2811 | 8629 |
| 7 | 130655100 | 130656700 | 100137803 | 100138267 | d7Mseg2812 | 8630 |
| 7 | 130752300 | 130754400 | 100254979 | 100256079 | d7Mseg2813 | 8631 |
| 7 | 130797450 | 130799450 | 100292087 | 100293710 | d7Mseg2815 | 8632 |
| 7 | 130807800 | 130809550 | 100303728 | 100304878 | d7Mseg2816 | 8633 |
| 7 | 130828950 | 130830850 | 100333054 | 100334779 | d7Mseg2817 | 8634 |
| 7 | 130851800 | 130853450 | 100364369 | 100365674 | d7Mseg2818 | 8635 |
| 7 | 130937750 | 130939600 | 100473217 | 100475321 | d7Mseg2822 | 8636 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 130948900 | 130951450 | 100480891 | 100483100 | d7Mseg2823 | 8637 |
| 7 | 130963450 | 130964950 | 100491267 | 100492543 | d7Mseg2824 | 8638 |
| 7 | 130989600 | 130991400 | 100517951 | 100520414 | d7Mseg2825 | 8639 |
| 7 | 131008100 | 131010000 | 100543536 | 100546418 | d7Mseg2826 | 8640 |
| 7 | 131075800 | 131078700 | 100603304 | 100605404 | d7Mseg2829 | 8641 |
| 7 | 131096700 | 131098100 | 100620371 | 100621777 | d7Mseg2830 | 8642 |
| 7 | 131119150 | 131121200 | 100644951 | 100646916 | d7Mseg2832 | 8643 |
| 7 | 131174700 | 131175950 | 100714413 | 100714797 | d7Mseg2835 | 8644 |
| 7 | 131220750 | 131223850 | 100740062 | 100743543 | d7Mseg2838 | 8645 |
| 7 | 131227050 | 131229250 | 100747241 | 100749019 | d7Mseg2839 | 8646 |
| 7 | 131231900 | 131235450 | 100751314 | 100752719 | d7Mseg2840 | 8647 |
| 7 | 131251300 | 131252300 | 100804104 | 100805328 | d7Mseg2841 | 8648 |
| 7 | 131254100 | 131255850 | 100807361 | 100809065 | d7Mseg2842 | 8649 |
| 7 | 131271900 | 131273550 | 100863960 | 100864836 | d7Mseg2843 | 8650 |
| 7 | 131283700 | 131286250 | 100870694 | 100873309 | d7Mseg2844 | 8651 |
| 7 | 131290750 | 131295500 | 100877742 | 100882345 | d7Mseg2845 | 8652 |
| 7 | 131296600 | 131298150 | 100883382 | 100885038 | d7Mseg2846 | 8653 |
| 7 | 131305800 | 131307800 | 100887333 | 100888281 | d7Mseg2847 | 8654 |
| 7 | 131321900 | 131323550 | 100892763 | 100896673 | d7Mseg2848 | 8655 |
| 7 | 131334250 | 131336150 | 100908270 | 100908977 | d7Mseg2850 | 8656 |
| 7 | 131342300 | 131343750 | 100913589 | 100915052 | d7Mseg2851 | 8657 |
| 7 | 131349000 | 131350800 | 100918041 | 100921182 | d7Mseg2852 | 8658 |
| 7 | 131391350 | 131393250 | 100963909 | 100972160 | d7Mseg2853 | 8659 |
| 7 | 131396300 | 131398250 | 100982323 | 100982929 | d7Mseg2854 | 8660 |
| 7 | 131438050 | 131439950 | 101017881 | 101018668 | d7Mseg2855 | 8661 |
| 7 | 131472250 | 131474050 | 101083233 | 101084118 | d7Mseg2857 | 8662 |
| 7 | 131475600 | 131477400 | 101084434 | 101085443 | d7Mseg2858 | 8663 |
| 7 | 131517850 | 131519600 | 101143167 | 101143454 | d7Mseg2861 | 8664 |
| 7 | 131533550 | 131535550 | 101176309 | 101177363 | d7Mseg2862 | 8665 |
| 7 | 131539450 | 131543100 | 101182998 | 101186406 | d7Mseg2863 | 8666 |
| 7 | 131545550 | 131547100 | 101187995 | 101188498 | d7Mseg2864 | 8667 |
| 7 | 131552350 | 131553600 | 101197511 | 101198948 | d7Mseg2865 | 8668 |
| 7 | 131742950 | 131744450 | 101395223 | 101396706 | d7Mseg2874 | 8669 |
| 7 | 131863400 | 131867450 | 101694196 | 101694977 | d7Mseg2883 | 8670 |
| 7 | 132117050 | 132121150 | 101617778 | 101621948 | d7Mseg2886 | 8671 |
| 7 | 132252250 | 132254050 | 101768859 | 101769828 | d7Mseg2892 | 8672 |
| 7 | 132276800 | 132278550 | 101853975 | 101855890 | d7Mseg2894 | 8673 |
| 7 | 132280000 | 132281350 | 101857354 | 101858560 | d7Mseg2895 | 8674 |
| 7 | 132330100 | 132331650 | 101905772 | 101907266 | d7Mseg2897 | 8675 |
| 7 | 132376400 | 132377850 | 101969762 | 101971242 | d7Mseg2899 | 8676 |
| 7 | 132508100 | 132510050 | 102088070 | 102091071 | d7Mseg2903 | 8677 |
| 7 | 132523850 | 132525500 | 102440289 | 102440722 | d7Mseg2904 | 8678 |
| 7 | 132584400 | 132586450 | 102306692 | 102307679 | d7Mseg2906 | 8679 |
| 7 | 132595900 | 132597250 | 102312482 | 102314440 | d7Mseg2907 | 8680 |
| 7 | 132603300 | 132605250 | 102319645 | 102320416 | d7Mseg2908 | 8681 |
| 7 | 132612150 | 132613950 | 102336374 | 102338376 | d7Mseg2909 | 8682 |
| 7 | 132615800 | 132617600 | 102340169 | 102340550 | d7Mseg2910 | 8683 |
| 7 | 132628650 | 132630300 | 102373401 | 102376459 | d7Mseg2911 | 8684 |
| 7 | 132672500 | 132674100 | 102469705 | 102470657 | d7Mseg2913 | 8685 |
| 7 | 132688550 | 132691800 | 102488905 | 102490451 | d7Mseg2915 | 8686 |
| 7 | 132751950 | 132753500 | 102570679 | 102572390 | d7Mseg2916 | 8687 |
| 7 | 132803350 | 132805150 | 102629513 | 102631774 | d7Mseg2918 | 8688 |
| 7 | 133163900 | 133165700 | 102796940 | 102799433 | d7Mseg2931 | 8689 |
| 7 | 133178750 | 133179800 | 102819701 | 102819849 | d7Mseg2933 | 8690 |
| 7 | 133200550 | 133203200 | 102862543 | 102865211 | d7Mseg2935 | 8691 |
| 7 | 133242550 | 133244400 | 102883877 | 102885870 | d7Mseg2936 | 8692 |
| 7 | 133277450 | 133279250 | 102943017 | 102943909 | d7Mseg2937 | 8693 |
| 7 | 133295750 | 133298500 | 102966529 | 102969721 | d7Mseg2938 | 8694 |
| 7 | 133318550 | 133320650 | 102987526 | 102989858 | d7Mseg2939 | 8695 |
| 7 | 133324650 | 133326000 | 102993077 | 102994538 | d7Mseg2940 | 8696 |
| 7 | 133339350 | 133340450 | 103010115 | 103011864 | d7Mseg2941 | 8697 |
| 7 | 133381700 | 133384950 | 103066136 | 103068374 | d7Mseg2942 | 8698 |
| 7 | 133400300 | 133404050 | 103084646 | 103087874 | d7Mseg2943 | 8699 |
| 7 | 133428100 | 133429500 | 103098720 | 103099647 | d7Mseg2945 | 8700 |
| 7 | 133651500 | 133659650 | 103497403 | 103501568 | d7Mseg2952 | 8701 |
| 7 | 133687650 | 133689200 | 103520117 | 103520775 | d7Mseg2955 | 8702 |
| 7 | 133711000 | 133714050 | 103541795 | 103544702 | d7Mseg2956 | 8703 |
| 7 | 133730950 | 133732750 | 103563228 | 103564744 | d7Mseg2957 | 8704 |
| 7 | 133955600 | 133957350 | 103717164 | 103717936 | d7Mseg2960 | 8705 |
| 7 | 133983300 | 133985050 | 103732911 | 103733977 | d7Mseg2961 | 8706 |
| 7 | 133987500 | 133990850 | 103735948 | 103738496 | d7Mseg2962 | 8707 |
| 7 | 133992750 | 133994750 | 103739582 | 103742239 | d7Mseg2963 | 8708 |
| 7 | 134003050 | 134004350 | 103751161 | 103751770 | d7Mseg2964 | 8709 |
| 7 | 134103350 | 134107500 | 103808956 | 103813140 | d7Mseg2967 | 8710 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 134135300 | 134136950 | 103835665 | 103836445 | d7Mseg2969 | 8711 |
| 7 | 134143300 | 134145000 | 103841454 | 103842819 | d7Mseg2970 | 8712 |
| 7 | 134161550 | 134163000 | 103870583 | 103870735 | d7Mseg2972 | 8713 |
| 7 | 134249200 | 134250200 | 103951239 | 103952239 | d7Mseg2973 | 8714 |
| 7 | 134264950 | 134267150 | 103980063 | 103980352 | d7Mseg2974 | 8715 |
| 7 | 134292950 | 134294650 | 103989534 | 103989913 | d7Mseg2975 | 8716 |
| 7 | 134321550 | 134323650 | 104017107 | 104019756 | d7Mseg2976 | 8717 |
| 7 | 134339100 | 134340850 | 104033297 | 104035279 | d7Mseg2977 | 8718 |
| 7 | 134384450 | 134385600 | 104100048 | 104100924 | d7Mseg2979 | 8719 |
| 7 | 134564000 | 134565900 | 104282526 | 104290859 | d7Mseg2982 | 8720 |
| 7 | 134633250 | 134634850 | 104357605 | 104358310 | d7Mseg2983 | 8721 |
| 7 | 134669600 | 134671000 | 104386408 | 104388399 | d7Mseg2984 | 8722 |
| 7 | 134748800 | 134750050 | 104473547 | 104474449 | d7Mseg2985 | 8723 |
| 7 | 134791700 | 134793550 | 104537116 | 104537499 | d7Mseg2986 | 8724 |
| 7 | 134824550 | 134825800 | 104566464 | 104567080 | d7Mseg2987 | 8725 |
| 7 | 134909200 | 134911000 | 104630711 | 104630974 | d7Mseg2990 | 8726 |
| 7 | 134966500 | 134967950 | 104662178 | 104663764 | d7Mseg2993 | 8727 |
| 7 | 134986650 | 134988150 | 104681898 | 104682819 | d7Mseg2995 | 8728 |
| 7 | 134992300 | 134994100 | 104695101 | 104697016 | d7Mseg2996 | 8729 |
| 7 | 135014150 | 135015950 | 104713272 | 104715237 | d7Mseg2997 | 8730 |
| 7 | 135066400 | 135068350 | 104746234 | 104748206 | d7Mseg2999 | 8731 |
| 7 | 135143400 | 135144900 | 104797378 | 104800214 | d7Mseg3000 | 8732 |
| 7 | 135256150 | 135258800 | 104879874 | 104882551 | d7Mseg3002 | 8733 |
| 7 | 135268800 | 135271750 | 104890808 | 104893265 | d7Mseg3003 | 8734 |
| 7 | 135326000 | 135330250 | 104962196 | 104964823 | d7Mseg3005 | 8735 |
| 7 | 135355800 | 135358300 | 104988195 | 104990876 | d7Mseg3006 | 8736 |
| 7 | 135446400 | 135451500 | 105063912 | 105069173 | d7Mseg3007 | 8737 |
| 7 | 135488250 | 135490000 | 105116090 | 105118380 | d7Mseg3008 | 8738 |
| 7 | 135501850 | 135503650 | 105142202 | 105143460 | d7Mseg3009 | 8739 |
| 7 | 135575950 | 135577350 | 105253181 | 105253748 | d7Mseg3011 | 8740 |
| 7 | 135639300 | 135644900 | 105302419 | 105303360 | d7Mseg3014 | 8741 |
| 7 | 135751400 | 135752650 | 105421015 | 105422213 | d7Mseg3016 | 8742 |
| 7 | 135787300 | 135790900 | 105461775 | 105463503 | d7Mseg3018 | 8743 |
| 7 | 135834800 | 135836250 | 105535890 | 105536614 | d7Mseg3020 | 8744 |
| 7 | 135891400 | 135893050 | 105638898 | 105639361 | d7Mseg3021 | 8745 |
| 7 | 136013150 | 136015350 | 105854114 | 105855626 | d7Mseg3026 | 8746 |
| 7 | 136026150 | 136027250 | 105864919 | 105865951 | d7Mseg3027 | 8747 |
| 7 | 136066050 | 136068150 | 105891334 | 105892267 | d7Mseg3028 | 8748 |
| 7 | 136122200 | 136123350 | 105954295 | 105955102 | d7Mseg3029 | 8749 |
| 7 | 136144350 | 136147100 | 105969149 | 105971877 | d7Mseg3030 | 8750 |
| 7 | 136153000 | 136154650 | 105977261 | 105977885 | d7Mseg3031 | 8751 |
| 7 | 136197250 | 136198750 | 106030161 | 106033128 | d7Mseg3032 | 8752 |
| 7 | 136207950 | 136209200 | 106040873 | 106041628 | d7Mseg3033 | 8753 |
| 7 | 136218150 | 136224400 | 106044395 | 106050619 | d7Mseg3034 | 8754 |
| 7 | 136237250 | 136239300 | 106062740 | 106064240 | d7Mseg3035 | 8755 |
| 7 | 136301150 | 136302850 | 106132234 | 106132558 | d7Mseg3037 | 8756 |
| 7 | 136355250 | 136356700 | 106182761 | 106184218 | d7Mseg3039 | 8757 |
| 7 | 136398400 | 136399850 | 106235706 | 106237160 | d7Mseg3040 | 8758 |
| 7 | 136403900 | 136405900 | 106241224 | 106243187 | d7Mseg3041 | 8759 |
| 7 | 136412600 | 136413600 | 106252729 | 106253249 | d7Mseg3043 | 8760 |
| 7 | 136465750 | 136469500 | 106268520 | 106269137 | d7Mseg3045 | 8761 |
| 7 | 136553250 | 136554500 | 106387278 | 106389492 | d7Mseg3048 | 8762 |
| 7 | 136592300 | 136602000 | 106445399 | 106454986 | d7Mseg3049 | 8763 |
| 7 | 136609250 | 136610850 | 106459802 | 106461378 | d7Mseg3050 | 8764 |
| 7 | 136613550 | 136615250 | 106463517 | 106465142 | d7Mseg3051 | 8765 |
| 7 | 136634350 | 136635500 | 106480643 | 106481487 | d7Mseg3052 | 8766 |
| 7 | 136672000 | 136673100 | 106538071 | 106538521 | d7Mseg3053 | 8767 |
| 7 | 136684650 | 136685800 | 106554821 | 106555966 | d7Mseg3054 | 8768 |
| 7 | 136707850 | 136709550 | 106577305 | 106579105 | d7Mseg3056 | 8769 |
| 7 | 136716850 | 136718800 | 106585270 | 106586229 | d7Mseg3057 | 8770 |
| 7 | 136721500 | 136722550 | 106589619 | 106590235 | d7Mseg3058 | 8771 |
| 7 | 136729450 | 136730650 | 106598516 | 106599733 | d7Mseg3059 | 8772 |
| 7 | 136736300 | 136737900 | 106603923 | 106605395 | d7Mseg3060 | 8773 |
| 7 | 136740500 | 136742250 | 106614710 | 106618409 | d7Mseg3061 | 8774 |
| 7 | 136793950 | 136795650 | 106675212 | 106677973 | d7Mseg3063 | 8775 |
| 7 | 136801250 | 136803550 | 106683726 | 106685337 | d7Mseg3064 | 8776 |
| 7 | 136807150 | 136814550 | 106688055 | 106694972 | d7Mseg3065 | 8777 |
| 7 | 136819600 | 136821300 | 106700784 | 106702512 | d7Mseg3066 | 8778 |
| 7 | 136830350 | 136831950 | 106709895 | 106711571 | d7Mseg3067 | 8779 |
| 7 | 136871650 | 136873150 | 106745707 | 106746745 | d7Mseg3070 | 8780 |
| 7 | 136874300 | 136877700 | 106747802 | 106750865 | d7Mseg3071 | 8781 |
| 7 | 136885850 | 136887200 | 106757232 | 106759029 | d7Mseg3072 | 8782 |
| 7 | 136897100 | 136899200 | 106770265 | 106772217 | d7Mseg3073 | 8783 |
| 7 | 136902500 | 136904300 | 106775963 | 106777498 | d7Mseg3074 | 8784 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 136940800 | 136942300 | 106809370 | 106810817 | d7Mseg3075 | 8785 |
| 7 | 136945200 | 136946850 | 106813880 | 106815226 | d7Mseg3076 | 8786 |
| 7 | 136949650 | 136951200 | 106817236 | 106818062 | d7Mseg3077 | 8787 |
| 7 | 136964300 | 136970500 | 106842102 | 106849053 | d7Mseg3078 | 8788 |
| 7 | 136974450 | 136976200 | 106852488 | 106854245 | d7Mseg3079 | 8789 |
| 7 | 136984050 | 136985650 | 106859156 | 106859525 | d7Mseg3080 | 8790 |
| 7 | 136989950 | 136993450 | 106870756 | 106873713 | d7Mseg3081 | 8791 |
| 7 | 137005400 | 137007250 | 106887245 | 106888793 | d7Mseg3083 | 8792 |
| 7 | 137026450 | 137028300 | 106903031 | 106905423 | d7Mseg3084 | 8793 |
| 7 | 137043700 | 137046750 | 106919655 | 106921526 | d7Mseg3085 | 8794 |
| 7 | 137052300 | 137053900 | 106925332 | 106927240 | d7Mseg3086 | 8795 |
| 7 | 137066100 | 137067250 | 106945299 | 106947884 | d7Mseg3087 | 8796 |
| 7 | 137074650 | 137078000 | 106956989 | 106960573 | d7Mseg3088 | 8797 |
| 7 | 137085350 | 137087050 | 106967779 | 106969103 | d7Mseg3089 | 8798 |
| 7 | 137094550 | 137095650 | 106977652 | 106977866 | d7Mseg3090 | 8799 |
| 7 | 137122300 | 137125750 | 107007407 | 107011076 | d7Mseg3091 | 8800 |
| 7 | 137131200 | 137137750 | 107016847 | 107022121 | d7Mseg3092 | 8801 |
| 7 | 137142050 | 137143600 | 107026911 | 107027327 | d7Mseg3093 | 8802 |
| 7 | 137168750 | 137170000 | 107037035 | 107038019 | d7Mseg3096 | 8803 |
| 7 | 137193950 | 137195500 | 107060391 | 107064080 | d7Mseg3097 | 8804 |
| 7 | 137198450 | 137202100 | 107068335 | 107072988 | d7Mseg3098 | 8805 |
| 7 | 137223600 | 137225000 | 107093763 | 107095058 | d7Mseg3099 | 8806 |
| 7 | 137252200 | 137255750 | 107134868 | 107137424 | d7Mseg3100 | 8807 |
| 7 | 137263800 | 137265550 | 107141530 | 107142547 | d7Mseg3101 | 8808 |
| 7 | 137272200 | 137273950 | 107147962 | 107149654 | d7Mseg3102 | 8809 |
| 7 | 137278000 | 137279250 | 107155153 | 107156168 | d7Mseg3103 | 8810 |
| 7 | 137283600 | 137285450 | 107158429 | 107160825 | d7Mseg3104 | 8811 |
| 7 | 137288600 | 137289800 | 107163530 | 107163971 | d7Mseg3105 | 8812 |
| 7 | 137294450 | 137296100 | 107166342 | 107167957 | d7Mseg3106 | 8813 |
| 7 | 137326250 | 137329900 | 107209009 | 107212410 | d7Mseg3107 | 8814 |
| 7 | 137342550 | 137346250 | 107220701 | 107224366 | d7Mseg3109 | 8815 |
| 7 | 137403650 | 137405450 | 107252202 | 107253411 | d7Mseg3115 | 8816 |
| 7 | 137440150 | 137441600 | 107285902 | 107287184 | d7Mseg3117 | 8817 |
| 7 | 137457750 | 137459850 | 107307978 | 107309388 | d7Mseg3118 | 8818 |
| 7 | 137466850 | 137468400 | 107315464 | 107316985 | d7Mseg3119 | 8819 |
| 7 | 137514600 | 137516400 | 107364837 | 107365401 | d7Mseg3120 | 8820 |
| 7 | 137593900 | 137594950 | 107394373 | 107395281 | d7Mseg3123 | 8821 |
| 7 | 137598500 | 137600100 | 107397620 | 107399000 | d7Mseg3124 | 8822 |
| 7 | 137606700 | 137608700 | 107404896 | 107407314 | d7Mseg3125 | 8823 |
| 7 | 137610750 | 137612550 | 107409521 | 107411504 | d7Mseg3126 | 8824 |
| 7 | 137619700 | 137624900 | 107417078 | 107420206 | d7Mseg3127 | 8825 |
| 7 | 137652250 | 137654450 | 107447414 | 107449123 | d7Mseg3128 | 8826 |
| 7 | 137658900 | 137659950 | 107453570 | 107454673 | d7Mseg3129 | 8827 |
| 7 | 137669550 | 137671550 | 107465427 | 107468408 | d7Mseg3130 | 8828 |
| 7 | 137675800 | 137677500 | 107473323 | 107475127 | d7Mseg3131 | 8829 |
| 7 | 137703100 | 137705150 | 107498361 | 107501096 | d7Mseg3132 | 8830 |
| 7 | 137761850 | 137763850 | 107553890 | 107554850 | d7Mseg3135 | 8831 |
| 7 | 137766050 | 137767700 | 107556077 | 107556563 | d7Mseg3136 | 8832 |
| 7 | 137784950 | 137786600 | 107568094 | 107568751 | d7Mseg3137 | 8833 |
| 7 | 137813400 | 137815250 | 107588374 | 107589515 | d7Mseg3139 | 8834 |
| 7 | 137829150 | 137831000 | 107601027 | 107603219 | d7Mseg3140 | 8835 |
| 7 | 137862250 | 137864200 | 107622146 | 107623383 | d7Mseg3142 | 8836 |
| 7 | 137888150 | 137889900 | 107656540 | 107658592 | d7Mseg3143 | 8837 |
| 7 | 137893100 | 137895000 | 107662459 | 107664319 | d7Mseg3144 | 8838 |
| 7 | 137909200 | 137911500 | 107682283 | 107684615 | d7Mseg3145 | 8839 |
| 7 | 137913900 | 137916250 | 107686917 | 107689639 | d7Mseg3146 | 8840 |
| 7 | 137950050 | 137952350 | 107756867 | 107757185 | d7Mseg3149 | 8841 |
| 7 | 137982700 | 137984150 | 107806090 | 107806409 | d7Mseg3150 | 8842 |
| 7 | 138027700 | 138030250 | 107831065 | 107832687 | d7Mseg3153 | 8843 |
| 7 | 138046350 | 138047900 | 107840494 | 107841803 | d7Mseg3155 | 8844 |
| 7 | 138052850 | 138054650 | 107850161 | 107852252 | d7Mseg3156 | 8845 |
| 7 | 138056650 | 138058350 | 107854912 | 107856349 | d7Mseg3157 | 8846 |
| 7 | 138087250 | 138088850 | 107908162 | 107909838 | d7Mseg3159 | 8847 |
| 7 | 138106400 | 138108400 | 107924839 | 107929467 | d7Mseg3160 | 8848 |
| 7 | 138111750 | 138113550 | 107932078 | 107932981 | d7Mseg3161 | 8849 |
| 7 | 138117300 | 138121300 | 107935418 | 107938688 | d7Mseg3162 | 8850 |
| 7 | 138124950 | 138127450 | 107941924 | 107942819 | d7Mseg3163 | 8851 |
| 7 | 138142300 | 138143700 | 107960303 | 107961582 | d7Mseg3166 | 8852 |
| 7 | 138147500 | 138149300 | 107965118 | 107967886 | d7Mseg3167 | 8853 |
| 7 | 138151800 | 138162300 | 107971425 | 107982189 | d7Mseg3168 | 8854 |
| 7 | 138217300 | 138219350 | 108103061 | 108104893 | d7Mseg3169 | 8855 |
| 7 | 138222150 | 138223400 | 108106539 | 108106916 | d7Mseg3170 | 8856 |
| 7 | 138232550 | 138234100 | 108117283 | 108118081 | d7Mseg3171 | 8857 |
| 7 | 138264500 | 138266550 | 108211591 | 108224000 | d7Mseg3174 | 8858 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 138281800 | 138283800 | 108243711 | 108244277 | d7Mseg3175 | 8859 |
| 7 | 138293800 | 138295350 | 108285957 | 108286337 | d7Mseg3176 | 8860 |
| 7 | 138408650 | 138409950 | 108471797 | 108477883 | d7Mseg3179 | 8861 |
| 7 | 138423200 | 138424850 | 108510414 | 108511696 | d7Mseg3180 | 8862 |
| 7 | 138518100 | 138519750 | 108614112 | 108615772 | d7Mseg3182 | 8863 |
| 7 | 138524200 | 138527000 | 108619894 | 108623746 | d7Mseg3183 | 8864 |
| 7 | 138528750 | 138530650 | 108625369 | 108627261 | d7Mseg3184 | 8865 |
| 7 | 138533200 | 138534950 | 108629707 | 108631757 | d7Mseg3185 | 8866 |
| 7 | 138561600 | 138567200 | 108671263 | 108677554 | d7Mseg3186 | 8867 |
| 7 | 138621550 | 138623400 | 108716644 | 108718159 | d7Mseg3188 | 8868 |
| 7 | 138659450 | 138660700 | 108777715 | 108778654 | d7Mseg3189 | 8869 |
| 7 | 138679600 | 138681500 | 108790747 | 108791192 | d7Mseg3192 | 8870 |
| 7 | 138692450 | 138694100 | 108821604 | 108823023 | d7Mseg3193 | 8871 |
| 7 | 138738800 | 138740900 | 108866609 | 108868579 | d7Mseg3196 | 8872 |
| 7 | 138766000 | 138767700 | 108905719 | 108908087 | d7Mseg3198 | 8873 |
| 7 | 138769250 | 138771150 | 108909443 | 108910691 | d7Mseg3199 | 8874 |
| 7 | 138802500 | 138803550 | 108951055 | 108951586 | d7Mseg3200 | 8875 |
| 7 | 138817050 | 138818450 | 108969689 | 108971382 | d7Mseg3201 | 8876 |
| 7 | 138820350 | 138822000 | 108972908 | 108973901 | d7Mseg3202 | 8877 |
| 7 | 138824350 | 138826200 | 108975868 | 108977708 | d7Mseg3203 | 8878 |
| 7 | 138863550 | 138864600 | 109019189 | 109020105 | d7Mseg3204 | 8879 |
| 7 | 138884550 | 138886500 | 109036918 | 109041452 | d7Mseg3205 | 8880 |
| 7 | 138917250 | 138919200 | 109086888 | 109087309 | d7Mseg3206 | 8881 |
| 7 | 138962400 | 138964050 | 109122175 | 109123179 | d7Mseg3207 | 8882 |
| 7 | 138981250 | 138982750 | 109149466 | 109152513 | d7Mseg3208 | 8883 |
| 7 | 138988900 | 138990450 | 109154404 | 109157400 | d7Mseg3209 | 8884 |
| 7 | 139000950 | 139002800 | 109160992 | 109164535 | d7Mseg3211 | 8885 |
| 7 | 139004650 | 139005800 | 109166314 | 109166873 | d7Mseg3212 | 8886 |
| 7 | 139017300 | 139018700 | 109176959 | 109177870 | d7Mseg3213 | 8887 |
| 7 | 139020200 | 139022150 | 109179238 | 109180283 | d7Mseg3214 | 8888 |
| 7 | 139052200 | 139054200 | 109201560 | 109202933 | d7Mseg3216 | 8889 |
| 7 | 139061350 | 139063050 | 109207875 | 109208490 | d7Mseg3218 | 8890 |
| 7 | 139092200 | 139093250 | 109219388 | 109220169 | d7Mseg3223 | 8891 |
| 7 | 139097850 | 139099350 | 109230553 | 109230762 | d7Mseg3224 | 8892 |
| 7 | 139162400 | 139164300 | 109290242 | 109291815 | d7Mseg3226 | 8893 |
| 7 | 139174600 | 139175950 | 109299347 | 109299990 | d7Mseg3227 | 8894 |
| 7 | 139212950 | 139214700 | 109362669 | 109363674 | d7Mseg3229 | 8895 |
| 7 | 139220550 | 139221750 | 109368319 | 109369594 | d7Mseg3230 | 8896 |
| 7 | 139228550 | 139229750 | 109374293 | 109375173 | d7Mseg3231 | 8897 |
| 7 | 139267400 | 139269050 | 109415001 | 109416739 | d7Mseg3233 | 8898 |
| 7 | 139378150 | 139379250 | 109535031 | 109536166 | d7Mseg3234 | 8899 |
| 7 | 139399350 | 139403250 | 109559439 | 109563236 | d7Mseg3235 | 8900 |
| 7 | 139423200 | 139425050 | 109580360 | 109581853 | d7Mseg3236 | 8901 |
| 7 | 139436550 | 139438500 | 109603573 | 109605145 | d7Mseg3237 | 8902 |
| 7 | 139443800 | 139445450 | 109610883 | 109616857 | d7Mseg3238 | 8903 |
| 7 | 139479300 | 139480350 | 109644807 | 109645113 | d7Mseg3240 | 8904 |
| 7 | 139495350 | 139497000 | 109658437 | 109660121 | d7Mseg3242 | 8905 |
| 7 | 139513950 | 139516200 | 109674292 | 109676555 | d7Mseg3243 | 8906 |
| 7 | 139517850 | 139519250 | 109678640 | 109679489 | d7Mseg3244 | 8907 |
| 7 | 139524850 | 139528650 | 109685038 | 109688559 | d7Mseg3245 | 8908 |
| 7 | 139529900 | 139531750 | 109689803 | 109691391 | d7Mseg3246 | 8909 |
| 7 | 139599250 | 139600400 | 109760060 | 109761082 | d7Mseg3248 | 8910 |
| 7 | 139819950 | 139821450 | 110030447 | 110031541 | d7Mseg3253 | 8911 |
| 7 | 139827450 | 139830300 | 110038100 | 110040925 | d7Mseg3254 | 8912 |
| 7 | 139832100 | 139833300 | 110042620 | 110043169 | d7Mseg3255 | 8913 |
| 7 | 139869350 | 139872550 | 110078155 | 110079210 | d7Mseg3256 | 8914 |
| 7 | 139936700 | 139940500 | 110158552 | 110161098 | d7Mseg3259 | 8915 |
| 7 | 139949100 | 139950350 | 110184289 | 110185133 | d7Mseg3261 | 8916 |
| 7 | 139952800 | 139955200 | 110187318 | 110189585 | d7Mseg3262 | 8917 |
| 7 | 140012500 | 140013750 | 110245776 | 110246469 | d7Mseg3263 | 8918 |
| 7 | 140015300 | 140017000 | 110248032 | 110249346 | d7Mseg3264 | 8919 |
| 7 | 140075050 | 140076950 | 110305481 | 110310141 | d7Mseg3266 | 8920 |
| 7 | 140099200 | 140101150 | 110339683 | 110341701 | d7Mseg3267 | 8921 |
| 7 | 140120500 | 140122300 | 110361199 | 110362042 | d7Mseg3268 | 8922 |
| 7 | 140124350 | 140127400 | 110364009 | 110365910 | d7Mseg3269 | 8923 |
| 7 | 140130050 | 140131150 | 110368675 | 110369855 | d7Mseg3270 | 8924 |
| 7 | 140178000 | 140179750 | 110415161 | 110418374 | d7Mseg3272 | 8925 |
| 7 | 140200100 | 140201850 | 110436064 | 110438052 | d7Mseg3273 | 8926 |
| 7 | 140207550 | 140209350 | 110438424 | 110439541 | d7Mseg3274 | 8927 |
| 7 | 140269400 | 140270750 | 110518960 | 110520340 | d7Mseg3275 | 8928 |
| 7 | 140284200 | 140286100 | 110530553 | 110532112 | d7Mseg3276 | 8929 |
| 7 | 140287350 | 140288650 | 110533461 | 110534446 | d7Mseg3277 | 8930 |
| 7 | 140318700 | 140321300 | 110591481 | 110594963 | d7Mseg3278 | 8931 |
| 7 | 140331400 | 140333250 | 110609285 | 110611393 | d7Mseg3279 | 8932 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 140345350 | 140347300 | 110625889 | 110628080 | d7Mseg3280 | 8933 |
| 7 | 140365550 | 140367400 | 110653329 | 110655158 | d7Mseg3281 | 8934 |
| 7 | 140541200 | 140542600 | 110735570 | 110736249 | d7Mseg3284 | 8935 |
| 7 | 140572500 | 140574100 | 110747285 | 110747744 | d7Mseg3285 | 8936 |
| 7 | 140588600 | 140590100 | 110755209 | 110756686 | d7Mseg3286 | 8937 |
| 7 | 140597000 | 140598250 | 110761855 | 110763057 | d7Mseg3287 | 8938 |
| 7 | 140600200 | 140601650 | 110765075 | 110766358 | d7Mseg3288 | 8939 |
| 7 | 140630750 | 140632450 | 110806446 | 110807444 | d7Mseg3290 | 8940 |
| 7 | 140753350 | 140755250 | 110925177 | 110926040 | d7Mseg3293 | 8941 |
| 7 | 140766800 | 140768750 | 110948098 | 110948959 | d7Mseg3294 | 8942 |
| 7 | 140784350 | 140786050 | 110968453 | 110970741 | d7Mseg3295 | 8943 |
| 7 | 140792500 | 140794450 | 110980426 | 110982130 | d7Mseg3296 | 8944 |
| 7 | 140816150 | 140818050 | 111018679 | 111020387 | d7Mseg3297 | 8945 |
| 7 | 140819500 | 140820700 | 111022027 | 111022506 | d7Mseg3298 | 8946 |
| 7 | 140895450 | 140899900 | 111127964 | 111130522 | d7Mseg3300 | 8947 |
| 7 | 140957250 | 140958650 | 111194459 | 111195910 | d7Mseg3303 | 8948 |
| 7 | 141062250 | 141064150 | 111263463 | 111265156 | d7Mseg3306 | 8949 |
| 7 | 141083500 | 141084750 | 111289905 | 111290648 | d7Mseg3307 | 8950 |
| 7 | 141094000 | 141095650 | 111305509 | 111306359 | d7Mseg3308 | 8951 |
| 7 | 141119500 | 141127700 | 111322217 | 111330457 | d7Mseg3309 | 8952 |
| 7 | 141220650 | 141221850 | 111400582 | 111401079 | d7Mseg3314 | 8953 |
| 7 | 141267700 | 141272150 | 111429188 | 111438980 | d7Mseg3316 | 8954 |
| 7 | 141314100 | 141315100 | 111462230 | 111462680 | d7Mseg3318 | 8955 |
| 7 | 141333400 | 141335250 | 111480444 | 111481290 | d7Mseg3319 | 8956 |
| 7 | 141349350 | 141351100 | 111490471 | 111491871 | d7Mseg3320 | 8957 |
| 7 | 141367700 | 141369400 | 111508506 | 111512804 | d7Mseg3321 | 8958 |
| 7 | 141405200 | 141407000 | 111537976 | 111538889 | d7Mseg3322 | 8959 |
| 7 | 141449950 | 141451950 | 111581820 | 111583018 | d7Mseg3323 | 8960 |
| 7 | 141453350 | 141455100 | 111584261 | 111585449 | d7Mseg3324 | 8961 |
| 7 | 141537700 | 141539250 | 111679833 | 111680409 | d7Mseg3325 | 8962 |
| 7 | 141543700 | 141545350 | 111689059 | 111690830 | d7Mseg3326 | 8963 |
| 7 | 141603900 | 141606000 | 111754275 | 111756680 | d7Mseg3327 | 8964 |
| 7 | 141617900 | 141619250 | 111768568 | 111769663 | d7Mseg3328 | 8965 |
| 7 | 141621750 | 141623450 | 111772015 | 111773002 | d7Mseg3329 | 8966 |
| 7 | 141764800 | 141767500 | 111907708 | 111908384 | d7Mseg3333 | 8967 |
| 7 | 141769600 | 141771100 | 111910145 | 111911273 | d7Mseg3334 | 8968 |
| 7 | 141787600 | 141790400 | 111925682 | 111926276 | d7Mseg3335 | 8969 |
| 7 | 141838200 | 141839650 | 111978992 | 111979520 | d7Mseg3336 | 8970 |
| 7 | 141844200 | 141845350 | 111984183 | 111984714 | d7Mseg3337 | 8971 |
| 7 | 141886300 | 141887900 | 112023445 | 112025773 | d7Mseg3338 | 8972 |
| 7 | 141895400 | 141897250 | 112034682 | 112036861 | d7Mseg3339 | 8973 |
| 7 | 141906350 | 141907950 | 112050181 | 112050777 | d7Mseg3340 | 8974 |
| 7 | 141916300 | 141917350 | 112060767 | 112061838 | d7Mseg3341 | 8975 |
| 7 | 141935250 | 141936550 | 112079617 | 112081072 | d7Mseg3342 | 8976 |
| 7 | 141938500 | 141942750 | 112083066 | 112087861 | d7Mseg3343 | 8977 |
| 7 | 142102950 | 142104900 | 112240339 | 112243025 | d7Mseg3348 | 8978 |
| 7 | 142123150 | 142124300 | 112281785 | 112282907 | d7Mseg3349 | 8979 |
| 7 | 142249800 | 142251500 | 112459907 | 112462746 | d7Mseg3351 | 8980 |
| 7 | 142264950 | 142266350 | 112467889 | 112468180 | d7Mseg3352 | 8981 |
| 7 | 142273600 | 142274850 | 112484419 | 112485260 | d7Mseg3353 | 8982 |
| 7 | 142451450 | 142452500 | 112621802 | 112622393 | d7Mseg3356 | 8983 |
| 7 | 142898600 | 142902200 | 113239476 | 113239928 | d7Mseg3361 | 8984 |
| 7 | 143010350 | 143011600 | 113343945 | 113344663 | d7Mseg3364 | 8985 |
| 7 | 143203700 | 143205300 | 113601424 | 113602052 | d7Mseg3367 | 8986 |
| 7 | 143322650 | 143324000 | 113760920 | 113761136 | d7Mseg3368 | 8987 |
| 7 | 143361100 | 143362950 | 113784437 | 113785624 | d7Mseg3369 | 8988 |
| 7 | 143391700 | 143399450 | 113813330 | 113820682 | d7Mseg3370 | 8989 |
| 7 | 143434600 | 143436400 | 113871299 | 113872955 | d7Mseg3371 | 8990 |
| 7 | 143493650 | 143494850 | 113941481 | 113941685 | d7Mseg3373 | 8991 |
| 7 | 143515400 | 143517300 | 113982665 | 113984434 | d7Mseg3374 | 8992 |
| 7 | 143622500 | 143624150 | 114135137 | 114135837 | d7Mseg3376 | 8993 |
| 7 | 143632850 | 143634550 | 114145020 | 114145660 | d7Mseg3377 | 8994 |
| 7 | 143798250 | 143800100 | 114213062 | 114214256 | d7Mseg3383 | 8995 |
| 7 | 143963900 | 143965650 | 114446851 | 114448580 | d7Mseg3385 | 8996 |
| 7 | 143988000 | 143989850 | 114468015 | 114469855 | d7Mseg3386 | 8997 |
| 7 | 144006300 | 144007350 | 114502213 | 114502652 | d7Mseg3387 | 8998 |
| 7 | 146942100 | 146943100 | 52971036 | 52971195 | d7Mseg3397 | 8999 |
| 7 | 146984600 | 146986000 | 55053197 | 55054435 | d7Mseg3398 | 9000 |
| 7 | 147006600 | 147007650 | 55032762 | 55033578 | d7Mseg3399 | 9001 |
| 7 | 147048400 | 147049400 | 54984813 | 54985377 | d7Mseg3401 | 9002 |
| 7 | 147079250 | 147080800 | 54957122 | 54958354 | d7Mseg3402 | 9003 |
| 7 | 147232000 | 147233000 | 54868422 | 54868599 | d7Mseg3410 | 9004 |
| 7 | 147238050 | 147239950 | 54844956 | 54846982 | d7Mseg3411 | 9005 |
| 7 | 147242050 | 147243450 | 54839795 | 54841281 | d7Mseg3412 | 9006 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 147251800 | 147254850 | 54828856 | 54830093 | d7Mseg3413 | 9007 |
| 7 | 147277250 | 147280500 | 54800904 | 54815394 | d7Mseg3414 | 9008 |
| 7 | 147286350 | 147288050 | 54780266 | 54781770 | d7Mseg3415 | 9009 |
| 7 | 147311600 | 147313300 | 54754944 | 54755417 | d7Mseg3416 | 9010 |
| 7 | 147421600 | 147423400 | 54583234 | 54586090 | d7Mseg3418 | 9011 |
| 7 | 147442200 | 147443900 | 54560614 | 54561460 | d7Mseg3419 | 9012 |
| 7 | 147465050 | 147468750 | 54531430 | 54537362 | d7Mseg3421 | 9013 |
| 7 | 147478700 | 147483450 | 54520505 | 54525870 | d7Mseg3422 | 9014 |
| 7 | 147491600 | 147495800 | 54505520 | 54507798 | d7Mseg3423 | 9015 |
| 7 | 147508100 | 147509100 | 54489526 | 54490295 | d7Mseg3424 | 9016 |
| 7 | 147623550 | 147625100 | 54365864 | 54366273 | d7Mseg3427 | 9017 |
| 7 | 147779150 | 147780400 | 54207955 | 54209261 | d7Mseg3431 | 9018 |
| 7 | 147954450 | 147956800 | 54069347 | 54071787 | d7Mseg3434 | 9019 |
| 7 | 147976150 | 147977650 | 54055511 | 54055761 | d7Mseg3436 | 9020 |
| 7 | 148070000 | 148072100 | 53961562 | 53962537 | d7Mseg3438 | 9021 |
| 7 | 148235950 | 148238050 | 53710937 | 53713068 | d7Mseg3446 | 9022 |
| 7 | 148277350 | 148278450 | 53671825 | 53672791 | d7Mseg3447 | 9023 |
| 7 | 148309350 | 148311000 | 53630304 | 53631519 | d7Mseg3448 | 9024 |
| 7 | 148351400 | 148352950 | 53576439 | 53578409 | d7Mseg3449 | 9025 |
| 7 | 148401250 | 148403000 | 53486649 | 53490244 | d7Mseg3451 | 9026 |
| 7 | 148436000 | 148437150 | 53460580 | 53461738 | d7Mseg3452 | 9027 |
| 7 | 148448100 | 148452250 | 53448361 | 53451724 | d7Mseg3453 | 9028 |
| 7 | 148466750 | 148468400 | 53432729 | 53434296 | d7Mseg3454 | 9029 |
| 7 | 148525550 | 148527250 | 53383097 | 53384418 | d7Mseg3456 | 9030 |
| 7 | 148530350 | 148532150 | 53381817 | 53382169 | d7Mseg3457 | 9031 |
| 7 | 148564650 | 148567200 | 53359327 | 53362767 | d7Mseg3459 | 9032 |
| 7 | 148578400 | 148581050 | 53348023 | 53350933 | d7Mseg3460 | 9033 |
| 7 | 148599100 | 148600650 | 53322029 | 53323583 | d7Mseg3461 | 9034 |
| 7 | 148605950 | 148608800 | 53315296 | 53317427 | d7Mseg3462 | 9035 |
| 7 | 148632800 | 148634100 | 53289589 | 53291266 | d7Mseg3463 | 9036 |
| 7 | 148635150 | 148636850 | 53285821 | 53287615 | d7Mseg3464 | 9037 |
| 7 | 148645700 | 148646700 | 53277282 | 53278119 | d7Mseg3465 | 9038 |
| 7 | 148649700 | 148651600 | 53269829 | 53273042 | d7Mseg3466 | 9039 |
| 7 | 148653000 | 148654250 | 53267506 | 53268880 | d7Mseg3467 | 9040 |
| 7 | 148656400 | 148658050 | 53263780 | 53265466 | d7Mseg3468 | 9041 |
| 7 | 148735200 | 148736850 | 53150809 | 53151406 | d7Mseg3469 | 9042 |
| 7 | 148775450 | 148777250 | 53111284 | 53113157 | d7Mseg3470 | 9043 |
| 7 | 148780600 | 148782500 | 53105176 | 53107227 | d7Mseg3471 | 9044 |
| 7 | 148791600 | 148793400 | 53094978 | 53096520 | d7Mseg3472 | 9045 |
| 7 | 149057600 | 149058800 | 9899748 | 9901003 | d7Mseg3482 | 9046 |
| 7 | 149203250 | 149205000 | 9753596 | 9755294 | d7Mseg3484 | 9047 |
| 7 | 149216550 | 149218150 | 9731609 | 9733894 | d7Mseg3486 | 9048 |
| 7 | 149232900 | 149234850 | 9707159 | 9707778 | d7Mseg3487 | 9049 |
| 7 | 149236050 | 149237750 | 9704243 | 9705597 | d7Mseg3488 | 9050 |
| 7 | 149250950 | 149252750 | 9661638 | 9661901 | d7Mseg3489 | 9051 |
| 7 | 149405900 | 149408400 | 55477112 | 55477642 | d7Mseg3494 | 9052 |
| 7 | 149433550 | 149434650 | 55492392 | 55493438 | d7Mseg3496 | 9053 |
| 7 | 149440700 | 149441900 | 55515319 | 55516529 | d7Mseg3497 | 9054 |
| 7 | 149448450 | 149450400 | 55517426 | 55517660 | d7Mseg3498 | 9055 |
| 7 | 149455050 | 149456700 | 55531701 | 55533137 | d7Mseg3499 | 9056 |
| 7 | 149474000 | 149475800 | 55556711 | 55557153 | d7Mseg3500 | 9057 |
| 7 | 149556350 | 149557850 | 55633524 | 55633795 | d7Mseg3505 | 9058 |
| 7 | 149559000 | 149560750 | 55634152 | 55635302 | d7Mseg3506 | 9059 |
| 7 | 149576600 | 149578300 | 55746681 | 55748238 | d7Mseg3508 | 9060 |
| 7 | 149675100 | 149676900 | 55936552 | 55937868 | d7Mseg3512 | 9061 |
| 7 | 149689800 | 149690850 | 55951120 | 55952650 | d7Mseg3513 | 9062 |
| 7 | 149724050 | 149725750 | 56049263 | 56049706 | d7Mseg3515 | 9063 |
| 7 | 149743900 | 149745650 | 56145263 | 56148059 | d7Mseg3516 | 9064 |
| 7 | 149794050 | 149795950 | 56258774 | 56260707 | d7Mseg3517 | 9065 |
| 7 | 149823750 | 149826250 | 56308384 | 56310177 | d7Mseg3518 | 9066 |
| 7 | 149931200 | 149934200 | 56588443 | 56591468 | d7Mseg3523 | 9067 |
| 7 | 149938300 | 149940100 | 56596230 | 56596915 | d7Mseg3524 | 9068 |
| 7 | 150133100 | 150136500 | 56640085 | 56640811 | d7Mseg3529 | 9069 |
| 7 | 150266350 | 150268050 | 57095794 | 57097543 | d7Mseg3533 | 9070 |
| 7 | 151460850 | 151462100 | 141234918 | 141235496 | d7Mseg3543 | 9071 |
| 7 | 151603350 | 151605050 | 23838101 | 23840843 | d7Mseg3547 | 9072 |
| 7 | 151685450 | 151686650 | 23792048 | 23792709 | d7Mseg3549 | 9073 |
| 7 | 151696250 | 151698050 | 23760756 | 23761726 | d7Mseg3550 | 9074 |
| 7 | 151947900 | 151949450 | 23498961 | 23499766 | d7Mseg3559 | 9075 |
| 7 | 151972050 | 151973200 | 23433517 | 23434186 | d7Mseg3561 | 9076 |
| 7 | 152020250 | 152022200 | 23397105 | 23399091 | d7Mseg3562 | 9077 |
| 7 | 152034050 | 152035800 | 23382968 | 23384712 | d7Mseg3563 | 9078 |
| 7 | 152040550 | 152041750 | 23368914 | 23370631 | d7Mseg3564 | 9079 |
| 7 | 152055450 | 152061650 | 23349239 | 23355376 | d7Mseg3565 | 9080 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| 7 | 152066700 | 152068350 | 23344902 | 23345899 | d7Mseg3566 | 9081 |
| 7 | 152084050 | 152085850 | 23327861 | 23328207 | d7Mseg3567 | 9082 |
| 7 | 152193050 | 152194850 | 23246260 | 23248154 | d7Mseg3569 | 9083 |
| 7 | 152317000 | 152318450 | 23169555 | 23170629 | d7Mseg3571 | 9084 |
| 7 | 152359450 | 152360700 | 23138093 | 23138412 | d7Mseg3572 | 9085 |
| 7 | 152538800 | 152540350 | 23056272 | 23056544 | d7Mseg3573 | 9086 |
| 7 | 152541650 | 152543200 | 23054454 | 23055361 | d7Mseg3574 | 9087 |
| 7 | 152570550 | 152573700 | 23029661 | 23032856 | d7Mseg3576 | 9088 |
| 7 | 152714750 | 152716400 | 22922511 | 22922946 | d7Mseg3578 | 9089 |
| 7 | 152943750 | 152945500 | 22726175 | 22727205 | d7Mseg3580 | 9090 |
| 7 | 153284700 | 153285700 | 22490321 | 22490459 | d7Mseg3589 | 9091 |
| 7 | 153321250 | 153322400 | 22465004 | 22465689 | d7Mseg3590 | 9092 |
| 7 | 153345750 | 153347250 | 22427283 | 22428966 | d7Mseg3591 | 9093 |
| 7 | 153354600 | 153356050 | 22419728 | 22420373 | d7Mseg3592 | 9094 |
| 7 | 153359500 | 153363650 | 22409298 | 22416916 | d7Mseg3593 | 9095 |
| 7 | 153517400 | 153518900 | 22315097 | 22316711 | d7Mseg3595 | 9096 |
| 7 | 153558300 | 153559550 | 22292827 | 22293525 | d7Mseg3596 | 9097 |
| 7 | 153599650 | 153601350 | 22265814 | 22266414 | d7Mseg3597 | 9098 |
| 7 | 153662350 | 153663350 | 22203565 | 22204211 | d7Mseg3598 | 9099 |
| 7 | 153770550 | 153771850 | 22138020 | 22138468 | d7Mseg3599 | 9100 |
| 7 | 153784650 | 153786150 | 22118840 | 22124325 | d7Mseg3600 | 9101 |
| 7 | 153813700 | 153815300 | 22090650 | 22091668 | d7Mseg3601 | 9102 |
| 7 | 153835650 | 153837300 | 22068131 | 22071744 | d7Mseg3602 | 9103 |
| 7 | 153914450 | 153916200 | 21974126 | 21976976 | d7Mseg3603 | 9104 |
| 7 | 153925100 | 153929050 | 21959662 | 21965543 | d7Mseg3604 | 9105 |
| 7 | 153974950 | 153976600 | 21920450 | 21920938 | d7Mseg3605 | 9106 |
| 7 | 154024050 | 154025900 | 21864898 | 21865863 | d7Mseg3606 | 9107 |
| 7 | 154029100 | 154030900 | 21861717 | 21863666 | d7Mseg3607 | 9108 |
| 7 | 154167750 | 154171300 | 21742716 | 21747077 | d7Mseg3608 | 9109 |
| 7 | 154184500 | 154186700 | 21728894 | 21731965 | d7Mseg3609 | 9110 |
| 7 | 154194750 | 154196550 | 21719063 | 21720797 | d7Mseg3610 | 9111 |
| 7 | 154254100 | 154257400 | 21674872 | 21678135 | d7Mseg3611 | 9112 |
| 7 | 154380900 | 154383000 | 21508922 | 21510647 | d7Mseg3612 | 9113 |
| 7 | 154427750 | 154429650 | 21458224 | 21458960 | d7Mseg3613 | 9114 |
| 7 | 154478350 | 154484050 | 21389368 | 21395519 | d7Mseg3614 | 9115 |
| 7 | 154488400 | 154489850 | 21378807 | 21379224 | d7Mseg3615 | 9116 |
| 7 | 154648550 | 154649750 | 21183339 | 21183461 | d7Mseg3619 | 9117 |
| 7 | 154678600 | 154679600 | 21165875 | 21167460 | d7Mseg3621 | 9118 |
| 7 | 154722900 | 154724000 | 21132154 | 21133292 | d7Mseg3622 | 9119 |
| 7 | 154857150 | 154858450 | 20989212 | 20991061 | d7Mseg3624 | 9120 |
| 7 | 154860400 | 154865200 | 20977540 | 20985474 | d7Mseg3625 | 9121 |
| 7 | 154881250 | 154882650 | 20962671 | 20963007 | d7Mseg3626 | 9122 |
| 7 | 154891400 | 154893000 | 20958210 | 20959832 | d7Mseg3627 | 9123 |
| 7 | 154898600 | 154900100 | 20952400 | 20953095 | d7Mseg3628 | 9124 |
| 7 | 155013800 | 155015450 | 20849446 | 20850148 | d7Mseg3630 | 9125 |
| 7 | 155018750 | 155020450 | 20844081 | 20844501 | d7Mseg3631 | 9126 |
| 7 | 155050350 | 155051350 | 20823092 | 20824468 | d7Mseg3632 | 9127 |
| 7 | 155104750 | 155106100 | 20751953 | 20753841 | d7Mseg3633 | 9128 |
| 7 | 155131750 | 155133450 | 20738380 | 20743875 | d7Mseg3634 | 9129 |
| 7 | 155141200 | 155142200 | 20732686 | 20733737 | d7Mseg3635 | 9130 |
| 7 | 155205700 | 155207350 | 20655507 | 20657151 | d7Mseg3637 | 9131 |
| 7 | 155208900 | 155210900 | 20652824 | 20653527 | d7Mseg3638 | 9132 |
| 7 | 155239600 | 155241250 | 20632847 | 20635035 | d7Mseg3639 | 9133 |
| 7 | 155273950 | 155275550 | 20614370 | 20615008 | d7Mseg3640 | 9134 |
| 7 | 155293600 | 155295400 | 20585892 | 20587631 | d7Mseg3641 | 9135 |
| 7 | 155358000 | 155359000 | 20549830 | 20550735 | d7Mseg3643 | 9136 |
| 7 | 155405700 | 155407450 | 20515014 | 20516017 | d7Mseg3645 | 9137 |
| 7 | 155430700 | 155431700 | 20491373 | 20492388 | d7Mseg3647 | 9138 |
| 7 | 155462550 | 155464250 | 20473783 | 20474427 | d7Mseg3648 | 9139 |
| 7 | 155477000 | 155478900 | 20463273 | 20466091 | d7Mseg3649 | 9140 |
| 7 | 155480650 | 155481850 | 20460549 | 20461795 | d7Mseg3650 | 9141 |
| 7 | 155499850 | 155501950 | 20447748 | 20449457 | d7Mseg3651 | 9142 |
| 7 | 155519150 | 155521100 | 20428353 | 20430233 | d7Mseg3652 | 9143 |
| 7 | 155613850 | 155615100 | 20356629 | 20356895 | d7Mseg3653 | 9144 |
| 7 | 155693500 | 155698350 | 20280719 | 20285258 | d7Mseg3654 | 9145 |
| 7 | 155714000 | 155715350 | 20260528 | 20261193 | d7Mseg3655 | 9146 |
| 7 | 155782900 | 155784550 | 20186390 | 20188004 | d7Mseg3656 | 9147 |
| 7 | 155805900 | 155807750 | 20162824 | 20168308 | d7Mseg3657 | 9148 |
| 7 | 155851050 | 155854450 | 20133359 | 20135681 | d7Mseg3660 | 9149 |
| 7 | 155863500 | 155866700 | 20116365 | 20116820 | d7Mseg3661 | 9150 |
| 7 | 155970350 | 155971650 | 20008177 | 20009478 | d7Mseg3665 | 9151 |
| 7 | 156030450 | 156031650 | 19933930 | 19934962 | d7Mseg3666 | 9152 |
| 7 | 156065150 | 156067100 | 19903898 | 19905882 | d7Mseg3667 | 9153 |
| 7 | 156082200 | 156083700 | 19886421 | 19887967 | d7Mseg3668 | 9154 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 156163900 | 156165350 | 19799037 | 19800050 | d7Mseg3669 | 9155 |
| 7 | 156202700 | 156204100 | 19762439 | 19763702 | d7Mseg3670 | 9156 |
| 7 | 156208000 | 156209950 | 19756581 | 19757848 | d7Mseg3671 | 9157 |
| 7 | 156223400 | 156225250 | 19741414 | 19742908 | d7Mseg3672 | 9158 |
| 7 | 156248200 | 156250000 | 19718352 | 19720075 | d7Mseg3673 | 9159 |
| 7 | 156264500 | 156266000 | 19702474 | 19703946 | d7Mseg3674 | 9160 |
| 7 | 156272650 | 156274300 | 19692640 | 19694087 | d7Mseg3675 | 9161 |
| 7 | 156327600 | 156329350 | 19635805 | 19638252 | d7Mseg3676 | 9162 |
| 7 | 156336700 | 156337750 | 19628440 | 19630205 | d7Mseg3677 | 9163 |
| 7 | 156353000 | 156354750 | 19610530 | 19612194 | d7Mseg3678 | 9164 |
| 7 | 156370950 | 156372450 | 19591353 | 19592414 | d7Mseg3679 | 9165 |
| 7 | 156396800 | 156398550 | 19565692 | 19567526 | d7Mseg3680 | 9166 |
| 7 | 156410850 | 156413050 | 19552602 | 19554763 | d7Mseg3681 | 9167 |
| 7 | 156421000 | 156428900 | 19530521 | 19539789 | d7Mseg3682 | 9168 |
| 7 | 156438500 | 156439650 | 19507194 | 19509568 | d7Mseg3683 | 9169 |
| 7 | 156516300 | 156518000 | 19433220 | 19442283 | d7Mseg3684 | 9170 |
| 7 | 156520400 | 156521950 | 19427941 | 19428602 | d7Mseg3685 | 9171 |
| 7 | 156573550 | 156576200 | 19362199 | 19364908 | d7Mseg3686 | 9172 |
| 7 | 156577950 | 156579850 | 19358186 | 19359792 | d7Mseg3687 | 9173 |
| 7 | 156637700 | 156639100 | 19318361 | 19318925 | d7Mseg3691 | 9174 |
| 7 | 156677050 | 156678350 | 19269741 | 19270971 | d7Mseg3692 | 9175 |
| 7 | 156693250 | 156694750 | 19255838 | 19256631 | d7Mseg3693 | 9176 |
| 7 | 156747750 | 156749200 | 19220733 | 19221544 | d7Mseg3694 | 9177 |
| 7 | 156751200 | 156754650 | 19217027 | 19217480 | d7Mseg3695 | 9178 |
| 7 | 156781350 | 156782900 | 19187590 | 19189211 | d7Mseg3696 | 9179 |
| 7 | 156793500 | 156795350 | 19180256 | 19181871 | d7Mseg3697 | 9180 |
| 7 | 156808400 | 156809400 | 19170885 | 19171807 | d7Mseg3698 | 9181 |
| 7 | 156819150 | 156824150 | 19144922 | 19151607 | d7Mseg3699 | 9182 |
| 7 | 156827050 | 156832350 | 19136810 | 19142338 | d7Mseg3700 | 9183 |
| 7 | 156847650 | 156850300 | 19119895 | 19122036 | d7Mseg3701 | 9184 |
| 7 | 156869500 | 156873650 | 19093266 | 19099449 | d7Mseg3702 | 9185 |
| 7 | 156885300 | 156886650 | 19074354 | 19074877 | d7Mseg3703 | 9186 |
| 7 | 156907450 | 156909250 | 19042535 | 19045689 | d7Mseg3704 | 9187 |
| 7 | 156924600 | 156925850 | 19017828 | 19019661 | d7Mseg3705 | 9188 |
| 7 | 156938150 | 156941850 | 19001009 | 19005346 | d7Mseg3706 | 9189 |
| 7 | 157034600 | 157036250 | 18906777 | 18908444 | d7Mseg3707 | 9190 |
| 7 | 157037950 | 157039650 | 18902896 | 18904851 | d7Mseg3708 | 9191 |
| 7 | 157075300 | 157077100 | 18807052 | 18818223 | d7Mseg3710 | 9192 |
| 7 | 157087900 | 157089000 | 18792722 | 18793330 | d7Mseg3711 | 9193 |
| 7 | 157136950 | 157138600 | 18740075 | 18740711 | d7Mseg3712 | 9194 |
| 7 | 157145700 | 157147100 | 18731761 | 18732705 | d7Mseg3713 | 9195 |
| 7 | 157172950 | 157174650 | 18717474 | 18718966 | d7Mseg3714 | 9196 |
| 7 | 157184600 | 157186450 | 18712330 | 18712944 | d7Mseg3715 | 9197 |
| 7 | 157193050 | 157194550 | 18704292 | 18706464 | d7Mseg3716 | 9198 |
| 7 | 157230350 | 157232000 | 18660553 | 18662100 | d7Mseg3717 | 9199 |
| 7 | 157241500 | 157242700 | 18650360 | 18651565 | d7Mseg3718 | 9200 |
| 7 | 157253100 | 157254750 | 18638158 | 18639878 | d7Mseg3719 | 9201 |
| 7 | 157268300 | 157269800 | 18624941 | 18626585 | d7Mseg3720 | 9202 |
| 7 | 157322300 | 157326650 | 18570053 | 18571290 | d7Mseg3722 | 9203 |
| 7 | 157337000 | 157338950 | 18555617 | 18555869 | d7Mseg3723 | 9204 |
| 7 | 157347250 | 157349350 | 18539273 | 18541551 | d7Mseg3724 | 9205 |
| 7 | 157360000 | 157361300 | 18530849 | 18531087 | d7Mseg3725 | 9206 |
| 7 | 157372600 | 157374450 | 18513158 | 18515812 | d7Mseg3726 | 9207 |
| 7 | 157378250 | 157380550 | 18508174 | 18509568 | d7Mseg3727 | 9208 |
| 7 | 157416900 | 157418500 | 18455960 | 18457412 | d7Mseg3728 | 9209 |
| 7 | 157431550 | 157434400 | 18441880 | 18444759 | d7Mseg3729 | 9210 |
| 7 | 157600100 | 157601850 | 18371731 | 18373454 | d7Mseg3737 | 9211 |
| 7 | 157806950 | 157810800 | 18162013 | 18162693 | d7Mseg3743 | 9212 |
| 7 | 157813300 | 157814500 | 18165052 | 18166634 | d7Mseg3744 | 9213 |
| 7 | 157884400 | 157886300 | 18129247 | 18129866 | d7Mseg3745 | 9214 |
| 7 | 157894250 | 157896750 | 18107141 | 18108043 | d7Mseg3746 | 9215 |
| 7 | 157909600 | 157910800 | 18093365 | 18094482 | d7Mseg3747 | 9216 |
| 7 | 157934300 | 157936200 | 18061687 | 18065612 | d7Mseg3748 | 9217 |
| 7 | 157942500 | 157944100 | 18056166 | 18058138 | d7Mseg3749 | 9218 |
| 7 | 157956150 | 157957800 | 18041407 | 18043092 | d7Mseg3750 | 9219 |
| 7 | 157966900 | 157968850 | 18030549 | 18031571 | d7Mseg3751 | 9220 |
| 7 | 157972950 | 157974750 | 18023228 | 18026100 | d7Mseg3752 | 9221 |
| 7 | 157989950 | 157991700 | 18016193 | 18018966 | d7Mseg3753 | 9222 |
| 7 | 158022100 | 158023900 | 17984861 | 17986656 | d7Mseg3754 | 9223 |
| 7 | 158032000 | 158034200 | 17976679 | 17978311 | d7Mseg3755 | 9224 |
| 7 | 158048750 | 158049900 | 17964595 | 17965716 | d7Mseg3756 | 9225 |
| 7 | 158099500 | 158100700 | 17914594 | 17915912 | d7Mseg3758 | 9226 |
| 7 | 158123700 | 158125400 | 17899971 | 17901823 | d7Mseg3760 | 9227 |
| 7 | 158131800 | 158132850 | 17893090 | 17893977 | d7Mseg3761 | 9228 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 158152800 | 158159150 | 17875193 | 17881545 | d7Mseg3762 | 9229 |
| 7 | 158160800 | 158165450 | 17869197 | 17873683 | d7Mseg3763 | 9230 |
| 7 | 158167500 | 158169750 | 17864739 | 17867567 | d7Mseg3764 | 9231 |
| 7 | 158171950 | 158175900 | 17858359 | 17862317 | d7Mseg3765 | 9232 |
| 7 | 158177800 | 158180200 | 17854021 | 17856909 | d7Mseg3766 | 9233 |
| 7 | 158187400 | 158189050 | 17845470 | 17847194 | d7Mseg3767 | 9234 |
| 7 | 158222800 | 158224650 | 17810797 | 17812620 | d7Mseg3768 | 9235 |
| 7 | 158227850 | 158231800 | 17805582 | 17807246 | d7Mseg3769 | 9236 |
| 7 | 158256150 | 158257750 | 17768522 | 17769580 | d7Mseg3772 | 9237 |
| 7 | 158266150 | 158267200 | 17760642 | 17761760 | d7Mseg3774 | 9238 |
| 7 | 158273150 | 158274350 | 17750984 | 17752196 | d7Mseg3775 | 9239 |
| 7 | 158281350 | 158282950 | 17741640 | 17743260 | d7Mseg3776 | 9240 |
| 7 | 158300000 | 158301200 | 17720045 | 17721921 | d7Mseg3777 | 9241 |
| 7 | 158307850 | 158309600 | 17710389 | 17711788 | d7Mseg3778 | 9242 |
| 7 | 158311950 | 158313050 | 17706139 | 17708100 | d7Mseg3779 | 9243 |
| 7 | 158332650 | 158333750 | 17686846 | 17687985 | d7Mseg3780 | 9244 |
| 7 | 158344900 | 158348950 | 17671633 | 17675749 | d7Mseg3781 | 9245 |
| 7 | 158354100 | 158356150 | 17662194 | 17666106 | d7Mseg3782 | 9246 |
| 7 | 158362350 | 158363600 | 17654308 | 17655578 | d7Mseg3783 | 9247 |
| 7 | 158366400 | 158367900 | 17647756 | 17651988 | d7Mseg3784 | 9248 |
| 7 | 158369900 | 158371600 | 17645250 | 17646047 | d7Mseg3785 | 9249 |
| 7 | 158372700 | 158374350 | 17641646 | 17642872 | d7Mseg3786 | 9250 |
| 7 | 158385000 | 158386450 | 17628573 | 17629690 | d7Mseg3787 | 9251 |
| 7 | 158400450 | 158402400 | 17612859 | 17614865 | d7Mseg3788 | 9252 |
| 7 | 158407100 | 158408950 | 17605732 | 17608201 | d7Mseg3789 | 9253 |
| 7 | 158411850 | 158413350 | 17600863 | 17602280 | d7Mseg3790 | 9254 |
| 7 | 158436300 | 158437750 | 17566158 | 17566874 | d7Mseg3791 | 9255 |
| 7 | 158439500 | 158441000 | 17563937 | 17564728 | d7Mseg3792 | 9256 |
| 7 | 158447000 | 158448350 | 17555628 | 17557193 | d7Mseg3793 | 9257 |
| 7 | 158452300 | 158453850 | 17549904 | 17551190 | d7Mseg3794 | 9258 |
| 7 | 158456400 | 158457750 | 17546584 | 17547101 | d7Mseg3795 | 9259 |
| 7 | 158467350 | 158468800 | 17536301 | 17537187 | d7Mseg3796 | 9260 |
| 7 | 158477750 | 158480550 | 17523733 | 17526556 | d7Mseg3797 | 9261 |
| 7 | 158512350 | 158514350 | 17486485 | 17488684 | d7Mseg3798 | 9262 |
| 7 | 158516450 | 158518100 | 17483117 | 17484456 | d7Mseg3799 | 9263 |
| 7 | 158544800 | 158545800 | 17448946 | 17450054 | d7Mseg3800 | 9264 |
| 7 | 158580050 | 158582050 | 17409254 | 17413200 | d7Mseg3801 | 9265 |
| 7 | 158594350 | 158598550 | 17392706 | 17396719 | d7Mseg3802 | 9266 |
| 7 | 158604100 | 158605600 | 17387098 | 17388655 | d7Mseg3803 | 9267 |
| 7 | 158655250 | 158657000 | 17348116 | 17349522 | d7Mseg3804 | 9268 |
| 7 | 158672700 | 158674300 | 17313280 | 17314399 | d7Mseg3805 | 9269 |
| 7 | 158703700 | 158705450 | 17270576 | 17271638 | d7Mseg3806 | 9270 |
| 7 | 158716500 | 158718050 | 17260053 | 17261508 | d7Mseg3807 | 9271 |
| 7 | 158763350 | 158764950 | 17217788 | 17218072 | d7Mseg3808 | 9272 |
| 7 | 158848300 | 158850200 | 17171100 | 17171878 | d7Mseg3810 | 9273 |
| 7 | 158959750 | 158961000 | 17070410 | 17071287 | d7Mseg3812 | 9274 |
| 7 | 158965750 | 158967350 | 17061835 | 17062371 | d7Mseg3813 | 9275 |
| 7 | 159005900 | 159007700 | 17020930 | 17022484 | d7Mseg3814 | 9276 |
| 7 | 159070450 | 159074800 | 16972503 | 16975038 | d7Mseg3816 | 9277 |
| 7 | 159081150 | 159082600 | 16963951 | 16965309 | d7Mseg3817 | 9278 |
| 7 | 159087800 | 159089350 | 16943710 | 16945316 | d7Mseg3818 | 9279 |
| 7 | 159090800 | 159092150 | 16942409 | 16942570 | d7Mseg3819 | 9280 |
| 7 | 159140650 | 159142400 | 16925579 | 16926170 | d7Mseg3821 | 9281 |
| 7 | 159196600 | 159198200 | 16888587 | 16890265 | d7Mseg3822 | 9282 |
| 7 | 159320700 | 159322150 | 16753321 | 16754269 | d7Mseg3823 | 9283 |
| 7 | 159325300 | 159326500 | 16737653 | 16738512 | d7Mseg3824 | 9284 |
| 7 | 159393400 | 159395300 | 16677446 | 16677747 | d7Mseg3828 | 9285 |
| 7 | 159465400 | 159467200 | 16609389 | 16609668 | d7Mseg3829 | 9286 |
| 7 | 159565600 | 159566750 | 16508485 | 16510219 | d7Mseg3830 | 9287 |
| 7 | 159568750 | 159570400 | 16502395 | 16502963 | d7Mseg3831 | 9288 |
| 7 | 159598350 | 159600400 | 16475880 | 16477721 | d7Mseg3832 | 9289 |
| 7 | 159629200 | 159630950 | 16449924 | 16451704 | d7Mseg3833 | 9290 |
| 7 | 159733200 | 159735050 | 16255454 | 16257479 | d7Mseg3836 | 9291 |
| 7 | 159767900 | 159769500 | 16307082 | 16308258 | d7Mseg3837 | 9292 |
| 7 | 159825000 | 159826750 | 16333884 | 16334119 | d7Mseg3838 | 9293 |
| 7 | 159856000 | 159857200 | 16231566 | 16232313 | d7Mseg3839 | 9294 |
| 7 | 159858700 | 159860300 | 16228672 | 16229883 | d7Mseg3840 | 9295 |
| 7 | 159862700 | 159864150 | 16226766 | 16227212 | d7Mseg3841 | 9296 |
| 7 | 159889050 | 159890850 | 16204511 | 16205766 | d7Mseg3842 | 9297 |
| 7 | 159950050 | 159952000 | 16171612 | 16173876 | d7Mseg3844 | 9298 |
| 7 | 160039650 | 160041300 | 16105055 | 16105359 | d7Mseg3845 | 9299 |
| 7 | 160050550 | 160052250 | 16099494 | 16100037 | d7Mseg3846 | 9300 |
| 7 | 160053700 | 160055250 | 16097410 | 16098623 | d7Mseg3847 | 9301 |
| 7 | 160074850 | 160076800 | 16079614 | 16081468 | d7Mseg3848 | 9302 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 160110900 | 160114550 | 16032227 | 16034284 | d7Mseg3849 | 9303 |
| 7 | 160125150 | 160126700 | 16020782 | 16022269 | d7Mseg3850 | 9304 |
| 7 | 160165300 | 160167050 | 16004352 | 16005544 | d7Mseg3854 | 9305 |
| 7 | 160175500 | 160179400 | 15998005 | 15999524 | d7Mseg3855 | 9306 |
| 7 | 160185900 | 160187550 | 15993783 | 15994666 | d7Mseg3856 | 9307 |
| 7 | 160242850 | 160244600 | 15960716 | 15961007 | d7Mseg3859 | 9308 |
| 7 | 160305750 | 160307450 | 15913061 | 15921504 | d7Mseg3860 | 9309 |
| 7 | 160319550 | 160320550 | 15903185 | 15904160 | d7Mseg3861 | 9310 |
| 7 | 160345250 | 160347350 | 15872654 | 15874787 | d7Mseg3862 | 9311 |
| 7 | 160365350 | 160367100 | 15848626 | 15850288 | d7Mseg3863 | 9312 |
| 7 | 160371650 | 160373050 | 15842639 | 15843879 | d7Mseg3864 | 9313 |
| 7 | 160394650 | 160396700 | 15808198 | 15811430 | d7Mseg3865 | 9314 |
| 7 | 160425400 | 160427050 | 15793002 | 15794628 | d7Mseg3866 | 9315 |
| 7 | 160465750 | 160467450 | 15755251 | 15756599 | d7Mseg3869 | 9316 |
| 7 | 160525750 | 160528700 | 15682438 | 15686472 | d7Mseg3871 | 9317 |
| 7 | 160536350 | 160538050 | 15671976 | 15672622 | d7Mseg3872 | 9318 |
| 7 | 160539750 | 160541200 | 15663972 | 15665034 | d7Mseg3873 | 9319 |
| 7 | 160562550 | 160564000 | 15635171 | 15637203 | d7Mseg3874 | 9320 |
| 7 | 160568700 | 160570700 | 15629434 | 15630996 | d7Mseg3875 | 9321 |
| 7 | 160591850 | 160593500 | 15610568 | 15612173 | d7Mseg3876 | 9322 |
| 7 | 160594900 | 160596700 | 15609012 | 15610231 | d7Mseg3877 | 9323 |
| 7 | 160609450 | 160610700 | 15593687 | 15594447 | d7Mseg3878 | 9324 |
| 7 | 160633550 | 160635350 | 15567581 | 15569062 | d7Mseg3879 | 9325 |
| 7 | 160665900 | 160667150 | 15546868 | 15547017 | d7Mseg3880 | 9326 |
| 7 | 160670400 | 160671400 | 15543003 | 15543166 | d7Mseg3881 | 9327 |
| 7 | 160681600 | 160683750 | 15530072 | 15533635 | d7Mseg3882 | 9328 |
| 7 | 160690250 | 160691800 | 15521928 | 15523039 | d7Mseg3883 | 9329 |
| 7 | 160731250 | 160732850 | 15478841 | 15480483 | d7Mseg3885 | 9330 |
| 7 | 160734400 | 160736800 | 15475688 | 15477656 | d7Mseg3886 | 9331 |
| 7 | 160751900 | 160753550 | 15457599 | 15463065 | d7Mseg3887 | 9332 |
| 7 | 160796900 | 160798850 | 15413668 | 15415549 | d7Mseg3889 | 9333 |
| 7 | 160806950 | 160808700 | 15406916 | 15408400 | d7Mseg3890 | 9334 |
| 7 | 160816950 | 160818100 | 15395182 | 15396967 | d7Mseg3891 | 9335 |
| 7 | 160884250 | 160886000 | 15319533 | 15320260 | d7Mseg3893 | 9336 |
| 7 | 160902900 | 160904000 | 62518794 | 62519151 | d7Mseg3894 | 9337 |
| 7 | 160943300 | 160948650 | 15281443 | 15289262 | d7Mseg3896 | 9338 |
| 7 | 160972350 | 160974000 | 15266541 | 15267669 | d7Mseg3898 | 9339 |
| 7 | 161075700 | 161076800 | 15187715 | 15188700 | d7Mseg3900 | 9340 |
| 7 | 161079700 | 161081400 | 15183461 | 15185574 | d7Mseg3901 | 9341 |
| 7 | 161236300 | 161238000 | 15088564 | 15089476 | d7Mseg3905 | 9342 |
| 7 | 161245750 | 161247500 | 15078794 | 15079222 | d7Mseg3906 | 9343 |
| 7 | 161281500 | 161282700 | 15045434 | 15050767 | d7Mseg3907 | 9344 |
| 7 | 161305050 | 161306250 | 15018950 | 15019189 | d7Mseg3908 | 9345 |
| 7 | 161380050 | 161381550 | 14934263 | 14935279 | d7Mseg3910 | 9346 |
| 7 | 161389200 | 161391000 | 14923116 | 14927495 | d7Mseg3911 | 9347 |
| 7 | 161489500 | 161491200 | 14817931 | 14819938 | d7Mseg3913 | 9348 |
| 7 | 161498000 | 161499650 | 14804662 | 14805869 | d7Mseg3914 | 9349 |
| 7 | 161554350 | 161555950 | 14763241 | 14764225 | d7Mseg3916 | 9350 |
| 7 | 161558450 | 161560200 | 14760841 | 14761695 | d7Mseg3917 | 9351 |
| 7 | 161623450 | 161624550 | 14700545 | 14707141 | d7Mseg3918 | 9352 |
| 7 | 161637200 | 161638600 | 14682156 | 14683516 | d7Mseg3919 | 9353 |
| 7 | 161661000 | 161664500 | 14662936 | 14665723 | d7Mseg3920 | 9354 |
| 7 | 161723200 | 161724950 | 14595902 | 14597908 | d7Mseg3921 | 9355 |
| 7 | 161742950 | 161746350 | 14565249 | 14569346 | d7Mseg3922 | 9356 |
| 7 | 161757400 | 161758600 | 14553216 | 14554433 | d7Mseg3923 | 9357 |
| 7 | 161772150 | 161773650 | 14537330 | 14539003 | d7Mseg3924 | 9358 |
| 7 | 162318400 | 162319800 | 14247638 | 14249710 | d7Mseg3928 | 9359 |
| 7 | 162490200 | 162491350 | 14117238 | 14117556 | d7Mseg3930 | 9360 |
| 7 | 162545650 | 162549900 | 14087147 | 14090777 | d7Mseg3932 | 9361 |
| 7 | 162571800 | 162575750 | 14078089 | 14078585 | d7Mseg3933 | 9362 |
| 7 | 162580250 | 162581750 | 14074400 | 14075622 | d7Mseg3934 | 9363 |
| 7 | 162649100 | 162650850 | 13989303 | 13989948 | d7Mseg3935 | 9364 |
| 7 | 162655350 | 162657350 | 13983977 | 13985610 | d7Mseg3936 | 9365 |
| 7 | 162673400 | 162679400 | 13954346 | 13967216 | d7Mseg3937 | 9366 |
| 7 | 162688100 | 162689800 | 13945319 | 13946151 | d7Mseg3938 | 9367 |
| 7 | 162694500 | 162695500 | 13938023 | 13939350 | d7Mseg3939 | 9368 |
| 7 | 162711350 | 162712750 | 13920659 | 13921757 | d7Mseg3940 | 9369 |
| 7 | 162715450 | 162716700 | 13917589 | 13918237 | d7Mseg3941 | 9370 |
| 7 | 162774350 | 162775450 | 13844855 | 13845263 | d7Mseg3942 | 9371 |
| 7 | 162783300 | 162785150 | 13832733 | 13834670 | d7Mseg3943 | 9372 |
| 7 | 162792050 | 162793750 | 13824572 | 13825325 | d7Mseg3944 | 9373 |
| 7 | 162794950 | 162796100 | 13822721 | 13823685 | d7Mseg3945 | 9374 |
| 7 | 162809550 | 162812800 | 13802456 | 13805049 | d7Mseg3946 | 9375 |
| 7 | 162869100 | 162870900 | 13756425 | 13757988 | d7Mseg3947 | 9376 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| 7 | 162877500 | 162879500 | 13750750 | 13753578 | d7Mseg3948 | 9377 |
| 7 | 162910650 | 162912350 | 13712690 | 13714036 | d7Mseg3949 | 9378 |
| 7 | 162925100 | 162926700 | 13694633 | 13695493 | d7Mseg3950 | 9379 |
| 7 | 162946950 | 162949350 | 13670688 | 13672284 | d7Mseg3951 | 9380 |
| 7 | 162955150 | 162956850 | 13665773 | 13666890 | d7Mseg3952 | 9381 |
| 7 | 162971200 | 162972350 | 13640589 | 13641010 | d7Mseg3953 | 9382 |
| 7 | 162993600 | 162995100 | 13618014 | 13618305 | d7Mseg3954 | 9383 |
| 7 | 163015600 | 163017100 | 13595709 | 13598183 | d7Mseg3955 | 9384 |
| 7 | 163022500 | 163026200 | 13585343 | 13588986 | d7Mseg3956 | 9385 |
| 7 | 163112100 | 163113100 | 13490965 | 13491333 | d7Mseg3957 | 9386 |
| 7 | 163115700 | 163116750 | 13488562 | 13489141 | d7Mseg3958 | 9387 |
| 7 | 163140600 | 163142350 | 13472970 | 13473661 | d7Mseg3959 | 9388 |
| 7 | 163197000 | 163198800 | 13419794 | 13421210 | d7Mseg3961 | 9389 |
| 7 | 163213850 | 163215350 | 13401755 | 13402474 | d7Mseg3962 | 9390 |
| 7 | 163232900 | 163234750 | 13383176 | 13385440 | d7Mseg3963 | 9391 |
| 7 | 163290550 | 163292150 | 13351902 | 13352109 | d7Mseg3964 | 9392 |
| 7 | 163329150 | 163330950 | 13307690 | 13307949 | d7Mseg3965 | 9393 |
| 7 | 163440450 | 163442000 | 13217591 | 13217945 | d7Mseg3966 | 9394 |
| 7 | 163448550 | 163450150 | 13208901 | 13211039 | d7Mseg3967 | 9395 |
| 7 | 163510900 | 163512850 | 13138849 | 13139323 | d7Mseg3968 | 9396 |
| 7 | 163538850 | 163540800 | 13110200 | 13111787 | d7Mseg3969 | 9397 |
| 7 | 163570500 | 163571850 | 13077748 | 13078839 | d7Mseg3970 | 9398 |
| 7 | 163576150 | 163577500 | 13069780 | 13070648 | d7Mseg3971 | 9399 |
| 7 | 163595000 | 163597000 | 13043120 | 13044105 | d7Mseg3972 | 9400 |
| 7 | 163635100 | 163636800 | 13002804 | 13004920 | d7Mseg3973 | 9401 |
| 7 | 163645250 | 163648400 | 12991834 | 12995106 | d7Mseg3974 | 9402 |
| 7 | 163650850 | 163652250 | 12988549 | 12989008 | d7Mseg3975 | 9403 |
| 7 | 163712250 | 163714450 | 12920512 | 12921530 | d7Mseg3976 | 9404 |
| 7 | 163790500 | 163791850 | 12836869 | 12837610 | d7Mseg3978 | 9405 |
| 7 | 163810250 | 163812250 | 12817303 | 12818970 | d7Mseg3979 | 9406 |
| 7 | 163818250 | 163825700 | 12804545 | 12811333 | d7Mseg3980 | 9407 |
| 7 | 163851150 | 163852900 | 12778335 | 12778683 | d7Mseg3981 | 9408 |
| 7 | 163855300 | 163856800 | 12773739 | 12775482 | d7Mseg3982 | 9409 |
| 7 | 163967950 | 163969150 | 12687052 | 12687310 | d7Mseg3984 | 9410 |
| 7 | 163977000 | 163978450 | 12677461 | 12677754 | d7Mseg3985 | 9411 |
| 7 | 163990500 | 163992150 | 12666294 | 12667710 | d7Mseg3986 | 9412 |
| 7 | 164044800 | 164046750 | 12629193 | 12630773 | d7Mseg3987 | 9413 |
| 7 | 164067000 | 164069100 | 12617812 | 12618660 | d7Mseg3988 | 9414 |
| 7 | 164072300 | 164075250 | 12614831 | 12615812 | d7Mseg3989 | 9415 |
| 7 | 164078000 | 164080000 | 12610568 | 12611868 | d7Mseg3990 | 9416 |
| 7 | 164090100 | 164091950 | 12597023 | 12598120 | d7Mseg3991 | 9417 |
| 7 | 164133650 | 164136100 | 12567467 | 12569464 | d7Mseg3992 | 9418 |
| 7 | 164164450 | 164166400 | 12517492 | 12518769 | d7Mseg3993 | 9419 |
| 7 | 164168350 | 164169400 | 12514816 | 12515872 | d7Mseg3994 | 9420 |
| 7 | 164211300 | 164212350 | 12470607 | 12471694 | d7Mseg3996 | 9421 |
| 7 | 164221200 | 164223700 | 12461865 | 12464316 | d7Mseg3998 | 9422 |
| 7 | 164225050 | 164226650 | 12459042 | 12460360 | d7Mseg3999 | 9423 |
| 7 | 164253550 | 164255000 | 12428520 | 12429933 | d7Mseg4000 | 9424 |
| 7 | 164299600 | 164301550 | 12390305 | 12391689 | d7Mseg4001 | 9425 |
| 7 | 164317450 | 164319850 | 12378648 | 12380082 | d7Mseg4002 | 9426 |
| 7 | 164330500 | 164332050 | 12362525 | 12364290 | d7Mseg4003 | 9427 |
| 7 | 164346750 | 164348000 | 12346699 | 12348304 | d7Mseg4004 | 9428 |
| 7 | 164354200 | 164355800 | 12340287 | 12341588 | d7Mseg4005 | 9429 |
| 7 | 164434950 | 164436800 | 12272025 | 12272718 | d7Mseg4006 | 9430 |
| 7 | 164447950 | 164449550 | 12260594 | 12262785 | d7Mseg4008 | 9431 |
| 7 | 164513100 | 164515200 | 12202605 | 12204549 | d7Mseg4009 | 9432 |
| 7 | 164552550 | 164554400 | 12162347 | 12163817 | d7Mseg4011 | 9433 |
| 7 | 164557250 | 164563100 | 12154660 | 12160662 | d7Mseg4012 | 9434 |
| 7 | 164635150 | 164636800 | 12097633 | 12098895 | d7Mseg4014 | 9435 |
| 7 | 164672800 | 164674200 | 12075323 | 12075826 | d7Mseg4016 | 9436 |
| 7 | 164714850 | 164717700 | 12034565 | 12038500 | d7Mseg4017 | 9437 |
| 7 | 164750200 | 164752150 | 12007922 | 12009274 | d7Mseg4018 | 9438 |
| 7 | 164758500 | 164760150 | 11996895 | 11998040 | d7Mseg4019 | 9439 |
| 7 | 164771200 | 164772450 | 11984879 | 11986032 | d7Mseg4020 | 9440 |
| 7 | 164777150 | 164778600 | 11977102 | 11978777 | d7Mseg4021 | 9441 |
| 7 | 164997350 | 165002300 | 11848071 | 11849766 | d7Mseg4025 | 9442 |
| 7 | 165006750 | 165008550 | 11843708 | 11845086 | d7Mseg4026 | 9443 |
| 7 | 165152700 | 165154600 | 11744793 | 11746727 | d7Mseg4029 | 9444 |
| 7 | 165161850 | 165163800 | 11736502 | 11738345 | d7Mseg4030 | 9445 |
| 7 | 165188800 | 165190500 | 11716811 | 11717463 | d7Mseg4031 | 9446 |
| 7 | 165210250 | 165211550 | 11705495 | 11706467 | d7Mseg4032 | 9447 |
| 7 | 165215800 | 165217400 | 11695662 | 11697464 | d7Mseg4033 | 9448 |
| 7 | 165221800 | 165224100 | 11689558 | 11691909 | d7Mseg4034 | 9449 |
| 7 | 165227600 | 165228750 | 11686051 | 11686880 | d7Mseg4035 | 9450 |

TABLE IVB-continued

Mouse Binding Sites with Human Liftovers

| Cell/ Day | Mouse Start | Mouse end | Human start | Human end | Segment name | SEQ ID NO: |
|---|---|---|---|---|---|---|
| 7 | 165232150 | 165237050 | 11680029 | 11685033 | d7Mseg4036 | 9451 |
| 7 | 165258400 | 165259750 | 11654579 | 11655709 | d7Mseg4037 | 9452 |
| 7 | 165300150 | 165301800 | 11623649 | 11624667 | d7Mseg4039 | 9453 |
| 7 | 165310300 | 165312200 | 11611236 | 11613127 | d7Mseg4040 | 9454 |
| 7 | 165330300 | 165331950 | 11587603 | 11588494 | d7Mseg4041 | 9455 |
| 7 | 165382350 | 165384050 | 11532746 | 11534360 | d7Mseg4042 | 9456 |
| 7 | 165394000 | 165395650 | 11517684 | 11518499 | d7Mseg4043 | 9457 |
| 7 | 165410700 | 165412600 | 11506593 | 11509034 | d7Mseg4044 | 9458 |
| 7 | 165460500 | 165462450 | 11456195 | 11457315 | d7Mseg4045 | 9459 |
| 7 | 165473150 | 165476600 | 11443827 | 11447248 | d7Mseg4046 | 9460 |
| 7 | 165555900 | 165557500 | 11363246 | 11365143 | d7Mseg4047 | 9461 |
| 7 | 165630250 | 165631250 | 11306984 | 11307601 | d7Mseg4048 | 9462 |
| 7 | 165635950 | 165637850 | 11298533 | 11299503 | d7Mseg4049 | 9463 |
| 7 | 165677150 | 165679000 | 11210925 | 11212213 | d7Mseg4050 | 9464 |
| 7 | 165720100 | 165721450 | 11173030 | 11174543 | d7Mseg4051 | 9465 |
| 7 | 165731800 | 165733450 | 11166321 | 11168458 | d7Mseg4052 | 9466 |
| 7 | 165791050 | 165792400 | 11102656 | 11104386 | d7Mseg4055 | 9467 |
| 7 | 165891050 | 165892850 | 11028156 | 11029924 | d7Mseg4058 | 9468 |
| 7 | 165904200 | 165905700 | 11010938 | 11012447 | d7Mseg4060 | 9469 |
| 7 | 165994900 | 165996350 | 10951348 | 10951854 | d7Mseg4062 | 9470 |
| 7 | 166121700 | 166123350 | 10851640 | 10853211 | d7Mseg4064 | 9471 |
| 7 | 166129550 | 166131300 | 10837425 | 10839146 | d7Mseg4065 | 9472 |
| 7 | 166170450 | 166174000 | 10737875 | 10791476 | d7Mseg4066 | 9473 |
| 7 | 166220100 | 166221350 | 10705777 | 10705972 | d7Mseg4067 | 9474 |
| 7 | 166280950 | 166282450 | 10628207 | 10630024 | d7Mseg4068 | 9475 |
| 7 | 166317350 | 166319550 | 10586688 | 10588813 | d7Mseg4069 | 9476 |
| 7 | 166340200 | 166341750 | 10564244 | 10566188 | d7Mseg4070 | 9477 |
| 7 | 166401250 | 166402300 | 10493356 | 10494554 | d7Mseg4071 | 9478 |
| 7 | 166404250 | 166406600 | 10488260 | 10491055 | d7Mseg4072 | 9479 |
| 7 | 166409850 | 166412250 | 10483386 | 10485756 | d7Mseg4073 | 9480 |
| 7 | 166415700 | 166417350 | 10460030 | 10461598 | d7Mseg4074 | 9481 |
| 7 | 166421500 | 166423550 | 10437413 | 10443204 | d7Mseg4075 | 9482 |
| M | 5748350 | 5749350 | 51076415 | 51076838 | MMseg11 | 9483 |
| M | 6151800 | 6153600 | 50387471 | 50389367 | MMseg13 | 9484 |
| M | 6251450 | 6253100 | 50297516 | 50298857 | MMseg14 | 9485 |
| M | 6354150 | 6359200 | 50210609 | 50215118 | MMseg15 | 9486 |
| M | 6444600 | 6445900 | 50174373 | 50175731 | MMseg16 | 9487 |
| M | 6451700 | 6453400 | 50164201 | 50166211 | MMseg17 | 9488 |
| M | 6645900 | 6647150 | 49964146 | 49964441 | MMseg20 | 9489 |
| M | 6871600 | 6873400 | 49721136 | 49722419 | MMseg21 | 9490 |
| M | 6895150 | 6896750 | 49686843 | 49688480 | MMseg22 | 9491 |
| M | 6963850 | 6965200 | 49628587 | 49629075 | MMseg23 | 9492 |
| M | 7182750 | 7184300 | 49089742 | 49091735 | MMseg26 | 9493 |
| M | 7216850 | 7218700 | 49053893 | 49055605 | MMseg27 | 9494 |
| M | 7307150 | 7308550 | 48927622 | 48930003 | MMseg28 | 9495 |
| M | 7365450 | 7366900 | 48858892 | 48860456 | MMseg29 | 9496 |
| M | 7498350 | 7500750 | 48689020 | 48692360 | MMseg30 | 9497 |
| M | 7752000 | 7753650 | 48397691 | 48399229 | MMseg32 | 9498 |
| M | 7766550 | 7767650 | 48381991 | 48382586 | MMseg33 | 9499 |
| M | 9012500 | 9013500 | 37672040 | 37673140 | MMseg36 | 9500 |
| M | 9365300 | 9367150 | 37800545 | 37802015 | MMseg39 | 9501 |
| M | 9740000 | 9741000 | 38132920 | 38133612 | MMseg41 | 9502 |
| M | 9762250 | 9763600 | 38152546 | 38154871 | MMseg42 | 9503 |
| M | 9815700 | 9817000 | 38200888 | 38202758 | MMseg43 | 9504 |
| M | 9943300 | 9944700 | 38315122 | 38315456 | MMseg44 | 9505 |
| M | 10221200 | 10222600 | 38606653 | 38607440 | MMseg45 | 9506 |
| M | 10251500 | 10253050 | 38626548 | 38627586 | MMseg46 | 9507 |
| M | 10486550 | 10487700 | 38875963 | 38877219 | MMseg47 | 9508 |
| M | 10751900 | 10753500 | 39082845 | 39084269 | MMseg49 | 9509 |
| M | 10759300 | 10760500 | 39089012 | 39090211 | MMseg50 | 9510 |
| M | 10778750 | 10780600 | 39108583 | 39110442 | MMseg51 | 9511 |
| M | 10971250 | 10972650 | 39284868 | 39286426 | MMseg52 | 9512 |
| M | 11124000 | 11125500 | 39430776 | 39432700 | MMseg53 | 9513 |
| M | 11262550 | 11264300 | 39569328 | 39570589 | MMseg54 | 9514 |
| M | 11383300 | 11385350 | 39679214 | 39681342 | MMseg55 | 9515 |
| M | 11550700 | 11551900 | 39837771 | 39838402 | MMseg56 | 9516 |
| M | 11576300 | 11578800 | 39865577 | 39868181 | MMseg57 | 9517 |
| M | 11582850 | 11585650 | 39872571 | 39875449 | MMseg58 | 9518 |
| M | 11645900 | 11647550 | 39945175 | 39946956 | MMseg59 | 9519 |
| M | 11654800 | 11659450 | 39954283 | 39958991 | MMseg60 | 9520 |
| M | 11662100 | 11669800 | 39961797 | 39969863 | MMseg61 | 9521 |
| M | 11703550 | 11705350 | 40003903 | 40005703 | MMseg62 | 9522 |
| M | 11707150 | 11708850 | 40007611 | 40009366 | MMseg63 | 9523 |
| M | 11710650 | 11718750 | 40011139 | 40018589 | MMseg64 | 9524 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| M | 11728200 | 11730500 | 40026472 | 40028777 | MMseg65 | 9525 |
| M | 11735100 | 11736450 | 40033943 | 40035274 | MMseg66 | 9526 |
| M | 11766750 | 11767900 | 40063878 | 40064124 | MMseg67 | 9527 |
| M | 12338050 | 12339450 | 40593930 | 40595293 | MMseg68 | 9528 |
| M | 12417200 | 12418250 | 40704659 | 40705382 | MMseg69 | 9529 |
| M | 12428000 | 12429350 | 40714842 | 40715317 | MMseg70 | 9530 |
| M | 12743200 | 12744650 | 41089659 | 41090124 | MMseg71 | 9531 |
| M | 12818100 | 12819950 | 41150505 | 41157947 | MMseg72 | 9532 |
| M | 12921500 | 12923400 | 41240932 | 41242415 | MMseg73 | 9533 |
| M | 13068150 | 13070050 | 41337552 | 41338312 | MMseg76 | 9534 |
| M | 13199900 | 13201100 | 41526219 | 41527502 | MMseg78 | 9535 |
| M | 13586650 | 13588100 | 41899542 | 41900594 | MMseg82 | 9536 |
| M | 13948700 | 13950050 | 42150821 | 42151310 | MMseg84 | 9537 |
| M | 14275600 | 14276850 | 42401359 | 42401723 | MMseg87 | 9538 |
| M | 15079050 | 15080900 | 42964831 | 42965428 | MMseg90 | 9539 |
| M | 15633350 | 15634500 | 43219518 | 43220620 | MMseg96 | 9540 |
| M | 16215950 | 16217100 | 43552275 | 43552776 | MMseg98 | 9541 |
| M | 16310150 | 16311550 | 43653789 | 43655204 | MMseg99 | 9542 |
| M | 16352600 | 16353700 | 43708265 | 43709514 | MMseg100 | 9543 |
| M | 16474850 | 16476200 | 43821516 | 43822646 | MMseg101 | 9544 |
| M | 16520600 | 16522000 | 43860750 | 43862275 | MMseg102 | 9545 |
| M | 16577900 | 16579200 | 43904022 | 43906946 | MMseg103 | 9546 |
| M | 17104850 | 17106650 | 44370097 | 44372478 | MMseg107 | 9547 |
| M | 17719850 | 17721600 | 44701005 | 44702677 | MMseg109 | 9548 |
| M | 17857950 | 17859250 | 44972915 | 44974806 | MMseg110 | 9549 |
| M | 18017950 | 18019350 | 45045628 | 45046309 | MMseg111 | 9550 |
| M | 18258950 | 18260700 | 45156771 | 45157187 | MMseg114 | 9551 |
| M | 18628650 | 18629650 | 45526439 | 45526711 | MMseg116 | 9552 |
| M | 19143000 | 19144250 | 45944608 | 45945570 | MMseg118 | 9553 |
| M | 19400450 | 19402100 | 46153370 | 46155321 | MMseg121 | 9554 |
| M | 19648350 | 19649700 | 46448372 | 46449437 | MMseg123 | 9555 |
| M | 19767600 | 19768650 | 46532957 | 46533394 | MMseg124 | 9556 |
| M | 19788100 | 19789650 | 46546448 | 46546847 | MMseg125 | 9557 |
| M | 19830550 | 19831800 | 46592650 | 46596786 | MMseg127 | 9558 |
| M | 19852500 | 19853950 | 46608662 | 46610205 | MMseg128 | 9559 |
| M | 19867300 | 19869950 | 46616951 | 46619601 | MMseg129 | 9560 |
| M | 20004300 | 20005900 | 46773536 | 46774882 | MMseg132 | 9561 |
| M | 20081300 | 20083100 | 46900462 | 46902001 | MMseg134 | 9562 |
| M | 20281100 | 20282500 | 47092449 | 47093871 | MMseg136 | 9563 |
| M | 20395550 | 20397400 | 47382119 | 47383886 | MMseg137 | 9564 |
| M | 20508200 | 20509400 | 47488820 | 47490031 | MMseg138 | 9565 |
| M | 20755850 | 20756900 | 47966043 | 47967443 | MMseg141 | 9566 |
| M | 21112950 | 21114100 | 115367118 | 115367917 | MMseg145 | 9567 |
| M | 21323400 | 21325100 | 115594479 | 115595982 | MMseg146 | 9568 |
| M | 21859450 | 21861050 | 116088825 | 116089315 | MMseg150 | 9569 |
| M | 22252950 | 22254200 | 116521907 | 116523099 | MMseg151 | 9570 |
| M | 22365000 | 22366700 | 116627963 | 116628490 | MMseg152 | 9571 |
| M | 22591250 | 22593200 | 116844814 | 116846302 | MMseg154 | 9572 |
| M | 22891300 | 22892700 | 117160204 | 117162745 | MMseg155 | 9573 |
| M | 22900300 | 22901850 | 117197807 | 117198634 | MMseg156 | 9574 |
| M | 23064000 | 23065200 | 117341955 | 117343454 | MMseg157 | 9575 |
| M | 23269850 | 23271200 | 117479737 | 117481070 | MMseg158 | 9576 |
| M | 31061350 | 31063000 | 57160736 | 57161825 | MMseg164 | 9577 |
| M | 33506600 | 33507900 | 117703737 | 117705042 | MMseg166 | 9578 |
| M | 33655950 | 33657600 | 117865709 | 117865993 | MMseg167 | 9579 |
| M | 33677500 | 33678650 | 117887912 | 117889641 | MMseg169 | 9580 |
| M | 33719150 | 33720800 | 117936088 | 117937432 | MMseg170 | 9581 |
| M | 33813200 | 33814300 | 118050315 | 118050806 | MMseg171 | 9582 |
| M | 33866800 | 33870650 | 118106993 | 118110700 | MMseg172 | 9583 |
| M | 34264100 | 34265200 | 118498370 | 118498922 | MMseg174 | 9584 |
| M | 34447150 | 34448350 | 118743838 | 118744484 | MMseg176 | 9585 |
| M | 34528700 | 34530250 | 118826374 | 118827918 | MMseg177 | 9586 |
| M | 34587900 | 34590700 | 118891626 | 118894438 | MMseg178 | 9587 |
| M | 34642500 | 34644100 | 118977552 | 118978563 | MMseg179 | 9588 |
| M | 35869800 | 35871200 | 119641379 | 119642247 | MMseg184 | 9589 |
| M | 35983400 | 35984750 | 119759361 | 119760471 | MMseg186 | 9590 |
| M | 36033000 | 36034750 | 119822855 | 119823422 | MMseg188 | 9591 |
| M | 36079100 | 36080150 | 119872729 | 119873853 | MMseg189 | 9592 |
| M | 36147600 | 36149700 | 119915366 | 119916215 | MMseg190 | 9593 |
| M | 36218750 | 36220550 | 119959781 | 119968254 | MMseg191 | 9594 |
| M | 36597100 | 36598600 | 120291848 | 120292317 | MMseg194 | 9595 |
| M | 36924550 | 36926150 | 120568820 | 120570886 | MMseg197 | 9596 |
| M | 37551900 | 37553550 | 120965147 | 120968022 | MMseg201 | 9597 |
| M | 37969400 | 37970450 | 121501507 | 121501725 | MMseg202 | 9598 |

TABLE IVB-continued

Mouse Binding Sites with Human Liftovers

| Cell/Day | Mouse | | Human | | Segment | |
| --- | --- | --- | --- | --- | --- | --- |
| | Start | end | start | end | name | SEQ ID NO: |
| M | 38079150 | 38080750 | 121618886 | 121619926 | MMseg203 | 9599 |
| M | 38281750 | 38283400 | 121879773 | 121881361 | MMseg204 | 9600 |
| M | 38444000 | 38445050 | 122013409 | 122013642 | MMseg206 | 9601 |
| M | 38561450 | 38563000 | 122121499 | 122122409 | MMseg209 | 9602 |
| M | 38731100 | 38732300 | 122294096 | 122294864 | MMseg210 | 9603 |
| M | 38790800 | 38792350 | 122352832 | 122354054 | MMseg211 | 9604 |
| M | 39492400 | 39494100 | 123081818 | 123083882 | MMseg213 | 9605 |
| M | 39805700 | 39807700 | 123426566 | 123428759 | MMseg215 | 9606 |
| M | 39846000 | 39847400 | 123470567 | 123471902 | MMseg216 | 9607 |
| M | 39967500 | 39969050 | 123590168 | 123591761 | MMseg217 | 9608 |
| M | 40023850 | 40025400 | 123642627 | 123643161 | MMseg218 | 9609 |
| M | 40425400 | 40426600 | 124026728 | 124028624 | MMseg219 | 9610 |
| M | 40781400 | 40785400 | 124337576 | 124341322 | MMseg220 | 9611 |
| M | 40953300 | 40954650 | 124462957 | 124463685 | MMseg221 | 9612 |
| M | 41102400 | 41103750 | 124544235 | 124544653 | MMseg223 | 9613 |
| M | 41718450 | 41719750 | 125297300 | 125298487 | MMseg226 | 9614 |
| M | 41756150 | 41757350 | 125334297 | 125334538 | MMseg227 | 9615 |
| M | 42069950 | 42071000 | 125601592 | 125601936 | MMseg229 | 9616 |
| M | 42181700 | 42182750 | 125731578 | 125731807 | MMseg230 | 9617 |
| M | 42202000 | 42203700 | 125740154 | 125741540 | MMseg231 | 9618 |
| M | 42450900 | 42452150 | 125959401 | 125959828 | MMseg232 | 9619 |
| M | 42819700 | 42821000 | 126373406 | 126373921 | MMseg233 | 9620 |
| M | 43831900 | 43833250 | 127461185 | 127466799 | MMseg241 | 9621 |
| M | 43886350 | 43887600 | 127479682 | 127481326 | MMseg243 | 9622 |
| M | 44252100 | 44253150 | 127832599 | 127832980 | MMseg244 | 9623 |
| M | 44378250 | 44379750 | 127951857 | 127952536 | MMseg245 | 9624 |
| M | 44806550 | 44808000 | 128238615 | 128238902 | MMseg247 | 9625 |
| M | 45404500 | 45405900 | 128808886 | 128810670 | MMseg249 | 9626 |
| M | 45449100 | 45452700 | 128856715 | 128859696 | MMseg250 | 9627 |
| M | 45518700 | 45520450 | 128933211 | 128934320 | MMseg251 | 9628 |
| M | 45696600 | 45698250 | 129116279 | 129117903 | MMseg253 | 9629 |
| M | 45817450 | 45818700 | 129256327 | 129256969 | MMseg254 | 9630 |
| M | 46526200 | 46527800 | 129921536 | 129923301 | MMseg257 | 9631 |
| M | 46589400 | 46590700 | 129991567 | 129995308 | MMseg258 | 9632 |
| M | 46730900 | 46732150 | 130129392 | 130130576 | MMseg259 | 9633 |
| M | 46786550 | 46787900 | 130159266 | 130160128 | MMseg260 | 9634 |
| M | 46845350 | 46847000 | 130214690 | 130216304 | MMseg261 | 9635 |
| M | 47096950 | 47098300 | 130370676 | 130372022 | MMseg266 | 9636 |
| M | 47277800 | 47278800 | 130480480 | 130481488 | MMseg268 | 9637 |
| M | 47820550 | 47821700 | 130740685 | 130741323 | MMseg271 | 9638 |
| M | 48193550 | 48196000 | 131156178 | 131158689 | MMseg275 | 9639 |
| M | 48251350 | 48252400 | 131215697 | 131216878 | MMseg276 | 9640 |
| M | 48284900 | 48286650 | 131251254 | 131253314 | MMseg277 | 9641 |
| M | 48343450 | 48344900 | 131321266 | 131322624 | MMseg279 | 9642 |
| M | 48483100 | 48484100 | 131524685 | 131525682 | MMseg280 | 9643 |
| M | 48522450 | 48523550 | 131578848 | 131579779 | MMseg281 | 9644 |
| M | 48526400 | 48528150 | 131590554 | 131591740 | MMseg282 | 9645 |
| M | 48558700 | 48559900 | 131623600 | 131624736 | MMseg283 | 9646 |
| M | 48856950 | 48859000 | 131881678 | 131884124 | MMseg284 | 9647 |
| M | 48862150 | 48863550 | 131887966 | 131889731 | MMseg285 | 9648 |
| M | 49064500 | 49065800 | 132122111 | 132122636 | MMseg287 | 9649 |
| M | 49405600 | 49407250 | 132436079 | 132437528 | MMseg288 | 9650 |
| M | 49497350 | 49498800 | 132526484 | 132527990 | MMseg289 | 9651 |
| M | 49510150 | 49511400 | 132540477 | 132541995 | MMseg290 | 9652 |
| M | 49571550 | 49572800 | 132617041 | 132619498 | MMseg291 | 9653 |
| M | 49740150 | 49741750 | 132824815 | 132826853 | MMseg292 | 9654 |
| M | 49809350 | 49810500 | 132929400 | 132930721 | MMseg293 | 9655 |
| M | 49899250 | 49900700 | 133043990 | 133045826 | MMseg294 | 9656 |
| M | 49917950 | 49919150 | 133067381 | 133069727 | MMseg295 | 9657 |
| M | 49942600 | 49944300 | 133093735 | 133095552 | MMseg296 | 9658 |
| M | 49965300 | 49968700 | 133117792 | 133121448 | MMseg297 | 9659 |
| M | 49997500 | 49998900 | 133151877 | 133153912 | MMseg298 | 9660 |
| M | 50096400 | 50100350 | 133304977 | 133309222 | MMseg299 | 9661 |
| M | 50143700 | 50145100 | 133370577 | 133371992 | MMseg300 | 9662 |
| M | 50209600 | 50210750 | 133429054 | 133429874 | MMseg301 | 9663 |
| M | 50282750 | 50284400 | 133524919 | 133527179 | MMseg303 | 9664 |
| M | 50634750 | 50635800 | 133947550 | 133948902 | MMseg304 | 9665 |
| M | 50641850 | 50643450 | 133956560 | 133960476 | MMseg305 | 9666 |
| M | 51018750 | 51021000 | 134231382 | 134233395 | MMseg308 | 9667 |
| M | 51194850 | 51195900 | 141433590 | 141434225 | MMseg312 | 9668 |
| M | 53704500 | 53706200 | 134650548 | 134652493 | MMseg318 | 9669 |
| M | 54161400 | 54163150 | 135423230 | 135425026 | MMseg321 | 9670 |
| M | 54279000 | 54280500 | 135545720 | 135547150 | MMseg323 | 9671 |
| M | 54756100 | 54757650 | 136115263 | 136116820 | MMseg325 | 9672 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| M | 54774300 | 54775600 | 136134507 | 136135864 | MMseg326 | 9673 |
| M | 55169950 | 55176500 | 136506849 | 136513628 | MMseg328 | 9674 |
| M | 55261000 | 55262400 | 136622712 | 136623264 | MMseg329 | 9675 |
| M | 55268150 | 55273600 | 136628118 | 136633739 | MMseg330 | 9676 |
| M | 55279300 | 55288700 | 136643767 | 136653231 | MMseg331 | 9677 |
| M | 55290250 | 55292700 | 136654785 | 136657531 | MMseg332 | 9678 |
| M | 55399650 | 55401100 | 136814120 | 136817847 | MMseg333 | 9679 |
| M | 55407300 | 55408950 | 136828203 | 136829801 | MMseg334 | 9680 |
| M | 55925700 | 55927050 | 137302884 | 137304328 | MMseg339 | 9681 |
| M | 56152550 | 56153650 | 137525692 | 137526681 | MMseg341 | 9682 |
| M | 56379050 | 56380550 | 137785121 | 137787005 | MMseg342 | 9683 |
| M | 56386350 | 56388150 | 137792291 | 137794091 | MMseg343 | 9684 |
| M | 56634900 | 56635950 | 138062404 | 138063181 | MMseg344 | 9685 |
| M | 56736450 | 56737550 | 138193708 | 138194646 | MMseg345 | 9686 |
| M | 56819900 | 56822800 | 138285889 | 138289094 | MMseg346 | 9687 |
| M | 56834000 | 56835200 | 138300941 | 138301824 | MMseg347 | 9688 |
| M | 57004650 | 57006100 | 138405725 | 138414513 | MMseg349 | 9689 |
| M | 57259550 | 57261150 | 138620974 | 138621419 | MMseg351 | 9690 |
| M | 57425750 | 57427250 | 138770044 | 138770603 | MMseg352 | 9691 |
| M | 57430550 | 57433250 | 138772853 | 138775256 | MMseg353 | 9692 |
| M | 57727450 | 57728900 | 139057731 | 139058887 | MMseg354 | 9693 |
| M | 57800350 | 57802150 | 139173183 | 139174842 | MMseg356 | 9694 |
| M | 58140650 | 58142300 | 139580864 | 139582747 | MMseg357 | 9695 |
| M | 58143500 | 58152650 | 139584079 | 139593995 | MMseg358 | 9696 |
| M | 58439750 | 58441150 | 139867257 | 139868724 | MMseg361 | 9697 |
| M | 58988650 | 58990100 | 140259998 | 140260628 | MMseg366 | 9698 |
| M | 59262150 | 59263950 | 140736943 | 140738104 | MMseg367 | 9699 |
| M | 59592700 | 59593750 | 141194357 | 141195534 | MMseg370 | 9700 |
| M | 60583050 | 60584350 | 141937515 | 141938138 | MMseg373 | 9701 |
| M | 61043950 | 61045450 | 142350411 | 142351908 | MMseg380 | 9702 |
| M | 61527800 | 61529150 | 142720439 | 142721781 | MMseg383 | 9703 |
| M | 61671850 | 61673650 | 142878749 | 142880327 | MMseg385 | 9704 |
| M | 61963800 | 61965550 | 143163639 | 143164033 | MMseg389 | 9705 |
| M | 63929250 | 63930400 | 144926811 | 144927653 | MMseg402 | 9706 |
| M | 63959550 | 63960750 | 144961489 | 144961806 | MMseg403 | 9707 |
| M | 64147050 | 64148450 | 145231449 | 145232903 | MMseg404 | 9708 |
| M | 64432550 | 64433850 | 145449800 | 145449964 | MMseg407 | 9709 |
| M | 64982900 | 64984650 | 145928315 | 145929114 | MMseg411 | 9710 |
| M | 65565600 | 65566600 | 146682637 | 146683663 | MMseg413 | 9711 |
| M | 66032050 | 66033150 | 147094190 | 147094515 | MMseg414 | 9712 |
| M | 66147050 | 66148400 | 148136452 | 148137558 | MMseg416 | 9713 |
| M | 66414450 | 66415550 | 147376479 | 147377512 | MMseg418 | 9714 |
| M | 66466200 | 66467250 | 147416032 | 147416633 | MMseg419 | 9715 |
| M | 66565900 | 66567800 | 147532436 | 147533070 | MMseg420 | 9716 |
| M | 66791050 | 66792100 | 147740529 | 147740681 | MMseg421 | 9717 |
| M | 66910950 | 66912600 | 147855324 | 147856060 | MMseg422 | 9718 |
| M | 67053550 | 67055100 | 148002184 | 148003665 | MMseg423 | 9719 |
| M | 67107250 | 67108750 | 148056834 | 148058356 | MMseg424 | 9720 |
| M | 67336350 | 67337900 | 148289250 | 148290266 | MMseg426 | 9721 |
| M | 67438050 | 67439250 | 148394750 | 148396004 | MMseg427 | 9722 |
| M | 67492950 | 67494400 | 148463656 | 148465512 | MMseg428 | 9723 |
| M | 67582600 | 67583950 | 148549872 | 148552716 | MMseg430 | 9724 |
| M | 68201300 | 68202800 | 149440019 | 149444320 | MMseg431 | 9725 |
| M | 68566200 | 68567250 | 149838808 | 149840325 | MMseg433 | 9726 |
| M | 68809850 | 68811350 | 150152649 | 150154190 | MMseg435 | 9727 |
| M | 68913850 | 68920450 | 150341780 | 150348993 | MMseg436 | 9728 |
| M | 69023100 | 69024500 | 150507372 | 150509706 | MMseg437 | 9729 |
| M | 69206150 | 69207800 | 150861757 | 150863431 | MMseg438 | 9730 |
| M | 69289200 | 69290200 | 150932386 | 150933007 | MMseg439 | 9731 |
| M | 69573500 | 69575000 | 151193056 | 151194306 | MMseg441 | 9732 |
| M | 69898700 | 69902050 | 151616721 | 151620206 | MMseg444 | 9733 |
| M | 70703250 | 70704700 | 152734500 | 152736473 | MMseg448 | 9734 |
| M | 70747600 | 70749950 | 152782383 | 152784617 | MMseg449 | 9735 |
| M | 70788600 | 70789950 | 152819817 | 152821149 | MMseg450 | 9736 |
| M | 70804450 | 70805500 | 152834446 | 152835361 | MMseg451 | 9737 |
| M | 70934050 | 70935750 | 152968441 | 152970287 | MMseg453 | 9738 |
| M | 71284600 | 71286450 | 153300874 | 153306329 | MMseg455 | 9739 |
| M | 71297900 | 71299400 | 153330015 | 153330874 | MMseg456 | 9740 |
| M | 71335900 | 71337000 | 153371046 | 153371498 | MMseg457 | 9741 |
| M | 71490050 | 71491150 | 153597854 | 153598989 | MMseg460 | 9742 |
| M | 71617950 | 71619050 | 153718278 | 153719140 | MMseg461 | 9743 |
| M | 72290150 | 72291600 | 153956437 | 153957872 | MMseg467 | 9744 |
| M | 72365450 | 72366450 | 154017342 | 154017499 | MMseg468 | 9745 |
| M | 72582600 | 72584050 | 154215357 | 154215869 | MMseg470 | 9746 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| M | 72624100 | 72625150 | 154250623 | 154250998 | MMseg471 | 9747 |
| M | 73054650 | 73055950 | 114860457 | 114861747 | MMseg473 | 9748 |
| M | 73071500 | 73072900 | 114844362 | 114844984 | MMseg474 | 9749 |
| M | 73155600 | 73157200 | 114767260 | 114768562 | MMseg475 | 9750 |
| M | 73261100 | 73262650 | 114691960 | 114692435 | MMseg476 | 9751 |
| M | 73327750 | 73329150 | 114644793 | 114645241 | MMseg478 | 9752 |
| M | 73341100 | 73342200 | 114627636 | 114628019 | MMseg479 | 9753 |
| M | 73349000 | 73350400 | 114615075 | 114616059 | MMseg480 | 9754 |
| M | 73643150 | 73644150 | 9936073 | 9936323 | MMseg482 | 9755 |
| M | 73943550 | 73944700 | 8802904 | 8808683 | MMseg486 | 9756 |
| M | 74132400 | 74133750 | 8891298 | 8892121 | MMseg487 | 9757 |
| M | 74765750 | 74767100 | 9439444 | 9445152 | MMseg492 | 9758 |
| M | 74813350 | 74814550 | 9517999 | 9518540 | MMseg494 | 9759 |
| M | 74824650 | 74825850 | 9526588 | 9527688 | MMseg495 | 9760 |
| M | 74836600 | 74837700 | 9541735 | 9542753 | MMseg496 | 9761 |
| M | 74849700 | 74851450 | 9568569 | 9570768 | MMseg497 | 9762 |
| M | 75704950 | 75706650 | 37305235 | 37305481 | MMseg503 | 9763 |
| M | 75868550 | 75870150 | 50648371 | 50648543 | MMseg504 | 9764 |
| M | 76513450 | 76514900 | 36399442 | 36400549 | Mmseg508 | 9765 |
| M | 77125950 | 77127250 | 35519498 | 35521293 | Mmseg510 | 9766 |
| M | 77574450 | 77575900 | 35150260 | 35160220 | MMseg514 | 9767 |
| M | 78182700 | 78184200 | 34748285 | 34748895 | MMseg520 | 9768 |
| M | 78325850 | 78327400 | 34660292 | 34661661 | MMseg521 | 9769 |
| M | 78385750 | 78387700 | 34610115 | 34612020 | MMseg522 | 9770 |
| M | 79062350 | 79063600 | 34199143 | 34199280 | MMseg526 | 9771 |
| M | 79173000 | 79174450 | 34038122 | 34038418 | MMseg528 | 9772 |
| M | 79501300 | 79502300 | 33814292 | 33814675 | MMseg530 | 9773 |
| M | 80079150 | 80080250 | 33335447 | 33336215 | MMseg533 | 9774 |
| M | 80214700 | 80215850 | 33211441 | 33212426 | MMseg534 | 9775 |
| M | 80289550 | 80291150 | 33143296 | 33145129 | MMseg535 | 9776 |
| M | 80951950 | 80953100 | 32598589 | 32599876 | MMseg539 | 9777 |
| M | 80986250 | 80987500 | 32547715 | 32548917 | MMseg540 | 9778 |
| M | 81013650 | 81014950 | 32525825 | 32527469 | MMseg541 | 9779 |
| M | 81201750 | 81202950 | 32321843 | 32326932 | MMseg542 | 9780 |
| M | 81227950 | 81229600 | 32274064 | 32278591 | MMseg543 | 9781 |
| M | 81279900 | 81281750 | 32217187 | 32218420 | MMseg544 | 9782 |
| M | 81329500 | 81330500 | 32165214 | 32165919 | MMseg545 | 9783 |
| M | 81504450 | 81505850 | 31991565 | 31993741 | MMseg546 | 9784 |
| M | 81921950 | 81922950 | 31614505 | 31615576 | MMseg547 | 9785 |
| M | 82168250 | 82169850 | 31382553 | 31384566 | MMseg548 | 9786 |
| M | 82230400 | 82232100 | 31329148 | 31332982 | MMseg549 | 9787 |
| M | 82607750 | 82609250 | 31029272 | 31030516 | MMseg551 | 9788 |
| M | 82630250 | 82631250 | 31020288 | 31024031 | MMseg552 | 9789 |
| M | 82936850 | 82937950 | 30752842 | 30753334 | MMseg553 | 9790 |
| M | 83220450 | 83222100 | 30492715 | 30493672 | MMseg554 | 9791 |
| M | 83313000 | 83314550 | 30436903 | 30437909 | MMseg555 | 9792 |
| M | 83567400 | 83568850 | 30257600 | 30258223 | MMseg559 | 9793 |
| M | 83691900 | 83693400 | 30203246 | 30205467 | MMseg561 | 9794 |
| M | 84027100 | 84028200 | 29940164 | 29940830 | MMseg562 | 9795 |
| M | 84064350 | 84066050 | 29904001 | 29906944 | MMseg563 | 9796 |
| M | 84476400 | 84477600 | 29474201 | 29476636 | MMseg564 | 9797 |
| M | 84508350 | 84509700 | 29458782 | 29460076 | MMseg565 | 9798 |
| M | 84762400 | 84763950 | 29208421 | 29208751 | MMseg567 | 9799 |
| M | 84897200 | 84898200 | 29066918 | 29067892 | MMseg568 | 9800 |
| M | 84910100 | 84911200 | 29051254 | 29052897 | MMseg569 | 9801 |
| M | 84961950 | 84963350 | 29000756 | 29002298 | MMseg570 | 9802 |
| M | 84978950 | 84980450 | 28981962 | 28982362 | MMseg571 | 9803 |
| M | 85005100 | 85006350 | 28936463 | 28938576 | MMseg572 | 9804 |
| M | 85562100 | 85563150 | 28487115 | 28487606 | MMseg574 | 9805 |
| M | 85703250 | 85704650 | 28368422 | 28370314 | MMseg576 | 9806 |
| M | 86279900 | 86281250 | 28017133 | 28018798 | MMseg579 | 9807 |
| M | 86798900 | 86800500 | 27646071 | 27646646 | MMseg580 | 9808 |
| M | 86802650 | 86804100 | 27637492 | 27641190 | MMseg581 | 9809 |
| M | 87221250 | 87222450 | 27271213 | 27272126 | MMseg582 | 9810 |
| M | 88018550 | 88020000 | 26584683 | 26585735 | MMseg589 | 9811 |
| M | 89366350 | 89367900 | 26149133 | 26156488 | MMseg597 | 9812 |
| M | 89562150 | 89563950 | 25920772 | 25921401 | MMseg598 | 9813 |
| M | 89828050 | 89829600 | 25563318 | 25564678 | MMseg599 | 9814 |
| M | 90202250 | 90204300 | 25254918 | 25256191 | MMseg602 | 9815 |
| M | 90256200 | 90257300 | 25217098 | 25218123 | MMseg605 | 9816 |
| M | 90492400 | 90495350 | 25070572 | 25072276 | MMseg607 | 9817 |
| M | 90525900 | 90545400 | 25019886 | 25040035 | MMseg608 | 9818 |
| M | 90579500 | 90580700 | 24992157 | 24994070 | MMseg609 | 9819 |
| M | 90607700 | 90609050 | 24961318 | 24962578 | MMseg610 | 9820 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| M | 90929350 | 90930500 | 24657766 | 24658741 | MMseg611 | 9821 |
| M | 90945250 | 90947150 | 24637311 | 24639225 | MMseg612 | 9822 |
| M | 90949050 | 90950550 | 24626926 | 24629015 | MMseg613 | 9823 |
| M | 91012250 | 91014050 | 24552230 | 24555573 | MMseg614 | 9824 |
| M | 91069350 | 91070800 | 24490772 | 24494009 | MMseg615 | 9825 |
| M | 91265450 | 91266800 | 24288541 | 24291243 | MMseg616 | 9826 |
| M | 91478500 | 91482600 | 24040129 | 24045037 | MMseg619 | 9827 |
| M | 91509800 | 91511600 | 24014166 | 24015401 | MMseg620 | 9828 |
| M | 91594050 | 91595650 | 23942739 | 23944821 | MMseg622 | 9829 |
| M | 91606250 | 91607550 | 23929612 | 23930914 | MMseg623 | 9830 |
| M | 91610000 | 91611950 | 23926353 | 23928328 | MMseg624 | 9831 |
| M | 91787200 | 91788950 | 51635116 | 51636882 | MMseg626 | 9832 |
| M | 91880600 | 91882350 | 51485545 | 51487465 | MMseg628 | 9833 |
| M | 91890700 | 91891950 | 51491994 | 51492497 | MMseg629 | 9834 |
| M | 91975350 | 91977250 | 57623737 | 57625519 | MMseg630 | 9835 |
| M | 92328500 | 92329550 | 62946889 | 62948473 | MMseg635 | 9836 |
| M | 92654950 | 92656600 | 63431904 | 63432726 | MMseg638 | 9837 |
| M | 93011600 | 93013100 | 64424882 | 64425267 | MMseg641 | 9838 |
| M | 93178550 | 93179550 | 64774397 | 64775385 | MMseg644 | 9839 |
| M | 93201000 | 93202800 | 64801053 | 64802481 | MMseg645 | 9840 |
| M | 93346300 | 93347850 | 64948633 | 64949287 | MMseg646 | 9841 |
| M | 93551450 | 93552700 | 65333221 | 65334136 | MMseg651 | 9842 |
| M | 93691200 | 93692500 | 65416247 | 65417202 | MMseg652 | 9843 |
| M | 93785250 | 93787100 | 65507408 | 65519374 | MMseg653 | 9844 |
| M | 93905900 | 93907550 | 65654925 | 65655818 | MMseg654 | 9845 |
| M | 94839450 | 94840900 | 66125640 | 66126153 | MMseg662 | 9846 |
| M | 95231150 | 95232550 | 66749817 | 66751352 | MMseg665 | 9847 |
| M | 95524350 | 95526200 | 66956140 | 66956678 | MMseg669 | 9848 |
| M | 96034550 | 96035750 | 67585112 | 67585837 | MMseg671 | 9849 |
| M | 96193450 | 96195200 | 67860712 | 67862062 | MMseg673 | 9850 |
| M | 96293100 | 96294700 | 67971552 | 67971788 | MMseg674 | 9851 |
| M | 96322100 | 96323600 | 68039404 | 68041384 | MMseg675 | 9852 |
| M | 96329300 | 96330550 | 68046721 | 68047958 | MMseg676 | 9853 |
| M | 96402650 | 96404150 | 68125654 | 68126415 | MMseg677 | 9854 |
| M | 96434900 | 96436150 | 68158317 | 68159610 | MMseg678 | 9855 |
| M | 96528000 | 96529350 | 68250249 | 68251386 | MMseg679 | 9856 |
| M | 96555200 | 96556400 | 68282865 | 68284098 | MMseg680 | 9857 |
| M | 96567850 | 96569300 | 68293701 | 68295952 | MMseg681 | 9858 |
| M | 96641750 | 96642850 | 68360234 | 68361899 | MMseg682 | 9859 |
| M | 96671450 | 96672700 | 68391414 | 68392929 | MMseg683 | 9860 |
| M | 97014600 | 97018200 | 68723299 | 68726946 | MMseg684 | 9861 |
| M | 97483900 | 97485300 | 69152100 | 69152567 | MMseg686 | 9862 |
| M | 97559900 | 97561600 | 69223359 | 69223957 | MMseg687 | 9863 |
| M | 97754400 | 97755900 | 69442930 | 69443397 | MMseg689 | 9864 |
| M | 97772150 | 97773850 | 69459091 | 69460567 | MMseg690 | 9865 |
| M | 97898200 | 97899350 | 69605476 | 69606446 | MMseg692 | 9866 |
| M | 97915450 | 97916650 | 69630187 | 69631537 | MMseg693 | 9867 |
| M | 97922950 | 97924000 | 69641034 | 69641198 | MMseg694 | 9868 |
| M | 98138900 | 98140200 | 69884475 | 69884970 | MMseg695 | 9869 |
| M | 98148200 | 98149400 | 69901327 | 69901844 | MMseg696 | 9870 |
| M | 98577450 | 98581300 | 70441275 | 70445393 | MMseg698 | 9871 |
| M | 98585400 | 98586850 | 70450799 | 70451047 | MMseg699 | 9872 |
| M | 98834400 | 98836350 | 70751877 | 70753896 | MMseg701 | 9873 |
| M | 98858150 | 98859400 | 70774823 | 70776014 | MMseg702 | 9874 |
| M | 99043850 | 99047200 | 71129786 | 71133325 | MMseg706 | 9875 |
| M | 99220750 | 99222500 | 71306682 | 71307389 | MMseg708 | 9876 |
| M | 99236450 | 99237800 | 71324304 | 71325351 | MMseg709 | 9877 |
| M | 99442050 | 99449500 | 71520901 | 71528981 | MMseg711 | 9878 |
| M | 99506100 | 99507650 | 71574921 | 71576860 | MMseg712 | 9879 |
| M | 99591750 | 99593400 | 71676716 | 71678233 | MMseg713 | 9880 |
| M | 99610950 | 99612600 | 71694597 | 71696111 | MMseg714 | 9881 |
| M | 99883150 | 99884950 | 72002658 | 72004150 | MMseg715 | 9882 |
| M | 100128600 | 100130250 | 72162720 | 72164453 | MMseg716 | 9883 |
| M | 100380450 | 100382750 | 72433129 | 72435454 | MMseg721 | 9884 |
| M | 100516450 | 100519300 | 72666631 | 72669541 | MMseg722 | 9885 |
| M | 100551250 | 100553100 | 72782399 | 72784236 | MMseg723 | 9886 |
| M | 100889900 | 100891800 | 73754833 | 73756926 | MMseg727 | 9887 |
| M | 100920200 | 100921800 | 73731598 | 73733113 | MMseg728 | 9888 |
| M | 101016150 | 101017800 | 73640803 | 73642498 | MMseg729 | 9889 |
| M | 101131950 | 101133750 | 73796281 | 73797015 | MMseg731 | 9890 |
| M | 101287900 | 101288950 | 73973440 | 73973792 | MMseg733 | 9891 |
| M | 101393850 | 101397150 | 74142849 | 74145904 | MMseg734 | 9892 |
| M | 101440500 | 101442050 | 74185725 | 74187823 | MMseg735 | 9893 |
| M | 101608350 | 101609750 | 74375221 | 74376789 | MMseg737 | 9894 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| M | 101624200 | 101625400 | 74384265 | 74384853 | MMseg738 | 9895 |
| M | 101758800 | 101760500 | 74641629 | 74644014 | MMseg739 | 9896 |
| M | 101883300 | 101884350 | 74799734 | 74800662 | MMseg740 | 9897 |
| M | 101942950 | 101944550 | 74835923 | 74842905 | MMseg742 | 9898 |
| M | 102400850 | 102402350 | 75938514 | 75938837 | MMseg745 | 9899 |
| M | 102759850 | 102761150 | 76438759 | 76439779 | MMseg747 | 9900 |
| M | 102957550 | 102961000 | 76703692 | 76704302 | MMseg750 | 9901 |
| M | 103179700 | 103181050 | 77110993 | 77112114 | MMseg752 | 9902 |
| M | 103222250 | 103223250 | 77165896 | 77166862 | MMseg753 | 9903 |
| M | 103797050 | 103798750 | 77581313 | 77582989 | MMseg759 | 9904 |
| M | 104041050 | 104042050 | 77920198 | 77923241 | MMseg764 | 9905 |
| M | 104099950 | 104101250 | 77979366 | 77980418 | MMseg765 | 9906 |
| M | 104463100 | 104465750 | 78411164 | 78413511 | MMseg767 | 9907 |
| M | 104556500 | 104558250 | 78540264 | 78542569 | MMseg769 | 9908 |
| M | 105066950 | 105068650 | 79699365 | 79701033 | MMseg773 | 9909 |
| M | 105983300 | 105984500 | 79983579 | 79984013 | MMseg780 | 9910 |
| M | 106050950 | 106052850 | 80129449 | 80129941 | MMseg781 | 9911 |
| M | 106212850 | 106214050 | 80381063 | 80382416 | MMseg782 | 9912 |
| M | 106612450 | 106613650 | 80774911 | 80776408 | MMseg784 | 9913 |
| M | 106910650 | 106912100 | 81166951 | 81168123 | MMseg786 | 9914 |
| M | 106955950 | 106957650 | 81327625 | 81328065 | MMseg787 | 9915 |
| M | 107128550 | 107129600 | 81575374 | 81576152 | MMseg788 | 9916 |
| M | 107389750 | 107390850 | 81863934 | 81864504 | MMseg789 | 9917 |
| M | 107489050 | 107490200 | 81952668 | 81953486 | MMseg790 | 9918 |
| M | 107965600 | 107967500 | 82707442 | 82708367 | MMseg793 | 9919 |
| M | 108384350 | 108385650 | 83186738 | 83189593 | MMseg794 | 9920 |
| M | 108496050 | 108497650 | 83311277 | 83312698 | MMseg795 | 9921 |
| M | 108577100 | 108578150 | 83443492 | 83444507 | MMseg796 | 9922 |
| M | 109472300 | 109473950 | 84325456 | 84326692 | MMseg806 | 9923 |
| M | 109713400 | 109717700 | 84498068 | 84502366 | MMseg809 | 9924 |
| M | 109867750 | 109869150 | 84686651 | 84687277 | MMseg811 | 9925 |
| M | 110000500 | 110001900 | 84791126 | 84791744 | MMseg812 | 9926 |
| M | 110207650 | 110208750 | 85181784 | 85182876 | MMseg813 | 9927 |
| M | 110275150 | 110276350 | 85284751 | 85286471 | MMseg815 | 9928 |
| M | 110386100 | 110387900 | 85386249 | 85387255 | MMseg816 | 9929 |
| M | 110411350 | 110412600 | 85402933 | 85404168 | MMseg817 | 9930 |
| M | 110439050 | 110440700 | 85456591 | 85457025 | MMseg818 | 9931 |
| M | 110486750 | 110488100 | 85493114 | 85493510 | MMseg819 | 9932 |
| M | 110560900 | 110562550 | 85625105 | 85627165 | MMseg820 | 9933 |
| M | 110578450 | 110579900 | 85643982 | 85645513 | MMseg821 | 9934 |
| M | 110610000 | 110611350 | 85713602 | 85714772 | MMseg822 | 9935 |
| M | 110950700 | 110951700 | 86089353 | 86089588 | MMseg823 | 9936 |
| M | 110992250 | 110993400 | 86140876 | 86141430 | MMseg825 | 9937 |
| M | 111466400 | 111468000 | 86645506 | 86646572 | MMseg827 | 9938 |
| M | 111514000 | 111515400 | 86681076 | 86681942 | MMseg828 | 9939 |
| M | 111659150 | 111660350 | 86882669 | 86883398 | MMseg829 | 9940 |
| M | 112319150 | 112320900 | 87221875 | 87224746 | MMseg831 | 9941 |
| M | 112660900 | 112662600 | 87499718 | 87499920 | MMseg832 | 9942 |
| M | 113009850 | 113011300 | 87649181 | 87650356 | MMseg834 | 9943 |
| M | 114285300 | 114286700 | 88407592 | 88408662 | MMseg839 | 9944 |
| M | 114516300 | 114517450 | 88631528 | 88632064 | MMseg842 | 9945 |
| M | 116209950 | 116211450 | 89785792 | 89786465 | MMseg852 | 9946 |
| M | 116417150 | 116419000 | 90000094 | 90001613 | MMseg853 | 9947 |
| M | 117145150 | 117146450 | 90801422 | 90802560 | MMseg856 | 9948 |
| M | 117349000 | 117350350 | 90980144 | 90981122 | MMseg858 | 9949 |
| M | 117402250 | 117407550 | 91032710 | 91037887 | MMseg860 | 9950 |
| M | 117618800 | 117620450 | 91331021 | 91331322 | MMseg861 | 9951 |
| M | 117696400 | 117698100 | 91431278 | 91433116 | MMseg863 | 9952 |
| M | 117701900 | 117702950 | 91446852 | 91450061 | MMseg864 | 9953 |
| M | 117779000 | 117780650 | 91578843 | 91580649 | MMseg865 | 9954 |
| M | 117808300 | 117809500 | 91613712 | 91614566 | MMseg866 | 9955 |
| M | 117859750 | 117861300 | 91658180 | 91658535 | MMseg867 | 9956 |
| M | 119283500 | 119285050 | 92797309 | 92803533 | MMseg872 | 9957 |
| M | 119509650 | 119511600 | 92927439 | 92929203 | MMseg874 | 9958 |
| M | 119858200 | 119859900 | 93177479 | 93180391 | MMseg875 | 9959 |
| M | 123745200 | 123746200 | 93753922 | 93754506 | MMseg882 | 9960 |
| M | 123952950 | 123954600 | 93884923 | 93887134 | MMseg885 | 9961 |
| M | 125052000 | 125053100 | 94984431 | 94985552 | MMseg892 | 9962 |
| M | 126010150 | 126011350 | 95714394 | 95714657 | MMseg896 | 9963 |
| M | 126128050 | 126129100 | 95811359 | 95811866 | MMseg897 | 9964 |
| M | 126134100 | 126135350 | 95818665 | 95819541 | MMseg898 | 9965 |
| M | 126335050 | 126338850 | 95990007 | 95993886 | MMseg900 | 9966 |
| M | 126476300 | 126478050 | 96169827 | 96171966 | MMseg901 | 9967 |
| M | 126491100 | 126492850 | 96193486 | 96195772 | MMseg902 | 9968 |

TABLE IVB-continued

Mouse Binding Sites with Human Liftovers

| Cell/ | Mouse | | Human | | Segment | |
|---|---|---|---|---|---|---|
| Day | Start | end | start | end | name | SEQ ID NO: |
| M | 127858250 | 127860200 | 97533217 | 97534531 | MMseg908 | 9969 |
| M | 127936450 | 127938050 | 97588006 | 97588532 | MMseg910 | 9970 |
| M | 127990550 | 127991950 | 97624348 | 97625702 | MMseg911 | 9971 |
| M | 128030850 | 128032500 | 97669577 | 97674316 | MMseg912 | 9972 |
| M | 128097900 | 128099450 | 97730698 | 97731095 | MMseg913 | 9973 |
| M | 128324700 | 128325800 | 97934513 | 97935472 | MMseg914 | 9974 |
| M | 128536450 | 128538050 | 98150460 | 98151481 | MMseg915 | 9975 |
| M | 128595000 | 128596400 | 98198615 | 98200051 | MMseg916 | 9976 |
| M | 128642500 | 128643600 | 98230930 | 98231359 | MMseg917 | 9977 |
| M | 128785100 | 128786450 | 98325940 | 98327127 | MMseg918 | 9978 |
| M | 128802650 | 128803900 | 98337034 | 98338007 | MMseg919 | 9979 |
| M | 128846350 | 128847450 | 98369489 | 98370229 | MMseg920 | 9980 |
| M | 129381700 | 129383100 | 98906297 | 98906620 | MMseg923 | 9981 |
| M | 129513350 | 129514750 | 99003189 | 99003961 | MMseg925 | 9982 |
| M | 129596000 | 129597300 | 99106530 | 99107422 | MMseg926 | 9983 |
| M | 129661550 | 129663100 | 99176861 | 99178047 | MMseg927 | 9984 |
| M | 130093500 | 130094900 | 99529255 | 99530631 | MMseg928 | 9985 |
| M | 130135200 | 130136250 | 99569187 | 99570014 | MMseg929 | 9986 |
| M | 130209050 | 130210200 | 99650657 | 99651760 | MMseg930 | 9987 |
| M | 130224300 | 130226000 | 99665979 | 99667550 | MMseg931 | 9988 |
| M | 130320100 | 130321900 | 99767037 | 99767713 | MMseg932 | 9989 |
| M | 130515200 | 130516800 | 99985954 | 99987439 | MMseg933 | 9990 |
| M | 130648400 | 130649900 | 100131007 | 100131589 | MMseg935 | 9991 |
| M | 130970750 | 130971750 | 100499362 | 100500206 | MMseg939 | 9992 |
| M | 131743800 | 131745450 | 101396017 | 101397733 | MMseg944 | 9993 |
| M | 132278600 | 132280000 | 101855946 | 101857354 | MMseg948 | 9994 |
| M | 132446250 | 132447450 | 102776478 | 102777421 | MMseg950 | 9995 |
| M | 132593250 | 132594900 | 102311063 | 102311634 | MMseg952 | 9996 |
| M | 132614950 | 132616550 | 102339045 | 102340550 | MMseg953 | 9997 |
| M | 132749600 | 132751200 | 102565461 | 102566671 | MMseg956 | 9998 |
| M | 132778000 | 132779550 | 102610275 | 102611320 | MMseg957 | 9999 |
| M | 133200550 | 133202600 | 102862543 | 102864520 | MMseg965 | 10000 |
| M | 133252200 | 133253750 | 102917394 | 102918313 | MMseg967 | 10001 |
| M | 133255450 | 133256950 | 102919433 | 102920854 | MMseg968 | 10002 |
| M | 133422650 | 133424150 | 103097167 | 103098085 | MMseg969 | 10003 |
| M | 133427250 | 133429050 | 103098720 | 103098948 | MMseg970 | 10004 |
| M | 133524100 | 133525100 | 103353886 | 103354572 | MMseg971 | 10005 |
| M | 133526500 | 133528150 | 103355958 | 103357778 | MMseg972 | 10006 |
| M | 133650600 | 133655950 | 103495632 | 103500851 | MMseg976 | 10007 |
| M | 133996300 | 133997600 | 103743455 | 103744895 | MMseg978 | 10008 |
| M | 134056750 | 134057900 | 103771272 | 103775617 | MMseg979 | 10009 |
| M | 134221850 | 134223150 | 103938931 | 103940001 | MMseg980 | 10010 |
| M | 134369750 | 134371200 | 104055433 | 104056038 | MMseg982 | 10011 |
| M | 134785850 | 134787600 | 104532420 | 104532985 | MMseg987 | 10012 |
| M | 135011900 | 135012950 | 104711775 | 104712044 | MMseg989 | 10013 |
| M | 135466650 | 135468200 | 105087702 | 105089227 | MMseg991 | 10014 |
| M | 135535550 | 135537550 | 105193829 | 105196084 | MMseg992 | 10015 |
| M | 136318750 | 136320400 | 106148299 | 106149674 | MMseg996 | 10016 |
| M | 136514200 | 136515550 | 106345421 | 106346746 | MMseg998 | 10017 |
| M | 136568750 | 136570250 | 106410404 | 106411812 | MMseg1000 | 10018 |
| M | 136600400 | 136602000 | 106453320 | 106454986 | MMseg1002 | 10019 |
| M | 136627450 | 136628700 | 106471463 | 106472244 | MMseg1003 | 10020 |
| M | 136630700 | 136632400 | 106475854 | 106477674 | MMseg1004 | 10021 |
| M | 136727100 | 136728350 | 106596842 | 106597598 | MMseg1005 | 10022 |
| M | 136745700 | 136746800 | 106626313 | 106627239 | MMseg1006 | 10023 |
| M | 136794150 | 136795900 | 106677025 | 106678088 | MMseg1007 | 10024 |
| M | 136805700 | 136807600 | 106687753 | 106688404 | MMseg1009 | 10025 |
| M | 136810900 | 136814000 | 106691572 | 106694448 | MMseg1010 | 10026 |
| M | 136887000 | 136888100 | 106758820 | 106761610 | MMseg1011 | 10027 |
| M | 137133700 | 137135950 | 107019244 | 107021093 | MMseg1013 | 10028 |
| M | 137149650 | 137150700 | 107032531 | 107033387 | MMseg1014 | 10029 |
| M | 137168150 | 137169300 | 107036909 | 107037517 | MMseg1015 | 10030 |
| M | 137249050 | 137250750 | 107125059 | 107127384 | MMseg1016 | 10031 |
| M | 137459150 | 137460700 | 107309195 | 107309955 | MMseg1018 | 10032 |
| M | 137509650 | 137511350 | 107360048 | 107361592 | MMseg1019 | 10033 |
| M | 137518150 | 137519300 | 107367247 | 107368380 | MMseg1020 | 10034 |
| M | 137609150 | 137610750 | 107407807 | 107409521 | MMseg1021 | 10035 |
| M | 137661150 | 137662400 | 107455959 | 107457400 | MMseg1022 | 10036 |
| M | 137814550 | 137815750 | 107588053 | 107588914 | MMseg1023 | 10037 |
| M | 137866850 | 137868200 | 107625514 | 107625717 | MMseg1024 | 10038 |
| M | 137909200 | 137910750 | 107682283 | 107683870 | MMseg1025 | 10039 |
| M | 138155550 | 138162100 | 107975275 | 107981988 | MMseg1027 | 10040 |
| M | 138344900 | 138346350 | 108371115 | 108371394 | MMseg1028 | 10041 |
| M | 138497500 | 138499200 | 108595607 | 108599114 | MMseg1030 | 10042 |

TABLE IVB-continued

Mouse Binding Sites with Human Liftovers

| Cell/Day | Mouse | | Human | | Segment | |
|---|---|---|---|---|---|---|
| | Start | end | start | end | name | SEQ ID NO: |
| M | 138577300 | 138578350 | 108684940 | 108685646 | MMseg1031 | 10043 |
| M | 138655950 | 138657600 | 108773752 | 108776368 | MMseg1033 | 10044 |
| M | 138861000 | 138862150 | 109017789 | 109018788 | MMseg1034 | 10045 |
| M | 138943650 | 138945000 | 109104066 | 109104577 | MMseg1035 | 10046 |
| M | 139058150 | 139059900 | 109206160 | 109206963 | MMseg1036 | 10047 |
| M | 139234500 | 139235900 | 109378304 | 109379245 | MMseg1037 | 10048 |
| M | 139316300 | 139317700 | 109463676 | 109465986 | MMseg1038 | 10049 |
| M | 139430050 | 139431350 | 109591776 | 109592916 | MMseg1039 | 10050 |
| M | 139458550 | 139459900 | 109629485 | 109630972 | MMseg1040 | 10051 |
| M | 139635450 | 139636700 | 109879988 | 109880299 | MMseg1041 | 10052 |
| M | 139697400 | 139698650 | 109805172 | 109805516 | MMseg1042 | 10053 |
| M | 139745550 | 139747050 | 109943807 | 109944715 | MMseg1043 | 10054 |
| M | 139987100 | 139988850 | 110226213 | 110228387 | MMseg1044 | 10055 |
| M | 140083250 | 140085000 | 110315590 | 110316674 | MMseg1045 | 10056 |
| M | 140155900 | 140157150 | 110398096 | 110399281 | MMseg1046 | 10057 |
| M | 140262750 | 140264100 | 110514566 | 110515987 | MMseg1047 | 10058 |
| M | 140324750 | 140325800 | 110599252 | 110599767 | MMseg1048 | 10059 |
| M | 141011100 | 141014550 | 111234907 | 111235760 | Mmseg1050 | 10060 |
| M | 141122750 | 141124850 | 111325473 | 111327688 | Mmseg1051 | 10061 |
| M | 141629350 | 141630950 | 111773174 | 111780006 | Mmseg1052 | 10062 |
| M | 141813150 | 141814300 | 111949839 | 111950020 | Mmseg1054 | 10063 |
| M | 142949600 | 142951350 | 113265897 | 113266178 | MMseg1056 | 10064 |
| M | 143325300 | 143326350 | 113762632 | 113762826 | MMseg1058 | 10065 |
| M | 143346200 | 143347600 | 113770324 | 113771336 | MMseg1059 | 10066 |
| M | 143396550 | 143399200 | 113818163 | 113820605 | MMseg1060 | 10067 |
| M | 143828450 | 143829600 | 114247925 | 114249029 | MMseg1062 | 10068 |
| M | 143832100 | 143833150 | 114251373 | 114252988 | MMseg1063 | 10069 |
| M | 143915100 | 143916350 | 114357412 | 114358718 | MMseg1064 | 10070 |
| M | 147004500 | 147006350 | 55033828 | 55036153 | MMseg1067 | 10071 |
| M | 147499650 | 147500750 | 54497893 | 54498387 | MMseg1070 | 10072 |
| M | 147668750 | 147670150 | 54319993 | 54320661 | MMseg1074 | 10073 |
| M | 147998550 | 148000100 | 54028933 | 54029207 | MMseg1075 | 10074 |
| M | 148054700 | 148056250 | 53988742 | 53989670 | MMseg1076 | 10075 |
| M | 148457400 | 148458950 | 53441694 | 53442006 | MMseg1077 | 10076 |
| M | 148511500 | 148512800 | 53393244 | 53394295 | MMseg1078 | 10077 |
| M | 148514600 | 148516600 | 53389862 | 53391858 | MMseg1079 | 10078 |
| M | 148666800 | 148668500 | 53253670 | 53255198 | MMseg1080 | 10079 |
| M | 149107700 | 149109050 | 9857299 | 9859449 | MMseg1085 | 10080 |
| M | 149139800 | 149141150 | 9829894 | 9830916 | MMseg1086 | 10081 |
| M | 149517250 | 149519000 | 55584450 | 55586933 | MMseg1089 | 10082 |
| M | 151469900 | 151471600 | 148630369 | 148630574 | MMseg1102 | 10083 |
| M | 152044650 | 152046100 | 23364640 | 23366242 | MMseg1103 | 10084 |
| M | 152055650 | 152060200 | 23350792 | 23355162 | MMseg1104 | 10085 |
| M | 152070600 | 152071700 | 23340912 | 23342050 | MMseg1105 | 10086 |
| M | 152133950 | 152135050 | 23302181 | 23303309 | MMseg1106 | 10087 |
| M | 152611900 | 152613600 | 22996612 | 22998738 | MMseg1107 | 10088 |
| M | 152708250 | 152709500 | 22922991 | 22924300 | MMseg1108 | 10089 |
| M | 153097150 | 153098600 | 22635976 | 22637590 | MMseg1109 | 10090 |
| M | 153259450 | 153260850 | 22514326 | 22516734 | MMseg1110 | 10091 |
| M | 153310450 | 153311550 | 22476010 | 22476361 | MMseg1112 | 10092 |
| M | 153457200 | 153458500 | 22354781 | 22356450 | MMseg1113 | 10093 |
| M | 153851750 | 153853150 | 22050675 | 22052078 | MMseg1114 | 10094 |
| M | 154266400 | 154267500 | 21664266 | 21665295 | MMseg1115 | 10095 |
| M | 154354450 | 154356600 | 21536146 | 21538465 | MMseg1116 | 10096 |
| M | 154359850 | 154360950 | 21531795 | 21532662 | MMseg1117 | 10097 |
| M | 154478850 | 154482050 | 21391694 | 21395006 | MMseg1118 | 10098 |
| M | 154979800 | 154981450 | 20881821 | 20883114 | MMseg1120 | 10099 |
| M | 155175600 | 155177250 | 20686110 | 20687356 | MMseg1121 | 10100 |
| M | 155592950 | 155594500 | 20380196 | 20381928 | MMseg1123 | 10101 |
| M | 155850850 | 155855650 | 20133359 | 20135681 | MMseg1125 | 10102 |
| M | 155914900 | 155916100 | 20047728 | 20050675 | MMseg1127 | 10103 |
| M | 155947200 | 155948500 | 20014121 | 20014391 | MMseg1128 | 10104 |
| M | 156050800 | 156052150 | 19916475 | 19916777 | MMseg1129 | 10105 |
| M | 156173800 | 156175150 | 19790322 | 19791596 | MMseg1130 | 10106 |
| M | 156332900 | 156334600 | 19632378 | 19633538 | MMseg1131 | 10107 |
| M | 156575900 | 156577400 | 19361539 | 19362523 | MMseg1132 | 10108 |
| M | 156615300 | 156616950 | 19336717 | 19337267 | MMseg1133 | 10109 |
| M | 156915950 | 156917400 | 19028709 | 19030593 | MMseg1134 | 10110 |
| M | 156939550 | 156941000 | 19001813 | 19003365 | MMseg1135 | 10111 |
| M | 157075450 | 157077200 | 18806997 | 18818223 | MMseg1136 | 10112 |
| M | 157082600 | 157084300 | 18797567 | 18799687 | MMseg1137 | 10113 |
| M | 157252000 | 157253500 | 18639528 | 18641140 | MMseg1138 | 10114 |
| M | 157291850 | 157293050 | 18603679 | 18604531 | MMseg1139 | 10115 |
| M | 157732500 | 157734300 | 18240144 | 18240870 | MMseg1142 | 10116 |

TABLE IVB-continued

Mouse Binding Sites with Human Liftovers

| Cell/Day | Mouse Start | Mouse end | Human start | Human end | Segment name | SEQ ID NO: |
|---|---|---|---|---|---|---|
| M | 157974800 | 157976550 | 18021746 | 18023162 | MMseg1143 | 10117 |
| M | 158154450 | 158157550 | 17876984 | 17879845 | MMseg1144 | 10118 |
| M | 158259100 | 158260650 | 17766275 | 17767756 | MMseg1145 | 10119 |
| M | 158345350 | 158347650 | 17672974 | 17675261 | MMseg1146 | 10120 |
| M | 158379950 | 158381000 | 17632722 | 17634330 | MMseg1147 | 10121 |
| M | 158599200 | 158600700 | 17390657 | 17392078 | MMseg1148 | 10122 |
| M | 158720550 | 158721550 | 17257216 | 17257769 | MMseg1150 | 10123 |
| M | 158851550 | 158852850 | 17168374 | 17169701 | MMseg1151 | 10124 |
| M | 158949900 | 158951400 | 17087437 | 17088674 | MMseg1153 | 10125 |
| M | 158959950 | 158961350 | 17070128 | 17071066 | MMseg1154 | 10126 |
| M | 159080250 | 159082650 | 16963853 | 16966209 | MMseg1156 | 10127 |
| M | 159203550 | 159205400 | 16883371 | 16884266 | MMseg1157 | 10128 |
| M | 159235100 | 159236450 | 16846153 | 16846456 | MMseg1158 | 10129 |
| M | 159319550 | 159321300 | 16753321 | 16754454 | MMseg1159 | 10130 |
| M | 159776150 | 159777650 | 16314342 | 16314768 | MMseg1161 | 10131 |
| M | 160001250 | 160002400 | 16130429 | 16131585 | MMseg1162 | 10132 |
| M | 160115400 | 160116950 | 16030242 | 16031393 | MMseg1163 | 10133 |
| M | 160365250 | 160367100 | 15848626 | 15850676 | MMseg1167 | 10134 |
| M | 160861100 | 160862850 | 15347026 | 15349529 | MMseg1169 | 10135 |
| M | 161072900 | 161074050 | 15189814 | 15190425 | MMseg1170 | 10136 |
| M | 161227600 | 161229100 | 15093224 | 15094638 | MMseg1171 | 10137 |
| M | 161323850 | 161324950 | 14993608 | 14994082 | MMseg1172 | 10138 |
| M | 161357200 | 161358200 | 14950467 | 14951475 | MMseg1173 | 10139 |
| M | 161419650 | 161421200 | 14882869 | 14883777 | MMseg1174 | 10140 |
| M | 161572150 | 161573150 | 14745213 | 14745814 | MMseg1176 | 10141 |
| M | 161921600 | 161922900 | 14448856 | 14449148 | MMseg1178 | 10142 |
| M | 162336100 | 162337150 | 14235632 | 14237829 | MMseg1179 | 10143 |
| M | 162434450 | 162435850 | 14163737 | 14164131 | MMseg1180 | 10144 |
| M | 162676200 | 162678100 | 13955587 | 13957519 | MMseg1181 | 10145 |
| M | 162717750 | 162718800 | 13915314 | 13916110 | MMseg1182 | 10146 |
| M | 163433400 | 163434550 | 13221669 | 13222560 | MMseg1184 | 10147 |
| M | 163630900 | 163632050 | 13007637 | 13008082 | MMseg1185 | 10148 |
| M | 163647200 | 163648550 | 12991689 | 12993122 | MMseg1186 | 10149 |
| M | 163730600 | 163731650 | 12909774 | 12910724 | MMseg1187 | 10150 |
| M | 163748650 | 163750400 | 12902034 | 12902693 | MMseg1188 | 10151 |
| M | 163819450 | 163820450 | 12809689 | 12810746 | MMseg1189 | 10152 |
| M | 163923300 | 163924500 | 12729068 | 12729246 | MMseg1190 | 10153 |
| M | 164201450 | 164202450 | 12484206 | 12484349 | MMseg1192 | 10154 |
| M | 164366800 | 164368400 | 12329590 | 12331008 | MMseg1193 | 10155 |
| M | 164471750 | 164472800 | 12238770 | 12240904 | MMseg1195 | 10156 |
| M | 164583450 | 164585100 | 12138301 | 12139476 | MMseg1197 | 10157 |
| M | 164589550 | 164590900 | 12134109 | 12134814 | MMseg1198 | 10158 |
| M | 164746300 | 164747750 | 12011972 | 12013034 | MMseg1199 | 10159 |
| M | 164964150 | 164965600 | 11881888 | 11882967 | MMseg1200 | 10160 |
| M | 165094850 | 165096750 | 11790174 | 11790869 | MMseg1201 | 10161 |
| M | 165232550 | 165235100 | 11681898 | 11684654 | MMseg1202 | 10162 |
| M | 165245650 | 165247050 | 11670574 | 11671232 | MMseg1203 | 10163 |
| M | 165283100 | 165284700 | 11636638 | 11638291 | MMseg1204 | 10164 |
| M | 165377800 | 165379300 | 11544817 | 11547072 | MMseg1205 | 10165 |
| M | 165445000 | 165446600 | 11469150 | 11471127 | MMseg1207 | 10166 |
| M | 165690100 | 165691550 | 11200197 | 11202213 | MMseg1210 | 10167 |
| M | 166306750 | 166308500 | 10599802 | 10602471 | MMseg1211 | 10168 |

For Table JVC: c/d: cell/day; 0, day 0 ES cells; 7, day 7 ES cells; M, MEF cells. These sites did not have human liftovers sequences corresponding to the empirically identified mouse binding sites.

TABLE IVC

Mouse Moderate Sites

| c/d | start | end | segment |
|---|---|---|---|
| 0 | 3013250 | 3014900 | d0Mseg1 |
| 0 | 3040500 | 3042200 | d0Mseg2 |
| 0 | 3199600 | 3201300 | d0Mseg3 |
| 0 | 3888800 | 3890200 | d0Mseg4 |
| 0 | 4299550 | 4301150 | d0Mseg5 |
| 0 | 4864500 | 4865900 | d0Mseg6 |
| 0 | 5043950 | 5046250 | d0Mseg7 |
| 0 | 5156500 | 5158150 | d0Mseg8 |
| 0 | 5243750 | 5245500 | d0Mseg9 |
| 0 | 5280750 | 5282600 | d0Mseg10 |
| 0 | 5365800 | 5367250 | d0Mseg11 |
| 0 | 5548600 | 5550350 | d0Mseg13 |
| 0 | 5557950 | 5559800 | d0Mseg14 |
| 0 | 6129350 | 6130550 | d0Mseg19 |
| 0 | 6189300 | 6190350 | d0Mseg20 |
| 0 | 7598600 | 7600450 | d0Mseg35 |
| 0 | 7656650 | 7658100 | d0Mseg36 |
| 0 | 7892450 | 7894150 | d0Mseg37 |

TABLE IVC-continued

Mouse Moderate Sites

| c/d | start | end | segment |
|---|---|---|---|
| 0 | 8153500 | 8154650 | d0Mseg38 |
| 0 | 8274000 | 8275850 | d0Mseg39 |
| 0 | 8468900 | 8470750 | d0Mseg40 |
| 0 | 8514150 | 8516000 | d0Mseg41 |
| 0 | 8572300 | 8573950 | d0Mseg42 |
| 0 | 8665550 | 8667200 | d0Mseg43 |
| 0 | 9129150 | 9130900 | d0Mseg47 |
| 0 | 9169600 | 9171000 | d0Mseg48 |
| 0 | 9600200 | 9602000 | d0Mseg49 |
| 0 | 9654550 | 9656200 | d0Mseg52 |
| 0 | 10265600 | 10267300 | d0Mseg61 |
| 0 | 11349600 | 11351300 | d0Mseg72 |
| 0 | 12219450 | 12220600 | d0Mseg90 |
| 0 | 12441150 | 12442800 | d0Mseg91 |
| 0 | 12966750 | 12968350 | d0Mseg92 |
| 0 | 13991600 | 13993200 | d0Mseg102 |
| 0 | 14101700 | 14103350 | d0Mseg103 |
| 0 | 14494250 | 14496000 | d0Mseg106 |
| 0 | 14735800 | 14737450 | d0Mseg108 |
| 0 | 14938450 | 14939950 | d0Mseg112 |
| 0 | 15005250 | 15006800 | d0Mseg113 |
| 0 | 15180550 | 15182200 | d0Mseg114 |
| 0 | 15539300 | 15541050 | d0Mseg117 |
| 0 | 16907700 | 16909450 | d0Mseg123 |
| 0 | 16933400 | 16935050 | d0Mseg124 |
| 0 | 18051250 | 18052650 | d0Mseg128 |
| 0 | 18099850 | 18101600 | d0Mseg129 |
| 0 | 18127350 | 18128500 | d0Mseg130 |
| 0 | 18326150 | 18327150 | d0Mseg131 |
| 0 | 18349150 | 18350600 | d0Mseg132 |
| 0 | 18380000 | 18381700 | d0Mseg133 |
| 0 | 18525150 | 18526200 | d0Mseg134 |
| 0 | 18588750 | 18590450 | d0Mseg135 |
| 0 | 18698450 | 18700250 | d0Mseg136 |
| 0 | 18705600 | 18706950 | d0Mseg137 |
| 0 | 18946750 | 18948350 | d0Mseg139 |
| 0 | 19045350 | 19047000 | d0Mseg141 |
| 0 | 19180550 | 19182250 | d0Mseg142 |
| 0 | 19225150 | 19226900 | d0Mseg143 |
| 0 | 19584700 | 19586600 | d0Mseg145 |
| 0 | 19612750 | 19614150 | d0Mseg146 |
| 0 | 19729650 | 19731250 | d0Mseg148 |
| 0 | 19896650 | 19898550 | d0Mseg150 |
| 0 | 20768800 | 20769850 | d0Mseg153 |
| 0 | 20937650 | 20940750 | d0Mseg154 |
| 0 | 21048500 | 21050250 | d0Mseg155 |
| 0 | 21388750 | 21390350 | d0Mseg159 |
| 0 | 21695650 | 21697500 | d0Mseg160 |
| 0 | 21731400 | 21733200 | d0Mseg161 |
| 0 | 21795550 | 21797450 | d0Mseg162 |
| 0 | 21915400 | 21917000 | d0Mseg164 |
| 0 | 21966550 | 21968200 | d0Mseg165 |
| 0 | 22058700 | 22060400 | d0Mseg166 |
| 0 | 22102100 | 22103850 | d0Mseg167 |
| 0 | 22222300 | 22223750 | d0Mseg172 |
| 0 | 23200050 | 23201850 | d0Mseg181 |
| 0 | 23833750 | 23835150 | d0Mseg184 |
| 0 | 23920150 | 23921750 | d0Mseg185 |
| 0 | 24065850 | 24067450 | d0Mseg186 |
| 0 | 24196000 | 24197650 | d0Mseg187 |
| 0 | 25178800 | 25179900 | d0Mseg188 |
| 0 | 25182350 | 25184100 | d0Mseg189 |
| 0 | 25237450 | 25239050 | d0Mseg190 |
| 0 | 25965050 | 25966450 | d0Mseg191 |
| 0 | 25997800 | 25999650 | d0Mseg192 |
| 0 | 26155850 | 26157700 | d0Mseg193 |
| 0 | 27398150 | 27399800 | d0Mseg194 |
| 0 | 30557050 | 30558950 | d0Mseg195 |
| 0 | 30626550 | 30628300 | d0Mseg196 |
| 0 | 32060900 | 32062500 | d0Mseg197 |
| 0 | 33110450 | 33111650 | d0Mseg198 |
| 0 | 33635000 | 33636550 | d0Mseg199 |
| 0 | 33945750 | 33947550 | d0Mseg202 |
| 0 | 34161650 | 34163250 | d0Mseg203 |
| 0 | 34449850 | 34451650 | d0Mseg205 |
| 0 | 34547150 | 34549000 | d0Mseg207 |
| 0 | 34703150 | 34704450 | d0Mseg210 |
| 0 | 34754750 | 34758750 | d0Mseg211 |
| 0 | 34840000 | 34841700 | d0Mseg212 |
| 0 | 34927800 | 34929000 | d0Mseg213 |
| 0 | 34999550 | 35001250 | d0Mseg214 |
| 0 | 35011550 | 35013300 | d0Mseg215 |
| 0 | 35074650 | 35076350 | d0Mseg216 |
| 0 | 35167550 | 35169200 | d0Mseg217 |
| 0 | 35253900 | 35255850 | d0Mseg218 |
| 0 | 35273000 | 35274700 | d0Mseg219 |
| 0 | 35533100 | 35535000 | d0Mseg220 |
| 0 | 36097300 | 36098550 | d0Mseg229 |
| 0 | 36243100 | 36244800 | d0Mseg231 |
| 0 | 36272000 | 36273000 | d0Mseg232 |
| 0 | 36331400 | 36332450 | d0Mseg233 |
| 0 | 36363600 | 36365350 | d0Mseg234 |
| 0 | 36428650 | 36430300 | d0Mseg235 |
| 0 | 36697800 | 36699550 | d0Mseg237 |
| 0 | 37126800 | 37128500 | d0Mseg239 |
| 0 | 37220600 | 37222150 | d0Mseg240 |
| 0 | 37754100 | 37756000 | d0Mseg241 |
| 0 | 37808500 | 37810100 | d0Mseg243 |
| 0 | 37893300 | 37894950 | d0Mseg245 |
| 0 | 38033100 | 38034650 | d0Mseg246 |
| 0 | 38153950 | 38155650 | d0Mseg247 |
| 0 | 38268000 | 38269650 | d0Mseg248 |
| 0 | 38427700 | 38429500 | d0Mseg249 |
| 0 | 38451300 | 38453000 | d0Mseg250 |
| 0 | 38549550 | 38551200 | d0Mseg252 |
| 0 | 39290250 | 39291450 | d0Mseg258 |
| 0 | 39392900 | 39394600 | d0Mseg260 |
| 0 | 39490350 | 39492000 | d0Mseg261 |
| 0 | 39682450 | 39684100 | d0Mseg264 |
| 0 | 40276600 | 40278350 | d0Mseg273 |
| 0 | 40562500 | 40564300 | d0Mseg277 |
| 0 | 40765100 | 40766850 | d0Mseg278 |
| 0 | 41442300 | 41444150 | d0Mseg286 |
| 0 | 41556450 | 41558050 | d0Mseg288 |
| 0 | 41780950 | 41782300 | d0Mseg290 |
| 0 | 41889350 | 41891000 | d0Mseg291 |
| 0 | 41971850 | 41973650 | d0Mseg292 |
| 0 | 41976150 | 41977200 | d0Mseg293 |
| 0 | 42412450 | 42414150 | d0Mseg294 |
| 0 | 42839400 | 42841100 | d0Mseg295 |
| 0 | 42886550 | 42888200 | d0Mseg296 |
| 0 | 42916700 | 42918400 | d0Mseg297 |
| 0 | 43051500 | 43052900 | d0Mseg298 |
| 0 | 43144850 | 43146550 | d0Mseg299 |
| 0 | 43152750 | 43154600 | d0Mseg300 |
| 0 | 43214150 | 43215250 | d0Mseg301 |
| 0 | 43569750 | 43571350 | d0Mseg302 |
| 0 | 43666950 | 43668750 | d0Mseg303 |
| 0 | 43689450 | 43691150 | d0Mseg304 |
| 0 | 43784050 | 43785800 | d0Mseg305 |
| 0 | 43971000 | 43972900 | d0Mseg307 |
| 0 | 43980600 | 43982400 | d0Mseg308 |
| 0 | 44065700 | 44067250 | d0Mseg309 |
| 0 | 44279100 | 44280750 | d0Mseg310 |
| 0 | 44987050 | 44988900 | d0Mseg317 |
| 0 | 45953400 | 45955000 | d0Mseg326 |
| 0 | 46107500 | 46109150 | d0Mseg327 |
| 0 | 46152600 | 46154350 | d0Mseg329 |
| 0 | 46451250 | 46453300 | d0Mseg333 |
| 0 | 46468750 | 46470500 | d0Mseg334 |
| 0 | 46499600 | 46501300 | d0Mseg335 |
| 0 | 46683350 | 46684350 | d0Mseg336 |
| 0 | 46774000 | 46775700 | d0Mseg337 |
| 0 | 46911200 | 46912900 | d0Mseg344 |
| 0 | 47334200 | 47335900 | d0Mseg351 |
| 0 | 47348150 | 47349900 | d0Mseg352 |
| 0 | 47725700 | 47728350 | d0Mseg354 |
| 0 | 47894500 | 47896200 | d0Mseg355 |
| 0 | 47991050 | 47992300 | d0Mseg356 |
| 0 | 48382050 | 48383500 | d0Mseg360 |
| 0 | 49215000 | 49216800 | d0Mseg371 |
| 0 | 49325650 | 49327300 | d0Mseg372 |

TABLE IVC-continued

Mouse Moderate Sites

| c/d | start | end | segment |
|---|---|---|---|
| 0 | 50042400 | 50043500 | d0Mseg379 |
| 0 | 50203300 | 50206100 | d0Mseg382 |
| 0 | 50250650 | 50252450 | d0Mseg383 |
| 0 | 50623900 | 50625700 | d0Mseg388 |
| 0 | 50727600 | 50729500 | d0Mseg390 |
| 0 | 50782000 | 50783700 | d0Mseg391 |
| 0 | 50809750 | 50810950 | d0Mseg392 |
| 0 | 50926250 | 50928200 | d0Mseg393 |
| 0 | 50937400 | 50939200 | d0Mseg394 |
| 0 | 51007100 | 51008750 | d0Mseg395 |
| 0 | 51075300 | 51080100 | d0Mseg397 |
| 0 | 51094900 | 51096750 | d0Mseg398 |
| 0 | 51124650 | 51126300 | d0Mseg399 |
| 0 | 51185500 | 51187350 | d0Mseg400 |
| 0 | 51276800 | 51281250 | d0Mseg401 |
| 0 | 51291900 | 51293600 | d0Mseg402 |
| 0 | 51408950 | 51410550 | d0Mseg403 |
| 0 | 51546600 | 51548350 | d0Mseg404 |
| 0 | 52539900 | 52541600 | d0Mseg405 |
| 0 | 52681550 | 52683150 | d0Mseg406 |
| 0 | 52756550 | 52758300 | d0Mseg407 |
| 0 | 52760800 | 52762650 | d0Mseg408 |
| 0 | 52825900 | 52827150 | d0Mseg409 |
| 0 | 52951300 | 52953000 | d0Mseg410 |
| 0 | 53077650 | 53079250 | d0Mseg411 |
| 0 | 53181550 | 53182550 | d0Mseg412 |
| 0 | 53201550 | 53203300 | d0Mseg413 |
| 0 | 53355200 | 53357250 | d0Mseg414 |
| 0 | 53783450 | 53785150 | d0Mseg416 |
| 0 | 55102050 | 55103050 | d0Mseg427 |
| 0 | 55258100 | 55259800 | d0Mseg429 |
| 0 | 55322800 | 55324500 | d0Mseg431 |
| 0 | 55453850 | 55455650 | d0Mseg432 |
| 0 | 56609400 | 56610950 | d0Mseg444 |
| 0 | 57133200 | 57136250 | d0Mseg450 |
| 0 | 57670200 | 57671950 | d0Mseg456 |
| 0 | 58108800 | 58110500 | d0Mseg462 |
| 0 | 58437300 | 58439000 | d0Mseg466 |
| 0 | 58580850 | 58582300 | d0Mseg467 |
| 0 | 58951850 | 58952950 | d0Mseg470 |
| 0 | 59288200 | 59289850 | d0Mseg473 |
| 0 | 59516900 | 59518800 | d0Mseg476 |
| 0 | 59522850 | 59524500 | d0Mseg477 |
| 0 | 59602250 | 59603600 | d0Mseg478 |
| 0 | 59640650 | 59642600 | d0Mseg479 |
| 0 | 59840600 | 59842450 | d0Mseg480 |
| 0 | 59877800 | 59879600 | d0Mseg481 |
| 0 | 59949400 | 59951400 | d0Mseg482 |
| 0 | 59992700 | 59994400 | d0Mseg483 |
| 0 | 60058250 | 60060100 | d0Mseg484 |
| 0 | 60265700 | 60267300 | d0Mseg486 |
| 0 | 60360500 | 60362250 | d0Mseg487 |
| 0 | 60389700 | 60391350 | d0Mseg488 |
| 0 | 60425250 | 60426950 | d0Mseg489 |
| 0 | 60531700 | 60533350 | d0Mseg490 |
| 0 | 60613450 | 60615300 | d0Mseg491 |
| 0 | 60756100 | 60757800 | d0Mseg493 |
| 0 | 60776250 | 60777950 | d0Mseg494 |
| 0 | 60900650 | 60902100 | d0Mseg495 |
| 0 | 60921800 | 60923550 | d0Mseg496 |
| 0 | 61005150 | 61006750 | d0Mseg497 |
| 0 | 61024750 | 61026500 | d0Mseg499 |
| 0 | 61144100 | 61145650 | d0Mseg500 |
| 0 | 61305700 | 61307400 | d0Mseg502 |
| 0 | 61787100 | 61788700 | d0Mseg504 |
| 0 | 62017400 | 62018450 | d0Mseg506 |
| 0 | 62119600 | 62121100 | d0Mseg507 |
| 0 | 62229900 | 62231500 | d0Mseg508 |
| 0 | 62272100 | 62273300 | d0Mseg509 |
| 0 | 62310850 | 62312200 | d0Mseg510 |
| 0 | 62346700 | 62348300 | d0Mseg512 |
| 0 | 62443800 | 62445600 | d0Mseg513 |
| 0 | 62626900 | 62628700 | d0Mseg514 |
| 0 | 63125250 | 63126400 | d0Mseg518 |
| 0 | 63147950 | 63149600 | d0Mseg519 |
| 0 | 63180600 | 63182250 | d0Mseg520 |
| 0 | 63305150 | 63306900 | d0Mseg521 |
| 0 | 63313750 | 63315550 | d0Mseg522 |
| 0 | 63465550 | 63467300 | d0Mseg524 |
| 0 | 63480800 | 63482350 | d0Mseg525 |
| 0 | 63500200 | 63501950 | d0Mseg526 |
| 0 | 63788250 | 63789850 | d0Mseg529 |
| 0 | 64122350 | 64123950 | d0Mseg532 |
| 0 | 64222650 | 64224400 | d0Mseg535 |
| 0 | 64545950 | 64547100 | d0Mseg536 |
| 0 | 64758250 | 64759950 | d0Mseg537 |
| 0 | 64815850 | 64817600 | d0Mseg538 |
| 0 | 64947250 | 64948850 | d0Mseg540 |
| 0 | 65108800 | 65110550 | d0Mseg542 |
| 0 | 65195350 | 65196400 | d0Mseg544 |
| 0 | 65306400 | 65308150 | d0Mseg545 |
| 0 | 65420550 | 65422200 | d0Mseg547 |
| 0 | 65457400 | 65459200 | d0Mseg548 |
| 0 | 65636550 | 65638450 | d0Mseg550 |
| 0 | 66062150 | 66063950 | d0Mseg552 |
| 0 | 66329550 | 66331500 | d0Mseg556 |
| 0 | 66502450 | 66504500 | d0Mseg557 |
| 0 | 67191500 | 67193150 | d0Mseg567 |
| 0 | 67382350 | 67384050 | d0Mseg569 |
| 0 | 67761400 | 67763200 | d0Mseg571 |
| 0 | 68225650 | 68227450 | d0Mseg574 |
| 0 | 68443350 | 68444800 | d0Mseg578 |
| 0 | 68581500 | 68583200 | d0Mseg579 |
| 0 | 68715750 | 68717450 | d0Mseg580 |
| 0 | 68892300 | 68893500 | d0Mseg581 |
| 0 | 68924800 | 68926650 | d0Mseg583 |
| 0 | 68933900 | 68935650 | d0Mseg584 |
| 0 | 69636950 | 69638700 | d0Mseg590 |
| 0 | 69769550 | 69771250 | d0Mseg591 |
| 0 | 70302000 | 70303900 | d0Mseg593 |
| 0 | 70340800 | 70342250 | d0Mseg594 |
| 0 | 70406500 | 70408450 | d0Mseg595 |
| 0 | 70456600 | 70457800 | d0Mseg596 |
| 0 | 70617550 | 70619400 | d0Mseg597 |
| 0 | 71416350 | 71418100 | d0Mseg606 |
| 0 | 71439900 | 71441500 | d0Mseg607 |
| 0 | 71717150 | 71718900 | d0Mseg610 |
| 0 | 71732200 | 71733900 | d0Mseg611 |
| 0 | 71766550 | 71768550 | d0Mseg612 |
| 0 | 71772050 | 71773900 | d0Mseg613 |
| 0 | 72261750 | 72263350 | d0Mseg614 |
| 0 | 72319900 | 72321600 | d0Mseg615 |
| 0 | 72719800 | 72721500 | d0Mseg617 |
| 0 | 72791900 | 72793650 | d0Mseg618 |
| 0 | 72979050 | 72980550 | d0Mseg619 |
| 0 | 73026250 | 73027900 | d0Mseg620 |
| 0 | 73168900 | 73170500 | d0Mseg621 |
| 0 | 73205500 | 73207200 | d0Mseg622 |
| 0 | 73209450 | 73210700 | d0Mseg623 |
| 0 | 73214300 | 73216200 | d0Mseg624 |
| 0 | 73395450 | 73396850 | d0Mseg626 |
| 0 | 73814500 | 73816250 | d0Mseg628 |
| 0 | 73985200 | 73986950 | d0Mseg630 |
| 0 | 74090600 | 74092300 | d0Mseg631 |
| 0 | 74099000 | 74100650 | d0Mseg632 |
| 0 | 74254350 | 74255850 | d0Mseg634 |
| 0 | 74383200 | 74384900 | d0Mseg636 |
| 0 | 74388350 | 74390050 | d0Mseg637 |
| 0 | 74422450 | 74424050 | d0Mseg638 |
| 0 | 74950550 | 74952500 | d0Mseg642 |
| 0 | 74989200 | 74991000 | d0Mseg643 |
| 0 | 75264800 | 75266500 | d0Mseg644 |
| 0 | 75302750 | 75304800 | d0Mseg645 |
| 0 | 75343350 | 75345300 | d0Mseg646 |
| 0 | 75503350 | 75505000 | d0Mseg647 |
| 0 | 75876500 | 75878100 | d0Mseg649 |
| 0 | 76059750 | 76061450 | d0Mseg650 |
| 0 | 76099950 | 76102350 | d0Mseg651 |
| 0 | 76774750 | 76776700 | d0Mseg657 |
| 0 | 76972550 | 76973900 | d0Mseg659 |
| 0 | 77056000 | 77057750 | d0Mseg660 |
| 0 | 77238250 | 77239850 | d0Mseg661 |

TABLE IVC-continued

Mouse Moderate Sites

| c/d | start | end | segment |
|---|---|---|---|
| 0 | 77280800 | 77282500 | d0Mseg662 |
| 0 | 77413950 | 77415650 | d0Mseg663 |
| 0 | 77477200 | 77479100 | d0Mseg664 |
| 0 | 77630850 | 77632150 | d0Mseg666 |
| 0 | 77648800 | 77650550 | d0Mseg667 |
| 0 | 77713150 | 77714800 | d0Mseg669 |
| 0 | 77795650 | 77797250 | d0Mseg670 |
| 0 | 77836600 | 77838250 | d0Mseg671 |
| 0 | 78041500 | 78042800 | d0Mseg672 |
| 0 | 78410650 | 78412350 | d0Mseg673 |
| 0 | 78415050 | 78416650 | d0Mseg674 |
| 0 | 78677450 | 78679000 | d0Mseg675 |
| 0 | 78723050 | 78724800 | d0Mseg676 |
| 0 | 78727050 | 78728050 | d0Mseg677 |
| 0 | 78814000 | 78815700 | d0Mseg679 |
| 0 | 78817450 | 78819400 | d0Mseg680 |
| 0 | 78826850 | 78828450 | d0Mseg681 |
| 0 | 79118850 | 79120500 | d0Mseg683 |
| 0 | 79307350 | 79309100 | d0Mseg685 |
| 0 | 79320650 | 79322350 | d0Mseg686 |
| 0 | 79333950 | 79335550 | d0Mseg687 |
| 0 | 79367850 | 79369450 | d0Mseg688 |
| 0 | 79413200 | 79414800 | d0Mseg689 |
| 0 | 79439900 | 79441550 | d0Mseg690 |
| 0 | 79505600 | 79507350 | d0Mseg691 |
| 0 | 79537450 | 79539250 | d0Mseg692 |
| 0 | 79682500 | 79684150 | d0Mseg694 |
| 0 | 79810850 | 79812850 | d0Mseg695 |
| 0 | 79876400 | 79878050 | d0Mseg697 |
| 0 | 80343250 | 80344500 | d0Mseg700 |
| 0 | 80478750 | 80480500 | d0Mseg701 |
| 0 | 80586950 | 80588350 | d0Mseg702 |
| 0 | 80859950 | 80861650 | d0Mseg703 |
| 0 | 82754950 | 82756550 | d0Mseg716 |
| 0 | 83059750 | 83060800 | d0Mseg719 |
| 0 | 83585800 | 83587900 | d0Mseg723 |
| 0 | 83604000 | 83605800 | d0Mseg724 |
| 0 | 83659000 | 83660750 | d0Mseg725 |
| 0 | 83681100 | 83682650 | d0Mseg727 |
| 0 | 83737900 | 83739700 | d0Mseg728 |
| 0 | 83875350 | 83877050 | d0Mseg729 |
| 0 | 83906200 | 83907650 | d0Mseg730 |
| 0 | 84393250 | 84394900 | d0Mseg737 |
| 0 | 85048800 | 85050500 | d0Mseg746 |
| 0 | 85486100 | 85487750 | d0Mseg754 |
| 0 | 85591450 | 85592850 | d0Mseg755 |
| 0 | 85738950 | 85740600 | d0Mseg756 |
| 0 | 85852450 | 85853600 | d0Mseg758 |
| 0 | 85965200 | 85969050 | d0Mseg759 |
| 0 | 86021850 | 86023500 | d0Mseg760 |
| 0 | 86380450 | 86382050 | d0Mseg761 |
| 0 | 86796950 | 86798800 | d0Mseg764 |
| 0 | 86831250 | 86832900 | d0Mseg765 |
| 0 | 87010550 | 87012150 | d0Mseg768 |
| 0 | 87068300 | 87069850 | d0Mseg769 |
| 0 | 87112450 | 87114100 | d0Mseg770 |
| 0 | 87268250 | 87270000 | d0Mseg772 |
| 0 | 87454700 | 87456000 | d0Mseg773 |
| 0 | 87649100 | 87650300 | d0Mseg775 |
| 0 | 87694300 | 87696050 | d0Mseg776 |
| 0 | 87708500 | 87710300 | d0Mseg777 |
| 0 | 87783600 | 87785350 | d0Mseg779 |
| 0 | 87856000 | 87857700 | d0Mseg780 |
| 0 | 87874500 | 87876200 | d0Mseg781 |
| 0 | 87996150 | 87997750 | d0Mseg783 |
| 0 | 88041950 | 88042950 | d0Mseg784 |
| 0 | 88141300 | 88142900 | d0Mseg785 |
| 0 | 88269800 | 88272300 | d0Mseg787 |
| 0 | 88301600 | 88303450 | d0Mseg788 |
| 0 | 88322200 | 88324100 | d0Mseg789 |
| 0 | 88387200 | 88388850 | d0Mseg790 |
| 0 | 88437450 | 88439050 | d0Mseg791 |
| 0 | 88457250 | 88459100 | d0Mseg792 |
| 0 | 88538350 | 88539950 | d0Mseg793 |
| 0 | 88656750 | 88657950 | d0Mseg794 |
| 0 | 88669850 | 88670850 | d0Mseg795 |
| 0 | 88763350 | 88764550 | d0Mseg796 |
| 0 | 88986100 | 88987700 | d0Mseg797 |
| 0 | 89117600 | 89119300 | d0Mseg798 |
| 0 | 89128400 | 89130050 | d0Mseg799 |
| 0 | 89440850 | 89442550 | d0Mseg801 |
| 0 | 89487850 | 89489250 | d0Mseg803 |
| 0 | 89600550 | 89602250 | d0Mseg804 |
| 0 | 89838800 | 89840450 | d0Mseg808 |
| 0 | 90230650 | 90233850 | d0Mseg810 |
| 0 | 90336850 | 90337850 | d0Mseg813 |
| 0 | 91224550 | 91226300 | d0Mseg817 |
| 0 | 91739800 | 91740800 | d0Mseg822 |
| 0 | 91793300 | 91795350 | d0Mseg823 |
| 0 | 92015650 | 92017400 | d0Mseg825 |
| 0 | 92019050 | 92022950 | d0Mseg826 |
| 0 | 92030050 | 92031750 | d0Mseg827 |
| 0 | 92036200 | 92038050 | d0Mseg828 |
| 0 | 92531400 | 92533100 | d0Mseg829 |
| 0 | 92699450 | 92701050 | d0Mseg831 |
| 0 | 92820250 | 92821950 | d0Mseg833 |
| 0 | 92937550 | 92939400 | d0Mseg835 |
| 0 | 93183200 | 93184850 | d0Mseg837 |
| 0 | 93261400 | 93263050 | d0Mseg838 |
| 0 | 93276700 | 93278350 | d0Mseg839 |
| 0 | 93482500 | 93484200 | d0Mseg840 |
| 0 | 93841300 | 93843000 | d0Mseg842 |
| 0 | 93858250 | 93860050 | d0Mseg843 |
| 0 | 93898000 | 93899900 | d0Mseg844 |
| 0 | 93976800 | 93978600 | d0Mseg846 |
| 0 | 94103700 | 94105300 | d0Mseg847 |
| 0 | 94138750 | 94140600 | d0Mseg848 |
| 0 | 94255700 | 94257350 | d0Mseg849 |
| 0 | 94259300 | 94261000 | d0Mseg850 |
| 0 | 94462750 | 94465550 | d0Mseg851 |
| 0 | 94468300 | 94470000 | d0Mseg852 |
| 0 | 94794950 | 94796450 | d0Mseg855 |
| 0 | 94871900 | 94873450 | d0Mseg858 |
| 0 | 95011000 | 95012600 | d0Mseg859 |
| 0 | 95045450 | 95046600 | d0Mseg860 |
| 0 | 95092700 | 95094750 | d0Mseg861 |
| 0 | 95111300 | 95113000 | d0Mseg862 |
| 0 | 95237850 | 95239550 | d0Mseg863 |
| 0 | 95277100 | 95279100 | d0Mseg864 |
| 0 | 95592350 | 95594050 | d0Mseg866 |
| 0 | 95671550 | 95673300 | d0Mseg867 |
| 0 | 95742400 | 95744100 | d0Mseg868 |
| 0 | 96175600 | 96177300 | d0Mseg871 |
| 0 | 96318100 | 96320200 | d0Mseg874 |
| 0 | 96537000 | 96538650 | d0Mseg882 |
| 0 | 96884250 | 96886000 | d0Mseg892 |
| 0 | 97941450 | 97943400 | d0Mseg899 |
| 0 | 98205400 | 98207250 | d0Mseg903 |
| 0 | 98221150 | 98222900 | d0Mseg904 |
| 0 | 98253750 | 98255900 | d0Mseg905 |
| 0 | 98305100 | 98306300 | d0Mseg906 |
| 0 | 99019450 | 99021350 | d0Mseg917 |
| 0 | 99116900 | 99118450 | d0Mseg923 |
| 0 | 99331900 | 99333350 | d0Mseg927 |
| 0 | 99376000 | 99377650 | d0Mseg928 |
| 0 | 100151300 | 100153200 | d0Mseg937 |
| 0 | 100359350 | 100360850 | d0Mseg938 |
| 0 | 100466650 | 100468450 | d0Mseg940 |
| 0 | 100679700 | 100681700 | d0Mseg942 |
| 0 | 100686100 | 100689200 | d0Mseg943 |
| 0 | 100707400 | 100708650 | d0Mseg944 |
| 0 | 100721700 | 100723700 | d0Mseg945 |
| 0 | 100957950 | 100959550 | d0Mseg952 |
| 0 | 101059500 | 101061600 | d0Mseg955 |
| 0 | 101098850 | 101100650 | d0Mseg957 |
| 0 | 101221650 | 101222800 | d0Mseg958 |
| 0 | 101257400 | 101258550 | d0Mseg959 |
| 0 | 101267550 | 101269250 | d0Mseg960 |
| 0 | 101627600 | 101629250 | d0Mseg963 |
| 0 | 101795650 | 101797350 | d0Mseg965 |
| 0 | 101906600 | 101907600 | d0Mseg966 |
| 0 | 102103500 | 102105200 | d0Mseg970 |

TABLE IVC-continued

Mouse Moderate Sites

| c/d | start | end | segment |
|---|---|---|---|
| 0 | 102214950 | 102217750 | d0Mseg971 |
| 0 | 102377950 | 102379550 | d0Mseg974 |
| 0 | 102401700 | 102402700 | d0Mseg975 |
| 0 | 102729050 | 102730850 | d0Mseg977 |
| 0 | 102951750 | 102953500 | d0Mseg978 |
| 0 | 103354300 | 103355650 | d0Mseg981 |
| 0 | 103375500 | 103377250 | d0Mseg982 |
| 0 | 103461400 | 103463100 | d0Mseg984 |
| 0 | 103532250 | 103534050 | d0Mseg985 |
| 0 | 103593900 | 103595600 | d0Mseg986 |
| 0 | 103674400 | 103676100 | d0Mseg987 |
| 0 | 103679000 | 103681250 | d0Mseg988 |
| 0 | 103713350 | 103715150 | d0Mseg989 |
| 0 | 103748650 | 103750400 | d0Mseg990 |
| 0 | 103838500 | 103840200 | d0Mseg992 |
| 0 | 103911200 | 103913150 | d0Mseg994 |
| 0 | 104191150 | 104192950 | d0Mseg996 |
| 0 | 104241650 | 104243300 | d0Mseg997 |
| 0 | 104518400 | 104520050 | d0Mseg998 |
| 0 | 104550000 | 104551400 | d0Mseg999 |
| 0 | 104820600 | 104822350 | d0Mseg1002 |
| 0 | 105116250 | 105117350 | d0Mseg1005 |
| 0 | 105490300 | 105491900 | d0Mseg1006 |
| 0 | 105626050 | 105627750 | d0Mseg1007 |
| 0 | 105637200 | 105638350 | d0Mseg1008 |
| 0 | 105691250 | 105692700 | d0Mseg1009 |
| 0 | 105824300 | 105825850 | d0Mseg1010 |
| 0 | 105882100 | 105883800 | d0Mseg1011 |
| 0 | 105894150 | 105895700 | d0Mseg1012 |
| 0 | 106399950 | 106401400 | d0Mseg1018 |
| 0 | 106470600 | 106472300 | d0Mseg1019 |
| 0 | 106490300 | 106492250 | d0Mseg1020 |
| 0 | 106594300 | 106596000 | d0Mseg1021 |
| 0 | 106691400 | 106692950 | d0Mseg1023 |
| 0 | 106869750 | 106871550 | d0Mseg1024 |
| 0 | 106979750 | 106981350 | d0Mseg1025 |
| 0 | 107294250 | 107295750 | d0Mseg1027 |
| 0 | 107625750 | 107627150 | d0Mseg1030 |
| 0 | 107631800 | 107633850 | d0Mseg1031 |
| 0 | 107947200 | 107948900 | d0Mseg1034 |
| 0 | 108116700 | 108118600 | d0Mseg1036 |
| 0 | 108122550 | 108124200 | d0Mseg1037 |
| 0 | 108642600 | 108644400 | d0Mseg1040 |
| 0 | 108779750 | 108781550 | d0Mseg1043 |
| 0 | 108906450 | 108908050 | d0Mseg1045 |
| 0 | 109003300 | 109004900 | d0Mseg1046 |
| 0 | 109006700 | 109011200 | d0Mseg1047 |
| 0 | 109252300 | 109253500 | d0Mseg1048 |
| 0 | 109255150 | 109256850 | d0Mseg1049 |
| 0 | 109393450 | 109395300 | d0Mseg1051 |
| 0 | 109593350 | 109594700 | d0Mseg1053 |
| 0 | 110143600 | 110145500 | d0Mseg1058 |
| 0 | 110632150 | 110633800 | d0Mseg1060 |
| 0 | 111326800 | 111329500 | d0Mseg1063 |
| 0 | 111405500 | 111406650 | d0Mseg1064 |
| 0 | 111545400 | 111547100 | d0Mseg1065 |
| 0 | 111815600 | 111817550 | d0Mseg1067 |
| 0 | 112020750 | 112022450 | d0Mseg1068 |
| 0 | 112145800 | 112148750 | d0Mseg1069 |
| 0 | 112393200 | 112395300 | d0Mseg1070 |
| 0 | 112601800 | 112603400 | d0Mseg1072 |
| 0 | 112787800 | 112789500 | d0Mseg1073 |
| 0 | 112848650 | 112850100 | d0Mseg1074 |
| 0 | 113048050 | 113049150 | d0Mseg1075 |
| 0 | 113546950 | 113549200 | d0Mseg1077 |
| 0 | 113646200 | 113647750 | d0Mseg1078 |
| 0 | 113669100 | 113670800 | d0Mseg1079 |
| 0 | 114135100 | 114136100 | d0Mseg1082 |
| 0 | 114684700 | 114686500 | d0Mseg1084 |
| 0 | 114700450 | 114702250 | d0Mseg1085 |
| 0 | 115025200 | 115027200 | d0Mseg1086 |
| 0 | 115415450 | 115417150 | d0Mseg1087 |
| 0 | 115684300 | 115685950 | d0Mseg1088 |
| 0 | 115919850 | 115921650 | d0Mseg1090 |
| 0 | 116024300 | 116025900 | d0Mseg1092 |
| 0 | 116036500 | 116038600 | d0Mseg1093 |
| 0 | 116123200 | 116124950 | d0Mseg1094 |
| 0 | 116217400 | 116219150 | d0Mseg1095 |
| 0 | 116353750 | 116355450 | d0Mseg1098 |
| 0 | 116365000 | 116366650 | d0Mseg1099 |
| 0 | 116559650 | 116561100 | d0Mseg1101 |
| 0 | 116629100 | 116630750 | d0Mseg1102 |
| 0 | 116635550 | 116637350 | d0Mseg1103 |
| 0 | 116675600 | 116677500 | d0Mseg1104 |
| 0 | 116732650 | 116734550 | d0Mseg1105 |
| 0 | 116871000 | 116872500 | d0Mseg1106 |
| 0 | 117228750 | 117230600 | d0Mseg1109 |
| 0 | 117244400 | 117246300 | d0Mseg1110 |
| 0 | 117428900 | 117430500 | d0Mseg1114 |
| 0 | 118006150 | 118007800 | d0Mseg1117 |
| 0 | 118062150 | 118063850 | d0Mseg1118 |
| 0 | 118205250 | 118206350 | d0Mseg1119 |
| 0 | 118364400 | 118365800 | d0Mseg1120 |
| 0 | 118567950 | 118569650 | d0Mseg1121 |
| 0 | 118736900 | 118738450 | d0Mseg1122 |
| 0 | 118856550 | 118858200 | d0Mseg1123 |
| 0 | 119019200 | 119020950 | d0Mseg1124 |
| 0 | 119201550 | 119203300 | d0Mseg1127 |
| 0 | 119232700 | 119234350 | d0Mseg1128 |
| 0 | 119313800 | 119315400 | d0Mseg1131 |
| 0 | 119607150 | 119608800 | d0Mseg1133 |
| 0 | 119628850 | 119632400 | d0Mseg1135 |
| 0 | 119972800 | 119974250 | d0Mseg1138 |
| 0 | 120027300 | 120029150 | d0Mseg1139 |
| 0 | 120074950 | 120077000 | d0Mseg1140 |
| 0 | 120144650 | 120146100 | d0Mseg1141 |
| 0 | 120148600 | 120150550 | d0Mseg1142 |
| 0 | 120489400 | 120491150 | d0Mseg1143 |
| 0 | 120562850 | 120564500 | d0Mseg1144 |
| 0 | 120660150 | 120661800 | d0Mseg1145 |
| 0 | 120789550 | 120791150 | d0Mseg1146 |
| 0 | 120962150 | 120963750 | d0Mseg1147 |
| 0 | 121212800 | 121214450 | d0Mseg1148 |
| 0 | 121272450 | 121273800 | d0Mseg1149 |
| 0 | 122608950 | 122610350 | d0Mseg1150 |
| 0 | 122631150 | 122632800 | d0Mseg1151 |
| 0 | 122772950 | 122774700 | d0Mseg1152 |
| 0 | 122939250 | 122940300 | d0Mseg1153 |
| 0 | 123015600 | 123017050 | d0Mseg1154 |
| 0 | 123109250 | 123110750 | d0Mseg1155 |
| 0 | 123363600 | 123365300 | d0Mseg1157 |
| 0 | 123398700 | 123400600 | d0Mseg1158 |
| 0 | 123511600 | 123513250 | d0Mseg1159 |
| 0 | 123600850 | 123602550 | d0Mseg1160 |
| 0 | 123769100 | 123770700 | d0Mseg1161 |
| 0 | 123943500 | 123945250 | d0Mseg1162 |
| 0 | 123995300 | 123996550 | d0Mseg1163 |
| 0 | 124134200 | 124135900 | d0Mseg1164 |
| 0 | 124497800 | 124499700 | d0Mseg1165 |
| 0 | 124592100 | 124593700 | d0Mseg1166 |
| 0 | 124694500 | 124696200 | d0Mseg1167 |
| 0 | 124831400 | 124833050 | d0Mseg1168 |
| 0 | 124847250 | 124848650 | d0Mseg1169 |
| 0 | 125017850 | 125019550 | d0Mseg1171 |
| 0 | 125260200 | 125261900 | d0Mseg1172 |
| 0 | 125404050 | 125405800 | d0Mseg1174 |
| 0 | 125503900 | 125505600 | d0Mseg1175 |
| 0 | 125604400 | 125606150 | d0Mseg1176 |
| 0 | 125637050 | 125638900 | d0Mseg1177 |
| 0 | 125759350 | 125761100 | d0Mseg1178 |
| 0 | 125762750 | 125764150 | d0Mseg1179 |
| 0 | 126147050 | 126149150 | d0Mseg1180 |
| 0 | 127919250 | 127920850 | d0Mseg1188 |
| 0 | 128141600 | 128143750 | d0Mseg1190 |
| 0 | 128620550 | 128622250 | d0Mseg1195 |
| 0 | 128761600 | 128762900 | d0Mseg1196 |
| 0 | 129730850 | 129732550 | d0Mseg1200 |
| 0 | 129743700 | 129745750 | d0Mseg1201 |
| 0 | 129954000 | 129955700 | d0Mseg1202 |
| 0 | 130336000 | 130340700 | d0Mseg1208 |
| 0 | 130368350 | 130369550 | d0Mseg1209 |
| 0 | 131027100 | 131028500 | d0Mseg1216 |

TABLE IVC-continued

Mouse Moderate Sites

| c/d | start | end | segment |
|---|---|---|---|
| 0 | 131204150 | 131205800 | d0Mseg1217 |
| 0 | 131346500 | 131348200 | d0Mseg1219 |
| 0 | 131354000 | 131355700 | d0Mseg1220 |
| 0 | 131497950 | 131499600 | d0Mseg1224 |
| 0 | 131514050 | 131515700 | d0Mseg1225 |
| 0 | 131732800 | 131736150 | d0Mseg1227 |
| 0 | 131756800 | 131758450 | d0Mseg1229 |
| 0 | 131782750 | 131784350 | d0Mseg1230 |
| 0 | 131790250 | 131791900 | d0Mseg1231 |
| 0 | 131793750 | 131795650 | d0Mseg1232 |
| 0 | 131842750 | 131844550 | d0Mseg1233 |
| 0 | 132266000 | 132267400 | d0Mseg1235 |
| 0 | 132302800 | 132304350 | d0Mseg1236 |
| 0 | 132559400 | 132560600 | d0Mseg1238 |
| 0 | 132641650 | 132643300 | d0Mseg1239 |
| 0 | 132901400 | 132903200 | d0Mseg1242 |
| 0 | 132965250 | 132967250 | d0Mseg1243 |
| 0 | 133196500 | 133198500 | d0Mseg1245 |
| 0 | 133632100 | 133635600 | d0Mseg1252 |
| 0 | 133638300 | 133640900 | d0Mseg1253 |
| 0 | 133661200 | 133664050 | d0Mseg1255 |
| 0 | 133665600 | 133667550 | d0Mseg1256 |
| 0 | 133698000 | 133699850 | d0Mseg1257 |
| 0 | 133704550 | 133706550 | d0Mseg1258 |
| 0 | 134039500 | 134041150 | d0Mseg1260 |
| 0 | 134075600 | 134077550 | d0Mseg1261 |
| 0 | 134130950 | 134132550 | d0Mseg1263 |
| 0 | 134317850 | 134319350 | d0Mseg1265 |
| 0 | 134533000 | 134534600 | d0Mseg1266 |
| 0 | 134920500 | 134921500 | d0Mseg1268 |
| 0 | 134955400 | 134956800 | d0Mseg1270 |
| 0 | 135178500 | 135180300 | d0Mseg1274 |
| 0 | 135232950 | 135234650 | d0Mseg1275 |
| 0 | 135240800 | 135242500 | d0Mseg1276 |
| 0 | 135547250 | 135548650 | d0Mseg1282 |
| 0 | 135556400 | 135559550 | d0Mseg1283 |
| 0 | 135633850 | 135635250 | d0Mseg1285 |
| 0 | 135723250 | 135724900 | d0Mseg1286 |
| 0 | 135726100 | 135728000 | d0Mseg1287 |
| 0 | 135987350 | 135989000 | d0Mseg1289 |
| 0 | 135997750 | 135999050 | d0Mseg1290 |
| 0 | 136051300 | 136053100 | d0Mseg1292 |
| 0 | 136594750 | 136597450 | d0Mseg1297 |
| 0 | 137140850 | 137142900 | d0Mseg1312 |
| 0 | 137156650 | 137159900 | d0Mseg1313 |
| 0 | 137355200 | 137358750 | d0Mseg1319 |
| 0 | 137682600 | 137684200 | d0Mseg1324 |
| 0 | 137715600 | 137717500 | d0Mseg1326 |
| 0 | 137770050 | 137771050 | d0Mseg1328 |
| 0 | 138174650 | 138176350 | d0Mseg1337 |
| 0 | 138192250 | 138194250 | d0Mseg1339 |
| 0 | 138205000 | 138206800 | d0Mseg1340 |
| 0 | 138240350 | 138241550 | d0Mseg1341 |
| 0 | 138667250 | 138668250 | d0Mseg1346 |
| 0 | 138995100 | 138996850 | d0Mseg1350 |
| 0 | 139065250 | 139069750 | d0Mseg1351 |
| 0 | 139076150 | 139078000 | d0Mseg1352 |
| 0 | 139095300 | 139097200 | d0Mseg1353 |
| 0 | 139808700 | 139810050 | d0Mseg1364 |
| 0 | 140443800 | 140445600 | d0Mseg1371 |
| 0 | 140453250 | 140455150 | d0Mseg1372 |
| 0 | 140712350 | 140713900 | d0Mseg1373 |
| 0 | 141481200 | 141482600 | d0Mseg1377 |
| 0 | 141592950 | 141594250 | d0Mseg1378 |
| 0 | 141602050 | 141603700 | d0Mseg1379 |
| 0 | 141680100 | 141681850 | d0Mseg1380 |
| 0 | 141720250 | 141721950 | d0Mseg1381 |
| 0 | 142259150 | 142261000 | d0Mseg1386 |
| 0 | 142436950 | 142439550 | d0Mseg1388 |
| 0 | 142609300 | 142611000 | d0Mseg1389 |
| 0 | 142784250 | 142785950 | d0Mseg1391 |
| 0 | 142929800 | 142931650 | d0Mseg1392 |
| 0 | 143034900 | 143036700 | d0Mseg1394 |
| 0 | 143114400 | 143116150 | d0Mseg1396 |
| 0 | 143126350 | 143128050 | d0Mseg1397 |
| 0 | 143612050 | 143614850 | d0Mseg1403 |
| 0 | 143718550 | 143720200 | d0Mseg1404 |
| 0 | 143726050 | 143727650 | d0Mseg1405 |
| 0 | 143743400 | 143745250 | d0Mseg1406 |
| 0 | 143893150 | 143894900 | d0Mseg1407 |
| 0 | 144049250 | 144051350 | d0Mseg1410 |
| 0 | 144088050 | 144089650 | d0Mseg1411 |
| 0 | 144229600 | 144231450 | d0Mseg1412 |
| 0 | 145294150 | 145295800 | d0Mseg1413 |
| 0 | 145307450 | 145309100 | d0Mseg1414 |
| 0 | 145399400 | 145401000 | d0Mseg1415 |
| 0 | 145455450 | 145456750 | d0Mseg1416 |
| 0 | 146206350 | 146207900 | d0Mseg1418 |
| 0 | 146288450 | 146290250 | d0Mseg1420 |
| 0 | 146456650 | 146458400 | d0Mseg1421 |
| 0 | 146533650 | 146535250 | d0Mseg1422 |
| 0 | 146639950 | 146641550 | d0Mseg1423 |
| 0 | 146762600 | 146764250 | d0Mseg1424 |
| 0 | 146800750 | 146802450 | d0Mseg1425 |
| 0 | 146825850 | 146827450 | d0Mseg1426 |
| 0 | 146900350 | 146903250 | d0Mseg1427 |
| 0 | 146936300 | 146937350 | d0Mseg1428 |
| 0 | 147253700 | 147254950 | d0Mseg1430 |
| 0 | 147394800 | 147396400 | d0Mseg1431 |
| 0 | 147578550 | 147580300 | d0Mseg1432 |
| 0 | 148265100 | 148266650 | d0Mseg1434 |
| 0 | 148543400 | 148545350 | d0Mseg1437 |
| 0 | 149508800 | 149510550 | d0Mseg1442 |
| 0 | 149531650 | 149533500 | d0Mseg1443 |
| 0 | 149652250 | 149653700 | d0Mseg1444 |
| 0 | 149762050 | 149763600 | d0Mseg1445 |
| 0 | 149876750 | 149878500 | d0Mseg1448 |
| 0 | 150103000 | 150104700 | d0Mseg1450 |
| 0 | 150242200 | 150243950 | d0Mseg1452 |
| 0 | 150429700 | 150431400 | d0Mseg1454 |
| 0 | 150504600 | 150506350 | d0Mseg1455 |
| 0 | 150603700 | 150605450 | d0Mseg1456 |
| 0 | 150695300 | 150697000 | d0Mseg1457 |
| 0 | 150849700 | 150851350 | d0Mseg1458 |
| 0 | 150969200 | 150971100 | d0Mseg1459 |
| 0 | 151195150 | 151196600 | d0Mseg1460 |
| 0 | 151325350 | 151327100 | d0Mseg1461 |
| 0 | 151436700 | 151438350 | d0Mseg1462 |
| 0 | 151513650 | 151515300 | d0Mseg1463 |
| 0 | 151959750 | 151961500 | d0Mseg1466 |
| 0 | 152105050 | 152106150 | d0Mseg1469 |
| 0 | 152179500 | 152181100 | d0Mseg1470 |
| 0 | 152303200 | 152305050 | d0Mseg1471 |
| 0 | 152412000 | 152413450 | d0Mseg1472 |
| 0 | 153284600 | 153286300 | d0Mseg1476 |
| 0 | 153370000 | 153371400 | d0Mseg1478 |
| 0 | 153400950 | 153402700 | d0Mseg1479 |
| 0 | 153534150 | 153535900 | d0Mseg1480 |
| 0 | 153757500 | 153758700 | d0Mseg1481 |
| 0 | 154499650 | 154500800 | d0Mseg1485 |
| 0 | 154551650 | 154553600 | d0Mseg1486 |
| 0 | 154681400 | 154682450 | d0Mseg1488 |
| 0 | 154732250 | 154734050 | d0Mseg1489 |
| 0 | 155046000 | 155047650 | d0Mseg1490 |
| 0 | 155256600 | 155258350 | d0Mseg1492 |
| 0 | 155277500 | 155279200 | d0Mseg1493 |
| 0 | 155351050 | 155353600 | d0Mseg1495 |
| 0 | 155555850 | 155557700 | d0Mseg1497 |
| 0 | 155832500 | 155834400 | d0Mseg1502 |
| 0 | 155980850 | 155982300 | d0Mseg1504 |
| 0 | 157516650 | 157518650 | d0Mseg1520 |
| 0 | 157556750 | 157558400 | d0Mseg1521 |
| 0 | 157572200 | 157573950 | d0Mseg1522 |
| 0 | 157735700 | 157737750 | d0Mseg1524 |
| 0 | 157750700 | 157752500 | d0Mseg1525 |
| 0 | 158820150 | 158821850 | d0Mseg1539 |
| 0 | 159074350 | 159076150 | d0Mseg1541 |
| 0 | 160189150 | 160191000 | d0Mseg1547 |
| 0 | 160197550 | 160199650 | d0Mseg1548 |
| 0 | 160474700 | 160475700 | d0Mseg1551 |
| 0 | 161477750 | 161479400 | d0Mseg1557 |
| 0 | 161848050 | 161849700 | d0Mseg1561 |

TABLE IVC-continued

Mouse Moderate Sites

| c/d | start | end | segment |
|---|---|---|---|
| 0 | 161957500 | 161959100 | d0Mseg1562 |
| 0 | 162659200 | 162661100 | d0Mseg1567 |
| 0 | 163084400 | 163086700 | d0Mseg1573 |
| 0 | 163150050 | 163151050 | d0Mseg1574 |
| 0 | 163335200 | 163336900 | d0Mseg1577 |
| 0 | 163895400 | 163897100 | d0Mseg1579 |
| 0 | 164403750 | 164405400 | d0Mseg1583 |
| 0 | 164632400 | 164633550 | d0Mseg1587 |
| 0 | 164670400 | 164672200 | d0Mseg1588 |
| 0 | 164979450 | 164981050 | d0Mseg1592 |
| 0 | 165294750 | 165296450 | d0Mseg1597 |
| 0 | 165360200 | 165361900 | d0Mseg1600 |
| 0 | 165528050 | 165530000 | d0Mseg1603 |
| 0 | 165802400 | 165804200 | d0Mseg1609 |
| 0 | 165928600 | 165930150 | d0Mseg1610 |
| 0 | 165951550 | 165953150 | d0Mseg1611 |
| 0 | 166284650 | 166286550 | d0Mseg1614 |
| 0 | 166425400 | 166429400 | d0Mseg1618 |
| 7 | 4307600 | 4309000 | d7Mseg1 |
| 7 | 4574750 | 4575950 | d7Mseg2 |
| 7 | 4723150 | 4724150 | d7Mseg3 |
| 7 | 5044850 | 5046800 | d7Mseg5 |
| 7 | 5334700 | 5336400 | d7Mseg6 |
| 7 | 5503100 | 5504200 | d7Mseg7 |
| 7 | 5567800 | 5569200 | d7Mseg8 |
| 7 | 5575150 | 5576950 | d7Mseg9 |
| 7 | 5578300 | 5579800 | d7Mseg10 |
| 7 | 5671100 | 5672450 | d7Mseg13 |
| 7 | 5685650 | 5686650 | d7Mseg14 |
| 7 | 5697100 | 5698800 | d7Mseg15 |
| 7 | 5702100 | 5703750 | d7Mseg16 |
| 7 | 5808300 | 5810000 | d7Mseg18 |
| 7 | 5857350 | 5858650 | d7Mseg20 |
| 7 | 5867000 | 5868500 | d7Mseg21 |
| 7 | 5888700 | 5890200 | d7Mseg22 |
| 7 | 6083650 | 6085250 | d7Mseg26 |
| 7 | 6223850 | 6225500 | d7Mseg28 |
| 7 | 6270050 | 6271050 | d7Mseg29 |
| 7 | 6492100 | 6493800 | d7Mseg37 |
| 7 | 6508850 | 6509950 | d7Mseg38 |
| 7 | 6550800 | 6551900 | d7Mseg41 |
| 7 | 6593600 | 6595300 | d7Mseg43 |
| 7 | 6687600 | 6689400 | d7Mseg48 |
| 7 | 6690650 | 6692300 | d7Mseg49 |
| 7 | 6695500 | 6700150 | d7Mseg50 |
| 7 | 6724100 | 6725200 | d7Mseg51 |
| 7 | 6780450 | 6782000 | d7Mseg54 |
| 7 | 6807950 | 6809500 | d7Mseg55 |
| 7 | 6878800 | 6882850 | d7Mseg60 |
| 7 | 6911300 | 6913200 | d7Mseg63 |
| 7 | 6923650 | 6925300 | d7Mseg64 |
| 7 | 6967700 | 6968850 | d7Mseg70 |
| 7 | 7005550 | 7007450 | d7Mseg72 |
| 7 | 7074300 | 7079600 | d7Mseg76 |
| 7 | 7099550 | 7101400 | d7Mseg77 |
| 7 | 7105800 | 7107500 | d7Mseg78 |
| 7 | 7110650 | 7112600 | d7Mseg79 |
| 7 | 7120550 | 7123400 | d7Mseg80 |
| 7 | 7129950 | 7131650 | d7Mseg81 |
| 7 | 7290700 | 7292500 | d7Mseg90 |
| 7 | 7328650 | 7330300 | d7Mseg92 |
| 7 | 7355500 | 7356800 | d7Mseg94 |
| 7 | 7526550 | 7528550 | d7Mseg108 |
| 7 | 7573250 | 7575000 | d7Mseg109 |
| 7 | 7600700 | 7602200 | d7Mseg112 |
| 7 | 7609400 | 7610500 | d7Mseg113 |
| 7 | 7623400 | 7624800 | d7Mseg114 |
| 7 | 7653550 | 7655750 | d7Mseg115 |
| 7 | 7672400 | 7673550 | d7Mseg116 |
| 7 | 7681350 | 7682450 | d7Mseg117 |
| 7 | 7689450 | 7691400 | d7Mseg118 |
| 7 | 7697200 | 7699100 | d7Mseg119 |
| 7 | 7714200 | 7715850 | d7Mseg121 |
| 7 | 7807400 | 7809100 | d7Mseg127 |
| 7 | 7932900 | 7934750 | d7Mseg129 |
| 7 | 7938250 | 7940150 | d7Mseg130 |
| 7 | 7979650 | 7981300 | d7Mseg131 |
| 7 | 7986300 | 7987850 | d7Mseg132 |
| 7 | 8111900 | 8113650 | d7Mseg133 |
| 7 | 8151800 | 8153350 | d7Mseg134 |
| 7 | 8208300 | 8209800 | d7Mseg136 |
| 7 | 8466450 | 8472550 | d7Mseg138 |
| 7 | 8902450 | 8904350 | d7Mseg142 |
| 7 | 9188300 | 9190200 | d7Mseg144 |
| 7 | 9259800 | 9261550 | d7Mseg146 |
| 7 | 9385400 | 9387100 | d7Mseg149 |
| 7 | 9410500 | 9412150 | d7Mseg150 |
| 7 | 9703150 | 9704300 | d7Mseg157 |
| 7 | 9901050 | 9902900 | d7Mseg163 |
| 7 | 9948550 | 9949800 | d7Mseg166 |
| 7 | 9952900 | 9954550 | d7Mseg167 |
| 7 | 10607000 | 10608500 | d7Mseg187 |
| 7 | 10749500 | 10751000 | d7Mseg195 |
| 7 | 10794200 | 10795950 | d7Mseg198 |
| 7 | 11001250 | 11003700 | d7Mseg205 |
| 7 | 11347350 | 11349000 | d7Mseg224 |
| 7 | 11611400 | 11612500 | d7Mseg237 |
| 7 | 11678450 | 11679550 | d7Mseg241 |
| 7 | 11743000 | 11746400 | d7Mseg246 |
| 7 | 11910800 | 11912450 | d7Mseg254 |
| 7 | 11971200 | 11972900 | d7Mseg257 |
| 7 | 12026000 | 12027700 | d7Mseg261 |
| 7 | 12235550 | 12237250 | d7Mseg268 |
| 7 | 12440350 | 12441500 | d7Mseg275 |
| 7 | 12457900 | 12459600 | d7Mseg276 |
| 7 | 12497350 | 12498850 | d7Mseg277 |
| 7 | 12501600 | 12503150 | d7Mseg278 |
| 7 | 12512850 | 12514750 | d7Mseg279 |
| 7 | 12592100 | 12593300 | d7Mseg283 |
| 7 | 12636400 | 12638050 | d7Mseg285 |
| 7 | 12782250 | 12784050 | d7Mseg288 |
| 7 | 12799150 | 12801200 | d7Mseg289 |
| 7 | 12816750 | 12819800 | d7Mseg291 |
| 7 | 12884800 | 12886500 | d7Mseg292 |
| 7 | 12891300 | 12893100 | d7Mseg293 |
| 7 | 12913800 | 12915100 | d7Mseg294 |
| 7 | 13010550 | 13011600 | d7Mseg296 |
| 7 | 13036750 | 13038100 | d7Mseg297 |
| 7 | 13446450 | 13448050 | d7Mseg314 |
| 7 | 13739350 | 13740450 | d7Mseg319 |
| 7 | 14100400 | 14101400 | d7Mseg324 |
| 7 | 14353050 | 14354550 | d7Mseg325 |
| 7 | 14648500 | 14650350 | d7Mseg326 |
| 7 | 14982850 | 14984400 | d7Mseg328 |
| 7 | 15419100 | 15420400 | d7Mseg329 |
| 7 | 15629000 | 15630000 | d7Mseg330 |
| 7 | 15723100 | 15725050 | d7Mseg331 |
| 7 | 15958500 | 15959950 | d7Mseg333 |
| 7 | 16001800 | 16003650 | d7Mseg334 |
| 7 | 16037250 | 16038550 | d7Mseg335 |
| 7 | 16566600 | 16568200 | d7Mseg343 |
| 7 | 16936050 | 16937650 | d7Mseg349 |
| 7 | 16949800 | 16951350 | d7Mseg350 |
| 7 | 17122450 | 17123500 | d7Mseg353 |
| 7 | 17162750 | 17164400 | d7Mseg356 |
| 7 | 17614200 | 17615400 | d7Mseg360 |
| 7 | 17903000 | 17904500 | d7Mseg361 |
| 7 | 18247500 | 18249100 | d7Mseg363 |
| 7 | 18409500 | 18411100 | d7Mseg364 |
| 7 | 19298050 | 19299850 | d7Mseg369 |
| 7 | 19329200 | 19331150 | d7Mseg370 |
| 7 | 19623550 | 19624950 | d7Mseg372 |
| 7 | 19627200 | 19628500 | d7Mseg373 |
| 7 | 19651650 | 19653350 | d7Mseg375 |
| 7 | 19661150 | 19663150 | d7Mseg376 |
| 7 | 19721450 | 19722500 | d7Mseg378 |
| 7 | 19875800 | 19876850 | d7Mseg380 |
| 7 | 20021900 | 20023350 | d7Mseg383 |
| 7 | 20049300 | 20050900 | d7Mseg384 |
| 7 | 20058500 | 20059900 | d7Mseg385 |
| 7 | 20116250 | 20118000 | d7Mseg386 |
| 7 | 20146100 | 20147850 | d7Mseg389 |

TABLE IVC-continued

Mouse Moderate Sites

| c/d | start | end | segment |
|---|---|---|---|
| 7 | 20155950 | 20157050 | d7Mseg390 |
| 7 | 20321200 | 20323000 | d7Mseg395 |
| 7 | 20324750 | 20325950 | d7Mseg396 |
| 7 | 20559800 | 20560800 | d7Mseg402 |
| 7 | 20573600 | 20575600 | d7Mseg403 |
| 7 | 20675950 | 20677300 | d7Mseg404 |
| 7 | 20727750 | 20729200 | d7Mseg407 |
| 7 | 20786900 | 20788250 | d7Mseg408 |
| 7 | 20802200 | 20803950 | d7Mseg409 |
| 7 | 20849300 | 20851000 | d7Mseg410 |
| 7 | 20856850 | 20858800 | d7Mseg411 |
| 7 | 20937100 | 20940950 | d7Mseg413 |
| 7 | 20947200 | 20949100 | d7Mseg414 |
| 7 | 21006200 | 21007650 | d7Mseg415 |
| 7 | 21023050 | 21024550 | d7Mseg416 |
| 7 | 21146750 | 21148150 | d7Mseg419 |
| 7 | 21247000 | 21248700 | d7Mseg422 |
| 7 | 21258400 | 21259700 | d7Mseg423 |
| 7 | 21283950 | 21285650 | d7Mseg424 |
| 7 | 21353150 | 21354300 | d7Mseg426 |
| 7 | 21430900 | 21432600 | d7Mseg427 |
| 7 | 21459950 | 21461500 | d7Mseg429 |
| 7 | 21529550 | 21531500 | d7Mseg430 |
| 7 | 21644650 | 21646150 | d7Mseg431 |
| 7 | 21806400 | 21807450 | d7Mseg432 |
| 7 | 21830050 | 21831250 | d7Mseg433 |
| 7 | 21862900 | 21863950 | d7Mseg434 |
| 7 | 22045600 | 22047350 | d7Mseg435 |
| 7 | 22055500 | 22057100 | d7Mseg436 |
| 7 | 22506550 | 22508200 | d7Mseg438 |
| 7 | 23168550 | 23169650 | d7Mseg443 |
| 7 | 23178400 | 23179800 | d7Mseg444 |
| 7 | 23215200 | 23216650 | d7Mseg445 |
| 7 | 23913100 | 23914300 | d7Mseg448 |
| 7 | 24378050 | 24379600 | d7Mseg449 |
| 7 | 25313250 | 25314650 | d7Mseg450 |
| 7 | 25496900 | 25498450 | d7Mseg451 |
| 7 | 25604450 | 25605850 | d7Mseg452 |
| 7 | 31083550 | 31085050 | d7Mseg453 |
| 7 | 32128850 | 32130300 | d7Mseg454 |
| 7 | 33094450 | 33096050 | d7Mseg455 |
| 7 | 33119700 | 33120700 | d7Mseg456 |
| 7 | 33346100 | 33347900 | d7Mseg457 |
| 7 | 33379550 | 33381050 | d7Mseg458 |
| 7 | 33409500 | 33411250 | d7Mseg460 |
| 7 | 33698550 | 33700100 | d7Mseg467 |
| 7 | 33754150 | 33756150 | d7Mseg471 |
| 7 | 33837600 | 33839450 | d7Mseg475 |
| 7 | 33841200 | 33842400 | d7Mseg476 |
| 7 | 33912350 | 33914300 | d7Mseg481 |
| 7 | 33959650 | 33961100 | d7Mseg483 |
| 7 | 34207150 | 34209200 | d7Mseg493 |
| 7 | 34448300 | 34449800 | d7Mseg501 |
| 7 | 34544000 | 34545700 | d7Mseg506 |
| 7 | 34570100 | 34573550 | d7Mseg509 |
| 7 | 34576350 | 34578100 | d7Mseg510 |
| 7 | 34595250 | 34597100 | d7Mseg512 |
| 7 | 34601050 | 34602600 | d7Mseg513 |
| 7 | 34654600 | 34657700 | d7Mseg516 |
| 7 | 34894000 | 34895650 | d7Mseg521 |
| 7 | 34911900 | 34912950 | d7Mseg522 |
| 7 | 35017350 | 35018500 | d7Mseg523 |
| 7 | 35044500 | 35046000 | d7Mseg524 |
| 7 | 35057150 | 35058850 | d7Mseg525 |
| 7 | 35065400 | 35067100 | d7Mseg526 |
| 7 | 35084450 | 35086050 | d7Mseg527 |
| 7 | 35096250 | 35097800 | d7Mseg528 |
| 7 | 35105250 | 35106450 | d7Mseg529 |
| 7 | 35111400 | 35112500 | d7Mseg530 |
| 7 | 35173650 | 35175350 | d7Mseg531 |
| 7 | 35178900 | 35181600 | d7Mseg532 |
| 7 | 35182900 | 35184500 | d7Mseg533 |
| 7 | 35220700 | 35222450 | d7Mseg535 |
| 7 | 35255600 | 35256800 | d7Mseg537 |
| 7 | 35285700 | 35287000 | d7Mseg538 |
| 7 | 35292450 | 35294250 | d7Mseg539 |
| 7 | 35334750 | 35336450 | d7Mseg540 |
| 7 | 35372350 | 35376050 | d7Mseg541 |
| 7 | 35378300 | 35379550 | d7Mseg542 |
| 7 | 35436950 | 35438350 | d7Mseg543 |
| 7 | 35443650 | 35444650 | d7Mseg544 |
| 7 | 35451450 | 35452850 | d7Mseg545 |
| 7 | 35473950 | 35476050 | d7Mseg548 |
| 7 | 35527100 | 35528350 | d7Mseg550 |
| 7 | 35532850 | 35535100 | d7Mseg551 |
| 7 | 35617400 | 35619250 | d7Mseg557 |
| 7 | 35653050 | 35654950 | d7Mseg558 |
| 7 | 35725400 | 35728650 | d7Mseg559 |
| 7 | 35746700 | 35748050 | d7Mseg561 |
| 7 | 35838750 | 35840450 | d7Mseg563 |
| 7 | 35862050 | 35863450 | d7Mseg564 |
| 7 | 35932250 | 35933900 | d7Mseg567 |
| 7 | 35989100 | 35992350 | d7Mseg572 |
| 7 | 36096400 | 36098050 | d7Mseg575 |
| 7 | 36249950 | 36251450 | d7Mseg576 |
| 7 | 36334250 | 36336200 | d7Mseg577 |
| 7 | 36548250 | 36550000 | d7Mseg578 |
| 7 | 36643200 | 36644750 | d7Mseg579 |
| 7 | 36725250 | 36726550 | d7Mseg581 |
| 7 | 36816250 | 36817900 | d7Mseg582 |
| 7 | 36935000 | 36936200 | d7Mseg585 |
| 7 | 37049500 | 37051050 | d7Mseg587 |
| 7 | 37115850 | 37117150 | d7Mseg588 |
| 7 | 37231500 | 37232950 | d7Mseg589 |
| 7 | 37318500 | 37320100 | d7Mseg593 |
| 7 | 37456700 | 37457900 | d7Mseg595 |
| 7 | 37497900 | 37499050 | d7Mseg596 |
| 7 | 37562700 | 37563750 | d7Mseg597 |
| 7 | 37579450 | 37581000 | d7Mseg598 |
| 7 | 37650950 | 37652750 | d7Mseg599 |
| 7 | 37753350 | 37755150 | d7Mseg600 |
| 7 | 37780800 | 37781800 | d7Mseg601 |
| 7 | 37925400 | 37926650 | d7Mseg604 |
| 7 | 38047200 | 38048900 | d7Mseg606 |
| 7 | 38113450 | 38115100 | d7Mseg607 |
| 7 | 38137250 | 38138850 | d7Mseg608 |
| 7 | 38269350 | 38270850 | d7Mseg610 |
| 7 | 38377250 | 38378800 | d7Mseg612 |
| 7 | 38409200 | 38411000 | d7Mseg613 |
| 7 | 38442150 | 38443550 | d7Mseg614 |
| 7 | 38534300 | 38536050 | d7Mseg615 |
| 7 | 38725750 | 38727250 | d7Mseg618 |
| 7 | 39119550 | 39122300 | d7Mseg633 |
| 7 | 39204900 | 39206450 | d7Mseg636 |
| 7 | 39294900 | 39296850 | d7Mseg639 |
| 7 | 39336050 | 39337800 | d7Mseg641 |
| 7 | 39364300 | 39365450 | d7Mseg642 |
| 7 | 39410450 | 39412000 | d7Mseg643 |
| 7 | 39416200 | 39418000 | d7Mseg644 |
| 7 | 39648400 | 39649800 | d7Mseg650 |
| 7 | 39680400 | 39682500 | d7Mseg651 |
| 7 | 39744700 | 39746250 | d7Mseg653 |
| 7 | 39813750 | 39815550 | d7Mseg656 |
| 7 | 40033700 | 40034900 | d7Mseg666 |
| 7 | 40343700 | 40345550 | d7Mseg672 |
| 7 | 40388250 | 40389250 | d7Mseg673 |
| 7 | 40899050 | 40900600 | d7Mseg681 |
| 7 | 41158650 | 41160000 | d7Mseg682 |
| 7 | 41539150 | 41540700 | d7Mseg683 |
| 7 | 41562500 | 41564200 | d7Mseg684 |
| 7 | 41579700 | 41581550 | d7Mseg685 |
| 7 | 41706000 | 41707200 | d7Mseg687 |
| 7 | 41736550 | 41738050 | d7Mseg690 |
| 7 | 41798400 | 41799700 | d7Mseg693 |
| 7 | 41941200 | 41942850 | d7Mseg694 |
| 7 | 41983450 | 41985050 | d7Mseg696 |
| 7 | 41999850 | 42001250 | d7Mseg697 |
| 7 | 42417350 | 42419400 | d7Mseg699 |
| 7 | 42493200 | 42495050 | d7Mseg700 |
| 7 | 42525000 | 42527050 | d7Mseg701 |
| 7 | 42688200 | 42690150 | d7Mseg703 |
| 7 | 42774550 | 42775600 | d7Mseg705 |

TABLE IVC-continued

Mouse Moderate Sites

| c/d | start | end | segment |
|---|---|---|---|
| 7 | 42916750 | 42918000 | d7Mseg706 |
| 7 | 43065350 | 43066850 | d7Mseg707 |
| 7 | 43123400 | 43124600 | d7Mseg708 |
| 7 | 43184400 | 43186300 | d7Mseg709 |
| 7 | 43255950 | 43257900 | d7Mseg710 |
| 7 | 43281250 | 43282450 | d7Mseg711 |
| 7 | 43338900 | 43340750 | d7Mseg712 |
| 7 | 43397050 | 43399050 | d7Mseg713 |
| 7 | 43402700 | 43404350 | d7Mseg714 |
| 7 | 43441500 | 43442600 | d7Mseg715 |
| 7 | 43456450 | 43457800 | d7Mseg716 |
| 7 | 43507300 | 43508800 | d7Mseg717 |
| 7 | 43584300 | 43586800 | d7Mseg718 |
| 7 | 43777350 | 43779350 | d7Mseg721 |
| 7 | 43836900 | 43838600 | d7Mseg723 |
| 7 | 43862600 | 43864200 | d7Mseg724 |
| 7 | 43872050 | 43873600 | d7Mseg725 |
| 7 | 43993650 | 43995250 | d7Mseg729 |
| 7 | 44215200 | 44216300 | d7Mseg734 |
| 7 | 44329900 | 44331400 | d7Mseg739 |
| 7 | 44409350 | 44410350 | d7Mseg742 |
| 7 | 44628400 | 44629950 | d7Mseg748 |
| 7 | 44765550 | 44767100 | d7Mseg755 |
| 7 | 44799800 | 44801200 | d7Mseg756 |
| 7 | 44855950 | 44857850 | d7Mseg758 |
| 7 | 45045300 | 45046800 | d7Mseg761 |
| 7 | 45052500 | 45053600 | d7Mseg762 |
| 7 | 45301150 | 45302900 | d7Mseg769 |
| 7 | 45324450 | 45326400 | d7Mseg770 |
| 7 | 45339250 | 45341850 | d7Mseg771 |
| 7 | 45362150 | 45363400 | d7Mseg774 |
| 7 | 45402450 | 45403800 | d7Mseg778 |
| 7 | 45572050 | 45573550 | d7Mseg786 |
| 7 | 45594500 | 45596100 | d7Mseg787 |
| 7 | 45652400 | 45653900 | d7Mseg789 |
| 7 | 45889850 | 45891100 | d7Mseg804 |
| 7 | 46078850 | 46081100 | d7Mseg810 |
| 7 | 46105000 | 46106000 | d7Mseg811 |
| 7 | 46141350 | 46143250 | d7Mseg813 |
| 7 | 46164200 | 46165950 | d7Mseg814 |
| 7 | 46198850 | 46200050 | d7Mseg815 |
| 7 | 46210100 | 46211150 | d7Mseg816 |
| 7 | 46865500 | 46866600 | d7Mseg838 |
| 7 | 46891550 | 46892600 | d7Mseg839 |
| 7 | 46933200 | 46934900 | d7Mseg840 |
| 7 | 46953400 | 46954450 | d7Mseg841 |
| 7 | 47004350 | 47006100 | d7Mseg842 |
| 7 | 47079200 | 47080750 | d7Mseg843 |
| 7 | 47191950 | 47193850 | d7Mseg846 |
| 7 | 47198800 | 47200450 | d7Mseg847 |
| 7 | 47208500 | 47209650 | d7Mseg848 |
| 7 | 47223250 | 47224550 | d7Mseg849 |
| 7 | 47260550 | 47261750 | d7Mseg850 |
| 7 | 47285500 | 47287100 | d7Mseg852 |
| 7 | 47329200 | 47330300 | d7Mseg854 |
| 7 | 47395200 | 47396850 | d7Mseg856 |
| 7 | 47499200 | 47500350 | d7Mseg860 |
| 7 | 47551250 | 47552550 | d7Mseg861 |
| 7 | 47579250 | 47580650 | d7Mseg863 |
| 7 | 47590200 | 47591600 | d7Mseg864 |
| 7 | 47609950 | 47611350 | d7Mseg865 |
| 7 | 47661300 | 47663050 | d7Mseg866 |
| 7 | 47669950 | 47671350 | d7Mseg867 |
| 7 | 47715900 | 47717100 | d7Mseg868 |
| 7 | 47726600 | 47729450 | d7Mseg869 |
| 7 | 47743200 | 47744400 | d7Mseg870 |
| 7 | 47772400 | 47774150 | d7Mseg871 |
| 7 | 47833700 | 47835600 | d7Mseg873 |
| 7 | 47941850 | 47943200 | d7Mseg876 |
| 7 | 47987350 | 47989500 | d7Mseg877 |
| 7 | 47991050 | 47992200 | d7Mseg878 |
| 7 | 48001850 | 48004550 | d7Mseg879 |
| 7 | 48008250 | 48010000 | d7Mseg880 |
| 7 | 48015600 | 48017250 | d7Mseg881 |
| 7 | 48025850 | 48026950 | d7Mseg882 |
| 7 | 48048700 | 48050400 | d7Mseg884 |
| 7 | 48297650 | 48299400 | d7Mseg895 |
| 7 | 48382400 | 48384400 | d7Mseg902 |
| 7 | 48595000 | 48596450 | d7Mseg909 |
| 7 | 48647300 | 48649400 | d7Mseg911 |
| 7 | 48653550 | 48655150 | d7Mseg912 |
| 7 | 48665150 | 48666800 | d7Mseg913 |
| 7 | 48682650 | 48684150 | d7Mseg914 |
| 7 | 48762150 | 48763750 | d7Mseg920 |
| 7 | 49007400 | 49008850 | d7Mseg933 |
| 7 | 49043550 | 49044600 | d7Mseg936 |
| 7 | 49158750 | 49160400 | d7Mseg944 |
| 7 | 49168750 | 49170400 | d7Mseg945 |
| 7 | 49187600 | 49188950 | d7Mseg946 |
| 7 | 49294700 | 49296100 | d7Mseg950 |
| 7 | 49315900 | 49317700 | d7Mseg952 |
| 7 | 49324900 | 49326500 | d7Mseg953 |
| 7 | 49658250 | 49660050 | d7Mseg968 |
| 7 | 49818400 | 49819550 | d7Mseg979 |
| 7 | 50078400 | 50080200 | d7Mseg989 |
| 7 | 50197700 | 50198950 | d7Mseg996 |
| 7 | 50235750 | 50237450 | d7Mseg998 |
| 7 | 50249250 | 50250700 | d7Mseg1000 |
| 7 | 50323700 | 50325300 | d7Mseg1002 |
| 7 | 50753750 | 50755600 | d7Mseg1021 |
| 7 | 50764300 | 50766200 | d7Mseg1022 |
| 7 | 50792600 | 50793700 | d7Mseg1023 |
| 7 | 50819900 | 50821550 | d7Mseg1024 |
| 7 | 50826400 | 50828500 | d7Mseg1025 |
| 7 | 50921700 | 50923050 | d7Mseg1026 |
| 7 | 50939150 | 50940450 | d7Mseg1027 |
| 7 | 50944050 | 50945250 | d7Mseg1028 |
| 7 | 50996200 | 50997800 | d7Mseg1030 |
| 7 | 51029050 | 51030800 | d7Mseg1031 |
| 7 | 51048600 | 51050200 | d7Mseg1033 |
| 7 | 51059000 | 51062650 | d7Mseg1034 |
| 7 | 51076300 | 51080000 | d7Mseg1035 |
| 7 | 51081700 | 51083600 | d7Mseg1036 |
| 7 | 51177650 | 51179400 | d7Mseg1037 |
| 7 | 51276550 | 51281350 | d7Mseg1038 |
| 7 | 52594000 | 52595200 | d7Mseg1039 |
| 7 | 52840650 | 52841850 | d7Mseg1040 |
| 7 | 52891650 | 52893250 | d7Mseg1041 |
| 7 | 53184100 | 53185150 | d7Mseg1042 |
| 7 | 53388350 | 53390300 | d7Mseg1043 |
| 7 | 53394400 | 53395650 | d7Mseg1044 |
| 7 | 53452500 | 53454200 | d7Mseg1045 |
| 7 | 53502100 | 53503350 | d7Mseg1047 |
| 7 | 53545000 | 53546650 | d7Mseg1049 |
| 7 | 53634950 | 53636550 | d7Mseg1051 |
| 7 | 53646300 | 53648150 | d7Mseg1052 |
| 7 | 53649500 | 53651000 | d7Mseg1053 |
| 7 | 53679050 | 53680450 | d7Mseg1054 |
| 7 | 53683700 | 53685500 | d7Mseg1055 |
| 7 | 53805400 | 53807850 | d7Mseg1058 |
| 7 | 53810550 | 53812150 | d7Mseg1059 |
| 7 | 53854350 | 53855550 | d7Mseg1061 |
| 7 | 54118100 | 54119900 | d7Mseg1080 |
| 7 | 54544250 | 54545800 | d7Mseg1093 |
| 7 | 54733150 | 54734200 | d7Mseg1100 |
| 7 | 54843050 | 54844750 | d7Mseg1106 |
| 7 | 54935400 | 54937250 | d7Mseg1109 |
| 7 | 54988950 | 54990200 | d7Mseg1113 |
| 7 | 55242800 | 55243850 | d7Mseg1126 |
| 7 | 55586150 | 55587950 | d7Mseg1140 |
| 7 | 55598800 | 55600650 | d7Mseg1141 |
| 7 | 55650700 | 55652650 | d7Mseg1142 |
| 7 | 55797200 | 55799000 | d7Mseg1144 |
| 7 | 55851300 | 55853150 | d7Mseg1148 |
| 7 | 55958950 | 55960250 | d7Mseg1150 |
| 7 | 55979700 | 55981450 | d7Mseg1151 |
| 7 | 55985600 | 55987750 | d7Mseg1152 |
| 7 | 56059200 | 56060450 | d7Mseg1153 |
| 7 | 56071000 | 56072200 | d7Mseg1154 |
| 7 | 56104400 | 56106000 | d7Mseg1156 |
| 7 | 56231350 | 56232400 | d7Mseg1158 |
| 7 | 56262150 | 56263750 | d7Mseg1159 |

TABLE IVC-continued

Mouse Moderate Sites

| c/d | start | end | segment |
|---|---|---|---|
| 7 | 56676950 | 56678600 | d7Mseg1173 |
| 7 | 56916200 | 56917900 | d7Mseg1182 |
| 7 | 57018350 | 57020050 | d7Mseg1185 |
| 7 | 57091550 | 57093000 | d7Mseg1188 |
| 7 | 57094750 | 57096150 | d7Mseg1189 |
| 7 | 57111600 | 57113100 | d7Mseg1190 |
| 7 | 57126550 | 57128200 | d7Mseg1191 |
| 7 | 57137000 | 57138300 | d7Mseg1192 |
| 7 | 57669650 | 57670700 | d7Mseg1207 |
| 7 | 57736800 | 57738100 | d7Mseg1209 |
| 7 | 57761900 | 57763800 | d7Mseg1210 |
| 7 | 57787600 | 57789100 | d7Mseg1211 |
| 7 | 57966500 | 57968200 | d7Mseg1218 |
| 7 | 58298700 | 58299750 | d7Mseg1229 |
| 7 | 58346850 | 58348050 | d7Mseg1230 |
| 7 | 58456700 | 58458100 | d7Mseg1232 |
| 7 | 58540250 | 58542650 | d7Mseg1235 |
| 7 | 58650750 | 58652350 | d7Mseg1236 |
| 7 | 58750450 | 58752000 | d7Mseg1240 |
| 7 | 58789900 | 58791200 | d7Mseg1241 |
| 7 | 58809900 | 58813500 | d7Mseg1242 |
| 7 | 58918900 | 58919950 | d7Mseg1244 |
| 7 | 58926800 | 58928500 | d7Mseg1245 |
| 7 | 58938550 | 58940150 | d7Mseg1247 |
| 7 | 59099800 | 59101400 | d7Mseg1251 |
| 7 | 59634550 | 59636150 | d7Mseg1253 |
| 7 | 59760600 | 59762100 | d7Mseg1256 |
| 7 | 59780850 | 59782300 | d7Mseg1257 |
| 7 | 59824750 | 59826300 | d7Mseg1258 |
| 7 | 60135900 | 60137350 | d7Mseg1259 |
| 7 | 61078300 | 61079950 | d7Mseg1267 |
| 7 | 61137050 | 61138250 | d7Mseg1268 |
| 7 | 61364300 | 61365650 | d7Mseg1270 |
| 7 | 61823450 | 61825100 | d7Mseg1272 |
| 7 | 61861500 | 61863300 | d7Mseg1273 |
| 7 | 62268650 | 62270400 | d7Mseg1274 |
| 7 | 62518100 | 62519850 | d7Mseg1275 |
| 7 | 62756250 | 62757800 | d7Mseg1276 |
| 7 | 63237600 | 63239350 | d7Mseg1277 |
| 7 | 63309300 | 63310750 | d7Mseg1278 |
| 7 | 63375900 | 63377500 | d7Mseg1280 |
| 7 | 63524800 | 63526350 | d7Mseg1281 |
| 7 | 63938750 | 63940350 | d7Mseg1287 |
| 7 | 64017900 | 64019750 | d7Mseg1288 |
| 7 | 64357750 | 64359350 | d7Mseg1290 |
| 7 | 64575700 | 64576950 | d7Mseg1293 |
| 7 | 64721600 | 64723150 | d7Mseg1294 |
| 7 | 65151000 | 65152300 | d7Mseg1295 |
| 7 | 65334400 | 65336050 | d7Mseg1296 |
| 7 | 65467000 | 65468300 | d7Mseg1297 |
| 7 | 65506700 | 65507950 | d7Mseg1299 |
| 7 | 65657250 | 65658300 | d7Mseg1300 |
| 7 | 65767700 | 65769250 | d7Mseg1301 |
| 7 | 65819650 | 65821250 | d7Mseg1302 |
| 7 | 65842700 | 65844650 | d7Mseg1303 |
| 7 | 65866300 | 65867300 | d7Mseg1304 |
| 7 | 65873650 | 65875050 | d7Mseg1305 |
| 7 | 65972100 | 65973500 | d7Mseg1310 |
| 7 | 65976250 | 65977850 | d7Mseg1311 |
| 7 | 66003950 | 66005550 | d7Mseg1312 |
| 7 | 66061950 | 66063850 | d7Mseg1313 |
| 7 | 66073900 | 66075450 | d7Mseg1314 |
| 7 | 66139500 | 66140600 | d7Mseg1315 |
| 7 | 66173400 | 66175550 | d7Mseg1316 |
| 7 | 66194200 | 66195650 | d7Mseg1317 |
| 7 | 66239000 | 66240200 | d7Mseg1318 |
| 7 | 66287100 | 66288350 | d7Mseg1319 |
| 7 | 66439450 | 66441100 | d7Mseg1325 |
| 7 | 66459200 | 66460800 | d7Mseg1326 |
| 7 | 66489000 | 66490500 | d7Mseg1327 |
| 7 | 66525200 | 66526450 | d7Mseg1328 |
| 7 | 66788950 | 66790450 | d7Mseg1333 |
| 7 | 66859150 | 66860650 | d7Mseg1334 |
| 7 | 66922000 | 66923200 | d7Mseg1338 |
| 7 | 66924400 | 66926150 | d7Mseg1339 |
| 7 | 67156950 | 67158700 | d7Mseg1345 |
| 7 | 67192450 | 67193950 | d7Mseg1346 |
| 7 | 67223050 | 67224800 | d7Mseg1350 |
| 7 | 67284600 | 67286400 | d7Mseg1352 |
| 7 | 67295150 | 67296850 | d7Mseg1353 |
| 7 | 67527900 | 67529600 | d7Mseg1355 |
| 7 | 68030850 | 68032150 | d7Mseg1366 |
| 7 | 68052750 | 68054250 | d7Mseg1367 |
| 7 | 68214100 | 68215950 | d7Mseg1377 |
| 7 | 68317400 | 68318700 | d7Mseg1384 |
| 7 | 68319800 | 68321000 | d7Mseg1385 |
| 7 | 68451400 | 68453050 | d7Mseg1389 |
| 7 | 68571150 | 68572450 | d7Mseg1392 |
| 7 | 68574150 | 68575800 | d7Mseg1393 |
| 7 | 68593000 | 68594250 | d7Mseg1394 |
| 7 | 68719250 | 68720500 | d7Mseg1399 |
| 7 | 68778500 | 68779500 | d7Mseg1401 |
| 7 | 68861200 | 68864600 | d7Mseg1406 |
| 7 | 68892850 | 68894150 | d7Mseg1408 |
| 7 | 68897950 | 68899800 | d7Mseg1409 |
| 7 | 68943950 | 68945850 | d7Mseg1412 |
| 7 | 68971950 | 68973700 | d7Mseg1414 |
| 7 | 69100650 | 69102300 | d7Mseg1418 |
| 7 | 69139550 | 69140600 | d7Mseg1419 |
| 7 | 69193700 | 69195200 | d7Mseg1422 |
| 7 | 69197200 | 69198250 | d7Mseg1423 |
| 7 | 69265650 | 69267050 | d7Mseg1427 |
| 7 | 69313750 | 69314950 | d7Mseg1429 |
| 7 | 69316400 | 69317850 | d7Mseg1430 |
| 7 | 69354100 | 69355850 | d7Mseg1432 |
| 7 | 69409350 | 69411150 | d7Mseg1434 |
| 7 | 69538900 | 69540600 | d7Mseg1437 |
| 7 | 69546550 | 69548450 | d7Mseg1438 |
| 7 | 69558300 | 69560100 | d7Mseg1439 |
| 7 | 69568050 | 69569250 | d7Mseg1440 |
| 7 | 69588100 | 69589850 | d7Mseg1441 |
| 7 | 69637550 | 69639400 | d7Mseg1442 |
| 7 | 69676250 | 69677650 | d7Mseg1444 |
| 7 | 69709300 | 69710950 | d7Mseg1447 |
| 7 | 69809050 | 69810700 | d7Mseg1450 |
| 7 | 69848600 | 69850300 | d7Mseg1452 |
| 7 | 69945350 | 69947100 | d7Mseg1454 |
| 7 | 69996600 | 69998450 | d7Mseg1455 |
| 7 | 70033000 | 70034650 | d7Mseg1456 |
| 7 | 70094650 | 70096200 | d7Mseg1459 |
| 7 | 70099900 | 70101300 | d7Mseg1460 |
| 7 | 70268100 | 70269400 | d7Mseg1467 |
| 7 | 70270650 | 70272000 | d7Mseg1468 |
| 7 | 70291500 | 70293000 | d7Mseg1470 |
| 7 | 70335350 | 70336750 | d7Mseg1472 |
| 7 | 70348050 | 70349250 | d7Mseg1473 |
| 7 | 70469400 | 70470700 | d7Mseg1474 |
| 7 | 70506150 | 70507700 | d7Mseg1477 |
| 7 | 70585400 | 70587050 | d7Mseg1480 |
| 7 | 70615600 | 70616650 | d7Mseg1482 |
| 7 | 70619800 | 70621550 | d7Mseg1483 |
| 7 | 70625150 | 70626250 | d7Mseg1484 |
| 7 | 70833800 | 70835450 | d7Mseg1499 |
| 7 | 70837300 | 70838700 | d7Mseg1500 |
| 7 | 70849300 | 70851050 | d7Mseg1501 |
| 7 | 70895500 | 70897350 | d7Mseg1505 |
| 7 | 70990450 | 70993350 | d7Mseg1511 |
| 7 | 70996100 | 70998000 | d7Mseg1512 |
| 7 | 71064950 | 71066550 | d7Mseg1514 |
| 7 | 71132100 | 71133350 | d7Mseg1519 |
| 7 | 71251100 | 71253700 | d7Mseg1528 |
| 7 | 71303750 | 71305250 | d7Mseg1531 |
| 7 | 71604250 | 71606100 | d7Mseg1544 |
| 7 | 71625450 | 71626850 | d7Mseg1545 |
| 7 | 71646950 | 71648400 | d7Mseg1546 |
| 7 | 71706750 | 71708300 | d7Mseg1549 |
| 7 | 71751500 | 71753050 | d7Mseg1550 |
| 7 | 71823600 | 71825250 | d7Mseg1551 |
| 7 | 71855400 | 71857200 | d7Mseg1552 |
| 7 | 71872250 | 71873500 | d7Mseg1553 |
| 7 | 72002400 | 72004050 | d7Mseg1555 |
| 7 | 72107200 | 72108850 | d7Mseg1556 |

TABLE IVC-continued

Mouse Moderate Sites

| c/d | start | end | segment |
|---|---|---|---|
| 7 | 72198400 | 72200050 | d7Mseg1557 |
| 7 | 72226450 | 72228150 | d7Mseg1559 |
| 7 | 72257350 | 72258400 | d7Mseg1560 |
| 7 | 72385650 | 72389350 | d7Mseg1564 |
| 7 | 72521600 | 72523200 | d7Mseg1567 |
| 7 | 72573300 | 72575000 | d7Mseg1569 |
| 7 | 72708100 | 72711150 | d7Mseg1571 |
| 7 | 72712300 | 72714200 | d7Mseg1572 |
| 7 | 72772100 | 72773300 | d7Mseg1575 |
| 7 | 72869150 | 72870500 | d7Mseg1578 |
| 7 | 73209650 | 73212600 | d7Mseg1584 |
| 7 | 73549600 | 73550650 | d7Mseg1587 |
| 7 | 73739700 | 73741450 | d7Mseg1588 |
| 7 | 73875550 | 73876550 | d7Mseg1589 |
| 7 | 73902100 | 73903350 | d7Mseg1590 |
| 7 | 73920800 | 73922400 | d7Mseg1591 |
| 7 | 74085350 | 74087200 | d7Mseg1593 |
| 7 | 74282300 | 74283350 | d7Mseg1594 |
| 7 | 74372100 | 74373900 | d7Mseg1595 |
| 7 | 74549300 | 74550700 | d7Mseg1596 |
| 7 | 74583900 | 74585500 | d7Mseg1597 |
| 7 | 74630000 | 74631600 | d7Mseg1598 |
| 7 | 74785250 | 74786600 | d7Mseg1603 |
| 7 | 74867250 | 74869250 | d7Mseg1604 |
| 7 | 74971350 | 74972400 | d7Mseg1606 |
| 7 | 75019350 | 75020850 | d7Mseg1607 |
| 7 | 75041950 | 75043150 | d7Mseg1608 |
| 7 | 75150900 | 75151950 | d7Mseg1609 |
| 7 | 75259000 | 75260900 | d7Mseg1610 |
| 7 | 75400300 | 75401750 | d7Mseg1611 |
| 7 | 76101300 | 76103050 | d7Mseg1614 |
| 7 | 76463300 | 76464950 | d7Mseg1615 |
| 7 | 76829900 | 76831550 | d7Mseg1617 |
| 7 | 77160900 | 77162600 | d7Mseg1618 |
| 7 | 77486000 | 77487400 | d7Mseg1620 |
| 7 | 77576950 | 77578850 | d7Mseg1621 |
| 7 | 77621200 | 77622850 | d7Mseg1622 |
| 7 | 77679000 | 77680550 | d7Mseg1623 |
| 7 | 78026800 | 78028300 | d7Mseg1624 |
| 7 | 78277700 | 78278800 | d7Mseg1625 |
| 7 | 78425900 | 78427400 | d7Mseg1630 |
| 7 | 79127150 | 79128700 | d7Mseg1631 |
| 7 | 79314800 | 79316200 | d7Mseg1632 |
| 7 | 79604200 | 79605850 | d7Mseg1633 |
| 7 | 79685550 | 79687300 | d7Mseg1635 |
| 7 | 79772650 | 79773850 | d7Mseg1636 |
| 7 | 80044500 | 80045800 | d7Mseg1637 |
| 7 | 80112650 | 80114450 | d7Mseg1638 |
| 7 | 80224900 | 80226500 | d7Mseg1640 |
| 7 | 80559250 | 80560450 | d7Mseg1645 |
| 7 | 80563150 | 80564300 | d7Mseg1646 |
| 7 | 80644850 | 80646000 | d7Mseg1648 |
| 7 | 80653800 | 80655500 | d7Mseg1649 |
| 7 | 80660600 | 80661700 | d7Mseg1650 |
| 7 | 80667950 | 80669650 | d7Mseg1651 |
| 7 | 80686750 | 80688600 | d7Mseg1652 |
| 7 | 80726050 | 80728050 | d7Mseg1653 |
| 7 | 80731550 | 80733750 | d7Mseg1654 |
| 7 | 80997600 | 80999450 | d7Mseg1658 |
| 7 | 81006200 | 81007600 | d7Mseg1659 |
| 7 | 81042250 | 81044100 | d7Mseg1661 |
| 7 | 81117750 | 81119450 | d7Mseg1662 |
| 7 | 81261850 | 81263600 | d7Mseg1665 |
| 7 | 81382100 | 81383450 | d7Mseg1667 |
| 7 | 81649050 | 81650850 | d7Mseg1673 |
| 7 | 81743200 | 81744850 | d7Mseg1675 |
| 7 | 82108450 | 82109950 | d7Mseg1687 |
| 7 | 82140650 | 82142150 | d7Mseg1691 |
| 7 | 82273850 | 82275550 | d7Mseg1699 |
| 7 | 82376300 | 82378100 | d7Mseg1705 |
| 7 | 82462000 | 82463550 | d7Mseg1708 |
| 7 | 82551950 | 82553050 | d7Mseg1711 |
| 7 | 82583900 | 82584900 | d7Mseg1712 |
| 7 | 82764350 | 82765600 | d7Mseg1716 |
| 7 | 82930750 | 82932500 | d7Mseg1722 |
| 7 | 82962000 | 82963000 | d7Mseg1723 |
| 7 | 82968650 | 82970550 | d7Mseg1724 |
| 7 | 83032600 | 83034300 | d7Mseg1726 |
| 7 | 83067200 | 83068650 | d7Mseg1727 |
| 7 | 83250450 | 83253200 | d7Mseg1733 |
| 7 | 83262400 | 83263550 | d7Mseg1734 |
| 7 | 83317050 | 83318600 | d7Mseg1735 |
| 7 | 83365600 | 83367250 | d7Mseg1737 |
| 7 | 83450200 | 83451800 | d7Mseg1740 |
| 7 | 83560850 | 83562500 | d7Mseg1743 |
| 7 | 83579100 | 83580900 | d7Mseg1744 |
| 7 | 83598400 | 83600300 | d7Mseg1746 |
| 7 | 83666200 | 83670050 | d7Mseg1749 |
| 7 | 83712000 | 83713750 | d7Mseg1751 |
| 7 | 83832800 | 83834350 | d7Mseg1753 |
| 7 | 83860050 | 83861050 | d7Mseg1754 |
| 7 | 84083800 | 84085250 | d7Mseg1761 |
| 7 | 84380200 | 84381550 | d7Mseg1768 |
| 7 | 84622300 | 84623600 | d7Mseg1772 |
| 7 | 84631300 | 84632550 | d7Mseg1773 |
| 7 | 84770700 | 84772450 | d7Mseg1777 |
| 7 | 84875650 | 84876700 | d7Mseg1778 |
| 7 | 85029300 | 85030300 | d7Mseg1783 |
| 7 | 85039400 | 85041050 | d7Mseg1784 |
| 7 | 85544550 | 85546200 | d7Mseg1794 |
| 7 | 85672050 | 85673500 | d7Mseg1795 |
| 7 | 86047150 | 86048700 | d7Mseg1799 |
| 7 | 86161550 | 86162650 | d7Mseg1800 |
| 7 | 86637350 | 86639350 | d7Mseg1801 |
| 7 | 86664300 | 86665550 | d7Mseg1802 |
| 7 | 86834100 | 86835300 | d7Mseg1803 |
| 7 | 86913350 | 86914850 | d7Mseg1804 |
| 7 | 86977100 | 86978300 | d7Mseg1805 |
| 7 | 87009300 | 87010850 | d7Mseg1806 |
| 7 | 87040700 | 87042300 | d7Mseg1807 |
| 7 | 88123050 | 88124550 | d7Mseg1809 |
| 7 | 88143100 | 88144750 | d7Mseg1810 |
| 7 | 88426250 | 88427900 | d7Mseg1812 |
| 7 | 88631350 | 88633150 | d7Mseg1814 |
| 7 | 88656050 | 88657250 | d7Mseg1815 |
| 7 | 88788950 | 88790700 | d7Mseg1816 |
| 7 | 89851450 | 89852900 | d7Mseg1826 |
| 7 | 89975900 | 89977050 | d7Mseg1830 |
| 7 | 90105400 | 90106750 | d7Mseg1834 |
| 7 | 90138500 | 90140200 | d7Mseg1835 |
| 7 | 90222300 | 90223400 | d7Mseg1837 |
| 7 | 90233300 | 90235150 | d7Mseg1838 |
| 7 | 90242900 | 90244450 | d7Mseg1839 |
| 7 | 90384750 | 90386550 | d7Mseg1843 |
| 7 | 90412350 | 90413850 | d7Mseg1845 |
| 7 | 90442800 | 90444250 | d7Mseg1846 |
| 7 | 90595700 | 90597450 | d7Mseg1851 |
| 7 | 90641400 | 90642800 | d7Mseg1852 |
| 7 | 90856400 | 90857900 | d7Mseg1858 |
| 7 | 90888300 | 90889850 | d7Mseg1859 |
| 7 | 91128750 | 91132950 | d7Mseg1872 |
| 7 | 91167350 | 91168700 | d7Mseg1876 |
| 7 | 91187150 | 91189200 | d7Mseg1877 |
| 7 | 91233600 | 91237800 | d7Mseg1880 |
| 7 | 91284700 | 91288400 | d7Mseg1883 |
| 7 | 91289450 | 91291250 | d7Mseg1884 |
| 7 | 91405250 | 91406650 | d7Mseg1889 |
| 7 | 91541050 | 91542500 | d7Mseg1896 |
| 7 | 91559900 | 91561500 | d7Mseg1897 |
| 7 | 91597950 | 91599250 | d7Mseg1902 |
| 7 | 91600700 | 91604600 | d7Mseg1903 |
| 7 | 91650300 | 91651600 | d7Mseg1907 |
| 7 | 91670700 | 91671700 | d7Mseg1908 |
| 7 | 91713250 | 91714850 | d7Mseg1910 |
| 7 | 91727350 | 91728700 | d7Mseg1911 |
| 7 | 91747100 | 91748300 | d7Mseg1912 |
| 7 | 91755800 | 91757500 | d7Mseg1913 |
| 7 | 91769350 | 91771250 | d7Mseg1914 |
| 7 | 91791500 | 91792700 | d7Mseg1917 |
| 7 | 91818050 | 91819700 | d7Mseg1919 |
| 7 | 91864550 | 91866450 | d7Mseg1920 |
| 7 | 91886000 | 91887000 | d7Mseg1922 |

TABLE IVC-continued

Mouse Moderate Sites

| c/d | start | end | segment |
|---|---|---|---|
| 7 | 91893900 | 91895050 | d7Mseg1924 |
| 7 | 91901750 | 91903650 | d7Mseg1925 |
| 7 | 91916750 | 91920300 | d7Mseg1926 |
| 7 | 91964250 | 91965350 | d7Mseg1927 |
| 7 | 91977800 | 91979550 | d7Mseg1929 |
| 7 | 92003150 | 92005050 | d7Mseg1930 |
| 7 | 92019100 | 92020400 | d7Mseg1931 |
| 7 | 92035250 | 92039800 | d7Mseg1932 |
| 7 | 92063300 | 92064800 | d7Mseg1933 |
| 7 | 92076550 | 92078300 | d7Mseg1934 |
| 7 | 92099050 | 92100650 | d7Mseg1935 |
| 7 | 92110950 | 92111950 | d7Mseg1936 |
| 7 | 92116800 | 92119750 | d7Mseg1937 |
| 7 | 92179650 | 92181300 | d7Mseg1938 |
| 7 | 92212450 | 92213650 | d7Mseg1939 |
| 7 | 92321100 | 92322550 | d7Mseg1946 |
| 7 | 92381000 | 92382850 | d7Mseg1951 |
| 7 | 92478100 | 92479900 | d7Mseg1952 |
| 7 | 92647200 | 92648350 | d7Mseg1957 |
| 7 | 92676050 | 92677250 | d7Mseg1960 |
| 7 | 92678350 | 92681100 | d7Mseg1961 |
| 7 | 92686450 | 92687750 | d7Mseg1962 |
| 7 | 92701300 | 92702400 | d7Mseg1963 |
| 7 | 92727750 | 92729400 | d7Mseg1965 |
| 7 | 92794200 | 92796000 | d7Mseg1966 |
| 7 | 92862350 | 92864200 | d7Mseg1967 |
| 7 | 92871050 | 92872650 | d7Mseg1968 |
| 7 | 92924000 | 92925550 | d7Mseg1971 |
| 7 | 92966050 | 92967650 | d7Mseg1972 |
| 7 | 92988700 | 92990750 | d7Mseg1973 |
| 7 | 93035700 | 93037300 | d7Mseg1974 |
| 7 | 93078700 | 93080750 | d7Mseg1975 |
| 7 | 93160450 | 93162000 | d7Mseg1977 |
| 7 | 93261400 | 93263450 | d7Mseg1982 |
| 7 | 93334400 | 93336100 | d7Mseg1987 |
| 7 | 93447300 | 93448950 | d7Mseg1990 |
| 7 | 93482600 | 93483750 | d7Mseg1991 |
| 7 | 93518500 | 93519750 | d7Mseg1994 |
| 7 | 93613750 | 93615350 | d7Mseg1995 |
| 7 | 93630850 | 93632600 | d7Mseg1996 |
| 7 | 93639800 | 93641500 | d7Mseg1997 |
| 7 | 93671250 | 93673150 | d7Mseg1998 |
| 7 | 93686750 | 93687750 | d7Mseg1999 |
| 7 | 93698300 | 93699600 | d7Mseg2001 |
| 7 | 93760100 | 93761600 | d7Mseg2003 |
| 7 | 93823400 | 93824900 | d7Mseg2004 |
| 7 | 93891750 | 93893450 | d7Mseg2005 |
| 7 | 93895900 | 93897450 | d7Mseg2006 |
| 7 | 94070200 | 94071800 | d7Mseg2007 |
| 7 | 94090250 | 94092300 | d7Mseg2008 |
| 7 | 94096350 | 94098050 | d7Mseg2009 |
| 7 | 94120450 | 94122950 | d7Mseg2010 |
| 7 | 94140900 | 94142850 | d7Mseg2011 |
| 7 | 94179250 | 94180550 | d7Mseg2013 |
| 7 | 94264000 | 94265550 | d7Mseg2014 |
| 7 | 94268500 | 94270150 | d7Mseg2015 |
| 7 | 94321100 | 94322850 | d7Mseg2016 |
| 7 | 94334850 | 94336550 | d7Mseg2017 |
| 7 | 94408500 | 94410000 | d7Mseg2018 |
| 7 | 94440600 | 94441900 | d7Mseg2019 |
| 7 | 94645350 | 94646450 | d7Mseg2024 |
| 7 | 94687150 | 94688500 | d7Mseg2025 |
| 7 | 94730450 | 94733550 | d7Mseg2026 |
| 7 | 94785700 | 94787200 | d7Mseg2027 |
| 7 | 94824850 | 94826450 | d7Mseg2028 |
| 7 | 94827500 | 94828550 | d7Mseg2029 |
| 7 | 94877300 | 94878450 | d7Mseg2030 |
| 7 | 94919550 | 94920650 | d7Mseg2032 |
| 7 | 94974750 | 94976250 | d7Mseg2033 |
| 7 | 95025800 | 95027500 | d7Mseg2034 |
| 7 | 95067450 | 95069150 | d7Mseg2036 |
| 7 | 95228050 | 95229850 | d7Mseg2037 |
| 7 | 95242500 | 95243500 | d7Mseg2038 |
| 7 | 95293250 | 95294500 | d7Mseg2039 |
| 7 | 95339750 | 95341600 | d7Mseg2040 |
| 7 | 95471650 | 95475650 | d7Mseg2049 |
| 7 | 95531000 | 95532000 | d7Mseg2050 |
| 7 | 95594400 | 95595900 | d7Mseg2051 |
| 7 | 95988850 | 95990400 | d7Mseg2060 |
| 7 | 96012100 | 96015100 | d7Mseg2061 |
| 7 | 96224400 | 96226250 | d7Mseg2069 |
| 7 | 96573750 | 96575400 | d7Mseg2099 |
| 7 | 96840950 | 96842900 | d7Mseg2119 |
| 7 | 96866250 | 96867750 | d7Mseg2122 |
| 7 | 96896450 | 96898750 | d7Mseg2125 |
| 7 | 96956300 | 96958300 | d7Mseg2126 |
| 7 | 96966450 | 96967950 | d7Mseg2127 |
| 7 | 96993650 | 96994900 | d7Mseg2128 |
| 7 | 97107350 | 97108950 | d7Mseg2133 |
| 7 | 97229950 | 97231100 | d7Mseg2140 |
| 7 | 97237150 | 97240100 | d7Mseg2141 |
| 7 | 97271350 | 97273300 | d7Mseg2142 |
| 7 | 97319800 | 97321300 | d7Mseg2145 |
| 7 | 97331950 | 97333200 | d7Mseg2146 |
| 7 | 97402500 | 97403950 | d7Mseg2151 |
| 7 | 97629450 | 97630600 | d7Mseg2154 |
| 7 | 97646000 | 97647750 | d7Mseg2156 |
| 7 | 97656450 | 97658400 | d7Mseg2157 |
| 7 | 97730150 | 97731700 | d7Mseg2161 |
| 7 | 97840050 | 97841800 | d7Mseg2166 |
| 7 | 98019650 | 98020800 | d7Mseg2175 |
| 7 | 98031050 | 98032900 | d7Mseg2176 |
| 7 | 98104100 | 98105800 | d7Mseg2178 |
| 7 | 98119550 | 98121850 | d7Mseg2179 |
| 7 | 98163500 | 98165400 | d7Mseg2181 |
| 7 | 98199250 | 98200300 | d7Mseg2182 |
| 7 | 98249300 | 98250550 | d7Mseg2184 |
| 7 | 98253850 | 98256950 | d7Mseg2185 |
| 7 | 98265150 | 98267050 | d7Mseg2186 |
| 7 | 98286800 | 98288200 | d7Mseg2188 |
| 7 | 98318150 | 98320000 | d7Mseg2189 |
| 7 | 98332350 | 98333600 | d7Mseg2190 |
| 7 | 98368200 | 98369800 | d7Mseg2191 |
| 7 | 98556150 | 98557900 | d7Mseg2200 |
| 7 | 98701800 | 98704650 | d7Mseg2209 |
| 7 | 98799700 | 98804050 | d7Mseg2210 |
| 7 | 98821350 | 98823250 | d7Mseg2211 |
| 7 | 98947250 | 98950200 | d7Mseg2218 |
| 7 | 98955400 | 98958650 | d7Mseg2219 |
| 7 | 98981300 | 98983100 | d7Mseg2221 |
| 7 | 98999450 | 99001100 | d7Mseg2223 |
| 7 | 99008200 | 99009950 | d7Mseg2224 |
| 7 | 99027350 | 99029050 | d7Mseg2225 |
| 7 | 99100850 | 99104750 | d7Mseg2233 |
| 7 | 99302700 | 99304600 | d7Mseg2246 |
| 7 | 99401150 | 99402750 | d7Mseg2252 |
| 7 | 99430550 | 99431550 | d7Mseg2253 |
| 7 | 99459250 | 99460750 | d7Mseg2256 |
| 7 | 99471500 | 99473200 | d7Mseg2257 |
| 7 | 99646350 | 99648100 | d7Mseg2266 |
| 7 | 99798500 | 99799900 | d7Mseg2271 |
| 7 | 99845100 | 99847100 | d7Mseg2273 |
| 7 | 99863350 | 99864500 | d7Mseg2274 |
| 7 | 99946750 | 99948300 | d7Mseg2278 |
| 7 | 99964000 | 99965550 | d7Mseg2279 |
| 7 | 99968500 | 99970450 | d7Mseg2280 |
| 7 | 99904950 | 99986500 | d7Mseg2282 |
| 7 | 99994250 | 99995450 | d7Mseg2283 |
| 7 | 100014150 | 100015850 | d7Mseg2284 |
| 7 | 100028950 | 100031050 | d7Mseg2286 |
| 7 | 100036850 | 100038650 | d7Mseg2287 |
| 7 | 100053600 | 100056350 | d7Mseg2288 |
| 7 | 100062000 | 100065450 | d7Mseg2289 |
| 7 | 100141500 | 100143100 | d7Mseg2292 |
| 7 | 100171450 | 100172900 | d7Mseg2293 |
| 7 | 100175800 | 100177150 | d7Mseg2294 |
| 7 | 100184100 | 100185600 | d7Mseg2295 |
| 7 | 100189250 | 100190250 | d7Mseg2296 |
| 7 | 100242750 | 100244400 | d7Mseg2298 |
| 7 | 100246950 | 100248700 | d7Mseg2299 |
| 7 | 100259250 | 100261150 | d7Mseg2300 |
| 7 | 100281350 | 100283000 | d7Mseg2301 |

TABLE IVC-continued

Mouse Moderate Sites

| c/d | start | end | segment |
|---|---|---|---|
| 7 | 100304650 | 100306000 | d7Mseg2302 |
| 7 | 100343800 | 100345400 | d7Mseg2303 |
| 7 | 100359250 | 100361100 | d7Mseg2304 |
| 7 | 100371600 | 100372800 | d7Mseg2305 |
| 7 | 100401400 | 100404400 | d7Mseg2306 |
| 7 | 100430850 | 100432600 | d7Mseg2307 |
| 7 | 100491450 | 100492900 | d7Mseg2308 |
| 7 | 100542500 | 100543850 | d7Mseg2312 |
| 7 | 100593650 | 100595150 | d7Mseg2315 |
| 7 | 100617500 | 100619350 | d7Mseg2317 |
| 7 | 100626400 | 100627550 | d7Mseg2318 |
| 7 | 100631800 | 100633850 | d7Mseg2319 |
| 7 | 100687100 | 100688800 | d7Mseg2321 |
| 7 | 100690700 | 100692350 | d7Mseg2322 |
| 7 | 100724000 | 100725850 | d7Mseg2323 |
| 7 | 100795550 | 100796950 | d7Mseg2324 |
| 7 | 100955000 | 100956600 | d7Mseg2330 |
| 7 | 101025150 | 101026500 | d7Mseg2337 |
| 7 | 101038600 | 101040600 | d7Mseg2338 |
| 7 | 101047850 | 101049800 | d7Mseg2339 |
| 7 | 101060950 | 101062550 | d7Mseg2340 |
| 7 | 101092200 | 101094200 | d7Mseg2342 |
| 7 | 101098550 | 101099650 | d7Mseg2343 |
| 7 | 101110650 | 101112550 | d7Mseg2344 |
| 7 | 101115300 | 101117250 | d7Mseg2345 |
| 7 | 101122750 | 101123750 | d7Mseg2346 |
| 7 | 101144300 | 101146050 | d7Mseg2347 |
| 7 | 101198250 | 101201800 | d7Mseg2352 |
| 7 | 101214150 | 101215650 | d7Mseg2354 |
| 7 | 101219800 | 101224350 | d7Mseg2355 |
| 7 | 101228050 | 101229950 | d7Mseg2356 |
| 7 | 101240100 | 101241800 | d7Mseg2357 |
| 7 | 101285250 | 101286450 | d7Mseg2360 |
| 7 | 101455800 | 101457700 | d7Mseg2364 |
| 7 | 101480450 | 101482200 | d7Mseg2365 |
| 7 | 101528100 | 101532450 | d7Mseg2367 |
| 7 | 101541300 | 101544300 | d7Mseg2368 |
| 7 | 101585100 | 101586800 | d7Mseg2370 |
| 7 | 101662800 | 101664850 | d7Mseg2375 |
| 7 | 101707850 | 101709500 | d7Mseg2379 |
| 7 | 101796600 | 101800900 | d7Mseg2383 |
| 7 | 101854300 | 101855650 | d7Mseg2386 |
| 7 | 101894700 | 101896000 | d7Mseg2390 |
| 7 | 101910200 | 101911600 | d7Mseg2391 |
| 7 | 101914900 | 101916700 | d7Mseg2392 |
| 7 | 101941250 | 101943000 | d7Mseg2393 |
| 7 | 101956100 | 101958100 | d7Mseg2394 |
| 7 | 101989100 | 101991000 | d7Mseg2396 |
| 7 | 102072700 | 102073700 | d7Mseg2399 |
| 7 | 102095500 | 102098550 | d7Mseg2400 |
| 7 | 102118050 | 102119750 | d7Mseg2401 |
| 7 | 102141200 | 102143500 | d7Mseg2402 |
| 7 | 102176450 | 102178200 | d7Mseg2404 |
| 7 | 102195400 | 102199000 | d7Mseg2405 |
| 7 | 102202900 | 102204350 | d7Mseg2406 |
| 7 | 102207450 | 102210200 | d7Mseg2407 |
| 7 | 102212350 | 102214050 | d7Mseg2408 |
| 7 | 102222300 | 102224050 | d7Mseg2409 |
| 7 | 102228100 | 102229200 | d7Mseg2410 |
| 7 | 102312250 | 102317450 | d7Mseg2411 |
| 7 | 102335100 | 102336150 | d7Mseg2412 |
| 7 | 102345400 | 102347100 | d7Mseg2413 |
| 7 | 102348750 | 102349750 | d7Mseg2414 |
| 7 | 102483200 | 102484850 | d7Mseg2417 |
| 7 | 102708300 | 102710250 | d7Mseg2425 |
| 7 | 102712550 | 102713550 | d7Mseg2426 |
| 7 | 102746000 | 102748100 | d7Mseg2428 |
| 7 | 102784250 | 102785450 | d7Mseg2430 |
| 7 | 102895600 | 102898450 | d7Mseg2433 |
| 7 | 102920350 | 102921650 | d7Mseg2434 |
| 7 | 102925850 | 102927350 | d7Mseg2435 |
| 7 | 102948850 | 102950050 | d7Mseg2436 |
| 7 | 102981950 | 102983200 | d7Mseg2439 |
| 7 | 103151550 | 103153500 | d7Mseg2444 |
| 7 | 103254000 | 103255800 | d7Mseg2447 |
| 7 | 103298500 | 103300250 | d7Mseg2450 |
| 7 | 103400100 | 103401500 | d7Mseg2451 |
| 7 | 103532500 | 103534450 | d7Mseg2454 |
| 7 | 103551950 | 103553400 | d7Mseg2456 |
| 7 | 103554800 | 103556200 | d7Mseg2457 |
| 7 | 103607350 | 103609600 | d7Mseg2458 |
| 7 | 103614500 | 103616200 | d7Mseg2459 |
| 7 | 103617800 | 103619650 | d7Mseg2460 |
| 7 | 103659000 | 103660900 | d7Mseg2463 |
| 7 | 103678450 | 103680550 | d7Mseg2464 |
| 7 | 103701400 | 103702950 | d7Mseg2465 |
| 7 | 103714450 | 103716100 | d7Mseg2466 |
| 7 | 103736950 | 103738400 | d7Mseg2467 |
| 7 | 103810800 | 103812550 | d7Mseg2468 |
| 7 | 103826550 | 103828400 | d7Mseg2469 |
| 7 | 103834900 | 103836400 | d7Mseg2471 |
| 7 | 103891800 | 103893250 | d7Mseg2472 |
| 7 | 103960650 | 103962650 | d7Mseg2473 |
| 7 | 103968100 | 103969650 | d7Mseg2474 |
| 7 | 103974800 | 103976000 | d7Mseg2475 |
| 7 | 103986650 | 103987800 | d7Mseg2476 |
| 7 | 104024500 | 104025650 | d7Mseg2480 |
| 7 | 104045400 | 104046750 | d7Mseg2483 |
| 7 | 104189500 | 104190900 | d7Mseg2489 |
| 7 | 104265000 | 104266050 | d7Mseg2490 |
| 7 | 104303300 | 104304650 | d7Mseg2492 |
| 7 | 104316900 | 104318900 | d7Mseg2493 |
| 7 | 104326650 | 104327650 | d7Mseg2494 |
| 7 | 104426450 | 104428500 | d7Mseg2497 |
| 7 | 104543100 | 104544900 | d7Mseg2500 |
| 7 | 104638500 | 104640150 | d7Mseg2503 |
| 7 | 104730500 | 104732300 | d7Mseg2504 |
| 7 | 104776450 | 104778200 | d7Mseg2505 |
| 7 | 104787150 | 104788600 | d7Mseg2506 |
| 7 | 104957950 | 104959000 | d7Mseg2508 |
| 7 | 105113750 | 105115000 | d7Mseg2512 |
| 7 | 105236000 | 105237750 | d7Mseg2513 |
| 7 | 105718850 | 105720750 | d7Mseg2514 |
| 7 | 105734400 | 105736150 | d7Mseg2515 |
| 7 | 105754800 | 105756350 | d7Mseg2516 |
| 7 | 105771800 | 105772950 | d7Mseg2517 |
| 7 | 105790250 | 105791750 | d7Mseg2518 |
| 7 | 105834850 | 105836000 | d7Mseg2519 |
| 7 | 105909850 | 105910850 | d7Mseg2520 |
| 7 | 105912900 | 105914350 | d7Mseg2521 |
| 7 | 106034050 | 106035400 | d7Mseg2523 |
| 7 | 106130650 | 106132450 | d7Mseg2525 |
| 7 | 106191250 | 106192800 | d7Mseg2526 |
| 7 | 106195700 | 106197350 | d7Mseg2527 |
| 7 | 106215800 | 106217800 | d7Mseg2530 |
| 7 | 106368300 | 106370150 | d7Mseg2536 |
| 7 | 106372850 | 106374450 | d7Mseg2537 |
| 7 | 106431000 | 106432500 | d7Mseg2539 |
| 7 | 106500900 | 106502500 | d7Mseg2540 |
| 7 | 106621050 | 106622350 | d7Mseg2541 |
| 7 | 106704400 | 106705550 | d7Mseg2542 |
| 7 | 107064150 | 107065650 | d7Mseg2546 |
| 7 | 107136000 | 107137350 | d7Mseg2547 |
| 7 | 107246700 | 107248150 | d7Mseg2550 |
| 7 | 107451300 | 107452800 | d7Mseg2551 |
| 7 | 107570650 | 107572100 | d7Mseg2553 |
| 7 | 107790100 | 107791400 | d7Mseg2554 |
| 7 | 107951050 | 107952500 | d7Mseg2558 |
| 7 | 107979300 | 107980900 | d7Mseg2560 |
| 7 | 107988500 | 107990000 | d7Mseg2561 |
| 7 | 107991550 | 107992600 | d7Mseg2562 |
| 7 | 108036800 | 108038650 | d7Mseg2565 |
| 7 | 108172050 | 108173250 | d7Mseg2566 |
| 7 | 108387950 | 108389400 | d7Mseg2567 |
| 7 | 108416950 | 108418050 | d7Mseg2568 |
| 7 | 108753500 | 108755100 | d7Mseg2578 |
| 7 | 108926650 | 108928400 | d7Mseg2582 |
| 7 | 109005500 | 109010500 | d7Mseg2583 |
| 7 | 109012800 | 109014600 | d7Mseg2584 |
| 7 | 109026400 | 109032350 | d7Mseg2585 |
| 7 | 109055700 | 109057400 | d7Mseg2586 |
| 7 | 109078950 | 109080450 | d7Mseg2587 |

TABLE IVC-continued

Mouse Moderate Sites

| c/d | start | end | segment |
|---|---|---|---|
| 7 | 109113750 | 109115050 | d7Mseg2588 |
| 7 | 109194450 | 109196250 | d7Mseg2589 |
| 7 | 109253950 | 109255750 | d7Mseg2591 |
| 7 | 109304150 | 109305750 | d7Mseg2592 |
| 7 | 109393800 | 109395700 | d7Mseg2594 |
| 7 | 109399400 | 109401250 | d7Mseg2595 |
| 7 | 109402850 | 109403900 | d7Mseg2596 |
| 7 | 109408000 | 109409300 | d7Mseg2597 |
| 7 | 109436700 | 109437900 | d7Mseg2599 |
| 7 | 109633300 | 109635150 | d7Mseg2605 |
| 7 | 109689050 | 109690900 | d7Mseg2606 |
| 7 | 109699600 | 109701400 | d7Mseg2607 |
| 7 | 109792300 | 109793950 | d7Mseg2611 |
| 7 | 109819000 | 109820350 | d7Mseg2613 |
| 7 | 109934350 | 109936000 | d7Mseg2615 |
| 7 | 110060600 | 110062500 | d7Mseg2617 |
| 7 | 110352400 | 110353400 | d7Mseg2621 |
| 7 | 110603300 | 110604850 | d7Mseg2629 |
| 7 | 110634100 | 110635550 | d7Mseg2631 |
| 7 | 110726250 | 110728150 | d7Mseg2632 |
| 7 | 110984800 | 110986000 | d7Mseg2636 |
| 7 | 111049350 | 111051000 | d7Mseg2638 |
| 7 | 111081150 | 111082250 | d7Mseg2639 |
| 7 | 111235600 | 111237550 | d7Mseg2640 |
| 7 | 111697650 | 111699350 | d7Mseg2643 |
| 7 | 111724750 | 111726250 | d7Mseg2644 |
| 7 | 111799650 | 111801400 | d7Mseg2646 |
| 7 | 111848150 | 111849550 | d7Mseg2647 |
| 7 | 111881950 | 111883350 | d7Mseg2648 |
| 7 | 112086950 | 112088450 | d7Mseg2649 |
| 7 | 112466650 | 112467650 | d7Mseg2651 |
| 7 | 112637950 | 112639450 | d7Mseg2652 |
| 7 | 112804550 | 112806250 | d7Mseg2653 |
| 7 | 112968450 | 112970450 | d7Mseg2654 |
| 7 | 113022200 | 113024050 | d7Mseg2655 |
| 7 | 113541850 | 113543250 | d7Mseg2656 |
| 7 | 113819300 | 113821250 | d7Mseg2657 |
| 7 | 114172100 | 114174100 | d7Mseg2658 |
| 7 | 114281400 | 114282950 | d7Mseg2659 |
| 7 | 114668600 | 114670100 | d7Mseg2660 |
| 7 | 114723350 | 114724850 | d7Mseg2661 |
| 7 | 114848500 | 114850000 | d7Mseg2663 |
| 7 | 115051000 | 115052850 | d7Mseg2664 |
| 7 | 115682900 | 115684350 | d7Mseg2665 |
| 7 | 115693000 | 115694250 | d7Mseg2666 |
| 7 | 115735700 | 115737000 | d7Mseg2667 |
| 7 | 115993000 | 115994800 | d7Mseg2668 |
| 7 | 116084650 | 116086150 | d7Mseg2669 |
| 7 | 116144250 | 116145500 | d7Mseg2670 |
| 7 | 116698050 | 116699850 | d7Mseg2671 |
| 7 | 116885550 | 116886550 | d7Mseg2672 |
| 7 | 117214700 | 117215950 | d7Mseg2674 |
| 7 | 117922650 | 117923950 | d7Mseg2683 |
| 7 | 118263700 | 118265300 | d7Mseg2684 |
| 7 | 118439050 | 118440350 | d7Mseg2685 |
| 7 | 118593200 | 118594700 | d7Mseg2687 |
| 7 | 118677800 | 118679500 | d7Mseg2688 |
| 7 | 118996700 | 118997800 | d7Mseg2689 |
| 7 | 119360500 | 119361500 | d7Mseg2692 |
| 7 | 120033400 | 120034650 | d7Mseg2696 |
| 7 | 121281300 | 121282850 | d7Mseg2697 |
| 7 | 123185600 | 123187450 | d7Mseg2698 |
| 7 | 123983400 | 123985350 | d7Mseg2699 |
| 7 | 124150350 | 124151550 | d7Mseg2700 |
| 7 | 124192000 | 124193650 | d7Mseg2701 |
| 7 | 124284800 | 124286200 | d7Mseg2702 |
| 7 | 124628600 | 124630200 | d7Mseg2703 |
| 7 | 125148500 | 125150100 | d7Mseg2706 |
| 7 | 125165400 | 125167000 | d7Mseg2707 |
| 7 | 125543700 | 125544700 | d7Mseg2709 |
| 7 | 125639150 | 125640450 | d7Mseg2710 |
| 7 | 126004100 | 126005650 | d7Mseg2712 |
| 7 | 127047750 | 127049950 | d7Mseg2728 |
| 7 | 127503700 | 127505300 | d7Mseg2736 |
| 7 | 127544050 | 127545750 | d7Mseg2737 |
| 7 | 127584100 | 127586000 | d7Mseg2738 |
| 7 | 127671650 | 127673150 | d7Mseg2742 |
| 7 | 127738500 | 127740000 | d7Mseg2743 |
| 7 | 127829050 | 127830450 | d7Mseg2744 |
| 7 | 128005000 | 128006650 | d7Mseg2746 |
| 7 | 128432000 | 128433700 | d7Mseg2751 |
| 7 | 128609250 | 128610600 | d7Mseg2754 |
| 7 | 128742000 | 128743100 | d7Mseg2756 |
| 7 | 128821450 | 128823250 | d7Mseg2757 |
| 7 | 129020550 | 129022050 | d7Mseg2761 |
| 7 | 129027200 | 129028700 | d7Mseg2762 |
| 7 | 129136650 | 129138100 | d7Mseg2763 |
| 7 | 129212450 | 129214350 | d7Mseg2764 |
| 7 | 129232850 | 129234450 | d7Mseg2765 |
| 7 | 129300400 | 129302100 | d7Mseg2767 |
| 7 | 129334500 | 129335700 | d7Mseg2769 |
| 7 | 129359600 | 129361250 | d7Mseg2770 |
| 7 | 129532800 | 129534300 | d7Mseg2775 |
| 7 | 129639850 | 129641450 | d7Mseg2776 |
| 7 | 129690350 | 129691400 | d7Mseg2777 |
| 7 | 129702100 | 129703300 | d7Mseg2778 |
| 7 | 129738650 | 129740350 | d7Mseg2780 |
| 7 | 129780550 | 129782500 | d7Mseg2781 |
| 7 | 129885550 | 129886650 | d7Mseg2783 |
| 7 | 130075900 | 130077700 | d7Mseg2786 |
| 7 | 130106200 | 130107600 | d7Mseg2787 |
| 7 | 130111200 | 130112450 | d7Mseg2788 |
| 7 | 130256750 | 130258450 | d7Mseg2794 |
| 7 | 130331350 | 130333050 | d7Mseg2796 |
| 7 | 130342050 | 130343850 | d7Mseg2797 |
| 7 | 130543650 | 130545400 | d7Mseg2807 |
| 7 | 130569200 | 130570700 | d7Mseg2809 |
| 7 | 130769200 | 130770500 | d7Mseg2814 |
| 7 | 130879700 | 130881350 | d7Mseg2819 |
| 7 | 130931100 | 130932550 | d7Mseg2820 |
| 7 | 130934650 | 130935750 | d7Mseg2821 |
| 7 | 131012650 | 131014050 | d7Mseg2827 |
| 7 | 131042550 | 131044100 | d7Mseg2828 |
| 7 | 131103050 | 131106850 | d7Mseg2831 |
| 7 | 131151100 | 131153300 | d7Mseg2833 |
| 7 | 131158250 | 131161550 | d7Mseg2834 |
| 7 | 131188900 | 131190900 | d7Mseg2836 |
| 7 | 131214300 | 131216200 | d7Mseg2837 |
| 7 | 131325300 | 131326600 | d7Mseg2849 |
| 7 | 131459800 | 131461700 | d7Mseg2856 |
| 7 | 131497800 | 131500350 | d7Mseg2859 |
| 7 | 131514150 | 131515300 | d7Mseg2860 |
| 7 | 131568500 | 131570050 | d7Mseg2866 |
| 7 | 131573100 | 131574800 | d7Mseg2867 |
| 7 | 131585350 | 131587050 | d7Mseg2868 |
| 7 | 131588500 | 131589700 | d7Mseg2869 |
| 7 | 131608250 | 131609250 | d7Mseg2870 |
| 7 | 131611450 | 131612750 | d7Mseg2871 |
| 7 | 131615450 | 131617050 | d7Mseg2872 |
| 7 | 131631200 | 131634000 | d7Mseg2873 |
| 7 | 131746800 | 131748700 | d7Mseg2875 |
| 7 | 131763000 | 131764600 | d7Mseg2876 |
| 7 | 131784950 | 131786450 | d7Mseg2877 |
| 7 | 131789150 | 131791000 | d7Mseg2878 |
| 7 | 131812950 | 131815000 | d7Mseg2879 |
| 7 | 131819150 | 131820600 | d7Mseg2880 |
| 7 | 131823550 | 131825000 | d7Mseg2881 |
| 7 | 131848150 | 131849700 | d7Mseg2882 |
| 7 | 132098750 | 132100350 | d7Mseg2884 |
| 7 | 132101750 | 132103400 | d7Mseg2885 |
| 7 | 132143250 | 132144450 | d7Mseg2887 |
| 7 | 132159850 | 132160950 | d7Mseg2888 |
| 7 | 132205100 | 132206250 | d7Mseg2889 |
| 7 | 132219750 | 132221250 | d7Mseg2890 |
| 7 | 132224350 | 132226300 | d7Mseg2891 |
| 7 | 132273100 | 132275300 | d7Mseg2893 |
| 7 | 132319400 | 132322000 | d7Mseg2896 |
| 7 | 132338850 | 132341700 | d7Mseg2898 |
| 7 | 132396450 | 132397550 | d7Mseg2900 |
| 7 | 132430600 | 132432050 | d7Mseg2901 |
| 7 | 132490150 | 132491700 | d7Mseg2902 |
| 7 | 132543350 | 132544600 | d7Mseg2905 |

TABLE IVC-continued

Mouse Moderate Sites

| c/d | start | end | segment |
|---|---|---|---|
| 7 | 132649200 | 132650350 | d7Mseg2912 |
| 7 | 132680800 | 132682800 | d7Mseg2914 |
| 7 | 132793400 | 132795100 | d7Mseg2917 |
| 7 | 132810650 | 132812200 | d7Mseg2919 |
| 7 | 132818400 | 132821150 | d7Mseg2920 |
| 7 | 132967500 | 132969600 | d7Mseg2921 |
| 7 | 132971550 | 132973550 | d7Mseg2922 |
| 7 | 133047600 | 133049150 | d7Mseg2923 |
| 7 | 133052400 | 133054000 | d7Mseg2924 |
| 7 | 133057650 | 133059300 | d7Mseg2925 |
| 7 | 133078850 | 133080250 | d7Mseg2926 |
| 7 | 133083450 | 133084500 | d7Mseg2927 |
| 7 | 133120400 | 133123200 | d7Mseg2928 |
| 7 | 133144950 | 133146450 | d7Mseg2929 |
| 7 | 133153800 | 133155900 | d7Mseg2930 |
| 7 | 133174250 | 133175850 | d7Mseg2932 |
| 7 | 133182050 | 133183650 | d7Mseg2934 |
| 7 | 133417700 | 133419150 | d7Mseg2944 |
| 7 | 133437800 | 133439750 | d7Mseg2946 |
| 7 | 133560350 | 133561650 | d7Mseg2947 |
| 7 | 133571250 | 133573150 | d7Mseg2948 |
| 7 | 133580300 | 133582250 | d7Mseg2949 |
| 7 | 133632500 | 133641950 | d7Mseg2950 |
| 7 | 133646250 | 133647850 | d7Mseg2951 |
| 7 | 133661400 | 133663150 | d7Mseg2953 |
| 7 | 133671200 | 133672800 | d7Mseg2954 |
| 7 | 133793050 | 133794450 | d7Mseg2958 |
| 7 | 133809900 | 133811050 | d7Mseg2959 |
| 7 | 134014700 | 134016100 | d7Mseg2965 |
| 7 | 134075300 | 134076850 | d7Mseg2966 |
| 7 | 134115900 | 134119950 | d7Mseg2968 |
| 7 | 134148050 | 134150100 | d7Mseg2971 |
| 7 | 134369350 | 134370650 | d7Mseg2978 |
| 7 | 134441600 | 134442850 | d7Mseg2980 |
| 7 | 134472600 | 134474300 | d7Mseg2981 |
| 7 | 134833150 | 134834900 | d7Mseg2988 |
| 7 | 134892600 | 134894400 | d7Mseg2989 |
| 7 | 134953950 | 134955350 | d7Mseg2991 |
| 7 | 134959200 | 134960500 | d7Mseg2992 |
| 7 | 134979950 | 134981400 | d7Mseg2994 |
| 7 | 135027250 | 135029200 | d7Mseg2998 |
| 7 | 135222300 | 135224200 | d7Mseg3001 |
| 7 | 135276350 | 135277600 | d7Mseg3004 |
| 7 | 135559750 | 135561450 | d7Mseg3010 |
| 7 | 135621300 | 135622450 | d7Mseg3012 |
| 7 | 135630250 | 135631750 | d7Mseg3013 |
| 7 | 135699650 | 135700900 | d7Mseg3015 |
| 7 | 135781300 | 135782400 | d7Mseg3017 |
| 7 | 135826900 | 135828650 | d7Mseg3019 |
| 7 | 135932550 | 135933850 | d7Mseg3022 |
| 7 | 135936650 | 135937750 | d7Mseg3023 |
| 7 | 135941500 | 135943050 | d7Mseg3024 |
| 7 | 135983250 | 135984900 | d7Mseg3025 |
| 7 | 136261800 | 136263250 | d7Mseg3036 |
| 7 | 136307000 | 136308150 | d7Mseg3038 |
| 7 | 136407750 | 136409300 | d7Mseg3042 |
| 7 | 136428200 | 136429900 | d7Mseg3044 |
| 7 | 136519700 | 136520800 | d7Mseg3046 |
| 7 | 136534750 | 136536300 | d7Mseg3047 |
| 7 | 136697000 | 136698350 | d7Mseg3055 |
| 7 | 136762050 | 136763850 | d7Mseg3062 |
| 7 | 136855650 | 136856750 | d7Mseg3068 |
| 7 | 136860950 | 136861950 | d7Mseg3069 |
| 7 | 136996100 | 136997500 | d7Mseg3082 |
| 7 | 137153100 | 137155850 | d7Mseg3094 |
| 7 | 137159200 | 137160550 | d7Mseg3095 |
| 7 | 137336500 | 137337550 | d7Mseg3108 |
| 7 | 137350550 | 137352250 | d7Mseg3110 |
| 7 | 137353950 | 137357900 | d7Mseg3111 |
| 7 | 137359800 | 137361700 | d7Mseg3112 |
| 7 | 137381450 | 137382550 | d7Mseg3113 |
| 7 | 137388600 | 137390100 | d7Mseg3114 |
| 7 | 137422400 | 137424300 | d7Mseg3116 |
| 7 | 137530800 | 137531900 | d7Mseg3121 |
| 7 | 137584500 | 137588700 | d7Mseg3122 |
| 7 | 137736000 | 137737550 | d7Mseg3133 |
| 7 | 137754050 | 137755800 | d7Mseg3134 |
| 7 | 137808250 | 137810450 | d7Mseg3138 |
| 7 | 137842050 | 137845850 | d7Mseg3141 |
| 7 | 137925850 | 137927750 | d7Mseg3147 |
| 7 | 137938600 | 137940650 | d7Mseg3148 |
| 7 | 137990950 | 137992150 | d7Mseg3151 |
| 7 | 138002550 | 138004000 | d7Mseg3152 |
| 7 | 138040900 | 138042400 | d7Mseg3154 |
| 7 | 138061650 | 138063400 | d7Mseg3158 |
| 7 | 138134800 | 138136400 | d7Mseg3164 |
| 7 | 138139050 | 138140800 | d7Mseg3165 |
| 7 | 138239550 | 138241300 | d7Mseg3172 |
| 7 | 138244300 | 138245450 | d7Mseg3173 |
| 7 | 138304550 | 138305700 | d7Mseg3177 |
| 7 | 138310750 | 138312450 | d7Mseg3178 |
| 7 | 138469300 | 138470950 | d7Mseg3181 |
| 7 | 138570600 | 138572550 | d7Mseg3187 |
| 7 | 138666750 | 138668350 | d7Mseg3190 |
| 7 | 138676200 | 138677300 | d7Mseg3191 |
| 7 | 138697950 | 138699500 | d7Mseg3194 |
| 7 | 138732100 | 138734000 | d7Mseg3195 |
| 7 | 138758200 | 138759950 | d7Mseg3197 |
| 7 | 138995800 | 138997250 | d7Mseg3210 |
| 7 | 139024250 | 139026200 | d7Mseg3215 |
| 7 | 139057050 | 139058750 | d7Mseg3217 |
| 7 | 139065800 | 139069750 | d7Mseg3219 |
| 7 | 139076700 | 139078350 | d7Mseg3220 |
| 7 | 139082500 | 139087250 | d7Mseg3221 |
| 7 | 139088600 | 139090350 | d7Mseg3222 |
| 7 | 139126250 | 139129650 | d7Mseg3225 |
| 7 | 139178050 | 139179600 | d7Mseg3228 |
| 7 | 139241750 | 139242800 | d7Mseg3232 |
| 7 | 139472200 | 139473350 | d7Mseg3239 |
| 7 | 139489450 | 139491050 | d7Mseg3241 |
| 7 | 139563200 | 139564200 | d7Mseg3247 |
| 7 | 139614600 | 139616150 | d7Mseg3249 |
| 7 | 139646050 | 139647600 | d7Mseg3250 |
| 7 | 139660450 | 139661700 | d7Mseg3251 |
| 7 | 139684250 | 139685500 | d7Mseg3252 |
| 7 | 139894300 | 139895650 | d7Mseg3257 |
| 7 | 139929350 | 139931050 | d7Mseg3258 |
| 7 | 139942550 | 139943800 | d7Mseg3260 |
| 7 | 140037600 | 140038950 | d7Mseg3265 |
| 7 | 140151800 | 140154000 | d7Mseg3271 |
| 7 | 140487450 | 140489000 | d7Mseg3282 |
| 7 | 140506700 | 140508050 | d7Mseg3283 |
| 7 | 140609750 | 140610750 | d7Mseg3289 |
| 7 | 140731800 | 140732800 | d7Mseg3291 |
| 7 | 140748800 | 140750450 | d7Mseg3292 |
| 7 | 140841150 | 140842750 | d7Mseg3299 |
| 7 | 140912650 | 140914550 | d7Mseg3301 |
| 7 | 140921200 | 140923050 | d7Mseg3302 |
| 7 | 140990450 | 140992200 | d7Mseg3304 |
| 7 | 141000400 | 141002150 | d7Mseg3305 |
| 7 | 141158250 | 141159450 | d7Mseg3310 |
| 7 | 141168950 | 141170000 | d7Mseg3311 |
| 7 | 141182300 | 141183450 | d7Mseg3312 |
| 7 | 141212850 | 141214050 | d7Mseg3313 |
| 7 | 141249600 | 141251100 | d7Mseg3315 |
| 7 | 141277900 | 141279600 | d7Mseg3317 |
| 7 | 141686950 | 141688700 | d7Mseg3330 |
| 7 | 141700400 | 141702400 | d7Mseg3331 |
| 7 | 141744400 | 141745900 | d7Mseg3332 |
| 7 | 142029150 | 142031150 | d7Mseg3344 |
| 7 | 142042400 | 142043400 | d7Mseg3345 |
| 7 | 142062650 | 142064300 | d7Mseg3346 |
| 7 | 142077550 | 142079000 | d7Mseg3347 |
| 7 | 142235850 | 142237300 | d7Mseg3350 |
| 7 | 142284450 | 142285950 | d7Mseg3354 |
| 7 | 142433750 | 142435050 | d7Mseg3355 |
| 7 | 142628500 | 142630400 | d7Mseg3357 |
| 7 | 142704250 | 142705350 | d7Mseg3358 |
| 7 | 142797900 | 142799150 | d7Mseg3359 |
| 7 | 142842900 | 142844550 | d7Mseg3360 |
| 7 | 142911150 | 142912400 | d7Mseg3362 |
| 7 | 142932500 | 142933850 | d7Mseg3363 |

TABLE IVC-continued

Mouse Moderate Sites

| c/d | start | end | segment |
|---|---|---|---|
| 7 | 143041500 | 143042700 | d7Mseg3365 |
| 7 | 143181450 | 143183100 | d7Mseg3366 |
| 7 | 143480350 | 143481950 | d7Mseg3372 |
| 7 | 143597750 | 143599250 | d7Mseg3375 |
| 7 | 143697850 | 143699650 | d7Mseg3378 |
| 7 | 143704050 | 143705600 | d7Mseg3379 |
| 7 | 143708950 | 143710500 | d7Mseg3380 |
| 7 | 143718800 | 143720350 | d7Mseg3381 |
| 7 | 143728900 | 143730500 | d7Mseg3382 |
| 7 | 143889000 | 143890600 | d7Mseg3384 |
| 7 | 144086450 | 144088200 | d7Mseg3388 |
| 7 | 145311050 | 145312900 | d7Mseg3389 |
| 7 | 146051350 | 146052700 | d7Mseg3390 |
| 7 | 146380650 | 146381950 | d7Mseg3391 |
| 7 | 146578200 | 146579500 | d7Mseg3392 |
| 7 | 146610750 | 146611800 | d7Mseg3393 |
| 7 | 146781550 | 146783350 | d7Mseg3394 |
| 7 | 146788750 | 146790050 | d7Mseg3395 |
| 7 | 146888900 | 146890600 | d7Mseg3396 |
| 7 | 147039950 | 147041350 | d7Mseg3400 |
| 7 | 147082100 | 147083900 | d7Mseg3403 |
| 7 | 147093800 | 147095450 | d7Mseg3404 |
| 7 | 147107800 | 147109800 | d7Mseg3405 |
| 7 | 147190800 | 147191850 | d7Mseg3406 |
| 7 | 147197500 | 147199200 | d7Mseg3407 |
| 7 | 147205500 | 147206850 | d7Mseg3408 |
| 7 | 147212800 | 147214000 | d7Mseg3409 |
| 7 | 147358550 | 147360350 | d7Mseg3417 |
| 7 | 147458150 | 147460000 | d7Mseg3420 |
| 7 | 147531750 | 147533500 | d7Mseg3425 |
| 7 | 147618650 | 147619850 | d7Mseg3426 |
| 7 | 147654950 | 147656800 | d7Mseg3428 |
| 7 | 147714800 | 147716200 | d7Mseg3429 |
| 7 | 147771350 | 147772450 | d7Mseg3430 |
| 7 | 147823450 | 147824600 | d7Mseg3432 |
| 7 | 147830900 | 147832850 | d7Mseg3433 |
| 7 | 147969600 | 147971150 | d7Mseg3435 |
| 7 | 147992750 | 147994200 | d7Mseg3437 |
| 7 | 148078450 | 148079900 | d7Mseg3439 |
| 7 | 148088650 | 148090350 | d7Mseg3440 |
| 7 | 148113300 | 148115050 | d7Mseg3441 |
| 7 | 148166600 | 148170950 | d7Mseg3442 |
| 7 | 148176550 | 148178150 | d7Mseg3443 |
| 7 | 148217250 | 148218500 | d7Mseg3444 |
| 7 | 148231300 | 148232800 | d7Mseg3445 |
| 7 | 148382100 | 148385300 | d7Mseg3450 |
| 7 | 148476800 | 148478500 | d7Mseg3455 |
| 7 | 148540350 | 148541650 | d7Mseg3458 |
| 7 | 148819900 | 148822150 | d7Mseg3473 |
| 7 | 148834300 | 148835850 | d7Mseg3474 |
| 7 | 148862600 | 148864250 | d7Mseg3475 |
| 7 | 148906350 | 148908000 | d7Mseg3476 |
| 7 | 148917800 | 148919250 | d7Mseg3477 |
| 7 | 148973150 | 148974850 | d7Mseg3478 |
| 7 | 148977250 | 148978900 | d7Mseg3479 |
| 7 | 148985850 | 148987500 | d7Mseg3480 |
| 7 | 149033200 | 149034650 | d7Mseg3481 |
| 7 | 149068250 | 149069550 | d7Mseg3483 |
| 7 | 149211650 | 149215250 | d7Mseg3485 |
| 7 | 149289500 | 149291150 | d7Mseg3490 |
| 7 | 149294900 | 149296400 | d7Mseg3491 |
| 7 | 149308600 | 149310250 | d7Mseg3492 |
| 7 | 149354500 | 149356300 | d7Mseg3493 |
| 7 | 149411750 | 149414200 | d7Mseg3495 |
| 7 | 149481000 | 149482700 | d7Mseg3501 |
| 7 | 149501850 | 149503450 | d7Mseg3502 |
| 7 | 149513850 | 149515100 | d7Mseg3503 |
| 7 | 149531800 | 149533050 | d7Mseg3504 |
| 7 | 149569100 | 149570250 | d7Mseg3507 |
| 7 | 149647450 | 149648800 | d7Mseg3509 |
| 7 | 149655250 | 149657200 | d7Mseg3510 |
| 7 | 149667600 | 149668600 | d7Mseg3511 |
| 7 | 149702250 | 149703350 | d7Mseg3514 |
| 7 | 149834500 | 149836300 | d7Mseg3519 |
| 7 | 149885200 | 149887150 | d7Mseg3520 |
| 7 | 149888650 | 149889750 | d7Mseg3521 |
| 7 | 149906250 | 149907950 | d7Mseg3522 |
| 7 | 149952550 | 149954500 | d7Mseg3525 |
| 7 | 149992800 | 149994550 | d7Mseg3526 |
| 7 | 150022000 | 150024250 | d7Mseg3527 |
| 7 | 150059550 | 150061000 | d7Mseg3528 |
| 7 | 150148450 | 150150050 | d7Mseg3530 |
| 7 | 150193900 | 150196000 | d7Mseg3531 |
| 7 | 150239000 | 150240650 | d7Mseg3532 |
| 7 | 150314500 | 150316200 | d7Mseg3534 |
| 7 | 150340600 | 150342100 | d7Mseg3535 |
| 7 | 150631950 | 150633000 | d7Mseg3536 |
| 7 | 150718850 | 150719950 | d7Mseg3537 |
| 7 | 150812450 | 150813950 | d7Mseg3538 |
| 7 | 151157750 | 151159100 | d7Mseg3539 |
| 7 | 151289300 | 151290750 | d7Mseg3540 |
| 7 | 151369800 | 151371500 | d7Mseg3541 |
| 7 | 151378800 | 151380050 | d7Mseg3542 |
| 7 | 151495350 | 151497100 | d7Mseg3544 |
| 7 | 151506650 | 151507900 | d7Mseg3545 |
| 7 | 151577700 | 151578800 | d7Mseg3546 |
| 7 | 151652800 | 151654150 | d7Mseg3548 |
| 7 | 151740100 | 151741400 | d7Mseg3551 |
| 7 | 151786900 | 151788100 | d7Mseg3552 |
| 7 | 151819500 | 151821100 | d7Mseg3553 |
| 7 | 151825500 | 151826500 | d7Mseg3554 |
| 7 | 151900150 | 151901750 | d7Mseg3555 |
| 7 | 151906150 | 151907850 | d7Mseg3556 |
| 7 | 151909700 | 151911400 | d7Mseg3557 |
| 7 | 151931200 | 151932250 | d7Mseg3558 |
| 7 | 151966600 | 151968100 | d7Mseg3560 |
| 7 | 152177250 | 152178650 | d7Mseg3568 |
| 7 | 152312800 | 152314250 | d7Mseg3570 |
| 7 | 152555900 | 152557050 | d7Mseg3575 |
| 7 | 152664500 | 152665900 | d7Mseg3577 |
| 7 | 152725700 | 152726800 | d7Mseg3579 |
| 7 | 152965750 | 152967350 | d7Mseg3581 |
| 7 | 152975250 | 152976800 | d7Mseg3582 |
| 7 | 152985900 | 152987450 | d7Mseg3583 |
| 7 | 153142500 | 153144300 | d7Mseg3584 |
| 7 | 153152750 | 153153850 | d7Mseg3585 |
| 7 | 153184500 | 153186250 | d7Mseg3586 |
| 7 | 153188400 | 153189950 | d7Mseg3587 |
| 7 | 153205600 | 153207050 | d7Mseg3588 |
| 7 | 153409500 | 153411250 | d7Mseg3594 |
| 7 | 154587400 | 154588700 | d7Mseg3616 |
| 7 | 154605550 | 154606750 | d7Mseg3617 |
| 7 | 154630650 | 154632100 | d7Mseg3618 |
| 7 | 154662550 | 154664200 | d7Mseg3620 |
| 7 | 154801300 | 154803250 | d7Mseg3623 |
| 7 | 154962100 | 154963650 | d7Mseg3629 |
| 7 | 155170750 | 155172350 | d7Mseg3636 |
| 7 | 155354800 | 155356700 | d7Mseg3642 |
| 7 | 155394250 | 155395750 | d7Mseg3644 |
| 7 | 155409350 | 155411150 | d7Mseg3646 |
| 7 | 155833950 | 155835450 | d7Mseg3658 |
| 7 | 155847650 | 155849300 | d7Mseg3659 |
| 7 | 155867750 | 155868950 | d7Mseg3662 |
| 7 | 155893550 | 155895050 | d7Mseg3663 |
| 7 | 155964400 | 155968450 | d7Mseg3664 |
| 7 | 156586600 | 156588000 | d7Mseg3688 |
| 7 | 156620350 | 156621750 | d7Mseg3689 |
| 7 | 156623550 | 156624650 | d7Mseg3690 |
| 7 | 157050850 | 157052650 | d7Mseg3709 |
| 7 | 157314650 | 157315850 | d7Mseg3721 |
| 7 | 157484650 | 157486350 | d7Mseg3730 |
| 7 | 157512450 | 157514100 | d7Mseg3731 |
| 7 | 157527600 | 157529050 | d7Mseg3732 |
| 7 | 157543050 | 157545000 | d7Mseg3733 |
| 7 | 157565850 | 157567750 | d7Mseg3734 |
| 7 | 157571600 | 157573100 | d7Mseg3735 |
| 7 | 157591450 | 157592650 | d7Mseg3736 |
| 7 | 157657300 | 157659150 | d7Mseg3738 |
| 7 | 157716750 | 157718400 | d7Mseg3739 |
| 7 | 157726150 | 157727550 | d7Mseg3740 |
| 7 | 157736550 | 157738300 | d7Mseg3741 |
| 7 | 157787400 | 157791450 | d7Mseg3742 |

TABLE IVC-continued

Mouse Moderate Sites

| c/d | start | end | segment |
|---|---|---|---|
| 7 | 158060900 | 158062450 | d7Mseg3757 |
| 7 | 158105850 | 158107600 | d7Mseg3759 |
| 7 | 158237250 | 158238400 | d7Mseg3770 |
| 7 | 158241550 | 158243300 | d7Mseg3771 |
| 7 | 158260200 | 158261950 | d7Mseg3773 |
| 7 | 158789950 | 158792150 | d7Mseg3809 |
| 7 | 158869150 | 158873000 | d7Mseg3811 |
| 7 | 159013100 | 159014150 | d7Mseg3815 |
| 7 | 159100500 | 159102350 | d7Mseg3820 |
| 7 | 159335350 | 159336700 | d7Mseg3825 |
| 7 | 159345850 | 159346900 | d7Mseg3826 |
| 7 | 159349250 | 159350950 | d7Mseg3827 |
| 7 | 159670550 | 159671950 | d7Mseg3834 |
| 7 | 159724200 | 159727450 | d7Mseg3835 |
| 7 | 159911500 | 159913150 | d7Mseg3843 |
| 7 | 160131000 | 160132050 | d7Mseg3851 |
| 7 | 160138600 | 160140100 | d7Mseg3852 |
| 7 | 160154950 | 160156500 | d7Mseg3853 |
| 7 | 160194600 | 160201150 | d7Mseg3857 |
| 7 | 160216100 | 160217500 | d7Mseg3858 |
| 7 | 160453400 | 160454550 | d7Mseg3867 |
| 7 | 160457750 | 160459400 | d7Mseg3868 |
| 7 | 160502150 | 160503750 | d7Mseg3870 |
| 7 | 160696650 | 160697650 | d7Mseg3884 |
| 7 | 160762300 | 160764000 | d7Mseg3888 |
| 7 | 160848350 | 160850050 | d7Mseg3892 |
| 7 | 160910200 | 160912050 | d7Mseg3895 |
| 7 | 160953000 | 160954700 | d7Mseg3897 |
| 7 | 161026850 | 161028100 | d7Mseg3899 |
| 7 | 161091000 | 161092450 | d7Mseg3902 |
| 7 | 161176700 | 161177950 | d7Mseg3903 |
| 7 | 161215650 | 161217550 | d7Mseg3904 |
| 7 | 161367850 | 161369050 | d7Mseg3909 |
| 7 | 161456600 | 161458450 | d7Mseg3912 |
| 7 | 161524850 | 161526300 | d7Mseg3915 |
| 7 | 161810350 | 161812000 | d7Mseg3925 |
| 7 | 161857150 | 161858850 | d7Mseg3926 |
| 7 | 161864550 | 161866100 | d7Mseg3927 |
| 7 | 162373800 | 162375600 | d7Mseg3929 |
| 7 | 162508800 | 162509900 | d7Mseg3931 |
| 7 | 163180250 | 163181450 | d7Mseg3960 |
| 7 | 163716000 | 163717750 | d7Mseg3977 |
| 7 | 163883350 | 163884650 | d7Mseg3983 |
| 7 | 164174100 | 164177400 | d7Mseg3995 |
| 7 | 164214300 | 164216150 | d7Mseg3997 |
| 7 | 164442250 | 164443800 | d7Mseg4007 |
| 7 | 164519350 | 164520600 | d7Mseg4010 |
| 7 | 164568950 | 164570250 | d7Mseg4013 |
| 7 | 164660250 | 164663750 | d7Mseg4015 |
| 7 | 164899200 | 164900500 | d7Mseg4022 |
| 7 | 164926200 | 164928000 | d7Mseg4023 |
| 7 | 164978000 | 164979750 | d7Mseg4024 |
| 7 | 165049550 | 165051250 | d7Mseg4027 |
| 7 | 165120350 | 165121750 | d7Mseg4028 |
| 7 | 165264000 | 165265700 | d7Mseg4038 |
| 7 | 165778100 | 165779700 | d7Mseg4053 |
| 7 | 165788300 | 165789800 | d7Mseg4054 |
| 7 | 165830800 | 165832450 | d7Mseg4056 |
| 7 | 165880900 | 165881950 | d7Mseg4057 |
| 7 | 165895350 | 165896700 | d7Mseg4059 |
| 7 | 165917350 | 165918700 | d7Mseg4061 |
| 7 | 166017800 | 166019650 | d7Mseg4063 |
| 7 | 166425600 | 166428850 | d7Mseg4076 |
| 7 | 166434450 | 166435950 | d7Mseg4077 |
| M | 3853650 | 3855000 | MMseg1 |
| M | 3913600 | 3914800 | MMseg2 |
| M | 4182500 | 4184150 | MMseg3 |
| M | 4758150 | 4759400 | MMseg4 |
| M | 5039250 | 5040550 | MMseg5 |
| M | 5418550 | 5419600 | MMseg6 |
| M | 5428450 | 5430450 | MMseg7 |
| M | 5502250 | 5503450 | MMseg8 |
| M | 5508350 | 5509900 | MMseg9 |
| M | 5651250 | 5652400 | MMseg10 |
| M | 5962150 | 5963800 | MMseg12 |
| M | 6560100 | 6561450 | MMseg18 |
| M | 6615900 | 6616950 | MMseg19 |
| M | 7011150 | 7012750 | MMseg24 |
| M | 7129050 | 7130650 | MMseg25 |
| M | 7558000 | 7559000 | MMseg31 |
| M | 8239550 | 8241250 | MMseg34 |
| M | 8905600 | 8906700 | MMseg35 |
| M | 9127600 | 9129200 | MMseg37 |
| M | 9287800 | 9288850 | MMseg38 |
| M | 9555150 | 9556750 | MMseg40 |
| M | 10621950 | 10623150 | MMseg48 |
| M | 12991250 | 12992550 | MMseg74 |
| M | 12999900 | 13001150 | MMseg75 |
| M | 13082550 | 13083550 | MMseg77 |
| M | 13353300 | 13354800 | MMseg79 |
| M | 13406700 | 13407700 | MMseg80 |
| M | 13503000 | 13504700 | MMseg81 |
| M | 13679750 | 13680900 | MMseg83 |
| M | 13985150 | 13986400 | MMseg85 |
| M | 14134000 | 14135250 | MMseg86 |
| M | 14490950 | 14492650 | MMseg88 |
| M | 15005150 | 15006850 | MMseg89 |
| M | 15139700 | 15141000 | MMseg91 |
| M | 15379600 | 15381300 | MMseg92 |
| M | 15393700 | 15394850 | MMseg93 |
| M | 15413700 | 15415150 | MMseg94 |
| M | 15588650 | 15590050 | MMseg95 |
| M | 15729750 | 15731250 | MMseg97 |
| M | 16775200 | 16776700 | MMseg104 |
| M | 16932850 | 16934350 | MMseg105 |
| M | 16940550 | 16942300 | MMseg106 |
| M | 17622900 | 17624800 | MMseg108 |
| M | 18065050 | 18066550 | MMseg112 |
| M | 18184600 | 18186150 | MMseg113 |
| M | 18400350 | 18402200 | MMseg115 |
| M | 18941550 | 18943100 | MMseg117 |
| M | 19251350 | 19253050 | MMseg119 |
| M | 19397250 | 19398500 | MMseg120 |
| M | 19557100 | 19558600 | MMseg122 |
| M | 19815300 | 19816600 | MMseg126 |
| M | 19908500 | 19909600 | MMseg130 |
| M | 19948200 | 19949800 | MMseg131 |
| M | 20036000 | 20037200 | MMseg133 |
| M | 20188800 | 20190600 | MMseg135 |
| M | 20562700 | 20564250 | MMseg139 |
| M | 20592400 | 20593750 | MMseg140 |
| M | 20899000 | 20900950 | MMseg142 |
| M | 20943950 | 20945350 | MMseg143 |
| M | 21002150 | 21003550 | MMseg144 |
| M | 21345950 | 21346950 | MMseg147 |
| M | 21459600 | 21461200 | MMseg148 |
| M | 21849650 | 21851100 | MMseg149 |
| M | 22518300 | 22519450 | MMseg153 |
| M | 23312100 | 23313450 | MMseg159 |
| M | 23502250 | 23503600 | MMseg160 |
| M | 24068550 | 24070050 | MMseg161 |
| M | 24784200 | 24785900 | MMseg162 |
| M | 25495850 | 25497200 | MMseg163 |
| M | 33282900 | 33283950 | MMseg165 |
| M | 33664350 | 33665550 | MMseg168 |
| M | 33938650 | 33940000 | MMseg173 |
| M | 34384450 | 34386250 | MMseg175 |
| M | 34654900 | 34656500 | MMseg180 |
| M | 34906250 | 34907450 | MMseg181 |
| M | 35106550 | 35107600 | MMseg182 |
| M | 35254900 | 35256700 | MMseg183 |
| M | 35912050 | 35913150 | MMseg185 |
| M | 36011250 | 36012300 | MMseg187 |
| M | 36289600 | 36290600 | MMseg192 |
| M | 36326900 | 36328200 | MMseg193 |
| M | 36784200 | 36785850 | MMseg195 |
| M | 36854050 | 36855500 | MMseg196 |
| M | 37066250 | 37068000 | MMseg198 |
| M | 37101450 | 37103500 | MMseg199 |
| M | 37347150 | 37348200 | MMseg200 |
| M | 38284900 | 38285900 | MMseg205 |
| M | 38464950 | 38466450 | MMseg207 |

TABLE IVC-continued

Mouse Moderate Sites

| c/d | start | end | segment |
|---|---|---|---|
| M | 38478150 | 38479750 | MMseg208 |
| M | 39070400 | 39071600 | MMseg212 |
| M | 39658500 | 39659950 | MMseg214 |
| M | 41053850 | 41055400 | MMseg222 |
| M | 41188600 | 41190350 | MMseg224 |
| M | 41475550 | 41477000 | MMseg225 |
| M | 41838950 | 41840250 | MMseg228 |
| M | 42952250 | 42953650 | MMseg234 |
| M | 43164050 | 43165700 | MMseg235 |
| M | 43300500 | 43301700 | MMseg236 |
| M | 43357850 | 43358850 | MMseg237 |
| M | 43428250 | 43429850 | MMseg238 |
| M | 43508100 | 43509350 | MMseg239 |
| M | 43513800 | 43515250 | MMseg240 |
| M | 43876250 | 43877650 | MMseg242 |
| M | 44741100 | 44742600 | MMseg246 |
| M | 44980800 | 44982100 | MMseg248 |
| M | 45542000 | 45543350 | MMseg252 |
| M | 46151950 | 46153350 | MMseg255 |
| M | 46246300 | 46247300 | MMseg256 |
| M | 46875250 | 46876600 | MMseg262 |
| M | 46897200 | 46899000 | MMseg263 |
| M | 47000050 | 47001600 | MMseg264 |
| M | 47079450 | 47081150 | MMseg265 |
| M | 47195000 | 47196750 | MMseg267 |
| M | 47571850 | 47573350 | MMseg269 |
| M | 47687500 | 47688700 | MMseg270 |
| M | 47930700 | 47932100 | MMseg272 |
| M | 48036250 | 48038000 | MMseg273 |
| M | 48093550 | 48094850 | MMseg274 |
| M | 48308050 | 48310000 | MMseg278 |
| M | 49014000 | 49015350 | MMseg286 |
| M | 50234600 | 50235950 | MMseg302 |
| M | 50735900 | 50737350 | MMseg306 |
| M | 50826250 | 50827500 | MMseg307 |
| M | 51044400 | 51045800 | MMseg309 |
| M | 51083050 | 51084050 | MMseg310 |
| M | 51136650 | 51137950 | MMseg311 |
| M | 51278250 | 51281050 | MMseg313 |
| M | 51482200 | 51486500 | MMseg314 |
| M | 53165750 | 53167450 | MMseg315 |
| M | 53249650 | 53251250 | MMseg316 |
| M | 53639200 | 53640800 | MMseg317 |
| M | 53820100 | 53821400 | MMseg319 |
| M | 53826350 | 53828150 | MMseg320 |
| M | 54236300 | 54238200 | MMseg322 |
| M | 54520000 | 54521000 | MMseg324 |
| M | 54999100 | 55000650 | MMseg327 |
| M | 55444450 | 55446000 | MMseg335 |
| M | 55483150 | 55484400 | MMseg336 |
| M | 55747650 | 55749450 | MMseg337 |
| M | 55900050 | 55901700 | MMseg338 |
| M | 56106050 | 56107450 | MMseg340 |
| M | 56965100 | 56966400 | MMseg348 |
| M | 57142100 | 57143250 | MMseg350 |
| M | 57730200 | 57731950 | MMseg355 |
| M | 58285000 | 58286650 | MMseg359 |
| M | 58341150 | 58342500 | MMseg360 |
| M | 58621950 | 58623450 | MMseg362 |
| M | 58721900 | 58723300 | MMseg363 |
| M | 58780650 | 58782050 | MMseg364 |
| M | 58865700 | 58867350 | MMseg365 |
| M | 59293500 | 59295250 | MMseg368 |
| M | 59540050 | 59541450 | MMseg369 |
| M | 59748650 | 59749700 | MMseg371 |
| M | 60453600 | 60455000 | MMseg372 |
| M | 60616600 | 60617950 | MMseg374 |
| M | 60698850 | 60700300 | MMseg375 |
| M | 60714950 | 60716650 | MMseg376 |
| M | 60790600 | 60792450 | MMseg377 |
| M | 61016450 | 61017650 | MMseg378 |
| M | 61040000 | 61041000 | MMseg379 |
| M | 61100400 | 61102150 | MMseg381 |
| M | 61436750 | 61437850 | MMseg382 |
| M | 61635600 | 61636950 | MMseg384 |
| M | 61753450 | 61754950 | MMseg386 |
| M | 61814600 | 61816300 | MMseg387 |
| M | 61908750 | 61910050 | MMseg388 |
| M | 62017450 | 62018850 | MMseg390 |
| M | 62055450 | 62056700 | MMseg391 |
| M | 62178300 | 62179350 | MMseg392 |
| M | 62287150 | 62288450 | MMseg393 |
| M | 62650950 | 62652550 | MMseg394 |
| M | 63122400 | 63123850 | MMseg395 |
| M | 63161850 | 63163150 | MMseg396 |
| M | 63173650 | 63175800 | MMseg397 |
| M | 63193700 | 63195550 | MMseg398 |
| M | 63220800 | 63222600 | MMseg399 |
| M | 63490650 | 63491900 | MMseg400 |
| M | 63678500 | 63680300 | MMseg401 |
| M | 64283600 | 64284900 | MMseg405 |
| M | 64305350 | 64306500 | MMseg406 |
| M | 64500200 | 64501550 | MMseg408 |
| M | 64679350 | 64680350 | MMseg409 |
| M | 64846350 | 64847550 | MMseg410 |
| M | 65009500 | 65010700 | MMseg412 |
| M | 66108350 | 66110150 | MMseg415 |
| M | 66332100 | 66333400 | MMseg417 |
| M | 67137700 | 67138900 | MMseg425 |
| M | 67496900 | 67498100 | MMseg429 |
| M | 68460650 | 68461800 | MMseg432 |
| M | 68588200 | 68589400 | MMseg434 |
| M | 69561150 | 69562600 | MMseg440 |
| M | 69870950 | 69872600 | MMseg442 |
| M | 69885650 | 69889050 | MMseg443 |
| M | 69913200 | 69914350 | MMseg445 |
| M | 70024950 | 70026350 | MMseg446 |
| M | 70651400 | 70652750 | MMseg447 |
| M | 70909300 | 70910550 | MMseg452 |
| M | 70946400 | 70947800 | MMseg454 |
| M | 71348700 | 71350300 | MMseg458 |
| M | 71380650 | 71382200 | MMseg459 |
| M | 71814350 | 71816050 | MMseg462 |
| M | 71846750 | 71848000 | MMseg463 |
| M | 71930850 | 71932050 | MMseg464 |
| M | 72217150 | 72218800 | MMseg465 |
| M | 72239800 | 72241600 | MMseg466 |
| M | 72396500 | 72398000 | MMseg469 |
| M | 72772150 | 72773250 | MMseg472 |
| M | 73302650 | 73303700 | MMseg477 |
| M | 73508550 | 73510300 | MMseg481 |
| M | 73721700 | 73723550 | MMseg483 |
| M | 73747600 | 73748900 | MMseg484 |
| M | 73907500 | 73909300 | MMseg485 |
| M | 74287750 | 74288900 | MMseg488 |
| M | 74371800 | 74373200 | MMseg489 |
| M | 74549700 | 74551200 | MMseg490 |
| M | 74702550 | 74703850 | MMseg491 |
| M | 74785350 | 74786750 | MMseg493 |
| M | 75212300 | 75213900 | MMseg498 |
| M | 75242700 | 75244200 | MMseg499 |
| M | 75332250 | 75333750 | MMseg500 |
| M | 75497000 | 75499000 | MMseg501 |
| M | 75613800 | 75615000 | MMseg502 |
| M | 75873650 | 75875150 | MMseg505 |
| M | 76088250 | 76089700 | MMseg506 |
| M | 76295900 | 76297600 | MMseg507 |
| M | 76844550 | 76845850 | MMseg509 |
| M | 77235800 | 77237100 | MMseg511 |
| M | 77545850 | 77547150 | MMseg512 |
| M | 77550750 | 77552250 | MMseg513 |
| M | 77577300 | 77578950 | MMseg515 |
| M | 77631150 | 77632900 | MMseg516 |
| M | 77681050 | 77682200 | MMseg517 |
| M | 77685850 | 77687000 | MMseg518 |
| M | 78018300 | 78019700 | MMseg519 |
| M | 78672950 | 78674250 | MMseg523 |
| M | 78809700 | 78811000 | MMseg524 |
| M | 78844550 | 78845800 | MMseg525 |
| M | 79106900 | 79108550 | MMseg527 |
| M | 79305500 | 79306550 | MMseg529 |
| M | 79523750 | 79525400 | MMseg531 |

TABLE IVC-continued

Mouse Moderate Sites

| c/d | start | end | segment |
|---|---|---|---|
| M | 79823200 | 79824450 | MMseg532 |
| M | 80564550 | 80566300 | MMseg536 |
| M | 80637150 | 80638600 | MMseg537 |
| M | 80913700 | 80914900 | MMseg538 |
| M | 82552300 | 82553650 | MMseg550 |
| M | 83364850 | 83366000 | MMseg556 |
| M | 83371600 | 83373350 | MMseg557 |
| M | 83511200 | 83513850 | MMseg558 |
| M | 83639250 | 83640500 | MMseg560 |
| M | 84621550 | 84623100 | MMseg566 |
| M | 85395650 | 85398150 | MMseg573 |
| M | 85649200 | 85650850 | MMseg575 |
| M | 85753300 | 85754350 | MMseg577 |
| M | 86013300 | 86014450 | MMseg578 |
| M | 87286950 | 87288150 | MMseg583 |
| M | 87334850 | 87336400 | MMseg584 |
| M | 87366750 | 87368350 | MMseg585 |
| M | 87410800 | 87411950 | MMseg586 |
| M | 87513100 | 87515100 | MMseg587 |
| M | 87643150 | 87644900 | MMseg588 |
| M | 88092300 | 88093550 | MMseg590 |
| M | 88288000 | 88289700 | MMseg591 |
| M | 88347150 | 88348500 | MMseg592 |
| M | 88473950 | 88475600 | MMseg593 |
| M | 88760900 | 88762400 | MMseg594 |
| M | 89226800 | 89228700 | MMseg595 |
| M | 89285950 | 89287000 | MMseg596 |
| M | 90006500 | 90008250 | MMseg600 |
| M | 90150550 | 90151950 | MMseg601 |
| M | 90231250 | 90232550 | MMseg603 |
| M | 90234150 | 90235500 | MMseg604 |
| M | 90474100 | 90475400 | MMseg606 |
| M | 91423400 | 91425250 | MMseg617 |
| M | 91471600 | 91473200 | MMseg618 |
| M | 91533550 | 91536400 | MMseg621 |
| M | 91665450 | 91666700 | MMseg625 |
| M | 91824650 | 91826250 | MMseg627 |
| M | 91995750 | 91997350 | MMseg631 |
| M | 92172350 | 92174150 | MMseg632 |
| M | 92195100 | 92196750 | MMseg633 |
| M | 92301050 | 92302350 | MMseg634 |
| M | 92578950 | 92580750 | MMseg636 |
| M | 92588050 | 92589650 | MMseg637 |
| M | 92683900 | 92685200 | MMseg639 |
| M | 92863400 | 92864450 | MMseg640 |
| M | 93050700 | 93051900 | MMseg642 |
| M | 93104900 | 93106750 | MMseg643 |
| M | 93398050 | 93399150 | MMseg647 |
| M | 93400750 | 93401800 | MMseg648 |
| M | 93469050 | 93470400 | MMseg649 |
| M | 93528700 | 93530300 | MMseg650 |
| M | 93957800 | 93958900 | MMseg655 |
| M | 94010400 | 94011500 | MMseg656 |
| M | 94108050 | 94109750 | MMseg657 |
| M | 94187400 | 94188650 | MMseg658 |
| M | 94224450 | 94226000 | MMseg659 |
| M | 94268400 | 94269750 | MMseg660 |
| M | 94482050 | 94483700 | MMseg661 |
| M | 94993450 | 94995150 | MMseg663 |
| M | 95214700 | 95215900 | MMseg664 |
| M | 95262100 | 95263800 | MMseg666 |
| M | 95282100 | 95283700 | MMseg667 |
| M | 95311950 | 95313750 | MMseg668 |
| M | 95672450 | 95673950 | MMseg670 |
| M | 96123950 | 96125100 | MMseg672 |
| M | 97391250 | 97392350 | MMseg685 |
| M | 97748050 | 97749300 | MMseg688 |
| M | 97849550 | 97851300 | MMseg691 |
| M | 98207550 | 98208550 | MMseg697 |
| M | 98801500 | 98802800 | MMseg700 |
| M | 98941550 | 98942600 | MMseg703 |
| M | 98974200 | 98976450 | MMseg704 |
| M | 99033300 | 99034500 | MMseg705 |
| M | 99133450 | 99134700 | MMseg707 |
| M | 99409750 | 99410850 | MMseg710 |
| M | 100233950 | 100235250 | MMseg717 |
| M | 100239700 | 100240700 | MMseg718 |
| M | 100251300 | 100253550 | MMseg719 |
| M | 100340950 | 100342500 | MMseg720 |
| M | 100602700 | 100604000 | MMseg724 |
| M | 100639200 | 100646300 | MMseg725 |
| M | 100781050 | 100782700 | MMseg726 |
| M | 101106000 | 101107850 | MMseg730 |
| M | 101148650 | 101150250 | MMseg732 |
| M | 101530950 | 101532550 | MMseg736 |
| M | 101898700 | 101900050 | MMseg741 |
| M | 102262900 | 102264050 | MMseg743 |
| M | 102368400 | 102370100 | MMseg744 |
| M | 102474500 | 102475800 | MMseg746 |
| M | 102788050 | 102789300 | MMseg748 |
| M | 102856700 | 102857950 | MMseg749 |
| M | 103127200 | 103130750 | MMseg751 |
| M | 103490600 | 103491700 | MMseg754 |
| M | 103526150 | 103527600 | MMseg755 |
| M | 103553950 | 103535550 | MMseg756 |
| M | 103581350 | 103582850 | MMseg757 |
| M | 103678550 | 103681250 | MMseg758 |
| M | 103845250 | 103846300 | MMseg760 |
| M | 103867650 | 103869200 | MMseg761 |
| M | 103917000 | 103918550 | MMseg762 |
| M | 103922650 | 103924250 | MMseg763 |
| M | 104411000 | 104412350 | MMseg766 |
| M | 104468900 | 104470050 | MMseg768 |
| M | 104772600 | 104773900 | MMseg770 |
| M | 104848950 | 104849950 | MMseg771 |
| M | 105027400 | 105028450 | MMseg772 |
| M | 105207500 | 105208750 | MMseg774 |
| M | 105220800 | 105222600 | MMseg775 |
| M | 105377450 | 105378800 | MMseg776 |
| M | 105384550 | 105385950 | MMseg777 |
| M | 105388100 | 105389550 | MMseg778 |
| M | 105658650 | 105660100 | MMseg779 |
| M | 106215950 | 106217450 | MMseg783 |
| M | 106746100 | 106747800 | MMseg785 |
| M | 107668600 | 107670350 | MMseg791 |
| M | 107836650 | 107838150 | MMseg792 |
| M | 108610550 | 108612400 | MMseg797 |
| M | 108827450 | 108828700 | MMseg798 |
| M | 108963050 | 108964600 | MMseg799 |
| M | 108968700 | 108970300 | MMseg800 |
| M | 108997650 | 108998950 | MMseg801 |
| M | 109018600 | 109019600 | MMseg802 |
| M | 109037600 | 109038600 | MMseg803 |
| M | 109220150 | 109221500 | MMseg804 |
| M | 109436500 | 109438250 | MMseg805 |
| M | 109526200 | 109527800 | MMseg807 |
| M | 109562700 | 109563750 | MMseg808 |
| M | 109773250 | 109774900 | MMseg810 |
| M | 110255000 | 110256750 | MMseg814 |
| M | 110962200 | 110963200 | MMseg824 |
| M | 111271550 | 111273200 | MMseg826 |
| M | 111924150 | 111925500 | MMseg830 |
| M | 112983650 | 112985150 | MMseg833 |
| M | 113241050 | 113242450 | MMseg835 |
| M | 113461050 | 113462100 | MMseg836 |
| M | 113730600 | 113732150 | MMseg837 |
| M | 114172850 | 114174300 | MMseg838 |
| M | 114387400 | 114388800 | MMseg840 |
| M | 114413850 | 114415200 | MMseg841 |
| M | 114768850 | 114769850 | MMseg843 |
| M | 115105200 | 115106800 | MMseg844 |
| M | 115134650 | 115136150 | MMseg845 |
| M | 115656900 | 115658850 | MMseg846 |
| M | 115665950 | 115667250 | MMseg847 |
| M | 115678600 | 115679900 | MMseg848 |
| M | 115893950 | 115895000 | MMseg849 |
| M | 115947800 | 115949300 | MMseg850 |
| M | 116100300 | 116101700 | MMseg851 |
| M | 116508800 | 116510200 | MMseg854 |
| M | 117079050 | 117080600 | MMseg855 |
| M | 117316100 | 117317600 | MMseg857 |
| M | 117351800 | 117353500 | MMseg859 |

TABLE IVC-continued

Mouse Moderate Sites

| c/d | start | end | segment |
|---|---|---|---|
| M | 117683700 | 117685300 | MMseg862 |
| M | 117971700 | 117973450 | MMseg868 |
| M | 118276100 | 118277550 | MMseg869 |
| M | 118521900 | 118523700 | MMseg870 |
| M | 118594300 | 118595550 | MMseg871 |
| M | 119374450 | 119375950 | MMseg873 |
| M | 119904150 | 119905300 | MMseg876 |
| M | 119953200 | 119954950 | MMseg877 |
| M | 122902500 | 122904050 | MMseg878 |
| M | 123006500 | 123007800 | MMseg879 |
| M | 123323350 | 123324600 | MMseg880 |
| M | 123707800 | 123708800 | MMseg881 |
| M | 123856850 | 123858100 | MMseg883 |
| M | 123864900 | 123865950 | MMseg884 |
| M | 124369850 | 124370950 | MMseg886 |
| M | 124444500 | 124445950 | MMseg887 |
| M | 124465050 | 124466050 | MMseg888 |
| M | 124515700 | 124517350 | MMseg889 |
| M | 124663250 | 124665000 | MMseg890 |
| M | 125022300 | 125023900 | MMseg891 |
| M | 125153700 | 125154800 | MMseg893 |
| M | 125618400 | 125619700 | MMseg894 |
| M | 125677650 | 125678850 | MMseg895 |
| M | 126265250 | 126266850 | MMseg899 |
| M | 127107200 | 127108200 | MMseg903 |
| M | 127440900 | 127442250 | MMseg904 |
| M | 127530150 | 127531850 | MMseg905 |
| M | 127593150 | 127594250 | MMseg906 |
| M | 127653450 | 127655150 | MMseg907 |
| M | 127913200 | 127914200 | MMseg909 |
| M | 128956900 | 128958250 | MMseg921 |
| M | 129162200 | 129163650 | MMseg922 |
| M | 129461050 | 129464000 | MMseg924 |
| M | 130582100 | 130583200 | MMseg934 |
| M | 130768750 | 130770100 | MMseg936 |
| M | 130837350 | 130838550 | MMseg937 |
| M | 130898050 | 130899150 | MMseg938 |
| M | 131086950 | 131088550 | MMseg940 |
| M | 131104100 | 131105650 | MMseg941 |
| M | 131495200 | 131496350 | MMseg942 |
| M | 131730800 | 131732550 | MMseg943 |
| M | 132207900 | 132209100 | MMseg945 |
| M | 132232300 | 132233850 | MMseg946 |
| M | 132236600 | 132237650 | MMseg947 |
| M | 132364300 | 132365300 | MMseg949 |
| M | 132465900 | 132467200 | MMseg951 |
| M | 132648000 | 132649350 | MMseg954 |
| M | 132666000 | 132667650 | MMseg955 |
| M | 132838750 | 132840350 | MMseg958 |
| M | 132856800 | 132858450 | MMseg959 |
| M | 132984650 | 132985800 | MMseg960 |
| M | 133065750 | 133067150 | MMseg961 |
| M | 133118500 | 133119950 | MMseg962 |
| M | 133123300 | 133124600 | MMseg963 |
| M | 133127600 | 133129200 | MMseg964 |
| M | 133204150 | 133205750 | MMseg966 |
| M | 133538050 | 133539800 | MMseg973 |
| M | 133632600 | 133634450 | MMseg974 |
| M | 133637850 | 133641150 | MMseg975 |
| M | 133872000 | 133873250 | MMseg977 |
| M | 134292600 | 134294150 | MMseg981 |
| M | 134410300 | 134411850 | MMseg983 |
| M | 134535700 | 134537300 | MMseg984 |
| M | 134681700 | 134683150 | MMseg985 |
| M | 134729700 | 134731250 | MMseg986 |
| M | 134961050 | 134962400 | MMseg988 |
| M | 135124500 | 135126000 | MMseg990 |
| M | 135596500 | 135598150 | MMseg993 |
| M | 135879850 | 135881100 | MMseg994 |
| M | 135973700 | 135975000 | MMseg995 |
| M | 136447100 | 136448550 | MMseg997 |
| M | 136545600 | 136547200 | MMseg999 |
| M | 136594600 | 136598150 | MMseg1001 |
| M | 136797750 | 136799150 | MMseg1008 |
| M | 137015750 | 137017450 | MMseg1012 |
| M | 137350250 | 137351400 | MMseg1017 |
| M | 137916950 | 137918200 | MMseg1026 |
| M | 138381100 | 138383600 | MMseg1029 |
| M | 138645950 | 138647500 | MMseg1032 |
| M | 140647750 | 140648950 | MMseg1049 |
| M | 141684600 | 141686000 | MMseg1053 |
| M | 142240800 | 142241850 | MMseg1055 |
| M | 143084800 | 143086400 | MMseg1057 |
| M | 143679800 | 143681250 | MMseg1061 |
| M | 144057050 | 144058600 | MMseg1065 |
| M | 146277150 | 146278500 | MMseg1066 |
| M | 147153000 | 147154300 | MMseg1068 |
| M | 147373100 | 147374650 | MMseg1069 |
| M | 147596450 | 147597650 | MMseg1071 |
| M | 147599300 | 147600850 | MMseg1072 |
| M | 147638800 | 147640450 | MMseg1073 |
| M | 148724200 | 148725650 | MMseg1081 |
| M | 148899600 | 148901450 | MMseg1082 |
| M | 148905550 | 148907100 | MMseg1083 |
| M | 149019850 | 149021250 | MMseg1084 |
| M | 149186650 | 149187900 | MMseg1087 |
| M | 149360600 | 149361750 | MMseg1088 |
| M | 149857900 | 149859350 | MMseg1090 |
| M | 149866150 | 149868050 | MMseg1091 |
| M | 149942350 | 149943700 | MMseg1092 |
| M | 149953200 | 149954600 | MMseg1093 |
| M | 149995100 | 149996350 | MMseg1094 |
| M | 150023050 | 150024400 | MMseg1095 |
| M | 150691950 | 150693700 | MMseg1096 |
| M | 150907200 | 150908300 | MMseg1097 |
| M | 150982700 | 150983700 | MMseg1098 |
| M | 151001400 | 151002900 | MMseg1099 |
| M | 151091950 | 151093300 | MMseg1100 |
| M | 151230750 | 151232000 | MMseg1101 |
| M | 153281400 | 153283100 | MMseg1111 |
| M | 154760350 | 154761550 | MMseg1119 |
| M | 155235150 | 155236150 | MMseg1122 |
| M | 155673900 | 155675850 | MMseg1124 |
| M | 155887750 | 155889200 | MMseg1126 |
| M | 157441650 | 157443000 | MMseg1140 |
| M | 157565700 | 157567200 | MMseg1141 |
| M | 158701750 | 158703100 | MMseg1149 |
| M | 158898550 | 158899800 | MMseg1152 |
| M | 159015800 | 159017200 | MMseg1155 |
| M | 159352300 | 159354000 | MMseg1160 |
| M | 160138050 | 160139900 | MMseg1164 |
| M | 160154050 | 160155450 | MMseg1165 |
| M | 160197700 | 160200400 | MMseg1166 |
| M | 160720100 | 160721150 | MMseg1168 |
| M | 161454650 | 161456650 | MMseg1175 |
| M | 161716050 | 161717500 | MMseg1177 |
| M | 163323300 | 163324550 | MMseg1183 |
| M | 164180300 | 164181350 | MMseg1191 |
| M | 164412050 | 164413400 | MMseg1194 |
| M | 164572500 | 164573850 | MMseg1196 |
| M | 165395050 | 165396550 | MMseg1206 |
| M | 165513000 | 165514700 | MMseg1208 |
| M | 165596800 | 165598350 | MMseg1209 |

Table V presents a full list of strong EZH2 sites on mouse Chr13. For Table V: 0, day 0 ES cells; 7, day 7 ES cells; M, MEF cells.

TABLE V

| | start | end | name |
|---|---|---|---|
| 0 | 3356950 | 3360750 | 13.0seg_1 |
| 0 | 10357650 | 10360200 | 13.0seg_2 |
| 0 | 22094300 | 22095300 | 13.0seg_3 |
| 0 | 23377600 | 23379350 | 13.0seg_4 |

TABLE V-continued

| start | end | name |
|---|---|---|
| 0 | 23401050 | 23406550 | 13.0seg_5 |
| 0 | 23486500 | 23488700 | 13.0seg_6 |
| 0 | 28976050 | 28977450 | 13.0seg_7 |
| 0 | 29042750 | 29044450 | 13.0seg_8 |
| 0 | 30840550 | 30843850 | 13.0seg_9 |
| 0 | 31648650 | 31652000 | 13.0seg_10 |
| 0 | 31706400 | 31723100 | 13.0seg_11 |
| 0 | 31891450 | 31904050 | 13.0seg_12 |
| 0 | 34742650 | 34745050 | 13.0seg_13 |
| 0 | 36815800 | 36828450 | 13.0seg_14 |
| 0 | 38437500 | 38439550 | 13.0seg_15 |
| 0 | 40796400 | 40801550 | 13.0seg_16 |
| 0 | 40822500 | 40838550 | 13.0seg_17 |
| 0 | 42396950 | 42398050 | 13.0seg_18 |
| 0 | 46061450 | 46063350 | 13.0seg_19 |
| 0 | 48357100 | 48358700 | 13.0seg_20 |
| 0 | 48752600 | 48765950 | 13.0seg_21 |
| 0 | 49342350 | 49343550 | 13.0seg_22 |
| 0 | 51661800 | 51665000 | 13.0seg_23 |
| 0 | 53073250 | 53076100 | 13.0seg_24 |
| 0 | 53557950 | 53562600 | 13.0seg_25 |
| 0 | 53566450 | 53572600 | 13.0seg_26 |
| 0 | 55049500 | 55050600 | 13.0seg_27 |
| 0 | 55924950 | 55939300 | 13.0seg_28 |
| 0 | 56323550 | 56325750 | 13.0seg_29 |
| 0 | 56348800 | 56356000 | 13.0seg_30 |
| 0 | 56357250 | 56361850 | 13.0seg_31 |
| 0 | 56538800 | 56540550 | 13.0seg_32 |
| 0 | 56853050 | 56856150 | 13.0seg_33 |
| 0 | 58008150 | 58010000 | 13.0seg_34 |
| 0 | 58908050 | 58911250 | 13.0seg_35 |
| 0 | 63672500 | 63675550 | 13.0seg_36 |
| 0 | 72093850 | 72101050 | 13.0seg_37 |
| 0 | 72760300 | 72763850 | 13.0seg_38 |
| 0 | 72764950 | 72769750 | 13.0seg_39 |
| 0 | 72774250 | 72777300 | 13.0seg_40 |
| 0 | 72953350 | 72954800 | 13.0seg_41 |
| 0 | 73396950 | 73403550 | 13.0seg_42 |
| 0 | 73404600 | 73405900 | 13.0seg_43 |
| 0 | 73407750 | 73410550 | 13.0seg_44 |
| 0 | 76091600 | 76093150 | 13.0seg_45 |
| 0 | 76192300 | 76195450 | 13.0seg_46 |
| 0 | 78320050 | 78322600 | 13.0seg_47 |
| 0 | 78332100 | 78342350 | 13.0seg_48 |
| 0 | 78347000 | 78350900 | 13.0seg_49 |
| 0 | 83854500 | 83857050 | 13.0seg_50 |
| 0 | 83858550 | 83860900 | 13.0seg_51 |
| 0 | 83863250 | 83867100 | 13.0seg_52 |
| 0 | 83871450 | 83873550 | 13.0seg_53 |
| 0 | 84484400 | 84486350 | 13.0seg_54 |
| 0 | 92900200 | 92902200 | 13.0seg_55 |
| 0 | 95472100 | 95473350 | 13.0seg_56 |
| 0 | 95479900 | 95481300 | 13.0seg_57 |
| 0 | 95638750 | 95648950 | 13.0seg_58 |
| 0 | 95650900 | 95656850 | 13.0seg_59 |
| 0 | 96899200 | 96900650 | 13.0seg_60 |
| 0 | 97128850 | 97130750 | 13.0seg_61 |
| 0 | 99122600 | 99130250 | 13.0seg_62 |
| 0 | 99133200 | 99137850 | 13.0seg_63 |
| 0 | 99159800 | 99162950 | 13.0seg_64 |
| 0 | 99199350 | 99200550 | 13.0seg_65 |
| 0 | 99272300 | 99274000 | 13.0seg_66 |
| 0 | 99342550 | 99343800 | 13.0seg_67 |
| 0 | 100668150 | 100669250 | 13.0seg_68 |
| 0 | 104123000 | 104126400 | 13.0seg_69 |
| 0 | 105842800 | 105845100 | 13.0seg_70 |
| 0 | 106233400 | 106237300 | 13.0seg_71 |
| 0 | 108681100 | 108682950 | 13.0seg_72 |
| 0 | 113777300 | 113785050 | 13.0seg_73 |
| 0 | 113824250 | 113826600 | 13.0seg_74 |
| 0 | 115244750 | 115251450 | 13.0seg_75 |
| 0 | 117092800 | 117097000 | 13.0seg_76 |
| 0 | 117099700 | 117101800 | 13.0seg_77 |
| 0 | 117103150 | 117104300 | 13.0seg_78 |
| 0 | 117814500 | 117815600 | 13.0seg_79 |
| 7 | 3356750 | 3361400 | 13.7seg_1 |
| 7 | 10357800 | 10361400 | 13.7seg_2 |
| 7 | 22072350 | 22075250 | 13.7seg_3 |
| 7 | 22097900 | 22100100 | 13.7seg_4 |
| 7 | 23403900 | 23406150 | 13.7seg_5 |
| 7 | 23486450 | 23489050 | 13.7seg_6 |
| 7 | 29043000 | 29045350 | 13.7seg_7 |
| 7 | 31648100 | 31652850 | 13.7seg_8 |
| 7 | 31706200 | 31724650 | 13.7seg_9 |
| 7 | 31892150 | 31905800 | 13.7seg_10 |
| 7 | 34743050 | 34745800 | 13.7seg_11 |
| 7 | 35055450 | 35057000 | 13.7seg_12 |
| 7 | 36059900 | 36062550 | 13.7seg_13 |
| 7 | 36814750 | 36828100 | 13.7seg_14 |
| 7 | 38436250 | 38439650 | 13.7seg_15 |
| 7 | 40796150 | 40810900 | 13.7seg_16 |
| 7 | 40822500 | 40841050 | 13.7seg_17 |
| 7 | 43397550 | 43399350 | 13.7seg_18 |
| 7 | 43879700 | 43881750 | 13.7seg_19 |
| 7 | 46060500 | 46062150 | 13.7seg_20 |
| 7 | 47217850 | 47219300 | 13.7seg_21 |
| 7 | 48751050 | 48769050 | 13.7seg_22 |
| 7 | 48826200 | 48827900 | 13.7seg_23 |
| 7 | 51660950 | 51665250 | 13.7seg_24 |
| 7 | 51942100 | 51945450 | 13.7seg_25 |
| 7 | 53557200 | 53562950 | 13.7seg_26 |
| 7 | 53566150 | 53570950 | 13.7seg_27 |
| 7 | 55051250 | 55052550 | 13.7seg_28 |
| 7 | 55057900 | 55059100 | 13.7seg_29 |
| 7 | 55490850 | 55492350 | 13.7seg_30 |
| 7 | 55573800 | 55575000 | 13.7seg_31 |
| 7 | 55924850 | 55940600 | 13.7seg_32 |
| 7 | 56322300 | 56325350 | 13.7seg_33 |
| 7 | 56349750 | 56364000 | 13.7seg_34 |
| 7 | 56395300 | 56398650 | 13.7seg_35 |
| 7 | 56538900 | 56540800 | 13.7seg_36 |
| 7 | 56853300 | 56856050 | 13.7seg_37 |
| 7 | 58008450 | 58009950 | 13.7seg_38 |
| 7 | 58097150 | 58098300 | 13.7seg_39 |
| 7 | 58213150 | 58215150 | 13.7seg_40 |
| 7 | 58907500 | 58910800 | 13.7seg_41 |
| 7 | 63671950 | 63675950 | 13.7seg_42 |
| 7 | 69875950 | 69879900 | 13.7seg_43 |
| 7 | 72093300 | 72102850 | 13.7seg_44 |
| 7 | 72760100 | 72763650 | 13.7seg_45 |
| 7 | 72764700 | 72770500 | 13.7seg_46 |
| 7 | 72773400 | 72779100 | 13.7seg_47 |
| 7 | 73396600 | 73410250 | 13.7seg_48 |
| 7 | 76192300 | 76194350 | 13.7seg_49 |
| 7 | 78302350 | 78303850 | 13.7seg_50 |
| 7 | 78311400 | 78313900 | 13.7seg_51 |
| 7 | 78315300 | 78326450 | 13.7seg_52 |
| 7 | 78328450 | 78329550 | 13.7seg_53 |
| 7 | 78331750 | 78345750 | 13.7seg_54 |
| 7 | 78347000 | 78351100 | 13.7seg_55 |
| 7 | 83853900 | 83862350 | 13.7seg_56 |
| 7 | 83863900 | 83869700 | 13.7seg_57 |
| 7 | 83871600 | 83873650 | 13.7seg_58 |
| 7 | 83878050 | 83879550 | 13.7seg_59 |
| 7 | 93196150 | 93198050 | 13.7seg_60 |
| 7 | 95479200 | 95481200 | 13.7seg_61 |
| 7 | 95639150 | 95656550 | 13.7seg_62 |
| 7 | 96213300 | 96214500 | 13.7seg_63 |
| 7 | 96900700 | 96904350 | 13.7seg_64 |
| 7 | 97693800 | 97696300 | 13.7seg_65 |
| 7 | 99122200 | 99139350 | 13.7seg_66 |
| 7 | 99160300 | 99162850 | 13.7seg_67 |
| 7 | 99271550 | 99276800 | 13.7seg_68 |
| 7 | 99342150 | 99344200 | 13.7seg_69 |
| 7 | 105842950 | 105845900 | 13.7seg_70 |
| 7 | 106234300 | 106236950 | 13.7seg_71 |
| 7 | 109004400 | 109006200 | 13.7seg_72 |
| 7 | 113775950 | 113785400 | 13.7seg_73 |
| 7 | 113787700 | 113790300 | 13.7seg_74 |
| 7 | 113823900 | 113826450 | 13.7seg_75 |
| 7 | 115246450 | 115250350 | 13.7seg_76 |
| 7 | 115890950 | 115892650 | 13.7seg_77 |
| 7 | 117082950 | 117105350 | 13.7seg_78 |
| 7 | 117495700 | 117497650 | 13.7seg_79 |
| 7 | 117813300 | 117816000 | 13.7seg_80 |
| 7 | 119502750 | 119504650 | 13.7seg_81 |

TABLE V-continued

|   | start | end | name |
|---|---|---|---|
| M | 3357350 | 3360800 | 13.Mseg_1 |
| M | 12197650 | 12199550 | 13.Mseg_2 |
| M | 12611450 | 12612950 | 13.Mseg_3 |
| M | 13875800 | 13877800 | 13.Mseg_4 |
| M | 19039700 | 19041400 | 13.Mseg_5 |
| M | 20181300 | 20183850 | 13.Mseg_6 |
| M | 21334350 | 21335400 | 13.Mseg_7 |
| M | 22086850 | 22089450 | 13.Mseg_8 |
| M | 22097600 | 22099800 | 13.Mseg_9 |
| M | 23400950 | 23406350 | 13.Mseg_10 |
| M | 23487000 | 23488600 | 13.Mseg_11 |
| M | 25146700 | 25149200 | 13.Mseg_12 |
| M | 30840050 | 30843450 | 13.Mseg_13 |
| M | 31649550 | 31652750 | 13.Mseg_14 |
| M | 31706200 | 31707550 | 13.Mseg_15 |
| M | 36060050 | 36061950 | 13.Mseg_16 |
| M | 38242350 | 38245450 | 13.Mseg_17 |
| M | 38436150 | 38439900 | 13.Mseg_18 |
| M | 40798050 | 40801350 | 13.Mseg_19 |
| M | 40803050 | 40806600 | 13.Mseg_20 |
| M | 40822600 | 40837900 | 13.Mseg_21 |
| M | 41209050 | 41210750 | 13.Mseg_22 |
| M | 43879750 | 43881300 | 13.Mseg_23 |
| M | 46512500 | 46515600 | 13.Mseg_24 |
| M | 48752700 | 48765900 | 13.Mseg_25 |
| M | 48825700 | 48828500 | 13.Mseg_26 |
| M | 49240400 | 49244450 | 13.Mseg_27 |
| M | 51661750 | 51664150 | 13.Mseg_28 |
| M | 53556650 | 53563050 | 13.Mseg_29 |
| M | 53566200 | 53572700 | 13.Mseg_30 |
| M | 54149750 | 54151600 | 13.Mseg_31 |
| M | 54866250 | 54868550 | 13.Mseg_32 |
| M | 54972950 | 54977050 | 13.Mseg_33 |
| M | 55050200 | 55052100 | 13.Mseg_34 |
| M | 55056400 | 55058200 | 13.Mseg_35 |
| M | 55479650 | 55480900 | 13.Mseg_36 |
| M | 55925150 | 55939650 | 13.Mseg_37 |
| M | 56321550 | 56326000 | 13.Mseg_38 |
| M | 56350700 | 56354900 | 13.Mseg_39 |
| M | 56357500 | 56362450 | 13.Mseg_40 |
| M | 56396300 | 56399550 | 13.Mseg_41 |
| M | 56538900 | 56540700 | 13.Mseg_42 |
| M | 56853850 | 56855800 | 13.Mseg_43 |
| M | 58008900 | 58010050 | 13.Mseg_44 |
| M | 58907300 | 58910550 | 13.Mseg_45 |
| M | 60703100 | 60704500 | 13.Mseg_46 |
| M | 63672900 | 63675800 | 13.Mseg_47 |
| M | 69876150 | 69879350 | 13.Mseg_48 |
| M | 72093600 | 72106600 | 13.Mseg_49 |
| M | 73397450 | 73403500 | 13.Mseg_50 |
| M | 73405300 | 73410050 | 13.Mseg_51 |
| M | 74776800 | 74777900 | 13.Mseg_52 |
| M | 76520800 | 76522700 | 13.Mseg_53 |
| M | 81771200 | 81773200 | 13.Mseg_54 |
| M | 83855650 | 83856850 | 13.Mseg_55 |
| M | 83859850 | 83861800 | 13.Mseg_56 |
| M | 83863850 | 83873800 | 13.Mseg_57 |
| M | 93195000 | 93197800 | 13.Mseg_58 |
| M | 93563650 | 93565150 | 13.Mseg_59 |
| M | 94443900 | 94445100 | 13.Mseg_60 |
| M | 95364800 | 95367500 | 13.Mseg_61 |
| M | 95454700 | 95456050 | 13.Mseg_62 |
| M | 95470950 | 95474500 | 13.Mseg_63 |
| M | 95476500 | 95482400 | 13.Mseg_64 |
| M | 95637750 | 95648350 | 13.Mseg_65 |
| M | 95651300 | 95656700 | 13.Mseg_66 |
| M | 96660450 | 96661950 | 13.Mseg_67 |
| M | 96900900 | 96904150 | 13.Mseg_68 |
| M | 97840950 | 97842850 | 13.Mseg_69 |
| M | 101320050 | 101323950 | 13.Mseg_70 |
| M | 104123300 | 104125050 | 13.Mseg_71 |
| M | 105843150 | 105845800 | 13.Mseg_72 |
| M | 106083650 | 106085350 | 13.Mseg_73 |
| M | 112141900 | 112143250 | 13.Mseg_74 |
| M | 113777450 | 113780200 | 13.Mseg_75 |
| M | 113782950 | 113785550 | 13.Mseg_76 |
| M | 113821150 | 113823500 | 13.Mseg_77 |
| M | 113824600 | 113826100 | 13.Mseg_78 |
| M | 117088200 | 117089450 | 13.Mseg_79 |
| M | 117093000 | 117094750 | 13.Mseg_80 |
| M | 117098050 | 117102350 | 13.Mseg_81 |
| M | 117493650 | 117500700 | 13.Mseg_82 |
| M | 118391300 | 118392850 | 13.Mseg_83 |

Example 8

Identification of lncRNAs Modifying X-linked Disease Genes

For the mouse inactive X-chromosome, strong and moderate PRC2 sites were identified by the allele-specific ChIP-seq analysis of days 0 and 7 mouse female ES cells, and MEFs (mouse embryonic fibroblasts) as described above. The transcriptome of day 7 differentiating female ES cells was also obtained by RNA-seq analysis. Transcripts in the RNA-seq library were aligned to the mouse July 2007 (NCBI37/mm9) genome using TopHat (Trapnell et al., Bioinformatics, 2009 May 1; 25(9):1105-11) to identify splice junctions, Additionally, Cufflinks (Trapnell et al., Nature Biotechnology 28, 511-515(2010)) was used to assemble full transcripts and quantitate their abundance. To call an lncRNA, transcripts were flagged that overlapped more than 80% with a protein-coding mRNA, The remaining transcripts were called "X-linked lncRNA", Previously annotated lncRNAs are given a specific ENSEMBL ID in Tables VI and VIII (e.g., ENSMUST00000083484). Novel predicted lncRNAs are given CUFF names (e.g., CUFF.14406) in Tables VI and VIII On the X chromosome, there are 54 disease genes known to date, To reactivate a specific gene for therapeutic purposes, it was reasoned that one could target a nearby strong or moderate site, or both. Relevant strong sites may reside several megabases away. Because there is one strong site for every 10 coding genes on average and there are 20-30 moderate sites on average in this interval, PRC2-associated lncRNAs were identified within strong and moderate sites in a +/−100 kb window from the TSS of the disease gene of interest. The following was done: first all EZH2 sites within +/−100 kb of the transcription start site (TSS) of a disease gene were identified. EZH2 segments that intersect the +/−100-kb window by ≥1 bp were included. This list of EZH2 segments was then intersected with the list of assembled "X-linked lncRNA" (identified by RNA-seq and TopHat/Cufflinks assembly, per above) to obtain Table VI. A total of 47 such lncRNAs were identified (See Table VI). There are 125 entries for these 47 distinct lncRNAs due to the fact that a single lncRNA can overlap multiple EZH2 sites.

TABLE VI

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information. "SIN" refers to the SEQ ID NO:. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2 hg19 start" and ezh2 hg19 stop". The nearest disease gene of interest corresponding to these PRC2-associated lncRNAs is shown in the last column ("disease gene").

| Start | Stop | Str | SIN: | Transcript_ID | Ezh2_ID | Ezh2_start | Ezh2_stop | Ezh2 type | h Chr | hg19_Start | hg19_Stop | hg19-str | SIN: | ezh2_hg19_start | ezh2_hg19_stop | Disease gene |
|---|---|---|---|---|---|---|---|---|---|---|---|---|---|---|---|---|
| 6948402 | 6952952 | − | 1 | ENSMUST00000134976 | seg_67 | 6952250 | 6954400 | M | chrX | 49644159 | 49648485 | + | 157 | 49642649 | 49644648 | CLCN5 |
| 6953051 | 6955168 | + | 2 | ENSMUST00000128858 | seg_67 | 6952250 | 6954400 | M | chrX | 49641851 | 49644052 | − | 158 | 49642649 | 49644648 | CLCN5 |
| 7418487 | 7449418 | + | 3 | CUFF.13987.1 | seg_100 | 7418000 | 7419950 | M | chrX | 48783029 | 48815641 | − | 174 | 48814127 | 48816443 | PQBP1 |
| 7418957 | 7453752 | + | 4 | CUFF.13988.3 | seg_100 | 7418000 | 7419950 | M | chrX | 48778055 | 48815149 | − | 175 | 48814127 | 48816443 | PQBP1 |
| 7418957 | 7452410 | + | 5 | CUFF.13988.4 | seg_100 | 7418000 | 7419950 | M | chrX | 48778055 | 48815149 | − | 222 | 48814127 | 48816443 | PQBP1 |
| 7419731 | 7452410 | + | 6 | ENSMUST00000150644 | seg_100 | 7418000 | 7419950 | M | chrX | 48779489 | 48814344 | − | 189 | 48814127 | 48816443 | PQBP1 |
| 7419731 | 7452750 | + | 7 | ENSMUST00000150644 | seg_102 | 7451100 | 7452750 | M | chrX | 48779489 | 48814344 | − | 190 | 48779300 | 48780883 | PQBP1 |
| 7476440 | 7483890 | + | 8 | CUFF.13992.1 | seg_105 | 7475700 | 7477250 | M | chrX | 48750837 | 48754815 | − | 176 | 48754430 | 48755836 | PQBP1 |
| 7476463 | 7497358 | + | 9 | CUFF.13985.1 | seg_105 | 7475700 | 7477250 | M | chrX | 48693572 | 48755112 | − | 177 | 48754430 | 48755836 | PQBP1 |
| 7476463 | 7497358 | + | 10 | CUFF.13985.1 | seg_106 | 7497150 | 7506950 | M | chrX | 48693572 | 48755112 | − | 178 | 48683657 | 48693841 | PQBP1 |
| 7476501 | 7476531 | + | 11 | CUFF.13986.1 | seg_105 | 7475700 | 7477250 | M | chrX | 48755060 | 48755074 | + | 179 | 48754430 | 48755836 | PQBP1 |
| 7476797 | 7483890 | + | 12 | CUFF.13992.3 | seg_105 | 7475700 | 7477250 | M | chrX | 48750837 | 48754815 | − | 183 | 48754430 | 48755836 | PQBP1 |
| 7527282 | 7527994 | − | 13 | ENSMUST00000117520 | seg_108 | 7526550 | 7528550 | M | other | 0 | 0 | + |  | 0 | 0 | OA1 = GPR143 |
| 7624355 | 7624525 | + | 14 | ENSMUST00000119726 | seg_114 | 7623400 | 7624800 | M | other | 0 | 0 | + |  | 0 | 0 | OA1 = GPR143 |
| 7624355 | 7624525 | + | 15 | ENSMUST00000119726 | seg_114 | 7623400 | 7624800 | M | other | 0 | 0 | + |  | 0 | 0 | OA1 = GPR143 |
| 7682420 | 7683239 | + | 16 | ENSMUST00000118546 | seg_117 | 7681350 | 7682450 | M | other | 0 | 0 | + |  | 0 | 0 | OA1 = GPR143 |
| 7682420 | 7683239 | + | 17 | ENSMUST00000118546 | seg_117 | 7681350 | 7682450 | M | other | 0 | 0 | + |  | 0 | 0 | OA1 = GPR143 |
| 7706844 | 7709637 | − | 18 | ENSMUST00000149257 | seg_120 | 7708050 | 7709850 | M | chrX | 48456197 | 48458240 | + | 223 | 48455984 | 48457509 | WAS |
| 7708468 | 7709984 | − | 19 | CUFF.13998.10 | seg_120 | 7708050 | 7709850 | M | chrX | 48455856 | 48457390 | + | 200 | 48455984 | 48457509 | WAS |
| 7731609 | 7753084 | − | 20 | ENSMUST00000133093 | seg_123 | 7752200 | 7753550 | M | chrX | 48398062 | 48419602 | + | 224 | 48397692 | 48398968 | WAS |
| 7731609 | 7753084 | − | 21 | ENSMUST100000133093 | seg_123 | 7752200 | 7753550 | M | chrX | 48398062 | 48419602 | + | 225 | 48397692 | 48398968 | WAS |
| 7731617 | 7753017 | − | 22 | ENSMUST00000143984 | seg_123 | 7752200 | 7753550 | M | chrX | 48398130 | 48419594 | + | 226 | 48397692 | 48398968 | WAS |
| 8903530 | 8904209 | − | 23 | CUFF.14023.1 | seg_142 | 8902450 | 8904350 | M | other | 0 | 0 | + |  | 0 | 0 | OA1 = GPR143 |
| 8904262 | 8904575 | − | 24 | CUFF.14022.1 | seg_142 | 8902450 | 8904350 | M | other | 0 | 0 | + |  | 0 | 0 | OA1 = GPR143 |

TABLE VI-continued

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information; "SIN" refers to the SEQ ID NO. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2 hg19 start" and ezh2 hg19 stop". The nearest disease gene of interest corresponding to these PRC2-associated lncRNAs is shown in the last column ("disease gene").

| Start | Stop | Str | SIN: | Transcript ID | Ezh2_ID | Ezh2_start | Ezh2_stop | Ezh2 type | h Chr | hg19_Start | hg19_Stop | hg19-str | SIN: | ezh2_hg19_start | ezh2_hg19_stop | Disease gene |
|---|---|---|---|---|---|---|---|---|---|---|---|---|---|---|---|---|
| 20194399 | 20225033 | + | 25 | CUFF.14074.1 | seg_17 | 20194000 | 20195500 | S | chrX | 47004091 | 47041189 | + | 137 | 47003630 | 47005197 | UBA1 |
| 20194399 | 20225033 | + | 26 | CUFF.14074.1 | seg_391 | 20193650 | 20196400 | M | chrX | 47004091 | 47041189 | + | 138 | 47003141 | 47006163 | UBA1 |
| 20194629 | 20228027 | + | 27 | CUFF.14095.1 | seg_17 | 20194000 | 20195500 | S | chrX | 47004307 | 47046225 | + | 196 | 47003630 | 47005197 | UBA1 |
| 20194629 | 20228027 | + | 28 | CUFF.14095.1 | seg_391 | 20193650 | 20196400 | M | chrX | 47004307 | 47046225 | + | 197 | 47003141 | 47006163 | UBA1 |
| 20194911 | 20226322 | + | 29 | ENSMUST00000141128 | seg_17 | 20194000 | 20195500 | S | chrX | 47004623 | 47044506 | + | 207 | 47003630 | 47005197 | UBA1 |
| 20194911 | 20226322 | + | 30 | ENSMUST00000141128 | seg_391 | 20193650 | 20196400 | M | chrX | 47004623 | 47044506 | + | 208 | 47003141 | 47006163 | UBA1 |
| 20194911 | 20226322 | + | 31 | ENSMUST00000141128 | seg_17 | 20194000 | 20195500 | S | chrX | 47004623 | 47044506 | + | 209 | 47003630 | 47005197 | UBA1 |
| 20194911 | 20226322 | + | 32 | ENSMUST00000141128 | seg_391 | 20193650 | 20196400 | M | chrX | 47004623 | 47044506 | + | 210 | 47003141 | 47006163 | UBA1 |
| 20281032 | 20294944 | + | 33 | CUFF.14075.2 | seg_394 | 20294250 | 20296200 | M | chrX | 47092379 | 47103954 | + | 139 | 47103171 | 47106480 | UBA1 |
| 45162547 | 45245729 | − | 34 | CUFF.14233.3 | seg_768 | 45243800 | 45248200 | M | chrX | 128580480 | 128657501 | − | 198 | 128655532 | 128659505 | OCRL |
| 45227508 | 45245609 | − | 35 | ENSMUST00000141084 | seg_768 | 45243800 | 45248200 | M | chrX | 128638885 | 128657382 | − | 211 | 128655532 | 128659505 | OCRL |
| 45363158 | 45363341 | + | 36 | CUFF.14229.1 | seg_774 | 45362150 | 45363400 | M | other | 0 | 0 | + | | 0 | 0 | OA1 = GPR143 |
| 45363178 | 45363342 | + | 37 | CUFF.14188.1 | seg_774 | 45362150 | 45363400 | M | other | 0 | 0 | + | | 0 | 0 | OA1 = GPR143 |
| 48368108 | 48371354 | − | 38 | CUFF.14256.2 | seg_899 | 48367900 | 48369550 | M | chrX | 131348118 | 131351566 | − | 184 | 131347929 | 131349656 | NYS1 = FRMD7 |
| 48371324 | 48371616 | − | 39 | CUFF.14209.1 | seg_900 | 48371400 | 48373300 | M | chrX | 131351532 | 131351823 | − | 140 | 131351609 | 131353535 | NYS1 = FRMD7 |
| 48371476 | 48371850 | − | 40 | CUFF.14210.1 | seg_900 | 48371400 | 48373300 | M | chrX | 131351714 | 131352061 | + | 141 | 131351609 | 131353535 | NYS1 = FRMD7 |
| 50341229 | 50374836 | + | 41 | CUFF.14271.1 | seg_1003 | 50340900 | 50342400 | M | chrX | 133594153 | 133634696 | + | 142 | 133593796 | 133595251 | HPRT1 = HPRT |
| 50341250 | 50341769 | + | 42 | CUFF.14224.1 | seg_1003 | 50340900 | 50342400 | M | chrX | 133594174 | 133594686 | + | 143 | 133593796 | 133595251 | HPRT1 = HPRT |
| 50407432 | 50407526 | − | 43 | ENSMUST00000083484 | seg_1004 | 50407500 | 50413850 | M | chrX | 133680658 | 133680753 | − | 144 | 133680727 | 133686885 | HPRT1 = HPRT |
| 50408223 | 50410367 | − | 44 | ENSMUST00000155622 | seg_1004 | 50407500 | 50413850 | M | chrX | 133681640 | 133683674 | − | 145 | 133680727 | 133686885 | HPRT1 = HPRT |
| 50408223 | 50410367 | − | 45 | ENSMUST00000155622 | seg_37 | 50410150 | 50413500 | S | chrX | 133681640 | 133683674 | − | 146 | 133683549 | 133686542 | HPRT1 = HPRT |
| 50408947 | 50410413 | − | 46 | CUFF.14272.4 | seg_1004 | 50407500 | 50413850 | M | chrX | 133682420 | 133683720 | − | 147 | 133680727 | 133686885 | HPRT1 = HPRT |

TABLE VI-continued

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information; "SIN" refers to the SEQ ID NO. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2 hg19 start" and ezh2 hg19 stop". The nearest disease gene of interest corresponding to these PRC2-associated lncRNAs is shown in the last column ("disease gene").

| Start | Stop | Str | SIN: | Transcript ID | Ezh2 ID | Ezh2_start | Ezh2_stop | Ezh2 type | h Chr | hg19_Start | hg19_Stop | hg19-str | SIN: | ezh2_hg19_start | ezh2_hg19_stop | Disease gene |
|---|---|---|---|---|---|---|---|---|---|---|---|---|---|---|---|---|
| 50408947 | 50410413 | − | 47 | CUFF.14272.4 | seg_37 | 50410150 | 50413500 | S | chrX | 133682420 | 133683720 | − | 148 | 133683549 | 133686542 | HPRT1 = HPRT |
| 50409370 | 50410367 | − | 48 | ENSMUST00000151099 | seg_1004 | 50407500 | 50413850 | M | chrX | 133682808 | 133683674 | − | 149 | 133680727 | 133686885 | HPRT1 = HPRT |
| 50409370 | 50410367 | − | 49 | ENSMUST00000151099 | seg_37 | 50410150 | 50413500 | S | chrX | 133682808 | 133683674 | − | 150 | 133683549 | 133686542 | HPRT1 = HPRT |
| 50409370 | 50410367 | − | 50 | ENSMUST00000151099 | seg_1004 | 50407500 | 50413850 | M | chrX | 133682808 | 133683674 | − | 151 | 133680727 | 133686885 | HPRT1 = HPRT |
| 50409370 | 50410367 | − | 51 | ENSMUST00000151099 | seg_37 | 50410150 | 50413500 | S | chrX | 133682808 | 133683674 | − | 152 | 133583549 | 133686547 | HPRT1 = HPRT |
| 65920689 | 65931574 | + | 52 | ENSMUST00000101520 | seg_1309 | 65930300 | 65933100 | M | chrX | 146974056 | 146993242 | + | 153 | 146992254 | 146994838 | FMR1 |
| 65931716 | 65951510 | + | 53 | CUFF.14287.2 | seg_1309 | 65930300 | 65933100 | M | chrX | 146993398 | 147012157 | + | 154 | 146992254 | 146994838 | FMR1 |
| 65931716 | 65970681 | + | 54 | CUFF.14287.3 | seg_1309 | 65930300 | 65933100 | M | chrX | 146993398 | 147032195 | + | 155 | 146992254 | 146994838 | FMR1 |
| 65931716 | 65970681 | + | 55 | CUFF.14352.1 | seg_1309 | 65930300 | 65933100 | M | chrX | 146993398 | 147032195 | + | 156 | 146992254 | 146994838 | FMR1 |
| 65932068 | 65932563 | + | 56 | CUFF.14288.1 | seg_1309 | 65930300 | 65933100 | M | chrX | 146993774 | 146994298 | + | 212 | 146992254 | 146994838 | FMR1 |
| 65932227 | 65932774 | + | 57 | CUFF.14353.1 | seg_1309 | 65930300 | 65933100 | M | chrX | 146993961 | 146994506 | + | 213 | 146992254 | 146994838 | FMR1 |
| 70884707 | 70887453 | + | 58 | CUFF.14399.1 | seg_1504 | 70880300 | 70886600 | M | chrX | 152912601 | 152915465 | + | 159 | 152907256 | 152914605 | ABCD1 |
| 70884707 | 70887453 | + | 59 | CUFF.14399.1 | seg_56 | 70884700 | 70886100 | S | chrX | 152912601 | 152915465 | + | 160 | 152912593 | 152913737 | ABCD1 |
| 70918489 | 70919425 | + | 60 | CUFF.14406.3 | seg_1507 | 70919050 | 70921750 | M | chrX | 152953368 | 152954327 | + | 161 | 152953952 | 152956569 | ABCD1 |
| 71038698 | 71070106 | − | 61 | CUFF.14350.4 | seg_1515 | 71069800 | 71072250 | M | chrX | 153067624 | 153096149 | − | 162 | 153095872 | 153098097 | L1CAM |
| 71167461 | 71171740 | + | 62 | ENSMUST00000135213 | seg_1524 | 71165700 | 71168200 | M | chrX | 153198707 | 153205716 | + | 214 | 153201262 | 153205716 | AVPR2 |
| 71188131 | 71212039 | − | 63 | CUFF.14346.3 | seg_1526 | 71210350 | 71212250 | M | chrX | 153213005 | 153236998 | − | 188 | 153235226 | 153237200 | AVPR2 |
| 71209543 | 71210383 | − | 64 | CUFF.14432.1 | seg_1526 | 71210350 | 71212250 | M | chrX | 153234378 | 153235269 | − | 215 | 153235226 | 153237200 | AVPR2 |
| 71212129 | 71212322 | + | 65 | CUFF.14347.1 | seg_1526 | 71210350 | 71212250 | M | chrX | 153237078 | 153237272 | + | 163 | 153235226 | 153237200 | AVPR2 |
| 71252041 | 71252841 | + | 66 | ENSMUST00000120692 | seg_1528 | 71251100 | 71253700 | M | other | 0 | 0 | + | 0 | 0 | 0 | OA1 = GPR143 |
| 71252041 | 71252841 | + | 67 | ENSMUST00000120692 | seg_1528 | 71251100 | 71253700 | M | other | 0 | 0 | + | 0 | 0 | 0 | OA1 = GPR143 |
| 71491032 | 71491211 | − | 63 | CUFF.14417.1 | seg_1536 | 71489000 | 71492050 | M | chrX | 153598856 | 153599051 | − | 216 | 153599880 | 153599880 | EMD |
| 71491144 | 71491278 | + | 69 | CUFF.14563.1 | seg_1536 | 71489000 | 71492050 | M | chrX | 153598983 | 153599133 | + | 217 | 153599880 | 153599880 | EMD |
| 71500026 | 71500436 | + | 70 | CUFF.14439.2 | seg_1537 | 71499550 | 71501250 | M | chrX | 153607566 | 153607980 | + | 164 | 153606662 | 153608766 | EMD |
| 71500100 | 71501024 | + | 71 | ENSMUST00000129516 | seg_1537 | 71499550 | 71501250 | M | chrX | 153607643 | 153608527 | + | 218 | 153606662 | 153608766 | EMD |
| 71527251 | 71528204 | + | 72 | ENSMUST00000146260 | seg_1538 | 71525800 | 71528950 | M | chrX | 153637932 | 153640001 | + | 165 | 153636852 | 153640773 | EMD |
| 71527251 | 71528254 | + | 73 | ENSMUST00000135012 | seg_1538 | 71525800 | 71528950 | M | chrX | 153637932 | 153640082 | + | 166 | 153636852 | 153640773 | EMD |

TABLE VI-continued

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information; "SIN" refers to the SEQ ID NO:. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2 hg19 start" and ezh2 hg19 stop". The nearest disease gene of interest corresponding to these PRC2-associated lncRNAs is shown in the last column ("disease gene").

| Start | Stop | Str | SIN: | Transcript ID | Ezh2 ID | Ezh2_start | Ezh2_stop | Ezh2 type | h Chr | hg19_Start | hg19_Stop | hg19 str | SIN: | ezh2_hg19_start | ezh2_hg19_stop | Disease gene |
|---|---|---|---|---|---|---|---|---|---|---|---|---|---|---|---|---|
| 71527980 | 71535490 | + | 74 | CUFF.14421.3 | seg_1538 | 71525800 | 71528950 | M | chrX | 153639773 | 153650067 | + | 167 | 153636852 | 153640773 | EMD |
| 71528089 | 71533374 | + | 75 | ENSMUST00000156880 | seg_1538 | 71525800 | 71528950 | M | chrX | 153639886 | 153647898 | + | 219 | 153636852 | 153640773 | EMD |
| 71528089 | 71535487 | + | 76 | ENSMUST00000124200 | seg_1538 | 71525800 | 71528950 | M | chrX | 153639886 | 153650064 | + | 220 | 153636852 | 153640773 | EMD |
| 71528090 | 71535488 | + | 77 | ENSMUST00000114182 | seg_1538 | 71525800 | 71528950 | M | chrX | 153639887 | 153650065 | + | 221 | 153636852 | 153640773 | EMD |
| 71550319 | 71553622 | + | 78 | CUFF.14360.1 | seg_1540 | 71549400 | 71551350 | M | chrX | 153665202 | 153668876 | + | 168 | 153664294 | 153666201 | EMD |
| 71550319 | 71557201 | + | 79 | CUFF.14360.2 | seg_1540 | 71549400 | 71551350 | M | chrX | 153665202 | 153671813 | + | 169 | 153664294 | 153666201 | EMD |
| 71550337 | 71553623 | + | 80 | CUFF.14449.2 | seg_1540 | 71549400 | 71551350 | M | chrX | 153665244 | 153668877 | + | 170 | 153664294 | 153666201 | EMD |
| 71574384 | 71597045 | + | 81 | CUFF.14364.2 | seg_1542 | 71572900 | 71574500 | M | chrX | 153686599 | 153702184 | + | 172 | 153686144 | 153686719 | IKBKG |
| 71574384 | 71590028 | + | 82 | CUFF.14364.1 | seg_1542 | 71572900 | 71574500 | M | chrX | 153686599 | 153702184 | + | 171 | 153686144 | 153686710 | IKBKG |
| 71574404 | 71588866 | + | 83 | CUFF.14453.2 | seg_1542 | 71572900 | 71574500 | M | chrX | 153686620 | 153701013 | + | 173 | 153686144 | 153686719 | IKBKG |
| 71598672 | 71598963 | − | 84 | CUFF.14450.4 | seg_1543 | 71597350 | 71599550 | M | chrX | 153707075 | 153707335 | − | 186 | 153706026 | 153707374 | IKBKG |
| 71598672 | 71598963 | + | 85 | CUFF.14450.4 | seg_58 | 71597850 | 71598950 | S | chrX | 153707075 | 153707335 | − | 187 | 153706412 | 153707323 | IKBKG |
| 71675010 | 71699193 | + | 86 | CUFF.14372.14 | seg_1547 | 71673000 | 71675050 | M | chrX | 153775825 | 153799420 | + | 199 | 153773591 | 153775852 | G6PD = G6PDX |
| 72388763 | 72388969 | + | 87 | ENSMUST00000121894 | seg_1564 | 72385650 | 72389350 | M | other | 0 | 0 | + | | 0 | 0 | OA1 = GPR143 |
| 72388763 | 72388969 | + | 88 | ENSMUST00000121894 | seg_1564 | 72385650 | 72389350 | M | other | 0 | 0 | + | | 0 | 0 | OA1 = GPR143 |
| 72389027 | 72389809 | + | 89 | ENSMUST00000116535 | seg_1564 | 72385650 | 72389350 | M | other | 0 | 0 | + | | 0 | 0 | OA1 = GPR143 |
| 72389027 | 72389809 | + | 90 | ENSMUST00000116535 | seg_1564 | 72385650 | 72389350 | M | other | 0 | 0 | + | | 0 | 0 | OA1 = GPR143 |
| 101531844 | 101543844 | − | 91 | CUFF.14676.1 | seg_2367 | 101528100 | 101532450 | M | other | 0 | 0 | + | | 0 | 0 | OA1 = GPR143 |
| 101531844 | 101543844 | − | 92 | CUFF.14676.1 | seg_2368 | 101541300 | 101544300 | M | other | 0 | 0 | + | | 0 | 0 | OA1 = GPR143 |
| 101541168 | 101543573 | − | 93 | ENSMUST00000120233 | seg_2368 | 101541300 | 101544300 | M | other | 0 | 0 | + | | 0 | 0 | OA1 = GPR143 |
| 103106842 | 103124685 | − | 94 | ENSMUST00000126345 | seg_2443 | 103106750 | 103108550 | M | chrX | 76995795 | 77041698 | − | 191 | 76995713 | 77031704 | ATRX |
| 131120171 | 131120713 | + | 95 | CUFF.14771.1 | seg_2832 | 131119150 | 131121200 | M | chrX | 100645947 | 100646543 | + | 126 | 100644952 | 100646916 | BTK |
| 131120229 | 131122601 | + | 96 | ENSMUST00000170828 | seg_2832 | 131119150 | 131121200 | M | chrX | 100646005 | 100650827 | + | 192 | 100644952 | 100646916 | BTK |
| 131216059 | 131216416 | + | 97 | ENSMUST00000117957 | seg_2837 | 131214300 | 131216200 | M | other | 0 | 0 | + | | 0 | 0 | OA1 = GPR143 |

TABLE VI-continued

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information; "SIN" refers to the SEQ ID NO. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2 hg19 start" and ezh2 hg19 stop". The nearest disease gene of interest corresponding to these PRC2-associated lncRNAs is shown in the last column ("disease gene").

| Start | Stop | Str | SIN: | Transcript ID | Ezh2_ID | Ezh2_start | Ezh2_stop | Ezh2 type | h Chr | hg19_Start | hg19_Stop | hg19-str | SIN: | ezh2_hg19_start | ezh2_hg19_stop | Disease gene |
|---|---|---|---|---|---|---|---|---|---|---|---|---|---|---|---|---|
| 131216059 | 131216416 | + | 98 | ENSMUST00000117957 | seg_2837 | 131214300 | 131216200 | M | other | 0 | 0 | + | 201 | 0 | 0 | OA1 = GPR143 |
| 131223346 | 131231296 | + | 99 | CUFF.14776.2 | seg_2838 | 131220750 | 131223850 | M | chrX | 100742982 | 100750790 | + | 127 | 100740062 | 100743543 | GLA |
| 136991152 | 136999981 | + | 100 | ENSMUST00000155235 | seg_3081 | 136989950 | 136993450 | M | chrX | 106871733 | 106882715 | + | 128 | 106870757 | 106873713 | PRPS1 |
| 136991152 | 136999981 | + | 101 | ENSMUST00000155235 | seg_3081 | 136989950 | 136993450 | M | chrX | 106871733 | 106882715 | + | 129 | 106870757 | 106873713 | PRPS1 |
| 137074067 | 137077207 | − | 102 | ENSMUST00000112995 | seg_3088 | 137074650 | 137078000 | M | chrX | 106956451 | 106959745 | − | 185 | 106955989 | 106960573 | PRPS1 |
| 137077642 | 137083068 | − | 103 | ENSMUST00000152048 | seg_3088 | 137074650 | 137078000 | M | chrX | 106960212 | 106965429 | − | | 106956989 | 106960573 | PRPS1 |
| 138062502 | 138063011 | + | 104 | ENSMUST00000118845 | seg_3158 | 138061650 | 138063400 | M | other | 0 | 0 | + | | 0 | 0 | OA1 = GPR143 |
| 147079847 | 147091979 | − | 105 | CUFF.14799.4 | seg_3402 | 147079250 | 147080800 | M | chrX | 54947223 | 54957868 | + | 182 | 54957123 | 54958355 | ALAS2 |
| 147417684 | 147442281 | − | 106 | CUFF.14800.3 | seg_3419 | 147442200 | 147443900 | M | chrX | 54561410 | 54591707 | + | 130 | 54560615 | 54561460 | FGD1 |
| 147481431 | 147502847 | + | 107 | CUFF.14802.3 | seg_3422 | 147478700 | 147483450 | M | chrX | 54475005 | 54522668 | − | 202 | 54520506 | 54525870 | FGD1 |
| 147481431 | 147521724 | + | 108 | CUFF.14907.2 | seg_3422 | 147478700 | 147483450 | M | chrX | 54475005 | 54522668 | − | 203 | 54520506 | 54525870 | FGD1 |
| 147481431 | 147521724 | + | 109 | CUFF.14802.2 | seg_3422 | 147478700 | 147483450 | M | chrX | 54475005 | 54522668 | − | 204 | 54520506 | 54525870 | FGD1 |
| 148089731 | 148090645 | + | 110 | ENSMUST00000121650 | seg_3440 | 148088650 | 148090350 | M | other | 0 | 0 | + | | 0 | 0 | OA1 = GPR143 |
| 148089731 | 148090645 | + | 111 | ENSMUST00000121650 | seg_3440 | 148088650 | 148090350 | M | other | 0 | 0 | + | | 0 | 0 | OA1 = GPR143 |
| 148578768 | 148639178 | + | 112 | CUFF.14816.1 | seg_119 | 148578700 | 148580800 | S | chrX | 53283545 | 53350548 | − | 131 | 53348417 | 53350616 | MRX1 = QSEC2 |
| 148578768 | 148639178 | + | 113 | CUFF.14816.1 | seg_3460 | 148578400 | 148581050 | M | chrX | 53283545 | 53350548 | − | 132 | 53348024 | 53350934 | MRX1 = QSEC2 |
| 149044052 | 149204222 | − | 114 | CUFF.14826.2 | seg_3484 | 149203250 | 149205000 | M | chrX | 9754409 | 9917528 | + | 193 | 9753597 | 9755295 | OA1 = GPR143 |
| 149057511 | 149204219 | − | 115 | CUFF.14936.7 | seg_3484 | 149203250 | 149205000 | M | chrX | 9754412 | 9901148 | + | 194 | 9753597 | 9755295 | OA1 = GPR143 |
| 151696962 | 151731456 | + | 116 | CUFF.14845.1 | seg_3550 | 151696250 | 151698050 | M | chrX | 23722764 | 23761432 | − | 133 | 23760757 | 23761726 | SAT = SAT1 |

TABLE VI-continued

LncRNAs associated with strong and moderate EZH2 sites

Table VI presents a total of 47 distinct lncRNAs with XCI-associated PRC2 sites located within +/−100 kb of a disease gene of interest. The "start" and "stop" columns show the Start and stop base numbers (coordinates) on the mm9 ChrX; STR, strand (+/−) information; "SIN" refers to the SEQ ID NO:. The predicted transcript is named under "Transcript ID" using ENSEMBL nomenclature when the transcript is a previously annotated RNA. In the case of novel lncRNAs, the transcript is identified as "CUFF.X" where X is a newly assigned numerical. "Ezh2 ID" refers to the PRC2 segment shown in Table IVA or B (a strong or moderate site, as designated in column I as "Ezh2 type"). The "start" and "stop" coordinates of the Ezh2 site are also indicated (Ezh2 start and Ezh2 stop). Human LiftOver chromosome and start and stop coordinates for the predicted corresponding human lncRNAs are shown in the columns "h Chr", "hg19 start" and "hg19 stop" with strand information (+/−); numbers correspond to human genome build 19. Predicted human EZH2 sites are shown in columns "ezh2_hg19_start" and ezh2_hg19 stop". The nearest disease gene of interest corresponding to these PRC2-associated lncRNAs is shown in the last column ("disease gene").

| Start | Stop | Str | SIN: | Transcript ID | Ezh2_ID | Ezh2_start | Ezh2_stop | Ezh2 type | h Chr | hg19_Start | hg19_Stop | hg19-str | SIN: | ezh2_hg19_start | ezh2_hg19_stop | Disease gene |
|---|---|---|---|---|---|---|---|---|---|---|---|---|---|---|---|---|
| 151696978 | 151697427 | + | 117 | CUFF.14962.1 | seg_3550 | 151696250 | 151698050 | M | chrX | 23761017 | 23761415 | − | 134 | 23760757 | 23761726 | SAT = SAT1 |
| 151696986 | 151698125 | + | 118 | ENSMUST00000134662 | seg_3550 | 151696250 | 151698050 | M | chrX | 23760757 | 23761407 | − | 135 | 23760757 | 23761726 | SAT = SAT1 |
| 151738742 | 151740292 | − | 119 | ENSMUST00000144428 | seg_3551 | 151740100 | 151741400 | M | other | 0 | 0 | + | | 0 | 0 | OA1 = GPR143 |
| 153915277 | 153915525 | − | 120 | CUFF.14971.1 | seg_3603 | 153914450 | 153916200 | M | chrX | 21971056 | 21975269 | + | 205 | 21974127 | 21976977 | PHEX |
| 157027663 | 157036207 | + | 121 | CUFF.15003.1 | seg_3707 | 157034600 | 157036250 | M | chrX | 18907129 | 18912800 | − | 181 | 18906778 | 18908445 | PHKA2 |
| 157241673 | 157241983 | − | 122 | CUFF.15005.1 | seg_3718 | 157241500 | 157242700 | M | chrX | 18651084 | 18651384 | + | 206 | 18650361 | 18651566 | RS1 |
| 157246270 | 157432634 | − | 123 | CUFF.15001.3 | seg_3729 | 157431550 | 157434400 | M | chrX | 18443703 | 18646844 | + | 180 | 18441881 | 18444750 | CDKL5 |
| 162827965 | 162878637 | − | 124 | CUFF.15054.2 | seg_3948 | 162877500 | 162879500 | M | chrX | 13752890 | 13788174 | + | 195 | 13750751 | 13753578 | OFD1 |
| 162948132 | 162948265 | + | 125 | CUFF.14908.1 | seg_3951 | 162946950 | 162949350 | M | chrX | 13671391 | 13671542 | − | 136 | 13670689 | 13672284 | SEDL = TRAPPC2 |

If the stringency were relaxed beyond +/−100 kb, a total of 230 distinct lncRNAs with XCI-associated PRC2 sites was observed; these are set forth in Table VII. There are 640 entries for these 230 distinct lncRNAs in Table VII, also due to the fact that a single lncRNA can overlap multiple EZH2 sites. A strong or moderate site located >100 kb away from a gene of interest may be involved in repressing the gene at long range. The present data suggests that a single strong EZH2 site (for example) could control genes over a 1-2 Mb domain,

TABLE VII

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 5976972 | 6214566 | + | CUFF.13967.2 | seg_25 | 5976300 | 5978850 | M | chrX | 50336327 | 50557310 | − | 124335918 | 124340213 | CLCN5 |
| 5977553 | 5977692 | + | CUFF.13962.1 | seg_25 | 5976300 | 5978850 | M | chrX | 50556592 | 50556724 | − | 124335918 | 124340213 | CLCN5 |
| 6356106 | 6474704 | + | CUFF.13966.1 | seg_1 | 6355950 | 6357900 | S | chrX | 50143999 | 50213570 | + | 50211825 | 50213570 | CLCN5 |
| 6356106 | 6474704 | + | CUFF.13966.1 | seg_33 | 6353350 | 6359000 | M | chrX | 50143999 | 50213570 | + | 50210632 | 50215941 | CLCN5 |
| 6948402 | 6952952 | − | ENSMUST00000134976 | seg_67 | 6952250 | 6954400 | M | chrX | 49644851 | 49648485 | + | 49642649 | 49644648 | CLCN5 |
| 6953051 | 6955168 | + | ENSMUST00000128858 | seg_67 | 6952250 | 6954400 | M | chrX | 49641851 | 49644052 | + | 49642649 | 49644648 | CLCN5 |
| 7134422 | 7154618 | − | CUFF.13970.2 | seg_82 | 7132850 | 7137250 | M | chrX | 49123140 | 49146158 | + | 49143046 | 49147196 | PQBP1 |
| 7215764 | 7224495 | + | ENSMUST00000149795 | seg_86 | 7224100 | 7226000 | M | chrX | 49049104 | 49056698 | − | 49143046 | 49147196 | PQBP1 |
| 7329256 | 7329540 | + | ENSMUST00000121084 | seg_92 | 7328650 | 7330300 | M | chrX | 114953264 | 114953549 | − | 73832957 | 73834636 | COL4A5 |
| 7329256 | 7329540 | + | ENSMUST00000121084 | seg_92 | 7328650 | 7330300 | M | chrX | 114953264 | 114953549 | − | 0 | 0 | COL4A5 |
| 7367144 | 7397082 | − | ENSMUST00000132456 | seg_95 | 7365650 | 7367450 | M | chrX | 48830738 | 48858649 | − | 95939522 | 95940514 | PQBP1 |
| 7367144 | 7397082 | − | ENSMUST00000132456 | seg_95 | 7365650 | 7367450 | M | chrX | 48830738 | 48858649 | − | 95939522 | 95940514 | PQBP1 |
| 7418487 | 7449418 | + | CUFF.13987.1 | seg_100 | 7418000 | 7419950 | M | chrX | 48783029 | 48815641 | − | 48814127 | 48816443 | PQBP1 |
| 7418957 | 7453752 | + | CUFF.13988.3 | seg_100 | 7418000 | 7419950 | M | chrX | 48778055 | 48815149 | − | 48814127 | 48816443 | PQBP1 |
| 7418957 | 7453752 | + | CUFF.13988.4 | seg_100 | 7418000 | 7419950 | M | chrX | 48778055 | 48815149 | − | 48814127 | 48816443 | PQBP1 |
| 7419731 | 7452410 | + | ENSMUST00000150644 | seg_100 | 7418000 | 7419950 | M | chrX | 48779489 | 48814344 | − | 48814127 | 48816443 | PQBP1 |
| 7419731 | 7452410 | + | ENSMUST00000150644 | seg_102 | 7451100 | 7452750 | M | chrX | 48779489 | 48814344 | − | 48779300 | 48780883 | PQBP1 |
| 7476440 | 7483890 | + | CUFF.13992.1 | seg_105 | 7475700 | 7477250 | M | chrX | 48750837 | 48754815 | − | 48754430 | 48755836 | PQBP1 |
| 7476463 | 7497358 | + | CUFF.13985.1 | seg_105 | 7475700 | 7477250 | M | chrX | 48693572 | 48755112 | − | 48754430 | 48755836 | PQBP1 |
| 7476463 | 7497358 | + | CUFF.13985.1 | seg_106 | 7497150 | 7506950 | M | chrX | 48693572 | 48755112 | − | 48683657 | 48693841 | PQBP1 |
| 7476501 | 7476531 | + | CUFF.13986.1 | seg_105 | 7475700 | 7477250 | M | chrX | 48755060 | 48755074 | − | 48754430 | 48755836 | PQBP1 |
| 7476797 | 7483890 | + | CUFF.13992.3 | seg_105 | 7475700 | 7477250 | M | chrX | 48750837 | 48754815 | + | 48754430 | 48755836 | PQBP1 |
| 7527282 | 7527994 | − | ENSMUST00000117520 | seg_108 | 7526550 | 7528550 | M | other | 0 | 0 | + | 106690970 | 106694548 | OA1 = GPR143 |
| 7624355 | 7624525 | + | ENSMUST00000119726 | seg_114 | 7623400 | 7624800 | M | other | 0 | 0 | + | 0 | 0 | OA1 = GPR143 |
| 7624355 | 7624525 | + | ENSMUST00000119726 | seg_114 | 7623400 | 7624800 | M | other | 0 | 0 | + | 0 | 0 | OA1 = GPR143 |
| 7682420 | 7683239 | + | ENSMUST00000118546 | seg_117 | 7681350 | 7682450 | M | other | 0 | 0 | + | 111324058 | 111328035 | OA1 = GPR143 |
| 7682420 | 7683239 | + | ENSMUST00000118546 | seg_117 | 7681350 | 7682450 | M | other | 0 | 0 | + | 111324058 | 111328035 | OA1 = GPR143 |
| 7706844 | 7709637 | + | ENSMUST00000149257 | seg_120 | 7708050 | 7709850 | M | chrX | 43456197 | 48458240 | + | 48455984 | 48457509 | WAS |
| 7708468 | 7709984 | + | CUFF.13998.10 | seg_120 | 7708050 | 7709850 | M | chrX | 48455856 | 48457390 | + | 48455984 | 48457509 | WAS |
| 7731609 | 7753084 | + | ENSMUST00000133093 | seg_123 | 7752200 | 7753550 | M | chrX | 48398062 | 48419602 | + | 48397692 | 48398968 | WAS |
| 7731609 | 7753084 | + | ENSMUST00000133093 | seg_123 | 7752200 | 7753550 | M | chrX | 48398062 | 48419602 | + | 48397692 | 48398968 | WAS |
| 7731617 | 7753017 | − | ENSMUST00000143984 | seg_123 | 7752200 | 7753550 | M | chrX | 48398130 | 48419594 | + | 48397692 | 48398968 | WAS |
| 7767001 | 7770024 | + | ENSMUST00000149495 | seg_124 | 7769500 | 7771450 | M | chrX | 48380199 | 48382586 | + | 48382586 | 23354524 | WAS |
| 7767001 | 7770024 | + | ENSMUST00000149495 | seg_124 | 7769500 | 7771450 | M | chrX | 48380199 | 48382586 | + | 48382586 | 23354524 | WAS |
| 7770971 | 7783651 | − | CUFF.14005.1 | seg_124 | 7769500 | 7771450 | M | chrX | 48367347 | 48371257 | + | 23349576 | 23354524 | WAS |
| 7770971 | 7783651 | − | CUFF.14005.1 | seg_125 | 7782550 | 7784550 | M | chrX | 48367347 | 48371257 | + | 48365856 | 48368481 | WAS |
| 7770974 | 7787507 | − | CUFF.13999.1 | seg_124 | 7769500 | 7771450 | M | chrX | 48363330 | 48379198 | + | 48363330 | 48364503 | WAS |
| 7770974 | 7787507 | − | CUFF.13999.1 | seg_126 | 7786050 | 7787900 | M | chrX | 48363330 | 48379198 | + | 48363330 | 48364503 | WAS |
| 7770979 | 7783623 | − | ENSMUST00000122943 | seg_124 | 7769500 | 7771450 | M | chrX | 48367374 | 48379193 | + | 23349576 | 23354524 | WAS |
| 7770979 | 7783623 | − | ENSMUST00000122943 | seg_125 | 7782550 | 7784550 | M | chrX | 48367374 | 48379193 | + | 48365856 | 48368481 | WAS |
| 7780134 | 7783651 | + | CUFF.13999.8 | seg_125 | 7782550 | 7784550 | M | chrX | 48367347 | 48371257 | + | 48365856 | 48368481 | WAS |
| 8769671 | 8792653 | + | CUFF.14016.1 | seg_139 | 8755150 | 8778300 | M | chrX | 37430765 | 37481482 | + | 37429656 | 37431928 | XK |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 8903530 | 8904209 | - | CUFF.14023.1 | seg_142 | 8902450 | 8904350 | M | other | 0 | 0 | + | 0 | 0 | OA1 = GPR143 |
| 8904262 | 8904575 | - | CUFF.14022.1 | seg_142 | 8902450 | 8904350 | M | other | 0 | 0 | + | 0 | 0 | OA1 = GPR143 |
| 9233402 | 9240129 | + | ENSMUST00000154091 | seg_145 | 9239450 | 9240700 | M | chrX | 37700168 | 37706872 | - | 37706179 | 37707339 | CYBB |
| 10062235 | 10173613 | + | CUFF.14024.1 | seg_170 | 10060250 | 10063600 | M | chrX | 38420746 | 38548056 | + | 38418377 | 38422130 | OTC |
| 10062248 | 10173731 | - | CUFF.14034.1 | seg_170 | 10060250 | 10063600 | M | chrX | 38420761 | 38548175 | - | 38418377 | 38422130 | OTC |
| 10284302 | 10295947 | - | CUFF.14026.1 | seg_176 | 10294100 | 10296950 | M | chrX | 38652969 | 38664787 | + | 38662899 | 38665833 | OTC |
| 10284302 | 10295947 | - | CUFF.14026.1 | seg_4 | 10294900 | 10296300 | S | chrX | 38652969 | 38664787 | + | 38663737 | 38665158 | OTC |
| 10292145 | 10296816 | + | CUFF.14027.3 | seg_176 | 10294100 | 10296950 | M | chrX | 38660685 | 38665692 | - | 38662899 | 38665833 | OTC |
| 10294443 | 10294862 | + | CUFF.14027.4 | seg_176 | 10294100 | 10296950 | M | chrX | 38663247 | 38663698 | - | 38662899 | 38665833 | OTC |
| 11241367 | 11241392 | - | CUFF.14028.1 | seg_222 | 11237650 | 11247250 | M | chrX | 39547664 | 39547694 | + | 39544481 | 39551310 | OTC |
| 11421805 | 11421826 | - | CUFF.14029.1 | seg_230 | 11421800 | 11423650 | M | other | 0 | 0 | - | 39719105 | 39720500 | OA1 = GPR143 |
| 11490217 | 11490415 | - | ENSMUST00000121919 | seg_233 | 11490400 | 11492200 | M | chrX | 39646386 | 39646595 | - | 39784049 | 39785370 | OTC |
| 11490217 | 11490415 | - | ENSMUST00000121919 | seg_233 | 11490400 | 11492200 | M | chrX | 39646386 | 39646595 | - | 39784049 | 39785370 | OTC |
| 11613866 | 11737559 | - | CUFF.14045.5 | seg_12 | 11727350 | 11738450 | 5 | chrX | 39910507 | 40036404 | - | 40025540 | 40037252 | OTC |
| 11613866 | 11737559 | - | CUFF.14045.5 | seg_245 | 11726100 | 11739000 | M | chrX | 39910507 | 40036404 | - | 40024407 | 40037420 | OTC |
| 11613866 | 11705532 | - | CUFF.14045.3 | seg_11 | 11699450 | 11718900 | S | chrX | 39910507 | 40005885 | - | 39999869 | 40018589 | OTC |
| 11613866 | 11705532 | - | CUFF.14045.3 | seg_243 | 11698650 | 11720400 | M | chrX | 39910507 | 40005885 | - | 39999141 | 40019359 | OTC |
| 11623972 | 11657682 | - | CUFF.14034.6 | seg_10 | 11650000 | 11672900 | S | chrX | 39921386 | 39957214 | - | 39949539 | 39972450 | OTC |
| 11623972 | 11657682 | - | CUFF.14034.6 | seg_239 | 11642000 | 11673350 | M | chrX | 39921386 | 39957214 | - | 39941129 | 39972450 | OTC |
| 11625208 | 11657693 | - | CUFF.14045.8 | seg_10 | 11650000 | 11672900 | S | chrX | 39922665 | 39957225 | - | 39949539 | 39972450 | OTC |
| 11625208 | 11657693 | - | CUFF.14045.8 | seg_239 | 11642000 | 11673350 | M | chrX | 39922665 | 39957225 | - | 39941129 | 39972450 | OTC |
| 12254777 | 12339238 | - | CUFF.14050.2 | seg_13 | 12338750 | 12340000 | S | chrX | 40511131 | 40595078 | - | 40594596 | 40595937 | CSNB1 = NYX |
| 12254777 | 12339238 | - | CUFF.14050.2 | seg_270 | 12338300 | 12340450 | M | chrX | 40511131 | 40595078 | - | 40594157 | 40596414 | CSNB1 = NYX |
| 12256875 | 12339199 | - | ENSMUST00000124053 | seg_13 | 12338750 | 12340000 | S | chrX | 40513127 | 40595044 | - | 40594596 | 40595937 | CSNB1 = NYX |
| 12256875 | 12339199 | - | ENSMUST00000124053 | seg_270 | 12338300 | 12340450 | M | chrX | 40513127 | 40595044 | - | 40594157 | 40596414 | CSNB1 = NYX |
| 12338584 | 12339240 | - | CUFF.14036.7 | seg_13 | 12338750 | 12340000 | S | chrX | 40594441 | 40595080 | - | 40594596 | 40595937 | CSNB1 = NYX |
| 12338584 | 12339240 | - | CUFF.14036.7 | seg_270 | 12338300 | 12340450 | M | chrX | 40594441 | 40595080 | - | 40594157 | 40596414 | CSNB1 = NYX |
| 12339404 | 12398618 | + | ENSMUST00000139163 | seg_13 | 12338750 | 12340000 | S | chrX | 40595245 | 40649934 | + | 40594596 | 40595937 | CSNB1 = NYX |
| 12339404 | 12398618 | + | ENSMUST00000139163 | seg_270 | 12338300 | 12340450 | M | chrX | 40595245 | 40649934 | + | 40594157 | 40596414 | CSNB1 = NYX |
| 12513998 | 12515254 | + | ENSMUST00000121924 | seg_279 | 12512850 | 12514750 | M | other | 0 | 0 | + | 0 | 0 | OA1 = GPR143 |
| 12513998 | 12515254 | + | ENSMUST00000121924 | seg_279 | 12512850 | 12514750 | M | other | 0 | 0 | + | 0 | 0 | OA1 = GPR143 |
| 12648548 | 12650070 | + | CUFF.14051.1 | seg_286 | 12648150 | 12650200 | M | chrX | 40944519 | 40945909 | + | 40944126 | 40946037 | CSNB1 = NYX |
| 12648599 | 12768156 | + | CUFF.14068.1 | seg_286 | 12648150 | 12650200 | M | chrX | 40944564 | 41100156 | + | 40944126 | 40946037 | CSNB1 = NYX |
| 12648599 | 12743898 | + | CUFF.14068.3 | seg_286 | 12648150 | 12650200 | M | chrX | 40944564 | 41089870 | + | 40944126 | 40946037 | CSNB1 = NYX |
| 12648599 | 12738071 | + | CUFF.14068.2 | seg_286 | 12648150 | 12650200 | M | chrX | 40944564 | 41082678 | + | 40944126 | 40946037 | CSNB1 = NYX |
| 12648884 | 12649225 | + | CUFF.14043.1 | seg_286 | 12648150 | 12650200 | M | chrX | 40944807 | 40945143 | + | 40944126 | 40946037 | CSNB1 = NYX |
| 12650018 | 12650277 | + | CUFF.14069.1 | seg_286 | 12648150 | 12650200 | M | chrX | 40945858 | 40946083 | + | 40944126 | 40946037 | CSNB1 = NYX |
| 12655982 | 12656311 | + | CUFF.14071.1 | seg_287 | 12656000 | 12657100 | M | chrX | 40950911 | 40950974 | + | 40950911 | 40951267 | CSNB1 = NYX |
| 13094206 | 13423886 | + | CUFF.14064.11 | seg_312 | 13422100 | 13425750 | M | chrX | 41374187 | 41782933 | - | 41781170 | 41784742 | CSNB1 = NYX |
| 13129411 | 13423893 | + | CUFF.14064.11 | seg_312 | 13422100 | 13425750 | M | chrX | 41416196 | 41782933 | - | 41781170 | 41784742 | CSNB1 = NYX |
| 13131747 | 13423893 | - | CUFF.14054.11 | seg_312 | 13422100 | 13425750 | M | chrX | 41418781 | 41782940 | - | 41781170 | 41784742 | CSNB1 = NYX |
| 13290060 | 13290192 | + | CUFF.14072.1 | seg_307 | 13289250 | 13291300 | M | other | 0 | 0 | + | 41643313 | 41645899 | OA1 = GPR143 |
| 16195694 | 16195958 | + | CUFF.14062.1 | seg_337 | 16195350 | 16197100 | M | chrX | 43514157 | 43514486 | - | 43513806 | 43515723 | NDP |
| 16196824 | 16254723 | + | CUFF.14077.1 | seg_337 | 16195350 | 16197100 | M | chrX | 43515447 | 43595516 | + | 43513806 | 43515723 | NDP |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 17135024 | 17148750 | − | ENSMUST00000127690 | seg_355 | 17147650 | 17149850 | M | chrX | 44383408 | 44401509 | − | 44400354 | 44402597 | NDP |
| 19636666 | 19674647 | + | CUFF.14085.1 | seg_16 | 19636100 | 19638650 | S | chrX | 46433208 | 46457778 | + | 46432903 | 46435184 | UBA1 |
| 19636666 | 19674647 | + | CUFF.14085.1 | seg_374 | 19635850 | 19639100 | M | chrX | 46433208 | 46457778 | + | 46432903 | 46435740 | UBA1 |
| 19636666 | 19638395 | + | CUFF.14085.2 | seg_16 | 19636100 | 19638650 | S | chrX | 46433208 | 46434914 | + | 46432903 | 46435184 | UBA1 |
| 19636666 | 19638395 | + | CUFF.14085.2 | seg_374 | 19635850 | 19639100 | M | chrX | 46433208 | 46434914 | + | 46432903 | 46435740 | UBA1 |
| 19772151 | 19868953 | − | CUFF.14069.5 | seg_379 | 19867400 | 19869550 | M | chrX | 46538672 | 46634914 | − | 46617058 | 46619162 | UBA1 |
| 20002814 | 20003061 | + | CUFF.14072.2 | seg_382 | 20001050 | 20006900 | M | chrX | 46772015 | 46772258 | + | 46770003 | 46775398 | UBA1 |
| 20003237 | 20003672 | + | CUFF.14092.1 | seg_382 | 20001050 | 20006900 | M | chrX | 46772434 | 46772864 | + | 46770003 | 46775398 | UBA1 |
| 20194399 | 20225033 | + | CUFF.14074.1 | seg_17 | 20193650 | 20195500 | S | chrX | 47004091 | 47041189 | + | 47003630 | 47005197 | UBA1 |
| 20194399 | 20225033 | + | CUFF.14074.1 | seg_391 | 20193650 | 20196400 | M | chrX | 47004091 | 47041189 | + | 47003141 | 47006163 | UBA1 |
| 20194629 | 20228027 | + | CUFF.14095.1 | seg_17 | 20193650 | 20195500 | S | chrX | 47004307 | 47046225 | + | 47003630 | 47005197 | UBA1 |
| 20194629 | 20228027 | + | CUFF.14095.1 | seg_391 | 20193650 | 20196400 | M | chrX | 47004307 | 47046225 | + | 47003141 | 47006163 | UBA1 |
| 20194911 | 20226322 | + | ENSMUST00000141128 | seg_17 | 20194000 | 20195500 | S | chrX | 47004623 | 47044506 | + | 47003630 | 47005197 | UBA1 |
| 20194911 | 20226322 | + | ENSMUST00000141128 | seg_391 | 20193650 | 20196400 | M | chrX | 47004623 | 47044506 | + | 47003141 | 47006163 | UBA1 |
| 20194911 | 20226322 | + | ENSMUST00000141128 | seg_17 | 20194000 | 20195500 | S | chrX | 47004623 | 47044506 | + | 47003630 | 47005197 | UBA1 |
| 20194911 | 20226322 | + | ENSMUST00000141128 | seg_391 | 20193650 | 20196400 | M | chrX | 47004623 | 47044506 | + | 47003141 | 47006163 | UBA1 |
| 20281032 | 20294944 | + | CUFF.14075.2 | seg_394 | 20294250 | 20296200 | M | chrX | 47092379 | 47103954 | + | 47103171 | 47106480 | UBA1 |
| 20539240 | 20563863 | + | ENSMUST00000136447 | seg_401 | 20538000 | 20539700 | M | other | 0 | 0 | + | 47517837 | 47518881 | OA1 = GPR143 |
| 20937991 | 20941748 | + | ENSMUST00000127554 | seg_413 | 20937100 | 20940950 | M | other | 0 | 0 | + | 0 | 0 | OA1 = GPR143 |
| 20938066 | 20940148 | + | ENSMUST00000132683 | seg_413 | 20937100 | 20940950 | M | other | 0 | 0 | + | 0 | 0 | OA1 = GPR143 |
| 20938066 | 20940148 | + | ENSMUST00000132683 | seg_413 | 20937100 | 20940950 | M | other | 0 | 0 | + | 0 | 0 | OA1 = GPR143 |
| 33428645 | 33616557 | + | CUFF.14157.1 | seg_461 | 33428350 | 33432700 | M | chrX | 117629607 | 117820108 | + | 117629279 | 117633627 | COL4A5 |
| 33523834 | 33616557 | + | CUFF.14123.1 | seg_461 | 33428350 | 33432700 | M | chrX | 117629622 | 117723351 | + | 117629279 | 117633627 | COL4A5 |
| 33428660 | 33616557 | + | CUFF.14123.2 | seg_461 | 33428350 | 33432700 | M | chrX | 117629622 | 117820108 | + | 117629279 | 117633627 | COL4A5 |
| 33735899 | 33739153 | + | CUFF.14150.2 | seg_470 | 33737800 | 33739750 | M | chrX | 117957705 | 117960935 | + | 117959581 | 117961051 | COL4A5 |
| 33868348 | 33882606 | + | CUFF.14151.3 | seg_19 | 33867300 | 33870050 | S | chrX | 118108524 | 118124402 | + | 118107473 | 118110151 | COL4A5 |
| 33868348 | 33882606 | + | CUFF.14151.3 | seg_478 | 33862700 | 33871850 | M | chrX | 118108524 | 118124402 | + | 118101867 | 118111814 | COL4A5 |
| 33868348 | 33902336 | + | CUFF.14151.5 | seg_19 | 33867300 | 33870050 | S | chrX | 118108524 | 118152100 | + | 118107473 | 118110151 | COL4A5 |
| 33868348 | 33902336 | + | CUFF.14151.5 | seg_478 | 33862700 | 33871850 | M | chrX | 118108524 | 118152100 | + | 118101867 | 118111814 | COL4A5 |
| 33868348 | 33902336 | + | CUFF.14151.4 | seg_19 | 33867300 | 33870050 | S | chrX | 118108524 | 118152100 | + | 118107473 | 118110151 | COL4A5 |
| 33868348 | 33902336 | + | CUFF.14151.4 | seg_478 | 33862700 | 33871850 | M | chrX | 118108524 | 118152100 | + | 118101867 | 118111814 | COL4A5 |
| 34138199 | 34138634 | + | CUFF.14127.1 | seg_490 | 34136250 | 34139900 | M | chrX | 118370243 | 118370677 | + | 118368673 | 118372101 | OCRL |
| 34139837 | 34139989 | + | CUFF.14154.1 | seg_490 | 34136250 | 34139900 | M | chrX | 118372040 | 118372343 | + | 118368673 | 118372101 | OCRL |
| 34148309 | 34185415 | + | CUFF.14129.2 | seg_492 | 34184100 | 34185750 | M | chrX | 118380626 | 118407635 | + | 118406356 | 118407906 | OCRL |
| 34148309 | 34185417 | − | CUFF.14156.1 | seg_492 | 34184100 | 34185750 | M | chrX | 118380626 | 118407637 | − | 118406356 | 118407906 | OCRL |
| 34190337 | 34208188 | − | CUFF.14126.1 | seg_493 | 34207150 | 34209200 | M | chrX | 118415403 | 118422937 | − | 0 | 0 | OCRL |
| 34208212 | 34209008 | + | ENSMUST00000118173 | seg_493 | 34207150 | 34209200 | M | other | 0 | 0 | + | 0 | 0 | OA1 = GPR143 |
| 34208212 | 34209008 | + | ENSMUST00000118173 | seg_493 | 34207150 | 34209200 | M | other | 0 | 0 | + | 0 | 0 | OA1 = GPR143 |
| 34354766 | 34357180 | − | ENSMUST00000170210 | seg_495 | 34353300 | 34354950 | M | chrX | 118627272 | 118628472 | − | 118625327 | 118626697 | OCRL |
| 34354766 | 34357180 | − | ENSMUST00000170210 | seg_495 | 34353300 | 34354950 | M | chrX | 118627272 | 118628472 | − | 118625327 | 118626697 | OCRL |
| 34391130 | 34404168 | − | ENSMUST00000143544 | seg_496 | 34403300 | 34405050 | M | chrX | 118673725 | 118699359 | − | 118693658 | 118699484 | OCRL |
| 34414316 | 34415329 | + | CUFF.14162.1 | seg_497 | 34414150 | 34417000 | M | chrX | 118708489 | 118709503 | + | 118708340 | 118710452 | OCRL |
| 34414316 | 34414834 | + | CUFF.14162.2 | seg_497 | 34414150 | 34417000 | M | chrX | 118708489 | 118708986 | + | 118708340 | 118710452 | OCRL |
| 34414323 | 34414681 | + | CUFF.14131.1 | seg_497 | 34414150 | 34417000 | M | chrX | 118708496 | 118708841 | + | 118708340 | 118710452 | OCRL |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 34427535 | 34443093 | - | CUFF.14163.2 | seg_500 | 34441550 | 34443350 | M | chrX | 118722300 | 118740065 | - | 118738473 | 118740315 | OCRL |
| 34442912 | 34442959 | + | CUFF.14135.1 | seg_500 | 34441550 | 34443350 | M | chrX | 118739875 | 118739921 | - | 118738473 | 118740315 | OCRL |
| 34443059 | 34443464 | + | CUFF.14136.1 | seg_500 | 34441550 | 34443350 | M | chrX | 118740012 | 118740391 | - | 118738473 | 118740315 | OCRL |
| 34443156 | 34443320 | - | CUFF.14161.1 | seg_500 | 34441550 | 34443350 | M | chrX | 118740127 | 118740291 | - | 118738473 | 118740315 | OCRL |
| 34631673 | 34650335 | - | CUFF.14138.2 | seg_515 | 34648750 | 34650650 | M | chrX | 118967985 | 118986994 | - | 118985453 | 118987309 | OCRL |
| 34648901 | 34650347 | - | CUFF.14169.5 | seg_515 | 34648750 | 34650650 | M | chrX | 118985453 | 118987006 | - | 118985453 | 118987309 | OCRL |
| 35180050 | 35183034 | + | CUFF.14184.1 | seg_532 | 35178900 | 35181600 | M | other | 0 | 0 | + | 0 | 0 | OA1 = GPR143 |
| 35180050 | 35183034 | + | CUFF.14184.1 | seg_533 | 35182900 | 35184500 | M | other | 0 | 0 | + | 0 | 0 | OA1 = GPR143 |
| 35533905 | 35534803 | + | ENSMUST00000118349 | seg_21 | 35533400 | 35534750 | M | other | 0 | 0 | + | 0 | 0 | OA1 = GPR143 |
| 35533905 | 35534803 | + | ENSMUST00000118349 | seg_551 | 35533250 | 35535100 | S | other | 0 | 0 | + | 0 | 0 | OA1 = GPR143 |
| 35533905 | 35534803 | + | ENSMUST00000118349 | seg_21 | 35533400 | 35534750 | M | other | 0 | 0 | + | 0 | 0 | OA1 = GPR143 |
| 35533905 | 35534803 | + | ENSMUST00000118349 | seg_551 | 35533250 | 35535100 | S | other | 0 | 0 | + | 0 | 0 | OA1 = GPR143 |
| 35542915 | 35550223 | + | CUFF.14157.1 | seg_552 | 35542250 | 35544050 | M | chrX | 117629607 | 119392253 | + | 119383881 | 119385797 | OCRL |
| 35542935 | 35550223 | + | CUFF.14192.1 | seg_552 | 35542250 | 35544050 | M | chrX | 119384666 | 119392253 | + | 119383881 | 119385797 | OCRL |
| 35600278 | 35604805 | - | CUFF.14159.1 | seg_22 | 35603700 | 35606500 | S | chrX | 119439594 | 119444569 | - | 119443375 | 119446145 | OCRL |
| 35600278 | 35604805 | - | CUFF.14159.1 | seg_556 | 35602250 | 35609250 | M | chrX | 119439594 | 119444569 | - | 119441828 | 119448975 | OCRL |
| 35897792 | 35917936 | - | CUFF.14166.5 | seg_566 | 35896800 | 35898250 | M | chrX | 119672390 | 119695039 | - | 119672194 | 119672859 | OCRL |
| 35961900 | 35966603 | + | ENSMUST00000133128 | seg_569 | 35960900 | 35962650 | M | chrX | 119742855 | 119746241 | + | 119742376 | 119742750 | OCRL |
| 38754031 | 38966276 | + | ENSMUST00000128197 | seg_23 | 38753650 | 38755500 | M | chrX | 122317775 | 122554831 | + | 122317397 | 122319184 | OCRL |
| 38754031 | 38966276 | + | ENSMUST00000128197 | seg_619 | 38753250 | 38755800 | S | chrX | 122317775 | 122554831 | + | 122316995 | 122319507 | OCRL |
| 38754659 | 39031778 | + | CUFF.14209.6 | seg_23 | 38753650 | 38755500 | M | chrX | 122318324 | 122624766 | + | 122317397 | 122319184 | OCRL |
| 38754659 | 39031778 | + | CUFF.14209.6 | seg_619 | 38753250 | 38755800 | S | chrX | 122318324 | 122624766 | + | 122316995 | 122319507 | OCRL |
| 38754659 | 38966731 | + | ENSMUST00000148212 | seg_23 | 38753650 | 38755500 | M | chrX | 122318324 | 122555502 | + | 122317397 | 122319184 | OCRL |
| 38754659 | 38966731 | + | ENSMUST00000148212 | seg_619 | 38753250 | 38755800 | S | chrX | 122318324 | 122555302 | + | 122316995 | 122319507 | OCRL |
| 39155509 | 39265102 | + | CUFF.14211.5 | seg_638 | 39262300 | 39268050 | M | chrX | 122744049 | 122866926 | + | 122863888 | 122867232 | OCRL |
| 39264775 | 39265102 | + | CUFF.14211.10 | seg_638 | 39262300 | 39268050 | M | chrX | 122754023 | 122866926 | + | 122863888 | 122867232 | OCRL |
| 39264775 | 39265789 | - | CUFF.14175.17 | seg_638 | 39262300 | 39268050 | M | chrX | 122866626 | 122866902 | + | 122863888 | 122867232 | OCRL |
| 40177535 | 40782180 | - | ENSMUST00000154433 | seg_25 | 40779750 | 40784250 | M | chrX | 123784986 | 124338187 | - | 124335918 | 124340213 | OCRL |
| 40177535 | 40782180 | - | ENSMUST00000154433 | seg_678 | 40779300 | 40784650 | M | chrX | 123784986 | 124338187 | - | 124335476 | 124340593 | OCRL |
| 40250312 | 40782303 | - | ENSMUST00000126161 | seg_25 | 40779750 | 40784250 | M | chrX | 123836202 | 124338304 | - | 124335918 | 124340213 | OCRL |
| 40250312 | 40782303 | - | ENSMUST00000126161 | seg_678 | 40779300 | 40784650 | M | chrX | 123836202 | 124338304 | - | 124335476 | 124340593 | OCRL |
| 40677132 | 40782180 | - | ENSMUST00000125231 | seg_25 | 40779750 | 40784250 | M | chrX | 124241111 | 124338187 | - | 124335918 | 124340213 | OCRL |
| 40677132 | 40782180 | - | ENSMUST00000125231 | seg_678 | 40779300 | 40784650 | M | chrX | 124241111 | 124338187 | - | 124335476 | 124340593 | OCRL |
| 40677132 | 40782180 | - | ENSMUST00000125231 | seg_25 | 40779750 | 40784250 | M | chrX | 124241111 | 124338187 | - | 124335918 | 124340213 | OCRL |
| 40677132 | 40782180 | - | ENSMUST00000125231 | seg_678 | 40779300 | 40784650 | M | chrX | 124241111 | 124338137 | - | 124335476 | 124340593 | OCRL |
| 45162547 | 45245729 | + | CUFF.14233.3 | seg_768 | 45243800 | 45248200 | M | chrX | 128580480 | 128657501 | + | 128655532 | 128659505 | OCRL |
| 45227508 | 45245609 | + | ENSMUST00000141084 | seg_768 | 45243800 | 45248200 | M | chrX | 128638886 | 128657382 | + | 128655532 | 128659505 | OCRL |
| 45363158 | 45363341 | + | CUFF.14229.1 | seg_774 | 45362150 | 45363400 | M | other | 0 | 0 | + | 0 | 0 | OA1 = GPR143 |
| 45363178 | 45363342 | + | CUFF.14188.1 | seg_774 | 45362150 | 45363400 | M | other | 0 | 0 | + | 0 | 0 | OA1 = GPR143 |
| 45694175 | 45694423 | - | CUFF.14198.1 | seg_28 | 45693200 | 45698600 | S | chrX | 129113942 | 129114135 | - | 129110141 | 129120295 | OCRL |
| 45694175 | 45694423 | - | CUFF.14198.1 | seg_28 | 45693200 | 45698600 | S | chrX | 129113942 | 129114135 | - | 129110141 | 129120295 | OCRL |
| 45694535 | 45755264 | + | CUFF.14240.2 | seg_793 | 45690600 | 45700600 | M | chrX | 129114248 | 129186162 | + | 129110141 | -129118262 | OCRL |
| 45694535 | 45755264 | + | CUFF.14240.2 | seg_793 | 45690600 | 45700600 | M | chrX | 129114248 | 129186162 | + | 129110141 | 129120295 | OCRL |
| 45694535 | 45761226 | + | CUFF.14240.3 | seg_28 | 45693200 | 45698600 | S | chrX | 129114248 | 129192040 | + | 129112931 | -129118262 | OCRL |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 45694535 | 45761226 | + | CUFF.14240.3 | seg_793 | 45690600 | 45700600 | M | chrX | 129114248 | 129119040 | + | 129110141 | 129120295 | OCRL |
| 45695238 | 45746514 | + | CUFF.14240.5 | seg_28 | 45693200 | 45698600 | S | chrX | 129114949 | 129173294 | + | 129112931 | -129118262 | OCRL |
| 45695238 | 45746514 | + | CUFF.14240.5 | seg_793 | 45690600 | 45700600 | M | chrX | 129114949 | 129173294 | + | 129110141 | 129120295 | OCRL |
| 45696947 | 45761226 | + | CUFF.14240.8 | seg_28 | 45693200 | 45698600 | S | chrX | 129116613 | 129192040 | + | 129112931 | 129118262 | OCRL |
| 45696947 | 45761226 | + | CUFF.14240.8 | seg_793 | 45690600 | 45700600 | M | chrX | 129116613 | 129192040 | + | 129110141 | 129120295 | OCRL |
| 45697574 | 45698600 | + | CUFF.14200.5 | seg_28 | 45693200 | 45698600 | S | chrX | 129117248 | 129118262 | - | 129112931 | -129118262 | OCRL |
| 45697574 | 45698600 | + | CUFF.14200.5 | seg_793 | 45690600 | 45700600 | M | chrX | 129117248 | 129118262 | - | 129110141 | 129120295 | OCRL |
| 45764223 | 45810380 | - | CUFF.14235.1 | seg_797 | 45799100 | 45810800 | M | chrX | 129195192 | 129248513 | + | 129237507 | 129249292 | OCRL |
| 45806529 | 45807451 | - | CUFF.14203.1 | seg_29 | 45805150 | 45807500 | S | chrX | 129244056 | 129244891 | - | 129242747 | 129244939 | OCRL |
| 45806529 | 45807451 | - | CUFF.14203.1 | seg_797 | 45799100 | 45810800 | M | chrX | 129244056 | 129244891 | - | 129237507 | 129249292 | OCRL |
| 45976590 | 46015471 | - | CUFF.14243.2 | seg_807 | 45976250 | 45977750 | M | chrX | 129473516 | 129507331 | + | 129473042 | 129474708 | OCRL |
| 45976926 | 46005231 | - | ENSMUST00000153047 | seg_807 | 45976250 | 45977750 | M | chrX | 129473871 | 129498726 | + | 129473042 | 129474708 | OCRL |
| 46838852 | 46848439 | - | ENSMUST00000151128 | seg_836 | 46835350 | 46841700 | M | chrX | 130207473 | 130217728 | + | 130204272 | 130210819 | NYS1 = FRMD7 |
| 46838852 | 46848439 | - | ENSMUST00000151128 | seg_837 | 46844950 | 46849750 | M | chrX | 130207473 | 130217728 | + | 130214253 | 130219020 | NYS1 = FRMD7 |
| 47135713 | 47150926 | - | CUFF.14205.9 | seg_844 | 47150550 | 47152600 | M | chrX | 130407480 | 130423284 | - | 130422906 | 130424949 | NYS1 = FRMD7 |
| 47139524 | 47150928 | - | CUFF.14249.5 | seg_844 | 47150550 | 47152600 | M | chrX | 130411301 | 130423286 | - | 130422906 | 130424949 | NYS1 = FRMD7 |
| 47148122 | 47150912 | - | ENSMUST00000135492 | seg_844 | 47150550 | 47152600 | M | chrX | 130420186 | 130423270 | - | 130422906 | 130424949 | NYS1 = FRMD7 |
| 47726321 | 47727201 | + | ENSMUST00000121522 | seg_869 | 47726600 | 47729450 | M | other | 0 | 0 | 0 | 0 | 0 | OA1 = GPR143 |
| 47727201 | 47727201 | + | ENSMUST00000121522 | seg_869 | 47726600 | 47729450 | M | other | 0 | 0 | 0 | 0 | 0 | OA1 = GPR143 |
| 47908438 | 47988438 | - | ENSMUST00000124842 | seg_877 | 47987350 | 47989500 | M | other | 0 | 0 | 0 | 0 | 0 | OA1 = GPR143 |
| 47930580 | 47930887 | - | CUFF.14345.1 | seg_875 | 47929100 | 47930850 | M | chrX | 130956109 | 130964776 | - | 130875046 | 130875479 | OA1 = GPR143 |
| 47948607 | 47988499 | - | CUFF.14211.3 | seg_877 | 47987350 | 47989500 | M | chrX | 130956109 | 130964775 | - | 0 | 0 | NYS1 = FRMD7 |
| 47968572 | 47988498 | - | ENSMUST00000143999 | seg_877 | 47987350 | 47989500 | M | chrX | 130956109 | 130964776 | - | 0 | 0 | NYS1 = FRMD7 |
| 47983977 | 47988499 | - | CUFF.14211.7 | seg_877 | 47987350 | 47989500 | M | chrX | 130960808 | 130964776 | - | 0 | 0 | NYS1 = FRMD7 |
| 48368108 | 48371354 | - | CUFF.14256.2 | seg_899 | 48367900 | 48369550 | M | chrX | 131348118 | 131351566 | - | 131347929 | 131349656 | NYS1 = FRMD7 |
| 48371324 | 48371616 | - | CUFF.14209.1 | seg_900 | 48371400 | 48373300 | M | chrX | 131351532 | 131351823 | - | 131351609 | 131353535 | NYS1 = FRMD7 |
| 48371476 | 48371850 | + | CUFF.14210.1 | seg_900 | 48371400 | 48373300 | M | chrX | 131351714 | 131352061 | + | 131351609 | 131353535 | NYS1 = FRMD7 |
| 49029960 | 49034525 | - | ENSMUST00000142738 | seg_34 | 49033400 | 49035850 | S | chrX | 132087343 | 132092376 | - | 132091169 | 132093740 | NYS1 = FRMD7 |
| 49029960 | 49034525 | - | ENSMUST00000142738 | seg_935 | 49029050 | 49041550 | M | chrX | 132087343 | 132092376 | - | 132086354 | 132099266 | NYS1 = FRMD7 |
| 49033169 | 49033742 | - | ENSMUST00000142983 | seg_34 | 49033400 | 49035850 | S | chrX | 132090938 | 132091521 | - | 132091169 | 132093740 | NYS1 = FRMD7 |
| 49033169 | 49033742 | - | ENSMUST00000142983 | seg_935 | 49029050 | 49041550 | M | chrX | 132090938 | 132091521 | - | 132086354 | 132099266 | NYS1 = FRMD7 |
| 49033355 | 49034263 | - | ENSMUST00000140145 | seg_34 | 49033400 | 49035850 | S | chrX | 132091124 | 132092112 | - | 132091169 | 132093740 | NYS1 = FRMD7 |
| 49033355 | 49034263 | - | ENSMUST00000140145 | seg_935 | 49029050 | 49041550 | M | chrX | 132091124 | 132092112 | - | 132086354 | 132099266 | NYS1 = FRMD7 |
| 49106697 | 49154410 | - | CUFF.14260.1 | seg_943 | 49154200 | 49156050 | M | chrX | 132159249 | 132231301 | - | 132231109 | 132231426 | NYS1 = FRMD7 |
| 49404740 | 49405157 | - | CUFF.14263.1 | seg_956 | 49404000 | 49405600 | M | chrX | 132435253 | 132435700 | - | 132434518 | 132436079 | NYS1 = FRMD7 |
| 49405289 | 49405837 | - | CUFF.14264.1 | seg_956 | 49404000 | 49405600 | M | chrX | 132435805 | 132436325 | - | 132434518 | 132436079 | NYS1 = FRMD7 |
| 49775584 | 49775692 | - | ENSMUST00000102259 | seg_976 | 49775500 | 49776800 | M | chrX | 132880759 | 132880877 | - | 132880685 | 132881912 | HPRT1 = HPRT |
| 50095234 | 50098237 | - | CUFF.14267.2 | seg_990 | 50096650 | 50098550 | M | chrX | 133303779 | 133307009 | - | 133305238 | 133307374 | HPRT1 = HPRT |
| 50095740 | 50097770 | - | ENSMUST00000133214 | seg_990 | 50096650 | 50098550 | M | chrX | 133304296 | 133306522 | - | 133305238 | 133307374 | HPRT1 = HPRT |
| 50095740 | 50097770 | - | ENSMUST00000138156 | seg_990 | 50096650 | 50098550 | M | chrX | 133304296 | 133306522 | - | 133305238 | 133307374 | HPRT1 = HPRT |
| 50095740 | 50097770 | - | ENSMUST00000143479 | seg_990 | 50096650 | 50098550 | M | chrX | 133304296 | 133306522 | - | 133305238 | 133307374 | HPRT1 = HPRT |
| 50095740 | 50097770 | - | ENSMUST00000138156 | seg_990 | 50096650 | 50098550 | M | chrX | 133304296 | 133306522 | - | 133305238 | 133307374 | HPRT1 = HPRT |
| 50095740 | 50097770 | - | ENSMUST00000143479 | seg_990 | 50096650 | 50098550 | M | chrX | 133304296 | 133306522 | - | 133305238 | 133307374 | HPRT1 = HPRT |
| 50265390 | 50265600 | + | CUFF.14269.1 | seg_1001 | 50264950 | 50267500 | M | chrX | 133507274 | 133507484 | + | 133506826 | 133509357 | HPRT1 = HPRT |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 50265421 | 50310120 | + | CUFF.14222.1 | seg_1001 | 50264950 | 50267500 | M | chrX | 133507305 | 133562820 | + | 133506826 | 133509357 | HPRT1 = HPRT |
| 50341229 | 50374836 | + | CUFF.14271.1 | seg_1003 | 50340900 | 50342400 | M | chrX | 133594153 | 133634696 | + | 133593796 | 133595251 | HPRT1 = HPRT |
| 50341250 | 50341769 | + | CUFF.14224.1 | seg_1003 | 50340900 | 50342400 | M | chrX | 133594174 | 133594686 | + | 133593796 | 133595251 | HPRT1 = HPRT |
| 50407432 | 50407526 | − | ENSMUST00000083484 | seg_1004 | 50407500 | 50413850 | M | chrX | 133680658 | 133680753 | − | 133680727 | 133686885 | HPRT1 = HPRT |
| 50408223 | 50410367 | − | ENSMUST00000155622 | seg_1004 | 50407500 | 50413850 | M | chrX | 133681640 | 133683674 | − | 133680727 | 133686885 | HPRT1 = HPRT |
| 50408223 | 50410367 | − | ENSMUST00000155622 | seg_37 | 50410150 | 50413850 | S | chrX | 133681640 | 133683674 | − | 133683549 | 133686542 | HPRT1 = HPRT |
| 50408947 | 50410413 | − | CUFF.14272.4 | seg_1004 | 50407500 | 50413850 | M | chrX | 133682420 | 133683720 | − | 133680727 | 133686885 | HPRT1 = HPRT |
| 50408947 | 50410413 | − | CUFF.14272.4 | seg_37 | 50410150 | 50413850 | S | chrX | 133682420 | 133683720 | − | 133683549 | 133686542 | HPRT1 = HPRT |
| 50409370 | 50410367 | − | ENSMUST00000151099 | seg_1004 | 50407500 | 50413850 | M | chrX | 133682808 | 133683674 | − | 133680727 | 133686885 | HPRT1 = HPRT |
| 50409370 | 50410367 | − | ENSMUST00000151099 | seg_37 | 50410150 | 50413850 | S | chrX | 133682808 | 133683674 | − | 133683549 | 133686542 | HPRT1 = HPRT |
| 50409370 | 50410367 | − | ENSMUST00000151099 | seg_1004 | 50407500 | 50413850 | M | chrX | 133682808 | 133683674 | − | 133680727 | 133686885 | HPRT1 = HPRT |
| 50409370 | 50410367 | − | ENSMUST00000151099 | seg_37 | 50410150 | 50413850 | S | chrX | 133682808 | 133683674 | − | 133683549 | 133686542 | HPRT1 = HPRT |
| 51076013 | 51076306 | + | ENSMUST00000119948 | seg_1035 | 51076300 | 51080000 | M | other | 0 | 0 | + | 0 | 0 | OA1 = GPR143 |
| 51272614 | 51278177 | − | ENSMUST00000152691 | seg_1038 | 51276550 | 51281350 | M | other | 0 | 0 | − | 0 | 0 | OA1 = GPR143 |
| 51272614 | 51278177 | − | ENSMUST00000152691 | seg_39 | 51277000 | 51280800 | S | other | 0 | 0 | − | 0 | 0 | OA1 = GPR143 |
| 53599576 | 53618851 | + | CUFF.14301.1 | seg_1050 | 53618100 | 53619850 | M | chrX | 134478720 | 134497065 | + | 134496269 | 134497771 | HPRT1 = HPRT |
| 53838689 | 53851246 | − | CUFF.14304.2 | seg_1060 | 53850250 | 53852000 | M | chrX | 135044238 | 135056037 | − | 135055069 | 135057268 | HPRT1 = HPRT |
| 53863012 | 53908257 | + | CUFF.14306.3 | seg_1062 | 53862950 | 53864950 | M | chrX | 135067645 | 135115687 | + | 135067584 | 135069491 | HPRT1 = HPRT |
| 53984857 | 54043843 | + | CUFF.14254.1 | seg_1073 | 53983050 | 53986450 | M | chrX | 135229664 | 135290816 | + | 135226915 | 135231187 | HPRT1 = HPRT |
| 53984936 | 54043843 | + | CUFF.14308.1 | seg_1073 | 53983050 | 53986450 | M | chrX | 135229664 | 135290816 | + | 135226915 | 135231187 | HPRT1 = HPRT |
| 54484662 | 54494066 | − | ENSMUST00000151768 | seg_1092 | 54492950 | 54494750 | M | chrX | 135747707 | 135759091 | − | 135758146 | 135759853 | HPRT1 = HPRT |
| 54644626 | 54644698 | − | ENSMUST00000083176 | seg_1095 | 54644100 | 54645900 | M | chrX | 135961358 | 135961432 | − | 135961062 | 135962620 | HPRT1 = HPRT |
| 54644626 | 54644698 | − | ENSMUST00000083176 | seg_1095 | 54644100 | 54645900 | M | chrX | 135961358 | 135961432 | − | 135961062 | 135962620 | HPRT1 = HPRT |
| 54939724 | 54991732 | + | ENSMUST00000117477 | seg_1113 | 54988950 | 54990200 | M | other | 0 | 0 | + | 0 | 0 | OA1 = GPR143 |
| 55175146 | 55175209 | + | CUFF.14315.1 | seg_1124 | 55168950 | 55177100 | M | chrX | 136512124 | 136512176 | + | 136505920 | 136514806 | F9 |
| 55175146 | 55175209 | + | CUFF.14315.1 | seg_43 | 55169850 | 55176350 | S | chrX | 136512124 | 136512176 | + | 136506771 | 136513469 | F9 |
| 55283804 | 55294913 | − | CUFF.14261.2 | seg_1129 | 55279400 | 55288000 | M | chrX | 136648285 | 136659851 | − | 136643868 | 136652525 | F9 |
| 55283804 | 55294913 | − | CUFF.14261.2 | seg_1130 | 55290400 | 55296750 | M | chrX | 136648285 | 136659851 | − | 136654976 | 136660703 | F9 |
| 55283804 | 55294913 | − | CUFF.14261.2 | seg_45 | 55283050 | 55287350 | S | chrX | 136648285 | 136659851 | − | 136647552 | 136651893 | F9 |
| 55283804 | 55286873 | − | CUFF.14316.3 | seg_1129 | 55279400 | 55288000 | M | chrX | 136648285 | 136651403 | − | 136643868 | 136652525 | F9 |
| 55283804 | 55286873 | − | CUFF.14316.3 | seg_45 | 55283050 | 55287350 | S | chrX | 136648285 | 136651403 | − | 136647552 | 136651893 | F9 |
| 55291586 | 55291918 | − | CUFF.14263.1 | seg_1130 | 55290400 | 55296750 | M | chrX | 136648285 | 132435700 | − | 136654976 | 136660703 | F9 |
| 56316667 | 56386391 | − | ENSMUST00000138503 | seg_1161 | 56386000 | 56388000 | M | chrX | 124352253 | 137714968 | − | 137791961 | 137793923 | HPRT1 = HPRT |
| 56421226 | 56421304 | − | CUFF.14323.1 | seg_1163 | 56418350 | 56421350 | M | chrX | 137714968 | 137792332 | − | 137820604 | 137823585 | F9 |
| 57309131 | 57432445 | − | CUFF.14324.1 | seg_1198 | 57428450 | 57434700 | M | chrX | 137823466 | 138663919 | − | 138771736 | 138771736 | F9 |
| 57377877 | 57431535 | − | CUFF.14324.7 | seg_1198 | 57428450 | 57434700 | M | chrX | 138663919 | 138773758 | − | 138771736 | 138780855 | F9 |
| 57392756 | 57392833 | − | CUFF.14325.1 | seg_1197 | 57391850 | 57393700 | M | other | 0 | 0 | − | 138714942 | 138716185 | OA1 = GPR143 |
| 57488638 | 57657223 | − | CUFF.14329.7 | seg_1205 | 57655000 | 57659550 | M | chrX | 138818955 | 139014388 | − | 139012164 | 139017130 | F9 |
| 57488638 | 57657479 | − | CUFF.14272.6 | seg_1205 | 57655000 | 57659550 | M | chrX | 138818955 | 139014657 | − | 139012164 | 139017130 | F9 |
| 57657230 | 57657464 | + | CUFF.14273.1 | seg_1205 | 57655000 | 57659550 | M | chrX | 139014395 | 139014642 | + | 139012164 | 139017130 | F9 |
| 57657681 | 57657808 | + | CUFF.14274.1 | seg_1205 | 57655000 | 57659550 | M | chrX | 139014914 | 139015030 | + | 139012164 | 139017130 | F9 |
| 57761975 | 57762010 | − | CUFF.14277.1 | seg_1210 | 57761900 | 57763800 | M | other | 0 | 0 | − | 0 | 0 | OA1 = GPR143 |
| 57801194 | 57802024 | + | ENSMUST00000117865 | seg_1212 | 57799400 | 57803350 | M | chrX | 139173902 | 139174723 | + | 139172227 | 139176447 | F9 |
| 57801194 | 57802024 | + | ENSMUST00000117865 | seg_1212 | 57799400 | 57803350 | M | chrX | 139173902 | 139174723 | + | 139172227 | 139176447 | F9 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 58144545 | 58146615 | − | CUFF.14269.1 | seg_1227 | 58140550 | 58155350 | M | chrX | 133507274 | 133507484 | + | 139580491 | 139597036 | HPRT1 = HPRT |
| 58144545 | 58146615 | − | CUFF.14269.1 | seg_49 | 58143750 | 58152800 | S | chrX | 133507274 | 133507484 | + | 139584340 | 139594145 | HPRT1 = HPRT |
| 58146828 | 58151242 | + | ENSMUST00000145552 | seg_1227 | 58140550 | 58155350 | M | chrX | 139587446 | 139592481 | + | 139580491 | 139597036 | F9 |
| 58146828 | 58151242 | + | ENSMUST00000145552 | seg_49 | 58143750 | 58152800 | S | chrX | 139587446 | 139592481 | + | 139584340 | 139594145 | F9 |
| 65920689 | 65931574 | + | ENSMUST00000101520 | seg_1309 | 65930300 | 65933100 | M | chrX | 146974056 | 146993242 | − | 146992254 | 146994838 | FMR1 |
| 65931716 | 65951510 | + | CUFF.14287.2 | seg_1309 | 65930300 | 65933100 | M | chrX | 146993398 | 147012157 | − | 146992254 | 146994838 | FMR1 |
| 65931716 | 65970681 | + | CUFF.14287.3 | seg_1309 | 65930300 | 65933100 | M | chrX | 146993398 | 147032195 | − | 146992254 | 146994838 | FMR1 |
| 65931716 | 65970681 | + | CUFF.14352.1 | seg_1309 | 65930300 | 65933100 | M | chrX | 146993398 | 147032195 | − | 146992254 | 146994838 | FMR1 |
| 65932068 | 65932563 | + | CUFF.14288.1 | seg_1309 | 65930300 | 65933100 | M | chrX | 146993774 | 146994298 | − | 146992254 | 146994838 | FMR1 |
| 65932227 | 65932774 | + | CUFF.14353.1 | seg_1309 | 65930300 | 65933100 | M | chrX | 146993961 | 146994506 | − | 146992254 | 146994838 | FMR1 |
| 66858632 | 66859423 | − | ENSMUST00000163828 | seg_1334 | 66859150 | 66860650 | M | other | 0 | 0 | + | 0 | 0 | OA1 = GPR143 |
| 66858632 | 66859428 | − | ENSMUST00000163828 | seg_1334 | 66859150 | 66860650 | M | other | 0 | 0 | + | 0 | 0 | OA1 = GPR143 |
| 66355671 | 66859420 | + | ENSMUST00000120762 | seg_1334 | 66859150 | 66860650 | M | other | 0 | 0 | + | 0 | 0 | OA1 = GPR143 |
| 67712928 | 67730355 | − | CUFF.14360.2 | seg_1361 | 67729150 | 67730900 | M | chrX | 148678210 | 148713485 | + | 148712175 | 148714034 | MTM1 |
| 67712928 | 67730355 | − | CUFF.14295.2 | seg_1361 | 67729150 | 67730900 | M | chrX | 148678210 | 148713485 | + | 148712175 | 148714034 | MTM1 |
| 67716098 | 67730317 | + | ENSMUST00000134954 | seg_1361 | 67729150 | 67730900 | M | chrX | 148682045 | 148713449 | + | 148712175 | 148714034 | MTM1 |
| 68291015 | 68303292 | + | CUFF.14296.1 | seg_1381 | 68301500 | 68306350 | M | chrX | 149520032 | 149531563 | + | 149529888 | 149534532 | MTM1 |
| 68291015 | 68303292 | + | CUFF.14296.1 | seg_51 | 68305200 | 68305800 | S | chrX | 149520032 | 149531563 | + | 149530085 | 149534002 | MTM1 |
| 68809081 | 68812693 | + | CUFF.14369.2 | seg_1404 | 68805250 | 68809850 | M | chrX | 150151747 | 150156053 | + | 150146455 | 150152649 | MTM1 |
| 68809092 | 68812471 | + | CUFF.14301.1 | seg_1404 | 68805250 | 68809850 | M | chrX | 134478720 | 134497065 | + | 150146455 | 150152649 | HPRT1 = HPRT |
| 68809408 | 68809659 | + | CUFF.14301.6 | seg_1404 | 68805250 | 68809850 | M | chrX | 150152106 | 150152390 | + | 150146455 | 150152649 | MTM1 |
| 68809643 | 68809983 | + | CUFF.14370.1 | seg_1404 | 68805250 | 68809850 | M | chrX | 150152374 | 150152784 | + | 150146455 | 150152649 | MTM1 |
| 68809715 | 68813851 | + | CUFF.14301.7 | seg_1404 | 68805250 | 68809850 | M | chrX | 150152444 | 150157265 | + | 150146455 | 150157265 | MTM1 |
| 68917141 | 68920567 | + | ENSMUST00000131554 | seg_1411 | 68914050 | 68921750 | M | chrX | 150345344 | 150349110 | + | 150341934 | 150350499 | MTM1 |
| 68917141 | 68920567 | + | ENSMUST00000131554 | seg_53 | 68914500 | 68919750 | S | chrX | 150345344 | 150349110 | + | 150342370 | 150348293 | MTM1 |
| 68917141 | 68920567 | + | ENSMUST00000144712 | seg_1411 | 68914050 | 68921750 | M | chrX | 150345344 | 150349110 | + | 150341934 | 150350499 | MTM1 |
| 68917141 | 68920567 | + | ENSMUST00000144712 | seg_53 | 68914500 | 68919750 | S | chrX | 150345344 | 150349110 | + | 150342370 | 150348293 | MTM1 |
| 69062152 | 69066323 | + | ENSMUST00000138979 | seg_1416 | 69061200 | 69063200 | M | chrX | 150565693 | 150573568 | + | 150564437 | 150567623 | MTM1 |
| 69062152 | 69066323 | + | ENSMUST00000138979 | seg_1416 | 69061200 | 69063200 | M | chrX | 150565698 | 150573568 | + | 150564437 | 150567623 | MTM1 |
| 69514307 | 69520142 | − | ENSMUST00000153740 | seg_1436 | 69517250 | 69520800 | M | chrX | 151137877 | 151143202 | − | 151139787 | 151143870 | MTM1 |
| 69519852 | 69520142 | − | CUFF.14310.4 | seg_1436 | 69517250 | 69520800 | M | chrX | 151142857 | 151143202 | − | 151139787 | 151143870 | MTM1 |
| 70232678 | 70261234 | + | CUFF.14389.3 | seg_1465 | 70232550 | 70233700 | M | chrX | 152066590 | 152132534 | + | 152066464 | 152067633 | ABCD1 |
| 70232678 | 70276882 | + | CUFF.14389.4 | seg_1465 | 70232550 | 70233700 | M | chrX | 152066590 | 152142042 | + | 152066464 | 152067633 | ABCD1 |
| 70232678 | 70276882 | + | CUFF.14389.4 | seg_1469 | 70276250 | 70277250 | M | chrX | 152066590 | 152142042 | + | 152141408 | 152142118 | ABCD1 |
| 70232678 | 70276882 | + | ENSMUST00000144712 | seg_1465 | 70232550 | 70233700 | M | chrX | 152066590 | 152142042 | + | 152066464 | 152067633 | ABCD1 |
| 70232678 | 70276882 | + | ENSMUST00000144712 | seg_1469 | 70276250 | 70277250 | M | chrX | 152066590 | 152142042 | + | 152141408 | 152142118 | ABCD1 |
| 70232678 | 70276882 | + | CUFF.14389.2 | seg_1469 | 70276250 | 70277250 | M | chrX | 152066590 | 152142042 | + | 152141408 | 152142118 | ABCD1 |
| 70659581 | 70659693 | + | CUFF.14395.1 | seg_1486 | 70655550 | 70660200 | M | other | 0 | 0 | + | 0 | 0 | OA1 = GPR143 |
| 70682654 | 70704414 | − | CUFF.14396.3 | seg_1489 | 70702900 | 70704800 | M | chrX | 152731126 | 152736112 | − | 152676030 | 152680458 | ABCD1 |
| 70748725 | 70748751 | − | CUFF.14493.1 | seg_1493 | 70748300 | 70751550 | M | chrX | 152783300 | 152783425 | − | 152731557 | 152736608 | ABCD1 |
| 70884707 | 70887453 | + | CUFF.14399.1 | seg_1504 | 70880250 | 70886600 | M | chrX | 152912601 | 152915465 | − | 152907256 | 152914605 | ABCD1 |
| 70884707 | 70887453 | + | CUFF.14399.1 | seg_56 | 70884700 | 70886100 | S | chrX | 152912601 | 152915465 | − | 152912593 | 152913737 | ABCD1 |
| 70918489 | 70919425 | + | CUFF.14406.3 | seg_1507 | 70919050 | 70921750 | M | chrX | 152953368 | 152954327 | − | 152953952 | 152956569 | ABCD1 |
| 71038698 | 71070106 | + | CUFF.14350.4 | seg_1515 | 71069800 | 71072250 | M | chrX | 153067624 | 153096149 | − | 153095872 | 153098097 | L1CAM |
| 71167461 | 71171740 | − | ENSMUST00000135213 | seg_1524 | 71165700 | 71168200 | M | chrX | 153200721 | 153205716 | − | 153198707 | 153201262 | AVPR2 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 71188131 | 71212039 | - | CUFF.14346.3 | seg_1526 | 71210350 | 71212250 | M | chrX | 153213005 | 153236998 | - | 153235226 | 153237200 | AVPR2 |
| 71209543 | 71210383 | - | CUFF.14432.1 | seg_1526 | 71210350 | 71212250 | M | chrX | 153234378 | 153235269 | - | 153235226 | 153237200 | AVPR2 |
| 71212129 | 71212322 | - | CUFF.14347.1 | seg_1526 | 71210350 | 71212250 | M | chrX | 153237078 | 153237272 | - | 153235226 | 153237200 | AVPR2 |
| 71252041 | 71252841 | + | ENSMUST00000120692 | seg_1528 | 71251100 | 71253700 | M | other | 0 | 0 | + | 0 | 0 | OA1 = GPR143 |
| 71252041 | 71252841 | + | ENSMUST00000120692 | seg_1528 | 71251100 | 71253700 | M | other | 0 | 0 | + | 0 | 0 | OA1 = GPR143 |
| 71491032 | 71491211 | - | CUFF.14417.1 | seg_1536 | 71489000 | 71492050 | M | chrX | 153598856 | 153599051 | + | 153596991 | 153599880 | EMD |
| 71491144 | 71491278 | - | CUFF.14563.1 | seg_1536 | 71489000 | 71492050 | M | chrX | 153598983 | 153599133 | + | 153596991 | 153599880 | EMD |
| 71500026 | 71500436 | + | CUFF.14439.2 | seg_1537 | 71499550 | 71501250 | M | chrX | 153607566 | 153607980 | + | 153606662 | 153608766 | EMD |
| 71500100 | 71501024 | + | ENSMUST00000129516 | seg_1537 | 71499550 | 71501250 | M | chrX | 153607643 | 153608527 | + | 153606662 | 153608766 | EMD |
| 71527251 | 71528204 | + | ENSMUST00000146260 | seg_1538 | 71525800 | 71528950 | M | chrX | 153637932 | 153640001 | + | 153636852 | 153640773 | EMD |
| 71527251 | 71528254 | + | ENSMUST00000135012 | seg_1538 | 71525800 | 71528950 | M | chrX | 153637932 | 153640082 | + | 153636852 | 153640773 | EMD |
| 71527980 | 71535490 | + | CUFF.14421.3 | seg_1538 | 71525800 | 71528950 | M | chrX | 153639773 | 153650067 | + | 153636852 | 153640773 | EMD |
| 71528089 | 71533374 | + | ENSMUST00000156880 | seg_1538 | 71525800 | 71528950 | M | chrX | 153639886 | 153647898 | + | 153636852 | 153640773 | EMD |
| 71528089 | 71535487 | + | ENSMUST00000124200 | seg_1538 | 71525800 | 71528950 | M | chrX | 153639886 | 153650064 | + | 153636852 | 153640773 | EMD |
| 71528090 | 71535488 | + | ENSMUST00000114182 | seg_1538 | 71525800 | 71528950 | M | chrX | 153639887 | 153650065 | + | 153636852 | 153640773 | EMD |
| 71550319 | 71557201 | + | CUFF.14360.2 | seg_1540 | 71549400 | 71551350 | M | chrX | 148678210 | 148713485 | + | 153664294 | 153666201 | MTM1 |
| 71550319 | 71553622 | + | CUFF.14360.1 | seg_1540 | 71549400 | 71551350 | M | chrX | 148678210 | 153668876 | + | 153664294 | 153666201 | OA1 = GPR143 |
| 71550337 | 71553623 | + | CUFF.14449.2 | seg_1540 | 71549400 | 71551350 | M | chrX | 153665244 | 153668877 | + | 153664294 | 153666201 | EMD |
| 71574384 | 71597045 | + | CUFF.14364.1 | seg_1542 | 71572900 | 71574500 | M | chrX | 153686599 | 153705719 | + | 153686144 | 153686719 | IKBKG |
| 71574384 | 71590028 | + | CUFF.14364.1 | seg_1542 | 71572900 | 71574500 | M | chrX | 153686599 | 153702184 | + | 153686144 | 153686719 | IKBKG |
| 71574404 | 71588866 | + | CUFF.14453.2 | seg_1542 | 71572900 | 71574500 | M | chrX | 153686620 | 153701013 | + | 153686144 | 153686719 | IKBKG |
| 71598672 | 71598963 | - | CUFF.14450.4 | seg_1543 | 71597350 | 71599950 | M | chrX | 153707075 | 153707335 | - | 153706026 | 153707314 | IKBKG |
| 71598672 | 71598963 | - | CUFF.14450.4 | seg_58 | 71597850 | 71599950 | S | chrX | 153707075 | 153707335 | - | 153706412 | 153707323 | IKBKG |
| 71675010 | 71699193 | + | CUFF.14372.14 | seg_1547 | 71673000 | 71675050 | M | chrX | 153773825 | 153799420 | + | 153773591 | 153775852 | G6PD = G6PDX |
| 72388763 | 72388969 | + | ENSMUST00000121894 | seg_1564 | 72385650 | 72389350 | M | other | 0 | 0 | + | 0 | 0 | OA1 = GPR143 |
| 72388763 | 72388969 | + | ENSMUST00000121894 | seg_1564 | 72385650 | 72389350 | M | other | 0 | 0 | + | 0 | 0 | OA1 = GPR143 |
| 72389027 | 72389809 | + | ENSMUST00000116535 | seg_1564 | 72385650 | 72389350 | M | other | 0 | 0 | + | 0 | 0 | OA1 = GPR143 |
| 72389027 | 72389809 | + | ENSMUST00000116535 | seg_1564 | 72385650 | 72389350 | M | other | 0 | 0 | + | 0 | 0 | OA1 = GPR143 |
| 72759615 | 72762429 | + | CUFF.14477.1 | seg_1574 | 72758200 | 72760250 | M | chrX | 154444700 | 154448461 | + | 154444033 | 154445346 | F8 |
| 72759656 | 72767094 | + | ENSMUST00000123419 | seg_1574 | 72758200 | 72760250 | M | chrX | 154444742 | 154456167 | + | 154444033 | 154445346 | F8 |
| 73030993 | 73120555 | - | CUFF.14480.2 | seg_1582 | 73118600 | 73123600 | M | chrX | 114795419 | 114885001 | - | 114793736 | 114797278 | COL4A5 |
| 73120309 | 73120521 | - | CUFF.14390.7 | seg_1582 | 73118600 | 73123600 | M | chrX | 114795453 | 114795667 | - | 114793736 | 114797278 | COL4A5 |
| 75715283 | 75829194 | + | ENSMUST00000126209 | seg_1613 | 75828600 | 75830000 | M | chrX | 37208552 | 37301473 | + | 37207651 | 37209173 | XK |
| 75715283 | 75829194 | + | ENSMUST00000126209 | seg_1613 | 75828600 | 75830000 | M | chrX | 37208552 | 373301473 | + | 37207651 | 37209173 | XK |
| 75726052 | 75829121 | + | ENSMUST00000126994 | seg_1613 | 75725050 | 75728900 | M | chrX | 37285442 | 37293306 | + | 37285442 | 37294050 | XK |
| 75726052 | 75829121 | + | ENSMUST00000126994 | seg_1613 | 75828600 | 75830000 | M | chrX | 37208635 | 37293306 | + | 37207651 | 37209173 | XK |
| 75762644 | 75829230 | + | ENSMUST00000148345 | seg_1613 | 75828600 | 75830000 | M | chrX | 37208533 | 37269301 | + | 37207651 | 37209173 | XK |
| 78316009 | 78316663 | + | CUFF.14419.1 | seg_1627 | 78315700 | 78317600 | M | chrX | 34645190 | 34675419 | - | 34673892 | 34675817 | XK |
| 78316009 | 78343211 | + | CUFF.14508.1 | seg_1627 | 78315700 | 78317600 | M | chrX | 34645190 | 34675419 | - | 34673892 | 34675817 | XK |
| 78316009 | 78343211 | + | CUFF.14508.1 | seg_1628 | 78342250 | 78344000 | M | chrX | 34645190 | 34675419 | - | 34644751 | 34646161 | XK |
| 78316037 | 78340115 | + | ENSMUST00000150052 | seg_1627 | 78315700 | 78317600 | M | chrX | 34648380 | 34675385 | - | 34673892 | 34675817 | XK |
| 82819228 | 82867039 | + | CUFF.14513.1 | seg_1719 | 82818550 | 82821050 | M | chrX | 30845559 | 30907504 | - | 30905718 | 30908242 | DAX1 = NROB1 |
| 82819228 | 82879808 | + | CUFF.14513.2 | seg_1719 | 82818550 | 82821050 | M | chrX | 30845559 | 30907504 | - | 30905718 | 30908242 | DAX1 = NROB1 |
| 82819378 | 82820964 | + | ENSMUST00000152880 | seg_1719 | 82818550 | 82821050 | M | chrX | 30905799 | 30907361 | - | 30905718 | 30908242 | DAX1 = NROB1 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 82961777 | 82962362 | + | ENSMUST00000121559 | seg_1723 | 82962000 | 82963000 | M | other | 0 | 0 | + | 0 | 0 | OA1 = GPR143 |
| 82961777 | 82962362 | + | ENSMUST00000121559 | seg_1723 | 82962000 | 82963000 | M | other | 0 | 0 | + | 0 | 0 | OA1 = GPR143 |
| 83561422 | 83564035 | + | ENSMUST00000119460 | seg_1743 | 83560850 | 83562500 | M | other | 0 | 0 | + | 0 | 0 | OA1 = GPR143 |
| 83561422 | 83564035 | + | ENSMUST00000119460 | seg_1743 | 83560850 | 83562500 | M | other | 0 | 0 | + | 0 | 0 | OA1 = GPR143 |
| 83591184 | 83591184 | − | ENSMUST00000116183 | seg_1745 | 83591000 | 83592600 | M | chrX | 30260253 | 30261290 | + | 30260067 | 30260445 | DAX1 = NROB1 |
| 83658987 | 83659063 | − | CUFF.14521.1 | seg_1747 | 83657500 | 83660550 | M | other | 0 | 0 | + | 30223407 | 30223935 | OA1 = GPR143 |
| 91077474 | 91077950 | + | CUFF.14448.1 | seg_1867 | 91076600 | 91079100 | M | chrX | 24482937 | 24483410 | − | 24481558 | 24484296 | SAT = SAT1 |
| 91780815 | 91787329 | + | ENSMUST00000153386 | seg_1916 | 91786200 | 91788100 | M | chrX | 51636754 | 51645448 | + | 51635991 | 51637836 | MRX1 = IQSEC2 |
| 91784323 | 91787522 | − | CUFF.14462.8 | seg_1915 | 91782700 | 91784350 | M | chrX | 51636562 | 51639796 | + | 51639769 | 51641672 | MRX1 = IQSEC2 |
| 91784323 | 91787522 | − | CUFF.14462.8 | seg_1916 | 91786200 | 91788100 | M | chrX | 51636562 | 51639796 | + | 51635991 | 51637836 | MRX1 = IQSEC2 |
| 91792302 | 91792908 | − | ENSMUST00000119908 | seg_1917 | 91791500 | 91792700 | M | other | 0 | 0 | + | 0 | 0 | OA1 = GPR143 |
| 91792302 | 91792908 | − | ENSMUST00000119908 | seg_1917 | 91791500 | 91792700 | M | other | 0 | 0 | + | 0 | 0 | OA1 = GPR143 |
| 91881387 | 91888583 | + | CUFF.14550.1 | seg_1921 | 91880500 | 91882850 | M | chrX | 51486509 | 51491404 | + | 51485472 | 51487965 | CLCN5 |
| 91881387 | 91888583 | + | CUFF.14550.1 | seg_65 | 91881050 | 91882300 | S | chrX | 51486509 | 51491404 | + | 51485154 | 51487415 | CLCN5 |
| 91881415 | 91888583 | + | ENSMUST00000137033 | seg_1921 | 91880500 | 91882850 | M | chrX | 51486537 | 51491404 | + | 51485472 | 51487965 | CLCN5 |
| 91881415 | 91888583 | + | ENSMUST00000137033 | seg_65 | 91881050 | 91882300 | S | chrX | 51486537 | 51491404 | + | 51486154 | 51487415 | CLCN5 |
| 91916842 | 91918459 | − | ENSMUST00000119588 | seg_1926 | 91916750 | 91920300 | M | other | 0 | 0 | + | 0 | 0 | OA1 = GPR143 |
| 91916842 | 91918459 | − | ENSMUST00000119588 | seg_1926 | 91916750 | 91920300 | M | other | 0 | 0 | + | 0 | 0 | OA1 = GPR143 |
| 92017958 | 92019373 | − | ENSMUST00000118127 | seg_1931 | 92019100 | 92020400 | M | other | 0 | 0 | + | 0 | 0 | OA1 = GPR143 |
| 92017958 | 92019373 | − | ENSMUST00000118127 | seg_1931 | 92019100 | 92020400 | M | other | 0 | 0 | + | 0 | 0 | OA1 = GPR143 |
| 92020317 | 92021016 | − | ENSMUST00000121899 | seg_1931 | 92019100 | 92020400 | M | other | 0 | 0 | + | 0 | 0 | OA1 = GPR143 |
| 92020317 | 92021016 | − | ENSMUST00000121899 | seg_1931 | 92019100 | 92020400 | M | other | 0 | 0 | + | 0 | 0 | OA1 = GPR143 |
| 92035056 | 92035685 | + | ENSMUST00000117813 | seg_1932 | 92035250 | 92039800 | M | other | 0 | 0 | + | 0 | 0 | OA1 = GPR143 |
| 92035056 | 92035685 | + | ENSMUST00000117813 | seg_1932 | 92035250 | 92039800 | M | other | 0 | 0 | + | 0 | 0 | OA1 = GPR143 |
| 92038442 | 92043576 | + | ENSMUST00000057963 | seg_1932 | 92035250 | 92039800 | M | chrX | 57931970 | 57936908 | + | 0 | 0 | ALAS2 |
| 92907017 | 93120097 | + | ENSMUST00000150123 | seg_1970 | 92906500 | 92907900 | M | other | 0 | 0 | + | 64253522 | 64255559 | OA1 = GPR143 |
| 92907017 | 93120097 | + | ENSMUST00000150123 | seg_1970 | 92905500 | 92907900 | M | other | 0 | 0 | + | 64253522 | 64255559 | OA1 = GPR143 |
| 93291330 | 93363894 | + | CUFF.14565.1 | seg_1985 | 93291150 | 93293200 | M | chrX | 64887470 | 64961795 | + | 64887278 | 64888973 | AR |
| 93291330 | 93363894 | + | CUFF.14565.2 | seg_1985 | 93291150 | 93293200 | M | chrX | 64887470 | 64961795 | + | 64887278 | 64888973 | AR |
| 96132488 | 96144356 | + | CUFF.14576.2 | seg_2066 | 96130800 | 96134100 | M | chrX | 67718666 | 67757125 | + | 67717473 | 67719790 | AR |
| 96132695 | 96144356 | + | CUFF.14576.5 | seg_2066 | 96130800 | 96134100 | M | chrX | 67718666 | 67757125 | + | 67717473 | 67719790 | AR |
| 96133100 | 96140245 | + | ENSMUST00000149082 | seg_2066 | 96130800 | 96134100 | M | chrX | 67718666 | 67751756 | + | 67717473 | 67719790 | AR |
| 96237920 | 96270067 | + | CUFF.14578.2 | seg_2070 | 96236650 | 96240350 | M | chrX | 67913429 | 67945678 | − | 67911949 | 67915944 | ED1 = EDA |
| 96237920 | 96265783 | + | CUFF.14486.3 | seg_2070 | 96236650 | 96240350 | M | chrX | 67913429 | 67942045 | − | 67911949 | 67915944 | ED1 = EDA |
| 96331411 | 96344330 | + | CUFF.14577.2 | seg_2076 | 96329150 | 96335250 | M | chrX | 68048806 | 68061977 | − | 68046540 | 68052833 | ED1 = EDA |
| 96331411 | 96344330 | + | CUFF.14577.1 | seg_2076 | 96329150 | 96335250 | M | chrX | 68048806 | 68061977 | − | 68046540 | 68052833 | ED1 = EDA |
| 96509316 | 96509440 | + | CUFF.14581.1 | seg_2092 | 96508650 | 96510100 | M | chrX | 68233310 | 68233735 | − | 68232377 | 68234110 | ED1 = EDA |
| 96600670 | 96639136 | + | CUFF.14585.1 | seg_2105 | 96638050 | 96640450 | M | chrX | 68316315 | 68357637 | − | 68356517 | 68358498 | ED1 = EDA |
| 96600670 | 96639136 | − | ENSMUST00000156494 | seg_69 | 96638500 | 96639900 | S | chrX | 68316315 | 68357637 | − | 68356970 | 68359344 | ED1 = EDA |
| 96600670 | 96639136 | − | ENSMUST00000156494 | seg_2105 | 96638050 | 96640450 | M | chrX | 68316315 | 68357637 | − | 68356517 | 68358498 | ED1 = EDA |
| 96600670 | 96639136 | − | ENSMUST00000156494 | seg_69 | 96638500 | 96639900 | S | chrX | 68316315 | 68357637 | − | 68356970 | 68359344 | ED1 = EDA |
| 97015446 | 97015868 | + | CUFF.14585.1 | seg_2130 | 97013850 | 97018550 | M | chrX | 68724170 | 68724592 | − | 68722532 | 68727304 | ED1 = EDA |
| 97015934 | 97016205 | + | CUFF.14494.1 | seg_2130 | 97013850 | 97018550 | M | chrX | 68724653 | 68724923 | − | 68722532 | 68727304 | ED1 = EDA |
| 97016120 | 97016273 | + | CUFF.14493.1 | seg_2130 | 97013850 | 97018550 | M | chrX | 68724838 | 68724991 | + | 68722532 | 68727304 | ED1 = EDA |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 97170822 | 97506638 | + | CUFF.14505.2 | seg_2136 | 97168850 | 97172800 | M | chrX | 68835853 | 69179424 | + | 68833901 | 68837825 | ED1 = EDA |
| 97170822 | 97596101 | + | CUFF.14505.1 | seg_2136 | 97168850 | 97172800 | M | chrX | 68835853 | 69259315 | + | 68833901 | 68837825 | ED1 = EDA |
| 97170904 | 97596101 | + | CUFF.14597.1 | seg_2136 | 97168850 | 97172800 | M | chrX | 68835936 | 69259315 | + | 68833901 | 68837825 | ED1 = EDA |
| 97170904 | 97596101 | + | CUFF.14597.1 | seg_71 | 97170850 | 97172350 | S | chrX | 68835936 | 69259315 | + | 68835881 | 68837401 | ED1 = EDA |
| 97925212 | 97927787 | + | ENSMUST00000144912 | seg_2169 | 97927300 | 97928500 | M | chrX | 69642906 | 69645256 | + | 69644718 | 69645993 | GJB1 |
| 97925212 | 97927787 | + | ENSMUST00000144912 | seg_2169 | 97927300 | 97928500 | M | chrX | 69642906 | 69645256 | + | 69644718 | 69645993 | GJB1 |
| 97962972 | 97982921 | − | CUFF.14507.1 | seg_2171 | 97962150 | 97963800 | M | chrX | 69664586 | 69686006 | − | 69663824 | 69665432 | GJB1 |
| 97962972 | 97972554 | − | CUFF.14507.2 | seg_2171 | 97962150 | 97963800 | M | chrX | 69664586 | 69674956 | − | 69663824 | 69665432 | GJB1 |
| 97968278 | 97968379 | − | CUFF.14599.1 | seg_2172 | 97964500 | 97968300 | M | chrX | 69670135 | 69670233 | − | 69968211 | 69670157 | GJB1 |
| 98254344 | 98254631 | − | ENSMUST00000119001 | seg_2185 | 98253850 | 98256950 | M | other | 0 | 0 | + | 0 | 0 | OA1 = GPR143 |
| 98449812 | 98456212 | + | CUFF.14512.1 | seg_2194 | 98449350 | 98457550 | M | chrX | 70316012 | 70323383 | + | 70315553 | 70324518 | GJB1 |
| 98835383 | 98849934 | + | CUFF.14619.1 | seg_2212 | 98834700 | 98836650 | M | chrX | 70752905 | 70766816 | + | 70751717 | 70753489 | GJB1 |
| 98835383 | 98849934 | + | CUFF.14619.1 | seg_74 | 98834700 | 98835950 | S | chrX | 70752905 | 70766816 | + | 70752200 | 70754177 | GJB1 |
| 98835399 | 98849983 | + | CUFF.14523.2 | seg_2212 | 98834700 | 98836650 | M | chrX | 70752921 | 70766864 | + | 70751717 | 70753489 | GJB1 |
| 98835399 | 98849983 | + | CUFF.14523.2 | seg_74 | 98834700 | 98835950 | S | chrX | 70752921 | 70766864 | + | 70752200 | 70754177 | GJB1 |
| 98835952 | 98836294 | + | CUFF.14620.1 | seg_2212 | 98834700 | 98836650 | M | chrX | 70753491 | 70753847 | + | 70751717 | 70754177 | GJB1 |
| 98866564 | 98988647 | − | ENSMUST00000056225 | seg_2222 | 98983950 | 98987350 | M | chrX | 70883692 | 70885694 | − | 70883129 | 70884479 | GJB1 |
| 98986564 | 98988647 | − | ENSMUST00000056225 | seg_2222 | 98985950 | 98987350 | M | chrX | 70883692 | 70885694 | − | 70883129 | 70884479 | GJB1 |
| 99044721 | 99287394 | + | CUFF.14621.1 | seg_2226 | 99040300 | 99051650 | M | chrX | 71130717 | 71373136 | + | 71125932 | 71136845 | GJB1 |
| 99044721 | 99287394 | + | CUFF.14621.1 | seg_2245 | 99286300 | 99288050 | M | chrX | 71130717 | 71373136 | + | 71372238 | 71373440 | GJB1 |
| 99044721 | 99287394 | + | CUFF.14621.1 | seg_77 | 99044000 | 99047000 | S | chrX | 71130717 | 71373136 | + | 71129999 | 71133070 | GJB1 |
| 99044724 | 99144974 | + | ENSMUST00000125115 | seg_2226 | 99040300 | 99051650 | M | chrX | 71130720 | 71230692 | + | 71125932 | 71136845 | GJB1 |
| 99044724 | 99144974 | + | ENSMUST00000125115 | seg_77 | 99044000 | 99047000 | S | chrX | 71130720 | 71230692 | + | 71129999 | 71133070 | GJB1 |
| 99044724 | 99358449 | + | ENSMUST00000133472 | seg_77 | 99044000 | 99047000 | S | chrX | 71130720 | 71230692 | + | 71129999 | 71133070 | GJB1 |
| 99337055 | 99352453 | − | CUFF.14618.1 | seg_2248 | 99352000 | 99354000 | M | chrX | 71423283 | 71458939 | − | 71458371 | 71460230 | GJB1 |
| 99337055 | 99352458 | − | CUFF.14618.2 | seg_2248 | 99352000 | 99354000 | M | chrX | 71423238 | 71458939 | − | 71458371 | 71460230 | GJB1 |
| 99709314 | 99839595 | − | CUFF.14533.2 | seg_2272 | 99838800 | 99841900 | M | chrX | 71798692 | 71934148 | − | 71933638 | 71937216 | GJB1 |
| 99750118 | 99839585 | − | CUFF.14637.7 | seg_2272 | 99838800 | 99841900 | M | chrX | 71838498 | 71934132 | − | 71933638 | 71937216 | GJB1 |
| 100355529 | 100360903 | + | CUFF.14548.1 | seg_2304 | 100359250 | 100361100 | M | other | 0 | 0 | + | 0 | 0 | OA1 = GPR143 |
| 100358233 | 100360766 | − | ENSMUST00000087891 | seg_2304 | 100359250 | 100361100 | M | other | 0 | 0 | + | 0 | 0 | OA1 = GPR143 |
| 100358233 | 100360766 | − | ENSMUST00000087891 | seg_2304 | 100359250 | 100361100 | M | other | 0 | 0 | + | 0 | 0 | OA1 = GPR143 |
| 100358449 | 100360746 | − | ENSMUST00000125115 | seg_2304 | 100359250 | 100361100 | M | other | 0 | 0 | + | 0 | 0 | OA1 = GPR143 |
| 100618468 | 100618584 | + | CUFF.14618.1 | seg_2317 | 100617500 | 100619350 | M | other | 0 | 0 | + | 0 | 0 | OA1 = GPR143 |
| 100724822 | 100725046 | − | ENSMUST00000117673 | seg_2323 | 100724000 | 100725850 | M | other | 0 | 0 | + | 0 | 0 | OA1 = GPR143 |
| 100891328 | 100891351 | + | CUFF.14559.1 | seg_2326 | 100885800 | 100893650 | M | chrX | 73755234 | 73755237 | − | 73752844 | 73758155 | ABCB7 |
| 101162901 | 101176626 | − | CUFF.14563.3 | seg_2349 | 101177750 | 101177750 | M | chrX | 73816770 | 73834464 | − | 73822504 | 73835755 | ABCB7 |
| 101162901 | 101176626 | − | CUFF.14563.3 | seg_86 | 101175150 | 101176300 | S | chrX | 73816770 | 73834464 | − | 73832957 | 73834636 | ABCB7 |
| 101272773 | 101396532 | + | CUFF.14564.2 | seg_2362 | 101392900 | 101398450 | M | chrX | 73953408 | 74145290 | + | 74141968 | 74147202 | ABCB7 |
| 101272773 | 101396549 | + | CUFF.14668.2 | seg_2362 | 101392900 | 101398450 | M | chrX | 73953408 | 74145305 | + | 74141968 | 74147202 | ABCB7 |
| 101396608 | 101396824 | − | CUFF.14673.1 | seg_2362 | 101392900 | 101398450 | M | chrX | 74145376 | 74145592 | − | 74141968 | 74147202 | ABCB7 |
| 101531844 | 101543844 | − | CUFF.14676.1 | seg_2367 | 101528100 | 101532450 | M | other | 0 | 0 | + | 0 | 0 | OA1 = GPR143 |
| 101531844 | 101543844 | − | CUFF.14676.1 | seg_2368 | 101541300 | 101544300 | M | other | 0 | 0 | + | 0 | 0 | OA1 = GPR143 |
| 101543168 | 101543573 | − | ENSMUST00000120233 | seg_2368 | 101541300 | 101544300 | M | other | 0 | 0 | + | 0 | 0 | OA1 = GPR143 |
| 101941821 | 101942111 | − | ENSMUST00000122247 | seg_2393 | 101941250 | 101943000 | M | other | 0 | 0 | + | 0 | 0 | OA1 = GPR143 |
| 101941821 | 101942111 | + | ENSMUST00000122247 | seg_2393 | 101941250 | 101943000 | M | other | 0 | 0 | + | 0 | 0 | OA1 = GPR143 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 102143124 | 102143621 | + | ENSMUST00000122012 | seg_2402 | 102141200 | 102143500 | M | other | 0 | 0 | + | 0 | 0 | OA1 = GPR143 |
| 102143124 | 102143621 | + | ENSMUST00000122012 | seg_2402 | 102141200 | 102143500 | M | other | 0 | 0 | + | 0 | 0 | OA1 = GPR143 |
| 102227925 | 102228705 | + | ENSMUST00000119287 | seg_2410 | 102228100 | 102229200 | M | other | 0 | 0 | + | 0 | 0 | OA1 = GPR143 |
| 102227925 | 102228705 | + | ENSMUST00000119287 | seg_2410 | 102228100 | 102229200 | M | other | 0 | 0 | + | 0 | 0 | OA1 = GPR143 |
| 102920467 | 102920853 | − | ENSMUST00000071515 | seg_2434 | 102920350 | 102921650 | M | other | 0 | 0 | + | 0 | 0 | OA1 = GPR143 |
| 102920467 | 102920853 | − | ENSMUST00000071515 | seg_2434 | 102920350 | 102921650 | M | other | 0 | 0 | + | 0 | 0 | OA1 = GPR143 |
| 103106842 | 103124685 | + | ENSMUST00000126345 | seg_2443 | 103106750 | 103108550 | M | chrX | 76995795 | 77041698 | − | 76995713 | 77031704 | ATRX |
| 103555795 | 103579410 | − | ENSMUST00000122015 | seg_2457 | 103554800 | 103556200 | M | chrX | 77422903 | 77428610 | + | 0 | 0 | PGK1 |
| 103828136 | 103828642 | + | ENSMUST00000117308 | seg_2469 | 103326550 | 103828400 | M | other | 0 | 0 | + | 0 | 0 | OA1 = GPR143 |
| 106030003 | 106034841 | + | ENSMUST00000145250 | seg_2523 | 106034050 | 106035400 | M | chrX | 80065639 | 80068874 | + | 0 | 0 | PGK1 |
| 106030003 | 106034841 | + | ENSMUST00000145250 | seg_2523 | 106034050 | 106035400 | M | chrX | 80065639 | 80068874 | + | 0 | 0 | PGK1 |
| 106196824 | 106197635 | + | ENSMUST00000120648 | seg_2527 | 106195700 | 106197350 | M | other | 0 | 0 | − | 0 | 0 | OA1 = GPR143 |
| 106196824 | 106197635 | + | ENSMUST00000120648 | seg_2527 | 106195700 | 106197350 | M | other | 0 | 0 | − | 0 | 0 | OA1 = GPR143 |
| 109008832 | 109008863 | − | CUFF.14605.1 | seg_2583 | 109005500 | 109010500 | M | other | 0 | 0 | + | 0 | 0 | OA1 = GPR143 |
| 109714135 | 109739682 | + | ENSMUST00000151972 | seg_2608 | 109707900 | 109717600 | M | chrX | 84498794 | 84521473 | − | 84495478 | 84502272 | CHM |
| 109935831 | 109936305 | − | ENSMUST00000117144 | seg_2615 | 109934350 | 109936000 | M | other | 0 | 0 | + | 0 | 0 | OA1 = GPR143 |
| 110411861 | 110869443 | + | ENSMUST00000146539 | seg_2622 | 110410900 | 110414150 | M | chrX | 85403464 | 85999861 | + | 85402511 | 85405628 | CHM |
| 123984075 | 123984154 | + | CUFF.14747.1 | seg_2699 | 123983400 | 123985350 | M | other | 0 | 0 | + | 0 | 0 | OA1 = GPR143 |
| 126284278 | 126577066 | + | CUFF.14645.2 | seg_2714 | 126283350 | 126285600 | M | chrX | 95939805 | 96319018 | + | 95938881 | 95941157 | BTK |
| 126284278 | 126577066 | + | CUFF.14645.2 | seg_95 | 126283950 | 126284950 | S | chrX | 95939805 | 96319018 | + | 95939522 | 95940514 | BTK |
| 126284278 | 126284832 | + | CUFF.14757.2 | seg_2714 | 126283350 | 126285600 | M | chrX | 95939805 | 95940396 | + | 95938881 | 95941157 | BTK |
| 126284278 | 126284832 | + | CUFF.14757.2 | seg_95 | 126283950 | 126284950 | S | chrX | 95939805 | 95940396 | + | 95939522 | 95940514 | BTK |
| 126284360 | 126863066 | + | ENSMUST00000155333 | seg_2714 | 126283350 | 126285600 | M | chrX | 95939886 | 96685244 | + | 95938881 | 95941157 | BTK |
| 126284360 | 126863066 | + | ENSMUST00000155333 | seg_95 | 126283950 | 126284950 | S | chrX | 95939886 | 96685244 | + | 95939522 | 95940514 | BTK |
| 130117402 | 130223532 | + | CUFF.14649.2 | seg_2793 | 130215450 | 130229700 | M | chrX | 99546628 | 99665277 | − | 99657327 | 99671435 | BTK |
| 130117402 | 130223532 | + | CUFF.14649.2 | seg_96 | 130218250 | 130227050 | S | chrX | 99546628 | 99665277 | − | 99660156 | 99668596 | BTK |
| 130155559 | 130223532 | − | CUFF.14760.5 | seg_2793 | 130215450 | 130229700 | M | chrX | 99657457 | 99665277 | − | 99657457 | 99671435 | BTK |
| 130155559 | 130223532 | − | CUFF.14760.5 | seg_96 | 130218250 | 130227050 | S | chrX | 99657457 | 99665277 | − | 99660156 | 99668596 | BTK |
| 130470924 | 130516351 | + | CUFF.14761.3 | seg_2806 | 130514450 | 130517050 | M | chrX | 99929475 | 99987138 | + | 99985303 | 99987553 | BTK |
| 130470924 | 130516351 | + | CUFF.14761.3 | seg_97 | 130515100 | 130516400 | S | chrX | 99929475 | 99987138 | + | 99985954 | 99987187 | BTK |
| 131004413 | 131009527 | + | ENSMUST00000170828 | seg_2826 | 131008100 | 131010000 | M | chrX | 100536586 | 100543536 | + | 100543536 | 100546418 | BTK |
| 131120171 | 131122601 | − | ENSMUST00000117957 | seg_2832 | 131119150 | 131121200 | M | chrX | 100643947 | 100646314 | + | 100644952 | 100646916 | BTK |
| 131120229 | 131122601 | − | ENSMUST00000117957 | seg_2832 | 131119150 | 131121200 | M | chrX | 100646005 | 100646543 | + | 100644952 | 100646916 | BTK |
| 131216059 | 131216416 | + | ENSMUST00000117957 | seg_2837 | 131214300 | 131216200 | M | chrX | 100646005 | 100650827 | + | 0 | 0 | BTK |
| 131216059 | 131216416 | + | ENSMUST00000117957 | seg_2837 | 131214300 | 131216200 | M | other | 0 | 0 | + | 0 | 0 | OA1 = GPR143 |
| 131223346 | 131231296 | + | CUFF.14776.1 | seg_2838 | 131220750 | 131223850 | M | chrX | 100742982 | 100750790 | + | 100740062 | 100743543 | GLA |
| 131282994 | 131285982 | − | CUFF.14778.2 | seg_2844 | 131283700 | 131286250 | M | chrX | 100870107 | 100872989 | + | 100870694 | 100873309 | GLA |
| 131291106 | 131295994 | + | CUFF.14779.1 | seg_2845 | 131290750 | 131295500 | M | chrX | 100878100 | 100882831 | + | 100877742 | 100882345 | GLA |
| 132277243 | 132332177 | + | CUFF.14679.2 | seg_2894 | 132276800 | 132278550 | M | chrX | 101854484 | 101907684 | + | 101853975 | 101855890 | GLA |
| 132277243 | 132336941 | + | CUFF.14679.1 | seg_2894 | 132276800 | 132278550 | M | chrX | 101854484 | 101912334 | + | 101853975 | 101855890 | GLA |
| 132330954 | 132331138 | + | CUFF.14680.1 | seg_2897 | 132330100 | 132331650 | M | chrX | 101906632 | 101906814 | + | 101905772 | 101907266 | GLA |
| 132331073 | 132331146 | + | CUFF.14836.1 | seg_2897 | 132330100 | 132331650 | M | chrX | 101906746 | 101906822 | + | 101905772 | 101907266 | GLA |
| 132673507 | 132674982 | + | CUFF.14803.1 | seg_2913 | 132672500 | 132674100 | M | chrX | 102469998 | 102471683 | + | 102469706 | 102470657 | GLA |
| 133243165 | 133246017 | + | CUFF.14802.2 | seg_2936 | 133242550 | 133244400 | M | chrX | 102884653 | 102887080 | + | 102883877 | 102885870 | GLA |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 133535557 | 133572844 | - | CUFF.14810.7 | seg_2948 | 133571250 | 133573150 | M | chrX | 103373884 | 103402391 | - | 0 | 103402391 | TBG = SERPINA7 |
| 133535594 | 133572841 | - | ENSMUST00000145842 | seg_2948 | 133571250 | 133573150 | M | chrX | 103373384 | 0 | - | 0 | 0 | OA1 = GPR143 |
| 133549811 | 133572838 | - | ENSMUST00000148253 | seg_2948 | 133571250 | 133573150 | M | chrX | 103381078 | 103402391 | - | 0 | 0 | TBG = SERPINA7 |
| 133566334 | 133572841 | + | ENSMUST00000132171 | seg_2948 | 133571250 | 133573150 | S | other | 0 | 0 | + | 0 | 0 | OA1 = GPR143 |
| 133634055 | 133634641 | + | ENSMUST00000119317 | seg_101 | 133633550 | 133635650 | M | other | 0 | 0 | + | 0 | 0 | OA1 = GPR143 |
| 133634055 | 133634641 | + | ENSMUST00000119317 | seg_101 | 133633550 | 133635650 | S | other | 0 | 0 | + | 0 | 0 | OA1 = GPR143 |
| 133634055 | 133634641 | + | ENSMUST00000119317 | seg_2950 | 133632500 | 133641950 | M | other | 0 | 0 | + | 0 | 0 | OA1 = GPR143 |
| 133638428 | 133639261 | + | ENSMUST00000119238 | seg_102 | 133638950 | 133640150 | S | other | 0 | 0 | + | 48779300 | 48780883 | OA1 = GPR143 |
| 133638428 | 133639261 | + | ENSMUST00000119238 | seg_102 | 133638950 | 133640150 | M | other | 0 | 0 | + | 0 | 0 | OA1 = GPR143 |
| 133638428 | 133639261 | + | ENSMUST00000119238 | seg_2950 | 133632500 | 133641950 | S | other | 0 | 0 | + | 48779300 | 48780883 | OA1 = GPR143 |
| 133638428 | 133639261 | + | ENSMUST00000119238 | seg_2950 | 133632500 | 133641950 | M | other | 0 | 0 | + | 0 | 0 | OA1 = GPR143 |
| 133641785 | 133642659 | + | ENSMUST00000118914 | seg_2950 | 133632500 | 133641950 | M | other | 0 | 0 | + | 0 | 0 | OA1 = GPR143 |
| 133641785 | 133642659 | + | ENSMUST00000118914 | seg_2950 | 133632500 | 133641950 | M | chrX | 0 | 0 | + | 0 | 0 | OA1 = GPR143 |
| 133645879 | 133647421 | + | ENSMUST00000118843 | seg_2951 | 133646250 | 133647850 | M | other | 0 | 0 | + | 0 | 0 | OA1 = GPR143 |
| 133645879 | 133647421 | + | ENSMUST00000118843 | seg_2951 | 133646250 | 133647850 | M | chrX | 0 | 0 | + | 0 | 0 | OA1 = GPR143 |
| 133662649 | 133664374 | + | ENSMUST00000118561 | seg_2953 | 133661400 | 133663150 | M | other | 0 | 0 | + | 0 | 0 | OA1 = GPR143 |
| 133810152 | 133810286 | - | CUFF.14819.1 | seg_2959 | 133809900 | 133811050 | M | other | 0 | 0 | + | 0 | 0 | OA1 = GPR143 |
| 134105558 | 135040850 | + | ENSMUST00000130879 | seg_104 | 134103900 | 134107150 | S | chrX | 103811122 | 104731475 | + | 103809534 | 103812755 | TBG = SERPINA7 |
| 134105558 | 135040850 | + | ENSMUST00000130879 | seg_104 | 134103900 | 134107150 | M | chrX | 103811122 | 104731475 | + | 103808956 | 103813140 | TBG = SERPINA7 |
| 134105558 | 135040850 | + | ENSMUST00000130879 | seg_2967 | 134103350 | 134107500 | S | chrX | 103811122 | 104731475 | + | 103809534 | 103812755 | TBG = SERPINA7 |
| 134105558 | 135040850 | + | ENSMUST00000130879 | seg_2967 | 134103350 | 134107500 | M | chrX | 103811122 | 104731475 | + | 103808956 | 103813140 | TBG = SERPINA7 |
| 134966460 | 134966551 | - | CUFF.14828.1 | seg_2993 | 134966500 | 134967950 | M | other | 0 | 0 | + | 104662179 | 104663764 | OA1 = GPR143 |
| 135448948 | 155545071 | + | CUFF.14822.1 | seg_3007 | 155446400 | 155451500 | M | chrX | 105066516 | 105202602 | + | 105063912 | 105069173 | TBG = SERPINA7 |
| 135448948 | 155524317 | + | CUFF.14822.2 | seg_3007 | 155446400 | 155451500 | M | chrX | 105066516 | 105178759 | + | 105063912 | 105069173 | TBG = SERPINA7 |
| 135448953 | 155545071 | + | CUFF.14710.1 | seg_3007 | 155446400 | 155451500 | M | chrX | 105066521 | 105202502 | + | 105063912 | 105069173 | TBG = SERPINA7 |
| 135882030 | 135892277 | - | ENSMUST00000126591 | seg_3021 | 135891400 | 135893050 | M | chrX | 105625325 | 105639361 | - | 105638898 | 105639361 | TBG = SERPINA7 |
| 135882030 | 135892277 | - | ENSMUST00000126591 | seg_3021 | 135891400 | 135893050 | M | chrX | 105625325 | 105639361 | + | 105638898 | 105639361 | TBG = SERPINA7 |
| 135893007 | 135893796 | + | ENSMUST00000122380 | seg_3021 | 135891400 | 135893050 | M | other | 0 | 0 | + | 105638898 | 105639361 | OA1 = GPR143 |
| 136144963 | 136145837 | + | ENSMUST00000113029 | seg_3030 | 136144350 | 136147100 | S | chrX | 105970772 | 105970636 | + | 105969146 | 105971877 | TBG = SERPINA7 |
| 136145906 | 136206280 | + | ENSMUST00000113029 | seg_3030 | 136144350 | 136147100 | M | chrX | 105970704 | 106003816 | + | 105969146 | 105971877 | TBG = SERPINA7 |
| 136219520 | 136287944 | - | CUFF.14832.1 | seg_3034 | 136218150 | 136224400 | M | chrX | 106045891 | 106118691 | - | 106044392 | 106050619 | TBG = SERPINA7 |
| 136224009 | 136224144 | + | CUFF.14834.1 | seg_3034 | 136218150 | 136224400 | M | other | 0 | 0 | + | 106044392 | 106050619 | OA1 = GPR143 |
| 136541344 | 136597251 | - | CUFF.14340.2 | seg_107 | 136594950 | 136598150 | S | chrX | 106366669 | 106449677 | - | 48661090 | 43663232 | PRPS1 |
| 136541344 | 136597251 | - | CUFF.14840.2 | seg_3049 | 136592300 | 136602000 | M | chrX | 106366669 | 106449677 | - | 106445400 | 106454986 | PRPS1 |
| 136991152 | 136999981 | + | ENSMUST00000155235 | seg_3081 | 136989950 | 136993450 | M | chrX | 106871733 | 106882715 | + | 106870757 | 106873713 | PRPS1 |
| 136991152 | 136999981 | + | ENSMUST00000155235 | seg_3081 | 136989950 | 136993450 | M | chrX | 106871733 | 106882715 | + | 106870757 | 106873713 | PRPS1 |
| 137074067 | 137077207 | + | ENSMUST00000112995 | seg_3088 | 137074650 | 137078000 | M | chrX | 106956451 | 106959745 | + | 106956989 | 106960573 | PRPS1 |
| 137074067 | 137133980 | - | CUFF.14847.2 | seg_109 | 137131450 | 137137100 | S | chrX | 106956451 | 107019412 | - | 107017134 | 107022121 | PRPS1 |
| 137074067 | 137133980 | - | CUFF.14847.2 | seg_3092 | 137131200 | 137137750 | M | chrX | 106956451 | 107019412 | - | 107016847 | 107022121 | PRPS1 |
| 137077642 | 137083068 | + | ENSMUST00000152048 | seg_3088 | 137074650 | 137078000 | M | chrX | 106960212 | 106965429 | + | 106956989 | 106960573 | PRPS1 |
| 137199310 | 137330254 | + | CUFF.14734.2 | seg_3098 | 137198450 | 137202100 | M | chrX | 107069159 | 107174866 | + | 107068335 | 107072988 | PRPS1 |
| 137199472 | 137330254 | + | CUFF.14852.2 | seg_3098 | 137198450 | 137202100 | M | chrX | 107069322 | 107174866 | + | 107068335 | 107072988 | PRPS1 |
| 137356477 | 137357062 | - | ENSMUST00000116438 | seg_3111 | 137353950 | 137357900 | M | other | 0 | 0 | + | 0 | 0 | OA1 = GPR143 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 137356477 | 137357062 | − | ENSMUST00000116438 | seg_3111 | 137353950 | 137357900 | M | other | 0 | 0 | | 0 | 0 | OA1 = GPR143 |
| 137599946 | 137764377 | − | CUFF.14856.2 | seg_3124 | 137598500 | 137600100 | M | chrX | 107398844 | 107554980 | + | 107397620 | 107399000 | COL4A5 |
| 137599946 | 137642145 | − | CUFF.14856.4 | seg_3124 | 137598500 | 137600100 | M | chrX | 107398844 | 107438474 | − | 107397620 | 107399000 | COL4A5 |
| 137599946 | 137908628 | − | CUFF.14856.3 | seg_3124 | 137598500 | 137600100 | M | chrX | 107398844 | 107681685 | − | 107397620 | 107399000 | COL4A5 |
| 137909928 | 138123778 | + | CUFF.14860.3 | seg_3145 | 137909200 | 137911500 | M | chrX | 107683031 | 107940825 | + | 107682283 | 107684615 | COL4A5 |
| 137909928 | 138123778 | + | CUFF.14860.2 | seg_3145 | 137909200 | 137911500 | M | chrX | 107683031 | 107940825 | + | 107682283 | 107684615 | COL4A5 |
| 137909928 | 138123778 | + | CUFF.14737.2 | seg_3145 | 137909200 | 137911500 | M | chrX | 107683031 | 107940825 | + | 107682283 | 107684615 | COL4A5 |
| 137909928 | 138123778 | + | CUFF.14860.6 | seg_3145 | 137909200 | 137911500 | M | chrX | 107683031 | 107940825 | + | 107682283 | 107684615 | COL4A5 |
| 137910111 | 138063011 | + | ENSMUST00000118845 | seg_3145 | 138061650 | 138063400 | M | other | 0 | 0 | | 0 | 0 | OA1 = GPR143 |
| 138062502 | 138304675 | + | ENSMUST00000074490 | seg_3158 | 138304550 | 138305700 | M | other | 0 | 0 | | 0 | 0 | OA1 = GPR143 |
| 138304947 | 138733073 | + | ENSMUST00000117081 | seg_3177 | 138732100 | 138734000 | M | other | 0 | 0 | | 0 | 0 | OA1 = GPR143 |
| 138732108 | 138733073 | + | ENSMUST00000117081 | seg_3195 | 138732100 | 138734000 | M | other | 0 | 0 | | 0 | 0 | OA1 = GPR143 |
| 138732108 | 138821158 | + | CUFF.14867.1 | seg_3195 | 138820350 | 138822000 | M | chrX | 108973213 | 108973350 | − | 108972909 | 108973901 | COL4A5 |
| 138820850 | 139057445 | − | ENSMUST00000118547 | seg_3202 | 139057050 | 139058750 | M | other | 0 | 0 | | 0 | 0 | OA1 = GPR143 |
| 139057035 | 139057445 | − | ENSMUST00000118547 | seg_3217 | 139057050 | 139058750 | M | other | 0 | 0 | | 0 | 0 | OA1 = GPR143 |
| 139057035 | 139068558 | − | CUFF.14862.1 | seg_3217 | 139065800 | 139069750 | M | other | 0 | 0 | | 0 | 0 | OA1 = GPR143 |
| 139065646 | 139068558 | − | ENSMUST00000155951 | seg_3219 | 139065800 | 139069750 | M | other | 0 | 0 | | 0 | 0 | OA1 = GPR143 |
| 139066026 | 139401362 | − | CUFF.14750.2 | seg_3219 | 139399350 | 139403250 | M | chrX | 109437413 | 109561405 | − | 109559439 | 109563236 | COL4A5 |
| 139285689 | 139401386 | − | CUFF.14865.1 | seg_3235 | 139399350 | 139403250 | M | chrX | 109437413 | 109561427 | − | 109559439 | 109563236 | COL4A5 |
| 139285689 | 139830157 | − | CUFF.14869.1 | seg_3254 | 139827450 | 139830300 | M | chrX | 110040716 | 110040731 | − | 110038100 | 110040925 | COL4A5 |
| 139830092 | 140232335 | + | CUFF.14876.1 | seg_3262 | 139952800 | 139955200 | M | chrX | 110187602 | 110470586 | + | 110187318 | 110189585 | COL4A5 |
| 139955067 | 140100407 | − | CUFF.14876.6 | seg_3267 | 140099200 | 140101150 | M | chrX | 110339366 | 110340933 | + | 110339683 | 110341701 | COL4A5 |
| 140098882 | 141122546 | − | ENSMUST00000148240 | seg_117 | 141121300 | 141125200 | M | chrX | 111039581 | 111325310 | − | 111324058 | 111328035 | COL4A5 |
| 140853218 | 141122546 | − | ENSMUST00000148240 | seg_3309 | 141119500 | 141127700 | M | chrX | 111089581 | 111325310 | + | 111322217 | 111330457 | COL4A5 |
| 140989754 | 140990880 | − | ENSMUST00000117991 | seg_3304 | 140990450 | 140992200 | M | chrX | 35820375 | 35821357 | + | 0 | 0 | XK |
| 141880968 | 141939813 | − | CUFF.14766.4 | seg_3343 | 141938500 | 141942750 | M | chrX | 112018106 | 112084182 | − | 112083066 | 112087861 | COL4A5 |
| 143904918 | 143988678 | − | CUFF.14892.1 | seg_3386 | 143988000 | 143989850 | M | chrX | 114345174 | 114468689 | + | 114468015 | 114469855 | COL4A5 |
| 143919223 | 143988699 | − | CUFF.14773.9 | seg_3386 | 143988000 | 143989850 | M | chrX | 114361317 | 114468712 | + | 114468015 | 114469855 | COL4A5 |
| 143943353 | 143988678 | − | CUFF.14892.10 | seg_3386 | 143988000 | 143989850 | M | chrX | 114400113 | 114468689 | + | 114468015 | 114469855 | COL4A5 |
| 147079847 | 147091979 | + | CUFF.14799.4 | seg_3402 | 147079250 | 147080800 | M | chrX | 54947223 | 54957868 | + | 54957123 | 54958355 | ALAS2 |
| 147242402 | 147242529 | − | ENSMUST00000116932 | seg_3412 | 147242050 | 147243450 | M | chrX | 54840803 | 54840922 | + | 54839796 | 54841282 | ALAS2 |
| 147359163 | 147360702 | − | ENSMUST00000117716 | seg_3417 | 147358550 | 147360350 | M | other | 0 | 0 | | 0 | 0 | OA1 = GPR143 |
| 147417684 | 147442281 | − | CUFF.14800.3 | seg_3419 | 147442200 | 147443900 | M | chrX | 54561410 | 54591707 | + | 54560615 | 54561460 | FGD1 |
| 147481431 | 147502847 | + | CUFF.14802.3 | seg_3422 | 147478700 | 147483450 | M | chrX | 54475005 | 54522668 | − | 54520506 | 54525870 | FGD1 |
| 147481431 | 147521724 | + | CUFF.14907.2 | seg_3422 | 147478700 | 147483450 | M | chrX | 54475005 | 54522668 | − | 54520506 | 54525870 | FGD1 |
| 147481431 | 147521724 | + | CUFF.14802.2 | seg_3422 | 147478700 | 147483450 | M | chrX | 54475005 | 54522668 | − | 54520506 | 54525870 | FGD1 |
| 147778718 | 147779728 | + | CUFF.14910.3 | seg_3431 | 147779150 | 147780400 | M | chrX | 54208636 | 54209706 | − | 54207956 | 54209262 | PHF8 |
| 147955198 | 147991026 | + | CUFF.14809.2 | seg_3434 | 147954450 | 147956800 | M | chrX | 53963676 | 54070922 | − | 54069348 | 54071788 | PHF8 |
| 147955198 | 148067814 | + | CUFF.14809.1 | seg_3434 | 147954450 | 147956800 | M | chrX | 53963676 | 54070908 | − | 54069348 | 54071788 | PHF8 |
| 147955208 | 148067814 | + | CUFF.14914.1 | seg_3434 | 147954450 | 147956800 | M | chrX | 53963676 | 54070908 | − | 54069348 | 54071788 | PHF8 |
| 147955471 | 147955656 | + | CUFF.14808.1 | seg_3434 | 147954450 | 147956800 | M | chrX | 54070443 | 54070616 | − | 54069348 | 54071788 | PHF8 |
| 148089731 | 148090645 | + | CUFF.14808.1 | seg_3440 | 148088650 | 148090350 | M | other | 0 | 0 | | 0 | 0 | OA1 = GPR143 |
| 148090645 | 148090645 | + | ENSMUST00000121650 | seg_3440 | 148088650 | 148090350 | M | other | 0 | 0 | | 0 | 0 | OA1 = GPR143 |
| 148355350 | 148352209 | + | CUFF.14830.1 | seg_3449 | 148351400 | 148352950 | M | chrX | 53577614 | 53713695 | − | 53576440 | 53578410 | MRX1 = IQSEC2 |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 148436388 | 148438986 | + | CUFF.14916.3 | seg_3452 | 148436000 | 148437150 | M | chrX | 53458207 | 53461346 | − | 53460581 | 53461739 | MRX1 = IQSEC2 |
| 148444127 | 148450813 | − | ENSMUST00000133517 | seg_3453 | 148448100 | 148452250 | M | chrX | 53449811 | 53453282 | + | 53448362 | 53451724 | MRX1 = IQSEC2 |
| 148444127 | 148450813 | − | ENSMUST00000133517 | seg_3453 | 148448100 | 148452250 | M | chrX | 53449811 | 53453282 | + | 53448362 | 53451724 | MRX1 = IQSEC2 |
| 148450971 | 148470755 | + | ENSMUST00000145518 | seg_3453 | 148448100 | 148452250 | M | chrX | 53405849 | 53449660 | − | 53448362 | 53451724 | MRX1 = IQSEC2 |
| 148450971 | 148497237 | + | CUFF.14814.3 | seg_3453 | 148448100 | 148452250 | M | chrX | 53405849 | 53449660 | − | 53448362 | 53451724 | MRX1 = IQSEC2 |
| 148451804 | 148451804 | + | CUFF.14921.1 | seg_3453 | 148448100 | 148452250 | M | chrX | 53448837 | 53449093 | − | 53448362 | 53451724 | MRX1 = IQSEC2 |
| 148477431 | 148478058 | − | CUFF.14920.1 | seg_3455 | 148476800 | 148478500 | M | other | 0 | 0 | + | 0 | 0 | OA1 = GPR143 |
| 148477592 | 148478055 | − | ENSMUST00000120888 | seg_3455 | 148476800 | 148478500 | M | other | 0 | 0 | + | 0 | 0 | OA1 = GPR143 |
| 148477592 | 148478055 | − | ENSMUST00000120888 | seg_3455 | 148476800 | 148478500 | M | other | 0 | 0 | + | 0 | 0 | OA1 = GPR143 |
| 148578768 | 148639178 | + | CUFF.14816.1 | seg_119 | 148578700 | 148580800 | S | chrX | 53283545 | 53350548 | − | 53334817 | 53350616 | MRX1 = IQSEC2 |
| 148578768 | 148639178 | + | CUFF.14816.1 | seg_3460 | 148578400 | 148581050 | M | chrX | 53283545 | 53350548 | − | 53348024 | 53350934 | MRX1 = IQSEC2 |
| 148771395 | 148776968 | + | ENSMUST00000138918 | seg_3470 | 148775450 | 148777250 | M | chrX | 53111515 | 53117727 | − | 53111285 | 53113158 | MRX1 = IQSEC2 |
| 148771395 | 148777019 | − | CUFF.14927.4 | seg_3470 | 148775450 | 148777250 | M | chrX | 53111515 | 53117727 | − | 53111285 | 53113158 | MRX1 = IQSEC2 |
| 148771395 | 148777019 | − | CUFF.14927.3 | seg_3470 | 148775450 | 148777250 | M | chrX | 53111515 | 53117727 | − | 53111285 | 53113158 | MRX1 = IQSEC2 |
| 148978796 | 148979698 | − | ENSMUST00000120079 | seg_3479 | 148977250 | 148978900 | M | other | 0 | 0 | + | 0 | 0 | OA1 = GPR143 |
| 149044052 | 149204222 | + | CUFF.14826.2 | seg_3484 | 149203250 | 149205000 | M | chrX | 9754409 | 9917528 | + | 9753597 | 9755295 | OA1 = GPR143 |
| 149057511 | 149204219 | + | CUFF.14936.7 | seg_3484 | 149203250 | 149205000 | M | chrX | 9754412 | 9901148 | + | 9753597 | 9755295 | OA1 = GPR143 |
| 149441009 | 149444230 | + | CUFF.14939.1 | seg_3497 | 149440700 | 149441900 | M | chrX | 55513030 | 55516285 | − | 55515320 | 55516529 | ALAS2 |
| 149655713 | 149655986 | + | ENSMUST00000119867 | seg_3510 | 149655250 | 149657200 | M | other | 0 | 0 | + | 0 | 0 | OA1 = GPR143 |
| 149794275 | 149830825 | + | CUFF.14942.5 | seg_3517 | 149794050 | 149795950 | M | chrX | 56259009 | 56314850 | − | 56258774 | 56260707 | ALAS2 |
| 150266767 | 150268786 | + | CUFF.14947.1 | seg_3533 | 150266350 | 150268050 | M | chrX | 57095072 | 57097138 | + | 57095795 | 57097544 | ALAS2 |
| 151696962 | 151731456 | + | CUFF.14845.1 | seg_3550 | 151696250 | 151698050 | M | chrX | 23722764 | 23761432 | − | 23760757 | 23761726 | SAT = SAT1 |
| 151696978 | 151697427 | − | CUFF.14962.1 | seg_3550 | 151696250 | 151698050 | M | chrX | 23761017 | 23761415 | − | 23760757 | 23761726 | SAT = SAT1 |
| 151696986 | 151698125 | + | ENSMUST00000134662 | seg_3550 | 151696250 | 151698050 | M | chrX | 23760757 | 23761407 | − | 23760757 | 23761726 | SAT = SAT1 |
| 151738742 | 151740292 | − | ENSMUST00000144428 | seg_3551 | 151740100 | 151741400 | M | other | 0 | 0 | + | 0 | 0 | OA1 = GPR143 |
| 153915277 | 153915525 | − | CUFF.14971.1 | seg_3603 | 153914450 | 153916200 | M | chrX | 21975056 | 21975269 | + | 21974127 | 21976977 | PHEX |
| 154588028 | 154589111 | + | ENSMUST00000120024 | seg_3616 | 154587400 | 154588700 | M | other | 0 | 0 | + | 0 | 0 | OA1 = GPR143 |
| 154588028 | 154589111 | + | ENSMUST00000120024 | seg_3616 | 154587400 | 154588700 | M | other | 0 | 0 | + | 0 | 0 | OA1 = GPR143 |
| 155693729 | 155693827 | + | CUFF.14862.1 | seg_3654 | 155693500 | 155698350 | M | chrX | 20039469 | 20137382 | − | 20280720 | 20285259 | OA1 = GPR143 |
| 155834188 | 155924555 | + | CUFF.14861.1 | seg_3658 | 155833950 | 155835450 | M | chrX | 0 | 0 | + | 0 | 0 | OA1 = GPR143 |
| 155848179 | 155848442 | − | ENSMUST00000122329 | seg_3659 | 155847650 | 155849300 | M | other | 0 | 0 | + | 0 | 0 | OA1 = GPR143 |
| 155848232 | 155848371 | + | CUFF.14983.1 | seg_3659 | 155847650 | 155849300 | M | other | 0 | 0 | + | 0 | 0 | OA1 = GPR143 |
| 155964620 | 155998280 | + | CUFF.14989.2 | seg_3664 | 155964400 | 155968450 | M | chrX | 19968429 | 20009740 | − | 20008178 | 20009479 | PHKA2 |
| 155970597 | 156031013 | + | CUFF.14989.3 | seg_3665 | 155970350 | 155971650 | M | chrX | 19934359 | 20009176 | − | 19933931 | 19934963 | PHKA2 |
| 155970597 | 156031013 | + | CUFF.14989.3 | seg_3666 | 156030450 | 156031650 | M | chrX | 19934359 | 20009176 | − | 19903899 | 19905883 | PHKA2 |
| 156065166 | 156416001 | + | CUFF.14994.1 | seg_3667 | 156065150 | 156067100 | M | chrX | 19550319 | 19905867 | − | 19552603 | 19554763 | PHKA2 |
| 156380844 | 156412099 | + | ENSMUST00000142426 | seg_3681 | 156410850 | 156413050 | M | chrX | 19553529 | 19587588 | − | 19552603 | 19554763 | PHKA2 |
| 157027663 | 157036207 | + | CUFF.15003.1 | seg_3707 | 157034600 | 157036250 | M | chrX | 18907129 | 18912800 | − | 18906778 | 18908445 | PHKA2 |
| 157241673 | 157241983 | + | CUFF.15005.1 | seg_3718 | 157241550 | 157242700 | M | chrX | 18651084 | 18651384 | − | 18650361 | 18651566 | RS1 |
| 157246270 | 157432634 | − | CUFF.15001.3 | seg_3729 | 157431550 | 157434400 | M | chrX | 18443703 | 18446844 | + | 18441881 | 18444760 | CDKL5 |
| 157573079 | 157573160 | + | CUFF.14875.1 | seg_3735 | 157571600 | 157573100 | M | other | 0 | 0 | + | 0 | 0 | OA1 = GPR143 |
| 158346155 | 158346709 | + | ENSMUST00000154188 | seg_134 | 158344900 | 158348950 | S | chrX | 17673951 | 17674501 | − | 17672667 | 17674599 | CC = NHS |
| 158346155 | 158346709 | + | ENSMUST00000154188 | seg_3781 | 158344900 | 158348950 | M | chrX | 17673951 | 17674501 | − | 17671634 | 17675750 | CC = NHS |
| 158346155 | 158346709 | + | ENSMUST00000154188 | seg_134 | 158346050 | 158347950 | S | chrX | 17673951 | 17674501 | − | 17672667 | 17674599 | CC = NHS |

TABLE VII-continued

Table VII presents 230 distinct lncRNAs with XCI-associated PRC2 sites (640 entries). This table is laid out in a similar manner to Table VI and lists all of the lncRNAs associated with strong and moderate sites on the X chromosome, irrespective of proximity to disease gene of interest. A strong or moderate site located >100 kb away from a gene of interest may be involved in repressing the gene a long range.

| Start | Stop | Str | Transcript_ID | Ezh2_ID | Ezh2_start | Ezh2_stop | Ezh2 type | h_Chr | hg19_Start | hg19_Stop | hg19-strand | ezh2_hg19_start | ezh2_hg19_stop | disease_gene |
|---|---|---|---|---|---|---|---|---|---|---|---|---|---|---|
| 158346155 | 158346709 | + | ENSMUST00000154188 | seg_3781 | 158344900 | 158348950 | M | chrX | 17673951 | 17674501 | − | 17671634 | 17675750 | CC = NHS |
| 158789528 | 158791808 | + | ENSMUST00000119454 | seg_3809 | 158789950 | 158792150 | M | other | 0 | 0 | + | 0 | 0 | OA1 = GPR143 |
| 158789528 | 158791808 | + | ENSMUST00000119454 | seg_3809 | 158789950 | 158792150 | M | other | 0 | 0 | + | 0 | 0 | OA1 = GPR143 |
| 159294918 | 159326390 | − | CUFF.15022.1 | seg_3824 | 159325300 | 159326500 | M | chrX | 16737682 | 16754364 | + | 16737654 | 16738513 | CC = NHS |
| 160198169 | 160198915 | − | ENSMUST00000119583 | seg_137 | 160197550 | 160199400 | S | other | 0 | 0 | + | 0 | 0 | OA1 = GPR143 |
| 160198169 | 160198915 | − | ENSMUST00000119583 | seg_3857 | 160194600 | 160201150 | S | other | 0 | 0 | + | 0 | 0 | OA1 = GPR143 |
| 160198169 | 160198915 | − | ENSMUST00000119583 | seg_137 | 160197550 | 160199400 | S | other | 0 | 0 | + | 0 | 0 | OA1 = GPR143 |
| 160198169 | 160198915 | − | ENSMUST00000119583 | seg_3857 | 160194600 | 160201150 | M | other | 0 | 0 | + | 0 | 0 | OA1 = GPR143 |
| 160346915 | 160347226 | + | CUFF.15036.1 | seg_138 | 160345550 | 160347000 | S | chrX | 15872785 | 15873088 | − | 15873004 | 15874466 | PIGA |
| 160346915 | 160347226 | + | CUFF.15036.1 | seg_3862 | 160345250 | 160347350 | M | chrX | 15872785 | 15873088 | − | 15872655 | 15874788 | PIGA |
| 160346922 | 160367478 | + | CUFF.14888.1 | seg_138 | 160345550 | 160347000 | S | chrX | 15848182 | 15873081 | − | 15873004 | 15874466 | PIGA |
| 160346922 | 160367478 | + | CUFF.14888.1 | seg_3862 | 160345250 | 160347350 | M | chrX | 15848182 | 15873081 | − | 15872655 | 15874788 | PIGA |
| 160391523 | 160396094 | − | ENSMUST00000139166 | seg_3865 | 160394650 | 160396700 | M | chrX | 15808883 | 15822299 | + | 15808199 | 15811430 | PIGA |
| 161381302 | 161418307 | − | CUFF.15049.4 | seg_3910 | 161380550 | 161381550 | M | chrX | 14891501 | 14934512 | + | 14934264 | 14935279 | PIGA |
| 162827965 | 162878637 | − | CUFF.15054.2 | seg_3948 | 162877500 | 162879500 | M | chrX | 13752890 | 13788174 | + | 13750751 | 13753578 | OFD1 |
| 162948132 | 162948265 | + | CUFF.14908.1 | seg_3951 | 162946950 | 162949350 | M | chrX | 13671391 | 13671542 | − | 13670689 | 13672284 | SEDL = TRAPPC2 |
| 163292134 | 163292985 | + | ENSMUST00000087025 | seg_3964 | 163290550 | 163292150 | M | other | 0 | 0 | + | 13351903 | 13352110 | OA1 = GPR143 |
| 163292134 | 163292985 | + | ENSMUST00000087025 | seg_3964 | 163290550 | 163292150 | M | other | 0 | 0 | + | 13351903 | 13352110 | OA1 = GPR143 |
| 163292143 | 163292943 | + | ENSMUST00000118791 | seg_3964 | 163290550 | 163292150 | M | chrX | 0 | 0 | + | 13351903 | 13352110 | OA1 = GPR143 |
| 163292143 | 163292943 | + | ENSMUST00000118791 | seg_3964 | 163290550 | 163292150 | M | other | 0 | 0 | + | 13351903 | 13352110 | OA1 = GPR143 |
| 163784254 | 163820681 | − | CUFF.15069.2 | seg_3980 | 163818250 | 163825700 | M | chrX | 12809471 | 12837836 | + | 12804546 | 12811334 | SEDL = TRAPPC2 |
| 163790030 | 163820681 | − | CUFF.15069.3 | seg_3980 | 163818250 | 163825700 | M | chrX | 12809471 | 12837836 | + | 12804546 | 12811334 | SEDL = TRAPPC2 |
| 163810341 | 163820642 | − | ENSMUST00000145456 | seg_3979 | 163818250 | 163812250 | M | chrX | 12809525 | 12818878 | + | 12817304 | 12818971 | SEDL = TRAPPC2 |
| 163810341 | 163820642 | − | ENSMUST00000145456 | seg_3980 | 163818250 | 163825700 | M | chrX | 12809525 | 12818878 | + | 12804546 | 12811334 | SEDL = TRAPPC2 |
| 164214193 | 164215488 | + | CUFF.14919.1 | seg_3997 | 164214300 | 164216150 | M | other | 0 | 0 | + | 0 | 0 | OA1 = GPR143 |
| 164214193 | 164215488 | + | ENSMUST00000119938 | seg_3997 | 164214300 | 164216150 | M | other | 0 | 0 | + | 0 | 0 | OA1 = GPR143 |

To obtain human paralogues, the mouse lncRNAs were lifted over (using uesc batch liftOver software genome.ucsc.edu/cgi-bin/hgLiftOver) to the February 2009 (CRCh37/hg19) human genome assembly.

Tables VIII and IX set forth the SEQ ID NOs. for the mouse and human lncRNAs from Table VII. Coordinates are in reference to genome assembly mm9 and hg19, respectively.

TABLE VIII lncRNAs for Mouse Ezh2 binding sites

| Start | Finish | Strand | Disease Gene | Mod/Strong | SEQ ID NO: |
|---|---|---|---|---|---|
| 100355529 | 100360903 | − | OA1 = GPR143 | moderate | 227 |
| 100358233 | 100360766 | − | OA1 = GPR143 | moderate | 228 |
| 100358233 | 100360766 | − | OA1 = GPR143 | moderate | 229 |
| 100358449 | 100360746 | − | OA1 = GPR143 | moderate | 230 |
| 10062235 | 10173613 | + | OTC | moderate | 231 |
| 10062248 | 10173731 | + | OTC | moderate | 232 |
| 100724822 | 100725046 | + | OA1 = GPR143 | moderate | 233 |
| 100891328 | 100891361 | + | ABCB7 | moderate | 234 |
| 101396608 | 101396824 | − | ABCB7 | moderate | 235 |
| 101941821 | 101942111 | + | OA1 = CPR143 | moderate | 236 |
| 101941821 | 101942111 | + | OA1 = CPR143 | moderate | 237 |
| 102143124 | 102143621 | + | OA1 = CPR143 | moderate | 238 |
| 102143124 | 102143621 | + | OA1 = CPR143 | moderate | 239 |
| 102227925 | 102228705 | + | OA1 = CPR143 | moderate | 240 |
| 102227925 | 102228705 | + | OA1 = CPR143 | moderate | 241 |
| 10284302 | 10295947 | − | OTC | moderate | 242 |
| 10284302 | 10295947 | − | OTC | strong | 243 |
| 102920467 | 102920853 | − | OA1 = CPR143 | moderate | 244 |
| 102920467 | 102920853 | − | OA1 = CPR143 | moderate | 245 |
| 103555795 | 103579410 | − | PGK1 | moderate | 246 |
| 103828136 | 103828642 | − | OA1 = CPR143 | moderate | 247 |
| 106030003 | 106034841 | + | PGK1 | moderate | 248 |
| 106030003 | 106034841 | + | PGK1 | moderate | 249 |
| 106196824 | 106197635 | + | OA1 = CPR143 | moderate | 250 |
| 106196824 | 106197635 | + | OA1 = CPR143 | moderate | 251 |
| 109008832 | 109008863 | − | OA1 = CPR143 | moderate | 252 |
| 109714135 | 109739682 | + | CHM | moderate | 253 |
| 109935831 | 109936305 | − | OA1 = CPR143 | moderate | 254 |
| 11241367 | 11241392 | − | OTC | moderate | 255 |
| 11421805 | 11421826 | − | OA1 = CPR143 | moderate | 256 |
| 11490217 | 11490415 | − | OTC | moderate | 257 |
| 11490217 | 11490415 | − | OTC | moderate | 258 |
| 12339404 | 12398618 | + | CSNB1 = NYX | strong | 259 |
| 12339404 | 12398618 | + | CSNB1 = NYX | moderate | 260 |
| 123984075 | 123984154 | − | OA1 = CPR143 | moderate | 261 |
| 12513998 | 12515254 | + | OA1 = CPR143 | moderate | 262 |
| 12513998 | 12515254 | + | OA1 = CPR143 | moderate | 263 |
| 126284278 | 126284832 | + | BTK | moderate | 264 |
| 126284278 | 126284832 | + | BTK | strong | 265 |
| 126284278 | 126577066 | + | BTK | moderate | 266 |
| 126284278 | 126577066 | + | BTK | strong | 267 |
| 12648548 | 12650070 | + | CSNB1 = NYX | moderate | 268 |
| 12658599 | 12738071 | + | CSNB1 = NYX | moderate | 269 |
| 12658599 | 12743898 | + | CSNB1 = NYX | moderate | 270 |
| 12658599 | 12768156 | + | CSNB1 = NYX | moderate | 271 |
| 131120171 | 131120713 | + | BTK | moderate | 272 |
| 131216059 | 131216416 | + | OA1 = CPR143 | moderate | 273 |
| 131216059 | 131216416 | + | OA1 = CPR143 | moderate | 274 |
| 131291106 | 131295994 | + | GLA | moderate | 275 |
| 132277243 | 132332177 | + | GLA | moderate | 276 |
| 132277243 | 132336941 | + | GLA | moderate | 277 |
| 132673507 | 132674982 | + | GLA | moderate | 278 |
| 133634055 | 133634641 | + | OA1 = CPR143 | strong | 279 |
| 133634055 | 133634641 | + | OA1 = CPR143 | moderate | 280 |
| 133634055 | 133634641 | + | OA1 = CPR143 | strong | 281 |
| 133634055 | 133634641 | + | OA1 = CPR143 | moderate | 282 |
| 133638428 | 133639261 | − | OA1 = CPR143 | strong | 283 |
| 133638428 | 133639261 | − | OA1 = CPR143 | moderate | 284 |
| 133638428 | 133639261 | − | OA1 = CPR143 | strong | 285 |
| 133638428 | 133639261 | − | OA1 = CPR143 | moderate | 286 |
| 133641785 | 133642659 | + | OA1 = CPR143 | moderate | 287 |
| 133641785 | 133642659 | + | OA1 = CPR143 | moderate | 288 |
| 133645879 | 133647421 | + | OA1 = CPR143 | moderate | 289 |

TABLE VIII-continued lncRNAs for Mouse Ezh2 binding sites

| Start | Finish | Strand | Disease Gene | Mod/Strong | SEQ ID NO: |
|---|---|---|---|---|---|
| 133645879 | 133647421 | + | OA1 = CPR143 | moderate | 290 |
| 133662649 | 133664374 | + | OA1 = CPR143 | moderate | 291 |
| 133810152 | 133810286 | − | OA1 = CPR143 | moderate | 292 |
| 134966460 | 134966551 | − | OA1 = CPR143 | moderate | 293 |
| 135448948 | 135524317 | + | TBG = SERPINA7 | moderate | 294 |
| 135448948 | 135545071 | + | TBG = SERPINA7 | moderate | 295 |
| 135448953 | 135545071 | + | TBG = SERPINA7 | moderate | 296 |
| 135882030 | 135892277 | − | TBG = SERPINA7 | moderate | 297 |
| 135882030 | 135892277 | − | TBG = SERPINA7 | moderate | 298 |
| 135893007 | 135893796 | + | OA1 = CPR143 | moderate | 299 |
| 136219520 | 136287944 | + | PRPS1 | moderate | 300 |
| 136991152 | 136999981 | + | PRPS1 | moderate | 301 |
| 136991152 | 136999981 | + | PRPS1 | moderate | 302 |
| 137074067 | 137077207 | − | PRPS1 | moderate | 303 |
| 137356477 | 137357062 | − | OA1 = GPR143 | moderate | 304 |
| 137356477 | 137357062 | − | OA1 = GPR143 | moderate | 305 |
| 137599946 | 137642145 | − | COL4A5 | moderate | 306 |
| 137599946 | 137764377 | − | COL4A5 | moderate | 307 |
| 138304675 | 138304947 | − | OA1 = GPR143 | moderate | 308 |
| 138732108 | 138733073 | + | OA1 = GPR143 | moderate | 309 |
| 138732108 | 138733073 | + | OA1 = GPR143 | moderate | 310 |
| 139057035 | 139057445 | − | OA1 = GPP143 | moderate | 311 |
| 139057035 | 139057445 | − | OA1 = CPR143 | moderate | 312 |
| 139065646 | 139068558 | − | OA1 = CPR143 | moderate | 313 |
| 139066026 | 139068558 | − | OA1 = GPR143 | moderate | 314 |
| 139830092 | 139830157 | − | COL4A5 | moderate | 315 |
| 139953067 | 140232335 | + | COL4A5 | moderate | 316 |
| 147359163 | 147360702 | − | OA1 = CPR143 | moderate | 317 |
| 147417684 | 147442281 | − | FGD1 | moderate | 318 |
| 147778718 | 147779728 | + | PHF8 | moderate | 319 |
| 147955198 | 147991026 | + | PHF8 | moderate | 320 |
| 147955198 | 148067814 | + | PHF8 | moderate | 321 |
| 147955208 | 148067814 | + | PHF8 | moderate | 322 |
| 147955471 | 147955656 | − | PHF8 | moderate | 323 |
| 148089731 | 148090645 | + | OA1 = GPR143 | moderate | 324 |
| 148089731 | 148090645 | + | OA1 = GPP143 | moderate | 325 |
| 148235350 | 148352209 | + | MRX1 = IQSEC2 | moderate | 326 |
| 148450971 | 148470755 | + | MRX1 = IQSEC2 | moderate | 327 |
| 148450971 | 148497237 | + | MRX1 = IQSEC2 | moderate | 328 |
| 148477431 | 148478058 | − | OA1 = GFR143 | moderate | 329 |
| 148477592 | 148478055 | − | OA1 = GPR143 | moderate | 330 |
| 148477592 | 148478055 | − | OA1 = GPR143 | moderate | 331 |
| 148578768 | 148639178 | + | MRX1 = IQSEC2 | strong | 332 |
| 148573768 | 148639178 | + | MRX1 = IQSEC2 | moderate | 333 |
| 148771395 | 148776968 | − | MRX1 = IQSEC2 | moderate | 334 |
| 148771395 | 148777019 | − | MRX1 = IQSEC2 | moderate | 335 |
| 148771395 | 148777019 | − | MRX1 = IQSEC2 | moderate | 336 |
| 148978796 | 148979698 | − | OA1 = GPR143 | moderate | 337 |
| 149441009 | 149444230 | + | ALAS2 | moderate | 338 |
| 149655713 | 149655986 | + | OA1 = GPR143 | moderate | 339 |
| 150266767 | 150268786 | + | ALAS2 | moderate | 340 |
| 151696962 | 151731456 | + | SAT = SAT1 | moderate | 341 |
| 151696978 | 151697427 | + | SAT = SAT1 | moderate | 342 |
| 151696986 | 151658125 | + | SAT = SAT1 | moderate | 343 |
| 151738742 | 151740292 | − | OA1 = GPR143 | moderate | 344 |
| 154588028 | 154589111 | + | OA1 = GPP143 | moderate | 345 |
| 154588028 | 154589111 | + | OA1 = GPR143 | moderate | 346 |
| 155693729 | 155693827 | − | OA1 = GPR143 | moderate | 347 |
| 155834188 | 155924555 | + | PHKA2 | moderate | 348 |
| 155848179 | 155848442 | − | OA1 = GPR143 | moderate | 349 |
| 155843232 | 155848371 | + | OA1 = GPR143 | moderate | 350 |
| 156065166 | 156416001 | + | PHKA2 | moderate | 351 |
| 158346155 | 158346705 | + | CC = NHS | strong | 352 |
| 158346155 | 158346709 | + | CC = NHS | moderate | 353 |
| 158346155 | 158346709 | + | CC = NHS | strong | 354 |
| 158346155 | 158346709 | + | CC = NHS | moderate | 355 |
| 158789528 | 158791808 | + | GA = CPR143 | moderate | 356 |
| 158739528 | 158791808 | + | OA1 = GPR143 | moderate | 357 |
| 159294918 | 159326390 | − | CC = NHS | moderate | 358 |
| 160198169 | 160198915 | − | OA1 = GPR143 | strong | 359 |
| 160198169 | 160198915 | − | OA1 = GPR143 | moderate | 360 |
| 160159169 | 160198915 | − | OA1 = GPR143 | strong | 361 |
| 160198169 | 160198915 | − | OA1 = GPR143 | moderate | 362 |
| 160346915 | 160347226 | + | PIGA | strong | 363 |

TABLE VIII-continued lncRNAs for Mouse Ezh2 binding sites

| Start | Finish | Strand | Disease Gene | Mod/Strong | SEQ ID NO: |
|---|---|---|---|---|---|
| 160346915 | 160347226 | + | PIGA | moderate | 364 |
| 160346922 | 160367478 | + | PIGA | strong | 365 |
| 160346922 | 160367478 | + | PICA | moderate | 366 |
| 16195654 | 16195958 | + | NDP | moderate | 367 |
| 16196824 | 16254723 | + | NDP | moderate | 368 |
| 162948132 | 162948265 | + | SEDL = TRAPPC2 | moderate | 369 |
| 163292134 | 163292985 | + | OA1 = GPR143 | moderate | 370 |
| 163292134 | 163292985 | + | OA1 = GPR143 | moderate | 371 |
| 163292143 | 163292943 | + | OA1 = GPR143 | moderate | 372 |
| 163292143 | 163292943 | + | OA1 = GPR143 | moderate | 373 |
| 163784254 | 163820681 | − | SEDL = TRAPPC2 | moderate | 374 |
| 164214193 | 164215488 | + | OA1 = GPR143 | moderate | 375 |
| 164214193 | 164215488 | + | OA1 = GPR143 | moderate | 376 |
| 19636666 | 19638395 | + | UBA1 | strong | 377 |
| 19636666 | 19638395 | + | UBA1 | moderate | 378 |
| 19636666 | 19674647 | + | UBA1 | strong | 379 |
| 13636666 | 19674647 | + | UBA1 | moderate | 380 |
| 20002814 | 20003061 | + | UBA1 | moderate | 381 |
| 20194399 | 20225033 | + | UBA1 | strong | 382 |
| 20194399 | 20225033 | + | UBA1 | moderate | 383 |
| 20281032 | 20294944 | + | UBA1 | moderate | 384 |
| 20539240 | 20563863 | + | OA1 = GPR143 | moderate | 385 |
| 20937991 | 20941748 | + | OA1 = GPR143 | moderate | 386 |
| 20938066 | 20940148 | + | OA1 = GPR143 | moderate | 387 |
| 20938066 | 20940148 | + | OA1 = GPR143 | moderate | 388 |
| 33428645 | 33616557 | + | COL4A5 | moderate | 389 |
| 33428660 | 33523834 | + | COL4A5 | moderate | 390 |
| 33428660 | 33616557 | + | COL4A5 | moderate | 391 |
| 33868348 | 33882606 | + | COL4A5 | strong | 392 |
| 33868348 | 33882606 | + | COL4A5 | moderate | 393 |
| 34138199 | 34138634 | + | OCRL | moderate | 394 |
| 34190337 | 34208188 | − | OCRL | moderate | 395 |
| 34208212 | 34209008 | + | OA1 = GPR143 | moderate | 396 |
| 34208212 | 34209008 | + | OA1 = GPR143 | moderate | 397 |
| 34354766 | 34357180 | − | OCRL | moderate | 398 |
| 34354766 | 34357180 | − | OCRL | moderate | 399 |
| 34414316 | 34414834 | + | OCRL | moderate | 400 |
| 34414316 | 34415329 | + | OCRL | moderate | 401 |
| 34414323 | 34414681 | + | OCRL | moderate | 402 |
| 34442912 | 34442959 | + | OCRL | moderate | 403 |
| 34443059 | 34443464 | − | OCRL | moderate | 404 |
| 34443156 | 34443320 | − | OCRL | moderate | 405 |
| 35180050 | 35183034 | + | OA1 = GPR143 | moderate | 406 |
| 35180050 | 35183034 | + | OA1 = GFR143 | moderate | 407 |
| 35533905 | 35534803 | + | OA1 = GPR143 | strong | 408 |
| 35533905 | 35534803 | + | OA1 = GPR143 | moderate | 409 |
| 35533905 | 35534803 | + | OA1 = GPR143 | strong | 410 |
| 35533905 | 35534803 | + | OA1 = GPR143 | moderate | 411 |
| 35542915 | 35550223 | + | OCRL | moderate | 412 |
| 35542935 | 35550223 | + | OCRL | moderate | 413 |
| 38754031 | 38966276 | + | OCRL | strong | 414 |
| 38754031 | 38966276 | + | OCRL | moderate | 415 |
| 40677132 | 40782180 | − | OCRL | strong | 416 |
| 40677132 | 40782180 | − | OCRL | moderate | 417 |
| 40677132 | 40782180 | − | OCRL | strong | 418 |
| 40677132 | 40782180 | − | OCRL | moderate | 419 |
| 45363158 | 45363341 | + | OA1 = GPR143 | moderate | 420 |
| 45363178 | 45363342 | + | OA1 = GPR143 | moderate | 421 |
| 45694175 | 45694423 | − | OCRL | strong | 422 |
| 45694175 | 45694423 | − | OCRL | moderate | 423 |
| 45694535 | 45755264 | − | OCRL | strong | 424 |
| 45694535 | 45755264 | + | OCRL | moderate | 425 |
| 45976590 | 46015471 | + | OCRL | moderate | 426 |
| 47726321 | 47727201 | + | OA1 = GPR143 | moderate | 427 |
| 47726321 | 47727201 | + | OA1 = GPP143 | moderate | 428 |
| 47908921 | 47988433 | − | OA1 = GPR143 | moderate | 429 |
| 47930580 | 47930887 | − | OA1 = GPR143 | moderate | 430 |
| 47948607 | 47988499 | − | NYS1 = FRMD7 | moderate | 431 |
| 47968572 | 47988498 | − | NYS1 = FRMD7 | moderate | 432 |
| 47983977 | 47988499 | − | NYS1 = FRMD7 | moderate | 433 |
| 48371324 | 48371616 | − | NYS1 = FRMD7 | moderate | 434 |
| 48371476 | 48371850 | + | NYS1 = FRMD7 | moderate | 435 |
| 49106697 | 49154410 | − | NYS1 = FRMD7 | moderate | 436 |
| 49404740 | 49405157 | − | HPRT1 = HPRT | moderate | 437 |
| 49405289 | 49405837 | − | HPRT1 = HPRT | moderate | 438 |
| 50095234 | 50098237 | − | HPRT1 = HPRT | moderate | 439 |
| 50095740 | 50097770 | − | HPRT1 = HPRT | moderate | 440 |
| 50095740 | 50097770 | − | HPRT1 = HPRT | moderate | 441 |
| 50095740 | 50097770 | − | HPRT1 = HPRT | moderate | 442 |
| 50095740 | 50097770 | − | HPRT1 = HPRT | moderate | 443 |
| 50095740 | 50097770 | − | HPRT1 = HPRT | moderate | 444 |
| 50265421 | 50310120 | + | HPRT1 = HPRT | moderate | 445 |
| 50341229 | 50374836 | + | HPRT1 = HPRT | moderate | 446 |
| 50341250 | 50341769 | + | HPRT1 = HPRT | moderate | 447 |
| 50407432 | 50407526 | − | HPRT1 = HPRT | moderate | 448 |
| 50408223 | 50410367 | − | HPRT1 = HPRT | moderate | 449 |
| 50408223 | 50410367 | − | HPRT1 = HPRT | strong | 450 |
| 50408947 | 50410413 | − | HPRT1 = HPRT | moderate | 451 |
| 50408947 | 50410413 | − | HPRT1 = HPRT | strong | 452 |
| 50409370 | 50410367 | − | HPRT1 = HPRT | moderate | 453 |
| 50409370 | 50410367 | − | HPRT1 = HPRT | strong | 454 |
| 50409370 | 50410367 | − | HPRT1 = HPRT | moderate | 455 |
| 50409370 | 50410367 | − | HPRT1 = HPRT | strong | 456 |
| 51076013 | 51076305 | + | GA1 = GPR143 | moderate | 457 |
| 51272614 | 51278177 | − | OA1 = GPR143 | moderate | 458 |
| 51272614 | 51278177 | − | OA1 = GPR143 | strong | 459 |
| 53599576 | 53618851 | + | HPRT1 = HPRT | moderate | 460 |
| 53984857 | 54043843 | + | HPRT1 = HPRT | moderate | 461 |
| 53984936 | 54043843 | + | HPRT1 = HPRT | moderate | 462 |
| 54484662 | 54494066 | − | HPRT1 = HPRT | moderate | 463 |
| 54989724 | 54991732 | + | OA1 = GPR143 | moderate | 464 |
| 55175146 | 55175209 | + | F9 | moderate | 465 |
| 55175146 | 55175209 | + | F9 | strong | 466 |
| 55291586 | 55291918 | − | HPRT1 = HPRT | moderate | 467 |
| 57657230 | 57657464 | + | F9 | moderate | 468 |
| 57657681 | 57657808 | + | F9 | moderate | 469 |
| 57801194 | 57802024 | + | F9 | moderate | 470 |
| 57801194 | 57802024 | + | F9 | moderate | 471 |
| 58146828 | 58151242 | + | F9 | moderate | 472 |
| 58146828 | 58151242 | + | F9 | strong | 473 |
| 6356106 | 6474704 | + | CLCN5 | strong | 474 |
| 6356106 | 6474704 | + | CLCN5 | moderate | 475 |
| 65920689 | 65931574 | − | FMR1 | moderate | 476 |
| 65931716 | 65951510 | + | FMR1 | moderate | 477 |
| 65931716 | 65970681 | + | FMR1 | moderate | 478 |
| 65931716 | 65970681 | + | FMR1 | moderate | 479 |
| 66858632 | 66859428 | − | OA1 = GPR143 | moderate | 480 |
| 66858632 | 66859428 | − | OA1 = GPR143 | moderate | 481 |
| 66858671 | 66859420 | − | OA1 = GPR143 | moderate | 482 |
| 67712928 | 67730355 | − | MTM1 | moderate | 483 |
| 68291015 | 68303292 | − | MTM1 | moderate | 484 |
| 68291015 | 68303292 | − | MTM1 | strong | 485 |
| 68809081 | 68812693 | + | MTM1 | moderate | 486 |
| 68809092 | 68812471 | + | HPRT1 = HPRT | moderate | 487 |
| 6948402 | 6952952 | − | CLCN5 | moderate | 488 |
| 6953051 | 6955168 | + | CLCN5 | moderate | 489 |
| 70232678 | 70261234 | + | ABCD1 | moderate | 490 |
| 70748725 | 70748751 | − | ABCD1 | moderate | 491 |
| 70884707 | 70887453 | + | ABCD1 | moderate | 492 |
| 70884707 | 70887453 | + | ABCD1 | strong | 493 |
| 70918489 | 70919425 | + | ABCD1 | moderate | 494 |
| 71038698 | 71070106 | − | L1CAM | moderate | 495 |
| 71212129 | 71212322 | − | AVPR2 | moderate | 496 |
| 71252041 | 71252841 | + | OA1 = GPR143 | moderate | 497 |
| 71252041 | 71252841 | + | OA1 = GPR143 | moderate | 498 |
| 71500026 | 71500436 | + | EMD | moderate | 499 |
| 71527251 | 71528204 | + | EMD | moderate | 500 |
| 71527251 | 71528254 | + | EMD | moderate | 501 |
| 71527980 | 71535490 | + | EMD | moderate | 502 |
| 71550319 | 71553622 | + | OA1 = GPR143 | moderate | 503 |
| 71550319 | 71557201 | + | MTM1 | moderate | 504 |
| 71550337 | 71553623 | + | EMD | moderate | 505 |
| 71574384 | 71590028 | + | IKBKG | moderate | 506 |
| 71574384 | 71597045 | + | IKBKG | moderate | 507 |
| 71574404 | 71588866 | + | IKBKG | moderate | 508 |
| 72388763 | 72388969 | + | OA1 = GPR143 | moderate | 509 |
| 72388763 | 72388969 | + | OA1 = GPR143 | moderate | 510 |
| 72389027 | 72389809 | + | OA1 = GPR143 | moderate | 511 |

TABLE VIII-continued lncRNAs for Mouse Ezh2 binding sites

| Start | Finish | Strand | Disease Gene | Mod/Strong | SEQ ID NO: |
|---|---|---|---|---|---|
| 72389027 | 72389809 | + | OA1 = GPR143 | moderate | 512 |
| 72759615 | 72762429 | + | F8 | moderate | 513 |
| 7329256 | 7329540 | + | COL4A5 | moderate | 514 |
| 7329256 | 7329540 | + | COL4A5 | moderate | 515 |
| 7418487 | 7449418 | + | PQBP1 | moderate | 516 |
| 7418957 | 7449384 | + | PQBP1 | moderate | 517 |
| 7476440 | 7483890 | + | PQBP1 | moderate | 518 |
| 7476463 | 7497358 | + | PQBP1 | moderate | 519 |
| 7476463 | 7497358 | + | PQBP1 | moderate | 520 |
| 7476501 | 7476531 | − | PQBP1 | moderate | 521 |
| 7527282 | 7527994 | − | OA1 = GPR143 | moderate | 522 |
| 7624355 | 7624525 | + | OA1 = GPR143 | moderate | 523 |
| 7624355 | 7624525 | + | OA1 = GPR143 | moderate | 524 |
| 7682420 | 7683239 | + | OA1 = GPR143 | moderate | 525 |
| 7682420 | 7683239 | + | OA1 = GPR143 | moderate | 526 |
| 7770971 | 7783651 | − | WAS | moderate | 527 |
| 7770971 | 7783651 | − | WAS | moderate | 528 |
| 78316009 | 78316663 | + | XK | moderate | 529 |
| 78316009 | 78343211 | + | XK | moderate | 530 |
| 78316009 | 78343211 | + | XK | moderate | 531 |
| 78316037 | 78340115 | + | XK | moderate | 532 |
| 82819228 | 82867039 | + | DAX1 = NR0B1 | moderate | 533 |
| 82819228 | 82879808 | + | DAX1 = NR0B1 | moderate | 534 |
| 82961777 | 82962362 | + | OA1 = GPR143 | moderate | 535 |
| 82961777 | 82962362 | + | OA1 = GPR143 | moderate | 536 |
| 83561422 | 83564035 | + | OA1 = GPR143 | moderate | 537 |
| 83561422 | 83564035 | + | OA1 = GPR143 | moderate | 538 |
| 83590162 | 83591184 | − | DAX1 = NR0B1 | moderate | 539 |
| 83658987 | 83659063 | − | OA1 = GPR143 | moderate | 540 |
| 8776971 | 8792653 | + | XK | moderate | 541 |
| 8903530 | 8904209 | − | OA1 = GPR143 | moderate | 542 |
| 8904262 | 8904575 | − | OA1 = GPR143 | moderate | 543 |
| 91077474 | 91077950 | + | SAT = SAT1 | moderate | 544 |
| 91792302 | 91792908 | − | OA1 = GPR143 | moderate | 545 |
| 91792302 | 91792908 | − | OA1 = GPR143 | moderate | 546 |
| 91881387 | 91888583 | + | CLCN5 | moderate | 547 |
| 91881387 | 91888583 | + | CLCN5 | strong | 548 |
| 91916842 | 91918459 | − | OA1 = GPR143 | moderate | 549 |
| 91916842 | 91918459 | − | OA1 = GPR143 | moderate | 550 |
| 92017958 | 92019373 | − | OA1 = GPR143 | moderate | 551 |
| 92017958 | 92019373 | − | OA1 = GPR143 | moderate | 552 |
| 92020317 | 92021016 | − | OA1 = GPR143 | moderate | 553 |
| 92020317 | 92021016 | − | OA1 = GPR143 | moderate | 554 |
| 92035056 | 92035685 | + | OA1 = GPR143 | moderate | 555 |
| 92035056 | 92035685 | + | OA1 = GPR143 | moderate | 556 |
| 92038442 | 92043576 | + | ALAS2 | moderate | 557 |
| 92907017 | 93120097 | + | OA1 = GFR143 | moderate | 558 |
| 92907017 | 93120097 | + | OA1 = GPR143 | moderate | 559 |
| 93291330 | 93363894 | + | AR | moderate | 560 |
| 93291330 | 93363894 | + | AR | moderate | 561 |
| 96331411 | 96344330 | + | ED1 = EDA | moderate | 562 |
| 96331411 | 96344330 | + | ED1 = EDA | moderate | 563 |
| 96509316 | 96509440 | + | ED1 = EDA | moderate | 564 |
| 96600670 | 96639136 | − | ED1 = EDA | moderate | 565 |
| 96600670 | 96639136 | − | ED1 = EDA | strong | 566 |
| 96600670 | 96639136 | − | ED1 = EDA | moderate | 567 |
| 96600670 | 36639136 | − | ED1 = EDA | strong | 568 |
| 97015446 | 97015868 | + | ED1 = EDA | moderate | 569 |
| 97015934 | 97016205 | − | ED1 = EDA | moderate | 570 |
| 97016120 | 97016273 | + | ED1 = EDA | moderate | 571 |
| 97170822 | 97506638 | + | ED1 = EDA | moderate | 572 |
| 97170822 | 97596101 | + | ED1 = EDA | moderate | 573 |
| 97170904 | 97596101 | + | ED1 = EDA | moderate | 574 |
| 97170904 | 97596101 | + | ED1 = EDA | strong | 575 |
| 97925212 | 97927787 | + | GJB1 | moderate | 576 |
| 97925212 | 97927787 | + | GJB1 | moderate | 577 |
| 97962972 | 97972554 | − | GJB1 | moderate | 578 |
| 97962972 | 97982921 | − | GJB1 | moderate | 579 |
| 97968278 | 97968379 | − | GJB1 | moderate | 580 |
| 98254349 | 98254631 | + | OA1 = GPR143 | moderate | 581 |
| 98449812 | 98456212 | + | GJB1 | moderate | 582 |
| 98835383 | 98849934 | + | GJB1 | moderate | 583 |
| 98835383 | 98849934 | + | GJB1 | strong | 584 |
| 98835399 | 98849983 | + | GJB1 | moderate | 585 |
| 98835399 | 98849983 | + | GJB1 | strong | 586 |
| 98986564 | 98988647 | − | GJB1 | moderate | 587 |
| 98986564 | 98988647 | − | GJB1 | moderate | 588 |
| 99044721 | 99287394 | + | GJB1 | moderate | 589 |
| 99044721 | 99287394 | + | GJB1 | moderate | 590 |
| 99044721 | 99287394 | + | GJB1 | strong | 591 |
| 99044724 | 99144974 | + | GJB1 | moderate | 592 |
| 99044724 | 99144974 | + | GJB1 | strong | 593 |
| 157246270 | 157432634 | − | CDKL5 | moderate | 594 |
| 137074067 | 137133980 | − | PRPS1 | strong | 595 |
| 137074067 | 137133980 | − | PRPS1 | moderate | 596 |
| 55283804 | 55294913 | + | F9 | moderate | 597 |
| 55283804 | 55294913 | + | F9 | moderate | 598 |
| 55283804 | 55294913 | + | F9 | strong | 599 |
| 137199310 | 137302254 | + | PRPS1 | moderate | 600 |
| 137199472 | 137302254 | + | PRPS1 | moderate | 601 |
| 47148122 | 47150912 | − | NYS1 = FRMD7 | moderate | 602 |
| 157027663 | 157036207 | + | PHKA2 | moderate | 603 |
| 55283804 | 55286873 | + | F9 | moderate | 604 |
| 55283804 | 55286873 | + | F9 | strong | 605 |
| 155970597 | 156031013 | + | PHKA2 | moderate | 606 |
| 155970597 | 156031013 | + | PHKA2 | moderate | 607 |
| 91881415 | 91888583 | + | CLCN5 | moderate | 608 |
| 91881415 | 91888583 | + | CLCN5 | strong | 609 |
| 11613866 | 11737559 | − | CSNB1 = NYX | strong | 610 |
| 11613866 | 11737559 | − | CSNB1 = NYX | moderate | 611 |
| 47135713 | 47150926 | − | NYS1 = FRMD7 | moderate | 612 |
| 57377877 | 57431535 | − | F9 | moderate | 613 |
| 12256875 | 12339199 | − | CSNB1 = NYX | strong | 614 |
| 12256875 | 12339199 | − | CSNB1 = NYX | moderate | 615 |
| 11613866 | 11705532 | − | CSNB1 = NYX | strong | 616 |
| 11613866 | 11705532 | − | CSNB1 = NYX | moderate | 617 |
| 143904918 | 143988678 | − | COL4A5 | moderate | 618 |
| 53863012 | 53908257 | + | HPRT1 = HPR7 | moderate | 619 |
| 57309131 | 57432445 | − | F9 | moderate | 620 |
| 96132695 | 96144356 | + | AR | moderate | 621 |
| 96132488 | 96144356 | + | AR | moderate | 622 |
| 40250312 | 40782303 | − | OCRL | strong | 623 |
| 40250312 | 40782303 | − | OCRL | moderate | 624 |
| 96237920 | 96270067 | + | ED1 = EDA | moderate | 625 |
| 10292145 | 10296816 | + | OTC | moderate | 626 |
| 131282994 | 131285982 | − | GLA | moderate | 627 |
| 155964620 | 155998280 | + | PHKA2 | moderate | 628 |
| 40177535 | 40782180 | − | OCRL | strong | 629 |
| 40177535 | 40782180 | − | OCRL | moderate | 630 |
| 7367144 | 7397082 | + | PQBP1 | moderate | 631 |
| 7367144 | 7397082 | + | PQBP1 | moderate | 632 |
| 7770974 | 7787507 | − | WAS | moderate | 633 |
| 7770974 | 7787507 | − | WAS | moderate | 634 |
| 147079847 | 147091979 | − | ALAS2 | moderate | 635 |
| 96133100 | 96140245 | + | AR | moderate | 636 |
| 96237920 | 96265783 | + | ED1 = EDA | moderate | 637 |
| 7134422 | 7154618 | − | PQBP1 | moderate | 638 |
| 45806529 | 45807451 | − | OCRL | strong | 639 |
| 45806529 | 45807451 | − | OCRL | moderate | 640 |
| 12338584 | 12339240 | − | CSNB1 = NYX | strong | 641 |
| 12338584 | 12339240 | − | CSNB1 = NYX | moderate | 642 |
| 45764223 | 45810380 | − | OCRL | moderate | 643 |
| 7476797 | 7483890 | + | PQBP1 | moderate | 644 |
| 48368108 | 48371354 | − | NYS1 = FRMD7 | moderate | 645 |
| 137077642 | 137083063 | − | PRPS1 | moderate | 646 |
| 156380844 | 156412099 | + | PHKA2 | moderate | 647 |
| 71598672 | 71598963 | − | IKBKG | moderate | 648 |
| 71598672 | 71598963 | − | IKBKG | strong | 649 |
| 34427535 | 34443093 | − | OCRL | moderate | 650 |
| 5976972 | 6214566 | + | CLCN5 | moderate | 651 |
| 71188131 | 71212039 | − | AVPR2 | moderate | 652 |
| 7419731 | 7452410 | + | PQBP1 | moderate | 653 |
| 7419731 | 7452410 | + | PQBP1 | moderate | 654 |
| 91784323 | 91787522 | − | MRX1 = IQSEC2 | moderate | 655 |
| 9178432 | 91787522 | − | MRX1 = IQSEC2 | moderate | 656 |
| 101162901 | 101176626 | − | ABCB7 | moderate | 657 |
| 101162901 | 101176626 | − | ABCB7 | strong | 658 |
| 101272773 | 101396532 | − | ABCB7 | moderate | 659 |

TABLE VIII-continued lncRNAs for Mouse Ezh2 binding sites

| Start | Finish | Strand | Disease Gene | Mod/Strong | SEQ ID NO: |
|---|---|---|---|---|---|
| 101272773 | 101396549 | − | ABCB7 | moderate | 660 |
| 103106842 | 103124685 | − | ATRX | moderate | 661 |
| 11623972 | 11657682 | − | CSNB1 = NYX | strong | 662 |
| 11623972 | 11657682 | − | CSNB1 = NYX | moderate | 663 |
| 11625208 | 11657693 | − | CSNB1 = NYX | strong | 664 |
| 11625208 | 11657693 | − | CSNB1 = NYX | moderate | 665 |
| 12254777 | 12339238 | − | CSNB1 = NYX | strong | 666 |
| 12254777 | 12339238 | − | CSNB1 = NYX | moderate | 667 |
| 130215559 | 130223532 | − | BTK | moderate | 668 |
| 130215559 | 130223532 | − | BTK | strong | 669 |
| 130470924 | 130516351 | − | BTK | moderate | 670 |
| 130470924 | 130516351 | − | BTK | strong | 671 |
| 13094206 | 13423886 | − | CSNB1 = NYX | moderate | 672 |
| 131120229 | 131122601 | + | BTK | moderate | 673 |
| 13129411 | 13423886 | − | CSNB1 = NYX | moderate | 674 |
| 13131747 | 13423893 | − | CSNB1 = NYX | moderate | 675 |
| 133535557 | 133572844 | − | TBG = SERPINA7 | moderate | 676 |
| 133535594 | 133572841 | − | OA1 = GPR143 | moderate | 677 |
| 133549811 | 133572838 | − | TBG = SERPINA7 | moderate | 678 |
| 133566334 | 133572841 | − | OA1 = GPR143 | moderate | 679 |
| 136541344 | 136597251 | − | PRPS1 | strong | 680 |
| 136541344 | 136597251 | − | PRPS1 | moderate | 681 |
| 137599946 | 137908628 | − | COL4A5 | moderate | 682 |
| 137909928 | 138123778 | + | COL4A5 | moderate | 683 |
| 137909928 | 138123778 | + | COL4A5 | moderate | 684 |
| 137909929 | 138123778 | + | COL4A5 | moderate | 685 |
| 137910111 | 138123773 | + | COL4A5 | moderate | 686 |
| 139285689 | 139401362 | − | COL4A5 | moderate | 687 |
| 139285689 | 139401386 | − | COL4A5 | moderate | 688 |
| 141880968 | 141939813 | − | COL4A5 | moderate | 689 |
| 143919223 | 143988699 | − | COL4A5 | moderate | 690 |
| 143943353 | 143988678 | − | COL4A5 | moderate | 691 |
| 148436388 | 148438986 | + | MPX1 = IQSEC2 | moderate | 692 |
| 149044052 | 149204222 | − | OA1 = GPR143 | moderate | 693 |
| 149057511 | 149204219 | − | OA1 = GPR143 | moderate | 694 |
| 149794275 | 149830825 | + | ALAS2 | moderate | 695 |
| 161381302 | 161418307 | − | PIGA | moderate | 696 |
| 162827965 | 162878637 | − | OFD1 | moderate | 697 |
| 19772151 | 19868953 | − | UBA1 | moderate | 698 |
| 20194629 | 20228027 | + | UBA1 | strong | 699 |
| 20194629 | 20228027 | + | UBA1 | moderate | 700 |
| 33735899 | 33739153 | + | COL4A5 | moderate | 701 |
| 34148309 | 34185415 | − | OCRL | moderate | 702 |
| 34148309 | 34185417 | − | OCRL | moderate | 703 |
| 34391130 | 34404168 | − | OCRL | moderate | 704 |
| 34631673 | 34650335 | − | OCRL | moderate | 705 |
| 34648901 | 34650347 | − | OCRL | moderate | 706 |
| 38754659 | 39031778 | + | OCRL | strong | 707 |
| 38754659 | 39031778 | + | OCRL | moderate | 708 |
| 39155509 | 39265102 | − | OCRL | moderate | 709 |
| 39166391 | 39265102 | − | OCRL | moderate | 710 |
| 45162547 | 45245729 | − | OCRL | moderate | 711 |
| 47139524 | 47150928 | − | NYS1 = FRMD7 | moderate | 712 |
| 50265390 | 50265600 | + | HPRT1 = HPRT | moderate | 713 |
| 57488638 | 57657223 | − | F9 | moderate | 714 |
| 57488638 | 57657479 | − | F9 | moderate | 715 |
| 58144545 | 58146615 | − | HPRT1 = HPRT | moderate | 716 |
| 58144545 | 58146615 | − | HPRT1 = HPRT | strong | 717 |
| 70682654 | 70704414 | − | ABCD1 | moderate | 718 |
| 71675010 | 71699193 | + | G6PD = G6PDX | moderate | 719 |
| 73030993 | 73120555 | − | COL4A5 | moderate | 720 |
| 7708468 | 7709984 | − | WAS | moderate | 721 |
| 7780134 | 7783651 | − | WAS | moderate | 722 |
| 99337055 | 99352458 | − | GJB1 | moderate | 723 |
| 99337055 | 99352453 | − | GJB1 | moderate | 724 |
| 99709314 | 99839595 | − | GJB1 | moderate | 725 |
| 100618468 | 100618584 | − | OA1 = GPR143 | moderate | 726 |
| 101531844 | 101543844 | − | OA1 = GPR143 | moderate | 727 |
| 101531844 | 101543844 | − | OA1 = GPR143 | moderate | 728 |
| 101541168 | 101543573 | − | OA1 = GPR143 | moderate | 729 |
| 10294443 | 10294862 | + | OTC | moderate | 730 |
| 110411861 | 110869443 | + | CHM | moderate | 731 |
| 126284360 | 126863066 | + | BTK | moderate | 732 |
| 126284360 | 126863066 | + | BTK | strong | 733 |
| 12648884 | 12649225 | + | CSNB1 = NYX | moderate | 734 |
| 12650018 | 12650277 | + | CSNB1 = NYX | moderate | 735 |
| 12655982 | 12656311 | + | CSNB1 = NYX | moderate | 736 |
| 130117402 | 130223532 | − | BTK | moderate | 737 |
| 130117402 | 130223532 | − | BTK | strong | 738 |
| 131004413 | 131009527 | − | BTK | moderate | 739 |
| 131223346 | 131231296 | + | GLA | moderate | 740 |
| 132330954 | 132331138 | + | GLA | moderate | 741 |
| 132331073 | 132331146 | + | GLA | moderate | 742 |
| 13290060 | 13290192 | − | OA1 = GPR143 | moderate | 743 |
| 133243165 | 133246017 | − | GLA | moderate | 744 |
| 134105558 | 135040850 | + | TBG = SERPINA7 | strong | 745 |
| 134105558 | 135040850 | + | TBG = SERPINA7 | moderate | 746 |
| 134105558 | 135040850 | + | TBG = SERPINA7 | strong | 747 |
| 134105558 | 135040850 | + | TBG = SERPINA7 | moderate | 748 |
| 136144963 | 136145837 | + | TBG = SERPINA7 | moderate | 749 |
| 136145906 | 136206280 | + | TBG = SERPINA7 | moderate | 750 |
| 136224009 | 136224144 | + | OA1 = GPR143 | moderate | 751 |
| 138062502 | 138063011 | + | OA1 = GPR143 | moderate | 752 |
| 138820850 | 138821158 | − | COL4A5 | moderate | 753 |
| 140098882 | 140100407 | + | COL4A5 | moderate | 754 |
| 140853218 | 141122546 | − | COL4A5 | strong | 755 |
| 140853218 | 141122546 | − | COL4A5 | moderate | 756 |
| 140989754 | 140990880 | − | XK | moderate | 757 |
| 147242402 | 147242529 | − | ALAS2 | moderate | 758 |
| 147481431 | 147502847 | + | FDG1 | moderate | 759 |
| 147481431 | 147521724 | + | FDG1 | moderate | 760 |
| 147481431 | 147521724 | + | FDG1 | moderate | 761 |
| 148444127 | 148450813 | − | MRX1 = IQSEC2 | moderate | 762 |
| 148444127 | 148450813 | − | MRX1 = IQSEC2 | moderate | 763 |
| 148451529 | 148451804 | + | MRX1 = IQSEC2 | moderate | 764 |
| 153915277 | 153915525 | − | PHEX | moderate | 765 |
| 157241673 | 157241983 | − | RS1 | moderate | 766 |
| 157573079 | 157573160 | + | OA1 = GPR143 | moderate | 767 |
| 160391523 | 160396094 | − | PIGA | moderate | 768 |
| 163790030 | 163820681 | − | SEDL = RAPPC2 | moderate | 769 |
| 163810341 | 163820642 | − | SEDL = RAPPC2 | moderate | 770 |
| 163810341 | 163820642 | − | SEDL = RAPPC2 | moderate | 771 |
| 17135024 | 17148750 | − | NDP | moderate | 772 |
| 20003237 | 20003672 | − | UBA1 | moderate | 773 |
| 20194911 | 20226322 | + | UBA1 | strong | 774 |
| 20194911 | 20226322 | + | UBA1 | moderate | 775 |
| 20194911 | 20226322 | + | UBA1 | strong | 776 |
| 20194911 | 20226322 | + | UBA1 | moderate | 777 |
| 33868348 | 33902336 | + | COL4A5 | strong | 778 |
| 33868348 | 33902336 | + | COL4A5 | moderate | 779 |
| 33868348 | 33902336 | + | COL4A5 | strong | 780 |
| 33868348 | 33902336 | + | COL4A5 | moderate | 781 |
| 34139837 | 34139989 | + | OCRL | moderate | 782 |
| 35600278 | 35604805 | − | OCRL | strong | 783 |
| 35600278 | 35604805 | − | OCRL | moderate | 784 |
| 35897792 | 35917936 | − | OCRL | moderate | 785 |
| 35961900 | 35966603 | + | OCRL | moderate | 786 |
| 38754659 | 38966731 | + | OCRL | strong | 787 |
| 38754659 | 38966731 | + | OCRL | moderate | 788 |
| 39264775 | 39265078 | − | OCRL | moderate | 789 |
| 45227508 | 45245609 | − | OCRL | moderate | 790 |
| 45694535 | 45761226 | + | OCRL | strong | 791 |
| 45694535 | 45761226 | + | OCRL | moderate | 792 |
| 45695238 | 45746514 | + | OCRL | strong | 793 |
| 45695238 | 45746514 | + | OCRL | moderate | 794 |
| 45696947 | 45761226 | + | OCRL | strong | 795 |
| 45696947 | 45761226 | + | OCRL | moderate | 796 |
| 45697574 | 45698600 | + | OCRL | strong | 797 |
| 45697574 | 45698600 | + | OCRL | moderate | 798 |
| 45976926 | 46005231 | + | OCRL | moderate | 799 |
| 46838852 | 46848439 | + | NYS1 = FRMD7 | moderate | 800 |
| 46838852 | 46848438 | + | NYS1 = FRMD7 | moderate | 801 |
| 49029960 | 49034525 | − | NYS1 = FRMD7 | strong | 802 |
| 49029960 | 49034525 | − | NYS1 = FRMD7 | moderate | 803 |
| 49033169 | 49033742 | − | NYS1 = FRMD7 | strong | 804 |
| 49033169 | 49033742 | − | NYS1 = FRMD7 | moderate | 805 |
| 49033355 | 49034263 | − | NYS1 = FRMD7 | strong | 806 |
| 49033355 | 49034263 | − | NYS1 = FRMD7 | moderate | 807 |

TABLE VIII-continued lncRNAs for Mouse Ezh2 binding sites

| Start | Finish | Strand | Disease Gene | Mod/Strong | SEQ ID NO: |
|---|---|---|---|---|---|
| 49775584 | 49775692 | − | HPRT1 = HPRT | moderate | 808 |
| 53838689 | 53851246 | − | HPRT1 = HPRT | moderate | 809 |
| 54644626 | 54644698 | − | HPRT1 = HPRT | moderate | 810 |
| 54644626 | 54644698 | − | HPRT1 = HPRT | moderate | 811 |
| 56316667 | 56386391 | − | F9 | moderate | 812 |
| 56421226 | 56421304 | − | F9 | moderate | 813 |
| 57392756 | 57392833 | − | OA1 = GPR143 | moderate | 814 |
| 57761975 | 57762010 | − | OA1 = GPR143 | moderate | 815 |
| 5977553 | 5977692 | + | CLCN5 | moderate | 816 |
| 65932068 | 65932563 | + | FMR1 | moderate | 817 |
| 65932227 | 65932774 | + | FMR1 | moderate | 818 |
| 67712928 | 67730355 | − | MTM1 | moderate | 819 |
| 67716098 | 67730317 | − | MTM1 | moderate | 820 |
| 68809408 | 68809659 | + | MTM1 | moderate | 821 |
| 68809643 | 68809983 | + | MTM1 | moderate | 822 |
| 68809715 | 68813851 | + | MTM1 | moderate | 823 |
| 68917141 | 68920567 | + | MTM1 | moderate | 824 |
| 68917141 | 68920567 | + | MTM1 | strong | 825 |
| 68917141 | 68920567 | + | MTM1 | moderate | 826 |
| 68917141 | 68920567 | + | MTM1 | strong | 827 |
| 69062152 | 69066323 | + | MTM1 | moderate | 828 |
| 69062152 | 69066323 | + | MTM1 | moderate | 829 |
| 69514307 | 69520142 | − | MTM1 | moderate | 830 |
| 69519852 | 69520142 | − | MTM1 | moderate | 831 |
| 70232678 | 70276882 | + | ABCD1 | moderate | 832 |
| 70232678 | 70276882 | + | ABCD1 | moderate | 833 |
| 70232678 | 70276882 | + | ABCD1 | moderate | 834 |
| 70232678 | 70276882 | + | ABCD1 | moderate | 835 |
| 70659581 | 70659693 | + | OA1 = GPR143 | moderate | 836 |
| 71167461 | 71171740 | − | AVPR2 | moderate | 837 |
| 71209543 | 71210333 | − | AVPR2 | moderate | 838 |
| 71491032 | 71491211 | − | EMD | moderate | 839 |
| 71491144 | 71491278 | − | EMD | moderate | 840 |
| 71500100 | 71501024 | + | EMD | moderate | 841 |
| 71528089 | 71533374 | + | EMD | moderate | 842 |
| 71528089 | 71535487 | + | EMD | moderate | 843 |
| 71528090 | 71535488 | + | EMD | moderate | 844 |
| 7215764 | 7224495 | + | PQBP1 | moderate | 845 |
| 72759656 | 72767094 | + | F8 | moderate | 846 |
| 73120309 | 73120521 | − | COL4A5 | moderate | 847 |
| 7418957 | 7453752 | + | PQBP1 | moderate | 848 |
| 75715283 | 75829194 | − | XK | moderate | 849 |
| 75715283 | 75829194 | − | XK | moderate | 850 |
| 75726052 | 75829121 | − | XK | moderate | 851 |
| 75726052 | 75829121 | − | XK | moderate | 852 |
| 75762644 | 75829230 | − | XK | moderate | 853 |
| 7706844 | 7709637 | − | WAS | moderate | 854 |
| 7731609 | 7753084 | − | WAS | moderate | 855 |
| 7731609 | 7753084 | − | WAS | moderate | 856 |
| 7731617 | 7753017 | − | WAS | moderate | 857 |
| 7767001 | 7770024 | − | WAS | moderate | 858 |
| 7767001 | 7770024 | − | WAS | moderate | 859 |
| 7770979 | 7783623 | − | WAS | moderate | 860 |
| 7770979 | 7783623 | − | WAS | moderate | 861 |
| 82819378 | 82820964 | + | DAX1 = NR0B1 | moderate | 862 |
| 91780815 | 91787329 | − | MRX1 = IQSEC2 | moderate | 863 |
| 9233402 | 9240129 | − | CYBB | moderate | 864 |
| 98835952 | 98836294 | + | GJB1 | moderate | 865 |
| 99750118 | 99839585 | − | GJB1 | moderate | 866 |

TABLE IX

Human LiftOver Ezh2 binding sites

| Start | Finish | Strand | Disease Gene | Mod/Strong | SEQ ID NO: |
|---|---|---|---|---|---|
| 38420746 | 38548056 | + | OTC | moderate | 867 |
| 38420761 | 38548175 | + | OTC | moderate | 868 |
| 73755234 | 73755237 | − | ABCB7 | moderate | 869 |
| 74145376 | 74145592 | − | ABCB7 | moderate | 870 |
| 38652969 | 38664787 | − | OTC | moderate | 871 |
| 38652969 | 38664787 | − | OTC | strong | 872 |
| 77422903 | 77423610 | − | PGK1 | moderate | 873 |
| 80065639 | 80068874 | + | PGK1 | moderate | 874 |
| 80065639 | 80068874 | + | PGK1 | moderate | 875 |
| 84498794 | 84521473 | + | CHM | moderate | 876 |
| 39547664 | 39547694 | − | OTC | moderate | 877 |
| 39646386 | 39646595 | − | OTC | moderate | 878 |
| 39646386 | 39646595 | − | OTC | moderate | 879 |
| 40595745 | 40649934 | + | CSNB1 = NYX | strong | 880 |
| 40595245 | 40649934 | + | CSNB1 = NYX | moderate | 881 |
| 95939805 | 95940396 | + | BTK | moderate | 882 |
| 95939805 | 95940396 | + | BTK | strong | 883 |
| 95939805 | 96319018 | + | BTK | moderate | 884 |
| 95939805 | 96319018 | + | BTK | strong | 885 |
| 40944519 | 40945909 | + | CSNB1 = NYX | moderate | 886 |
| 40944564 | 41082678 | + | CSNB1 = NYX | moderate | 887 |
| 40944564 | 41089870 | + | CSNB1 = NYX | moderate | 888 |
| 40944564 | 41100156 | + | CSNB1 = NYX | moderate | 889 |
| 1.01E+08 | 1.01E+08 | + | BTK | moderate | 890 |
| 1.01E+08 | 1.01E+08 | + | GLA | moderate | 891 |
| 1.02E+08 | 1.02E+08 | + | GLA | moderate | 892 |
| 1.02E+08 | 1.02E+08 | + | GLA | moderate | 893 |
| 1.02E+08 | 1.02E+08 | + | GLA | moderate | 894 |
| 1.05E+08 | 1.05E+08 | + | TBG = SERPINA7 | moderate | 895 |
| 1.05E+08 | 1.05E+08 | + | TBG = SERPINA7 | moderate | 896 |
| 1.05E+08 | 1.05E+08 | + | TBG = SERPINA7 | moderate | 897 |
| 1.06E+08 | 1.06E+08 | − | TBG = SERPINA7 | moderate | 898 |
| 1.06E+08 | 1.06E+08 | − | TBG = SERPINA7 | moderate | 899 |
| 1.06E+08 | 1.06E+08 | + | PRPS1 | moderate | 900 |
| 1.07E+08 | 1.07E+08 | + | PRPS1 | moderate | 901 |
| 1.07E+08 | 1.07E+08 | + | PRPS1 | moderate | 902 |
| 1.07E+08 | 1.07E+08 | − | PRPS1 | moderate | 903 |
| 1.07E+08 | 1.07E+08 | − | COL4A5 | moderate | 904 |
| 1.07E+08 | 1.08E+08 | − | COL4A5 | moderate | 905 |
| 1.1E+08 | 1.1E+08 | − | COL4A5 | moderate | 906 |
| 1.1E+08 | 1.1E+08 | + | COL4A5 | moderate | 907 |
| 54561410 | 54591707 | + | FGD1 | moderate | 908 |
| 54208636 | 54209706 | − | PHF8 | moderate | 909 |
| 53963676 | 54070922 | − | PHF8 | moderate | 910 |
| 53963676 | 54070908 | − | PHF8 | moderate | 911 |
| 53963676 | 54070908 | − | PHF8 | moderate | 912 |
| 54070048 | 54070616 | + | PHF8 | moderate | 913 |
| 53577614 | 53713695 | − | MRX1 = IQSEC2 | moderate | 914 |
| 53405849 | 53449660 | − | MRX1 = IQSEC2 | moderate | 915 |
| 53405849 | 53449660 | − | MRX1 = IQSEC2 | moderate | 916 |
| 53283545 | 53350548 | − | MRX1 = IQSEC2 | strong | 917 |
| 53283545 | 53350548 | − | MRX1 = IQSEC2 | moderate | 918 |
| 53111515 | 53117727 | + | MRX1 = IQSEC2 | moderate | 919 |
| 53111515 | 53117727 | + | MRX1 = IQSEC2 | moderate | 920 |
| 53111515 | 53117777 | + | MRX1 = IQSEC2 | moderate | 921 |
| 55513030 | 55516285 | − | ALAS2 | moderate | 922 |
| 57095072 | 57097138 | − | ALAS2 | moderate | 923 |
| 23722764 | 23761432 | − | SAT = SAT1 | moderate | 924 |
| 23761017 | 23761415 | − | SAT = SAT1 | moderate | 925 |
| 23760757 | 23761407 | − | SAT = SAT1 | moderate | 926 |
| 20039469 | 20137382 | − | PHKA2 | moderate | 927 |
| 19550319 | 19905867 | − | PHKA2 | moderate | 928 |
| 17673951 | 17674501 | − | CC = NHS | strong | 929 |
| 17673951 | 17674501 | − | CC = NHS | moderate | 930 |
| 17673951 | 17674501 | − | CC = NHS | strong | 931 |
| 17673951 | 17674501 | − | CC = NHS | moderate | 932 |
| 16737682 | 16754364 | + | CC = NHS | moderate | 933 |
| 15872785 | 15873088 | − | PIGA | strong | 934 |
| 15872785 | 15873088 | − | PIGA | moderate | 935 |
| 15848182 | 15873081 | − | PIGA | strong | 936 |
| 15848182 | 15873081 | − | PIGA | moderate | 937 |
| 43514157 | 43514486 | − | NDP | moderate | 938 |
| 43515447 | 43595516 | + | NDP | moderate | 939 |
| 13671391 | 13671542 | − | SEDL = TRAPPC2 | moderate | 940 |
| 12809471 | 12837836 | + | SEDL = TRAPPC2 | moderate | 941 |
| 46433208 | 46434914 | + | UBA1 | strong | 942 |
| 46433208 | 46434914 | + | UBA1 | moderate | 943 |

TABLE IX-continued

Human LiftOver Ezh2 binding sites

| Start | Finish | Strand | Disease Gene | Mod/Strong | SEQ ID NO: |
|---|---|---|---|---|---|
| 46433208 | 46457778 | + | UBA1 | strong | 944 |
| 46433208 | 46457778 | − | UBA1 | moderate | 945 |
| 46772015 | 46772258 | + | UBA1 | moderate | 946 |
| 47004091 | 47041189 | + | UBA1 | strong | 947 |
| 47004091 | 47041189 | + | UBA1 | moderate | 948 |
| 47092379 | 47103954 | + | UBA1 | moderate | 949 |
| 1.18E+08 | 1.18E+08 | + | COL4A5 | moderate | 950 |
| 1.18E+08 | 1.18E+08 | + | COL4A5 | moderate | 951 |
| 1.18E+08 | 1.18E+08 | − | COL4A5 | moderate | 952 |
| 1.18E+08 | 1.18E+08 | + | COL4A5 | strong | 953 |
| 1.18E+08 | 1.18E+08 | + | COL4A5 | moderate | 954 |
| 1.18E+08 | 1.18E+08 | + | OCRL | moderate | 955 |
| 1.18E+08 | 1.18E+08 | − | OCRL | moderate | 956 |
| 1.19E+08 | 1.19E+08 | − | OCRL | moderate | 957 |
| 1.19E+08 | 1.19E+08 | − | OCRL | moderate | 958 |
| 1.19E+08 | 1.19E+08 | + | OCRL | moderate | 959 |
| 1.19E+08 | 1.19E+08 | + | OCRL | moderate | 960 |
| 1.19E+08 | 1.19E+08 | + | OCRL | moderate | 961 |
| 1.19E+08 | 1.19E+08 | + | OCRL | moderate | 962 |
| 1.19E+08 | 1.19E+08 | − | OCRL | moderate | 963 |
| 1.19E+08 | 1.19E+08 | − | OCRL | moderate | 964 |
| 1.18E+08 | 1.19E+08 | + | OCRL | moderate | 965 |
| 1.19E+08 | 1.19E+08 | + | OCRL | moderate | 966 |
| 1.22E+08 | 1.23E+08 | + | OCRL | strong | 967 |
| 1.22E+08 | 1.23E+08 | + | OCRL | moderate | 968 |
| 1.24E+08 | 1.24E+08 | − | OCRL | strong | 969 |
| 1.24E+08 | 1.24E+08 | − | OCRL | moderate | 970 |
| 1.24E+08 | 1.24E+08 | − | OCRL | strong | 971 |
| 1.24E+08 | 1.24E+08 | − | OCRL | moderate | 972 |
| 1.29E+08 | 1.29E+08 | − | OCRL | strong | 973 |
| 1.29E+08 | 1.29E+08 | − | OCRL | moderate | 974 |
| 1.29E+08 | 1.29E+08 | + | OCRL | strong | 975 |
| 1.29E+08 | 1.29E+08 | + | OCRL | moderate | 976 |
| 1.29E+08 | 1.31E+08 | + | OCRL | moderate | 977 |
| 1.31E+08 | 1.31E+08 | − | NYS1 = FRMD7 | moderate | 978 |
| 1.31E+08 | 1.31E+08 | − | NYS1 = FRMD7 | moderate | 979 |
| 1.31E+08 | 1.31E+08 | − | NYS1 = FRMD7 | moderate | 980 |
| 1.31E+08 | 1.31E+08 | − | NYS1 = FRMD7 | moderate | 981 |
| 1.31E+08 | 1.31E+08 | + | NYS1 = FRMD7 | moderate | 982 |
| 1.32E+08 | 1.32E+08 | − | NYS1 = FRMD7 | moderate | 983 |
| 1.32E+08 | 1.32E+08 | − | HPRT1 = HPRT | moderate | 984 |
| 1.32E+08 | 1.32E+08 | − | HPRT1 = HPRT | moderate | 985 |
| 1.33E+08 | 1.33E+08 | − | HPRT1 = HPRT | moderate | 986 |
| 1.33E+08 | 1.33E+08 | − | HPRT1 = HPRT | moderate | 987 |
| 1.33E+08 | 1.33E+08 | − | HPRT1 = HPRT | moderate | 988 |
| 1.33E+08 | 1.33E+08 | − | HPRT1 = HPRT | moderate | 989 |
| 1.33E+08 | 1.33E+38 | − | HPRT1 = HPRT | moderate | 990 |
| 1.33E+08 | 1.33E+08 | − | HPRT1 = HPRT | moderate | 991 |
| 1.34E+08 | 1.34E+08 | + | HPRT1 = HPRT | moderate | 992 |
| 1.34E+08 | 1.34E+08 | + | HPRT1 = HPRT | moderate | 993 |
| 1.34E+08 | 1.34E+08 | + | HPRT1 = HPRT | moderate | 994 |
| 1.34E+08 | 1.34E+08 | − | HPRT1 = HPRT | moderate | 995 |
| 1.34E+08 | 1.34E+08 | − | HPRT1 = HPRT | moderate | 996 |
| 1.34E+08 | 1.34E+08 | − | HPRT1 = HPRT | strong | 997 |
| 1.34E+08 | 1.34E+08 | − | HPRT1 = HPRT | moderate | 998 |
| 1.34E+08 | 1.34E+08 | − | HPRT1 = HPRT | strong | 999 |
| 1.34E+08 | 1.34E+08 | − | HPRT1 = HPRT | moderate | 1000 |
| 1.34E+08 | 1.34E+08 | − | HPRT1 = HPRT | strong | 1001 |
| 1.34E+08 | 1.34E+08 | − | HPRT1 = HPRT | moderate | 1002 |
| 1.34E+08 | 1.34E+08 | − | HPRT1 = HPRT | strong | 1003 |
| 1.34E+08 | 1.34E+08 | + | HPRT1 = HPRT | moderate | 1004 |
| 1.35E+08 | 1.35E+08 | + | HPRT1 = HPRT | moderate | 1005 |
| 1.35E+08 | 1.35E+08 | + | HPRT1 = HPRT | moderate | 1006 |
| 1.36E+08 | 1.36E+08 | − | HPRT1 = HPRT | moderate | 1007 |
| 1.37E+08 | 1.37E+08 | + | F9 | moderate | 1008 |
| 1.37E+08 | 1.37E+08 | + | F9 | strong | 1009 |
| 1.32E+08 | 1.32E+08 | − | HPRT1 = HPRT | moderate | 1010 |
| 1.39E+08 | 1.39E+08 | + | F9 | moderate | 1011 |
| 1.39E+08 | 1.39E+08 | + | F9 | moderate | 1012 |
| 1.39E+08 | 1.39E+08 | + | F9 | moderate | 1013 |
| 1.39E+08 | 1.39E+08 | + | F9 | moderate | 1014 |
| 1.4E+08 | 1.4E+08 | + | F9 | moderate | 1015 |
| 1.4E+08 | 1.4E+08 | + | F9 | strong | 1016 |
| 50143999 | 50213570 | − | CLCN5 | strong | 1017 |
| 50143999 | 50213570 | − | CLCN5 | moderate | 1018 |
| 1.47E+08 | 1.47E+08 | − | FMR1 | moderate | 1019 |
| 1.47E+08 | 1.47E+08 | + | FMR1 | moderate | 1020 |
| 1.47E+08 | 1.47E+08 | + | FMR1 | moderate | 1021 |
| 1.47E+08 | 1.47E+08 | + | FMR1 | moderate | 1022 |
| 1.49E+08 | 1.49E+08 | − | MTM1 | moderate | 1023 |
| 1.5E+08 | 1.5E+08 | − | MTM1 | moderate | 1024 |
| 1.5E+08 | 1.5E+08 | − | MTM1 | strong | 1025 |
| 1.5E+08 | 1.5E+08 | + | MTM1 | moderate | 1026 |
| 1.34E+08 | 1.34E+08 | + | HPRT1 = HPRT | moderate | 1027 |
| 49644159 | 49648485 | + | CLCN5 | moderate | 1028 |
| 49641851 | 49644052 | − | CLCN5 | moderate | 1029 |
| 1.52E+08 | 1.52E+08 | + | ABCD1 | moderate | 1030 |
| 1.53E+08 | 1.53E+08 | − | ABCD1 | moderate | 1031 |
| 1.53E+08 | 1.53E+08 | − | ABCD1 | moderate | 1032 |
| 1.53E+08 | 1.53E+08 | + | ABCD1 | strong | 1033 |
| 1.53E+08 | 1.53E+08 | + | ABCD1 | moderate | 1034 |
| 1.53E+08 | 1.53E+08 | − | L1CAM | moderate | 1035 |
| 1.53E+08 | 1.53E+08 | − | AVPR2 | moderate | 1036 |
| 1.54E+08 | 1.54E+08 | + | EMD | moderate | 1037 |
| 1.54E+08 | 1.54E+08 | + | EMD | moderate | 1038 |
| 1.54E+08 | 1.54E+08 | + | EMD | moderate | 1039 |
| 1.54E+08 | 1.54E+08 | + | EMD | moderate | 1040 |
| 1.49E+08 | −1.5E+08 | − | OA1 = GPR143 | moderate | 1041 |
| 1.49E+08 | 1.49E+08 | − | MTM1 | moderate | 1042 |
| 1.54E+08 | 1.54E+08 | + | EMD | moderate | 1043 |
| 1.54E+08 | 1.54E+08 | + | IKBKG | moderate | 1044 |
| 1.54E+08 | 1.54E+08 | + | IKBKG | moderate | 1045 |
| 1.54E+08 | 1.54E+08 | + | IKBKG | moderate | 1046 |
| 1.54E+08 | 1.54E+08 | + | F8 | moderate | 1047 |
| 1.15E+08 | 1.15E+08 | − | COL4A5 | moderate | 1048 |
| 1.15E+08 | 1.15E+08 | − | COL4A5 | moderate | 1049 |
| 48783029 | 48815641 | − | PQBP1 | moderate | 1050 |
| 48778055 | 48815149 | − | PQBP1 | moderate | 1051 |
| 48750837 | 48754815 | − | PQBP1 | moderate | 1052 |
| 48693572 | 48755112 | − | PQBP1 | moderate | 1053 |
| 48693572 | 48755112 | − | PQBP1 | moderate | 1054 |
| 48755060 | 48755074 | + | PQBP1 | moderate | 1055 |
| 48367347 | 48371257 | + | WAS | moderate | 1056 |
| 48367347 | 48371257 | − | WAS | moderate | 1057 |
| 34645190 | 34675419 | − | XK | moderate | 1058 |
| 34645190 | 34675419 | − | XK | moderate | 1059 |
| 34645190 | 34675419 | − | XK | moderate | 1060 |
| 34648788 | 34675385 | − | XK | moderate | 1061 |
| 30845559 | 30907504 | − | DAX1 = NR0B1 | moderate | 1062 |
| 30845559 | 30907504 | − | DAX1 = NR0B1 | moderate | 1063 |
| 30260253 | 30261290 | + | DAX1 = NR0B1 | moderate | 1064 |
| 37430765 | 37481482 | − | XK | moderate | 1065 |
| 24482937 | 24483410 | − | SAT = SAT1 | moderate. | 1066 |
| 51486509 | 51491404 | + | CLCN5 | moderate | 1067 |
| 51486509 | 51491404 | + | CLCN5 | strong | 1068 |
| 57931970 | 57936908 | + | ALAS2 | moderate | 1069 |
| 64887470 | 64961793 | + | AR | moderate | 1070 |
| 64887470 | 64961795 | + | AR | moderate | 1071 |
| 68048806 | 68061977 | + | ED1 = EDA | moderate | 1072 |
| 68048806 | 68061977 | + | ED1 = EDA | moderate | 1073 |
| 68233310 | 68233735 | + | ED1 = EDA | moderate | 1074 |
| 68316315 | 68357637 | − | ED1 = EDA | moderate | 1075 |
| 68316315 | 68351637 | − | ED1 = EDA | strong | 1076 |
| 68316315 | 68357637 | − | ED1 = EDA | moderate | 1077 |
| 68316315 | 68357637 | − | ED1 = EDA | strong | 1078 |
| 68724170 | 68724592 | + | ED1 = EDA | moderate | 1079 |
| 68724653 | 68724923 | − | ED1 = EDA | moderate | 1080 |
| 68724838 | 68724991 | + | ED1 = EDA | moderate | 1081 |
| 68835853 | 69179424 | + | ED1 = EDA | moderate | 1032 |
| 68835353 | 69259315 | + | ED1 = EDA | moderate | 1083 |
| 68835936 | 69259315 | + | ED1 = EDA | moderate | 1084 |
| 68835936 | 69259315 | + | ED1 = EDA | strong | 1085 |
| 69642906 | 69645256 | + | GJB1 | moderate | 1086 |
| 69642906 | 69645256 | + | GJB1 | moderate | 1087 |
| 69664586 | 69674956 | − | GJB1 | moderate | 1088 |
| 69664586 | 69686006 | − | GJB1 | moderate | 1089 |
| 69670135 | 69670233 | − | GJB1 | moderate | 1090 |
| 70316012 | 70323383 | + | GJB1 | moderate | 1091 |

TABLE IX-continued

Human LiftOver Ezh2 binding sites

| Start | Finish | Strand | Disease Gene | Mod/Strong | SEQ ID NO: |
|---|---|---|---|---|---|
| 70752905 | 70766316 | + | GJB1 | moderate | 1092 |
| 70152905 | 70766816 | + | GJB1 | strong | 1093 |
| 70752921 | 70766864 | + | GJB1 | moderate | 1094 |
| 70752921 | 70766864 | + | GJB1 | strong | 1095 |
| 70883692 | 70885694 | − | GJB1 | moderate | 1096 |
| 70883692 | 70885694 | − | GJB1 | moderate | 1097 |
| 71130717 | 71373136 | + | GJB1 | moderate | 1098 |
| 71130717 | 71373136 | + | GJB1 | moderate | 1099 |
| 71130717 | 71373136 | + | GJB1 | strong | 1100 |
| 71130720 | 71230692 | + | GJB1 | moderate | 1101 |
| 71130720 | 71230692 | + | GJB1 | strong | 1102 |
| 18443703 | 18646844 | + | CDKL5 | moderate | 1103 |
| 1.07E+08 | 1.07E+08 | − | PRPS1 | strong | 1104 |
| 1.07E+08 | 1.07E+08 | − | PRPS1 | moderate | 1105 |
| 1.37E+08 | 1.37E+08 | + | F9 | moderate | 1106 |
| 1.37E+08 | 1.37E+08 | + | F9 | moderate | 1107 |
| 1.37E+08 | 1.37E+08 | + | F9 | strong | 1108 |
| 1.07E+08 | 1.07E+08 | − | PRPS1 | moderate | 1109 |
| 1.07E+08 | 1.07E+08 | − | PRPS1 | moderate | 1110 |
| 1.3E+08 | 1.3E+08 | − | NYS1 = FRMD7 | moderate | 1111 |
| 18907129 | 18912300 | − | PHKA2 | moderate | 1112 |
| 1.37E+08 | 1.37E+08 | + | F9 | moderate | 1113 |
| 1.37E+08 | 1.37E+08 | + | F9 | strong | 1114 |
| 19934359 | 20009176 | − | PHKA2 | moderate | 1115 |
| 19934359 | 20009176 | − | PHKA2 | moderate | 1116 |
| 51486531 | 51491404 | + | CLCN5 | moderate | 1117 |
| 51486537 | 51491404 | + | CLCN5 | strong | 1118 |
| 39910507 | 40036404 | − | CSNB1 = NYX | strong | 1119 |
| 39910507 | 40036404 | − | CSNB1 = NYX | moderate | 1120 |
| 1.3E+08 | 1.3E+08 | − | NYS1 = FRMD7 | moderate | 1121 |
| 1.39E+08 | 1.39E+08 | − | F9 | moderate | 1122 |
| 40513127 | 40595044 | − | CSNB1 = NYX | strong | 1123 |
| 40513127 | 40595044 | − | CSNB1 = NYX | moderate | 1124 |
| 39910507 | 40005885 | − | CSNB1 = NYX | strong | 1125 |
| 39910507 | 40005885 | − | CSNB1 = NYX | moderate | 1126 |
| 1.14E+08 | 1.14E+08 | − | COL4A5 | moderate | 1127 |
| 1.35E+08 | 1.35E+08 | + | HPRT1 = HPRT | moderate | 1128 |
| 1.39E+08 | 1.39E+08 | − | F9 | moderate | 1129 |
| 61718666 | 61157125 | + | AR | moderate | 1130 |
| 67718666 | 67757125 | + | AR | moderate | 1131 |
| 1.24E+08 | 1.24E+08 | − | OCRL | strong | 1132 |
| 1.24E+08 | 1.24E+08 | − | OCRL | moderate | 1133 |
| 67913429 | 67945678 | + | ED1 = EDA | moderate | 1134 |
| 38660685 | 38665692 | − | OTC | moderate | 1135 |
| 1.01E+08 | 1.01E+08 | − | GLA | moderate | 1136 |
| 19968429 | 20009740 | − | PHKA2 | moderate | 1137 |
| 1.24E+08 | 1.24E+08 | − | OCRL | strong | 1138 |
| 1.24E+08 | 1.24E+08 | − | OCRL | moderate | 1139 |
| 48830738 | 48858649 | − | PQBP1 | moderate | 1140 |
| 48830738 | 48853649 | − | PQBP1 | moderate | 1141 |
| 48363330 | 48379198 | + | WAS | moderate | 1142 |
| 48363330 | 48379198 | + | WAS | moderate | 1143 |
| 54947223 | 54957868 | + | ALAS2 | moderate | 1144 |
| 67718666 | 67751756 | + | AR | moderate | 1145 |
| 67913429 | 67942045 | + | ED1 = EDA | moderate | 1146 |
| 49123140 | 49146158 | + | PQBP1 | moderate | 1147 |
| 1.29E+08 | 1.29E+08 | − | OCRL | strong | 1148 |
| 1.29E+08 | 1.29E+08 | − | OCRL | moderate | 1149 |
| 40594441 | 40595080 | − | CSNB1 = NYX | strong | 1150 |
| 40594441 | 40595080 | − | CSNB1 = NYX | moderate | 1151 |
| 1.29E+08 | 1.29E+08 | − | OCRL | moderate | 1152 |
| 48750337 | 48754315 | − | PQBP1 | moderate | 1153 |
| 1.31E+08 | 1.31E+08 | − | NYS1 = FRMD7 | moderate | 1154 |
| 1.07E+08 | 1.07E+08 | − | PRPS1 | moderate | 1155 |
| 19553529 | 19587588 | − | PHKA2 | moderate | 1156 |
| 1.54E+08 | 1.54E+08 | − | IKBKG | moderate | 1157 |
| 1.34E+08 | 1.54E+08 | − | IKBKG | strong | 1158 |
| 1.19E+08 | 1.19E+08 | − | OCRL | moderate | 1159 |
| 50336570 | 50551310 | − | CLCN5 | moderate | 1160 |
| 1.53E+08 | 1.53E+08 | − | AVPR2 | moderate | 1161 |
| 48779439 | 48814344 | − | PQBP1 | moderate | 1162 |
| 48779489 | 48814344 | − | PQBP1 | moderate | 1163 |
| 51636562 | 51639796 | + | MRX1 = IQSEC2 | moderate | 1164 |
| 51636562 | 51639796 | + | MRX1 = IQSEC2 | moderate | 1165 |
| 73816770 | 73834464 | − | ABCB7 | moderate | 1166 |
| 73816770 | 73834464 | − | ABCB7 | strong | 1167 |
| 73953408 | 74145290 | − | ABCB7 | moderate | 1168 |
| 73953408 | 74145305 | − | ABCB7 | moderate | 1169 |
| 76995795 | 77041698 | − | ATRX | moderate | 1170 |
| 39921386 | 39957214 | − | CSNB1 = NYX | strong | 1171 |
| 39921386 | 39957214 | − | CSNB1= NYX. | moderate | 1172 |
| 39922665 | 39957225 | − | CSNB1 = NYX | strong | 1173 |
| 39922665 | 39957225 | − | CSNB1 = NYX | moderate | 1174 |
| 40511131 | 40595078 | − | CSNB1 = NYX | strong | 1175 |
| 40511131 | 40595078 | − | CSNB1 = NYX | moderate | 1176 |
| 99657457 | 99665277 | − | BTK | moderate | 1177 |
| 99657457 | 99665277 | − | BTK | strong | 1178 |
| 99929475 | 99987138 | − | BTK | moderate | 1179 |
| 99929475 | 99987138 | − | BTK | strong | 1180 |
| 41374187 | 41782933 | − | CSNB1 = NYX | moderate | 1181 |
| 1.01E+08 | 1.01E+08 | + | BTK | moderate | 1182 |
| 41416196 | 41782933 | − | CSNB1 = NYX | moderate | 1183 |
| 41418781 | 41782940 | − | CSNB1 = NYX | moderate | 1184 |
| 1.03E+08 | 1.03E+08 | − | TBG = SERPINA7 | moderate | 1185 |
| 1.03E+08 | 0 | − | OA1 = GPR143 | moderate | 1186 |
| 1.03E+08 | 1.03E+08 | − | TBG = SERPINA7 | moderate | 1187 |
| 1.06E+08 | 1.06E+08 | − | PRPS1 | strong | 1188 |
| 1.06E+08 | 1.06E+08 | − | PRPS1 | moderate | 1189 |
| 1.07E+08 | 1.08E+08 | − | COL4A5 | moderate | 1190 |
| 1.08E+08 | 1.08E+08 | − | COL4A5 | moderate | 1191 |
| 1.08E+08 | 1.08E+08 | + | COL4A5 | moderate | 1192 |
| 1.08E+08 | 1.08E+08 | + | COL4A5 | moderate | 1193 |
| 1.08E+08 | 1.08E+08 | + | COL4A5 | moderate | 1194 |
| 1.09E+08 | 1.1E+08 | − | COL4A5 | moderate | 1195 |
| 1.09E+08 | 1.1E+08 | − | COL4A5 | moderate | 1196 |
| 1.12E+08 | 1.12E+08 | − | COL4A5 | moderate | 1197 |
| 1.14E+08 | 1.14E+08 | − | COL4A5 | moderate | 1198 |
| 1.14E+08 | 1.14E+08 | − | COL4A5 | moderate | 1199 |
| 53458207 | 53461346 | − | MRX1 = IQSEC2 | moderate | 1200 |
| 9754409 | 9917528 | + | OA1 = GPR143 | moderate | 1201 |
| 9754412 | 9901148 | + | OA1 = GPR143 | moderate | 1202 |
| 56259009 | 56314850 | − | ALAS2 | moderate | 1203 |
| 14891501 | 14934512 | + | PIGA | moderate | 1204 |
| 13752890 | 13788174 | + | OFD1 | moderate | 1205 |
| 46533672 | 46613615 | − | UBA1 | moderate | 1206 |
| 47004307 | 47046225 | + | UBA1 | strong | 1207 |
| 47004307 | 47046225 | + | UBA1 | moderate | 1208 |
| 1.18E+08 | 1.18E+08 | − | COL4A5 | moderate | 1209 |
| 1.18E+08 | 1.18E+08 | − | OCRL | moderate | 1210 |
| 1.13E+08 | 1.18E+08 | − | OCRL | moderate | 1211 |
| 1.19E+08 | 1.19E+08 | − | OCRL | moderate | 1212 |
| 1.19E+08 | 1.19E+08 | − | OCRL | moderate | 1213 |
| 1.19E+08 | 1.19E+08 | − | OCRL | moderate | 1214 |
| 1.22E+03 | 1.23E+08 | + | OCRL | strong | 1715 |
| 1.22E+08 | 1.23E+08 | + | OCRL | moderate | 1216 |
| 1.23E+08 | 1.23E+08 | − | OCRL | moderate | 1217 |
| 1.23E+08 | 1.23E+08 | − | OCRL | moderate | 1218 |
| 1.29E+08 | 1.29E+08 | − | OCRL | moderate | 1219 |
| 1.3E+08 | 1.3E+08 | − | NYS1 = FRMD7 | moderate | 1220 |
| 1.34E+08 | 1.34E+08 | + | HPRT1 = HPRT | moderate | 1221 |
| 1.39E+08 | 1.39E+08 | − | F9 | moderate | 1222 |
| 1.39E+08 | 1.39E+08 | − | F9 | moderate | 1223 |
| 1.34E+08 | 1.34E+08 | + | HPRT1 = HPRT | moderate | 1224 |
| 1.34E+08 | 1.34E+08 | + | HPRT1 = HPRT | strong | 1225 |
| 1.53E+08 | 1.53E+08 | − | ABCD1 | moderate | 1226 |
| 1.54E+08 | 1.54E+08 | + | G6PD = G6PDX | moderate | 1227 |
| 1.15E+08 | 1.15E+08 | + | COL4A5 | moderate | 1228 |
| 48455856 | 48457390 | + | WAS | moderate | 1229 |
| 48367347 | 48371257 | + | WAS | moderate | 1230 |
| 71423288 | 71458939 | − | GJB1 | moderate | 1231 |
| 71423288 | 71458939 | − | GJB1 | moderate | 1232 |
| 71798692 | 71934148 | − | GJB1 | moderate | 1233 |
| 38663247 | 38663699 | + | OTC | moderate | 1234 |
| 85403464 | 85999361 | + | CHM | moderate | 1235 |
| 95939886 | 96685244 | + | BTK | moderate | 1236 |
| 95939336 | 96635244 | + | BTK | strong | 1237 |
| 40944807 | 40945143 | + | CSNB1 = NYX | moderate | 1238 |
| 40945858 | 40946083 | + | CSNB1 = NYX | moderate | 1239 |

TABLE IX-continued

Human LiftOver Ezh2 binding sites

| Start | Finish | Strand | Disease Gene | Mod/Strong | SEQ ID NO: |
|---|---|---|---|---|---|
| 40950911 | 40950974 | + | CSNB1 = NYX | moderate | 1240 |
| 99546628 | 99665277 | − | BTK | moderate | 1241 |
| 99546628 | 99665277 | − | BTK | strong | 1242 |
| 1.01E+08 | 1.01E+08 | − | BTK | moderate | 1243 |
| 1.01E+08 | 1.01E+08 | + | GLA | moderate | 1244 |
| 1.02E+08 | 1.02E+08 | + | GLA | moderate | 1245 |
| 1.02E+08 | 1.02E+08 | + | GLA | moderate | 1246 |
| 1.03E+08 | 1.03E+08 | + | GLA | moderate | 1247 |
| 1.04E+08 | 1.05E+08 | + | TBG = SERPINA7 | strong | 1248 |
| 1.04E+08 | 1.05E+08 | + | TBG = SERPINA7 | moderate | 1249 |
| 1.04E+08 | 1.05E+08 | + | TBG = SERPINA7 | strong | 1250 |
| 1.04E+08 | 1.05E+08 | + | TBG = SERPINA7 | moderate | 1251 |
| 1.06E+08 | 1.06E+08 | + | TBG = SERPINA7 | moderate | 1252 |
| 1.06E+08 | 1.06E+08 | + | TBG = SERPINA7 | moderate | 1253 |
| 1.09E+08 | 1.09E+08 | − | COL4A5 | moderate | 1254 |
| 1.1E+08 | 1.1E+08 | + | COL4A5 | moderate | 1255 |
| 1.11E+08 | 1.11E+08 | − | COL4A5 | strong | 1256 |
| 1.11E+08 | 1.11E+08 | − | COL4A5 | moderate | 1257 |
| 35820375 | 35821357 | + | XK | moderate | 1258 |
| 54840303 | 54840922 | + | ALAS2 | moderate | 1259 |
| 54475005 | 54522668 | − | FGD1 | moderate | 1260 |
| 54475005 | 54527668 | − | FGD1 | moderate | 1261 |
| 54475005 | 54522668 | − | FGD1 | moderate | 1262 |
| 53449811 | 53453282 | + | MRX1 = IQSEC2 | moderate | 1263 |
| 53449811 | 53453282 | + | MRX1 = IQSEC2 | moderate | 1264 |
| 53448837 | 53449093 | − | MRX1 = IQSEC2 | moderate | 1265 |
| 21975056 | 21975269 | + | PHEX | moderate | 1266 |
| 18651084 | 18651384 | + | RS1 | moderate | 1267 |
| 15808383 | 15822299 | + | PIGA | moderate | 1268 |
| 12809471 | 12837836 | + | SEDL = TRAPPC2 | moderate | 1269 |
| 12809525 | 12818878 | + | SEDL = TRAPPC2 | moderate | 1270 |
| 12809525 | 12818818 | + | SEDL = TRAPPC2 | moderate | 1271 |
| 44383408 | 44401509 | − | NDP | moderate | 1272 |
| 46772434 | 46772364 | + | UBA1 | moderate | 1273 |
| 47004623 | 47044505 | + | UBA1 | strong | 1274 |
| 47004623 | 47044506 | + | UBA1 | moderate | 1275 |
| 47004623 | 47044506 | + | UBA1 | strong | 1276 |
| 47004623 | 47044506 | + | UBA1 | moderate | 1277 |
| 1.18E+08 | 1.18E+08 | + | COL4A5 | strong | 1278 |
| 1.18E+08 | 1.18E+08 | + | COL4A5 | moderate | 1279 |
| 1.18E+08 | 1.18E+08 | + | COL4A5 | strong | 1280 |
| 1.18E+08 | 1.18E+08 | + | COL4A5 | moderate | 1281 |
| 1.18E+08 | 1.18E+08 | + | OCRL | moderate | 1282 |
| 1.19E+08 | 1.19E+08 | − | OCRL | strong | 1283 |
| 1.19E+08 | 1.19E+08 | − | OCRL | moderate | 1284 |
| 1.2E+08 | 1.2E+08 | − | OCRL | moderate | 1285 |
| 1.2E+08 | 1.2E+08 | + | OCRL | moderate | 1286 |
| 1.22E+08 | 1.23E+08 | + | OCRL | strong | 1287 |
| 1.22E+08 | 1.23E+08 | + | OCRL | moderate | 1288 |
| 1.23E+08 | 1.23E+08 | − | OCRL | moderate | 1289 |
| 1.29E+08 | 1.29E+08 | − | OCRL | moderate | 1290 |
| 1.29E+08 | 1.29E+08 | + | OCRL | strong | 1291 |
| 1.29E+08 | 1.29E+08 | + | OCRL | moderate | 1292 |
| 1.29E+08 | 1.29E+08 | + | OCRL | strong | 1293 |
| 1.29E+08 | 1.29E+08 | + | OCRL | moderate | 1294 |
| 1.29E+08 | 1.29E+08 | + | OCRL | strong | 1295 |
| 1.29E+08 | 1.29E+08 | + | OCRL | moderate | 1296 |
| 1.29E+08 | 1.29E+08 | + | OCRL | strong | 1297 |
| 1.29E+08 | 1.29E+08 | + | OCRL | moderate | 1298 |
| 1.29E+08 | 1.29E+08 | + | OCRL | moderate | 1299 |
| 1.3E+08 | 1.3E+08 | + | NYS1 = FRMD7 | moderate | 1300 |
| 1.3E+08 | 1.3E+08 | + | NYS1 = FRMD7 | moderate | 1301 |
| 1.32E+08 | 1.32E+08 | − | NYS1 = FRMD7 | strong | 1302 |
| 1.32E+08 | 1.32E+08 | − | NYS1 = FRMD7 | moderate | 1303 |
| 1.32E+08 | 1.32E+08 | − | NYS1 = FRMD7 | strong | 1304 |
| 1.32E+08 | 1.32E+08 | − | NYS1 = FRMD7 | moderate | 1305 |
| 1.32E+08 | 1.32E+08 | − | NYS1 = FRMD7 | strong | 1306 |
| 1.32E+08 | 1.32E+08 | − | NYS1 = FRMD7 | moderate | 1307 |
| 1.33E+08 | 1.38E+08 | − | HPRT1 = HPRT | moderate | 1308 |
| 1.35E+08 | 1.35E+08 | − | HPRT1 = HPRT | moderate | 1309 |
| 1.36E+08 | 1.36E+08 | − | HPRT1 = HPRT | moderate | 1310 |
| 1.36E+08 | 1.36E+08 | − | HPRT1 = HPRT | moderate | 1311 |
| 1.38E+08 | 1.38E+08 | − | F9 | moderate | 1312 |
| 1.38E+08 | 1.38E+08 | − | F9 | moderate | 1313 |
| 50556592 | 50556774 | − | CLCN5 | moderate | 1314 |
| 1.47E+08 | 1.47E+08 | + | FMR1 | moderate | 1315 |
| 1.47E+08 | 1.47E+08 | + | FMR1 | moderate | 1316 |
| 1.49E+08 | 1.49E+08 | − | MTM1 | moderate | 1317 |
| 1.49E+08 | 1.49E+08 | − | MTM1 | moderate | 1318 |
| 1.5E+08 | 1.5E+08 | + | MTM1 | moderate | 1319 |
| 1.5E+08 | 1.5E+08 | + | MTM1 | moderate | 1320 |
| 1.5E+08 | 1.5E+08 | + | MTM1 | moderate | 1321 |
| 1.5E+08 | 1.5E+08 | + | MTM1 | moderate | 1322 |
| 1.5E+08 | 1.5E+08 | + | MTM1 | strong | 1323 |
| 1.5E+08 | 1.5E+08 | + | MTM1 | moderate | 1324 |
| 1.5E+08 | 1.5E+08 | + | MTM1 | strong | 1325 |
| 1.51E+08 | 1.51E+08 | + | MTM1 | moderate | 1326 |
| 1.51E+08 | 1.51E+08 | + | MTM1 | moderate | 1327 |
| 1.51E+08 | 1.51E+08 | − | MTM1 | moderate | 1328 |
| 1.51E+08 | 1.51E+08 | − | MTM1 | moderate | 1329 |
| 1.52E+08 | 1.52E+08 | + | ABCD1 | moderate | 1330 |
| 1.52E+08 | 1.52E+08 | + | ABCD1 | moderate | 1331 |
| 1.32E+08 | 1.52E+08 | + | ABCD1 | moderate | 1332 |
| 1.52E+08 | 1.52E+08 | + | ABCD1 | moderate | 1333 |
| 1.53E+08 | 1.53E+08 | − | AVPR2 | moderate | 1334 |
| 1.53E+08 | 1.53E+08 | − | AVPR2 | moderate | 1335 |
| 1.54E+08 | 1.54E+08 | − | EMD | moderate | 1336 |
| 1.54E+08 | 1.54E+08 | − | EMD | moderate | 1337 |
| 1.54E+03 | 1.54E+08 | + | EMD | moderate | 1338 |
| 1.34E+08 | 1.54E+08 | + | EMD | moderate | 1339 |
| 1.54E+08 | 1.54E+08 | + | EMD | moderate | 1340 |
| 1.54E+08 | 1.54E+08 | + | EMD | moderate | 1341 |
| 49049104 | 49056698 | − | PQBP1 | moderate | 1342 |
| 1.54E+03 | 1.54E+08 | + | F8 | moderate | 1343 |
| 1.15E+08 | 1.15E+08 | + | COL4A5 | moderate | 1344 |
| 48778055 | 48815149 | − | PQBP1 | moderate | 1345 |
| 37208552 | 37301473 | + | XK | moderate | 1346 |
| 37208552 | 37301473 | + | XK | moderate | 1347 |
| 37208635 | 37293306 | + | XK | moderate | 1348 |
| 37208635 | 37293306 | + | XK | moderate | 1349 |
| 37208533 | 37269301 | + | XK | moderate | 1350 |
| 48436197 | 48458240 | + | WAS | moderate | 1351 |
| 48398062 | 48419602 | + | WAS | moderate | 1352 |
| 48398062 | 48419602 | + | WAS | moderate | 1353 |
| 48398130 | 48419594 | + | WAS | moderate | 1354 |
| 43330199 | 48382586 | + | WAS | moderate | 1355 |
| 48380199 | 48382586 | + | WAS | moderate | 1356 |
| 48367374 | 48379193 | + | WAS | moderate | 1357 |
| 48367374 | 48379193 | + | WAS | moderate | 1358 |
| 30905799 | 30907361 | − | DAX1 = NR0B1 | moderate | 1359 |
| 51636754 | 51645448 | + | MRX1 = IQSEC2 | moderate | 1360 |
| 37700168 | 37706872 | − | CYBB | moderate | 1361 |
| 70753491 | 70753347 | + | GJB1 | moderate | 1362 |
| 71838498 | 71934132 | − | GJB1 | moderate | 1363 |

Oligonucleotide drugs targeting the disease genes are designed using the reverse complement of the lncRNA sequence listed in the LncRNA Tables VI and VII.

Example 9

Targeting paRNAs to Treat X-linked Diseases

As described above, there are over 40 X-linked diseases associated with the presence of a mutation on the active X. These diseases would be treatable or even curable if the normal allele, present on the inactive X, could be reactivated. It would not be desirable to reactivate the entire X chromosome, as over-dosage could lead to other problems such as cancer. Thus, locus-specific reactivation is desirable, but the presence of many layers of heterochromatin may make this difficult using standard methods.

To determine whether locus-specific reactivation can be achieved by taking advantage of Polycomb spreading sites, reactivation of the Mecp2 gene was attempted.

Mecp2 mutations cause Rett syndrome, an autism spectrum disorder that is fatal in affected males and that results in autistic, progressive neurological symptoms, with regression of language and motor control, seizures, and respiratory diseases in females beginning at about 1-3 years of age. It is not a degenerative disease, and mouse models show that the condition is reversible if Mecp2 expression is restored postnatally, even after onset of symptoms (Guy et al., Science. 315(5815):1143-7 (2007)).

In mice, Mecp2 resides within a 5 mb gene-rich cluster. Using the methods described in Examples 1-8 above, strong and moderate PRC2 binding sites in the cluster were identified, There are 6 PRC2 strong sites or "spreading elements" for this gene cluster present in d0ES, d7 ES, and/or MEF, and over 170 PRC2 moderate sites. The PRC2 binding sites had paRNAs associated with them, as shown by methods outlined above in Tables VI and VII. Mecp2 has an antisense paRNA; the Mecp2 gene is on the − strand of the chromosome. See WO 2012/065143 and WO 2012/087983.

Three approaches were used to increase Mecp2 expression: first, targeting the Mecp2 antisense lncRNA; second, targeting the strong Polycomb binding sites in the region; and third, targeting both. Gapmer antisense oligos were designed to the small regions of interest. The selected regions for targeting the Polycomb sites were the transcripts crossing two strong binding sites closest to the Mecp2 gene, corresponding to seg_57 and seg_58 in Table IVA, above. For targeting the Mecp2 antisense, gapmers were designed against the antisense RNA that overlaps the gene body of Mecp2 region. The gapmers carried LNA bases at the ends and have full phosphorothioate backbone.

Mecp2-AS (antisense transcript)-targeting oligos were as shown in Table X; oligos targeting the PRC2 strong binding sites are shown in Table XL All sequences are shown 5'-3'.

TABLE X

| LNA | Sequence | SEQ ID NO: |
|---|---|---|
| LNA 17 | +AGA+TCA+GGA+TGT+AG+C-Phos | 1364 |
| LNA 22 | +T+C+AG*T*C*C*T*C*A*C+T+C+C-Phos | 1365 |

+indicates placement of LNA nucleotides;
*refers to phosphorothioate backbone

TABLE XI

| LNA | Sequence | SEQ ID NO: |
|---|---|---|
| | Segment 57 | |
| 57 plus-94-LNA A | CGGTGCCTAGCATGCA | 1366 |
| 57 minus-226-LNA B | GTTGATTGATAGGA | 1367 |
| 57 Plus-548-LNA E | TGGAAAGGAGGAGGTG | 1368 |
| 57 minus-857-LNA F | GTGTATGCGTGTGA | 1369 |
| | Segment 58 | |
| 58 Plus-614-LNA C | GAAAGGCACGAAGAG | 1370 |
| 58 minus-771-LNA D | GGATGCTTGAAACA | 1371 |

TABLE XI-continued

| LNA | Sequence | SEQ ID NO: |
|---|---|---|
| 58 Plus-549-LNA G | CCTTACCCCTCTAAAA | 1372 |
| 58 minus-381-LNA H | AGGAGCTTAAAGTGAG | 1373 |

To determine the ability of the selected oligos to reactivate Mecp2 from the inactive X chromosome, assays were carried out using genetically marked cells. An F1 mus/cas Mecp2:GFP reporter cell line was created as follows, Mecp2:GFP knock-in mice (M. musculus background [mus]) were crossed with wildtype Mus castancus [cas] male mice to generate F1 progeny in which the two X chromosomes can be distinguished by SNPs. Tail tip fibroblasts were outgrown and immortalized using SV40 large T antigen. Clones in which the Mecp2:GFP-bearing musculus X chromosome was inactivated were used for the X-reactivation assays.

Mecp2-GFP Xi cells derived from imortalized Tail tip Fibroblasts (as described above) were grown and passaged in standard Fibroblast HEPES buffered DMEM media with 10% Calf Serum and 1% Penicillin Streptomycin.

Each LNA from Exiqon A/S Vedbaek, Denmark was resuspended, from HPLC Purified Lyophilized powder, in DEPC treated water to make a 100 uM stock solution and a 10 uM working solution and both were stored at −20° C.

All transfections were done using Lipofectamine LTX and Plus reagent (Invitrogen Catalog #15338-100) in 24 well plates. Each transfection used a mix of three component mixtures that were made and then added to each well in the plate as follows:

1) Mix 1 consisted of: 50 ul of Optimem reduced Serum Medium (Gibco 31985-070)+3 ul of Lipofectamine LTX (Invitrogen Catalog #15338-100) and was added to and allowed to stand at room temperature for at least 5 minutes.

2) Mix 2 consisted of: 50 ul of Optimem LNA to 20-100 nM each +1.5 ul of Plus reagent from the Lipofectamine LTX kit. This mix was allowed to stand for 5 minutes at room temperature.

3) Mix 1 was added dropwise to Mix 2 and allowed to stand at room temperature for at least 5 minutes then 100 ul of this mixture was added dropwise to 400 ul DMEM FCS media containing $5 \times 10^4$ cells in suspension/well of a 24 well plate. Transfected plates of cells were in placed in the incubator, 37 C/5% CO2 for 24 hours.

Post transfection, cells from each well were harvested by trypsinization, spun into a pellet at 1000×g for 5 minutes and then lysed in 1 ml Trizol (Invitrogen 15596-026) to extract the RNA using reagent instructions. The RNA pellet was suspended in DEPC treated water and then DNA was removed using Ambion® TURBO™ DNase AM2238 which was inactivated using the inactivation beads supplied with the kit. RNA was converted to cDNA using SuperScript® Reverse Transcriptase from Invitrogen (Catalog #18080093). QPCR was performed in a 20 ul reaction volume using iQ™ SYBR® Green Supermix Catalog #170-8880 in Biorad CFX96 and CFX384 Real-Time PCR Detection System with the primers shown in Table XII below. All qPCR values are normalized to the housekeeping gene Gapdh.

TABLE XII

| Name | F/R | Sequence 5'-3' | SEQ ID NO: |
|---|---|---|---|
| GapdhBP1F | F | ATGAATACGGCTACAGCAACAGG | 1374 |
| GapdhBP1R | R | CTCTTGCTCAGTGTCCTTGCTG | 1375 |
| mMecp2 275852F AC-Mus | R | GCTTGCTACACAGCCATTAC | 1376 |
| mMecp2 275852F AT-Cast | R | GCTTGCTACACAGCCATTAT | 1377 |
| mMecp2 275852F | F | TAGAAGGCCCAGCACAAAGT | 1378 |

F, forward;
R, reverse

In the absence of any of the oligos, the Mecp2 allele of the active X was expressed at about 500 times the level of the allele on the inactive X.

FIG. 15A shows the results of treating the cells with each of the LNAs, singly or in combination. There was approximately 4-5× upregulation of expression after treating the cells pith LNA 22. Single oligos targeting the PRC2 binding site were also effective; see, e.g., C, D. The combination of oligos ABCD was also effective, oligos E, F, and G in combinations of two were mildly effective, but the EFG combination was exemplary, with approximately 41× upregulation. As shown in FIG. 15B, by comparison, expression of Mecp2 from the Castaneus X (active X) was less affected by the LNA transfections. Cas Xa may have some upregulation because the strong polycomb stations are also present on the Xa, Expression of a distant gene, GPC4 (which is about 20 Mb away from Mecp2) was also evaluated after treatment with the various oligos. Little to no upregulation was seen, providing evidence for the locus-specificity of the approach described herein.

To increase expression of mcp2 in human cells, e.g., cells in a living human, oligos are designed to target the human Mecp2-associated antisense lncRNA, the sequence of which is included herein as SEQ ID NO:10169. In some embodiments, oligos are designed that target a strong or moderate binding site in or near the MECP2 gene, e.g., as shown in table A.

Example 10

Human Allele-Specific ChIP-seq—Human paRNAs and PRC2 Binding Sites

Using the methods and criteria described above, PRC2 strong binding sites and their associated paRNAs were identified in two different human cell types cells by analysis of ChIP-scq data for SUZ12 and the catalytic subunit EZH2 in two cell lines, K562 (an erythroleukemia cell line) and GM12878 (a lymphoblastoid cell line). Accession numbers are:
SUZ12 in K562: wgEncodeEH00311:2(exp)/wgEncodeEH000052(input)
EZH2 in K562: wgEncodeEH002089 (exp)/wgEncodeEH000052(input),
EZH2 GM12878: wgEncodeE14003112 (exp)/wgEncodeEH000037(input))

In K562 cells, a total of 578 EZH2 strong sites were identified (Table XIII), and a total of 666 SUZ12 strong sites were found (Table XIV). In GM12878, 215 EZH2 strong sites were found (Table XV). These likely serve as spreading elements for silencing by PRC2 and by other chromatin modifiers. Shown in the Tables are (in column order): the start and end positions (base number on X-chromosome), segment number (name) for the strong EZH2 or SUZ12 site; and the sequence identifier (SEQ ID NO:). All coordinates refer to hg19. Table XIII sets forth the coordinates and SEQ NOs. for the EZH2 strong binding sites identified in K562 cells.

TABLE XIII

EZH2 in K562

| start | end | name | SEQ ID NO: |
|---|---|---|---|
| 372800 | 374450 | seg_1 | 1379 |
| 379550 | 383950 | seg_2 | 1380 |
| 387200 | 393050 | seg_3 | 1381 |
| 419950 | 421200 | seg_4 | 1382 |
| 425800 | 427350 | seg_5 | 1383 |
| 436400 | 439050 | seg_6 | 1384 |
| 458450 | 460500 | seg_7 | 1385 |
| 610100 | 614650 | seg_8 | 1386 |
| 631850 | 633750 | seg_9 | 1387 |
| 750450 | 752100 | seg_10 | 1388 |
| 920750 | 921950 | seg_11 | 1389 |
| 928850 | 930150 | seg_12 | 1390 |
| 961300 | 964500 | seg_13 | 1391 |
| 965950 | 967550 | seg_14 | 1392 |
| 977100 | 979150 | seg_15 | 1393 |
| 988950 | 996900 | seg_16 | 1394 |
| 1232150 | 1233250 | seg_17 | 1395 |
| 1235100 | 1236300 | seg_18 | 1396 |
| 1238350 | 1241400 | seg_19 | 1397 |
| 1324000 | 1325900 | seg_20 | 1398 |
| 1348200 | 1349900 | seg_21 | 1399 |
| 1392500 | 1394100 | seg_22 | 1400 |
| 1403850 | 1405100 | seg_23 | 1401 |
| 1460050 | 1461400 | seg_24 | 1402 |
| 1464650 | 1468000 | seg_25 | 1403 |
| 1672250 | 1674650 | seg_26 | 1404 |
| 1733950 | 1735600 | seg_27 | 1405 |
| 1747250 | 1749200 | seg_28 | 1406 |
| 2368950 | 2371350 | seg_29 | 1407 |
| 2374650 | 2376750 | seg_30 | 1408 |
| 2381200 | 2383650 | seg_31 | 1409 |
| 2391700 | 2394350 | seg_32 | 1410 |
| 2444150 | 2446650 | seg_33 | 1411 |
| 2451150 | 2452250 | seg_34 | 1412 |
| 2454950 | 2457000 | seg_35 | 1413 |
| 2461000 | 2462500 | seg_36 | 1414 |
| 2664000 | 2667450 | seg_37 | 1415 |
| 2669000 | 2672950 | seg_38 | 1416 |
| 2681550 | 2683000 | seg_39 | 1417 |
| 2684450 | 2685950 | seg_40 | 1418 |
| 2699450 | 2703000 | seg_41 | 1419 |
| 2854000 | 2856700 | seg_42 | 1420 |
| 2873200 | 2874800 | seg_43 | 1421 |
| 2876400 | 2879500 | seg_44 | 1422 |
| 2887500 | 2888650 | seg_45 | 1423 |
| 2936900 | 2938400 | seg_46 | 1424 |
| 2957200 | 2959050 | seg_47 | 1425 |
| 3466650 | 3467850 | seg_48 | 1426 |
| 3482000 | 3483150 | seg_49 | 1427 |
| 3507050 | 3508700 | seg_50 | 1428 |
| 3705050 | 3707200 | seg_51 | 1429 |
| 3708300 | 3710150 | seg_52 | 1430 |
| 3712800 | 3713800 | seg_53 | 1431 |
| 3724050 | 3726750 | seg_54 | 1432 |
| 9153950 | 9155700 | seg_55 | 1433 |
| 9229800 | 9231600 | seg_56 | 1434 |
| 9241950 | 9244700 | seg_57 | 1435 |
| 9246150 | 9248050 | seg_58 | 1436 |
| 9255400 | 9263150 | seg_59 | 1437 |
| 9268600 | 9269950 | seg_60 | 1438 |
| 9273550 | 9277500 | seg_61 | 1439 |
| 9371100 | 9382750 | seg_62 | 1440 |
| 9483500 | 9485050 | seg_63 | 1441 |
| 9793150 | 9794450 | seg_64 | 1442 |
| 9806050 | 9807500 | seg_65 | 1443 |
| 9814250 | 9818150 | seg_66 | 1444 |
| 9823350 | 9824550 | seg_67 | 1445 |
| 9863450 | 9867000 | seg_68 | 1446 |

TABLE XIII-continued

EZH2 in K562

| start | end | name | SEQ ID NO: |
|---|---|---|---|
| 9880300 | 9881950 | seg_69 | 1447 |
| 9883800 | 9885000 | seg_70 | 1448 |
| 9913900 | 9916050 | seg_71 | 1449 |
| 9929000 | 9930050 | seg_72 | 1450 |
| 10048550 | 10049650 | seg_73 | 1451 |
| 10180950 | 10182200 | seg_74 | 1452 |
| 10189550 | 10190550 | seg_75 | 1453 |
| 10405900 | 10406950 | seg_76 | 1454 |
| 10549850 | 10550950 | seg_77 | 1455 |
| 10575350 | 10576400 | seg_78 | 1456 |
| 10577550 | 10579300 | seg_79 | 1457 |
| 10587800 | 10589900 | seg_80 | 1458 |
| 10837250 | 10839150 | seg_81 | 1459 |
| 11358850 | 11360300 | seg_82 | 1460 |
| 11385800 | 11386800 | seg_83 | 1461 |
| 11478950 | 11480450 | seg_84 | 1462 |
| 11482700 | 11483900 | seg_85 | 1463 |
| 11735400 | 11736450 | seg_86 | 1464 |
| 12726850 | 12727900 | seg_87 | 1465 |
| 12750450 | 12751500 | seg_88 | 1466 |
| 12790000 | 12792000 | seg_89 | 1467 |
| 12793350 | 12796700 | seg_90 | 1468 |
| 12801350 | 12803400 | seg_91 | 1469 |
| 12995250 | 12996450 | seg_92 | 1470 |
| 13374100 | 13375150 | seg_93 | 1471 |
| 13450850 | 13452000 | seg_94 | 1472 |
| 13469850 | 13471200 | seg_95 | 1473 |
| 13476300 | 13477400 | seg_96 | 1474 |
| 13508450 | 13509700 | seg_97 | 1475 |
| 13587150 | 13589150 | seg_98 | 1476 |
| 13634850 | 13636950 | seg_99 | 1477 |
| 13800750 | 13802000 | seg_100 | 1478 |
| 13803050 | 13806050 | seg_101 | 1479 |
| 13820050 | 13821950 | seg_102 | 1480 |
| 13832300 | 13835750 | seg_103 | 1481 |
| 13917650 | 13919650 | seg_104 | 1482 |
| 13941900 | 13943750 | seg_105 | 1483 |
| 13954250 | 13956600 | seg_106 | 1484 |
| 13970300 | 13971650 | seg_107 | 1485 |
| 13982450 | 13985700 | seg_108 | 1486 |
| 14056900 | 14058300 | seg_109 | 1487 |
| 14082450 | 14083900 | seg_110 | 1488 |
| 14943900 | 14945100 | seg_111 | 1489 |
| 15286800 | 15288500 | seg_112 | 1490 |
| 15301150 | 15302150 | seg_113 | 1491 |
| 15321650 | 15322700 | seg_114 | 1492 |
| 15354950 | 15359650 | seg_115 | 1493 |
| 15382100 | 15387750 | seg_116 | 1494 |
| 15391300 | 15392750 | seg_117 | 1495 |
| 15661050 | 15663600 | seg_118 | 1496 |
| 16141650 | 16142650 | seg_119 | 1497 |
| 16548550 | 16550900 | seg_120 | 1498 |
| 16919800 | 16921600 | seg_121 | 1499 |
| 16927950 | 16929000 | seg_122 | 1500 |
| 16965250 | 16968400 | seg_123 | 1501 |
| 17028550 | 17029750 | seg_124 | 1502 |
| 17113350 | 17114550 | seg_125 | 1503 |
| 17749950 | 17751500 | seg_126 | 1504 |
| 17876650 | 17878250 | seg_127 | 1505 |
| 18211700 | 18212750 | seg_128 | 1506 |
| 18234150 | 18238350 | seg_129 | 1507 |
| 18249900 | 18251000 | seg_130 | 1508 |
| 18378400 | 18380050 | seg_131 | 1509 |
| 18382850 | 18383900 | seg_132 | 1510 |
| 18412350 | 18413650 | seg_133 | 1511 |
| 18416550 | 18418150 | seg_134 | 1512 |
| 18443550 | 18447600 | seg_135 | 1513 |
| 18451450 | 18452650 | seg_136 | 1514 |
| 18624850 | 18626400 | seg_137 | 1515 |
| 18651650 | 18653200 | seg_138 | 1516 |
| 18659400 | 18661000 | seg_139 | 1517 |
| 18663000 | 18664250 | seg_140 | 1518 |
| 18689000 | 18690200 | seg_141 | 1519 |
| 18694650 | 18696250 | seg_142 | 1520 |
| 18704800 | 18705850 | seg_143 | 1521 |
| 18814500 | 18815800 | seg_144 | 1522 |
| 18850450 | 18852300 | seg_145 | 1523 |
| 18858250 | 18862600 | seg_146 | 1524 |
| 18865700 | 18867200 | seg_147 | 1525 |
| 18891000 | 18894600 | seg_148 | 1526 |
| 19012650 | 19013750 | seg_149 | 1527 |
| 19038700 | 19039900 | seg_150 | 1528 |
| 19065750 | 19066850 | seg_151 | 1529 |
| 19141200 | 19142550 | seg_152 | 1530 |
| 19307900 | 19310300 | seg_153 | 1531 |
| 19348850 | 19352250 | seg_154 | 1532 |
| 19393250 | 19401800 | seg_155 | 1533 |
| 19415800 | 19417450 | seg_156 | 1534 |
| 19474150 | 19475400 | seg_157 | 1535 |
| 19554750 | 19556200 | seg_158 | 1536 |
| 19560350 | 19561400 | seg_159 | 1537 |
| 19570450 | 19571550 | seg_160 | 1538 |
| 19620350 | 19621400 | seg_161 | 1539 |
| 19638050 | 19639150 | seg_162 | 1540 |
| 19813200 | 19814750 | seg_163 | 1541 |
| 19817600 | 19819100 | seg_164 | 1542 |
| 19879900 | 19881050 | seg_165 | 1543 |
| 19883900 | 19887350 | seg_166 | 1544 |
| 19890300 | 19891400 | seg_167 | 1545 |
| 19894150 | 19895700 | seg_168 | 1546 |
| 19902750 | 19905650 | seg_169 | 1547 |
| 19922300 | 19923750 | seg_170 | 1548 |
| 20019400 | 20021100 | seg_171 | 1549 |
| 20041050 | 20042600 | seg_172 | 1550 |
| 20128750 | 20130450 | seg_173 | 1551 |
| 20288800 | 20290300 | seg_174 | 1552 |
| 20297600 | 20299550 | seg_175 | 1553 |
| 20311300 | 20312350 | seg_176 | 1554 |
| 20341300 | 20343100 | seg_177 | 1555 |
| 20350450 | 20352350 | seg_178 | 1556 |
| 20412250 | 20413300 | seg_179 | 1557 |
| 20427800 | 20429700 | seg_180 | 1558 |
| 20432100 | 20434300 | seg_181 | 1559 |
| 21924250 | 21925300 | seg_182 | 1560 |
| 22051000 | 22052100 | seg_183 | 1561 |
| 22073800 | 22074800 | seg_184 | 1562 |
| 23660850 | 23662600 | seg_185 | 1563 |
| 23774100 | 23775150 | seg_186 | 1564 |
| 24270650 | 24272400 | seg_187 | 1565 |
| 24276700 | 24278300 | seg_188 | 1566 |
| 24285100 | 24289350 | seg_189 | 1567 |
| 24328750 | 24333600 | seg_190 | 1568 |
| 24379500 | 24384800 | seg_191 | 1569 |
| 24483500 | 24485500 | seg_192 | 1570 |
| 24544700 | 24546050 | seg_193 | 1571 |
| 25026650 | 25045650 | seg_194 | 1572 |
| 25046800 | 25048550 | seg_195 | 1573 |
| 31007050 | 31009050 | seg_196 | 1574 |
| 31014200 | 31015250 | seg_197 | 1575 |
| 31022150 | 31023300 | seg_198 | 1576 |
| 37191850 | 37193450 | seg_199 | 1577 |
| 38037000 | 38038300 | seg_200 | 1578 |
| 38078450 | 38080750 | seg_201 | 1579 |
| 38195400 | 38197000 | seg_202 | 1580 |
| 38211800 | 38213050 | seg_203 | 1581 |
| 38475900 | 38477150 | seg_204 | 1582 |
| 38511700 | 38513450 | seg_205 | 1583 |
| 38537300 | 38539300 | seg_206 | 1584 |
| 39061650 | 39062900 | seg_207 | 1585 |
| 39551800 | 39553100 | seg_208 | 1586 |
| 39763900 | 39765400 | seg_209 | 1587 |
| 39775200 | 39777050 | seg_210 | 1588 |
| 40355900 | 40357500 | seg_211 | 1589 |
| 40389550 | 40391550 | seg_212 | 1590 |
| 40597850 | 40599200 | seg_213 | 1591 |
| 40869500 | 40870650 | seg_214 | 1592 |
| 41125350 | 41126800 | seg_215 | 1593 |
| 41167750 | 41169450 | seg_216 | 1594 |
| 41209650 | 41210900 | seg_217 | 1595 |
| 41814600 | 41816250 | seg_218 | 1596 |

TABLE XIII-continued

EZH2 in K562

| start | end | name | SEQ ID NO: |
|---|---|---|---|
| 43831100 | 43833350 | seg_219 | 1597 |
| 43888350 | 43890300 | seg_220 | 1598 |
| 44172850 | 44174600 | seg_221 | 1599 |
| 44538100 | 44539300 | seg_222 | 1600 |
| 45627800 | 45629350 | seg_223 | 1601 |
| 45708500 | 45709500 | seg_224 | 1602 |
| 46263300 | 46264350 | seg_225 | 1603 |
| 46465650 | 46466700 | seg_226 | 1604 |
| 46639450 | 46641100 | seg_227 | 1605 |
| 47125900 | 47127750 | seg_228 | 1606 |
| 47145650 | 47147250 | seg_229 | 1607 |
| 47232600 | 47233700 | seg_230 | 1608 |
| 47382350 | 47383400 | seg_231 | 1609 |
| 47542100 | 47544050 | seg_232 | 1610 |
| 47676000 | 47677900 | seg_233 | 1611 |
| 47981500 | 47983400 | seg_234 | 1612 |
| 48042250 | 48043650 | seg_235 | 1613 |
| 48045350 | 48046450 | seg_236 | 1614 |
| 48051300 | 48052550 | seg_237 | 1615 |
| 48063100 | 48065000 | seg_238 | 1616 |
| 48096650 | 48098100 | seg_239 | 1617 |
| 48155300 | 48156750 | seg_240 | 1618 |
| 48171500 | 48177300 | seg_241 | 1619 |
| 48288050 | 48289600 | seg_242 | 1620 |
| 48475350 | 48476950 | seg_243 | 1621 |
| 48511900 | 48513550 | seg_244 | 1622 |
| 49004850 | 49005850 | seg_245 | 1623 |
| 49420650 | 49421700 | seg_246 | 1624 |
| 49429000 | 49430200 | seg_247 | 1625 |
| 49463400 | 49464600 | seg_248 | 1626 |
| 49517800 | 49519800 | seg_249 | 1627 |
| 49594450 | 49595600 | seg_250 | 1628 |
| 51419250 | 51421950 | seg_251 | 1629 |
| 51423850 | 51425400 | seg_252 | 1630 |
| 51454600 | 51455900 | seg_253 | 1631 |
| 51458450 | 51460250 | seg_254 | 1632 |
| 51798900 | 51802500 | seg_255 | 1633 |
| 51935050 | 51936300 | seg_256 | 1634 |
| 51939700 | 51941850 | seg_257 | 1635 |
| 52543850 | 52545000 | seg_258 | 1636 |
| 52596350 | 52597600 | seg_259 | 1637 |
| 52603150 | 52604300 | seg_260 | 1638 |
| 52673200 | 52675150 | seg_261 | 1639 |
| 52713100 | 52714950 | seg_262 | 1640 |
| 52851450 | 52852550 | seg_263 | 1641 |
| 52854250 | 52855350 | seg_264 | 1642 |
| 52896900 | 52898050 | seg_265 | 1643 |
| 52996700 | 52998100 | seg_266 | 1644 |
| 53188000 | 53189350 | seg_267 | 1645 |
| 53347500 | 53352900 | seg_268 | 1646 |
| 53356450 | 53357750 | seg_269 | 1647 |
| 53360100 | 53362200 | seg_270 | 1648 |
| 53516400 | 53517800 | seg_271 | 1649 |
| 53759850 | 53761200 | seg_272 | 1650 |
| 53823250 | 53824350 | seg_273 | 1651 |
| 53842300 | 53844450 | seg_274 | 1652 |
| 54317850 | 54320600 | seg_275 | 1653 |
| 54386500 | 54387850 | seg_276 | 1654 |
| 54389200 | 54390400 | seg_277 | 1655 |
| 54495250 | 54496750 | seg_278 | 1656 |
| 55040550 | 55042350 | seg_279 | 1657 |
| 55142250 | 55144000 | seg_280 | 1658 |
| 55146600 | 55147900 | seg_281 | 1659 |
| 55209800 | 55211250 | seg_282 | 1660 |
| 55683550 | 55684650 | seg_283 | 1661 |
| 61880850 | 61882700 | seg_284 | 1662 |
| 64771000 | 64772400 | seg_285 | 1663 |
| 67652200 | 67654900 | seg_286 | 1664 |
| 68341700 | 68343050 | seg_287 | 1665 |
| 68353000 | 68354550 | seg_288 | 1666 |
| 68483250 | 68485150 | seg_289 | 1667 |
| 68525100 | 68526300 | seg_290 | 1668 |
| 68836050 | 68838050 | seg_291 | 1669 |
| 68918100 | 68920050 | seg_292 | 1670 |
| 69352950 | 69354000 | seg_293 | 1671 |
| 69697700 | 69699050 | seg_294 | 1672 |
| 70432400 | 70434300 | seg_295 | 1673 |
| 70436000 | 70437500 | seg_296 | 1674 |
| 70474400 | 70475600 | seg_297 | 1675 |
| 70877700 | 70883450 | seg_298 | 1676 |
| 70919900 | 70923050 | seg_299 | 1677 |
| 70926200 | 70950300 | seg_300 | 1678 |
| 70972100 | 70989450 | seg_301 | 1679 |
| 70992300 | 70994500 | seg_302 | 1680 |
| 70997850 | 70999500 | seg_303 | 1681 |
| 71003450 | 71005550 | seg_304 | 1682 |
| 71031900 | 71034450 | seg_305 | 1683 |
| 71094050 | 71095700 | seg_306 | 1684 |
| 71238100 | 71239150 | seg_307 | 1685 |
| 71261650 | 71263400 | seg_308 | 1686 |
| 71319750 | 71321300 | seg_309 | 1687 |
| 71348750 | 71353050 | seg_310 | 1688 |
| 71503150 | 71504200 | seg_311 | 1689 |
| 71512450 | 71513550 | seg_312 | 1690 |
| 71526450 | 71528800 | seg_313 | 1691 |
| 71945800 | 71946950 | seg_314 | 1692 |
| 71953450 | 71955300 | seg_315 | 1693 |
| 73398500 | 73400100 | seg_316 | 1694 |
| 73535100 | 73536450 | seg_317 | 1695 |
| 73638950 | 73640300 | seg_318 | 1696 |
| 73642000 | 73643200 | seg_319 | 1697 |
| 85339200 | 85340950 | seg_320 | 1698 |
| 100106050 | 100107200 | seg_321 | 1699 |
| 100119950 | 100121600 | seg_322 | 1700 |
| 100193650 | 100195150 | seg_323 | 1701 |
| 100471350 | 100473200 | seg_324 | 1702 |
| 100514900 | 100516350 | seg_325 | 1703 |
| 100532400 | 100533600 | seg_326 | 1704 |
| 101800900 | 101804000 | seg_327 | 1705 |
| 102378800 | 102380350 | seg_328 | 1706 |
| 102430600 | 102432050 | seg_329 | 1707 |
| 102530950 | 102533100 | seg_330 | 1708 |
| 102564900 | 102566400 | seg_331 | 1709 |
| 102584350 | 102585450 | seg_332 | 1710 |
| 102861350 | 102862700 | seg_333 | 1711 |
| 102917800 | 102919350 | seg_334 | 1712 |
| 103087250 | 103088400 | seg_335 | 1713 |
| 103166900 | 103168400 | seg_336 | 1714 |
| 103172500 | 103174800 | seg_337 | 1715 |
| 103216000 | 103218450 | seg_338 | 1716 |
| 103230800 | 103233250 | seg_339 | 1717 |
| 103253050 | 103254100 | seg_340 | 1718 |
| 103261650 | 103262700 | seg_341 | 1719 |
| 103301600 | 103303200 | seg_342 | 1720 |
| 103306050 | 103309200 | seg_343 | 1721 |
| 103311200 | 103312950 | seg_344 | 1722 |
| 103314600 | 103315800 | seg_345 | 1723 |
| 103355850 | 103358850 | seg_346 | 1724 |
| 103812100 | 103813500 | seg_347 | 1725 |
| 105065250 | 105066350 | seg_348 | 1726 |
| 105968700 | 105970600 | seg_349 | 1727 |
| 106044350 | 106046150 | seg_350 | 1728 |
| 106482900 | 106485150 | seg_351 | 1729 |
| 106748850 | 106751050 | seg_352 | 1730 |
| 106766500 | 106768400 | seg_353 | 1731 |
| 106839200 | 106841100 | seg_354 | 1732 |
| 106844750 | 106845950 | seg_355 | 1733 |
| 106857050 | 106858450 | seg_356 | 1734 |
| 106984400 | 106985900 | seg_357 | 1735 |
| 107012550 | 107013950 | seg_358 | 1736 |
| 107015700 | 107021050 | seg_359 | 1737 |
| 107067200 | 107071350 | seg_360 | 1738 |
| 107167050 | 107168350 | seg_361 | 1739 |
| 107318400 | 107320100 | seg_362 | 1740 |
| 107680300 | 107682050 | seg_363 | 1741 |
| 107800800 | 107802650 | seg_364 | 1742 |
| 108823900 | 108825300 | seg_365 | 1743 |
| 108842500 | 108844650 | seg_366 | 1744 |
| 109664500 | 109668200 | seg_367 | 1745 |
| 109675200 | 109677300 | seg_368 | 1746 |

TABLE XIII-continued

EZH2 in K562

| start | end | name | SEQ ID NO: |
|---|---|---|---|
| 109681600 | 109683350 | seg_369 | 1747 |
| 109687600 | 109689250 | seg_370 | 1748 |
| 109763200 | 109764700 | seg_371 | 1749 |
| 110037400 | 110040400 | seg_372 | 1750 |
| 110089850 | 110091400 | seg_373 | 1751 |
| 110338150 | 110339500 | seg_374 | 1752 |
| 111326550 | 111327950 | seg_375 | 1753 |
| 113342550 | 113344100 | seg_376 | 1754 |
| 113352150 | 113353850 | seg_377 | 1755 |
| 113418750 | 113420450 | seg_378 | 1756 |
| 113814950 | 113817950 | seg_379 | 1757 |
| 114206400 | 114207900 | seg_380 | 1758 |
| 114467100 | 114468700 | seg_381 | 1759 |
| 114956100 | 114958000 | seg_382 | 1760 |
| 117249800 | 117250800 | seg_383 | 1761 |
| 117862300 | 117863400 | seg_384 | 1762 |
| 117940450 | 117941800 | seg_385 | 1763 |
| 117956850 | 117963900 | seg_386 | 1764 |
| 117965550 | 117966650 | seg_387 | 1765 |
| 118052350 | 118054150 | seg_388 | 1766 |
| 118081300 | 118083250 | seg_389 | 1767 |
| 118109050 | 118110300 | seg_390 | 1768 |
| 118205950 | 118208800 | seg_391 | 1769 |
| 118212900 | 118215850 | seg_392 | 1770 |
| 118282850 | 118287450 | seg_393 | 1771 |
| 118346000 | 118349200 | seg_394 | 1772 |
| 118359850 | 118363400 | seg_395 | 1773 |
| 118366950 | 118370450 | seg_396 | 1774 |
| 118441450 | 118445300 | seg_397 | 1775 |
| 118449700 | 118451000 | seg_398 | 1776 |
| 118457400 | 118458500 | seg_399 | 1777 |
| 118475800 | 118478400 | seg_400 | 1778 |
| 118493600 | 118495250 | seg_401 | 1779 |
| 118496550 | 118498200 | seg_402 | 1780 |
| 118503050 | 118504750 | seg_403 | 1781 |
| 118513250 | 118514500 | seg_404 | 1782 |
| 118869150 | 118873850 | seg_405 | 1783 |
| 119086550 | 119088100 | seg_406 | 1784 |
| 119119400 | 119121600 | seg_407 | 1785 |
| 119123100 | 119136250 | seg_408 | 1786 |
| 119146350 | 119147850 | seg_409 | 1787 |
| 119149100 | 119157100 | seg_410 | 1788 |
| 119467950 | 119469350 | seg_411 | 1789 |
| 119504000 | 119505500 | seg_412 | 1790 |
| 119514900 | 119515950 | seg_413 | 1791 |
| 119865950 | 119867450 | seg_414 | 1792 |
| 120299600 | 120300600 | seg_415 | 1793 |
| 122316650 | 122320500 | seg_416 | 1794 |
| 122402300 | 122404250 | seg_417 | 1795 |
| 123373100 | 123375050 | seg_418 | 1796 |
| 124335350 | 124337600 | seg_419 | 1797 |
| 128781700 | 128784050 | seg_420 | 1798 |
| 128788300 | 128792400 | seg_421 | 1799 |
| 128811850 | 128813500 | seg_422 | 1800 |
| 128829500 | 128831000 | seg_423 | 1801 |
| 128834150 | 128836250 | seg_424 | 1802 |
| 128852750 | 128855450 | seg_425 | 1803 |
| 128996850 | 128998800 | seg_426 | 1804 |
| 129312750 | 129314600 | seg_427 | 1805 |
| 129429500 | 129430650 | seg_428 | 1806 |
| 129518000 | 129519450 | seg_429 | 1807 |
| 129685850 | 129687000 | seg_430 | 1808 |
| 130182350 | 130183950 | seg_431 | 1809 |
| 130192100 | 130193800 | seg_432 | 1810 |
| 130765450 | 130766550 | seg_433 | 1811 |
| 130814550 | 130815550 | seg_434 | 1812 |
| 131217450 | 131219600 | seg_435 | 1813 |
| 131226100 | 131227550 | seg_436 | 1814 |
| 131234500 | 131238250 | seg_437 | 1815 |
| 131552950 | 131554550 | seg_438 | 1816 |
| 131555800 | 131556900 | seg_439 | 1817 |
| 131706550 | 131707650 | seg_440 | 1818 |
| 133307050 | 133308100 | seg_441 | 1819 |
| 133367850 | 133369000 | seg_442 | 1820 |
| 133370100 | 133372950 | seg_443 | 1821 |
| 133751450 | 133752450 | seg_444 | 1822 |
| 133779700 | 133780700 | seg_445 | 1823 |
| 133810300 | 133811300 | seg_446 | 1824 |
| 133937450 | 133939000 | seg_447 | 1825 |
| 133984050 | 133985200 | seg_448 | 1826 |
| 133996850 | 133998300 | seg_449 | 1827 |
| 134096600 | 134097900 | seg_450 | 1828 |
| 134115350 | 134116650 | seg_451 | 1829 |
| 134141750 | 134143050 | seg_452 | 1830 |
| 134144200 | 134147750 | seg_453 | 1831 |
| 134153750 | 134155600 | seg_454 | 1832 |
| 134232350 | 134234600 | seg_455 | 1833 |
| 134262000 | 134263300 | seg_456 | 1834 |
| 134267150 | 134272000 | seg_457 | 1835 |
| 134313200 | 134319300 | seg_458 | 1836 |
| 134322900 | 134324600 | seg_459 | 1837 |
| 134342600 | 134344200 | seg_460 | 1838 |
| 134345900 | 134351900 | seg_461 | 1839 |
| 134368650 | 134375600 | seg_462 | 1840 |
| 134383050 | 134384100 | seg_463 | 1841 |
| 134557050 | 134558100 | seg_464 | 1842 |
| 134567350 | 134570450 | seg_465 | 1843 |
| 134582350 | 134583400 | seg_466 | 1844 |
| 134630300 | 134631800 | seg_467 | 1845 |
| 134725600 | 134726800 | seg_468 | 1846 |
| 134730400 | 134732000 | seg_469 | 1847 |
| 134841450 | 134843250 | seg_470 | 1848 |
| 134974900 | 134976100 | seg_471 | 1849 |
| 135142850 | 135149600 | seg_472 | 1850 |
| 135153750 | 135158600 | seg_473 | 1851 |
| 135164850 | 135166450 | seg_474 | 1852 |
| 135200900 | 135202500 | seg_475 | 1853 |
| 135227100 | 135229300 | seg_476 | 1854 |
| 135230550 | 135237050 | seg_477 | 1855 |
| 135238700 | 135240650 | seg_478 | 1856 |
| 135247650 | 135253150 | seg_479 | 1857 |
| 135255700 | 135257250 | seg_480 | 1858 |
| 135261000 | 135263500 | seg_481 | 1859 |
| 135278300 | 135279400 | seg_482 | 1860 |
| 135280500 | 135283000 | seg_483 | 1861 |
| 135286200 | 135288850 | seg_484 | 1862 |
| 135570450 | 135571950 | seg_485 | 1863 |
| 135573250 | 135575700 | seg_486 | 1864 |
| 135605150 | 135606400 | seg_487 | 1865 |
| 135623250 | 135624500 | seg_488 | 1866 |
| 135635700 | 135637100 | seg_489 | 1867 |
| 135700350 | 135703200 | seg_490 | 1868 |
| 135705250 | 135706450 | seg_491 | 1869 |
| 135736900 | 135741150 | seg_492 | 1870 |
| 136111350 | 136117550 | seg_493 | 1871 |
| 136134350 | 136135800 | seg_494 | 1872 |
| 136507400 | 136511500 | seg_495 | 1873 |
| 136629000 | 136633450 | seg_496 | 1874 |
| 136650650 | 136652500 | seg_497 | 1875 |
| 138637250 | 138639450 | seg_498 | 1876 |
| 138772500 | 138776000 | seg_499 | 1877 |
| 139024650 | 139025850 | seg_500 | 1878 |
| 139053450 | 139055300 | seg_501 | 1879 |
| 143224150 | 143226300 | seg_502 | 1880 |
| 148673150 | 148680900 | seg_503 | 1881 |
| 148682650 | 148684100 | seg_504 | 1882 |
| 148711650 | 148713850 | seg_505 | 1883 |
| 148735200 | 148736900 | seg_506 | 1884 |
| 148805000 | 148806550 | seg_507 | 1885 |
| 148826750 | 148829150 | seg_508 | 1886 |
| 148852950 | 148862150 | seg_509 | 1887 |
| 149108000 | 149109350 | seg_510 | 1888 |
| 149530200 | 149534000 | seg_511 | 1889 |
| 149646300 | 149649450 | seg_512 | 1890 |
| 149650500 | 149652300 | seg_513 | 1891 |
| 149673500 | 149676800 | seg_514 | 1892 |
| 149680400 | 149683100 | seg_515 | 1893 |
| 149691650 | 149693050 | seg_516 | 1894 |
| 150131750 | 150132800 | seg_517 | 1895 |
| 150134250 | 150137250 | seg_518 | 1896 |

TABLE XIII-continued

EZH2 in K562

| start | end | name | SEQ ID NO: |
|---|---|---|---|
| 150159250 | 150160300 | seg_519 | 1897 |
| 150256200 | 150257200 | seg_520 | 1898 |
| 150341400 | 150347800 | seg_521 | 1899 |
| 150394350 | 150398150 | seg_522 | 1900 |
| 150515800 | 150516800 | seg_523 | 1901 |
| 150721650 | 150722950 | seg_524 | 1902 |
| 150765850 | 150766900 | seg_525 | 1903 |
| 150827300 | 150828750 | seg_526 | 1904 |
| 150871800 | 150872900 | seg_527 | 1905 |
| 150911500 | 150912750 | seg_528 | 1906 |
| 150916300 | 150917600 | seg_529 | 1907 |
| 150941700 | 150943250 | seg_530 | 1908 |
| 151095050 | 151096600 | seg_531 | 1909 |
| 151989450 | 151991100 | seg_532 | 1910 |
| 152046300 | 152047500 | seg_533 | 1911 |
| 152051700 | 152053600 | seg_534 | 1912 |
| 152061800 | 152071500 | seg_535 | 1913 |
| 152072750 | 152074300 | seg_536 | 1914 |
| 152076150 | 152079750 | seg_537 | 1915 |
| 152101250 | 152104800 | seg_538 | 1916 |
| 152393100 | 152402450 | seg_539 | 1917 |
| 152522450 | 152523650 | seg_540 | 1918 |
| 152529100 | 152538150 | seg_541 | 1919 |
| 152565900 | 152567100 | seg_542 | 1920 |
| 152664400 | 152665900 | seg_543 | 1921 |
| 152749250 | 152750350 | seg_544 | 1922 |
| 152757900 | 152759300 | seg_545 | 1923 |
| 152786250 | 152787250 | seg_546 | 1924 |
| 152788650 | 152794100 | seg_547 | 1925 |
| 152800850 | 152804450 | seg_548 | 1926 |
| 152814800 | 152828650 | seg_549 | 1927 |
| 152830250 | 152836300 | seg_550 | 1928 |
| 152838450 | 152845550 | seg_551 | 1929 |
| 152868250 | 152873400 | seg_552 | 1930 |
| 152886950 | 152890650 | seg_553 | 1931 |
| 152892700 | 152894800 | seg_554 | 1932 |
| 152896000 | 152904000 | seg_555 | 1933 |
| 152929350 | 152932250 | seg_556 | 1934 |
| 153075300 | 153076350 | seg_557 | 1935 |
| 153078100 | 153079800 | seg_558 | 1936 |
| 153083600 | 153087450 | seg_559 | 1937 |
| 153088800 | 153098300 | seg_560 | 1938 |
| 153118550 | 153120150 | seg_561 | 1939 |
| 153123650 | 153124700 | seg_562 | 1940 |
| 153127450 | 153132350 | seg_563 | 1941 |
| 153150300 | 153151550 | seg_564 | 1942 |
| 153157700 | 153161200 | seg_565 | 1943 |
| 153162600 | 153164350 | seg_566 | 1944 |
| 153438400 | 153439700 | seg_567 | 1945 |
| 153455250 | 153457100 | seg_568 | 1946 |
| 153547800 | 153558950 | seg_569 | 1947 |
| 153829500 | 153833250 | seg_570 | 1948 |
| 153877100 | 153878700 | seg_571 | 1949 |
| 153883050 | 153884900 | seg_572 | 1950 |
| 153886450 | 153887600 | seg_573 | 1951 |
| 153979700 | 153981100 | seg_574 | 1952 |
| 154129300 | 154130500 | seg_575 | 1953 |
| 154214850 | 154216450 | seg_576 | 1954 |
| 154443300 | 154445000 | seg_577 | 1955 |
| 155118300 | 155119400 | seg_578 | 1956 |

Table XIV sets forth the hg19 coordinates and SEQ ID NOs, or the SUZ12 strong binding sites identified in K562.

TABLE XIV

SUZ12 in K562

| start | end | name | SEQ ID NO: |
|---|---|---|---|
| 169650 | 171500 | seg_1 | 1957 |
| 373150 | 374900 | seg_2 | 1958 |
| 376150 | 377150 | seg_3 | 1959 |
| 379350 | 383850 | seg_4 | 1960 |
| 385450 | 391000 | seg_5 | 1961 |
| 392750 | 393800 | seg_6 | 1962 |
| 397400 | 399300 | seg_7 | 1963 |
| 419800 | 421150 | seg_8 | 1964 |
| 426250 | 427400 | seg_9 | 1965 |
| 457200 | 458700 | seg_10 | 1966 |
| 605350 | 606900 | seg_11 | 1967 |
| 610200 | 612700 | seg_12 | 1968 |
| 751200 | 752650 | seg_13 | 1969 |
| 754300 | 755950 | seg_14 | 1970 |
| 843900 | 845100 | seg_15 | 1971 |
| 976900 | 978400 | seg_16 | 1972 |
| 989000 | 993500 | seg_17 | 1973 |
| 995100 | 996500 | seg_18 | 1974 |
| 1029100 | 1031050 | seg_19 | 1975 |
| 1240150 | 1241200 | seg_20 | 1976 |
| 1259600 | 1261050 | seg_21 | 1977 |
| 1329250 | 1330400 | seg_22 | 1978 |
| 1392750 | 1394000 | seg_23 | 1979 |
| 1397900 | 1399150 | seg_24 | 1980 |
| 1447300 | 1450000 | seg_25 | 1981 |
| 1464250 | 1469050 | seg_26 | 1982 |
| 1571500 | 1573550 | seg_27 | 1983 |
| 1589950 | 1591400 | seg_28 | 1984 |
| 1666750 | 1668400 | seg_29 | 1985 |
| 1736000 | 1737000 | seg_30 | 1986 |
| 1750100 | 1751300 | seg_31 | 1987 |
| 1776200 | 1777750 | seg_32 | 1988 |
| 2143700 | 2144900 | seg_33 | 1989 |
| 2441800 | 2442900 | seg_34 | 1990 |
| 2455900 | 2457600 | seg_35 | 1991 |
| 2499200 | 2503800 | seg_36 | 1992 |
| 2598050 | 2601800 | seg_37 | 1993 |
| 2608500 | 2610050 | seg_38 | 1994 |
| 2663650 | 2667050 | seg_39 | 1995 |
| 2685100 | 2686250 | seg_40 | 1996 |
| 2710300 | 2713050 | seg_41 | 1997 |
| 2718100 | 2719250 | seg_42 | 1998 |
| 2722300 | 2723400 | seg_43 | 1999 |
| 2985150 | 2986300 | seg_44 | 2000 |
| 3262450 | 3264450 | seg_45 | 2001 |
| 3705150 | 3706850 | seg_46 | 2002 |
| 3718850 | 3720100 | seg_47 | 2003 |
| 3836600 | 3837850 | seg_48 | 2004 |
| 4762000 | 4763100 | seg_49 | 2005 |
| 8433250 | 8434450 | seg_50 | 2006 |
| 9230300 | 9231800 | seg_51 | 2007 |
| 9245050 | 9246200 | seg_52 | 2008 |
| 9275350 | 9276800 | seg_53 | 2009 |
| 9291250 | 9292250 | seg_54 | 2010 |
| 9337400 | 9338550 | seg_55 | 2011 |
| 9372050 | 9382550 | seg_56 | 2012 |
| 9433800 | 9434800 | seg_57 | 2013 |
| 9465900 | 9467000 | seg_58 | 2014 |
| 9732550 | 9734250 | seg_59 | 2015 |
| 9754100 | 9755600 | seg_60 | 2016 |
| 9815800 | 9817450 | seg_61 | 2017 |
| 9861700 | 9864800 | seg_62 | 2018 |
| 9935000 | 9936000 | seg_63 | 2019 |
| 9943250 | 9944350 | seg_64 | 2020 |
| 9982300 | 9983400 | seg_65 | 2021 |
| 10066550 | 10068450 | seg_66 | 2022 |
| 10587800 | 10589000 | seg_67 | 2023 |
| 10995600 | 10996600 | seg_68 | 2024 |
| 11002150 | 11003400 | seg_69 | 2025 |
| 11317250 | 11318400 | seg_70 | 2026 |
| 11671200 | 11672400 | seg_71 | 2027 |
| 11681150 | 11684100 | seg_72 | 2028 |
| 11754000 | 11755100 | seg_73 | 2029 |
| 11778800 | 11779850 | seg_74 | 2030 |
| 12601150 | 12602900 | seg_75 | 2031 |
| 12791300 | 12794950 | seg_76 | 2032 |
| 12799050 | 12800050 | seg_77 | 2033 |

TABLE XIV-continued

SUZ12 in K562

| start | end | name | SEQ ID NO: |
|---|---|---|---|
| 12812950 | 12814100 | seg_78 | 2034 |
| 12857600 | 12858700 | seg_79 | 2035 |
| 12897150 | 12898350 | seg_80 | 2036 |
| 12993000 | 12994200 | seg_81 | 2037 |
| 13445800 | 13446850 | seg_82 | 2038 |
| 13503550 | 13504700 | seg_83 | 2039 |
| 13518050 | 13519350 | seg_84 | 2040 |
| 13587150 | 13589000 | seg_85 | 2041 |
| 13804100 | 13806050 | seg_86 | 2042 |
| 13834050 | 13835850 | seg_87 | 2043 |
| 13898100 | 13899500 | seg_88 | 2044 |
| 13955300 | 13956550 | seg_89 | 2045 |
| 14247250 | 14248400 | seg_90 | 2046 |
| 14596250 | 14597350 | seg_91 | 2047 |
| 14958750 | 14959900 | seg_92 | 2048 |
| 15134850 | 15135950 | seg_93 | 2049 |
| 15330250 | 15331650 | seg_94 | 2050 |
| 16488650 | 16489900 | seg_95 | 2051 |
| 16927400 | 16928750 | seg_96 | 2052 |
| 16967100 | 16968150 | seg_97 | 2053 |
| 17047350 | 17048350 | seg_98 | 2054 |
| 17793100 | 17794100 | seg_99 | 2055 |
| 17877100 | 17879400 | seg_100 | 2056 |
| 18001050 | 18002050 | seg_101 | 2057 |
| 18140450 | 18141600 | seg_102 | 2058 |
| 18179450 | 18180550 | seg_103 | 2059 |
| 18232100 | 18233200 | seg_104 | 2060 |
| 18236850 | 18239450 | seg_105 | 2061 |
| 18244700 | 18245900 | seg_106 | 2062 |
| 18442500 | 18445000 | seg_107 | 2063 |
| 18661950 | 18663150 | seg_108 | 2064 |
| 18667450 | 18668950 | seg_109 | 2065 |
| 18889600 | 18891200 | seg_110 | 2066 |
| 18892400 | 18894300 | seg_111 | 2067 |
| 18904350 | 18905750 | seg_112 | 2068 |
| 18931800 | 18932800 | seg_113 | 2069 |
| 19141050 | 19142200 | seg_114 | 2070 |
| 19285300 | 19286350 | seg_115 | 2071 |
| 19307300 | 19309350 | seg_116 | 2072 |
| 19349800 | 19351800 | seg_117 | 2073 |
| 19390850 | 19391950 | seg_118 | 2074 |
| 19395050 | 19396500 | seg_119 | 2075 |
| 19398600 | 19399850 | seg_120 | 2076 |
| 19504100 | 19505200 | seg_121 | 2077 |
| 19602850 | 19605250 | seg_122 | 2078 |
| 19627300 | 19628350 | seg_123 | 2079 |
| 19874700 | 19875850 | seg_124 | 2080 |
| 19904300 | 19906050 | seg_125 | 2081 |
| 20021350 | 20023050 | seg_126 | 2082 |
| 20099150 | 20100450 | seg_127 | 2083 |
| 20129200 | 20134650 | seg_128 | 2084 |
| 20159600 | 20160600 | seg_129 | 2085 |
| 20348600 | 20349750 | seg_130 | 2086 |
| 20366200 | 20367200 | seg_131 | 2087 |
| 21294850 | 21295950 | seg_132 | 2088 |
| 21991750 | 21992750 | seg_133 | 2089 |
| 22180550 | 22181700 | seg_134 | 2090 |
| 22537550 | 22538650 | seg_135 | 2091 |
| 22961950 | 22963000 | seg_136 | 2092 |
| 23093050 | 23094400 | seg_137 | 2093 |
| 23349300 | 23351100 | seg_138 | 2094 |
| 23412800 | 23413800 | seg_139 | 2095 |
| 23519800 | 23520850 | seg_140 | 2096 |
| 23889950 | 23891000 | seg_141 | 2097 |
| 23925150 | 23926350 | seg_142 | 2098 |
| 24147850 | 24148850 | seg_143 | 2099 |
| 24286700 | 24289050 | seg_144 | 2100 |
| 24301450 | 24303550 | seg_145 | 2101 |
| 24328700 | 24333250 | seg_146 | 2102 |
| 24379450 | 24382100 | seg_147 | 2103 |
| 24408550 | 24410100 | seg_148 | 2104 |
| 24504450 | 24505550 | seg_149 | 2105 |
| 24574200 | 24575400 | seg_150 | 2106 |
| 24644850 | 24646050 | seg_151 | 2107 |
| 25025650 | 25045000 | seg_152 | 2108 |
| 25046850 | 25048300 | seg_153 | 2109 |
| 25118300 | 25119350 | seg_154 | 2110 |
| 25302550 | 25303800 | seg_155 | 2111 |
| 26860050 | 26861050 | seg_156 | 2112 |
| 28053850 | 28054900 | seg_157 | 2113 |
| 30325950 | 30328550 | seg_158 | 2114 |
| 30797500 | 30798500 | seg_159 | 2115 |
| 30955050 | 30956300 | seg_160 | 2116 |
| 30992350 | 30993350 | seg_161 | 2117 |
| 31010750 | 31012250 | seg_162 | 2118 |
| 31691100 | 31692100 | seg_163 | 2119 |
| 33817650 | 33818700 | seg_164 | 2120 |
| 35897350 | 35898350 | seg_165 | 2121 |
| 37016650 | 37018000 | seg_166 | 2122 |
| 37064150 | 37065200 | seg_167 | 2123 |
| 37351000 | 37352100 | seg_168 | 2124 |
| 37733800 | 37734850 | seg_169 | 2125 |
| 38078900 | 38081100 | seg_170 | 2126 |
| 38663050 | 38664250 | seg_171 | 2127 |
| 38778550 | 38779750 | seg_172 | 2128 |
| 39021100 | 39022250 | seg_173 | 2129 |
| 39371550 | 39372650 | seg_174 | 2130 |
| 39382850 | 39383850 | seg_175 | 2131 |
| 39413850 | 39415500 | seg_176 | 2132 |
| 39458100 | 39459400 | seg_177 | 2133 |
| 39685600 | 39687150 | seg_178 | 2134 |
| 39740700 | 39741800 | seg_179 | 2135 |
| 39763700 | 39765450 | seg_180 | 2136 |
| 39843400 | 39844400 | seg_181 | 2137 |
| 39873150 | 39874450 | seg_182 | 2138 |
| 40027900 | 40029300 | seg_183 | 2139 |
| 40149800 | 40151100 | seg_184 | 2140 |
| 40263700 | 40265000 | seg_185 | 2141 |
| 40359650 | 40360750 | seg_186 | 2142 |
| 40375050 | 40376700 | seg_187 | 2143 |
| 40390200 | 40391900 | seg_188 | 2144 |
| 40602000 | 40603200 | seg_189 | 2145 |
| 40828200 | 40829350 | seg_190 | 2146 |
| 40890100 | 40891600 | seg_191 | 2147 |
| 41112400 | 41113550 | seg_192 | 2148 |
| 41306350 | 41307400 | seg_193 | 2149 |
| 41958050 | 41959450 | seg_194 | 2150 |
| 41983850 | 41985000 | seg_195 | 2151 |
| 42505050 | 42506050 | seg_196 | 2152 |
| 43471800 | 43472900 | seg_197 | 2153 |
| 43830050 | 43831700 | seg_198 | 2154 |
| 43964400 | 43965900 | seg_199 | 2155 |
| 44203200 | 44204350 | seg_200 | 2156 |
| 44997500 | 44998600 | seg_201 | 2157 |
| 46464100 | 46465450 | seg_202 | 2158 |
| 47127000 | 47128150 | seg_203 | 2159 |
| 47145550 | 47146800 | seg_204 | 2160 |
| 47175050 | 47176550 | seg_205 | 2161 |
| 47363250 | 47364350 | seg_206 | 2162 |
| 47371600 | 47373400 | seg_207 | 2163 |
| 47476800 | 47478350 | seg_208 | 2164 |
| 47595750 | 47596900 | seg_209 | 2165 |
| 47661850 | 47663050 | seg_210 | 2166 |
| 47984500 | 47985650 | seg_211 | 2167 |
| 48165350 | 48166500 | seg_212 | 2168 |
| 48175100 | 48176600 | seg_213 | 2169 |
| 48193350 | 48194400 | seg_214 | 2170 |
| 48199400 | 48200550 | seg_215 | 2171 |
| 48240000 | 48241200 | seg_216 | 2172 |
| 48828300 | 48829300 | seg_217 | 2173 |
| 48963250 | 48964250 | seg_218 | 2174 |
| 49029700 | 49030700 | seg_219 | 2175 |
| 49068450 | 49069750 | seg_220 | 2176 |
| 49074200 | 49075450 | seg_221 | 2177 |
| 49104450 | 49105650 | seg_222 | 2178 |
| 49409000 | 49410150 | seg_223 | 2179 |
| 49420300 | 49421700 | seg_224 | 2180 |
| 49551450 | 49552750 | seg_225 | 2181 |
| 49906350 | 49907600 | seg_226 | 2182 |
| 49917850 | 49919100 | seg_227 | 2183 |

TABLE XIV-continued

SUZ12 in K562

| start | end | name | SEQ ID NO: |
|---|---|---|---|
| 50213900 | 50215200 | seg_228 | 2184 |
| 50450650 | 50451850 | seg_229 | 2185 |
| 50555600 | 50557750 | seg_230 | 2186 |
| 50694600 | 50695650 | seg_231 | 2187 |
| 50918150 | 50919200 | seg_232 | 2188 |
| 51126600 | 51128150 | seg_233 | 2189 |
| 51316600 | 51317600 | seg_234 | 2190 |
| 51419250 | 51420500 | seg_235 | 2191 |
| 51424500 | 51426000 | seg_236 | 2192 |
| 51452900 | 51456150 | seg_237 | 2193 |
| 51458700 | 51460100 | seg_238 | 2194 |
| 51545600 | 51546650 | seg_239 | 2195 |
| 51800050 | 51801050 | seg_240 | 2196 |
| 51805500 | 51812400 | seg_241 | 2197 |
| 51929300 | 51932300 | seg_242 | 2198 |
| 51935000 | 51936100 | seg_243 | 2199 |
| 51939150 | 51940750 | seg_244 | 2200 |
| 52239900 | 52241050 | seg_245 | 2201 |
| 52267050 | 52268250 | seg_246 | 2202 |
| 52496400 | 52497400 | seg_247 | 2203 |
| 52526900 | 52528150 | seg_248 | 2204 |
| 52530600 | 52532500 | seg_249 | 2205 |
| 52543750 | 52545000 | seg_250 | 2206 |
| 52692900 | 52694100 | seg_251 | 2207 |
| 52705000 | 52706750 | seg_252 | 2208 |
| 52755450 | 52756450 | seg_253 | 2209 |
| 52809850 | 52811650 | seg_254 | 2210 |
| 52919850 | 52921300 | seg_255 | 2211 |
| 52925850 | 52927100 | seg_256 | 2212 |
| 52989600 | 52990850 | seg_257 | 2213 |
| 52994300 | 52995300 | seg_258 | 2214 |
| 53069800 | 53070900 | seg_259 | 2215 |
| 53284450 | 53286250 | seg_260 | 2216 |
| 53329950 | 53331050 | seg_261 | 2217 |
| 53348300 | 53351800 | seg_262 | 2218 |
| 53360200 | 53362250 | seg_263 | 2219 |
| 53510800 | 53511850 | seg_264 | 2220 |
| 53893900 | 53895050 | seg_265 | 2221 |
| 53947550 | 53948650 | seg_266 | 2222 |
| 54070050 | 54071100 | seg_267 | 2223 |
| 54221650 | 54222700 | seg_268 | 2224 |
| 54315000 | 54316050 | seg_269 | 2225 |
| 54386700 | 54387800 | seg_270 | 2226 |
| 54521250 | 54522900 | seg_271 | 2227 |
| 54776750 | 54777850 | seg_272 | 2228 |
| 55026400 | 55027550 | seg_273 | 2229 |
| 55142950 | 55144000 | seg_274 | 2230 |
| 55195550 | 55197050 | seg_275 | 2231 |
| 56029500 | 56030800 | seg_276 | 2232 |
| 56625450 | 56626500 | seg_277 | 2233 |
| 56787300 | 56788350 | seg_278 | 2234 |
| 57633650 | 57634750 | seg_279 | 2235 |
| 58499950 | 58501350 | seg_280 | 2236 |
| 58556450 | 58557650 | seg_281 | 2237 |
| 58564350 | 58569550 | seg_282 | 2238 |
| 58572250 | 58575150 | seg_283 | 2239 |
| 58576450 | 58579850 | seg_284 | 2240 |
| 61687500 | 61693950 | seg_285 | 2241 |
| 61696500 | 61697900 | seg_286 | 2242 |
| 61705150 | 61707200 | seg_287 | 2243 |
| 61709550 | 61713800 | seg_288 | 2244 |
| 61715700 | 61717700 | seg_289 | 2245 |
| 61718950 | 61720050 | seg_290 | 2246 |
| 61722850 | 61725350 | seg_291 | 2247 |
| 61735200 | 61737150 | seg_292 | 2248 |
| 61745250 | 61748350 | seg_293 | 2249 |
| 61759400 | 61765200 | seg_294 | 2250 |
| 61767100 | 61768400 | seg_295 | 2251 |
| 61771650 | 61773500 | seg_296 | 2252 |
| 61812750 | 61816700 | seg_297 | 2253 |
| 61825850 | 61827800 | seg_298 | 2254 |
| 61833050 | 61834950 | seg_299 | 2255 |
| 61836400 | 61840450 | seg_300 | 2256 |
| 61848600 | 61850050 | seg_301 | 2257 |
| 61871000 | 61872850 | seg_302 | 2258 |
| 61880650 | 61882600 | seg_303 | 2259 |
| 62373750 | 62375100 | seg_304 | 2260 |
| 62381350 | 62382900 | seg_305 | 2261 |
| 62967650 | 62969200 | seg_306 | 2262 |
| 63267250 | 63268250 | seg_307 | 2263 |
| 63412200 | 63413300 | seg_308 | 2264 |
| 64138750 | 64139800 | seg_309 | 2265 |
| 64770000 | 64772700 | seg_310 | 2266 |
| 66313800 | 66314950 | seg_311 | 2267 |
| 66763900 | 66766950 | seg_312 | 2268 |
| 67871900 | 67872900 | seg_313 | 2269 |
| 68048550 | 68051950 | seg_314 | 2270 |
| 68132200 | 68133300 | seg_315 | 2271 |
| 68233300 | 68234300 | seg_316 | 2272 |
| 68270750 | 68271850 | seg_317 | 2273 |
| 68406000 | 68407300 | seg_318 | 2274 |
| 68423100 | 68425000 | seg_319 | 2275 |
| 68482450 | 68484700 | seg_320 | 2276 |
| 68524950 | 68526550 | seg_321 | 2277 |
| 68836650 | 68837650 | seg_322 | 2278 |
| 69354600 | 69355600 | seg_323 | 2279 |
| 69394450 | 69395900 | seg_324 | 2280 |
| 69663950 | 69665850 | seg_325 | 2281 |
| 70013100 | 70014100 | seg_326 | 2282 |
| 70368600 | 70369750 | seg_327 | 2283 |
| 70435950 | 70436950 | seg_328 | 2284 |
| 70443150 | 70444550 | seg_329 | 2285 |
| 70839050 | 70840250 | seg_330 | 2286 |
| 70877750 | 70883200 | seg_331 | 2287 |
| 70920450 | 70921550 | seg_332 | 2288 |
| 70931300 | 70944400 | seg_333 | 2289 |
| 70945900 | 70947000 | seg_334 | 2290 |
| 70948700 | 70950550 | seg_335 | 2291 |
| 70973450 | 70990950 | seg_336 | 2292 |
| 71033300 | 71034650 | seg_337 | 2293 |
| 71091950 | 71093750 | seg_338 | 2294 |
| 71130200 | 71132050 | seg_339 | 2295 |
| 71237900 | 71239300 | seg_340 | 2296 |
| 71241400 | 71242500 | seg_341 | 2297 |
| 71279100 | 71280300 | seg_342 | 2298 |
| 71350200 | 71352700 | seg_343 | 2299 |
| 71364150 | 71365850 | seg_344 | 2300 |
| 71525750 | 71529400 | seg_345 | 2301 |
| 71800550 | 71801550 | seg_346 | 2302 |
| 71951850 | 71953000 | seg_347 | 2303 |
| 72011750 | 72013700 | seg_348 | 2304 |
| 72136450 | 72138350 | seg_349 | 2305 |
| 72146600 | 72148500 | seg_350 | 2306 |
| 72157050 | 72158200 | seg_351 | 2307 |
| 72666800 | 72668350 | seg_352 | 2308 |
| 73134450 | 73135450 | seg_353 | 2309 |
| 73397650 | 73399200 | seg_354 | 2310 |
| 73498350 | 73499350 | seg_355 | 2311 |
| 73642400 | 73643800 | seg_356 | 2312 |
| 74055400 | 74056550 | seg_357 | 2313 |
| 77165200 | 77166850 | seg_358 | 2314 |
| 77223450 | 77224850 | seg_359 | 2315 |
| 77296400 | 77297850 | seg_360 | 2316 |
| 78307850 | 78308850 | seg_361 | 2317 |
| 79181150 | 79182150 | seg_362 | 2318 |
| 79277400 | 79278700 | seg_363 | 2319 |
| 79717550 | 79718700 | seg_364 | 2320 |
| 80106100 | 80107250 | seg_365 | 2321 |
| 80258650 | 80259800 | seg_366 | 2322 |
| 83187600 | 83188750 | seg_367 | 2323 |
| 85105500 | 85106600 | seg_368 | 2324 |
| 85317700 | 85318700 | seg_369 | 2325 |
| 86337800 | 86339100 | seg_370 | 2326 |
| 88482200 | 88483250 | seg_371 | 2327 |
| 89470750 | 89472100 | seg_372 | 2328 |
| 91035500 | 91036850 | seg_373 | 2329 |
| 93266850 | 93268000 | seg_374 | 2330 |
| 99556100 | 99557150 | seg_375 | 2331 |
| 99830600 | 99831700 | seg_376 | 2332 |
| 99891050 | 99892300 | seg_377 | 2333 |

TABLE XIV-continued

SUZ12 in K562

| start | end | name | SEQ ID NO: |
|---|---|---|---|
| 99934950 | 99936050 | seg_378 | 2334 |
| 99999850 | 100001500 | seg_379 | 2335 |
| 100334000 | 100335900 | seg_380 | 2336 |
| 100509100 | 100510450 | seg_381 | 2337 |
| 100672350 | 100673500 | seg_382 | 2338 |
| 100744750 | 100745800 | seg_383 | 2339 |
| 100793500 | 100794650 | seg_384 | 2340 |
| 100852500 | 100853550 | seg_385 | 2341 |
| 100867500 | 100868650 | seg_386 | 2342 |
| 101564000 | 101565000 | seg_387 | 2343 |
| 101730800 | 101732700 | seg_388 | 2344 |
| 101770350 | 101771700 | seg_389 | 2345 |
| 102529150 | 102533650 | seg_390 | 2346 |
| 102564750 | 102566250 | seg_391 | 2347 |
| 102585450 | 102586700 | seg_392 | 2348 |
| 102840700 | 102841750 | seg_393 | 2349 |
| 102918500 | 102920100 | seg_394 | 2350 |
| 102982800 | 102984450 | seg_395 | 2351 |
| 103086000 | 103088000 | seg_396 | 2352 |
| 103172500 | 103174100 | seg_397 | 2353 |
| 103216950 | 103218150 | seg_398 | 2354 |
| 103231050 | 103232850 | seg_399 | 2355 |
| 103241500 | 103242650 | seg_400 | 2356 |
| 103305100 | 103306050 | seg_401 | 2357 |
| 103355950 | 103358450 | seg_402 | 2358 |
| 103526000 | 103527100 | seg_403 | 2359 |
| 103809050 | 103810850 | seg_404 | 2360 |
| 105065050 | 105067650 | seg_405 | 2361 |
| 105960300 | 105961850 | seg_406 | 2362 |
| 106047050 | 106048050 | seg_407 | 2363 |
| 106172400 | 106173500 | seg_408 | 2364 |
| 106686250 | 106687400 | seg_499 | 2365 |
| 106748850 | 106751450 | seg_410 | 2366 |
| 106766900 | 106768200 | seg_411 | 2367 |
| 106793100 | 106794250 | seg_412 | 2368 |
| 106843800 | 106846550 | seg_413 | 2369 |
| 106991800 | 106993500 | seg_414 | 2370 |
| 107018250 | 107019350 | seg_415 | 2371 |
| 107067850 | 107070850 | seg_416 | 2372 |
| 107223950 | 107225250 | seg_417 | 2373 |
| 107509250 | 107510600 | seg_418 | 2374 |
| 107621250 | 107622550 | seg_419 | 2375 |
| 107964200 | 107965250 | seg_420 | 2376 |
| 107975000 | 107976700 | seg_421 | 2377 |
| 108199300 | 108200550 | seg_422 | 2378 |
| 108296850 | 108298000 | seg_423 | 2379 |
| 108674800 | 108676200 | seg_424 | 2380 |
| 108703300 | 108705200 | seg_425 | 2381 |
| 108793550 | 108795100 | seg_426 | 2382 |
| 108811600 | 108812750 | seg_427 | 2383 |
| 108842800 | 108843800 | seg_428 | 2384 |
| 109133400 | 109135000 | seg_429 | 2385 |
| 109247900 | 109249000 | seg_430 | 2386 |
| 109686900 | 109688500 | seg_431 | 2387 |
| 110038450 | 110040100 | seg_432 | 2388 |
| 111148500 | 111149550 | seg_433 | 2389 |
| 111323950 | 111326100 | seg_434 | 2390 |
| 111377450 | 111378600 | seg_435 | 2391 |
| 111877350 | 111878350 | seg_436 | 2392 |
| 112067850 | 112068950 | seg_437 | 2393 |
| 113251050 | 113252200 | seg_438 | 2394 |
| 113815000 | 113819700 | seg_439 | 2395 |
| 114795000 | 114796050 | seg_440 | 2396 |
| 114954500 | 114955550 | seg_441 | 2397 |
| 114957400 | 114958700 | seg_442 | 2398 |
| 115997450 | 115998650 | seg_443 | 2399 |
| 117249550 | 117251250 | seg_444 | 2400 |
| 117349200 | 117350550 | seg_445 | 2401 |
| 117956850 | 117960550 | seg_446 | 2402 |
| 118109900 | 118111100 | seg_447 | 2403 |
| 118206800 | 118209350 | seg_448 | 2404 |
| 118214300 | 118215550 | seg_449 | 2405 |
| 118240400 | 118241500 | seg_450 | 2406 |
| 118283750 | 118285900 | seg_451 | 2407 |
| 118367150 | 118368400 | seg_452 | 2408 |
| 118532900 | 118534700 | seg_453 | 2409 |
| 118552150 | 118553350 | seg_454 | 2410 |
| 118636600 | 118637750 | seg_455 | 2411 |
| 118868550 | 118869800 | seg_456 | 2412 |
| 119123450 | 119126250 | seg_457 | 2413 |
| 119128250 | 119130300 | seg_458 | 2414 |
| 119133050 | 119135500 | seg_459 | 2415 |
| 119147300 | 119149300 | seg_460 | 2416 |
| 119152200 | 119153950 | seg_461 | 2417 |
| 119443650 | 119445500 | seg_462 | 2418 |
| 119503950 | 119505200 | seg_463 | 2419 |
| 119626450 | 119627500 | seg_464 | 2420 |
| 120007900 | 120009150 | seg_465 | 2421 |
| 120122250 | 120123600 | seg_466 | 2422 |
| 120742050 | 120743100 | seg_467 | 2423 |
| 121110750 | 121111750 | seg_468 | 2424 |
| 121201700 | 121202750 | seg_469 | 2425 |
| 122004000 | 122005250 | seg_470 | 2426 |
| 122317650 | 122321300 | seg_471 | 2427 |
| 122323700 | 122324850 | seg_472 | 2428 |
| 124416550 | 124417650 | seg_473 | 2429 |
| 126645100 | 126646650 | seg_474 | 2430 |
| 127166250 | 127167250 | seg_475 | 2431 |
| 127302450 | 127303900 | seg_476 | 2432 |
| 128393800 | 128394950 | seg_477 | 2433 |
| 128756950 | 128758000 | seg_478 | 2434 |
| 128781850 | 128783650 | seg_479 | 2435 |
| 128787750 | 128789650 | seg_480 | 2436 |
| 128812100 | 128813800 | seg_481 | 2437 |
| 128822550 | 128823650 | seg_482 | 2438 |
| 128833600 | 128834700 | seg_483 | 2439 |
| 128882700 | 128883950 | seg_484 | 2440 |
| 129429400 | 129430750 | seg_485 | 2441 |
| 129444800 | 129445800 | seg_486 | 2442 |
| 129517950 | 129519000 | seg_487 | 2443 |
| 129598850 | 129599900 | seg_488 | 2444 |
| 129617200 | 129618400 | seg_489 | 2445 |
| 129671600 | 129672750 | seg_490 | 2446 |
| 130182550 | 130183750 | seg_491 | 2447 |
| 130211050 | 130212100 | seg_492 | 2448 |
| 130215900 | 130218550 | seg_493 | 2449 |
| 130409100 | 130410150 | seg_494 | 2450 |
| 130804750 | 130805950 | seg_495 | 2451 |
| 131351450 | 131352650 | seg_496 | 2452 |
| 131556050 | 131558450 | seg_497 | 2453 |
| 131752700 | 131753800 | seg_498 | 2454 |
| 132008150 | 132009150 | seg_499 | 2455 |
| 132086850 | 132088300 | seg_500 | 2456 |
| 132264250 | 132264500 | seg_501 | 2457 |
| 133370100 | 133372850 | seg_502 | 2458 |
| 133384600 | 133385600 | seg_503 | 2459 |
| 133682650 | 133684050 | seg_504 | 2460 |
| 134003650 | 134004750 | seg_505 | 2461 |
| 134133250 | 134134300 | seg_506 | 2462 |
| 134141600 | 134142800 | seg_507 | 2463 |
| 134233350 | 134234550 | seg_508 | 2464 |
| 134280300 | 134282050 | seg_509 | 2465 |
| 134314000 | 134315050 | seg_510 | 2466 |
| 134346900 | 134347900 | seg_511 | 2467 |
| 134349000 | 134350350 | seg_512 | 2468 |
| 134358450 | 134359550 | seg_513 | 2469 |
| 134368700 | 134369700 | seg_514 | 2470 |
| 134370750 | 134373750 | seg_515 | 2471 |
| 134478200 | 134479400 | seg_516 | 2472 |
| 134512850 | 134514000 | seg_517 | 2473 |
| 134555850 | 134556850 | seg_518 | 2474 |
| 134566100 | 134571950 | seg_519 | 2475 |
| 134731350 | 134732350 | seg_520 | 2476 |
| 134753150 | 134754200 | seg_521 | 2477 |
| 134775800 | 134776800 | seg_522 | 2478 |
| 134871500 | 134872550 | seg_523 | 2479 |
| 134888100 | 134889150 | seg_524 | 2480 |
| 134931900 | 134933650 | seg_525 | 2481 |
| 134947700 | 134950650 | seg_526 | 2482 |
| 134998700 | 134999900 | seg_527 | 2483 |

TABLE XIV-continued

SUZ12 in K562

| start | end | name | SEQ ID NO: |
|---|---|---|---|
| 135033500 | 135035000 | seg_528 | 2484 |
| 135138100 | 135139300 | seg_529 | 2485 |
| 135141350 | 135147300 | seg_530 | 2486 |
| 135212600 | 135213950 | seg_531 | 2487 |
| 135228300 | 135230300 | seg_532 | 2488 |
| 135233600 | 135234900 | seg_533 | 2489 |
| 135250050 | 135251600 | seg_534 | 2490 |
| 135436600 | 135438050 | seg_535 | 2491 |
| 135572450 | 135573650 | seg_536 | 2492 |
| 135634450 | 135636250 | seg_537 | 2493 |
| 135736550 | 135737900 | seg_538 | 2494 |
| 135741150 | 135742750 | seg_539 | 2495 |
| 135906100 | 135907150 | seg_540 | 2496 |
| 136114400 | 136117300 | seg_541 | 2497 |
| 136132050 | 136133500 | seg_542 | 2498 |
| 136318450 | 136319900 | seg_543 | 2499 |
| 136507450 | 136511100 | seg_544 | 2500 |
| 136628850 | 136633350 | seg_545 | 2501 |
| 136650850 | 136652450 | seg_546 | 2502 |
| 137064300 | 137065400 | seg_547 | 2503 |
| 138313850 | 138315100 | seg_548 | 2504 |
| 138501150 | 138502400 | seg_549 | 2505 |
| 138689350 | 138690400 | seg_550 | 2506 |
| 138772800 | 138775400 | seg_551 | 2507 |
| 139015500 | 139016750 | seg_552 | 2508 |
| 139172400 | 139174100 | seg_553 | 2509 |
| 139253700 | 139254950 | seg_554 | 2510 |
| 139584250 | 139586100 | seg_555 | 2511 |
| 139589450 | 139593950 | seg_556 | 2512 |
| 140096200 | 140097500 | seg_557 | 2513 |
| 140130900 | 140131900 | seg_558 | 2514 |
| 143215950 | 143217150 | seg_559 | 2515 |
| 147095200 | 147096350 | seg_560 | 2516 |
| 147627750 | 147628750 | seg_561 | 2517 |
| 147670600 | 147671600 | seg_562 | 2518 |
| 148425850 | 148426900 | seg_563 | 2519 |
| 148432950 | 148434000 | seg_564 | 2520 |
| 148552100 | 148554200 | seg_565 | 2521 |
| 148640200 | 148641350 | seg_566 | 2522 |
| 148673650 | 148678650 | seg_567 | 2523 |
| 148679900 | 148684000 | seg_568 | 2524 |
| 148712800 | 148714250 | seg_569 | 2525 |
| 148749000 | 148750600 | seg_570 | 2526 |
| 148752850 | 148753850 | seg_571 | 2527 |
| 148816200 | 148817450 | seg_572 | 2528 |
| 148848550 | 148851050 | seg_573 | 2529 |
| 148853750 | 148858950 | seg_574 | 2530 |
| 148885600 | 148886800 | seg_575 | 2531 |
| 149087550 | 149088750 | seg_576 | 2532 |
| 149221300 | 149222500 | seg_577 | 2533 |
| 149326200 | 149327250 | seg_578 | 2534 |
| 149527800 | 149533900 | seg_579 | 2535 |
| 149646250 | 149648200 | seg_580 | 2536 |
| 149670700 | 149671900 | seg_581 | 2537 |
| 149681150 | 149683750 | seg_582 | 2538 |
| 149715600 | 149716650 | seg_583 | 2539 |
| 150103250 | 150104600 | seg_584 | 2540 |
| 150133850 | 150135550 | seg_585 | 2541 |
| 150137200 | 150138250 | seg_586 | 2542 |
| 150140550 | 150141850 | seg_587 | 2543 |
| 150166150 | 150167250 | seg_588 | 2544 |
| 150188550 | 150189700 | seg_589 | 2545 |
| 150342250 | 150347350 | seg_590 | 2546 |
| 150395650 | 150397300 | seg_591 | 2547 |
| 150554150 | 150555950 | seg_592 | 2548 |
| 150565200 | 150566300 | seg_593 | 2549 |
| 150903100 | 150904100 | seg_594 | 2550 |
| 150934500 | 150935550 | seg_595 | 2551 |
| 151097500 | 151098700 | seg_596 | 2552 |
| 151891100 | 151892300 | seg_597 | 2553 |
| 151910750 | 151912800 | seg_598 | 2554 |
| 151973850 | 151975150 | seg_599 | 2555 |
| 152044600 | 152046350 | seg_600 | 2556 |
| 152049050 | 152050250 | seg_601 | 2557 |
| 152051700 | 152054800 | seg_602 | 2558 |
| 152057500 | 152058500 | seg_603 | 2559 |
| 152061950 | 152063850 | seg_604 | 2560 |
| 152065900 | 152071400 | seg_605 | 2561 |
| 152076500 | 152078400 | seg_606 | 2562 |
| 152096400 | 152098350 | seg_607 | 2563 |
| 152101500 | 152102750 | seg_608 | 2564 |
| 152155100 | 152156400 | seg_609 | 2565 |
| 152346450 | 152347600 | seg_610 | 2566 |
| 152349600 | 152351300 | seg_611 | 2567 |
| 152392250 | 152393600 | seg_612 | 2568 |
| 152397400 | 152399350 | seg_613 | 2569 |
| 152530950 | 152538400 | seg_614 | 2570 |
| 152639750 | 152640900 | seg_615 | 2571 |
| 152662500 | 152664500 | seg_616 | 2572 |
| 152695700 | 152696750 | seg_617 | 2573 |
| 152757650 | 152760600 | seg_618 | 2574 |
| 152773950 | 152775950 | seg_619 | 2575 |
| 152789000 | 152790950 | seg_620 | 2576 |
| 152792050 | 152797450 | seg_621 | 2577 |
| 152801800 | 152804350 | seg_622 | 2578 |
| 152811300 | 152813150 | seg_623 | 2579 |
| 152815500 | 152817200 | seg_624 | 2580 |
| 152818800 | 152828200 | seg_625 | 2581 |
| 152831650 | 152837100 | seg_626 | 2582 |
| 152839000 | 152842300 | seg_627 | 2583 |
| 152870900 | 152872850 | seg_628 | 2584 |
| 152875300 | 152879100 | seg_629 | 2585 |
| 152887500 | 152889300 | seg_630 | 2586 |
| 152891850 | 152893950 | seg_631 | 2587 |
| 152896800 | 152900700 | seg_632 | 2588 |
| 152903550 | 152905450 | seg_633 | 2589 |
| 152908450 | 152909650 | seg_634 | 2590 |
| 153070100 | 153072100 | seg_635 | 2591 |
| 153075150 | 153076450 | seg_636 | 2592 |
| 153078150 | 153079950 | seg_637 | 2593 |
| 153089000 | 153091450 | seg_638 | 2594 |
| 153093650 | 153097850 | seg_639 | 2595 |
| 153123550 | 153131800 | seg_640 | 2596 |
| 153133350 | 153135150 | seg_641 | 2597 |
| 153150200 | 153151550 | seg_642 | 2598 |
| 153157550 | 153159050 | seg_643 | 2599 |
| 153199600 | 153200600 | seg_644 | 2600 |
| 153405550 | 153406900 | seg_645 | 2601 |
| 153409000 | 153412050 | seg_646 | 2602 |
| 153423450 | 153426400 | seg_647 | 2603 |
| 153438400 | 153439900 | seg_648 | 2604 |
| 153447400 | 153449250 | seg_649 | 2605 |
| 153454750 | 153456450 | seg_650 | 2606 |
| 153460750 | 153463050 | seg_651 | 2607 |
| 153477600 | 153479200 | seg_652 | 2608 |
| 153481700 | 153485800 | seg_653 | 2609 |
| 153498150 | 153500900 | seg_654 | 2610 |
| 153551150 | 153553600 | seg_655 | 2611 |
| 153559500 | 153561300 | seg_656 | 2612 |
| 153563100 | 153564150 | seg_657 | 2613 |
| 153604800 | 153605900 | seg_658 | 2614 |
| 153617600 | 153619700 | seg_659 | 2615 |
| 153803300 | 153804700 | seg_660 | 2616 |
| 153827800 | 153828850 | seg_661 | 2617 |
| 153830300 | 153833450 | seg_662 | 2618 |
| 155235050 | 155236450 | seg_663 | 2619 |
| 155245550 | 155247000 | seg_664 | 2620 |
| 155253000 | 155254000 | seg_665 | 2621 |
| 155259200 | 155260550 | seg_666 | 2622 |

Table XV sets forth the hg19 coordinates and SEQ NOs. for the strong EZH2 binding sites identified in GM12878 cells.

TABLE XV

EZH2 in GM12878

| start | end | name | SEQ ID NO: |
|---|---|---|---|
| 334650 | 336100 | seg_1 | 2623 |
| 1330550 | 1331800 | seg_2 | 2624 |
| 1610000 | 1611450 | seg_3 | 2625 |
| 1639800 | 1641400 | seg_4 | 2626 |
| 2500300 | 2501650 | seg_5 | 2627 |
| 2730100 | 2731700 | seg_6 | 2628 |
| 3728950 | 3730750 | seg_7 | 2629 |
| 7001450 | 7003250 | seg_8 | 2630 |
| 7066750 | 7067800 | seg_9 | 2631 |
| 7247600 | 7248900 | seg_10 | 2632 |
| 8007900 | 8008900 | seg_11 | 2633 |
| 8706300 | 8707500 | seg_12 | 2634 |
| 8796200 | 8797750 | seg_13 | 2635 |
| 9754800 | 9756400 | seg_14 | 2636 |
| 10123700 | 10128400 | seg_15 | 2637 |
| 10587050 | 10589450 | seg_16 | 2638 |
| 11777450 | 11778850 | seg_17 | 2639 |
| 11807750 | 11809050 | seg_18 | 2640 |
| 12328750 | 12329950 | seg_19 | 2641 |
| 12511300 | 12512400 | seg_20 | 2642 |
| 12789700 | 12791650 | seg_21 | 2643 |
| 12861500 | 12862950 | seg_22 | 2644 |
| 12907600 | 12908700 | seg_23 | 2645 |
| 13002150 | 13005550 | seg_24 | 2646 |
| 13022550 | 13023650 | seg_25 | 2647 |
| 13104600 | 13106550 | seg_26 | 2648 |
| 13140400 | 13141450 | seg_27 | 2649 |
| 13275200 | 13276500 | seg_28 | 2650 |
| 13400400 | 13401500 | seg_29 | 2651 |
| 13690350 | 13691400 | seg_30 | 2652 |
| 13769950 | 13771750 | seg_31 | 2653 |
| 13861350 | 13862450 | seg_32 | 2654 |
| 13954750 | 13956950 | seg_33 | 2655 |
| 14044850 | 14046750 | seg_34 | 2656 |
| 15161350 | 15162400 | seg_35 | 2657 |
| 15221450 | 15222600 | seg_36 | 2658 |
| 15366600 | 15367950 | seg_37 | 2659 |
| 15635900 | 15637200 | seg_38 | 2660 |
| 15661250 | 15663050 | seg_39 | 2661 |
| 15691700 | 15692750 | seg_40 | 2662 |
| 15870450 | 15871500 | seg_41 | 2663 |
| 15873100 | 15875050 | seg_42 | 2664 |
| 16038450 | 16039750 | seg_43 | 2665 |
| 16042200 | 16043200 | seg_44 | 2666 |
| 16728700 | 16730250 | seg_45 | 2667 |
| 16900250 | 16901750 | seg_46 | 2668 |
| 17016300 | 17017600 | seg_47 | 2669 |
| 17092400 | 17093800 | seg_48 | 2670 |
| 17395100 | 17396350 | seg_49 | 2671 |
| 17502900 | 17504050 | seg_50 | 2672 |
| 17784350 | 17785350 | seg_51 | 2673 |
| 17814350 | 17815500 | seg_52 | 2674 |
| 18371700 | 18372700 | seg_53 | 2675 |
| 18873500 | 18875100 | seg_54 | 2676 |
| 19140800 | 19142750 | seg_55 | 2677 |
| 20313350 | 20314350 | seg_56 | 2678 |
| 21392500 | 21393700 | seg_57 | 2679 |
| 21456000 | 21457350 | seg_58 | 2680 |
| 22244450 | 22245550 | seg_59 | 2681 |
| 22543750 | 22544950 | seg_60 | 2682 |
| 23349400 | 23350400 | seg_61 | 2683 |
| 24071600 | 24072950 | seg_62 | 2684 |
| 24163650 | 24165150 | seg_63 | 2685 |
| 24664100 | 24665300 | seg_64 | 2686 |
| 25024050 | 25042800 | seg_65 | 2687 |
| 29296100 | 29297200 | seg_66 | 2688 |
| 29464050 | 29465100 | seg_67 | 2689 |
| 29572800 | 29574700 | seg_68 | 2690 |
| 30201850 | 30203000 | seg_69 | 2691 |
| 30358350 | 30359600 | seg_70 | 2692 |
| 30553550 | 30554600 | seg_71 | 2693 |
| 30731150 | 30732450 | seg_72 | 2694 |
| 30753250 | 30754400 | seg_73 | 2695 |
| 30989450 | 30990650 | seg_74 | 2696 |
| 31188900 | 31190050 | seg_75 | 2697 |
| 31789800 | 31791200 | seg_76 | 2698 |
| 32372400 | 32373550 | seg_77 | 2699 |
| 32690150 | 32691150 | seg_78 | 2700 |
| 37222250 | 37223300 | seg_79 | 2701 |
| 37645650 | 37647450 | seg_80 | 2702 |
| 37765500 | 37766650 | seg_81 | 2703 |
| 38135850 | 38136950 | seg_82 | 2704 |
| 38537450 | 38538750 | seg_83 | 2705 |
| 39511450 | 39512600 | seg_84 | 2706 |
| 39546900 | 39548650 | seg_85 | 2707 |
| 39634900 | 39635950 | seg_86 | 2708 |
| 39871150 | 39873000 | seg_87 | 2709 |
| 40265250 | 40266350 | seg_88 | 2710 |
| 41095400 | 41096450 | seg_89 | 2711 |
| 41209250 | 41211000 | seg_90 | 2712 |
| 41579300 | 41581500 | seg_91 | 2713 |
| 43208150 | 43209200 | seg_92 | 2714 |
| 45627750 | 45630900 | seg_93 | 2715 |
| 45708550 | 45711000 | seg_94 | 2716 |
| 46497450 | 46498550 | seg_95 | 2717 |
| 46692050 | 46693500 | seg_96 | 2718 |
| 46772150 | 46774250 | seg_97 | 2719 |
| 46819250 | 46820950 | seg_98 | 2720 |
| 46839750 | 46841250 | seg_99 | 2721 |
| 50489150 | 50490250 | seg_100 | 2722 |
| 53349050 | 53352550 | seg_101 | 2723 |
| 53356550 | 53357650 | seg_102 | 2724 |
| 53467000 | 53468050 | seg_103 | 2725 |
| 53659750 | 53660850 | seg_104 | 2726 |
| 53677550 | 53678650 | seg_105 | 2727 |
| 56267800 | 56269150 | seg_106 | 2728 |
| 61838500 | 61840400 | seg_107 | 2729 |
| 62599850 | 62601050 | seg_108 | 2730 |
| 62906550 | 62907850 | seg_109 | 2731 |
| 64255700 | 64256850 | seg_110 | 2732 |
| 64754100 | 64755650 | seg_111 | 2733 |
| 64801300 | 64802950 | seg_112 | 2734 |
| 68049150 | 68050700 | seg_113 | 2735 |
| 68230350 | 68231550 | seg_114 | 2736 |
| 68392000 | 68393100 | seg_115 | 2737 |
| 68607150 | 68608150 | seg_116 | 2738 |
| 68725350 | 68726600 | seg_117 | 2739 |
| 69416400 | 69418200 | seg_118 | 2740 |
| 69555900 | 69556900 | seg_119 | 2741 |
| 69663400 | 69665750 | seg_120 | 2742 |
| 69690000 | 69691650 | seg_121 | 2743 |
| 71320100 | 71321750 | seg_122 | 2744 |
| 71351100 | 71353000 | seg_123 | 2745 |
| 71495000 | 71496100 | seg_124 | 2746 |
| 71523650 | 71529700 | seg_125 | 2747 |
| 71833400 | 71834600 | seg_126 | 2748 |
| 73639250 | 73642650 | seg_127 | 2749 |
| 78177750 | 78179500 | seg_128 | 2750 |
| 78196450 | 78197450 | seg_129 | 2751 |
| 78211700 | 78214250 | seg_130 | 2752 |
| 78408600 | 78409850 | seg_131 | 2753 |
| 78413000 | 78414000 | seg_132 | 2754 |
| 78416550 | 78417950 | seg_133 | 2755 |
| 78513750 | 78515600 | seg_134 | 2756 |
| 80385100 | 80386100 | seg_135 | 2757 |
| 82723300 | 82724450 | seg_136 | 2758 |
| 88458350 | 88460200 | seg_137 | 2759 |
| 91034350 | 91035850 | seg_138 | 2760 |
| 96703000 | 96704200 | seg_139 | 2761 |
| 99622650 | 99623950 | seg_140 | 2762 |
| 99666250 | 99668550 | seg_141 | 2763 |
| 99880550 | 99881650 | seg_142 | 2764 |
| 99985450 | 99986650 | seg_143 | 2765 |
| 102632100 | 102633150 | seg_144 | 2766 |
| 102942900 | 102943950 | seg_145 | 2767 |
| 105218650 | 105219800 | seg_146 | 2768 |
| 105938200 | 105940150 | seg_147 | 2769 |
| 105968900 | 105969900 | seg_148 | 2770 |
| 106044700 | 106046300 | seg_149 | 2771 |
| 106117050 | 106118200 | seg_150 | 2772 |

TABLE XV-continued

EZH2 in GM12878

| start | end | name | SEQ ID NO: |
|---|---|---|---|
| 106691800 | 106694950 | seg_151 | 2773 |
| 106750650 | 106751900 | seg_152 | 2774 |
| 107067250 | 107070800 | seg_153 | 2775 |
| 107314500 | 107315550 | seg_154 | 2776 |
| 107494550 | 107495800 | seg_155 | 2777 |
| 107670350 | 107671350 | seg_156 | 2778 |
| 108728500 | 108730000 | seg_157 | 2779 |
| 109388700 | 109390200 | seg_158 | 2780 |
| 109606250 | 109607300 | seg_159 | 2781 |
| 109634900 | 109636050 | seg_160 | 2782 |
| 109693150 | 109694700 | seg_161 | 2783 |
| 109938700 | 109940350 | seg_162 | 2784 |
| 110094600 | 110096000 | seg_163 | 2785 |
| 110955050 | 110956250 | seg_164 | 2786 |
| 111165850 | 111167200 | seg_165 | 2787 |
| 111431200 | 111432300 | seg_166 | 2788 |
| 111921950 | 111923200 | seg_167 | 2789 |
| 112094000 | 112095700 | seg_168 | 2790 |
| 114642350 | 114643450 | seg_169 | 2791 |
| 117505350 | 117506550 | seg_170 | 2792 |
| 117661700 | 117662750 | seg_171 | 2793 |
| 117957150 | 117960300 | seg_172 | 2794 |
| 117985600 | 117986600 | seg_173 | 2795 |
| 118109100 | 118110500 | seg_174 | 2796 |
| 119124200 | 119126100 | seg_175 | 2797 |
| 119130600 | 119136250 | seg_176 | 2798 |
| 119149750 | 119150850 | seg_177 | 2799 |
| 119283750 | 119285050 | seg_178 | 2800 |
| 119443250 | 119445250 | seg_179 | 2801 |
| 119475500 | 119476550 | seg_180 | 2802 |
| 120440750 | 120442950 | seg_181 | 2803 |
| 120630700 | 120631700 | seg_182 | 2804 |
| 124337400 | 124339100 | seg_183 | 2805 |
| 125673400 | 125674600 | seg_184 | 2806 |
| 128265000 | 128266000 | seg_185 | 2807 |
| 129114500 | 129116250 | seg_186 | 2808 |
| 129398550 | 129399700 | seg_187 | 2809 |
| 129750050 | 129751050 | seg_188 | 2810 |
| 131866700 | 131867750 | seg_189 | 2811 |
| 132547800 | 132548950 | seg_190 | 2812 |
| 133307500 | 133308850 | seg_191 | 2813 |
| 133603350 | 133604800 | seg_192 | 2814 |
| 133681150 | 133683450 | seg_193 | 2815 |
| 133684650 | 133685700 | seg_194 | 2816 |
| 134491550 | 134493250 | seg_195 | 2817 |
| 135228150 | 135229350 | seg_196 | 2818 |
| 135231600 | 135232650 | seg_197 | 2819 |
| 136114000 | 136117750 | seg_198 | 2820 |
| 136133300 | 136135150 | seg_199 | 2821 |
| 136507800 | 136510950 | seg_200 | 2822 |
| 136650000 | 136652650 | seg_201 | 2823 |
| 138275750 | 138278250 | seg_202 | 2824 |
| 138285450 | 138287700 | seg_203 | 2825 |
| 139172250 | 139173500 | seg_204 | 2826 |
| 139583350 | 139585350 | seg_205 | 2827 |
| 139847900 | 139849150 | seg_206 | 2828 |
| 147582000 | 147584900 | seg_207 | 2829 |
| 148958200 | 148959900 | seg_208 | 2830 |
| 149394250 | 149395700 | seg_209 | 2831 |
| 149529400 | 149535200 | seg_210 | 2832 |
| 150315200 | 150316600 | seg_211 | 2833 |
| 150345300 | 150346350 | seg_212 | 2834 |
| 152910650 | 152911850 | seg_213 | 2835 |
| 153094250 | 153095900 | seg_214 | 2836 |
| 153097200 | 153098250 | seg_215 | 2837 |

Each PRC2 strong site or the paRNA(s) associated with each PRC2 strong site is a candidate drug target against with antisense oligonucleotides (ASO) can be designed.

PRC2-associated RNAs were called by analyzing RNA-seq datasets for the corresponding cell lines (wgEncodeEH000187, wgEncodeEH000170, wgEncodeEH000182) and identifying those that overlap the PRC2 site in either orientation by at least 1 base pair.

Again, the PRC2 site-associated RNAs can be noncoding (long noncoding RNA, lncRNA) or occasionally part of a coding mRNA; for simplicity, we will discuss them together as polycomb-associated RNAs (paRNAs). In K562 cells, there are 1275 paRNAs associated with the EZH2 strong sites (Table XVI), 1317 paRNAs associated with strong SUZ12 sites (Table XVII), In GM12878 cells, there are 503 paRNAs associated with the EZH2 strong sites (Table XVIII), Previously annotated RNAs were given a specific ENSEMBL ID in Tables XVI-XVIII (e.g., ENST00000433425.1).

Shown in the following Tables XVI-XVIII are (in column order): Transcript ID number (Ensemble nomenclature); SIN (SEQ NO:); START and STOP, the Start and stop base numbers (coordinates) on the X-chromosome; STRAND, the strand of the X-chromosome (+, -); SUZ12_ID or EZH2_ID, the segment number with which the paRNA is associated; EZH2_START and EZH2_END or SUZ_START and SUZ_END, the start and end base numbers of the segment on the X chr; NEAREST GENE, the name of the closest annotated gene; DISEASE GENE; the name of the closest disease gene. In the sequence listing submitted herewith, the transcripts are represented in DNA sequences; replacement of the "T" nucleotides with "U" would render the original RNA sequence.

TABLE XVI paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000334060.3 | 2838 | 585079 | 620146 | + | seg_8 | 610100 | 614650 | SHOX | OA1 = GPR143 |
| ENST00000381575.1 | 2839 | 591542 | 620146 | + | seg_8 | 610100 | 614650 | SHOX | OA1 = GPR143 |
| ENST00000381566.1 | 2840 | 1317790 | 1331527 | − | seg_20 | 1324000 | 1325900 | CRLF2 | OA1 = GPR143 |
| ENST00000381567.3 | 2841 | 1314890 | 1331527 | − | seg_20 | 1324000 | 1325900 | CRLF2 | OA1 = GPR143 |
| ENST00000467626.1 | 2842 | 1314894 | 1331616 | − | seg_20 | 1324000 | 1325900 | CRLF2 | OA1 = GPR143 |
| ENST00000400841.2 | 2843 | 1314894 | 1331530 | − | seg_20 | 1324000 | 1325900 | CRLF2 | OA1 = GPR143 |
| ENST00000486791.1 | 2844 | 1387738 | 1428827 | + | seg_22 | 1392500 | 1394100 | CSF2RA | OA1 = GPR143 |
| ENST00000381524.3 | 2845 | 1387701 | 1429274 | + | seg_22 | 1392500 | 1394100 | CSF2RA | OA1 = GPR143 |
| ENST00000412290.1 | 2846 | 1387711 | 1413288 | + | seg_22 | 1392500 | 1394100 | CSF2RA | OA1 = GPR143 |
| ENST00000501036.2 | 2847 | 1387693 | 1428828 | + | seg_22 | 1392500 | 1394100 | CSF2RA | OA1 = GPR143 |
| ENST00000381529.3 | 2848 | 1387693 | 1428815 | + | seg_22 | 1392500 | 1394100 | CSF2RA | OA1 = GPR143 |
| ENST00000361536.3 | 2849 | 1387693 | 1428828 | + | seg_22 | 1392500 | 1394100 | CSF2RA | OA1 = GPR143 |
| ENST00000355432.3 | 2850 | 1387738 | 1428827 | + | seg_22 | 1392500 | 1394100 | CSF2RA | OA1 = GPR143 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000355805.2 | 2851 | 1387738 | 1428827 | + | seg_22 | 1392500 | 1394100 | CSF2RA | OA1 = GPR143 |
| ENST00000419094.1 | 2852 | 1387723 | 1409320 | + | seg_22 | 1392500 | 1394100 | CSF2RA | OA1 = GPR143 |
| ENST00000493312.1 | 2853 | 1387707 | 1419436 | + | seg_22 | 1392500 | 1394100 | CSF2RA | OA1 = GPR143 |
| ENST00000381507.4 | 2854 | 1387693 | 1428828 | + | seg_22 | 1392500 | 1394100 | CSF2RA | OA1 = GPR143 |
| ENST00000381509.3 | 2855 | 1387725 | 1424834 | + | seg_22 | 1392500 | 1394100 | CSF2RA | OA1 = GPR143 |
| ENST00000494969.1 | 2856 | 1387725 | 1428815 | + | seg_22 | 1392500 | 1394100 | CSF2RA | OA1 = GPR143 |
| ENST00000432318.2 | 2857 | 1387693 | 1428828 | + | seg_22 | 1392500 | 1394100 | CSF2RA | OA1 = GPR143 |
| ENST00000481245.1 | 2858 | 1387728 | 1401113 | + | seg_22 | 1392500 | 1394100 | CSF2RA | OA1 = GPR143 |
| ENST00000477940.1 | 2859 | 1404545 | 1407533 | + | seg_23 | 1403850 | 1405100 | CSF2RA | OA1 = GPR143 |
| ENST00000486791.1 | 2860 | 1387738 | 1428827 | + | seg_23 | 1403850 | 1405100 | CSF2RA | OA1 = GPR143 |
| ENST00000381500.1 | 2861 | 1401579 | 1428531 | + | seg_23 | 1403850 | 1405100 | CSF2RA | OA1 = GPR143 |
| ENST00000381524.3 | 2862 | 1387701 | 1429274 | + | seg_23 | 1403850 | 1405100 | CSF2RA | OA1 = GPR143 |
| ENST00000417535.2 | 2863 | 1401571 | 1428828 | + | seg_23 | 1403850 | 1405100 | CSF2RA | OA1 = GPR143 |
| ENST00000412290.1 | 2864 | 1387711 | 1413288 | + | seg_23 | 1403850 | 1405100 | CSF2RA | OA1 = GPR143 |
| ENST00000501036.2 | 2865 | 1387693 | 1428828 | + | seg_23 | 1403850 | 1405100 | CSF2RA | OA1 = GPR143 |
| ENST00000381529.3 | 2866 | 1387693 | 1428815 | + | seg_23 | 1403850 | 1405100 | CSF2RA | OA1 = GPR143 |
| ENST00000361536.3 | 2867 | 1387693 | 1428828 | + | seg_23 | 1403850 | 1405100 | CSF2RA | OA1 = GPR143 |
| ENST00000355432.3 | 2868 | 1387738 | 1428827 | + | seg_23 | 1403850 | 1405100 | CSF2RA | OA1 = GPR143 |
| ENST00000355805.2 | 2869 | 1387738 | 1428827 | + | seg_23 | 1403850 | 1405100 | CSF2RA | OA1 = GPR143 |
| ENST00000419094.1 | 2870 | 1387723 | 1409320 | + | seg_23 | 1403850 | 1405100 | CSF2RA | OA1 = GPR143 |
| ENST00000493312.1 | 2871 | 1387707 | 1419436 | + | seg_23 | 1403850 | 1405100 | CSF2RA | OA1 = GPR143 |
| ENST00000381507.4 | 2872 | 1387693 | 1428828 | + | seg_23 | 1403850 | 1405100 | CSF2RA | OA1 = GPR143 |
| ENST00000381509.3 | 2873 | 1387725 | 1424834 | + | seg_23 | 1403850 | 1405100 | CSF2RA | OA1 = GPR143 |
| ENST00000494969.1 | 2874 | 1387725 | 1428815 | + | seg_23 | 1403850 | 1405100 | CSF2RA | OA1 = GPR143 |
| ENST00000432318.2 | 2875 | 1387693 | 1428828 | + | seg_23 | 1403850 | 1405100 | CSF2RA | OA1 = GPR143 |
| ENST00000381469.2 | 2876 | 1460659 | 1501358 | + | seg_24 | 1460050 | 1461400 | IL3RA | OA1 = GPR143 |
| ENST00000331035.4 | 2877 | 1455509 | 1501578 | + | seg_24 | 1460050 | 1461400 | IL3RA | OA1 = GPR143 |
| ENST00000432757.1 | 2878 | 1455689 | 1475224 | + | seg_24 | 1460050 | 1461400 | IL3RA | OA1 = GPR143 |
| ENST00000381469.2 | 2879 | 1460659 | 1501358 | + | seg_25 | 1464650 | 1468000 | IL3RA | OA1 = GPR143 |
| ENST00000331035.4 | 2880 | 1455509 | 1501578 | + | seg_25 | 1464650 | 1468000 | IL3RA | OA1 = GPR143 |
| ENST00000432757.1 | 2881 | 1455689 | 1475224 | + | seg_25 | 1464650 | 1468000 | IL3RA | OA1 = GPR143 |
| ENST00000381229.4 | 2882 | 1734057 | 1761920 | + | seg_27 | 1733950 | 1735600 | ASMT | OA1 = GPR143 |
| ENST00000381233.3 | 2883 | 1734068 | 1761974 | + | seg_27 | 1733950 | 1735600 | ASMT | OA1 = GPR143 |
| ENST00000381241.3 | 2884 | 1733894 | 1761974 | + | seg_27 | 1733950 | 1735600 | ASMT | OA1 = GPR143 |
| ENST00000381229.4 | 2885 | 1734057 | 1761920 | + | seg_28 | 1747250 | 1749200 | ASMT | OA1 = GPR143 |
| ENST00000381233.3 | 2886 | 1734068 | 1761974 | + | seg_28 | 1747250 | 1749200 | ASMT | OA1 = GPR143 |
| ENST00000381241.3 | 2887 | 1733894 | 1761974 | + | seg_28 | 1747250 | 1749200 | ASMT | OA1 = GPR143 |
| ENST00000509780.1 | 2888 | 1746639 | 1755356 | + | seg_28 | 1747250 | 1749200 | ASMT | OA1 = GPR143 |
| ENST00000430536.2 | 2889 | 2255872 | 2419001 | − | seg_29 | 2368950 | 2371350 | DHRSX | OA1 = GPR143 |
| ENST00000441131.2 | 2890 | 2184895 | 2420846 | − | seg_29 | 2368950 | 2371350 | DHRSX | OA1 = GPR143 |
| ENST00000334651.5 | 2891 | 2137557 | 2419019 | − | seg_29 | 2368950 | 2371350 | DHRSX | OA1 = GPR143 |
| ENST00000444280.1 | 2892 | 2184811 | 2418691 | − | seg_29 | 2368950 | 2371350 | DHRSX | OA1 = GPR143 |
| ENST00000478825.1 | 2893 | 2209543 | 2418630 | − | seg_29 | 2368950 | 2371350 | DHRSX | OA1 = GPR143 |
| ENST00000412516.2 | 2894 | 2161103 | 2419014 | − | seg_29 | 2368950 | 2371350 | DHRSX | OA1 = GPR143 |
| ENST00000430536.2 | 2895 | 2255872 | 2419001 | − | seg_30 | 2374650 | 2376750 | DHRSX | OA1 = GPR143 |
| ENST00000441131.2 | 2896 | 2184895 | 2420846 | − | seg_30 | 2374650 | 2376750 | DHRSX | OA1 = GPR143 |
| ENST00000334651.5 | 2897 | 2137557 | 2419019 | − | seg_30 | 2374650 | 2376750 | DHRSX | OA1 = GPR143 |
| ENST00000444280.1 | 2898 | 2184811 | 2418691 | − | seg_30 | 2374650 | 2376750 | DHRSX | OA1 = GPR143 |
| ENST00000478825.1 | 2899 | 2209543 | 2418630 | − | seg_30 | 2374650 | 2376750 | DHRSX | OA1 = GPR143 |
| ENST00000412516.2 | 2900 | 2161103 | 2419014 | − | seg_30 | 2374650 | 2376750 | DHRSX | OA1 = GPR143 |
| ENST00000430536.2 | 2901 | 2255872 | 2419001 | − | seg_31 | 2381200 | 2383650 | ZBED1 | OA1 = GPR143 |
| ENST00000441131.2 | 2902 | 2184895 | 2420846 | − | seg_31 | 2381200 | 2383650 | ZBED1 | OA1 = GPR143 |
| ENST00000334651.5 | 2903 | 2137557 | 2419019 | − | seg_31 | 2381200 | 2383650 | ZBED1 | OA1 = GPR143 |
| ENST00000444280.1 | 2904 | 2184811 | 2418691 | − | seg_31 | 2381200 | 2383650 | ZBED1 | OA1 = GPR143 |
| ENST00000478825.1 | 2905 | 2209543 | 2418630 | − | seg_31 | 2381200 | 2383650 | ZBED1 | OA1 = GPR143 |
| ENST00000412516.2 | 2906 | 2161103 | 2419014 | − | seg_31 | 2381200 | 2383650 | ZBED1 | OA1 = GPR143 |
| ENST00000430536.2 | 2907 | 2255872 | 2419001 | − | seg_32 | 2391700 | 2394350 | ZBED1 | OA1 = GPR143 |
| ENST00000441131.2 | 2908 | 2184895 | 2420846 | − | seg_32 | 2391700 | 2394350 | ZBED1 | OA1 = GPR143 |
| ENST00000334651.5 | 2909 | 2137557 | 2419019 | − | seg_32 | 2391700 | 2394350 | ZBED1 | OA1 = GPR143 |
| ENST00000444280.1 | 2910 | 2184811 | 2418691 | − | seg_32 | 2391700 | 2394350 | ZBED1 | OA1 = GPR143 |
| ENST00000478825.1 | 2911 | 2209543 | 2418630 | − | seg_32 | 2391700 | 2394350 | ZBED1 | OA1 = GPR143 |
| ENST00000412516.2 | 2912 | 2161103 | 2419014 | − | seg_32 | 2391700 | 2394350 | ZBED1 | OA1 = GPR143 |
| ENST00000426774.1 | 2913 | 2670093 | 2734539 | + | seg_38 | 2669000 | 2672950 | XG | OA1 = GPR143 |
| ENST00000533923.2 | 2914 | 2670231 | 2732581 | + | seg_38 | 2669000 | 2672950 | XG | OA1 = GPR143 |
| ENST00000381174.5 | 2915 | 2670091 | 2733968 | + | seg_38 | 2669000 | 2672950 | XG | OA1 = GPR143 |
| ENST00000503018.1 | 2916 | 2670337 | 2693037 | + | seg_38 | 2669000 | 2672950 | XG | OA1 = GPR143 |
| ENST00000419513.2 | 2917 | 2670093 | 2732589 | + | seg_38 | 2669000 | 2672950 | XG | OA1 = GPR143 |
| ENST00000509484.2 | 2918 | 2670186 | 2729477 | + | seg_38 | 2669000 | 2672950 | XG | OA1 = GPR143 |
| ENST00000426774.1 | 2919 | 2670093 | 2734539 | + | seg_39 | 2681550 | 2683000 | XG | OA1 = GPR143 |
| ENST00000533923.2 | 2920 | 2670231 | 2732581 | + | seg_39 | 2681550 | 2683000 | XG | OA1 = GPR143 |
| ENST00000381174.5 | 2921 | 2670091 | 2733968 | + | seg_39 | 2681550 | 2683000 | XG | OA1 = GPR143 |
| ENST00000503018.1 | 2922 | 2670337 | 2693037 | + | seg_39 | 2681550 | 2683000 | XG | OA1 = GPR143 |
| ENST00000419513.2 | 2923 | 2670093 | 2732589 | + | seg_39 | 2681550 | 2683000 | XG | OA1 = GPR143 |
| ENST00000509484.2 | 2924 | 2670186 | 2729477 | + | seg_39 | 2681550 | 2683000 | XG | OA1 = GPR143 |
| ENST00000426774.1 | 2925 | 2670093 | 2734539 | + | seg_40 | 2684450 | 2685950 | XG | OA1 = GPR143 |
| ENST00000533923.2 | 2926 | 2670231 | 2732581 | + | seg_40 | 2684450 | 2685950 | XG | OA1 = GPR143 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000381174.5 | 2927 | 2670091 | 2733968 | + | seg_40 | 2684450 | 2685950 | XG | OA1 = GPR143 |
| ENST00000503018.1 | 2928 | 2670337 | 2693037 | + | seg_40 | 2684450 | 2685950 | XG | OA1 = GPR143 |
| ENST00000419513.2 | 2929 | 2670093 | 2732589 | + | seg_40 | 2684450 | 2685950 | XG | OA1 = GPR143 |
| ENST00000509484.2 | 2930 | 2670186 | 2729477 | + | seg_40 | 2684450 | 2685950 | XG | OA1 = GPR143 |
| ENST00000426774.1 | 2931 | 2670093 | 2734539 | + | seg_41 | 2699450 | 2703000 | XG | OA1 = GPR143 |
| ENST00000533923.2 | 2932 | 2670231 | 2732581 | + | seg_41 | 2699450 | 2703000 | XG | OA1 = GPR143 |
| ENST00000381174.5 | 2933 | 2670091 | 2733968 | + | seg_41 | 2699450 | 2703000 | XG | OA1 = GPR143 |
| ENST00000419513.2 | 2934 | 2670093 | 2732589 | + | seg_41 | 2699450 | 2703000 | XG | OA1 = GPR143 |
| ENST00000509484.2 | 2935 | 2670186 | 2729477 | + | seg_41 | 2699450 | 2703000 | XG | OA1 = GPR143 |
| ENST00000381134.3 | 2936 | 2852857 | 2882311 | − | seg_42 | 2854000 | 2856700 | ARSD | OA1 = GPR143 |
| ENST00000545496.1 | 2937 | 2852852 | 2882325 | − | seg_42 | 2854000 | 2856700 | ARSD | OA1 = GPR143 |
| ENST00000540563.1 | 2938 | 2852699 | 2886286 | − | seg_42 | 2854000 | 2856700 | ARSD | OA1 = GPR143 |
| ENST00000438544.1 | 2939 | 2867664 | 2882305 | − | seg_43 | 2873200 | 2874800 | ARSE | OA1 = GPR143 |
| ENST00000381134.3 | 2940 | 2852857 | 2882311 | − | seg_43 | 2873200 | 2874800 | ARSE | OA1 = GPR143 |
| ENST00000545496.1 | 2941 | 2852852 | 2882325 | − | seg_43 | 2873200 | 2874800 | ARSE | OA1 = GPR143 |
| ENST00000540563.1 | 2942 | 2852699 | 2886286 | − | seg_43 | 2873200 | 2874800 | ARSE | OA1 = GPR143 |
| ENST00000496095.1 | 2943 | 2876452 | 2882305 | − | seg_44 | 2876400 | 2879500 | ARSE | OA1 = GPR143 |
| ENST00000438544.1 | 2944 | 2867664 | 2882305 | − | seg_44 | 2876400 | 2879500 | ARSE | OA1 = GPR143 |
| ENST00000381134.3 | 2945 | 2852857 | 2882311 | − | seg_44 | 2876400 | 2879500 | ARSE | OA1 = GPR143 |
| ENST00000545496.1 | 2946 | 2852852 | 2882325 | − | seg_44 | 2876400 | 2879500 | ARSE | OA1 = GPR143 |
| ENST00000540563.1 | 2947 | 2852699 | 2886286 | − | seg_44 | 2876400 | 2879500 | ARSE | OA1 = GPR143 |
| ENST00000381130.2 | 2948 | 2924654 | 2951612 | + | seg_46 | 2936900 | 2938400 | ARSH | OA1 = GPR143 |
| ENST00000432442.1 | 2949 | 9217960 | 9243246 | + | seg_56 | 9229800 | 9231600 | FAM9B | OA1 = GPR143 |
| ENST00000432442.1 | 2950 | 9217960 | 9243246 | + | seg_57 | 9241950 | 9244700 | FAM9B | OA1 = GPR143 |
| ENST00000416620.1 | 2951 | 9370791 | 9382606 | + | seg_62 | 9371100 | 9382750 | TBL1X | OA1 = GPR143 |
| ENST00000441088.1 | 2952 | 9431360 | 9622328 | + | seg_63 | 9483500 | 9485000 | TBL1X | OA1 = GPR143 |
| ENST00000217964.7 | 2953 | 9433048 | 9687778 | + | seg_63 | 9483500 | 9485000 | TBL1X | OA1 = GPR143 |
| ENST00000380961.1 | 2954 | 9431369 | 9686902 | + | seg_63 | 9483500 | 9485000 | TBL1X | OA1 = GPR143 |
| ENST00000407597.2 | 2955 | 9431335 | 9687780 | + | seg_63 | 9483500 | 9485000 | TBL1X | OA1 = GPR143 |
| ENST00000424279.1 | 2956 | 9431335 | 9687780 | + | seg_63 | 9483500 | 9485000 | TBL1X | OA1 = GPR143 |
| ENST00000415293.1 | 2957 | 9431371 | 9656077 | + | seg_63 | 9483500 | 9485000 | TBL1X | OA1 = GPR143 |
| ENST00000536365.1 | 2958 | 9431352 | 9684302 | + | seg_63 | 9483500 | 9485000 | TBL1X | OA1 = GPR143 |
| ENST00000422314.1 | 2959 | 9433334 | 9652158 | + | seg_63 | 9483500 | 9485000 | TBL1X | OA1 = GPR143 |
| ENST00000380913.3 | 2960 | 9754496 | 9917483 | + | seg_64 | 9793150 | 9794450 | SHROOM2 | OA1 = GPR143 |
| ENST00000380913.3 | 2961 | 9754496 | 9917483 | + | seg_65 | 9806050 | 9807500 | SHROOM2 | OA1 = GPR143 |
| ENST00000380913.3 | 2962 | 9754496 | 9917483 | + | seg_66 | 9814250 | 9818150 | SHROOM2 | OA1 = GPR143 |
| ENST00000380913.3 | 2963 | 9754496 | 9917483 | + | seg_67 | 9823350 | 9824550 | SHROOM2 | OA1 = GPR143 |
| ENST00000493668.1 | 2964 | 9866185 | 9905186 | + | seg_68 | 9863450 | 9867000 | SHROOM2 | OA1 = GPR143 |
| ENST00000380913.3 | 2965 | 9754496 | 9917483 | + | seg_68 | 9863450 | 9867000 | SHROOM2 | OA1 = GPR143 |
| ENST00000493668.1 | 2966 | 9866185 | 9905186 | + | seg_69 | 9880300 | 9881950 | SHROOM2 | OA1 = GPR143 |
| ENST00000418909.2 | 2967 | 9880412 | 9916398 | + | seg_69 | 9880300 | 9881950 | SHROOM2 | OA1 = GPR143 |
| ENST00000540923.1 | 2968 | 9880723 | 9917476 | + | seg_69 | 9880300 | 9881950 | SHROOM2 | OA1 = GPR143 |
| ENST00000452575.1 | 2969 | 9880723 | 9914748 | + | seg_69 | 9880300 | 9881950 | SHROOM2 | OA1 = GPR143 |
| ENST00000380913.3 | 2970 | 9754496 | 9917483 | + | seg_69 | 9880300 | 9881950 | SHROOM2 | OA1 = GPR143 |
| ENST00000493668.1 | 2971 | 9866185 | 9905186 | + | seg_70 | 9883800 | 9885000 | SHROOM2 | OA1 = GPR143 |
| ENST00000418909.2 | 2972 | 9880412 | 9916398 | + | seg_70 | 9883800 | 9885000 | SHROOM2 | OA1 = GPR143 |
| ENST00000540923.1 | 2973 | 9880723 | 9917476 | + | seg_70 | 9883800 | 9885000 | SHROOM2 | OA1 = GPR143 |
| ENST00000452575.1 | 2974 | 9880723 | 9914748 | + | seg_70 | 9883800 | 9885000 | SHROOM2 | OA1 = GPR143 |
| ENST00000380913.3 | 2975 | 9754496 | 9917483 | + | seg_70 | 9883800 | 9885000 | SHROOM2 | OA1 = GPR143 |
| ENST00000418909.2 | 2976 | 9880412 | 9916398 | + | seg_71 | 9913900 | 9916050 | SHROOM2 | OA1 = GPR143 |
| ENST00000540923.1 | 2977 | 9880723 | 9917476 | + | seg_71 | 9913900 | 9916050 | SHROOM2 | OA1 = GPR143 |
| ENST00000452575.1 | 2978 | 9880723 | 9914748 | + | seg_71 | 9913900 | 9916050 | SHROOM2 | OA1 = GPR143 |
| ENST00000380913.3 | 2979 | 9754496 | 9917483 | + | seg_71 | 9913900 | 9916050 | SHROOM2 | OA1 = GPR143 |
| ENST00000543293.1 | 2980 | 10031499 | 10086141 | + | seg_73 | 10048550 | 10049650 | WWC3 | OA1 = GPR143 |
| ENST00000398613.4 | 2981 | 10035291 | 10109658 | + | seg_73 | 10048550 | 10049650 | WWC3 | OA1 = GPR143 |
| ENST00000380861.4 | 2982 | 9983602 | 10112518 | + | seg_73 | 10048550 | 10049650 | WWC3 | OA1 = GPR143 |
| ENST00000454666.1 | 2983 | 10031499 | 10109658 | + | seg_73 | 10048550 | 10049650 | WWC3 | OA1 = GPR143 |
| ENST00000421085.2 | 2984 | 10126540 | 10201760 | + | seg_74 | 10180950 | 10182200 | CLCN4 | OA1 = GPR143 |
| ENST00000380829.1 | 2985 | 10126488 | 10201737 | + | seg_74 | 10180950 | 10182200 | CLCN4 | OA1 = GPR143 |
| ENST00000380833.4 | 2986 | 10125024 | 10205700 | + | seg_74 | 10180950 | 10182200 | CLCN4 | OA1 = GPR143 |
| ENST00000421085.2 | 2987 | 10126540 | 10201760 | + | seg_75 | 10189550 | 10190550 | CLCN4 | OA1 = GPR143 |
| ENST00000380829.1 | 2988 | 10126488 | 10201737 | + | seg_75 | 10189550 | 10190550 | CLCN4 | OA1 = GPR143 |
| ENST00000380833.4 | 2989 | 10125024 | 10205700 | + | seg_75 | 10189550 | 10190550 | CLCN4 | OA1 = GPR143 |
| ENST00000384473.1 | 2990 | 10550857 | 10550959 | + | seg_77 | 10549850 | 10550950 | MID1 | OA1 = GPR143 |
| ENST00000423614.1 | 2991 | 10534995 | 10588625 | − | seg_77 | 10549850 | 10550950 | MID1 | OA1 = GPR143 |
| ENST00000453318.2 | 2992 | 10413350 | 10645779 | − | seg_77 | 10549850 | 10550950 | MID1 | OA1 = GPR143 |
| ENST00000380782.1 | 2993 | 10413596 | 10588459 | − | seg_77 | 10549850 | 10550950 | MID1 | OA1 = GPR143 |
| ENST00000380787.1 | 2994 | 10413596 | 10851773 | − | seg_77 | 10549850 | 10550950 | MID1 | OA1 = GPR143 |
| ENST00000380785.1 | 2995 | 10413596 | 10851762 | − | seg_77 | 10549850 | 10550950 | MID1 | OA1 = GPR143 |
| ENST00000317552.4 | 2996 | 10413350 | 10588674 | − | seg_77 | 10549850 | 10550950 | MID1 | OA1 = GPR143 |
| ENST00000413894.1 | 2997 | 10423115 | 10645727 | − | seg_77 | 10549850 | 10550950 | MID1 | OA1 = GPR143 |
| ENST00000380780.1 | 2998 | 10413596 | 10557949 | − | seg_77 | 10549850 | 10550950 | MID1 | OA1 = GPR143 |
| ENST00000423614.1 | 2999 | 10534995 | 10588625 | − | seg_78 | 10575350 | 10576400 | MID1 | OA1 = GPR143 |
| ENST00000453318.2 | 3000 | 10413350 | 10645779 | − | seg_78 | 10575350 | 10576400 | MID1 | OA1 = GPR143 |
| ENST00000380782.1 | 3001 | 10413596 | 10588459 | − | seg_78 | 10575350 | 10576400 | MID1 | OA1 = GPR143 |
| ENST00000380787.1 | 3002 | 10413596 | 10851773 | − | seg_78 | 10575350 | 10576400 | MID1 | OA1 = GPR143 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000380785.1 | 3003 | 10413596 | 10851762 | − | seg__78 | 10575350 | 10576400 | MID1 | OA1 = GPR143 |
| ENST00000317552.4 | 3004 | 10413350 | 10588674 | − | seg__78 | 10575350 | 10576400 | MID1 | OA1 = GPR143 |
| ENST00000413894.1 | 3005 | 10423115 | 10645727 | − | seg__78 | 10575350 | 10576400 | MID1 | OA1 = GPR143 |
| ENST00000423614.1 | 3006 | 10534995 | 10588625 | − | seg__79 | 10577550 | 10579300 | MID1 | OA1 = GPR143 |
| ENST00000453318.2 | 3007 | 10413350 | 10645779 | − | seg__79 | 10577550 | 10579300 | MID1 | OA1 = GPR143 |
| ENST00000380782.1 | 3008 | 10413596 | 10588459 | − | seg__79 | 10577550 | 10579300 | MID1 | OA1 = GPR143 |
| ENST00000380787.1 | 3009 | 10413596 | 10851773 | − | seg__79 | 10577550 | 10579300 | MID1 | OA1 = GPR143 |
| ENST00000380785.1 | 3010 | 10413596 | 10851762 | − | seg__79 | 10577550 | 10579300 | MID1 | OA1 = GPR143 |
| ENST00000317552.4 | 3011 | 10413350 | 10588674 | − | seg__79 | 10577550 | 10579300 | MID1 | OA1 = GPR143 |
| ENST00000413894.1 | 3012 | 10423115 | 10645727 | − | seg__79 | 10577550 | 10579300 | MID1 | OA1 = GPR143 |
| ENST00000423614.1 | 3013 | 10534995 | 10588625 | − | seg__80 | 10587800 | 10589900 | MID1 | OA1 = GPR143 |
| ENST00000453318.2 | 3014 | 10413350 | 10645779 | − | seg__80 | 10587800 | 10589900 | MID1 | OA1 = GPR143 |
| ENST00000380782.1 | 3015 | 10413596 | 10588459 | − | seg__80 | 10587800 | 10589900 | MID1 | OA1 = GPR143 |
| ENST00000380787.1 | 3016 | 10413596 | 10851773 | − | seg__80 | 10587800 | 10589900 | MID1 | OA1 = GPR143 |
| ENST00000380785.1 | 3017 | 10413596 | 10851762 | − | seg__80 | 10587800 | 10589900 | MID1 | OA1 = GPR143 |
| ENST00000317552.4 | 3018 | 10413350 | 10588674 | − | seg__80 | 10587800 | 10589900 | MID1 | OA1 = GPR143 |
| ENST00000413894.1 | 3019 | 10423115 | 10645727 | − | seg__80 | 10587800 | 10589900 | MID1 | OA1 = GPR143 |
| ENST00000380787.1 | 3020 | 10413596 | 10851773 | − | seg__81 | 10837250 | 10839150 | HCCS | OA1 = GPR143 |
| ENST00000380785.1 | 3021 | 10413596 | 10851762 | − | seg__81 | 10837250 | 10839150 | HCCS | OA1 = GPR143 |
| ENST00000380736.1 | 3022 | 11155663 | 11445893 | − | seg__82 | 11358850 | 11360300 | ARHGAP6 | OA1 = GPR143 |
| ENST00000413512.3 | 3023 | 11162134 | 11369656 | − | seg__82 | 11358850 | 11360300 | ARHGAP6 | OA1 = GPR143 |
| ENST00000380732.3 | 3024 | 11166770 | 11682948 | − | seg__82 | 11358850 | 11360300 | ARHGAP6 | OA1 = GPR143 |
| ENST00000489330.1 | 3025 | 11155667 | 11683203 | − | seg__82 | 11358850 | 11360300 | ARHGAP6 | OA1 = GPR143 |
| ENST00000337414.4 | 3026 | 11155664 | 11683821 | − | seg__82 | 11358850 | 11360300 | ARHGAP6 | OA1 = GPR143 |
| ENST00000495242.1 | 3027 | 11155664 | 11683821 | − | seg__82 | 11358850 | 11360300 | ARHGAP6 | OA1 = GPR143 |
| ENST00000380718.1 | 3028 | 11161517 | 11683821 | − | seg__82 | 11358850 | 11360300 | ARHGAP6 | OA1 = GPR143 |
| ENST00000380736.1 | 3029 | 11155663 | 11445893 | − | seg__83 | 11385800 | 11386800 | ARHGAP6 | OA1 = GPR143 |
| ENST00000380732.3 | 3030 | 11166770 | 11682948 | − | seg__83 | 11385800 | 11386800 | ARHGAP6 | OA1 = GPR143 |
| ENST00000489330.1 | 3031 | 11155667 | 11683203 | − | seg__83 | 11385800 | 11386800 | ARHGAP6 | OA1 = GPR143 |
| ENST00000337414.4 | 3032 | 11155664 | 11683821 | − | seg__83 | 11385800 | 11386800 | ARHGAP6 | OA1 = GPR143 |
| ENST00000495242.1 | 3033 | 11155664 | 11683821 | − | seg__83 | 11385800 | 11386800 | ARHGAP6 | OA1 = GPR143 |
| ENST00000380718.1 | 3034 | 11161517 | 11683821 | − | seg__83 | 11385800 | 11386800 | ARHGAP6 | OA1 = GPR143 |
| ENST00000380732.3 | 3035 | 11166770 | 11682948 | − | seg__84 | 11478950 | 11480450 | ARHGAP6 | OA1 = GPR143 |
| ENST00000489330.1 | 3036 | 11155667 | 11683203 | − | seg__84 | 11478950 | 11480450 | ARHGAP6 | OA1 = GPR143 |
| ENST00000337414.4 | 3037 | 11155664 | 11683821 | − | seg__84 | 11478950 | 11480450 | ARHGAP6 | OA1 = GPR143 |
| ENST00000495242.1 | 3038 | 11155664 | 11683821 | − | seg__84 | 11478950 | 11480450 | ARHGAP6 | OA1 = GPR143 |
| ENST00000380718.1 | 3039 | 11161517 | 11683821 | − | seg__84 | 11478950 | 11480450 | ARHGAP6 | OA1 = GPR143 |
| ENST00000380732.3 | 3040 | 11166770 | 11682948 | − | seg__85 | 11482700 | 11483900 | ARHGAP6 | OA1 = GPR143 |
| ENST00000489330.1 | 3041 | 11155667 | 11683203 | − | seg__85 | 11482700 | 11483900 | ARHGAP6 | OA1 = GPR143 |
| ENST00000337414.4 | 3042 | 11155664 | 11683821 | − | seg__85 | 11482700 | 11483900 | ARHGAP6 | OA1 = GPR143 |
| ENST00000495242.1 | 3043 | 11155664 | 11683821 | − | seg__85 | 11482700 | 11483900 | ARHGAP6 | OA1 = GPR143 |
| ENST00000380718.1 | 3044 | 11161517 | 11683821 | − | seg__85 | 11482700 | 11483900 | ARHGAP6 | OA1 = GPR143 |
| ENST00000304087.6 | 3045 | 12516791 | 12742633 | + | seg__87 | 12726850 | 12727900 | PRPS2 | SEDL = TRAPPC2 |
| ENST00000380682.1 | 3046 | 12156585 | 12742642 | + | seg__87 | 12726850 | 12727900 | PRPS2 | SEDL = TRAPPC2 |
| ENST00000429478.2 | 3047 | 12516714 | 12736911 | + | seg__87 | 12726850 | 12727900 | PRPS2 | SEDL = TRAPPC2 |
| ENST00000451311.2 | 3048 | 12993227 | 12995346 | + | seg__92 | 12995250 | 12996450 | TMSB4X | SEDL = TRAPPC2 |
| ENST00000380635.1 | 3049 | 12993363 | 12995346 | + | seg__92 | 12995250 | 12996450 | TMSB4X | SEDL = TRAPPC2 |
| ENST00000380636.1 | 3050 | 12993229 | 12995345 | + | seg__92 | 12995250 | 12996450 | TMSB4X | SEDL = TRAPPC2 |
| ENST00000456091.1 | 3051 | 13354500 | 13391753 | + | seg__93 | 13374100 | 13375150 | ATXN3L | SEDL = TRAPPC2 |
| ENST00000380602.3 | 3052 | 13587741 | 13651694 | + | seg__98 | 13587150 | 13589150 | EGFL6 | SEDL = TRAPPC2 |
| ENST00000361306.1 | 3053 | 13587724 | 13651693 | + | seg__98 | 13587150 | 13589150 | EGFL6 | SEDL = TRAPPC2 |
| ENST00000380602.3 | 3054 | 13587741 | 13651694 | + | seg__99 | 13634850 | 13636950 | TCEANC | SEDL = TRAPPC2 |
| ENST00000361306.1 | 3055 | 13587724 | 13651693 | + | seg__99 | 13634850 | 13636950 | TCEANC | SEDL = TRAPPC2 |
| ENST00000493677.1 | 3056 | 13790818 | 13835188 | − | seg__100 | 13800750 | 13802000 | GPM6B | OFD1 |
| ENST00000355135.2 | 3057 | 13792073 | 13835188 | − | seg__100 | 13800750 | 13802000 | GPM6B | OFD1 |
| ENST00000316715.4 | 3058 | 13789150 | 13835461 | − | seg__100 | 13800750 | 13802000 | GPM6B | OFD1 |
| ENST00000495211.1 | 3059 | 13794286 | 13802040 | − | seg__100 | 13800750 | 13802000 | GPM6B | OFD1 |
| ENST00000356942.5 | 3060 | 13792073 | 13835465 | − | seg__100 | 13800750 | 13802000 | GPM6B | OFD1 |
| ENST00000475307.1 | 3061 | 13801568 | 13835442 | − | seg__100 | 13800750 | 13802000 | GPM6B | OFD1 |
| ENST00000493085.1 | 3062 | 13797972 | 13907176 | − | seg__100 | 13800750 | 13802000 | GPM6B | OFD1 |
| ENST00000398361.3 | 3063 | 13792456 | 13956534 | − | seg__100 | 13800750 | 13802000 | GPM6B | OFD1 |
| ENST00000468080.1 | 3064 | 13798027 | 13907731 | − | seg__100 | 13800750 | 13802000 | GPM6B | OFD1 |
| ENST00000454189.2 | 3065 | 13789575 | 13956757 | − | seg__100 | 13800750 | 13802000 | GPM6B | OFD1 |
| ENST00000493677.1 | 3066 | 13790818 | 13835188 | − | seg__101 | 13803050 | 13806050 | GPM6B | OFD1 |
| ENST00000355135.2 | 3067 | 13792073 | 13835188 | − | seg__101 | 13803050 | 13806050 | GPM6B | OFD1 |
| ENST00000316715.4 | 3068 | 13789150 | 13835461 | − | seg__101 | 13803050 | 13806050 | GPM6B | OFD1 |
| ENST00000356942.5 | 3069 | 13792073 | 13835465 | − | seg__101 | 13803050 | 13806050 | GPM6B | OFD1 |
| ENST00000475307.1 | 3070 | 13801568 | 13835442 | − | seg__101 | 13803050 | 13806050 | GPM6B | OFD1 |
| ENST00000493085.1 | 3071 | 13797972 | 13907176 | − | seg__101 | 13803050 | 13806050 | GPM6B | OFD1 |
| ENST00000398361.3 | 3072 | 13792456 | 13956534 | − | seg__101 | 13803050 | 13806050 | GPM6B | OFD1 |
| ENST00000468080.1 | 3073 | 13798027 | 13907731 | − | seg__101 | 13803050 | 13806050 | GPM6B | OFD1 |
| ENST00000454189.2 | 3074 | 13789575 | 13956757 | − | seg__101 | 13803050 | 13806050 | GPM6B | OFD1 |
| ENST00000493677.1 | 3075 | 13790818 | 13835188 | − | seg__102 | 13820050 | 13821950 | GPM6B | OFD1 |
| ENST00000355135.2 | 3076 | 13792073 | 13835188 | − | seg__102 | 13820050 | 13821950 | GPM6B | OFD1 |
| ENST00000316715.4 | 3077 | 13789150 | 13835461 | − | seg__102 | 13820050 | 13821950 | GPM6B | OFD1 |
| ENST00000356942.5 | 3078 | 13792073 | 13835465 | − | seg__102 | 13820050 | 13821950 | GPM6B | OFD1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000475307.1 | 3079 | 13801568 | 13835442 | − | seg_102 | 13820050 | 13821950 | GPM6B | OFD1 |
| ENST00000493085.1 | 3080 | 13797972 | 13907176 | − | seg_102 | 13820050 | 13821950 | GPM6B | OFD1 |
| ENST00000398361.3 | 3081 | 13792456 | 13956534 | − | seg_102 | 13820050 | 13821950 | GPM6B | OFD1 |
| ENST00000468080.1 | 3082 | 13798027 | 13907731 | − | seg_102 | 13820050 | 13821950 | GPM6B | OFD1 |
| ENST00000454189.2 | 3083 | 13789575 | 13956757 | − | seg_102 | 13820050 | 13821950 | GPM6B | OFD1 |
| ENST00000493677.1 | 3084 | 13790818 | 13835188 | − | seg_103 | 13832300 | 13835750 | GPM6B | OFD1 |
| ENST00000355135.2 | 3085 | 13792073 | 13835188 | − | seg_103 | 13832300 | 13835750 | GPM6B | OFD1 |
| ENST00000316715.4 | 3086 | 13789150 | 13835461 | − | seg_103 | 13832300 | 13835750 | GPM6B | OFD1 |
| ENST00000356942.5 | 3087 | 13792073 | 13835465 | − | seg_103 | 13832300 | 13835750 | GPM6B | OFD1 |
| ENST00000475307.1 | 3088 | 13801568 | 13835442 | − | seg_103 | 13832300 | 13835750 | GPM6B | OFD1 |
| ENST00000493085.1 | 3089 | 13797972 | 13907176 | − | seg_103 | 13832300 | 13835750 | GPM6B | OFD1 |
| ENST00000398361.3 | 3090 | 13792456 | 13956534 | − | seg_103 | 13832300 | 13835750 | GPM6B | OFD1 |
| ENST00000468080.1 | 3091 | 13798027 | 13907731 | − | seg_103 | 13832300 | 13835750 | GPM6B | OFD1 |
| ENST00000454189.2 | 3092 | 13789575 | 13956757 | − | seg_103 | 13832300 | 13835750 | GPM6B | OFD1 |
| ENST00000398361.3 | 3093 | 13792456 | 13956534 | − | seg_104 | 13917650 | 13919650 | GPM6B | OFD1 |
| ENST00000454189.2 | 3094 | 13789575 | 13956757 | − | seg_104 | 13917650 | 13919650 | GPM6B | OFD1 |
| ENST00000398361.3 | 3095 | 13792456 | 13956534 | − | seg_105 | 13941900 | 13943750 | GPM6B | OFD1 |
| ENST00000454189.2 | 3096 | 13789575 | 13956757 | − | seg_105 | 13941900 | 13943750 | GPM6B | OFD1 |
| ENST00000398361.3 | 3097 | 13792456 | 13956534 | − | seg_106 | 13954250 | 13956600 | GPM6B | OFD1 |
| ENST00000454189.2 | 3098 | 13789575 | 13956757 | − | seg_106 | 13954250 | 13956600 | GPM6B | OFD1 |
| ENST00000380488.4 | 3099 | 15262109 | 15288270 | − | seg_112 | 15286800 | 15288500 | ASB9 | PIGA |
| ENST00000473862.1 | 3100 | 15262412 | 15288135 | − | seg_112 | 15286800 | 15288500 | ASB9 | PIGA |
| ENST00000546332.1 | 3101 | 15262111 | 15288589 | − | seg_112 | 15286800 | 15288500 | ASB9 | PIGA |
| ENST00000380483.3 | 3102 | 15262109 | 15288173 | − | seg_112 | 15286800 | 15288500 | ASB9 | PIGA |
| ENST00000380485.3 | 3103 | 15262109 | 15288183 | − | seg_112 | 15286800 | 15288500 | ASB9 | PIGA |
| ENST00000470015.1 | 3104 | 15268652 | 15288281 | − | seg_112 | 15286800 | 15288500 | ASB9 | PIGA |
| ENST00000380470.3 | 3105 | 15299819 | 15333746 | − | seg_113 | 15301150 | 15302150 | ASB9 | PIGA |
| ENST00000537676.1 | 3106 | 15298053 | 15332681 | − | seg_113 | 15301150 | 15302150 | ASB9 | PIGA |
| ENST00000344384.4 | 3107 | 15300441 | 15332681 | − | seg_113 | 15301150 | 15302150 | ASB9 | PIGA |
| ENST00000485437.1 | 3108 | 15301628 | 15333727 | − | seg_113 | 15301150 | 15302150 | ASB9 | PIGA |
| ENST00000480796.1 | 3109 | 15301166 | 15333778 | − | seg_113 | 15301150 | 15302150 | ASB9 | PIGA |
| ENST00000380470.3 | 3110 | 15299819 | 15333746 | − | seg_114 | 15321650 | 15322700 | ASB11 | PIGA |
| ENST00000537676.1 | 3111 | 15298053 | 15332681 | − | seg_114 | 15321650 | 15322700 | ASB11 | PIGA |
| ENST00000344384.4 | 3112 | 15300441 | 15332681 | − | seg_114 | 15321650 | 15322700 | ASB11 | PIGA |
| ENST00000485437.1 | 3113 | 15301628 | 15333727 | − | seg_114 | 15321650 | 15322700 | ASB11 | PIGA |
| ENST00000480796.1 | 3114 | 15301166 | 15333778 | − | seg_114 | 15321650 | 15322700 | ASB11 | PIGA |
| ENST00000297904.3 | 3115 | 15363713 | 15402498 | − | seg_116 | 15382100 | 15387750 | FIGF | PIGA |
| ENST00000297904.3 | 3116 | 15363713 | 15402498 | − | seg_117 | 15391300 | 15392750 | FIGF | PIGA |
| ENST00000380342.3 | 3117 | 15645441 | 15683154 | − | seg_118 | 15661050 | 15663600 | TMEM27 | PIGA |
| ENST00000380289.2 | 3118 | 16141679 | 16171144 | + | seg_119 | 16141650 | 16142650 | GRPR | PIGA |
| ENST00000535371.1 | 3119 | 16142045 | 16170808 | + | seg_119 | 16141650 | 16142650 | GRPR | PIGA |
| ENST00000357277.3 | 3120 | 16964814 | 17171395 | + | seg_123 | 16965250 | 16968400 | REPS2 | CC = NHS |
| ENST00000380063.2 | 3121 | 16964814 | 17167136 | + | seg_123 | 16965250 | 16968400 | REPS2 | CC = NHS |
| ENST00000481792.1 | 3122 | 16965193 | 17040494 | + | seg_123 | 16965250 | 16968400 | REPS2 | CC = NHS |
| ENST00000303843.7 | 3123 | 16964985 | 17171395 | + | seg_123 | 16965250 | 16968400 | REPS2 | CC = NHS |
| ENST00000357277.3 | 3124 | 16964814 | 17171395 | + | seg_124 | 17028550 | 17029750 | REPS2 | CC = NHS |
| ENST00000380063.2 | 3125 | 16964814 | 17167136 | + | seg_124 | 17028550 | 17029750 | REPS2 | CC = NHS |
| ENST00000380064.4 | 3126 | 16996667 | 17165745 | + | seg_124 | 17028550 | 17029750 | REPS2 | CC = NHS |
| ENST00000481792.1 | 3127 | 16965193 | 17040494 | + | seg_124 | 17028550 | 17029750 | REPS2 | CC = NHS |
| ENST00000303843.7 | 3128 | 16964985 | 17171395 | + | seg_124 | 17028550 | 17029750 | REPS2 | CC = NHS |
| ENST00000469714.1 | 3129 | 17092636 | 17165752 | + | seg_125 | 17113350 | 17114550 | REPS2 | CC = NHS |
| ENST00000357277.3 | 3130 | 16964814 | 17171395 | + | seg_125 | 17113350 | 17114550 | REPS2 | CC = NHS |
| ENST00000380063.2 | 3131 | 16964814 | 17167136 | + | seg_125 | 17113350 | 17114550 | REPS2 | CC = NHS |
| ENST00000380064.4 | 3132 | 16996667 | 17165745 | + | seg_125 | 17113350 | 17114550 | REPS2 | CC = NHS |
| ENST00000303843.7 | 3133 | 16964985 | 17171395 | + | seg_125 | 17113350 | 17114550 | REPS2 | CC = NHS |
| ENST00000380057.4 | 3134 | 17705832 | 17754111 | + | seg_126 | 17749950 | 17751500 | SCML1 | CC = NHS |
| ENST00000398097.3 | 3135 | 17653413 | 17754098 | + | seg_126 | 17749950 | 17751500 | SCML1 | CC = NHS |
| ENST00000380060.3 | 3136 | 17393543 | 17754114 | + | seg_126 | 17749950 | 17751500 | SCML1 | CC = NHS |
| ENST00000360011.1 | 3137 | 17818171 | 17878827 | − | seg_127 | 17876650 | 17878250 | RAI2 | CC = NHS |
| ENST00000331511.1 | 3138 | 17818171 | 17879356 | − | seg_127 | 17876650 | 17878250 | RAI2 | CC = NHS |
| ENST00000545871.1 | 3139 | 17818171 | 17879457 | − | seg_127 | 17876650 | 17878250 | RAI2 | CC = NHS |
| ENST00000451717.1 | 3140 | 17818171 | 17879457 | − | seg_127 | 17876650 | 17878250 | RAI2 | CC = NHS |
| ENST00000415486.2 | 3141 | 17818171 | 17879457 | − | seg_127 | 17876650 | 17878250 | RAI2 | CC = NHS |
| ENST00000380033.4 | 3142 | 18181051 | 18239003 | − | seg_128 | 18211700 | 18212750 | BEND2 | CDKL5 |
| ENST00000380030.3 | 3143 | 18189095 | 18239024 | − | seg_128 | 18211700 | 18212750 | BEND2 | CDKL5 |
| ENST00000380033.4 | 3144 | 18181051 | 18239003 | − | seg_129 | 18234150 | 18238350 | BEND2 | CDKL5 |
| ENST00000380030.3 | 3145 | 18189095 | 18239024 | − | seg_129 | 18234150 | 18238350 | BEND2 | CDKL5 |
| ENST00000379996.3 | 3146 | 18443703 | 18671749 | + | seg_135 | 18443550 | 18447600 | CDKL5 | CDKL5 |
| ENST00000379996.3 | 3147 | 18443703 | 18671749 | + | seg_136 | 18451450 | 18452650 | CDKL5 | CDKL5 |
| ENST00000463994.1 | 3148 | 18622067 | 18638077 | + | seg_137 | 18624850 | 18626400 | RS1 | RS1 |
| ENST00000379996.3 | 3149 | 18443703 | 18671749 | + | seg_137 | 18624850 | 18626400 | RS1 | RS1 |
| ENST00000379989.3 | 3150 | 18460308 | 18671745 | + | seg_137 | 18624850 | 18626400 | RS1 | RS1 |
| ENST00000379996.3 | 3151 | 18443703 | 18671749 | + | seg_138 | 18651650 | 18653200 | RS1 | RS1 |
| ENST00000379989.3 | 3152 | 18460308 | 18671745 | + | seg_138 | 18651650 | 18653200 | RS1 | RS1 |
| ENST00000476595.1 | 3153 | 18660044 | 18668657 | − | seg_139 | 18659400 | 18661000 | RS1 | RS1 |
| ENST00000379984.3 | 3154 | 18658030 | 18690229 | − | seg_139 | 18659400 | 18661000 | RS1 | RS1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000379996.3 | 3155 | 18443703 | 18671749 | + | seg_139 | 18659400 | 18661000 | RS1 | RS1 |
| ENST00000379989.3 | 3156 | 18460308 | 18671745 | + | seg_139 | 18659400 | 18661000 | RS1 | RS1 |
| ENST00000476595.1 | 3157 | 18660044 | 18668657 | − | seg_140 | 18663000 | 18664250 | RS1 | RS1 |
| ENST00000379984.3 | 3158 | 18658030 | 18690229 | − | seg_140 | 18663000 | 18664250 | RS1 | RS1 |
| ENST00000379996.3 | 3159 | 18443703 | 18671749 | + | seg_140 | 18663000 | 18664250 | RS1 | RS1 |
| ENST00000379989.3 | 3160 | 18460308 | 18671745 | + | seg_140 | 18663000 | 18664250 | RS1 | RS1 |
| ENST00000379984.3 | 3161 | 18658030 | 18690229 | − | seg_141 | 18689000 | 18690200 | RS1 | RS1 |
| ENST00000486029.1 | 3162 | 18694029 | 18716028 | + | seg_142 | 18694650 | 18696250 | RS1 | RS1 |
| ENST00000486029.1 | 3163 | 18694029 | 18716028 | + | seg_143 | 18704800 | 18705850 | RS1 | RS1 |
| ENST00000379962.2 | 3164 | 18748282 | 18845778 | + | seg_144 | 18814500 | 18815800 | PPEF1 | RS1 |
| ENST00000359763.6 | 3165 | 18709046 | 18846039 | + | seg_144 | 18814500 | 18815800 | PPEF1 | RS1 |
| ENST00000349874.5 | 3166 | 18709046 | 18846039 | + | seg_144 | 18814500 | 18815800 | PPEF1 | RS1 |
| ENST00000543630.1 | 3167 | 18709046 | 18846039 | + | seg_144 | 18814500 | 18815800 | PPEF1 | RS1 |
| ENST00000544635.1 | 3168 | 18725773 | 18845806 | + | seg_144 | 18814500 | 18815800 | PPEF1 | RS1 |
| ENST00000361511.3 | 3169 | 18709032 | 18846035 | + | seg_144 | 18814500 | 18815800 | PPEF1 | RS1 |
| ENST00000340581.3 | 3170 | 19008128 | 19100861 | − | seg_149 | 19012650 | 19013750 | PHKA2 | PHKA2 |
| ENST00000397917.4 | 3171 | 19008829 | 19049228 | − | seg_149 | 19012650 | 19013750 | PHKA2 | PHKA2 |
| ENST00000357991.3 | 3172 | 19007432 | 19140579 | − | seg_149 | 19012650 | 19013750 | PHKA2 | PHKA2 |
| ENST00000379869.3 | 3173 | 19007432 | 19140677 | − | seg_149 | 19012650 | 19013750 | PHKA2 | PHKA2 |
| ENST00000379876.1 | 3174 | 19007427 | 19140755 | − | seg_149 | 19012650 | 19013750 | PHKA2 | PHKA2 |
| ENST00000354791.3 | 3175 | 19007427 | 19140755 | − | seg_149 | 19012650 | 19013750 | PHKA2 | PHKA2 |
| ENST00000356606.4 | 3176 | 19007433 | 19140582 | − | seg_149 | 19012650 | 19013750 | PHKA2 | PHKA2 |
| ENST00000379873.2 | 3177 | 19007427 | 19140755 | − | seg_149 | 19012650 | 19013750 | PHKA2 | PHKA2 |
| ENST00000360279.4 | 3178 | 19007432 | 19140677 | − | seg_149 | 19012650 | 19013750 | PHKA2 | PHKA2 |
| ENST00000357544.3 | 3179 | 19007432 | 19140677 | − | seg_149 | 19012650 | 19013750 | PHKA2 | PHKA2 |
| ENST00000379878.3 | 3180 | 19007427 | 19140755 | − | seg_149 | 19012650 | 19013750 | PHKA2 | PHKA2 |
| ENST00000340581.3 | 3181 | 19008128 | 19100861 | − | seg_150 | 19038700 | 19039900 | PHKA2 | PHKA2 |
| ENST00000397917.4 | 3182 | 19008829 | 19049228 | − | seg_150 | 19038700 | 19039900 | PHKA2 | PHKA2 |
| ENST00000479496.1 | 3183 | 19037686 | 19054506 | − | seg_150 | 19038700 | 19039900 | PHKA2 | PHKA2 |
| ENST00000357991.3 | 3184 | 19007432 | 19140579 | − | seg_150 | 19038700 | 19039900 | PHKA2 | PHKA2 |
| ENST00000379869.3 | 3185 | 19007432 | 19140677 | − | seg_150 | 19038700 | 19039900 | PHKA2 | PHKA2 |
| ENST00000379876.1 | 3186 | 19007427 | 19140755 | − | seg_150 | 19038700 | 19039900 | PHKA2 | PHKA2 |
| ENST00000354791.3 | 3187 | 19007427 | 19140755 | − | seg_150 | 19038700 | 19039900 | PHKA2 | PHKA2 |
| ENST00000356606.4 | 3188 | 19007433 | 19140582 | − | seg_150 | 19038700 | 19039900 | PHKA2 | PHKA2 |
| ENST00000379873.2 | 3189 | 19007427 | 19140755 | − | seg_150 | 19038700 | 19039900 | PHKA2 | PHKA2 |
| ENST00000360279.4 | 3190 | 19007432 | 19140677 | − | seg_150 | 19038700 | 19039900 | PHKA2 | PHKA2 |
| ENST00000357544.3 | 3191 | 19007432 | 19140677 | − | seg_150 | 19038700 | 19039900 | PHKA2 | PHKA2 |
| ENST00000379878.3 | 3192 | 19007427 | 19140755 | − | seg_150 | 19038700 | 19039900 | PHKA2 | PHKA2 |
| ENST00000340581.3 | 3193 | 19008128 | 19100861 | − | seg_151 | 19065750 | 19066850 | GPR64 | PHKA2 |
| ENST00000357991.3 | 3194 | 19007432 | 19140579 | − | seg_151 | 19065750 | 19066850 | GPR64 | PHKA2 |
| ENST00000379869.3 | 3195 | 19007432 | 19140677 | − | seg_151 | 19065750 | 19066850 | GPR64 | PHKA2 |
| ENST00000379876.1 | 3196 | 19007427 | 19140755 | − | seg_151 | 19065750 | 19066850 | GPR64 | PHKA2 |
| ENST00000354791.3 | 3197 | 19007427 | 19140755 | − | seg_151 | 19065750 | 19066850 | GPR64 | PHKA2 |
| ENST00000356606.4 | 3198 | 19007433 | 19140582 | − | seg_151 | 19065750 | 19066850 | GPR64 | PHKA2 |
| ENST00000379873.2 | 3199 | 19007427 | 19140755 | − | seg_151 | 19065750 | 19066850 | GPR64 | PHKA2 |
| ENST00000360279.4 | 3200 | 19007432 | 19140677 | − | seg_151 | 19065750 | 19066850 | GPR64 | PHKA2 |
| ENST00000357544.3 | 3201 | 19007432 | 19140677 | − | seg_151 | 19065750 | 19066850 | GPR64 | PHKA2 |
| ENST00000379878.3 | 3202 | 19007427 | 19140755 | − | seg_151 | 19065750 | 19066850 | GPR64 | PHKA2 |
| ENST00000365274.1 | 3203 | 19394892 | 19394993 | + | seg_155 | 19393250 | 19401800 | PDHA1 | PHKA2 |
| ENST00000338883.4 | 3204 | 19378174 | 19533379 | − | seg_155 | 19393250 | 19401800 | PDHA1 | PHKA2 |
| ENST00000359173.3 | 3205 | 19378176 | 19478245 | − | seg_155 | 19393250 | 19401800 | PDHA1 | PHKA2 |
| ENST00000469203.2 | 3206 | 19378797 | 19504642 | − | seg_155 | 19393250 | 19401800 | PDHA1 | PHKA2 |
| ENST00000518578.1 | 3207 | 19378174 | 19500394 | − | seg_155 | 19393250 | 19401800 | PDHA1 | PHKA2 |
| ENST00000338883.4 | 3208 | 19378174 | 19533379 | − | seg_156 | 19415800 | 19417450 | MAP3K15 | PHKA2 |
| ENST00000359173.3 | 3209 | 19378176 | 19478245 | − | seg_156 | 19415800 | 19417450 | MAP3K15 | PHKA2 |
| ENST00000469203.2 | 3210 | 19378797 | 19504642 | − | seg_156 | 19415800 | 19417450 | MAP3K15 | PHKA2 |
| ENST00000518578.1 | 3211 | 19378174 | 19500394 | − | seg_156 | 19415800 | 19417450 | MAP3K15 | PHKA2 |
| ENST00000338883.4 | 3212 | 19378174 | 19533379 | − | seg_157 | 19474150 | 19475400 | MAP3K15 | PHKA2 |
| ENST00000359173.3 | 3213 | 19378176 | 19478245 | − | seg_157 | 19474150 | 19475400 | MAP3K15 | PHKA2 |
| ENST00000469203.2 | 3214 | 19378797 | 19504642 | − | seg_157 | 19474150 | 19475400 | MAP3K15 | PHKA2 |
| ENST00000518578.1 | 3215 | 19378174 | 19500394 | − | seg_157 | 19474150 | 19475400 | MAP3K15 | PHKA2 |
| ENST00000397804.1 | 3216 | 19553520 | 19725207 | − | seg_158 | 19554750 | 19556200 | MAP3K15 | PHKA2 |
| ENST00000379698.4 | 3217 | 19553811 | 19817869 | − | seg_158 | 19554750 | 19556200 | MAP3K15 | PHKA2 |
| ENST00000397821.3 | 3218 | 19552093 | 19905719 | − | seg_158 | 19554750 | 19556200 | MAP3K15 | PHKA2 |
| ENST00000379702.2 | 3219 | 19552083 | 19905719 | − | seg_158 | 19554750 | 19556200 | MAP3K15 | PHKA2 |
| ENST00000379726.3 | 3220 | 19554532 | 19764529 | − | seg_158 | 19554750 | 19556200 | MAP3K15 | PHKA2 |
| ENST00000541422.1 | 3221 | 19554308 | 19688480 | − | seg_158 | 19554750 | 19556200 | MAP3K15 | PHKA2 |
| ENST00000379716.1 | 3222 | 19552125 | 19689116 | − | seg_158 | 19554750 | 19556200 | MAP3K15 | PHKA2 |
| ENST00000397804.1 | 3223 | 19553520 | 19725207 | − | seg_159 | 19560350 | 19561400 | MAP3K15 | PHKA2 |
| ENST00000379698.4 | 3224 | 19553811 | 19817869 | − | seg_159 | 19560350 | 19561400 | MAP3K15 | PHKA2 |
| ENST00000397821.3 | 3225 | 19552093 | 19905719 | − | seg_159 | 19560350 | 19561400 | MAP3K15 | PHKA2 |
| ENST00000379702.2 | 3226 | 19552083 | 19905719 | − | seg_159 | 19560350 | 19561400 | MAP3K15 | PHKA2 |
| ENST00000379726.3 | 3227 | 19554532 | 19765429 | − | seg_159 | 19560350 | 19561400 | MAP3K15 | PHKA2 |
| ENST00000541422.1 | 3228 | 19554308 | 19688480 | − | seg_159 | 19560350 | 19561400 | MAP3K15 | PHKA2 |
| ENST00000379716.1 | 3229 | 19552125 | 19689116 | − | seg_159 | 19560350 | 19561400 | MAP3K15 | PHKA2 |
| ENST00000397804.1 | 3230 | 19553520 | 19725207 | − | seg_160 | 19570450 | 19571550 | MAP3K15 | PHKA2 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000379698.4 | 3231 | 19553811 | 19817869 | − | seg_160 | 19570450 | 19571550 | MAP3K15 | PHKA2 |
| ENST00000397821.3 | 3232 | 19552093 | 19905719 | − | seg_160 | 19570450 | 19571550 | MAP3K15 | PHKA2 |
| ENST00000379702.2 | 3233 | 19552083 | 19905719 | − | seg_160 | 19570450 | 19571550 | MAP3K15 | PHKA2 |
| ENST00000379726.3 | 3234 | 19554532 | 19764529 | − | seg_160 | 19570450 | 19571550 | MAP3K15 | PHKA2 |
| ENST00000541422.1 | 3235 | 19554308 | 19688480 | − | seg_160 | 19570450 | 19571550 | MAP3K15 | PHKA2 |
| ENST00000379716.1 | 3236 | 19552125 | 19689116 | − | seg_160 | 19570450 | 19571550 | MAP3K15 | PHKA2 |
| ENST00000397804.1 | 3237 | 19553520 | 19725207 | − | seg_161 | 19620350 | 19621400 | SH3KBP1 | PHKA2 |
| ENST00000379698.4 | 3238 | 19553811 | 19817869 | − | seg_161 | 19620350 | 19621400 | SH3KBP1 | PHKA2 |
| ENST00000397821.3 | 3239 | 19552093 | 19905719 | − | seg_161 | 19620350 | 19621400 | SH3KBP1 | PHKA2 |
| ENST00000477102.1 | 3240 | 19610186 | 19682833 | − | seg_161 | 19620350 | 19621400 | SH3KBP1 | PHKA2 |
| ENST00000379697.3 | 3241 | 19606396 | 19905577 | − | seg_161 | 19620350 | 19621400 | SH3KBP1 | PHKA2 |
| ENST00000494961.1 | 3242 | 19606802 | 19713819 | − | seg_161 | 19620350 | 19621400 | SH3KBP1 | PHKA2 |
| ENST00000379702.2 | 3243 | 19552083 | 19905719 | − | seg_161 | 19620350 | 19621400 | SH3KBP1 | PHKA2 |
| ENST00000379726.3 | 3244 | 19554532 | 19764529 | − | seg_161 | 19620350 | 19621400 | SH3KBP1 | PHKA2 |
| ENST00000541422.1 | 3245 | 19554308 | 19688480 | − | seg_161 | 19620350 | 19621400 | SH3KBP1 | PHKA2 |
| ENST00000379716.1 | 3246 | 19552125 | 19689116 | − | seg_161 | 19620350 | 19621400 | SH3KBP1 | PHKA2 |
| ENST00000397804.1 | 3247 | 19553520 | 19725207 | − | seg_162 | 19638050 | 19639150 | SH3KBP1 | PHKA2 |
| ENST00000379698.4 | 3248 | 19553811 | 19817869 | − | seg_162 | 19638050 | 19639150 | SH3KBP1 | PHKA2 |
| ENST00000397821.3 | 3249 | 19552093 | 19905719 | − | seg_162 | 19638050 | 19639150 | SH3KBP1 | PHKA2 |
| ENST00000477102.1 | 3250 | 19610186 | 19682833 | − | seg_162 | 19638050 | 19639150 | SH3KBP1 | PHKA2 |
| ENST00000379697.3 | 3251 | 19606396 | 19905577 | − | seg_162 | 19638050 | 19639150 | SH3KBP1 | PHKA2 |
| ENST00000494961.1 | 3252 | 19606802 | 19713819 | − | seg_162 | 19638050 | 19639150 | SH3KBP1 | PHKA2 |
| ENST00000379702.2 | 3253 | 19552083 | 19905719 | − | seg_162 | 19638050 | 19639150 | SH3KBP1 | PHKA2 |
| ENST00000379726.3 | 3254 | 19554532 | 19764529 | − | seg_162 | 19638050 | 19639150 | SH3KBP1 | PHKA2 |
| ENST00000541422.1 | 3255 | 19554308 | 19688480 | − | seg_162 | 19638050 | 19639150 | SH3KBP1 | PHKA2 |
| ENST00000379716.1 | 3256 | 19552125 | 19689116 | − | seg_162 | 19638050 | 19639150 | SH3KBP1 | PHKA2 |
| ENST00000379698.4 | 3257 | 19553811 | 19817869 | − | seg_163 | 19813200 | 19814750 | SH3KBP1 | PHKA2 |
| ENST00000397821.3 | 3258 | 19552093 | 19905719 | − | seg_163 | 19813200 | 19814750 | SH3KBP1 | PHKA2 |
| ENST00000379697.3 | 3259 | 19606396 | 19905577 | − | seg_163 | 19813200 | 19814750 | SH3KBP1 | PHKA2 |
| ENST00000379702.2 | 3260 | 19552083 | 19905719 | − | seg_163 | 19813200 | 19814750 | SH3KBP1 | PHKA2 |
| ENST00000379698.4 | 3261 | 19553811 | 19817869 | − | seg_164 | 19817600 | 19819100 | SH3KBP1 | PHKA2 |
| ENST00000397821.3 | 3262 | 19552093 | 19905719 | − | seg_164 | 19817600 | 19819100 | SH3KBP1 | PHKA2 |
| ENST00000379697.3 | 3263 | 19606396 | 19905577 | − | seg_164 | 19817600 | 19819100 | SH3KBP1 | PHKA2 |
| ENST00000379702.2 | 3264 | 19552083 | 19905719 | − | seg_164 | 19817600 | 19819100 | SH3KBP1 | PHKA2 |
| ENST00000397821.3 | 3265 | 19552093 | 19905719 | − | seg_165 | 19879900 | 19881050 | SH3KBP1 | PHKA2 |
| ENST00000379697.3 | 3266 | 19606396 | 19905577 | − | seg_165 | 19879900 | 19881050 | SH3KBP1 | PHKA2 |
| ENST00000379702.2 | 3267 | 19552083 | 19905719 | − | seg_165 | 19879900 | 19881050 | SH3KBP1 | PHKA2 |
| ENST00000397821.3 | 3268 | 19552093 | 19905719 | − | seg_166 | 19883900 | 19887350 | SH3KBP1 | PHKA2 |
| ENST00000379697.3 | 3269 | 19606396 | 19905577 | − | seg_166 | 19883900 | 19887350 | SH3KBP1 | PHKA2 |
| ENST00000379702.2 | 3270 | 19552083 | 19905719 | − | seg_166 | 19883900 | 19887350 | SH3KBP1 | PHKA2 |
| ENST00000397821.3 | 3271 | 19552093 | 19905719 | − | seg_167 | 19890300 | 19891400 | SH3KBP1 | PHKA2 |
| ENST00000379697.3 | 3272 | 19606396 | 19905577 | − | seg_167 | 19890300 | 19891400 | SH3KBP1 | PHKA2 |
| ENST00000379702.2 | 3273 | 19552083 | 19905719 | − | seg_167 | 19890300 | 19891400 | SH3KBP1 | PHKA2 |
| ENST00000397821.3 | 3274 | 19552093 | 19905719 | − | seg_168 | 19894150 | 19895700 | SH3KBP1 | PHKA2 |
| ENST00000379697.3 | 3275 | 19606396 | 19905577 | − | seg_168 | 19894150 | 19895700 | SH3KBP1 | PHKA2 |
| ENST00000379702.2 | 3276 | 19552083 | 19905719 | − | seg_168 | 19894150 | 19895700 | SH3KBP1 | PHKA2 |
| ENST00000397821.3 | 3277 | 19552093 | 19905719 | − | seg_169 | 19902750 | 19905650 | SH3KBP1 | PHKA2 |
| ENST00000379697.3 | 3278 | 19606396 | 19905577 | − | seg_169 | 19902750 | 19905650 | SH3KBP1 | PHKA2 |
| ENST00000379702.2 | 3279 | 19552083 | 19905719 | − | seg_169 | 19902750 | 19905650 | SH3KBP1 | PHKA2 |
| ENST00000466145.1 | 3280 | 20039466 | 20044061 | − | seg_172 | 20041050 | 20042600 | MAP7D2 | PHKA2 |
| ENST00000379643.4 | 3281 | 20024833 | 20135114 | − | seg_172 | 20041050 | 20042600 | MAP7D2 | PHKA2 |
| ENST00000544957.1 | 3282 | 20026440 | 20135022 | − | seg_172 | 20041050 | 20042600 | MAP7D2 | PHKA2 |
| ENST00000543767.1 | 3283 | 20024989 | 20074895 | − | seg_172 | 20041050 | 20042600 | MAP7D2 | PHKA2 |
| ENST00000443379.2 | 3284 | 20024833 | 20135114 | − | seg_172 | 20041050 | 20042600 | MAP7D2 | PHKA2 |
| ENST00000379651.3 | 3285 | 20024831 | 20135016 | − | seg_172 | 20041050 | 20042600 | MAP7D2 | PHKA2 |
| ENST00000452324.2 | 3286 | 20024833 | 20134756 | − | seg_172 | 20041050 | 20042600 | MAP7D2 | PHKA2 |
| ENST00000485173.1 | 3287 | 20025227 | 20082856 | − | seg_172 | 20041050 | 20042600 | MAP7D2 | PHKA2 |
| ENST00000330274.7 | 3288 | 20070519 | 20135114 | − | seg_173 | 20128750 | 20130450 | MAP7D2 | PHKA2 |
| ENST00000379643.4 | 3289 | 20024833 | 20135114 | − | seg_173 | 20128750 | 20130450 | MAP7D2 | PHKA2 |
| ENST00000544957.1 | 3290 | 20026440 | 20135022 | − | seg_173 | 20128750 | 20130450 | MAP7D2 | PHKA2 |
| ENST00000443379.2 | 3291 | 20024833 | 20135114 | − | seg_173 | 20128750 | 20130450 | MAP7D2 | PHKA2 |
| ENST00000379651.3 | 3292 | 20024831 | 20135016 | − | seg_173 | 20128750 | 20130450 | MAP7D2 | PHKA2 |
| ENST00000452324.2 | 3293 | 20024833 | 20134756 | − | seg_173 | 20128750 | 20130450 | MAP7D2 | PHKA2 |
| ENST00000379374.4 | 3294 | 22050559 | 22269427 | + | seg_183 | 22051000 | 22052100 | PHEX | PHEX |
| ENST00000537599.1 | 3295 | 22051016 | 22266300 | + | seg_183 | 22051000 | 22052100 | PHEX | PHEX |
| ENST00000379374.4 | 3296 | 22050559 | 22269427 | + | seg_184 | 22073800 | 22074800 | PHEX | PHEX |
| ENST00000537599.1 | 3297 | 22051016 | 22266300 | + | seg_184 | 22073800 | 22074800 | PHEX | PHEX |
| ENST00000535894.1 | 3298 | 22056171 | 22266413 | + | seg_184 | 22073800 | 22074800 | PHEX | PHEX |
| ENST00000379295.1 | 3299 | 23721801 | 23784592 | − | seg_186 | 23774100 | 23775150 | ACOT9 | SAT = SAT1 |
| ENST00000486479.1 | 3300 | 24329024 | 24331432 | − | seg_190 | 24328750 | 24333600 | ZFX | SAT = SAT1 |
| ENST00000536351.1 | 3301 | 24328979 | 24331432 | − | seg_190 | 24328750 | 24333600 | ZFX | SAT = SAT1 |
| ENST00000413856.1 | 3302 | 24380878 | 24383541 | + | seg_191 | 24379500 | 24384800 | PDK3 | SAT = SAT1 |
| ENST00000436466.1 | 3303 | 24380878 | 24383495 | + | seg_191 | 24379500 | 24384800 | PDK3 | SAT = SAT1 |
| ENST00000441463.2 | 3304 | 24483573 | 24557954 | + | seg_192 | 24483500 | 24485500 | PDK3 | SAT = SAT1 |
| ENST00000379162.4 | 3305 | 24483338 | 24552542 | + | seg_192 | 24483500 | 24485500 | PDK3 | SAT = SAT1 |
| ENST00000441463.2 | 3306 | 24483573 | 24557954 | + | seg_193 | 24544700 | 24546050 | PDK3 | SAT = SAT1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000379162.4 | 3307 | 24483338 | 24552542 | + | seg_193 | 24544700 | 24546050 | PDK3 | SAT = SAT1 |
| ENST00000379044.4 | 3308 | 25021811 | 25034065 | − | seg_194 | 25026650 | 25045650 | ARX | SAT = SAT1 |
| ENST00000438281.1 | 3309 | 25047662 | 25048352 | + | seg_195 | 25046800 | 25048550 | ARX | SAT = SAT1 |
| ENST00000432886.2 | 3310 | 38008589 | 38080177 | − | seg_200 | 38037000 | 38038300 | SRPX | RPGR |
| ENST00000378533.3 | 3311 | 38008592 | 38080152 | − | seg_200 | 38037000 | 38038300 | SRPX | RPGR |
| ENST00000538295.1 | 3312 | 38008589 | 38080177 | − | seg_200 | 38037000 | 38038300 | SRPX | RPGR |
| ENST00000343800.6 | 3313 | 38008595 | 38080696 | − | seg_200 | 38037000 | 38038300 | SRPX | RPGR |
| ENST00000544439.1 | 3314 | 38008589 | 38080177 | − | seg_200 | 38037000 | 38038300 | SRPX | RPGR |
| ENST00000465127.1 | 3315 | 37208583 | 38546928 | + | seg_200 | 38037000 | 38038300 | SRPX | RPGR |
| ENST00000423919.1 | 3316 | 38080644 | 38082920 | + | seg_201 | 38078450 | 38080750 | SRPX | RPGR |
| ENST00000432886.2 | 3317 | 38008589 | 38080177 | − | seg_201 | 38078450 | 38080750 | SRPX | RPGR |
| ENST00000378533.3 | 3318 | 38008592 | 38080152 | − | seg_201 | 38078450 | 38080750 | SRPX | RPGR |
| ENST00000538295.1 | 3319 | 38008589 | 38080177 | − | seg_201 | 38078450 | 38080750 | SRPX | RPGR |
| ENST00000343800.6 | 3320 | 38008595 | 38080696 | − | seg_201 | 38078450 | 38080750 | SRPX | RPGR |
| ENST00000544439.1 | 3321 | 38008589 | 38080177 | − | seg_201 | 38078450 | 38080750 | SRPX | RPGR |
| ENST00000465127.1 | 3322 | 37208583 | 38546928 | + | seg_201 | 38078450 | 38080750 | SRPX | RPGR |
| ENST00000465127.1 | 3323 | 37208583 | 38546928 | + | seg_202 | 38195400 | 38197000 | RPGR | RPGR |
| ENST00000488812.1 | 3324 | 38211858 | 38262920 | + | seg_203 | 38211800 | 38213050 | OTC | OTC |
| ENST00000039007.4 | 3325 | 38211798 | 38280703 | + | seg_203 | 38211800 | 38213050 | OTC | OTC |
| ENST00000465127.1 | 3326 | 37208583 | 38546928 | + | seg_203 | 38211800 | 38213050 | OTC | OTC |
| ENST00000480976.1 | 3327 | 38420797 | 38533519 | + | seg_204 | 38475900 | 38477150 | TSPAN7 | OTC |
| ENST00000494037.1 | 3328 | 38471575 | 38530670 | + | seg_204 | 38475900 | 38477150 | TSPAN7 | OTC |
| ENST00000488893.1 | 3329 | 38429936 | 38535070 | + | seg_204 | 38475900 | 38477150 | TSPAN7 | OTC |
| ENST00000471410.1 | 3330 | 38420795 | 38547422 | + | seg_204 | 38475900 | 38477150 | TSPAN7 | OTC |
| ENST00000545599.1 | 3331 | 38420797 | 38547525 | + | seg_204 | 38475900 | 38477150 | TSPAN7 | OTC |
| ENST00000378482.2 | 3332 | 38420623 | 38548167 | + | seg_204 | 38475900 | 38477150 | TSPAN7 | OTC |
| ENST00000422612.2 | 3333 | 38420795 | 38547422 | + | seg_204 | 38475900 | 38477150 | TSPAN7 | OTC |
| ENST00000286824.6 | 3334 | 38420797 | 38547651 | + | seg_204 | 38475900 | 38477150 | TSPAN7 | OTC |
| ENST00000475216.1 | 3335 | 38420797 | 38547525 | + | seg_204 | 38475900 | 38477150 | TSPAN7 | OTC |
| ENST00000465127.1 | 3336 | 37208583 | 38546928 | + | seg_204 | 38475900 | 38477150 | TSPAN7 | OTC |
| ENST00000480976.1 | 3337 | 38420797 | 38533519 | + | seg_205 | 38511700 | 38513450 | TSPAN7 | OTC |
| ENST00000494037.1 | 3338 | 38471575 | 38530670 | + | seg_205 | 38511700 | 38513450 | TSPAN7 | OTC |
| ENST00000488893.1 | 3339 | 38429936 | 38535070 | + | seg_205 | 38511700 | 38513450 | TSPAN7 | OTC |
| ENST00000471410.1 | 3340 | 38420795 | 38547422 | + | seg_205 | 38511700 | 38513450 | TSPAN7 | OTC |
| ENST00000545599.1 | 3341 | 38420797 | 38547525 | + | seg_205 | 38511700 | 38513450 | TSPAN7 | OTC |
| ENST00000378482.2 | 3342 | 38420623 | 38548167 | + | seg_205 | 38511700 | 38513450 | TSPAN7 | OTC |
| ENST00000422612.2 | 3343 | 38420795 | 38547422 | + | seg_205 | 38511700 | 38513450 | TSPAN7 | OTC |
| ENST00000286824.6 | 3344 | 38420797 | 38547651 | + | seg_205 | 38511700 | 38513450 | TSPAN7 | OTC |
| ENST00000475216.1 | 3345 | 38420797 | 38547525 | + | seg_205 | 38511700 | 38513450 | TSPAN7 | OTC |
| ENST00000465127.1 | 3346 | 37208583 | 38546928 | + | seg_205 | 38511700 | 38513450 | TSPAN7 | OTC |
| ENST00000471410.1 | 3347 | 38420795 | 38547422 | + | seg_206 | 38537300 | 38539300 | TSPAN7 | OTC |
| ENST00000545599.1 | 3348 | 38420797 | 38547525 | + | seg_206 | 38537300 | 38539300 | TSPAN7 | OTC |
| ENST00000378482.2 | 3349 | 38420623 | 38548167 | + | seg_206 | 38537300 | 38539300 | TSPAN7 | OTC |
| ENST00000422612.2 | 3350 | 38420795 | 38547422 | + | seg_206 | 38537300 | 38539300 | TSPAN7 | OTC |
| ENST00000286824.6 | 3351 | 38420797 | 38547651 | + | seg_206 | 38537300 | 38539300 | TSPAN7 | OTC |
| ENST00000419600.2 | 3352 | 38525350 | 38548169 | + | seg_206 | 38537300 | 38539300 | TSPAN7 | OTC |
| ENST00000475216.1 | 3353 | 38420797 | 38547525 | + | seg_206 | 38537300 | 38539300 | TSPAN7 | OTC |
| ENST00000465127.1 | 3354 | 37208583 | 38546928 | + | seg_206 | 38537300 | 38539300 | TSPAN7 | OTC |
| ENST00000456333.1 | 3355 | 40594652 | 40597950 | + | seg_213 | 40597850 | 40599200 | MED14 | CSNB1 = NYX |
| ENST00000478993.1 | 3356 | 41192651 | 41223725 | + | seg_217 | 41209650 | 41210900 | DDX3X | CSNB1 = NYX |
| ENST00000378062.5 | 3357 | 43808022 | 43832750 | − | seg_219 | 43831100 | 43833350 | NDP | NDP |
| ENST00000470584.1 | 3358 | 43808928 | 43832632 | − | seg_219 | 43831100 | 43833350 | NDP | NDP |
| ENST00000397254.2 | 3359 | 43888578 | 43890167 | + | seg_220 | 43888350 | 43890300 | NDP | NDP |
| ENST00000378056.5 | 3360 | 44094631 | 44202923 | − | seg_221 | 44172850 | 44174600 | EFHC2 | NDP |
| ENST00000441230.1 | 3361 | 44007958 | 44202911 | − | seg_221 | 44172850 | 44174600 | EFHC2 | NDP |
| ENST00000333807.6 | 3362 | 44007129 | 44202923 | − | seg_221 | 44172850 | 44174600 | EFHC2 | NDP |
| ENST00000420999.1 | 3363 | 44007911 | 44202918 | − | seg_221 | 44172850 | 44174600 | EFHC2 | NDP |
| ENST00000414772.1 | 3364 | 45707328 | 45710447 | − | seg_224 | 45708500 | 45709500 | KRBOX4 | UBA1 |
| ENST00000456532.1 | 3365 | 45707509 | 45710920 | − | seg_224 | 45708500 | 45709500 | KRBOX4 | UBA1 |
| ENST00000491894.1 | 3366 | 46465730 | 46480451 | − | seg_226 | 46465650 | 46466700 | CHST7 | UBA1 |
| ENST00000464933.1 | 3367 | 46465696 | 46495069 | − | seg_226 | 46465650 | 46466700 | CHST7 | UBA1 |
| ENST00000489574.1 | 3368 | 46465730 | 46529121 | − | seg_226 | 46465650 | 46466700 | CHST7 | UBA1 |
| ENST00000328306.4 | 3369 | 46464753 | 46618490 | − | seg_226 | 46465650 | 46466700 | CHST7 | UBA1 |
| ENST00000377073.3 | 3370 | 47229982 | 47273704 | + | seg_230 | 47232600 | 47233700 | ZNF157 | UBA1 |
| ENST00000403001.3 | 3371 | 48046211 | 48051817 | − | seg_236 | 48045350 | 48046450 | SSX5 | WAS |
| ENST00000311798.1 | 3372 | 48045656 | 48056199 | − | seg_236 | 48045350 | 48046450 | SSX5 | WAS |
| ENST00000347757.1 | 3373 | 48045656 | 48056199 | − | seg_236 | 48045350 | 48046450 | SSX5 | WAS |
| ENST00000376923.1 | 3374 | 48045656 | 48054794 | − | seg_236 | 48045350 | 48046450 | SSX5 | WAS |
| ENST00000403001.3 | 3375 | 48046211 | 48051817 | − | seg_237 | 48051300 | 48052550 | SSX5 | WAS |
| ENST00000311798.1 | 3376 | 48045656 | 48056199 | − | seg_237 | 48051300 | 48052550 | SSX5 | WAS |
| ENST00000347757.1 | 3377 | 48045656 | 48056199 | − | seg_237 | 48051300 | 48052550 | SSX5 | WAS |
| ENST00000376923.1 | 3378 | 48045656 | 48054794 | − | seg_237 | 48051300 | 48052550 | SSX5 | WAS |
| ENST00000407081.2 | 3379 | 48156255 | 48165614 | − | seg_240 | 48155300 | 48156750 | SSX9 | WAS |
| ENST00000376909.1 | 3380 | 48154885 | 48165675 | − | seg_240 | 48155300 | 48156750 | SSX9 | WAS |
| ENST00000438101.1 | 3381 | 49429447 | 49433283 | − | seg_247 | 49429000 | 49430200 | PAGE1 | CLCN5 |
| ENST00000474146.1 | 3382 | 49595287 | 49598570 | + | seg_250 | 49594450 | 49595600 | PAGE4 | CLCN5 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000376141.1 | 3383 | 49593863 | 49598576 | + | seg_250 | 49594450 | 49595600 | PAGE4 | CLCN5 |
| ENST00000218068.6 | 3384 | 49593906 | 49598576 | + | seg_250 | 49594450 | 49595600 | PAGE4 | CLCN5 |
| ENST00000478785.1 | 3385 | 49593951 | 49595934 | + | seg_250 | 49594450 | 49595600 | PAGE4 | CLCN5 |
| ENST00000491883.1 | 3386 | 51425000 | 51425485 | − | seg_252 | 51423850 | 51425400 | GSPT2 | CLCN5 |
| ENST00000477634.1 | 3387 | 51928008 | 51935364 | + | seg_256 | 51935050 | 51936300 | MAGED4 | MRX1 = IQSEC2 |
| ENST00000497416.1 | 3388 | 51933114 | 51935352 | + | seg_256 | 51935050 | 51936300 | MAGED4 | MRX1 = IQSEC2 |
| ENST00000416960.1 | 3389 | 51927919 | 51935364 | + | seg_256 | 51935050 | 51936300 | MAGED4 | MRX1 = IQSEC2 |
| ENST00000497348.1 | 3390 | 51934138 | 51935280 | + | seg_256 | 51935050 | 51936300 | MAGED4 | MRX1 = IQSEC2 |
| ENST00000488430.1 | 3391 | 51927983 | 51935364 | + | seg_256 | 51935050 | 51936300 | MAGED4 | MRX1 = IQSEC2 |
| ENST00000459685.1 | 3392 | 51927972 | 51935364 | + | seg_256 | 51935050 | 51936300 | MAGED4 | MRX1 = IQSEC2 |
| ENST00000471932.1 | 3393 | 51927943 | 51935364 | + | seg_256 | 51935050 | 51936300 | MAGED4 | MRX1 = IQSEC2 |
| ENST00000479281.1 | 3394 | 51930729 | 51935364 | + | seg_256 | 51935050 | 51936300 | MAGED4 | MRX1 = IQSEC2 |
| ENST00000375626.3 | 3395 | 51928008 | 51935364 | + | seg_256 | 51935050 | 51936300 | MAGED4 | MRX1 = IQSEC2 |
| ENST00000498483.1 | 3396 | 51928008 | 51935364 | + | seg_256 | 51935050 | 51936300 | MAGED4 | MRX1 = IQSEC2 |
| ENST00000375563.4 | 3397 | 52541053 | 52545988 | − | seg_258 | 52543850 | 52545000 | XAGE1E | MRX1 = IQSEC2 |
| ENST00000375567.3 | 3398 | 52541053 | 52546033 | − | seg_258 | 52543850 | 52545000 | XAGE1E | MRX1 = IQSEC2 |
| ENST00000375570.1 | 3399 | 52541053 | 52546189 | − | seg_258 | 52543850 | 52545000 | XAGE1E | MRX1 = IQSEC2 |
| ENST00000463689.1 | 3400 | 52541053 | 52544001 | − | seg_258 | 52543850 | 52545000 | XAGE1E | MRX1 = IQSEC2 |
| ENST00000429372.2 | 3401 | 52541053 | 52546197 | − | seg_258 | 52543850 | 52545000 | XAGE1E | MRX1 = IQSEC2 |
| ENST00000298181.5 | 3402 | 52673140 | 52683950 | − | seg_261 | 52673200 | 52675150 | SSX7 | MRX1 = IQSEC2 |
| ENST00000375496.2 | 3403 | 52854316 | 52858317 | − | seg_264 | 52854250 | 52855350 | XAGE5 | MRX1 = IQSEC2 |
| ENST00000502642.1 | 3404 | 52853318 | 52858317 | − | seg_264 | 52854250 | 52855350 | XAGE5 | MRX1 = IQSEC2 |
| ENST00000305824.4 | 3405 | 52853316 | 52858317 | − | seg_264 | 52854250 | 52855350 | XAGE5 | MRX1 = IQSEC2 |
| ENST00000346279.3 | 3406 | 52891557 | 52897099 | − | seg_265 | 52896900 | 52898050 | XAGE3 | MRX1 = IQSEC2 |
| ENST00000515858.1 | 3407 | 52994637 | 53024651 | − | seg_266 | 52996700 | 52998100 | FAM156A | MRX1 = IQSEC2 |
| ENST00000451084.2 | 3408 | 52977462 | 53024634 | − | seg_266 | 52996700 | 52998100 | FAM156A | MRX1 = IQSEC2 |
| ENST00000416923.1 | 3409 | 52977768 | 53024632 | − | seg_266 | 52996700 | 52998100 | FAM156A | MRX1 = IQSEC2 |
| ENST00000511863.1 | 3410 | 52984353 | 53024651 | − | seg_266 | 52996700 | 52998100 | FAM156A | MRX1 = IQSEC2 |
| ENST00000414076.2 | 3411 | 52976960 | 53024551 | − | seg_266 | 52996700 | 52998100 | FAM156A | MRX1 = IQSEC2 |
| ENST00000505988.1 | 3412 | 52977787 | 53024551 | − | seg_266 | 52996700 | 52998100 | FAM156A | MRX1 = IQSEC2 |
| ENST00000512364.1 | 3413 | 52976462 | 53024644 | − | seg_266 | 52996700 | 52998100 | FAM156A | MRX1 = IQSEC2 |
| ENST00000505062.1 | 3414 | 52994760 | 53024651 | − | seg_266 | 52996700 | 52998100 | FAM156A | MRX1 = IQSEC2 |
| ENST00000475552.1 | 3415 | 52977803 | 53024634 | − | seg_266 | 52996700 | 52998100 | FAM156A | MRX1 = IQSEC2 |
| ENST00000432596.1 | 3416 | 53352187 | 53352973 | + | seg_268 | 53347500 | 53352900 | IQSEC2 | MRX1 = IQSEC2 |
| ENST00000396435.3 | 3417 | 53262058 | 53350522 | − | seg_268 | 53347500 | 53352900 | IQSEC2 | MRX1 = IQSEC2 |
| ENST00000375368.5 | 3418 | 53262059 | 53350522 | − | seg_268 | 53347500 | 53352900 | IQSEC2 | MRX1 = IQSEC2 |
| ENST00000375159.2 | 3419 | 54224757 | 54360106 | − | seg_275 | 54317850 | 54320600 | WNK3 | FGD1 |
| ENST00000354646.2 | 3420 | 54219258 | 54384438 | − | seg_275 | 54317850 | 54320600 | WNK3 | FGD1 |
| ENST00000375169.3 | 3421 | 54219256 | 54384438 | − | seg_275 | 54317850 | 54320600 | WNK3 | FGD1 |
| ENST00000375135.3 | 3422 | 54471887 | 54522599 | − | seg_278 | 54495250 | 54496750 | FGD1 | FGD1 |
| ENST00000537277.1 | 3423 | 54475243 | 54522322 | − | seg_278 | 54495250 | 54496750 | FGD1 | FGD1 |
| ENST00000498636.1 | 3424 | 55035546 | 55046866 | − | seg_279 | 55040550 | 55042350 | ALAS2 | ALAS2 |
| ENST00000335854.4 | 3425 | 55035522 | 55057410 | − | seg_279 | 55040550 | 55042350 | ALAS2 | ALAS2 |
| ENST00000396198.3 | 3426 | 55035488 | 55057410 | − | seg_279 | 55040550 | 55042350 | ALAS2 | ALAS2 |
| ENST00000330807.5 | 3427 | 55035488 | 55057497 | − | seg_279 | 55040550 | 55042350 | ALAS2 | ALAS2 |
| ENST00000473660.1 | 3428 | 55210389 | 55210459 | − | seg_282 | 55209800 | 55211250 | MTRNR2L10 | ALAS2 |
| ENST00000440433.1 | 3429 | 64770778 | 64772301 | − | seg_285 | 64771000 | 64772400 | LAS1L | AR |
| ENST00000491714.1 | 3430 | 67652773 | 67653755 | − | seg_286 | 67652200 | 67654900 | OPHN1 | AR |
| ENST00000540071.1 | 3431 | 67266504 | 67653369 | − | seg_286 | 67652200 | 67654900 | OPHN1 | AR |
| ENST00000355520.5 | 3432 | 67262186 | 67653647 | − | seg_286 | 67652200 | 67654900 | OPHN1 | AR |
| ENST00000338901.3 | 3433 | 68835911 | 68890104 | + | seg_291 | 68836050 | 68838050 | EDA | ED1 = EDA |
| ENST00000374548.1 | 3434 | 68835911 | 69177354 | + | seg_291 | 68836050 | 68838050 | EDA | ED1 = EDA |
| ENST00000525810.1 | 3435 | 68835911 | 69080892 | + | seg_291 | 68836050 | 68838050 | EDA | ED1 = EDA |
| ENST00000513754.2 | 3436 | 68835911 | 69177327 | + | seg_291 | 68836050 | 68838050 | EDA | ED1 = EDA |
| ENST00000533317.1 | 3437 | 68835911 | 69177327 | + | seg_291 | 68836050 | 68838050 | EDA | ED1 = EDA |
| ENST00000527388.1 | 3438 | 68835911 | 69080892 | + | seg_291 | 68836050 | 68838050 | EDA | ED1 = EDA |
| ENST00000502251.1 | 3439 | 68835911 | 69177354 | + | seg_291 | 68836050 | 68838050 | EDA | ED1 = EDA |
| ENST00000374552.4 | 3440 | 68835911 | 69259319 | + | seg_291 | 68836050 | 68838050 | EDA | ED1 = EDA |
| ENST00000374553.2 | 3441 | 68835911 | 69259319 | + | seg_291 | 68836050 | 68838050 | EDA | ED1 = EDA |
| ENST00000524573.1 | 3442 | 68835961 | 69255487 | + | seg_291 | 68836050 | 68838050 | EDA | ED1 = EDA |
| ENST00000374548.1 | 3443 | 68835911 | 69177354 | + | seg_292 | 68918100 | 68920050 | EDA | ED1 = EDA |
| ENST00000525810.1 | 3444 | 68835911 | 69080892 | + | seg_292 | 68918100 | 68920050 | EDA | ED1 = EDA |
| ENST00000513754.2 | 3445 | 68835911 | 69177327 | + | seg_292 | 68918100 | 68920050 | EDA | ED1 = EDA |
| ENST00000510681.2 | 3446 | 68840273 | 69080948 | + | seg_292 | 68918100 | 68920050 | EDA | ED1 = EDA |
| ENST00000533317.1 | 3447 | 68835911 | 69177327 | + | seg_292 | 68918100 | 68920050 | EDA | ED1 = EDA |
| ENST00000527388.1 | 3448 | 68835911 | 69080892 | + | seg_292 | 68918100 | 68920050 | EDA | ED1 = EDA |
| ENST00000502251.1 | 3449 | 68835911 | 69177354 | + | seg_292 | 68918100 | 68920050 | EDA | ED1 = EDA |
| ENST00000530321.1 | 3450 | 68840300 | 69080892 | + | seg_292 | 68918100 | 68920050 | EDA | ED1 = EDA |
| ENST00000503592.1 | 3451 | 68840254 | 69253260 | + | seg_292 | 68918100 | 68920050 | EDA | ED1 = EDA |
| ENST00000374552.4 | 3452 | 68835911 | 69259319 | + | seg_292 | 68918100 | 68920050 | EDA | ED1 = EDA |
| ENST00000374553.2 | 3453 | 68835911 | 69259319 | + | seg_292 | 68918100 | 68920050 | EDA | ED1 = EDA |
| ENST00000524573.1 | 3454 | 68835961 | 69255487 | + | seg_292 | 68918100 | 68920050 | EDA | ED1 = EDA |
| ENST00000342206.6 | 3455 | 69353299 | 69386174 | + | seg_293 | 69352950 | 69354000 | IGBP1 | ED1 = EDA |
| ENST00000356413.4 | 3456 | 69353313 | 69386174 | + | seg_293 | 69352950 | 69354000 | IGBP1 | ED1 = EDA |
| ENST00000374355.3 | 3457 | 69672155 | 69725337 | + | seg_294 | 69697700 | 69699050 | DLG3 | GJB1 |
| ENST00000194900.4 | 3458 | 69664711 | 69725337 | + | seg_294 | 69697700 | 69699050 | DLG3 | GJB1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000542398.1 | 3459 | 69674946 | 69725335 | + | seg__294 | 69697700 | 69699050 | DLG3 | GJB1 |
| ENST00000466140.1 | 3460 | 69698968 | 69719753 | + | seg__294 | 69697700 | 69699050 | DLG3 | GJB1 |
| ENST00000494493.1 | 3461 | 69674957 | 69712087 | + | seg__294 | 69697700 | 69699050 | DLG3 | GJB1 |
| ENST00000489733.1 | 3462 | 69674953 | 69718408 | + | seg__294 | 69697700 | 69699050 | DLG3 | GJB1 |
| ENST00000463252.1 | 3463 | 69664986 | 69723796 | + | seg__294 | 69697700 | 69699050 | DLG3 | GJB1 |
| ENST00000374360.3 | 3464 | 69664819 | 69725337 | + | seg__294 | 69697700 | 69699050 | DLG3 | GJB1 |
| ENST00000447581.1 | 3465 | 70435109 | 70443810 | + | seg__296 | 70436000 | 70437500 | GJB1 | GJB1 |
| ENST00000374029.1 | 3466 | 70435044 | 70445050 | + | seg__296 | 70436000 | 70437500 | GJB1 | GJB1 |
| ENST00000374022.3 | 3467 | 70435062 | 70445366 | + | seg__296 | 70436000 | 70437500 | GJB1 | GJB1 |
| ENST00000373981.1 | 3468 | 70469054 | 70474425 | − | seg__297 | 70474400 | 70475600 | ZMYM3 | GJB1 |
| ENST00000373988.1 | 3469 | 70459476 | 70474910 | − | seg__297 | 70474400 | 70475600 | ZMYM3 | GJB1 |
| ENST00000373998.1 | 3470 | 70459474 | 70474996 | − | seg__297 | 70474400 | 70475600 | ZMYM3 | GJB1 |
| ENST00000353904.2 | 3471 | 70459474 | 70474499 | − | seg__297 | 70474400 | 70475600 | ZMYM3 | GJB1 |
| ENST00000422194.1 | 3472 | 70882845 | 70885603 | − | seg__298 | 70877700 | 70883450 | CXCR3 | GJB1 |
| ENST00000433410.1 | 3473 | 70882848 | 70884121 | − | seg__298 | 70877700 | 70883450 | CXCR3 | GJB1 |
| ENST00000508574.1 | 3474 | 70917046 | 70926305 | + | seg__299 | 70919900 | 70923050 | CXCR3 | GJB1 |
| ENST00000508574.1 | 3475 | 70917046 | 70926305 | + | seg__300 | 70926200 | 70950300 | CXCR3 | GJB1 |
| ENST00000417668.1 | 3476 | 70938992 | 70939460 | + | seg__300 | 70926200 | 70950300 | CXCR3 | GJB1 |
| ENST00000457716.1 | 3477 | 70939766 | 70940650 | + | seg__300 | 70926200 | 70950300 | CXCR3 | GJB1 |
| ENST00000535490.1 | 3478 | 70934224 | 70938135 | − | seg__300 | 70926200 | 70950300 | CXCR3 | GJB1 |
| ENST00000452468.1 | 3479 | 70934221 | 70936237 | − | seg__300 | 70926200 | 70950300 | CXCR3 | GJB1 |
| ENST00000456199.1 | 3480 | 70981815 | 70982283 | − | seg__301 | 70972100 | 70989450 | CXCR3 | GJB1 |
| ENST00000439926.1 | 3481 | 70980625 | 70981509 | − | seg__301 | 70972100 | 70989450 | CXCR3 | GJB1 |
| ENST00000440412.1 | 3482 | 70985038 | 70987054 | + | seg__301 | 70972100 | 70989450 | CXCR3 | GJB1 |
| ENST00000542739.1 | 3483 | 70983140 | 70987051 | + | seg__301 | 70972100 | 70989450 | CXCR3 | GJB1 |
| ENST00000408757.1 | 3484 | 70979235 | 70979305 | − | seg__301 | 70972100 | 70989450 | CXCR3 | GJB1 |
| ENST00000515698.1 | 3485 | 70994970 | 71004228 | − | seg__303 | 70997850 | 70999500 | NHSL2 | GJB1 |
| ENST00000515698.1 | 3486 | 70994970 | 71004228 | − | seg__304 | 71003450 | 71005550 | NHSL2 | GJB1 |
| ENST00000540800.1 | 3487 | 71130938 | 71363424 | + | seg__307 | 71238100 | 71239150 | NHSL2 | GJB1 |
| ENST00000540800.1 | 3488 | 71130938 | 71363424 | + | seg__308 | 71261650 | 71263400 | RGAG4 | GJB1 |
| ENST00000540800.1 | 3489 | 71130938 | 71363424 | + | seg__309 | 71319750 | 71321300 | RGAG4 | GJB1 |
| ENST00000479991.1 | 3490 | 71346960 | 71351751 | − | seg__310 | 71348750 | 71353050 | RGAG4 | GJB1 |
| ENST00000545866.1 | 3491 | 71346958 | 71351758 | − | seg__310 | 71348750 | 71353050 | RGAG4 | GJB1 |
| ENST00000513469.1 | 3492 | 71352000 | 71354556 | + | seg__310 | 71348750 | 71353050 | RGAG4 | GJB1 |
| ENST00000540800.1 | 3493 | 71130938 | 71363424 | + | seg__310 | 71348750 | 71353050 | RGAG4 | GJB1 |
| ENST00000439980.2 | 3494 | 71401615 | 71522776 | + | seg__311 | 71503150 | 71504200 | RPS4X | GJB1 |
| ENST00000439980.2 | 3495 | 71401615 | 71522776 | + | seg__312 | 71512450 | 71513550 | CITED1 | GJB1 |
| ENST00000246139.5 | 3496 | 71521500 | 71526837 | − | seg__313 | 71526450 | 71528800 | CITED1 | GJB1 |
| ENST00000453707.2 | 3497 | 71521488 | 71527000 | − | seg__313 | 71526450 | 71528800 | CITED1 | GJB1 |
| ENST00000454225.1 | 3498 | 71522056 | 71526757 | − | seg__313 | 71526450 | 71528800 | CITED1 | GJB1 |
| ENST00000373619.3 | 3499 | 71521497 | 71527037 | − | seg__313 | 71526450 | 71528800 | CITED1 | GJB1 |
| ENST00000365612.1 | 3500 | 71945976 | 71946190 | − | seg__314 | 71945800 | 71946750 | PHKA1 | GJB1 |
| ENST00000276033.4 | 3501 | 73640638 | 73753752 | + | seg__319 | 73642000 | 73643200 | SLC16A2 | ABCB7 |
| ENST00000394563.3 | 3502 | 85339719 | 85341344 | − | seg__320 | 85339200 | 85340950 | CHM | CHM |
| ENST00000372964.1 | 3503 | 100098322 | 100129198 | − | seg__321 | 100106050 | 100107200 | NOX1 | BTK |
| ENST00000372961.3 | 3504 | 100098334 | 100129334 | − | seg__321 | 100106050 | 100107200 | NOX1 | BTK |
| ENST00000372966.3 | 3505 | 100098313 | 100129334 | − | seg__321 | 100106050 | 100107200 | NOX1 | BTK |
| ENST00000217885.5 | 3506 | 100098825 | 100129198 | − | seg__321 | 100106050 | 100107200 | NOX1 | BTK |
| ENST00000372960.4 | 3507 | 100098941 | 100129128 | − | seg__321 | 100106050 | 100107200 | NOX1 | BTK |
| ENST00000372957.2 | 3508 | 100098941 | 100129334 | − | seg__321 | 100106050 | 100107200 | NOX1 | BTK |
| ENST00000372964.1 | 3509 | 100098322 | 100129198 | − | seg__322 | 100119950 | 100121600 | NOX1 | BTK |
| ENST00000372961.3 | 3510 | 100098334 | 100129334 | − | seg__322 | 100119950 | 100121600 | NOX1 | BTK |
| ENST00000372966.3 | 3511 | 100098313 | 100129334 | − | seg__322 | 100119950 | 100121600 | NOX1 | BTK |
| ENST00000217885.5 | 3512 | 100098825 | 100129198 | − | seg__322 | 100119950 | 100121600 | NOX1 | BTK |
| ENST00000372960.4 | 3513 | 100098941 | 100129128 | − | seg__322 | 100119950 | 100121600 | NOX1 | BTK |
| ENST00000372957.2 | 3514 | 100098941 | 100129334 | − | seg__322 | 100119950 | 100121600 | NOX1 | BTK |
| ENST00000538510.1 | 3515 | 100486534 | 100519485 | + | seg__325 | 100514900 | 100516350 | DRP2 | BTK |
| ENST00000541709.1 | 3516 | 100474933 | 100519485 | + | seg__325 | 100514900 | 100516350 | DRP2 | BTK |
| ENST00000402866.1 | 3517 | 100474758 | 100519486 | + | seg__325 | 100514900 | 100516350 | DRP2 | BTK |
| ENST00000395209.3 | 3518 | 100474775 | 100519486 | + | seg__325 | 100514900 | 100516350 | DRP2 | BTK |
| ENST00000324762.6 | 3519 | 100523245 | 100542793 | − | seg__326 | 100532400 | 100533600 | TAF7L | BTK |
| ENST00000372907.3 | 3520 | 100523241 | 100548045 | − | seg__326 | 100532400 | 100533600 | TAF7L | BTK |
| ENST00000356784.1 | 3521 | 100523848 | 100546324 | − | seg__326 | 100532400 | 100533600 | TAF7L | BTK |
| ENST00000372905.2 | 3522 | 100523242 | 100548059 | − | seg__326 | 100532400 | 100533600 | TAF7L | BTK |
| ENST00000325117.7 | 3523 | 101801665 | 101803141 | − | seg__327 | 101800900 | 101804000 | TMSB15A | GLA |
| ENST00000372680.1 | 3524 | 102528619 | 102531800 | − | seg__330 | 102530950 | 102533100 | TCEAL5 | GLA |
| ENST00000449185.1 | 3525 | 102564600 | 102565863 | − | seg__331 | 102564900 | 102566400 | BEX2 | GLA |
| ENST00000372674.1 | 3526 | 102564430 | 102565935 | − | seg__331 | 102564900 | 102566400 | BEX2 | GLA |
| ENST00000372677.3 | 3527 | 102564274 | 102565974 | − | seg__331 | 102564900 | 102566400 | BEX2 | GLA |
| ENST00000536889.1 | 3528 | 102564282 | 102565883 | − | seg__331 | 102564900 | 102566400 | BEX2 | GLA |
| ENST00000332431.4 | 3529 | 102585124 | 102587254 | + | seg__332 | 102584350 | 102585450 | TCEAL7 | GLA |
| ENST00000372666.1 | 3530 | 102585157 | 102587016 | + | seg__332 | 102584350 | 102585450 | TCEAL7 | GLA |
| ENST00000372628.1 | 3531 | 102862379 | 102864855 | + | seg__333 | 102861350 | 102862700 | TCEAL3 | GLA |
| ENST00000447281.1 | 3532 | 103172005 | 103174131 | − | seg__337 | 103172500 | 103174800 | TMSB15B | TBG = SERPINA7 |
| ENST00000455723.1 | 3533 | 103173770 | 103187485 | + | seg__337 | 103172500 | 103174800 | TMSB15B | TBG = SERPINA7 |
| ENST00000419165.1 | 3534 | 103173479 | 103220554 | + | seg__337 | 103172500 | 103174800 | TMSB15B | TBG = SERPINA7 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000448050.1 | 3535 | 103216417 | 103216861 | − | seg_338 | 103216000 | 103218450 | TMSB15B | TBG = SERPINA7 |
| ENST00000451146.1 | 3536 | 103216382 | 103216864 | − | seg_338 | 103216000 | 103218450 | TMSB15B | TBG = SERPINA7 |
| ENST00000540220.1 | 3537 | 103217224 | 103220868 | + | seg_338 | 103216000 | 103218450 | TMSB15B | TBG = SERPINA7 |
| ENST00000436583.1 | 3538 | 103217242 | 103220554 | + | seg_338 | 103216000 | 103218450 | TMSB15B | TBG = SERPINA7 |
| ENST00000419165.1 | 3539 | 103173479 | 103220554 | + | seg_338 | 103216000 | 103218450 | TMSB15B | TBG = SERPINA7 |
| ENST00000422550.1 | 3540 | 103230404 | 103230880 | + | seg_339 | 103230800 | 103233250 | TMSB15B | TBG = SERPINA7 |
| ENST00000423478.1 | 3541 | 103356822 | 103357563 | + | seg_346 | 103355850 | 103358850 | SLC25A53 | TBG = SERPINA7 |
| ENST00000422784.1 | 3542 | 103357235 | 103360533 | + | seg_346 | 103355850 | 103358850 | SLC25A53 | TBG = SERPINA7 |
| ENST00000537356.1 | 3543 | 103357107 | 103360531 | + | seg_346 | 103355850 | 103358850 | SLC25A53 | TBG = SERPINA7 |
| ENST00000357421.4 | 3544 | 103343898 | 103401708 | − | seg_346 | 103355850 | 103358850 | SLC25A53 | TBG = SERPINA7 |
| ENST00000372582.1 | 3545 | 103810996 | 105011822 | + | seg_347 | 103812100 | 103813500 | IL1RAPL2 | TBG = SERPINA7 |
| ENST00000418562.1 | 3546 | 105937024 | 106033435 | + | seg_349 | 105968700 | 105970600 | RNF128 | TBG = SERPINA7 |
| ENST00000324342.3 | 3547 | 105937068 | 106040223 | + | seg_349 | 105968700 | 105970600 | RNF128 | TBG = SERPINA7 |
| ENST00000255499.2 | 3548 | 105969894 | 106040223 | + | seg_349 | 105968700 | 105970600 | RNF128 | TBG = SERPINA7 |
| ENST00000357242.5 | 3549 | 106045910 | 106119375 | + | seg_350 | 106044350 | 106046150 | TBC1D8B | TBG = SERPINA7 |
| ENST00000481617.2 | 3550 | 106045935 | 106073313 | + | seg_350 | 106044350 | 106046150 | TBC1D8B | TBG = SERPINA7 |
| ENST00000276175.3 | 3551 | 106046043 | 106117347 | + | seg_350 | 106044350 | 106046150 | TBC1D8B | TBG = SERPINA7 |
| ENST00000310452.2 | 3552 | 106045919 | 106093061 | + | seg_350 | 106044350 | 106046150 | TBC1D8B | TBG = SERPINA7 |
| ENST00000372453.3 | 3553 | 106449862 | 106487473 | + | seg_351 | 106482900 | 106485150 | PIH1D3 | PRPS1 |
| ENST00000535523.1 | 3554 | 106449862 | 106487472 | + | seg_351 | 106482900 | 106485150 | PIH1D3 | PRPS1 |
| ENST00000336387.4 | 3555 | 106450378 | 106486594 | + | seg_351 | 106482900 | 106485150 | PIH1D3 | PRPS1 |
| ENST00000415252.1 | 3556 | 106756213 | 106789051 | − | seg_353 | 106766500 | 106768400 | FRMPD3 | PRPS1 |
| ENST00000276185.4 | 3557 | 106765680 | 106846603 | + | seg_353 | 106766500 | 106768400 | FRMPD3 | PRPS1 |
| ENST00000276185.4 | 3558 | 106765680 | 106846603 | + | seg_354 | 106839200 | 106841100 | PRPS1 | PRPS1 |
| ENST00000439554.1 | 3559 | 106769876 | 106848481 | + | seg_354 | 106839200 | 106841100 | PRPS1 | PRPS1 |
| ENST00000276185.4 | 3560 | 106765680 | 106846603 | + | seg_355 | 106844750 | 106845950 | PRPS1 | PRPS1 |
| ENST00000439554.1 | 3561 | 106769876 | 106848481 | + | seg_355 | 106844750 | 106845950 | PRPS1 | PRPS1 |
| ENST00000372384.2 | 3562 | 106956454 | 107019218 | − | seg_357 | 106984400 | 106985900 | TSC22D3 | PRPS1 |
| ENST00000372383.4 | 3563 | 106956454 | 107019017 | − | seg_357 | 106984400 | 106985900 | TSC22D3 | PRPS1 |
| ENST00000394928.2 | 3564 | 106957214 | 107018890 | − | seg_357 | 106984400 | 106985900 | TSC22D3 | PRPS1 |
| ENST00000315660.4 | 3565 | 106956451 | 107019215 | − | seg_357 | 106984400 | 106985900 | TSC22D3 | PRPS1 |
| ENST00000506081.1 | 3566 | 106957600 | 107020297 | − | seg_357 | 106984400 | 106985900 | TSC22D3 | PRPS1 |
| ENST00000514426.1 | 3567 | 106957717 | 107020308 | − | seg_357 | 106984400 | 106985900 | TSC22D3 | PRPS1 |
| ENST00000510887.1 | 3568 | 106959142 | 107019944 | − | seg_357 | 106984400 | 106985900 | TSC22D3 | PRPS1 |
| ENST00000502650.1 | 3569 | 106959153 | 107019345 | − | seg_357 | 106984400 | 106985900 | TSC22D3 | PRPS1 |
| ENST00000514897.1 | 3570 | 106959128 | 107020572 | − | seg_357 | 106984400 | 106985900 | TSC22D3 | PRPS1 |
| ENST00000480691.2 | 3571 | 106959133 | 107020285 | − | seg_357 | 106984400 | 106985900 | TSC22D3 | PRPS1 |
| ENST00000372384.2 | 3572 | 106956454 | 107019218 | − | seg_358 | 107012550 | 107013950 | TSC22D3 | PRPS1 |
| ENST00000372383.4 | 3573 | 106956454 | 107019017 | − | seg_358 | 107012550 | 107013950 | TSC22D3 | PRPS1 |
| ENST00000394928.2 | 3574 | 106957214 | 107018890 | − | seg_358 | 107012550 | 107013950 | TSC22D3 | PRPS1 |
| ENST00000315660.4 | 3575 | 106956451 | 107019215 | − | seg_358 | 107012550 | 107013950 | TSC22D3 | PRPS1 |
| ENST00000506081.1 | 3576 | 106957600 | 107020297 | − | seg_358 | 107012550 | 107013950 | TSC22D3 | PRPS1 |
| ENST00000514426.1 | 3577 | 106957717 | 107020308 | − | seg_358 | 107012550 | 107013950 | TSC22D3 | PRPS1 |
| ENST00000510887.1 | 3578 | 106959142 | 107019944 | − | seg_358 | 107012550 | 107013950 | TSC22D3 | PRPS1 |
| ENST00000502650.1 | 3579 | 106959153 | 107019345 | − | seg_358 | 107012550 | 107013950 | TSC22D3 | PRPS1 |
| ENST00000514897.1 | 3580 | 106959128 | 107020572 | − | seg_358 | 107012550 | 107013950 | TSC22D3 | PRPS1 |
| ENST00000480691.2 | 3581 | 106959133 | 107020285 | − | seg_358 | 107012550 | 107013950 | TSC22D3 | PRPS1 |
| ENST00000506724.1 | 3582 | 107018348 | 107019488 | − | seg_359 | 107015700 | 107021050 | TSC22D3 | PRPS1 |
| ENST00000509000.1 | 3583 | 107020963 | 107037689 | + | seg_359 | 107015700 | 107021050 | TSC22D3 | PRPS1 |
| ENST00000372384.2 | 3584 | 106956454 | 107019218 | − | seg_359 | 107015700 | 107021050 | TSC22D3 | PRPS1 |
| ENST00000505965.1 | 3585 | 107018397 | 107020567 | − | seg_359 | 107015700 | 107021050 | TSC22D3 | PRPS1 |
| ENST00000372383.4 | 3586 | 106956454 | 107019017 | − | seg_359 | 107015700 | 107021050 | TSC22D3 | PRPS1 |
| ENST00000394928.2 | 3587 | 106957214 | 107018890 | − | seg_359 | 107015700 | 107021050 | TSC22D3 | PRPS1 |
| ENST00000315660.4 | 3588 | 106956451 | 107019215 | − | seg_359 | 107015700 | 107021050 | TSC22D3 | PRPS1 |
| ENST00000506081.1 | 3589 | 106957600 | 107020297 | − | seg_359 | 107015700 | 107021050 | TSC22D3 | PRPS1 |
| ENST00000514426.1 | 3590 | 106957717 | 107020308 | − | seg_359 | 107015700 | 107021050 | TSC22D3 | PRPS1 |
| ENST00000502961.1 | 3591 | 107018476 | 107020559 | − | seg_359 | 107015700 | 107021050 | TSC22D3 | PRPS1 |
| ENST00000510887.1 | 3592 | 106959142 | 107019944 | − | seg_359 | 107015700 | 107021050 | TSC22D3 | PRPS1 |
| ENST00000502650.1 | 3593 | 106959153 | 107019345 | − | seg_359 | 107015700 | 107021050 | TSC22D3 | PRPS1 |
| ENST00000514897.1 | 3594 | 106959128 | 107020572 | − | seg_359 | 107015700 | 107021050 | TSC22D3 | PRPS1 |
| ENST00000480691.2 | 3595 | 106959133 | 107020285 | − | seg_359 | 107015700 | 107021050 | TSC22D3 | PRPS1 |
| ENST00000451923.1 | 3596 | 107068985 | 107084611 | + | seg_360 | 107067200 | 107071350 | MID2 | PRPS1 |
| ENST00000443968.2 | 3597 | 107069644 | 107170423 | + | seg_360 | 107067200 | 107071350 | MID2 | PRPS1 |
| ENST00000262843.6 | 3598 | 107069109 | 107170423 | + | seg_360 | 107067200 | 107071350 | MID2 | PRPS1 |
| ENST00000430140.1 | 3599 | 107137827 | 107179210 | − | seg_361 | 107167050 | 107168350 | TEX13B | PRPS1 |
| ENST00000474517.1 | 3600 | 107160732 | 107169702 | + | seg_361 | 107167050 | 107168350 | TEX13B | PRPS1 |
| ENST00000443968.2 | 3601 | 107069644 | 107170423 | + | seg_361 | 107167050 | 107168350 | TEX13B | PRPS1 |
| ENST00000262843.6 | 3602 | 107069109 | 107170423 | + | seg_361 | 107167050 | 107168350 | TEX13B | PRPS1 |
| ENST00000415430.3 | 3603 | 107288200 | 107322414 | + | seg_362 | 107318400 | 107320100 | PSMD10 | COL4A5 |
| ENST00000217957.5 | 3604 | 107288244 | 107322327 | + | seg_362 | 107318400 | 107320100 | PSMD10 | COL4A5 |
| ENST00000545689.1 | 3605 | 107399275 | 107681556 | − | seg_363 | 107680300 | 107682050 | COL4A6 | COL4A5 |
| ENST00000538570.1 | 3606 | 107399275 | 107681556 | − | seg_363 | 107680300 | 107682050 | COL4A6 | COL4A5 |
| ENST00000394872.2 | 3607 | 107398838 | 107681658 | − | seg_363 | 107680300 | 107682050 | COL4A6 | COL4A5 |
| ENST00000461897.1 | 3608 | 107510872 | 107681660 | − | seg_363 | 107680300 | 107682050 | COL4A6 | COL4A5 |
| ENST00000468338.1 | 3609 | 107457022 | 107682702 | − | seg_363 | 107680300 | 107682050 | COL4A6 | COL4A5 |
| ENST00000541389.1 | 3610 | 107399121 | 107681660 | − | seg_363 | 107680300 | 107682050 | COL4A6 | COL4A5 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000334504.7 | 3611 | 107398837 | 107681660 | − | seg_363 | 107680300 | 107682050 | COL4A6 | COL4A5 |
| ENST00000372216.4 | 3612 | 107398837 | 107682702 | − | seg_363 | 107680300 | 107682050 | COL4A6 | COL4A5 |
| ENST00000477085.1 | 3613 | 107510872 | 107682727 | − | seg_363 | 107680300 | 107682050 | COL4A6 | COL4A5 |
| ENST00000508186.1 | 3614 | 107683236 | 107940014 | + | seg_364 | 107800800 | 107802650 | COL4A5 | COL4A5 |
| ENST00000470339.1 | 3615 | 107683172 | 107812265 | + | seg_364 | 107800800 | 107802650 | COL4A5 | COL4A5 |
| ENST00000328300.6 | 3616 | 107683112 | 107940771 | + | seg_364 | 107800800 | 107802650 | COL4A5 | COL4A5 |
| ENST00000361603.2 | 3617 | 107683112 | 107940775 | + | seg_364 | 107800800 | 107802650 | COL4A5 | COL4A5 |
| ENST00000520821.1 | 3618 | 109602044 | 109694109 | + | seg_367 | 109664500 | 109668200 | RGAG1 | COL4A5 |
| ENST00000465301.2 | 3619 | 109662285 | 109699562 | + | seg_367 | 109664500 | 109668200 | RGAG1 | COL4A5 |
| ENST00000372057.1 | 3620 | 109439638 | 109683461 | − | seg_367 | 109664500 | 109668200 | RGAG1 | COL4A5 |
| ENST00000520821.1 | 3621 | 109602044 | 109694109 | + | seg_368 | 109675200 | 109677300 | RGAG1 | COL4A5 |
| ENST00000465301.2 | 3622 | 109662285 | 109699562 | + | seg_368 | 109675200 | 109677300 | RGAG1 | COL4A5 |
| ENST00000372057.1 | 3623 | 109439638 | 109683461 | − | seg_368 | 109675200 | 109677300 | RGAG1 | COL4A5 |
| ENST00000520821.1 | 3624 | 109602044 | 109694109 | + | seg_369 | 109681600 | 109683350 | RGAG1 | COL4A5 |
| ENST00000465301.2 | 3625 | 109662285 | 109699562 | + | seg_369 | 109681600 | 109683350 | RGAG1 | COL4A5 |
| ENST00000372057.1 | 3626 | 109439638 | 109683461 | − | seg_369 | 109681600 | 109683350 | RGAG1 | COL4A5 |
| ENST00000520821.1 | 3627 | 109602044 | 109694109 | + | seg_370 | 109687600 | 109689250 | RGAG1 | COL4A5 |
| ENST00000465301.2 | 3628 | 109662285 | 109699562 | + | seg_370 | 109687600 | 109689250 | RGAG1 | COL4A5 |
| ENST00000493351.1 | 3629 | 109764358 | 109764924 | + | seg_371 | 109763200 | 109764700 | RGAG1 | COL4A5 |
| ENST00000218054.4 | 3630 | 109917092 | 110039076 | − | seg_372 | 110037400 | 110040400 | CHRDL1 | COL4A5 |
| ENST00000394797.4 | 3631 | 109918473 | 110038993 | − | seg_372 | 110037400 | 110040400 | CHRDL1 | COL4A5 |
| ENST00000434224.1 | 3632 | 109917092 | 110039286 | − | seg_372 | 110037400 | 110040400 | CHRDL1 | COL4A5 |
| ENST00000372045.1 | 3633 | 109917084 | 110038993 | − | seg_372 | 110037400 | 110040400 | CHRDL1 | COL4A5 |
| ENST00000482160.1 | 3634 | 109919169 | 110039047 | − | seg_372 | 110037400 | 110040400 | CHRDL1 | COL4A5 |
| ENST00000372042.1 | 3635 | 109919004 | 110039039 | − | seg_372 | 110037400 | 110040400 | CHRDL1 | COL4A5 |
| ENST00000444321.2 | 3636 | 109919285 | 110039047 | − | seg_372 | 110037400 | 110040400 | CHRDL1 | COL4A5 |
| ENST00000446737.1 | 3637 | 110187513 | 110464146 | + | seg_374 | 110338150 | 110339500 | PAK3 | COL4A5 |
| ENST00000425146.1 | 3638 | 110187513 | 110464146 | + | seg_374 | 110338150 | 110339500 | PAK3 | COL4A5 |
| ENST00000317135.8 | 3639 | 114345185 | 114468635 | − | seg_381 | 114467100 | 114468700 | LRCH2 | COL4A5 |
| ENST00000536655.1 | 3640 | 114345189 | 114468627 | − | seg_381 | 114467100 | 114468700 | LRCH2 | COL4A5 |
| ENST00000538422.1 | 3641 | 114345686 | 114468628 | − | seg_381 | 114467100 | 114468700 | LRCH2 | COL4A5 |
| ENST00000451869.1 | 3642 | 114957297 | 114959381 | + | seg_382 | 114956100 | 114958000 | RP1-241P17.4 | COL4A5 |
| ENST00000415394.1 | 3643 | 114957343 | 114959383 | + | seg_382 | 114956100 | 114958000 | RP1-241P17.4 | COL4A5 |
| ENST00000436163.1 | 3644 | 117250225 | 117250763 | − | seg_383 | 117249800 | 117250800 | KLHL13 | COL4A5 |
| ENST00000371882.1 | 3645 | 117031776 | 117250761 | − | seg_383 | 117249800 | 117250800 | KLHL13 | COL4A5 |
| ENST00000540167.1 | 3646 | 117031777 | 117250828 | − | seg_383 | 117249800 | 117250800 | KLHL13 | COL4A5 |
| ENST00000541812.1 | 3647 | 117031777 | 117251303 | − | seg_383 | 117249800 | 117250800 | KLHL13 | COL4A5 |
| ENST00000545703.1 | 3648 | 117031777 | 117250828 | − | seg_383 | 117249800 | 117250800 | KLHL13 | COL4A5 |
| ENST00000371642.1 | 3649 | 117861565 | 117895483 | + | seg_384 | 117862300 | 117863400 | IL13RA1 | COL4A5 |
| ENST00000371666.3 | 3650 | 117861535 | 117928502 | + | seg_384 | 117862300 | 117863400 | IL13RA1 | COL4A5 |
| ENST00000310164.2 | 3651 | 117957753 | 117960931 | + | seg_386 | 117956850 | 117963900 | ZCCHC12 | COL4A5 |
| ENST00000481285.1 | 3652 | 118108581 | 118151946 | + | seg_390 | 118109050 | 118110300 | LONRF3 | COL4A5 |
| ENST00000304778.7 | 3653 | 118108581 | 118152318 | + | seg_390 | 118109050 | 118110300 | LONRF3 | COL4A5 |
| ENST00000439603.1 | 3654 | 118109325 | 118151950 | + | seg_390 | 118109050 | 118110300 | LONRF3 | COL4A5 |
| ENST00000371628.3 | 3655 | 118108713 | 118151892 | + | seg_390 | 118109050 | 118110300 | LONRF3 | COL4A5 |
| ENST00000422289.2 | 3656 | 118110295 | 118151947 | + | seg_390 | 118109050 | 118110300 | LONRF3 | COL4A5 |
| ENST00000472173.1 | 3657 | 118110295 | 118151946 | + | seg_390 | 118109050 | 118110300 | LONRF3 | COL4A5 |
| ENST00000365713.2 | 3658 | 118108581 | 118156888 | + | seg_390 | 118109050 | 118110300 | LONRF3 | COL4A5 |
| ENST00000440399.1 | 3659 | 118212598 | 118223411 | − | seg_392 | 118212900 | 118215850 | KIAA1210 | OCRL |
| ENST00000402510.2 | 3660 | 118212598 | 118284542 | − | seg_392 | 118212900 | 118215850 | KIAA1210 | OCRL |
| ENST00000402510.2 | 3661 | 118212598 | 118284542 | − | seg_393 | 118282850 | 118287450 | KIAA1210 | OCRL |
| ENST00000535419.1 | 3662 | 118370288 | 118378428 | + | seg_396 | 118366950 | 118370450 | PGRMC1 | OCRL |
| ENST00000217971.7 | 3663 | 118370216 | 118378429 | + | seg_396 | 118366950 | 118370450 | PGRMC1 | OCRL |
| ENST00000428222.1 | 3664 | 118425492 | 118469573 | + | seg_397 | 118441450 | 118445300 | PGRMC1 | OCRL |
| ENST00000428222.1 | 3665 | 118425492 | 118469573 | + | seg_398 | 118449700 | 118451000 | PGRMC1 | OCRL |
| ENST00000428222.1 | 3666 | 118425492 | 118469573 | + | seg_399 | 118457400 | 118458500 | SLC25A43 | OCRL |
| ENST00000413240.1 | 3667 | 118490264 | 118527558 | − | seg_401 | 118493600 | 118495250 | SLC25A43 | OCRL |
| ENST00000413240.1 | 3668 | 118490264 | 118527558 | − | seg_402 | 118496550 | 118498200 | SLC25A43 | OCRL |
| ENST00000413240.1 | 3669 | 118490264 | 118527558 | − | seg_403 | 118503050 | 118504750 | SLC25A43 | OCRL |
| ENST00000511924.1 | 3670 | 118513675 | 118514067 | + | seg_404 | 118513250 | 118514500 | SLC25A43 | OCRL |
| ENST00000413240.1 | 3671 | 118490264 | 118527558 | − | seg_404 | 118513250 | 118514500 | SLC25A43 | OCRL |
| ENST00000454625.1 | 3672 | 119144675 | 119149501 | − | seg_409 | 119146350 | 119147850 | RHOXF2B | OCRL |
| ENST00000454625.1 | 3673 | 119144675 | 119149501 | − | seg_410 | 119149700 | 119157100 | RHOXF2B | OCRL |
| ENST00000218008.3 | 3674 | 119495967 | 119516226 | + | seg_412 | 119504000 | 119505500 | ATP1B4 | OCRL |
| ENST00000539306.1 | 3675 | 119495997 | 119513514 | + | seg_412 | 119504000 | 119505500 | ATP1B4 | OCRL |
| ENST00000361319.3 | 3676 | 119495967 | 119516226 | + | seg_412 | 119504000 | 119505500 | ATP1B4 | OCRL |
| ENST00000218008.3 | 3677 | 119495967 | 119516226 | + | seg_413 | 119514900 | 119515950 | ATP1B4 | OCRL |
| ENST00000361319.3 | 3678 | 119495967 | 119516226 | + | seg_413 | 119514900 | 119515950 | ATP1B4 | OCRL |
| ENST00000427955.1 | 3679 | 119866948 | 119867250 | + | seg_414 | 119865950 | 119867450 | C1GALT1C1 | OCRL |
| ENST00000479118.1 | 3680 | 122318412 | 122387553 | + | seg_416 | 122316650 | 122320500 | GRIA3 | OCRL |
| ENST00000371264.3 | 3681 | 122318152 | 122338534 | + | seg_416 | 122316650 | 122320500 | GRIA3 | OCRL |
| ENST00000371266.1 | 3682 | 122318006 | 122338534 | + | seg_416 | 122316650 | 122320500 | GRIA3 | OCRL |
| ENST00000335161.8 | 3683 | 122318224 | 122338270 | + | seg_416 | 122316650 | 122320500 | GRIA3 | OCRL |
| ENST00000541091.1 | 3684 | 122318765 | 122551942 | + | seg_416 | 122316650 | 122320500 | GRIA3 | OCRL |
| ENST00000371251.1 | 3685 | 122318336 | 122616897 | + | seg_416 | 122316650 | 122320500 | GRIA3 | OCRL |
| ENST00000264357.5 | 3686 | 122318096 | 122624756 | + | seg_416 | 122316650 | 122320500 | GRIA3 | OCRL |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000371256.5 | 3687 | 122318336 | 122624766 | + | seg_416 | 122316650 | 122320500 | GRIA3 | OCRL |
| ENST00000542149.1 | 3688 | 122318224 | 122622587 | + | seg_416 | 122316650 | 122320500 | GRIA3 | OCRL |
| ENST00000541091.1 | 3689 | 122318765 | 122551942 | + | seg_417 | 122402300 | 122404250 | GRIA3 | OCRL |
| ENST00000371251.1 | 3690 | 122318336 | 122616897 | + | seg_417 | 122402300 | 122404250 | GRIA3 | OCRL |
| ENST00000264357.5 | 3691 | 122318096 | 122624756 | + | seg_417 | 122402300 | 122404250 | GRIA3 | OCRL |
| ENST00000371256.5 | 3692 | 122318336 | 122624766 | + | seg_417 | 122402300 | 122404250 | GRIA3 | OCRL |
| ENST00000542149.1 | 3693 | 122318224 | 122622587 | + | seg_417 | 122402300 | 122404250 | GRIA3 | OCRL |
| ENST00000469481.1 | 3694 | 123094545 | 123556514 | + | seg_418 | 123373100 | 123375500 | SH2D1A | OCRL |
| ENST00000429967.1 | 3695 | 128779786 | 128788914 | − | seg_420 | 128781700 | 128784050 | APLN | OCRL |
| ENST00000427399.1 | 3696 | 128781653 | 128782742 | − | seg_420 | 128781700 | 128784050 | APLN | OCRL |
| ENST00000307484.6 | 3697 | 128779240 | 128788933 | − | seg_420 | 128781700 | 128784050 | APLN | OCRL |
| ENST00000429967.1 | 3698 | 128779786 | 128788914 | − | seg_421 | 128788300 | 128792400 | APLN | OCRL |
| ENST00000307484.6 | 3699 | 128779240 | 128788933 | − | seg_421 | 128788300 | 128792400 | APLN | OCRL |
| ENST00000257017.4 | 3700 | 129305623 | 129318844 | + | seg_427 | 129312750 | 129314600 | RAB33A | OCRL |
| ENST00000276218.2 | 3701 | 129518319 | 129519511 | − | seg_429 | 129518000 | 129519450 | GPR119 | OCRL |
| ENST00000412420.1 | 3702 | 130150443 | 130192120 | − | seg_431 | 130182350 | 130183950 | ARHGAP36 | NYS1 = FRMD7 |
| ENST00000370922.1 | 3703 | 130192331 | 130223857 | + | seg_432 | 130192100 | 130193800 | ARHGAP36 | NYS1 = FRMD7 |
| ENST00000276211.5 | 3704 | 130192216 | 130223853 | + | seg_432 | 130192100 | 130193800 | ARHGAP36 | NYS1 = FRMD7 |
| ENST00000412420.1 | 3705 | 130150443 | 130192120 | − | seg_432 | 130192100 | 130193800 | ARHGAP36 | NYS1 = FRMD7 |
| ENST00000464296.1 | 3706 | 131211900 | 131261872 | − | seg_435 | 131217450 | 131219600 | FRMD7 | NYS1 = FRMD7 |
| ENST00000298542.4 | 3707 | 131211023 | 131262048 | − | seg_435 | 131217450 | 131219600 | FRMD7 | NYS1 = FRMD7 |
| ENST00000370879.1 | 3708 | 131211021 | 131228291 | − | seg_435 | 131217450 | 131219600 | FRMD7 | NYS1 = FRMD7 |
| ENST00000464296.1 | 3709 | 131211900 | 131261872 | − | seg_436 | 131226100 | 131227550 | FRMD7 | NYS1 = FRMD7 |
| ENST00000298542.4 | 3710 | 131211023 | 131262048 | − | seg_436 | 131226100 | 131227550 | FRMD7 | NYS1 = FRMD7 |
| ENST00000370879.1 | 3711 | 131211021 | 131228291 | − | seg_436 | 131226100 | 131227550 | FRMD7 | NYS1 = FRMD7 |
| ENST00000464296.1 | 3712 | 131211900 | 131261872 | − | seg_437 | 131234500 | 131238250 | FRMD7 | NYS1 = FRMD7 |
| ENST00000298542.4 | 3713 | 131211023 | 131262048 | − | seg_437 | 131234500 | 131238250 | FRMD7 | NYS1 = FRMD7 |
| ENST00000513703.1 | 3714 | 131234662 | 131261900 | − | seg_437 | 131234500 | 131238250 | FRMD7 | NYS1 = FRMD7 |
| ENST00000370853.3 | 3715 | 131512177 | 131573718 | − | seg_438 | 131552950 | 131554550 | MBNL3 | NYS1 = FRMD7 |
| ENST00000370857.3 | 3716 | 131506029 | 131573705 | − | seg_438 | 131552950 | 131554550 | MBNL3 | NYS1 = FRMD7 |
| ENST00000370839.3 | 3717 | 131513232 | 131573718 | − | seg_438 | 131552950 | 131554550 | MBNL3 | NYS1 = FRMD7 |
| ENST00000370844.1 | 3718 | 131513232 | 131623996 | − | seg_438 | 131552950 | 131554550 | MBNL3 | NYS1 = FRMD7 |
| ENST00000421707.1 | 3719 | 131518691 | 131623043 | − | seg_438 | 131552950 | 131554550 | MBNL3 | NYS1 = FRMD7 |
| ENST00000421483.1 | 3720 | 131351175 | 131564190 | + | seg_438 | 131552950 | 131554550 | MBNL3 | NYS1 = FRMD7 |
| ENST00000436215.1 | 3721 | 131516244 | 131623894 | − | seg_438 | 131552950 | 131554550 | MBNL3 | NYS1 = FRMD7 |
| ENST00000441399.1 | 3722 | 131352535 | 131566890 | + | seg_438 | 131552950 | 131554550 | MBNL3 | NYS1 = FRMD7 |
| ENST00000370853.3 | 3723 | 131512177 | 131573718 | − | seg_439 | 131555800 | 131556900 | MBNL3 | NYS1 = FRMD7 |
| ENST00000370857.3 | 3724 | 131506029 | 131573705 | − | seg_439 | 131555800 | 131556900 | MBNL3 | NYS1 = FRMD7 |
| ENST00000370839.3 | 3725 | 131513232 | 131573718 | − | seg_439 | 131555800 | 131556900 | MBNL3 | NYS1 = FRMD7 |
| ENST00000370844.1 | 3726 | 131513232 | 131623996 | − | seg_439 | 131555800 | 131556900 | MBNL3 | NYS1 = FRMD7 |
| ENST00000421707.1 | 3727 | 131518691 | 131623043 | − | seg_439 | 131555800 | 131556900 | MBNL3 | NYS1 = FRMD7 |
| ENST00000421483.1 | 3728 | 131351175 | 131564190 | + | seg_439 | 131555800 | 131556900 | MBNL3 | NYS1 = FRMD7 |
| ENST00000436215.1 | 3729 | 131516244 | 131623894 | − | seg_439 | 131555800 | 131556900 | MBNL3 | NYS1 = FRMD7 |
| ENST00000441399.1 | 3730 | 131352535 | 131566890 | + | seg_439 | 131555800 | 131556900 | MBNL3 | NYS1 = FRMD7 |
| ENST00000517294.1 | 3731 | 133371077 | 133380237 | + | seg_443 | 133370100 | 133372950 | CCDC160 | HPRT1 = HPRT |
| ENST00000370809.1 | 3732 | 133371077 | 133379808 | + | seg_443 | 133370100 | 133372950 | CCDC160 | HPRT1 = HPRT |
| ENST00000359237.4 | 3733 | 133699868 | 133792513 | − | seg_444 | 133751450 | 133752450 | PLAC1 | HPRT1 = HPRT |
| ENST00000476971.1 | 3734 | 133699907 | 133867666 | − | seg_444 | 133751450 | 133752450 | PLAC1 | HPRT1 = HPRT |
| ENST00000466797.1 | 3735 | 133735587 | 133898352 | − | seg_444 | 133751450 | 133752450 | PLAC1 | HPRT1 = HPRT |
| ENST00000473897.1 | 3736 | 133700540 | 133898293 | − | seg_444 | 133751450 | 133752450 | PLAC1 | HPRT1 = HPRT |
| ENST00000359237.4 | 3737 | 133699868 | 133792513 | − | seg_445 | 133779700 | 133780700 | PLAC1 | HPRT1 = HPRT |
| ENST00000476971.1 | 3738 | 133699907 | 133867666 | − | seg_445 | 133779700 | 133780700 | PLAC1 | HPRT1 = HPRT |
| ENST00000466797.1 | 3739 | 133735587 | 133898352 | − | seg_445 | 133779700 | 133780700 | PLAC1 | HPRT1 = HPRT |
| ENST00000473897.1 | 3740 | 133700540 | 133898293 | − | seg_445 | 133779700 | 133780700 | PLAC1 | HPRT1 = HPRT |
| ENST00000390132.2 | 3741 | 133811215 | 133811301 | + | seg_446 | 133810300 | 133811300 | PLAC1 | HPRT1 = HPRT |
| ENST00000476971.1 | 3742 | 133699907 | 133867666 | − | seg_446 | 133810300 | 133811300 | PLAC1 | HPRT1 = HPRT |
| ENST00000466797.1 | 3743 | 133735587 | 133898352 | − | seg_446 | 133810300 | 133811300 | PLAC1 | HPRT1 = HPRT |
| ENST00000473897.1 | 3744 | 133700540 | 133898293 | − | seg_446 | 133810300 | 133811300 | PLAC1 | HPRT1 = HPRT |
| ENST00000414371.2 | 3745 | 133930819 | 133957005 | + | seg_447 | 133937450 | 133939700 | FAM122C | HPRT1 = HPRT |
| ENST00000463842.1 | 3746 | 133979255 | 133988320 | + | seg_448 | 133984050 | 133985200 | FAM122C | HPRT1 = HPRT |
| ENST00000460216.1 | 3747 | 133973203 | 133988213 | + | seg_448 | 133984050 | 133985200 | FAM122C | HPRT1 = HPRT |
| ENST00000470657.1 | 3748 | 133941283 | 133986921 | + | seg_448 | 133984050 | 133985200 | FAM122C | HPRT1 = HPRT |
| ENST00000370784.4 | 3749 | 133941223 | 133988640 | + | seg_448 | 133984050 | 133985200 | FAM122C | HPRT1 = HPRT |
| ENST00000370785.3 | 3750 | 133941224 | 133988621 | + | seg_448 | 133984050 | 133985200 | FAM122C | HPRT1 = HPRT |
| ENST00000445123.1 | 3751 | 133941267 | 133988640 | + | seg_448 | 133984050 | 133985200 | FAM122C | HPRT1 = HPRT |
| ENST00000538706.1 | 3752 | 134155544 | 134156172 | − | seg_454 | 134153750 | 134155600 | FAM127C | HPRT1 = HPRT |
| ENST00000391440.1 | 3753 | 134154543 | 134156559 | − | seg_454 | 134153750 | 134155600 | FAM127C | HPRT1 = HPRT |
| ENST00000455568.1 | 3754 | 134229143 | 134232388 | − | seg_455 | 134232350 | 134234600 | FAM127B | HPRT1 = HPRT |
| ENST00000433425.1 | 3755 | 134230877 | 134232654 | − | seg_455 | 134232350 | 134234600 | FAM127B | HPRT1 = HPRT |
| ENST00000535837.1 | 3756 | 134232427 | 134232630 | − | seg_455 | 134232350 | 134234600 | FAM127B | HPRT1 = HPRT |
| ENST00000454984.1 | 3757 | 134269077 | 134269698 | − | seg_457 | 134267150 | 134272000 | CXorf48 | HPRT1 = HPRT |
| ENST00000461224.1 | 3758 | 134317162 | 134317234 | − | seg_458 | 134313200 | 134319300 | CXorf48 | HPRT1 = HPRT |
| ENST00000441416.1 | 3759 | 134314179 | 134328610 | − | seg_458 | 134313200 | 134319300 | CXorf48 | HPRT1 = HPRT |
| ENST00000441416.1 | 3760 | 134314179 | 134328610 | − | seg_459 | 134322900 | 134324600 | CXorf48 | HPRT1 = HPRT |
| ENST00000445718.1 | 3761 | 134335662 | 134349163 | + | seg_460 | 134342600 | 134344200 | CXorf48 | HPRT1 = HPRT |
| ENST00000445718.1 | 3762 | 134335662 | 134349163 | + | seg_461 | 134345900 | 134351900 | CXorf48 | HPRT1 = HPRT |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000442950.1 | 3763 | 134370740 | 134371295 | + | seg_462 | 134368650 | 134375600 | ZNF75D | HPRT1 = HPRT |
| ENST00000494295.1 | 3764 | 134382867 | 134478012 | − | seg_463 | 134383050 | 134384100 | ZNF75D | HPRT1 = HPRT |
| ENST00000417443.1 | 3765 | 134555868 | 134559682 | + | seg_464 | 134557050 | 134558100 | ZNF449 | HPRT1 = HPRT |
| ENST00000426910.1 | 3766 | 134566885 | 134572559 | + | seg_465 | 134567350 | 134570450 | DDX26B | HPRT1 = HPRT |
| ENST00000537770.1 | 3767 | 134975885 | 134995175 | + | seg_471 | 134974900 | 134976100 | SAGE1 | HPRT1 = HPRT |
| ENST00000324447.3 | 3768 | 134971374 | 134995175 | + | seg_471 | 134974900 | 134976100 | SAGE1 | HPRT1 = HPRT |
| ENST00000535938.1 | 3769 | 134975785 | 134995219 | + | seg_471 | 134974900 | 134976100 | SAGE1 | HPRT1 = HPRT |
| ENST00000536581.1 | 3770 | 135229692 | 135292637 | + | seg_477 | 135230550 | 135237050 | FHL1 | HPRT1 = HPRT |
| ENST00000420362.1 | 3771 | 135229825 | 135290725 | + | seg_477 | 135230550 | 135237050 | FHL1 | HPRT1 = HPRT |
| ENST00000370690.3 | 3772 | 135229624 | 135293518 | + | seg_477 | 135230550 | 135237050 | FHL1 | HPRT1 = HPRT |
| ENST00000535737.1 | 3773 | 135230737 | 135293518 | + | seg_477 | 135230550 | 135237050 | FHL1 | HPRT1 = HPRT |
| ENST00000394155.2 | 3774 | 135229559 | 135293518 | + | seg_477 | 135230550 | 135237050 | FHL1 | HPRT1 = HPRT |
| ENST00000458357.1 | 3775 | 135230270 | 135290084 | + | seg_477 | 135230550 | 135237050 | FHL1 | HPRT1 = HPRT |
| ENST00000536581.1 | 3776 | 135229692 | 135292637 | + | seg_478 | 135238700 | 135240650 | FHL1 | HPRT1 = HPRT |
| ENST00000420362.1 | 3777 | 135229825 | 135290725 | + | seg_478 | 135238700 | 135240650 | FHL1 | HPRT1 = HPRT |
| ENST00000370690.3 | 3778 | 135229624 | 135293518 | + | seg_478 | 135238700 | 135240650 | FHL1 | HPRT1 = HPRT |
| ENST00000535737.1 | 3779 | 135230737 | 135293518 | + | seg_478 | 135238700 | 135240650 | FHL1 | HPRT1 = HPRT |
| ENST00000394155.2 | 3780 | 135229559 | 135293518 | + | seg_478 | 135238700 | 135240650 | FHL1 | HPRT1 = HPRT |
| ENST00000458357.1 | 3781 | 135230270 | 135290084 | + | seg_478 | 135238700 | 135240650 | FHL1 | HPRT1 = HPRT |
| ENST00000345434.3 | 3782 | 135252085 | 135293518 | + | seg_479 | 135247650 | 135253150 | FHL1 | HPRT1 = HPRT |
| ENST00000536581.1 | 3783 | 135229692 | 135292637 | + | seg_479 | 135247650 | 135253150 | FHL1 | HPRT1 = HPRT |
| ENST00000434885.1 | 3784 | 135250353 | 135290734 | + | seg_479 | 135247650 | 135253150 | FHL1 | HPRT1 = HPRT |
| ENST00000543669.1 | 3785 | 135251455 | 135293518 | + | seg_479 | 135247650 | 135253150 | FHL1 | HPRT1 = HPRT |
| ENST00000449474.1 | 3786 | 135252050 | 135290042 | + | seg_479 | 135247650 | 135253150 | FHL1 | HPRT1 = HPRT |
| ENST00000420362.1 | 3787 | 135229825 | 135290725 | + | seg_479 | 135247650 | 135253150 | FHL1 | HPRT1 = HPRT |
| ENST00000452016.1 | 3788 | 135249163 | 135290734 | + | seg_479 | 135247650 | 135253150 | FHL1 | HPRT1 = HPRT |
| ENST00000456218.2 | 3789 | 135251962 | 135293518 | + | seg_479 | 135247650 | 135253150 | FHL1 | HPRT1 = HPRT |
| ENST00000394153.2 | 3790 | 135251796 | 135293518 | + | seg_479 | 135247650 | 135253150 | FHL1 | HPRT1 = HPRT |
| ENST00000370690.3 | 3791 | 135229624 | 135293518 | + | seg_479 | 135247650 | 135253150 | FHL1 | HPRT1 = HPRT |
| ENST00000535737.1 | 3792 | 135230737 | 135293518 | + | seg_479 | 135247650 | 135253150 | FHL1 | HPRT1 = HPRT |
| ENST00000456445.1 | 3793 | 135251835 | 135290729 | + | seg_479 | 135247650 | 135253150 | FHL1 | HPRT1 = HPRT |
| ENST00000394155.2 | 3794 | 135229559 | 135293518 | + | seg_479 | 135247650 | 135253150 | FHL1 | HPRT1 = HPRT |
| ENST00000458357.1 | 3795 | 135230270 | 135290084 | + | seg_479 | 135247650 | 135253150 | FHL1 | HPRT1 = HPRT |
| ENST00000345434.3 | 3796 | 135252085 | 135293518 | + | seg_480 | 135255700 | 135257250 | FHL1 | HPRT1 = HPRT |
| ENST00000536581.1 | 3797 | 135229692 | 135292637 | + | seg_480 | 135255700 | 135257250 | FHL1 | HPRT1 = HPRT |
| ENST00000434885.1 | 3798 | 135250353 | 135290734 | + | seg_480 | 135255700 | 135257250 | FHL1 | HPRT1 = HPRT |
| ENST00000543669.1 | 3799 | 135251455 | 135293518 | + | seg_480 | 135255700 | 135257250 | FHL1 | HPRT1 = HPRT |
| ENST00000449474.1 | 3800 | 135252050 | 135290042 | + | seg_480 | 135255700 | 135257250 | FHL1 | HPRT1 = HPRT |
| ENST00000420362.1 | 3801 | 135229825 | 135290725 | + | seg_480 | 135255700 | 135257250 | FHL1 | HPRT1 = HPRT |
| ENST00000452016.1 | 3802 | 135249163 | 135290734 | + | seg_480 | 135255700 | 135257250 | FHL1 | HPRT1 = HPRT |
| ENST00000456218.2 | 3803 | 135251962 | 135293518 | + | seg_480 | 135255700 | 135257250 | FHL1 | HPRT1 = HPRT |
| ENST00000394153.2 | 3804 | 135251796 | 135293518 | + | seg_480 | 135255700 | 135257250 | FHL1 | HPRT1 = HPRT |
| ENST00000370690.3 | 3805 | 135229624 | 135293518 | + | seg_480 | 135255700 | 135257250 | FHL1 | HPRT1 = HPRT |
| ENST00000535737.1 | 3806 | 135230737 | 135293518 | + | seg_480 | 135255700 | 135257250 | FHL1 | HPRT1 = HPRT |
| ENST00000456445.1 | 3807 | 135251835 | 135290729 | + | seg_480 | 135255700 | 135257250 | FHL1 | HPRT1 = HPRT |
| ENST00000394155.2 | 3808 | 135229559 | 135293518 | + | seg_480 | 135255700 | 135257250 | FHL1 | HPRT1 = HPRT |
| ENST00000458357.1 | 3809 | 135230270 | 135290084 | + | seg_480 | 135255700 | 135257250 | FHL1 | HPRT1 = HPRT |
| ENST00000345434.3 | 3810 | 135252085 | 135293518 | + | seg_481 | 135261000 | 135263500 | FHL1 | HPRT1 = HPRT |
| ENST00000536581.1 | 3811 | 135229692 | 135292637 | + | seg_481 | 135261000 | 135263500 | FHL1 | HPRT1 = HPRT |
| ENST00000434885.1 | 3812 | 135250353 | 135290734 | + | seg_481 | 135261000 | 135263500 | FHL1 | HPRT1 = HPRT |
| ENST00000543669.1 | 3813 | 135251455 | 135293518 | + | seg_481 | 135261000 | 135263500 | FHL1 | HPRT1 = HPRT |
| ENST00000449474.1 | 3814 | 135252050 | 135290042 | + | seg_481 | 135261000 | 135263500 | FHL1 | HPRT1 = HPRT |
| ENST00000420362.1 | 3815 | 135229825 | 135290725 | + | seg_481 | 135261000 | 135263500 | FHL1 | HPRT1 = HPRT |
| ENST00000452016.1 | 3816 | 135249163 | 135290734 | + | seg_481 | 135261000 | 135263500 | FHL1 | HPRT1 = HPRT |
| ENST00000456218.2 | 3817 | 135251962 | 135293518 | + | seg_481 | 135261000 | 135263500 | FHL1 | HPRT1 = HPRT |
| ENST00000394153.2 | 3818 | 135251796 | 135293518 | + | seg_481 | 135261000 | 135263500 | FHL1 | HPRT1 = HPRT |
| ENST00000370690.3 | 3819 | 135229624 | 135293518 | + | seg_481 | 135261000 | 135263500 | FHL1 | HPRT1 = HPRT |
| ENST00000535737.1 | 3820 | 135230737 | 135293518 | + | seg_481 | 135261000 | 135263500 | FHL1 | HPRT1 = HPRT |
| ENST00000456445.1 | 3821 | 135251835 | 135290729 | + | seg_481 | 135261000 | 135263500 | FHL1 | HPRT1 = HPRT |
| ENST00000394155.2 | 3822 | 135229559 | 135293518 | + | seg_481 | 135261000 | 135263500 | FHL1 | HPRT1 = HPRT |
| ENST00000458357.1 | 3823 | 135230270 | 135290084 | + | seg_481 | 135261000 | 135263500 | FHL1 | HPRT1 = HPRT |
| ENST00000542704.1 | 3824 | 135279212 | 135292265 | + | seg_482 | 135278300 | 135279400 | FHL1 | HPRT1 = HPRT |
| ENST00000477204.1 | 3825 | 135279222 | 135289710 | + | seg_482 | 135278300 | 135279400 | FHL1 | HPRT1 = HPRT |
| ENST00000370676.3 | 3826 | 135279185 | 135292226 | + | seg_482 | 135278300 | 135279400 | FHL1 | HPRT1 = HPRT |
| ENST00000539015.1 | 3827 | 135278913 | 135293518 | + | seg_482 | 135278300 | 135279400 | FHL1 | HPRT1 = HPRT |
| ENST00000370683.1 | 3828 | 135278932 | 135293518 | + | seg_482 | 135278300 | 135279400 | FHL1 | HPRT1 = HPRT |
| ENST00000345434.3 | 3829 | 135252085 | 135293518 | + | seg_482 | 135278300 | 135279400 | FHL1 | HPRT1 = HPRT |
| ENST00000536581.1 | 3830 | 135229692 | 135292637 | + | seg_482 | 135278300 | 135279400 | FHL1 | HPRT1 = HPRT |
| ENST00000434885.1 | 3831 | 135250353 | 135290734 | + | seg_482 | 135278300 | 135279400 | FHL1 | HPRT1 = HPRT |
| ENST00000543669.1 | 3832 | 135251455 | 135293518 | + | seg_482 | 135278300 | 135279400 | FHL1 | HPRT1 = HPRT |
| ENST00000449474.1 | 3833 | 135252050 | 135290042 | + | seg_482 | 135278300 | 135279400 | FHL1 | HPRT1 = HPRT |
| ENST00000420362.1 | 3834 | 135229825 | 135290725 | + | seg_482 | 135278300 | 135279400 | FHL1 | HPRT1 = HPRT |
| ENST00000452016.1 | 3835 | 135249163 | 135290734 | + | seg_482 | 135278300 | 135279400 | FHL1 | HPRT1 = HPRT |
| ENST00000456218.2 | 3836 | 135251962 | 135293518 | + | seg_482 | 135278300 | 135279400 | FHL1 | HPRT1 = HPRT |
| ENST00000394153.2 | 3837 | 135251796 | 135293518 | + | seg_482 | 135278300 | 135279400 | FHL1 | HPRT1 = HPRT |
| ENST00000370690.3 | 3838 | 135229624 | 135293518 | + | seg_482 | 135278300 | 135279400 | FHL1 | HPRT1 = HPRT |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000535737.1 | 3839 | 135230737 | 135293518 | + | seg_482 | 135278300 | 135279400 | FHL1 | HPRT1 = HPRT |
| ENST00000456445.1 | 3840 | 135251835 | 135290729 | + | seg_482 | 135278300 | 135279400 | FHL1 | HPRT1 = HPRT |
| ENST00000394155.2 | 3841 | 135229559 | 135293518 | + | seg_482 | 135278300 | 135279400 | FHL1 | HPRT1 = HPRT |
| ENST00000458357.1 | 3842 | 135230270 | 135290084 | + | seg_482 | 135278300 | 135279400 | FHL1 | HPRT1 = HPRT |
| ENST00000542704.1 | 3843 | 135279212 | 135292265 | + | seg_483 | 135280500 | 135283000 | FHL1 | HPRT1 = HPRT |
| ENST00000477204.1 | 3844 | 135279222 | 135289710 | + | seg_483 | 135280500 | 135283000 | FHL1 | HPRT1 = HPRT |
| ENST00000370676.3 | 3845 | 135279185 | 135292226 | + | seg_483 | 135280500 | 135283000 | FHL1 | HPRT1 = HPRT |
| ENST00000539015.1 | 3846 | 135278913 | 135293518 | + | seg_483 | 135280500 | 135283000 | FHL1 | HPRT1 = HPRT |
| ENST00000370683.1 | 3847 | 135278932 | 135293518 | + | seg_483 | 135280500 | 135283000 | FHL1 | HPRT1 = HPRT |
| ENST00000345434.3 | 3848 | 135252085 | 135293518 | + | seg_483 | 135280500 | 135283000 | FHL1 | HPRT1 = HPRT |
| ENST00000536581.1 | 3849 | 135229692 | 135292637 | + | seg_483 | 135280500 | 135283000 | FHL1 | HPRT1 = HPRT |
| ENST00000434885.1 | 3850 | 135250353 | 135290734 | + | seg_483 | 135280500 | 135283000 | FHL1 | HPRT1 = HPRT |
| ENST00000543669.1 | 3851 | 135251455 | 135293518 | + | seg_483 | 135280500 | 135283000 | FHL1 | HPRT1 = HPRT |
| ENST00000449474.1 | 3852 | 135252050 | 135290042 | + | seg_483 | 135280500 | 135283000 | FHL1 | HPRT1 = HPRT |
| ENST00000420362.1 | 3853 | 135229825 | 135290725 | + | seg_483 | 135280500 | 135283000 | FHL1 | HPRT1 = HPRT |
| ENST00000452016.1 | 3854 | 135249163 | 135290734 | + | seg_483 | 135280500 | 135283000 | FHL1 | HPRT1 = HPRT |
| ENST00000456218.2 | 3855 | 135251962 | 135293518 | + | seg_483 | 135280500 | 135283000 | FHL1 | HPRT1 = HPRT |
| ENST00000394153.2 | 3856 | 135251796 | 135293518 | + | seg_483 | 135280500 | 135283000 | FHL1 | HPRT1 = HPRT |
| ENST00000370690.3 | 3857 | 135229624 | 135293518 | + | seg_483 | 135280500 | 135283000 | FHL1 | HPRT1 = HPRT |
| ENST00000535737.1 | 3858 | 135230737 | 135293518 | + | seg_483 | 135280500 | 135283000 | FHL1 | HPRT1 = HPRT |
| ENST00000456445.1 | 3859 | 135251835 | 135290729 | + | seg_483 | 135280500 | 135283000 | FHL1 | HPRT1 = HPRT |
| ENST00000394155.2 | 3860 | 135229559 | 135293518 | + | seg_483 | 135280500 | 135283000 | FHL1 | HPRT1 = HPRT |
| ENST00000458357.1 | 3861 | 135230270 | 135290084 | + | seg_483 | 135280500 | 135283000 | FHL1 | HPRT1 = HPRT |
| ENST00000477080.1 | 3862 | 135287068 | 135289820 | + | seg_484 | 135286200 | 135288850 | FHL1 | HPRT1 = HPRT |
| ENST00000370674.1 | 3863 | 135286880 | 135292113 | + | seg_484 | 135286200 | 135288850 | FHL1 | HPRT1 = HPRT |
| ENST00000542704.1 | 3864 | 135279212 | 135292265 | + | seg_484 | 135286200 | 135288850 | FHL1 | HPRT1 = HPRT |
| ENST00000477204.1 | 3865 | 135279222 | 135289710 | + | seg_484 | 135286200 | 135288850 | FHL1 | HPRT1 = HPRT |
| ENST00000370676.3 | 3866 | 135279185 | 135292226 | + | seg_484 | 135286200 | 135288850 | FHL1 | HPRT1 = HPRT |
| ENST00000539015.1 | 3867 | 135278913 | 135293518 | + | seg_484 | 135286200 | 135288850 | FHL1 | HPRT1 = HPRT |
| ENST00000370683.1 | 3868 | 135278932 | 135293518 | + | seg_484 | 135286200 | 135288850 | FHL1 | HPRT1 = HPRT |
| ENST00000345434.3 | 3869 | 135252085 | 135293518 | + | seg_484 | 135286200 | 135288850 | FHL1 | HPRT1 = HPRT |
| ENST00000536581.1 | 3870 | 135229692 | 135292637 | + | seg_484 | 135286200 | 135288850 | FHL1 | HPRT1 = HPRT |
| ENST00000434885.1 | 3871 | 135250353 | 135290734 | + | seg_484 | 135286200 | 135288850 | FHL1 | HPRT1 = HPRT |
| ENST00000543669.1 | 3872 | 135251455 | 135293518 | + | seg_484 | 135286200 | 135288850 | FHL1 | HPRT1 = HPRT |
| ENST00000449474.1 | 3873 | 135252050 | 135290042 | + | seg_484 | 135286200 | 135288850 | FHL1 | HPRT1 = HPRT |
| ENST00000420362.1 | 3874 | 135229825 | 135290725 | + | seg_484 | 135286200 | 135288850 | FHL1 | HPRT1 = HPRT |
| ENST00000452016.1 | 3875 | 135249163 | 135290734 | + | seg_484 | 135286200 | 135288850 | FHL1 | HPRT1 = HPRT |
| ENST00000456218.2 | 3876 | 135251962 | 135293518 | + | seg_484 | 135286200 | 135288850 | FHL1 | HPRT1 = HPRT |
| ENST00000394153.2 | 3877 | 135251796 | 135293518 | + | seg_484 | 135286200 | 135288850 | FHL1 | HPRT1 = HPRT |
| ENST00000370690.3 | 3878 | 135229624 | 135293518 | + | seg_484 | 135286200 | 135288850 | FHL1 | HPRT1 = HPRT |
| ENST00000535737.1 | 3879 | 135230737 | 135293518 | + | seg_484 | 135286200 | 135288850 | FHL1 | HPRT1 = HPRT |
| ENST00000456445.1 | 3880 | 135251835 | 135290729 | + | seg_484 | 135286200 | 135288850 | FHL1 | HPRT1 = HPRT |
| ENST00000394155.2 | 3881 | 135229559 | 135293518 | + | seg_484 | 135286200 | 135288850 | FHL1 | HPRT1 = HPRT |
| ENST00000458357.1 | 3882 | 135230270 | 135290084 | + | seg_484 | 135286200 | 135288850 | FHL1 | HPRT1 = HPRT |
| ENST00000370648.3 | 3883 | 135570046 | 135575939 | + | seg_485 | 135570450 | 135571950 | BRS3 | HPRT1 = HPRT |
| ENST00000370648.3 | 3884 | 135570046 | 135575939 | + | seg_486 | 135573250 | 135575700 | BRS3 | HPRT1 = HPRT |
| ENST00000440515.1 | 3885 | 135618287 | 135638655 | + | seg_488 | 135623250 | 135624500 | VGLL1 | HPRT1 = HPRT |
| ENST00000370634.3 | 3886 | 135614311 | 135638966 | + | seg_488 | 135623250 | 135624500 | VGLL1 | HPRT1 = HPRT |
| ENST00000456412.1 | 3887 | 135618354 | 135638966 | + | seg_488 | 135623250 | 135624500 | VGLL1 | HPRT1 = HPRT |
| ENST00000430688.2 | 3888 | 135614311 | 135638965 | + | seg_488 | 135623250 | 135624500 | VGLL1 | HPRT1 = HPRT |
| ENST00000470358.1 | 3889 | 135632601 | 135638966 | + | seg_489 | 135635700 | 135637100 | VGLL1 | HPRT1 = HPRT |
| ENST00000440515.1 | 3890 | 135618287 | 135638655 | + | seg_489 | 135635700 | 135637100 | VGLL1 | HPRT1 = HPRT |
| ENST00000370634.3 | 3891 | 135614311 | 135638966 | + | seg_489 | 135635700 | 135637100 | VGLL1 | HPRT1 = HPRT |
| ENST00000456412.1 | 3892 | 135618354 | 135638966 | + | seg_489 | 135635700 | 135637100 | VGLL1 | HPRT1 = HPRT |
| ENST00000430688.2 | 3893 | 135614311 | 135638965 | + | seg_489 | 135635700 | 135637100 | VGLL1 | HPRT1 = HPRT |
| ENST00000370628.2 | 3894 | 135730386 | 135742549 | + | seg_492 | 135736900 | 135741150 | CD40LG | HPRT1 = HPRT |
| ENST00000370629.2 | 3895 | 135730352 | 135742549 | + | seg_492 | 135736900 | 135741150 | CD40LG | HPRT1 = HPRT |
| ENST00000298110.1 | 3896 | 136112307 | 136113833 | − | seg_493 | 136111350 | 136117550 | GPR101 | F9 |
| ENST00000287538.5 | 3897 | 136648301 | 136653744 | + | seg_497 | 136650650 | 136652500 | ZIC3 | F9 |
| ENST00000478471.1 | 3898 | 136650964 | 136652154 | + | seg_497 | 136650650 | 136652500 | ZIC3 | F9 |
| ENST00000370606.3 | 3899 | 136648677 | 136659850 | + | seg_497 | 136650650 | 136652500 | ZIC3 | F9 |
| ENST00000545711.1 | 3900 | 138638452 | 138638784 | − | seg_498 | 138637250 | 138639450 | F9 | F9 |
| ENST00000218099.2 | 3901 | 138612917 | 138645617 | + | seg_498 | 138637250 | 138639450 | F9 | F9 |
| ENST00000394090.2 | 3902 | 138612924 | 138644230 | + | seg_498 | 138637250 | 138639450 | F9 | F9 |
| ENST00000519895.1 | 3903 | 138664456 | 138790386 | − | seg_499 | 138772500 | 138776000 | MCF2 | F9 |
| ENST00000520602.1 | 3904 | 138663929 | 138774315 | − | seg_499 | 138772500 | 138776000 | MCF2 | F9 |
| ENST00000370578.4 | 3905 | 138663930 | 138774284 | − | seg_499 | 138772500 | 138776000 | MCF2 | F9 |
| ENST00000414978.1 | 3906 | 138663930 | 138790375 | − | seg_499 | 138772500 | 138776000 | MCF2 | F9 |
| ENST00000485626.1 | 3907 | 138884461 | 139027435 | − | seg_500 | 139024650 | 139025850 | ATP11C | F9 |
| ENST00000543618.1 | 3908 | 148678217 | 148683886 | − | seg_503 | 148673150 | 148680900 | HSFX2 | MTM1 |
| ENST00000522155.1 | 3909 | 148674868 | 148676436 | − | seg_503 | 148673150 | 148680900 | HSFX2 | MTM1 |
| ENST00000524178.1 | 3910 | 148674172 | 148676974 | − | seg_503 | 148673150 | 148680900 | HSFX2 | MTM1 |
| ENST00000519015.1 | 3911 | 148678217 | 148683886 | − | seg_503 | 148673150 | 148680900 | HSFX2 | MTM1 |
| ENST00000316916.8 | 3912 | 148678216 | 148713568 | − | seg_503 | 148673150 | 148680900 | HSFX2 | MTM1 |
| ENST00000502858.2 | 3913 | 148679625 | 148690438 | − | seg_503 | 148673150 | 148680900 | HSFX2 | MTM1 |
| ENST00000536359.1 | 3914 | 148678216 | 148713487 | − | seg_503 | 148673150 | 148680900 | HSFX2 | MTM1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000513505.2 | 3915 | 148678216 | 148713402 | − | seg_503 | 148673150 | 148680900 | HSFX2 | MTM1 |
| ENST00000543618.1 | 3916 | 148678217 | 148683886 | − | seg_504 | 148682650 | 148684100 | HSFX2 | MTM1 |
| ENST00000519015.1 | 3917 | 148678217 | 148683886 | − | seg_504 | 148682650 | 148684100 | HSFX2 | MTM1 |
| ENST00000316916.8 | 3918 | 148678216 | 148713568 | − | seg_504 | 148682650 | 148684100 | HSFX2 | MTM1 |
| ENST00000502858.2 | 3919 | 148679625 | 148690438 | − | seg_504 | 148682650 | 148684100 | HSFX2 | MTM1 |
| ENST00000536359.1 | 3920 | 148678216 | 148713487 | − | seg_504 | 148682650 | 148684100 | HSFX2 | MTM1 |
| ENST00000513505.2 | 3921 | 148678216 | 148713402 | − | seg_504 | 148682650 | 148684100 | HSFX2 | MTM1 |
| ENST00000502618.1 | 3922 | 148681969 | 148693146 | − | seg_504 | 148682650 | 148684100 | HSFX2 | MTM1 |
| ENST00000316916.8 | 3923 | 148678216 | 148713568 | − | seg_505 | 148711650 | 148713850 | TMEM185A | MTM1 |
| ENST00000502900.1 | 3924 | 148686838 | 148713403 | − | seg_505 | 148711650 | 148713850 | TMEM185A | MTM1 |
| ENST00000536359.1 | 3925 | 148678216 | 148713487 | − | seg_505 | 148711650 | 148713850 | TMEM185A | MTM1 |
| ENST00000511776.1 | 3926 | 148690379 | 148713365 | − | seg_505 | 148711650 | 148713850 | TMEM185A | MTM1 |
| ENST00000513505.2 | 3927 | 148678216 | 148713402 | − | seg_505 | 148711650 | 148713850 | TMEM185A | MTM1 |
| ENST00000507237.1 | 3928 | 148685375 | 148713381 | − | seg_505 | 148711650 | 148713850 | TMEM185A | MTM1 |
| ENST00000428022.1 | 3929 | 148848815 | 148854483 | + | seg_509 | 148852950 | 148862150 | HSFX1 | MTM1 |
| ENST00000370416.4 | 3930 | 148855726 | 148858525 | + | seg_509 | 148852950 | 148862150 | HSFX1 | MTM1 |
| ENST00000524311.1 | 3931 | 148850558 | 148853029 | + | seg_509 | 148852950 | 148862150 | HSFX1 | MTM1 |
| ENST00000458274.1 | 3932 | 149107957 | 149109050 | + | seg_510 | 149108000 | 149109350 | CXorf40B | MTM1 |
| ENST00000444489.1 | 3933 | 149108374 | 149185018 | + | seg_510 | 149108000 | 149109350 | CXorf40B | MTM1 |
| ENST00000449111.1 | 3934 | 149106846 | 149392815 | + | seg_510 | 149108000 | 149109350 | CXorf40B | MTM1 |
| ENST00000468306.1 | 3935 | 149529689 | 149638367 | + | seg_511 | 149530200 | 149534000 | MAMLD1 | MTM1 |
| ENST00000432680.2 | 3936 | 149531686 | 149681395 | + | seg_511 | 149530200 | 149534000 | MAMLD1 | MTM1 |
| ENST00000445612.2 | 3937 | 149529836 | 149680503 | + | seg_511 | 149530200 | 149534000 | MAMLD1 | MTM1 |
| ENST00000370401.2 | 3938 | 149531551 | 149682448 | + | seg_511 | 149530200 | 149534000 | MAMLD1 | MTM1 |
| ENST00000426613.2 | 3939 | 149613720 | 149682448 | + | seg_512 | 149646300 | 149649450 | MAMLD1 | MTM1 |
| ENST00000455522.2 | 3940 | 149639280 | 149680512 | + | seg_512 | 149646300 | 149649450 | MAMLD1 | MTM1 |
| ENST00000262858.5 | 3941 | 149613720 | 149682448 | + | seg_512 | 149646300 | 149649450 | MAMLD1 | MTM1 |
| ENST00000432680.2 | 3942 | 149531686 | 149681395 | + | seg_512 | 149646300 | 149649450 | MAMLD1 | MTM1 |
| ENST00000445612.2 | 3943 | 149529836 | 149680503 | + | seg_512 | 149646300 | 149649450 | MAMLD1 | MTM1 |
| ENST00000370401.2 | 3944 | 149531551 | 149682448 | + | seg_512 | 149646300 | 149649450 | MAMLD1 | MTM1 |
| ENST00000426613.2 | 3945 | 149613720 | 149682448 | + | seg_513 | 149650500 | 149652300 | MAMLD1 | MTM1 |
| ENST00000455522.2 | 3946 | 149639280 | 149680512 | + | seg_513 | 149650500 | 149652300 | MAMLD1 | MTM1 |
| ENST00000262858.5 | 3947 | 149613720 | 149682448 | + | seg_513 | 149650500 | 149652300 | MAMLD1 | MTM1 |
| ENST00000432680.2 | 3948 | 149531686 | 149681395 | + | seg_513 | 149650500 | 149652300 | MAMLD1 | MTM1 |
| ENST00000445612.2 | 3949 | 149529836 | 149680503 | + | seg_513 | 149650500 | 149652300 | MAMLD1 | MTM1 |
| ENST00000370401.2 | 3950 | 149531551 | 149682448 | + | seg_513 | 149650500 | 149652300 | MAMLD1 | MTM1 |
| ENST00000426613.2 | 3951 | 149613720 | 149682448 | + | seg_514 | 149673500 | 149676800 | MAMLD1 | MTM1 |
| ENST00000455522.2 | 3952 | 149639280 | 149680512 | + | seg_514 | 149673500 | 149676800 | MAMLD1 | MTM1 |
| ENST00000262858.5 | 3953 | 149613720 | 149682448 | + | seg_514 | 149673500 | 149676800 | MAMLD1 | MTM1 |
| ENST00000432680.2 | 3954 | 149531686 | 149681395 | + | seg_514 | 149673500 | 149676800 | MAMLD1 | MTM1 |
| ENST00000445612.2 | 3955 | 149529836 | 149680503 | + | seg_514 | 149673500 | 149676800 | MAMLD1 | MTM1 |
| ENST00000370401.2 | 3956 | 149531551 | 149682448 | + | seg_514 | 149673500 | 149676800 | MAMLD1 | MTM1 |
| ENST00000464149.1 | 3957 | 149677595 | 149682439 | + | seg_515 | 149680400 | 149683100 | MAMLD1 | MTM1 |
| ENST00000426613.2 | 3958 | 149613720 | 149682448 | + | seg_515 | 149680400 | 149683100 | MAMLD1 | MTM1 |
| ENST00000455522.2 | 3959 | 149639280 | 149680512 | + | seg_515 | 149680400 | 149683100 | MAMLD1 | MTM1 |
| ENST00000262858.5 | 3960 | 149613720 | 149682448 | + | seg_515 | 149680400 | 149683100 | MAMLD1 | MTM1 |
| ENST00000432680.2 | 3961 | 149531686 | 149681395 | + | seg_515 | 149680400 | 149683100 | MAMLD1 | MTM1 |
| ENST00000445612.2 | 3962 | 149529836 | 149680503 | + | seg_515 | 149680400 | 149683100 | MAMLD1 | MTM1 |
| ENST00000370401.2 | 3963 | 149531551 | 149682448 | + | seg_515 | 149680400 | 149683100 | MAMLD1 | MTM1 |
| ENST00000454196.1 | 3964 | 150343664 | 150346308 | − | seg_521 | 150341400 | 150347800 | GPR50 | MTM1 |
| ENST00000535473.1 | 3965 | 150345056 | 150348932 | − | seg_521 | 150341400 | 150347800 | GPR50 | MTM1 |
| ENST00000218316.3 | 3966 | 150345125 | 150349937 | + | seg_521 | 150341400 | 150347800 | GPR50 | MTM1 |
| ENST00000458074.1 | 3967 | 150394701 | 150396187 | − | seg_522 | 150394350 | 150398150 | GPR50 | MTM1 |
| ENST00000464219.1 | 3968 | 150732201 | 150844987 | + | seg_525 | 150765850 | 150766900 | PASD1 | MTM1 |
| ENST00000370357.4 | 3969 | 150732094 | 150845211 | + | seg_525 | 150765850 | 150766900 | PASD1 | MTM1 |
| ENST00000413236.1 | 3970 | 150780136 | 150839668 | + | seg_526 | 150827300 | 150828750 | PRRG3 | MTM1 |
| ENST00000464219.1 | 3971 | 150732201 | 150844987 | + | seg_526 | 150827300 | 150828750 | PRRG3 | MTM1 |
| ENST00000370357.4 | 3972 | 150732094 | 150845211 | + | seg_526 | 150827300 | 150828750 | PRRG3 | MTM1 |
| ENST00000448324.1 | 3973 | 150869023 | 150873975 | + | seg_527 | 150871800 | 150872900 | PRRG3 | MTM1 |
| ENST00000370353.3 | 3974 | 150866779 | 150874396 | + | seg_527 | 150871800 | 150872900 | PRRG3 | MTM1 |
| ENST00000329903.4 | 3975 | 150906923 | 150913776 | + | seg_528 | 150911500 | 150912750 | CNGA2 | MTM1 |
| ENST00000535156.1 | 3976 | 152082986 | 152142024 | + | seg_538 | 152101250 | 152104800 | ZNF185 | ABCD1 |
| ENST00000539731.1 | 3977 | 152082986 | 152142024 | + | seg_538 | 152101250 | 152104800 | ZNF185 | ABCD1 |
| ENST00000447088.1 | 3978 | 152088893 | 152106707 | + | seg_538 | 152101250 | 152104800 | ZNF185 | ABCD1 |
| ENST00000318504.7 | 3979 | 152082986 | 152142024 | + | seg_538 | 152101250 | 152104800 | ZNF185 | ABCD1 |
| ENST00000436731.1 | 3980 | 152100283 | 152128354 | + | seg_538 | 152101250 | 152104800 | ZNF185 | ABCD1 |
| ENST00000370270.1 | 3981 | 152086665 | 152142025 | + | seg_538 | 152101250 | 152104800 | ZNF185 | ABCD1 |
| ENST00000324823.6 | 3982 | 152082986 | 152142024 | + | seg_538 | 152101250 | 152104800 | ZNF185 | ABCD1 |
| ENST00000426821.1 | 3983 | 152087545 | 152142017 | + | seg_538 | 152101250 | 152104800 | ZNF185 | ABCD1 |
| ENST00000447792.1 | 3984 | 152089251 | 152106707 | + | seg_538 | 152101250 | 152104800 | ZNF185 | ABCD1 |
| ENST00000449285.2 | 3985 | 152082986 | 152142024 | + | seg_538 | 152101250 | 152104800 | ZNF185 | ABCD1 |
| ENST00000318529.8 | 3986 | 152086409 | 152142024 | + | seg_538 | 152101250 | 152104800 | ZNF185 | ABCD1 |
| ENST00000535861.1 | 3987 | 152082986 | 152142024 | + | seg_538 | 152101250 | 152104800 | ZNF185 | ABCD1 |
| ENST00000433245.2 | 3988 | 152082986 | 152128407 | + | seg_538 | 152101250 | 152104800 | ZNF185 | ABCD1 |
| ENST00000370268.4 | 3989 | 152082997 | 152142015 | + | seg_538 | 152101250 | 152104800 | ZNF185 | ABCD1 |
| ENST00000456193.1 | 3990 | 152387940 | 152393740 | − | seg_539 | 152393100 | 152402450 | PNMA6B | ABCD1 |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000415779.1 | 3991 | 152537078 | 152543256 | + | seg__541 | 152529100 | 152538150 | MAGEA1 | ABCD1 |
| ENST00000421080.2 | 3992 | 152713128 | 152760978 | − | seg__544 | 152749250 | 152750350 | U82695.9 | ABCD1 |
| ENST00000453918.2 | 3993 | 152721747 | 152760940 | − | seg__544 | 152749250 | 152750350 | U82695.9 | ABCD1 |
| ENST00000370210.1 | 3994 | 152727018 | 152760974 | − | seg__544 | 152749250 | 152750350 | U82695.9 | ABCD1 |
| ENST00000421080.2 | 3995 | 152713128 | 152760978 | − | seg__545 | 152757900 | 152759300 | U82695.9 | ABCD1 |
| ENST00000453918.2 | 3996 | 152721747 | 152760940 | − | seg__545 | 152757900 | 152759300 | U82695.9 | ABCD1 |
| ENST00000370210.1 | 3997 | 152727018 | 152760974 | − | seg__545 | 152757900 | 152759300 | U82695.9 | ABCD1 |
| ENST00000349466.2 | 3998 | 152783134 | 152846047 | + | seg__546 | 152786250 | 152787250 | ATP2B3 | ABCD1 |
| ENST00000370186.1 | 3999 | 152783134 | 152848397 | + | seg__546 | 152786250 | 152787250 | ATP2B3 | ABCD1 |
| ENST00000349466.2 | 4000 | 152783134 | 152846047 | + | seg__547 | 152788650 | 152794100 | ATP2B3 | ABCD1 |
| ENST00000370186.1 | 4001 | 152783134 | 152848397 | + | seg__547 | 152788650 | 152794100 | ATP2B3 | ABCD1 |
| ENST00000263519.4 | 4002 | 152801580 | 152848387 | + | seg__548 | 152800850 | 152804450 | ATP2B3 | ABCD1 |
| ENST00000349466.2 | 4003 | 152783134 | 152846047 | + | seg__548 | 152800850 | 152804450 | ATP2B3 | ABCD1 |
| ENST00000359149.3 | 4004 | 152801580 | 152846047 | + | seg__548 | 152800850 | 152804450 | ATP2B3 | ABCD1 |
| ENST00000370181.2 | 4005 | 152801580 | 152848387 | + | seg__548 | 152800850 | 152804450 | ATP2B3 | ABCD1 |
| ENST00000393842.1 | 4006 | 152798392 | 152835420 | + | seg__548 | 152800850 | 152804450 | ATP2B3 | ABCD1 |
| ENST00000370186.1 | 4007 | 152783134 | 152848397 | + | seg__548 | 152800850 | 152804450 | ATP2B3 | ABCD1 |
| ENST00000460549.1 | 4008 | 152822404 | 152826282 | + | seg__549 | 152814800 | 152828650 | ATP2B3 | ABCD1 |
| ENST00000263519.4 | 4009 | 152801580 | 152848387 | + | seg__549 | 152814800 | 152828650 | ATP2B3 | ABCD1 |
| ENST00000349466.2 | 4010 | 152783134 | 152846047 | + | seg__549 | 152814800 | 152828650 | ATP2B3 | ABCD1 |
| ENST00000359149.3 | 4011 | 152801580 | 152846047 | + | seg__549 | 152814800 | 152828650 | ATP2B3 | ABCD1 |
| ENST00000370181.2 | 4012 | 152801580 | 152848387 | + | seg__549 | 152814800 | 152828650 | ATP2B3 | ABCD1 |
| ENST00000393842.1 | 4013 | 152798392 | 152835420 | + | seg__549 | 152814800 | 152828650 | ATP2B3 | ABCD1 |
| ENST00000370186.1 | 4014 | 152783134 | 152848397 | + | seg__549 | 152814800 | 152828650 | ATP2B3 | ABCD1 |
| ENST00000496610.1 | 4015 | 152835106 | 152846027 | + | seg__550 | 152830250 | 152836300 | FAM58A | ABCD1 |
| ENST00000263519.4 | 4016 | 152801580 | 152848387 | + | seg__550 | 152830250 | 152836300 | FAM58A | ABCD1 |
| ENST00000349466.2 | 4017 | 152783134 | 152846047 | + | seg__550 | 152830250 | 152836300 | FAM58A | ABCD1 |
| ENST00000359149.3 | 4018 | 152801580 | 152846047 | + | seg__550 | 152830250 | 152836300 | FAM58A | ABCD1 |
| ENST00000370181.2 | 4019 | 152801580 | 152848387 | + | seg__550 | 152830250 | 152836300 | FAM58A | ABCD1 |
| ENST00000393842.1 | 4020 | 152798392 | 152835420 | + | seg__550 | 152830250 | 152836300 | FAM58A | ABCD1 |
| ENST00000370186.1 | 4021 | 152783134 | 152848397 | + | seg__550 | 152830250 | 152836300 | FAM58A | ABCD1 |
| ENST00000496610.1 | 4022 | 152835106 | 152846027 | + | seg__551 | 152838450 | 152845550 | FAM58A | ABCD1 |
| ENST00000263519.4 | 4023 | 152801580 | 152848387 | + | seg__551 | 152838450 | 152845550 | FAM58A | ABCD1 |
| ENST00000349466.2 | 4024 | 152783134 | 152846047 | + | seg__551 | 152838450 | 152845550 | FAM58A | ABCD1 |
| ENST00000359149.3 | 4025 | 152801580 | 152846047 | + | seg__551 | 152838450 | 152845550 | FAM58A | ABCD1 |
| ENST00000370181.2 | 4026 | 152801580 | 152848387 | + | seg__551 | 152838450 | 152845550 | FAM58A | ABCD1 |
| ENST00000370186.1 | 4027 | 152783134 | 152848397 | + | seg__551 | 152838450 | 152845550 | FAM58A | ABCD1 |
| ENST00000406288.2 | 4028 | 152871972 | 152872343 | − | seg__552 | 152868250 | 152873400 | FAM58A | ABCD1 |
| ENST00000434763.1 | 4029 | 152869952 | 152870803 | − | seg__552 | 152868250 | 152873400 | FAM58A | ABCD1 |
| ENST00000480496.1 | 4030 | 152931688 | 152931971 | + | seg__556 | 152929350 | 152932250 | PNCK | ABCD1 |
| ENST00000468491.1 | 4031 | 153072782 | 153095125 | − | seg__557 | 153075300 | 153076350 | PDZD4 | L1CAM |
| ENST00000480418.1 | 4032 | 153071037 | 153096020 | − | seg__557 | 153075300 | 153076350 | PDZD4 | L1CAM |
| ENST00000480650.1 | 4033 | 153073438 | 153095792 | − | seg__557 | 153075300 | 153076350 | PDZD4 | L1CAM |
| ENST00000164640.4 | 4034 | 153067621 | 153095945 | − | seg__557 | 153075300 | 153076350 | PDZD4 | L1CAM |
| ENST00000544474.1 | 4035 | 153068742 | 153095813 | − | seg__557 | 153075300 | 153076350 | PDZD4 | L1CAM |
| ENST00000483693.1 | 4036 | 153071000 | 153095598 | − | seg__557 | 153075300 | 153076350 | PDZD4 | L1CAM |
| ENST00000393758.2 | 4037 | 153067623 | 153095351 | − | seg__557 | 153075300 | 153076350 | PDZD4 | L1CAM |
| ENST00000475140.1 | 4038 | 153070548 | 153095311 | − | seg__557 | 153075300 | 153076350 | PDZD4 | L1CAM |
| ENST00000468491.1 | 4039 | 153072782 | 153095125 | − | seg__558 | 153078100 | 153079800 | PDZD4 | L1CAM |
| ENST00000480418.1 | 4040 | 153071037 | 153096020 | − | seg__558 | 153078100 | 153079800 | PDZD4 | L1CAM |
| ENST00000480650.1 | 4041 | 153073438 | 153095792 | − | seg__558 | 153078100 | 153079800 | PDZD4 | L1CAM |
| ENST00000164640.4 | 4042 | 153067621 | 153095945 | − | seg__558 | 153078100 | 153079800 | PDZD4 | L1CAM |
| ENST00000544474.1 | 4043 | 153068742 | 153095813 | − | seg__558 | 153078100 | 153079800 | PDZD4 | L1CAM |
| ENST00000483693.1 | 4044 | 153071000 | 153095598 | − | seg__558 | 153078100 | 153079800 | PDZD4 | L1CAM |
| ENST00000393758.2 | 4045 | 153067623 | 153095351 | − | seg__558 | 153078100 | 153079800 | PDZD4 | L1CAM |
| ENST00000475140.1 | 4046 | 153070548 | 153095311 | − | seg__558 | 153078100 | 153079800 | PDZD4 | L1CAM |
| ENST00000468491.1 | 4047 | 153072782 | 153095125 | − | seg__559 | 153083600 | 153087450 | PDZD4 | L1CAM |
| ENST00000480418.1 | 4048 | 153071037 | 153096020 | − | seg__559 | 153083600 | 153087450 | PDZD4 | L1CAM |
| ENST00000480650.1 | 4049 | 153073438 | 153095792 | − | seg__559 | 153083600 | 153087450 | PDZD4 | L1CAM |
| ENST00000164640.4 | 4050 | 153067621 | 153095945 | − | seg__559 | 153083600 | 153087450 | PDZD4 | L1CAM |
| ENST00000544474.1 | 4051 | 153068742 | 153095813 | − | seg__559 | 153083600 | 153087450 | PDZD4 | L1CAM |
| ENST00000483693.1 | 4052 | 153071000 | 153095598 | − | seg__559 | 153083600 | 153087450 | PDZD4 | L1CAM |
| ENST00000393758.2 | 4053 | 153067623 | 153095351 | − | seg__559 | 153083600 | 153087450 | PDZD4 | L1CAM |
| ENST00000475140.1 | 4054 | 153070548 | 153095311 | − | seg__559 | 153083600 | 153087450 | PDZD4 | L1CAM |
| ENST00000468491.1 | 4055 | 153072782 | 153095125 | − | seg__560 | 153088800 | 153098300 | PDZD4 | L1CAM |
| ENST00000480418.1 | 4056 | 153071037 | 153096020 | − | seg__560 | 153088800 | 153098300 | PDZD4 | L1CAM |
| ENST00000480650.1 | 4057 | 153073438 | 153095792 | − | seg__560 | 153088800 | 153098300 | PDZD4 | L1CAM |
| ENST00000164640.4 | 4058 | 153067621 | 153095945 | − | seg__560 | 153088800 | 153098300 | PDZD4 | L1CAM |
| ENST00000544474.1 | 4059 | 153068742 | 153095813 | − | seg__560 | 153088800 | 153098300 | PDZD4 | L1CAM |
| ENST00000483693.1 | 4060 | 153071000 | 153095598 | − | seg__560 | 153088800 | 153098300 | PDZD4 | L1CAM |
| ENST00000393758.2 | 4061 | 153067623 | 153095351 | − | seg__560 | 153088800 | 153098300 | PDZD4 | L1CAM |
| ENST00000475140.1 | 4062 | 153070548 | 153095311 | − | seg__560 | 153088800 | 153098300 | PDZD4 | L1CAM |
| ENST00000455590.1 | 4063 | 153132227 | 153133832 | − | seg__563 | 153127450 | 153132350 | L1CAM | L1CAM |
| ENST00000370058.3 | 4064 | 153127888 | 153129933 | − | seg__563 | 153127450 | 153132350 | L1CAM | L1CAM |
| ENST00000491983.1 | 4065 | 153128247 | 153129424 | − | seg__563 | 153127450 | 153132350 | L1CAM | L1CAM |
| ENST00000474853.1 | 4066 | 153130419 | 153131370 | − | seg__563 | 153127450 | 153132350 | L1CAM | L1CAM |

TABLE XVI-continued paRNAs associated with EZH2 STRONG sites in K562 cells

| Transcript ID | SIN: | Start | Stop | Strand | Ezh2 ID | Ezh2 Start | Ezh2 End | Nearest gene | Disease gene |
|---|---|---|---|---|---|---|---|---|---|
| ENST00000370055.1 | 4067 | 153127408 | 153151608 | − | seg_563 | 153127450 | 153132350 | L1CAM | L1CAM |
| ENST00000370057.3 | 4068 | 153126973 | 153141399 | − | seg_563 | 153127450 | 153132350 | L1CAM | L1CAM |
| ENST00000361699.4 | 4069 | 153128003 | 153141302 | − | seg_563 | 153127450 | 153132350 | L1CAM | L1CAM |
| ENST00000540065.1 | 4070 | 153126995 | 153151569 | − | seg_563 | 153127450 | 153132350 | L1CAM | L1CAM |
| ENST00000361981.3 | 4071 | 153126973 | 153141399 | − | seg_563 | 153127450 | 153132350 | L1CAM | L1CAM |
| ENST00000538883.1 | 4072 | 153126973 | 153141399 | − | seg_563 | 153127450 | 153132350 | L1CAM | L1CAM |
| ENST00000370060.1 | 4073 | 153126969 | 153151600 | − | seg_563 | 153127450 | 153132350 | L1CAM | L1CAM |
| ENST00000543994.1 | 4074 | 153126973 | 153141399 | − | seg_563 | 153127450 | 153132350 | L1CAM | L1CAM |
| ENST00000357566.1 | 4075 | 153146127 | 153154425 | + | seg_564 | 153150300 | 153151550 | LCA10 | L1CAM |
| ENST00000484587.1 | 4076 | 153149319 | 153151615 | + | seg_564 | 153150300 | 153151550 | LCA10 | L1CAM |
| ENST00000452593.1 | 4077 | 153146127 | 153154444 | + | seg_564 | 153150300 | 153151550 | LCA10 | L1CAM |
| ENST00000370055.1 | 4078 | 153127408 | 153151608 | − | seg_564 | 153150300 | 153151550 | LCA10 | L1CAM |
| ENST00000540065.1 | 4079 | 153126995 | 153151569 | − | seg_564 | 153150300 | 153151550 | LCA10 | L1CAM |
| ENST00000460553.1 | 4080 | 153138404 | 153151596 | − | seg_564 | 153150300 | 153151550 | LCA10 | L1CAM |
| ENST00000464967.1 | 4081 | 153137676 | 153174677 | − | seg_564 | 153150300 | 153151550 | LCA10 | L1CAM |
| ENST00000420165.1 | 4082 | 153137722 | 153151627 | − | seg_564 | 153150300 | 153151550 | LCA10 | L1CAM |
| ENST00000370060.1 | 4083 | 153126969 | 153151600 | − | seg_564 | 153150300 | 153151550 | LCA10 | L1CAM |
| ENST00000464967.1 | 4084 | 153137676 | 153174677 | − | seg_565 | 153157700 | 153161200 | LCA10 | AVPR2 |
| ENST00000464967.1 | 4085 | 153137676 | 153174677 | − | seg_566 | 153162600 | 153164350 | AVPR2 | AVPR2 |
| ENST00000369941.4 | 4086 | 153424682 | 153445634 | − | seg_567 | 153438400 | 153439700 | TEX28P2 | OPN1MW |
| ENST00000430054.1 | 4087 | 153455547 | 153461628 | + | seg_568 | 153455250 | 153457100 | OPN1MW | OPN1MW |
| ENST00000468495.1 | 4088 | 153448157 | 153459002 | + | seg_568 | 153455250 | 153457100 | OPN1MW | OPN1MW |
| ENST00000369935.5 | 4089 | 153448107 | 153461633 | + | seg_568 | 153455250 | 153457100 | OPN1MW | OPN1MW |
| ENST00000463884.1 | 4090 | 153555722 | 153558038 | + | seg_569 | 153547800 | 153558950 | TKTL1 | EMD |
| ENST00000482044.1 | 4091 | 153555530 | 153556245 | + | seg_569 | 153547800 | 153558950 | TKTL1 | EMD |
| ENST00000217905.7 | 4092 | 153524152 | 153558076 | + | seg_569 | 153547800 | 153558950 | TKTL1 | EMD |
| ENST00000441970.3 | 4093 | 153524027 | 153558713 | + | seg_569 | 153547800 | 153558950 | TKTL1 | EMD |
| ENST00000369915.3 | 4094 | 153524024 | 153558700 | + | seg_569 | 153547800 | 153558950 | TKTL1 | EMD |
| ENST00000465168.1 | 4095 | 153548651 | 153553731 | + | seg_569 | 153547800 | 153558950 | TKTL1 | EMD |
| ENST00000369912.2 | 4096 | 153533409 | 153558700 | + | seg_569 | 153547800 | 153558950 | TKTL1 | EMD |
| ENST00000442033.1 | 4097 | 153882820 | 153883599 | + | seg_572 | 153883050 | 153884900 | CTAG2 | DKC1 |
| ENST00000437536.1 | 4098 | 153887064 | 153887956 | − | seg_573 | 153886450 | 153887600 | CTAG2 | DKC1 |
| ENST00000496390.1 | 4099 | 153903529 | 153979858 | − | seg_574 | 153979700 | 153981100 | GAB3 | DKC1 |
| ENST00000393517.4 | 4100 | 154065133 | 154255215 | − | seg_575 | 154129300 | 154130500 | F8A1 | F8 |
| ENST00000360256.4 | 4101 | 154064070 | 154251028 | − | seg_575 | 154129300 | 154130500 | F8A1 | F8 |
| ENST00000423959.1 | 4102 | 154212976 | 154255215 | − | seg_576 | 154214850 | 154216450 | F8 | F8 |
| ENST00000393517.4 | 4103 | 154065133 | 154255215 | − | seg_576 | 154214850 | 154216450 | F8 | F8 |
| ENST00000360256.4 | 4104 | 154064070 | 154251028 | − | seg_576 | 154214850 | 154216450 | F8 | F8 |
| ENST00000286428.5 | 4105 | 154444643 | 154468098 | + | seg_577 | 154443300 | 154445000 | VBP1 | F8 |
| ENST00000535916.1 | 4106 | 154425284 | 154467325 | + | seg_577 | 154443300 | 154445000 | VBP1 | F8 |
| ENST00000488344.1 | 4107 | 155111023 | 155171608 | + | seg_578 | 155118300 | 155119400 | VAMP7 | F8 |
| ENST00000286448.6 | 4108 | 155110956 | 155173433 | + | seg_578 | 155118300 | 155119400 | VAMP7 | F8 |
| ENST00000460621.1 | 4109 | 155111041 | 155171653 | + | seg_578 | 155118300 | 155119400 | VAMP7 | F8 |
| ENST00000479687.1 | 4110 | 155111021 | 155171573 | + | seg_578 | 155118300 | 155119400 | VAMP7 | F8 |
| ENST00000463317.1 | 4111 | 155111035 | 155169454 | + | seg_578 | 155118300 | 155119400 | VAMP7 | F8 |
| ENST00000262640.6 | 4112 | 155111038 | 155173433 | + | seg_578 | 155118300 | 155119400 | VAMP7 | F8 |

TABLE XVII paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000431238.1 | 4113 | 170410 | 172712 | + | seg_1 | 169650 | 171500 | PLCXD1 | OA1 = GPR143 |
| ENST00000334060.3 | 4114 | 585079 | 620146 | + | seg_11 | 605350 | 606900 | SHOX | OA1 = GPR143 |
| ENST00000381578.1 | 4115 | 585079 | 607558 | + | seg_11 | 605350 | 606900 | SHOX | OA1 = GPR143 |
| ENST00000381575.1 | 4116 | 591542 | 620146 | + | seg_11 | 605350 | 606900 | SHOX | OA1 = GPR143 |
| ENST00000334060.3 | 4117 | 585079 | 620146 | + | seg_12 | 610200 | 612700 | SHOX | OA1 = GPR143 |
| ENST00000381575.1 | 4118 | 591542 | 620146 | + | seg_12 | 610200 | 612700 | SHOX | OA1 = GPR143 |
| ENST00000381566.1 | 4119 | 1317790 | 1331527 | − | seg_22 | 1329250 | 1330400 | CRLF2 | OA1 = GPR143 |
| ENST00000381567.3 | 4120 | 1314890 | 1331527 | − | seg_22 | 1329250 | 1330400 | CRLF2 | OA1 = GPR143 |
| ENST00000467626.1 | 4121 | 1314894 | 1331616 | − | seg_22 | 1329250 | 1330400 | CRLF2 | OA1 = GPR143 |
| ENST00000400841.2 | 4122 | 1314894 | 1331530 | − | seg_22 | 1329250 | 1330400 | CRLF2 | OA1 = GPR143 |
| ENST00000486791.1 | 4123 | 1387738 | 1428827 | + | seg_23 | 1392750 | 1394000 | CSF2RA | OA1 = GPR143 |
| ENST00000381524.3 | 4124 | 1387701 | 1429274 | + | seg_23 | 1392750 | 1394000 | CSF2RA | OA1 = GPR143 |
| ENST00000412290.1 | 4125 | 1387711 | 1413288 | + | seg_23 | 1392750 | 1394000 | CSF2RA | OA1 = GPR143 |
| ENST00000501036.2 | 4126 | 1387693 | 1428828 | + | seg_23 | 1392750 | 1394000 | CSF2RA | OA1 = GPR143 |
| ENST00000381529.3 | 4127 | 1387693 | 1428815 | + | seg_23 | 1392750 | 1394000 | CSF2RA | OA1 = GPR143 |
| ENST00000361536.3 | 4128 | 1387693 | 1428828 | + | seg_23 | 1392750 | 1394000 | CSF2RA | OA1 = GPR143 |
| ENST00000355432.3 | 4129 | 1387738 | 1428827 | + | seg_23 | 1392750 | 1394000 | CSF2RA | OA1 = GPR143 |
| ENST00000355805.2 | 4130 | 1387738 | 1428827 | + | seg_23 | 1392750 | 1394000 | CSF2RA | OA1 = GPR143 |
| ENST00000419094.1 | 4131 | 1387723 | 1409320 | + | seg_23 | 1392750 | 1394000 | CSF2RA | OA1 = GPR143 |
| ENST00000493312.1 | 4132 | 1387707 | 1419436 | + | seg_23 | 1392750 | 1394000 | CSF2RA | OA1 = GPR143 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000381507.4 | 4133 | 1387693 | 1428828 | + | seg_23 | 1392750 | 1394000 | CSF2RA | OA1 = GPR143 |
| ENST00000381509.3 | 4134 | 1387725 | 1424834 | + | seg_23 | 1392750 | 1394000 | CSF2RA | OA1 = GPR143 |
| ENST00000494969.1 | 4135 | 1387725 | 1428815 | + | seg_23 | 1392750 | 1394000 | CSF2RA | OA1 = GPR143 |
| ENST00000432318.2 | 4136 | 1387693 | 1428828 | + | seg_23 | 1392750 | 1394000 | CSF2RA | OA1 = GPR143 |
| ENST00000481245.1 | 4137 | 1387728 | 1401113 | + | seg_23 | 1392750 | 1394000 | CSF2RA | OA1 = GPR143 |
| ENST00000486791.1 | 4138 | 1387738 | 1428827 | + | seg_24 | 1397900 | 1399150 | CSF2RA | OA1 = GPR143 |
| ENST00000381524.3 | 4139 | 1387701 | 1429274 | + | seg_24 | 1397900 | 1399150 | CSF2RA | OA1 = GPR143 |
| ENST00000412290.1 | 4140 | 1387711 | 1413288 | + | seg_24 | 1397900 | 1399150 | CSF2RA | OA1 = GPR143 |
| ENST00000501036.2 | 4141 | 1387693 | 1428828 | + | seg_24 | 1397900 | 1399150 | CSF2RA | OA1 = GPR143 |
| ENST00000381529.3 | 4142 | 1387693 | 1428815 | + | seg_24 | 1397900 | 1399150 | CSF2RA | OA1 = GPR143 |
| ENST00000361536.3 | 4143 | 1387693 | 1428828 | + | seg_24 | 1397900 | 1399150 | CSF2RA | OA1 = GPR143 |
| ENST00000355432.3 | 4144 | 1387738 | 1428827 | + | seg_24 | 1397900 | 1399150 | CSF2RA | OA1 = GPR143 |
| ENST00000355805.2 | 4145 | 1387738 | 1428827 | + | seg_24 | 1397900 | 1399150 | CSF2RA | OA1 = GPR143 |
| ENST00000419094.1 | 4146 | 1387723 | 1409320 | + | seg_24 | 1397900 | 1399150 | CSF2RA | OA1 = GPR143 |
| ENST00000493312.1 | 4147 | 1387707 | 1419436 | + | seg_24 | 1397900 | 1399150 | CSF2RA | OA1 = GPR143 |
| ENST00000381507.4 | 4148 | 1387693 | 1428828 | + | seg_24 | 1397900 | 1399150 | CSF2RA | OA1 = GPR143 |
| ENST00000381509.3 | 4149 | 1387725 | 1424834 | + | seg_24 | 1397900 | 1399150 | CSF2RA | OA1 = GPR143 |
| ENST00000494969.1 | 4150 | 1387725 | 1428815 | + | seg_24 | 1397900 | 1399150 | CSF2RA | OA1 = GPR143 |
| ENST00000432318.2 | 4151 | 1387693 | 1428828 | + | seg_24 | 1397900 | 1399150 | CSF2RA | OA1 = GPR143 |
| ENST00000481245.1 | 4152 | 1387728 | 1401113 | + | seg_24 | 1397900 | 1399150 | CSF2RA | OA1 = GPR143 |
| ENST00000381469.2 | 4153 | 1460659 | 1501358 | + | seg_26 | 1464250 | 1469050 | IL3RA | OA1 = GPR143 |
| ENST00000331035.4 | 4154 | 1455509 | 1501578 | + | seg_26 | 1464250 | 1469050 | IL3RA | OA1 = GPR143 |
| ENST00000432757.1 | 4155 | 1455689 | 1475224 | + | seg_26 | 1464250 | 1469050 | IL3RA | OA1 = GPR143 |
| ENST00000474865.1 | 4156 | 1560485 | 1571765 | − | seg_27 | 1571500 | 1573550 | ASMTL | OA1 = GPR143 |
| ENST00000534940.1 | 4157 | 1522032 | 1572655 | − | seg_27 | 1571500 | 1573550 | ASMTL | OA1 = GPR143 |
| ENST00000416733.2 | 4158 | 1522032 | 1571768 | − | seg_27 | 1571500 | 1573550 | ASMTL | OA1 = GPR143 |
| ENST00000381333.4 | 4159 | 1522034 | 1571822 | − | seg_27 | 1571500 | 1573550 | ASMTL | OA1 = GPR143 |
| ENST00000381317.3 | 4160 | 1522034 | 1571766 | − | seg_27 | 1571500 | 1573550 | ASMTL | OA1 = GPR143 |
| ENST00000381297.4 | 4161 | 1581465 | 1656000 | − | seg_28 | 1589950 | 1591400 | P2RY8 | OA1 = GPR143 |
| ENST00000460672.1 | 4162 | 1585330 | 1613246 | − | seg_28 | 1589950 | 1591400 | P2RY8 | OA1 = GPR143 |
| ENST00000381229.4 | 4163 | 1734057 | 1761920 | + | seg_30 | 1736000 | 1737000 | ASMT | OA1 = GPR143 |
| ENST00000381233.3 | 4164 | 1734068 | 1761974 | + | seg_30 | 1736000 | 1737000 | ASMT | OA1 = GPR143 |
| ENST00000381241.3 | 4165 | 1733894 | 1761974 | + | seg_30 | 1736000 | 1737000 | ASMT | OA1 = GPR143 |
| ENST00000381229.4 | 4166 | 1734057 | 1761920 | + | seg_31 | 1750100 | 1751300 | ASMT | OA1 = GPR143 |
| ENST00000381233.3 | 4167 | 1734068 | 1761974 | + | seg_31 | 1750100 | 1751300 | ASMT | OA1 = GPR143 |
| ENST00000381241.3 | 4168 | 1733894 | 1761974 | + | seg_31 | 1750100 | 1751300 | ASMT | OA1 = GPR143 |
| ENST00000509780.1 | 4169 | 1746639 | 1755356 | + | seg_31 | 1750100 | 1751300 | ASMT | OA1 = GPR143 |
| ENST00000334651.5 | 4170 | 2137557 | 2419019 | − | seg_33 | 2143700 | 2144900 | DHRSX | OA1 = GPR143 |
| ENST00000381180.3 | 4171 | 2609402 | 2610291 | + | seg_38 | 2608500 | 2610050 | CD99 | OA1 = GPR143 |
| ENST00000381187.3 | 4172 | 2609317 | 2659142 | + | seg_38 | 2608500 | 2610050 | CD99 | OA1 = GPR143 |
| ENST00000381184.1 | 4173 | 2609321 | 2651708 | + | seg_38 | 2608500 | 2610050 | CD99 | OA1 = GPR143 |
| ENST00000381192.3 | 4174 | 2609220 | 2659350 | + | seg_38 | 2608500 | 2610050 | CD99 | OA1 = GPR143 |
| ENST00000449611.1 | 4175 | 2609541 | 2644414 | + | seg_38 | 2608500 | 2610050 | CD99 | OA1 = GPR143 |
| ENST00000426774.1 | 4176 | 2670093 | 2734539 | + | seg_40 | 2685100 | 2686250 | XG | OA1 = GPR143 |
| ENST00000533923.2 | 4177 | 2670231 | 2732581 | + | seg_40 | 2685100 | 2686250 | XG | OA1 = GPR143 |
| ENST00000381174.5 | 4178 | 2670091 | 2733968 | + | seg_40 | 2685100 | 2686250 | XG | OA1 = GPR143 |
| ENST00000503018.1 | 4179 | 2670337 | 2693037 | + | seg_40 | 2685100 | 2686250 | XG | OA1 = GPR143 |
| ENST00000419513.2 | 4180 | 2670093 | 2732589 | + | seg_40 | 2685100 | 2686250 | XG | OA1 = GPR143 |
| ENST00000509484.2 | 4181 | 2670186 | 2729477 | + | seg_40 | 2685100 | 2686250 | XG | OA1 = GPR143 |
| ENST00000519244.1 | 4182 | 2712576 | 2726418 | + | seg_41 | 2710300 | 2713050 | GYG2 | OA1 = GPR143 |
| ENST00000426774.1 | 4183 | 2670093 | 2734539 | + | seg_41 | 2710300 | 2713050 | GYG2 | OA1 = GPR143 |
| ENST00000533923.2 | 4184 | 2670231 | 2732581 | + | seg_41 | 2710300 | 2713050 | GYG2 | OA1 = GPR143 |
| ENST00000381174.5 | 4185 | 2670091 | 2733968 | + | seg_41 | 2710300 | 2713050 | GYG2 | OA1 = GPR143 |
| ENST00000419513.2 | 4186 | 2670093 | 2732589 | + | seg_41 | 2710300 | 2713050 | GYG2 | OA1 = GPR143 |
| ENST00000509484.2 | 4187 | 2670186 | 2729477 | + | seg_41 | 2710300 | 2713050 | GYG2 | OA1 = GPR143 |
| ENST00000519244.1 | 4188 | 2712576 | 2726418 | + | seg_42 | 2718100 | 2719250 | GYG2 | OA1 = GPR143 |
| ENST00000426774.1 | 4189 | 2670093 | 2734539 | + | seg_42 | 2718100 | 2719250 | GYG2 | OA1 = GPR143 |
| ENST00000533923.2 | 4190 | 2670231 | 2732581 | + | seg_42 | 2718100 | 2719250 | GYG2 | OA1 = GPR143 |
| ENST00000381174.5 | 4191 | 2670091 | 2733968 | + | seg_42 | 2718100 | 2719250 | GYG2 | OA1 = GPR143 |
| ENST00000419513.2 | 4192 | 2670093 | 2732589 | + | seg_42 | 2718100 | 2719250 | GYG2 | OA1 = GPR143 |
| ENST00000509484.2 | 4193 | 2670186 | 2729477 | + | seg_42 | 2718100 | 2719250 | GYG2 | OA1 = GPR143 |
| ENST00000519244.1 | 4194 | 2712576 | 2726418 | + | seg_43 | 2722300 | 2723400 | GYG2 | OA1 = GPR143 |
| ENST00000426774.1 | 4195 | 2670093 | 2734539 | + | seg_43 | 2722300 | 2723400 | GYG2 | OA1 = GPR143 |
| ENST00000533923.2 | 4196 | 2670231 | 2732581 | + | seg_43 | 2722300 | 2723400 | GYG2 | OA1 = GPR143 |
| ENST00000381174.5 | 4197 | 2670091 | 2733968 | + | seg_43 | 2722300 | 2723400 | GYG2 | OA1 = GPR143 |
| ENST00000419513.2 | 4198 | 2670093 | 2732589 | + | seg_43 | 2722300 | 2723400 | GYG2 | OA1 = GPR143 |
| ENST00000509484.2 | 4199 | 2670186 | 2729477 | + | seg_43 | 2722300 | 2723400 | GYG2 | OA1 = GPR143 |
| ENST00000537104.1 | 4200 | 2976652 | 3030747 | + | seg_44 | 2985150 | 2986300 | ARSF | OA1 = GPR143 |
| ENST00000359361.2 | 4201 | 2984874 | 3030747 | + | seg_44 | 2985150 | 2986300 | ARSF | OA1 = GPR143 |
| ENST00000381127.1 | 4202 | 2959512 | 3030767 | + | seg_44 | 2985150 | 2986300 | ARSF | OA1 = GPR143 |
| ENST00000217939.5 | 4203 | 3226611 | 3264684 | − | seg_45 | 3262450 | 3264450 | MXRA5 | OA1 = GPR143 |
| ENST00000381114.1 | 4204 | 3226606 | 3264682 | − | seg_45 | 3262450 | 3264450 | MXRA5 | OA1 = GPR143 |
| ENST00000381106.3 | 4205 | 3820866 | 3838787 | − | seg_48 | 3836600 | 3837850 | RP11-706O15.1 | OA1 = GPR143 |
| ENST00000453306.1 | 4206 | 8432871 | 8434550 | + | seg_50 | 8433250 | 8434450 | VCX3B | OA1 = GPR143 |
| ENST00000381029.4 | 4207 | 8433467 | 8434510 | + | seg_50 | 8433250 | 8434450 | VCX3B | OA1 = GPR143 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000440654.2 | 4208 | 8433376 | 8434522 | + | seg_50 | 8433250 | 8434450 | VCX3B | OA1 = GPR143 |
| ENST00000381032.1 | 4209 | 8432871 | 8434547 | + | seg_50 | 8433250 | 8434450 | VCX3B | OA1 = GPR143 |
| ENST00000444481.1 | 4210 | 8432871 | 8434424 | + | seg_50 | 8433250 | 8434450 | VCX3B | OA1 = GPR143 |
| ENST00000432442.1 | 4211 | 9217960 | 9243246 | + | seg_51 | 9230300 | 9231800 | FAM9B | OA1 = GPR143 |
| ENST00000416620.1 | 4212 | 9370791 | 9382606 | + | seg_56 | 9372050 | 9382550 | TBL1X | OA1 = GPR143 |
| ENST00000441088.1 | 4213 | 9431360 | 9622328 | + | seg_57 | 9433800 | 9434800 | TBL1X | OA1 = GPR143 |
| ENST00000217964.7 | 4214 | 9433048 | 9687778 | + | seg_57 | 9433800 | 9434800 | TBL1X | OA1 = GPR143 |
| ENST00000380961.1 | 4215 | 9431369 | 9686902 | + | seg_57 | 9433800 | 9434800 | TBL1X | OA1 = GPR143 |
| ENST00000407597.2 | 4216 | 9431335 | 9687780 | + | seg_57 | 9433800 | 9434800 | TBL1X | OA1 = GPR143 |
| ENST00000424279.1 | 4217 | 9431335 | 9687780 | + | seg_57 | 9433800 | 9434800 | TBL1X | OA1 = GPR143 |
| ENST00000415293.1 | 4218 | 9431371 | 9656077 | + | seg_57 | 9433800 | 9434800 | TBL1X | OA1 = GPR143 |
| ENST00000536365.1 | 4219 | 9431352 | 9684302 | + | seg_57 | 9433800 | 9434800 | TBL1X | OA1 = GPR143 |
| ENST00000422314.1 | 4220 | 9433334 | 9652158 | + | seg_57 | 9433800 | 9434800 | TBL1X | OA1 = GPR143 |
| ENST00000441088.1 | 4221 | 9431360 | 9622328 | + | seg_58 | 9465900 | 9467000 | TBL1X | OA1 = GPR143 |
| ENST00000217964.7 | 4222 | 9433048 | 9687778 | + | seg_58 | 9465900 | 9467000 | TBL1X | OA1 = GPR143 |
| ENST00000380961.1 | 4223 | 9431369 | 9686902 | + | seg_58 | 9465900 | 9467000 | TBL1X | OA1 = GPR143 |
| ENST00000407597.2 | 4224 | 9431335 | 9687780 | + | seg_58 | 9465900 | 9467000 | TBL1X | OA1 = GPR143 |
| ENST00000424279.1 | 4225 | 9431335 | 9687780 | + | seg_58 | 9465900 | 9467000 | TBL1X | OA1 = GPR143 |
| ENST00000415293.1 | 4226 | 9431371 | 9656077 | + | seg_58 | 9465900 | 9467000 | TBL1X | OA1 = GPR143 |
| ENST00000536365.1 | 4227 | 9431352 | 9684302 | + | seg_58 | 9465900 | 9467000 | TBL1X | OA1 = GPR143 |
| ENST00000422314.1 | 4228 | 9433334 | 9652158 | + | seg_58 | 9465900 | 9467000 | TBL1X | OA1 = GPR143 |
| ENST00000447366.1 | 4229 | 9707592 | 9754337 | − | seg_59 | 9732550 | 9734250 | GPR143 | OA1 = GPR143 |
| ENST00000431126.1 | 4230 | 9711605 | 9734229 | − | seg_59 | 9732550 | 9734250 | GPR143 | OA1 = GPR143 |
| ENST00000467482.1 | 4231 | 9693386 | 9734004 | − | seg_59 | 9732550 | 9734250 | GPR143 | OA1 = GPR143 |
| ENST00000380929.2 | 4232 | 9693454 | 9734005 | − | seg_59 | 9732550 | 9734250 | GPR143 | OA1 = GPR143 |
| ENST00000447366.1 | 4233 | 9707592 | 9754337 | − | seg_60 | 9754100 | 9755600 | SHROOM2 | OA1 = GPR143 |
| ENST00000380913.3 | 4234 | 9754496 | 9917483 | + | seg_60 | 9754100 | 9755600 | SHROOM2 | OA1 = GPR143 |
| ENST00000380913.3 | 4235 | 9754496 | 9917483 | + | seg_61 | 9815800 | 9817450 | SHROOM2 | OA1 = GPR143 |
| ENST00000380913.3 | 4236 | 9754496 | 9917483 | + | seg_62 | 9861700 | 9864800 | SHROOM2 | OA1 = GPR143 |
| ENST00000445307.2 | 4237 | 9935392 | 9936134 | + | seg_63 | 9935000 | 9936000 | AC002365.1 | OA1 = GPR143 |
| ENST00000543293.1 | 4238 | 10031499 | 10086141 | + | seg_66 | 10066550 | 10068450 | WWC3 | OA1 = GPR143 |
| ENST00000398613.4 | 4239 | 10035291 | 10109658 | + | seg_66 | 10066550 | 10068450 | WWC3 | OA1 = GPR143 |
| ENST00000380861.4 | 4240 | 9983602 | 10112518 | + | seg_66 | 10066550 | 10068450 | WWC3 | OA1 = GPR143 |
| ENST00000454666.1 | 4241 | 10031499 | 10109658 | + | seg_66 | 10066550 | 10068450 | WWC3 | OA1 = GPR143 |
| ENST00000423614.1 | 4242 | 10534995 | 10588625 | − | seg_67 | 10587800 | 10589000 | MID1 | OA1 = GPR143 |
| ENST00000453318.2 | 4243 | 10413350 | 10645779 | − | seg_67 | 10587800 | 10589000 | MID1 | OA1 = GPR143 |
| ENST00000380782.1 | 4244 | 10413596 | 10588459 | − | seg_67 | 10587800 | 10589000 | MID1 | OA1 = GPR143 |
| ENST00000380787.1 | 4245 | 10413596 | 10851773 | − | seg_67 | 10587800 | 10589000 | MID1 | OA1 = GPR143 |
| ENST00000380785.1 | 4246 | 10413596 | 10851762 | − | seg_67 | 10587800 | 10589000 | MID1 | OA1 = GPR143 |
| ENST00000317552.4 | 4247 | 10413350 | 10588674 | − | seg_67 | 10587800 | 10589000 | MID1 | OA1 = GPR143 |
| ENST00000413894.1 | 4248 | 10423115 | 10645727 | − | seg_67 | 10587800 | 10589000 | MID1 | OA1 = GPR143 |
| ENST00000433747.1 | 4249 | 10981960 | 11129258 | − | seg_68 | 10995600 | 10996600 | HCCS | OA1 = GPR143 |
| ENST00000433747.1 | 4250 | 10981960 | 11129258 | − | seg_69 | 11002150 | 11003400 | HCCS | OA1 = GPR143 |
| ENST00000380712.3 | 4251 | 11311533 | 11318881 | + | seg_70 | 11317250 | 11318400 | AMELX | OA1 = GPR143 |
| ENST00000380714.3 | 4252 | 11311533 | 11318881 | + | seg_70 | 11317250 | 11318400 | AMELX | OA1 = GPR143 |
| ENST00000348912.4 | 4253 | 11311533 | 11318873 | + | seg_70 | 11317250 | 11318400 | AMELX | OA1 = GPR143 |
| ENST00000380736.1 | 4254 | 11155663 | 11445893 | − | seg_70 | 11317250 | 11318400 | AMELX | OA1 = GPR143 |
| ENST00000413512.3 | 4255 | 11162134 | 11369656 | − | seg_70 | 11317250 | 11318400 | AMELX | OA1 = GPR143 |
| ENST00000380732.3 | 4256 | 11166770 | 11682948 | − | seg_70 | 11317250 | 11318400 | AMELX | OA1 = GPR143 |
| ENST00000489330.1 | 4257 | 11155667 | 11683203 | − | seg_70 | 11317250 | 11318400 | AMELX | OA1 = GPR143 |
| ENST00000337414.4 | 4258 | 11155664 | 11683821 | − | seg_70 | 11317250 | 11318400 | AMELX | OA1 = GPR143 |
| ENST00000495242.1 | 4259 | 11155664 | 11683821 | − | seg_70 | 11317250 | 11318400 | AMELX | OA1 = GPR143 |
| ENST00000380718.1 | 4260 | 11161517 | 11683821 | − | seg_70 | 11317250 | 11318400 | AMELX | OA1 = GPR143 |
| ENST00000380732.3 | 4261 | 11166770 | 11682948 | − | seg_71 | 11671200 | 11672400 | ARHGAP6 | OA1 = GPR143 |
| ENST00000489330.1 | 4262 | 11155667 | 11683203 | − | seg_71 | 11671200 | 11672400 | ARHGAP6 | OA1 = GPR143 |
| ENST00000337414.4 | 4263 | 11155664 | 11683821 | − | seg_71 | 11671200 | 11672400 | ARHGAP6 | OA1 = GPR143 |
| ENST00000495242.1 | 4264 | 11155664 | 11683821 | − | seg_71 | 11671200 | 11672400 | ARHGAP6 | OA1 = GPR143 |
| ENST00000380718.1 | 4265 | 11161517 | 11683821 | − | seg_71 | 11671200 | 11672400 | ARHGAP6 | OA1 = GPR143 |
| ENST00000380732.3 | 4266 | 11166770 | 11682948 | − | seg_72 | 11681150 | 11684100 | ARHGAP6 | OA1 = GPR143 |
| ENST00000489330.1 | 4267 | 11155667 | 11683203 | − | seg_72 | 11681150 | 11684100 | ARHGAP6 | OA1 = GPR143 |
| ENST00000337414.4 | 4268 | 11155664 | 11683821 | − | seg_72 | 11681150 | 11684100 | ARHGAP6 | OA1 = GPR143 |
| ENST00000495242.1 | 4269 | 11155664 | 11683821 | − | seg_72 | 11681150 | 11684100 | ARHGAP6 | OA1 = GPR143 |
| ENST00000380718.1 | 4270 | 11161517 | 11683821 | − | seg_72 | 11681150 | 11684100 | ARHGAP6 | OA1 = GPR143 |
| ENST00000473806.1 | 4271 | 11778257 | 11779701 | + | seg_74 | 11778800 | 11779850 | MSL3 | SEDL = TRAPPC2 |
| ENST00000478462.1 | 4272 | 11777760 | 11779173 | + | seg_74 | 11778800 | 11779850 | MSL3 | SEDL = TRAPPC2 |
| ENST00000380693.3 | 4273 | 11777671 | 11793870 | + | seg_74 | 11778800 | 11779850 | MSL3 | SEDL = TRAPPC2 |
| ENST00000337339.2 | 4274 | 11776356 | 11786096 | + | seg_74 | 11778800 | 11779850 | MSL3 | SEDL = TRAPPC2 |
| ENST00000312196.4 | 4275 | 11776278 | 11793870 | + | seg_74 | 11778800 | 11779850 | MSL3 | SEDL = TRAPPC2 |
| ENST00000398527.2 | 4276 | 11776728 | 11793574 | + | seg_74 | 11778800 | 11779850 | MSL3 | SEDL = TRAPPC2 |
| ENST00000468149.1 | 4277 | 11776372 | 11793350 | + | seg_74 | 11778800 | 11779850 | MSL3 | SEDL = TRAPPC2 |
| ENST00000494268.1 | 4278 | 11778341 | 11782370 | + | seg_74 | 11778800 | 11779850 | MSL3 | SEDL = TRAPPC2 |
| ENST00000421368.2 | 4279 | 11776705 | 11781076 | + | seg_74 | 11778800 | 11779850 | MSL3 | SEDL = TRAPPC2 |
| ENST00000487782.1 | 4280 | 11778594 | 11786803 | + | seg_74 | 11778800 | 11779850 | MSL3 | SEDL = TRAPPC2 |
| ENST00000476743.1 | 4281 | 11776701 | 11780338 | + | seg_74 | 11778800 | 11779850 | MSL3 | SEDL = TRAPPC2 |
| ENST00000483645.1 | 4282 | 11778305 | 11781043 | + | seg_74 | 11778800 | 11779850 | MSL3 | SEDL = TRAPPC2 |
| ENST00000361672.2 | 4283 | 11776410 | 11793350 | + | seg_74 | 11778800 | 11779850 | MSL3 | SEDL = TRAPPC2 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000380692.2 | 4284 | 11777747 | 11783765 | + | seg_74 | 11778800 | 11779850 | MSL3 | SEDL = TRAPPC2 |
| ENST00000482871.1 | 4285 | 11778162 | 11781026 | + | seg_74 | 11778800 | 11779850 | MSL3 | SEDL = TRAPPC2 |
| ENST00000304087.6 | 4286 | 12516791 | 12742633 | + | seg_75 | 12601150 | 12602900 | PRPS2 | SEDL = TRAPPC2 |
| ENST00000380682.1 | 4287 | 12156585 | 12742642 | + | seg_75 | 12601150 | 12602900 | PRPS2 | SEDL = TRAPPC2 |
| ENST00000429478.2 | 4288 | 12516714 | 12736911 | + | seg_75 | 12601150 | 12602900 | PRPS2 | SEDL = TRAPPC2 |
| ENST00000489404.1 | 4289 | 12809607 | 12828488 | + | seg_78 | 12812950 | 12814100 | PRPS2 | SEDL = TRAPPC2 |
| ENST00000398491.2 | 4290 | 12809525 | 12841205 | + | seg_78 | 12812950 | 12814100 | PRPS2 | SEDL = TRAPPC2 |
| ENST00000380668.5 | 4291 | 12809489 | 12842341 | + | seg_78 | 12812950 | 12814100 | PRPS2 | SEDL = TRAPPC2 |
| ENST00000380663.3 | 4292 | 12809474 | 12828238 | + | seg_78 | 12812950 | 12814100 | PRPS2 | SEDL = TRAPPC2 |
| ENST00000380659.3 | 4293 | 12885202 | 12908499 | + | seg_80 | 12897150 | 12898350 | TLR7 | SEDL = TRAPPC2 |
| ENST00000451311.2 | 4294 | 12993227 | 12995346 | + | seg_81 | 12993000 | 12994200 | TMSB4X | SEDL = TRAPPC2 |
| ENST00000380633.1 | 4295 | 12993777 | 12995200 | + | seg_81 | 12993000 | 12994200 | TMSB4X | SEDL = TRAPPC2 |
| ENST00000380635.1 | 4296 | 12993363 | 12995346 | + | seg_81 | 12993000 | 12994200 | TMSB4X | SEDL = TRAPPC2 |
| ENST00000380636.1 | 4297 | 12993229 | 12995345 | + | seg_81 | 12993000 | 12994200 | TMSB4X | SEDL = TRAPPC2 |
| ENST00000380602.3 | 4298 | 13587741 | 13651694 | + | seg_85 | 13587150 | 13589000 | EGFL6 | SEDL = TRAPPC2 |
| ENST00000361306.1 | 4299 | 13587724 | 13651693 | + | seg_85 | 13587150 | 13589000 | EGFL6 | SEDL = TRAPPC2 |
| ENST00000493677.1 | 4300 | 13790818 | 13835188 | − | seg_86 | 13804100 | 13806050 | GPM6B | OFD1 |
| ENST00000355135.2 | 4301 | 13792073 | 13835188 | − | seg_86 | 13804100 | 13806050 | GPM6B | OFD1 |
| ENST00000316715.4 | 4302 | 13789150 | 13835461 | − | seg_86 | 13804100 | 13806050 | GPM6B | OFD1 |
| ENST00000356942.5 | 4303 | 13792073 | 13835465 | − | seg_86 | 13804100 | 13806050 | GPM6B | OFD1 |
| ENST00000475307.1 | 4304 | 13801568 | 13835442 | − | seg_86 | 13804100 | 13806050 | GPM6B | OFD1 |
| ENST00000493085.1 | 4305 | 13797972 | 13907176 | − | seg_86 | 13804100 | 13806050 | GPM6B | OFD1 |
| ENST00000398361.3 | 4306 | 13792456 | 13956534 | − | seg_86 | 13804100 | 13806050 | GPM6B | OFD1 |
| ENST00000468080.1 | 4307 | 13798027 | 13907731 | − | seg_86 | 13804100 | 13806050 | GPM6B | OFD1 |
| ENST00000454189.2 | 4308 | 13789575 | 13956757 | − | seg_86 | 13804100 | 13806050 | GPM6B | OFD1 |
| ENST00000493677.1 | 4309 | 13790818 | 13835188 | − | seg_87 | 13834050 | 13835850 | GPM6B | OFD1 |
| ENST00000355135.2 | 4310 | 13792073 | 13835188 | − | seg_87 | 13834050 | 13835850 | GPM6B | OFD1 |
| ENST00000316715.4 | 4311 | 13789150 | 13835461 | − | seg_87 | 13834050 | 13835850 | GPM6B | OFD1 |
| ENST00000356942.5 | 4312 | 13792073 | 13835465 | − | seg_87 | 13834050 | 13835850 | GPM6B | OFD1 |
| ENST00000475307.1 | 4313 | 13801568 | 13835442 | − | seg_87 | 13834050 | 13835850 | GPM6B | OFD1 |
| ENST00000493085.1 | 4314 | 13797972 | 13907176 | − | seg_87 | 13834050 | 13835850 | GPM6B | OFD1 |
| ENST00000398361.3 | 4315 | 13792456 | 13956534 | − | seg_87 | 13834050 | 13835850 | GPM6B | OFD1 |
| ENST00000468080.1 | 4316 | 13798027 | 13907731 | − | seg_87 | 13834050 | 13835850 | GPM6B | OFD1 |
| ENST00000454189.2 | 4317 | 13789575 | 13956757 | − | seg_87 | 13834050 | 13835850 | GPM6B | OFD1 |
| ENST00000493085.1 | 4318 | 13797972 | 13907176 | − | seg_88 | 13898100 | 13899500 | GPM6B | OFD1 |
| ENST00000398361.3 | 4319 | 13792456 | 13956534 | − | seg_88 | 13898100 | 13899500 | GPM6B | OFD1 |
| ENST00000468080.1 | 4320 | 13798027 | 13907731 | − | seg_88 | 13898100 | 13899500 | GPM6B | OFD1 |
| ENST00000454189.2 | 4321 | 13789575 | 13956757 | − | seg_88 | 13898100 | 13899500 | GPM6B | OFD1 |
| ENST00000398361.3 | 4322 | 13792456 | 13956534 | − | seg_89 | 13955300 | 13956550 | GPM6B | OFD1 |
| ENST00000454189.2 | 4323 | 13789575 | 13956757 | − | seg_89 | 13955300 | 13956550 | GPM6B | OFD1 |
| ENST00000415367.1 | 4324 | 14549268 | 14625369 | + | seg_91 | 14596250 | 14597350 | GLRA2 | PIGA |
| ENST00000443437.2 | 4325 | 14547420 | 14749931 | + | seg_91 | 14596250 | 14597350 | GLRA2 | PIGA |
| ENST00000355020.4 | 4326 | 14547894 | 14748692 | + | seg_91 | 14596250 | 14597350 | GLRA2 | PIGA |
| ENST00000218075.4 | 4327 | 14547650 | 14749934 | + | seg_91 | 14596250 | 14597350 | GLRA2 | PIGA |
| ENST00000444401.1 | 4328 | 15135563 | 15135890 | − | seg_93 | 15134850 | 15135950 | ASB9 | PIGA |
| ENST00000380470.3 | 4329 | 15299819 | 15333746 | − | seg_94 | 15330250 | 15331650 | ASB11 | PIGA |
| ENST00000537676.1 | 4330 | 15298053 | 15332681 | − | seg_94 | 15330250 | 15331650 | ASB11 | PIGA |
| ENST00000344384.4 | 4331 | 15300441 | 15332681 | − | seg_94 | 15330250 | 15331650 | ASB11 | PIGA |
| ENST00000485437.1 | 4332 | 15301628 | 15333727 | − | seg_94 | 15330250 | 15331650 | ASB11 | PIGA |
| ENST00000480796.1 | 4333 | 15301166 | 15333778 | − | seg_94 | 15330250 | 15331650 | ASB11 | PIGA |
| ENST00000357277.3 | 4334 | 16964814 | 17171395 | + | seg_97 | 16967100 | 16968150 | REPS2 | CC = NHS |
| ENST00000380063.2 | 4335 | 16964814 | 17167136 | + | seg_97 | 16967100 | 16968150 | REPS2 | CC = NHS |
| ENST00000481792.1 | 4336 | 16965193 | 17040494 | + | seg_97 | 16967100 | 16968150 | REPS2 | CC = NHS |
| ENST00000303843.7 | 4337 | 16964985 | 17171395 | + | seg_97 | 16967100 | 16968150 | REPS2 | CC = NHS |
| ENST00000357277.3 | 4338 | 16964814 | 17171395 | + | seg_98 | 17047350 | 17048350 | REPS2 | CC = NHS |
| ENST00000380063.2 | 4339 | 16964814 | 17167136 | + | seg_98 | 17047350 | 17048350 | REPS2 | CC = NHS |
| ENST00000380064.4 | 4340 | 16996667 | 17165745 | + | seg_98 | 17047350 | 17048350 | REPS2 | CC = NHS |
| ENST00000303843.7 | 4341 | 16964985 | 17171395 | + | seg_98 | 17047350 | 17048350 | REPS2 | CC = NHS |
| ENST00000360011.1 | 4342 | 17818171 | 17878827 | − | seg_100 | 17877100 | 17879400 | RAI2 | CC = NHS |
| ENST00000331511.1 | 4343 | 17818171 | 17879356 | − | seg_100 | 17877100 | 17879400 | RAI2 | CC = NHS |
| ENST00000545871.1 | 4344 | 17818171 | 17879457 | − | seg_100 | 17877100 | 17879400 | RAI2 | CC = NHS |
| ENST00000451717.1 | 4345 | 17818171 | 17879457 | − | seg_100 | 17877100 | 17879400 | RAI2 | CC = NHS |
| ENST00000415486.2 | 4346 | 17818171 | 17879457 | − | seg_100 | 17877100 | 17879400 | RAI2 | CC = NHS |
| ENST00000453902.1 | 4347 | 17988317 | 18122764 | − | seg_101 | 18001050 | 18002050 | RAI2 | CDKL5 |
| ENST00000380033.4 | 4348 | 18181051 | 18239003 | − | seg_104 | 18232100 | 18233200 | BEND2 | CDKL5 |
| ENST00000380030.3 | 4349 | 18189095 | 18239024 | − | seg_104 | 18232100 | 18233200 | BEND2 | CDKL5 |
| ENST00000380033.4 | 4350 | 18181051 | 18239003 | − | seg_105 | 18236850 | 18239450 | BEND2 | CDKL5 |
| ENST00000380030.3 | 4351 | 18189095 | 18239024 | − | seg_105 | 18236850 | 18239450 | BEND2 | CDKL5 |
| ENST00000379996.3 | 4352 | 18443703 | 18671749 | + | seg_107 | 18442500 | 18445000 | CDKL5 | CDKL5 |
| ENST00000476595.1 | 4353 | 18660044 | 18668657 | − | seg_108 | 18661950 | 18663150 | RS1 | RS1 |
| ENST00000379984.3 | 4354 | 18658030 | 18690229 | − | seg_108 | 18661950 | 18663150 | RS1 | RS1 |
| ENST00000379996.3 | 4355 | 18443703 | 18671749 | + | seg_108 | 18661950 | 18663150 | RS1 | RS1 |
| ENST00000379989.3 | 4356 | 18460308 | 18671745 | + | seg_108 | 18661950 | 18663150 | RS1 | RS1 |
| ENST00000476595.1 | 4357 | 18660044 | 18668657 | − | seg_109 | 18667450 | 18668950 | RS1 | RS1 |
| ENST00000379984.3 | 4358 | 18658030 | 18690229 | − | seg_109 | 18667450 | 18668950 | RS1 | RS1 |
| ENST00000379996.3 | 4359 | 18443703 | 18671749 | + | seg_109 | 18667450 | 18668950 | RS1 | RS1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000379989.3 | 4360 | 18460308 | 18671745 | + | seg_109 | 18667450 | 18668950 | RS1 | RS1 |
| ENST00000379942.4 | 4361 | 18910418 | 19002716 | − | seg_113 | 18931800 | 18932800 | PHKA2 | PHKA2 |
| ENST00000470101.1 | 4362 | 19378178 | 19391296 | − | seg_118 | 19390850 | 19391950 | PDHA1 | PHKA2 |
| ENST00000338883.4 | 4363 | 19378174 | 19533379 | − | seg_118 | 19390850 | 19391950 | PDHA1 | PHKA2 |
| ENST00000359173.3 | 4364 | 19378176 | 19478245 | − | seg_118 | 19390850 | 19391950 | PDHA1 | PHKA2 |
| ENST00000469203.2 | 4365 | 19378797 | 19504642 | − | seg_118 | 19390850 | 19391950 | PDHA1 | PHKA2 |
| ENST00000518578.1 | 4366 | 19378174 | 19500394 | − | seg_118 | 19390850 | 19391950 | PDHA1 | PHKA2 |
| ENST00000338883.4 | 4367 | 19378174 | 19533379 | − | seg_119 | 19395050 | 19396500 | PDHA1 | PHKA2 |
| ENST00000359173.3 | 4368 | 19378176 | 19478245 | − | seg_119 | 19395050 | 19396500 | PDHA1 | PHKA2 |
| ENST00000469203.2 | 4369 | 19378797 | 19504642 | − | seg_119 | 19395050 | 19396500 | PDHA1 | PHKA2 |
| ENST00000518578.1 | 4370 | 19378174 | 19500394 | − | seg_119 | 19395050 | 19396500 | PDHA1 | PHKA2 |
| ENST00000338883.4 | 4371 | 19378174 | 19533379 | − | seg_120 | 19398600 | 19399850 | PDHA1 | PHKA2 |
| ENST00000359173.3 | 4372 | 19378176 | 19478245 | − | seg_120 | 19398600 | 19399850 | PDHA1 | PHKA2 |
| ENST00000469203.2 | 4373 | 19378797 | 19504642 | − | seg_120 | 19398600 | 19399850 | PDHA1 | PHKA2 |
| ENST00000518578.1 | 4374 | 19378174 | 19500394 | − | seg_120 | 19398600 | 19399850 | PDHA1 | PHKA2 |
| ENST00000338883.4 | 4375 | 19378174 | 19533379 | − | seg_121 | 19504100 | 19505200 | MAP3K15 | PHKA2 |
| ENST00000469203.2 | 4376 | 19378797 | 19504642 | − | seg_121 | 19504100 | 19505200 | MAP3K15 | PHKA2 |
| ENST00000397804.1 | 4377 | 19553520 | 19725207 | − | seg_122 | 19602850 | 19605500 | SH3KBP1 | PHKA2 |
| ENST00000379698.4 | 4378 | 19553811 | 19817869 | − | seg_122 | 19602850 | 19605500 | SH3KBP1 | PHKA2 |
| ENST00000397821.3 | 4379 | 19552093 | 19905719 | − | seg_122 | 19602850 | 19605500 | SH3KBP1 | PHKA2 |
| ENST00000379702.2 | 4380 | 19552083 | 19905719 | − | seg_122 | 19602850 | 19605500 | SH3KBP1 | PHKA2 |
| ENST00000379726.3 | 4381 | 19554532 | 19764529 | − | seg_122 | 19602850 | 19605500 | SH3KBP1 | PHKA2 |
| ENST00000541422.1 | 4382 | 19554308 | 19688480 | − | seg_122 | 19602850 | 19605500 | SH3KBP1 | PHKA2 |
| ENST00000379716.1 | 4383 | 19552125 | 19689116 | − | seg_122 | 19602850 | 19605500 | SH3KBP1 | PHKA2 |
| ENST00000397804.1 | 4384 | 19553520 | 19725207 | − | seg_123 | 19627300 | 19628350 | SH3KBP1 | PHKA2 |
| ENST00000379698.4 | 4385 | 19553811 | 19817869 | − | seg_123 | 19627300 | 19628350 | SH3KBP1 | PHKA2 |
| ENST00000397821.3 | 4386 | 19552093 | 19905719 | − | seg_123 | 19627300 | 19628350 | SH3KBP1 | PHKA2 |
| ENST00000477102.1 | 4387 | 19610186 | 19682833 | − | seg_123 | 19627300 | 19628350 | SH3KBP1 | PHKA2 |
| ENST00000379697.3 | 4388 | 19606396 | 19905577 | − | seg_123 | 19627300 | 19628350 | SH3KBP1 | PHKA2 |
| ENST00000494961.1 | 4389 | 19606802 | 19713819 | − | seg_123 | 19627300 | 19628350 | SH3KBP1 | PHKA2 |
| ENST00000379702.2 | 4390 | 19552083 | 19905719 | − | seg_123 | 19627300 | 19628350 | SH3KBP1 | PHKA2 |
| ENST00000379726.3 | 4391 | 19554532 | 19764529 | − | seg_123 | 19627300 | 19628350 | SH3KBP1 | PHKA2 |
| ENST00000541422.1 | 4392 | 19554308 | 19688480 | − | seg_123 | 19627300 | 19628350 | SH3KBP1 | PHKA2 |
| ENST00000379716.1 | 4393 | 19552125 | 19689116 | − | seg_123 | 19627300 | 19628350 | SH3KBP1 | PHKA2 |
| ENST00000397821.3 | 4394 | 19552093 | 19905719 | − | seg_124 | 19874700 | 19875850 | SH3KBP1 | PHKA2 |
| ENST00000379697.3 | 4395 | 19606396 | 19905577 | − | seg_124 | 19874700 | 19875850 | SH3KBP1 | PHKA2 |
| ENST00000379702.2 | 4396 | 19552083 | 19905719 | − | seg_124 | 19874700 | 19875850 | SH3KBP1 | PHKA2 |
| ENST00000397821.3 | 4397 | 19552093 | 19905719 | − | seg_125 | 19904300 | 19906050 | SH3KBP1 | PHKA2 |
| ENST00000379697.3 | 4398 | 19606396 | 19905577 | − | seg_125 | 19904300 | 19906050 | SH3KBP1 | PHKA2 |
| ENST00000379702.2 | 4399 | 19552083 | 19905719 | − | seg_125 | 19904300 | 19906050 | SH3KBP1 | PHKA2 |
| ENST00000330274.7 | 4400 | 20070519 | 20135114 | − | seg_127 | 20099150 | 20100450 | MAP7D2 | PHKA2 |
| ENST00000379643.4 | 4401 | 20024833 | 20135114 | − | seg_127 | 20099150 | 20100450 | MAP7D2 | PHKA2 |
| ENST00000544957.1 | 4402 | 20026440 | 20135022 | − | seg_127 | 20099150 | 20100450 | MAP7D2 | PHKA2 |
| ENST00000443379.2 | 4403 | 20024833 | 20135114 | − | seg_127 | 20099150 | 20100450 | MAP7D2 | PHKA2 |
| ENST00000379651.3 | 4404 | 20024831 | 20135016 | − | seg_127 | 20099150 | 20100450 | MAP7D2 | PHKA2 |
| ENST00000452324.2 | 4405 | 20024833 | 20134756 | − | seg_127 | 20099150 | 20100450 | MAP7D2 | PHKA2 |
| ENST00000330274.7 | 4406 | 20070519 | 20135114 | − | seg_128 | 20129200 | 20134650 | MAP7D2 | PHKA2 |
| ENST00000379643.4 | 4407 | 20024833 | 20135114 | − | seg_128 | 20129200 | 20134650 | MAP7D2 | PHKA2 |
| ENST00000544957.1 | 4408 | 20026440 | 20135022 | − | seg_128 | 20129200 | 20134650 | MAP7D2 | PHKA2 |
| ENST00000443379.2 | 4409 | 20024833 | 20135114 | − | seg_128 | 20129200 | 20134650 | MAP7D2 | PHKA2 |
| ENST00000379651.3 | 4410 | 20024831 | 20135016 | − | seg_128 | 20129200 | 20134650 | MAP7D2 | PHKA2 |
| ENST00000452324.2 | 4411 | 20024833 | 20134756 | − | seg_128 | 20129200 | 20134650 | MAP7D2 | PHKA2 |
| ENST00000379607.5 | 4412 | 20142636 | 20159962 | − | seg_129 | 20159600 | 20160600 | EIF1AX | PHKA2 |
| ENST00000379593.1 | 4413 | 20146196 | 20159944 | − | seg_129 | 20159600 | 20160600 | EIF1AX | PHKA2 |
| ENST00000404933.2 | 4414 | 21958691 | 22012953 | + | seg_133 | 21991750 | 21992750 | SMS | PHEX |
| ENST00000379404.1 | 4415 | 21958833 | 22012591 | + | seg_133 | 21991750 | 21992750 | SMS | PHEX |
| ENST00000457085.1 | 4416 | 21959163 | 21996229 | + | seg_133 | 21991750 | 21992750 | SMS | PHEX |
| ENST00000478094.1 | 4417 | 21958896 | 21996107 | + | seg_133 | 21991750 | 21992750 | SMS | PHEX |
| ENST00000415881.2 | 4418 | 21958853 | 22025798 | + | seg_133 | 21991750 | 21992750 | SMS | PHEX |
| ENST00000424650.1 | 4419 | 22180850 | 22191100 | + | seg_134 | 22180550 | 22181700 | PHEX | PHEX |
| ENST00000379374.4 | 4420 | 22050559 | 22269427 | + | seg_134 | 22180550 | 22181700 | PHEX | PHEX |
| ENST00000537599.1 | 4421 | 22051016 | 22266300 | + | seg_134 | 22180550 | 22181700 | PHEX | PHEX |
| ENST00000535894.1 | 4422 | 22056171 | 22266413 | + | seg_134 | 22180550 | 22181700 | PHEX | PHEX |
| ENST00000418858.3 | 4423 | 22115822 | 22266209 | + | seg_134 | 22180550 | 22181700 | PHEX | PHEX |
| ENST00000455399.1 | 4424 | 22407432 | 23082236 | − | seg_135 | 22537550 | 22538650 | ZNF645 | PHEX |
| ENST00000455399.1 | 4425 | 22407432 | 23082236 | − | seg_136 | 22961950 | 22963000 | DDX53 | SAT = SAT1 |
| ENST00000312214.5 | 4426 | 23093875 | 23094884 | + | seg_137 | 23093050 | 23094400 | DDX53 | SAT = SAT1 |
| ENST00000508288.1 | 4427 | 23093708 | 23096495 | − | seg_137 | 23093050 | 23094400 | DDX53 | SAT = SAT1 |
| ENST00000379361.4 | 4428 | 23352133 | 23422489 | + | seg_139 | 23412800 | 23413800 | PTCHD1 | SAT = SAT1 |
| ENST00000439528.1 | 4429 | 23851480 | 23899018 | − | seg_141 | 23889950 | 23891000 | APOO | SAT = SAT1 |
| ENST00000379226.4 | 4430 | 23851470 | 23926051 | − | seg_141 | 23889950 | 23891000 | APOO | SAT = SAT1 |
| ENST00000379220.3 | 4431 | 23851481 | 23926057 | − | seg_141 | 23889950 | 23891000 | APOO | SAT = SAT1 |
| ENST00000490078.1 | 4432 | 23851484 | 23926020 | − | seg_141 | 23889950 | 23891000 | APOO | SAT = SAT1 |
| ENST00000379211.3 | 4433 | 23925918 | 23957624 | + | seg_142 | 23925150 | 23926350 | APOO | SAT = SAT1 |
| ENST00000379226.4 | 4434 | 23851470 | 23926051 | − | seg_142 | 23925150 | 23926350 | APOO | SAT = SAT1 |
| ENST00000379220.3 | 4435 | 23851481 | 23926057 | − | seg_142 | 23925150 | 23926350 | APOO | SAT = SAT1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000490078.1 | 4436 | 23851484 | 23926020 | − | seg_142 | 23925150 | 23926350 | APOO | SAT = SAT1 |
| ENST00000486479.1 | 4437 | 24329024 | 24331432 | − | seg_146 | 24328700 | 24333250 | ZFX | SAT = SAT1 |
| ENST00000536351.1 | 4438 | 24328979 | 24331432 | − | seg_146 | 24328700 | 24333250 | ZFX | SAT = SAT1 |
| ENST00000413856.1 | 4439 | 24380878 | 24383541 | + | seg_147 | 24379450 | 24382100 | PDK3 | SAT = SAT1 |
| ENST00000436466.1 | 4440 | 24380878 | 24383495 | + | seg_147 | 24379450 | 24382100 | PDK3 | SAT = SAT1 |
| ENST00000441463.2 | 4441 | 24483573 | 24557954 | + | seg_149 | 24504450 | 24505550 | PDK3 | SAT = SAT1 |
| ENST00000379162.4 | 4442 | 24483338 | 24552542 | + | seg_149 | 24504450 | 24505550 | PDK3 | SAT = SAT1 |
| ENST00000379144.2 | 4443 | 24579959 | 24665353 | − | seg_151 | 24644850 | 24646050 | PCYT1B | SAT = SAT1 |
| ENST00000356768.4 | 4444 | 24579959 | 24665275 | − | seg_151 | 24644850 | 24646050 | PCYT1B | SAT = SAT1 |
| ENST00000379145.1 | 4445 | 24576204 | 24690794 | − | seg_151 | 24644850 | 24646050 | PCYT1B | SAT = SAT1 |
| ENST00000496020.1 | 4446 | 24580518 | 24665155 | − | seg_151 | 24644850 | 24646050 | PCYT1B | SAT = SAT1 |
| ENST00000379044.4 | 4447 | 25021811 | 25034065 | − | seg_152 | 25025650 | 25045000 | ARX | SAT = SAT1 |
| ENST00000438281.1 | 4448 | 25047662 | 25048352 | + | seg_153 | 25046850 | 25048300 | ARX | SAT = SAT1 |
| ENST00000378963.1 | 4449 | 30323791 | 30326605 | − | seg_158 | 30325950 | 30328550 | NR0B1 | DAX1 = NR0B1 |
| ENST00000453287.1 | 4450 | 30323938 | 30327495 | − | seg_158 | 30325950 | 30328550 | NR0B1 | DAX1 = NR0B1 |
| ENST00000378970.4 | 4451 | 30322323 | 30327715 | − | seg_158 | 30325950 | 30328550 | NR0B1 | DAX1 = NR0B1 |
| ENST00000378932.2 | 4452 | 30848454 | 30993201 | − | seg_160 | 30955050 | 30956300 | TAB3 | DAX1 = NR0B1 |
| ENST00000288422.2 | 4453 | 30848454 | 30993201 | − | seg_160 | 30955050 | 30956300 | TAB3 | DAX1 = NR0B1 |
| ENST00000378932.2 | 4454 | 30848454 | 30993201 | − | seg_161 | 30992350 | 30993350 | FTHL17 | DAX1 = NR0B1 |
| ENST00000288422.2 | 4455 | 30848454 | 30993201 | − | seg_161 | 30992350 | 30993350 | FTHL17 | DAX1 = NR0B1 |
| ENST00000474231.1 | 4456 | 31139514 | 32173586 | − | seg_163 | 31691100 | 31692100 | DMD | DAX1 = NR0B1 |
| ENST00000378684.4 | 4457 | 31132808 | 32430174 | − | seg_163 | 31691100 | 31692100 | DMD | DAX1 = NR0B1 |
| ENST00000343523.2 | 4458 | 31137345 | 32173586 | − | seg_163 | 31691100 | 31692100 | DMD | DAX1 = NR0B1 |
| ENST00000541735.1 | 4459 | 31137345 | 32173586 | − | seg_163 | 31691100 | 31692100 | DMD | DAX1 = NR0B1 |
| ENST00000378682.4 | 4460 | 31132808 | 32430326 | − | seg_163 | 31691100 | 31692100 | DMD | DAX1 = NR0B1 |
| ENST00000357033.4 | 4461 | 31137345 | 33229636 | − | seg_163 | 31691100 | 31692100 | DMD | DAX1 = NR0B1 |
| ENST00000542849.1 | 4462 | 31137345 | 33229673 | − | seg_163 | 31691100 | 31692100 | DMD | DAX1 = NR0B1 |
| ENST00000359836.1 | 4463 | 31137345 | 32173586 | − | seg_163 | 31691100 | 31692100 | DMD | DAX1 = NR0B1 |
| ENST00000535280.1 | 4464 | 31137345 | 33146544 | − | seg_163 | 31691100 | 31692100 | DMD | DAX1 = NR0B1 |
| ENST00000378707.3 | 4465 | 31137345 | 32173586 | − | seg_163 | 31691100 | 31692100 | DMD | DAX1 = NR0B1 |
| ENST00000378677.2 | 4466 | 31137345 | 33146477 | − | seg_163 | 31691100 | 31692100 | DMD | DAX1 = NR0B1 |
| ENST00000358062.2 | 4467 | 31137338 | 31893490 | − | seg_163 | 31691100 | 31692100 | DMD | DAX1 = NR0B1 |
| ENST00000534884.1 | 4468 | 31132808 | 33038324 | − | seg_163 | 31691100 | 31692100 | DMD | DAX1 = NR0B1 |
| ENST00000465285.1 | 4469 | 31139514 | 31947809 | − | seg_163 | 31691100 | 31692100 | DMD | DAX1 = NR0B1 |
| ENST00000439992.1 | 4470 | 33744625 | 33960397 | + | seg_164 | 33817650 | 33818700 | FAM47A | DAX1 = NR0B1 |
| ENST00000445233.1 | 4471 | 33760235 | 33960352 | + | seg_164 | 33817650 | 33818700 | FAM47A | DAX1 = NR0B1 |
| ENST00000402402.2 | 4472 | 37351274 | 37351801 | + | seg_168 | 37351000 | 37352100 | LANCL3 | XK |
| ENST00000465127.1 | 4473 | 37208583 | 38546928 | + | seg_168 | 37351000 | 37352100 | LANCL3 | XK |
| ENST00000465127.1 | 4474 | 37208583 | 38546928 | + | seg_169 | 37733800 | 37734850 | DYNLT3 | CYBB |
| ENST00000423919.1 | 4475 | 38080644 | 38082920 | + | seg_170 | 38078900 | 38081100 | SRPX | RPGR |
| ENST00000432886.2 | 4476 | 38008589 | 38080177 | − | seg_170 | 38078900 | 38081100 | SRPX | RPGR |
| ENST00000378533.3 | 4477 | 38008592 | 38080152 | − | seg_170 | 38078900 | 38081100 | SRPX | RPGR |
| ENST00000538295.1 | 4478 | 38008589 | 38080177 | − | seg_170 | 38078900 | 38081100 | SRPX | RPGR |
| ENST00000343800.6 | 4479 | 38008595 | 38080696 | − | seg_170 | 38078900 | 38081100 | SRPX | RPGR |
| ENST00000544439.1 | 4480 | 38008589 | 38080177 | − | seg_170 | 38078900 | 38081100 | SRPX | RPGR |
| ENST00000465127.1 | 4481 | 37208583 | 38546928 | + | seg_170 | 38078900 | 38081100 | SRPX | RPGR |
| ENST00000457894.1 | 4482 | 38660685 | 38665781 | + | seg_171 | 38663050 | 38664250 | MID1IP1 | OTC |
| ENST00000336949.6 | 4483 | 38662986 | 38665790 | + | seg_171 | 38663050 | 38664250 | MID1IP1 | OTC |
| ENST00000436893.1 | 4484 | 38660821 | 38663136 | − | seg_171 | 38663050 | 38664250 | MID1IP1 | OTC |
| ENST00000378474.3 | 4485 | 38660707 | 38665686 | + | seg_171 | 38663050 | 38664250 | MID1IP1 | OTC |
| ENST00000342274.4 | 4486 | 39910501 | 40036582 | − | seg_183 | 40027900 | 40029300 | BCOR | CSNB1 = NYX |
| ENST00000378455.4 | 4487 | 39910499 | 40036582 | − | seg_183 | 40027900 | 40029300 | BCOR | CSNB1 = NYX |
| ENST00000406200.2 | 4488 | 39922208 | 40036573 | − | seg_183 | 40027900 | 40029300 | BCOR | CSNB1 = NYX |
| ENST00000342595.2 | 4489 | 41306687 | 41334963 | + | seg_193 | 41306350 | 41307400 | NYX | CSNB1 = NYX |
| ENST00000378220.1 | 4490 | 41306713 | 41334905 | + | seg_193 | 41306350 | 41307400 | NYX | CSNB1 = NYX |
| ENST00000442175.1 | 4491 | 41958007 | 41958426 | − | seg_194 | 41958050 | 41959450 | CASK | CSNB1 = NYX |
| ENST00000440002.1 | 4492 | 42315830 | 42558636 | + | seg_196 | 42505050 | 42506050 | CASK | CSNB1 = NYX |
| ENST00000411879.1 | 4493 | 42111712 | 42558542 | + | seg_196 | 42505050 | 42506050 | CASK | CSNB1 = NYX |
| ENST00000378062.5 | 4494 | 43808022 | 43832750 | − | seg_198 | 43830050 | 43831700 | NDP | NDP |
| ENST00000470584.1 | 4495 | 43808928 | 43832632 | − | seg_198 | 43830050 | 43831700 | NDP | NDP |
| ENST00000328306.4 | 4496 | 46464753 | 46618490 | − | seg_202 | 46464100 | 46465450 | CHST7 | UBA1 |
| ENST00000446295.1 | 4497 | 47372001 | 47372882 | − | seg_207 | 47371600 | 47373400 | CXorf24 | UBA1 |
| ENST00000340666.4 | 4498 | 47431303 | 47479252 | − | seg_208 | 47476800 | 47478350 | SYN1 | UBA1 |
| ENST00000295987.7 | 4499 | 47431303 | 47479252 | − | seg_208 | 47476800 | 47478350 | SYN1 | UBA1 |
| ENST00000483225.1 | 4500 | 47566590 | 47596027 | + | seg_209 | 47595750 | 47596900 | UXT | UBA1 |
| ENST00000444248.1 | 4501 | 47662695 | 47664188 | + | seg_210 | 47661850 | 47663050 | ZNF81 | UBA1 |
| ENST00000338709.3 | 4502 | 47657325 | 47664188 | + | seg_210 | 47661850 | 47663050 | ZNF81 | UBA1 |
| ENST00000453735.1 | 4503 | 48166204 | 48168490 | + | seg_212 | 48165350 | 48166500 | SSX9 | WAS |
| ENST00000407081.2 | 4504 | 48156255 | 48165614 | − | seg_212 | 48165350 | 48166500 | SSX9 | WAS |
| ENST00000376909.1 | 4505 | 48154885 | 48165675 | − | seg_212 | 48165350 | 48166500 | SSX9 | WAS |
| ENST00000424410.1 | 4506 | 48193110 | 48193874 | − | seg_214 | 48193350 | 48194400 | SSX3 | WAS |
| ENST00000413071.1 | 4507 | 48239582 | 48242564 | − | seg_216 | 48240000 | 48241200 | SSX4 | WAS |
| ENST00000376327.5 | 4508 | 49028273 | 49031588 | + | seg_219 | 49029700 | 49030700 | PLP2 | PQBP1 |
| ENST00000376322.3 | 4509 | 49028273 | 49030030 | + | seg_219 | 49029700 | 49030700 | PLP2 | PQBP1 |
| ENST00000323022.5 | 4510 | 49061523 | 49089833 | − | seg_220 | 49068450 | 49069750 | CACNA1F | PQBP1 |
| ENST00000376265.2 | 4511 | 49061523 | 49089833 | − | seg_220 | 49068450 | 49069750 | CACNA1F | PQBP1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000376251.1 | 4512 | 49061523 | 49089771 | − | seg_220 | 49068450 | 49069750 | CACNA1F | PQBP1 |
| ENST00000323022.5 | 4513 | 49061523 | 49089833 | − | seg_221 | 49074200 | 49075450 | CACNA1F | PQBP1 |
| ENST00000376265.2 | 4514 | 49061523 | 49089833 | − | seg_221 | 49074200 | 49075450 | CACNA1F | PQBP1 |
| ENST00000376251.1 | 4515 | 49061523 | 49089771 | − | seg_221 | 49074200 | 49075450 | CACNA1F | PQBP1 |
| ENST00000492334.1 | 4516 | 49104172 | 49106976 | + | seg_222 | 49104450 | 49105650 | FOXP3 | PQBP1 |
| ENST00000538876.1 | 4517 | 49091932 | 49106980 | + | seg_222 | 49104450 | 49105650 | FOXP3 | PQBP1 |
| ENST00000376227.3 | 4518 | 49091927 | 49106987 | + | seg_222 | 49104450 | 49105650 | FOXP3 | PQBP1 |
| ENST00000289292.7 | 4519 | 50334647 | 50557302 | − | seg_229 | 50450650 | 50451850 | SHROOM4 | CLCN5 |
| ENST00000376020.2 | 4520 | 50334647 | 50557044 | − | seg_229 | 50450650 | 50451850 | SHROOM4 | CLCN5 |
| ENST00000289292.7 | 4521 | 50334647 | 50557302 | − | seg_230 | 50555600 | 50557750 | SHROOM4 | CLCN5 |
| ENST00000376020.2 | 4522 | 50334647 | 50557044 | − | seg_230 | 50555600 | 50557750 | SHROOM4 | CLCN5 |
| ENST00000425150.1 | 4523 | 51099796 | 51139314 | − | seg_233 | 51126600 | 51128150 | CXorf67 | CLCN5 |
| ENST00000491883.1 | 4524 | 51425000 | 51425485 | − | seg_236 | 51424500 | 51426000 | GSPT2 | CLCN5 |
| ENST00000480752.1 | 4525 | 51453887 | 51454372 | + | seg_237 | 51452900 | 51456150 | GSPT2 | CLCN5 |
| ENST00000375772.3 | 4526 | 51546103 | 51645450 | + | seg_239 | 51545600 | 51546650 | GSPT2 | MRX1 = IQSEC2 |
| ENST00000408778.1 | 4527 | 51806443 | 51806570 | − | seg_241 | 51805500 | 51812400 | MAGED4B | MRX1 = IQSEC2 |
| ENST00000514560.1 | 4528 | 51809141 | 51809753 | − | seg_241 | 51805500 | 51812400 | MAGED4B | MRX1 = IQSEC2 |
| ENST00000486010.1 | 4529 | 51810106 | 51812268 | − | seg_241 | 51805500 | 51812400 | MAGED4B | MRX1 = IQSEC2 |
| ENST00000486469.1 | 4530 | 51810098 | 51810701 | − | seg_241 | 51805500 | 51812400 | MAGED4B | MRX1 = IQSEC2 |
| ENST00000480114.1 | 4531 | 51804925 | 51812303 | − | seg_241 | 51805500 | 51812400 | MAGED4B | MRX1 = IQSEC2 |
| ENST00000470594.1 | 4532 | 51804923 | 51812278 | − | seg_241 | 51805500 | 51812400 | MAGED4B | MRX1 = IQSEC2 |
| ENST00000471617.1 | 4533 | 51804935 | 51807173 | − | seg_241 | 51805500 | 51812400 | MAGED4B | MRX1 = IQSEC2 |
| ENST00000497164.1 | 4534 | 51804923 | 51812278 | − | seg_241 | 51805500 | 51812400 | MAGED4B | MRX1 = IQSEC2 |
| ENST00000481193.2 | 4535 | 51805652 | 51808388 | − | seg_241 | 51805500 | 51812400 | MAGED4B | MRX1 = IQSEC2 |
| ENST00000490581.2 | 4536 | 51804923 | 51807639 | − | seg_241 | 51805500 | 51812400 | MAGED4B | MRX1 = IQSEC2 |
| ENST00000335504.5 | 4537 | 51804923 | 51812344 | − | seg_241 | 51805500 | 51812400 | MAGED4B | MRX1 = IQSEC2 |
| ENST00000360134.6 | 4538 | 51804923 | 51812294 | − | seg_241 | 51805500 | 51812400 | MAGED4B | MRX1 = IQSEC2 |
| ENST00000431659.1 | 4539 | 51804923 | 51812368 | − | seg_241 | 51805500 | 51812400 | MAGED4B | MRX1 = IQSEC2 |
| ENST00000481096.2 | 4540 | 51804923 | 51809773 | − | seg_241 | 51805500 | 51812400 | MAGED4B | MRX1 = IQSEC2 |
| ENST00000485287.1 | 4541 | 51804923 | 51812315 | − | seg_241 | 51805500 | 51812400 | MAGED4B | MRX1 = IQSEC2 |
| ENST00000477634.1 | 4542 | 51928008 | 51935364 | + | seg_242 | 51929300 | 51932300 | MAGED4 | MRX1 = IQSEC2 |
| ENST00000416960.1 | 4543 | 51927919 | 51935364 | + | seg_242 | 51929300 | 51932300 | MAGED4 | MRX1 = IQSEC2 |
| ENST00000474812.1 | 4544 | 51929586 | 51930176 | + | seg_242 | 51929300 | 51932300 | MAGED4 | MRX1 = IQSEC2 |
| ENST00000488430.1 | 4545 | 51927983 | 51935364 | + | seg_242 | 51929300 | 51932300 | MAGED4 | MRX1 = IQSEC2 |
| ENST00000459685.1 | 4546 | 51927972 | 51935364 | + | seg_242 | 51929300 | 51932300 | MAGED4 | MRX1 = IQSEC2 |
| ENST00000471932.1 | 4547 | 51927943 | 51935364 | + | seg_242 | 51929300 | 51932300 | MAGED4 | MRX1 = IQSEC2 |
| ENST00000467526.1 | 4548 | 51928019 | 51930190 | + | seg_242 | 51929300 | 51932300 | MAGED4 | MRX1 = IQSEC2 |
| ENST00000479281.1 | 4549 | 51930729 | 51935364 | + | seg_242 | 51929300 | 51932300 | MAGED4 | MRX1 = IQSEC2 |
| ENST00000375626.3 | 4550 | 51928008 | 51935364 | + | seg_242 | 51929300 | 51932300 | MAGED4 | MRX1 = IQSEC2 |
| ENST00000498483.1 | 4551 | 51928008 | 51935364 | + | seg_242 | 51929300 | 51932300 | MAGED4 | MRX1 = IQSEC2 |
| ENST00000477634.1 | 4552 | 51928008 | 51935364 | + | seg_243 | 51935000 | 51936100 | MAGED4 | MRX1 = IQSEC2 |
| ENST00000494716.1 | 4553 | 51933114 | 51935352 | + | seg_243 | 51935000 | 51936100 | MAGED4 | MRX1 = IQSEC2 |
| ENST00000416960.1 | 4554 | 51927919 | 51935364 | + | seg_243 | 51935000 | 51936100 | MAGED4 | MRX1 = IQSEC2 |
| ENST00000497348.1 | 4555 | 51934138 | 51935280 | + | seg_243 | 51935000 | 51936100 | MAGED4 | MRX1 = IQSEC2 |
| ENST00000488430.1 | 4556 | 51927983 | 51935364 | + | seg_243 | 51935000 | 51936100 | MAGED4 | MRX1 = IQSEC2 |
| ENST00000459685.1 | 4557 | 51927972 | 51935364 | + | seg_243 | 51935000 | 51936100 | MAGED4 | MRX1 = IQSEC2 |
| ENST00000471932.1 | 4558 | 51927943 | 51935364 | + | seg_243 | 51935000 | 51936100 | MAGED4 | MRX1 = IQSEC2 |
| ENST00000479281.1 | 4559 | 51930729 | 51935364 | + | seg_243 | 51935000 | 51936100 | MAGED4 | MRX1 = IQSEC2 |
| ENST00000375626.3 | 4560 | 51928008 | 51935364 | + | seg_243 | 51935000 | 51936100 | MAGED4 | MRX1 = IQSEC2 |
| ENST00000498483.1 | 4561 | 51928008 | 51935364 | + | seg_243 | 51935000 | 51936100 | MAGED4 | MRX1 = IQSEC2 |
| ENST00000518075.1 | 4562 | 52235228 | 52243951 | + | seg_245 | 52239900 | 52241050 | XAGE1B | MRX1 = IQSEC2 |
| ENST00000375612.4 | 4563 | 52239019 | 52243954 | + | seg_245 | 52239900 | 52241050 | XAGE1B | MRX1 = IQSEC2 |
| ENST00000375616.1 | 4564 | 52238818 | 52243954 | + | seg_245 | 52239900 | 52241050 | XAGE1B | MRX1 = IQSEC2 |
| ENST00000399805.2 | 4565 | 52240504 | 52243954 | + | seg_245 | 52239900 | 52241050 | XAGE1B | MRX1 = IQSEC2 |
| ENST00000437949.2 | 4566 | 52238810 | 52243954 | + | seg_245 | 52239900 | 52241050 | XAGE1B | MRX1 = IQSEC2 |
| ENST00000494039.1 | 4567 | 52241006 | 52243954 | + | seg_245 | 52239900 | 52241050 | XAGE1B | MRX1 = IQSEC2 |
| ENST00000519579.1 | 4568 | 52238925 | 52240863 | + | seg_245 | 52239900 | 52241050 | XAGE1B | MRX1 = IQSEC2 |
| ENST00000375613.3 | 4569 | 52238974 | 52243954 | + | seg_245 | 52239900 | 52241050 | XAGE1B | MRX1 = IQSEC2 |
| ENST00000478767.1 | 4570 | 52528159 | 52531107 | − | seg_249 | 52530600 | 52532500 | XAGE1D | MRX1 = IQSEC2 |
| ENST00000374959.3 | 4571 | 52528162 | 52533139 | − | seg_249 | 52530600 | 52532500 | XAGE1D | MRX1 = IQSEC2 |
| ENST00000375578.1 | 4572 | 52528159 | 52533295 | − | seg_249 | 52530600 | 52532500 | XAGE1D | MRX1 = IQSEC2 |
| ENST00000396497.3 | 4573 | 52528159 | 52533303 | − | seg_249 | 52530600 | 52532500 | XAGE1D | MRX1 = IQSEC2 |
| ENST00000438079.1 | 4574 | 52528159 | 52531609 | − | seg_249 | 52530600 | 52532500 | XAGE1D | MRX1 = IQSEC2 |
| ENST00000375572.4 | 4575 | 52528159 | 52533094 | − | seg_249 | 52530600 | 52532500 | XAGE1D | MRX1 = IQSEC2 |
| ENST00000375563.4 | 4576 | 52541053 | 52545988 | − | seg_250 | 52543750 | 52545000 | XAGE1E | MRX1 = IQSEC2 |
| ENST00000375567.3 | 4577 | 52541053 | 52546033 | − | seg_250 | 52543750 | 52545000 | XAGE1E | MRX1 = IQSEC2 |
| ENST00000375570.1 | 4578 | 52541053 | 52546189 | − | seg_250 | 52543750 | 52545000 | XAGE1E | MRX1 = IQSEC2 |
| ENST00000463689.1 | 4579 | 52541053 | 52544001 | − | seg_250 | 52543750 | 52545000 | XAGE1E | MRX1 = IQSEC2 |
| ENST00000429372.2 | 4580 | 52541053 | 52546197 | − | seg_250 | 52543750 | 52545000 | XAGE1E | MRX1 = IQSEC2 |
| ENST00000443473.1 | 4581 | 52701768 | 52706101 | + | seg_252 | 52705000 | 52706750 | SSX7 | MRX1 = IQSEC2 |
| ENST00000434905.1 | 4582 | 52810501 | 52814830 | − | seg_254 | 52809850 | 52811650 | SPANXN5 | MRX1 = IQSEC2 |
| ENST00000414788.1 | 4583 | 52920646 | 52929617 | + | seg_255 | 52919850 | 52921300 | FAM156B | MRX1 = IQSEC2 |
| ENST00000452154.2 | 4584 | 52920336 | 52937089 | + | seg_255 | 52919850 | 52921300 | FAM156B | MRX1 = IQSEC2 |
| ENST00000458697.1 | 4585 | 52925995 | 52929686 | + | seg_256 | 52925850 | 52927100 | FAM156B | MRX1 = IQSEC2 |
| ENST00000414788.1 | 4586 | 52920646 | 52929617 | + | seg_256 | 52925850 | 52927100 | FAM156B | MRX1 = IQSEC2 |
| ENST00000430150.2 | 4587 | 52926322 | 52937587 | + | seg_256 | 52925850 | 52927100 | FAM156B | MRX1 = IQSEC2 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000452154.2 | 4588 | 52920336 | 52937089 | + | seg_256 | 52925850 | 52927100 | FAM156B | MRX1 = IQSEC2 |
| ENST00000452021.2 | 4589 | 52926351 | 52937562 | + | seg_256 | 52925850 | 52927100 | FAM156B | MRX1 = IQSEC2 |
| ENST00000412319.1 | 4590 | 52926426 | 52937587 | + | seg_256 | 52925850 | 52927100 | FAM156B | MRX1 = IQSEC2 |
| ENST00000451084.2 | 4591 | 52977462 | 53024634 | − | seg_257 | 52989600 | 52990850 | FAM156A | MRX1 = IQSEC2 |
| ENST00000510893.1 | 4592 | 52985477 | 52993695 | − | seg_257 | 52989600 | 52990850 | FAM156A | MRX1 = IQSEC2 |
| ENST00000416923.1 | 4593 | 52977768 | 53024632 | − | seg_257 | 52989600 | 52990850 | FAM156A | MRX1 = IQSEC2 |
| ENST00000511863.1 | 4594 | 52984353 | 53024651 | − | seg_257 | 52989600 | 52990850 | FAM156A | MRX1 = IQSEC2 |
| ENST00000414076.2 | 4595 | 52976960 | 53024551 | − | seg_257 | 52989600 | 52990850 | FAM156A | MRX1 = IQSEC2 |
| ENST00000505988.1 | 4596 | 52977787 | 53024551 | − | seg_257 | 52989600 | 52990850 | FAM156A | MRX1 = IQSEC2 |
| ENST00000512364.1 | 4597 | 52976462 | 53024644 | − | seg_257 | 52989600 | 52990850 | FAM156A | MRX1 = IQSEC2 |
| ENST00000447562.1 | 4598 | 52977471 | 52993386 | − | seg_257 | 52989600 | 52990850 | FAM156A | MRX1 = IQSEC2 |
| ENST00000475552.1 | 4599 | 52977803 | 53024634 | − | seg_257 | 52989600 | 52990850 | FAM156A | MRX1 = IQSEC2 |
| ENST00000515858.1 | 4600 | 52994637 | 53024651 | − | seg_258 | 52994300 | 52995300 | FAM156A | MRX1 = IQSEC2 |
| ENST00000451084.2 | 4601 | 52977462 | 53024634 | − | seg_258 | 52994300 | 52995300 | FAM156A | MRX1 = IQSEC2 |
| ENST00000416923.1 | 4602 | 52977768 | 53024632 | − | seg_258 | 52994300 | 52995300 | FAM156A | MRX1 = IQSEC2 |
| ENST00000511863.1 | 4603 | 52984353 | 53024651 | − | seg_258 | 52994300 | 52995300 | FAM156A | MRX1 = IQSEC2 |
| ENST00000414076.2 | 4604 | 52976960 | 53024551 | − | seg_258 | 52994300 | 52995300 | FAM156A | MRX1 = IQSEC2 |
| ENST00000505988.1 | 4605 | 52977787 | 53024551 | − | seg_258 | 52994300 | 52995300 | FAM156A | MRX1 = IQSEC2 |
| ENST00000512364.1 | 4606 | 52976462 | 53024644 | − | seg_258 | 52994300 | 52995300 | FAM156A | MRX1 = IQSEC2 |
| ENST00000505062.1 | 4607 | 52994760 | 53024651 | − | seg_258 | 52994300 | 52995300 | FAM156A | MRX1 = IQSEC2 |
| ENST00000475552.1 | 4608 | 52977803 | 53024634 | − | seg_258 | 52994300 | 52995300 | FAM156A | MRX1 = IQSEC2 |
| ENST00000375365.2 | 4609 | 53263292 | 53310796 | − | seg_260 | 53284450 | 53286250 | IQSEC2 | MRX1 = IQSEC2 |
| ENST00000396435.3 | 4610 | 53262058 | 53350522 | − | seg_260 | 53284450 | 53286250 | IQSEC2 | MRX1 = IQSEC2 |
| ENST00000375368.5 | 4611 | 53262059 | 53350522 | − | seg_260 | 53284450 | 53286250 | IQSEC2 | MRX1 = IQSEC2 |
| ENST00000396435.3 | 4612 | 53262058 | 53350522 | − | seg_261 | 53329950 | 53331050 | IQSEC2 | MRX1 = IQSEC2 |
| ENST00000375368.5 | 4613 | 53262059 | 53350522 | − | seg_261 | 53329950 | 53331050 | IQSEC2 | MRX1 = IQSEC2 |
| ENST00000396435.3 | 4614 | 53262058 | 53350522 | − | seg_262 | 53348300 | 53351800 | IQSEC2 | MRX1 = IQSEC2 |
| ENST00000375368.5 | 4615 | 53262059 | 53350522 | − | seg_262 | 53348300 | 53351800 | IQSEC2 | MRX1 = IQSEC2 |
| ENST00000453905.1 | 4616 | 54044212 | 54075368 | − | seg_267 | 54070050 | 54071100 | PHF8 | PHF8 |
| ENST00000415025.1 | 4617 | 54044204 | 54070495 | − | seg_267 | 54070050 | 54071100 | PHF8 | PHF8 |
| ENST00000437224.1 | 4618 | 54044203 | 54075391 | − | seg_267 | 54070050 | 54071100 | PHF8 | PHF8 |
| ENST00000338154.6 | 4619 | 53963109 | 54070607 | − | seg_267 | 54070050 | 54071100 | PHF8 | PHF8 |
| ENST00000357988.5 | 4620 | 53963109 | 54071682 | − | seg_267 | 54070050 | 54071100 | PHF8 | PHF8 |
| ENST00000396277.3 | 4621 | 53963115 | 54070607 | − | seg_267 | 54070050 | 54071100 | PHF8 | PHF8 |
| ENST00000338946.6 | 4622 | 53963115 | 54070607 | − | seg_267 | 54070050 | 54071100 | PHF8 | PHF8 |
| ENST00000354646.2 | 4623 | 54219258 | 54384438 | − | seg_268 | 54221650 | 54222700 | FAM120C | PHF8 |
| ENST00000375169.3 | 4624 | 54219256 | 54384438 | − | seg_268 | 54221650 | 54222700 | FAM120C | PHF8 |
| ENST00000375159.2 | 4625 | 54224757 | 54360106 | − | seg_269 | 54315000 | 54316050 | WNK3 | FGD1 |
| ENST00000354646.2 | 4626 | 54219258 | 54384438 | − | seg_269 | 54315000 | 54316050 | WNK3 | FGD1 |
| ENST00000375169.3 | 4627 | 54219256 | 54384438 | − | seg_269 | 54315000 | 54316050 | WNK3 | FGD1 |
| ENST00000375135.3 | 4628 | 54471887 | 54522599 | − | seg_271 | 54521250 | 54522900 | FGD1 | FGD1 |
| ENST00000537277.1 | 4629 | 54475243 | 54522322 | − | seg_271 | 54521250 | 54522900 | FGD1 | FGD1 |
| ENST00000218436.6 | 4630 | 54775332 | 54824673 | − | seg_272 | 54776750 | 54777850 | ITIH6 | FGD1 |
| ENST00000471758.1 | 4631 | 55026826 | 55033190 | + | seg_273 | 55026400 | 55027550 | APEX2 | ALAS2 |
| ENST00000374987.3 | 4632 | 55026790 | 55035490 | + | seg_273 | 55026400 | 55027550 | APEX2 | ALAS2 |
| ENST00000452532.1 | 4633 | 55934556 | 56041606 | + | seg_276 | 56029500 | 56030800 | AL353698.1 | ALAS2 |
| ENST00000423617.1 | 4634 | 56755789 | 56844059 | + | seg_278 | 56787300 | 56788350 | UBQLN2 | ALAS2 |
| ENST00000451583.1 | 4635 | 56755806 | 56843809 | + | seg_278 | 56787300 | 56788350 | UBQLN2 | ALAS2 |
| ENST00000374922.4 | 4636 | 56755692 | 56844813 | + | seg_278 | 56787300 | 56788350 | UBQLN2 | ALAS2 |
| ENST00000437625.1 | 4637 | 56755677 | 56843883 | + | seg_278 | 56787300 | 56788350 | UBQLN2 | ALAS2 |
| ENST00000374870.4 | 4638 | 62854856 | 62975031 | − | seg_306 | 62967650 | 62969200 | ARHGEF9 | AR |
| ENST00000437457.2 | 4639 | 62854856 | 63005426 | − | seg_306 | 62967650 | 62969200 | ARHGEF9 | AR |
| ENST00000374878.1 | 4640 | 62854847 | 63005413 | − | seg_306 | 62967650 | 62969200 | ARHGEF9 | AR |
| ENST00000495564.1 | 4641 | 62857860 | 62974991 | − | seg_306 | 62967650 | 62969200 | ARHGEF9 | AR |
| ENST00000253401.6 | 4642 | 62854847 | 62974993 | − | seg_306 | 62967650 | 62969200 | ARHGEF9 | AR |
| ENST00000374872.1 | 4643 | 62857862 | 62974988 | − | seg_306 | 62967650 | 62969200 | ARHGEF9 | AR |
| ENST00000374869.3 | 4644 | 63404997 | 63425624 | − | seg_308 | 63412200 | 63413300 | AMER1 | AR |
| ENST00000403336.1 | 4645 | 63405997 | 63413166 | − | seg_308 | 63412200 | 63413300 | AMER1 | AR |
| ENST00000330258.3 | 4646 | 63404997 | 63425624 | − | seg_308 | 63412200 | 63413300 | AMER1 | AR |
| ENST00000488406.1 | 4647 | 64137280 | 64140007 | − | seg_309 | 64138750 | 64139800 | ZC4H2 | AR |
| ENST00000447788.2 | 4648 | 64136250 | 64196413 | − | seg_309 | 64138750 | 64139800 | ZC4H2 | AR |
| ENST00000374839.3 | 4649 | 64136261 | 64196364 | − | seg_309 | 64138750 | 64139800 | ZC4H2 | AR |
| ENST00000476032.1 | 4650 | 64137738 | 64196243 | − | seg_309 | 64138750 | 64139800 | ZC4H2 | AR |
| ENST00000488608.1 | 4651 | 64136368 | 64196413 | − | seg_309 | 64138750 | 64139800 | ZC4H2 | AR |
| ENST00000545618.1 | 4652 | 64136250 | 64196328 | − | seg_309 | 64138750 | 64139800 | ZC4H2 | AR |
| ENST0000492653.1 | 4653 | 64137660 | 64196353 | − | seg_309 | 64138750 | 64139800 | ZC4H2 | AR |
| ENST00000337990.2 | 4654 | 64136262 | 64254593 | − | seg_309 | 64138750 | 64139800 | ZC4H2 | AR |
| ENST00000488831.1 | 4655 | 64137720 | 64254549 | − | seg_309 | 64138750 | 64139800 | ZC4H2 | AR |
| ENST00000440433.1 | 4656 | 64770778 | 64772301 | − | seg_310 | 64770000 | 64772700 | LAS1L | AR |
| ENST00000538891.1 | 4657 | 66764989 | 66766608 | + | seg_312 | 66763900 | 66766950 | AR | AR |
| ENST00000396044.3 | 4658 | 66764986 | 66943778 | + | seg_312 | 66763900 | 66766950 | AR | AR |
| ENST00000513847.1 | 4659 | 66764662 | 66909605 | + | seg_312 | 66763900 | 66766950 | AR | AR |
| ENST00000544984.1 | 4660 | 66763874 | 66944119 | + | seg_312 | 66763900 | 66766950 | AR | AR |
| ENST00000514029.1 | 4661 | 66764662 | 66915917 | + | seg_312 | 66763900 | 66766950 | AR | AR |
| ENST00000374690.3 | 4662 | 66764465 | 66950461 | + | seg_312 | 66763900 | 66766950 | AR | AR |
| ENST00000504326.1 | 4663 | 66764662 | 66915917 | + | seg_312 | 66763900 | 66766950 | AR | AR |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000488088.1 | 4664 | 67867508 | 67876393 | + | seg_313 | 67871900 | 67872900 | STARD8 | ED1 = EDA |
| ENST00000374599.3 | 4665 | 67867610 | 67945678 | + | seg_313 | 67871900 | 67872900 | STARD8 | ED1 = EDA |
| ENST00000523864.1 | 4666 | 67867511 | 67945684 | + | seg_313 | 67871900 | 67872900 | STARD8 | ED1 = EDA |
| ENST00000252336.6 | 4667 | 67867511 | 67945682 | + | seg_313 | 67871900 | 67872900 | STARD8 | ED1 = EDA |
| ENST00000204961.4 | 4668 | 68048840 | 68061990 | + | seg_314 | 68048550 | 68051950 | EFNB1 | ED1 = EDA |
| ENST00000399711.1 | 4669 | 68399400 | 68429767 | + | seg_318 | 68406000 | 68407300 | PJA1 | ED1 = EDA |
| ENST00000399711.1 | 4670 | 68399400 | 68429767 | + | seg_319 | 68423100 | 68425000 | PJA1 | ED1 = EDA |
| ENST00000338901.3 | 4671 | 68835911 | 68890104 | + | seg_322 | 68836650 | 68837650 | EDA | ED1 = EDA |
| ENST00000374548.1 | 4672 | 68835911 | 69177354 | + | seg_322 | 68836650 | 68837650 | EDA | ED1 = EDA |
| ENST00000525810.1 | 4673 | 68835911 | 69080892 | + | seg_322 | 68836650 | 68837650 | EDA | ED1 = EDA |
| ENST00000513754.2 | 4674 | 68835911 | 69177327 | + | seg_322 | 68836650 | 68837650 | EDA | ED1 = EDA |
| ENST00000533317.1 | 4675 | 68835911 | 69177327 | + | seg_322 | 68836650 | 68837650 | EDA | ED1 = EDA |
| ENST00000527388.1 | 4676 | 68835911 | 69080892 | + | seg_322 | 68836650 | 68837650 | EDA | ED1 = EDA |
| ENST00000502251.1 | 4677 | 68835911 | 69177354 | + | seg_322 | 68836650 | 68837650 | EDA | ED1 = EDA |
| ENST00000374552.4 | 4678 | 68835911 | 69259319 | + | seg_322 | 68836650 | 68837650 | EDA | ED1 = EDA |
| ENST00000374553.2 | 4679 | 68835911 | 69259319 | + | seg_322 | 68836650 | 68837650 | EDA | ED1 = EDA |
| ENST00000524573.1 | 4680 | 68835961 | 69255487 | + | seg_322 | 68836650 | 68837650 | EDA | ED1 = EDA |
| ENST00000342206.6 | 4681 | 69353299 | 69386174 | + | seg_323 | 69354600 | 69355600 | IGBP1 | ED1 = EDA |
| ENST00000356413.4 | 4682 | 69353313 | 69386174 | + | seg_323 | 69354600 | 69355600 | IGBP1 | ED1 = EDA |
| ENST00000194900.4 | 4683 | 69664711 | 69725337 | + | seg_325 | 69663950 | 69665850 | DLG3 | GJB1 |
| ENST00000463252.1 | 4684 | 69664986 | 69723796 | + | seg_325 | 69663950 | 69665850 | DLG3 | GJB1 |
| ENST00000374360.3 | 4685 | 69664819 | 69725337 | + | seg_325 | 69663950 | 69665850 | DLG3 | GJB1 |
| ENST00000344304.3 | 4686 | 69748791 | 70117396 | − | seg_326 | 70013100 | 70014100 | TEX11 | GJB1 |
| ENST00000395889.2 | 4687 | 69748791 | 70128561 | − | seg_326 | 70013100 | 70014100 | TEX11 | GJB1 |
| ENST00000374333.2 | 4688 | 69748790 | 70128581 | − | seg_326 | 70013100 | 70014100 | TEX11 | GJB1 |
| ENST00000374051.3 | 4689 | 70364693 | 70391051 | + | seg_327 | 70368600 | 70369750 | NLGN3 | GJB1 |
| ENST00000395855.2 | 4690 | 70364693 | 70387607 | + | seg_327 | 70368600 | 70369750 | NLGN3 | GJB1 |
| ENST00000536169.1 | 4691 | 70364681 | 70391049 | + | seg_327 | 70368600 | 70369750 | NLGN3 | GJB1 |
| ENST00000358741.3 | 4692 | 70364712 | 70390143 | + | seg_327 | 70368600 | 70369750 | NLGN3 | GJB1 |
| ENST00000542063.1 | 4693 | 70364686 | 70390964 | + | seg_327 | 70368600 | 70369750 | NLGN3 | GJB1 |
| ENST00000447581.1 | 4694 | 70435109 | 70443810 | + | seg_328 | 70435950 | 70436950 | GJB1 | GJB1 |
| ENST00000374029.1 | 4695 | 70435044 | 70445050 | + | seg_328 | 70435950 | 70436950 | GJB1 | GJB1 |
| ENST00000374022.3 | 4696 | 70435062 | 70445366 | + | seg_328 | 70435950 | 70436950 | GJB1 | GJB1 |
| ENST00000447581.1 | 4697 | 70435109 | 70443810 | + | seg_329 | 70443150 | 70444550 | GJB1 | GJB1 |
| ENST00000374029.1 | 4698 | 70435044 | 70445050 | + | seg_329 | 70443150 | 70444550 | GJB1 | GJB1 |
| ENST00000361726.6 | 4699 | 70443056 | 70445048 | + | seg_329 | 70443150 | 70444550 | GJB1 | GJB1 |
| ENST00000374022.3 | 4700 | 70435062 | 70445366 | + | seg_329 | 70443150 | 70444550 | GJB1 | GJB1 |
| ENST00000422194.1 | 4701 | 70882845 | 70885603 | − | seg_331 | 70877750 | 70883200 | CXCR3 | GJB1 |
| ENST00000433410.1 | 4702 | 70882848 | 70884121 | − | seg_331 | 70877750 | 70883200 | CXCR3 | GJB1 |
| ENST00000508574.1 | 4703 | 70917046 | 70926305 | + | seg_332 | 70920450 | 70921550 | CXCR3 | GJB1 |
| ENST00000417668.1 | 4704 | 70938992 | 70939460 | + | seg_333 | 70931300 | 70944400 | CXCR3 | GJB1 |
| ENST00000457716.1 | 4705 | 70939766 | 70940650 | + | seg_333 | 70931300 | 70944400 | CXCR3 | GJB1 |
| ENST00000535490.1 | 4706 | 70934224 | 70938135 | − | seg_333 | 70931300 | 70944400 | CXCR3 | GJB1 |
| ENST00000452468.1 | 4707 | 70934221 | 70936237 | − | seg_333 | 70931300 | 70944400 | CXCR3 | GJB1 |
| ENST00000456199.1 | 4708 | 70981815 | 70982283 | − | seg_336 | 70973450 | 70990950 | CXCR3 | GJB1 |
| ENST00000439926.1 | 4709 | 70980625 | 70981509 | − | seg_336 | 70973450 | 70990950 | CXCR3 | GJB1 |
| ENST00000440412.1 | 4710 | 70985038 | 70987054 | + | seg_336 | 70973450 | 70990950 | CXCR3 | GJB1 |
| ENST00000542739.1 | 4711 | 70983140 | 70987051 | + | seg_336 | 70973450 | 70990950 | CXCR3 | GJB1 |
| ENST00000408757.1 | 4712 | 70979235 | 70979305 | − | seg_336 | 70973450 | 70990950 | CXCR3 | GJB1 |
| ENST00000540800.1 | 4713 | 71130938 | 71363424 | + | seg_339 | 71130200 | 71132050 | NHSL2 | GJB1 |
| ENST00000540800.1 | 4714 | 71130938 | 71363424 | + | seg_340 | 71237900 | 71239300 | NHSL2 | GJB1 |
| ENST00000540800.1 | 4715 | 71130938 | 71363424 | + | seg_341 | 71241400 | 71242500 | RGAG4 | GJB1 |
| ENST00000540800.1 | 4716 | 71130938 | 71363424 | + | seg_342 | 71279100 | 71280300 | RGAG4 | GJB1 |
| ENST00000479991.1 | 4717 | 71346960 | 71351751 | − | seg_343 | 71350200 | 71352700 | RGAG4 | GJB1 |
| ENST00000545866.1 | 4718 | 71346958 | 71351758 | − | seg_343 | 71350200 | 71352700 | RGAG4 | GJB1 |
| ENST00000513469.1 | 4719 | 71352000 | 71354556 | + | seg_343 | 71350200 | 71352700 | RGAG4 | GJB1 |
| ENST00000540800.1 | 4720 | 71130938 | 71363424 | + | seg_343 | 71350200 | 71352700 | RGAG4 | GJB1 |
| ENST00000456343.2 | 4721 | 71364034 | 71381600 | + | seg_344 | 71364150 | 71365850 | NHSL2 | GJB1 |
| ENST00000246139.5 | 4722 | 71521500 | 71526837 | − | seg_345 | 71525750 | 71529400 | CITED1 | GJB1 |
| ENST00000445983.1 | 4723 | 71521490 | 71525764 | − | seg_345 | 71525750 | 71529400 | CITED1 | GJB1 |
| ENST00000431381.1 | 4724 | 71521490 | 71525764 | − | seg_345 | 71525750 | 71529400 | CITED1 | GJB1 |
| ENST00000453707.2 | 4725 | 71521488 | 71527000 | − | seg_345 | 71525750 | 71529400 | CITED1 | GJB1 |
| ENST00000454225.1 | 4726 | 71522056 | 71526757 | − | seg_345 | 71525750 | 71529400 | CITED1 | GJB1 |
| ENST00000373619.3 | 4727 | 71521497 | 71527037 | − | seg_345 | 71525750 | 71529400 | CITED1 | GJB1 |
| ENST00000339490.3 | 4728 | 71798665 | 71934029 | − | seg_346 | 71800550 | 71801550 | HDAC8 | GJB1 |
| ENST00000373542.4 | 4729 | 71798664 | 71933888 | − | seg_346 | 71800550 | 71801550 | HDAC8 | GJB1 |
| ENST00000541944.1 | 4730 | 71798665 | 71934029 | − | seg_346 | 71800550 | 71801550 | HDAC8 | GJB1 |
| ENST00000373545.3 | 4731 | 71798664 | 71934167 | − | seg_346 | 71800550 | 71801550 | HDAC8 | GJB1 |
| ENST00000373539.3 | 4732 | 71800477 | 71934106 | − | seg_346 | 71800550 | 71801550 | HDAC8 | GJB1 |
| ENST00000472595.1 | 4733 | 71996833 | 72068636 | + | seg_348 | 72011750 | 72013700 | DMRTC1B | GJB1 |
| ENST00000334036.5 | 4734 | 71996972 | 72068632 | + | seg_348 | 72011750 | 72013700 | DMRTC1B | GJB1 |
| ENST00000483816.1 | 4735 | 72091859 | 72163653 | + | seg_349 | 72136450 | 72138350 | LINC00684 | GJB1 |
| ENST00000483816.1 | 4736 | 72091859 | 72163653 | − | seg_350 | 72146600 | 72148500 | LINC00684 | GJB1 |
| ENST00000373527.1 | 4737 | 72158003 | 72158798 | + | seg_351 | 72157050 | 72158200 | LINC00684 | GJB1 |
| ENST00000373524.1 | 4738 | 72158069 | 72158780 | + | seg_351 | 72157050 | 72158200 | LINC00684 | GJB1 |
| ENST00000483816.1 | 4739 | 72091859 | 72163653 | − | seg_351 | 72157050 | 72158200 | LINC00684 | GJB1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000373514.1 | 4740 | 72667088 | 72675081 | + | seg_352 | 72666800 | 72668350 | CDX4 | ABCB7 |
| ENST00000430772.1 | 4741 | 73467699 | 73513362 | − | seg_355 | 73498350 | 73499350 | ZCCHC13 | ABCB7 |
| ENST00000429124.1 | 4742 | 73498209 | 73512435 | − | seg_355 | 73498350 | 73499350 | ZCCHC13 | ABCB7 |
| ENST00000276033.4 | 4743 | 73640638 | 73753752 | + | seg_356 | 73642400 | 73643800 | SLC16A2 | ABCB7 |
| ENST00000055682.5 | 4744 | 73952692 | 74145287 | + | seg_357 | 74055400 | 74056550 | KIAA2022 | ABCB7 |
| ENST00000373468.1 | 4745 | 73952684 | 74145320 | − | seg_357 | 74055400 | 74056550 | KIAA2022 | ABCB7 |
| ENST00000350425.4 | 4746 | 77166194 | 77305892 | + | seg_358 | 77165200 | 77166850 | COX7B | ATP7A |
| ENST00000341514.6 | 4747 | 77166199 | 77305892 | + | seg_358 | 77165200 | 77166850 | COX7B | ATP7A |
| ENST00000343533.5 | 4748 | 77166194 | 77305892 | + | seg_358 | 77165200 | 77166850 | COX7B | ATP7A |
| ENST00000400860.5 | 4749 | 77166224 | 77302211 | + | seg_358 | 77165200 | 77166850 | COX7B | ATP7A |
| ENST00000343912.6 | 4750 | 77166194 | 77301057 | + | seg_358 | 77165200 | 77166850 | COX7B | ATP7A |
| ENST00000458128.1 | 4751 | 77223458 | 77225135 | − | seg_359 | 77223450 | 77224850 | PGAM4 | ATP7A |
| ENST00000355691.5 | 4752 | 77220936 | 77268087 | + | seg_359 | 77223450 | 77224850 | PGAM4 | ATP7A |
| ENST00000350425.4 | 4753 | 77166194 | 77305892 | + | seg_359 | 77223450 | 77224850 | PGAM4 | ATP7A |
| ENST00000341514.6 | 4754 | 77166199 | 77305892 | + | seg_359 | 77223450 | 77224850 | PGAM4 | ATP7A |
| ENST00000343533.5 | 4755 | 77166194 | 77305892 | + | seg_359 | 77223450 | 77224850 | PGAM4 | ATP7A |
| ENST00000400860.5 | 4756 | 77166224 | 77302211 | + | seg_359 | 77223450 | 77224850 | PGAM4 | ATP7A |
| ENST00000343912.6 | 4757 | 77166194 | 77301057 | + | seg_359 | 77223450 | 77224850 | PGAM4 | ATP7A |
| ENST00000350425.4 | 4758 | 77166194 | 77305892 | + | seg_360 | 77296400 | 77297850 | PGK1 | PGK1 |
| ENST00000341514.6 | 4759 | 77166199 | 77305892 | + | seg_360 | 77296400 | 77297850 | PGK1 | PGK1 |
| ENST00000343533.5 | 4760 | 77166194 | 77305892 | + | seg_360 | 77296400 | 77297850 | PGK1 | PGK1 |
| ENST00000400860.5 | 4761 | 77166224 | 77302211 | + | seg_360 | 77296400 | 77297850 | PGK1 | PGK1 |
| ENST00000343912.6 | 4762 | 77166194 | 77301057 | + | seg_360 | 77296400 | 77297850 | PGK1 | PGK1 |
| ENST00000476373.1 | 4763 | 79270268 | 79278153 | + | seg_363 | 79277400 | 79278700 | TBX22 | PGK1 |
| ENST00000373296.3 | 4764 | 79270255 | 79286872 | + | seg_363 | 79277400 | 79278700 | TBX22 | PGK1 |
| ENST00000373291.1 | 4765 | 79278568 | 79287268 | + | seg_363 | 79277400 | 79278700 | TBX22 | PGK1 |
| ENST00000373294.5 | 4766 | 79277741 | 79287268 | + | seg_363 | 79277400 | 79278700 | TBX22 | PGK1 |
| ENST00000442340.1 | 4767 | 79270255 | 79287268 | + | seg_363 | 79277400 | 79278700 | TBX22 | PGK1 |
| ENST00000544771.1 | 4768 | 83116170 | 83254350 | + | seg_367 | 83187500 | 83188750 | CYLC1 | CHM |
| ENST00000437961.1 | 4769 | 85106580 | 85106687 | − | seg_368 | 85105500 | 85106600 | CHM | CHM |
| ENST00000395337.2 | 4770 | 91034260 | 91139006 | + | seg_373 | 91035500 | 91036850 | PCDH11X | CHM |
| ENST00000373034.4 | 4771 | 99546642 | 99665271 | − | seg_375 | 99556100 | 99557150 | PCDH19 | BTK |
| ENST00000255531.7 | 4772 | 99546644 | 99665271 | − | seg_375 | 99556100 | 99557150 | PCDH19 | BTK |
| ENST00000420881.2 | 4773 | 99546642 | 99663595 | − | seg_375 | 99556100 | 99557150 | PCDH19 | BTK |
| ENST00000373020.4 | 4774 | 99883667 | 99891803 | − | seg_377 | 99891050 | 99892300 | TSPAN6 | BTK |
| ENST00000431386.2 | 4775 | 99884765 | 99891848 | − | seg_377 | 99891050 | 99892300 | TSPAN6 | BTK |
| ENST00000496771.1 | 4776 | 99887538 | 99891686 | − | seg_377 | 99891050 | 99892300 | TSPAN6 | BTK |
| ENST00000494424.1 | 4777 | 99888439 | 99894988 | − | seg_377 | 99891050 | 99892300 | TSPAN6 | BTK |
| ENST00000455616.1 | 4778 | 99929491 | 99986522 | − | seg_378 | 99934950 | 99936050 | SYTL4 | BTK |
| ENST00000372989.1 | 4779 | 99929488 | 99986498 | − | seg_378 | 99934950 | 99936050 | SYTL4 | BTK |
| ENST00000276141.6 | 4780 | 99929491 | 99986522 | − | seg_378 | 99934950 | 99936050 | SYTL4 | BTK |
| ENST00000454200.2 | 4781 | 99929491 | 99986522 | − | seg_378 | 99934950 | 99936050 | SYTL4 | BTK |
| ENST00000263033.5 | 4782 | 99930894 | 99987108 | − | seg_378 | 99934950 | 99936050 | SYTL4 | BTK |
| ENST00000444892.2 | 4783 | 100333871 | 100350296 | + | seg_380 | 100334000 | 100335900 | TMEM35 | BTK |
| ENST00000372930.4 | 4784 | 100333709 | 100351353 | + | seg_380 | 100334000 | 100335900 | TMEM35 | BTK |
| ENST00000538510.1 | 4785 | 100486534 | 100519485 | + | seg_381 | 100509100 | 100510450 | DRP2 | BTK |
| ENST00000541709.1 | 4786 | 100474933 | 100519485 | + | seg_381 | 100509100 | 100510450 | DRP2 | BTK |
| ENST00000402866.1 | 4787 | 100474758 | 100519486 | + | seg_381 | 100509100 | 100510450 | DRP2 | BTK |
| ENST00000395209.3 | 4788 | 100474775 | 100519486 | + | seg_381 | 100509100 | 100510450 | DRP2 | BTK |
| ENST00000453574.1 | 4789 | 100673287 | 100674171 | + | seg_382 | 100672350 | 100673500 | HNRNPH2 | GLA |
| ENST00000430461.1 | 4790 | 100673286 | 100701120 | + | seg_382 | 100672350 | 100673500 | HNRNPH2 | GLA |
| ENST00000433011.1 | 4791 | 100673275 | 100788446 | + | seg_382 | 100672350 | 100673500 | HNRNPH2 | GLA |
| ENST00000452188.1 | 4792 | 100740420 | 100788446 | + | seg_383 | 100744750 | 100745800 | ARMCX4 | GLA |
| ENST00000455331.1 | 4793 | 100740440 | 100754031 | + | seg_383 | 100744750 | 100745800 | ARMCX4 | GLA |
| ENST00000442270.1 | 4794 | 100740443 | 100788446 | + | seg_383 | 100744750 | 100745800 | ARMCX4 | GLA |
| ENST00000354842.4 | 4795 | 100740462 | 100788446 | + | seg_383 | 100744750 | 100745800 | ARMCX4 | GLA |
| ENST00000433011.1 | 4796 | 100673275 | 100788446 | + | seg_383 | 100744750 | 100745800 | ARMCX4 | GLA |
| ENST00000423738.2 | 4797 | 100740440 | 100750794 | + | seg_383 | 100744750 | 100745800 | ARMCX4 | GLA |
| ENST00000445416.1 | 4798 | 100740241 | 100771941 | + | seg_383 | 100744750 | 100745800 | ARMCX4 | GLA |
| ENST00000392722.2 | 4799 | 100792472 | 100794237 | − | seg_384 | 100793500 | 100794650 | ARMCX1 | GLA |
| ENST00000372828.2 | 4800 | 100852488 | 100853049 | + | seg_385 | 100852500 | 100853550 | ARMCX6 | GLA |
| ENST00000448512.1 | 4801 | 101470280 | 101567445 | + | seg_387 | 101564000 | 101565000 | NXF2 | GLA |
| ENST00000372758.1 | 4802 | 101478939 | 101581631 | + | seg_387 | 101564000 | 101565000 | NXF2 | GLA |
| ENST00000372763.1 | 4803 | 101478829 | 101581634 | + | seg_387 | 101564000 | 101565000 | NXF2 | GLA |
| ENST00000330252.5 | 4804 | 101470280 | 101581631 | + | seg_387 | 101564000 | 101565000 | NXF2 | GLA |
| ENST00000372757.1 | 4805 | 101502170 | 101581631 | + | seg_387 | 101564000 | 101565000 | NXF2 | GLA |
| ENST00000395088.2 | 4806 | 101470280 | 101581634 | + | seg_387 | 101564000 | 101565000 | NXF2 | GLA |
| ENST00000289373.4 | 4807 | 101768604 | 101771712 | − | seg_389 | 101770350 | 101771700 | TMSB15A | GLA |
| ENST00000372680.1 | 4808 | 102528619 | 102531800 | − | seg_390 | 102529150 | 102533650 | TCEAL5 | GLA |
| ENST00000449185.1 | 4809 | 102564600 | 102565863 | − | seg_391 | 102564750 | 102566250 | BEX2 | GLA |
| ENST00000372674.1 | 4810 | 102564430 | 102565935 | − | seg_391 | 102564750 | 102566250 | BEX2 | GLA |
| ENST00000372677.3 | 4811 | 102564274 | 102565974 | − | seg_391 | 102564750 | 102566250 | BEX2 | GLA |
| ENST00000536889.1 | 4812 | 102564282 | 102565883 | − | seg_391 | 102564750 | 102566250 | BEX2 | GLA |
| ENST00000332431.4 | 4813 | 102585124 | 102587254 | + | seg_392 | 102585450 | 102586700 | TCEAL7 | GLA |
| ENST00000372666.1 | 4814 | 102585157 | 102587016 | + | seg_392 | 102585450 | 102586700 | TCEAL7 | GLA |
| ENST00000425011.1 | 4815 | 102840543 | 102841777 | + | seg_393 | 102840700 | 102841750 | TCEAL4 | GLA |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000481555.1 | 4816 | 102840433 | 102841427 | + | seg_393 | 102840700 | 102841750 | TCEAL4 | GLA |
| ENST00000490644.1 | 4817 | 102840451 | 102841833 | + | seg_393 | 102840700 | 102841750 | TCEAL4 | GLA |
| ENST00000469586.1 | 4818 | 102841064 | 102841991 | + | seg_393 | 102840700 | 102841750 | TCEAL4 | GLA |
| ENST00000434216.2 | 4819 | 102840506 | 102841753 | + | seg_393 | 102840700 | 102841750 | TCEAL4 | GLA |
| ENST00000459722.1 | 4820 | 102840456 | 102841877 | + | seg_393 | 102840700 | 102841750 | TCEAL4 | GLA |
| ENST00000472484.1 | 4821 | 102840441 | 102842657 | + | seg_393 | 102840700 | 102841750 | TCEAL4 | GLA |
| ENST00000468024.1 | 4822 | 102840420 | 102842446 | + | seg_393 | 102840700 | 102841750 | TCEAL4 | GLA |
| ENST00000472745.1 | 4823 | 102840461 | 102842622 | + | seg_393 | 102840700 | 102841750 | TCEAL4 | GLA |
| ENST00000494801.1 | 4824 | 102840491 | 102842454 | + | seg_393 | 102840700 | 102841750 | TCEAL4 | GLA |
| ENST00000415568.2 | 4825 | 102840443 | 102842430 | + | seg_393 | 102840700 | 102841750 | TCEAL4 | GLA |
| ENST00000372629.4 | 4826 | 102831159 | 102842446 | + | seg_393 | 102840700 | 102841750 | TCEAL4 | GLA |
| ENST00000414064.2 | 4827 | 102840445 | 102842653 | + | seg_393 | 102840700 | 102841750 | TCEAL4 | GLA |
| ENST00000480725.1 | 4828 | 102973502 | 102983552 | − | seg_395 | 102982800 | 102984450 | GLRA4 | TBG = SERPINA7 |
| ENST00000372617.4 | 4829 | 102962152 | 102983552 | − | seg_395 | 102982800 | 102984450 | GLRA4 | TBG = SERPINA7 |
| ENST00000436213.1 | 4830 | 102962228 | 102983583 | − | seg_395 | 102982800 | 102984450 | GLRA4 | TBG = SERPINA7 |
| ENST00000243298.2 | 4831 | 103077252 | 103087158 | − | seg_396 | 103086000 | 103088000 | RAB9B | TBG = SERPINA7 |
| ENST00000447281.1 | 4832 | 103172005 | 103174131 | − | seg_397 | 103172500 | 103174100 | TMSB15B | TBG = SERPINA7 |
| ENST00000455723.1 | 4833 | 103173770 | 103187485 | + | seg_397 | 103172500 | 103174100 | TMSB15B | TBG = SERPINA7 |
| ENST00000419165.1 | 4834 | 103173479 | 103220554 | + | seg_397 | 103172500 | 103174100 | TMSB15B | TBG = SERPINA7 |
| ENST00000540220.1 | 4835 | 103217224 | 103220868 | + | seg_398 | 103216950 | 103218150 | TMSB15B | TBG = SERPINA7 |
| ENST00000436583.1 | 4836 | 103217242 | 103220554 | + | seg_398 | 103216950 | 103218150 | TMSB15B | TBG = SERPINA7 |
| ENST00000419165.1 | 4837 | 103173479 | 103220554 | + | seg_398 | 103216950 | 103218150 | TMSB15B | TBG = SERPINA7 |
| ENST00000423478.1 | 4838 | 103356822 | 103357563 | + | seg_402 | 103355950 | 103358450 | SLC25A53 | TBG = SERPINA7 |
| ENST00000422784.1 | 4839 | 103357235 | 103360533 | + | seg_402 | 103355950 | 103358450 | SLC25A53 | TBG = SERPINA7 |
| ENST00000537356.1 | 4840 | 103357107 | 103360531 | + | seg_402 | 103355950 | 103358450 | SLC25A53 | TBG = SERPINA7 |
| ENST00000357421.4 | 4841 | 103343898 | 103401708 | − | seg_402 | 103355950 | 103358450 | SLC25A53 | TBG = SERPINA7 |
| ENST00000243300.9 | 4842 | 105066536 | 105202602 | + | seg_405 | 105065050 | 105067850 | NRK | TBG = SERPINA7 |
| ENST00000536164.1 | 4843 | 105066574 | 105139308 | + | seg_405 | 105065050 | 105067850 | NRK | TBG = SERPINA7 |
| ENST00000428173.2 | 4844 | 105066536 | 105202601 | + | seg_405 | 105065050 | 105067850 | NRK | TBG = SERPINA7 |
| ENST00000418562.1 | 4845 | 105937024 | 106033435 | + | seg_406 | 105960300 | 105961850 | RNF128 | TBG = SERPINA7 |
| ENST00000324342.3 | 4846 | 105937068 | 106040223 | + | seg_406 | 105960300 | 105961850 | RNF128 | TBG = SERPINA7 |
| ENST00000357242.5 | 4847 | 106045910 | 106119375 | + | seg_407 | 106047050 | 106048050 | TBC1D8B | TBG = SERPINA7 |
| ENST00000481617.2 | 4848 | 106045935 | 106073313 | + | seg_407 | 106047050 | 106048050 | TBC1D8B | TBG = SERPINA7 |
| ENST00000276175.3 | 4849 | 106046043 | 106117347 | + | seg_407 | 106047050 | 106048050 | TBC1D8B | TBG = SERPINA7 |
| ENST00000310452.2 | 4850 | 106045919 | 106093061 | + | seg_407 | 106047050 | 106048050 | TBC1D8B | TBG = SERPINA7 |
| ENST00000540876.1 | 4851 | 106161590 | 106174089 | + | seg_408 | 106172400 | 106173500 | CLDN2 | PRPS1 |
| ENST00000541806.1 | 4852 | 106143394 | 106174089 | + | seg_408 | 106172400 | 106173500 | CLDN2 | PRPS1 |
| ENST00000358740.3 | 4853 | 106057103 | 106236570 | − | seg_408 | 106172400 | 106173500 | CLDN2 | PRPS1 |
| ENST00000336803.1 | 4854 | 106163634 | 106174091 | + | seg_408 | 106172400 | 106173500 | CLDN2 | PRPS1 |
| ENST00000415252.1 | 4855 | 106756213 | 106789051 | − | seg_411 | 106766900 | 106768200 | FRMPD3 | PRPS1 |
| ENST00000276185.4 | 4856 | 106765680 | 106846603 | + | seg_411 | 106766900 | 106768200 | FRMPD3 | PRPS1 |
| ENST00000477796.1 | 4857 | 106787813 | 106798427 | + | seg_412 | 106794250 | 106794250 | FRMPD3 | PRPS1 |
| ENST00000276185.4 | 4858 | 106765680 | 106846603 | + | seg_412 | 106793100 | 106794250 | FRMPD3 | PRPS1 |
| ENST00000439554.1 | 4859 | 106769876 | 106848481 | + | seg_412 | 106793100 | 106794250 | FRMPD3 | PRPS1 |
| ENST00000276185.4 | 4860 | 106765680 | 106846603 | + | seg_413 | 106843800 | 106846550 | PRPS1 | PRPS1 |
| ENST00000439554.1 | 4861 | 106769876 | 106848481 | + | seg_413 | 106843800 | 106846550 | PRPS1 | PRPS1 |
| ENST00000372384.2 | 4862 | 106956454 | 107019218 | − | seg_414 | 106991800 | 106993500 | TSC22D3 | PRPS1 |
| ENST00000372383.4 | 4863 | 106956454 | 107019017 | − | seg_414 | 106991800 | 106993500 | TSC22D3 | PRPS1 |
| ENST00000394928.2 | 4864 | 106957214 | 107018890 | − | seg_414 | 106991800 | 106993500 | TSC22D3 | PRPS1 |
| ENST00000315660.4 | 4865 | 106956451 | 107019215 | − | seg_414 | 106991800 | 106993500 | TSC22D3 | PRPS1 |
| ENST00000506081.1 | 4866 | 106957600 | 107020297 | − | seg_414 | 106991800 | 106993500 | TSC22D3 | PRPS1 |
| ENST00000514426.1 | 4867 | 106957717 | 107020308 | − | seg_414 | 106991800 | 106993500 | TSC22D3 | PRPS1 |
| ENST00000510887.1 | 4868 | 106959142 | 107019944 | − | seg_414 | 106991800 | 106993500 | TSC22D3 | PRPS1 |
| ENST00000502650.1 | 4869 | 106959153 | 107019345 | − | seg_414 | 106991800 | 106993500 | TSC22D3 | PRPS1 |
| ENST00000514897.1 | 4870 | 106959128 | 107020572 | − | seg_414 | 106991800 | 106993500 | TSC22D3 | PRPS1 |
| ENST00000480691.2 | 4871 | 106959133 | 107020285 | − | seg_414 | 106991800 | 106993500 | TSC22D3 | PRPS1 |
| ENST00000506724.1 | 4872 | 107018348 | 107019488 | − | seg_415 | 107018250 | 107019350 | TSC22D3 | PRPS1 |
| ENST00000372384.2 | 4873 | 106956454 | 107019218 | − | seg_415 | 107018250 | 107019350 | TSC22D3 | PRPS1 |
| ENST00000505965.1 | 4874 | 107018397 | 107020567 | − | seg_415 | 107018250 | 107019350 | TSC22D3 | PRPS1 |
| ENST00000372383.4 | 4875 | 106956454 | 107019017 | − | seg_415 | 107018250 | 107019350 | TSC22D3 | PRPS1 |
| ENST00000394928.2 | 4876 | 106957214 | 107018890 | − | seg_415 | 107018250 | 107019350 | TSC22D3 | PRPS1 |
| ENST00000315660.4 | 4877 | 106956451 | 107019215 | − | seg_415 | 107018250 | 107019350 | TSC22D3 | PRPS1 |
| ENST00000506081.1 | 4878 | 106957600 | 107020297 | − | seg_415 | 107018250 | 107019350 | TSC22D3 | PRPS1 |
| ENST00000514426.1 | 4879 | 106957717 | 107020308 | − | seg_415 | 107018250 | 107019350 | TSC22D3 | PRPS1 |
| ENST00000502961.1 | 4880 | 107018476 | 107020559 | − | seg_415 | 107018250 | 107019350 | TSC22D3 | PRPS1 |
| ENST00000510887.1 | 4881 | 106959142 | 107019944 | − | seg_415 | 107018250 | 107019350 | TSC22D3 | PRPS1 |
| ENST00000502650.1 | 4882 | 106959153 | 107019345 | − | seg_415 | 107018250 | 107019350 | TSC22D3 | PRPS1 |
| ENST00000514897.1 | 4883 | 106959128 | 107020572 | − | seg_415 | 107018250 | 107019350 | TSC22D3 | PRPS1 |
| ENST00000480691.2 | 4884 | 106959133 | 107020285 | − | seg_415 | 107018250 | 107019350 | TSC22D3 | PRPS1 |
| ENST00000451923.1 | 4885 | 107068985 | 107084611 | + | seg_416 | 107067850 | 107070850 | MID2 | PRPS1 |
| ENST00000443968.2 | 4886 | 107069644 | 107170423 | + | seg_416 | 107067850 | 107070850 | MID2 | PRPS1 |
| ENST00000262843.6 | 4887 | 107069109 | 107170423 | + | seg_416 | 107067850 | 107070850 | MID2 | PRPS1 |
| ENST00000302917.1 | 4888 | 107224094 | 107225600 | − | seg_417 | 107223950 | 107225250 | TEX13B | PRPS1 |
| ENST00000545689.1 | 4889 | 107399275 | 107681556 | − | seg_418 | 107509250 | 107510600 | COL4A6 | COL4A5 |
| ENST00000538570.1 | 4890 | 107399275 | 107681556 | − | seg_418 | 107509250 | 107510600 | COL4A6 | COL4A5 |
| ENST00000394872.2 | 4891 | 107398838 | 107681658 | − | seg_418 | 107509250 | 107510600 | COL4A6 | COL4A5 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000468338.1 | 4892 | 107457022 | 107682702 | − | seg_418 | 107509250 | 107510600 | COL4A6 | COL4A5 |
| ENST00000541389.1 | 4893 | 107399121 | 107681660 | − | seg_418 | 107509250 | 107510600 | COL4A6 | COL4A5 |
| ENST00000334504.7 | 4894 | 107398837 | 107681660 | − | seg_418 | 107509250 | 107510600 | COL4A6 | COL4A5 |
| ENST00000372216.4 | 4895 | 107398837 | 107682702 | − | seg_418 | 107509250 | 107510600 | COL4A6 | COL4A5 |
| ENST00000545689.1 | 4896 | 107399275 | 107681556 | − | seg_419 | 107621250 | 107622550 | COL4A6 | COL4A5 |
| ENST00000538570.1 | 4897 | 107399275 | 107681556 | − | seg_419 | 107621250 | 107622550 | COL4A6 | COL4A5 |
| ENST00000394872.2 | 4898 | 107398838 | 107681658 | − | seg_419 | 107621250 | 107622550 | COL4A6 | COL4A5 |
| ENST00000461897.1 | 4899 | 107510872 | 107681660 | − | seg_419 | 107621250 | 107622550 | COL4A6 | COL4A5 |
| ENST00000468338.1 | 4900 | 107457022 | 107682702 | − | seg_419 | 107621250 | 107622550 | COL4A6 | COL4A5 |
| ENST00000541389.1 | 4901 | 107399121 | 107681660 | − | seg_419 | 107621250 | 107622550 | COL4A6 | COL4A5 |
| ENST00000334504.7 | 4902 | 107398837 | 107681660 | − | seg_419 | 107621250 | 107622550 | COL4A6 | COL4A5 |
| ENST00000372216.4 | 4903 | 107398837 | 107682702 | − | seg_419 | 107621250 | 107622550 | COL4A6 | COL4A5 |
| ENST00000477085.1 | 4904 | 107510872 | 107682727 | − | seg_419 | 107621250 | 107622550 | COL4A6 | COL4A5 |
| ENST00000372129.2 | 4905 | 107975712 | 107979651 | − | seg_421 | 107975000 | 107976700 | RP6-24A23.6 | COL4A5 |
| ENST00000419932.1 | 4906 | 108297361 | 108297792 | − | seg_423 | 108296850 | 108298000 | IRS4 | COL4A5 |
| ENST00000516235.1 | 4907 | 108297553 | 108297626 | + | seg_423 | 108296850 | 108298000 | IRS4 | COL4A5 |
| ENST00000218006.2 | 4908 | 108616135 | 108725301 | − | seg_424 | 108674800 | 108676200 | GUCY2F | COL4A5 |
| ENST00000218006.2 | 4909 | 108616135 | 108725301 | − | seg_425 | 108703300 | 108705200 | GUCY2F | COL4A5 |
| ENST00000440201.1 | 4910 | 108811707 | 108813521 | + | seg_427 | 108811600 | 108812750 | NXT2 | COL4A5 |
| ENST00000471255.1 | 4911 | 109245915 | 109310624 | + | seg_430 | 109247900 | 109249000 | TMEM164 | COL4A5 |
| ENST00000288381.4 | 4912 | 109246343 | 109421016 | + | seg_430 | 109247900 | 109249000 | TMEM164 | COL4A5 |
| ENST00000372073.1 | 4913 | 109246323 | 109421016 | + | seg_430 | 109247900 | 109249000 | TMEM164 | COL4A5 |
| ENST00000372068.2 | 4914 | 109246342 | 109421012 | + | seg_430 | 109247900 | 109249000 | TMEM164 | COL4A5 |
| ENST00000501872.2 | 4915 | 109246343 | 109420900 | + | seg_430 | 109247900 | 109249000 | TMEM164 | COL4A5 |
| ENST00000372072.3 | 4916 | 109245863 | 109421012 | + | seg_430 | 109247900 | 109249000 | TMEM164 | COL4A5 |
| ENST00000520821.1 | 4917 | 109602044 | 109694109 | + | seg_431 | 109686900 | 109688500 | RGAG1 | COL4A5 |
| ENST00000465301.2 | 4918 | 109662285 | 109699562 | + | seg_431 | 109686900 | 109688500 | RGAG1 | COL4A5 |
| ENST00000218054.4 | 4919 | 109917092 | 110039076 | − | seg_432 | 110038450 | 110040100 | CHRDL1 | COL4A5 |
| ENST00000394797.4 | 4920 | 109918473 | 110038993 | − | seg_432 | 110038450 | 110040100 | CHRDL1 | COL4A5 |
| ENST00000434224.1 | 4921 | 109917092 | 110039286 | − | seg_432 | 110038450 | 110040100 | CHRDL1 | COL4A5 |
| ENST00000372045.1 | 4922 | 109917084 | 110038993 | − | seg_432 | 110038450 | 110040100 | CHRDL1 | COL4A5 |
| ENST00000482160.1 | 4923 | 109919169 | 110039047 | − | seg_432 | 110038450 | 110040100 | CHRDL1 | COL4A5 |
| ENST00000372042.1 | 4924 | 109919004 | 110039039 | − | seg_432 | 110038450 | 110040100 | CHRDL1 | COL4A5 |
| ENST00000444321.2 | 4925 | 109919285 | 110039047 | − | seg_432 | 110038450 | 110040100 | CHRDL1 | COL4A5 |
| ENST00000262839.2 | 4926 | 111017543 | 111326004 | − | seg_433 | 111148500 | 111149550 | TRPC5 | COL4A5 |
| ENST00000262839.2 | 4927 | 111017543 | 111326004 | − | seg_434 | 111323950 | 111326100 | TRPC5 | COL4A5 |
| ENST00000371968.3 | 4928 | 111873876 | 111923282 | − | seg_436 | 111877350 | 111878350 | LHFPL1 | COL4A5 |
| ENST00000536453.1 | 4929 | 111873879 | 111923375 | − | seg_436 | 111877350 | 111878350 | LHFPL1 | COL4A5 |
| ENST00000478229.1 | 4930 | 111874502 | 111923282 | − | seg_436 | 111877350 | 111878350 | LHFPL1 | COL4A5 |
| ENST00000462114.1 | 4931 | 112066365 | 112083911 | − | seg_437 | 112067850 | 112068950 | AMOT | COL4A5 |
| ENST00000524145.1 | 4932 | 112021795 | 112068356 | − | seg_437 | 112067850 | 112068950 | AMOT | COL4A5 |
| ENST00000304758.1 | 4933 | 112017731 | 112084043 | − | seg_437 | 112067850 | 112068950 | AMOT | COL4A5 |
| ENST00000371951.1 | 4934 | 113818551 | 114143070 | + | seg_439 | 113815000 | 113819700 | HTR2C | COL4A5 |
| ENST00000371950.3 | 4935 | 113818555 | 114144624 | + | seg_439 | 113815000 | 113819700 | HTR2C | COL4A5 |
| ENST00000276198.1 | 4936 | 113818551 | 114144624 | + | seg_439 | 113815000 | 113819700 | HTR2C | COL4A5 |
| ENST00000543279.1 | 4937 | 114752497 | 114797058 | − | seg_440 | 114795000 | 114796050 | PLS3 | COL4A5 |
| ENST00000441988.2 | 4938 | 114795501 | 114883831 | + | seg_440 | 114795000 | 114796050 | PLS3 | COL4A5 |
| ENST00000289290.3 | 4939 | 114795582 | 114884078 | + | seg_440 | 114795000 | 114796050 | PLS3 | COL4A5 |
| ENST00000537301.1 | 4940 | 114795555 | 114884078 | + | seg_440 | 114795000 | 114796050 | PLS3 | COL4A5 |
| ENST00000489283.1 | 4941 | 114795501 | 114864228 | + | seg_440 | 114795000 | 114796050 | PLS3 | COL4A5 |
| ENST00000355899.3 | 4942 | 114795509 | 114885177 | + | seg_440 | 114795000 | 114796050 | PLS3 | COL4A5 |
| ENST00000451869.1 | 4943 | 114957297 | 114959381 | + | seg_442 | 114957400 | 114958700 | RP1-241P17.4 | COL4A5 |
| ENST00000415394.1 | 4944 | 114957343 | 114959383 | + | seg_442 | 114957400 | 114958700 | RP1-241P17.4 | COL4A5 |
| ENST00000436163.1 | 4945 | 117250225 | 117250763 | − | seg_444 | 117249550 | 117251250 | KLHL13 | COL4A5 |
| ENST00000371882.1 | 4946 | 117031776 | 117250761 | − | seg_444 | 117249550 | 117251250 | KLHL13 | COL4A5 |
| ENST00000540167.1 | 4947 | 117031777 | 117250828 | − | seg_444 | 117249550 | 117251250 | KLHL13 | COL4A5 |
| ENST00000541812.1 | 4948 | 117031777 | 117251303 | − | seg_444 | 117249550 | 117251250 | KLHL13 | COL4A5 |
| ENST00000545703.1 | 4949 | 117031777 | 117250828 | − | seg_444 | 117249550 | 117251250 | KLHL13 | COL4A5 |
| ENST00000310164.2 | 4950 | 117957753 | 117960931 | + | seg_446 | 117956850 | 117960550 | ZCCHC12 | COL4A5 |
| ENST00000481285.1 | 4951 | 118108581 | 118151946 | + | seg_447 | 118109900 | 118111100 | LONRF3 | COL4A5 |
| ENST00000304778.7 | 4952 | 118108581 | 118152318 | + | seg_447 | 118109900 | 118111100 | LONRF3 | COL4A5 |
| ENST00000439603.1 | 4953 | 118109325 | 118151950 | + | seg_447 | 118109900 | 118111100 | LONRF3 | COL4A5 |
| ENST00000371628.3 | 4954 | 118108713 | 118151892 | + | seg_447 | 118109900 | 118111100 | LONRF3 | COL4A5 |
| ENST00000422289.2 | 4955 | 118110295 | 118151947 | + | seg_447 | 118109900 | 118111100 | LONRF3 | COL4A5 |
| ENST00000472173.1 | 4956 | 118110295 | 118151946 | + | seg_447 | 118109900 | 118111100 | LONRF3 | COL4A5 |
| ENST00000365713.2 | 4957 | 118108581 | 118156888 | + | seg_447 | 118109900 | 118111100 | LONRF3 | COL4A5 |
| ENST00000440399.1 | 4958 | 118212598 | 118223411 | − | seg_449 | 118214300 | 118215550 | KIAA1210 | OCRL |
| ENST00000402510.2 | 4959 | 118212598 | 118284542 | − | seg_449 | 118214300 | 118215550 | KIAA1210 | OCRL |
| ENST00000420240.1 | 4960 | 118227676 | 118250616 | − | seg_450 | 118240400 | 118241500 | KIAA1210 | OCRL |
| ENST00000402510.2 | 4961 | 118212598 | 118284542 | − | seg_450 | 118240400 | 118241500 | KIAA1210 | OCRL |
| ENST00000402510.2 | 4962 | 118212598 | 118284542 | − | seg_451 | 118283750 | 118285900 | KIAA1210 | OCRL |
| ENST00000488158.1 | 4963 | 118533343 | 118588435 | + | seg_453 | 118532900 | 118534700 | SLC25A43 | OCRL |
| ENST00000217909.7 | 4964 | 118533023 | 118588441 | + | seg_453 | 118532900 | 118534700 | SLC25A43 | OCRL |
| ENST00000326714.7 | 4965 | 118533367 | 118588431 | + | seg_453 | 118532900 | 118534700 | SLC25A43 | OCRL |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000495750.1 | 4966 | 118533463 | 118586860 | + | seg_453 | 118532900 | 118534700 | SLC25A43 | OCRL |
| ENST00000336249.7 | 4967 | 118533343 | 118587183 | + | seg_453 | 118532900 | 118534700 | SLC25A43 | OCRL |
| ENST00000493093.1 | 4968 | 118533372 | 118587145 | + | seg_453 | 118532900 | 118534700 | SLC25A43 | OCRL |
| ENST00000488158.1 | 4969 | 118533343 | 118588435 | + | seg_454 | 118552150 | 118553350 | SLC25A43 | OCRL |
| ENST00000217909.7 | 4970 | 118533023 | 118588441 | + | seg_454 | 118552150 | 118553350 | SLC25A43 | OCRL |
| ENST00000326714.7 | 4971 | 118533367 | 118588431 | + | seg_454 | 118552150 | 118553350 | SLC25A43 | OCRL |
| ENST00000495750.1 | 4972 | 118533463 | 118586860 | + | seg_454 | 118552150 | 118553350 | SLC25A43 | OCRL |
| ENST00000484058.1 | 4973 | 118540519 | 118586904 | + | seg_454 | 118552150 | 118553350 | SLC25A43 | OCRL |
| ENST00000336249.7 | 4974 | 118533343 | 118587183 | + | seg_454 | 118552150 | 118553350 | SLC25A43 | OCRL |
| ENST00000493093.1 | 4975 | 118533372 | 118587145 | + | seg_454 | 118552150 | 118553350 | SLC25A43 | OCRL |
| ENST00000454625.1 | 4976 | 119144675 | 119149501 | − | seg_460 | 119147300 | 119149300 | RHOXF2B | OCRL |
| ENST00000480821.1 | 4977 | 119443748 | 119445257 | − | seg_462 | 119443650 | 119445500 | TMEM255A | OCRL |
| ENST00000309720.5 | 4978 | 119392505 | 119445288 | − | seg_462 | 119443650 | 119445500 | TMEM255A | OCRL |
| ENST00000440464.1 | 4979 | 119392506 | 119445391 | − | seg_462 | 119443650 | 119445500 | TMEM255A | OCRL |
| ENST00000371369.4 | 4980 | 119392505 | 119445391 | − | seg_462 | 119443650 | 119445500 | TMEM255A | OCRL |
| ENST00000519908.1 | 4981 | 119402218 | 119445411 | − | seg_462 | 119443650 | 119445500 | TMEM255A | OCRL |
| ENST00000218008.3 | 4982 | 119495967 | 119516226 | + | seg_463 | 119503950 | 119505200 | ATP1B4 | OCRL |
| ENST00000539306.1 | 4983 | 119495997 | 119513514 | + | seg_463 | 119503950 | 119505200 | ATP1B4 | OCRL |
| ENST00000361319.3 | 4984 | 119495967 | 119516226 | + | seg_463 | 119503950 | 119505200 | ATP1B4 | OCRL |
| ENST00000371311.3 | 4985 | 120006457 | 120009779 | − | seg_465 | 120007900 | 120009150 | CT47B1 | OCRL |
| ENST00000479118.1 | 4986 | 122318412 | 122387553 | + | seg_471 | 122317650 | 122321300 | GRIA3 | OCRL |
| ENST00000371264.3 | 4987 | 122318152 | 122338534 | + | seg_471 | 122317650 | 122321300 | GRIA3 | OCRL |
| ENST00000371266.1 | 4988 | 122318006 | 122338534 | + | seg_471 | 122317650 | 122321300 | GRIA3 | OCRL |
| ENST00000335161.8 | 4989 | 122318224 | 122338270 | + | seg_471 | 122317650 | 122321300 | GRIA3 | OCRL |
| ENST00000541091.1 | 4990 | 122318765 | 122551942 | + | seg_471 | 122317650 | 122321300 | GRIA3 | OCRL |
| ENST00000371251.1 | 4991 | 122318336 | 122616897 | + | seg_471 | 122317650 | 122321300 | GRIA3 | OCRL |
| ENST00000264357.5 | 4992 | 122318096 | 122624756 | + | seg_471 | 122317650 | 122321300 | GRIA3 | OCRL |
| ENST00000371256.5 | 4993 | 122318336 | 122624766 | + | seg_471 | 122317650 | 122321300 | GRIA3 | OCRL |
| ENST00000542149.1 | 4994 | 122318224 | 122622587 | + | seg_471 | 122317650 | 122321300 | GRIA3 | OCRL |
| ENST00000479118.1 | 4995 | 122318412 | 122387553 | + | seg_472 | 122323700 | 122324850 | GRIA3 | OCRL |
| ENST00000371264.3 | 4996 | 122318152 | 122338534 | + | seg_472 | 122323700 | 122324850 | GRIA3 | OCRL |
| ENST00000371266.1 | 4997 | 122318006 | 122338534 | + | seg_472 | 122323700 | 122324850 | GRIA3 | OCRL |
| ENST00000335161.8 | 4998 | 122318224 | 122338270 | + | seg_472 | 122323700 | 122324850 | GRIA3 | OCRL |
| ENST00000541091.1 | 4999 | 122318765 | 122551942 | + | seg_472 | 122323700 | 122324850 | GRIA3 | OCRL |
| ENST00000371251.1 | 5000 | 122318336 | 122616897 | + | seg_472 | 122323700 | 122324850 | GRIA3 | OCRL |
| ENST00000264357.5 | 5001 | 122318096 | 122624756 | + | seg_472 | 122323700 | 122324850 | GRIA3 | OCRL |
| ENST00000371256.5 | 5002 | 122318336 | 122624766 | + | seg_472 | 122323700 | 122324850 | GRIA3 | OCRL |
| ENST00000542149.1 | 5003 | 122318224 | 122622587 | + | seg_472 | 122323700 | 122324850 | GRIA3 | OCRL |
| ENST00000429967.1 | 5004 | 128779786 | 128788914 | − | seg_479 | 128781850 | 128783650 | APLN | OCRL |
| ENST00000427399.1 | 5005 | 128781653 | 128782742 | − | seg_479 | 128781850 | 128783650 | APLN | OCRL |
| ENST00000307484.6 | 5006 | 128779240 | 128788933 | − | seg_479 | 128781850 | 128783650 | APLN | OCRL |
| ENST00000429967.1 | 5007 | 128779786 | 128788914 | − | seg_480 | 128787750 | 128789650 | APLN | OCRL |
| ENST00000307484.6 | 5008 | 128779240 | 128788933 | − | seg_480 | 128787750 | 128789650 | APLN | OCRL |
| ENST00000371106.3 | 5009 | 128872998 | 128903514 | + | seg_484 | 128882700 | 128883950 | XPNPEP2 | OCRL |
| ENST00000276218.2 | 5010 | 129518319 | 129519511 | − | seg_487 | 129517950 | 129519000 | GPR119 | OCRL |
| ENST00000458525.1 | 5011 | 129611043 | 129619850 | − | seg_489 | 129617200 | 129618900 | RBMX2 | OCRL |
| ENST00000412420.1 | 5012 | 130150443 | 130192120 | − | seg_491 | 130182550 | 130183750 | ARHGAP36 | NYS1 = FRMD7 |
| ENST00000423277.1 | 5013 | 130206962 | 130218649 | + | seg_492 | 130211050 | 130212100 | ARHGAP36 | NYS1 = FRMD7 |
| ENST00000370922.1 | 5014 | 130192331 | 130223857 | + | seg_492 | 130211050 | 130212100 | ARHGAP36 | NYS1 = FRMD7 |
| ENST00000276211.5 | 5015 | 130192216 | 130223853 | + | seg_492 | 130211050 | 130212100 | ARHGAP36 | NYS1 = FRMD7 |
| ENST00000423277.1 | 5016 | 130206962 | 130218649 | + | seg_493 | 130215900 | 130218550 | ARHGAP36 | NYS1 = FRMD7 |
| ENST00000412432.2 | 5017 | 130212691 | 130223857 | + | seg_493 | 130215900 | 130218550 | ARHGAP36 | NYS1 = FRMD7 |
| ENST00000370921.1 | 5018 | 130217684 | 130223857 | + | seg_493 | 130215900 | 130218550 | ARHGAP36 | NYS1 = FRMD7 |
| ENST00000370922.1 | 5019 | 130192331 | 130223857 | + | seg_493 | 130215900 | 130218550 | ARHGAP36 | NYS1 = FRMD7 |
| ENST00000276211.5 | 5020 | 130192216 | 130223853 | + | seg_493 | 130215900 | 130218550 | ARHGAP36 | NYS1 = FRMD7 |
| ENST00000467244.1 | 5021 | 130409953 | 130411491 | − | seg_494 | 130409100 | 130410150 | IGSF1 | NYS1 = FRMD7 |
| ENST00000370910.1 | 5022 | 130407480 | 130423252 | − | seg_494 | 130409100 | 130410150 | IGSF1 | NYS1 = FRMD7 |
| ENST00000370903.3 | 5023 | 130407485 | 130423403 | − | seg_494 | 130409100 | 130410150 | IGSF1 | NYS1 = FRMD7 |
| ENST00000361420.3 | 5024 | 130407483 | 130423200 | − | seg_494 | 130409100 | 130410150 | IGSF1 | NYS1 = FRMD7 |
| ENST00000370904.1 | 5025 | 130407485 | 130533677 | − | seg_494 | 130409100 | 130410150 | IGSF1 | NYS1 = FRMD7 |
| ENST00000490400.1 | 5026 | 131351694 | 131353471 | − | seg_496 | 131351450 | 131352650 | RAP2C | NYS1 = FRMD7 |
| ENST00000370874.1 | 5027 | 131338678 | 131353461 | − | seg_496 | 131351450 | 131352650 | RAP2C | NYS1 = FRMD7 |
| ENST00000342983.2 | 5028 | 131337053 | 131352152 | − | seg_496 | 131351450 | 131352650 | RAP2C | NYS1 = FRMD7 |
| ENST00000460462.1 | 5029 | 131339477 | 131352360 | − | seg_496 | 131351450 | 131352650 | RAP2C | NYS1 = FRMD7 |
| ENST00000421483.1 | 5030 | 131351175 | 131564190 | + | seg_496 | 131351450 | 131352650 | RAP2C | NYS1 = FRMD7 |
| ENST00000441399.1 | 5031 | 131352535 | 131566890 | + | seg_496 | 131351450 | 131352650 | RAP2C | NYS1 = FRMD7 |
| ENST00000370853.3 | 5032 | 131512177 | 131573718 | − | seg_497 | 131556050 | 131558450 | MBNL3 | NYS1 = FRMD7 |
| ENST00000370857.3 | 5033 | 131506029 | 131573705 | − | seg_497 | 131556050 | 131558450 | MBNL3 | NYS1 = FRMD7 |
| ENST00000370839.3 | 5034 | 131513232 | 131573718 | − | seg_497 | 131556050 | 131558450 | MBNL3 | NYS1 = FRMD7 |
| ENST00000370844.1 | 5035 | 131513232 | 131623996 | − | seg_497 | 131556050 | 131558450 | MBNL3 | NYS1 = FRMD7 |
| ENST00000421707.1 | 5036 | 131518691 | 131623043 | − | seg_497 | 131556050 | 131558450 | MBNL3 | NYS1 = FRMD7 |
| ENST00000421483.1 | 5037 | 131351175 | 131564190 | + | seg_497 | 131556050 | 131558450 | MBNL3 | NYS1 = FRMD7 |
| ENST00000436215.1 | 5038 | 131516244 | 131623894 | − | seg_497 | 131556050 | 131558450 | MBNL3 | NYS1 = FRMD7 |
| ENST00000441399.1 | 5039 | 131352535 | 131566890 | + | seg_497 | 131556050 | 131558450 | MBNL3 | NYS1 = FRMD7 |
| ENST00000370836.2 | 5040 | 131760044 | 132095423 | − | seg_499 | 132008150 | 132009150 | HS6ST2 | NYS1 = FRMD7 |
| ENST00000370833.2 | 5041 | 131762251 | 132091344 | − | seg_499 | 132008150 | 132009150 | HS6ST2 | NYS1 = FRMD7 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000461959.1 | 5042 | 131760044 | 132091354 | − | seg_499 | 132008150 | 132009150 | HS6ST2 | NYS1 = FRMD7 |
| ENST00000319809.6 | 5043 | 131762877 | 132091305 | − | seg_499 | 132008150 | 132009150 | HS6ST2 | NYS1 = FRMD7 |
| ENST00000521489.1 | 5044 | 131761998 | 132095423 | − | seg_499 | 132008150 | 132009150 | HS6ST2 | NYS1 = FRMD7 |
| ENST00000370837.1 | 5045 | 131760038 | 132091358 | − | seg_499 | 132008150 | 132009150 | HS6ST2 | NYS1 = FRMD7 |
| ENST00000370836.2 | 5046 | 131760044 | 132095423 | − | seg_500 | 132086850 | 132088300 | HS6ST2 | NYS1 = FRMD7 |
| ENST00000370833.2 | 5047 | 131762251 | 132091344 | − | seg_500 | 132086850 | 132088300 | HS6ST2 | NYS1 = FRMD7 |
| ENST00000461959.1 | 5048 | 131760044 | 132091354 | − | seg_500 | 132086850 | 132088300 | HS6ST2 | NYS1 = FRMD7 |
| ENST00000319809.6 | 5049 | 131762877 | 132091305 | − | seg_500 | 132086850 | 132088300 | HS6ST2 | NYS1 = FRMD7 |
| ENST00000521489.1 | 5050 | 131761998 | 132095423 | − | seg_500 | 132086850 | 132088300 | HS6ST2 | NYS1 = FRMD7 |
| ENST00000370837.1 | 5051 | 131760038 | 132091358 | − | seg_500 | 132086850 | 132088300 | HS6ST2 | NYS1 = FRMD7 |
| ENST00000517294.1 | 5052 | 133371077 | 133380237 | + | seg_502 | 133370100 | 133372850 | CCDC160 | HPRT1 = HPRT |
| ENST00000370809.4 | 5053 | 133371077 | 133379808 | + | seg_502 | 133370100 | 133372850 | CCDC160 | HPRT1 = HPRT |
| ENST00000434384.1 | 5054 | 133684003 | 133693953 | + | seg_504 | 133682650 | 133684050 | PLAC1 | HPRT1 = HPRT |
| ENST00000441416.1 | 5055 | 134314179 | 134328610 | + | seg_510 | 134314000 | 134315000 | CXorf48 | HPRT1 = HPRT |
| ENST00000445718.1 | 5056 | 134335662 | 134349163 | + | seg_511 | 134346900 | 134347900 | CXorf48 | HPRT1 = HPRT |
| ENST00000445718.1 | 5057 | 134335662 | 134349163 | + | seg_512 | 134349000 | 134350350 | CXorf48 | HPRT1 = HPRT |
| ENST00000442950.1 | 5058 | 134370740 | 134371295 | + | seg_515 | 134370750 | 134373750 | ZNF75D | HPRT1 = HPRT |
| ENST00000339249.4 | 5059 | 134478721 | 134497077 | + | seg_516 | 134478200 | 134479400 | ZNF449 | HPRT1 = HPRT |
| ENST00000370761.3 | 5060 | 134478721 | 134482954 | + | seg_516 | 134478200 | 134479400 | ZNF449 | HPRT1 = HPRT |
| ENST00000370760.3 | 5061 | 134478721 | 134482708 | + | seg_516 | 134478200 | 134479400 | ZNF449 | HPRT1 = HPRT |
| ENST00000417443.1 | 5062 | 134555868 | 134559682 | + | seg_518 | 134555850 | 134556850 | ZNF449 | HPRT1 = HPRT |
| ENST00000426910.1 | 5063 | 134566885 | 134572559 | + | seg_519 | 134566100 | 134571950 | DDX26B | HPRT1 = HPRT |
| ENST00000471213.1 | 5064 | 134866214 | 134875839 | + | seg_523 | 134871500 | 134872550 | CT45A2 | HPRT1 = HPRT |
| ENST00000370736.3 | 5065 | 134866214 | 134874250 | + | seg_523 | 134871500 | 134872550 | CT45A2 | HPRT1 = HPRT |
| ENST00000495729.1 | 5066 | 134866399 | 134874235 | + | seg_523 | 134871500 | 134872550 | CT45A2 | HPRT1 = HPRT |
| ENST00000370734.3 | 5067 | 134883488 | 134891521 | + | seg_524 | 134888100 | 134889150 | CT45A3 | HPRT1 = HPRT |
| ENST00000461216.1 | 5068 | 134883673 | 134891482 | + | seg_524 | 134888100 | 134889150 | CT45A3 | HPRT1 = HPRT |
| ENST00000485366.1 | 5069 | 134883488 | 134893393 | + | seg_524 | 134888100 | 134889150 | CT45A3 | HPRT1 = HPRT |
| ENST00000443882.1 | 5070 | 134887233 | 134891519 | + | seg_524 | 134888100 | 134889150 | CT45A3 | HPRT1 = HPRT |
| ENST00000487941.1 | 5071 | 134926788 | 134936735 | − | seg_525 | 134931900 | 134933650 | CT45A4 | HPRT1 = HPRT |
| ENST00000494421.1 | 5072 | 134928706 | 134936550 | − | seg_525 | 134931900 | 134933650 | CT45A4 | HPRT1 = HPRT |
| ENST00000434966.2 | 5073 | 134928695 | 134936735 | − | seg_525 | 134931900 | 134933650 | CT45A4 | HPRT1 = HPRT |
| ENST00000420087.2 | 5074 | 134928697 | 134953994 | − | seg_525 | 134931900 | 134933650 | CT45A4 | HPRT1 = HPRT |
| ENST00000463085.1 | 5075 | 134944381 | 134953994 | − | seg_526 | 134947700 | 134950650 | CT45A4 | HPRT1 = HPRT |
| ENST00000370724.3 | 5076 | 134945962 | 134953994 | − | seg_526 | 134947700 | 134950650 | CT45A4 | HPRT1 = HPRT |
| ENST00000491480.1 | 5077 | 134945973 | 134953809 | − | seg_526 | 134947700 | 134950650 | CT45A4 | HPRT1 = HPRT |
| ENST00000420087.2 | 5078 | 134928697 | 134953994 | − | seg_526 | 134947700 | 134950650 | CT45A4 | HPRT1 = HPRT |
| ENST00000536581.1 | 5079 | 135229692 | 135292637 | + | seg_532 | 135228300 | 135230300 | FHL1 | HPRT1 = HPRT |
| ENST00000420362.1 | 5080 | 135229825 | 135290725 | + | seg_532 | 135228300 | 135230300 | FHL1 | HPRT1 = HPRT |
| ENST00000370690.3 | 5081 | 135229624 | 135293518 | + | seg_532 | 135228300 | 135230300 | FHL1 | HPRT1 = HPRT |
| ENST00000394155.2 | 5082 | 135229559 | 135293518 | + | seg_532 | 135228300 | 135230300 | FHL1 | HPRT1 = HPRT |
| ENST00000458357.1 | 5083 | 135230270 | 135290084 | + | seg_532 | 135228300 | 135230300 | FHL1 | HPRT1 = HPRT |
| ENST00000536581.1 | 5084 | 135229692 | 135292637 | + | seg_533 | 135233600 | 135234900 | FHL1 | HPRT1 = HPRT |
| ENST00000420362.1 | 5085 | 135229825 | 135290725 | + | seg_533 | 135233600 | 135234900 | FHL1 | HPRT1 = HPRT |
| ENST00000370690.3 | 5086 | 135229624 | 135293518 | + | seg_533 | 135233600 | 135234900 | FHL1 | HPRT1 = HPRT |
| ENST00000535737.1 | 5087 | 135230737 | 135293518 | + | seg_533 | 135233600 | 135234900 | FHL1 | HPRT1 = HPRT |
| ENST00000394155.2 | 5088 | 135229559 | 135293518 | + | seg_533 | 135233600 | 135234900 | FHL1 | HPRT1 = HPRT |
| ENST00000458357.1 | 5089 | 135230270 | 135290084 | + | seg_533 | 135233600 | 135234900 | FHL1 | HPRT1 = HPRT |
| ENST00000536581.1 | 5090 | 135229692 | 135292637 | + | seg_534 | 135250050 | 135251600 | FHL1 | HPRT1 = HPRT |
| ENST00000434885.1 | 5091 | 135250353 | 135290734 | + | seg_534 | 135250050 | 135251600 | FHL1 | HPRT1 = HPRT |
| ENST00000543669.1 | 5092 | 135251455 | 135293518 | + | seg_534 | 135250050 | 135251600 | FHL1 | HPRT1 = HPRT |
| ENST00000420362.1 | 5093 | 135229825 | 135290725 | + | seg_534 | 135250050 | 135251600 | FHL1 | HPRT1 = HPRT |
| ENST00000452016.1 | 5094 | 135249163 | 135290734 | + | seg_534 | 135250050 | 135251600 | FHL1 | HPRT1 = HPRT |
| ENST00000370690.3 | 5095 | 135229624 | 135293518 | + | seg_534 | 135250050 | 135251600 | FHL1 | HPRT1 = HPRT |
| ENST00000535737.1 | 5096 | 135230737 | 135293518 | + | seg_534 | 135250050 | 135251600 | FHL1 | HPRT1 = HPRT |
| ENST00000394155.2 | 5097 | 135229559 | 135293518 | + | seg_534 | 135250050 | 135251600 | FHL1 | HPRT1 = HPRT |
| ENST00000458357.1 | 5098 | 135230270 | 135290084 | + | seg_534 | 135250050 | 135251600 | FHL1 | HPRT1 = HPRT |
| ENST00000394141.1 | 5099 | 135388180 | 135498843 | + | seg_535 | 135436600 | 135438050 | GPR112 | HPRT1 = HPRT |
| ENST00000287534.4 | 5100 | 135387012 | 135519215 | + | seg_535 | 135436600 | 135438050 | GPR112 | HPRT1 = HPRT |
| ENST00000394143.1 | 5101 | 135383122 | 135499047 | + | seg_535 | 135436600 | 135438050 | GPR112 | HPRT1 = HPRT |
| ENST00000412101.1 | 5102 | 135387012 | 135499047 | + | seg_535 | 135436600 | 135438050 | GPR112 | HPRT1 = HPRT |
| ENST00000370652.1 | 5103 | 135387012 | 135499047 | + | seg_535 | 135436600 | 135438050 | GPR112 | HPRT1 = HPRT |
| ENST00000370648.3 | 5104 | 135570046 | 135575939 | + | seg_536 | 135572450 | 135573650 | BRS3 | HPRT1 = HPRT |
| ENST00000470358.1 | 5105 | 135632601 | 135638966 | + | seg_537 | 135634450 | 135636250 | VGLL1 | HPRT1 = HPRT |
| ENST00000440515.1 | 5106 | 135618287 | 135638655 | + | seg_537 | 135634450 | 135636250 | VGLL1 | HPRT1 = HPRT |
| ENST00000370634.3 | 5107 | 135614311 | 135638966 | + | seg_537 | 135634450 | 135636250 | VGLL1 | HPRT1 = HPRT |
| ENST00000456412.1 | 5108 | 135618354 | 135638966 | + | seg_537 | 135634450 | 135636250 | VGLL1 | HPRT1 = HPRT |
| ENST00000430688.2 | 5109 | 135614311 | 135638965 | + | seg_537 | 135634450 | 135636250 | VGLL1 | HPRT1 = HPRT |
| ENST00000370628.2 | 5110 | 135730386 | 135742549 | + | seg_538 | 135736550 | 135737900 | CD40LG | HPRT1 = HPRT |
| ENST00000370629.2 | 5111 | 135730352 | 135742549 | + | seg_538 | 135736550 | 135737900 | CD40LG | HPRT1 = HPRT |
| ENST00000370628.2 | 5112 | 135730386 | 135742549 | + | seg_539 | 135741150 | 135742750 | CD40LG | HPRT1 = HPRT |
| ENST00000370629.2 | 5113 | 135730352 | 135742549 | + | seg_539 | 135741150 | 135742750 | CD40LG | HPRT1 = HPRT |
| ENST00000287538.5 | 5114 | 136648301 | 136653744 | + | seg_546 | 136650850 | 136652450 | ZIC3 | F9 |
| ENST00000478471.1 | 5115 | 136650964 | 136652154 | + | seg_546 | 136650850 | 136652450 | ZIC3 | F9 |
| ENST00000370606.3 | 5116 | 136648677 | 136659850 | + | seg_546 | 136650850 | 136652450 | ZIC3 | F9 |
| ENST00000483690.1 | 5117 | 138689343 | 138697109 | − | seg_550 | 138689350 | 138690400 | MCF2 | F9 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000519895.1 | 5118 | 138664456 | 138790386 | − | seg_550 | 138689350 | 138690400 | MCF2 | F9 |
| ENST00000446225.1 | 5119 | 138664301 | 138697211 | − | seg_550 | 138689350 | 138690400 | MCF2 | F9 |
| ENST00000520602.1 | 5120 | 138663929 | 138774315 | − | seg_550 | 138689350 | 138690400 | MCF2 | F9 |
| ENST00000536274.1 | 5121 | 138663930 | 138725000 | − | seg_550 | 138689350 | 138690400 | MCF2 | F9 |
| ENST00000370573.4 | 5122 | 138664602 | 138724677 | − | seg_550 | 138689350 | 138690400 | MCF2 | F9 |
| ENST00000370576.4 | 5123 | 138663930 | 138724887 | − | seg_550 | 138689350 | 138690400 | MCF2 | F9 |
| ENST00000370578.4 | 5124 | 138663930 | 138774284 | − | seg_550 | 138689350 | 138690400 | MCF2 | F9 |
| ENST00000338585.6 | 5125 | 138664630 | 138724677 | − | seg_550 | 138689350 | 138690400 | MCF2 | F9 |
| ENST00000414978.1 | 5126 | 138663930 | 138790375 | − | seg_550 | 138689350 | 138690400 | MCF2 | F9 |
| ENST00000519895.1 | 5127 | 138664456 | 138790386 | − | seg_551 | 138772800 | 138775400 | MCF2 | F9 |
| ENST00000520602.1 | 5128 | 138663929 | 138774315 | − | seg_551 | 138772800 | 138775400 | MCF2 | F9 |
| ENST00000370578.4 | 5129 | 138663930 | 138774284 | − | seg_551 | 138772800 | 138775400 | MCF2 | F9 |
| ENST00000414978.1 | 5130 | 138663930 | 138790375 | − | seg_551 | 138772800 | 138775400 | MCF2 | F9 |
| ENST00000485626.1 | 5131 | 138884461 | 139027435 | − | seg_552 | 139015500 | 139016750 | ATP11C | F9 |
| ENST00000453380.1 | 5132 | 139173902 | 139174720 | + | seg_553 | 139172400 | 139174100 | CXorf66 | F9 |
| ENST00000370536.2 | 5133 | 139585152 | 139587225 | − | seg_555 | 139584250 | 139586100 | SOX3 | F9 |
| ENST00000370530.1 | 5134 | 140096761 | 140097876 | + | seg_557 | 140096200 | 140097500 | SPANXB1 | F9 |
| ENST00000370467.3 | 5135 | 147062849 | 147108187 | + | seg_560 | 147095200 | 147096350 | FMR1NB | FMR1 |
| ENST00000489034.1 | 5136 | 147088336 | 147108185 | + | seg_560 | 147095200 | 147096350 | FMR1NB | FMR1 |
| ENST00000435346.1 | 5137 | 147628399 | 147628918 | + | seg_561 | 147627750 | 147628750 | AFF2 | FMR1 |
| ENST00000370457.5 | 5138 | 147582139 | 148082193 | + | seg_561 | 147627750 | 147628750 | AFF2 | FMR1 |
| ENST00000370460.2 | 5139 | 147582139 | 148082193 | + | seg_561 | 147627750 | 147628750 | AFF2 | FMR1 |
| ENST00000370458.1 | 5140 | 147582529 | 147985907 | + | seg_561 | 147627750 | 147628750 | AFF2 | FMR1 |
| ENST00000342251.3 | 5141 | 147582228 | 148075954 | + | seg_561 | 147627750 | 147628750 | AFF2 | FMR1 |
| ENST00000370457.5 | 5142 | 147582139 | 148082193 | + | seg_562 | 147670600 | 147671600 | AFF2 | FMR1 |
| ENST00000370460.2 | 5143 | 147582139 | 148082193 | + | seg_562 | 147670600 | 147671600 | AFF2 | FMR1 |
| ENST00000370458.1 | 5144 | 147582529 | 147985907 | + | seg_562 | 147670600 | 147671600 | AFF2 | FMR1 |
| ENST00000342251.3 | 5145 | 147582228 | 148075954 | + | seg_562 | 147670600 | 147671600 | AFF2 | FMR1 |
| ENST00000543618.1 | 5146 | 148678217 | 148683886 | − | seg_567 | 148673650 | 148678650 | HSFX2 | MTM1 |
| ENST00000522155.1 | 5147 | 148674868 | 148676436 | − | seg_567 | 148673650 | 148678650 | HSFX2 | MTM1 |
| ENST00000524178.1 | 5148 | 148674172 | 148676974 | − | seg_567 | 148673650 | 148678650 | HSFX2 | MTM1 |
| ENST00000519015.1 | 5149 | 148678217 | 148683886 | − | seg_567 | 148673650 | 148678650 | HSFX2 | MTM1 |
| ENST00000316916.8 | 5150 | 148678216 | 148713568 | − | seg_567 | 148673650 | 148678650 | HSFX2 | MTM1 |
| ENST00000536359.1 | 5151 | 148678216 | 148713487 | − | seg_567 | 148673650 | 148678650 | HSFX2 | MTM1 |
| ENST00000513505.2 | 5152 | 148678216 | 148713402 | − | seg_567 | 148673650 | 148678650 | HSFX2 | MTM1 |
| ENST00000543618.1 | 5153 | 148678217 | 148683886 | − | seg_568 | 148679900 | 148684000 | HSFX2 | MTM1 |
| ENST00000519015.1 | 5154 | 148678217 | 148683886 | − | seg_568 | 148679900 | 148684000 | HSFX2 | MTM1 |
| ENST00000316916.8 | 5155 | 148678216 | 148713568 | − | seg_568 | 148679900 | 148684000 | HSFX2 | MTM1 |
| ENST00000502858.2 | 5156 | 148679625 | 148690438 | − | seg_568 | 148679900 | 148684000 | HSFX2 | MTM1 |
| ENST00000536359.1 | 5157 | 148678216 | 148713487 | − | seg_568 | 148679900 | 148684000 | HSFX2 | MTM1 |
| ENST00000513505.2 | 5158 | 148678216 | 148713402 | − | seg_568 | 148679900 | 148684000 | HSFX2 | MTM1 |
| ENST00000502618.1 | 5159 | 148681969 | 148693146 | − | seg_568 | 148679900 | 148684000 | HSFX2 | MTM1 |
| ENST00000316916.8 | 5160 | 148678216 | 148713568 | − | seg_569 | 148712800 | 148714250 | TMEM185A | MTM1 |
| ENST00000502900.1 | 5161 | 148686838 | 148713403 | − | seg_569 | 148712800 | 148714250 | TMEM185A | MTM1 |
| ENST00000536359.1 | 5162 | 148678216 | 148713487 | − | seg_569 | 148712800 | 148714250 | TMEM185A | MTM1 |
| ENST00000511776.1 | 5163 | 148690379 | 148713365 | − | seg_569 | 148712800 | 148714250 | TMEM185A | MTM1 |
| ENST00000513505.2 | 5164 | 148678216 | 148713402 | − | seg_569 | 148712800 | 148714250 | TMEM185A | MTM1 |
| ENST00000507237.1 | 5165 | 148685375 | 148713381 | − | seg_569 | 148712800 | 148714250 | TMEM185A | MTM1 |
| ENST00000428022.1 | 5166 | 148848815 | 148854483 | + | seg_573 | 148848550 | 148851050 | HSFX1 | MTM1 |
| ENST00000524311.1 | 5167 | 148850558 | 148853029 | + | seg_573 | 148848550 | 148851050 | HSFX1 | MTM1 |
| ENST00000428022.1 | 5168 | 148848815 | 148854483 | + | seg_574 | 148853750 | 148858950 | HSFX1 | MTM1 |
| ENST00000370416.4 | 5169 | 148855726 | 148858525 | + | seg_574 | 148853750 | 148858950 | HSFX1 | MTM1 |
| ENST00000449111.1 | 5170 | 149106846 | 149392815 | + | seg_577 | 149221300 | 149222500 | CXorf40B | MTM1 |
| ENST00000449111.1 | 5171 | 149106846 | 149392815 | + | seg_578 | 149326200 | 149327250 | CXorf40B | MTM1 |
| ENST00000468306.1 | 5172 | 149529689 | 149638367 | + | seg_579 | 149527800 | 149533900 | MAMLD1 | MTM1 |
| ENST00000432680.2 | 5173 | 149531686 | 149681395 | + | seg_579 | 149527800 | 149533900 | MAMLD1 | MTM1 |
| ENST00000445612.2 | 5174 | 149529836 | 149680503 | + | seg_579 | 149527800 | 149533900 | MAMLD1 | MTM1 |
| ENST00000370401.2 | 5175 | 149531551 | 149682448 | + | seg_579 | 149527800 | 149533900 | MAMLD1 | MTM1 |
| ENST00000426613.2 | 5176 | 149613720 | 149682448 | + | seg_580 | 149646250 | 149648200 | MAMLD1 | MTM1 |
| ENST00000455522.2 | 5177 | 149639280 | 149680512 | + | seg_580 | 149646250 | 149648200 | MAMLD1 | MTM1 |
| ENST00000262858.5 | 5178 | 149613720 | 149682448 | + | seg_580 | 149646250 | 149648200 | MAMLD1 | MTM1 |
| ENST00000432680.2 | 5179 | 149531686 | 149681395 | + | seg_580 | 149646250 | 149648200 | MAMLD1 | MTM1 |
| ENST00000445612.2 | 5180 | 149529836 | 149680503 | + | seg_580 | 149646250 | 149648200 | MAMLD1 | MTM1 |
| ENST00000370401.2 | 5181 | 149531551 | 149682448 | + | seg_580 | 149646250 | 149648200 | MAMLD1 | MTM1 |
| ENST00000426613.2 | 5182 | 149613720 | 149682448 | + | seg_581 | 149670700 | 149671900 | MAMLD1 | MTM1 |
| ENST00000455522.2 | 5183 | 149639280 | 149680512 | + | seg_581 | 149670700 | 149671900 | MAMLD1 | MTM1 |
| ENST00000262858.5 | 5184 | 149613720 | 149682448 | + | seg_581 | 149670700 | 149671900 | MAMLD1 | MTM1 |
| ENST00000432680.2 | 5185 | 149531686 | 149681395 | + | seg_581 | 149670700 | 149671900 | MAMLD1 | MTM1 |
| ENST00000445612.2 | 5186 | 149529836 | 149680503 | + | seg_581 | 149670700 | 149671900 | MAMLD1 | MTM1 |
| ENST00000370401.2 | 5187 | 149531551 | 149682448 | + | seg_581 | 149670700 | 149671900 | MAMLD1 | MTM1 |
| ENST00000464149.1 | 5188 | 149677595 | 149682439 | + | seg_582 | 149681150 | 149683750 | MAMLD1 | MTM1 |
| ENST00000426613.2 | 5189 | 149613720 | 149682448 | + | seg_582 | 149681150 | 149683750 | MAMLD1 | MTM1 |
| ENST00000262858.5 | 5190 | 149613720 | 149682448 | + | seg_582 | 149681150 | 149683750 | MAMLD1 | MTM1 |
| ENST00000432680.2 | 5191 | 149531686 | 149681395 | + | seg_582 | 149681150 | 149683750 | MAMLD1 | MTM1 |
| ENST00000370401.2 | 5192 | 149531551 | 149682448 | + | seg_582 | 149681150 | 149683750 | MAMLD1 | MTM1 |
| ENST00000454196.1 | 5193 | 150343664 | 150346308 | − | seg_590 | 150342250 | 150347350 | GPR50 | MTM1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000535473.1 | 5194 | 150345056 | 150348932 | + | seg_590 | 150342250 | 150347350 | GPR50 | MTM1 |
| ENST00000218316.3 | 5195 | 150345125 | 150349937 | + | seg_590 | 150342250 | 150347350 | GPR50 | MTM1 |
| ENST00000458074.1 | 5196 | 150394701 | 150396187 | − | seg_591 | 150395650 | 150397300 | GPR50 | MTM1 |
| ENST00000370361.1 | 5197 | 150565038 | 150573629 | + | seg_593 | 150565200 | 150566300 | VMA21 | MTM1 |
| ENST00000330374.6 | 5198 | 150565676 | 150577836 | + | seg_593 | 150565200 | 150566300 | VMA21 | MTM1 |
| ENST00000477649.1 | 5199 | 150564987 | 150573629 | + | seg_593 | 150565200 | 150566300 | VMA21 | MTM1 |
| ENST00000535156.1 | 5200 | 152082986 | 152142024 | + | seg_607 | 152096400 | 152098350 | ZNF185 | ABCD1 |
| ENST00000539731.1 | 5201 | 152082986 | 152142024 | + | seg_607 | 152096400 | 152098350 | ZNF185 | ABCD1 |
| ENST00000447088.1 | 5202 | 152088893 | 152106707 | + | seg_607 | 152096400 | 152098350 | ZNF185 | ABCD1 |
| ENST00000318504.7 | 5203 | 152082986 | 152142024 | + | seg_607 | 152096400 | 152098350 | ZNF185 | ABCD1 |
| ENST00000370270.1 | 5204 | 152086665 | 152142025 | + | seg_607 | 152096400 | 152098350 | ZNF185 | ABCD1 |
| ENST00000324823.6 | 5205 | 152082986 | 152142024 | + | seg_607 | 152096400 | 152098350 | ZNF185 | ABCD1 |
| ENST00000426821.1 | 5206 | 152087545 | 152142017 | + | seg_607 | 152096400 | 152098350 | ZNF185 | ABCD1 |
| ENST00000447792.1 | 5207 | 152089251 | 152106707 | + | seg_607 | 152096400 | 152098350 | ZNF185 | ABCD1 |
| ENST00000449285.2 | 5208 | 152082986 | 152142024 | + | seg_607 | 152096400 | 152098350 | ZNF185 | ABCD1 |
| ENST00000318529.8 | 5209 | 152086409 | 152142024 | + | seg_607 | 152096400 | 152098350 | ZNF185 | ABCD1 |
| ENST00000535861.1 | 5210 | 152082986 | 152142024 | + | seg_607 | 152096400 | 152098350 | ZNF185 | ABCD1 |
| ENST00000433245.2 | 5211 | 152082986 | 152128407 | + | seg_607 | 152096400 | 152098350 | ZNF185 | ABCD1 |
| ENST00000370268.4 | 5212 | 152082997 | 152142015 | + | seg_607 | 152096400 | 152098350 | ZNF185 | ABCD1 |
| ENST00000535156.1 | 5213 | 152082986 | 152142024 | + | seg_608 | 152101500 | 152102750 | ZNF185 | ABCD1 |
| ENST00000539731.1 | 5214 | 152082986 | 152142024 | + | seg_608 | 152101500 | 152102750 | ZNF185 | ABCD1 |
| ENST00000447088.1 | 5215 | 152088893 | 152106707 | + | seg_608 | 152101500 | 152102750 | ZNF185 | ABCD1 |
| ENST00000318504.7 | 5216 | 152082986 | 152142024 | + | seg_608 | 152101500 | 152102750 | ZNF185 | ABCD1 |
| ENST00000436731.1 | 5217 | 152100283 | 152128354 | + | seg_608 | 152101500 | 152102750 | ZNF185 | ABCD1 |
| ENST00000370270.1 | 5218 | 152086665 | 152142025 | + | seg_608 | 152101500 | 152102750 | ZNF185 | ABCD1 |
| ENST00000324823.6 | 5219 | 152082986 | 152142024 | + | seg_608 | 152101500 | 152102750 | ZNF185 | ABCD1 |
| ENST00000426821.1 | 5220 | 152087545 | 152142017 | + | seg_608 | 152101500 | 152102750 | ZNF185 | ABCD1 |
| ENST00000447792.1 | 5221 | 152089251 | 152106707 | + | seg_608 | 152101500 | 152102750 | ZNF185 | ABCD1 |
| ENST00000449285.2 | 5222 | 152082986 | 152142024 | + | seg_608 | 152101500 | 152102750 | ZNF185 | ABCD1 |
| ENST00000318529.8 | 5223 | 152086409 | 152142024 | + | seg_608 | 152101500 | 152102750 | ZNF185 | ABCD1 |
| ENST00000535861.1 | 5224 | 152082986 | 152142024 | + | seg_608 | 152101500 | 152102750 | ZNF185 | ABCD1 |
| ENST00000433245.2 | 5225 | 152082986 | 152128407 | + | seg_608 | 152101500 | 152102750 | ZNF185 | ABCD1 |
| ENST00000370268.4 | 5226 | 152082997 | 152142015 | + | seg_608 | 152101500 | 152102750 | ZNF185 | ABCD1 |
| ENST00000456193.1 | 5227 | 152387940 | 152393740 | − | seg_612 | 152392250 | 152393600 | PNMA6B | ABCD1 |
| ENST00000415779.1 | 5228 | 152537078 | 152543256 | − | seg_614 | 152530950 | 152538400 | MAGEA1 | ABCD1 |
| ENST00000427876.1 | 5229 | 152663209 | 152664240 | − | seg_616 | 152662500 | 152664500 | ZFP92 | ABCD1 |
| ENST00000445091.1 | 5230 | 152662421 | 152664307 | − | seg_616 | 152662500 | 152664500 | ZFP92 | ABCD1 |
| ENST00000431891.2 | 5231 | 152760451 | 152772084 | + | seg_618 | 152757650 | 152760600 | U82695.9 | ABCD1 |
| ENST00000331595.4 | 5232 | 152760397 | 152775012 | + | seg_618 | 152757650 | 152760600 | U82695.9 | ABCD1 |
| ENST00000480756.1 | 5233 | 152760441 | 152775004 | + | seg_618 | 152757650 | 152760600 | U82695.9 | ABCD1 |
| ENST00000421080.2 | 5234 | 152713128 | 152760978 | − | seg_618 | 152757650 | 152760600 | U82695.9 | ABCD1 |
| ENST00000431270.2 | 5235 | 152760411 | 152773996 | + | seg_618 | 152757650 | 152760600 | U82695.9 | ABCD1 |
| ENST00000453918.2 | 5236 | 152721747 | 152760940 | − | seg_618 | 152757650 | 152760600 | U82695.9 | ABCD1 |
| ENST00000472615.1 | 5237 | 152760439 | 152775004 | + | seg_618 | 152757650 | 152760600 | U82695.9 | ABCD1 |
| ENST00000370210.1 | 5238 | 152727018 | 152760974 | − | seg_618 | 152757650 | 152760600 | U82695.9 | ABCD1 |
| ENST00000418899.2 | 5239 | 152770145 | 152774295 | + | seg_619 | 152773950 | 152775950 | BGN | ABCD1 |
| ENST00000492658.1 | 5240 | 152771327 | 152774263 | + | seg_619 | 152773950 | 152775950 | BGN | ABCD1 |
| ENST00000370204.1 | 5241 | 152767902 | 152775004 | + | seg_619 | 152773950 | 152775950 | BGN | ABCD1 |
| ENST00000430380.2 | 5242 | 152767902 | 152774998 | + | seg_619 | 152773950 | 152775950 | BGN | ABCD1 |
| ENST00000331595.4 | 5243 | 152760397 | 152775012 | + | seg_619 | 152773950 | 152775950 | BGN | ABCD1 |
| ENST00000480756.1 | 5244 | 152760441 | 152775004 | + | seg_619 | 152773950 | 152775950 | BGN | ABCD1 |
| ENST00000431270.2 | 5245 | 152760411 | 152773996 | + | seg_619 | 152773950 | 152775950 | BGN | ABCD1 |
| ENST00000472615.1 | 5246 | 152760439 | 152775004 | + | seg_619 | 152773950 | 152775950 | BGN | ABCD1 |
| ENST00000349466.2 | 5247 | 152783134 | 152846047 | + | seg_620 | 152789000 | 152790950 | ATP2B3 | ABCD1 |
| ENST00000370186.1 | 5248 | 152783134 | 152848397 | + | seg_620 | 152789000 | 152790950 | ATP2B3 | ABCD1 |
| ENST00000349466.2 | 5249 | 152783134 | 152846047 | + | seg_621 | 152792050 | 152797450 | ATP2B3 | ABCD1 |
| ENST00000370186.1 | 5250 | 152783134 | 152848397 | + | seg_621 | 152792050 | 152797450 | ATP2B3 | ABCD1 |
| ENST00000263519.4 | 5251 | 152801580 | 152848387 | + | seg_622 | 152801800 | 152804350 | ATP2B3 | ABCD1 |
| ENST00000349466.2 | 5252 | 152783134 | 152846047 | + | seg_622 | 152801800 | 152804350 | ATP2B3 | ABCD1 |
| ENST00000359149.3 | 5253 | 152801580 | 152846047 | + | seg_622 | 152801800 | 152804350 | ATP2B3 | ABCD1 |
| ENST00000370181.2 | 5254 | 152801580 | 152848387 | + | seg_622 | 152801800 | 152804350 | ATP2B3 | ABCD1 |
| ENST00000393842.1 | 5255 | 152798392 | 152835420 | + | seg_622 | 152801800 | 152804350 | ATP2B3 | ABCD1 |
| ENST00000370186.1 | 5256 | 152783134 | 152848397 | + | seg_622 | 152801800 | 152804350 | ATP2B3 | ABCD1 |
| ENST00000263519.4 | 5257 | 152801580 | 152848387 | + | seg_623 | 152811300 | 152813150 | ATP2B3 | ABCD1 |
| ENST00000349466.2 | 5258 | 152783134 | 152846047 | + | seg_623 | 152811300 | 152813150 | ATP2B3 | ABCD1 |
| ENST00000359149.3 | 5259 | 152801580 | 152846047 | + | seg_623 | 152811300 | 152813150 | ATP2B3 | ABCD1 |
| ENST00000370181.2 | 5260 | 152801580 | 152848387 | + | seg_623 | 152811300 | 152813150 | ATP2B3 | ABCD1 |
| ENST00000393842.1 | 5261 | 152798392 | 152835420 | + | seg_623 | 152811300 | 152813150 | ATP2B3 | ABCD1 |
| ENST00000370186.1 | 5262 | 152783134 | 152848397 | + | seg_623 | 152811300 | 152813150 | ATP2B3 | ABCD1 |
| ENST00000263519.4 | 5263 | 152801580 | 152848387 | + | seg_624 | 152815500 | 152817200 | ATP2B3 | ABCD1 |
| ENST00000349466.2 | 5264 | 152783134 | 152846047 | + | seg_624 | 152815500 | 152817200 | ATP2B3 | ABCD1 |
| ENST00000359149.3 | 5265 | 152801580 | 152846047 | + | seg_624 | 152815500 | 152817200 | ATP2B3 | ABCD1 |
| ENST00000370181.2 | 5266 | 152801580 | 152848387 | + | seg_624 | 152815500 | 152817200 | ATP2B3 | ABCD1 |
| ENST00000393842.1 | 5267 | 152798392 | 152835420 | + | seg_624 | 152815500 | 152817200 | ATP2B3 | ABCD1 |
| ENST00000370186.1 | 5268 | 152783134 | 152848397 | + | seg_624 | 152815500 | 152817200 | ATP2B3 | ABCD1 |
| ENST00000460549.1 | 5269 | 152822404 | 152826282 | + | seg_625 | 152818800 | 152828200 | ATP2B3 | ABCD1 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000263519.4 | 5270 | 152801580 | 152848387 | + | seg_625 | 152818800 | 152828200 | ATP2B3 | ABCD1 |
| ENST00000349466.2 | 5271 | 152783134 | 152846047 | + | seg_625 | 152818800 | 152828200 | ATP2B3 | ABCD1 |
| ENST00000359149.3 | 5272 | 152801580 | 152846047 | + | seg_625 | 152818800 | 152828200 | ATP2B3 | ABCD1 |
| ENST00000370181.2 | 5273 | 152801580 | 152848387 | + | seg_625 | 152818800 | 152828200 | ATP2B3 | ABCD1 |
| ENST00000393842.1 | 5274 | 152798392 | 152835420 | + | seg_625 | 152818800 | 152828200 | ATP2B3 | ABCD1 |
| ENST00000370186.1 | 5275 | 152783134 | 152848397 | + | seg_625 | 152818800 | 152828200 | ATP2B3 | ABCD1 |
| ENST00000496610.1 | 5276 | 152835106 | 152846027 | + | seg_626 | 152831650 | 152837100 | FAM58A | ABCD1 |
| ENST00000263519.4 | 5277 | 152801580 | 152848387 | + | seg_626 | 152831650 | 152837100 | FAM58A | ABCD1 |
| ENST00000349466.2 | 5278 | 152783134 | 152846047 | + | seg_626 | 152831650 | 152837100 | FAM58A | ABCD1 |
| ENST00000359149.3 | 5279 | 152801580 | 152846047 | + | seg_626 | 152831650 | 152837100 | FAM58A | ABCD1 |
| ENST00000370181.2 | 5280 | 152801580 | 152848387 | + | seg_626 | 152831650 | 152837100 | FAM58A | ABCD1 |
| ENST00000393842.1 | 5281 | 152798392 | 152835420 | + | seg_626 | 152831650 | 152837100 | FAM58A | ABCD1 |
| ENST00000370186.1 | 5282 | 152783134 | 152848397 | + | seg_626 | 152831650 | 152837100 | FAM58A | ABCD1 |
| ENST00000496610.1 | 5283 | 152835106 | 152846027 | + | seg_627 | 152839000 | 152842300 | FAM58A | ABCD1 |
| ENST00000263519.4 | 5284 | 152801580 | 152848387 | + | seg_627 | 152839000 | 152842300 | FAM58A | ABCD1 |
| ENST00000349466.2 | 5285 | 152783134 | 152846047 | + | seg_627 | 152839000 | 152842300 | FAM58A | ABCD1 |
| ENST00000359149.3 | 5286 | 152801580 | 152846047 | + | seg_627 | 152839000 | 152842300 | FAM58A | ABCD1 |
| ENST00000370181.2 | 5287 | 152801580 | 152848387 | + | seg_627 | 152839000 | 152842300 | FAM58A | ABCD1 |
| ENST00000370186.1 | 5288 | 152783134 | 152848397 | + | seg_627 | 152839000 | 152842300 | FAM58A | ABCD1 |
| ENST00000406288.2 | 5289 | 152871972 | 152872343 | + | seg_628 | 152870900 | 152872850 | FAM58A | ABCD1 |
| ENST00000446370.1 | 5290 | 152876149 | 152878380 | + | seg_629 | 152875300 | 152879100 | FAM58A | ABCD1 |
| ENST00000477033.1 | 5291 | 152907946 | 152913467 | + | seg_634 | 152908450 | 152909650 | DUSP9 | ABCD1 |
| ENST00000370167.4 | 5292 | 152907988 | 152916781 | + | seg_634 | 152908450 | 152909650 | DUSP9 | ABCD1 |
| ENST00000433144.1 | 5293 | 152908932 | 152916777 | + | seg_634 | 152908450 | 152909650 | DUSP9 | ABCD1 |
| ENST00000537633.1 | 5294 | 153069624 | 153073873 | − | seg_635 | 153070100 | 153072100 | PDZD4 | L1CAM |
| ENST00000484792.1 | 5295 | 153070334 | 153073594 | − | seg_635 | 153070100 | 153072100 | PDZD4 | L1CAM |
| ENST00000480418.1 | 5296 | 153071037 | 153096020 | − | seg_635 | 153070100 | 153072100 | PDZD4 | L1CAM |
| ENST00000164640.4 | 5297 | 153067621 | 153095945 | − | seg_635 | 153070100 | 153072100 | PDZD4 | L1CAM |
| ENST00000544474.1 | 5298 | 153068742 | 153095813 | − | seg_635 | 153070100 | 153072100 | PDZD4 | L1CAM |
| ENST00000483693.1 | 5299 | 153071000 | 153095598 | − | seg_635 | 153070100 | 153072100 | PDZD4 | L1CAM |
| ENST00000393758.2 | 5300 | 153067623 | 153095351 | − | seg_635 | 153070100 | 153072100 | PDZD4 | L1CAM |
| ENST00000475140.1 | 5301 | 153070548 | 153095311 | − | seg_635 | 153070100 | 153072100 | PDZD4 | L1CAM |
| ENST00000468491.1 | 5302 | 153072782 | 153095125 | − | seg_636 | 153075150 | 153076450 | PDZD4 | L1CAM |
| ENST00000480418.1 | 5303 | 153071037 | 153096020 | − | seg_636 | 153075150 | 153076450 | PDZD4 | L1CAM |
| ENST00000480650.1 | 5304 | 153073438 | 153095792 | − | seg_636 | 153075150 | 153076450 | PDZD4 | L1CAM |
| ENST00000164640.4 | 5305 | 153067621 | 153095945 | − | seg_636 | 153075150 | 153076450 | PDZD4 | L1CAM |
| ENST00000544474.1 | 5306 | 153068742 | 153095813 | − | seg_636 | 153075150 | 153076450 | PDZD4 | L1CAM |
| ENST00000483693.1 | 5307 | 153071000 | 153095598 | − | seg_636 | 153075150 | 153076450 | PDZD4 | L1CAM |
| ENST00000393758.2 | 5308 | 153067623 | 153095351 | − | seg_636 | 153075150 | 153076450 | PDZD4 | L1CAM |
| ENST00000475140.1 | 5309 | 153070548 | 153095311 | − | seg_636 | 153075150 | 153076450 | PDZD4 | L1CAM |
| ENST00000468491.1 | 5310 | 153072782 | 153095125 | − | seg_637 | 153078150 | 153079950 | PDZD4 | L1CAM |
| ENST00000480418.1 | 5311 | 153071037 | 153096020 | − | seg_637 | 153078150 | 153079950 | PDZD4 | L1CAM |
| ENST00000480650.1 | 5312 | 153073438 | 153095792 | − | seg_637 | 153078150 | 153079950 | PDZD4 | L1CAM |
| ENST00000164640.4 | 5313 | 153067621 | 153095945 | − | seg_637 | 153078150 | 153079950 | PDZD4 | L1CAM |
| ENST00000544474.1 | 5314 | 153068742 | 153095813 | − | seg_637 | 153078150 | 153079950 | PDZD4 | L1CAM |
| ENST00000483693.1 | 5315 | 153071000 | 153095598 | − | seg_637 | 153078150 | 153079950 | PDZD4 | L1CAM |
| ENST00000393758.2 | 5316 | 153067623 | 153095351 | − | seg_637 | 153078150 | 153079950 | PDZD4 | L1CAM |
| ENST00000475140.1 | 5317 | 153070548 | 153095311 | − | seg_637 | 153078150 | 153079950 | PDZD4 | L1CAM |
| ENST00000468491.1 | 5318 | 153072782 | 153095125 | − | seg_638 | 153089000 | 153091450 | PDZD4 | L1CAM |
| ENST00000480418.1 | 5319 | 153071037 | 153096020 | − | seg_638 | 153089000 | 153091450 | PDZD4 | L1CAM |
| ENST00000480650.1 | 5320 | 153073438 | 153095792 | − | seg_638 | 153089000 | 153091450 | PDZD4 | L1CAM |
| ENST00000164640.4 | 5321 | 153067621 | 153095945 | − | seg_638 | 153089000 | 153091450 | PDZD4 | L1CAM |
| ENST00000544474.1 | 5322 | 153068742 | 153095813 | − | seg_638 | 153089000 | 153091450 | PDZD4 | L1CAM |
| ENST00000483693.1 | 5323 | 153071000 | 153095598 | − | seg_638 | 153089000 | 153091450 | PDZD4 | L1CAM |
| ENST00000393758.2 | 5324 | 153067623 | 153095351 | − | seg_638 | 153089000 | 153091450 | PDZD4 | L1CAM |
| ENST00000475140.1 | 5325 | 153070548 | 153095311 | − | seg_638 | 153089000 | 153091450 | PDZD4 | L1CAM |
| ENST00000468491.1 | 5326 | 153072782 | 153095125 | − | seg_639 | 153093650 | 153097850 | PDZD4 | L1CAM |
| ENST00000480418.1 | 5327 | 153071037 | 153096020 | − | seg_639 | 153093650 | 153097850 | PDZD4 | L1CAM |
| ENST00000480650.1 | 5328 | 153073438 | 153095792 | − | seg_639 | 153093650 | 153097850 | PDZD4 | L1CAM |
| ENST00000164640.4 | 5329 | 153067621 | 153095945 | − | seg_639 | 153093650 | 153097850 | PDZD4 | L1CAM |
| ENST00000544474.1 | 5330 | 153068742 | 153095813 | − | seg_639 | 153093650 | 153097850 | PDZD4 | L1CAM |
| ENST00000483693.1 | 5331 | 153071000 | 153095598 | − | seg_639 | 153093650 | 153097850 | PDZD4 | L1CAM |
| ENST00000393758.2 | 5332 | 153067623 | 153095351 | − | seg_639 | 153093650 | 153097850 | PDZD4 | L1CAM |
| ENST00000475140.1 | 5333 | 153070548 | 153095311 | − | seg_639 | 153093650 | 153097850 | PDZD4 | L1CAM |
| ENST00000370058.3 | 5334 | 153127888 | 153129933 | − | seg_640 | 153123550 | 153131800 | L1CAM | L1CAM |
| ENST00000491983.1 | 5335 | 153128247 | 153129424 | − | seg_640 | 153123550 | 153131800 | L1CAM | L1CAM |
| ENST00000474853.1 | 5336 | 153130419 | 153131370 | − | seg_640 | 153123550 | 153131800 | L1CAM | L1CAM |
| ENST00000370055.1 | 5337 | 153127408 | 153151608 | − | seg_640 | 153123550 | 153131800 | L1CAM | L1CAM |
| ENST00000370057.3 | 5338 | 153126973 | 153141399 | − | seg_640 | 153123550 | 153131800 | L1CAM | L1CAM |
| ENST00000361699.4 | 5339 | 153128003 | 153141302 | − | seg_640 | 153123550 | 153131800 | L1CAM | L1CAM |
| ENST00000540065.1 | 5340 | 153126995 | 153151569 | − | seg_640 | 153123550 | 153131800 | L1CAM | L1CAM |
| ENST00000361981.3 | 5341 | 153126973 | 153141399 | − | seg_640 | 153123550 | 153131800 | L1CAM | L1CAM |
| ENST00000538883.1 | 5342 | 153126973 | 153141399 | − | seg_640 | 153123550 | 153131800 | L1CAM | L1CAM |
| ENST00000370060.1 | 5343 | 153126969 | 153151600 | − | seg_640 | 153123550 | 153131800 | L1CAM | L1CAM |
| ENST00000543994.1 | 5344 | 153126973 | 153141399 | − | seg_640 | 153123550 | 153131800 | L1CAM | L1CAM |
| ENST00000455590.1 | 5345 | 153132227 | 153133832 | − | seg_641 | 153133350 | 153135150 | L1CAM | L1CAM |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000484652.1 | 5346 | 153133862 | 153134627 | − | seg_641 | 153133350 | 153135150 | L1CAM | L1CAM |
| ENST00000496122.1 | 5347 | 153133006 | 153134078 | − | seg_641 | 153133350 | 153135150 | L1CAM | L1CAM |
| ENST00000370055.1 | 5348 | 153127408 | 153151608 | − | seg_641 | 153133350 | 153135150 | L1CAM | L1CAM |
| ENST00000370057.3 | 5349 | 153126973 | 153141399 | − | seg_641 | 153133350 | 153135150 | L1CAM | L1CAM |
| ENST00000361699.4 | 5350 | 153128003 | 153141302 | − | seg_641 | 153133350 | 153135150 | L1CAM | L1CAM |
| ENST00000540065.1 | 5351 | 153126995 | 153151569 | − | seg_641 | 153133350 | 153135150 | L1CAM | L1CAM |
| ENST00000361981.3 | 5352 | 153126973 | 153141399 | − | seg_641 | 153133350 | 153135150 | L1CAM | L1CAM |
| ENST00000538883.1 | 5353 | 153126973 | 153141399 | − | seg_641 | 153133350 | 153135150 | L1CAM | L1CAM |
| ENST00000370060.1 | 5354 | 153126969 | 153151600 | − | seg_641 | 153133350 | 153135150 | L1CAM | L1CAM |
| ENST00000543994.1 | 5355 | 153126973 | 153141399 | − | seg_641 | 153133350 | 153135150 | L1CAM | L1CAM |
| ENST00000357566.1 | 5356 | 153146127 | 153154425 | + | seg_642 | 153150200 | 153151550 | LCA10 | L1CAM |
| ENST00000484587.1 | 5357 | 153149319 | 153151615 | − | seg_642 | 153150200 | 153151550 | LCA10 | L1CAM |
| ENST00000452593.1 | 5358 | 153146127 | 153154444 | + | seg_642 | 153150200 | 153151550 | LCA10 | L1CAM |
| ENST00000370055.1 | 5359 | 153127408 | 153151608 | − | seg_642 | 153150200 | 153151550 | LCA10 | L1CAM |
| ENST00000540065.1 | 5360 | 153126995 | 153151569 | − | seg_642 | 153150200 | 153151550 | LCA10 | L1CAM |
| ENST00000460553.1 | 5361 | 153138404 | 153151596 | − | seg_642 | 153150200 | 153151550 | LCA10 | L1CAM |
| ENST00000464967.1 | 5362 | 153137676 | 153174677 | − | seg_642 | 153150200 | 153151550 | LCA10 | L1CAM |
| ENST00000420165.1 | 5363 | 153137722 | 153151627 | − | seg_642 | 153150200 | 153151550 | LCA10 | L1CAM |
| ENST00000370060.1 | 5364 | 153126969 | 153151600 | − | seg_642 | 153150200 | 153151550 | LCA10 | L1CAM |
| ENST00000464967.1 | 5365 | 153137676 | 153174677 | − | seg_643 | 153157550 | 153159050 | LCA10 | AVPR2 |
| ENST00000370011.3 | 5366 | 153195658 | 153200468 | − | seg_644 | 153199600 | 153200600 | NAA10 | AVPR2 |
| ENST00000545734.1 | 5367 | 153195383 | 153200462 | − | seg_644 | 153199600 | 153200600 | NAA10 | AVPR2 |
| ENST00000432089.1 | 5368 | 153196232 | 153200519 | − | seg_644 | 153199600 | 153200600 | NAA10 | AVPR2 |
| ENST00000466877.1 | 5369 | 153195379 | 153200468 | − | seg_644 | 153199600 | 153200600 | NAA10 | AVPR2 |
| ENST00000393710.3 | 5370 | 153197407 | 153200468 | − | seg_644 | 153199600 | 153200600 | NAA10 | AVPR2 |
| ENST00000464845.1 | 5371 | 153194695 | 153200676 | − | seg_644 | 153199600 | 153200600 | NAA10 | AVPR2 |
| ENST00000460996.1 | 5372 | 153195529 | 153200238 | − | seg_644 | 153199600 | 153200600 | NAA10 | AVPR2 |
| ENST00000477750.1 | 5373 | 153197224 | 153200533 | − | seg_644 | 153199600 | 153200600 | NAA10 | AVPR2 |
| ENST00000393712.3 | 5374 | 153195374 | 153200411 | − | seg_644 | 153199600 | 153200600 | NAA10 | AVPR2 |
| ENST00000370015.4 | 5375 | 153195367 | 153200494 | − | seg_644 | 153199600 | 153200600 | NAA10 | AVPR2 |
| ENST00000478177.1 | 5376 | 153199113 | 153200468 | − | seg_644 | 153199600 | 153200600 | NAA10 | AVPR2 |
| ENST00000370009.1 | 5377 | 153195377 | 153200468 | − | seg_644 | 153199600 | 153200600 | NAA10 | AVPR2 |
| ENST00000488481.1 | 5378 | 153199483 | 153200459 | − | seg_644 | 153199600 | 153200600 | NAA10 | AVPR2 |
| ENST00000494813.1 | 5379 | 153178664 | 153200452 | − | seg_644 | 153199600 | 153200600 | NAA10 | AVPR2 |
| ENST00000369951.4 | 5380 | 153409698 | 153424507 | + | seg_646 | 153409000 | 153412050 | OPN1LW | OPN1MW |
| ENST00000463296.1 | 5381 | 153409748 | 153421872 | + | seg_646 | 153409000 | 153412050 | OPN1LW | OPN1MW |
| ENST00000369941.4 | 5382 | 153424682 | 153445634 | − | seg_647 | 153423450 | 153426400 | OPN1LW | OPN1MW |
| ENST00000369951.4 | 5383 | 153409698 | 153424507 | + | seg_647 | 153423450 | 153426400 | OPN1LW | OPN1MW |
| ENST00000442922.1 | 5384 | 153418415 | 153424498 | + | seg_647 | 153423450 | 153426400 | OPN1LW | OPN1MW |
| ENST00000369941.4 | 5385 | 153424682 | 153445634 | − | seg_648 | 153438400 | 153439900 | TEX28P2 | OPN1MW |
| ENST00000468495.1 | 5386 | 153448157 | 153459002 | + | seg_649 | 153447400 | 153449250 | OPN1MW | OPN1MW |
| ENST00000369935.5 | 5387 | 153448107 | 153461633 | + | seg_649 | 153447400 | 153449250 | OPN1MW | OPN1MW |
| ENST00000430054.1 | 5388 | 153455547 | 153461628 | + | seg_650 | 153454750 | 153456450 | OPN1MW | OPN1MW |
| ENST00000468495.1 | 5389 | 153448157 | 153459002 | + | seg_650 | 153454750 | 153456450 | OPN1MW | OPN1MW |
| ENST00000369935.5 | 5390 | 153448107 | 153461633 | + | seg_650 | 153454750 | 153456450 | OPN1MW | OPN1MW |
| ENST00000430054.1 | 5391 | 153455547 | 153461628 | + | seg_651 | 153460750 | 153463050 | OPN1MW | OPN1MW |
| ENST00000369935.5 | 5392 | 153448107 | 153461633 | + | seg_651 | 153460750 | 153463050 | OPN1MW | OPN1MW |
| ENST00000369932.3 | 5393 | 153461812 | 153482755 | − | seg_651 | 153460750 | 153463050 | OPN1MW | OPN1MW |
| ENST00000369932.3 | 5394 | 153461812 | 153482755 | − | seg_652 | 153477600 | 153479200 | TEX28P1 | OPN1MW |
| ENST00000369932.3 | 5395 | 153461812 | 153482755 | − | seg_653 | 153481700 | 153485800 | TEX28P1 | OPN1MW |
| ENST00000488220.1 | 5396 | 153485266 | 153496120 | + | seg_653 | 153481700 | 153485800 | TEX28P1 | OPN1MW |
| ENST00000369929.4 | 5397 | 153485225 | 153498755 | + | seg_653 | 153481700 | 153485800 | TEX28P1 | OPN1MW |
| ENST00000430419.1 | 5398 | 153492665 | 153498746 | + | seg_654 | 153498150 | 153500900 | OPN1MW2 | OPN1MW |
| ENST00000361930.3 | 5399 | 153498932 | 153523462 | − | seg_654 | 153498150 | 153500900 | OPN1MW2 | OPN1MW |
| ENST00000369926.1 | 5400 | 153498930 | 153523564 | − | seg_654 | 153498150 | 153500900 | OPN1MW2 | OPN1MW |
| ENST00000369929.4 | 5401 | 153485225 | 153498755 | + | seg_654 | 153498150 | 153500900 | OPN1MW2 | OPN1MW |
| ENST00000217905.7 | 5402 | 153524152 | 153558076 | + | seg_655 | 153551150 | 153553600 | TKTL1 | EMD |
| ENST00000441970.3 | 5403 | 153524027 | 153558713 | + | seg_655 | 153551150 | 153553600 | TKTL1 | EMD |
| ENST00000369915.3 | 5404 | 153524024 | 153558700 | + | seg_655 | 153551150 | 153553600 | TKTL1 | EMD |
| ENST00000465168.1 | 5405 | 153548651 | 153553731 | + | seg_655 | 153551150 | 153553600 | TKTL1 | EMD |
| ENST00000369912.2 | 5406 | 153533409 | 153558700 | + | seg_655 | 153551150 | 153553600 | TKTL1 | EMD |
| ENST00000433825.1 | 5407 | 153562310 | 153563387 | − | seg_657 | 153563100 | 153564150 | FLNA | EMD |
| ENST00000474786.1 | 5408 | 153618315 | 153628507 | + | seg_659 | 153617900 | 153619700 | RPL10 | EMD |
| ENST00000455739.2 | 5409 | 155227361 | 155237484 | + | seg_663 | 155235050 | 155236450 | IL9R | F8 |
| ENST00000494962.1 | 5410 | 155235779 | 155237711 | + | seg_663 | 155235050 | 155236450 | IL9R | F8 |
| ENST00000424344.3 | 5411 | 155227246 | 155240482 | + | seg_663 | 155235050 | 155236450 | IL9R | F8 |
| ENST00000244174.5 | 5412 | 155227246 | 155240273 | + | seg_663 | 155235050 | 155236450 | IL9R | F8 |
| ENST00000540897.1 | 5413 | 155227371 | 155240482 | + | seg_663 | 155235050 | 155236450 | IL9R | F8 |
| ENST00000369423.2 | 5414 | 155227371 | 155240482 | + | seg_663 | 155235050 | 155236450 | IL9R | F8 |
| ENST00000483543.1 | 5415 | 155233883 | 155251689 | + | seg_663 | 155235050 | 155236450 | IL9R | F8 |
| ENST00000399966.4 | 5416 | 155244288 | 155246502 | − | seg_664 | 155245550 | 155247000 | WASH6P | F8 |
| ENST00000483543.1 | 5417 | 155233883 | 155251689 | + | seg_664 | 155245550 | 155247000 | WASH6P | F8 |
| ENST00000482170.1 | 5418 | 155251664 | 155253054 | + | seg_665 | 155253000 | 155254000 | WASH6P | F8 |
| ENST00000483079.1 | 5419 | 155252451 | 155253196 | + | seg_665 | 155253000 | 155254000 | WASH6P | F8 |
| ENST00000484415.1 | 5420 | 155251664 | 155255328 | + | seg_665 | 155253000 | 155254000 | WASH6P | F8 |
| ENST00000492963.1 | 5421 | 155251353 | 155255331 | + | seg_665 | 155253000 | 155254000 | WASH6P | F8 |

TABLE XVII-continued paRNAs associated with SUZ12 STRONG sites in K562 cells

| Transcript ID | SIN | Start | Stop | Strand | Suz12 ID | Suz12 Start | Suz12 End | Closest gene | disease gene |
|---|---|---|---|---|---|---|---|---|---|
| ENST00000496301.1 | 5422 | 155253032 | 155255331 | + | seg_665 | 155253000 | 155254000 | WASH6P | F8 |
| ENST00000359512.2 | 5423 | 155249967 | 155255327 | + | seg_665 | 155253000 | 155254000 | WASH6P | F8 |
| ENST00000461007.1 | 5424 | 155250993 | 155255328 | + | seg_665 | 155253000 | 155254000 | WASH6P | F8 |
| ENST00000460206.1 | 5425 | 155251353 | 155255375 | + | seg_665 | 155253000 | 155254000 | WASH6P | F8 |
| ENST00000483286.1 | 5426 | 155253489 | 155255219 | + | seg_665 | 155253000 | 155254000 | WASH6P | F8 |
| ENST00000464205.1 | 5427 | 155253736 | 155255219 | + | seg_665 | 155253000 | 155254000 | WASH6P | F8 |
| ENST00000285718.7 | 5428 | 155250706 | 155255299 | + | seg_665 | 155253000 | 155254000 | WASH6P | F8 |
| ENST00000340131.7 | 5429 | 155251353 | 155255331 | + | seg_665 | 155253000 | 155254000 | WASH6P | F8 |

TABLE XVIII

Table XVIII lists the 503 paRNAs associated with strong EZH2 sites in GM12878 cells. Coordinates in reference to hg19 assembly.

paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000390665.3 | 5430 | 294698 | 347445 | − | seg_1 | 334650 | 336100 | PPP2R3B | OA1 = GPR143 |
| ENST00000445792.2 | 5431 | 305631 | 347690 | − | seg_1 | 334650 | 336100 | PPP2R3B | OA1 = GPR143 |
| ENST00000381625.4 | 5432 | 308346 | 334779 | − | seg_1 | 334650 | 336100 | PPP2R3B | OA1 = GPR143 |
| ENST00000381567.3 | 5433 | 1314890 | 1331527 | − | seg_2 | 1330550 | 1331800 | CRLF2 | OA1 = GPR143 |
| ENST00000400841.2 | 5434 | 1314894 | 1331530 | − | seg_2 | 1330550 | 1331800 | CRLF2 | OA1 = GPR143 |
| ENST00000467626.1 | 5435 | 1314894 | 1331616 | − | seg_2 | 1330550 | 1331800 | CRLF2 | OA1 = GPR143 |
| ENST00000381566.1 | 5436 | 1317790 | 1331527 | − | seg_2 | 1330550 | 1331800 | CRLF2 | OA1 = GPR143 |
| ENST00000381297.4 | 5437 | 1581465 | 1656000 | − | seg_3 | 1610000 | 1611450 | P2RY8 | OA1 = GPR143 |
| ENST00000381297.4 | 5438 | 1581465 | 1656000 | − | seg_4 | 1639800 | 1641400 | P2RY8 | OA1 = GPR143 |
| ENST00000460672.1 | 5439 | 1585330 | 1613246 | − | seg_3 | 1610000 | 1611450 | P2RY8 | OA1 = GPR143 |
| ENST00000381174.5 | 5440 | 2670091 | 2733968 | + | seg_6 | 2730100 | 2731700 | GYG2 | OA1 = GPR143 |
| ENST00000419513.2 | 5441 | 2670093 | 2732589 | + | seg_6 | 2730100 | 2731700 | GYG2 | OA1 = GPR143 |
| ENST00000426774.1 | 5442 | 2670093 | 2734539 | + | seg_6 | 2730100 | 2731700 | GYG2 | OA1 = GPR143 |
| ENST00000533923.2 | 5443 | 2670231 | 2732581 | + | seg_6 | 2730100 | 2731700 | GYG2 | OA1 = GPR143 |
| ENST00000381077.5 | 5444 | 6966961 | 7066231 | − | seg_8 | 7001450 | 7003250 | HDHD1 | OA1 = GPR143 |
| ENST00000544385.1 | 5445 | 6966961 | 7066231 | − | seg_8 | 7001450 | 7003250 | HDHD1 | OA1 = GPR143 |
| ENST00000412827.2 | 5446 | 6967559 | 7066194 | − | seg_8 | 7001450 | 7003250 | HDHD1 | OA1 = GPR143 |
| ENST00000424830.2 | 5447 | 6967804 | 7066199 | − | seg_8 | 7001450 | 7003250 | HDHD1 | OA1 = GPR143 |
| ENST00000540122.1 | 5448 | 6975627 | 7066231 | − | seg_8 | 7001450 | 7003250 | HDHD1 | OA1 = GPR143 |
| ENST00000486446.2 | 5449 | 6975801 | 7066166 | − | seg_8 | 7001450 | 7003250 | HDHD1 | OA1 = GPR143 |
| ENST00000498474.2 | 5450 | 7002792 | 7066193 | − | seg_8 | 7001450 | 7003250 | HDHD1 | OA1 = GPR143 |
| ENST00000217961.4 | 5451 | 7137497 | 7272851 | + | seg_10 | 7247600 | 7248900 | STS | OA1 = GPR143 |
| ENST00000380913.3 | 5452 | 9754496 | 9917483 | + | seg_14 | 9754800 | 9756400 | SHROOM2 | OA1 = GPR143 |
| ENST00000380833.4 | 5453 | 10125024 | 10205700 | + | seg_15 | 10123700 | 10128400 | CLCN4 | OA1 = GPR143 |
| ENST00000380829.1 | 5454 | 10126488 | 10201737 | + | seg_15 | 10123700 | 10128400 | CLCN4 | OA1 = GPR143 |
| ENST00000421085.2 | 5455 | 10126540 | 10201760 | + | seg_15 | 10123700 | 10128400 | CLCN4 | OA1 = GPR143 |
| ENST00000454850.1 | 5456 | 10126572 | 10174759 | + | seg_15 | 10123700 | 10128400 | CLCN4 | OA1 = GPR143 |
| ENST00000317552.4 | 5457 | 10413350 | 10588674 | − | seg_16 | 10587050 | 10589450 | MID1 | OA1 = GPR143 |
| ENST00000453318.2 | 5458 | 10413350 | 10645779 | − | seg_16 | 10587050 | 10589450 | MID1 | OA1 = GPR143 |
| ENST00000380782.1 | 5459 | 10413596 | 10588459 | − | seg_16 | 10587050 | 10589450 | MID1 | OA1 = GPR143 |
| ENST00000380785.1 | 5460 | 10413596 | 10851762 | − | seg_16 | 10587050 | 10589450 | MID1 | OA1 = GPR143 |
| ENST00000380787.1 | 5461 | 10413596 | 10851773 | − | seg_16 | 10587050 | 10589450 | MID1 | OA1 = GPR143 |
| ENST00000413894.1 | 5462 | 10423115 | 10645727 | − | seg_16 | 10587050 | 10589450 | MID1 | OA1 = GPR143 |
| ENST00000423614.1 | 5463 | 10534995 | 10588625 | − | seg_16 | 10587050 | 10589450 | MID1 | OA1 = GPR143 |
| ENST00000312196.4 | 5464 | 11776278 | 11793870 | + | seg_17 | 11777450 | 11778850 | MSL3 | SEDL = TRAPPC2 |
| ENST00000337339.2 | 5465 | 11776356 | 11786096 | + | seg_17 | 11777450 | 11778850 | MSL3 | SEDL = TRAPPC2 |
| ENST00000468149.1 | 5466 | 11776372 | 11793350 | + | seg_17 | 11777450 | 11778850 | MSL3 | SEDL = TRAPPC2 |
| ENST00000361672.2 | 5467 | 11776410 | 11793350 | + | seg_17 | 11777450 | 11778850 | MSL3 | SEDL = TRAPPC2 |
| ENST00000476743.1 | 5468 | 11776701 | 11780338 | + | seg_17 | 11777450 | 11778850 | MSL3 | SEDL = TRAPPC2 |
| ENST00000421368.2 | 5469 | 11776705 | 11781076 | + | seg_17 | 11777450 | 11778850 | MSL3 | SEDL = TRAPPC2 |
| ENST00000398527.2 | 5470 | 11776728 | 11793574 | + | seg_17 | 11777450 | 11778850 | MSL3 | SEDL = TRAPPC2 |
| ENST00000380693.3 | 5471 | 11777671 | 11793870 | + | seg_17 | 11777450 | 11778850 | MSL3 | SEDL = TRAPPC2 |
| ENST00000380692.2 | 5472 | 11777747 | 11783765 | + | seg_17 | 11777450 | 11778850 | MSL3 | SEDL = TRAPPC2 |
| ENST00000478462.1 | 5473 | 11777760 | 11779173 | + | seg_17 | 11777450 | 11778850 | MSL3 | SEDL = TRAPPC2 |
| ENST00000482871.1 | 5474 | 11778162 | 11781026 | + | seg_17 | 11777450 | 11778850 | MSL3 | SEDL = TRAPPC2 |
| ENST00000473806.1 | 5475 | 11778257 | 11779701 | + | seg_17 | 11777450 | 11778850 | MSL3 | SEDL = TRAPPC2 |
| ENST00000483645.1 | 5476 | 11778305 | 11781043 | + | seg_17 | 11777450 | 11778850 | MSL3 | SEDL = TRAPPC2 |
| ENST00000494268.1 | 5477 | 11778341 | 11782370 | + | seg_17 | 11777450 | 11778850 | MSL3 | SEDL = TRAPPC2 |
| ENST00000487782.1 | 5478 | 11778594 | 11786803 | + | seg_17 | 11777450 | 11778850 | MSL3 | SEDL = TRAPPC2 |
| ENST00000380682.1 | 5479 | 12156585 | 12742642 | + | seg_19 | 12328750 | 12329950 | FRMPD4 | SEDL = TRAPPC2 |
| ENST00000380682.1 | 5480 | 12156585 | 12742642 | + | seg_20 | 12511300 | 12512400 | PRPS2 | SEDL = TRAPPC2 |
| ENST00000380659.3 | 5481 | 12885202 | 12908499 | + | seg_23 | 12907700 | 12908700 | TLR8 | SEDL = TRAPPC2 |
| ENST00000446964.1 | 5482 | 13395307 | 13421138 | + | seg_29 | 13400400 | 13401500 | ATXN3L | SEDL = TRAPPC2 |
| ENST00000467590.1 | 5483 | 13680863 | 13700083 | + | seg_30 | 13690350 | 13691400 | TCEANC | SEDL = TRAPPC2 |
| ENST00000380550.3 | 5484 | 13752832 | 13787480 | + | seg_31 | 13769950 | 13771750 | OFD1 | OFD1 |
| ENST00000398395.3 | 5485 | 13752851 | 13771024 | + | seg_31 | 13769950 | 13771750 | OFD1 | OFD1 |
| ENST00000340096.6 | 5486 | 13752864 | 13787472 | + | seg_31 | 13769950 | 13771750 | OFD1 | OFD1 |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000380567.1 | 5487 | 13752864 | 13787472 | + | seg_31 | 13769950 | 13771750 | OFD1 | OFD1 |
| ENST00000490265.1 | 5488 | 13752880 | 13787472 | + | seg_31 | 13769950 | 13771750 | OFD1 | OFD1 |
| ENST00000543598.1 | 5489 | 13753017 | 13787430 | + | seg_31 | 13769950 | 13771750 | OFD1 | OFD1 |
| ENST00000454189.2 | 5490 | 13789575 | 13956757 | − | seg_32 | 13861350 | 13862450 | GPM6B | OFD1 |
| ENST00000454189.2 | 5491 | 13789575 | 13956757 | − | seg_33 | 13954750 | 13956950 | GPM6B | OFD1 |
| ENST00000398361.3 | 5492 | 13792456 | 13956534 | − | seg_32 | 13861350 | 13862450 | GPM6B | OFD1 |
| ENST00000398361.3 | 5493 | 13792456 | 13956534 | − | seg_33 | 13954750 | 13956950 | GPM6B | OFD1 |
| ENST00000493085.1 | 5494 | 13797972 | 13907176 | − | seg_32 | 13861350 | 13862450 | GPM6B | OFD1 |
| ENST00000468080.1 | 5495 | 13798027 | 13907731 | − | seg_32 | 13861350 | 13862450 | GPM6B | OFD1 |
| ENST00000380523.4 | 5496 | 14026398 | 14048011 | − | seg_34 | 14044850 | 14046750 | GEMIN8 | OFD1 |
| ENST00000398355.3 | 5497 | 14026792 | 14048012 | − | seg_34 | 14044850 | 14046750 | GEMIN8 | OFD1 |
| ENST00000332885.3 | 5498 | 14027230 | 14047734 | − | seg_34 | 14044850 | 14046750 | GEMIN8 | OFD1 |
| ENST00000477386.1 | 5499 | 14038196 | 14045263 | − | seg_34 | 14044850 | 14046750 | GEMIN8 | OFD1 |
| ENST00000297904.3 | 5500 | 15363713 | 15402498 | − | seg_37 | 15366600 | 15367950 | PIGA | PIGA |
| ENST00000421585.1 | 5501 | 15621004 | 15639607 | + | seg_38 | 15635900 | 15637200 | ACE2 | PIGA |
| ENST00000380342.3 | 5502 | 15645441 | 15683154 | − | seg_39 | 15661250 | 15663050 | TMEM27 | PIGA |
| ENST00000329235.2 | 5503 | 15843929 | 15873054 | − | seg_41 | 15870450 | 15871500 | AP1S2 | PIGA |
| ENST00000452376.1 | 5504 | 15845015 | 15870636 | − | seg_41 | 15870450 | 15871500 | AP1S2 | PIGA |
| ENST00000380291.1 | 5505 | 15848182 | 15872927 | − | seg_41 | 15870450 | 15871500 | AP1S2 | PIGA |
| ENST00000545766.1 | 5506 | 15849325 | 15872936 | − | seg_41 | 15870450 | 15871500 | AP1S2 | PIGA |
| ENST00000450644.1 | 5507 | 15849566 | 15870625 | − | seg_41 | 15870450 | 15871500 | AP1S2 | PIGA |
| ENST00000421527.2 | 5508 | 15850187 | 15872936 | − | seg_41 | 15870450 | 15871500 | AP1S2 | PIGA |
| ENST00000340245.5 | 5509 | 15858670 | 15872939 | − | seg_41 | 15870450 | 15871500 | AP1S2 | PIGA |
| ENST00000443824.1 | 5510 | 16606126 | 16730340 | − | seg_45 | 16728700 | 16730200 | SYAP1 | CC = NHS |
| ENST00000359276.4 | 5511 | 16606429 | 16730775 | − | seg_45 | 16728700 | 16730200 | SYAP1 | CC = NHS |
| ENST00000380241.3 | 5512 | 16606429 | 16731059 | − | seg_45 | 16728700 | 16730200 | SYAP1 | CC = NHS |
| ENST00000380207.1 | 5513 | 16656945 | 16731059 | − | seg_45 | 16728700 | 16730200 | SYAP1 | CC = NHS |
| ENST00000380063.2 | 5514 | 16964814 | 17167136 | + | seg_47 | 17016300 | 17017600 | REPS2 | CC = NHS |
| ENST00000380063.2 | 5515 | 16964814 | 17167136 | + | seg_48 | 17092400 | 17093800 | REPS2 | CC = NHS |
| ENST00000357277.3 | 5516 | 16964814 | 17171395 | + | seg_47 | 17016300 | 17017600 | REPS2 | CC = NHS |
| ENST00000357277.3 | 5517 | 16964814 | 17171395 | + | seg_48 | 17092400 | 17093800 | REPS2 | CC = NHS |
| ENST00000303843.7 | 5518 | 16964985 | 17171395 | + | seg_47 | 17016300 | 17017600 | REPS2 | CC = NHS |
| ENST00000303843.7 | 5519 | 16964985 | 17171395 | + | seg_48 | 17092400 | 17093800 | REPS2 | CC = NHS |
| ENST00000481792.1 | 5520 | 16965193 | 17040494 | + | seg_47 | 17016300 | 17017600 | REPS2 | CC = NHS |
| ENST00000380064.4 | 5521 | 16996667 | 17165745 | + | seg_47 | 17016300 | 17017600 | REPS2 | CC = NHS |
| ENST00000380064.4 | 5522 | 16996667 | 17165745 | + | seg_48 | 17092400 | 17093800 | REPS2 | CC = NHS |
| ENST00000469714.1 | 5523 | 17092636 | 17165752 | + | seg_48 | 17092400 | 17093800 | REPS2 | CC = NHS |
| ENST00000380060.3 | 5524 | 17393543 | 17754114 | + | seg_49 | 17395100 | 17396300 | NHS | CC = NHS |
| ENST00000380060.3 | 5525 | 17393543 | 17754114 | + | seg_50 | 17502900 | 17504050 | NHS | CC = NHS |
| ENST00000251900.4 | 5526 | 18257434 | 18372847 | − | seg_53 | 18371700 | 18372700 | SCML2 | CDKL5 |
| ENST00000442006.2 | 5527 | 18259388 | 18372806 | − | seg_53 | 18371700 | 18372700 | SCML2 | CDKL5 |
| ENST00000543067.1 | 5528 | 21392536 | 21660980 | + | seg_57 | 21392500 | 21393700 | CNKSR2 | PHEX |
| ENST00000543067.1 | 5529 | 21392536 | 21660980 | + | seg_58 | 21456000 | 21457750 | CNKSR2 | PHEX |
| ENST00000425654.2 | 5530 | 21392536 | 21672812 | + | seg_57 | 21392500 | 21393700 | CNKSR2 | PHEX |
| ENST00000425654.2 | 5531 | 21392536 | 21672812 | + | seg_58 | 21456000 | 21457750 | CNKSR2 | PHEX |
| ENST00000279451.4 | 5532 | 21392560 | 21660980 | + | seg_57 | 21392500 | 21393700 | CNKSR2 | PHEX |
| ENST00000279451.4 | 5533 | 21392560 | 21660980 | + | seg_58 | 21456000 | 21457750 | CNKSR2 | PHEX |
| ENST00000379510.3 | 5534 | 21392980 | 21672813 | + | seg_57 | 21392500 | 21393700 | CNKSR2 | PHEX |
| ENST00000379510.3 | 5535 | 21392980 | 21672813 | + | seg_58 | 21456000 | 21457750 | CNKSR2 | PHEX |
| ENST00000480138.1 | 5536 | 21450755 | 21488996 | + | seg_58 | 21456000 | 21457750 | CNKSR2 | PHEX |
| ENST00000379374.4 | 5537 | 22050559 | 22269427 | + | seg_59 | 22244450 | 22245550 | ZNF645 | PHEX |
| ENST00000537599.1 | 5538 | 22051016 | 22266300 | + | seg_59 | 22244450 | 22245550 | ZNF645 | PHEX |
| ENST00000535894.1 | 5539 | 22056171 | 22266413 | + | seg_59 | 22244450 | 22245550 | ZNF645 | PHEX |
| ENST00000418858.3 | 5540 | 22115822 | 22266209 | + | seg_59 | 22244450 | 22245550 | ZNF645 | PHEX |
| ENST00000455399.1 | 5541 | 22407432 | 23082236 | − | seg_60 | 22543750 | 22544950 | ZNF645 | PHEX |
| ENST00000253039.4 | 5542 | 24072833 | 24096088 | + | seg_62 | 24071600 | 24072950 | EIF2S3 | SAT = SAT1 |
| ENST00000427551.1 | 5543 | 24164342 | 24167771 | − | seg_63 | 24163650 | 24165150 | ZFX | SAT = SAT1 |
| ENST00000379145.2 | 5544 | 24576204 | 24690794 | − | seg_64 | 24664100 | 24665300 | PCYT1B | SAT = SAT1 |
| ENST00000356768.4 | 5545 | 24579959 | 24665275 | − | seg_64 | 24664100 | 24665300 | PCYT1B | SAT = SAT1 |
| ENST00000379144.2 | 5546 | 24579959 | 24665353 | − | seg_64 | 24664100 | 24665300 | PCYT1B | SAT = SAT1 |
| ENST00000496020.1 | 5547 | 24580518 | 24665155 | − | seg_64 | 24664100 | 24665300 | PCYT1B | SAT = SAT1 |
| ENST00000379044.4 | 5548 | 25021811 | 25034065 | − | seg_65 | 25024050 | 25042800 | ARX | SAT = SAT1 |
| ENST00000378993.1 | 5549 | 28605516 | 29974840 | + | seg_66 | 29296100 | 29297200 | IL1RAPL1 | DAX1 = NR0B1 |
| ENST00000378993.1 | 5550 | 28605516 | 29974840 | + | seg_67 | 29464050 | 29465100 | IL1RAPL1 | DAX1 = NR0B1 |
| ENST00000378993.1 | 5551 | 28605516 | 29974840 | + | seg_68 | 29572800 | 29574700 | MAGEB2 | DAX1 = NR0B1 |
| ENST00000302196.4 | 5552 | 28807461 | 29973937 | + | seg_66 | 29296100 | 29297200 | IL1RAPL1 | DAX1 = NR0B1 |
| ENST00000302196.4 | 5553 | 28807461 | 29973937 | + | seg_67 | 29464050 | 29465100 | IL1RAPL1 | DAX1 = NR0B1 |
| ENST00000302196.4 | 5554 | 28807461 | 29973937 | + | seg_68 | 29572800 | 29574700 | MAGEB2 | DAX1 = NR0B1 |
| ENST00000378943.3 | 5555 | 30671476 | 30748725 | + | seg_72 | 30731150 | 30732450 | GK | DAX1 = NR0B1 |
| ENST00000378946.3 | 5556 | 30671476 | 30748725 | + | seg_72 | 30731150 | 30732450 | GK | DAX1 = NR0B1 |
| ENST00000534212.2 | 5557 | 30671476 | 30748725 | + | seg_72 | 30731150 | 30732450 | GK | DAX1 = NR0B1 |
| ENST00000378945.3 | 5558 | 30671595 | 30747287 | + | seg_72 | 30731150 | 30732450 | GK | DAX1 = NR0B1 |
| ENST00000427190.1 | 5559 | 30671606 | 30747366 | + | seg_72 | 30731150 | 30732450 | GK | DAX1 = NR0B1 |
| ENST00000481024.1 | 5560 | 30671606 | 30747366 | + | seg_72 | 30731150 | 30732450 | GK | DAX1 = NR0B1 |
| ENST00000451432.2 | 5561 | 30671613 | 30747555 | + | seg_72 | 30731150 | 30732450 | GK | DAX1 = NR0B1 |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000497961.1 | 5562 | 30716324 | 30740049 | + | seg_72 | 30731150 | 30732450 | GK | DAX1 = NR0B1 |
| ENST00000464659.1 | 5563 | 30718115 | 30742291 | − | seg_72 | 30731150 | 30732450 | GK | DAX1 = NR0B1 |
| ENST00000288422.2 | 5564 | 30848454 | 30993201 | − | seg_74 | 30989450 | 30990650 | FTHL17 | DAX1 = NR0B1 |
| ENST00000378932.2 | 5565 | 30848454 | 30993201 | − | seg_74 | 30989450 | 30990650 | FTHL17 | DAX1 = NR0B1 |
| ENST00000378684.4 | 5566 | 31132808 | 32430174 | − | seg_75 | 31188900 | 31190050 | DMD | DAX1 = NR0B1 |
| ENST00000378684.4 | 5567 | 31132808 | 32430174 | − | seg_76 | 31789800 | 31791200 | DMD | DAX1 = NR0B1 |
| ENST00000378684.4 | 5568 | 31132808 | 32430174 | − | seg_77 | 32372400 | 32373550 | DMD | DAX1 = NR0B1 |
| ENST00000378682.4 | 5569 | 31132808 | 32430326 | − | seg_75 | 31188900 | 31190050 | DMD | DAX1 = NR0B1 |
| ENST00000378682.4 | 5570 | 31132808 | 32430326 | − | seg_76 | 31789800 | 31791200 | DMD | DAX1 = NR0B1 |
| ENST00000378682.4 | 5571 | 31132808 | 32430326 | − | seg_77 | 32372400 | 32373550 | DMD | DAX1 = NR0B1 |
| ENST00000534884.1 | 5572 | 31132808 | 33038324 | − | seg_75 | 31188900 | 31190050 | DMD | DAX1 = NR0B1 |
| ENST00000534884.1 | 5573 | 31132808 | 33038324 | − | seg_76 | 31789800 | 31791200 | DMD | DAX1 = NR0B1 |
| ENST00000534884.1 | 5574 | 31132808 | 33038324 | − | seg_77 | 32372400 | 32373550 | DMD | DAX1 = NR0B1 |
| ENST00000534884.1 | 5575 | 31132808 | 33038324 | − | seg_78 | 32690150 | 32691150 | DMD | DAX1 = NR0B1 |
| ENST00000378723.3 | 5576 | 31137336 | 31285069 | − | seg_75 | 31188900 | 31190050 | DMD | DAX1 = NR0B1 |
| ENST00000358062.2 | 5577 | 31137338 | 31893490 | − | seg_75 | 31188900 | 31190050 | DMD | DAX1 = NR0B1 |
| ENST00000358062.2 | 5578 | 31137338 | 31893490 | − | seg_76 | 31789800 | 31791200 | DMD | DAX1 = NR0B1 |
| ENST00000343523.2 | 5579 | 31137345 | 32173586 | − | seg_75 | 31188900 | 31190050 | DMD | DAX1 = NR0B1 |
| ENST00000343523.2 | 5580 | 31137345 | 32173586 | − | seg_76 | 31789800 | 31791200 | DMD | DAX1 = NR0B1 |
| ENST00000359836.1 | 5581 | 31137345 | 32173586 | − | seg_75 | 31188900 | 31190050 | DMD | DAX1 = NR0B1 |
| ENST00000359836.1 | 5582 | 31137345 | 32173586 | − | seg_76 | 31789800 | 31791200 | DMD | DAX1 = NR0B1 |
| ENST00000378707.3 | 5583 | 31137345 | 32173586 | − | seg_75 | 31188900 | 31190050 | DMD | DAX1 = NR0B1 |
| ENST00000378707.3 | 5584 | 31137345 | 32173586 | − | seg_76 | 31789800 | 31791200 | DMD | DAX1 = NR0B1 |
| ENST00000541735.1 | 5585 | 31137345 | 32173586 | − | seg_75 | 31188900 | 31190050 | DMD | DAX1 = NR0B1 |
| ENST00000541735.1 | 5586 | 31137345 | 32173586 | − | seg_76 | 31789800 | 31791200 | DMD | DAX1 = NR0B1 |
| ENST00000378677.2 | 5587 | 31137345 | 33146477 | − | seg_75 | 31188900 | 31190050 | DMD | DAX1 = NR0B1 |
| ENST00000378677.2 | 5588 | 31137345 | 33146477 | − | seg_76 | 31789800 | 31791200 | DMD | DAX1 = NR0B1 |
| ENST00000378677.2 | 5589 | 31137345 | 33146477 | − | seg_77 | 32372400 | 32373550 | DMD | DAX1 = NR0B1 |
| ENST00000378677.2 | 5590 | 31137345 | 33146477 | − | seg_78 | 32690150 | 32691150 | DMD | DAX1 = NR0B1 |
| ENST00000535280.1 | 5591 | 31137345 | 33146544 | − | seg_75 | 31188900 | 31190050 | DMD | DAX1 = NR0B1 |
| ENST00000535280.1 | 5592 | 31137345 | 33146544 | − | seg_76 | 31789800 | 31791200 | DMD | DAX1 = NR0B1 |
| ENST00000535280.1 | 5593 | 31137345 | 33146544 | − | seg_77 | 32372400 | 32373550 | DMD | DAX1 = NR0B1 |
| ENST00000535280.1 | 5594 | 31137345 | 33146544 | − | seg_78 | 32690150 | 32691150 | DMD | DAX1 = NR0B1 |
| ENST00000357033.4 | 5595 | 31137345 | 33229636 | − | seg_75 | 31188900 | 31190050 | DMD | DAX1 = NR0B1 |
| ENST00000357033.4 | 5596 | 31137345 | 33229636 | − | seg_76 | 31789800 | 31791200 | DMD | DAX1 = NR0B1 |
| ENST00000357033.4 | 5597 | 31137345 | 33229636 | − | seg_77 | 32372400 | 32373550 | DMD | DAX1 = NR0B1 |
| ENST00000357033.4 | 5598 | 31137345 | 33229636 | − | seg_78 | 32690150 | 32691150 | DMD | DAX1 = NR0B1 |
| ENST00000542849.1 | 5599 | 31137345 | 33229673 | − | seg_75 | 31188900 | 31190050 | DMD | DAX1 = NR0B1 |
| ENST00000542849.1 | 5600 | 31137345 | 33229673 | − | seg_76 | 31789800 | 31791200 | DMD | DAX1 = NR0B1 |
| ENST00000542849.1 | 5601 | 31137345 | 33229673 | − | seg_77 | 32372400 | 32373550 | DMD | DAX1 = NR0B1 |
| ENST00000542849.1 | 5602 | 31137345 | 33229673 | − | seg_78 | 32690150 | 32691150 | DMD | DAX1 = NR0B1 |
| ENST00000378702.4 | 5603 | 31139301 | 31284974 | − | seg_75 | 31188900 | 31190050 | DMD | DAX1 = NR0B1 |
| ENST00000465285.1 | 5604 | 31139514 | 31947809 | − | seg_75 | 31188900 | 31190050 | DMD | DAX1 = NR0B1 |
| ENST00000465285.1 | 5605 | 31139514 | 31947809 | − | seg_76 | 31789800 | 31791200 | DMD | DAX1 = NR0B1 |
| ENST00000474231.1 | 5606 | 31139514 | 32173586 | − | seg_75 | 31188900 | 31190050 | DMD | DAX1 = NR0B1 |
| ENST00000474231.1 | 5607 | 31139514 | 32173586 | − | seg_76 | 31789800 | 31791200 | DMD | DAX1 = NR0B1 |
| ENST00000361471.4 | 5608 | 31139673 | 31285024 | − | seg_75 | 31188900 | 31190050 | DMD | DAX1 = NR0B1 |
| ENST00000378680.2 | 5609 | 31139790 | 31285066 | − | seg_75 | 31188900 | 31190050 | DMD | DAX1 = NR0B1 |
| ENST00000378705.3 | 5610 | 31187703 | 31224717 | − | seg_75 | 31188900 | 31190050 | DMD | DAX1 = NR0B1 |
| ENST00000471779.1 | 5611 | 31747803 | 31854900 | − | seg_76 | 31789800 | 31791200 | DMD | DAX1 = NR0B1 |
| ENST00000488902.1 | 5612 | 31950233 | 33229671 | − | seg_77 | 32372400 | 32373550 | DMD | DAX1 = NR0B1 |
| ENST00000488902.1 | 5613 | 31950233 | 33229671 | − | seg_78 | 32690150 | 32691150 | DMD | DAX1 = NR0B1 |
| ENST00000420596.1 | 5614 | 32382798 | 33229429 | − | seg_78 | 32690150 | 32691150 | DMD | DAX1 = NR0B1 |
| ENST00000448370.1 | 5615 | 32382798 | 33229429 | − | seg_78 | 32690150 | 32691150 | DMD | DAX1 = NR0B1 |
| ENST00000288447.4 | 5616 | 32534713 | 33357558 | − | seg_78 | 32690150 | 32691150 | DMD | DAX1 = NR0B1 |
| ENST00000480751.1 | 5617 | 32591709 | 32834670 | − | seg_78 | 32690150 | 32691150 | DMD | DAX1 = NR0B1 |
| ENST00000447523.1 | 5618 | 32591728 | 32867919 | − | seg_78 | 32690150 | 32691150 | DMD | DAX1 = NR0B1 |
| ENST00000378628.4 | 5619 | 37208528 | 37316548 | + | seg_79 | 37222250 | 37223300 | PRRG1 | XK |
| ENST00000491253.1 | 5620 | 37208562 | 37312900 | + | seg_79 | 37222250 | 37223300 | PRRG1 | XK |
| ENST00000466533.1 | 5621 | 37208583 | 37312664 | + | seg_79 | 37222250 | 37223300 | PRRG1 | XK |
| ENST00000542554.1 | 5622 | 37208583 | 37316545 | + | seg_79 | 37222250 | 37223300 | PRRG1 | XK |
| ENST00000543642.1 | 5623 | 37208583 | 37316545 | + | seg_79 | 37222250 | 37223300 | PRRG1 | XK |
| ENST00000465127.1 | 5624 | 37208583 | 38546928 | + | seg_79 | 37222250 | 37223300 | PRRG1 | XK |
| ENST00000465127.1 | 5625 | 37208583 | 38546928 | + | seg_80 | 37645650 | 37647450 | CYBB | CYBB |
| ENST00000465127.1 | 5626 | 37208583 | 38546928 | + | seg_81 | 37765500 | 37766650 | DYNLT3 | CYBB |
| ENST00000465127.1 | 5627 | 37208583 | 38546928 | + | seg_82 | 38135850 | 38136950 | RPGR | RPGR |
| ENST00000465127.1 | 5628 | 37208583 | 38546928 | + | seg_83 | 38537450 | 38538750 | TSPAN7 | OTC |
| ENST00000484460.1 | 5629 | 37208617 | 37312561 | + | seg_79 | 37222250 | 37223300 | PRRG1 | XK |
| ENST00000449135.2 | 5630 | 37208625 | 37316542 | + | seg_79 | 37222250 | 37223300 | PRRG1 | XK |
| ENST00000463135.1 | 5631 | 37208632 | 37301477 | + | seg_79 | 37222250 | 37223300 | PRRG1 | XK |
| ENST00000378588.4 | 5632 | 37639264 | 37672714 | + | seg_80 | 37645650 | 37647450 | CYBB | CYBB |
| ENST00000545017.1 | 5633 | 37639312 | 37670356 | + | seg_80 | 37645650 | 37647450 | CYBB | CYBB |
| ENST00000536160.1 | 5634 | 37639317 | 37670388 | + | seg_80 | 37645650 | 37647450 | CYBB | CYBB |
| ENST00000449263.1 | 5635 | 37765400 | 37808658 | + | seg_81 | 37765500 | 37766650 | DYNLT3 | CYBB |
| ENST00000309513.3 | 5636 | 38128424 | 38186788 | − | seg_82 | 38135850 | 38136950 | RPGR | RPGR |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000338898.3 | 5637 | 38128424 | 38186788 | − | seg_82 | 38135850 | 38136950 | RPGR | RPGR |
| ENST00000339363.3 | 5638 | 38128424 | 38186788 | − | seg_82 | 38135850 | 38136950 | RPGR | RPGR |
| ENST00000482855.1 | 5639 | 38128602 | 38186675 | − | seg_82 | 38135850 | 38136950 | RPGR | RPGR |
| ENST00000318842.6 | 5640 | 38128606 | 38186817 | − | seg_82 | 38135850 | 38136950 | RPGR | RPGR |
| ENST00000474584.1 | 5641 | 38128773 | 38186759 | − | seg_82 | 38135850 | 38136950 | RPGR | RPGR |
| ENST00000494707.1 | 5642 | 38132688 | 38150718 | − | seg_82 | 38135850 | 38136950 | RPGR | RPGR |
| ENST00000378482.2 | 5643 | 38420623 | 38548167 | + | seg_83 | 38537450 | 38538750 | TSPAN7 | OTC |
| ENST00000422612.2 | 5644 | 38420795 | 38547422 | + | seg_83 | 38537450 | 38538750 | TSPAN7 | OTC |
| ENST00000471410.1 | 5645 | 38420795 | 38547422 | + | seg_83 | 38537450 | 38538750 | TSPAN7 | OTC |
| ENST00000475216.1 | 5646 | 38420797 | 38547525 | + | seg_83 | 38537450 | 38538750 | TSPAN7 | OTC |
| ENST00000545599.1 | 5647 | 38420797 | 38547525 | + | seg_83 | 38537450 | 38538750 | TSPAN7 | OTC |
| ENST00000286824.6 | 5648 | 38420797 | 38547651 | + | seg_83 | 38537450 | 38538750 | TSPAN7 | OTC |
| ENST00000419600.2 | 5649 | 38525350 | 38548169 | + | seg_83 | 38537450 | 38538750 | TSPAN7 | OTC |
| ENST00000447651.1 | 5650 | 39868529 | 39871435 | + | seg_87 | 39871150 | 39873000 | BCOR | CSNB1 = NYX |
| EN6T00000399959.2 | 5651 | 41192651 | 41209462 | + | seg_90 | 41209250 | 41211000 | DDX3X | CSNB1 = NYX |
| ENST00000478993.1 | 5652 | 41192651 | 41223725 | + | seg_90 | 41209250 | 41211000 | DDX3X | CSNB1 = NYX |
| ENST00000421587.2 | 5653 | 41374187 | 41782265 | − | seg_91 | 41579300 | 41581500 | GPR82 | CSNB1 = NYX |
| ENST00000318588.9 | 5654 | 41374187 | 41782287 | − | seg_91 | 41579300 | 41581500 | GPR82 | CSNB1 = NYX |
| ENST00000361962.4 | 5655 | 41374187 | 41782287 | − | seg_91 | 41579300 | 41581500 | GPR82 | CSNB1 = NYX |
| ENST00000378163.1 | 5656 | 41378518 | 41782716 | − | seg_91 | 41579300 | 41581500 | GPR82 | CSNB1 = NYX |
| ENST00000378158.1 | 5657 | 41378906 | 41782592 | − | seg_91 | 41579300 | 41581500 | GPR82 | CSNB1 = NYX |
| ENST00000378166.4 | 5658 | 41379343 | 41782268 | − | seg_91 | 41579300 | 41581500 | GPR82 | CSNB1 = NYX |
| ENST00000442742.2 | 5659 | 41379589 | 41782260 | − | seg_91 | 41579300 | 41581500 | GPR82 | CSNB1 = NYX |
| ENST00000378154.1 | 5660 | 41418750 | 41782716 | − | seg_91 | 41579300 | 41581500 | GPR82 | CSNB1 = NYX |
| ENST00000414772.1 | 5661 | 45707328 | 45710447 | − | seg_94 | 45708550 | 45711000 | KRBOX4 | UBA1 |
| ENST00000456532.1 | 5662 | 45707509 | 45710920 | − | seg_94 | 45708550 | 45711000 | KRBOX4 | UBA1 |
| ENST00000328306.4 | 5663 | 46464753 | 46618490 | − | seg_95 | 46497450 | 46498550 | CHST7 | UBA1 |
| ENST00000489574.1 | 5664 | 46465730 | 46529121 | − | seg_95 | 46497450 | 46498550 | CHST7 | UBA1 |
| ENST00000424392.1 | 5665 | 46771711 | 46887378 | + | seg_97 | 46772150 | 46774250 | CXorf31 | UBA1 |
| ENST00000424392.1 | 5666 | 46771711 | 46887378 | + | seg_98 | 46819250 | 46820950 | PHF16 | UBA1 |
| ENST00000424392.1 | 5667 | 46771711 | 46887378 | + | seg_99 | 46839750 | 46841250 | PHF16 | UBA1 |
| ENST00000397189.1 | 5668 | 46771736 | 46920641 | + | seg_97 | 46772150 | 46774250 | CXorf31 | UBA1 |
| ENST00000397189.1 | 5669 | 46771736 | 46920641 | + | seg_98 | 46819250 | 46820950 | PHF16 | UBA1 |
| ENST00000397189.1 | 5670 | 46771736 | 46920641 | + | seg_99 | 46839750 | 46841250 | PHF16 | UBA1 |
| ENST00000218343.4 | 5671 | 46771868 | 46920640 | + | seg_97 | 46772150 | 46774250 | CXorf31 | UBA1 |
| ENST00000218343.4 | 5672 | 46771868 | 46920640 | + | seg_98 | 46819250 | 46820950 | PHF16 | UBA1 |
| ENST00000218343.4 | 5673 | 46771868 | 46920640 | + | seg_99 | 46839750 | 46841250 | PHF16 | UBA1 |
| ENST00000455411.1 | 5674 | 46772231 | 46884185 | + | seg_97 | 46772150 | 46774250 | CXorf31 | UBAI |
| ENST00000455411.1 | 5675 | 46772231 | 46884185 | + | seg_98 | 46819250 | 46820950 | PHF16 | UBA1 |
| ENST00000455411.1 | 5676 | 46772231 | 46884185 | + | seg_99 | 46839750 | 46841250 | PHF16 | UBA1 |
| ENST00000376020.2 | 5677 | 50334647 | 50557044 | − | seg_100 | 50489150 | 50490250 | SHROOM4 | CLCN5 |
| ENST00000289292.7 | 5678 | 50334647 | 50557302 | − | seg_100 | 50489150 | 50490250 | SHROOM4 | CLCN5 |
| ENST00000396435.3 | 5679 | 53262058 | 53350522 | − | seg_101 | 53349050 | 53352550 | IQSEC2 | MRX1 = IQSEC2 |
| ENST00000375368.5 | 5680 | 53262059 | 53350522 | − | seg_101 | 53349050 | 53352550 | IQSEC2 | MRX1 = IQSEC2 |
| ENST00000432596.1 | 5681 | 53352187 | 53352973 | + | seg_101 | 53349050 | 53352550 | IQSEC2 | MRX1 = IQSEC2 |
| ENST00000342160.3 | 5682 | 53559057 | 53711114 | − | seg_104 | 53659750 | 53660850 | HUWE1 | MRX1 = IQSEC2 |
| ENST00000342160.3 | 5683 | 53559057 | 53711114 | − | seg_105 | 53677550 | 53678650 | HUWE1 | MRX1 = IQSEC2 |
| ENST00000262854.6 | 5684 | 53559105 | 53713673 | − | seg_104 | 53659750 | 53660850 | HUWE1 | MRX1 = IQSEC2 |
| ENST00000262854.6 | 5685 | 53559105 | 53713673 | − | seg_105 | 53677550 | 53678650 | HUWE1 | MRX1 = IQSEC2 |
| ENST00000218328.8 | 5686 | 53611171 | 53713673 | − | seg_104 | 53659750 | 53660850 | HUWE1 | MRX1 = IQSEC2 |
| ENST00000218328.8 | 5687 | 53611171 | 53713673 | − | seg_105 | 53677550 | 53678650 | HUWE1 | MRX1 = IQSEC2 |
| ENST00000432528.2 | 5688 | 53659006 | 53713673 | − | seg_104 | 53659750 | 53660850 | HUWE1 | MRX1 = IQSEC2 |
| ENST00000432528.2 | 5689 | 53659006 | 53713673 | − | seg_105 | 53677550 | 53678650 | HUWE1 | MRX1 = IQSEC2 |
| ENST00000446750.1 | 5690 | 53674384 | 53711114 | − | seg_105 | 53677550 | 53678650 | HUWE1 | MRX1 = IQSEC2 |
| ENST00000476898.1 | 5691 | 56258854 | 56295641 | + | seg_106 | 56267800 | 56269150 | KLF8 | ALAS2 |
| ENST00000374928.3 | 5692 | 56258870 | 56314322 | + | seg_106 | 56267800 | 56269150 | KLF8 | ALAS2 |
| ENST00000462627.1 | 5693 | 56258907 | 56314317 | + | seg_106 | 56267800 | 56269150 | KLF8 | ALAS2 |
| ENST00000468660.1 | 5694 | 56259480 | 56311102 | + | seg_106 | 56267800 | 56269150 | KLF8 | ALAS2 |
| ENST00000358094.5 | 5695 | 56259622 | 56311530 | + | seg_106 | 56267800 | 56269150 | KLF8 | ALAS2 |
| ENST00000253401.6 | 5696 | 62854847 | 62974993 | − | seg_109 | 62906550 | 62907850 | ARHGEF9 | AR |
| ENST00000374878.1 | 5697 | 62854847 | 63005413 | − | seg_109 | 62906550 | 62907850 | ARHGEF9 | AR |
| ENST00000374870.4 | 5698 | 62854856 | 62975031 | − | seg_109 | 62906550 | 62907850 | ARHGEF9 | AR |
| ENST00000437457.2 | 5699 | 62854856 | 63005426 | − | seg_109 | 62906550 | 62907850 | ARHGEF9 | AR |
| ENST00000495564.1 | 5700 | 62857860 | 62974991 | − | seg_109 | 62906550 | 62907850 | ARHGEF9 | AR |
| ENST00000374872.1 | 5701 | 62857862 | 62974988 | − | seg_109 | 62906550 | 62907850 | ARHGEF9 | AR |
| ENST00000374807.5 | 5702 | 64732462 | 64754634 | − | seg_111 | 64754100 | 64755650 | LAS1L | AR |
| ENST00000374811.3 | 5703 | 64732462 | 64754636 | − | seg_111 | 64754100 | 64755650 | LAS1L | AR |
| ENST00000312391.8 | 5704 | 64732463 | 64754636 | − | seg_111 | 64754100 | 64755650 | LAS1L | AR |
| ENST00000374804.5 | 5705 | 64732463 | 64754636 | − | seg_111 | 64754100 | 64755650 | LAS1L | AR |
| ENST00000484069.1 | 5706 | 64732463 | 64754655 | − | seg_111 | 64754100 | 64755650 | LAS1L | AR |
| ENST00000544310.1 | 5707 | 64741799 | 64754636 | − | seg_111 | 64754100 | 64755650 | LAS1L | AR |
| ENST00000204961.4 | 5708 | 68048840 | 68061990 | + | seg_113 | 68049150 | 68050700 | EFNB1 | ED1 = EDA |
| ENST00000252338.4 | 5709 | 68725084 | 68752351 | + | seg_117 | 68725350 | 68726600 | FAM155B | ED1 = EDA |
| ENST00000333026.3 | 5710 | 69397333 | 69425395 | + | seg_118 | 69416400 | 69418200 | DGAT2L6 | ED1 = EDA |
| ENST00000374388.3 | 5711 | 69509879 | 69635312 | + | seg_119 | 69555900 | 69556900 | KIF4A | ED1 = EDA |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000374403.3 | 5712 | 69509940 | 69640682 | + | seg_119 | 69555900 | 69556900 | KIF4A | ED1 = EDA |
| ENST00000194900.4 | 5713 | 69664711 | 69725337 | + | seg_120 | 69663400 | 69665750 | DLG3 | GJB1 |
| ENST00000194900.4 | 5714 | 69664711 | 69725337 | + | seg_121 | 69690000 | 69691650 | DLG3 | GJB1 |
| ENST00000374360.3 | 5715 | 69664819 | 69725337 | + | seg_120 | 69663400 | 69665750 | DLG3 | GJB1 |
| ENST00000374360.3 | 5716 | 69664819 | 69725337 | + | seg_121 | 69690000 | 69691650 | DLG3 | GJB1 |
| ENST00000463252.1 | 5717 | 69664986 | 69723796 | + | seg_120 | 69663400 | 69665750 | DLG3 | GJB1 |
| ENST00000463252.1 | 5718 | 69664986 | 69723796 | + | seg_121 | 69690000 | 69691650 | DLG3 | GJB1 |
| ENST00000374355.3 | 5719 | 69672155 | 69725337 | + | seg_121 | 69690000 | 69691650 | DLG3 | GJB1 |
| ENST00000542398.1 | 5720 | 69674946 | 69725335 | + | seg_121 | 69690000 | 69691650 | DLG3 | GJB1 |
| ENST00000489733.1 | 5721 | 69674953 | 69718408 | + | seg_121 | 69690000 | 69691650 | DLG3 | GJB1 |
| ENST00000494493.1 | 5722 | 69674957 | 69712087 | + | seg_121 | 69690000 | 69691650 | DLG3 | GJB1 |
| ENST00000540800.1 | 5723 | 71130938 | 71363424 | + | seg_122 | 71320750 | 71321750 | RGAG4 | GJB1 |
| ENST00000540800.1 | 5724 | 71130938 | 71363424 | + | seg_123 | 71351100 | 71353000 | RGAG4 | GJB1 |
| ENST00000545866.1 | 5725 | 71346958 | 71351758 | − | seg_123 | 71351100 | 71353000 | RGAG4 | GJB1 |
| ENST00000479991.1 | 5726 | 71346960 | 71351751 | − | seg_123 | 71351100 | 71353000 | RGAG4 | GJB1 |
| ENST00000513469.1 | 5727 | 71352000 | 71354556 | + | seg_123 | 71351100 | 71353000 | RGAG4 | GJB1 |
| ENST00000439980.2 | 5728 | 71401615 | 71522776 | + | seg_124 | 71495000 | 71496100 | RPS4X | GJB1 |
| ENST00000316084.6 | 5729 | 71491892 | 71497150 | − | seg_124 | 71495000 | 71496100 | RPS4X | GJB1 |
| ENST00000486733.1 | 5730 | 71492563 | 71496077 | − | seg_124 | 71495000 | 71496100 | RPS4X | GJB1 |
| ENST00000373626.3 | 5731 | 71494105 | 71497098 | − | seg_124 | 71495000 | 71496100 | RPS4X | GJB1 |
| ENST00000453707.2 | 5732 | 71521488 | 71527000 | − | seg_125 | 71523650 | 71529700 | CITED1 | GJB1 |
| ENST00000431381.1 | 5733 | 71521490 | 71525764 | − | seg_125 | 71523650 | 71529700 | CITED1 | GJB1 |
| ENST00000445983.1 | 5734 | 71521490 | 71525764 | − | seg_125 | 71523650 | 71529700 | CITED1 | GJB1 |
| ENST00000373619.3 | 5735 | 71521497 | 71527037 | − | seg_125 | 71523650 | 71529700 | CITED1 | GJB1 |
| ENST00000246139.5 | 5736 | 71521500 | 71526837 | − | seg_125 | 71523650 | 71529700 | CITED1 | GJB1 |
| ENST00000417400.1 | 5737 | 71521733 | 71525747 | − | seg_125 | 71523650 | 71529700 | CITED1 | GJB1 |
| ENST00000427412.1 | 5738 | 71521818 | 71525415 | − | seg_125 | 71523650 | 71529700 | CITED1 | GJB1 |
| ENST00000450875.1 | 5739 | 71521904 | 71525742 | − | seg_125 | 71523650 | 71529700 | CITED1 | GJB1 |
| ENST00000454225.1 | 5740 | 71522056 | 71526757 | − | seg_125 | 71523650 | 71529700 | CITED1 | GJB1 |
| ENST00000373542.4 | 5741 | 71798664 | 71933888 | − | seg_126 | 71833400 | 71834600 | HDAC8 | GJB1 |
| ENST00000373545.3 | 5742 | 71798664 | 71934167 | − | seg_126 | 71833400 | 71834600 | HDAC8 | GJB1 |
| ENST00000339490.3 | 5743 | 71798665 | 71934029 | − | seg_126 | 71833400 | 71834600 | HDAC8 | GJB1 |
| ENST00000541944.1 | 5744 | 71798665 | 71934029 | − | seg_126 | 71833400 | 71834600 | HDAC8 | GJB1 |
| ENST00000373539.3 | 5745 | 71800477 | 71934106 | − | seg_126 | 71833400 | 71834600 | HDAC8 | GJB1 |
| ENST00000276033.4 | 5746 | 73640638 | 73753752 | + | seg_127 | 73639250 | 73642650 | SLC16A2 | ABCB7 |
| ENST00000544091.1 | 5747 | 78200829 | 78217437 | + | seg_130 | 78211700 | 78214250 | P2RY10 | PGK1 |
| ENST00000461541.1 | 5748 | 78200918 | 78216368 | + | seg_130 | 78211700 | 78214250 | P2RY10 | PGK1 |
| ENST00000475374.1 | 5749 | 78200918 | 78216577 | + | seg_130 | 78211700 | 78214250 | P2RY10 | PGK1 |
| ENST00000171757.2 | 5750 | 78200918 | 78217451 | + | seg_130 | 78211700 | 78214250 | P2RY10 | PGK1 |
| ENST00000358130.2 | 5751 | 80369200 | 80457441 | − | seg_135 | 80385100 | 80386100 | HMGN5 | PGK1 |
| ENST00000436386.1 | 5752 | 80370691 | 80457412 | − | seg_135 | 80385100 | 80386100 | HMGN5 | PGK1 |
| ENST00000451455.1 | 5753 | 80371703 | 80457385 | − | seg_135 | 80385100 | 80386100 | HMGN5 | PGK1 |
| ENST00000395337.2 | 5754 | 91034260 | 91139006 | + | seg_138 | 91034350 | 91035850 | PCDH11X | CHM |
| ENST00000355827.4 | 5755 | 95939662 | 96724837 | + | seg_139 | 96703000 | 96704200 | RPA4 | BTK |
| ENST00000373054.4 | 5756 | 95939662 | 96854316 | + | seg_139 | 96703000 | 96704200 | RPA4 | BTK |
| ENST00000373061.3 | 5757 | 95939662 | 96855597 | + | seg_139 | 96703000 | 96704200 | RPA4 | BTK |
| ENST00000373049.4 | 5758 | 95939711 | 96724834 | + | seg_139 | 96703000 | 96704200 | RPA4 | BTK |
| ENST00000324765.8 | 5759 | 95939711 | 96859996 | + | seg_139 | 96703000 | 96704200 | RPA4 | BTK |
| ENST00000537885.1 | 5760 | 95940016 | 96724764 | + | seg_139 | 96703000 | 96704200 | RPA4 | BTK |
| ENST00000439759.1 | 5761 | 96686257 | 96819492 | − | seg_139 | 96703000 | 96704200 | RPA4 | BTK |
| ENST00000420881.2 | 5762 | 99546642 | 99663595 | − | seg_140 | 99622650 | 99623950 | PCDH19 | BTK |
| ENST00000373034.4 | 5763 | 99546642 | 99665271 | − | seg_140 | 99622650 | 99623950 | PCDH19 | BTK |
| ENST00000255531.7 | 5764 | 99546644 | 99665271 | − | seg_140 | 99622650 | 99623950 | PCDH19 | BTK |
| ENST00000372989.1 | 5765 | 99929488 | 99986498 | − | seg_143 | 99985450 | 99986650 | SYTL4 | BTK |
| ENST00000276141.6 | 5766 | 99929491 | 99986522 | − | seg_143 | 99985450 | 99986650 | SYTL4 | BTK |
| ENST00000454200.2 | 5767 | 99929491 | 99986522 | − | seg_143 | 99985450 | 99986650 | SYTL4 | BTK |
| ENST00000455616.1 | 5768 | 99929491 | 99986522 | − | seg_143 | 99985450 | 99986650 | SYTL4 | BTK |
| ENST00000263033.5 | 5769 | 99930894 | 99987108 | − | seg_143 | 99985450 | 99986650 | SYTL4 | BTK |
| ENST00000372981.1 | 5770 | 99939693 | 99987107 | − | seg_143 | 99985450 | 99986650 | SYTL4 | BTK |
| ENST00000491326.1 | 5771 | 99986402 | 99987110 | − | seg_143 | 99985450 | 99986650 | SYTL4 | BTK |
| ENST00000361298.4 | 5772 | 102631268 | 102633005 | + | seg_144 | 102632100 | 102633150 | NGFRAP1 | GLA |
| ENST00000372645.3 | 5773 | 102631323 | 102633005 | + | seg_144 | 102632100 | 102633150 | NGFRAP1 | GLA |
| ENST00000372635.1 | 5774 | 102631335 | 102632988 | + | seg_144 | 102632100 | 102633150 | NGFRAP1 | GLA |
| ENST00000372634.1 | 5775 | 102631844 | 102632999 | + | seg_144 | 102632100 | 102633150 | NGFRAP1 | GLA |
| ENST00000299872.7 | 5776 | 102632109 | 102632992 | + | seg_144 | 102632100 | 102633150 | NGFRAP1 | GLA |
| ENST00000360458.1 | 5777 | 102930424 | 102942992 | − | seg_145 | 102942900 | 102943900 | MORF4L2 | GLA |
| ENST00000433176.2 | 5778 | 102930428 | 102943086 | − | seg_145 | 102942900 | 102943900 | MORF4L2 | GLA |
| ENST00000434230.1 | 5779 | 102931423 | 102942966 | − | seg_145 | 102942900 | 102943900 | MORF4L2 | GLA |
| ENST00000418819.1 | 5780 | 102931425 | 102942969 | − | seg_145 | 102942900 | 102943900 | MORF4L2 | GLA |
| ENST00000492116.1 | 5781 | 102931622 | 102943050 | − | seg_145 | 102942900 | 102943900 | MORF4L2 | GLA |
| ENST00000488331.1 | 5782 | 102939902 | 102942955 | − | seg_145 | 102942900 | 102943900 | MORF4L2 | GLA |
| ENST00000435306.1 | 5783 | 102942212 | 102946700 | + | seg_145 | 102942900 | 102943900 | MORF4L2 | GLA |
| ENST00000418562.1 | 5784 | 105937024 | 106033435 | + | seg_147 | 105938200 | 105940150 | RNF128 | TBG = SERPINA7 |
| ENST00000418562.1 | 5785 | 105937024 | 106033435 | + | seg_148 | 105968900 | 105969900 | RNF128 | TBG = SERPINA7 |
| ENST00000324342.3 | 5786 | 105937068 | 106040223 | + | seg_147 | 105938200 | 105940150 | RNF128 | TBG = SERPINA7 |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000324342.3 | 5787 | 105937068 | 106040223 | + | seg_148 | 105968900 | 105969900 | RNF128 | TBG = SERPINA7 |
| ENST00000255499.2 | 5788 | 105969894 | 106040223 | + | seg_148 | 105968900 | 105969900 | RNF128 | TBG = SERPINA7 |
| ENST00000357242.5 | 5789 | 106045910 | 106119375 | + | seg_149 | 106044700 | 106046300 | TBC1D8B | TBG = SERPINA7 |
| ENST00000357242.5 | 5790 | 106045910 | 106119375 | + | seg_150 | 106117050 | 106118200 | TBC1D8B | PRPS1 |
| ENST00000310452.2 | 5791 | 106045919 | 106093061 | + | seg_149 | 106044700 | 106046300 | TBC1D8B | TBG = SERPINA7 |
| ENST00000481617.2 | 5792 | 106045935 | 106073313 | + | seg_149 | 106044700 | 106046300 | TBC1D8B | TBG = SERPINA7 |
| ENST00000276175.3 | 5793 | 106046043 | 106117347 | + | seg_149 | 106044700 | 106046300 | TBC1D8B | TBG = SERPINA7 |
| ENST00000276175.3 | 5794 | 106046043 | 106117347 | + | seg_150 | 106117050 | 106118200 | TBC1D8B | PRPS1 |
| ENST00000358740.3 | 5795 | 106057103 | 106236570 | − | seg_150 | 106117050 | 106118200 | TBC1D8B | PRPS1 |
| ENST00000413086.3 | 5796 | 106083914 | 106119375 | + | seg_150 | 106117050 | 106118200 | TBC1D8B | PRPS1 |
| ENST00000394972.3 | 5797 | 106096743 | 106118337 | + | seg_150 | 106117050 | 106118200 | TBC1D8B | PRPS1 |
| ENST00000451923.1 | 5798 | 107068985 | 107084611 | + | seg_153 | 107067250 | 107070800 | MID2 | PRPS1 |
| ENST00000262843.6 | 5799 | 107069109 | 107170423 | + | seg_153 | 107067250 | 107070800 | MID2 | PRPS1 |
| ENST00000443968.2 | 5800 | 107069644 | 107170423 | + | seg_153 | 107067250 | 107070800 | MID2 | PRPS1 |
| ENST00000415430.3 | 5801 | 107288200 | 107322414 | + | seg_154 | 107314500 | 107315550 | PSMD10 | COL4A5 |
| ENST00000217957.5 | 5802 | 107288244 | 107322327 | + | seg_154 | 107314500 | 107315550 | PSMD10 | COL4A5 |
| ENST00000485533.1 | 5803 | 107307969 | 107316494 | + | seg_154 | 107314500 | 107315550 | PSMD10 | COL4A5 |
| ENST00000334504.7 | 5804 | 107398837 | 107681660 | − | seg_155 | 107494550 | 107495800 | COL4A6 | COL4A5 |
| ENST00000334504.7 | 5805 | 107398837 | 107681660 | − | seg_156 | 107670350 | 107671350 | COL4A6 | COL4A5 |
| ENST00000372216.4 | 5806 | 107398837 | 107682702 | − | seg_155 | 107494550 | 107495800 | COL4A6 | COL4A5 |
| ENST00000372216.4 | 5807 | 107398837 | 107682702 | − | seg_156 | 107670350 | 107671350 | COL4A6 | COL4A5 |
| ENST00000394872.2 | 5808 | 107398838 | 107681658 | − | seg_155 | 107494550 | 107495800 | COL4A6 | COL4A5 |
| ENST00000394872.2 | 5809 | 107398838 | 107681658 | − | seg_156 | 107670350 | 107671350 | COL4A6 | COL4A5 |
| ENST00000541389.1 | 5810 | 107399121 | 107681660 | − | seg_155 | 107494550 | 107495800 | COL4A6 | COL4A5 |
| ENST00000541389.1 | 5811 | 107399121 | 107681660 | − | seg_156 | 107670350 | 107671350 | COL4A6 | COL4A5 |
| ENST00000538570.1 | 5812 | 107399275 | 107681556 | − | seg_155 | 107494550 | 107495800 | COL4A6 | COL4A5 |
| ENST00000538570.1 | 5813 | 107399275 | 107681556 | − | seg_156 | 107670350 | 107671350 | COL4A6 | COL4A5 |
| ENST00000545689.1 | 5814 | 107399275 | 107681556 | − | seg_155 | 107494550 | 107495800 | COL4A6 | COL4A5 |
| ENST00000545689.1 | 5815 | 107399275 | 107681556 | − | seg_156 | 107670350 | 107671350 | COL4A6 | COL4A5 |
| ENST00000468338.1 | 5816 | 107457022 | 107682702 | − | seg_155 | 107494550 | 107495800 | COL4A6 | COL4A5 |
| ENST00000468338.1 | 5817 | 107457022 | 107682702 | − | seg_156 | 107670350 | 107671350 | COL4A6 | COL4A5 |
| ENST00000461897.1 | 5818 | 107510872 | 107681660 | − | seg_156 | 107670350 | 107671350 | COL4A6 | COL4A5 |
| ENST00000477085.1 | 5819 | 107510872 | 107682727 | − | seg_156 | 107670350 | 107671350 | COL4A6 | COL4A5 |
| ENST00000372072.3 | 5820 | 109245863 | 109421012 | + | seg_158 | 109388700 | 109390200 | TMEM164 | COL4A5 |
| ENST00000372073.1 | 5821 | 109246323 | 109421016 | + | seg_158 | 109388700 | 109390200 | TMEM164 | COL4A5 |
| ENST00000372068.2 | 5822 | 109246342 | 109421012 | + | seg_158 | 109388700 | 109390200 | TMEM164 | COL4A5 |
| ENST00000501872.2 | 5823 | 109246343 | 109420900 | + | seg_158 | 109388700 | 109390200 | TMEM164 | COL4A5 |
| ENST00000288381.4 | 5824 | 109246343 | 109421016 | + | seg_158 | 109388700 | 109390200 | TMEM164 | COL4A5 |
| ENST00000461715.1 | 5825 | 109308329 | 109414739 | + | seg_158 | 109388700 | 109390200 | TMEM164 | COL4A5 |
| ENST00000464177.1 | 5826 | 109388083 | 109425962 | + | seg_158 | 109388700 | 109390200 | TMEM164 | COL4A5 |
| ENST00000372057.1 | 5827 | 109439638 | 109683461 | − | seg_159 | 109606250 | 109607300 | GNG5P2 | COL4A5 |
| ENST00000372057.1 | 5828 | 109439638 | 109683461 | − | seg_160 | 109634900 | 109636050 | GNG5P2 | COL4A5 |
| ENST00000520821.1 | 5829 | 109602044 | 109694109 | + | seg_159 | 109606250 | 109607300 | GNG5P2 | COL4A5 |
| ENST00000520821.1 | 5830 | 109602044 | 109694109 | + | seg_160 | 109634900 | 109636050 | GNG5P2 | COL4A5 |
| ENST00000520821.1 | 5831 | 109602044 | 109694109 | + | seg_161 | 109693150 | 109694700 | RGAG1 | COL4A5 |
| ENST00000465301.2 | 5832 | 109662285 | 109699562 | + | seg_161 | 109693150 | 109694700 | RGAG1 | COL4A5 |
| ENST00000540483.1 | 5833 | 109693793 | 109698741 | + | seg_161 | 109693150 | 109694700 | RGAG1 | COL4A5 |
| ENST00000540313.1 | 5834 | 109693793 | 109699554 | + | seg_161 | 109693150 | 109694700 | RGAG1 | COL4A5 |
| ENST00000372045.1 | 5835 | 109917084 | 110038993 | − | seg_162 | 109938700 | 109940350 | CHRDL1 | COL4A5 |
| ENST00000218054.4 | 5836 | 109917092 | 110039076 | − | seg_162 | 109938700 | 109940350 | CHRDL1 | COL4A5 |
| ENST00000434224.1 | 5837 | 109917092 | 110039286 | − | seg_162 | 109938700 | 109940350 | CHRDL1 | COL4A5 |
| ENST00000394797.4 | 5838 | 109918473 | 110038993 | − | seg_162 | 109938700 | 109940350 | CHRDL1 | COL4A5 |
| ENST00000372042.1 | 5839 | 109919004 | 110039039 | − | seg_162 | 109938700 | 109940350 | CHRDL1 | COL4A5 |
| ENST00000482160.1 | 5840 | 109919169 | 110039047 | − | seg_162 | 109938700 | 109940350 | CHRDL1 | COL4A5 |
| ENST00000444321.2 | 5841 | 109919285 | 110039047 | − | seg_162 | 109938700 | 109940350 | CHRDL1 | COL4A5 |
| ENST00000487141.1 | 5842 | 110909043 | 110956525 | + | seg_164 | 110955050 | 110956250 | ALG13 | COL4A5 |
| ENST00000251943.4 | 5843 | 110924346 | 111003873 | + | seg_164 | 110955050 | 110956250 | ALG13 | COL4A5 |
| ENST00000394780.3 | 5844 | 110924435 | 111003872 | + | seg_164 | 110955050 | 110956250 | ALG13 | COL4A5 |
| ENST00000495283.1 | 5845 | 110924460 | 110967105 | + | seg_164 | 110955050 | 110956250 | ALG13 | COL4A5 |
| ENST00000262839.2 | 5846 | 111017543 | 111326004 | − | seg_165 | 111165850 | 111167200 | TRPC5 | COL4A5 |
| ENST00000371968.3 | 5847 | 111873876 | 111923282 | − | seg_167 | 111921950 | 111923200 | LHFPL1 | COL4A5 |
| ENST00000536453.1 | 5848 | 111873879 | 111923375 | − | seg_167 | 111921950 | 111923200 | LHFPL1 | COL4A5 |
| ENST00000478229.1 | 5849 | 111874502 | 111923282 | − | seg_167 | 111921950 | 111923200 | LHFPL1 | COL4A5 |
| ENST00000371822.5 | 5850 | 117480036 | 117583921 | + | seg_170 | 117505350 | 117506550 | WDR44 | COL4A5 |
| ENST00000254029.3 | 5851 | 117480072 | 117583924 | + | seg_170 | 117505350 | 117506550 | WDR44 | COL4A5 |
| ENST00000371825.3 | 5852 | 117480106 | 117583900 | + | seg_170 | 117505350 | 117506550 | WDR44 | COL4A5 |
| ENST00000493448.1 | 5853 | 117480162 | 117527178 | + | seg_170 | 117505350 | 117506550 | WDR44 | COL4A5 |
| ENST00000276204.6 | 5854 | 117629861 | 117820126 | + | seg_171 | 117661700 | 117662750 | DOCK11 | COL4A5 |
| ENST00000276202.7 | 5855 | 117629872 | 117820110 | + | seg_171 | 117661700 | 117662750 | DOCK11 | COL4A5 |
| ENST00000310164.2 | 5856 | 117957753 | 117960931 | + | seg_172 | 117957150 | 117960300 | ZCCHC12 | COL4A5 |
| ENST00000412422.1 | 5857 | 117973519 | 117991849 | + | seg_173 | 117985600 | 117986600 | ZCCHC12 | COL4A5 |
| ENST00000481285.1 | 5858 | 118108581 | 118151946 | + | seg_174 | 118109100 | 118110500 | LONRF3 | COL4A5 |
| ENST00000304778.7 | 5859 | 118108581 | 118152318 | + | seg_174 | 118109100 | 118110500 | LONRF3 | COL4A5 |
| ENST00000365713.2 | 5860 | 118108581 | 118156888 | + | seg_174 | 118109100 | 118110500 | LONRF3 | COL4A5 |
| ENST00000371628.3 | 5861 | 118108713 | 118151892 | + | seg_174 | 118109100 | 118110500 | LONRF3 | COL4A5 |

TABLE XVIII-continued

Table XVIII lists the 503 paRNAs associated with strong EZH2 sites in GM12878 cells. Coordinates in reference to hg19 assembly.
paRNAs associated with EZH2 STRONG sites in GM12878 cells

| Transcript ID | SIN | Start | Stop | Strand | Ezh2 ID | Ezh2 Start | Ezh2 End | Closest gene | Disease gene |
|---|---|---|---|---|---|---|---|---|---|
| ENST00000439603.1 | 5862 | 118109325 | 118151950 | + | seg_174 | 118109100 | 118110500 | LONRF3 | COL4A5 |
| ENST00000472173.1 | 5863 | 118110295 | 118151946 | + | seg_174 | 118109100 | 118110500 | LONRF3 | COL4A5 |
| ENST00000422289.2 | 5864 | 118110295 | 118151947 | + | seg_174 | 118109100 | 118110500 | LONRF3 | COL4A5 |
| ENST00000309720.5 | 5865 | 119392505 | 119445288 | − | seg_179 | 119443250 | 119445250 | TMEM255A | OCRL |
| ENST00000371369.4 | 5866 | 119392505 | 119445391 | − | seg_179 | 119443250 | 119445250 | TMEM255A | OCRL |
| ENST00000440464.1 | 5867 | 119392506 | 119445391 | − | seg_179 | 119443250 | 119445250 | TMEM255A | OCRL |
| ENST00000519908.1 | 5868 | 119402218 | 119445411 | − | seg_179 | 119443250 | 119445250 | TMEM255A | OCRL |
| ENST00000480821.1 | 5869 | 119443748 | 119445257 | − | seg_179 | 119443250 | 119445250 | TMEM255A | OCRL |
| ENST00000422498.1 | 5870 | 124337654 | 124338187 | − | seg_183 | 124337400 | 124339100 | TENM1 | OCRL |
| ENST00000488135.1 | 5871 | 129115083 | 129147127 | + | seg_186 | 129114500 | 129116250 | BCORL1 | OCRL |
| ENST00000066465.7 | 5872 | 129336682 | 129402873 | − | seg_187 | 129398550 | 129399700 | ZNF280C | OCRL |
| ENST00000370978.4 | 5873 | 129336685 | 129402873 | − | seg_187 | 129398550 | 129399700 | ZNF280C | OCRL |
| ENST00000447817.1 | 5874 | 129349167 | 129402857 | − | seg_187 | 129398550 | 129399700 | ZNF280C | OCRL |
| ENST00000370837.1 | 5875 | 131760038 | 132091358 | − | seg_189 | 131866700 | 131867750 | HS6ST2 | NYS1 = FRMD7 |
| ENST00000461959.1 | 5876 | 131760044 | 132091354 | − | seg_189 | 131866700 | 131867750 | HS6ST2 | NYS1 = FRMD7 |
| ENST00000370836.2 | 5877 | 131760044 | 132095423 | − | seg_189 | 131866700 | 131867750 | HS6ST2 | NYS1 = FRMD7 |
| ENST00000521489.1 | 5878 | 131761998 | 132095423 | − | seg_189 | 131866700 | 131867750 | HS6ST2 | NYS1 = FRMD7 |
| ENST00000370833.2 | 5879 | 131762251 | 132091344 | − | seg_189 | 131866700 | 131867750 | HS6ST2 | NYS1 = FRMD7 |
| ENST00000319809.6 | 5880 | 131762877 | 132091305 | − | seg_189 | 131866700 | 131867750 | HS6ST2 | NYS1 = FRMD7 |
| ENST00000370828.3 | 5881 | 132434131 | 132549518 | − | seg_190 | 132547800 | 132548950 | GPC4 | HPRT1 = HPRT |
| ENST00000536418.1 | 5882 | 132435064 | 132549205 | − | seg_190 | 132547800 | 132548950 | GPC4 | HPRT1 = HPRT |
| ENST00000535467.1 | 5883 | 132436668 | 132548587 | − | seg_190 | 132547800 | 132548950 | GPC4 | HPRT1 = HPRT |
| ENST00000298556.7 | 5884 | 133594183 | 133634698 | + | seg_192 | 133603350 | 133604800 | HPRT1 | HPRT1 = HPRT |
| ENST00000370796.4 | 5885 | 133594195 | 133634107 | + | seg_192 | 133603350 | 133604800 | HPRT1 | HPRT1 = HPRT |
| ENST00000462974.1 | 5886 | 133594381 | 133632671 | + | seg_192 | 133603350 | 133604800 | HPRT1 | HPRT1 = HPRT |
| ENST00000434384.1 | 5887 | 133684003 | 133693953 | + | seg_194 | 133684650 | 133685700 | PLAC1 | HPRT1 = HPRT |
| ENST00000339249.4 | 5888 | 134478721 | 134497077 | + | seg_195 | 134491550 | 134493250 | ZNF449 | HPRT1 = HPRT |
| ENST00000394155.2 | 5889 | 135229559 | 135293518 | + | seg_197 | 135231600 | 135232650 | FHL1 | HPRT1 = HPRT |
| ENST00000370690.3 | 5890 | 135229624 | 135293518 | + | seg_197 | 135231600 | 135232650 | FHL1 | HPRT1 = HPRT |
| ENST00000536581.1 | 5891 | 135229692 | 135292637 | + | seg_197 | 135231600 | 135232650 | FHL1 | HPRT1 = HPRT |
| ENST00000420362.1 | 5892 | 135229825 | 135290725 | + | seg_197 | 135231600 | 135232650 | FHL1 | HPRT1 = HPRT |
| ENST00000458357.1 | 5893 | 135230270 | 135290084 | + | seg_197 | 135231600 | 135232650 | FHL1 | HPRT1 = HPRT |
| ENST00000535737.1 | 5894 | 135230737 | 135293518 | + | seg_197 | 135231600 | 135232650 | FHL1 | HPRT1 = HPRT |
| ENST00000287538.5 | 5895 | 136648301 | 136653744 | + | seg_201 | 136650000 | 136652650 | ZIC3 | F9 |
| ENST00000370606.3 | 5896 | 136648677 | 136659850 | + | seg_201 | 136650000 | 136652650 | ZIC3 | F9 |
| ENST00000478471.1 | 5897 | 136650964 | 136652154 | + | seg_201 | 136650000 | 136652650 | ZIC3 | F9 |
| ENST00000370603.3 | 5898 | 137715011 | 138286269 | − | seg_202 | 138275750 | 138278250 | FGF13 | F9 |
| ENST00000370603.3 | 5899 | 137715011 | 138286269 | − | seg_203 | 138285450 | 138287700 | FGF13 | F9 |
| ENST00000541469.1 | 5900 | 137715011 | 138286269 | − | seg_202 | 138275750 | 138278250 | FGF13 | F9 |
| ENST00000541469.1 | 5901 | 137715011 | 138286269 | − | seg_203 | 138285450 | 138287700 | FGF13 | F9 |
| ENST00000436198.1 | 5902 | 137715116 | 138287168 | − | seg_202 | 138275750 | 138278250 | FGF13 | F9 |
| ENST00000436198.1 | 5903 | 137715116 | 138287168 | − | seg_203 | 138285450 | 138287700 | FGF13 | F9 |
| ENST00000448673.1 | 5904 | 137791014 | 138304939 | − | seg_202 | 138275750 | 138278250 | FGF13 | F9 |
| ENST00000448673.1 | 5905 | 137791014 | 138304939 | − | seg_203 | 138285450 | 138287700 | FGF13 | F9 |
| ENST00000421460.1 | 5906 | 137939674 | 138285687 | − | seg_202 | 138275750 | 138278250 | FGF13 | F9 |
| ENST00000421460.1 | 5907 | 137939674 | 138285687 | − | seg_203 | 138285450 | 138287700 | FGF13 | F9 |
| ENST00000370536.2 | 5908 | 139585152 | 139587225 | − | seg_205 | 139583350 | 139585350 | SOX3 | F9 |
| ENST00000498732.1 | 5909 | 139791945 | 139854839 | + | seg_206 | 139847900 | 139849150 | CDR1 | F9 |
| ENST00000456981.1 | 5910 | 147579633 | 147582135 | − | seg_207 | 147582000 | 147584900 | AFF2 | FMR1 |
| ENST00000370457.5 | 5911 | 147582139 | 148082193 | + | seg_207 | 147582000 | 147584900 | AFF2 | FMR1 |
| ENST00000370460.2 | 5912 | 147582139 | 148082193 | + | seg_207 | 147582000 | 147584900 | AFF2 | FMR1 |
| ENST00000342251.3 | 5913 | 147582228 | 148075954 | + | seg_207 | 147582000 | 147584900 | AFF2 | FMR1 |
| ENST00000370458.1 | 5914 | 147582529 | 147985907 | + | seg_207 | 147582000 | 147584900 | AFF2 | FMR1 |
| ENST00000468306.1 | 5915 | 149529689 | 149638367 | + | seg_210 | 149529400 | 149535200 | MAMLD1 | MTM1 |
| ENST00000445612.2 | 5916 | 149529836 | 149680503 | + | seg_210 | 149529400 | 149535200 | MAMLD1 | MTM1 |
| ENST00000370401.2 | 5917 | 149531551 | 149682448 | + | seg_210 | 149529400 | 149535200 | MAMLD1 | MTM1 |
| ENST00000432680.2 | 5918 | 149531686 | 149681395 | + | seg_210 | 149529400 | 149535200 | MAMLD1 | MTM1 |
| ENST00000454196.1 | 5919 | 150343664 | 150346308 | − | seg_212 | 150345300 | 150346350 | GPR50 | MTM1 |
| ENST00000535473.1 | 5920 | 150345056 | 150348932 | + | seg_212 | 150345300 | 150346350 | GPR50 | MTM1 |
| ENST00000218316.3 | 5921 | 150345125 | 150349937 | + | seg_212 | 150345300 | 150346350 | GPR50 | MTMI |
| ENST00000477033.1 | 5922 | 152907946 | 152913467 | + | seg_213 | 152910650 | 152911850 | DUSP9 | ABCD1 |
| ENST00000370167.4 | 5923 | 152907988 | 152916781 | + | seg_213 | 152910650 | 152911850 | DUSP9 | ABCD1 |
| ENST00000433144.1 | 5924 | 152908932 | 152916777 | + | seg_213 | 152910650 | 152911850 | DUSP9 | ABCD1 |
| ENST00000164640.4 | 5925 | 153067621 | 153095945 | − | seg_214 | 153094250 | 153095900 | PDZD4 | L1CAM |
| ENST00000393758.2 | 5926 | 153067623 | 153095351 | − | seg_214 | 153094250 | 153095900 | PDZD4 | L1CAM |
| ENST00000544474.1 | 5927 | 153068742 | 153095813 | − | seg_214 | 153094250 | 153095900 | PDZD4 | L1CAM |
| ENST00000475140.1 | 5928 | 153070548 | 153095311 | − | seg_214 | 153094250 | 153095900 | PDZD4 | L1CAM |
| ENST00000483693.1 | 5929 | 153071000 | 153095598 | − | seg_214 | 153094250 | 153095900 | PDZD4 | L1CAM |
| ENST00000480418.1 | 5930 | 153071037 | 153096020 | − | seg_214 | 153094250 | 153095900 | PDZD4 | L1CAM |
| ENST00000468491.1 | 5931 | 153072782 | 153095125 | − | seg_214 | 153094250 | 153095900 | PDZD4 | L1CAM |
| ENST00000480650.1 | 5932 | 153073438 | 153095792 | − | seg_214 | 153094250 | 153095900 | PDZD4 | L1CAM |

REFERENCES

Bailey, J. A., Carrel, L., Chakravarti, A., and Eichler, E. E. 2000. Molecular evidence for a relationship between LINE-1 elements and X chromosome inactivation: the Lyon repeat hypothesis. *Proc Natl Acad Sci USA* 97: 6634-6639.

Bailey, T. L., Williams, N., Misleh, C., and Li, W. W. 2006. MEME: discovering and analyzing DNA and protein sequence motifs. *Nucleic Acids Res* 34: W369-373.

Barski, A., Cuddapah, S., Cui, K., Roh, T. Y., Schones, D. E., Wang, Z., Wei, G., Chepelev, I., and Zhao, K. 2007. High-resolution profiling of histone methylations in the human genome. *Cell* 129: 823-837.

Berletch, J. B., Yang, F., and Disteche, C. M. 2010. Escape from X inactivation in mice and humans. *Genome Biol* 11: 213.

Bernstein, B. E., Mikkelsen, T. S., Xie, X., Kamal, M., Huebert, D. J., Cuff, J., Fry, B., Meissner, A., Wernig, M., Plath, K. et al. 2006. A bivalent chromatin structure marks key developmental genes in embryonic stem cells. *Cell* 125: 315-326.

Boyer, L. A., Plath, K., Zeitlinger, J., Brambrink, T., Medeiros, L. A., Lee, T. I., Levine, S. S., Wernig, M., Tajonar, A., Ray, M. K. et al. 2006. Polycomb complexes repress developmental regulators in murine embryonic stem cells. *Nature* 441: 349-353.

Brockdorff, N., Ashworth, A., Kay, G. F., McCabe, V. M., Norris, D. P., Cooper, P. J., Swift, S., and Rastan, S. 1992. The product of the mouse Xist gene is a 15 kb inactive X-specific transcript containing no conserved ORF and located in the nucleus. *Cell* 71: 515-526.

Brown, C. J., Hendrich, B. D., Rupert, J. L., Lafreniere, R. G., Xing, Y., Lawrence, J., and Willard, H. F. 1992. The human XIST gene: analysis of a 17 kb inactive X-specific RNA that contains conserved repeats and is highly localized within the nucleus. *Cell* 71: 527-542.

Cantrell, M. A., Carstens, B. C., and Wichman, H. A. 2009. X chromosome inactivation and Xist evolution in a rodent lacking LINE-1 activity. *PLoS One* 4: e6252.

Carrel, L. and Willard, H. F. 2005. X-inactivation profile reveals extensive variability in X-linked gene expression in females. *Nature* 434: 400-404.

Chow, J. C., Ciaudo, C., Fazzari, M. J., Mise, N., Servant, N., Glass, J. L., Attreed, M., Avner, P., Wutz, A., Barillot, E. et al. 2010. LINE-1 activity in facultative heterochromatin formation during X chromosome inactivation. *Cell* 141: 956-969.

Chow, J. C., Yen, Z., Ziesche, S. M., and Brown, C. J. 2005. Silencing of the mammalian X chromosome. *Annu Rev Genomics Hum Genet* 6: 69-92.

Chureau, C., Chantalat, S., Romito, A., Galvani, A., Duret, L., Avner, P., and Rougeulle, C. 2011. Ftx is a non-coding RNA which affects Xist expression and chromatin structure within the X-inactivation center region. *Hum Mol Genet* 20: 705-718.

Clemson, C. M., McNeil, J. A., Willard, H. F., and Lawrence, J. B. 1996. XIST RNA paints the inactive X chromosome at interphase: evidence for a novel RNA involved in nuclear/chromosome structure. *J Cell Biol* 132: 259-275.

Gartler, S. M. and Riggs, A. D. 1983. Mammalian X-chromosome inactivation. *Annu Rev Genet* 17: 155-190.

Greenfield, A., Carrel, L., Pennisi, D., Philippe, C., Quaderi, N., Siggers, P., Steiner, K., Tam, P. P., Monaco, A. P.,
Willard, H. F. et al. 1998. The UTX gene escapes X inactivation in mice and humans. *Hum Mol Genet* 7: 737-742.

Hasegawa, Y., Brockdorff, N., Kawano, S., Tsutui, K., and Nakagawa, S. 2010. The matrix protein hnRNP U is required for chromosomal localization of Xist RNA. *Dev Cell* 19: 469-476.

Helbig, R. and Fackelmayer, F. O. 2003. Scaffold attachment factor A (SAF-A) is concentrated in inactive X chromosome territories through its RGG domain. *Chromosoma* 112: 173-182.

Jeon, Y. and Lee, J. T. 2011. YY1 tethers Xist RNA to the inactive X nucleation center. *Cell* 146: 119-133.

Johnston, C. M., Newall, A. E., Brockdorff, N., and Nesterova, T. B. 2002. Enox, a novel gene that maps 10 kb upstream of Xist and partially escapes X inactivation. *Genomics* 80: 236-244.

Keane, T. M., Goodstadt, L., Danecek, P., White, M. A., Wong, K., Yalcin, B., Heger, A., Again, A., Slater, G., Goodson, M. et al. 2011. Mouse genomic variation and its effect on phenotypes and gene regulation. *Nature* 477: 289-294.

Ku, M., Koche, R. P., Rheinbay, E., Mendenhall, E. M., Endoh, M., Mikkelsen, T. S., Presser, A., Nusbaum, C., Xie, X., Chi, A. S. et al. 2008. Genomewide analysis of PRC1 and PRC2 occupancy identifies two classes of bivalent domains. *PLoS Genet* 4: e1000242.

Lee, J. T. 2011. Gracefully ageing at 50, X-chromosome inactivation becomes a paradigm for RNA and chromatin control. *Nat Rev Mol Cell Biol* 12: 815-826.

Lee, J. T., Davidow, L. S., and Warshawsky, D. 1999. Tsix, a gene antisense to Xist at the X-inactivation centre. *Nat Genet* 21: 400-404.

Lee, T. I., Johnstone, S. E., and Young, R. A. 2006. Chromatin immunoprecipitation and microarray-based analysis of protein location. *Nat Protoc* 1: 729-748.

Lyon, M. F. 1999. Imprinting and X-chromosome inactivation. *Results Probl Cell Differ* 25: 73-90.

Lyon, M. F. 2000. LINE-1 elements and X chromosome inactivation: a function for "junk" DNA? *Proc Natl Acad Sci USA* 97: 6248-6249.

Marks, H., Chow, J. C., Denissov, S., Francoijs, K. J., Brockdorff, N., Heard, E., and Stunnenberg, H. G. 2009. High-resolution analysis of epigenetic changes associated with X inactivation. *Genome Res* 19: 1361-1373.

Mikkelsen, T. S., Ku, M., Jaffe, D. B., Issac, B., Lieberman, E., Giannoukos, G., Alvarez, P., Brockman, W., Kim, T. K., Koche, R. P. et al. 2007. Genome-wide maps of chromatin state in pluripotent and lineage-committed cells. *Nature* 448: 553-560.

Namekawa, S. H., Payer, B., Huynh, K. D., Jaenisch, R., and Lee, J. T. 2010. Two-step imprinted X inactivation: repeat versus genic silencing in the mouse. *Mol Cell Biol* 30: 3187-3205.

Ogawa, Y., Sun, B. K., and Lee, J. T. 2008. Intersection of the RNA interference and X-inactivation pathways. *Science* 320: 1336-1341.

Payer, B. and Lee, J. T. 2008. X chromosome dosage compensation: how mammals keep the balance. *Annu Rev Genet* 42: 733-772.

Plath, K., Fang, J., Mlynarczyk-Evans, S. K., Cao, R., Worringer, K. A., Wang, H., de la Cruz, C. C., Otte, A. P., Panning, B., and Zhang, Y. 2003. Role of histone H3 lysine 27 methylation in X inactivation. *Science* 300: 131-135.

Pullirsch, D., Hartel, R., Kishimoto, H., Leeb, M., Steiner, G., and Wutz, A. 2010. The Trithorax group protein Ash2l and Saf-A are recruited to the inactive X chromosome at the onset of stable X inactivation. *Development* 137: 935-943.

Reinius, B., Shi, C., Hengshuo, L., Sandhu, K. S., Radomska, K. J., Rosen, G. D., Lu, L., Kullander, K., Williams, R. W., and Jazin, E. 2010. Female-biased expression of long non-coding RNAs in domains that escape X-inactivation in mouse. *BMC Genomics* 11: 614.

Silva, J., Mak, W., Zvetkova, I., Appanah, R., Nesterova, T. B., Webster, Z., Peters, A. H., Jenuwein, T., Otte, A. P., and Brockdorff, N. 2003. Establishment of histone h3 methylation on the inactive X chromosome requires transient recruitment of Eed-Enx1 polycomb group complexes. *Dev Cell* 4: 481-495.

Simon, J. A. and Kingston, R. E. 2009. Mechanisms of polycomb gene silencing: knowns and unknowns. *Nat Rev Mol Cell Biol* 10: 697-708.

Splinter, E., de Wit, E., Nora, E. P., Klous, P., van de Werken, H. J., Zhu, Y., Kaaij, L. J., van Ijcken, W., Gribnau, J., Heard, E. et al. 2011. The inactive X chromosome adopts a unique three-dimensional conformation that is dependent on Xist RNA. *Genes Dev* 25: 1371-1383.

Wang, Z., Willard, H. F., Mukherjee, S., and Furey, T. S. 2006. Evidence of influence of genomic DNA sequence on human X chromosome inactivation. *PLoS Comput Biol* 2: e113.

Wutz, A. and Gribnau, J. 2007. X inactivation Xplained. *Curr Opin Genet Dev* 17: 387-393.

Yang, F., Babak, T., Shendure, J., and Disteche, C. M. 2010. Global survey of escape from X inactivation by RNA-sequencing in mouse. *Genome Res* 20: 614-622.

Zhao, J., Sun, B. K., Erwin, J. A., Song, J. J., and Lee, J. T. 2008. Polycomb proteins targeted by a short repeat RNA to the mouse X chromosome. *Science* 322: 750-756.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

For example, other embodiments can include the following:

2. The method of claim 1, wherein the inactive X-linked allele is associated with an X-linked disorder, and the oligonucleotide is administered in a therapeutically effective amount.

3. The method of claim 1, wherein the cell is in a living subject.

4. The method of claim 1, wherein the inhibitory oligonucleotide is identical or complementary to at least 8 consecutive nucleotides of a nucleotide sequence of a PRC2 binding site in a region of a gene encoding the allele on the X Chromosome that is marked concurrently by H3K4me3 and H3K27me3 and coincides with a CpG island.

5. The method of claim 1, wherein the oligonucleotide does not comprise three or more consecutive guanosine nucleotides.

6. The method of claim 1, wherein the oligonucleotide is 8 to 30 nucleotides in length.

7. The method of claim 1, wherein at least one nucleotide of the oligonucleotide is a nucleotide analogue.

8. The method of claim 1, wherein at least one nucleotide of the oligonucleotide comprises a 2' O-methyl.

9. The method of claim 1, wherein the oligonucleotide comprises at least one ribonucleotide, at least one deoxyribonucleotide, or at least one bridged nucleotide.

10. The method of claim 9, wherein the bridged nucleotide is a LNA nucleotide, a cEt nucleotide or a ENA modified nucleotide.

11. The method of claim 1, wherein each nucleotide of the oligonucleotide is a LNA nucleotide.

12. The method of claim 1, wherein one or more of the nucleotides of the oligonucleotide comprise 2'-fluoro-deoxyribonucleotides, 2'-O-methyl nucleotides, ENA nucleotide analogues, or LNA nucleotides.

13. The method of claim 1, wherein the nucleotides of the oligonucleotide comprise phosphorothioate internucleotide linkages between at least two nucleotides.

14. The method of claim 1, wherein the nucleotides of the oligonucleotide comprise phosphorothioate internucleotide linkages between at least two nucleotides.

15. The method of claim 1, wherein the oligonucleotide is a gapmer or a mixmer.

16. A method of activating an inactive X-linked allele of Mecp2 in a cell, the method comprising administering to the cell an inhibitory oligonucleotide complementary to 10 to 50 nucleotides of a PRC2 binding site in a region of a gene

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09567581B2). An electronic copy of the "Sequence Listing" will also be available from the USPTO upon request and payment of the fee set forth in 37 CFR 1.19(b)(3).

What is claimed is:

1. A method of activating an inactive X-linked allele in a cell, the method comprising administering to the cell
an inhibitory oligonucleotide targeting a PRC2 binding site in a region of a gene encoding the allele on the X Chromosome that is marked concurrently by H3K4me3 and H3K27me3 and coincides with a CpG island.

encoding Mecp2 on the X Chromosome that is marked concurrently by H3K4me3 and H3K27me3 and coincides with a CpG island.

17. The method of claim 16, further comprising administering to the cell an inhibitory oligonucleotide targeting a polycomb-associated RNA (pa-RNA) associated with Mecp2.

18. The method of claim 16, wherein the cell is in a living subject.

19. The method of claim 16, wherein the inactive X-linked allele is associated with an X-linked disorder, and the oligonucleotide is administered in a therapeutically effective amount.

20. The method of claim 16, wherein the cell is in a living subject.

21. The method of claim 16, wherein the oligonucleotide does not comprise three or more consecutive guanosine nucleotides.

22. The method of claim 16, wherein the oligonucleotide is 8 to 30 nucleotides in length.

23. The method of claim 16, wherein at least one nucleotide of the oligonucleotide is a nucleotide analogue.

24. The method of claim 16, wherein at least one nucleotide of the oligonucleotide comprises a 2' O-methyl.

25. The method of claim 16, wherein the oligonucleotide comprises at least one ribonucleotide, at least one deoxyribonucleotide, or at least one bridged nucleotide.

26. The method of claim 25, wherein the bridged nucleotide is a LNA nucleotide, a cEt nucleotide or a ENA modified nucleotide.

27. The method of claim 16, wherein each nucleotide of the oligonucleotide is a LNA nucleotide.

28. The method of claim 16, wherein one or more of the nucleotides of the oligonucleotide comprise 2'-fluoro-deoxyribonucleotides, 2'-O-methyl nucleotides, ENA nucleotide analogues, or LNA nucleotides.

29. The method of claim 16, wherein the nucleotides of the oligonucleotide comprise phosphorothioate internucleotide linkages between at least two nucleotides.

30. The method of claim 16, wherein the nucleotides of the oligonucleotide comprise phosphorothioate internucleotide linkages between at least two nucleotides.

31. The method of claim 16, wherein the oligonucleotide is a gapmer or a mixmer.

32. The method of claim 1, wherein the cell is a cell of a female heterozygous subject.

33. The method of claim 16, wherein the cell is a cell of a female heterozygous subject.

34. The method of claim 16, wherein the inhibitory nucleotide is complementary to 10 to 50 nucleotides of SEQ ID NO: 6030 or 6031.

* * * * *